(12) United States Patent
Barda et al.

(10) Patent No.: US 12,351,591 B2
(45) Date of Patent: Jul. 8, 2025

(54) KRAS INHIBITORS

(71) Applicant: ELI LILLY AND COMPANY, Indianapolis, IN (US)

(72) Inventors: David Anthony Barda, Indianapolis, IN (US); Jolie Anne Bastian, Indianapolis, IN (US); Kelly Wayne Furness, Avon, IN (US); Deqi Guo, Carmel, IN (US); James Robert Henry, Indianapolis, IN (US); Richard Duane Johnston, Greenfield, IN (US); Jason Eric Lamar, Indianapolis, IN (US); Tao Liu, San Diego, CA (US); Michael John Rodriguez, Indianapolis, IN (US); Almudena Rubio, Carmel, IN (US); Chong Si, Zionsville, IN (US); Gaiying Zhao, Carmel, IN (US); Mohammad Sadegh Zia-Ebrahimi, Indianapolis, IN (US); Matthew Patrick Baumgartner, Aldan, PA (US); Isabel Rojo, Madrid (ES); Mario Barberis, Madrid (ES); Santiago Carballares Martin, Madrid (ES); Pablo Garcia Losada, Madrid (ES); Sonia Maria Gutierrez Sanfeliciano, Madrid (ES); Wenceslao Lumeras Amador, Madrid (ES); Victoriano Molero Florez, Madrid (ES); Maria Lourdes Prieto Vallejo, Madrid (ES)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 18/189,713

(22) Filed: Mar. 24, 2023

(65) Prior Publication Data

US 2024/0043451 A1    Feb. 8, 2024

Related U.S. Application Data

(60) Provisional application No. 63/386,404, filed on Dec. 7, 2022, provisional application No. 63/406,906, filed on Sep. 15, 2022, provisional application No. 63/323,607, filed on Mar. 25, 2022.

(51) Int. Cl.
*C07D 519/00* (2006.01)
*C07D 491/048* (2006.01)

(52) U.S. Cl.
CPC ....... *C07D 519/00* (2013.01); *C07D 491/048* (2013.01); *C07B 2200/05* (2013.01)

(58) Field of Classification Search
CPC . A61P 35/00; C07B 2200/05; C07D 491/048; C07D 519/00
See application file for complete search history.

(56) References Cited

FOREIGN PATENT DOCUMENTS

| WO | 2020/081282 A1 | 4/2020 |
|----|---------------|--------|
| WO | 2021/118877 A1 | 6/2021 |
| WO | 2022/002018 A1 | 1/2022 |
| WO | 2022/152233 A1 | 7/2022 |
| WO | 2022/184178 A1 | 9/2022 |
| WO | 2022/261154 A1 | 12/2022 |
| WO | 2023/061294 A1 | 4/2023 |

OTHER PUBLICATIONS

PCT International Search Report and the Written Opinion of the International Searching Authority pertaining to international Application No. PCT/ US2023/016257; Date of Mailing: Jun. 2, 2023; 12 pages.

*Primary Examiner* — Jeffrey H Murray
*Assistant Examiner* — Daniel John Burkett
(74) *Attorney, Agent, or Firm* — Stefan O. Ochiana

(57) ABSTRACT

The present invention provides compounds of the formula:

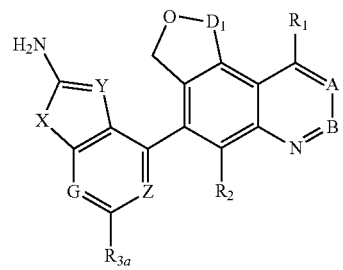

wherein A, B, $D_1$, X, Y, Z, G, $R_1$, $R_2$, and $R_{3a}$ are as described herein, pharmaceutically acceptable salts thereof, and methods of using these compounds and pharmaceutically acceptable salts thereof for treating patients for cancer.

33 Claims, No Drawings

KRAS INHIBITORS

BACKGROUND

The MAPK/ERK signaling pathway relays extracellular stimuli to the nucleus, thereby regulating diverse cellular responses including cell proliferation, differentiation, and apoptosis. KRas protein is an initiator of the MAPK/ERK signaling pathway and functions as a switch responsible for inducing cell division. In its inactive state, KRas binds guanosine diphosphate (GDP), effectively sending a negative signal to suppress cell division. In response to an extracellular signal, KRas is allosterically activated allowing for nucleotide exchange of GDP for guanosine triphosphate (GTP). In its GTP-bound active state, KRas recruits and activates proteins necessary for the propagation of growth factor induced signaling, as well as other cell signaling receptors. Examples of the proteins recruited by KRas-GTP are c-Raf and PI3-kinase. KRas, as a GTP-ase, converts the bound GTP back to GDP, thereby returning itself to an inactive state, and again propagating signals to suppress cell division. KRas gain of function mutations exhibit an increased degree of GTP binding and a decreased ability to convert GTP into GDP. The result is an increased MAPK/ERK signal which promotes cancerous cell growth. Missense mutations of KRas at codon 12 are the most common mutations and markedly diminish GTPase activity.

Oncogenic KRas mutations have been identified in approximately 30% of human cancers and have been demonstrated to activate multiple downstream signaling pathways. Despite the prevalence of KRas mutations, it has been a difficult therapeutic target. (Cox, A. D. *Drugging the Undruggable RAS: Mission Possible?* Nat. Rev. Drug Disc. 2014, 13, 828-851; Pylayeva-Gupta, y et al. *RAS Oncogenes: Weaving a Tumorigenic Web.* Nat. Rev. Cancer 2011, 11, 761-774).

Thus far, work has focused on KRas G12C mutant inhibitors (e.g., WO2019/099524, WO2020/081282, WO2020/101736, WO2020/146613, and WO2021/118877 disclose KRas G12C inhibitors), whereas WO2021/041671 discloses small molecules inhibitors of KRas G12D and WO2017/011920 discloses small molecule inhibitors of KRas G12C, G12D, and G12V.

There remains a need to provide alternative, small molecule KRas inhibitors. In particular, there is a need to provide more potent, orally deliverable KRas inhibitors that are useful for treating cancer. More particularly, there is a need to provide small molecule inhibitors that specifically inhibit KRas GTP activity. There is also a need to provide small molecule KRas inhibitors that exhibit greater efficacy at the same or reduced KRas inhibitory activity. Further, there is a desire to provide KRas inhibitors that exhibit better pharmacokinetic/pharmacodynamic properties. Also, there is a need to provide more potent KRas inhibitors that exhibit increased efficacy with reduced or minimized untoward or undesired effects. Further, there is a need to provide more potent KRas inhibitors that exhibit selective inhibition preference for KRas G12D mutant over KRas wild-type. Further, there is also a need to provide more potent KRas inhibitors that exhibit selective inhibition preference for KRas G12C, G12D, and/or G12V mutants over HRAS or NRAS. The present invention addresses one or more of these needs by providing novel KRas inhibitors.

SUMMARY

Compounds of Formula I are provided herein:

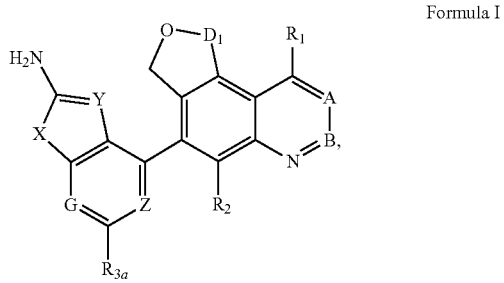

Formula I pharmaceutically acceptable salts thereof, and pharmaceutical compositions thereof. In Formula I,
A is —C(H)— or —N—;
B is —C($R_4$)— or —N—;
$D_1$ is —$CH_2$—, —$CH_2CH_2$—, or —CH($CH_2$CN)—;
X is —O— or —S—;
Y is —C(CN)— or —N—;
Z is —C($R_{3c}$)— or —N—;
G is —C($R_{3b}$)— or —N—;
$R_1$ is H, hydroxyl, methoxy, $C_{1-4}$ alkyl, $C_{2-4}$ heteroalkyl, azetidine, N-linked piperazine, piperidine, morpholine, or a group of the formula selected from

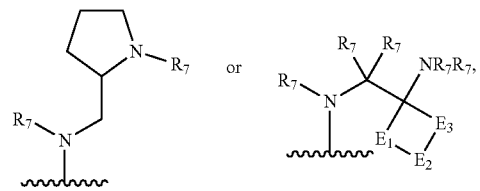

wherein the $C_{1-4}$ alkyl, $C_{2-4}$ heteroalkyl, azetidine, piperidine, or N-linked piperazine are optionally substituted with one or more of amino, hydroxyl, methyl, trideuteromethyl, methoxy, oxetane, or $C_{1-3}$ alkyl, wherein the $C_{1-3}$ alkyl is optionally substituted by one or more halogen, hydroxyl, methyl, hydroxymethyl, methoxy, trifluoromethoxy, difluoromethoxy, —O-trideuteromethyl, cyclopropyl, oxetane, pyrazole, imidazole, amino, —$CONR_7R_7$, —O—($CH_2$)$_p$—$OC_{1-3}$ alkyl, —O—($CH_2$)$_p$—OH, or —O—CO—$C_{1-3}$ alkyl, wherein the piperidine or the N-linked piperazine are optionally bridged by a $C_{1-3}$ alkyl and wherein the cyclopropyl, imidazole, or pyrazole are each optionally substituted with a hydroxyl, or a $C_{1-3}$ alkyl substituted with one or more hydroxyl;
$E_1$ is —($CR_7R_7$—)$_n$, $E_2$ is —$CR_7R_7$—, —$NR_7$— or —O— and $E_3$ is —($CR_7R_7$—)$_m$, wherein m+n is 1, 2, 3 or 4;
p is 1, 2, or 3;
$R_2$ is H, halogen, or methyl;
$R_{3a}$, $R_{3b}$, and $R_{3c}$ are each independently H, methyl or halogen;
$R_4$ is H, methyl, —$CH_2$—OH, —O—$R_5$-$R_6$, —O—$R_6$, or azetidine optionally substituted with $NR_7R_7$, wherein $R_5$ is —$CH_2$—, —CH($CH_3$)—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl, 2-oxo-1,3-dihydrobenzimidazole, imidazole, or pyrazole, wherein the $C_{1-3}$ alkyl, $C_{3-6}$ cycloalkyl, or $C_{4-6}$ heterocycloalkyl are optionally substituted with one or more oxo, halogen, hydroxyl, methoxy, difluoromethoxy, $NR_7R_7$, $C_{1-4}$ alkyl, $C_{1-4}$ alkenyl, —CN, or —CO—$CH_2OH$, wherein the $C_{1-4}$ alkyl is optionally substituted with one or more halogen, hydroxyl, methoxy, or $NR_7R_7$, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl and wherein if $R_4$ is H then $R_1$ is not H; and each $R_7$ is independently H, or $C_{1-3}$ alkyl.

Also provided herein are methods of using the compounds of Formulae I-VIII (including Ia-VIIa), pharmaceutically acceptable salts thereof, and pharmaceutical compositions thereof, to treat cancer, in particular for the treatment of lung cancer, pancreatic cancer, cervical cancer, esophageal cancer, endometrial cancer, ovarian cancer, cholangiocarcinoma, and colorectal cancer. The methods include administering a therapeutically effective amount of a compound of Formulae I-VIII (including Ia-VIIa), or a pharmaceutically acceptable salt thereof, to a patient in need thereof.

Further provided herein, are compounds of Formulae I-VIII (including Ia-VIIa), and pharmaceutically acceptable salts thereof, for use in therapy. Additionally provided herein, are the compounds of Formulae I-VIII (including Ia-VIIa), and pharmaceutically acceptable salts thereof, for use in the treatment of cancer, in particular for the treatment of lung cancer, pancreatic cancer, cervical cancer, esophageal cancer, endometrial cancer, ovarian cancer, cholangiocarcinoma, and colorectal cancer. Also additionally provided herein is the use of compounds of Formulae I-VIII (including Ia-VIIa), or pharmaceutically acceptable salts thereof, in the manufacture of a medicament for treating cancer, in particular for the treatment of lung cancer, pancreatic cancer, cervical cancer, esophageal cancer, endometrial cancer, ovarian cancer, cholangiocarcinoma, and colorectal cancer.

DETAILED DESCRIPTION

Novel inhibitors of the KRas gain of function mutation G12D are described herein. These new compounds could address the needs noted above for inhibitors of KRas GTP activity in gain of function mutants in the treatment of cancers such as lung cancer, colorectal cancer, pancreatic cancer, bladder cancer, cervical cancer, endometrial cancer, ovarian cancer, cholangiocarcinoma or esophageal cancer. Some of these new KRas G12D mutant inhibitor compounds are selective to KRas G12D mutants over wild-type KRas (and likely other mutant types such as G12C or G12V). Additionally, some of these new KRas G12D mutant inhibitor compounds are non-selective and inhibit both wild-type KRas and KRas G12D mutants (and possibly other mutant types such as G12C or G12V). Also, some of these new KRas compounds are non-selective and inhibit both wild-type KRas and Kras G12C, G12D, and/or G12V mutants.

The present invention provides a compound of Formula I:

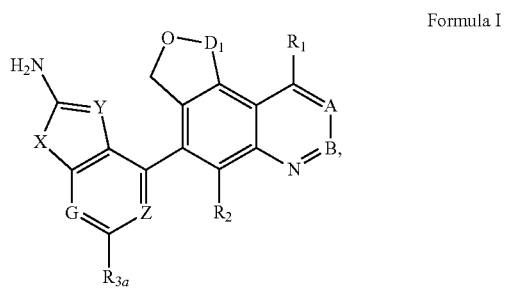

Formula I wherein A, B, $D_1$, X, Y, Z, G, $R_1$, $R_2$, and $R_{3a}$ are as defined above, or a pharmaceutically acceptable salt thereof.

In an embodiment a compound of Formula II is provided:

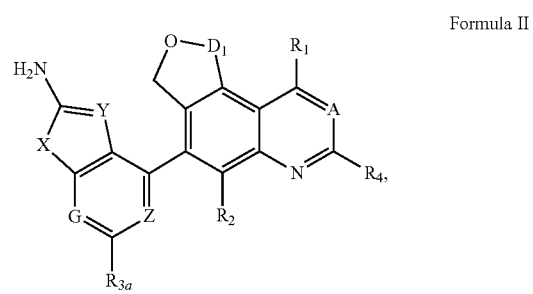

Formula II wherein $R_1$, $R_2$, $R_{3a}$, $R_4$, A, $D_1$, X, Y, Z, and G are as defined above, or a pharmaceutically acceptable salt thereof.

In an embodiment a compound of Formula III is provided:

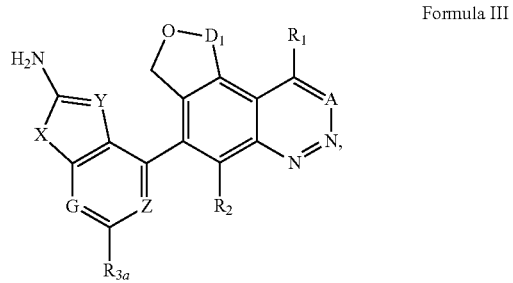

Formula III wherein $R_1$, $R_2$, $R_{3a}$, A, $D_1$, X, Y, Z, and G are as defined above, or a pharmaceutically acceptable salt thereof.

In an embodiment a compound of Formula IV is provided:

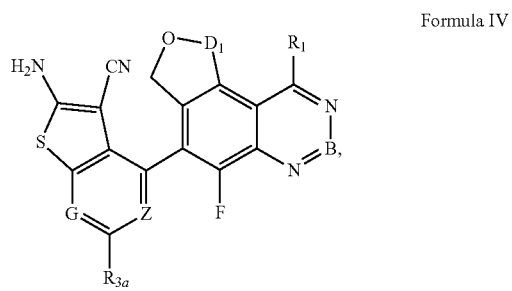

Formula IV wherein $R_1$, $R_{3a}$, B, $D_1$, Z, and G are as defined above, or a pharmaceutically acceptable salt thereof.

In an embodiment a compound of Formula V is provided:

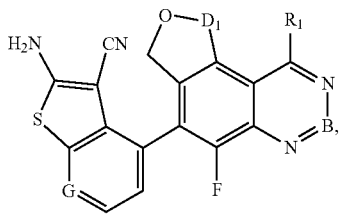

Formula V wherein $R_1$, B, $D_1$, and G are as defined above, or a pharmaceutically acceptable salt thereof.

In an embodiment a compound of Formula VI is provided:

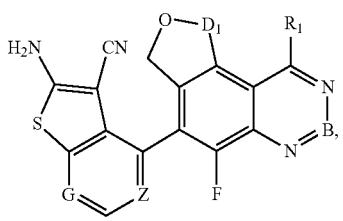

Formula VI wherein $R_1$, B, $D_1$, Z, and G are as defined above, or a pharmaceutically acceptable salt thereof.

In an embodiment a compound of Formula VII is provided:

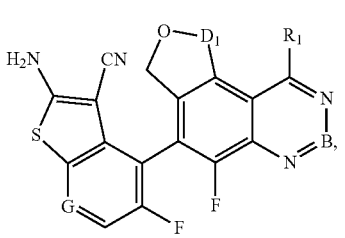

Formula VII wherein $R_1$, B, $D_1$, and G are as defined above, or a pharmaceutically acceptable salt thereof.

In an embodiment a compound of Formula VIII is provided:

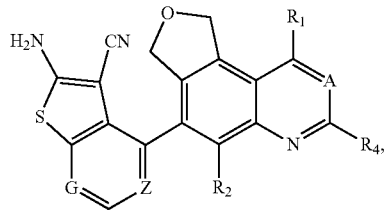

wherein $R_1$, $R_2$, $R_4$, A, Z, and G are as defined above, or a pharmaceutically acceptable salt thereof.

The present invention provides a compound of Formula Ia:

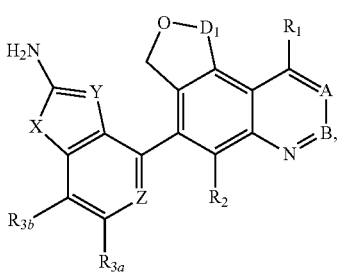

Formula Ia wherein A, B, $D_1$, X, Y, Z, $R_1$, $R_2$, $R_{3a}$, and $R_{3b}$ are as defined above, or a pharmaceutically acceptable salt thereof.

In an embodiment a compound of Formula IIa is provided:

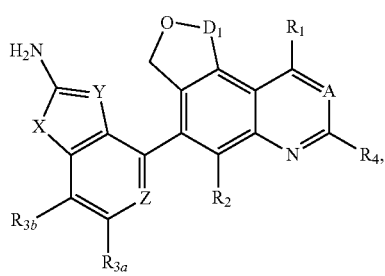

Formula IIa wherein $R_1$, $R_2$, $R_{3a}$, $R_{3b}$, $R_4$, A, $D_1$, X, Y, and Z are as defined above, or a pharmaceutically acceptable salt thereof.

In an embodiment a compound of Formula IIIa is provided:

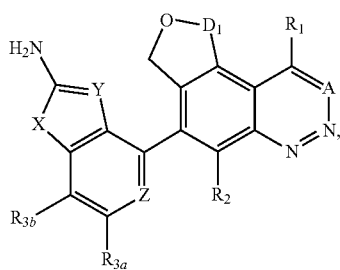

Formula IIIa wherein $R_1$, $R_2$, $R_{3a}$, $R_{3b}$, A, $D_1$, X, Y, and Z are as defined above, or a pharmaceutically acceptable salt thereof.

In an embodiment a compound of Formula IVa is provided:

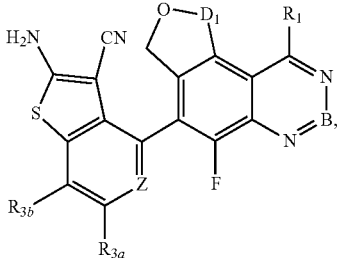

Formula IVa wherein $R_1$, $R_{3a}$, $R_{3b}$, B, $D_1$, and Z are as defined above, or a pharmaceutically acceptable salt thereof.

In an embodiment a compound of Formula Va is provided:

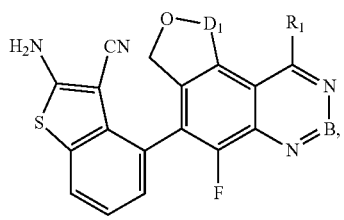

Formula Va wherein $R_1$, B, and $D_1$ are as defined above, or a pharmaceutically acceptable salt thereof.

In an embodiment a compound of Formula VIa is provided:

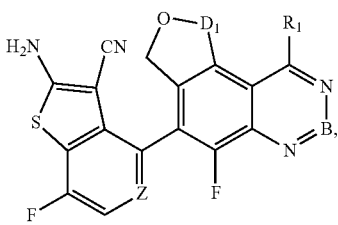

Formula VIa wherein $R_1$, B, $D_1$, and Z are as defined above, or a pharmaceutically acceptable salt thereof.

In an embodiment a compound of Formula VIIa is provided:

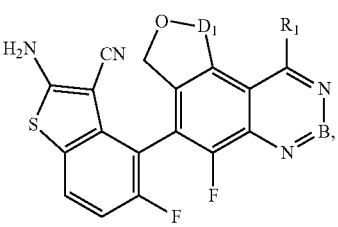

Formula VIIa wherein $R_1$, B, and $D_1$ are as defined above, or a pharmaceutically acceptable salt thereof.

As used herein, the term halogen means fluoro (F), chloro (Cl), bromo (Br), or iodo (I). As used herein, the term alkyl means saturated linear or branched-chain monovalent hydrocarbon radicals of one to a specified number of carbon atoms, e.g., "$C_{1-4}$ alkyl" or "$C_{1-3}$ alkyl." Examples of alkyls include, but are not limited to, methyl, ethyl, propyl, 1-propyl, isopropyl, butyl, and iso-butyl. As used herein, the term cycloalkyl means saturated cyclic monovalent hydrocarbon radicals containing a specified number of carbon atoms, e.g., "$C_{4-6}$ cycloalkyl." As used herein, the term heteroalkyl means saturated linear or branched-chain monovalent hydrocarbon radicals containing a specified number of atoms including both carbon atoms and one or more heteroatoms, e.g., "$C_{2-3}$ heteroalkyl" and "$C_{2-4}$ heteroalkyl." For example, $C_4$ heteroalkyl means a saturated linear or branched-chain monovalent hydrocarbon radical containing at least one carbon atoms and at least one heteroatoms, wherein the total number of carbon and heteroatoms adds up to 4 atoms. As used herein, the term heterocycloalkyl means saturated cyclic heteroalkyl groups containing a specified number of atoms including both carbon atoms and one or more heteroatoms, e.g., "$C_{4-6}$ heterocycloalkyl." Examples of heteroatoms include, but are not limited to, nitrogen and oxygen.

For $R_1$, the N-linked piperazine (or the piperidine) is optionally bridged by the $C_{1-3}$ alkyl. As used herein, the term "bridged" for the $R_1$ group means the $R_1$ group is bicyclic with the $C_{1-3}$ alkyl connecting to two, non-adjacent atoms of the N-linked piperazine ring. Examples of bridged N-linked piperazine ring groups include, but are not limited to:

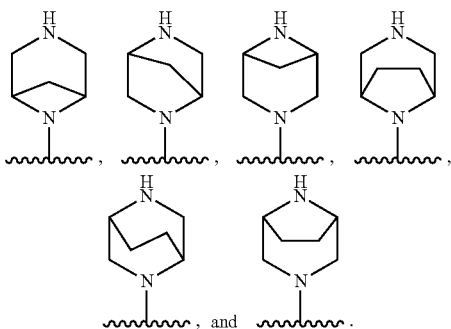

When acting as a bridge, the $C_{1-3}$ alkyl can optionally be substituted as defined, e.g., with a halogen like fluorine such as:

In $R_1$, the N-linked piperazine group is not specified to be bonded through a carbon or nitrogen and could be either. Similarly, optional substitutions onto the $C_{2-4}$ heteroalkyl, or N-linked piperazine groups of $R_1$ can be on a carbon or heteroatom.

For $R_6$, the $C_{4-6}$ cycloalkyl or $C_{4-6}$ heterocycloalkyl are optionally fused with a $C_{1-4}$ alkyl to form a bicyclic ring. As used herein, the term "fused" for the $R_7$ group means the $R_6$ group is bicyclic with the $C_{1-4}$ alkyl connecting to two, adjacent atoms of the $C_{4-6}$ cycloalkyl or $C_{4-6}$ heterocycloalkyl ring. Examples of fused $R_6$ groups include:

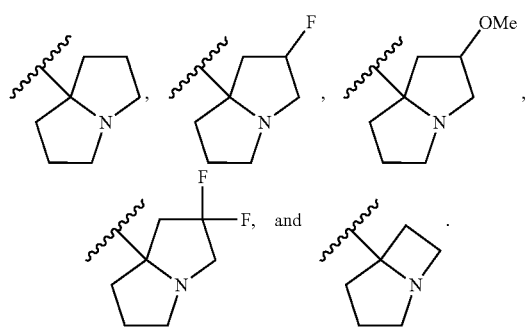

In $R_6$, the $C_{4-6}$ heterocycloalkyl group is not specified to be bonded through a carbon or nitrogen and could be either. Similarly, substitutions onto the $R_6$ $C_{4-6}$ heterocycloalkyl group can be on a carbon or heteroatom.

In an embodiment of a compound of Formula Ia, or a pharmaceutically acceptable salt thereof, A is —C(H)— or —N—; B is —C($R_4$)— or —N—; $D_1$ is —$CH_2$—, —$CH_2CH_2$—, or —CH($CH_2$CN)—; X is —O— or —S—; Y is —C(CN)— or —N—; Z is —C($R_3$)— or —N—; $R_1$ is H, $C_{1-4}$ alkyl, $C_{1-4}$ heteroalkyl, or N-linked piperazine, wherein the $C_{1-4}$ alkyl, $C_{1-4}$ heteroalkyl, or N-linked piperazine are optionally substituted with one or more of amino, hydroxyl, methyl, oxetane, and $C_{1-3}$ alkyl, wherein the $C_{1-3}$ alkyl is optionally substituted by one or more halogen, hydroxyl, methyl, hydroxymethyl, methoxy, cyclopropyl, oxetane, or amino, and wherein the N-linked piperazine is optionally bridged by the $C_{1-3}$ alkyl; $R_2$ is H, halogen, or methyl; $R_{3a}$, $R_{3b}$, and $R_{3c}$ are each independently H or halogen; and $R_4$ is H, methyl, —$CH_2$—OH, —O—$R_5$-$R_6$, or —O—$R_6$, wherein $R_5$ is —$CH_2$—, —CH($CH_3$)—, or —$CH_2$—$CH_2$—, wherein $R_6$ is H, $C_{1-3}$ alkyl, $C_{2-3}$ heterocycloalkyl, $C_{4-6}$ cycloalkyl, or $C_{4-6}$ heterocycloalkyl, wherein the $C_{1-3}$ alkyl, $C_{4-6}$ cycloalkyl, or $C_{4-6}$ heterocycloalkyl are optionally substituted with one or more halogen, hydroxyl, methoxy, $C_{1-4}$ alkyl, or $C_{1-4}$ alkenyl, wherein the $C_{1-4}$ alkyl is optionally substituted with one or more halogen or hydroxyl, wherein the $C_{4-6}$ cycloalkyl or $C_{4-6}$ heterocycloalkyl are optionally fused with the $C_{1-4}$ alkyl to form a bicyclic ring, and wherein if $R_4$ is H then $R_1$ is not H.

In an embodiment of a compound of Formulae I, Ia, II, IIa, III, IIIa, or VIII or a pharmaceutically acceptable salt thereof, A is —N—.

In an embodiment of a compound of Formulae I, Ia, II, IIa, III, IIIa, or VIII or a pharmaceutically acceptable salt thereof, A is —C(H)—.

In an embodiment of a compound of Formulae I, Ia, IV, IVa, V, Va, VI, VIa, VII, or VIIa or a pharmaceutically acceptable salt thereof, B is —N—.

In an embodiment of a compound of Formulae I, Ia, IV, IVa, V, Va, VI, VIa, VII, or VIIa or a pharmaceutically acceptable salt thereof, B is —CH—.

In an embodiment of a compound of Formulae I, Ia, IV, IVa, V, Va, VI, VIa, VII, or VIIa or a pharmaceutically acceptable salt thereof, B is —C($R_4$)—.

In an embodiment of a compound of Formulae I, Ia, II, IIa, III, IIIa, IV, IVa, V, Va, VI, VIa, VII, or VIIa or a pharmaceutically acceptable salt thereof, $D_1$ is —$CH_2$—.

In an embodiment of a compound of Formulae I, Ia, II, IIa, III, or IIIa or a pharmaceutically acceptable salt thereof, X is —S—.

In an embodiment of a compound of Formulae I, Ia, II, IIa, III, or IIIa or a pharmaceutically acceptable salt thereof, Y is —C(CN)—.

In an embodiment of a compound of any of Formulae I, Ia, II, IIa, III, IIIa, IV, or IVa or a pharmaceutically acceptable salt thereof, Z is —C($R_{3c}$)—.

In an embodiment of a compound of any of Formulae I, Ia, II, IIa, III, IIIa, IV, or IVa or a pharmaceutically acceptable salt thereof, Z is —N—.

In an embodiment of a compound of any of Formulae I, II, III, IV, V, or VII or a pharmaceutically acceptable salt thereof, G is —C($R_{3b}$)—.

In an embodiment of a compound of any of Formulae I, II, III, IV, V, or VII or a pharmaceutically acceptable salt thereof, G is —N—.

In an embodiment of a compound of any of Formulae I, II, III, IV, or VII or a pharmaceutically acceptable salt thereof, G is —N—, and Z is —C($R_{3c}$)—.

In an embodiment of a compound of any of Formulae I, II, III, IV, V, or VII or a pharmaceutically acceptable salt thereof, G is —C($R_{3b}$)—.

In an embodiment of a compound of any of Formulae I, II, III, IV, or VII or a pharmaceutically acceptable salt thereof, G is —C($R_{3b}$)—, and Z is —N—.

In an embodiment of a compound of any of Formulae I, II, III, or IV or a pharmaceutically acceptable salt thereof, $R_{3b}$ is F, or a pharmaceutically acceptable salt thereof.

In an embodiment of a compound of any of Formulae I, Ia, II, IIa, III, IIIa, IV, IVa, V, Va, VI, VIa, VII, VIIa, or VIII or a pharmaceutically acceptable salt thereof, $R_1$ is H.

In an embodiment of a compound of any of Formulae I, Ia, II, IIa, III, IIIa, IV, IVa, V, Va, VI, VIa, VII, VIIa, or VIII or a pharmaceutically acceptable salt thereof, $R_1$ is N-linked piperazine, which can be optionally substituted as defined above.

In an embodiment of a compound of any of Formulae I, Ia, II, IIa, III, IIIa, IV, IVa, V, Va, VI, VIa, VII, VIIa, or VIII or a pharmaceutically acceptable salt thereof, $R_1$ is an optionally substituted N-linked piperazine bridged by a $C_{1-3}$ alkyl.

In an embodiment of a compound of any of Formulae I, Ia, II, IIa, III, IIIa, IV, IVa, V, Va, VI, VIa, VII, VIIa, or VIII or a pharmaceutically acceptable salt thereof, $R_1$ is N-linked piperazine substituted with one or more of methyl, trideuteromethyl, or $C_{1-3}$ alkyl, wherein the $C_{1-3}$ alkyl is optionally substituted by one or more halogen, hydroxyl, methyl, hydroxymethyl, methoxy, trifluoromethoxy, difluoromethoxy, —O-trideuteromethyl, cyclopropyl, oxetane, pyrazole, imidazole, —$CONR_7R_7$, —O—($CH_2$)$_p$—$OC_{1-3}$ alkyl, —O—($CH_2$)$_p$—OH, or —O—CO—$C_{1-3}$ alkyl, and wherein the cyclopropyl, imidazole, or pyrazole are each optionally substituted with a hydroxyl or a $C_{1-3}$ alkyl substituted with one or more hydroxyl; and wherein the N-linked piperazine is bridged by a $C_{1-3}$ alkyl, or a pharmaceutically acceptable salt thereof.

In an embodiment of a compound of any of Formulae I, Ia, II, IIa, III, IIIa, IV, IVa, V, Va, VI, VIa, VII, VIIa, or VIII or a pharmaceutically acceptable salt thereof, $R_1$ is selected from

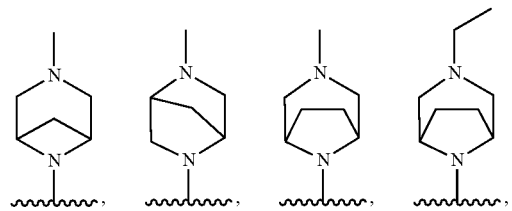

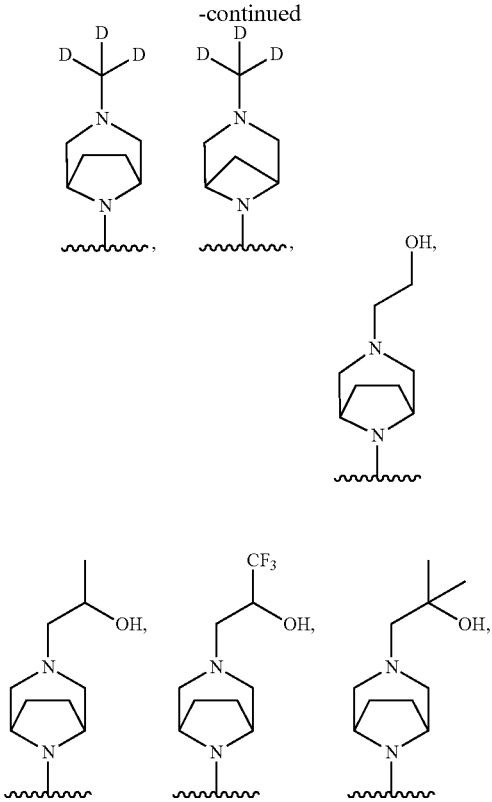
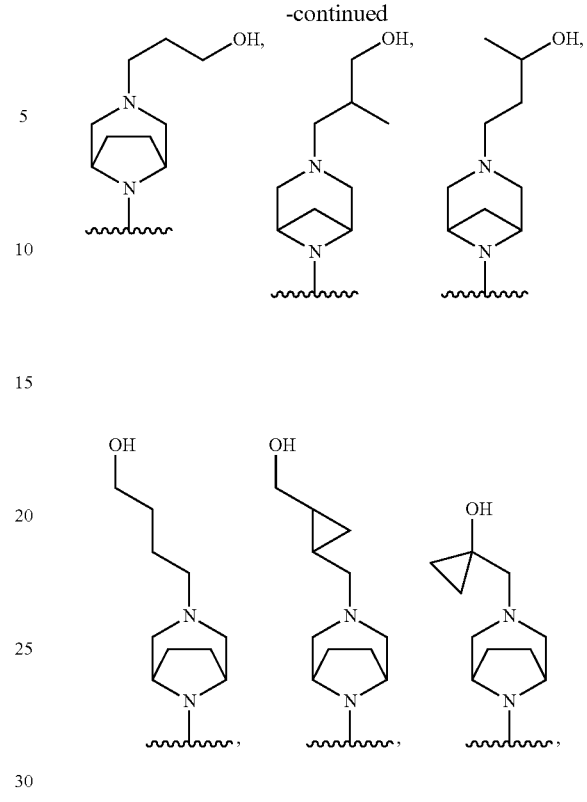
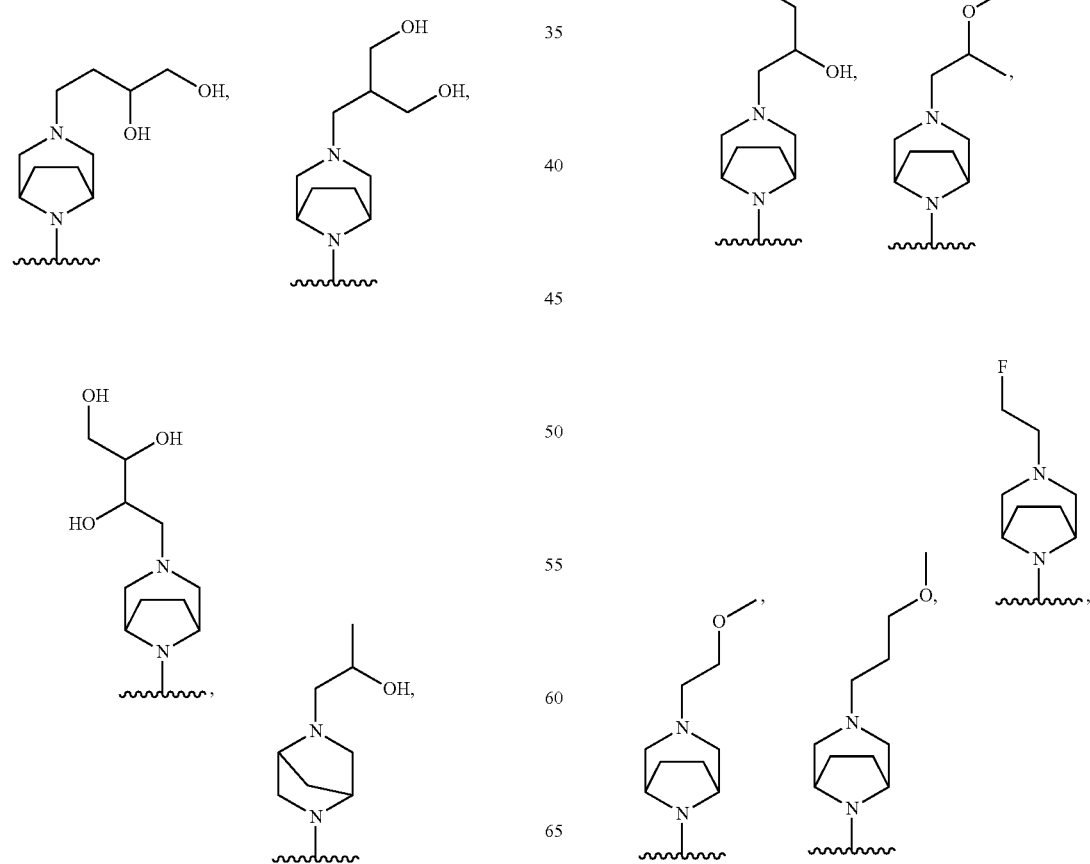

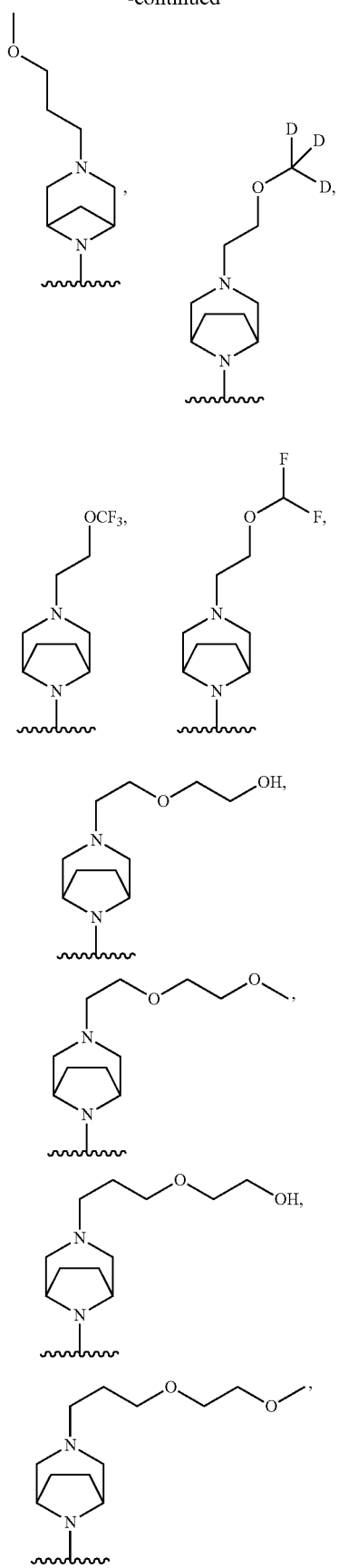
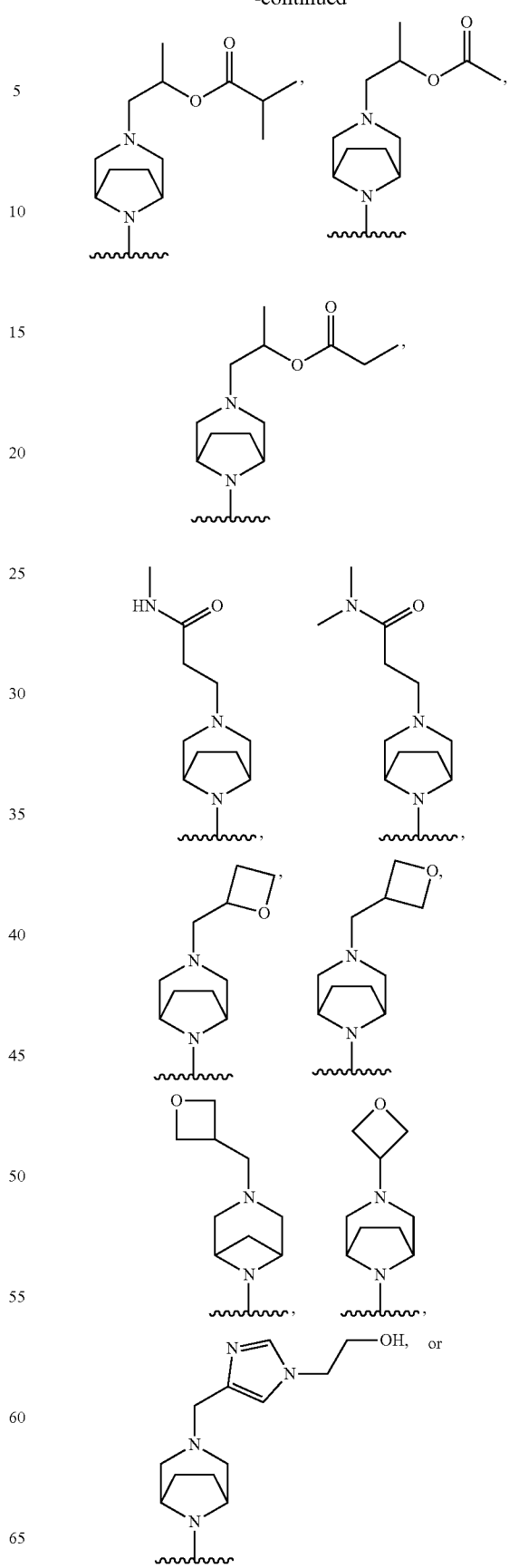

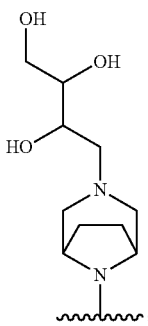
In an embodiment of a compound of any of Formulae I, Ia, II, IIa, III, IIIa, IV, IVa, V, Va, VI, VIa, VII, VIIa, or VIII or a pharmaceutically acceptable salt thereof, $R_1$ is H, methoxy, —CH$_2$—CH$_2$—NH$_2$, or a group of the formula
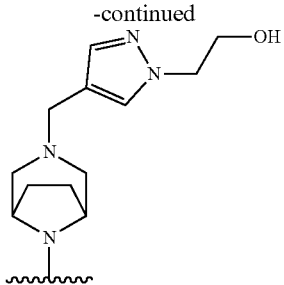
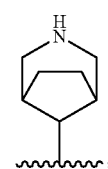
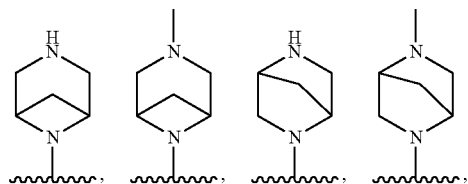
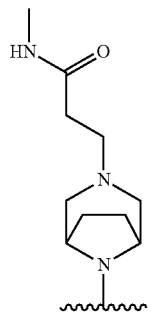 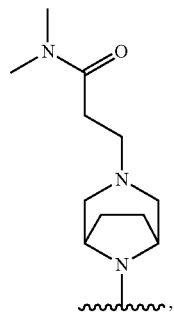
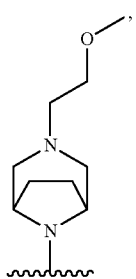
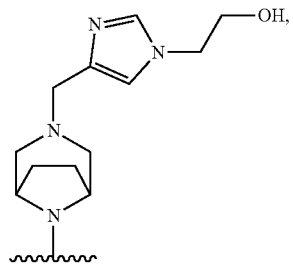
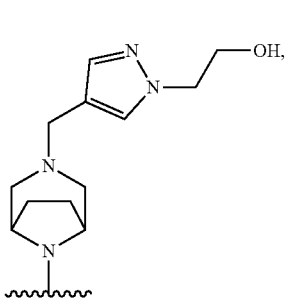 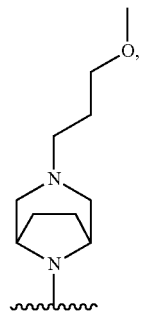
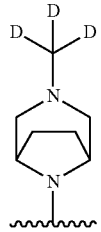 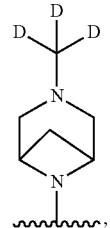
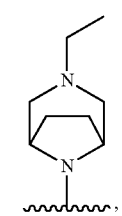
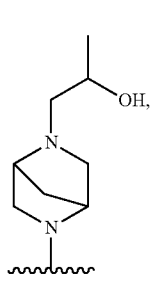 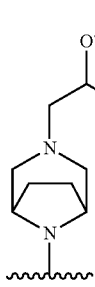

-continued
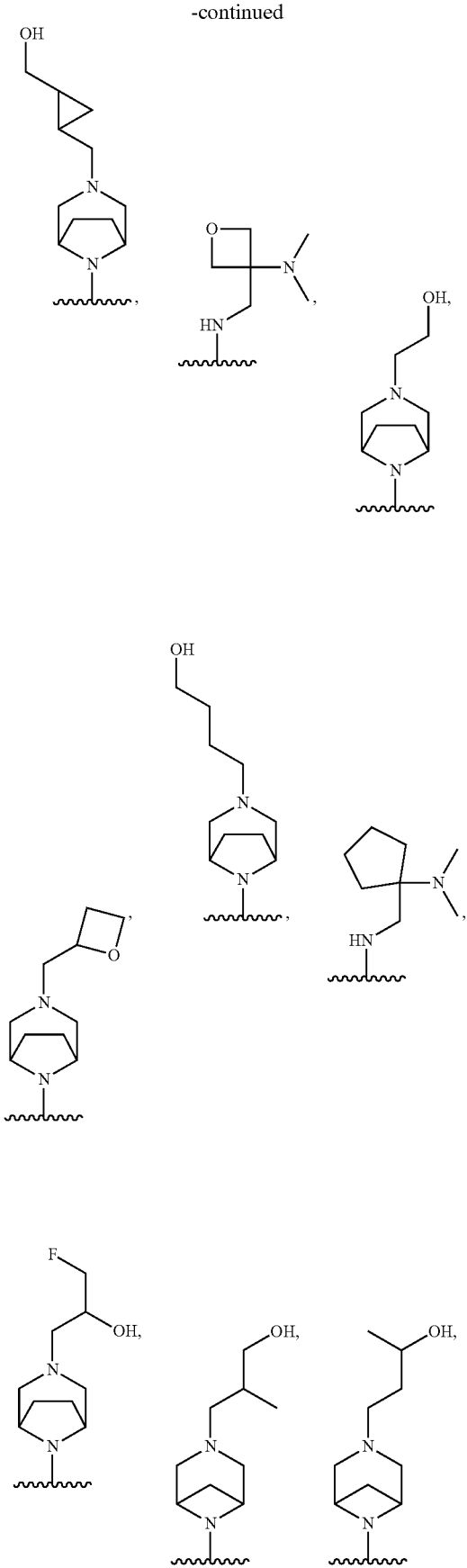
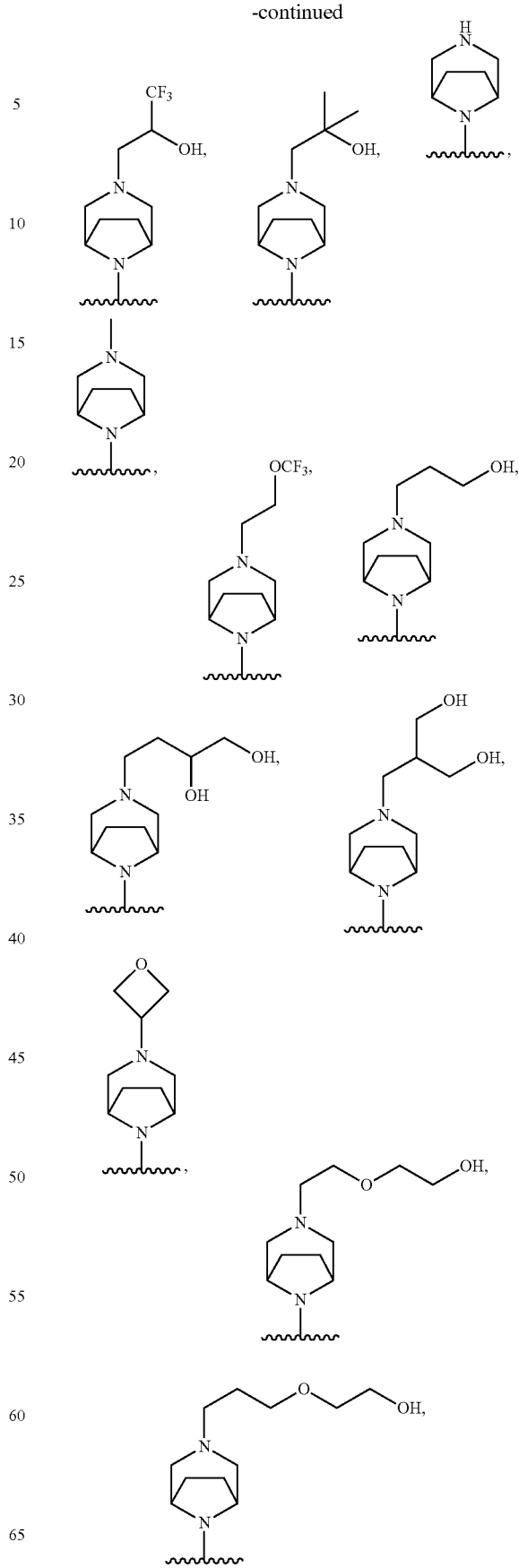

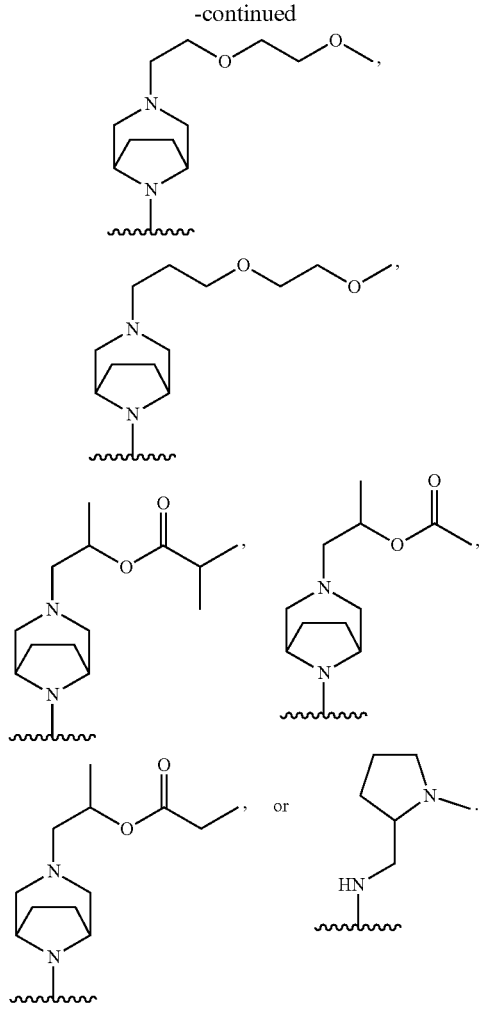
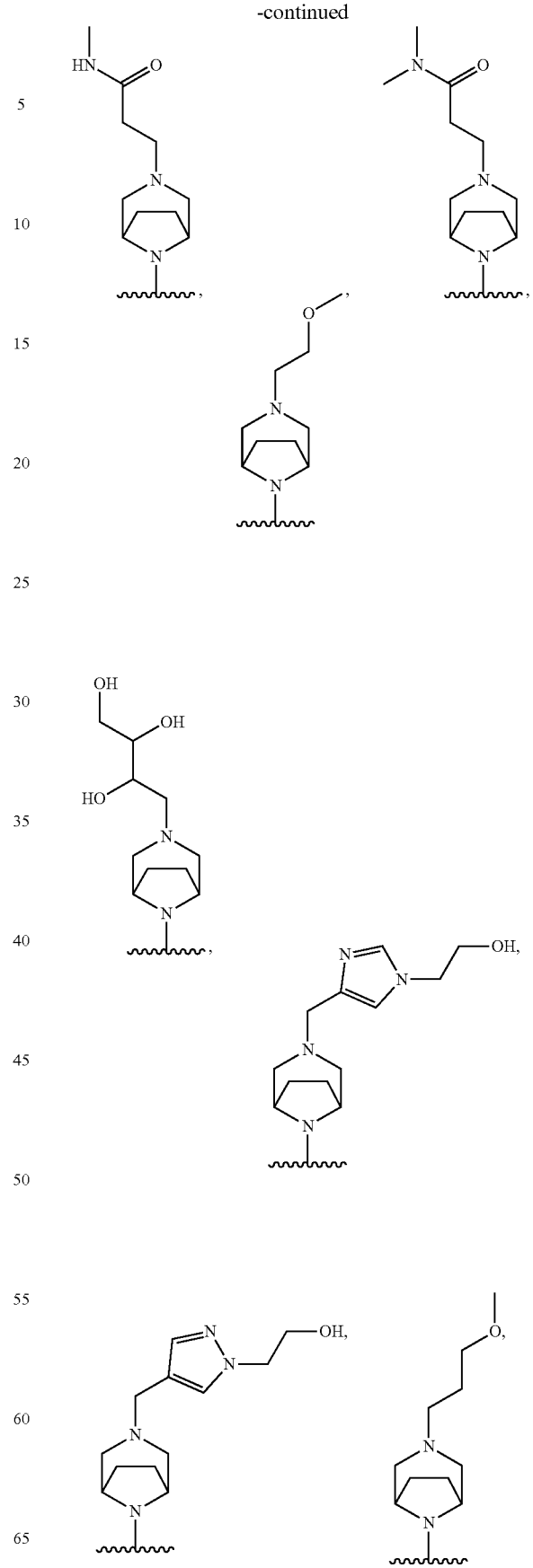
In an embodiment of a compound of any of Formulae I, Ia, II, IIa, III, IIIa, IV, IVa, V, Va, VI, VIa, VII, VIIa, or VIII or a pharmaceutically acceptable salt thereof, $R_1$ is
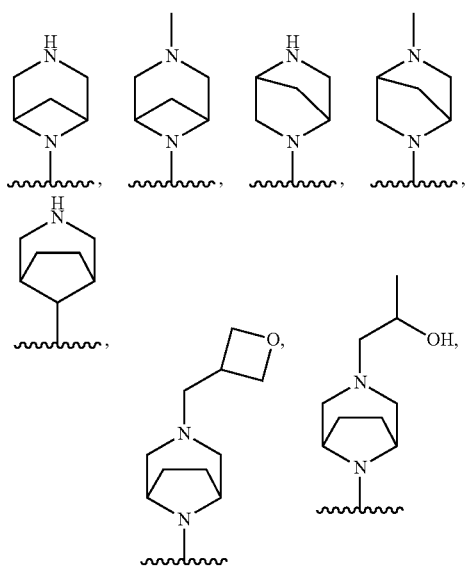

-continued
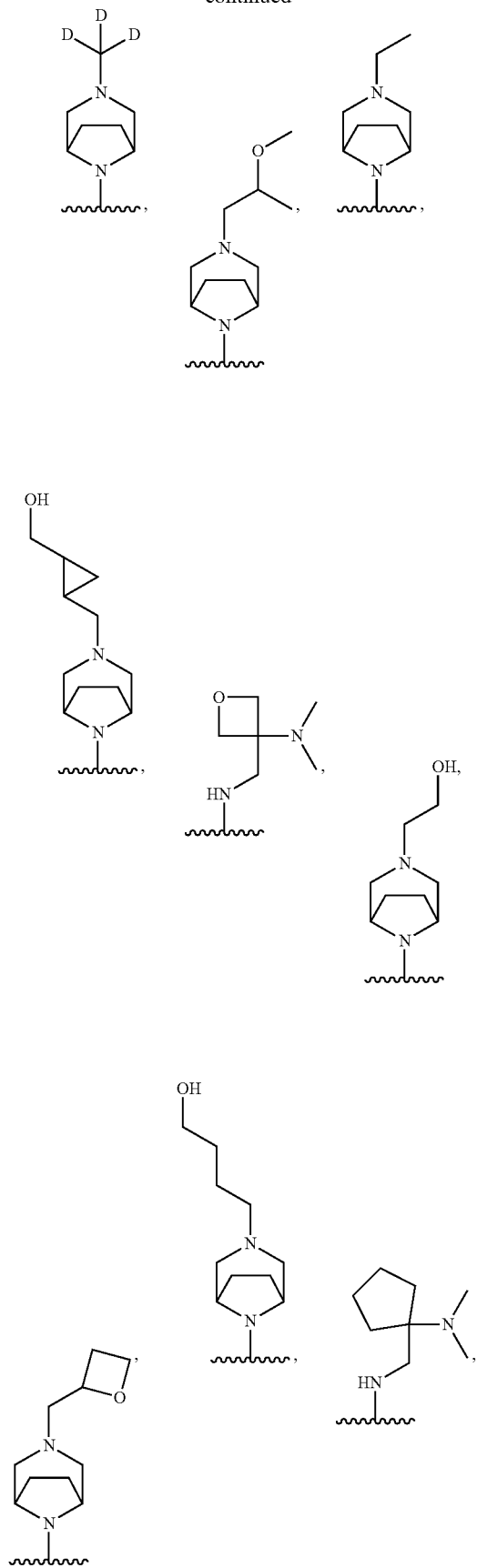
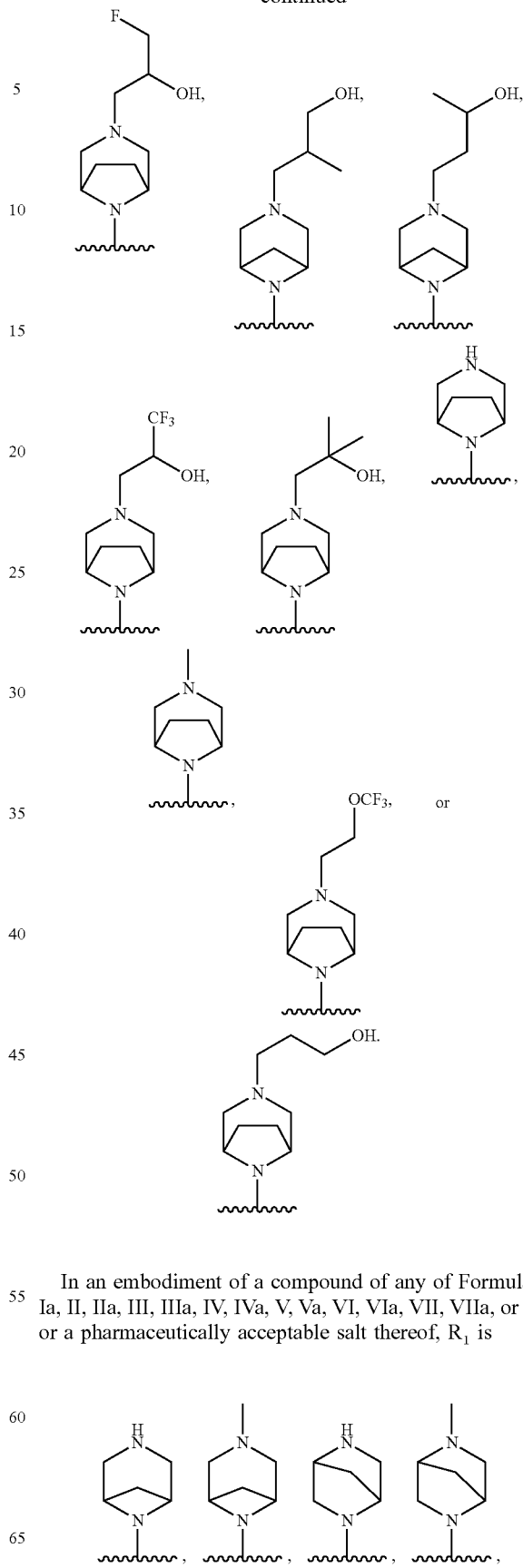
In an embodiment of a compound of any of Formulae I, Ia, II, IIa, III, IIIa, IV, IVa, V, Va, VI, VIa, VII, VIIa, or VIII or a pharmaceutically acceptable salt thereof, R₁ is

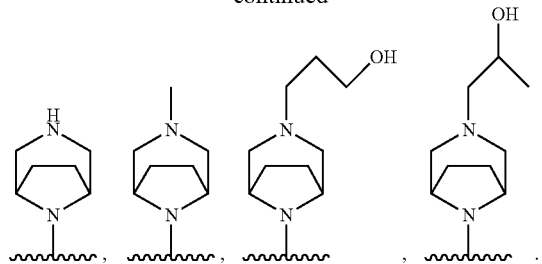

In an embodiment of a compound of any of Formulae I, Ia, II, IIa, III, IIIa, IV, IVa, V, Va, VI, VIa, VII, VIIa, or VIII or a pharmaceutically acceptable salt thereof, $R_1$ is H, methoxy, $C_{1-4}$ alkyl, $C_{2-4}$ heteroalkyl, N-linked piperazine, piperidine, or a group of the formula

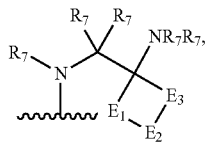

wherein the $C_{1-4}$ alkyl, $C_{2-4}$ heteroalkyl, piperidine, or N-linked piperazine are optionally substituted with one or more of amino, hydroxyl, methyl, trideuteromethyl, oxetane, or $C_{1-3}$ alkyl, wherein the $C_{1-3}$ alkyl is optionally substituted by one or more halogen, hydroxyl, methyl, hydroxymethyl, methoxy, trifluoromethoxy, cyclopropyl, oxetane, pyrazole, imidazole, amino, —$CONR_7R_7$, wherein the piperidine or the N-linked piperazine are optionally bridged by a $C_{1-3}$ alkyl and wherein the cyclopropyl, imidazole, or pyrazole are each optionally substituted with a $C_{1-3}$ alkyl substituted with one or more hydroxyl.

In an embodiment of a compound of Formulae I, Ia, II, IIa, IV, IVa, V, Va, VI, VIa, VII, VIIa, or VIII or a pharmaceutically acceptable salt thereof, $R_4$ is H, methyl, —$CH_2$—OH, —O—$R_5$-$R_6$, or —O—$R_6$, wherein $R_5$ is —$CH_2$—, —$CH_2(CH_3)$—, or —$CH_2$—$CH_2$—, wherein $R_6$ is H, $C_{1-3}$ alkyl, $C_{2-3}$ heterocycloalkyl, $C_{4-6}$ cycloalkyl, or $C_{4-6}$ heterocycloalkyl, wherein the $C_{1-3}$ alkyl, $C_{4-6}$ cycloalkyl, or $C_{4-6}$ heterocycloalkyl are optionally substituted with one or more halogen, hydroxyl, methoxy, $C_{1-4}$ alkyl, or $C_{1-4}$ alkenyl, wherein the $C_{1-4}$ alkyl is optionally substituted with one or more halogen or hydroxyl, wherein the $C_{4-6}$ cycloalkyl or $C_{4-6}$ heterocycloalkyl are optionally fused with the $C_{1-4}$ alkyl to form a bicyclic ring, and wherein if $R_4$ is H then $R_1$ is not H.

In an embodiment of a compound of Formula Ia, or a pharmaceutically acceptable salt thereof, $R_{3a}$, $R_{3b}$, and $R_{3c}$ are each independently H, or halogen; and $R_1$ is H, methoxy, $C_{1-4}$ alkyl, $C_{2-4}$ heteroalkyl, N-linked piperazine, piperidine, or a group of the formula

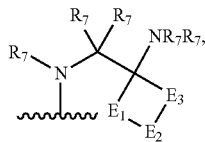

wherein the $C_{1-4}$ alkyl, $C_{2-4}$ heteroalkyl, piperidine, or N-linked piperazine are optionally substituted with one or more of amino, hydroxyl, methyl, trideuteromethyl, oxetane, or $C_{1-3}$ alkyl, wherein the $C_{1-3}$ alkyl is optionally substituted by one or more halogen, hydroxyl, methyl, hydroxymethyl, methoxy, trifluoromethoxy, cyclopropyl, oxetane, pyrazole, imidazole, amino, —$CONR_7R_7$, —O—$(CH_2)_p$—$OC_{1-3}$ alkyl, —O—$(CH_2)_p$—OH, or —O—CO—$C_{1-3}$ alkyl, wherein the piperidine or the N-linked piperazine are optionally bridged by a $C_{1-3}$ alkyl and wherein the cyclopropyl, imidazole, or pyrazole are each optionally substituted with a $C_{1-3}$ alkyl substituted with one or more hydroxyl; and $R_4$ is H, methyl, —$CH_2$—OH, —O—$R_5$-$R_6$, —O—$R_6$, or azetidine optionally substituted with $NR_7R_7$, wherein $R_5$ is —$CH_2$—, —$CH(CH_3)$—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl and wherein if $R_4$ is H then $R_1$ is not H; or a pharmaceutically acceptable salt thereof.

In an embodiment of a compound of Formula Ia, or a pharmaceutically acceptable salt thereof, $R_{3a}$, $R_{3b}$, and $R_{3c}$ are each independently H, or halogen; and $R_1$ is H, methoxy, $C_{1-4}$ alkyl, $C_{2-4}$ heteroalkyl, N-linked piperazine, piperidine, or a group of the formula

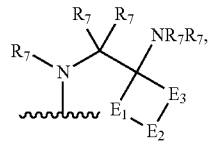

wherein the $C_{1-4}$ alkyl, $C_{2-4}$ heteroalkyl, piperidine, or N-linked piperazine are optionally substituted with one or more of amino, hydroxyl, methyl, trideuteromethyl, oxetane, or $C_{1-3}$ alkyl, wherein the $C_{1-3}$ alkyl is optionally substituted by one or more halogen, hydroxyl, methyl, hydroxymethyl, methoxy, trifluoromethoxy, cyclopropyl, oxetane, pyrazole, imidazole, amino, or —$CONR_7R_7$, wherein the piperidine or the N-linked piperazine are optionally bridged by a $C_{1-3}$ alkyl and wherein the cyclopropyl, imidazole, or pyrazole are each optionally substituted with a $C_{1-3}$ alkyl substituted with one or more hydroxyl; and $R_4$ is H, methyl, —$CH_2$—OH, —O—$R_5$-$R_6$, —O—$R_6$, or azetidine optionally substituted with $NR_7R_7$, wherein $R_5$ is —$CH_2$—, —$CH(CH_3)$—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl or 2-oxo-1,3-dihydrobenzimidazole, wherein the $C_{1-3}$ alkyl, $C_{3-6}$ cycloalkyl, or $C_{4-6}$ heterocycloalkyl are optionally substituted with one or more halogen, hydroxyl, methoxy, $NR_7R_7$, $C_{1-4}$ alkyl, or $C_{1-4}$ alkenyl, wherein the $C_{1-4}$ alkyl is optionally substituted with one or more halogen or hydroxyl, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl and wherein if $R_4$ is H then $R_1$ is not H; or a pharmaceutically acceptable salt thereof.

In an embodiment of a compound of Formula Ia, or a pharmaceutically acceptable salt thereof, $R_{3a}$, $R_{3b}$, and $R_{3c}$ are each independently H, or halogen; $R_1$ is H, $C_{1-4}$ alkyl, $C_{2-4}$ heteroalkyl, or N-linked piperazine, wherein the $C_{1-4}$ alkyl, $C_{2-4}$ heteroalkyl, or N-linked piperazine are optionally substituted with one or more of amino, hydroxyl, methyl, oxetane, or $C_{1-3}$ alkyl, wherein the $C_{1-3}$ alkyl is optionally substituted by one or more halogen, hydroxyl, methyl, hydroxymethyl, methoxy, cyclopropyl, oxetane, or amino, and wherein the N-linked piperazine is optionally bridged by the $C_{1-3}$ alkyl; and $R_4$ is H, methyl, —$CH_2$—OH, —O—$R_5$-$R_6$, or —O—$R_6$, wherein $R_5$ is —$CH_2$—, —$CH_2(CH_3)$—, or —$CH_2$—$CH_2$—, wherein $R_6$ is H, $C_{1-3}$ alkyl, $C_{2-3}$ heteroalkyl, $C_{4-6}$ cycloalkyl, or $C_{4-6}$ heterocycloalkyl, wherein the $C_{1-3}$ alkyl, $C_{4-6}$ cycloalkyl, or $C_{4-6}$ heterocycloalkyl are optionally substituted with one or more halogen, hydroxyl, methoxy, $C_{1-4}$ alkyl, or $C_{1-4}$ alkenyl, wherein the $C_{1-4}$ alkyl is optionally substituted with one or more halogen or hydroxyl, wherein the $C_{4-6}$ cycloalkyl or $C_{4-6}$ heterocycloalkyl are optionally fused with the $C_{1-4}$ alkyl to form a bicyclic ring, and wherein if $R_4$ is H then $R_1$ is not H; or a pharmaceutically acceptable salt thereof.

In an embodiment of a compound of Formulae Formulae I, Ia, II, IIa, IV, IVa, V, Va, VI, VIa, VII, VIIa, or VIII or a pharmaceutically acceptable salt thereof, $R_4$ is —O—$CH_2$—$R_6$.

In an embodiment of a compound of Formulae II, IIa, IV or IVa or a pharmaceutically acceptable salt thereof, $R_6$ is azetidine, pyrrolidine, piperidine, oxetane, tetrahydrofuran, morpholine, cyclobutane, or 1,4-dioxane.

In an embodiment of a compound of Formulae Formulae I, Ia, II, IIa, IV, IVa, V, Va, VI, VIa, VII, VIIa, or VIII or a pharmaceutically acceptable salt thereof, $R_4$ is methyl, methoxy, —$CH_2$—OH, or a group of the formula

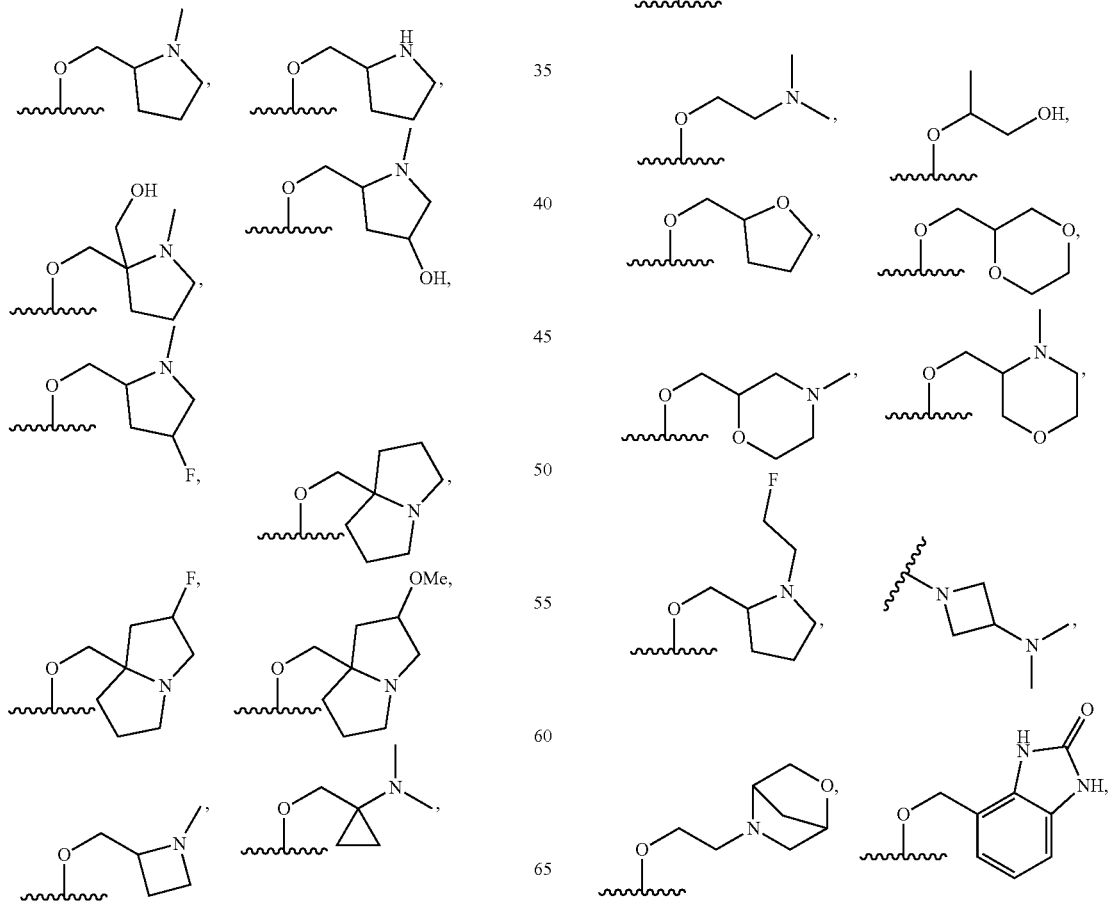

-continued
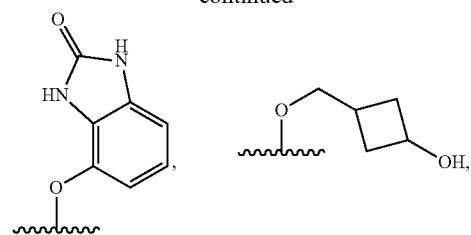
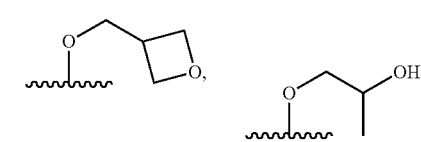
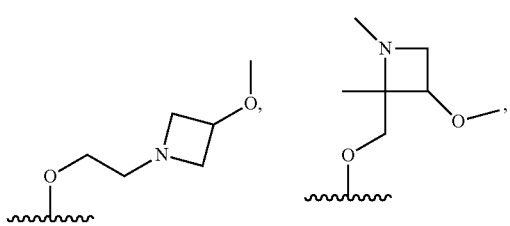
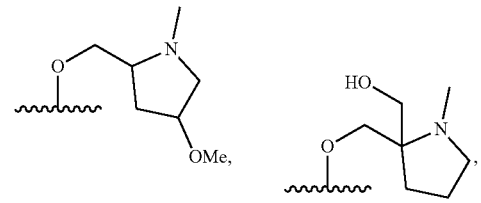
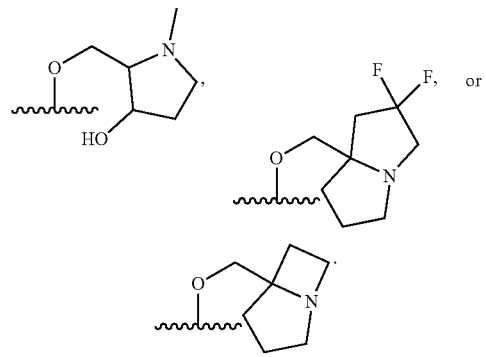
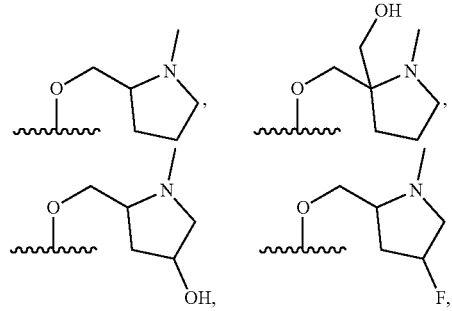
In an embodiment of a compound of Formulae Formulae I, Ia, II, IIa, IV, IVa, V, Va, VI, VIa, VII, VIIa, or VIII or a pharmaceutically acceptable salt thereof, R₄ is
-continued
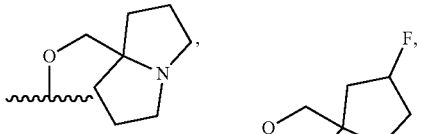
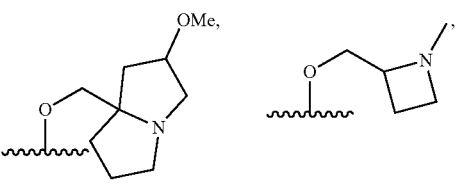
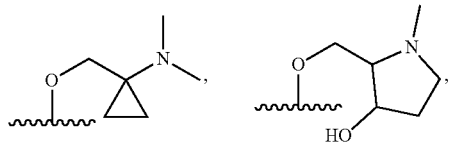
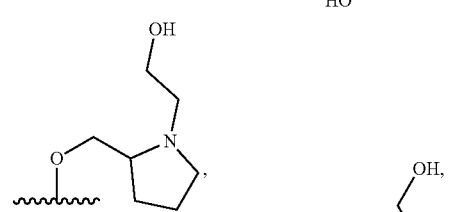
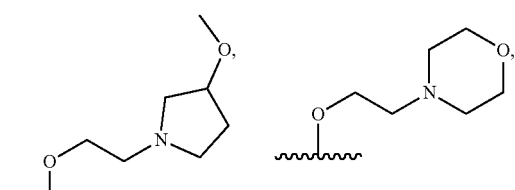
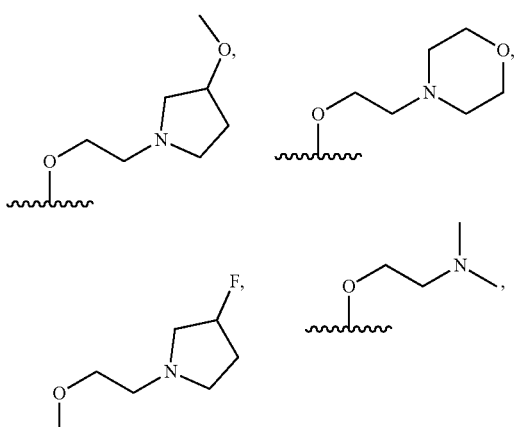
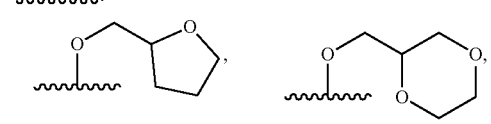
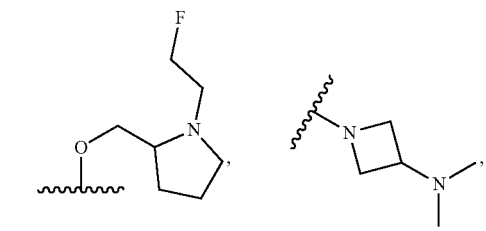

-continued

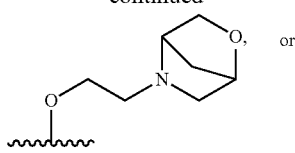

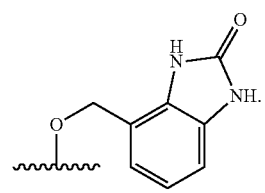

In an embodiment of a compound of Formulae I, Ia, II, IIa, IV, IVa, V, Va, VI, VIa, VII, VIIa, or VIII or a pharmaceutically acceptable salt thereof, R$_4$ is

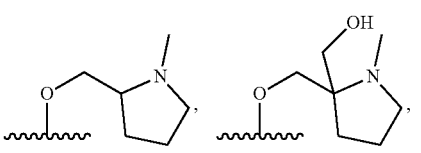

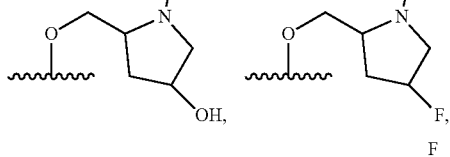

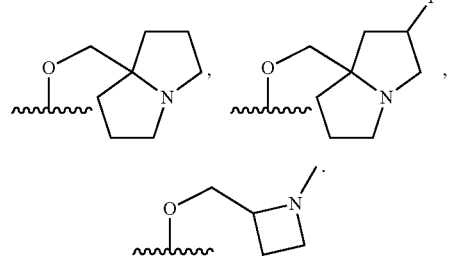

In an embodiment of a compound of Formulae Formulae I, Ia, II, IIa, IV, IVa, V, Va, VI, VIa, VII, VIIa, or VIII or a pharmaceutically acceptable salt thereof, R$_4$ is

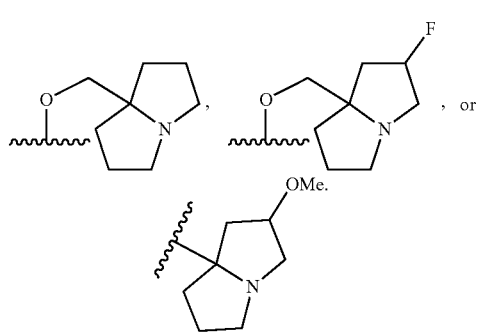

In an embodiment of a compound of Formulae Formulae I, Ia, II, IIa, IV, IVa, V, Va, VI, VIa, VII, VIIa, or VIII or a pharmaceutically acceptable salt thereof, R$_4$ is

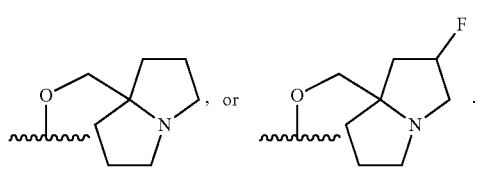 [SMILES: *OCC12CCCN1CCC2 ; *OCC12CCCN1CC(F)C2]

In an embodiment of a compound of Formulae Formulae I, Ia, II, IIa, IV, IVa, V, Va, VI, VIa, VII, VIIa, or VIII or a pharmaceutically acceptable salt thereof, R$_4$ is selected from

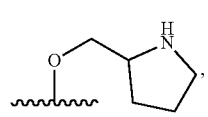 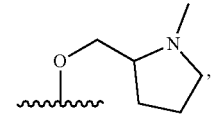

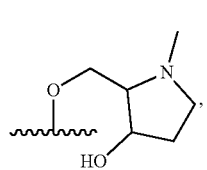 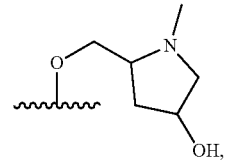

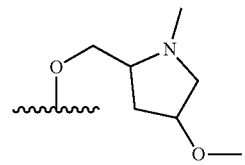 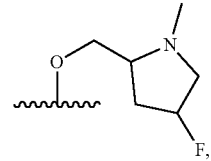

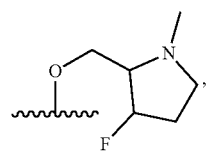 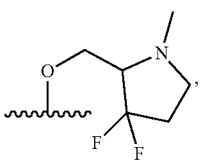

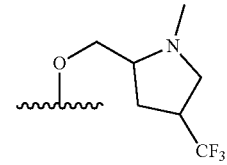 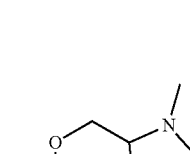

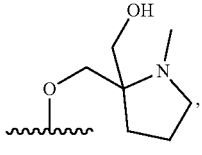 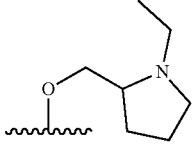

-continued
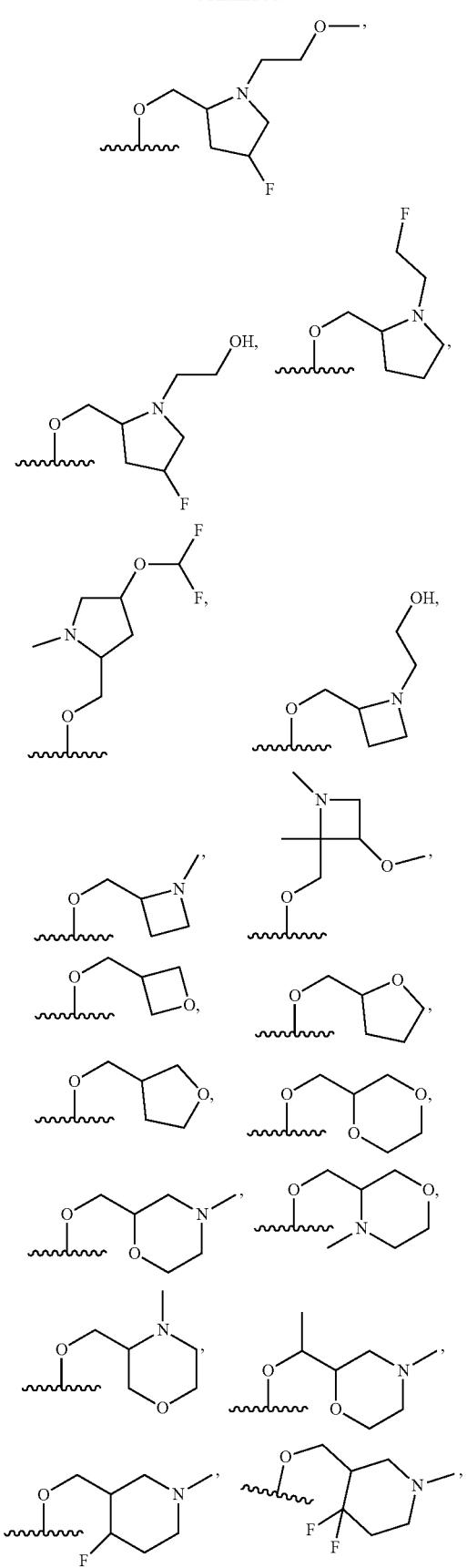
-continued
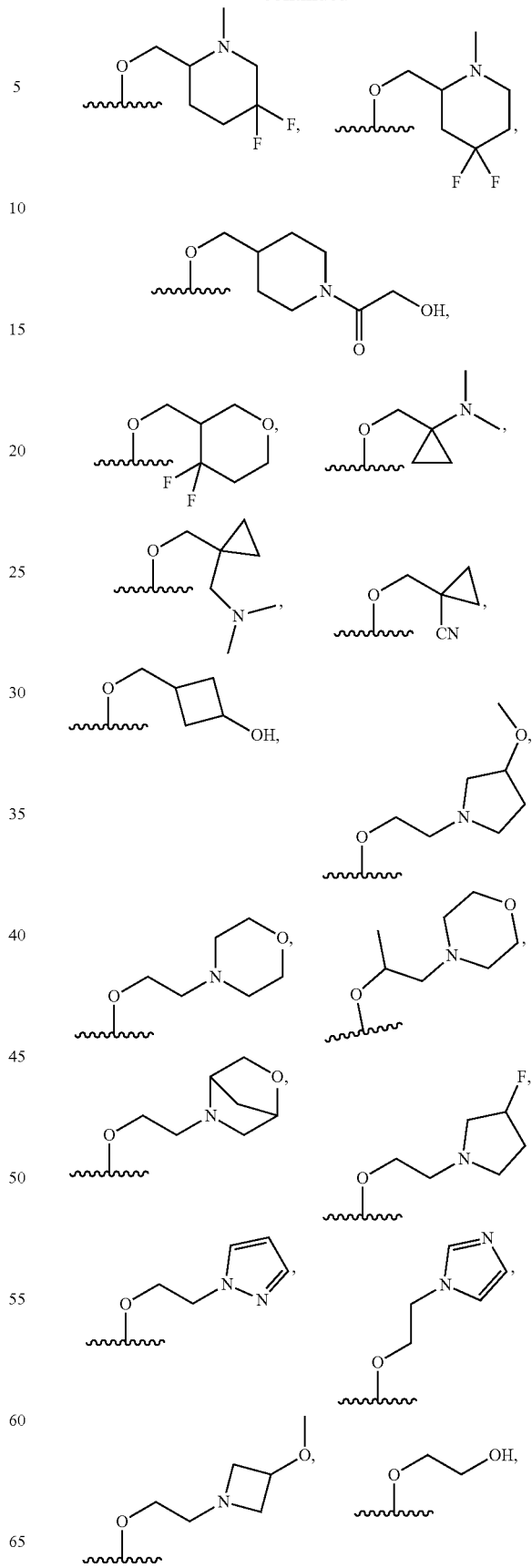

-continued

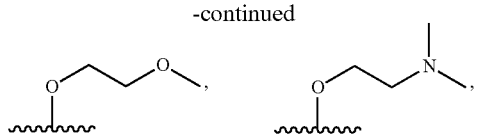

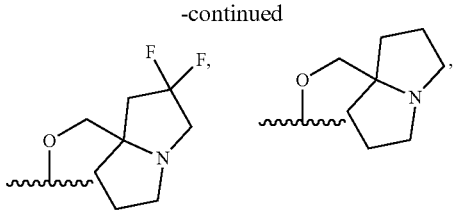

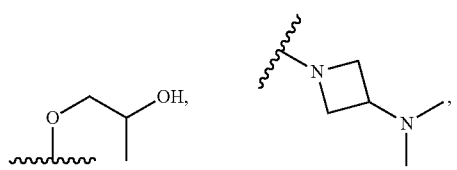

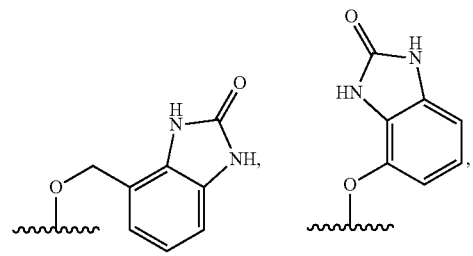

In an embodiment of a compound of Formulae I, Ia, II, IIa, III, IIIa or VIII or a pharmaceutically acceptable salt thereof, $R_2$ is F or Cl.

In an embodiment of a compound of Formulae I, Ia, II, IIa, III, IIIa, IV, or IVa or a pharmaceutically acceptable salt thereof, $R_{3b}$ and $R_{3c}$ are each independently H or F.

In an embodiment of a compound of Formulae I, Ia, II, or a or a pharmaceutically acceptable salt thereof, X is S, Y is —C(CN)—, $R_2$ is F or Cl, $R_{3a}$ is H, $R_{3b}$ is H, $R_{3c}$ is F, and $D_1$ is —CH$_2$—.

In the above embodiments of the compounds of Formulae I-VIII (including Ia-VIIa), the chemical drawings are shown flat without chiral information. These compounds often have multiple chiral centers and are contemplated to exist is various forms with various combinations of chiral centers. Additionally, these compounds have various enantiomers, diastereomers, and atropisomers that can exist and are included herein.

Examples of compounds described herein include the compounds of Table A and pharmaceutically acceptable salts thereof.

TABLE A

| Ex. # | Compound |
|---|---|
| 1 | |

TABLE A-continued
Example Compounds
| Ex. # | Compound |
|---|---|
| 2 | 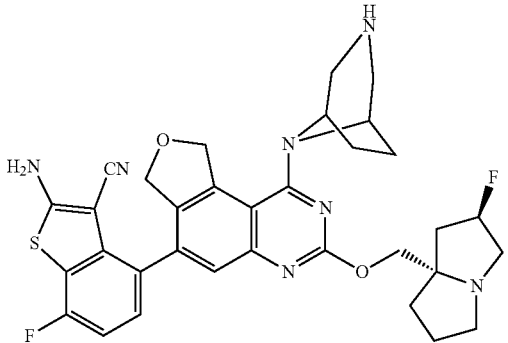 [SMILES: N#Cc1c(N)sc2c(F)ccc(-c3cc4nc(OC[C@@]56CCCN5C[C@H](F)C6)nc(N5C6CCC5CNC6)c4c4c3COC4)c12] |
| 3 | 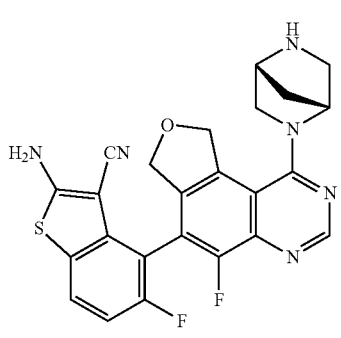 [SMILES: N#Cc1c(N)sc2ccc(F)c(-c3c4c(c5c(N6C[C@H]7C[C@@H]6CN7)ncnc5c3F)COC4)c12] |
| 4 | 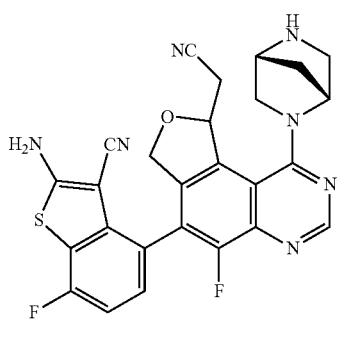 [SMILES: N#CCC1OCc2c(-c3ccc(F)c4sc(N)c(C#N)c34)c(F)c3ncnc(N4C[C@H]5C[C@@H]4CN5)c3c21] |
| 5 | 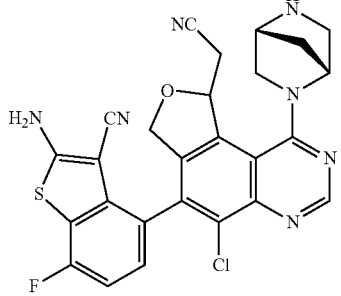 |

TABLE A-continued
Example Compounds
| Ex. # | Compound |
|---|---|
| 6 | 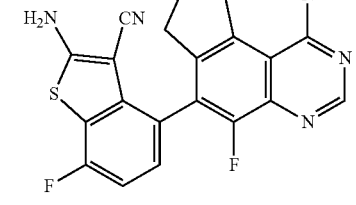 |
| 7 | 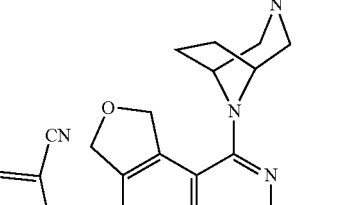 |
| 8 | 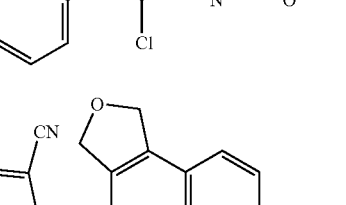 |
| 9 | 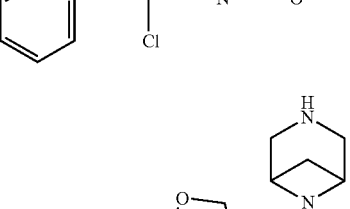 |
| 10 | 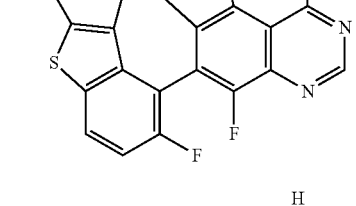 |

TABLE A-continued

Example Compounds

| Ex. # | Compound |
|---|---|
| 11 | |
| 12 | |
| 13 | |
| 14 | |

TABLE A-continued
Example Compounds
| Ex. # | Compound |
|---|---|
| 15 | 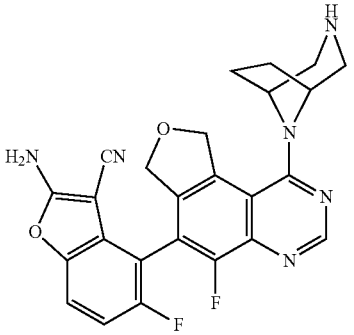 [SMILES: N#Cc1c(N)oc2ccc(F)c(-c3c4c(c5c(N6C7CCC6CNC7)ncnc5c3F)COC4)c12] |
| 16 | 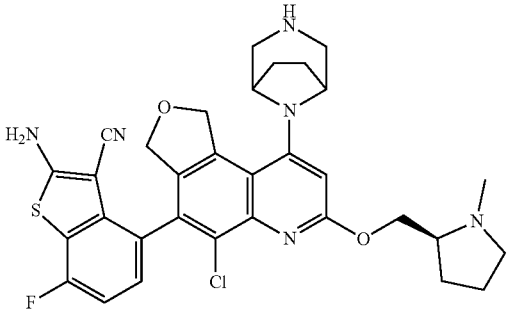 [SMILES: CN1CCC[C@H]1COc1cc(N2C3CCC2CNC3)c2c3c(c(-c4ccc(F)c5sc(N)c(C#N)c45)c(Cl)c2n1)COC3] |
| 17 | 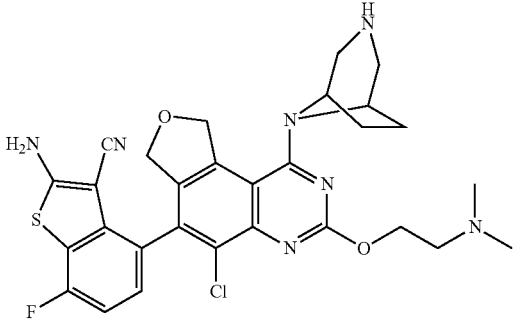 [SMILES: CN(C)CCOc1nc(N2C3CCC2CNC3)c2c3c(c(-c4ccc(F)c5sc(N)c(C#N)c45)c(Cl)c2n1)COC3] |
| 18 | 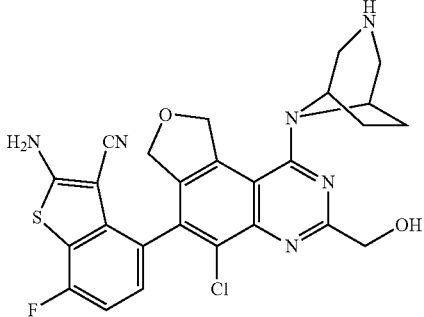 [SMILES: N#Cc1c(N)sc2c(F)ccc(-c3c4c(c5c(N6C7CCC6CNC7)nc(CO)nc5c3Cl)COC4)c12] |
| 19 | 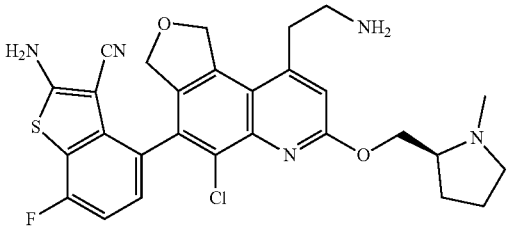 [SMILES: CN1CCC[C@H]1COc1cc(CCN)c2c3c(c(-c4ccc(F)c5sc(N)c(C#N)c45)c(Cl)c2n1)COC3] |

TABLE A-continued
Example Compounds
| Ex. # | Compound |
| --- | --- |
| 20 | 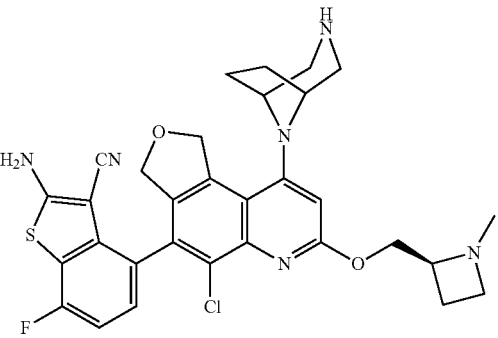 [SMILES: CN1CC[C@H]1COc1cc(N2C3CCC2CNC3)c2c3c(c(-c4ccc(F)c5sc(N)c(C#N)c45)c(Cl)c2n1)COC3] |
| 21 | 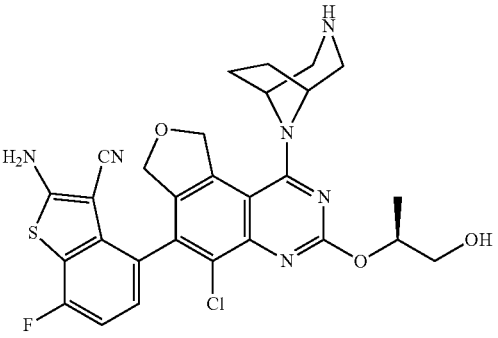 [SMILES: C[C@@H](CO)Oc1nc(N2C3CCC2CNC3)c2c3c(c(-c4ccc(F)c5sc(N)c(C#N)c45)c(Cl)c2n1)COC3] |
| 22 | 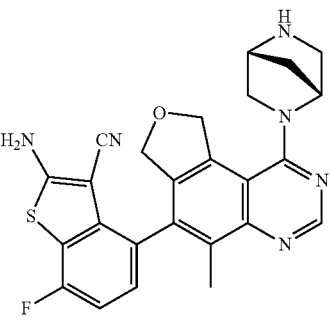 [SMILES: Cc1c(-c2ccc(F)c3sc(N)c(C#N)c23)c2c(c3c(N4C[C@H]5C[C@@H]4CN5)ncnc13)COC2] |
| 23 | 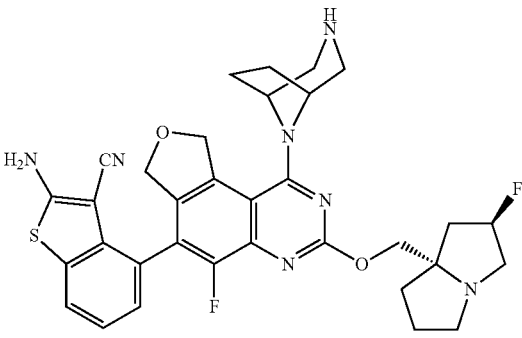 |

TABLE A-continued
Example Compounds
| Ex. # | Compound |
|---|---|
| 24 | 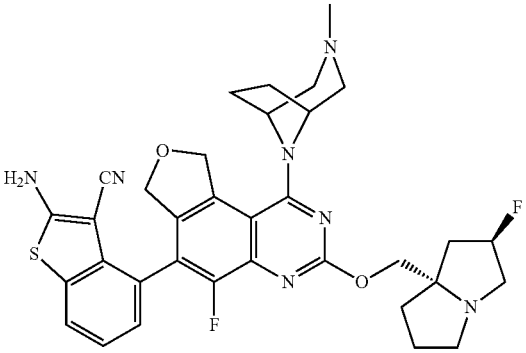 [SMILES: CN1CC2CCC(C1)N2c1nc(OC[C@@]23CCCN2C[C@H](F)C3)nc2c(F)c(-c3cccc4sc(N)c(C#N)c34)c3c(c12)COC3] |
| 25 | 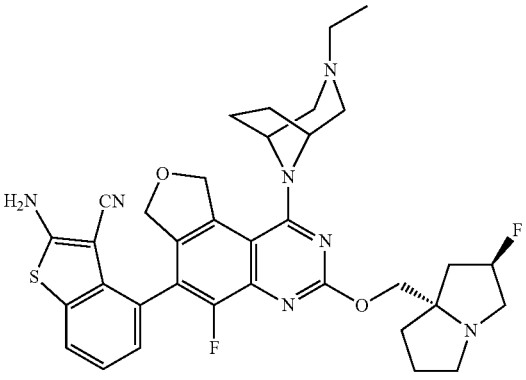 [SMILES: CCN1CC2CCC(C1)N2c1nc(OC[C@@]23CCCN2C[C@H](F)C3)nc2c(F)c(-c3cccc4sc(N)c(C#N)c34)c3c(c12)COC3] |
| 26 | 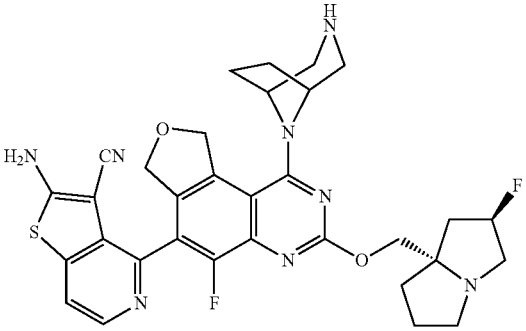 [SMILES: N#Cc1c(N)sc2ccnc(-c3c4c(c5c(N6C7CCC6CNC7)nc(OC[C@@]67CCCN6C[C@H](F)C7)nc5c3F)COC4)c12] |
| 27 | 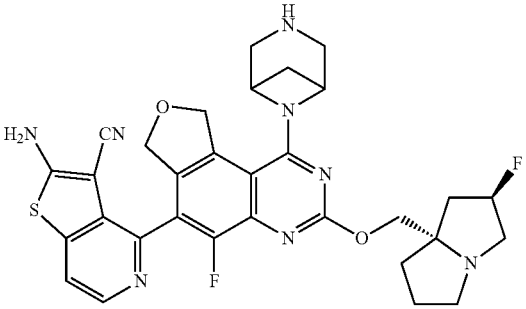 [SMILES: N#Cc1c(N)sc2ccnc(-c3c4c(c5c(N6C7CNCC6C7)nc(OC[C@@]67CCCN6C[C@H](F)C7)nc5c3F)COC4)c12] |

TABLE A-continued

Example Compounds

| Ex. # | Compound |
|---|---|
| 28 | |
| 29 | |
| 30 | |
| 31 | |
| 32 | |
| 33 | |

TABLE A-continued

Example Compounds

| Ex. # | Compound |
|---|---|
| 34 | |
| 35 | |
| 36 | |
| 37 | |
| 38 | |
| 39 | |

TABLE A-continued
Example Compounds
| Ex. # | Compound |
|---|---|
| 40 | 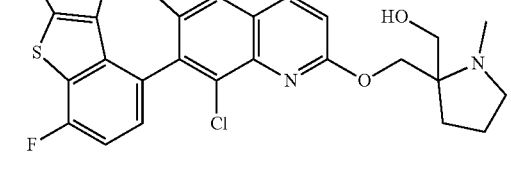 |
| 41 | 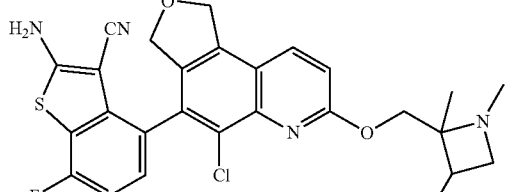 |
| 42 | 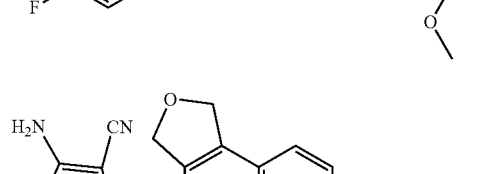 |
| 43 | 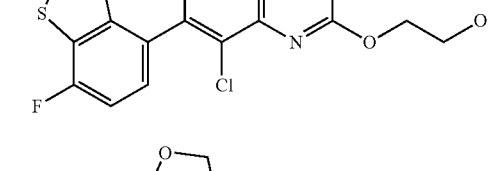 |
| 44 | 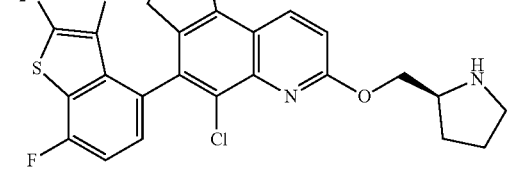 |
| 45 | 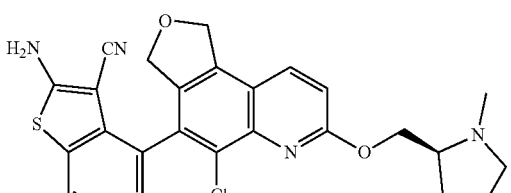 |

TABLE A-continued

Example Compounds

| Ex. # | Compound |
|---|---|
| 46 | |
| 47 | |
| 48 | |
| 49 | |

TABLE A-continued
Example Compounds
| Ex. # | Compound |
|---|---|
| 50 | 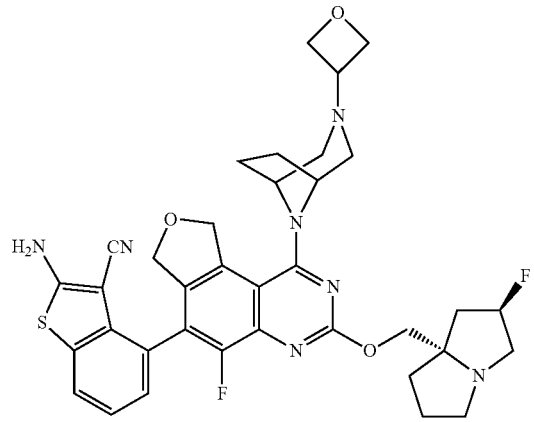 [SMILES: N#Cc1c(N)sc2cccc(-c3c4c(c5c(N6C7CCC6CN(C6COC6)C7)nc(OC[C@@]67CCCN6C[C@H](F)C7)nc5c3F)COC4)c12] |
| 51 | 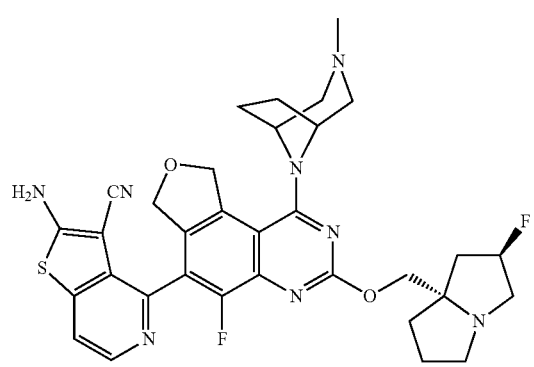 [SMILES: CN1CC2CCC(C1)N2c1nc(OC[C@@]23CCCN2C[C@H](F)C3)nc2c(F)c(-c3nccc4sc(N)c(C#N)c34)c3c(c12)COC3] |
| 52 | 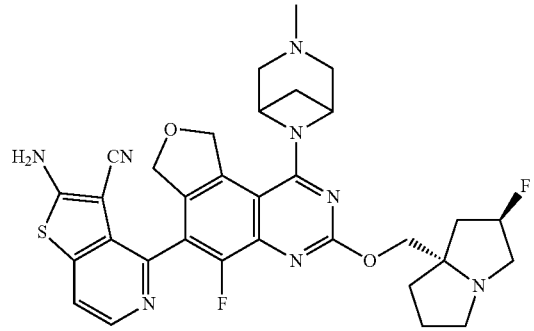 [SMILES: CN1CC2CC(C1)N2c1nc(OC[C@@]23CCCN2C[C@H](F)C3)nc2c(F)c(-c3nccc4sc(N)c(C#N)c34)c3c(c12)COC3] |
| 53 | 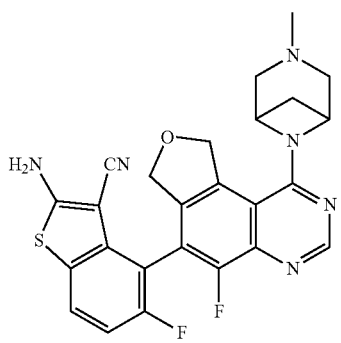 [SMILES: CN1CC2CC(C1)N2c1ncnc2c(F)c(-c3c(F)ccc4sc(N)c(C#N)c34)c3c(c12)COC3] |

TABLE A-continued
Example Compounds
| Ex. # | Compound |
|---|---|
| 54 | 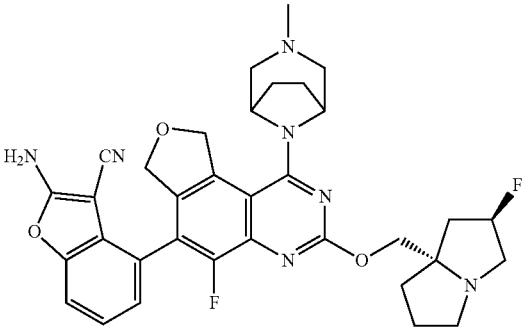 [SMILES: CN1CC2CCC(C1)N2c1nc(OC[C@@]23CCCN2C[C@H](F)C3)nc2c(F)c(-c3cccc4oc(N)c(C#N)c34)c3c(c12)COC3] |
| 55 | 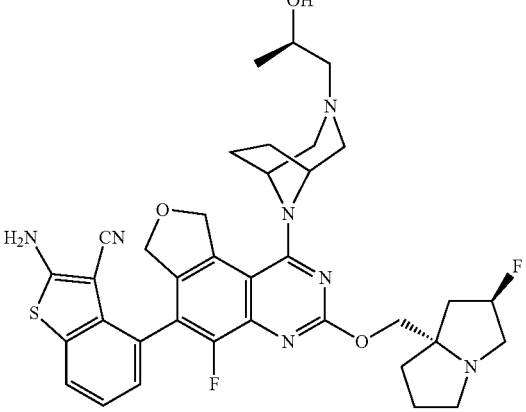 |
| 56 | 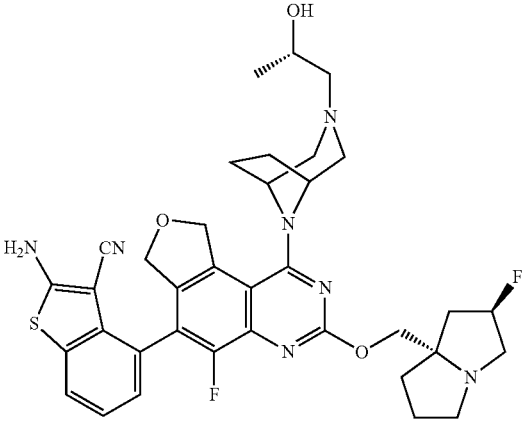 [SMILES: C[C@H](O)CN1CC2CCC(C1)N2c1nc(OC[C@@]23CCCN2C[C@H](F)C3)nc2c(F)c(-c3cccc4sc(N)c(C#N)c34)c3c(c12)COC3] |

TABLE A-continued
Example Compounds
| Ex. # | Compound |
|---|---|
| 57 | 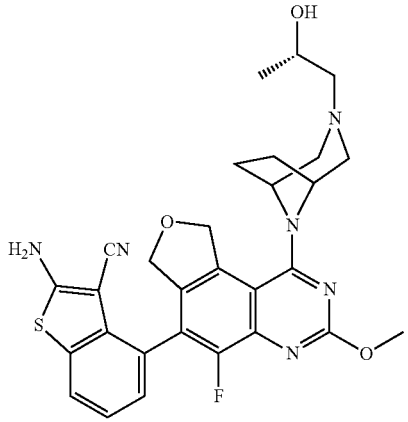 [SMILES: COc1nc(N2C3CCC2CN(C[C@H](C)O)C3)c2c3c(c(-c4cccc5sc(N)c(C#N)c45)c(F)c2n1)COC3] |
| 58 | 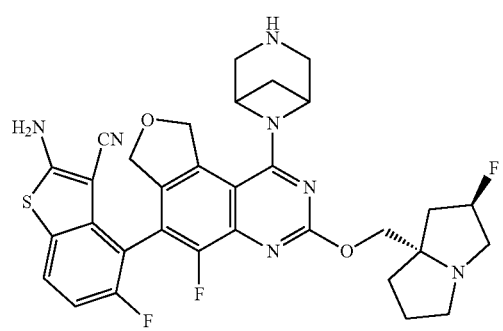 [SMILES: N#Cc1c(N)sc2ccc(F)c(-c3c4c(c5c(N6C7CNCC6C7)nc(OC[C@@]67CCCN6C[C@H](F)C7)nc5c3F)COC4)c12] |
| 59 | 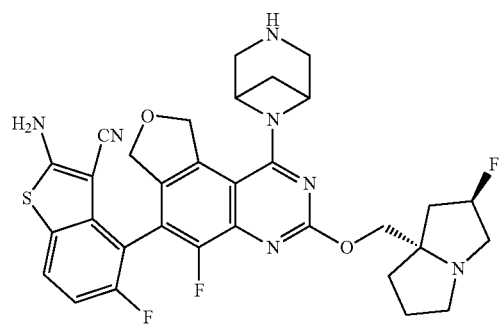 [SMILES: N#Cc1c(N)sc2ccc(F)c(-c3c4c(c5c(N6C7CNCC6C7)nc(OC[C@@]67CCCN6C[C@H](F)C7)nc5c3F)COC4)c12] |
| 60 | 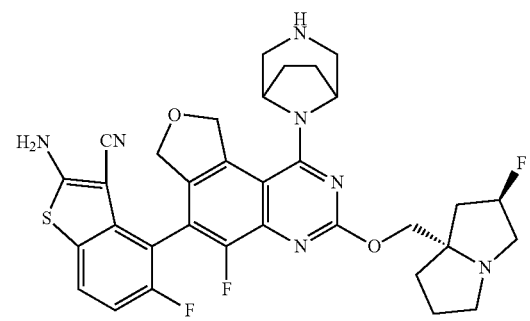 |

TABLE A-continued
Example Compounds
| Ex. # | Compound |
|---|---|
| 61 | 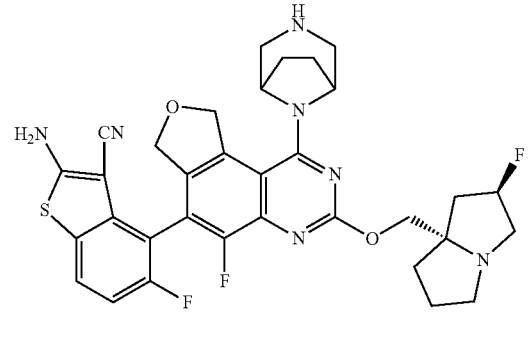 |
| 62 | 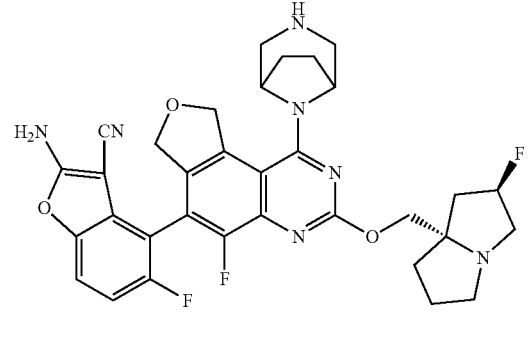 |
| 63 | 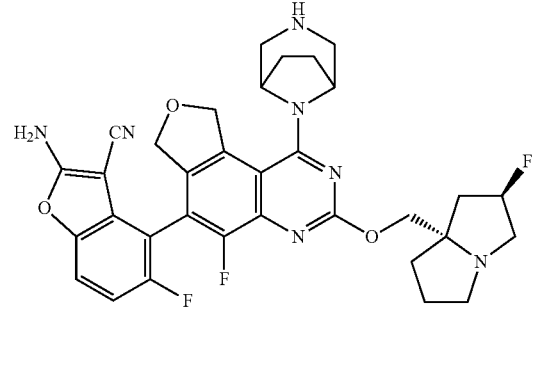 [SMILES: N#Cc1c(N)oc2ccc(F)c(-c3c4c(c5c(N6C7CCC6CNC7)nc(OC[C@@]67CCCN6C[C@H](F)C7)nc5c3F)COC4)c12] |
| 64 | 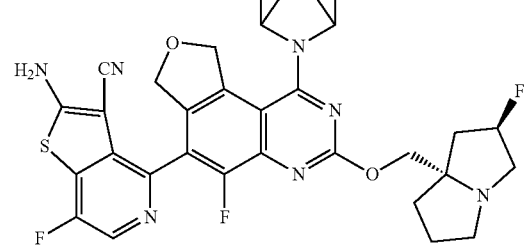 |

TABLE A-continued
Example Compounds
| Ex. # | Compound |
|---|---|
| 65 | 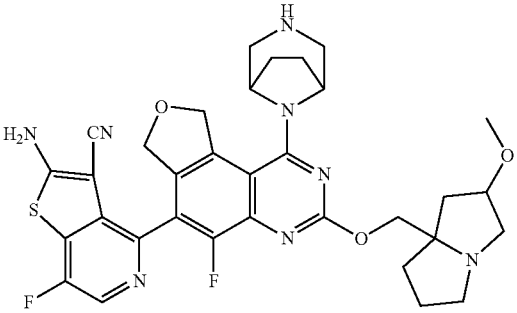 |
| 66 | 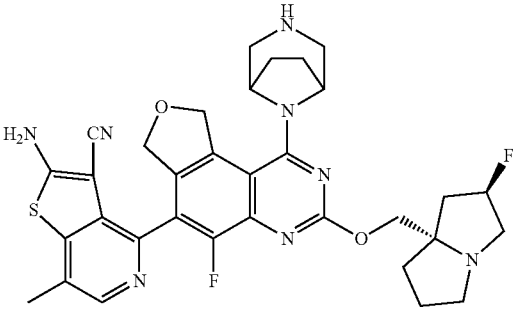 [SMILES: Cc1cnc(-c2c3c(c4c(N5C6CCC5CNC6)nc(OC[C@@]56CCCN5C[C@H](F)C6)nc4c2F)COC3)c2c(C#N)c(N)sc12] |
| 67 | 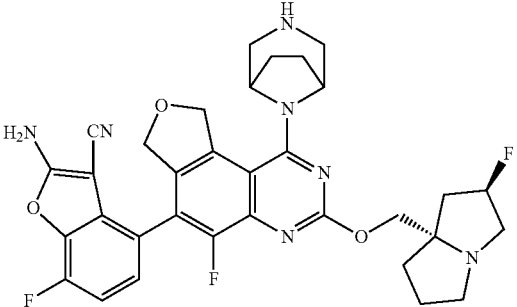 |
| 68 | 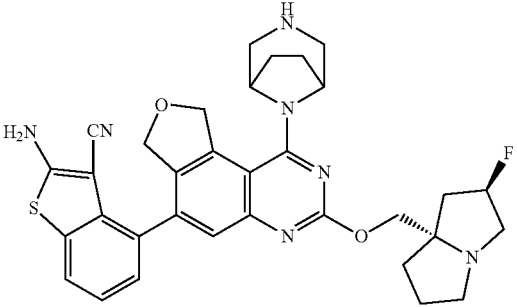 [SMILES: N#Cc1c(N)sc2cccc(-c3cc4nc(OC[C@@]56CCCN5C[C@H](F)C6)nc(N5C6CCC5CNC6)c4c4c3COC4)c12] |

TABLE A-continued
Example Compounds
| Ex. # | Compound |
|---|---|
| 69 | 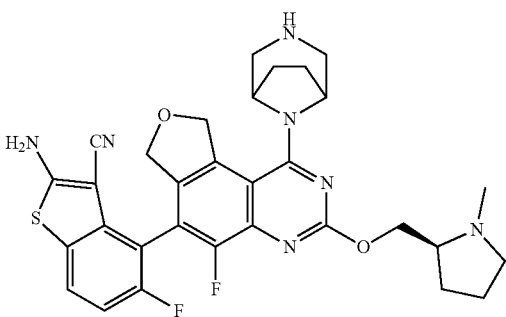 [SMILES: CN1CCC[C@H]1COc1nc(N2C3CCC2CNC3)c2c3c(c(-c4c(F)ccc5sc(N)c(C#N)c45)c(F)c2n1)COC3] |
| 70 | 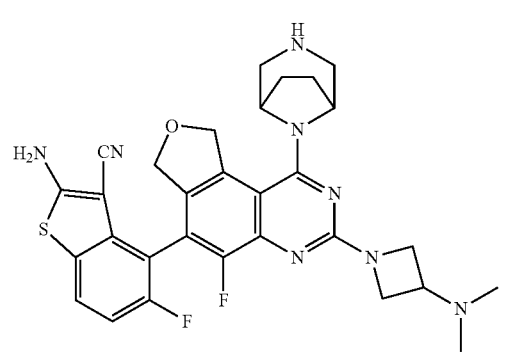 [SMILES: CN(C)C1CN(c2nc(N3C4CCC3CNC4)c3c4c(c(-c5c(F)ccc6sc(N)c(C#N)c56)c(F)c3n2)COC4)C1] |
| 71 | 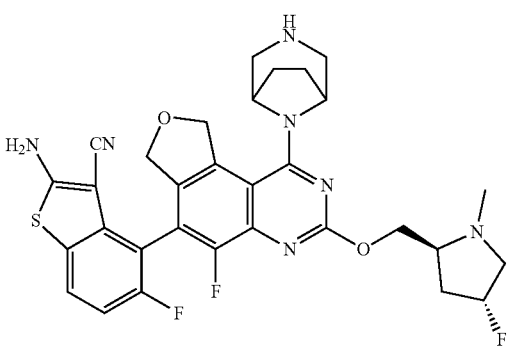 [SMILES: CN1C[C@H](F)C[C@H]1COc1nc(N2C3CCC2CNC3)c2c3c(c(-c4c(F)ccc5sc(N)c(C#N)c45)c(F)c2n1)COC3] |
| 72 | 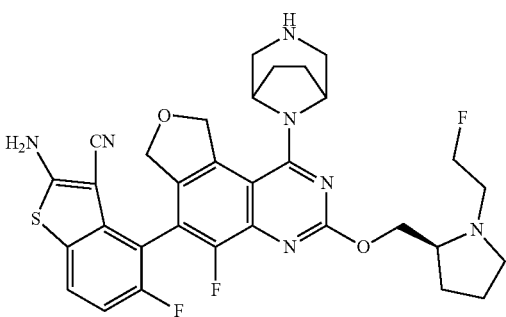 |

TABLE A-continued
Example Compounds
| Ex. # | Compound |
|---|---|
| 73 | 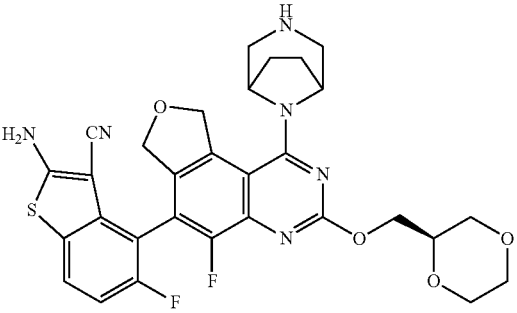 [SMILES: N#Cc1c(N)sc2ccc(F)c(-c3c4c(c5c(N6C7CCC6CNC7)nc(OC[C@H]6COCCO6)nc5c3F)COC4)c12] |
| 74 | 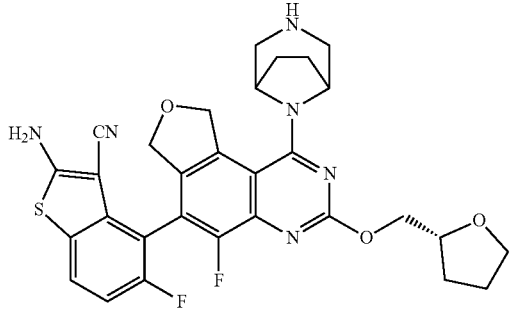 [SMILES: N#Cc1c(N)sc2ccc(F)c(-c3c4c(c5c(N6C7CCC6CNC7)nc(OC[C@H]6CCCO6)nc5c3F)COC4)c12] |
| 75 | 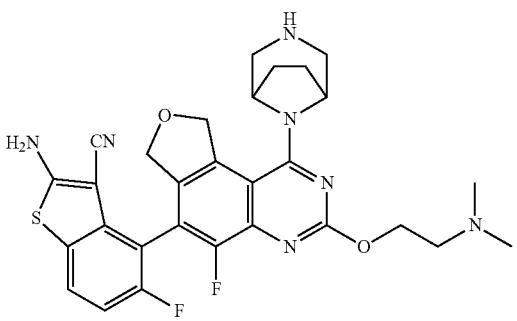 [SMILES: CN(C)CCOc1nc(N2C3CCC2CNC3)c2c3c(c(-c4c(F)ccc5sc(N)c(C#N)c45)c(F)c2n1)COC3] |
| 76 | 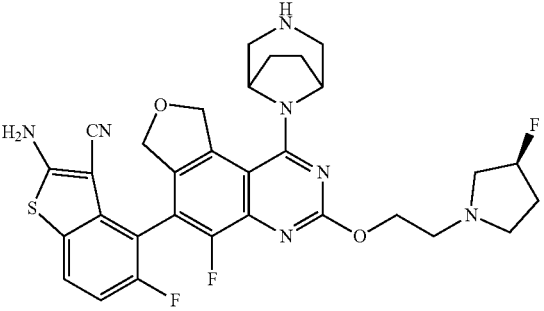 [SMILES: N#Cc1c(N)sc2ccc(F)c(-c3c4c(c5c(N6C7CCC6CNC7)nc(OCCN6CC[C@H](F)C6)nc5c3F)COC4)c12] |

TABLE A-continued

Example Compounds

| Ex. # | Compound |
|---|---|
| 77 | |
| 78 | |
| 79 | |
| 80 | |

TABLE A-continued
Example Compounds
| Ex. # | Compound |
|---|---|
| 81 | 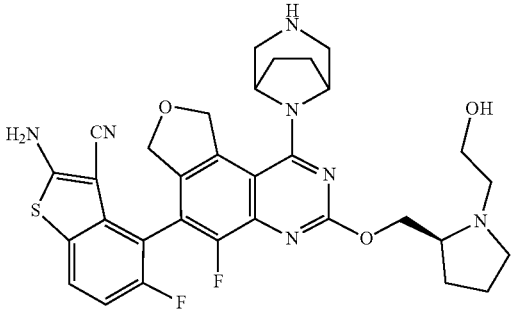 [SMILES: N#Cc1c(N)sc2ccc(F)c(-c3c4c(c5c(N6C7CCC6CNC7)nc(OC[C@@H]6CCCN6CCO)nc5c3F)COC4)c12] |
| 82 | 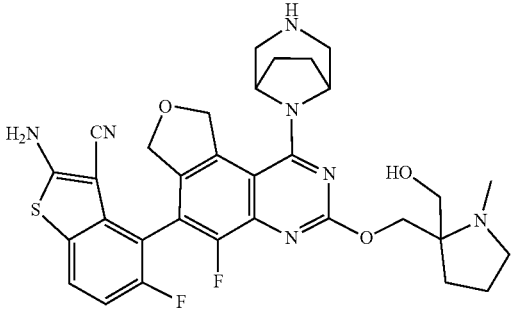 [SMILES: CN1CCCC1(CO)COc1nc(N2C3CCC2CNC3)c2c3c(c(-c4c(F)ccc5sc(N)c(C#N)c45)c(F)c2n1)COC3] |
| 83 | 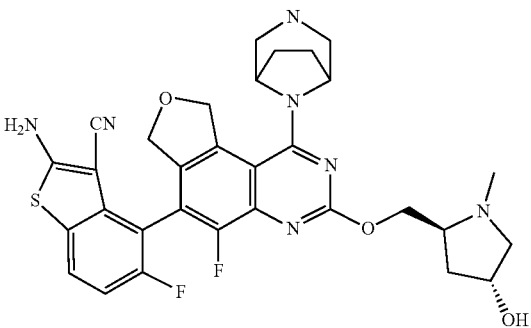 |
| 84 | 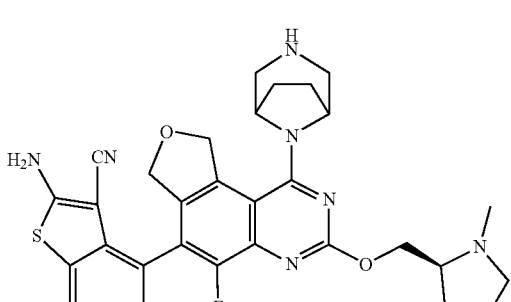 |

TABLE A-continued
Example Compounds
| Ex. # | Compound |
|---|---|
| 85 | 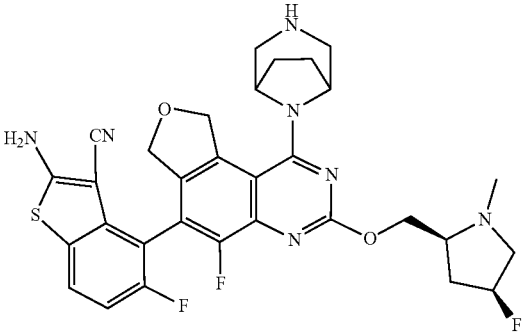 [SMILES: CN1C[C@@H](F)C[C@H]1COc1nc(N2C3CCC2CNC3)c2c3c(c(-c4c(F)ccc5sc(N)c(C#N)c45)c(F)c2n1)COC3] |
| 86 | 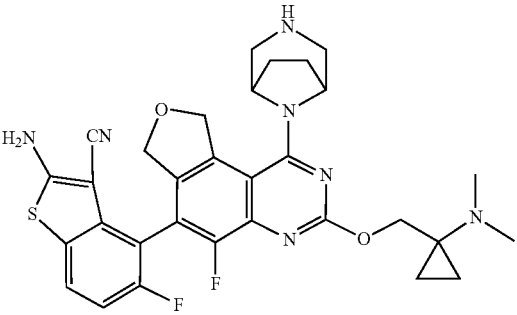 [SMILES: CN(C)C1(COc2nc(N3C4CCC3CNC4)c3c4c(c(-c5c(F)ccc6sc(N)c(C#N)c56)c(F)c3n2)COC4)CC1] |
| 87 | 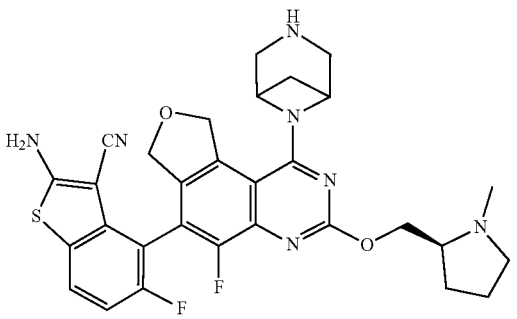 [SMILES: CN1CCC[C@H]1COc1nc(N2C3CNCC2C3)c2c3c(c(-c4c(F)ccc5sc(N)c(C#N)c45)c(F)c2n1)COC3] |
| 88 | 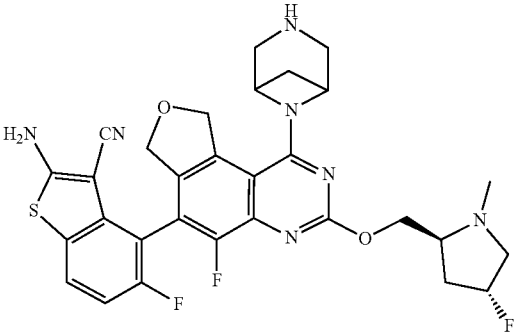 [SMILES: CN1C[C@H](F)C[C@H]1COc1nc(N2C3CNCC2C3)c2c3c(c(-c4c(F)ccc5sc(N)c(C#N)c45)c(F)c2n1)COC3] |

TABLE A-continued
Example Compounds
| Ex. # | Compound |
|---|---|
| 89 | 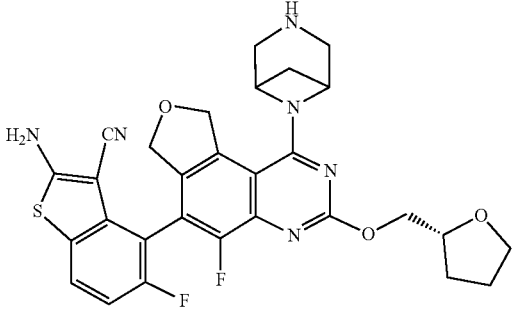 [SMILES: N#Cc1c(N)sc2ccc(F)c(-c3c4c(c5c(N6C7CNCC6C7)nc(OC[C@H]6CCCO6)nc5c3F)COC4)c12] |
| 90 | 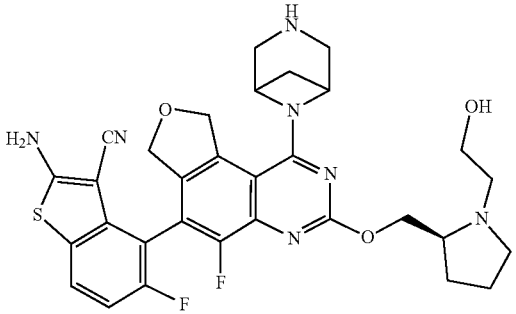 [SMILES: N#Cc1c(N)sc2ccc(F)c(-c3c4c(c5c(N6C7CNCC6C7)nc(OC[C@@H]6CCCN6CCO)nc5c3F)COC4)c12] |
| 91 | 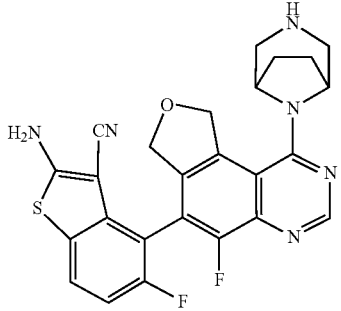 [SMILES: N#Cc1c(N)sc2ccc(F)c(-c3c4c(c5c(N6C7CCC6CNC7)ncnc5c3F)COC4)c12] |
| 92 | 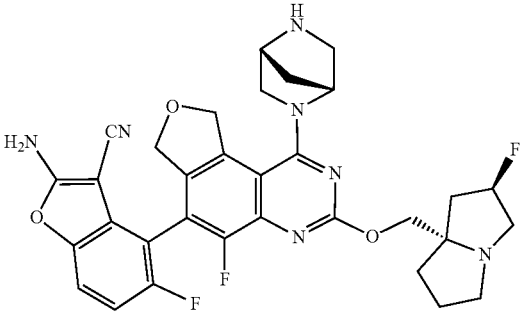 [SMILES: N#Cc1c(N)oc2ccc(F)c(-c3c4c(c5c(N6C[C@H]7C[C@@H]6CN7)nc(OC[C@@]67CCCN6C[C@H](F)C7)nc5c3F)COC4)c12] |

TABLE A-continued
Example Compounds
| Ex. # | Compound |
|---|---|
| 93 | 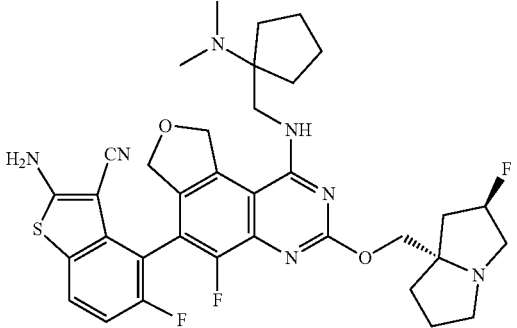 [SMILES: CN(C)C1(CNc2nc(OC[C@@]34CCCN3C[C@H](F)C4)nc3c(F)c(-c4c(F)ccc5sc(N)c(C#N)c45)c4c(c23)COC4)CCCC1] |
| 94 | 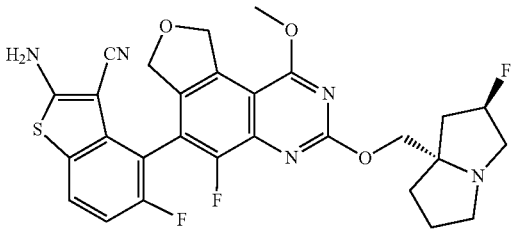 [SMILES: COc1nc(OC[C@@]23CCCN2C[C@H](F)C3)nc2c(F)c(-c3c(F)ccc4sc(N)c(C#N)c34)c3c(c12)COC3] |
| 95 | 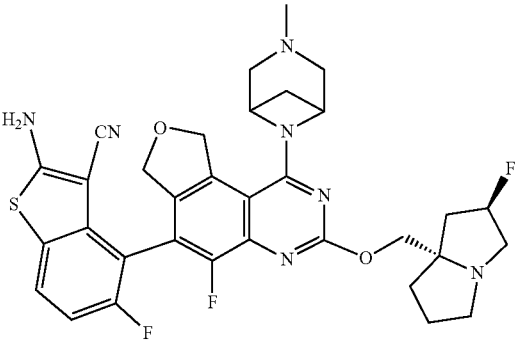 [SMILES: CN1CC2CC(C1)N2c1nc(OC[C@@]23CCCN2C[C@H](F)C3)nc2c(F)c(-c3c(F)ccc4sc(N)c(C#N)c34)c3c(c12)COC3] |
| 96 | 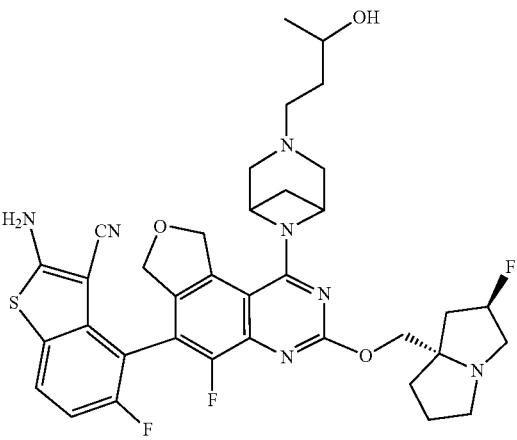 [SMILES: CC(O)CCN1CC2CC(C1)N2c1nc(OC[C@@]23CCCN2C[C@H](F)C3)nc2c(F)c(-c3c(F)ccc4sc(N)c(C#N)c34)c3c(c12)COC3] |

TABLE A-continued
Example Compounds
| Ex. # | Compound |
|---|---|
| 97 | 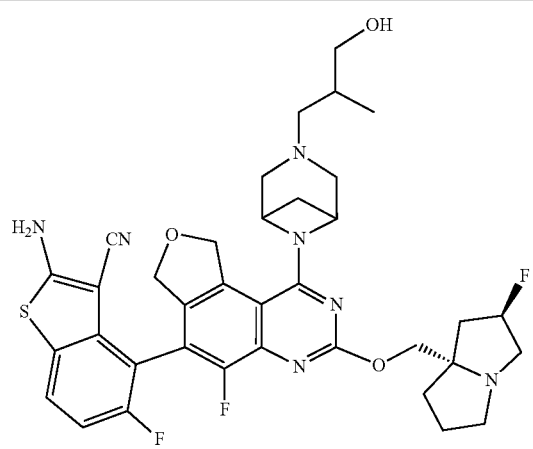 [SMILES: CC(CO)CN1CC2CC(C1)N2c1nc(OC[C@@]23CCCN2C[C@H](F)C3)nc2c(F)c(-c3c(F)ccc4sc(N)c(C#N)c34)c3c(c12)COC3] |
| 98 | 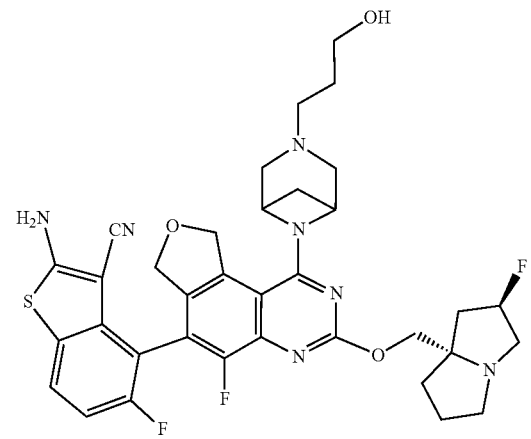 [SMILES: N#Cc1c(N)sc2ccc(F)c(-c3c4c(c5c(N6C7CC6CN(CCCO)C7)nc(OC[C@@]67CCCN6C[C@H](F)C7)nc5c3F)COC4)c12] |
| 99 | 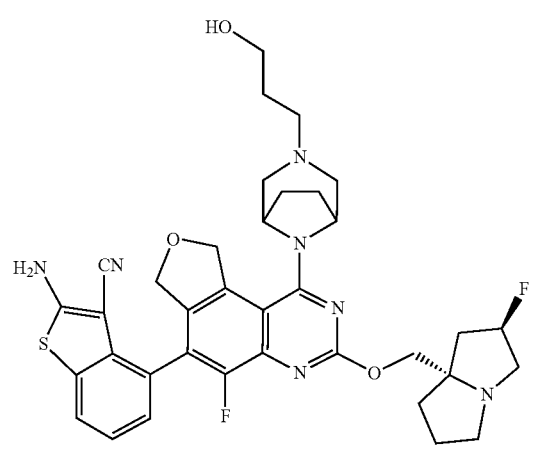 [SMILES: N#Cc1c(N)sc2cccc(-c3c4c(c5c(N6C7CCC6CN(CCCO)C7)nc(OC[C@@]67CCCN6C[C@H](F)C7)nc5c3F)COC4)c12] |

TABLE A-continued
Example Compounds
| Ex. # | Compound |
|---|---|
| 100 | 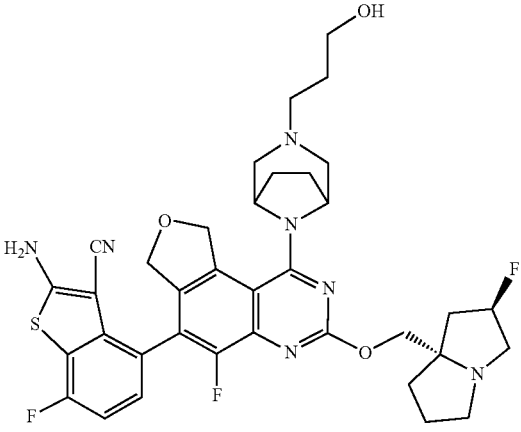 [SMILES: N#Cc1c(N)sc2c(F)ccc(-c3c4c(c5c(N6C7CCC6CN(CCCO)C7)nc(OC[C@@]67CCCN6C[C@H](F)C7)nc5c3F)COC4)c12] |
| 101 | 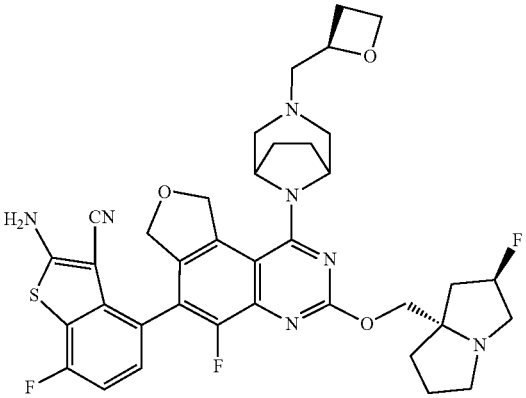 [SMILES: N#Cc1c(N)sc2c(F)ccc(-c3c4c(c5c(N6C7CCC6CN(C[C@H]6CCO6)C7)nc(OC[C@@]67CCCN6C[C@H](F)C7)nc5c3F)COC4)c12] |
| 102 | 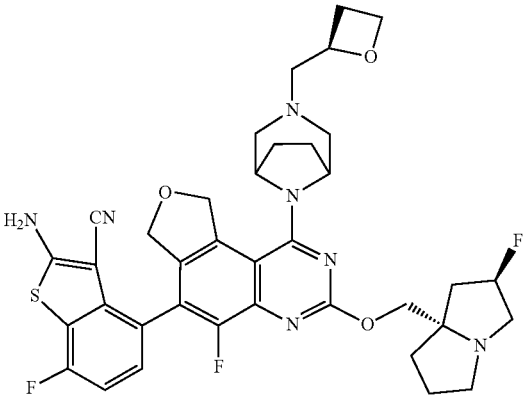 [SMILES: N#Cc1c(N)sc2c(F)ccc(-c3c4c(c5c(N6C7CCC6CN(C[C@H]6CCO6)C7)nc(OC[C@@]67CCCN6C[C@H](F)C7)nc5c3F)COC4)c12] |

TABLE A-continued
Example Compounds
| Ex. # | Compound |
|---|---|
| 103 | 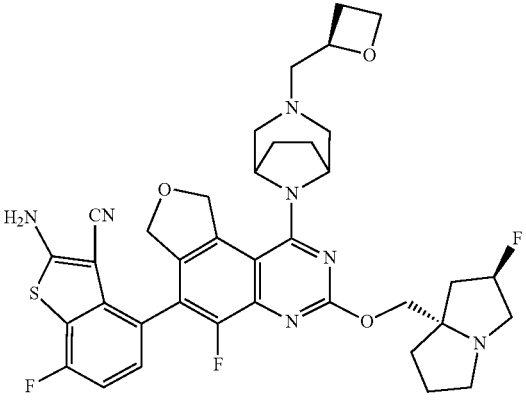 [SMILES: N#Cc1c(N)sc2c(F)ccc(-c3c4c(c5c(N6C7CCC6CN(C[C@H]6CCO6)C7)nc(OC[C@@]67CCCN6C[C@H](F)C7)nc5c3F)COC4)c12] |
| 104 | 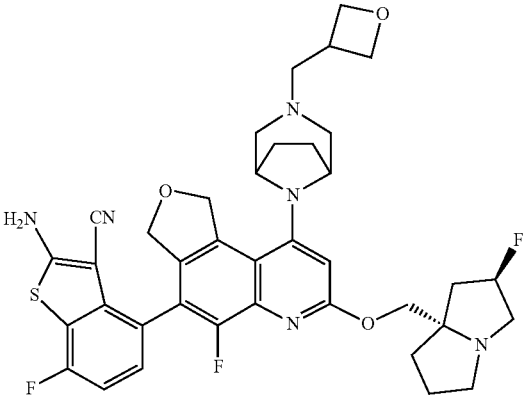 [SMILES: N#Cc1c(N)sc2c(F)ccc(-c3c4c(c5c(N6C7CCC6CN(CC6COC6)C7)cc(OC[C@@]67CCCN6C[C@H](F)C7)nc5c3F)COC4)c12] |
| 105 | 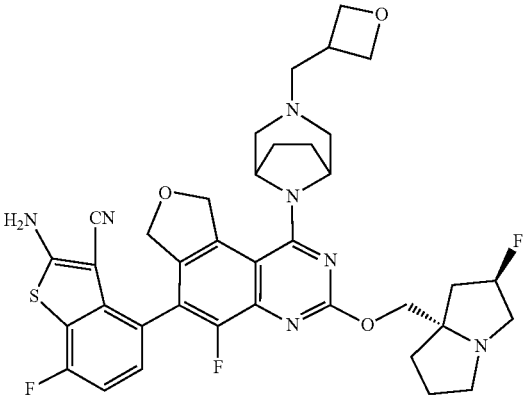 [SMILES: N#Cc1c(N)sc2c(F)ccc(-c3c4c(c5c(N6C7CCC6CN(CC6COC6)C7)nc(OC[C@@]67CCCN6C[C@H](F)C7)nc5c3F)COC4)c12] |

TABLE A-continued
Example Compounds
| Ex. # | Compound |
|---|---|
| 106 | 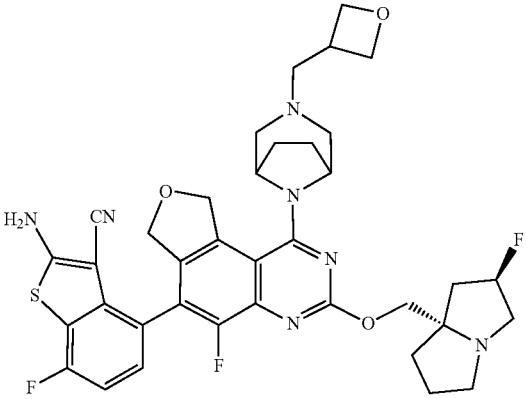 [SMILES: N#Cc1c(N)sc2c(F)ccc(-c3c4c(c5c(N6C7CCC6CN(CC6COC6)C7)nc(OC[C@@]67CCCN6C[C@H](F)C7)nc5c3F)COC4)c12] |
| 107 | 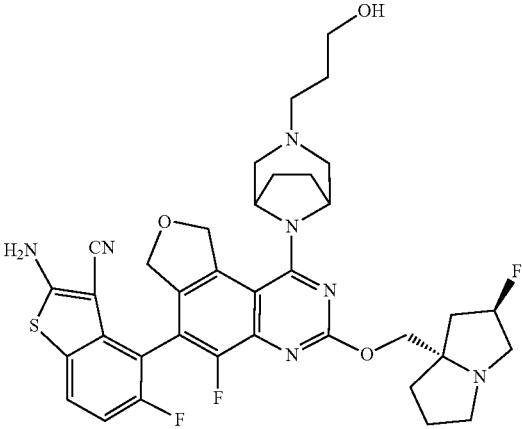 [SMILES: N#Cc1c(N)sc2ccc(F)c(-c3c4c(c5c(N6C7CCC6CN(CCCO)C7)nc(OC[C@@]67CCCN6C[C@H](F)C7)nc5c3F)COC4)c12] |
| 108 | 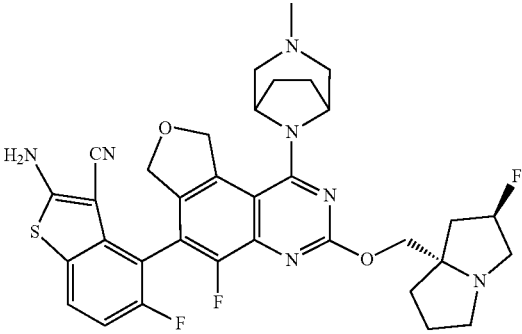 [SMILES: CN1CC2CCC(C1)N2c1nc(OC[C@@]23CCCN2C[C@H](F)C3)nc2c(F)c(-c3c(F)ccc4sc(N)c(C#N)c34)c3c(c12)COC3] |

TABLE A-continued
Example Compounds
| Ex. # | Compound |
|---|---|
| 109 | 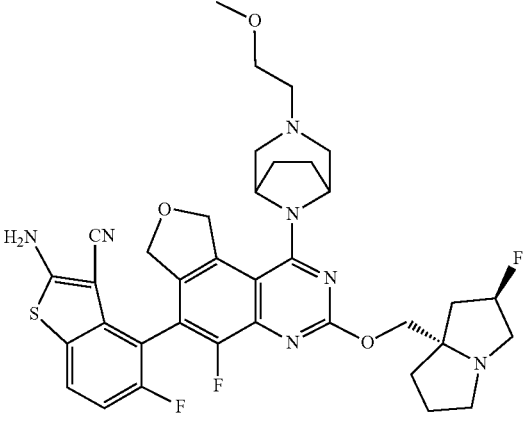 [SMILES: COCCN1CC2CCC(C1)N2c1nc(OC[C@@]23CCCN2C[C@H](F)C3)nc2c(F)c(-c3c(F)ccc4sc(N)c(C#N)c34)c3c(c12)COC3] |
| 110 | 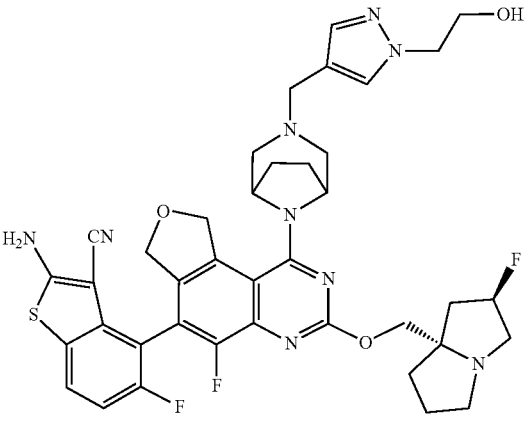 [SMILES: N#Cc1c(N)sc2ccc(F)c(-c3c4c(c5c(N6C7CCC6CN(Cc6cnn(CCO)c6)C7)nc(OC[C@@]67CCCN6C[C@H](F)C7)nc5c3F)COC4)c12] |
| 111 | 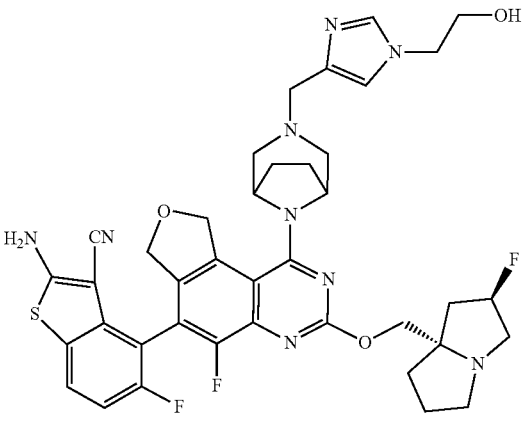 |

TABLE A-continued
Example Compounds
| Ex. # | Compound |
|---|---|
| 112 | 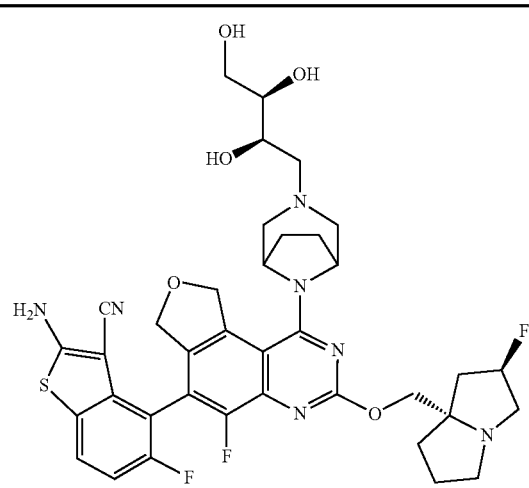 |
| 113 | 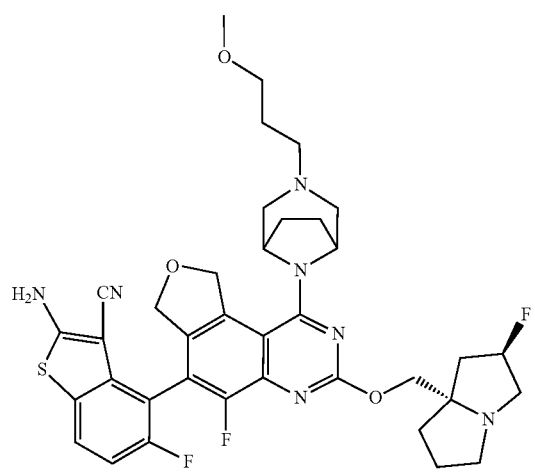 [SMILES: COCCCN1CC2CCC(C1)N2c1nc(OC[C@@]23CCCN2C[C@H](F)C3)nc2c(F)c(-c3c(F)ccc4sc(N)c(C#N)c34)c3c(c12)COC3] |
| 114 | 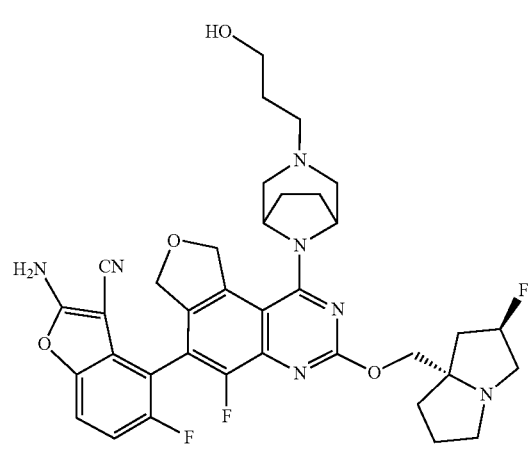 [SMILES: N#Cc1c(N)oc2ccc(F)c(-c3c4c(c5c(N6C7CCC6CN(CCCO)C7)nc(OC[C@@]67CCCN6C[C@H](F)C7)nc5c3F)COC4)c12] |

TABLE A-continued
Example Compounds
| Ex. # | Compound |
|---|---|
| 115 | 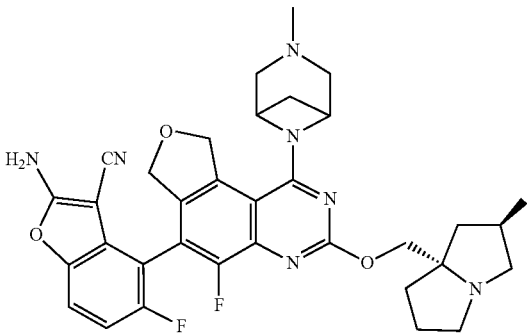 |
| 116 | 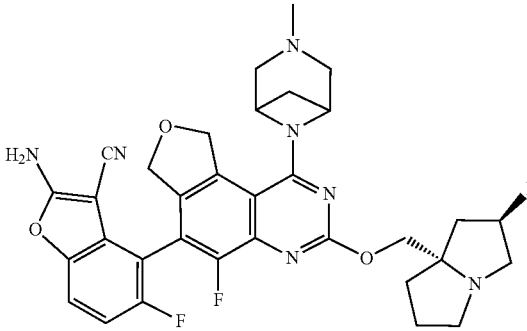 |
| 117 | 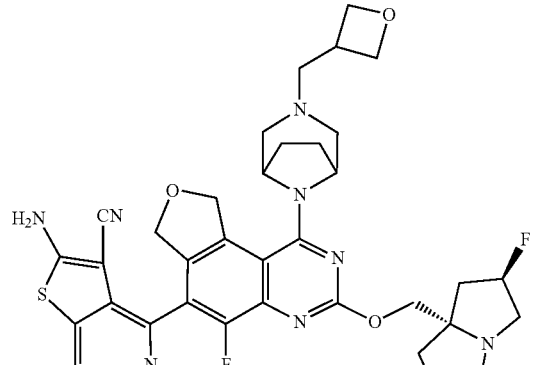 |
| 118 | 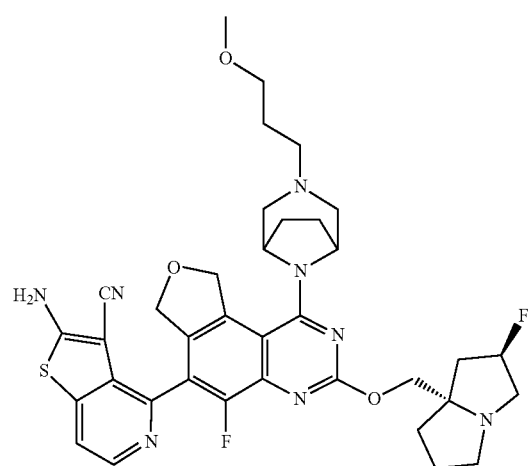 |

TABLE A-continued
Example Compounds
| Ex. # | Compound |
|---|---|
| 119 | 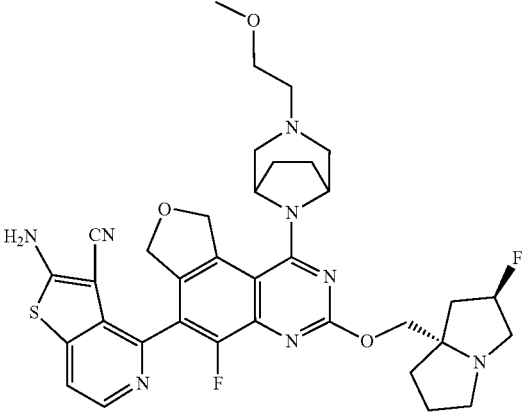 [SMILES: COCCN1CC2CCC(C1)N2c1nc(OC[C@@]23CCCN2C[C@H](F)C3)nc2c(F)c(-c3nccc4sc(N)c(C#N)c34)c3c(c12)COC3] |
| 120 | 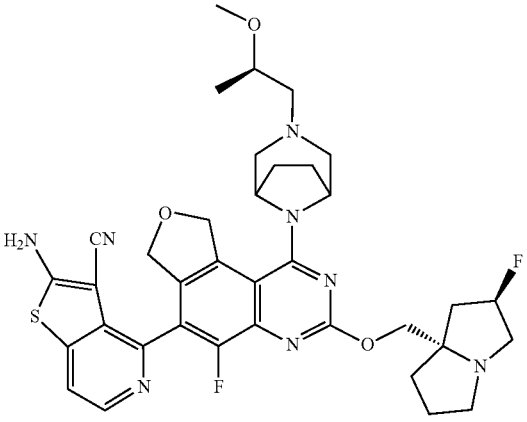 [SMILES: CO[C@H](C)CN1CC2CCC(C1)N2c1nc(OC[C@@]23CCCN2C[C@H](F)C3)nc2c(F)c(-c3nccc4sc(N)c(C#N)c34)c3c(c12)COC3] |
| 121 | 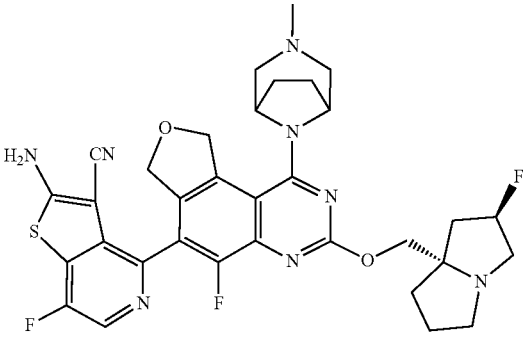 [SMILES: CN1CC2CCC(C1)N2c1nc(OC[C@@]23CCCN2C[C@H](F)C3)nc2c(F)c(-c3ncc(F)c4sc(N)c(C#N)c34)c3c(c12)COC3] |

TABLE A-continued
Example Compounds
| Ex. # | Compound |
|---|---|
| 122 | 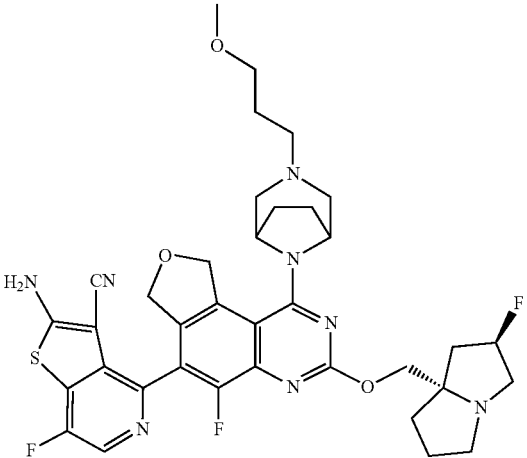 [SMILES: COCCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 123 | 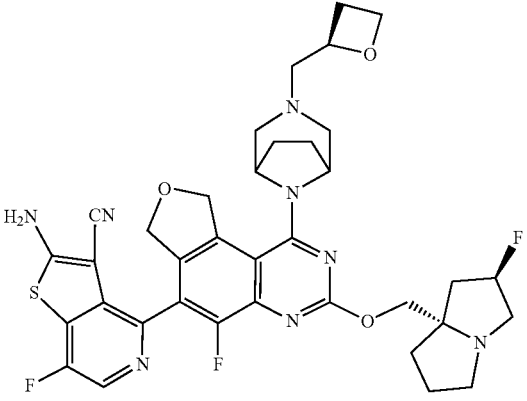 [SMILES: N#Cc1c(N)sc2c(F)cnc(-c3c4c(c5c(N6C7CCC6CN(C[C@H]6CCO6)C7)nc(OC[C@@]67CCCN6C[C@H](F)C7)nc5c3F)COC4)c12] |
| 124 | 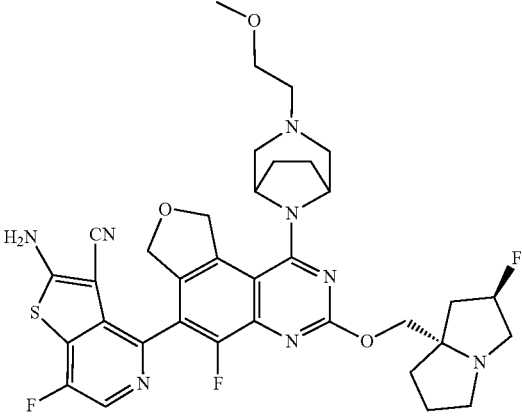 [SMILES: COCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] |

TABLE A-continued
Example Compounds
| Ex. # | Compound |
|---|---|
| 125 | 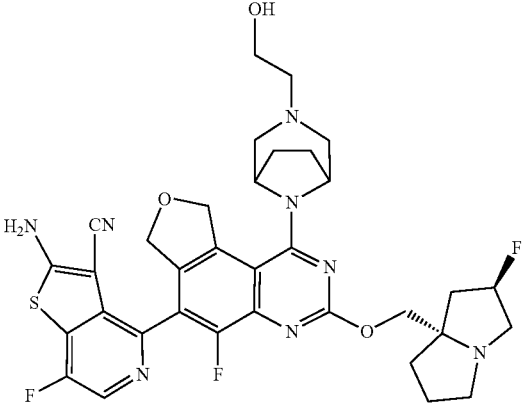 [SMILES: N#Cc1c(N)sc2c(F)cnc(-c3c4c(c5c(N6C7CCC6CN(CCO)C7)nc(OC[C@@]67CCCN6C[C@H](F)C7)nc5c3F)COC4)c12] |
| 126 | 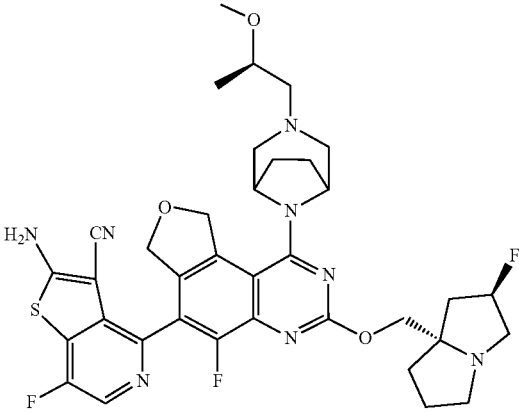 [SMILES: CO[C@H](C)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 127 | 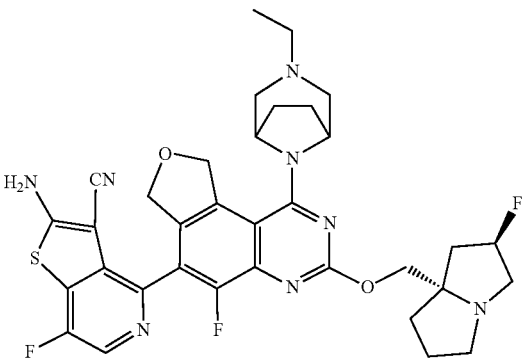 [SMILES: CCN1CC2CCC(C1)N2c1nc(OC[C@@]23CCCN2C[C@H](F)C3)nc2c(F)c(-c3ncc(F)c4sc(N)c(C#N)c34)c3c(c12)COC3] |

TABLE A-continued
Example Compounds
| Ex. # | Compound |
|---|---|
| 128 | 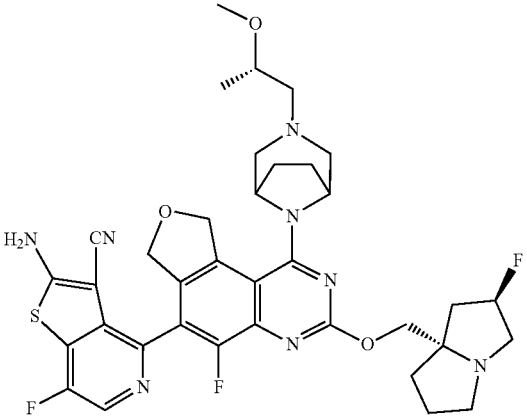 [SMILES: CO[C@@H](C)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 129 | 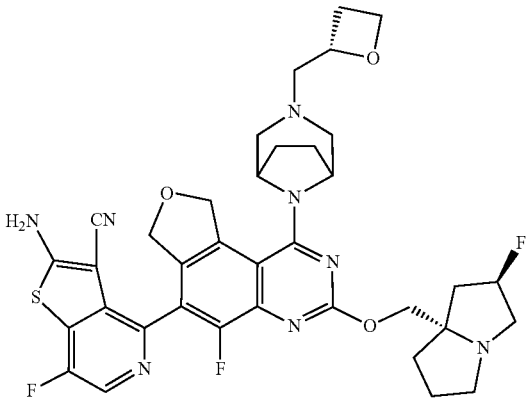 [SMILES: N#Cc1c(N)sc2c(F)cnc(-c3c4c(c5c(N6C7CCC6CN(C[C@@H]6CCO6)C7)nc(OC[C@@]67CCCN6C[C@H](F)C7)nc5c3F)COC4)c12] |
| 130 | 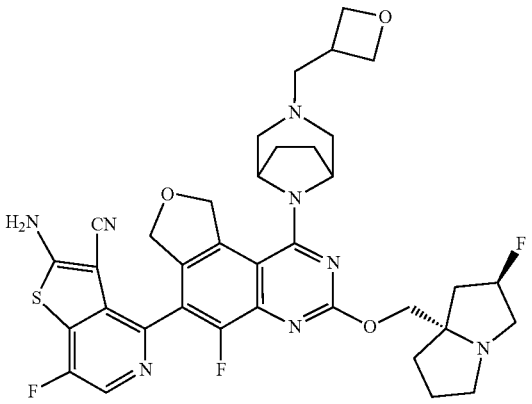 [SMILES: N#Cc1c(N)sc2c(F)cnc(-c3c4c(c5c(N6C7CCC6CN(CC6COC6)C7)nc(OC[C@@]67CCCN6C[C@H](F)C7)nc5c3F)COC4)c12] |

101 102
TABLE A-continued
Example Compounds
| Ex. # | Compound |
|---|---|
| 131 | 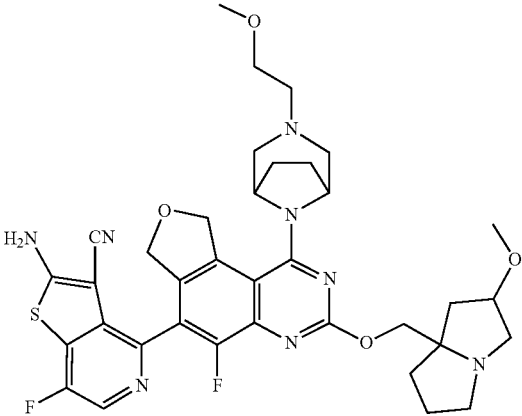 [SMILES: COCCN1CC2CCC(C1)N2c1nc(OCC23CCCN2CC(OC)C3)nc2c(F)c(-c3ncc(F)c4sc(N)c(C#N)c34)c3c(c12)COC3] |
| 132 | 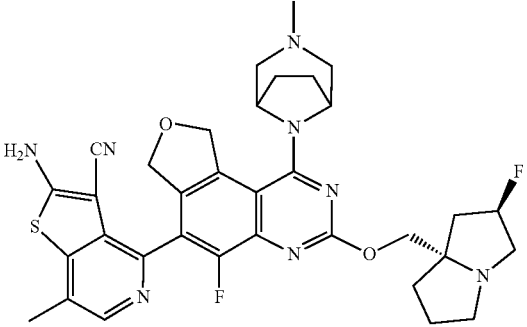 [SMILES: Cc1cnc(-c2c3c(c4c(N5C6CCC5CN(C)C6)nc(OC[C@@]56CCCN5C[C@H](F)C6)nc4c2F)COC3)c2c(C#N)c(N)sc12] |
| 133 | 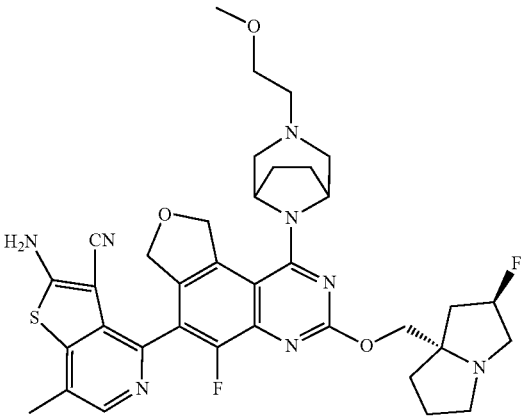 [SMILES: COCCN1CC2CCC(C1)N2c1nc(OC[C@@]23CCCN2C[C@H](F)C3)nc2c(F)c(-c3ncc(C)c4sc(N)c(C#N)c34)c3c(c12)COC3] |
| 134 | 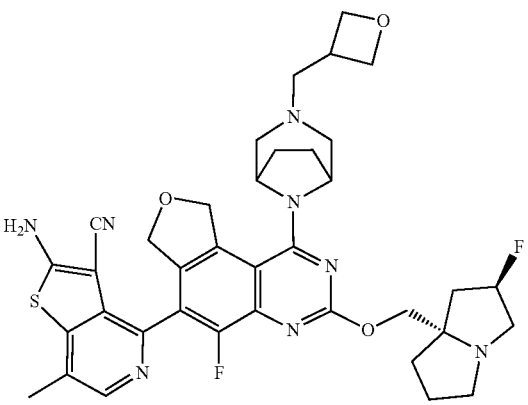 [SMILES: Cc1cnc(-c2c3c(c4c(N5C6CCC5CN(CC5COC5)C6)nc(OC[C@@]56CCCN5C[C@H](F)C6)nc4c2F)COC3)c2c(C#N)c(N)sc12] |

TABLE A-continued
Example Compounds
| Ex. # | Compound |
|---|---|
| 135 | 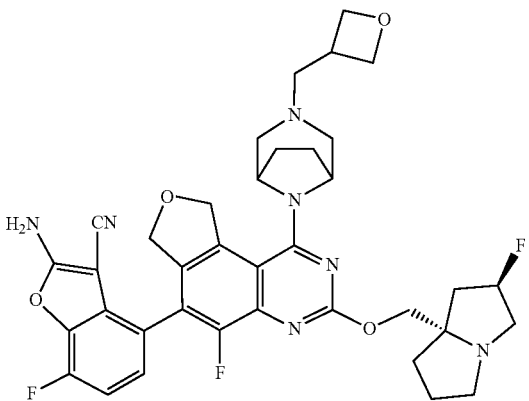 [SMILES: N#Cc1c(N)oc2c(F)ccc(-c3c4c(c5c(N6C7CCC6CN(CC6COC6)C7)nc(OC[C@@]67CCCN6C[C@H](F)C7)nc5c3F)COC4)c12] |
| 136 | 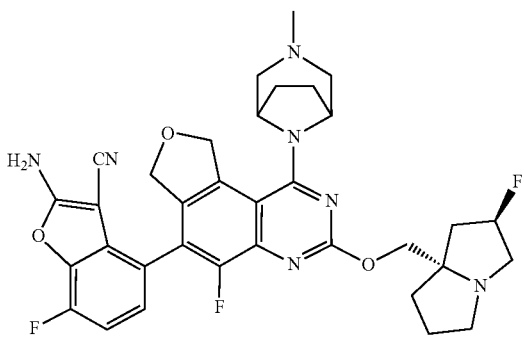 [SMILES: CN1CC2CCC(C1)N2c1nc(OC[C@@]23CCCN2C[C@H](F)C3)nc2c(F)c(-c3ccc(F)c4oc(N)c(C#N)c34)c3c(c12)COC3] |
| 137 | 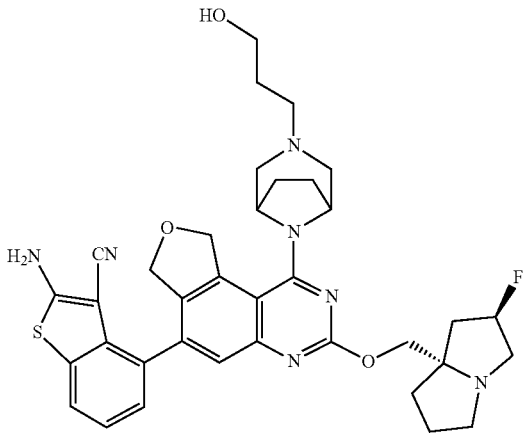 [SMILES: N#Cc1c(N)sc2cccc(-c3cc4nc(OC[C@@]56CCCN5C[C@H](F)C6)nc(N5C6CCC5CN(CCCO)C6)c4c4c3COC4)c12] |

TABLE A-continued
Example Compounds
| Ex. # | Compound |
|---|---|
| 138 | 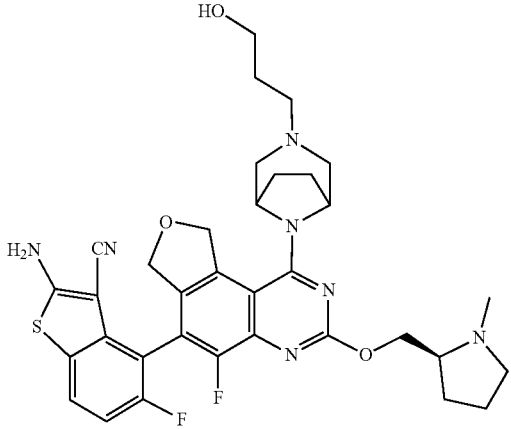 [SMILES: CN1CCC[C@H]1COc1nc(N2C3CCC2CN(CCCO)C3)c2c3c(c(-c4c(F)ccc5sc(N)c(C#N)c45)c(F)c2n1)COC3] |
| 139 | 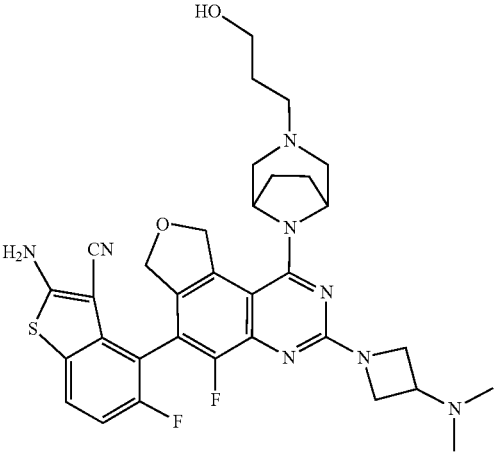 [SMILES: CN(C)C1CN(c2nc(N3C4CCC3CN(CCCO)C4)c3c4c(c(-c5c(F)ccc6sc(N)c(C#N)c56)c(F)c3n2)COC4)C1] |
| 140 | 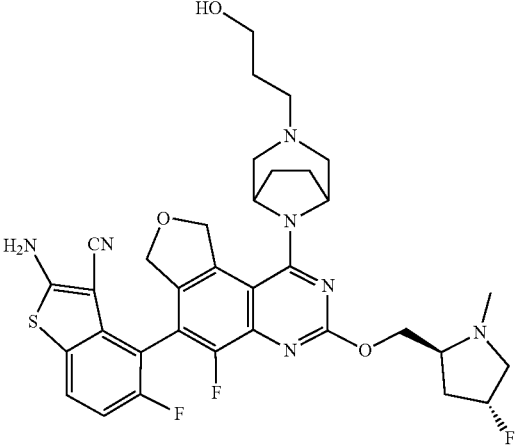 [SMILES: CN1C[C@H](F)C[C@H]1COc1nc(N2C3CCC2CN(CCCO)C3)c2c3c(c(-c4c(F)ccc5sc(N)c(C#N)c45)c(F)c2n1)COC3] |

TABLE A-continued
Example Compounds
| Ex. # | Compound |
|---|---|
| 141 | 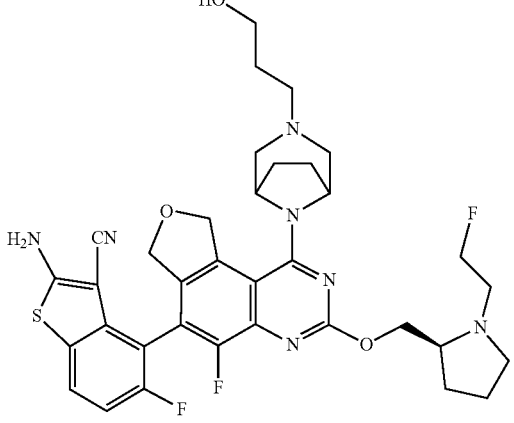 |
| 142 | 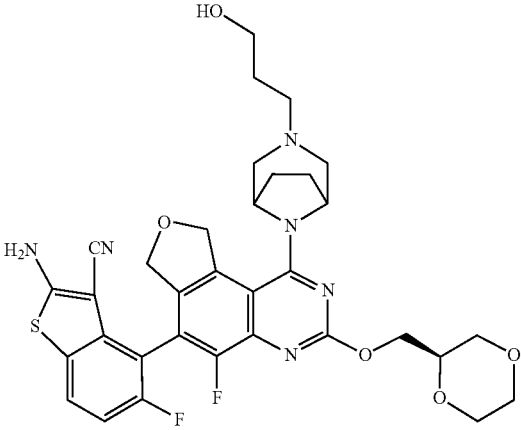 [SMILES: N#Cc1c(N)sc2ccc(F)c(-c3c4c(c5c(N6C7CCC6CN(CCCO)C7)nc(OC[C@H]6COCCO6)nc5c3F)COC4)c12] |
| 143 | 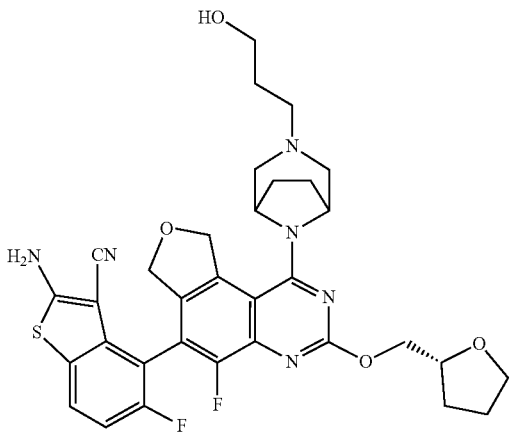 [SMILES: N#Cc1c(N)sc2ccc(F)c(-c3c4c(c5c(N6C7CCC6CN(CCCO)C7)nc(OC[C@H]6CCCO6)nc5c3F)COC4)c12] |

TABLE A-continued
Example Compounds
| Ex. # | Compound |
|---|---|
| 144 | 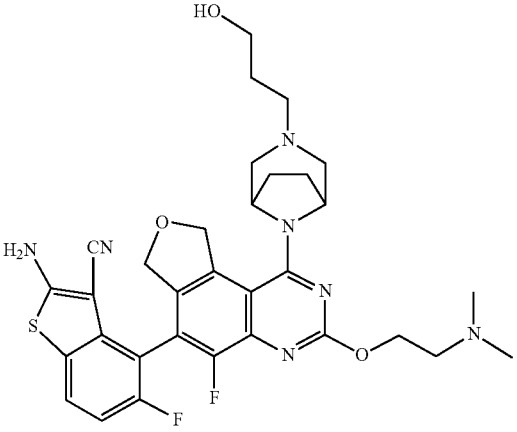 [SMILES: CN(C)CCOc1nc(N2C3CCC2CN(CCCO)C3)c2c3c(c(-c4c(F)ccc5sc(N)c(C#N)c45)c(F)c2n1)COC3] |
| 145 | 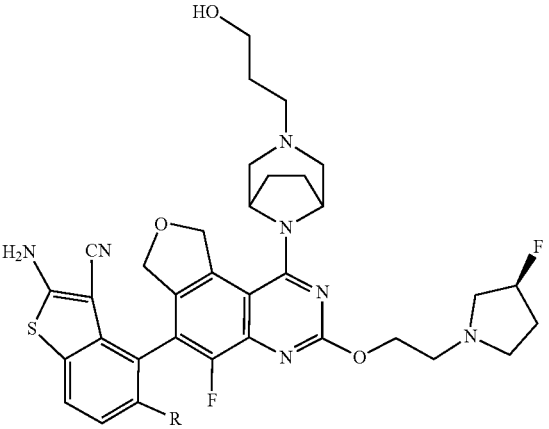 |
| 146 | 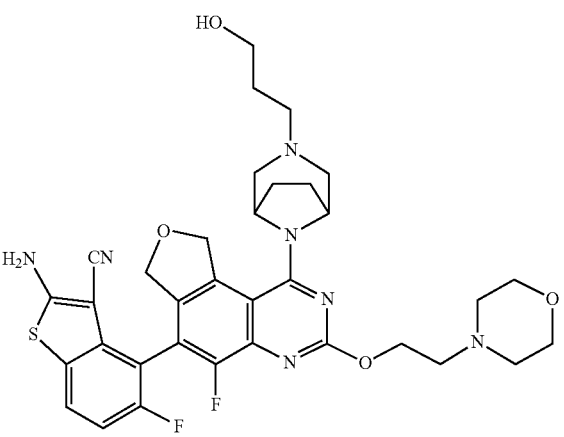 [SMILES: N#Cc1c(N)sc2ccc(F)c(-c3c4c(c5c(N6C7CCC6CN(CCCO)C7)nc(OCCN6CCOCC6)nc5c3F)COC4)c12] |

TABLE A-continued
Example Compounds
| Ex. # | Compound |
|---|---|
| 147 | 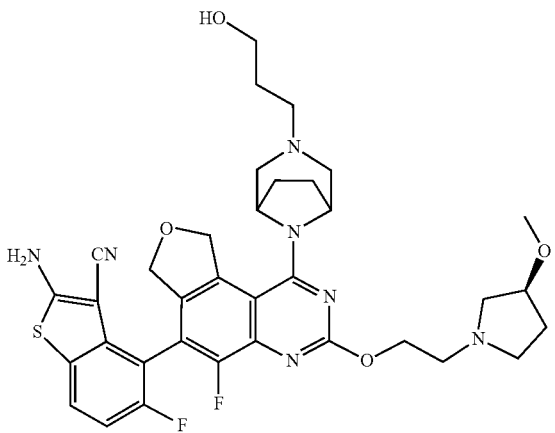 [SMILES: CO[C@H]1CCN(CCOc2nc(N3C4CCC3CN(CCCO)C4)c3c4c(c(-c5c(F)ccc6sc(N)c(C#N)c56)c(F)c3n2)COC4)C1] |
| 148 | 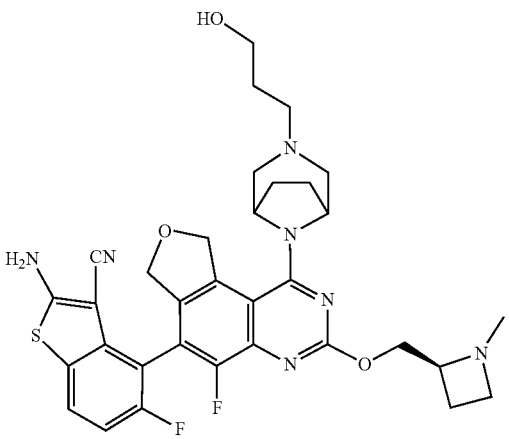 [SMILES: CN1CC[C@H]1COc1nc(N2C3CCC2CN(CCCO)C3)c2c3c(c(-c4c(F)ccc5sc(N)c(C#N)c45)c(F)c2n1)COC3] |
| 149 | 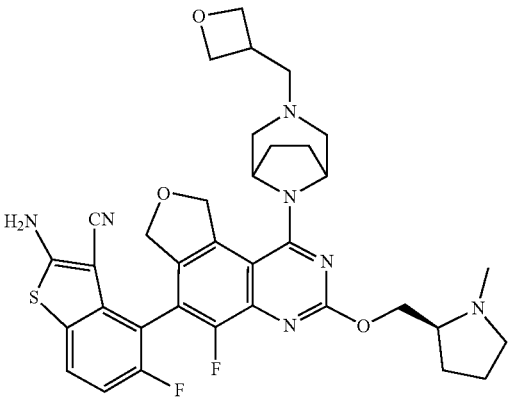 [SMILES: CN1CCC[C@H]1COc1nc(N2C3CCC2CN(CC2COC2)C3)c2c3c(c(-c4c(F)ccc5sc(N)c(C#N)c45)c(F)c2n1)COC3] |

TABLE A-continued
Example Compounds
| Ex. # | Compound |
|---|---|
| 150 | 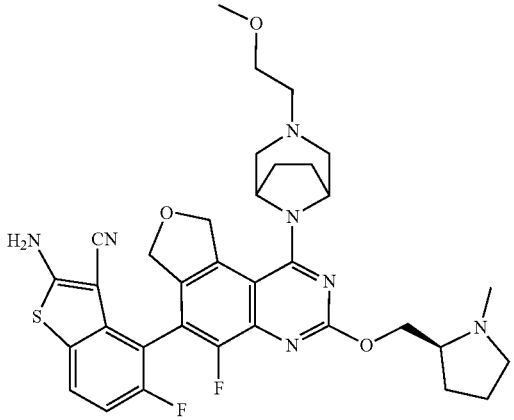 [SMILES: COCCN1CC2CCC(C1)N2c1nc(OC[C@@H]2CCCN2C)nc2c(F)c(-c3c(F)ccc4sc(N)c(C#N)c34)c3c(c12)COC3] |
| 151 | 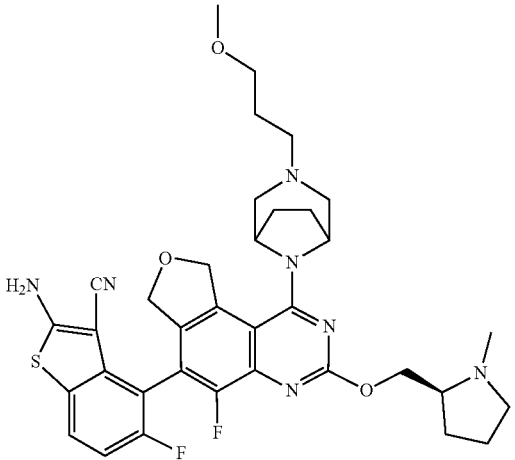 [SMILES: COCCCN1CC2CCC(C1)N2c1nc(OC[C@@H]2CCCN2C)nc2c(F)c(-c3c(F)ccc4sc(N)c(C#N)c34)c3c(c12)COC3] |
| 152 | 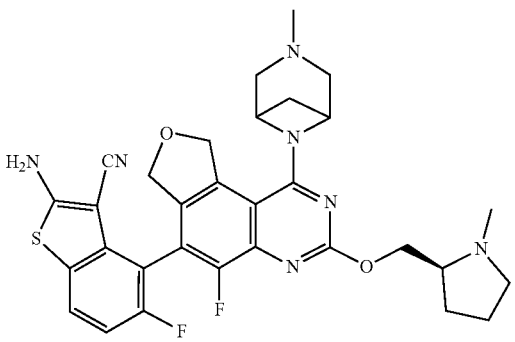 [SMILES: CN1CC2CC(C1)N2c1nc(OC[C@@H]2CCCN2C)nc2c(F)c(-c3c(F)ccc4sc(N)c(C#N)c34)c3c(c12)COC3] |

TABLE A-continued
Example Compounds
| Ex. # | Compound |
|---|---|
| 153 | 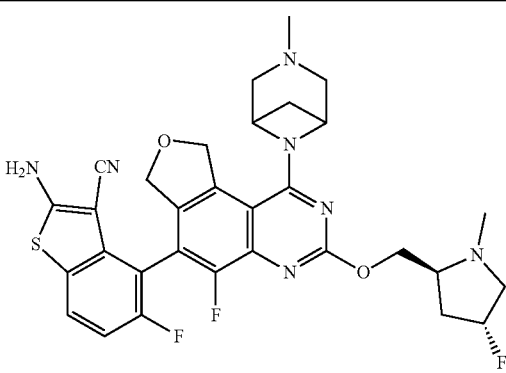 |
| 154 | 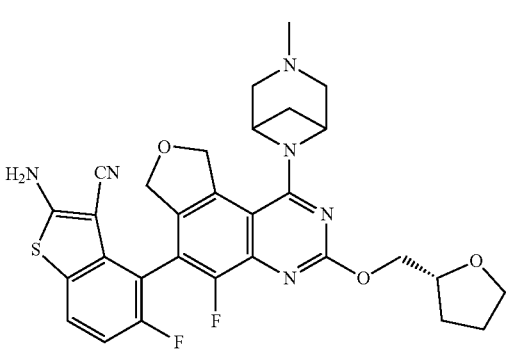 [SMILES: CN1CC2CC(C1)N2c1nc(OC[C@H]2CCCO2)nc2c(F)c(-c3c(F)ccc4sc(N)c(C#N)c34)c3c(c12)COC3] |
| 155 | 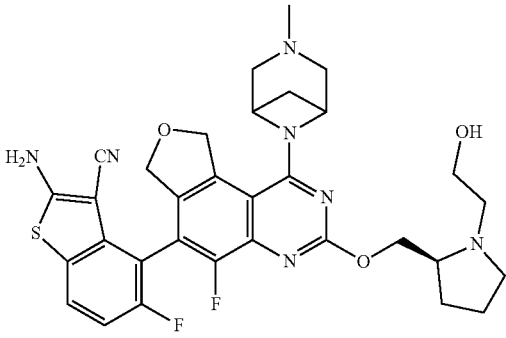 [SMILES: CN1CC2CC(C1)N2c1nc(OC[C@@H]2CCCN2CCO)nc2c(F)c(-c3c(F)ccc4sc(N)c(C#N)c34)c3c(c12)COC3] |
| 156 | 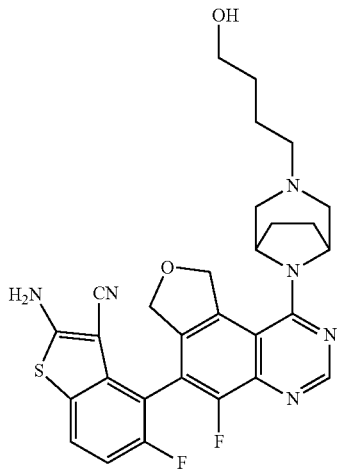 [SMILES: N#Cc1c(N)sc2ccc(F)c(-c3c4c(c5c(N6C7CCC6CN(CCCCO)C7)ncnc5c3F)COC4)c12] |

TABLE A-continued
Example Compounds
| Ex. # | Compound |
|---|---|
| 157 | 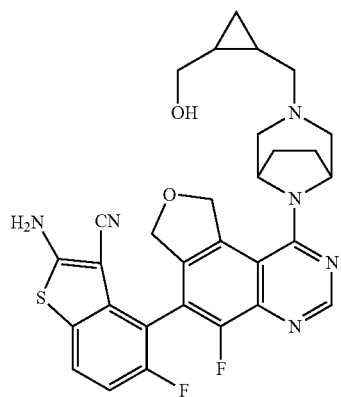 [SMILES: N#Cc1c(N)sc2ccc(F)c(-c3c4c(c5c(N6C7CCC6CN(CC6CC6CO)C7)ncnc5c3F)COC4)c12] |
| 158 | 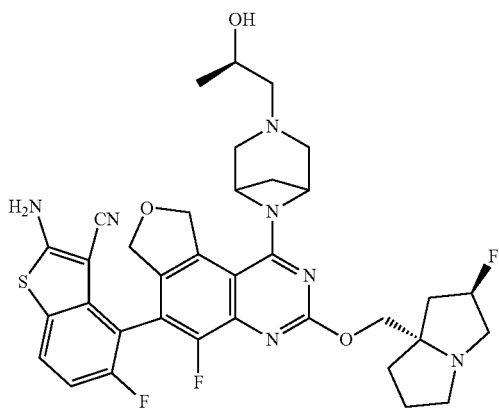 [SMILES: C[C@@H](O)CN1CC2CC(C1)N2c1nc(OC[C@@]23CCCN2C[C@H](F)C3)nc2c(F)c(-c3c(F)ccc4sc(N)c(C#N)c34)c3c(c12)COC3] |
| 159 | 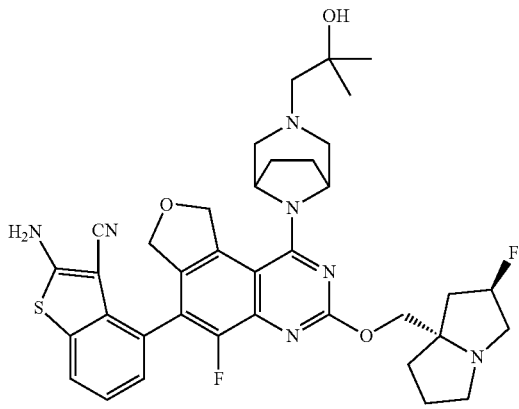 [SMILES: CC(C)(O)CN1CC2CCC(C1)N2c1nc(OC[C@@]23CCCN2C[C@H](F)C3)nc2c(F)c(-c3cccc4sc(N)c(C#N)c34)c3c(c12)COC3] |

119
120
TABLE A-continued
Example Compounds
| Ex. # | Compound |
|---|---|
| 160 | 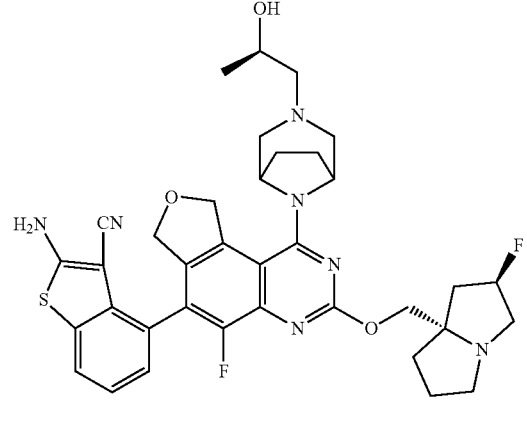 [SMILES: C[C@@H](O)CN1CC2CCC(C1)N2c1nc(OC[C@@]23CCCN2C[C@H](F)C3)nc2c(F)c(-c3cccc4sc(N)c(C#N)c34)c3c(c12)COC3] |
| 161 | 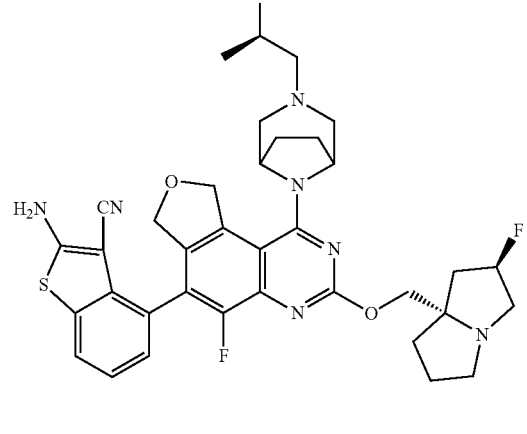 |
| 162 | 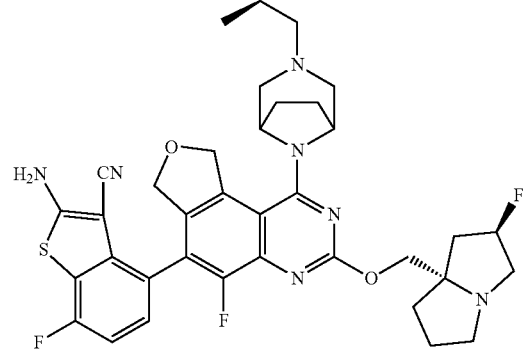 |

TABLE A-continued
Example Compounds
| Ex. # | Compound |
|---|---|
| 163 | 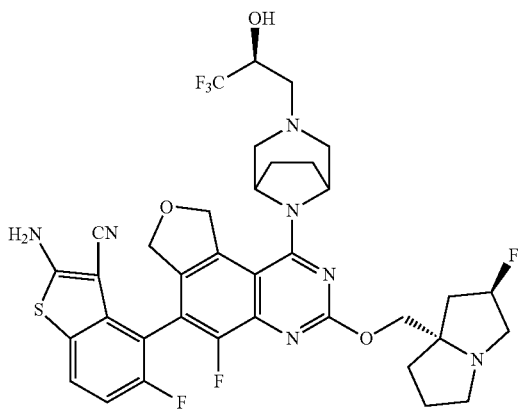 [SMILES: N#Cc1c(N)sc2ccc(F)c(-c3c4c(c5c(N6C7CCC6CN(C[C@H](O)C(F)(F)F)C7)nc(OC[C@@]67CCCN6C[C@H](F)C7)nc5c3F)COC4)c12] |
| 164 | 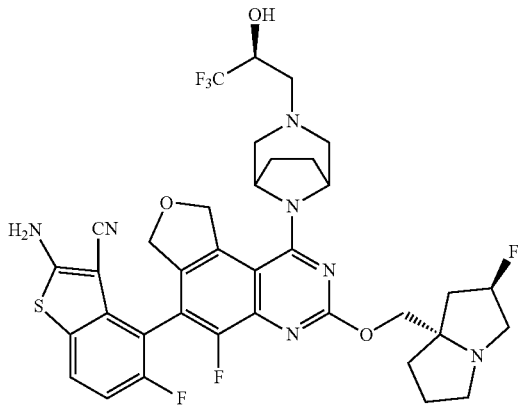 [SMILES: N#Cc1c(N)sc2ccc(F)c(-c3c4c(c5c(N6C7CCC6CN(C[C@H](O)C(F)(F)F)C7)nc(OC[C@@]67CCCN6C[C@H](F)C7)nc5c3F)COC4)c12] |
| 165 | 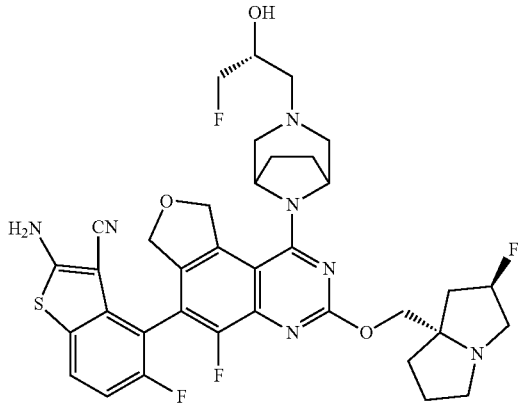 [SMILES: N#Cc1c(N)sc2ccc(F)c(-c3c4c(c5c(N6C7CCC6CN(C[C@@H](O)CF)C7)nc(OC[C@@]67CCCN6C[C@H](F)C7)nc5c3F)COC4)c12] |

TABLE A-continued
Example Compounds
| Ex. # | Compound |
|---|---|
| 166 | 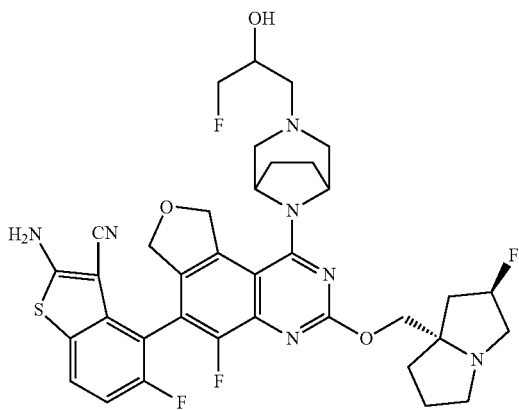 [SMILES: N#Cc1c(N)sc2ccc(F)c(-c3c4c(c5c(N6C7CCC6CN(CC(O)CF)C7)nc(OC[C@@]67CCCN6C[C@H](F)C7)nc5c3F)COC4)c12] |
| 167 | 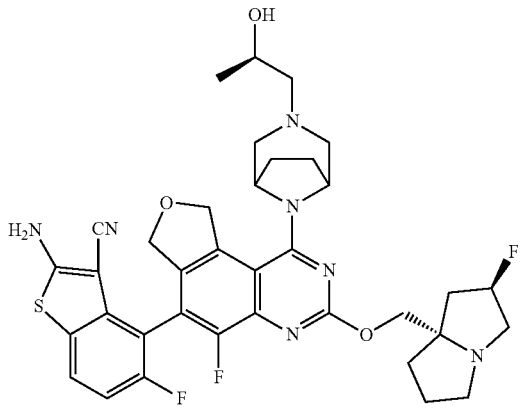 [SMILES: C[C@@H](O)CN1CC2CCC(C1)N2c1nc(OC[C@@]23CCCN2C[C@H](F)C3)nc2c(F)c(-c3c(F)ccc4sc(N)c(C#N)c34)c3c(c12)COC3] |
| 168 | 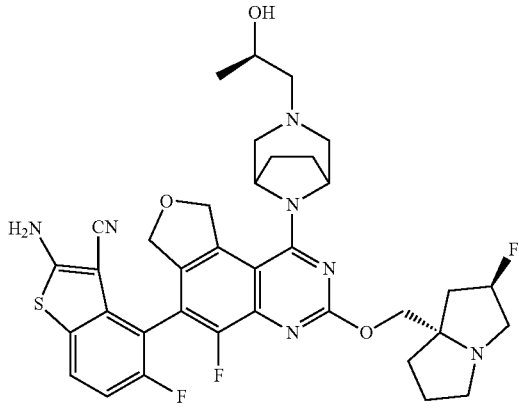 [SMILES: C[C@@H](O)CN1CC2CCC(C1)N2c1nc(OC[C@@]23CCCN2C[C@H](F)C3)nc2c(F)c(-c3c(F)ccc4sc(N)c(C#N)c34)c3c(c12)COC3] |

TABLE A-continued
Example Compounds
| Ex. # | Compound |
|---|---|
| 169 | 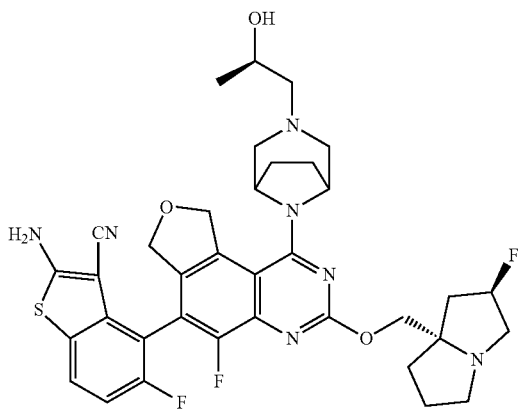 [SMILES: C[C@@H](O)CN1CC2CCC(C1)N2c1nc(OC[C@@]23CCCN2C[C@H](F)C3)nc2c(F)c(-c3c(F)ccc4sc(N)c(C#N)c34)c3c(c12)COC3] |
| 170 | 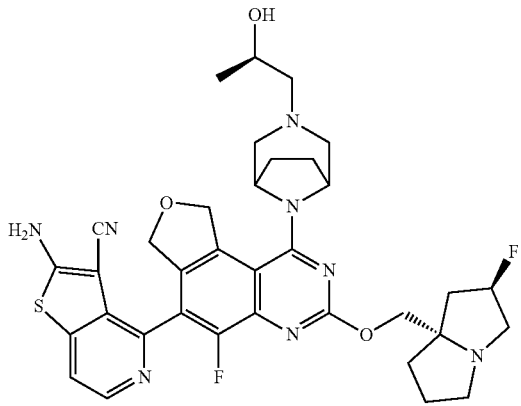 [SMILES: C[C@@H](O)CN1CC2CCC(C1)N2c1nc(OC[C@@]23CCCN2C[C@H](F)C3)nc2c(F)c(-c3nccc4sc(N)c(C#N)c34)c3c(c12)COC3] |
| 171 | 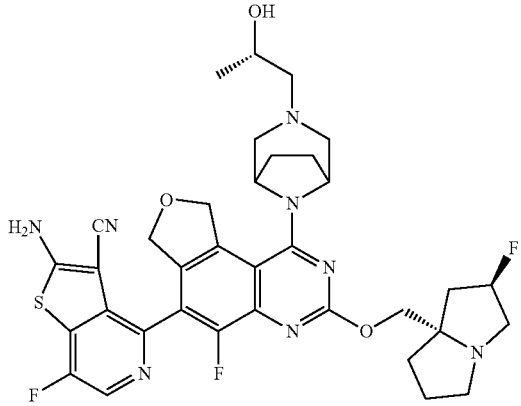 [SMILES: C[C@H](O)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] |

TABLE A-continued
Example Compounds
| Ex. # | Compound |
|---|---|
| 172 | 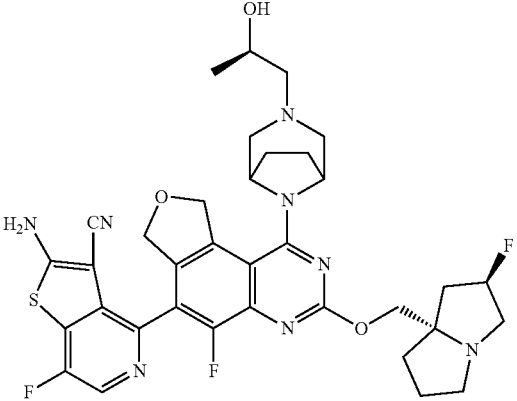 [SMILES: C[C@@H](O)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 173 | 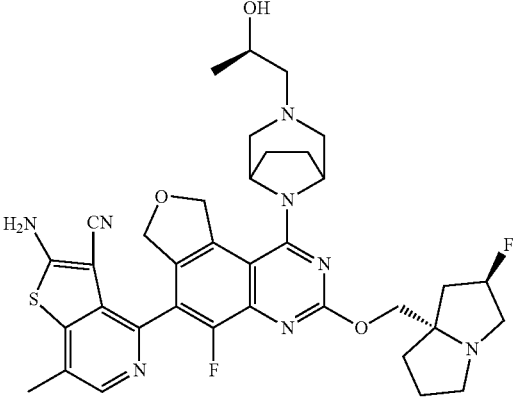 [SMILES: Cc1cnc(-c2c3c(c4c(N5C6CCC5CN(C[C@@H](C)O)C6)nc(OC[C@@]56CCCN5C[C@H](F)C6)nc4c2F)COC3)c2c(C#N)c(N)sc12] |
| 174 | 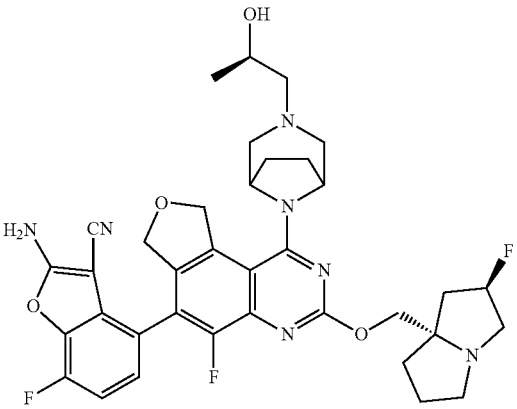 [SMILES: C[C@@H](O)CN1CC2CCC(C1)N2c1nc(OC[C@@]23CCCN2C[C@H](F)C3)nc2c(F)c(-c3ccc(F)c4oc(N)c(C#N)c34)c3c(c12)COC3] |

TABLE A-continued
Example Compounds
| Ex. # | Compound |
|---|---|
| 175 | 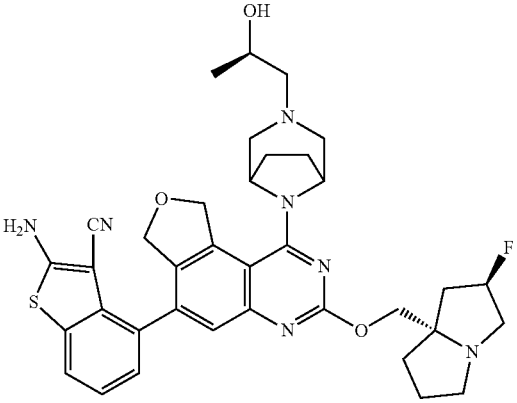 [SMILES: C[C@@H](O)CN1CC2CCC(C1)N2c1nc(OC[C@@]23CCCN2C[C@H](F)C3)nc2cc(-c3cccc4sc(N)c(C#N)c34)c3c(c12)COC3] |
| 176 | 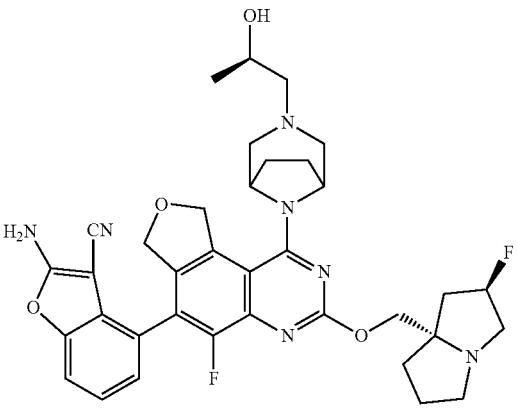 [SMILES: C[C@@H](O)CN1CC2CCC(C1)N2c1nc(OC[C@@]23CCCN2C[C@H](F)C3)nc2c(F)c(-c3cccc4oc(N)c(C#N)c34)c3c(c12)COC3] |
| 177 | 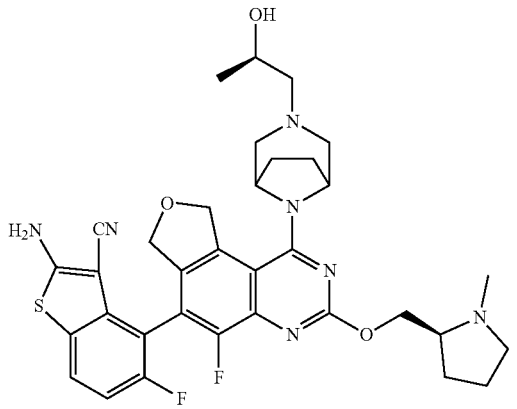 [SMILES: C[C@@H](O)CN1CC2CCC(C1)N2c1nc(OC[C@@H]2CCCN2C)nc2c(F)c(-c3c(F)ccc4sc(N)c(C#N)c34)c3c(c12)COC3] |

TABLE A-continued
Example Compounds
| Ex. # | Compound |
|---|---|
| 178 | 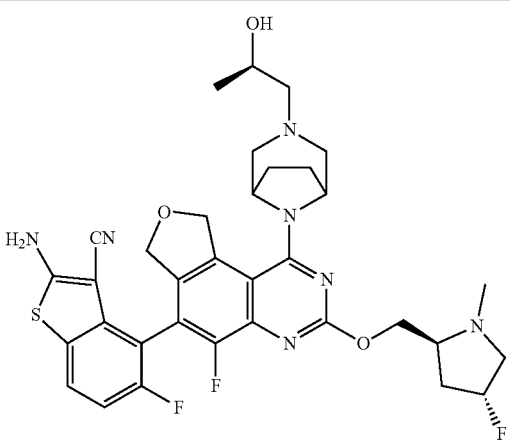 [SMILES: C[C@@H](O)CN1CC2CCC(C1)N2c1nc(OC[C@@H]2C[C@@H](F)CN2C)nc2c(F)c(-c3c(F)ccc4sc(N)c(C#N)c34)c3c(c12)COC3] |
| 179 | 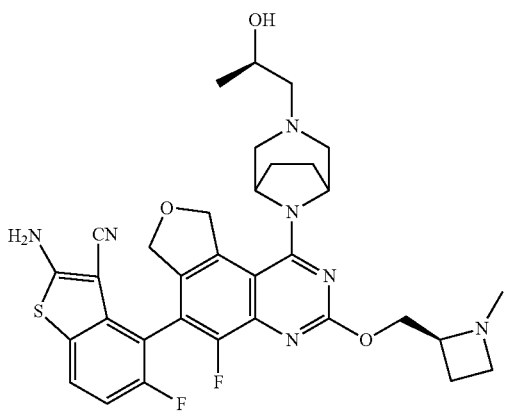 [SMILES: C[C@@H](O)CN1CC2CCC(C1)N2c1nc(OC[C@@H]2CCN2C)nc2c(F)c(-c3c(F)ccc4sc(N)c(C#N)c34)c3c(c12)COC3] |
| 180 | 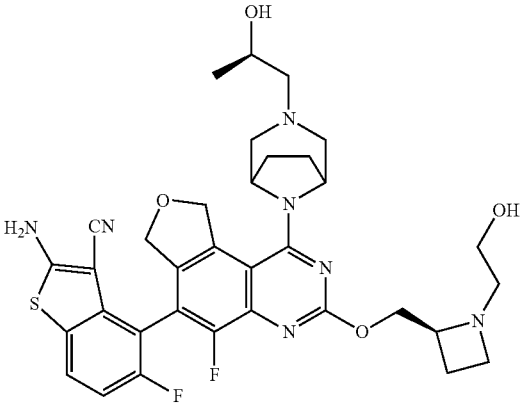 [SMILES: C[C@@H](O)CN1CC2CCC(C1)N2c1nc(OC[C@@H]2CCN2CCO)nc2c(F)c(-c3c(F)ccc4sc(N)c(C#N)c34)c3c(c12)COC3] |

TABLE A-continued
Example Compounds
| Ex. # | Compound |
|---|---|
| 181 | 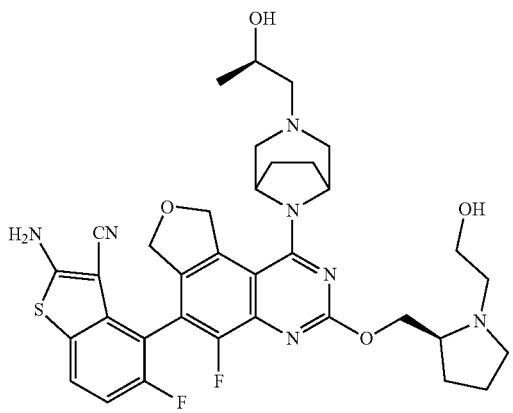 [SMILES: C[C@@H](O)CN1CC2CCC(C1)N2c1nc(OC[C@@H]2CCCN2CCO)nc2c(F)c(-c3c(F)ccc4sc(N)c(C#N)c34)c3c(c12)COC3] |
| 182 | 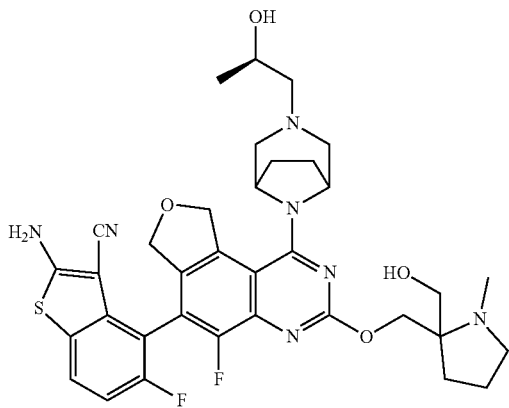 [SMILES: C[C@@H](O)CN1CC2CCC(C1)N2c1nc(OCC2(CO)CCCN2C)nc2c(F)c(-c3c(F)ccc4sc(N)c(C#N)c34)c3c(c12)COC3] |
| 183 | 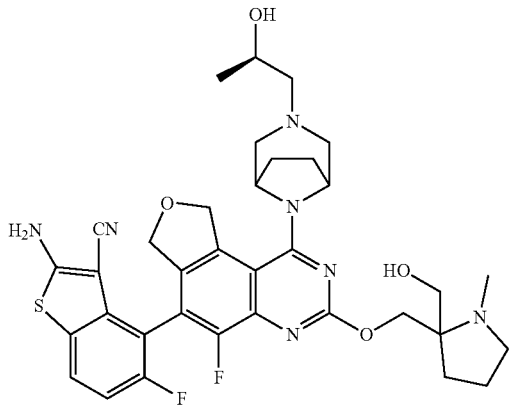 [SMILES: C[C@@H](O)CN1CC2CCC(C1)N2c1nc(OCC2(CO)CCCN2C)nc2c(F)c(-c3c(F)ccc4sc(N)c(C#N)c34)c3c(c12)COC3] |

TABLE A-continued
Example Compounds
| Ex. # | Compound |
|---|---|
| 184 | 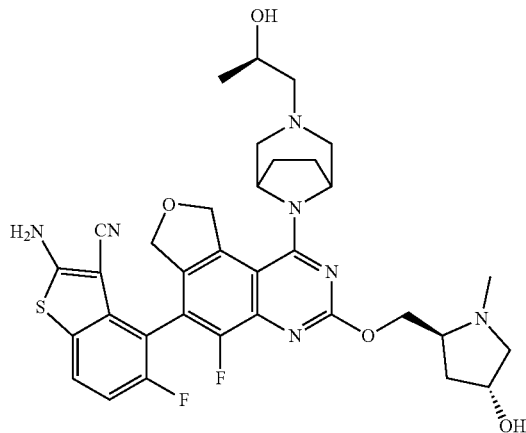 [SMILES: C[C@@H](O)CN1CC2CCC(C1)N2c1nc(OC[C@@H]2C[C@@H](O)CN2C)nc2c(F)c(-c3c(F)ccc4sc(N)c(C#N)c34)c3c(c12)COC3] |
| 185 | 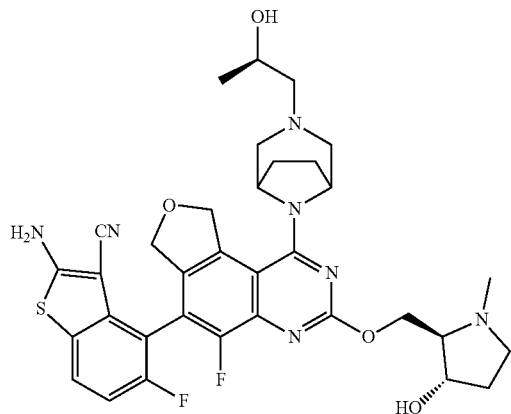 [SMILES: C[C@@H](O)CN1CC2CCC(C1)N2c1nc(OC[C@@H]2[C@@H](O)CCN2C)nc2c(F)c(-c3c(F)ccc4sc(N)c(C#N)c34)c3c(c12)COC3] |
| 186 | 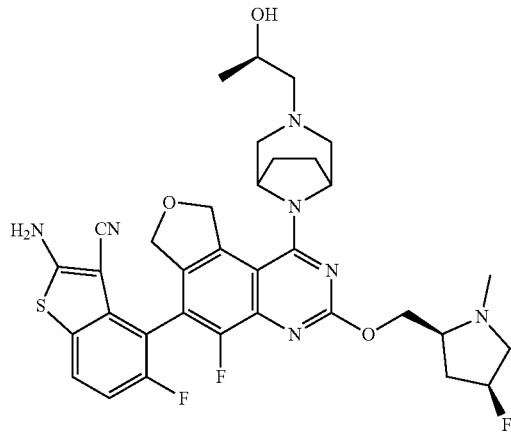 [SMILES: C[C@@H](O)CN1CC2CCC(C1)N2c1nc(OC[C@@H]2C[C@H](F)CN2C)nc2c(F)c(-c3c(F)ccc4sc(N)c(C#N)c34)c3c(c12)COC3] |

137
TABLE A-continued
Example Compounds
| Ex. # | Compound |
|---|---|
| 187 | 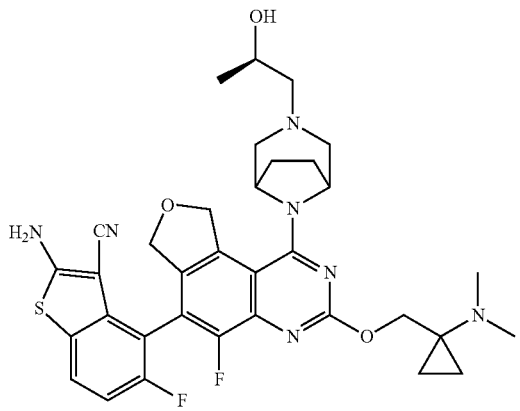 [SMILES: C[C@@H](O)CN1CC2CCC(C1)N2c1nc(OCC2(N(C)C)CC2)nc2c(F)c(-c3c(F)ccc4sc(N)c(C#N)c34)c3c(c12)COC3] |
| 188 | 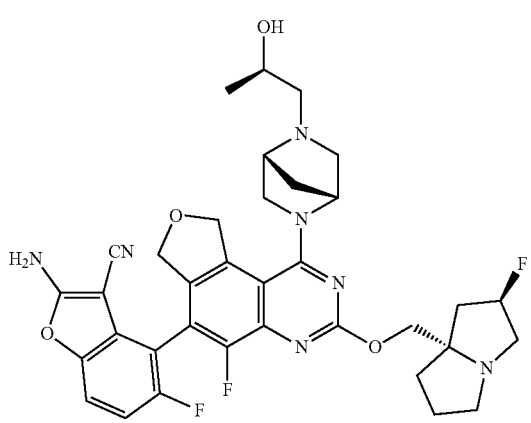 [SMILES: C[C@@H](O)CN1C[C@H]2C[C@@H]1CN2c1nc(OC[C@@]23CCCN2C[C@H](F)C3)nc2c(F)c(-c3c(F)ccc4oc(N)c(C#N)c34)c3c(c12)COC3] |
| 189 | 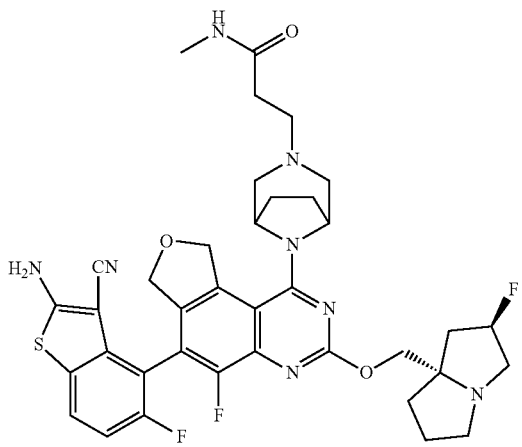 [SMILES: CNC(=O)CCN1CC2CCC(C1)N2c1nc(OC[C@@]23CCCN2C[C@H](F)C3)nc2c(F)c(-c3c(F)ccc4sc(N)c(C#N)c34)c3c(c12)COC3] |

139
TABLE A-continued
Example Compounds
| Ex. # | Compound |
|---|---|
| 190 | 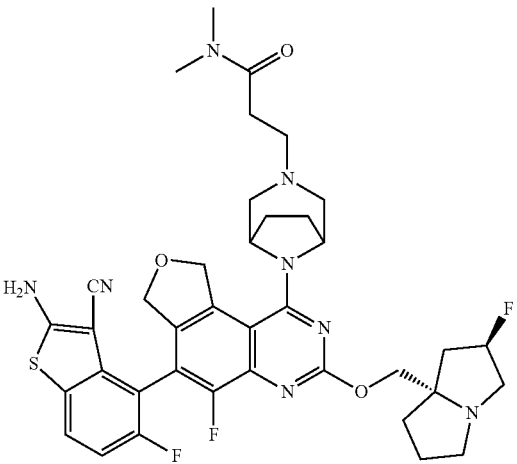 [SMILES: CN(C)C(=O)CCN1CC2CCC(C1)N2c1nc(OC[C@@]23CCCN2C[C@H](F)C3)nc2c(F)c(-c3c(F)ccc4sc(N)c(C#N)c34)c3c(c12)COC3] |
| 191 | 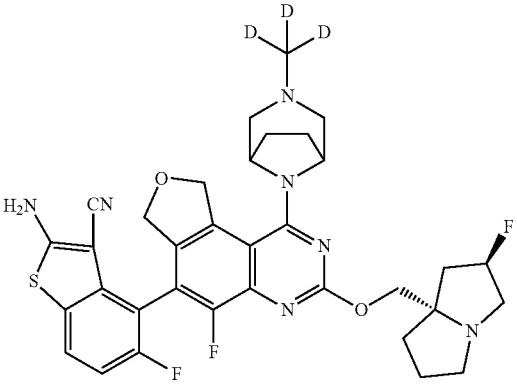 [SMILES: [2H]C([2H])([2H])N1CC2CCC(C1)N2c1nc(OC[C@@]23CCCN2C[C@H](F)C3)nc2c(F)c(-c3c(F)ccc4sc(N)c(C#N)c34)c3c(c12)COC3] |
| 192 | 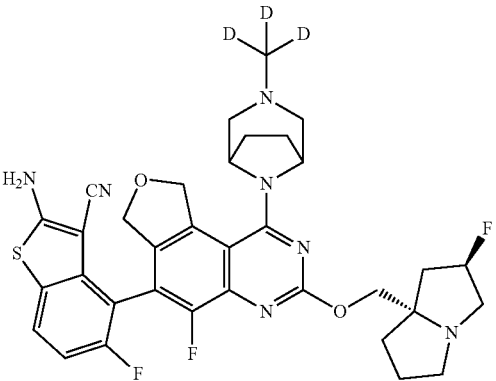 [SMILES: [2H]C([2H])([2H])N1CC2CCC(C1)N2c1nc(OC[C@@]23CCCN2C[C@H](F)C3)nc2c(F)c(-c3c(F)ccc4sc(N)c(C#N)c34)c3c(c12)COC3] |

TABLE A-continued
Example Compounds
| Ex. # | Compound |
|---|---|
| 193 | 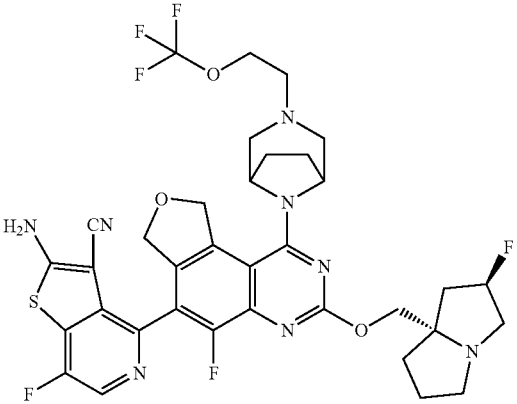 [SMILES: N#Cc1c(N)sc2c(F)cnc(-c3c4c(c5c(N6C7CCC6CN(CCOC(F)(F)F)C7)nc(OC[C@@]67CCCN6C[C@H](F)C7)nc5c3F)COC4)c12] |
| 194 | 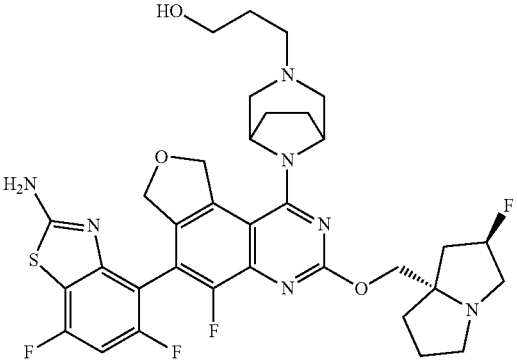 [SMILES: Nc1nc2c(-c3c4c(c5c(N6C7CCC6CN(CCCO)C7)nc(OC[C@@]67CCCN6C[C@H](F)C7)nc5c3F)COC4)c(F)cc(F)c2s1] |
| 195 | 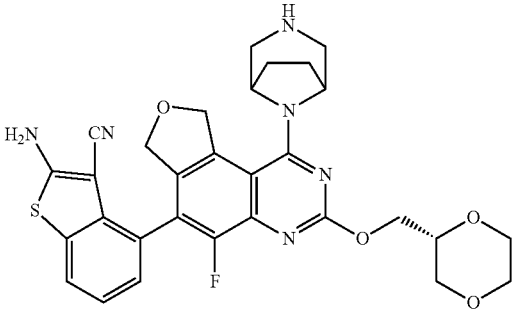 [SMILES: N#Cc1c(N)sc2cccc(-c3c4c(c5c(N6C7CCC6CNC7)nc(OC[C@H]6COCCO6)nc5c3F)COC4)c12] |
| 196 | 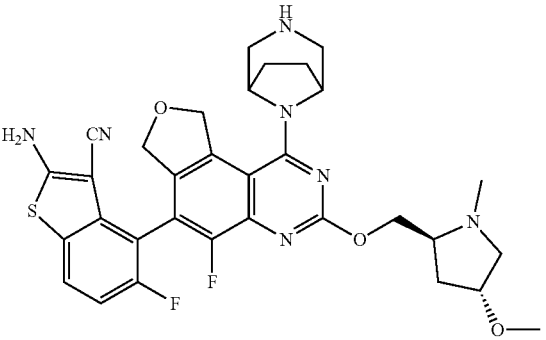 [SMILES: CO[C@@H]1C[C@@H](COc2nc(N3C4CCC3CNC4)c3c4c(c(-c5c(F)ccc6sc(N)c(C#N)c56)c(F)c3n2)COC4)N(C)C1] |

TABLE A-continued
Example Compounds
| Ex. # | Compound |
|---|---|
| 197 | 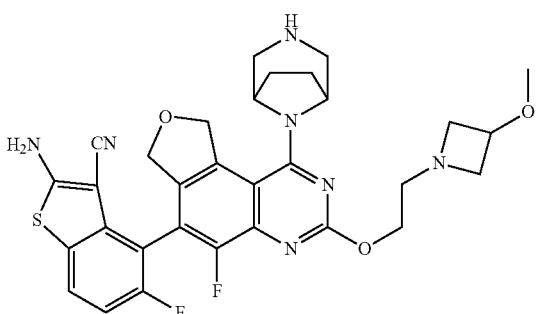 |
| 198 | 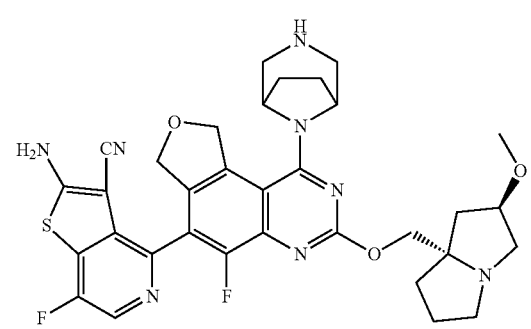 [SMILES: CO[C@H]1CN2CCC[C@@]2(COc2nc(N3C4CCC3CNC4)c3c4c(c(-c5ncc(F)c6sc(N)c(C#N)c56)c(F)c3n2)COC4)C1] |
| 199 | 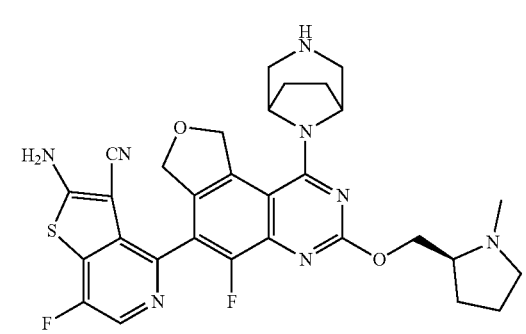 [SMILES: CN1CCC[C@H]1COc1nc(N2C3CCC2CNC3)c2c3c(c(-c4ncc(F)c5sc(N)c(C#N)c45)c(F)c2n1)COC3] |
| 200 | 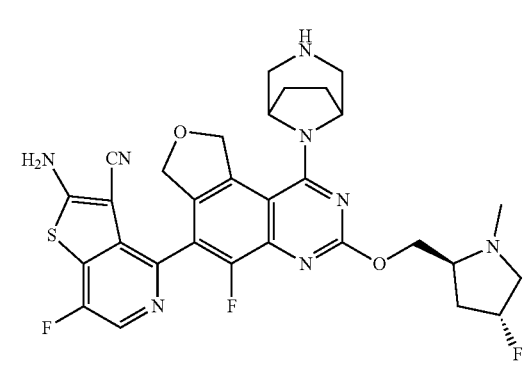 [SMILES: CN1C[C@H](F)C[C@H]1COc1nc(N2C3CCC2CNC3)c2c3c(c(-c4ncc(F)c5sc(N)c(C#N)c45)c(F)c2n1)COC3] |

TABLE A-continued
Example Compounds
| Ex. # | Compound |
|---|---|
| 201 | 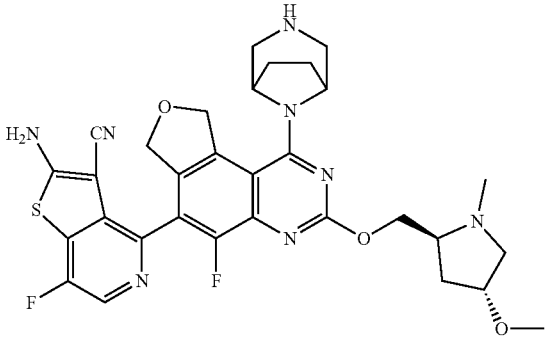 [SMILES: CO[C@@H]1C[C@@H](COc2nc(N3C4CCC3CNC4)c3c4c(c(-c5ncc(F)c6sc(N)c(C#N)c56)c(F)c3n2)COC4)N(C)C1] |
| 202 | 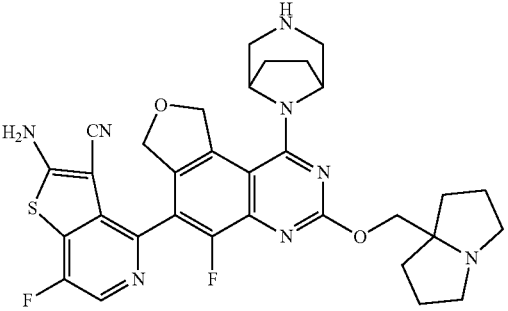 [SMILES: N#Cc1c(N)sc2c(F)cnc(-c3c4c(c5c(N6C7CCC6CNC7)nc(OCC67CCCN6CCC7)nc5c3F)COC4)c12] |
| 203 | 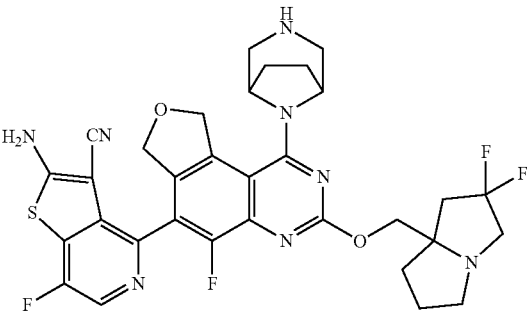 [SMILES: N#Cc1c(N)sc2c(F)cnc(-c3c4c(c5c(N6C7CCC6CNC7)nc(OCC67CCCN6CC(F)(F)C7)nc5c3F)COC4)c12] |
| 204 | 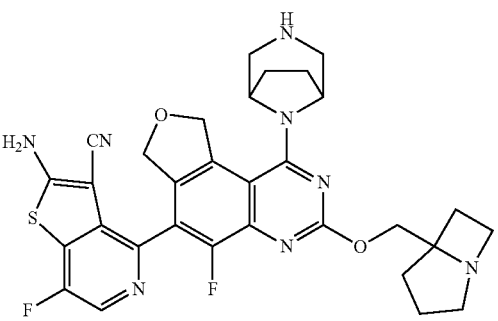 [SMILES: N#Cc1c(N)sc2c(F)cnc(-c3c4c(c5c(N6C7CCC6CNC7)nc(OCC67CCCN6CC7)nc5c3F)COC4)c12] |

TABLE A-continued

Example Compounds

| Ex. # | Compound |
|---|---|
| 205 | |
| 206 | |
| 207 | |
| 208 | |
| 209 | |
| 210 | |

TABLE A-continued

Example Compounds

| Ex. # | Compound |
|---|---|
| 211 | |
| 212 | |
| 213 | |
| 214 | |

TABLE A-continued
Example Compounds
| Ex. # | Compound |
|---|---|
| 215 | 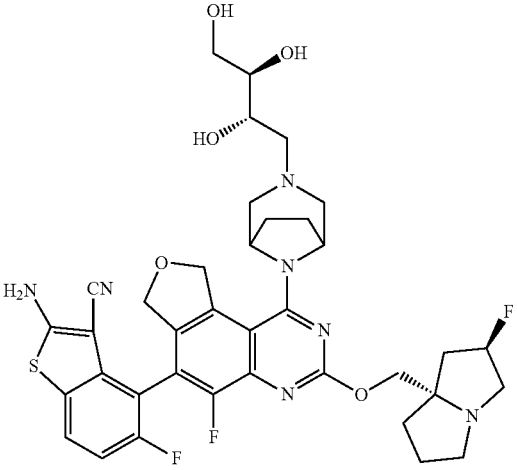 [SMILES: N#Cc1c(N)sc2ccc(F)c(-c3c4c(c5c(N6C7CCC6CN(C[C@H](O)[C@H](O)CO)C7)nc(OC[C@@]67CCCN6C[C@H](F)C7)nc5c3F)COC4)c12] |
| 216 | 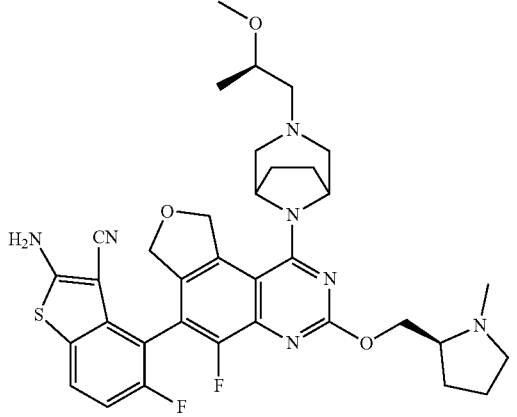 [SMILES: CO[C@H](C)CN1CC2CCC(C1)N2c1nc(OC[C@@H]2CCCN2C)nc2c(F)c(-c3c(F)ccc4sc(N)c(C#N)c34)c3c(c12)COC3] |
| 217 | 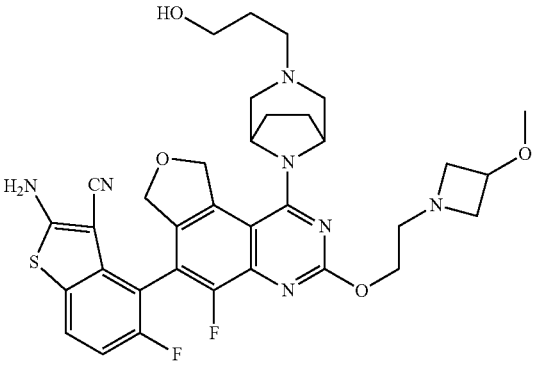 [SMILES: COC1CN(CCOc2nc(N3C4CCC3CN(CCCO)C4)c3c4c(c(-c5c(F)ccc6sc(N)c(C#N)c56)c(F)c3n2)COC4)C1] |

TABLE A-continued
Example Compounds
| Ex. # | Compound |
|---|---|
| 218 | 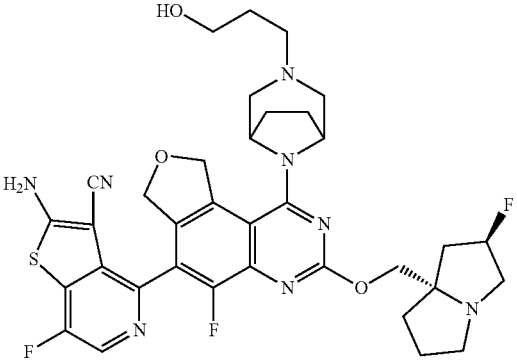 [SMILES: N#Cc1c(N)sc2c(F)cnc(-c3c4c(c5c(N6C7CCC6CN(CCCO)C7)nc(OC[C@@]67CCCN6C[C@H](F)C7)nc5c3F)COC4)c12] |
| 219 | 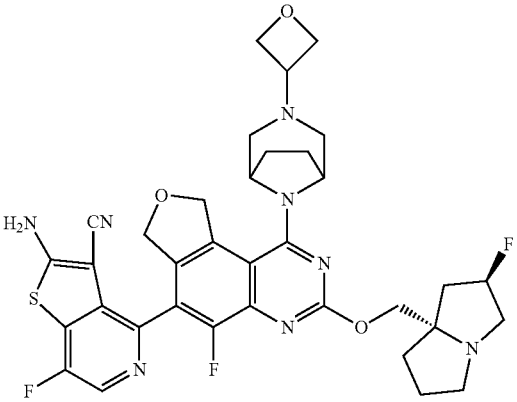 [SMILES: N#Cc1c(N)sc2c(F)cnc(-c3c4c(c5c(N6C7CCC6CN(C6COC6)C7)nc(OC[C@@]67CCCN6C[C@H](F)C7)nc5c3F)COC4)c12] |
| 220 | 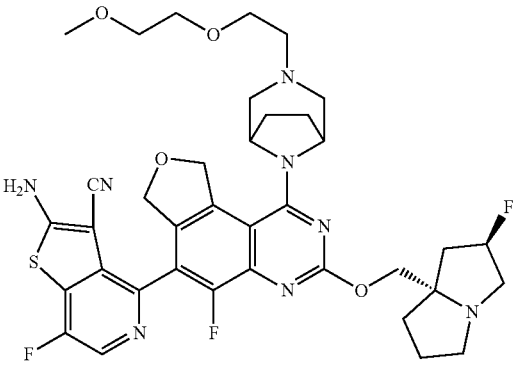 [SMILES: COCCOCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] |

TABLE A-continued
Example Compounds
| Ex. # | Compound |
|---|---|
| 221 | 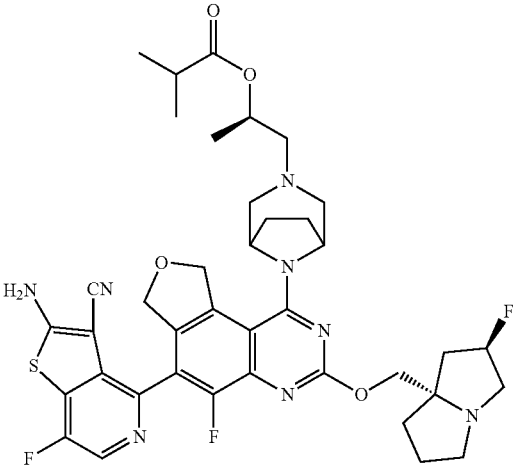 [SMILES: CC(C)C(=O)O[C@H](C)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 222 | 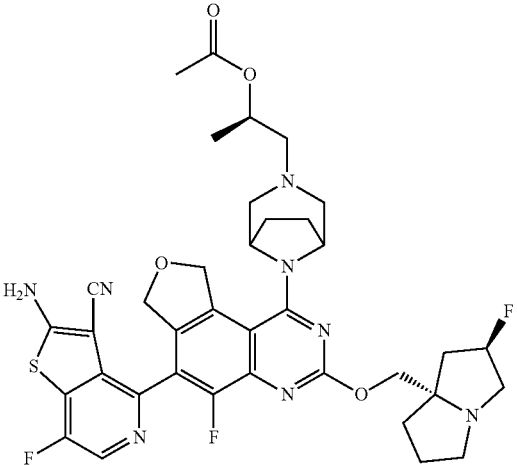 [SMILES: CC(=O)O[C@H](C)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 223 | 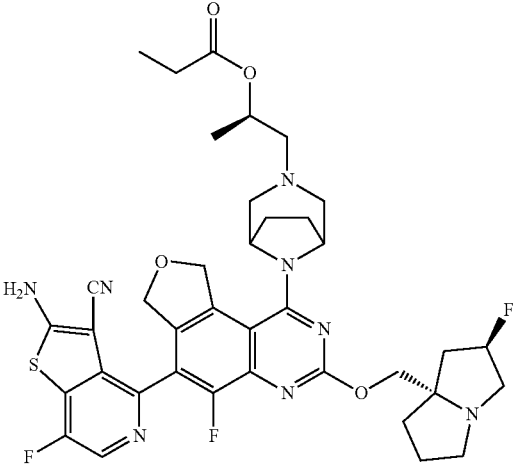 [SMILES: CCC(=O)O[C@H](C)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] |

TABLE A-continued
Example Compounds
| Ex. # | Compound |
|---|---|
| 224 | 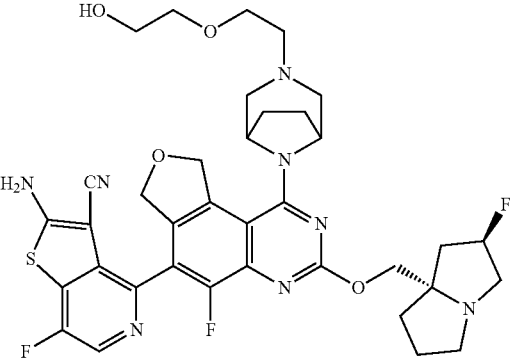 [SMILES: N#Cc1c(N)sc2c(F)cnc(-c3c4c(c5c(N6C7CCC6CN(CCOCCO)C7)nc(OC[C@@]67CCCN6C[C@H](F)C7)nc5c3F)COC4)c12] |
| 225 | 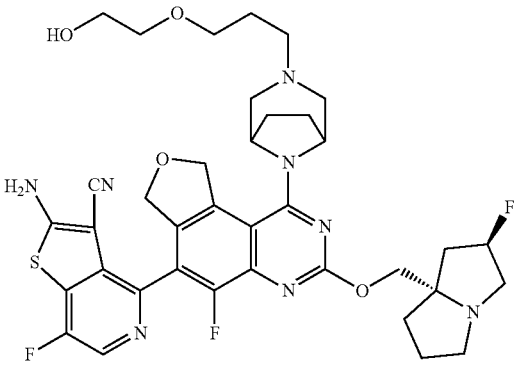 [SMILES: N#Cc1c(N)sc2c(F)cnc(-c3c4c(c5c(N6C7CCC6CN(CCCOCCO)C7)nc(OC[C@@]67CCCN6C[C@H](F)C7)nc5c3F)COC4)c12] |
| 226 | 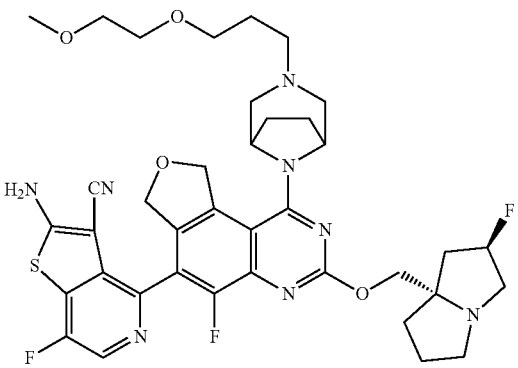 [SMILES: COCCOCCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 227 | 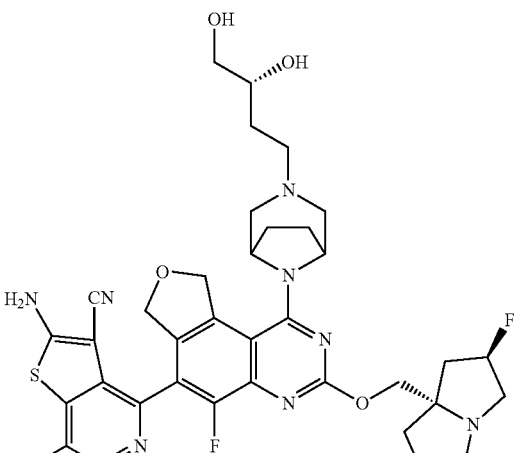 |

US 12,351,591 B2
TABLE A-continued
Example Compounds
| Ex. # | Compound |
|---|---|
| 228 | 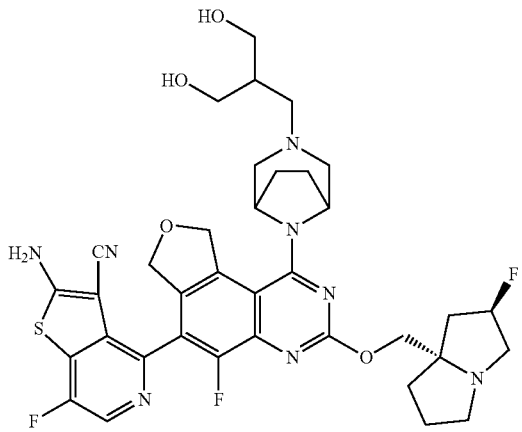 [SMILES: N#Cc1c(N)sc2c(F)cnc(-c3c4c(c5c(N6C7CCC6CN(CC(CO)CO)C7)nc(OC[C@@]67CCCN6C[C@H](F)C7)nc5c3F)COC4)c12] |
| 229 | 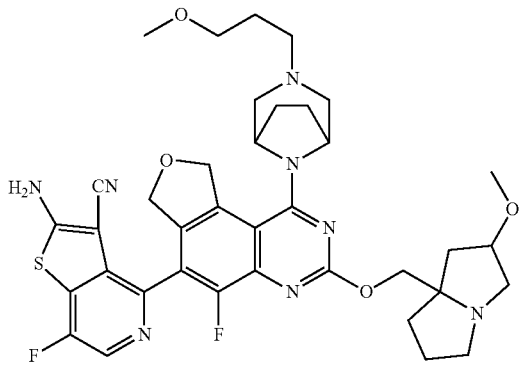 [SMILES: COCCCN1CC2CCC(C1)N2c1nc(OCC23CCCN2CC(OC)C3)nc2c(F)c(-c3ncc(F)c4sc(N)c(C#N)c34)c3c(c12)COC3] |
| 230 | 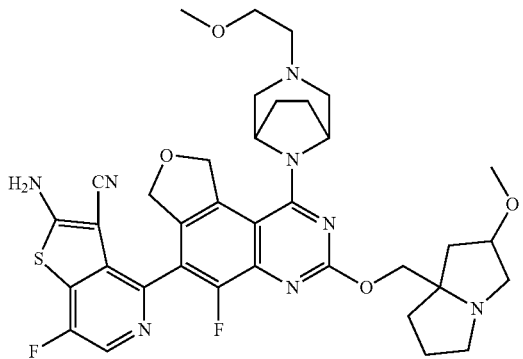 [SMILES: COCCN1CC2CCC(C1)N2c1nc(OCC23CCCN2CC(OC)C3)nc2c(F)c(-c3ncc(F)c4sc(N)c(C#N)c34)c3c(c12)COC3] |

TABLE A-continued
Example Compounds
| Ex. # | Compound |
|---|---|
| 231 | 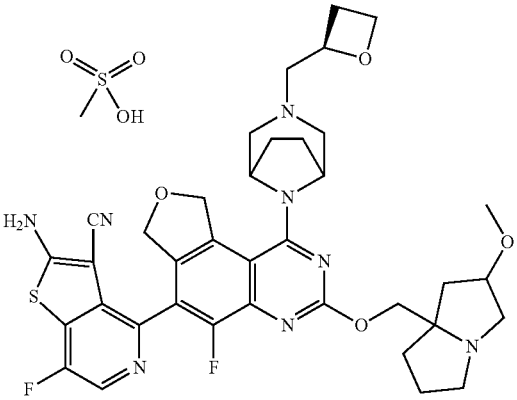 |
| 232 | 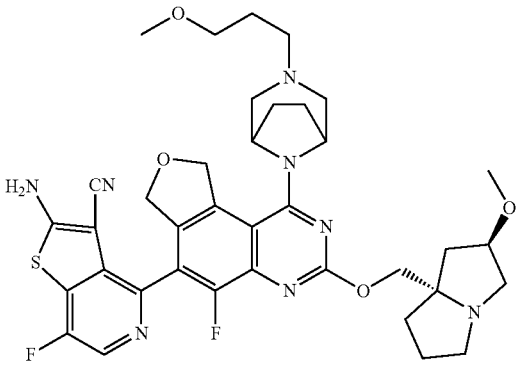 [SMILES: COCCCN1CC2CCC(C1)N2c1nc(OC[C@@]23CCCN2C[C@H](OC)C3)nc2c(F)c(-c3ncc(F)c4sc(N)c(C#N)c34)c3c(c12)COC3] |
| 233 | 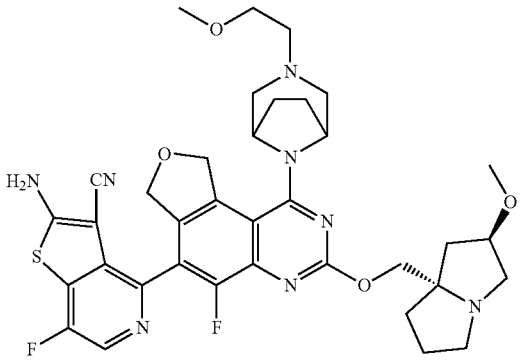 [SMILES: COCCN1CC2CCC(C1)N2c1nc(OC[C@@]23CCCN2C[C@H](OC)C3)nc2c(F)c(-c3ncc(F)c4sc(N)c(C#N)c34)c3c(c12)COC3] |
| 234 | 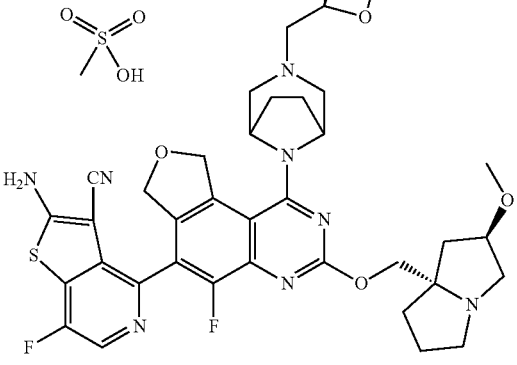 |

TABLE A-continued
Example Compounds
| Ex. # | Compound |
|---|---|
| 235 | 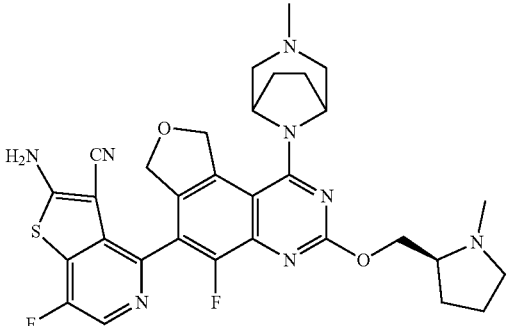 |
| 236 | 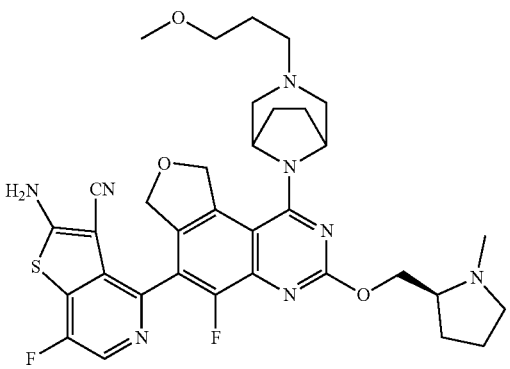 [SMILES: COCCCN1CC2CCC(C1)N2c1nc(OC[C@@H]2CCCN2C)nc2c(F)c(-c3ncc(F)c4sc(N)c(C#N)c34)c3c(c12)COC3] |
| 237 | 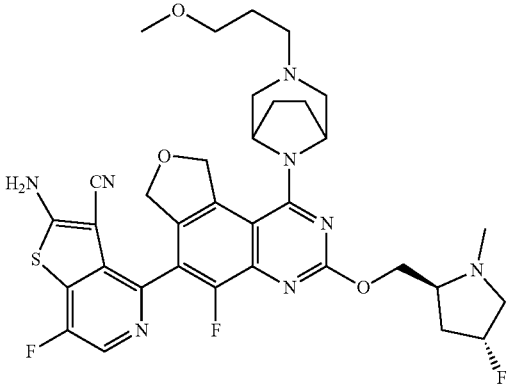 [SMILES: COCCCN1CC2CCC(C1)N2c1nc(OC[C@@H]2C[C@@H](F)CN2C)nc2c(F)c(-c3ncc(F)c4sc(N)c(C#N)c34)c3c(c12)COC3] |
| 238 | 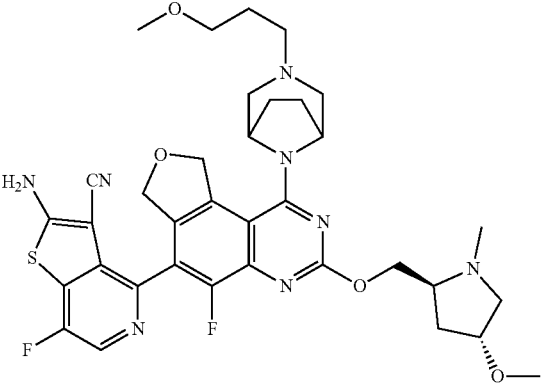 [SMILES: COCCCN1CC2CCC(C1)N2c1nc(OC[C@@H]2C[C@@H](OC)CN2C)nc2c(F)c(-c3ncc(F)c4sc(N)c(C#N)c34)c3c(c12)COC3] |

TABLE A-continued
Example Compounds
| Ex. # | Compound |
|---|---|
| 239 | 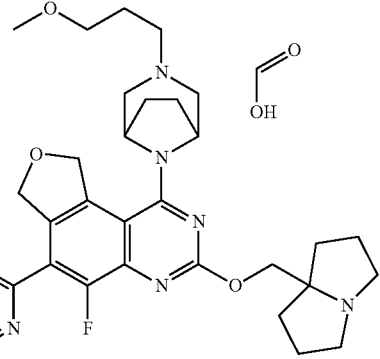 |
| 240 | 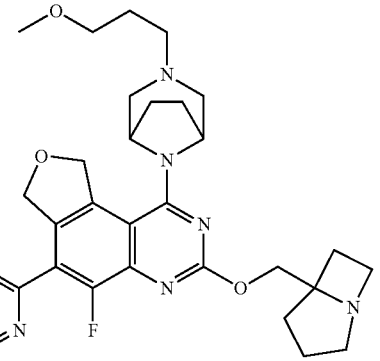 |
| 241 | 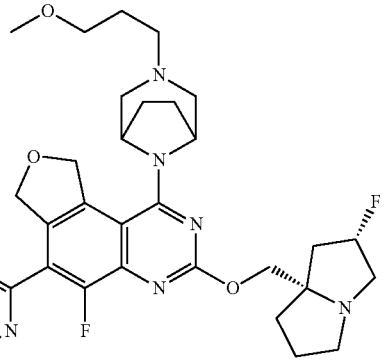 |
| 242 | 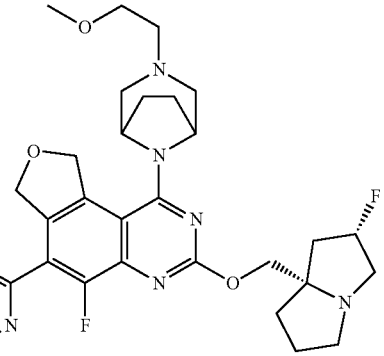 |

TABLE A-continued
Example Compounds
| Ex. # | Compound |
|---|---|
| 243 | 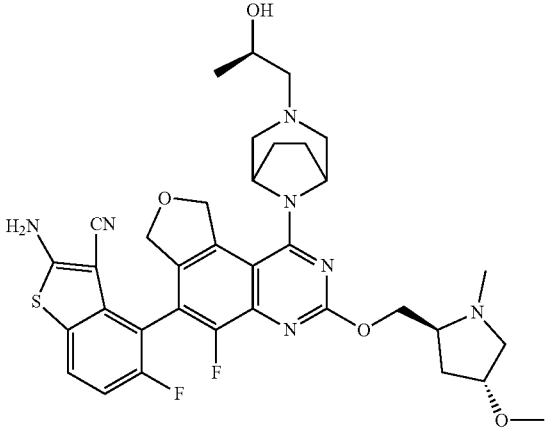 [SMILES: CO[C@@H]1C[C@@H](COc2nc(N3C4CCC3CN(C[C@@H](C)O)C4)c3c4c(c(-c5c(F)ccc6sc(N)c(C#N)c56)c(F)c3n2)COC4)N(C)C1] |
| 244 | 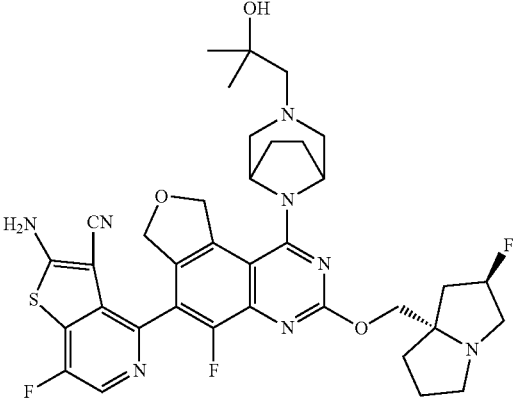 [SMILES: CC(C)(O)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 245 | 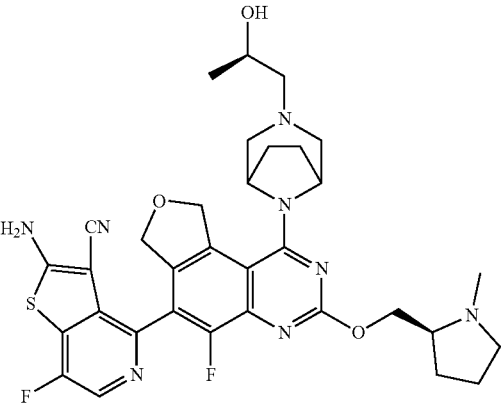 [SMILES: C[C@@H](O)CN1CC2CCC(C1)N2c1nc(OC[C@@H]2CCCN2C)nc2c(F)c(-c3ncc(F)c4sc(N)c(C#N)c34)c3c(c12)COC3] |

TABLE A-continued
Example Compounds
| Ex. # | Compound |
|---|---|
| 246 | 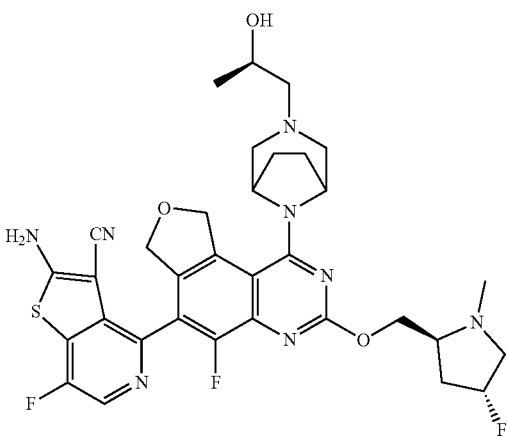 [SMILES: C[C@@H](O)CN1CC2CCC(C1)N2c1nc(OC[C@@H]2C[C@@H](F)CN2C)nc2c(F)c(-c3ncc(F)c4sc(N)c(C#N)c34)c3c(c12)COC3] |
| 247 | 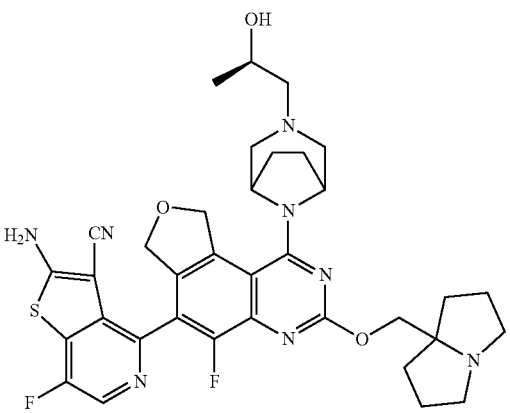 [SMILES: C[C@@H](O)CN1CC2CCC(C1)N2c1nc(OCC23CCCN2CCC3)nc2c(F)c(-c3ncc(F)c4sc(N)c(C#N)c34)c3c(c12)COC3] |
| 248 | 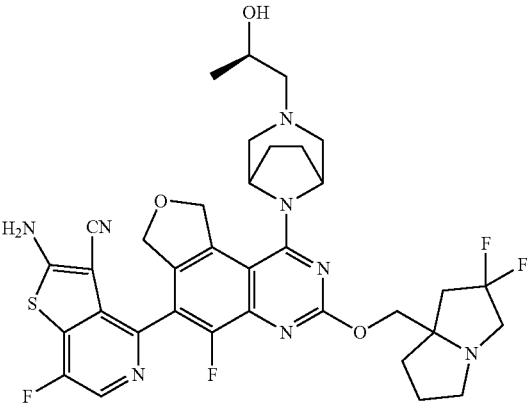 [SMILES: C[C@@H](O)CN1CC2CCC(C1)N2c1nc(OCC23CCCN2CC(F)(F)C3)nc2c(F)c(-c3ncc(F)c4sc(N)c(C#N)c34)c3c(c12)COC3] |

TABLE A-continued
Example Compounds
| Ex. # | Compound |
|---|---|
| 249 | 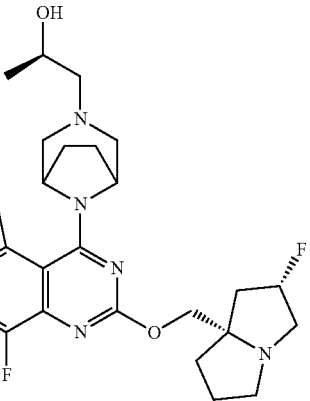 |
| 250 | 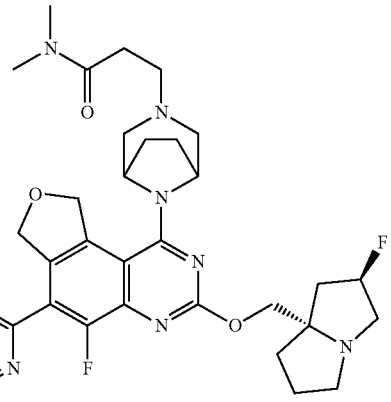 |
| 251 | 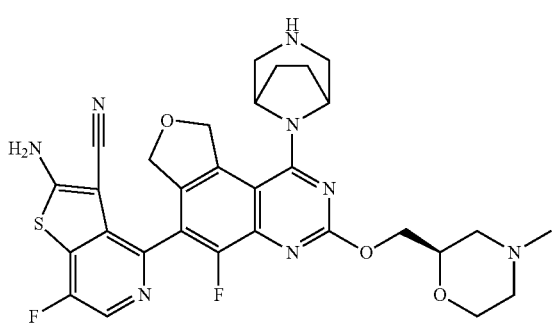 |
| 252 | 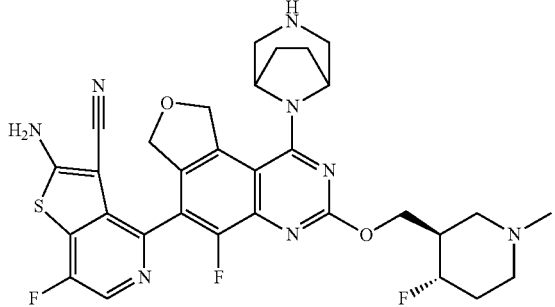 [SMILES: CN1CC[C@H](F)[C@@H](COc2nc(N3C4CCC3CNC4)c3c4c(c(-c5ncc(F)c6sc(N)c(C#N)c56)c(F)c3n2)COC4)C1] |

173 174
TABLE A-continued
Example Compounds
| Ex. # | Compound |
|---|---|
| 253 | 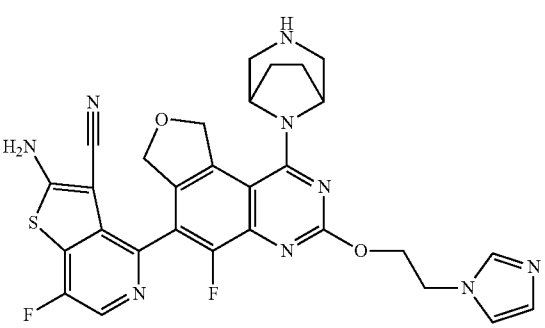 [SMILES: N#Cc1c(N)sc2c(F)cnc(-c3c4c(c5c(N6C7CCC6CNC7)nc(OCCn6ccnc6)nc5c3F)COC4)c12] |
| 254 | 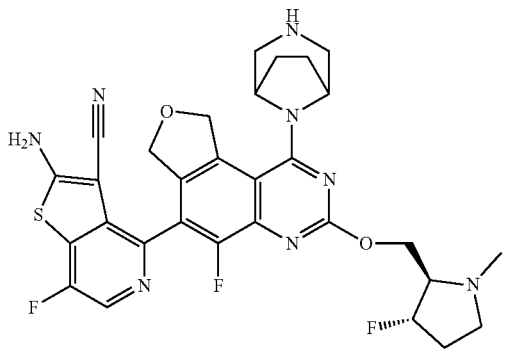 [SMILES: CN1CC[C@H](F)[C@H]1COc1nc(N2C3CCC2CNC3)c2c3c(c(-c4ncc(F)c5sc(N)c(C#N)c45)c(F)c2n1)COC3] |
| 255 | 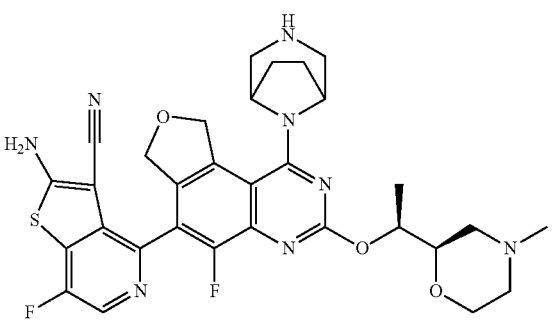 [SMILES: C[C@H](Oc1nc(N2C3CCC2CNC3)c2c3c(c(-c4ncc(F)c5sc(N)c(C#N)c45)c(F)c2n1)COC3)[C@H]1CN(C)CCO1] |
| 256 | 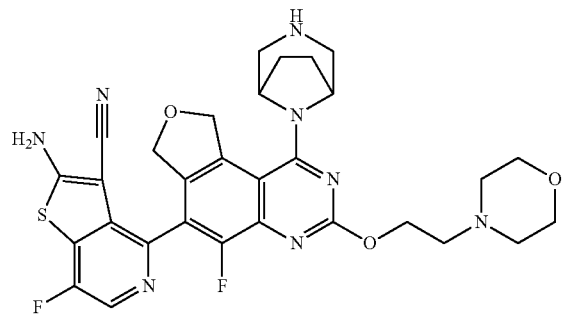 [SMILES: N#Cc1c(N)sc2c(F)cnc(-c3c4c(c5c(N6C7CCC6CNC7)nc(OCCN6CCOCC6)nc5c3F)COC4)c12] |

175 176
TABLE A-continued
Example Compounds
| Ex. # | Compound |
|---|---|
| 257 | 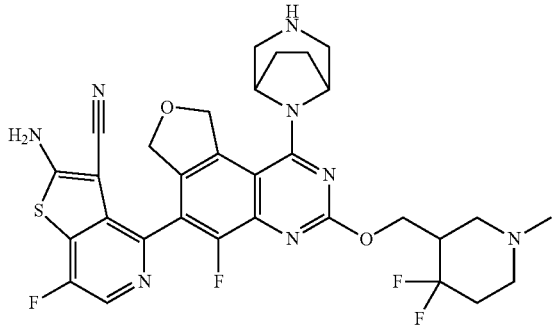 [SMILES: CN1CCC(F)(F)C(COc2nc(N3C4CCC3CNC4)c3c4c(c(-c5ncc(F)c6sc(N)c(C#N)c56)c(F)c3n2)COC4)C1] |
| 258 | 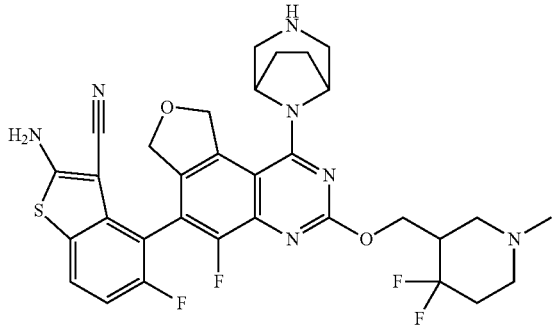 |
| 259 | 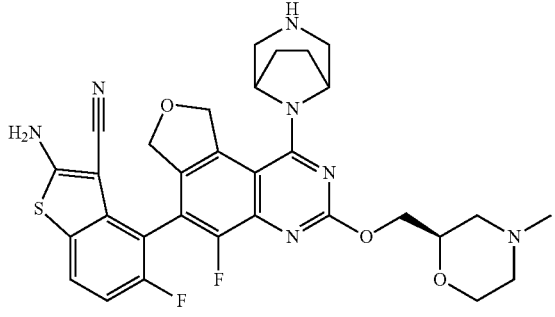 [SMILES: CN1CCO[C@@H](COc2nc(N3C4CCC3CNC4)c3c4c(c(-c5c(F)ccc6sc(N)c(C#N)c56)c(F)c3n2)COC4)C1] |
| 260 | 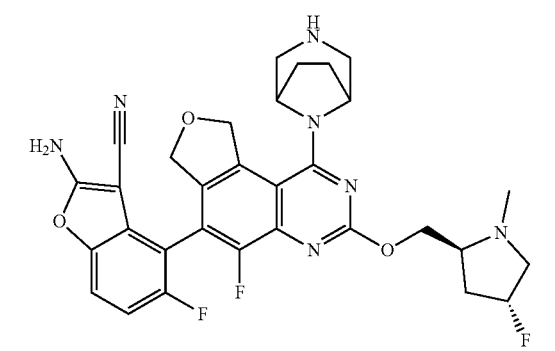 [SMILES: CN1C[C@H](F)C[C@H]1COc1nc(N2C3CCC2CNC3)c2c3c(c(-c4c(F)ccc5oc(N)c(C#N)c45)c(F)c2n1)COC3] |

TABLE A-continued
Example Compounds
| Ex. # | Compound |
|---|---|
| 261 | 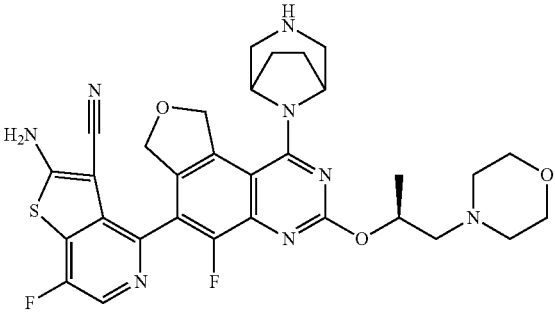 [SMILES: C[C@@H](CN1CCOCC1)Oc1nc(N2C3CCC2CNC3)c2c3c(c(-c4ncc(F)c5sc(N)c(C#N)c45)c(F)c2n1)COC3] |
| 262 | 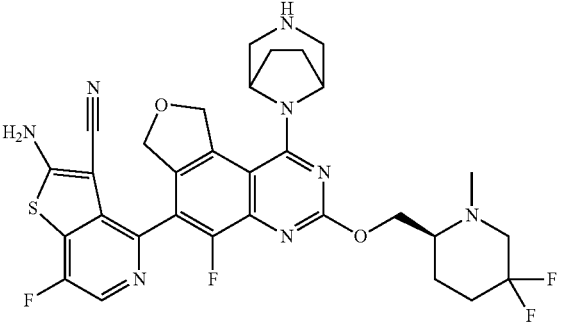 [SMILES: CN1CC(F)(F)CC[C@H]1COc1nc(N2C3CCC2CNC3)c2c3c(c(-c4ncc(F)c5sc(N)c(C#N)c45)c(F)c2n1)COC3] |
| 263 | 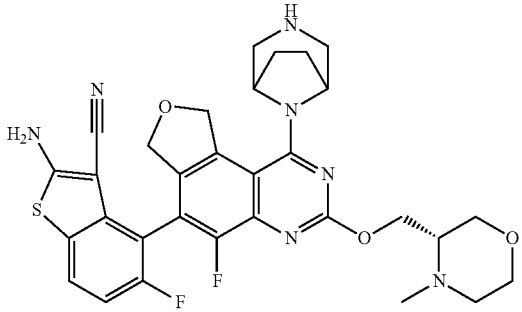 [SMILES: CN1CCOC[C@H]1COc1nc(N2C3CCC2CNC3)c2c3c(c(-c4c(F)ccc5sc(N)c(C#N)c45)c(F)c2n1)COC3] |
| 264 | 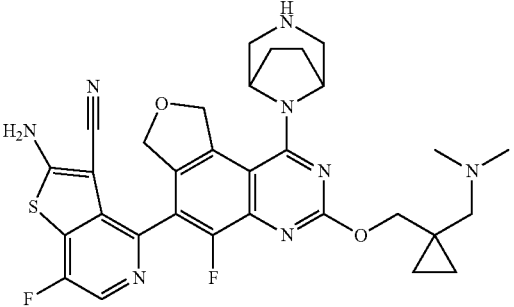 [SMILES: CN(C)CC1(COc2nc(N3C4CCC3CNC4)c3c4c(c(-c5ncc(F)c6sc(N)c(C#N)c56)c(F)c3n2)COC4)CC1] |

TABLE A-continued

Example Compounds

| Ex. # | Compound |
|---|---|
| 265 | |
| 266 | |
| 267 | |
| 268 | |

TABLE A-continued
Example Compounds
| Ex. # | Compound |
|---|---|
| 269 | 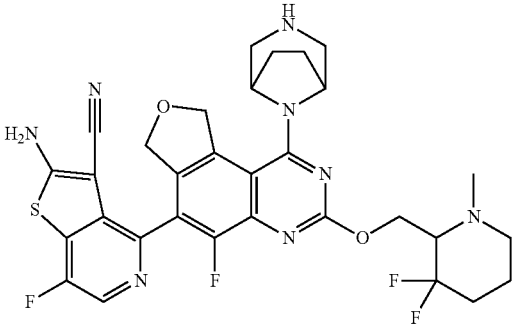 [SMILES: CN1CCCC(F)(F)C1COc1nc(N2C3CCC2CNC3)c2c3c(c(-c4ncc(F)c5sc(N)c(C#N)c45)c(F)c2n1)COC3] |
| 270 | 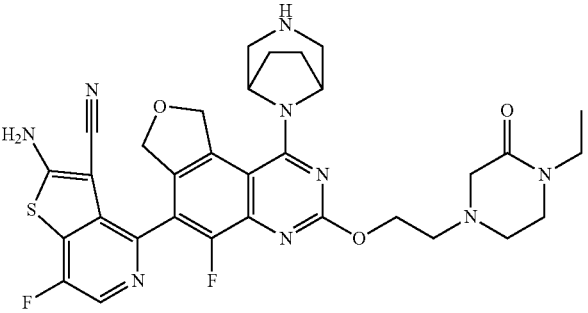 [SMILES: CCN1CCN(CCOc2nc(N3C4CCC3CNC4)c3c4c(c(-c5ncc(F)c6sc(N)c(C#N)c56)c(F)c3n2)COC4)CC1=O] |
| 271 | 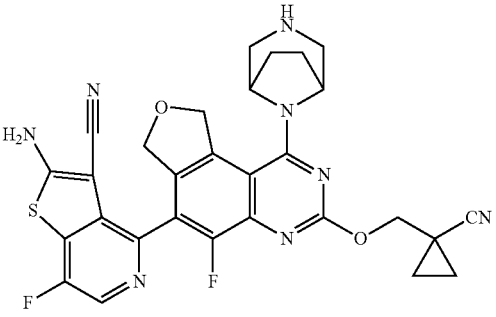 [SMILES: N#Cc1c(N)sc2c(F)cnc(-c3c4c(c5c(N6C7CCC6CNC7)nc(OCC6(C#N)CC6)nc5c3F)COC4)c12] |
| 272 | 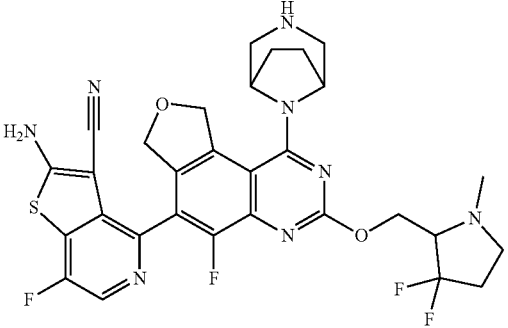 [SMILES: CN1CCC(F)(F)C1COc1nc(N2C3CCC2CNC3)c2c3c(c(-c4ncc(F)c5sc(N)c(C#N)c45)c(F)c2n1)COC3] |

TABLE A-continued
Example Compounds
| Ex. # | Compound |
|---|---|
| 273 | 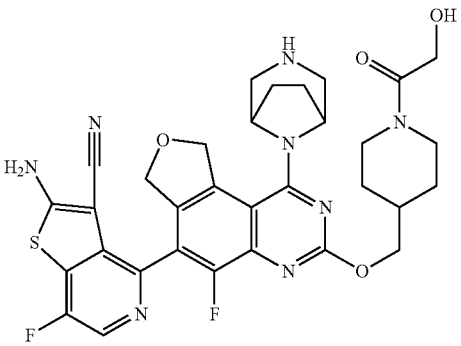 [SMILES: N#Cc1c(N)sc2c(F)cnc(-c3c4c(c5c(N6C7CCC6CNC7)nc(OCC6CCN(C(=O)CO)CC6)nc5c3F)COC4)c12] |
| 274 | 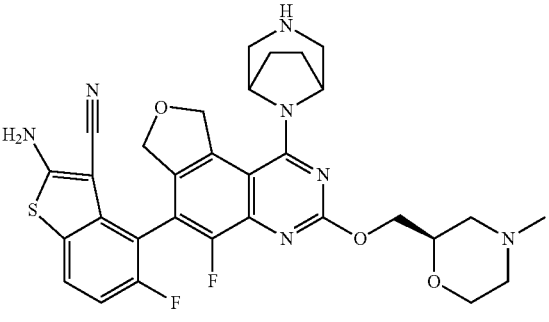 [SMILES: CN1CCO[C@@H](COc2nc(N3C4CCC3CNC4)c3c4c(c(-c5c(F)ccc6sc(N)c(C#N)c56)c(F)c3n2)COC4)C1] |
| 275 | 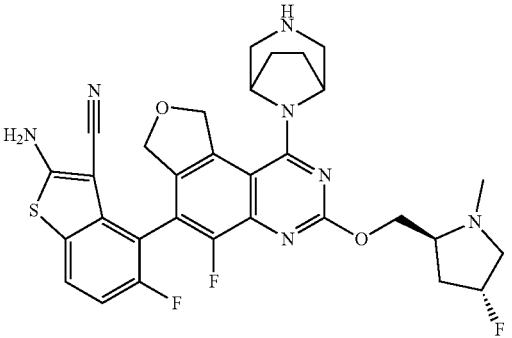 [SMILES: CN1C[C@H](F)C[C@H]1COc1nc(N2C3CCC2CNC3)c2c3c(c(-c4c(F)ccc5sc(N)c(C#N)c45)c(F)c2n1)COC3] |
| 276 | 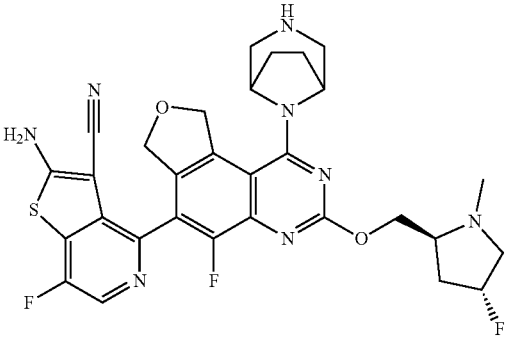 [SMILES: CN1C[C@H](F)C[C@H]1COc1nc(N2C3CCC2CNC3)c2c3c(c(-c4ncc(F)c5sc(N)c(C#N)c45)c(F)c2n1)COC3] |

TABLE A-continued

Example Compounds

| Ex. # | Compound |
|---|---|
| 277 | |
| 278 | |
| 279 | |
| 280 | |
| 281 | |

TABLE A-continued

Example Compounds

| Ex. # | Compound |
|---|---|
| 282 | |
| 283 | |
| 284 | |
| 285 | |
| 286 | |

TABLE A-continued

Example Compounds

| Ex. # | Compound |
|---|---|
| 287 | |
| 288 | |
| 289 | |
| 290 | |
| 291 | |
| 292 | |

TABLE A-continued

Example Compounds

| Ex. # | Compound |
|---|---|
| 293 | |
| 294 | |
| 295 | |
| 296 | |
| 297 | |
| 298 | |

TABLE A-continued
Example Compounds
| Ex. # | Compound |
|---|---|
| 299 | 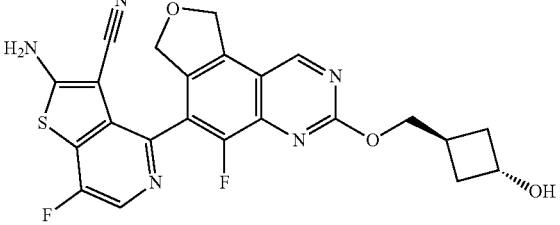 |
| 300 | 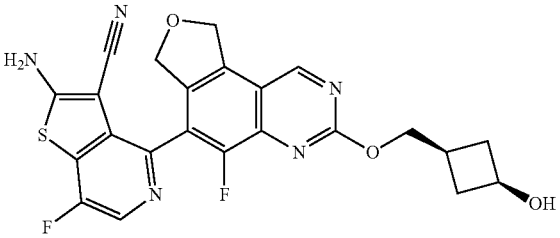 [SMILES: N#Cc1c(N)sc2c(F)cnc(-c3c4c(c5cnc(OC[C@H]6C[C@@H](O)C6)nc5c3F)COC4)c12] |
| 301 | 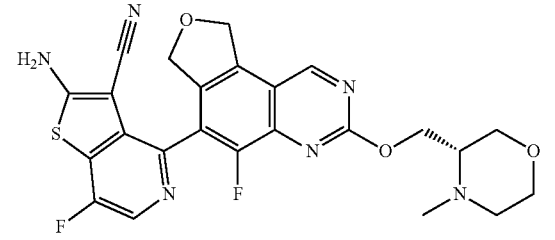 [SMILES: CN1CCOC[C@H]1COc1ncc2c3c(c(-c4ncc(F)c5sc(N)c(C#N)c45)c(F)c2n1)COC3] |
| 302 | 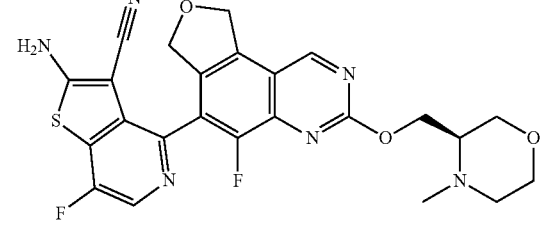 |
| 303 | 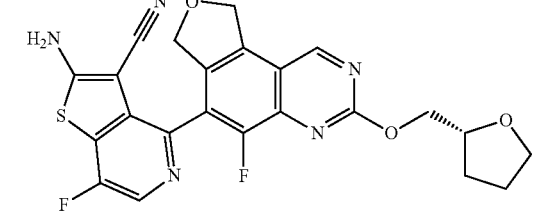 |
| 304 | 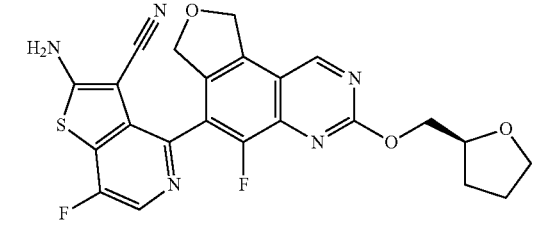 [SMILES: N#Cc1c(N)sc2c(F)cnc(-c3c4c(c5cnc(OC[C@@H]6CCCO6)nc5c3F)COC4)c12] |

TABLE A-continued

Example Compounds

| Ex. # | Compound |
|---|---|
| 305 | |
| 306 | |
| 307 | |
| 308 | |
| 309 | |
| 310 | |

TABLE A-continued
Example Compounds
| Ex. # | Compound |
|---|---|
| 311 | 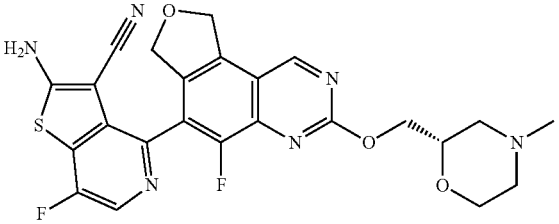 [SMILES: CN1CCO[C@H](COc2ncc3c4c(c(-c5ncc(F)c6sc(N)c(C#N)c56)c(F)c3n2)COC4)C1] |
| 312 | 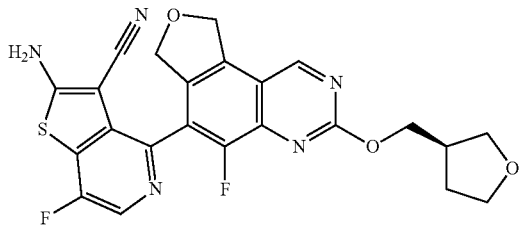 [SMILES: N#Cc1c(N)sc2c(F)cnc(-c3c4c(c5cnc(OC[C@@H]6CCOC6)nc5c3F)COC4)c12] |
| 313 | 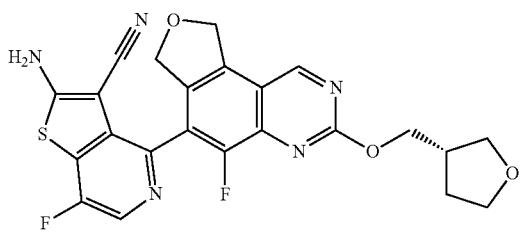 [SMILES: N#Cc1c(N)sc2c(F)cnc(-c3c4c(c5cnc(OC[C@H]6CCOC6)nc5c3F)COC4)c12] |
| 314 | 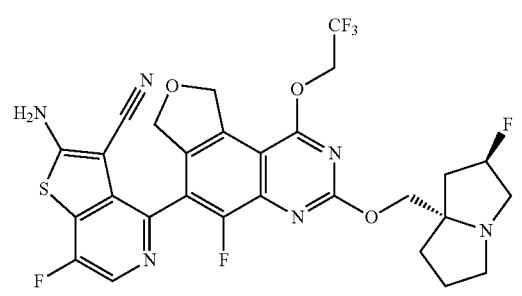 [SMILES: N#Cc1c(N)sc2c(F)cnc(-c3c4c(c5c(OCC(F)(F)F)nc(OC[C@@]67CCCN6C[C@H](F)C7)nc5c3F)COC4)c12] |
| 315 | 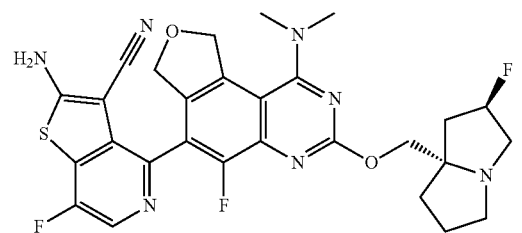 [SMILES: CN(C)c1nc(OC[C@@]23CCCN2C[C@H](F)C3)nc2c(F)c(-c3ncc(F)c4sc(N)c(C#N)c34)c3c(c12)COC3] |
| 316 | 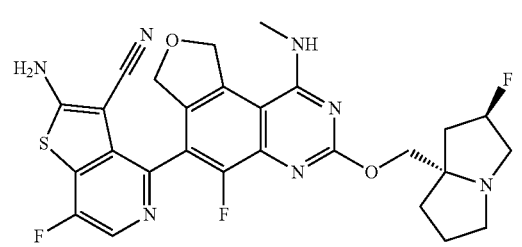 [SMILES: CNc1nc(OC[C@@]23CCCN2C[C@H](F)C3)nc2c(F)c(-c3ncc(F)c4sc(N)c(C#N)c34)c3c(c12)COC3] |

TABLE A-continued
Example Compounds
| Ex. # | Compound |
|---|---|
| 317 | 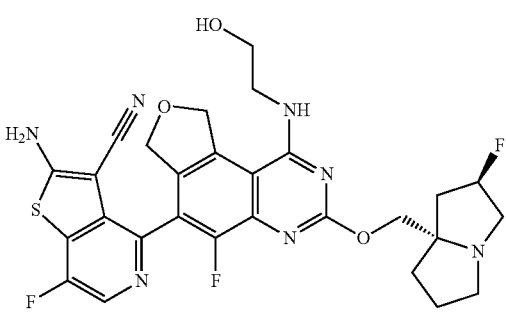 [SMILES: N#Cc1c(N)sc2c(F)cnc(-c3c4c(c5c(NCCO)nc(OC[C@@]67CCCN6C[C@H](F)C7)nc5c3F)COC4)c12] |
| 318 | 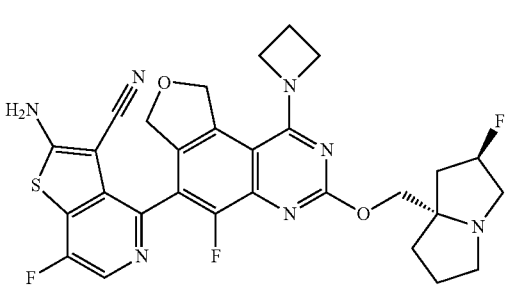 [SMILES: N#Cc1c(N)sc2c(F)cnc(-c3c4c(c5c(N6CCC6)nc(OC[C@@]67CCCN6C[C@H](F)C7)nc5c3F)COC4)c12] |
| 319 | 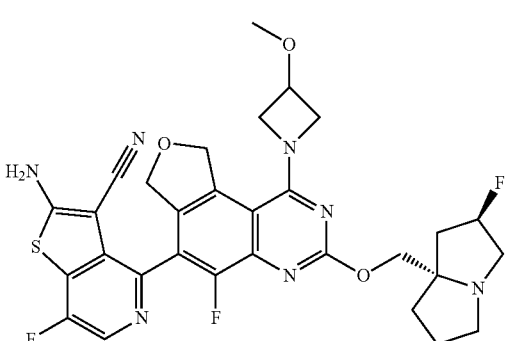 |
| 320 | 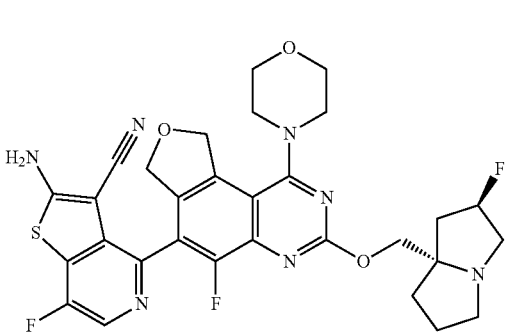 [SMILES: N#Cc1c(N)sc2c(F)cnc(-c3c4c(c5c(N6CCOCC6)nc(OC[C@@]67CCCN6C[C@H](F)C7)nc5c3F)COC4)c12] |

TABLE A-continued
Example Compounds
| Ex. # | Compound |
|---|---|
| 321 | 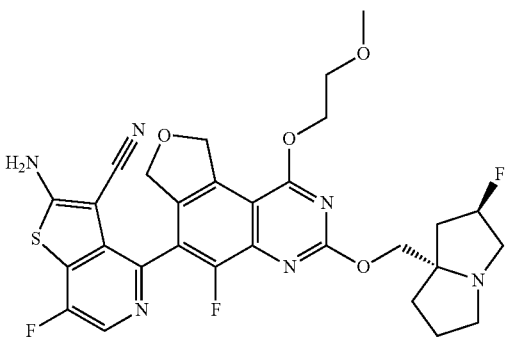 [SMILES: COCCOc1nc(OC[C@@]23CCCN2C[C@H](F)C3)nc2c(F)c(-c3ncc(F)c4sc(N)c(C#N)c34)c3c(c12)COC3] |
| 322 | 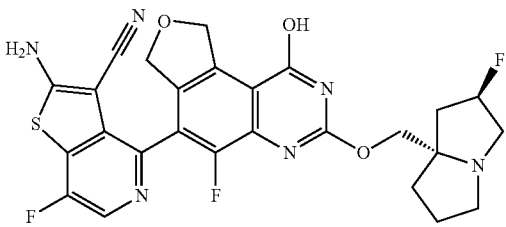 [SMILES: N#Cc1c(N)sc2c(F)cnc(-c3c4c(c5c(O)nc(OC[C@@]67CCCN6C[C@H](F)C7)nc5c3F)COC4)c12] |
| 323 | 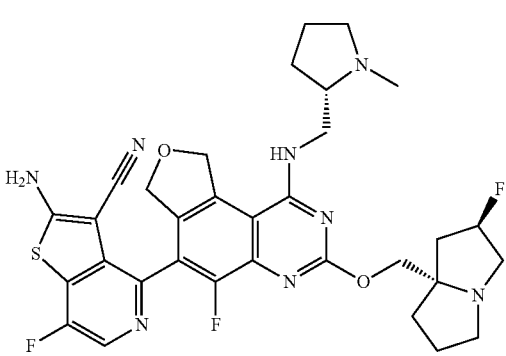 [SMILES: CN1CCC[C@H]1CNc1nc(OC[C@@]23CCCN2C[C@H](F)C3)nc2c(F)c(-c3ncc(F)c4sc(N)c(C#N)c34)c3c(c12)COC3] |
| 324 | 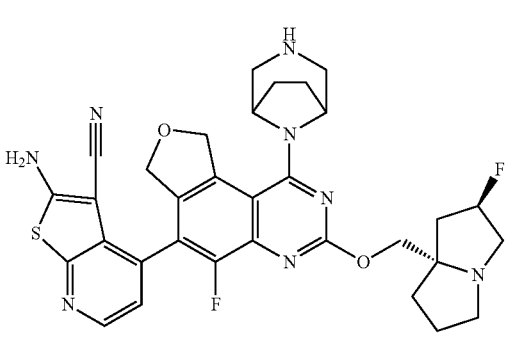 [SMILES: N#Cc1c(N)sc2nccc(-c3c4c(c5c(N6C7CCC6CNC7)nc(OC[C@@]67CCCN6C[C@H](F)C7)nc5c3F)COC4)c12] |

TABLE A-continued
Example Compounds
| Ex. # | Compound |
|---|---|
| 325 | 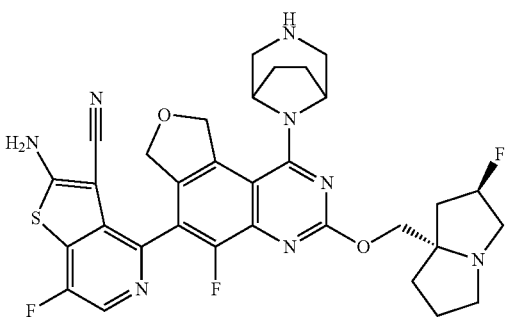 [SMILES: N#Cc1c(N)sc2c(F)cnc(-c3c4c(c5c(N6C7CCC6CNC7)nc(OC[C@@]67CCCN6C[C@H](F)C7)nc5c3F)COC4)c12] |
| 326 | 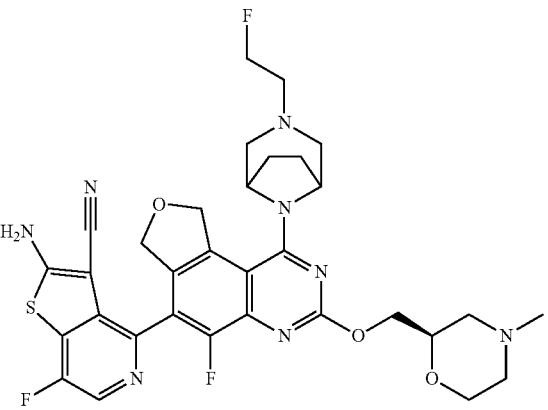 [SMILES: CN1CCO[C@@H](COc2nc(N3C4CCC3CN(CCF)C4)c3c4c(c(-c5ncc(F)c6sc(N)c(C#N)c56)c(F)c3n2)COC4)C1] |
| 327 | 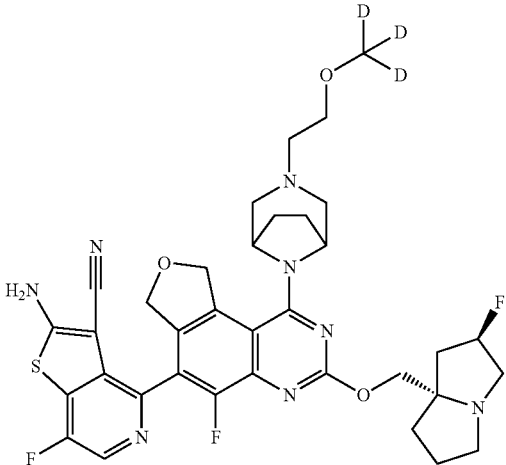 [SMILES: [2H]C([2H])([2H])OCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] |

TABLE A-continued
Example Compounds
| Ex. # | Compound |
|---|---|
| 328 | 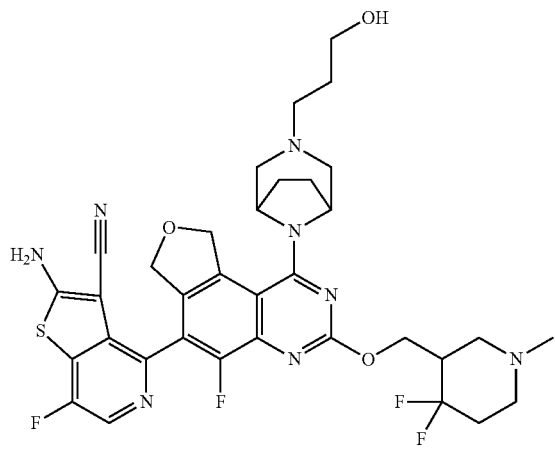 [SMILES: CN1CCC(F)(F)C(COc2nc(N3C4CCC3CN(CCCO)C4)c3c4c(c(-c5ncc(F)c6sc(N)c(C#N)c56)c(F)c3n2)COC4)C1] |
| 329 | 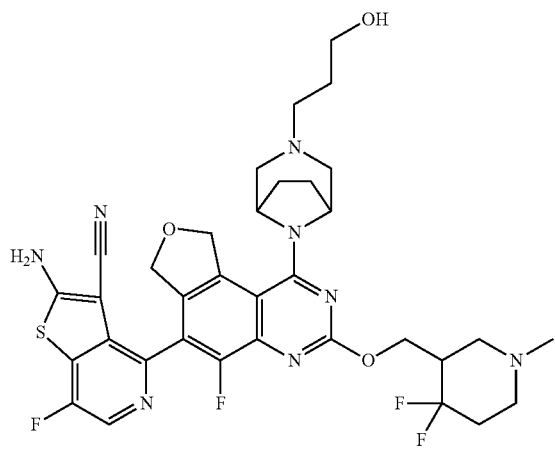 [SMILES: CN1CCC(F)(F)C(COc2nc(N3C4CCC3CN(CCCO)C4)c3c4c(c(-c5ncc(F)c6sc(N)c(C#N)c56)c(F)c3n2)COC4)C1] |
| 330 | 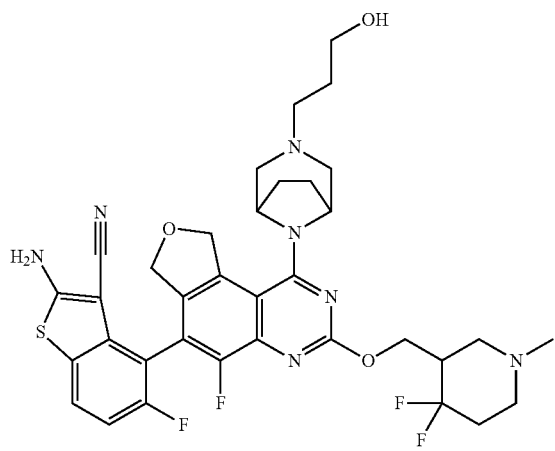 [SMILES: CN1CCC(F)(F)C(COc2nc(N3C4CCC3CN(CCCO)C4)c3c4c(c(-c5c(F)ccc6sc(N)c(C#N)c56)c(F)c3n2)COC4)C1] |

TABLE A-continued
Example Compounds
| Ex. # | Compound |
|---|---|
| 331 | 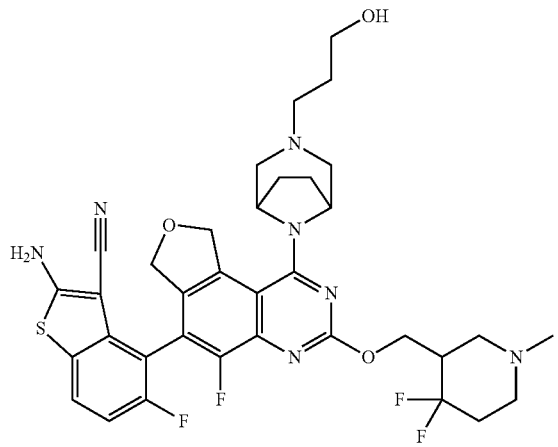 [SMILES: CN1CCC(F)(F)C(COc2nc(N3C4CCC3CN(CCCO)C4)c3c4c(c(-c5c(F)ccc6sc(N)c(C#N)c56)c(F)c3n2)COC4)C1] |
| 332 | 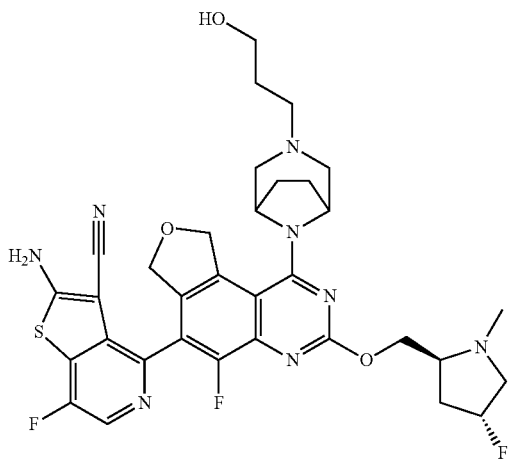 [SMILES: CN1C[C@H](F)C[C@H]1COc1nc(N2C3CCC2CN(CCCO)C3)c2c3c(c(-c4ncc(F)c5sc(N)c(C#N)c45)c(F)c2n1)COC3] |
| 333 | 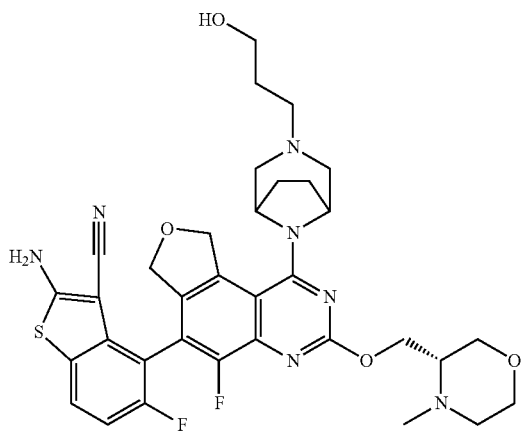 [SMILES: CN1CCOC[C@H]1COc1nc(N2C3CCC2CN(CCCO)C3)c2c3c(c(-c4c(F)ccc5sc(N)c(C#N)c45)c(F)c2n1)COC3] |

TABLE A-continued
Example Compounds
| Ex. # | Compound |
|---|---|
| 334 | 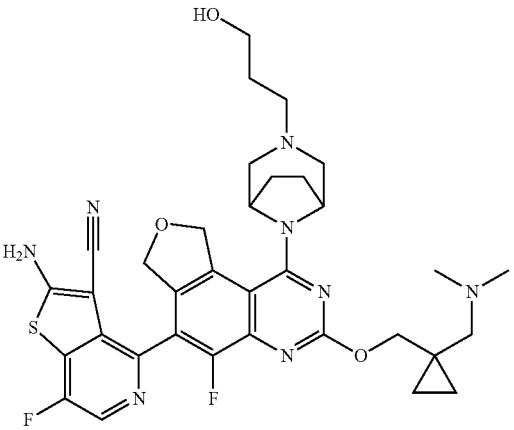 [SMILES: CN(C)CC1(COc2nc(N3C4CCC3CN(CCCO)C4)c3c4c(c(-c5ncc(F)c6sc(N)c(C#N)c56)c(F)c3n2)COC4)CC1] |
| 335 | 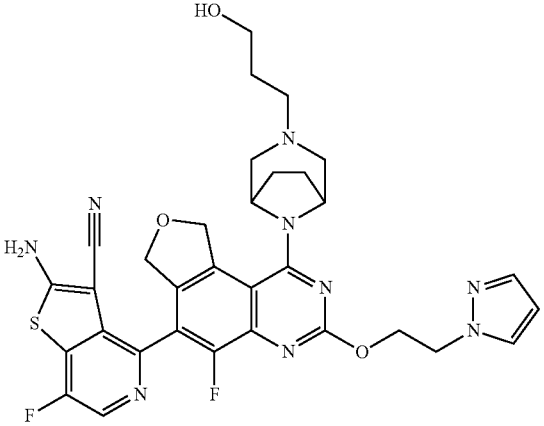 [SMILES: N#Cc1c(N)sc2c(F)cnc(-c3c4c(c5c(N6C7CCC6CN(CCCO)C7)nc(OCCn6cccn6)nc5c3F)COC4)c12] |
| 336 | 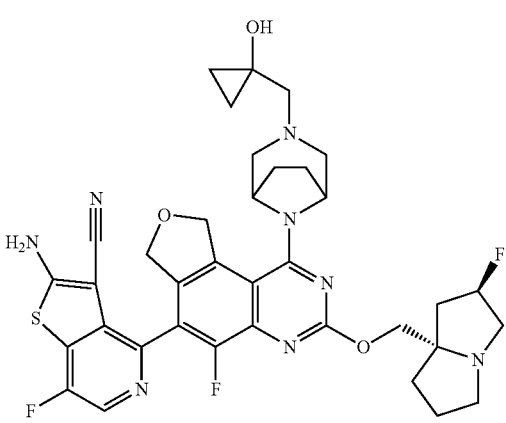 [SMILES: N#Cc1c(N)sc2c(F)cnc(-c3c4c(c5c(N6C7CCC6CN(CC6(O)CC6)C7)nc(OC[C@@]67CCCN6C[C@H](F)C7)nc5c3F)COC4)c12] |

TABLE A-continued
Example Compounds
| Ex. # | Compound |
|---|---|
| 337 | 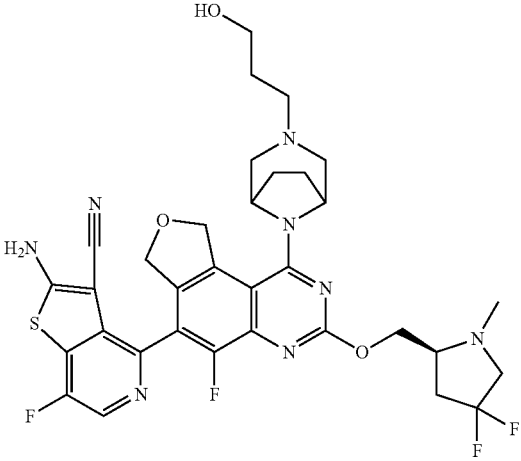 [SMILES: CN1CC(F)(F)C[C@H]1COc1nc(N2C3CCC2CN(CCCO)C3)c2c3c(c(-c4ncc(F)c5sc(N)c(C#N)c45)c(F)c2n1)COC3] |
| 338 | 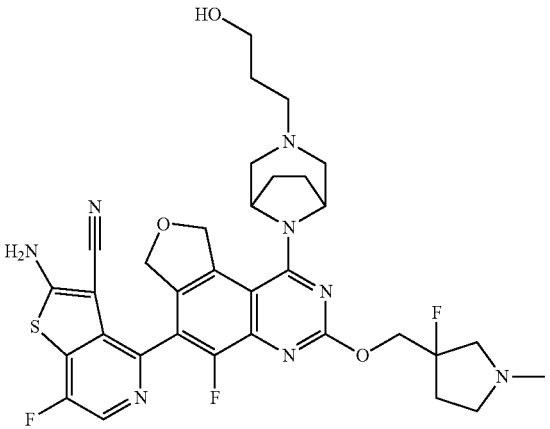 [SMILES: CN1CCC(F)(COc2nc(N3C4CCC3CN(CCCO)C4)c3c4c(c(-c5ncc(F)c6sc(N)c(C#N)c56)c(F)c3n2)COC4)C1] |
| 339 | 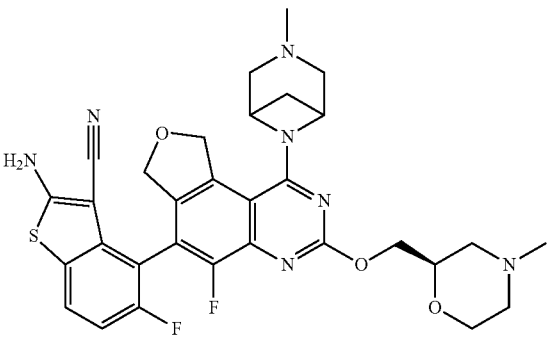 |

TABLE A-continued

Example Compounds

| Ex. # | Compound |
|---|---|
| 340 | |
| 341 | |
| 342 | |
| 343 | |

TABLE A-continued
Example Compounds
| Ex. # | Compound |
|---|---|
| 344 | 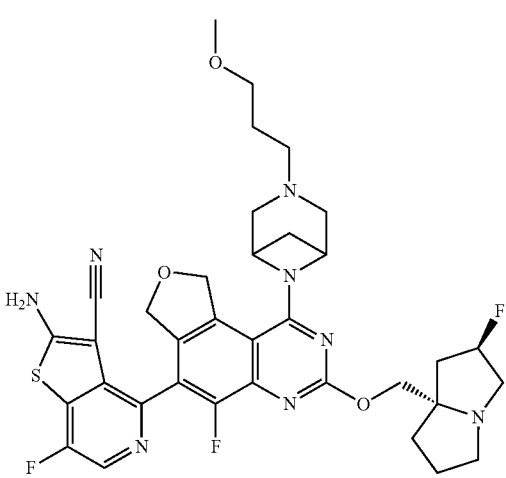 [SMILES: COCCCN1CC2CC(C1)N2c1nc(OC[C@@]23CCCN2C[C@H](F)C3)nc2c(F)c(-c3ncc(F)c4sc(N)c(C#N)c34)c3c(c12)COC3] |
| 345 | 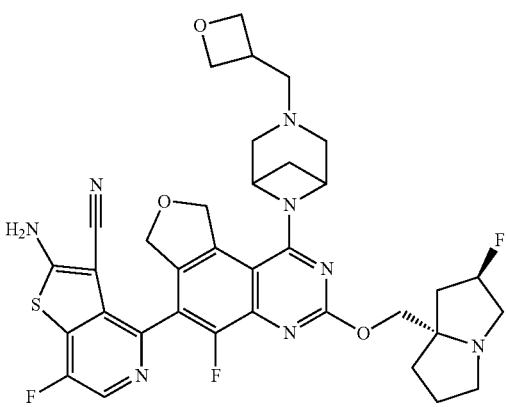 [SMILES: N#Cc1c(N)sc2c(F)cnc(-c3c4c(c5c(N6C7CC6CN(CC6COC6)C7)nc(OC[C@@]67CCCN6C[C@H](F)C7)nc5c3F)COC4)c12] |
| 346 | 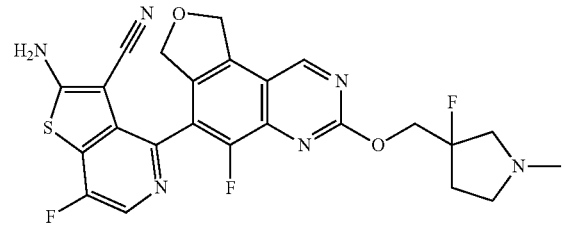 [SMILES: CN1CCC(F)(COc2ncc3c4c(c(-c5ncc(F)c6sc(N)c(C#N)c56)c(F)c3n2)COC4)C1] |
| 347 | 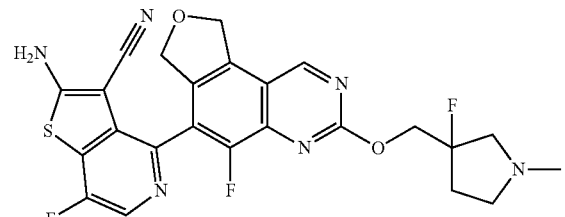 |

217
TABLE A-continued
Example Compounds
| Ex. # | Compound |
|---|---|
| 348 | 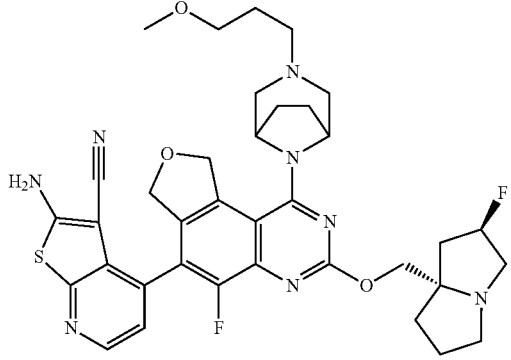 [SMILES: COCCCN1CC2CCC(C1)N2c1nc(OC[C@@]23CCCN2C[C@H](F)C3)nc2c(F)c(-c3ccnc4sc(N)c(C#N)c34)c3c(c12)COC3] |
| 349 | 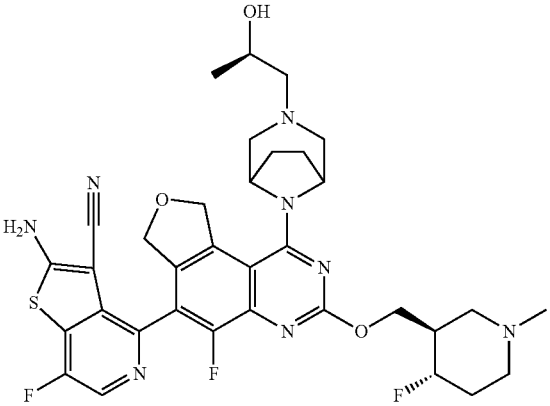 [SMILES: C[C@@H](O)CN1CC2CCC(C1)N2c1nc(OC[C@H]2CN(C)CC[C@@H]2F)nc2c(F)c(-c3ncc(F)c4sc(N)c(C#N)c34)c3c(c12)COC3] |
| 350 | 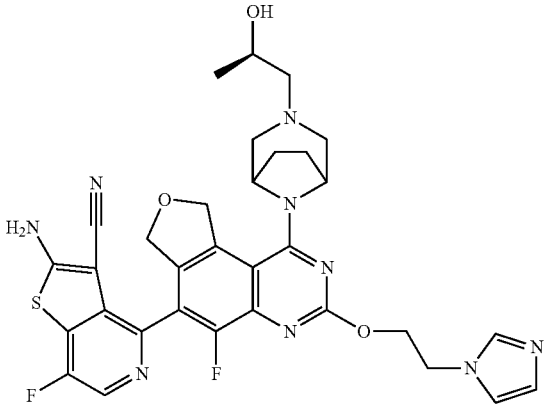 [SMILES: C[C@@H](O)CN1CC2CCC(C1)N2c1nc(OCCn2ccnc2)nc2c(F)c(-c3ncc(F)c4sc(N)c(C#N)c34)c3c(c12)COC3] |

TABLE A-continued
Example Compounds
| Ex. # | Compound |
|---|---|
| 351 | 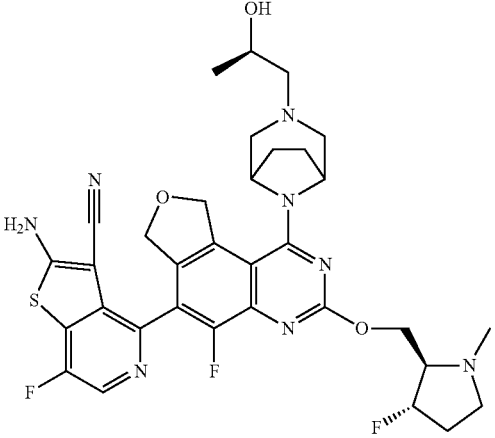 [SMILES: C[C@@H](O)CN1CC2CCC(C1)N2c1nc(OC[C@@H]2[C@@H](F)CCN2C)nc2c(F)c(-c3ncc(F)c4sc(N)c(C#N)c34)c3c(c12)COC3] |
| 352 | 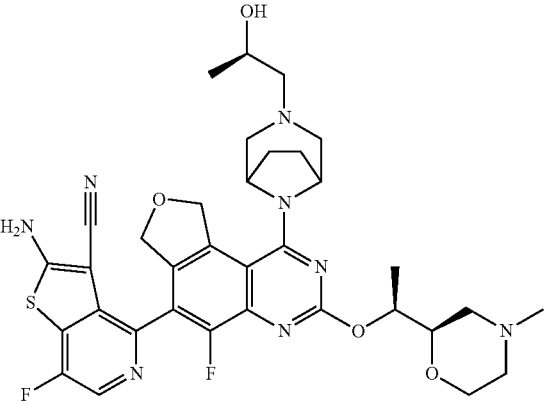 [SMILES: C[C@H](Oc1nc(N2C3CCC2CN(C[C@@H](C)O)C3)c2c3c(c(-c4ncc(F)c5sc(N)c(C#N)c45)c(F)c2n1)COC3)[C@H]1CN(C)CCO1] |
| 353 | 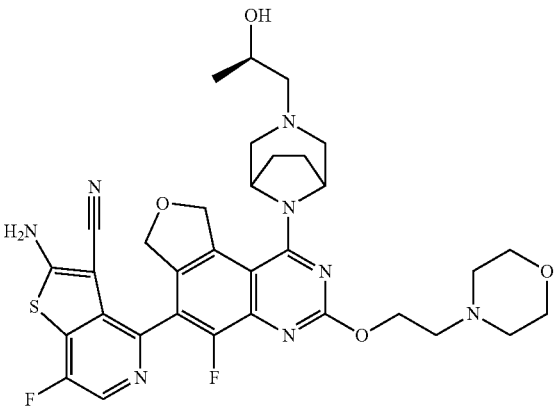 [SMILES: C[C@@H](O)CN1CC2CCC(C1)N2c1nc(OCCN2CCOCC2)nc2c(F)c(-c3ncc(F)c4sc(N)c(C#N)c34)c3c(c12)COC3] |

TABLE A-continued
Example Compounds
| Ex. # | Compound |
|---|---|
| 354 | 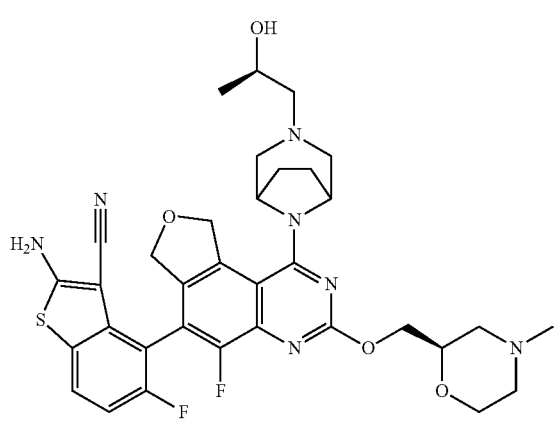 [SMILES: C[C@@H](O)CN1CC2CCC(C1)N2c1nc(OC[C@H]2CN(C)CCO2)nc2c(F)c(-c3c(F)ccc4sc(N)c(C#N)c34)c3c(c12)COC3] |
| 355 | 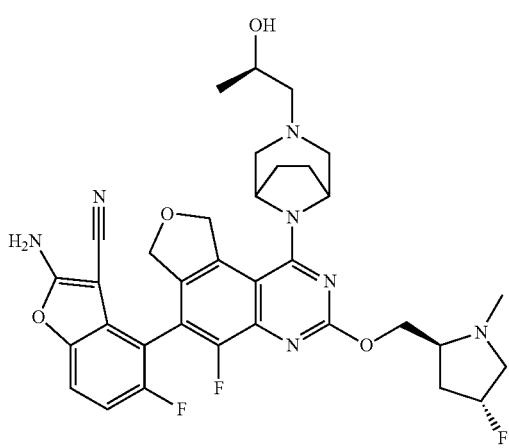 [SMILES: C[C@@H](O)CN1CC2CCC(C1)N2c1nc(OC[C@@H]2C[C@@H](F)CN2C)nc2c(F)c(-c3c(F)ccc4oc(N)c(C#N)c34)c3c(c12)COC3] |
| 356 | 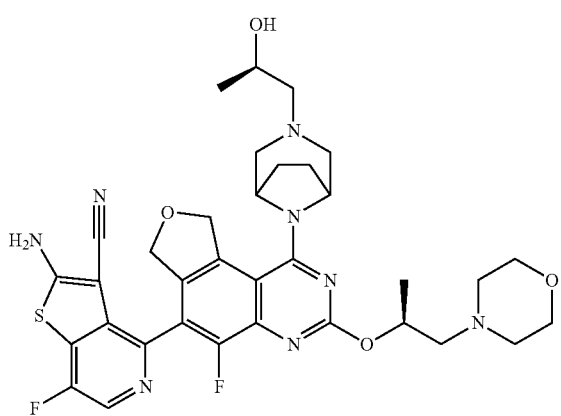 [SMILES: C[C@@H](O)CN1CC2CCC(C1)N2c1nc(O[C@@H](C)CN2CCOCC2)nc2c(F)c(-c3ncc(F)c4sc(N)c(C#N)c34)c3c(c12)COC3] |

TABLE A-continued
Example Compounds
| Ex. # | Compound |
|---|---|
| 357 | 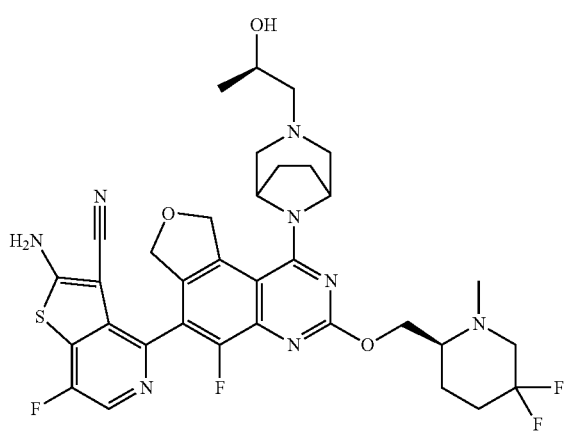 [SMILES: C[C@@H](O)CN1CC2CCC(C1)N2c1nc(OC[C@@H]2CCC(F)(F)CN2C)nc2c(F)c(-c3ncc(F)c4sc(N)c(C#N)c34)c3c(c12)COC3] |
| 358 | 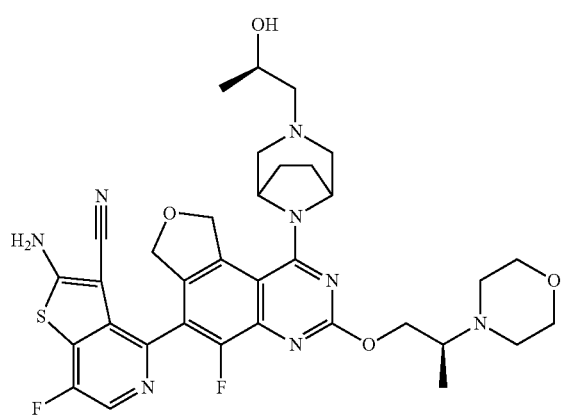 [SMILES: C[C@@H](O)CN1CC2CCC(C1)N2c1nc(OC[C@H](C)N2CCOCC2)nc2c(F)c(-c3ncc(F)c4sc(N)c(C#N)c34)c3c(c12)COC3] |
| 359 | 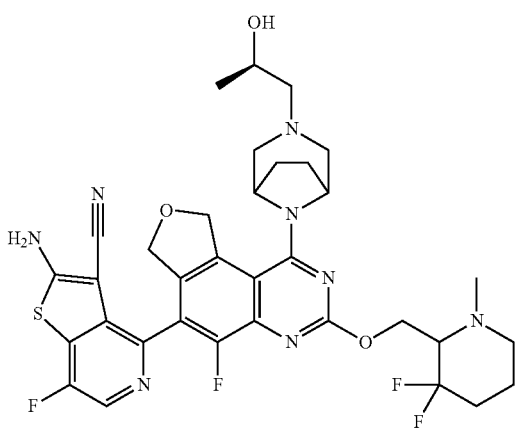 [SMILES: C[C@@H](O)CN1CC2CCC(C1)N2c1nc(OCC2N(C)CCCC2(F)F)nc2c(F)c(-c3ncc(F)c4sc(N)c(C#N)c34)c3c(c12)COC3] |

TABLE A-continued
Example Compounds
| Ex. # | Compound |
|---|---|
| 360 | 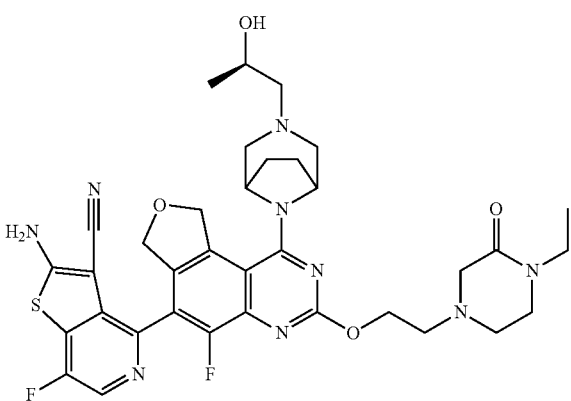 [SMILES: CCN1CCN(CCOc2nc(N3C4CCC3CN(C[C@@H](C)O)C4)c3c4c(c(-c5ncc(F)c6sc(N)c(C#N)c56)c(F)c3n2)COC4)CC1=O] |
| 361 | 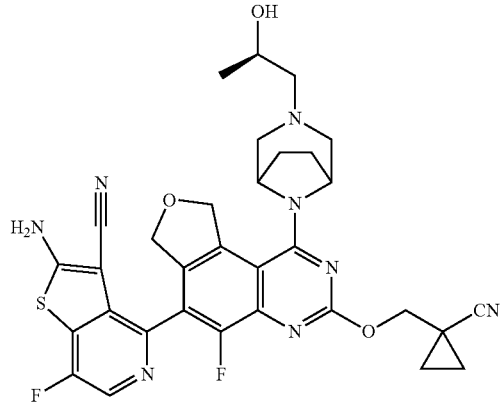 [SMILES: C[C@@H](O)CN1CC2CCC(C1)N2c1nc(OCC2(C#N)CC2)nc2c(F)c(-c3ncc(F)c4sc(N)c(C#N)c34)c3c(c12)COC3] |
| 362 | 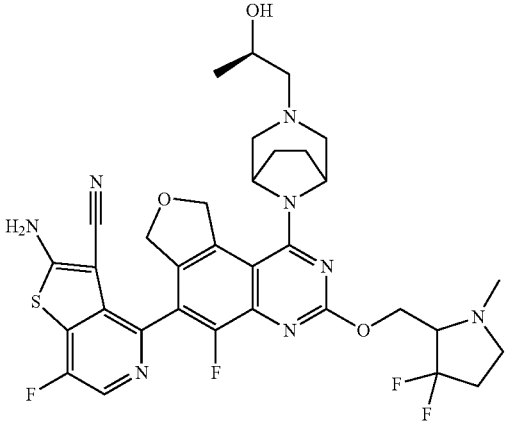 [SMILES: C[C@@H](O)CN1CC2CCC(C1)N2c1nc(OCC2N(C)CCC2(F)F)nc2c(F)c(-c3ncc(F)c4sc(N)c(C#N)c34)c3c(c12)COC3] |

TABLE A-continued
Example Compounds
| Ex. # | Compound |
|---|---|
| 363 | 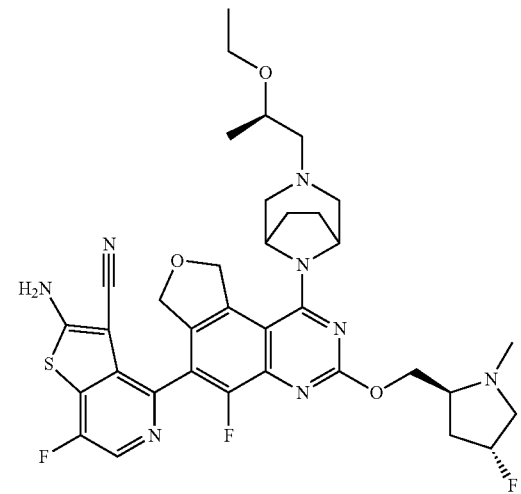 [SMILES: CCO[C@H](C)CN1CC2CCC(C1)N2c1nc(OC[C@@H]2C[C@@H](F)CN2C)nc2c(F)c(-c3ncc(F)c4sc(N)c(C#N)c34)c3c(c12)COC3] |
| 364 | 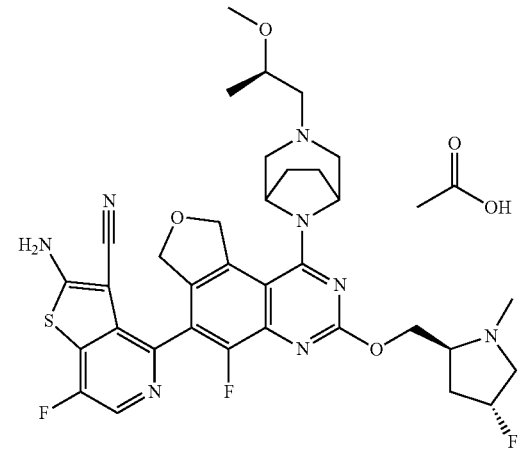 |
| 365 | 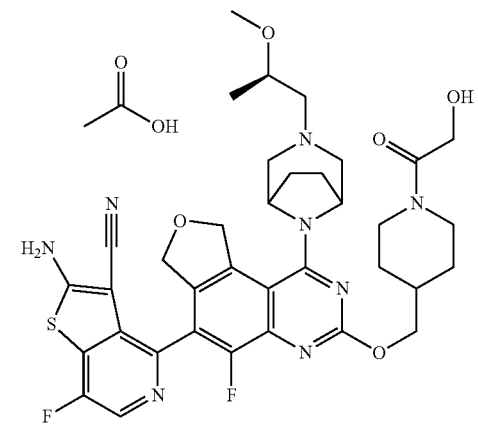 |

TABLE A-continued
Example Compounds
| Ex. # | Compound |
|---|---|
| 366 | 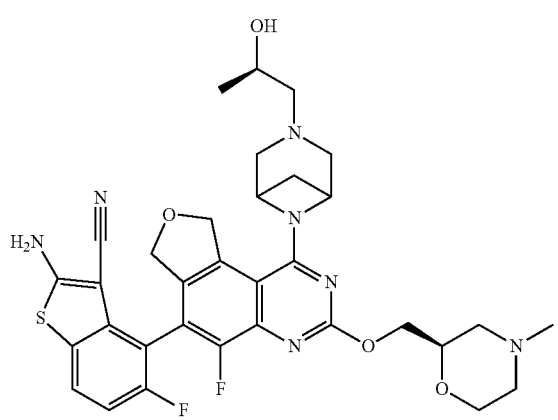 [SMILES: C[C@@H](O)CN1CC2CC(C1)N2c1nc(OC[C@H]2CN(C)CCO2)nc2c(F)c(-c3c(F)ccc4sc(N)c(C#N)c34)c3c(c12)COC3] |
| 367 | 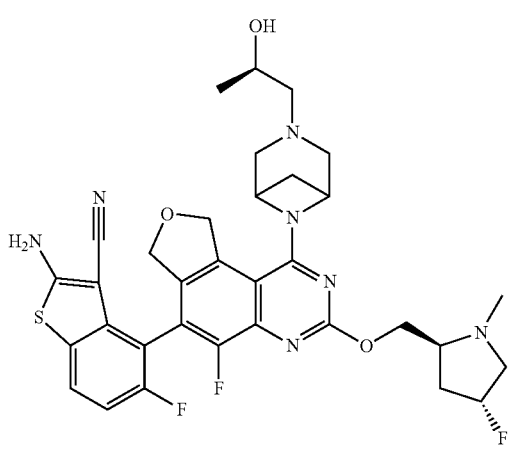 [SMILES: C[C@@H](O)CN1CC2CC(C1)N2c1nc(OC[C@@H]2C[C@@H](F)CN2C)nc2c(F)c(-c3c(F)ccc4sc(N)c(C#N)c34)c3c(c12)COC3] |
| 368 | 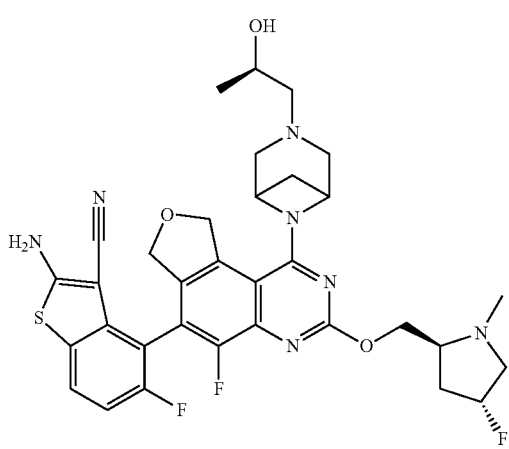 [SMILES: C[C@@H](O)CN1CC2CC(C1)N2c1nc(OC[C@@H]2C[C@@H](F)CN2C)nc2c(F)c(-c3c(F)ccc4sc(N)c(C#N)c34)c3c(c12)COC3] |

TABLE A-continued

Example Compounds

| Ex. # | Compound |
|---|---|
| 369 | (structure) |
| 370 | (structure) |
| 371 | (structure) |

TABLE A-continued
Example Compounds
| Ex. # | Compound |
|---|---|
| 372 | 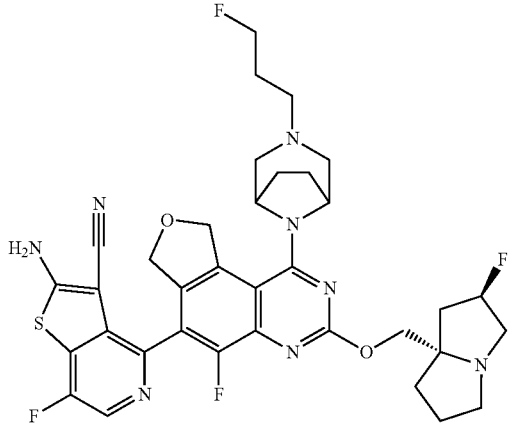 [SMILES: N#Cc1c(N)sc2c(F)cnc(-c3c4c(c5c(N6C7CCC6CN(CCCF)C7)nc(OC[C@@]67CCCN6C[C@H](F)C7)nc5c3F)COC4)c12] |
| 373 | 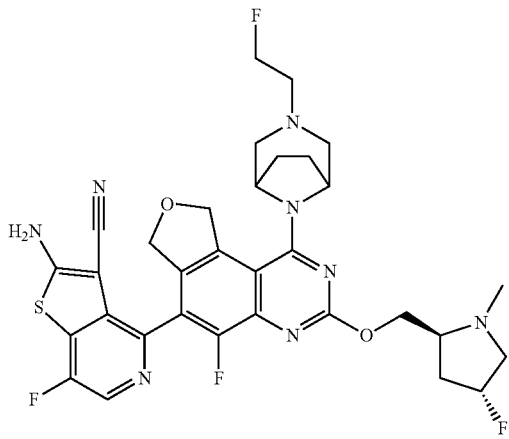 [SMILES: CN1C[C@H](F)C[C@H]1COc1nc(N2C3CCC2CN(CCF)C3)c2c3c(c(-c4ncc(F)c5sc(N)c(C#N)c45)c(F)c2n1)COC3] |
| 374 | 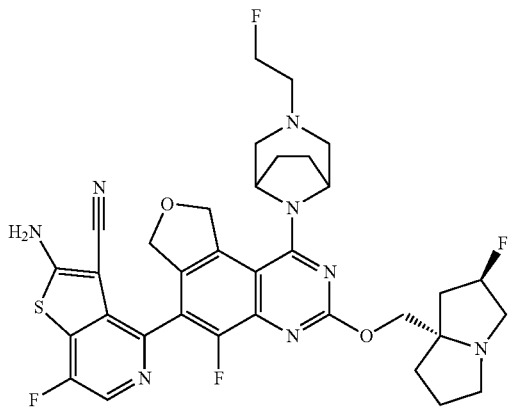 [SMILES: N#Cc1c(N)sc2c(F)cnc(-c3c4c(c5c(N6C7CCC6CN(CCF)C7)nc(OC[C@@]67CCCN6C[C@H](F)C7)nc5c3F)COC4)c12] |
| 375 | 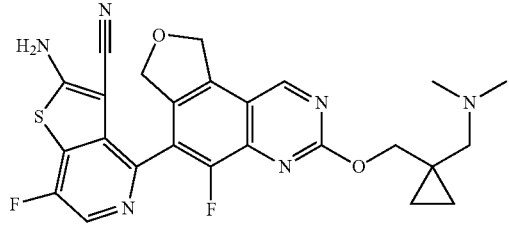 [SMILES: CN(C)CC1(COc2ncc3c4c(c(-c5ncc(F)c6sc(N)c(C#N)c56)c(F)c3n2)COC4)CC1] |

The chemical drawings in Table A contain indications of chiral aspects of the specific compounds shown. However, the chemical drawings in Table A do not contain all the possible chiral features of these compounds and the chiral indications shown are not intended to exclude changes to the chiral aspects shown. Thus, alternate chiral versions of the compounds as well as different combinations of chiral attributes are contemplated and included herein.

In a compound of Formulae I, Ia, II, IIa, III, IIIa, IV or IVa or a pharmaceutically acceptable salt thereof, the compound is selected from

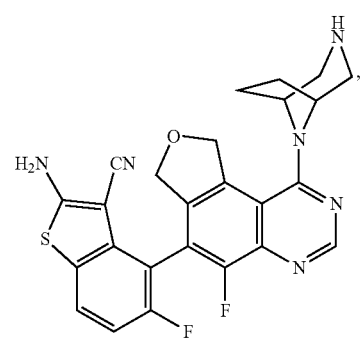

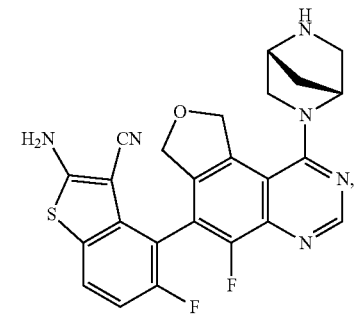

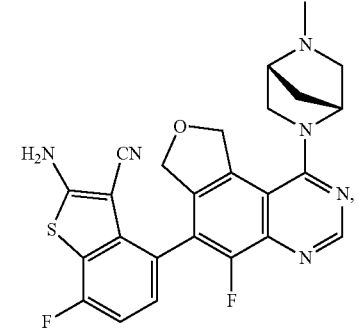

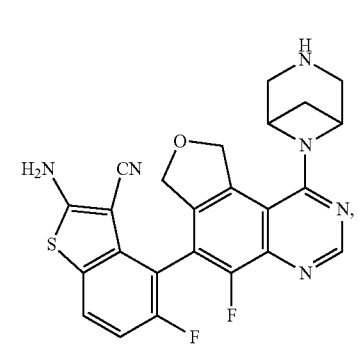

-continued

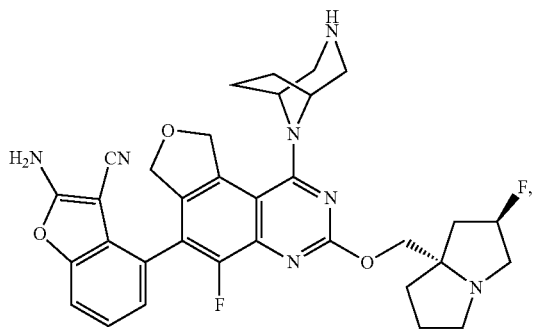

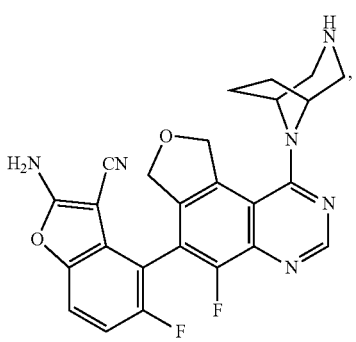

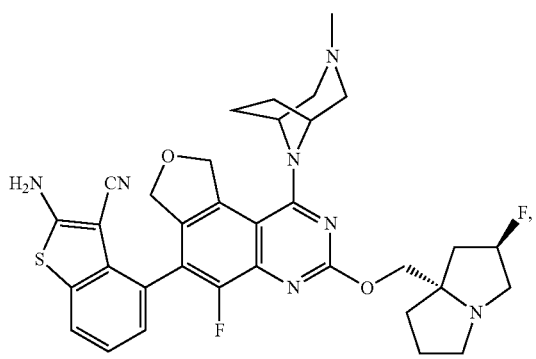

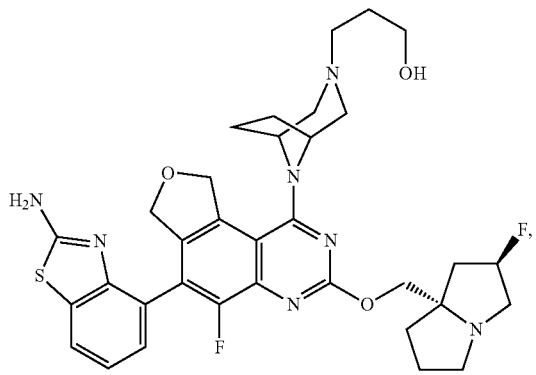

237
-continued
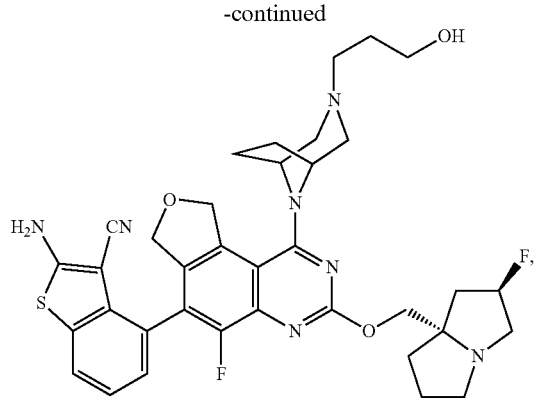
238
-continued
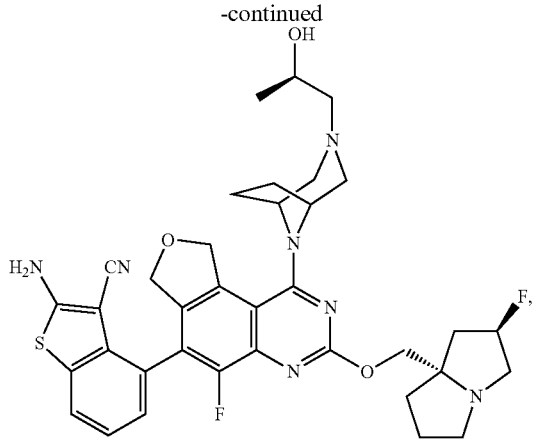
or a pharmaceutically acceptable salt thereof.
A further compound of Formulae I, Ia, II, IIa, III, IIIa, IV, or IVa or a pharmaceutically acceptable salt thereof, the compound is selected from
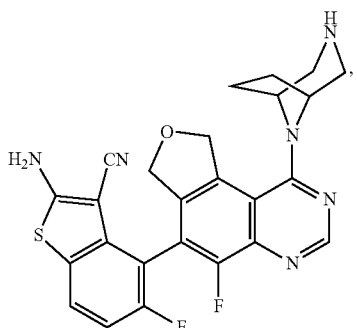
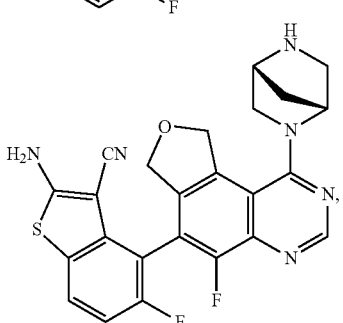
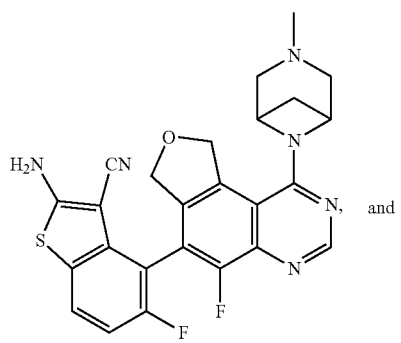
and

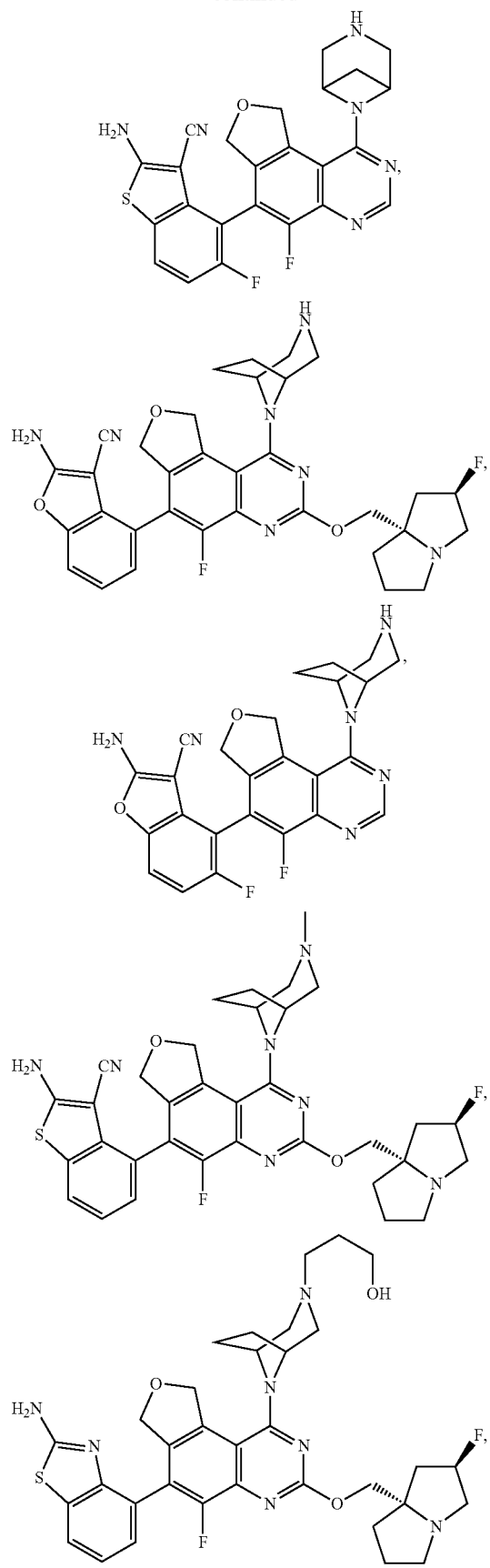
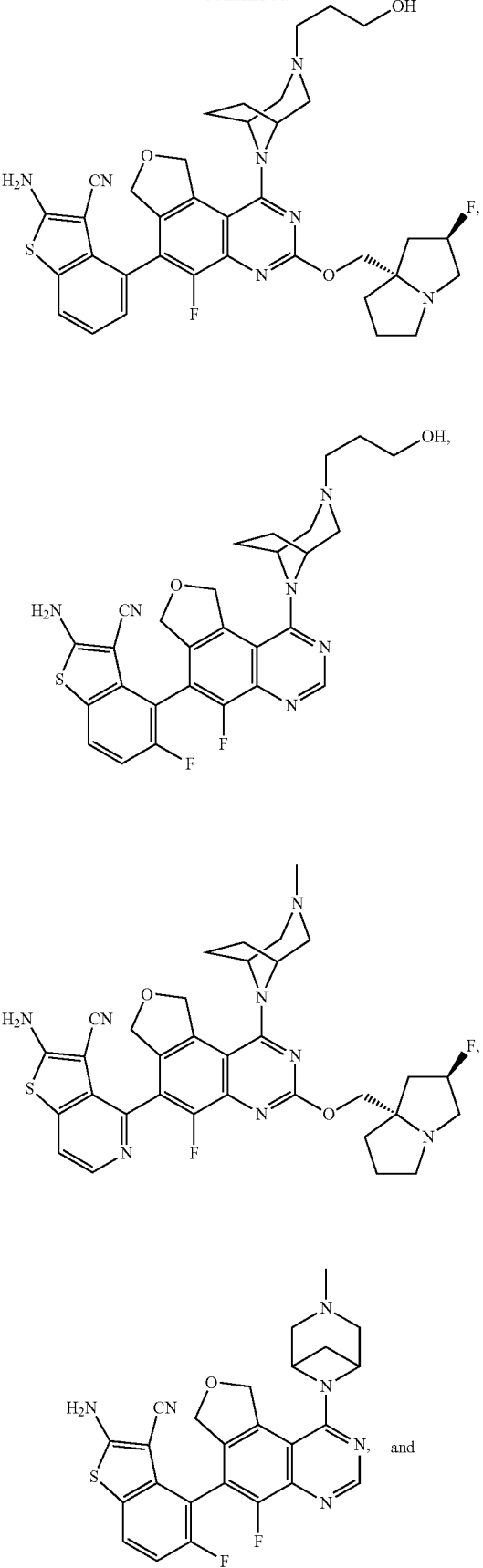

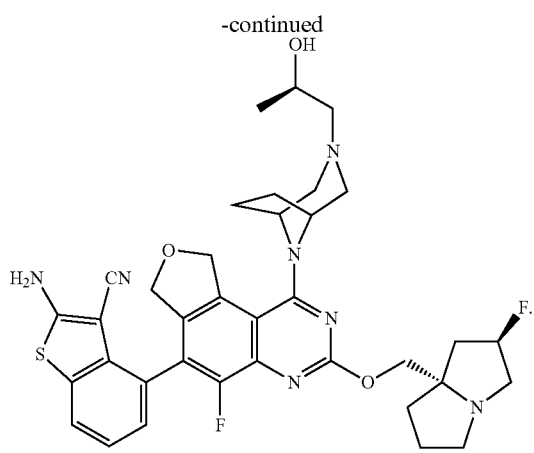
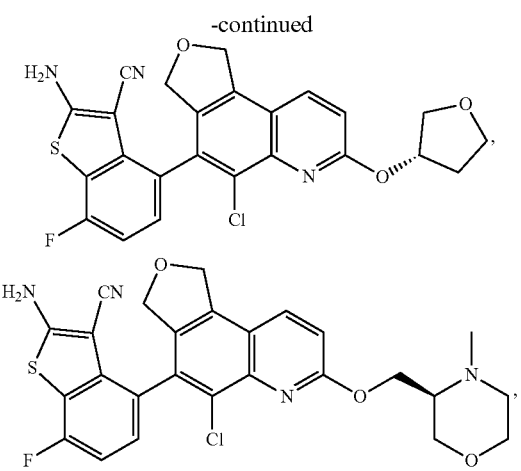
A further compound of Formulae I, Ia, II, IIa, III, IIIa, IV, or IVa or a pharmaceutically acceptable salt thereof, the compound is selected from
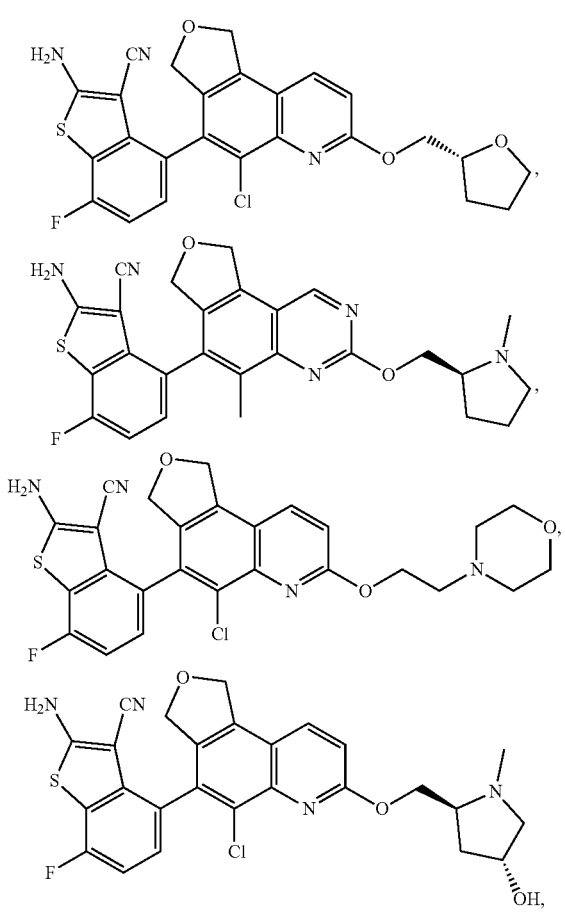
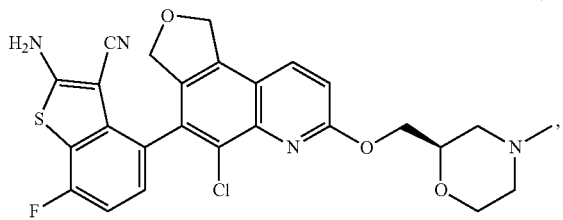

243
-continued
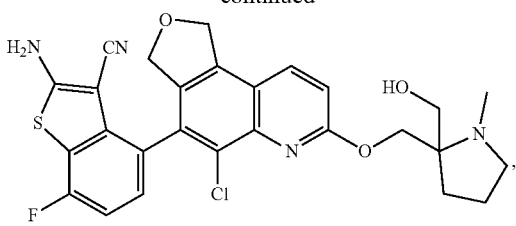
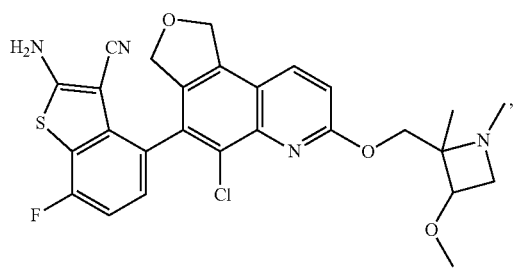
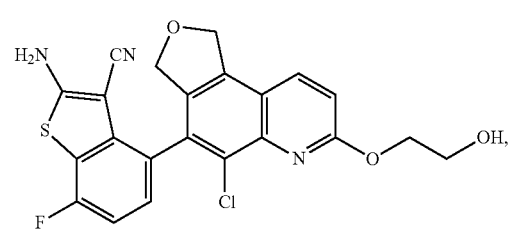
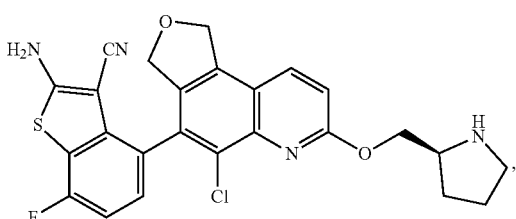
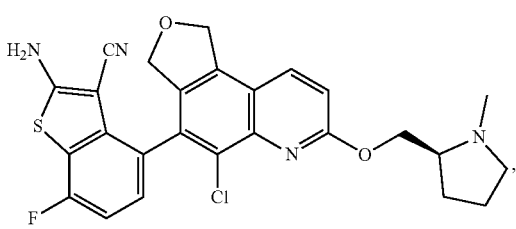
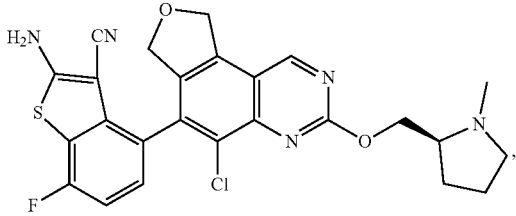
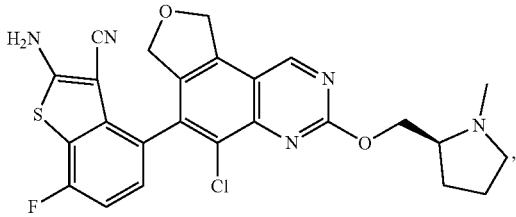
244
-continued
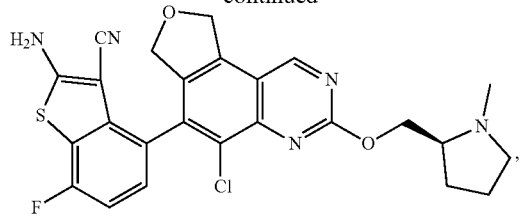
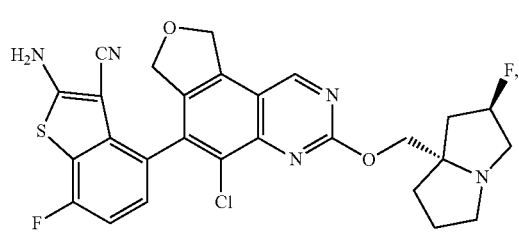
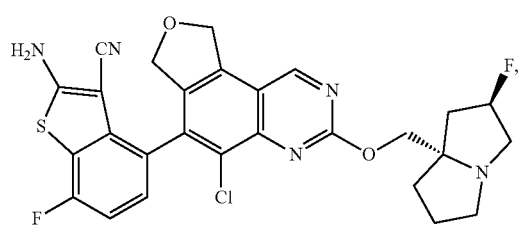
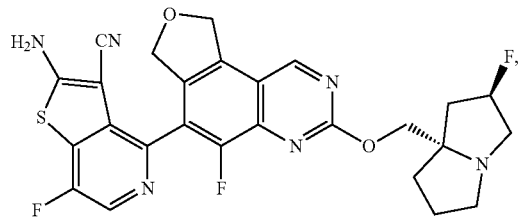
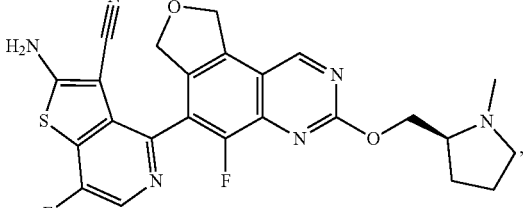
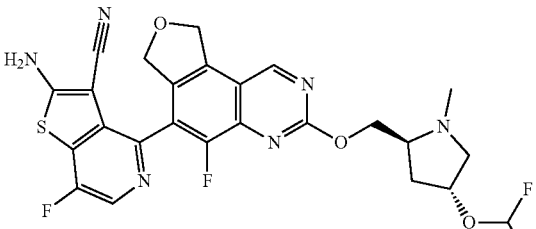
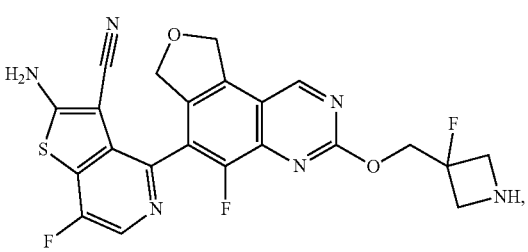

245
-continued
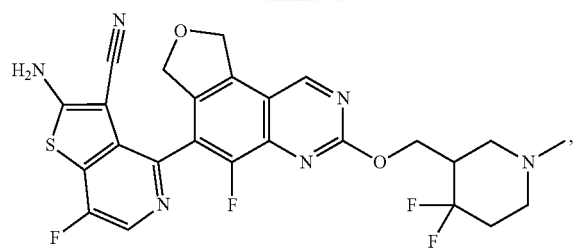
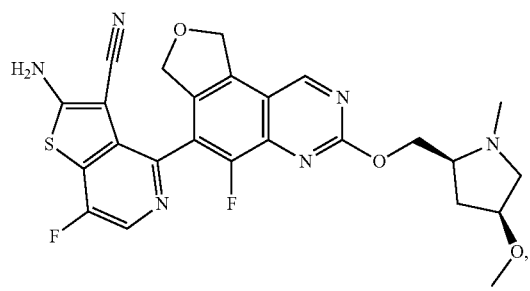
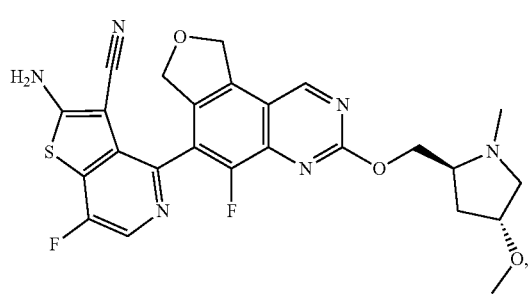
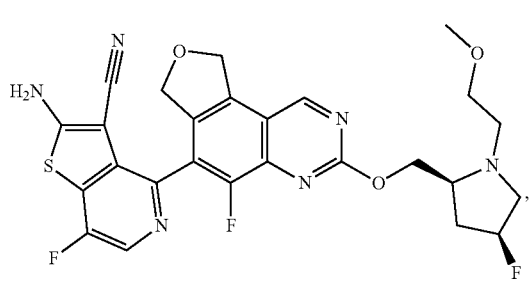
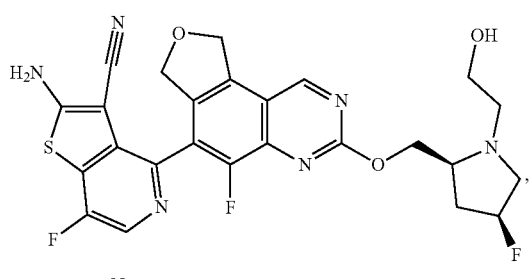
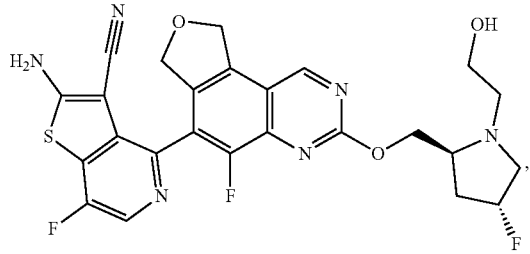
246
-continued
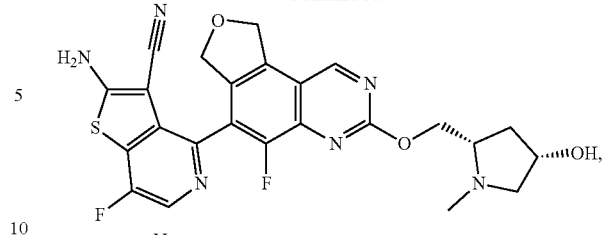
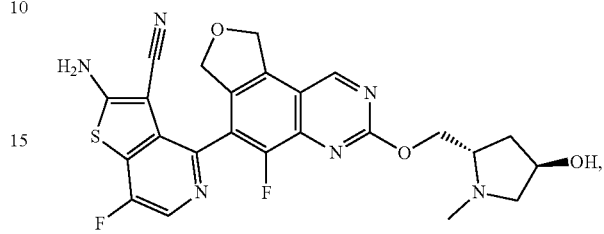
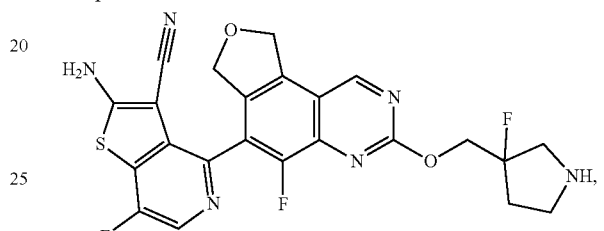
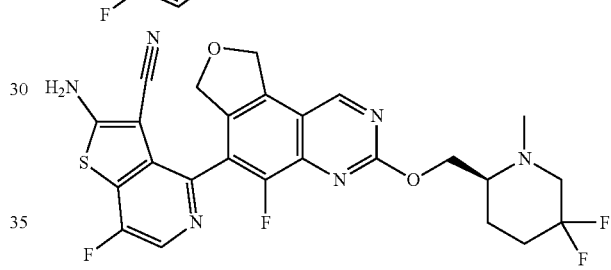
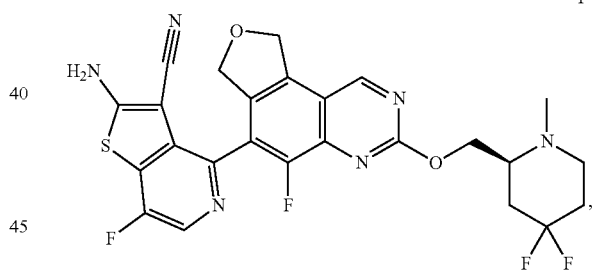
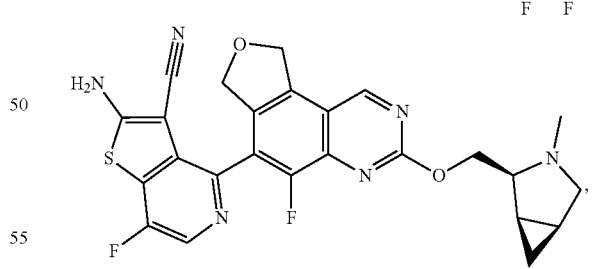
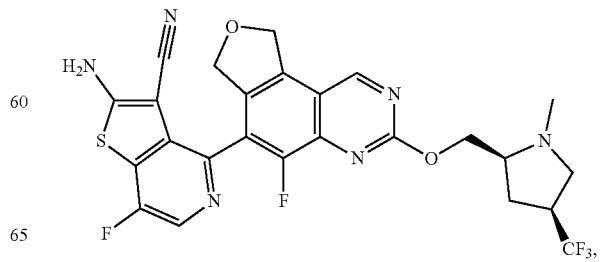

247
-continued
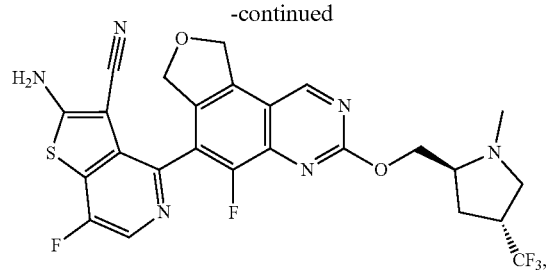
248
-continued
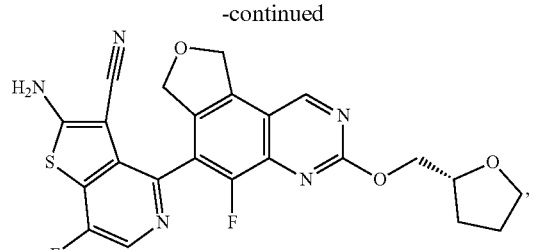
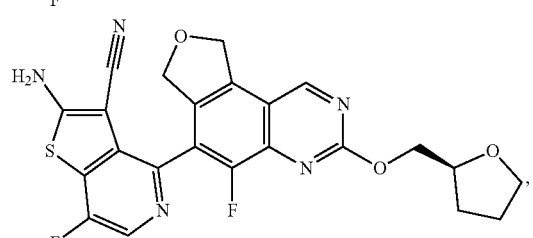
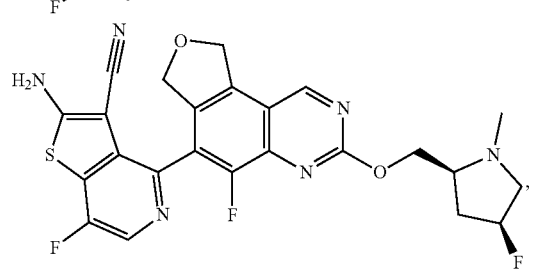
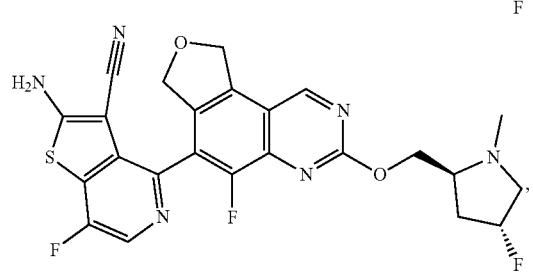
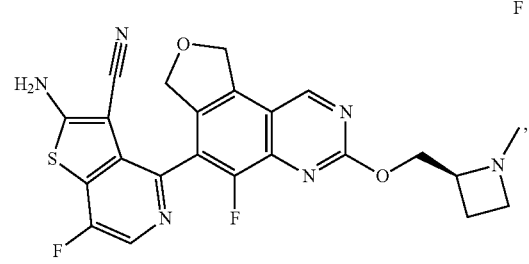
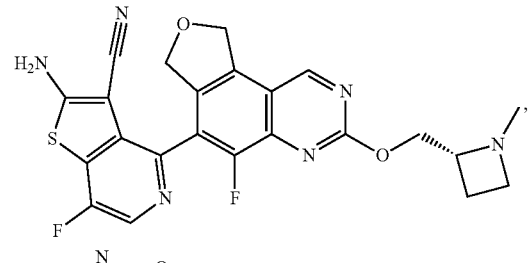
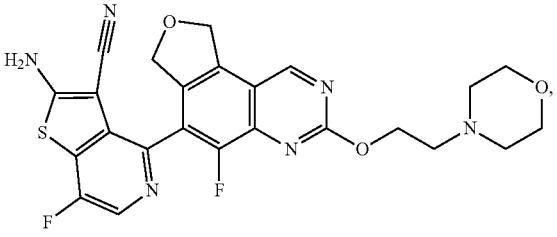

249
-continued
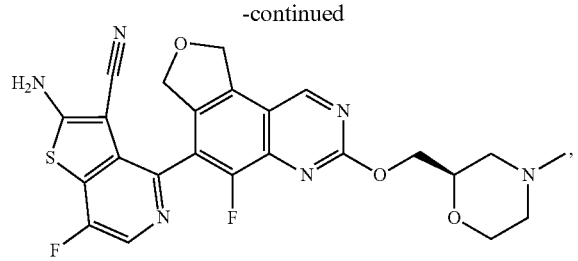
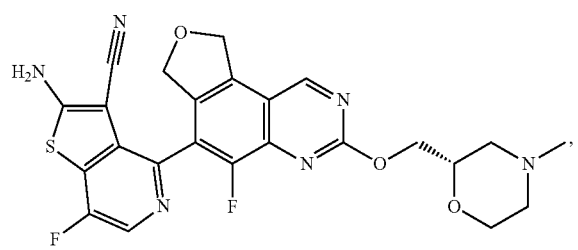
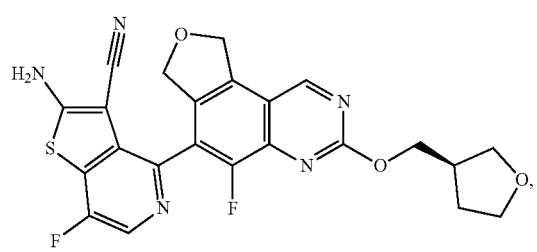
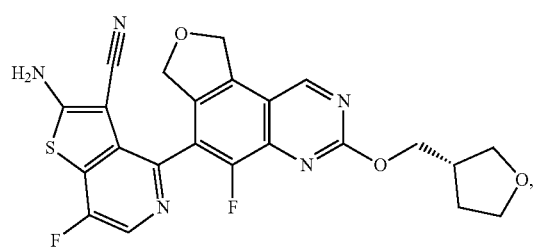
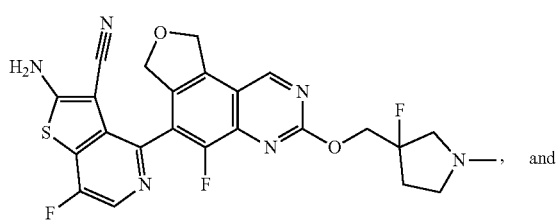
, and
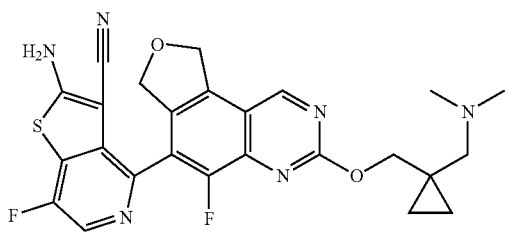
or a pharmaceutically acceptable salt thereof.
A further compound of Formulae I, Ia, II, IIa, III, IIIa, IV, or IVa or a pharmaceutically acceptable salt thereof, the compound is selected from
250
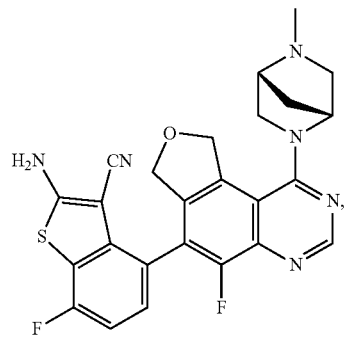
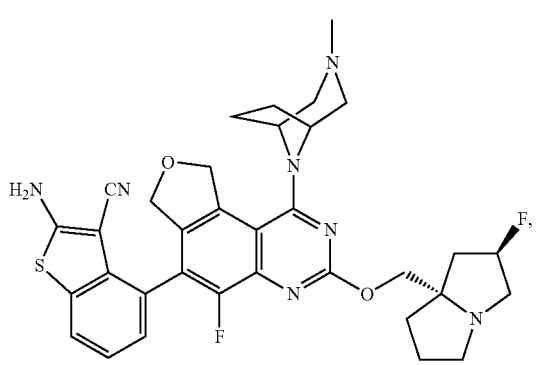
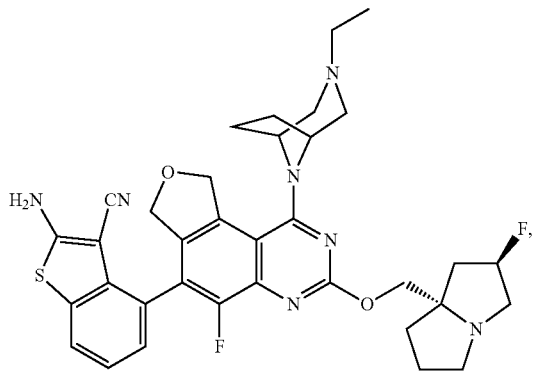
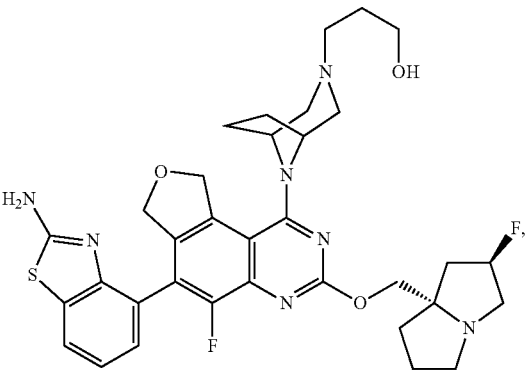

251
-continued
252
-continued
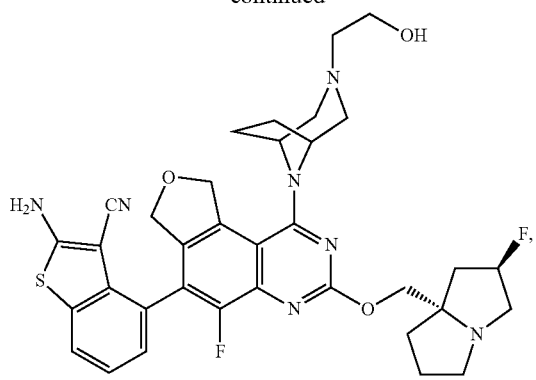
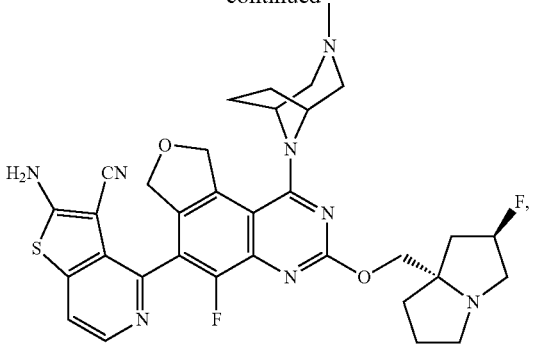

253
-continued
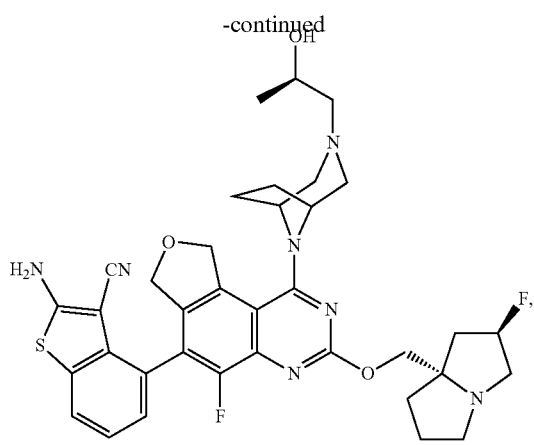
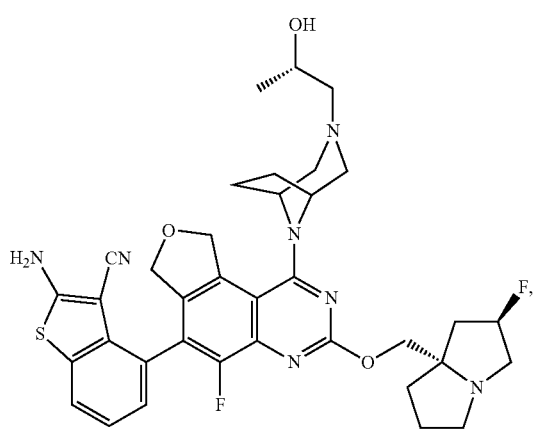
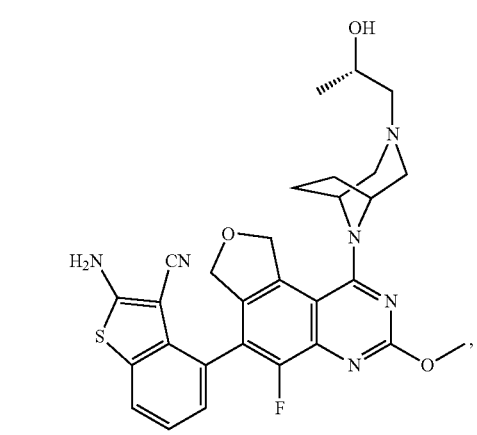
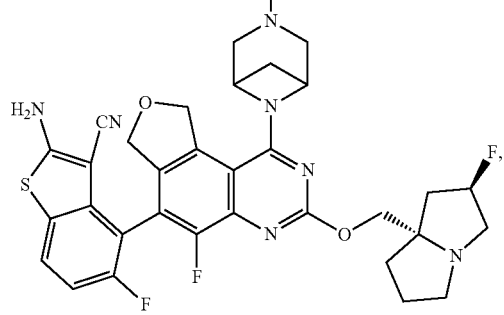
254
-continued
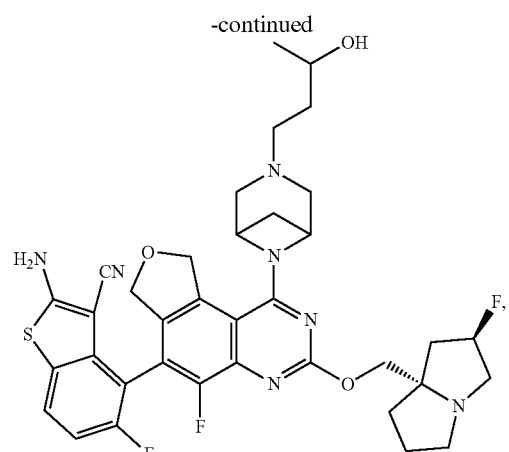
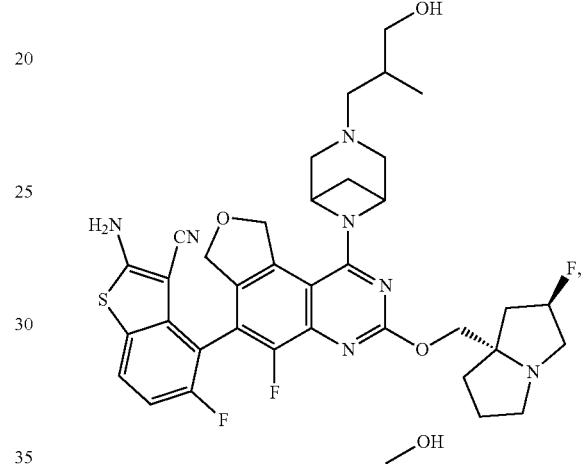
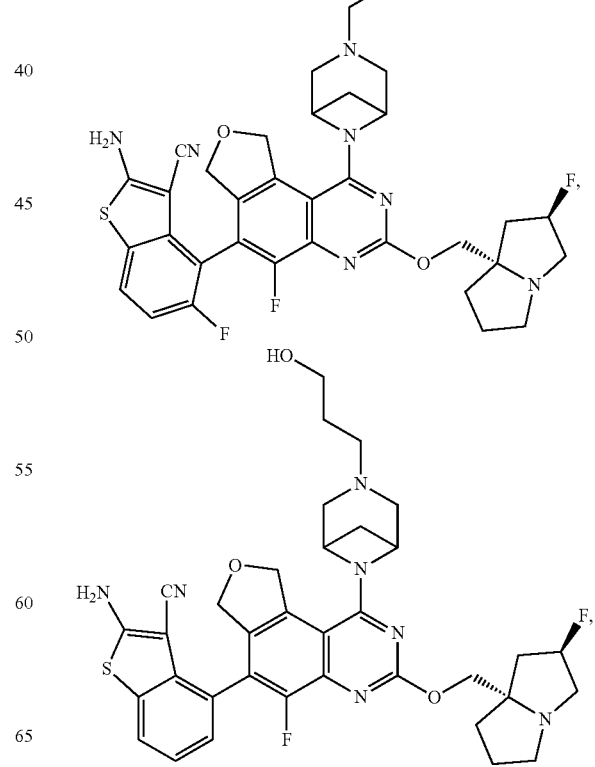

-continued
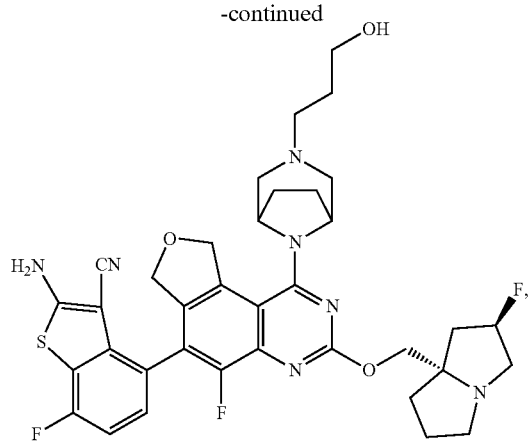
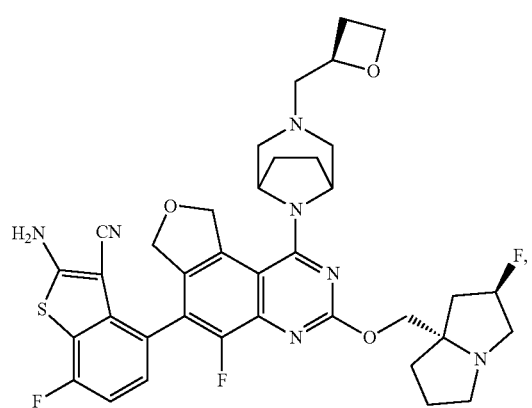
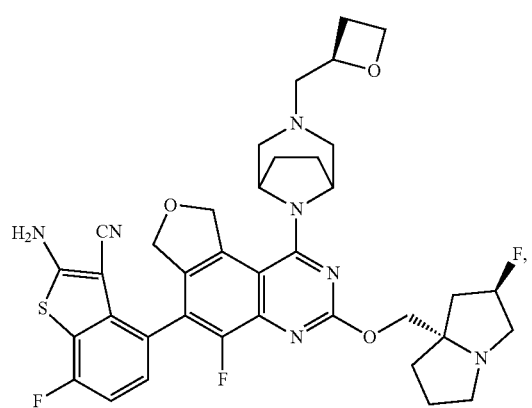
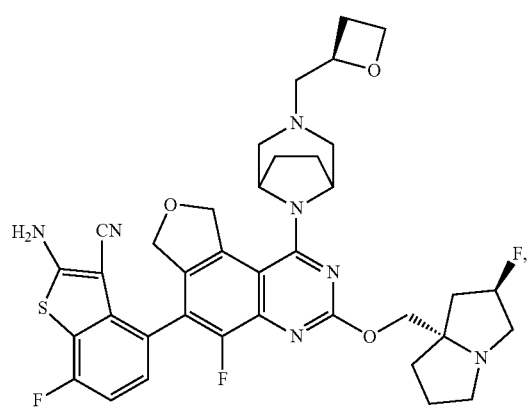
-continued
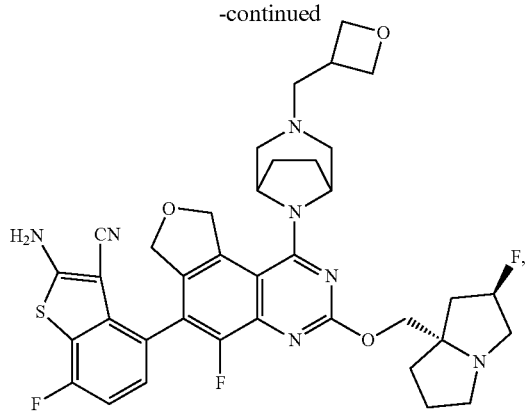
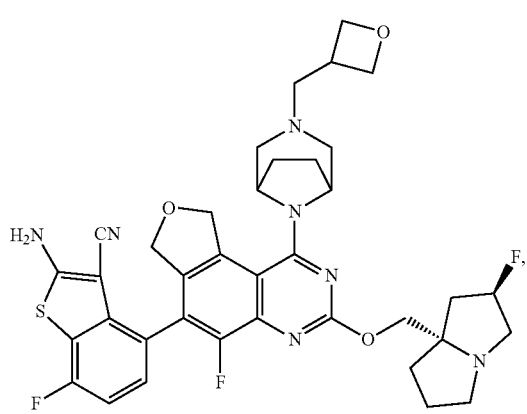
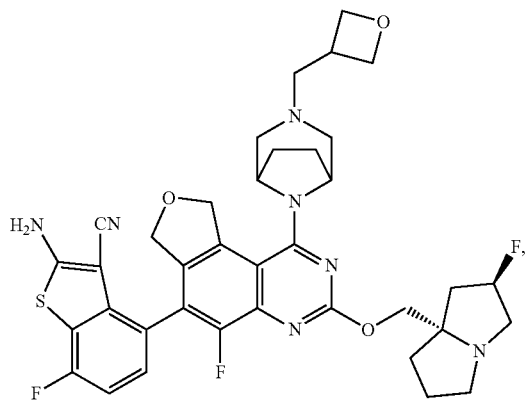
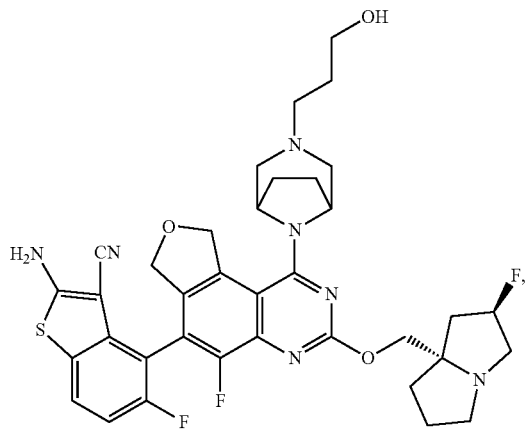

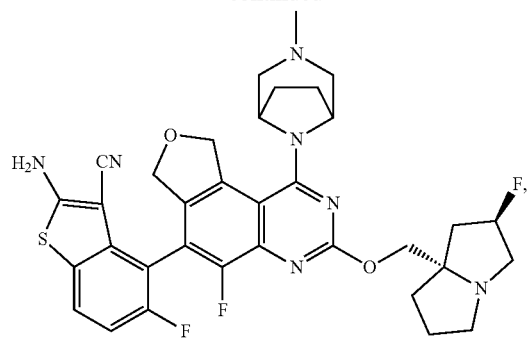
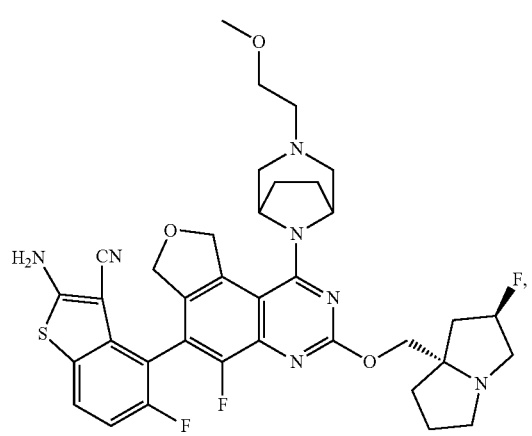
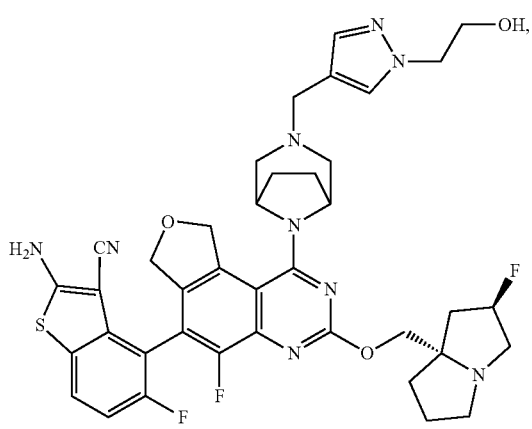
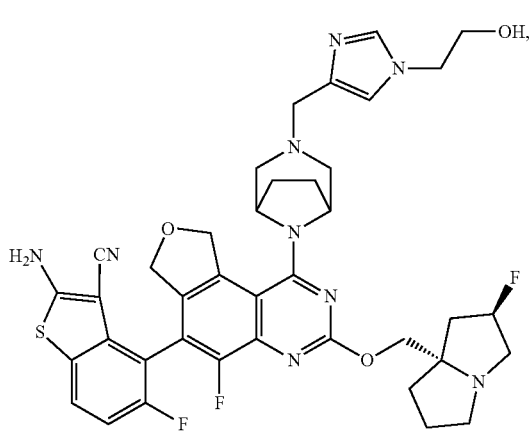
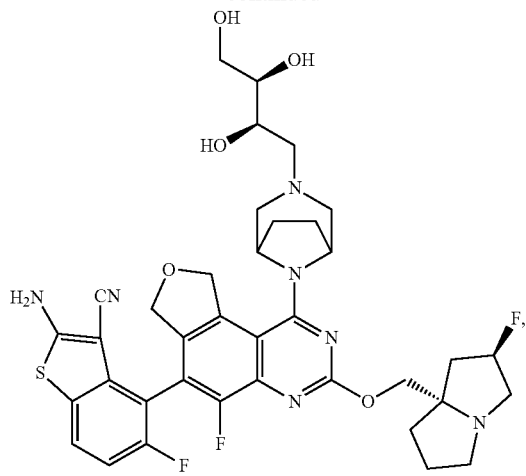
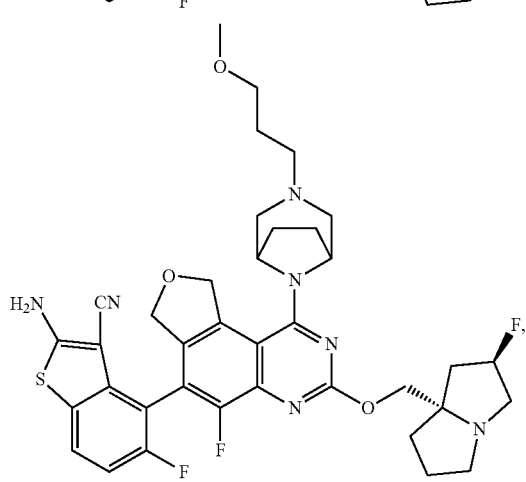
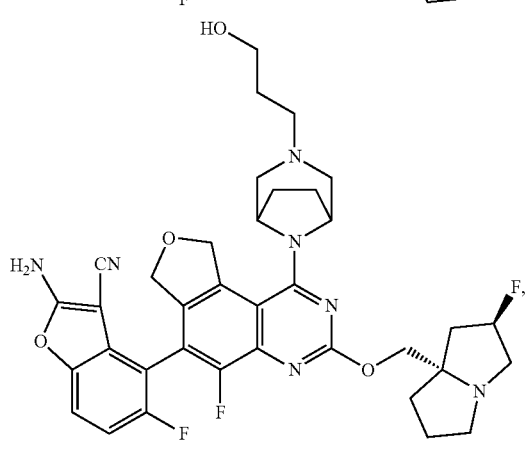
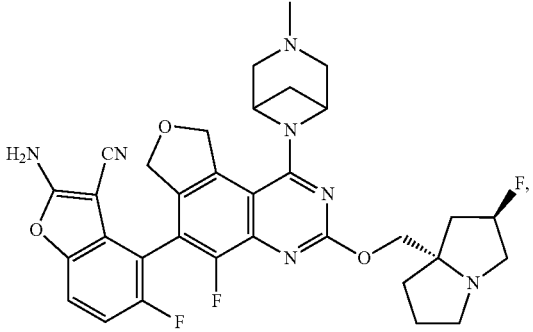

259
-continued

260
-continued

261
-continued
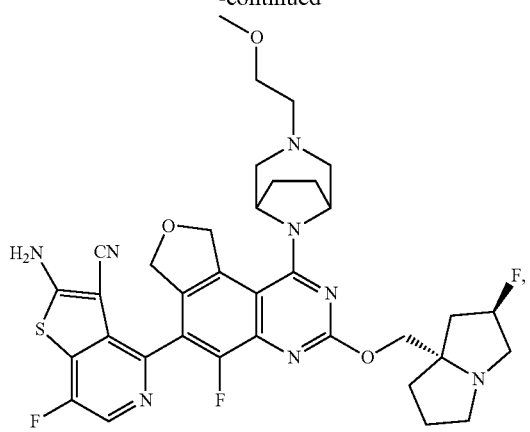
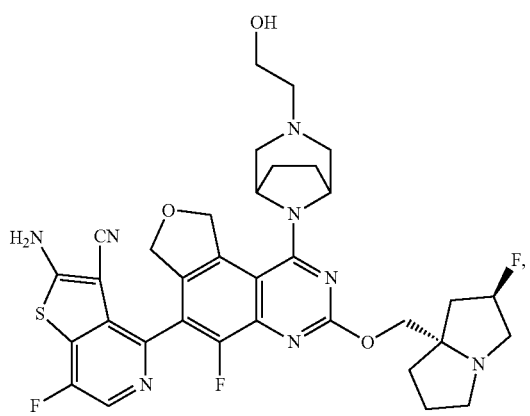
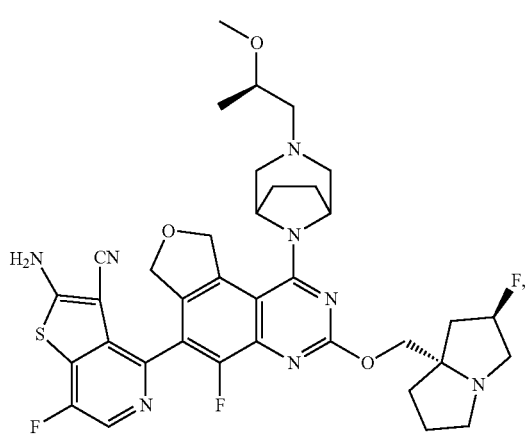
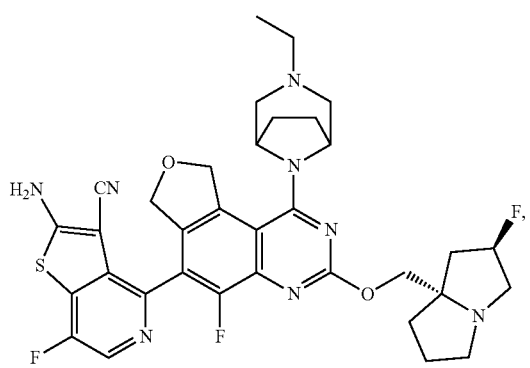
262
-continued
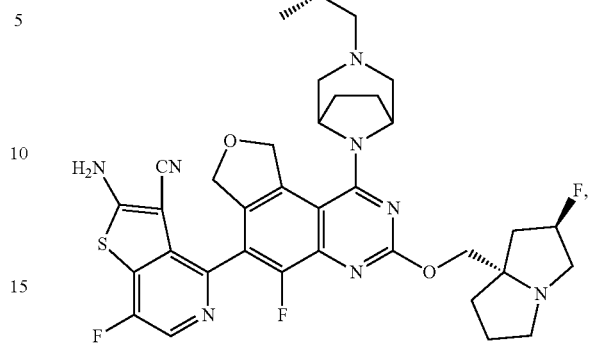
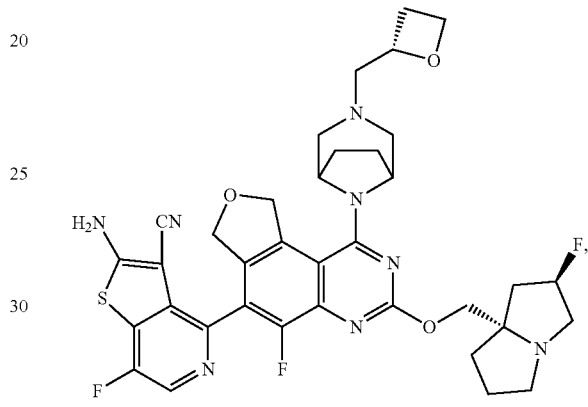
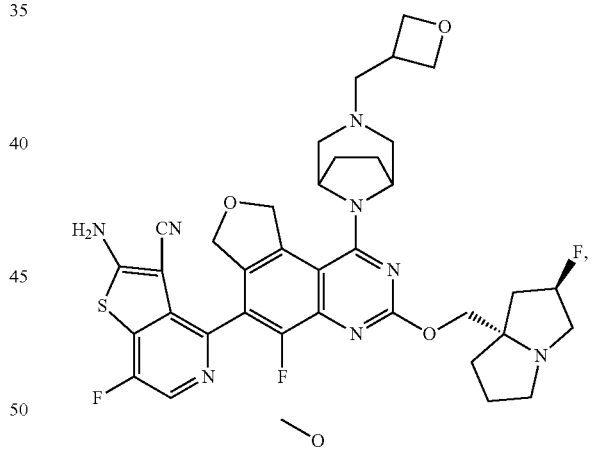
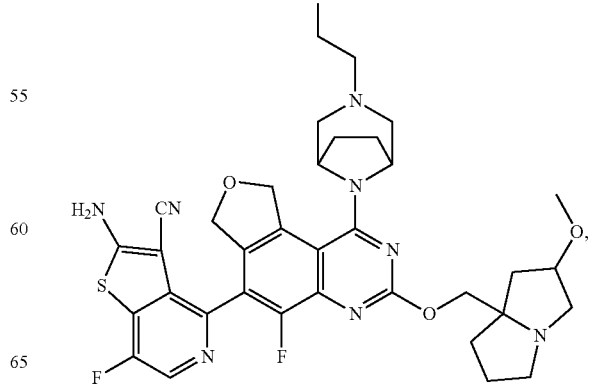

263
-continued
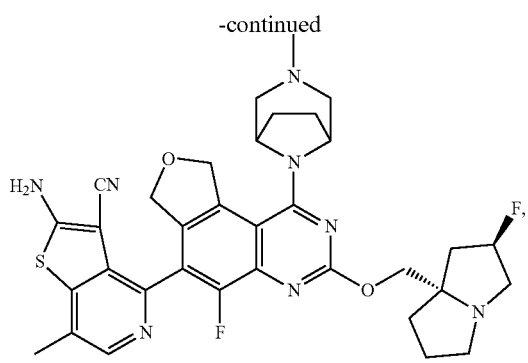
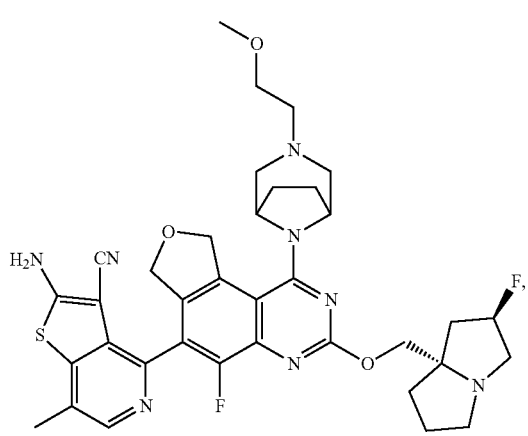
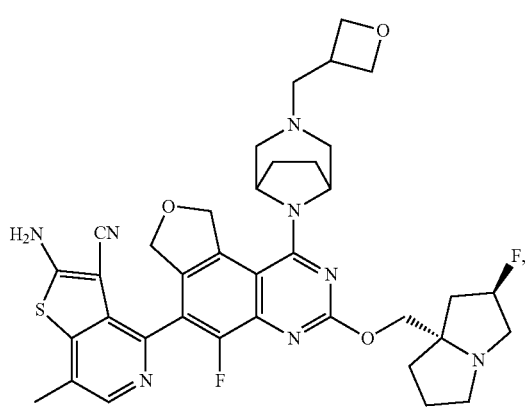
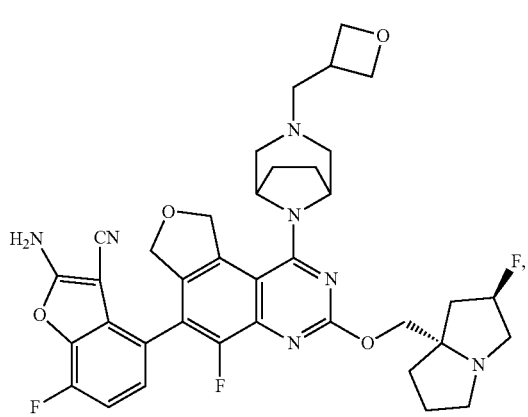
264
-continued
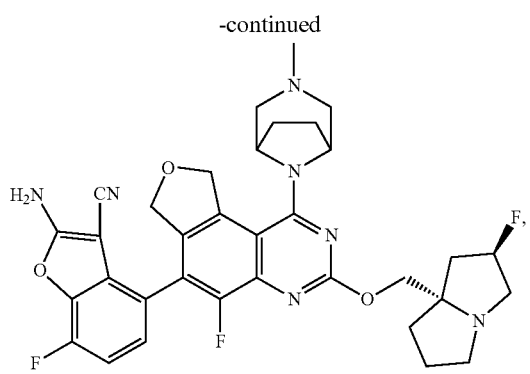
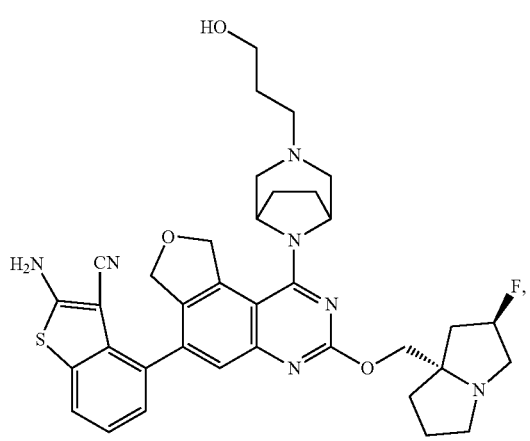
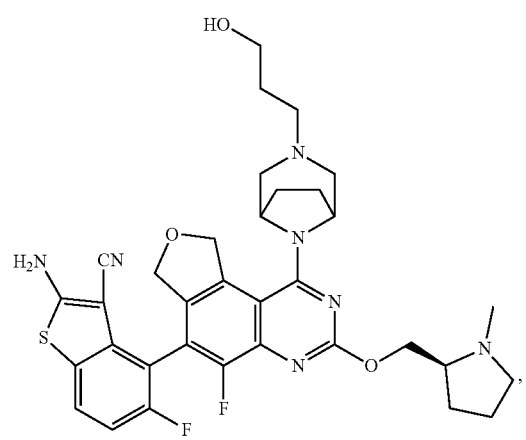
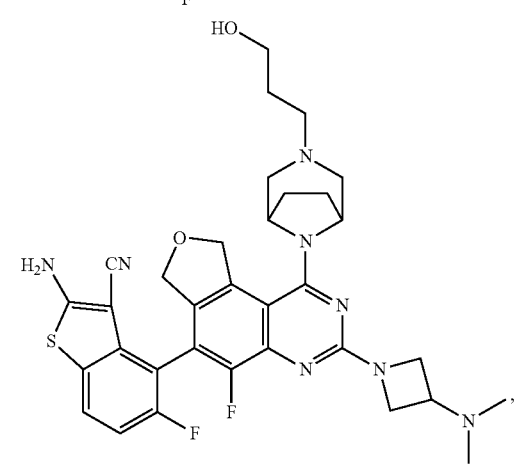

265
-continued
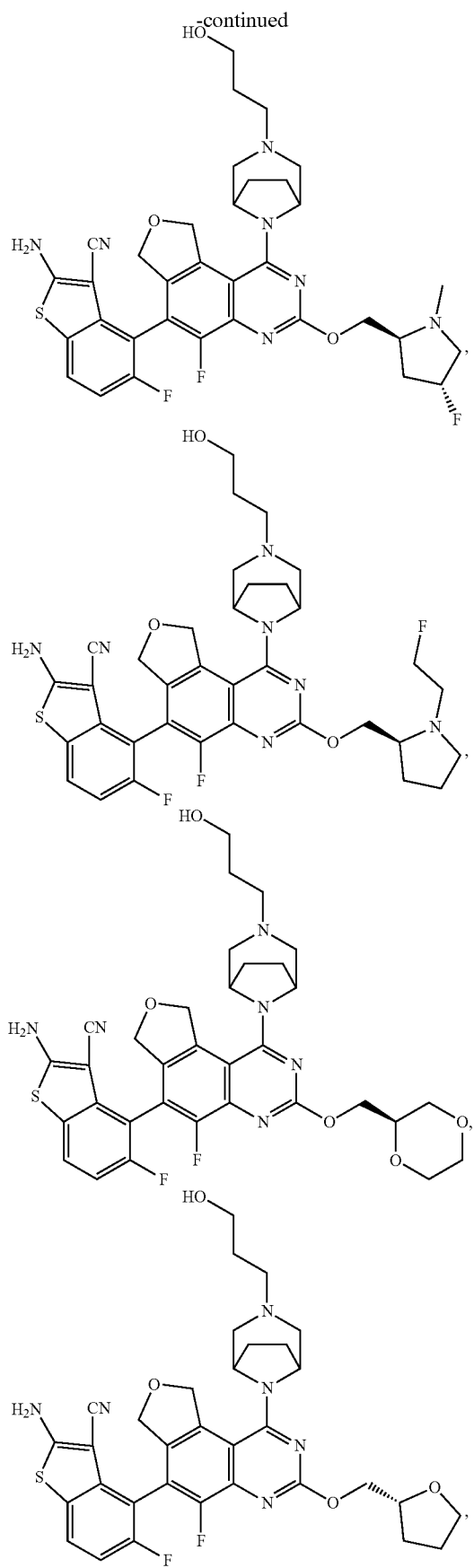
266
-continued
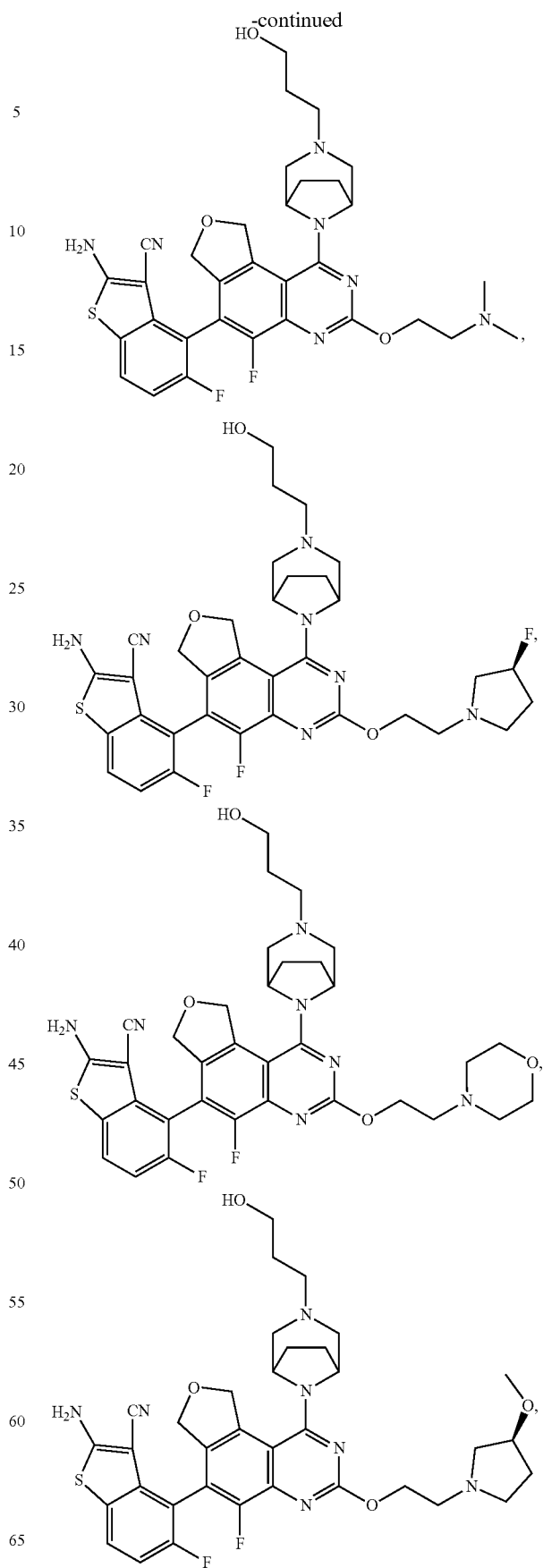

267
-continued
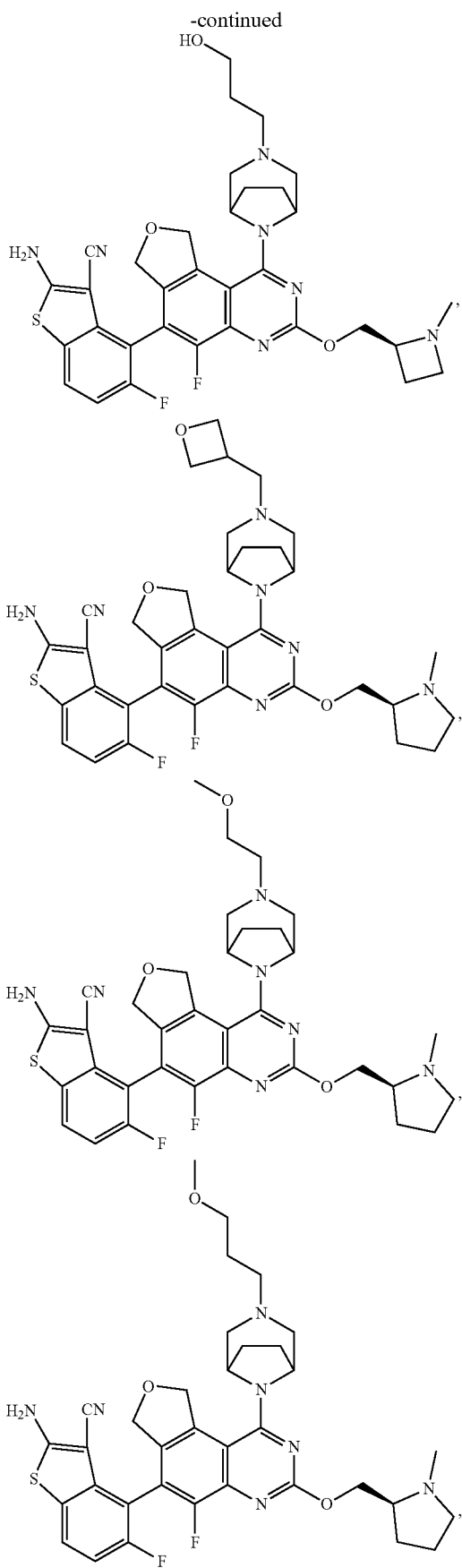
268
-continued
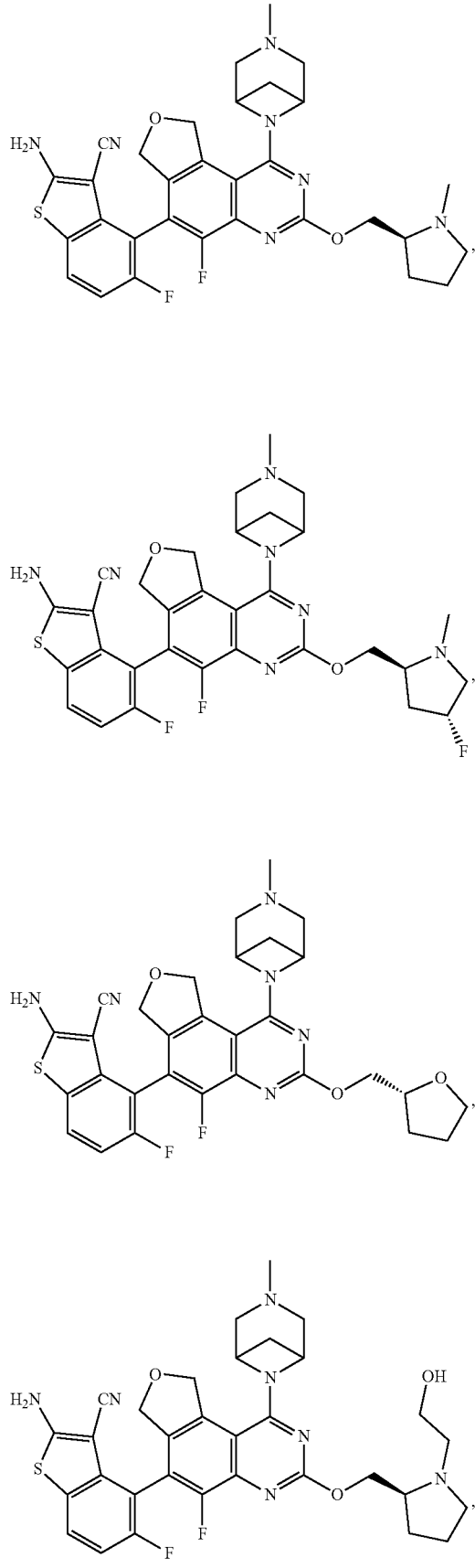

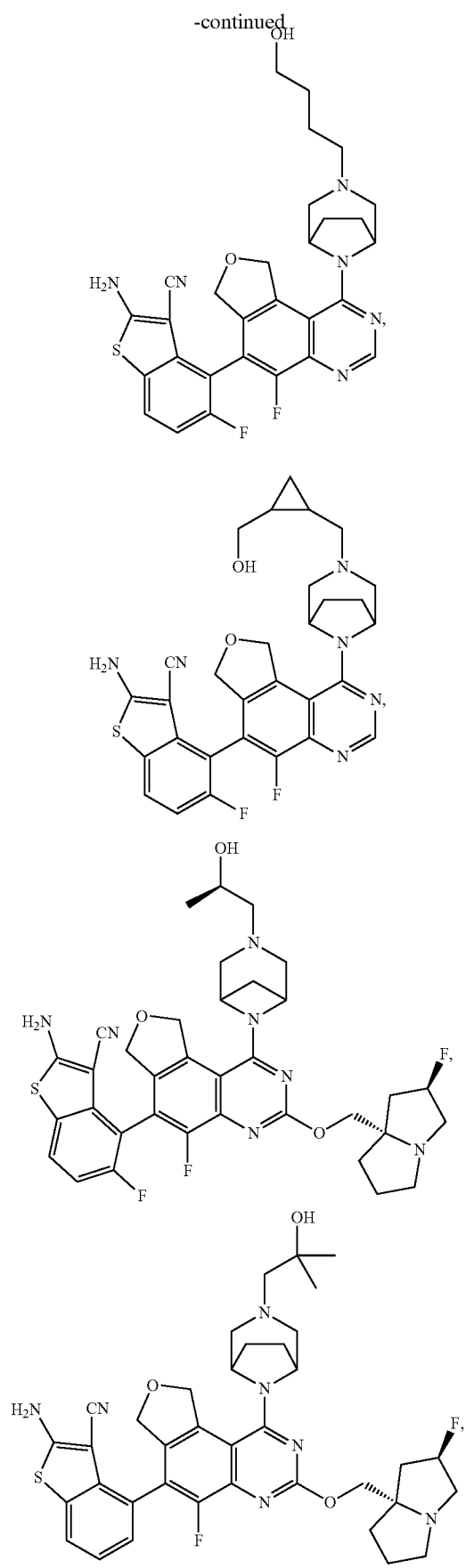

271
-continued
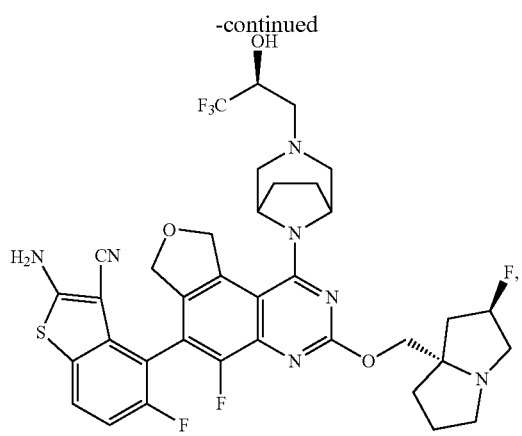
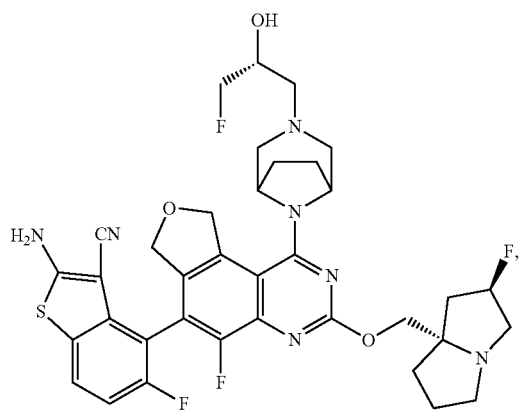
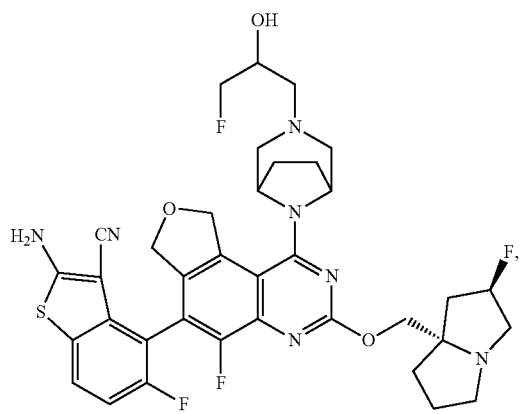
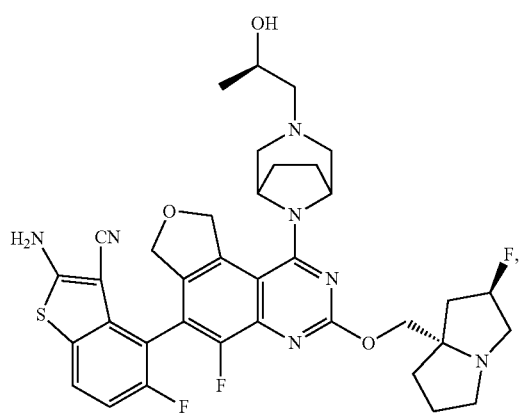
272
-continued
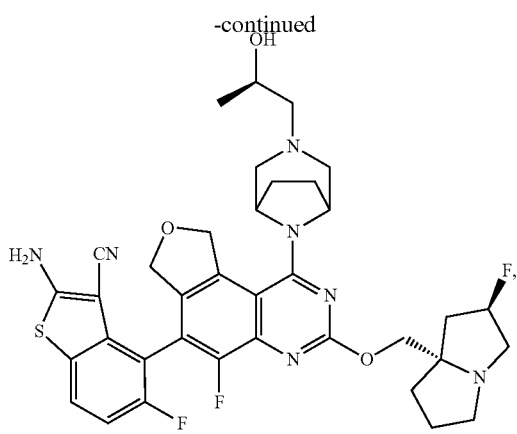
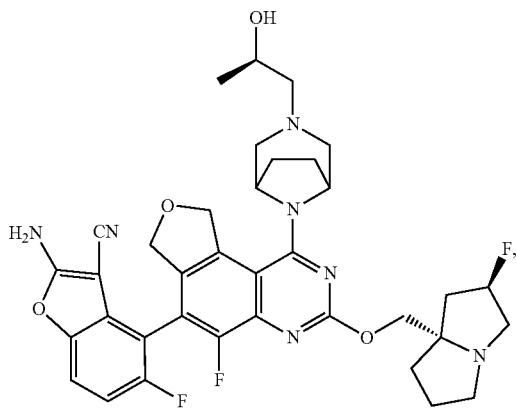
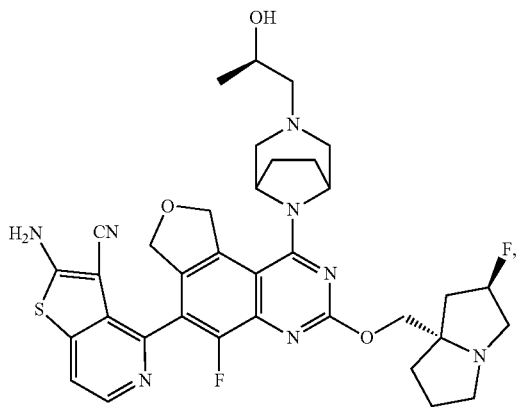
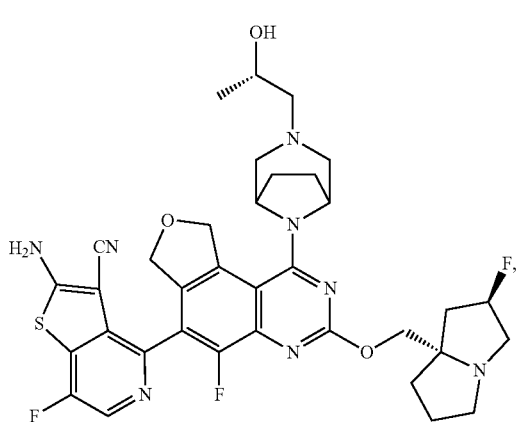

-continued
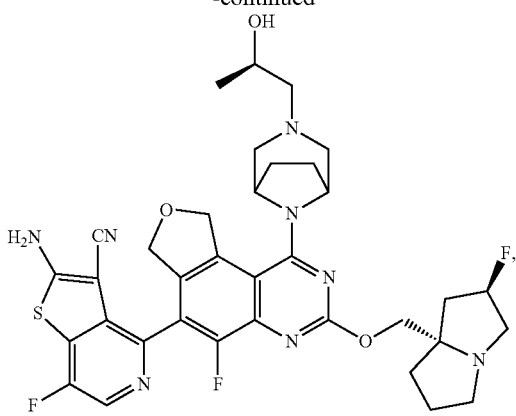
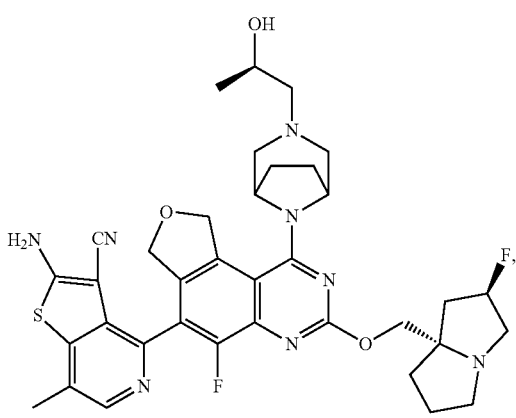
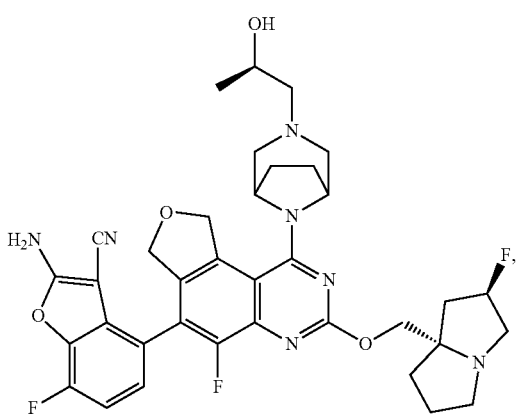
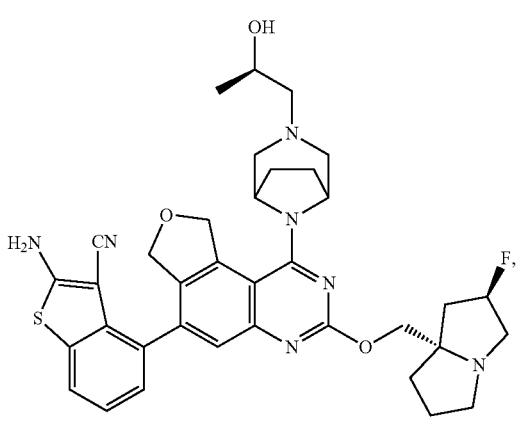
-continued
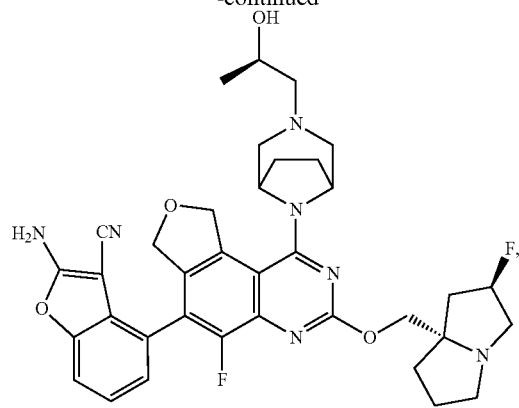
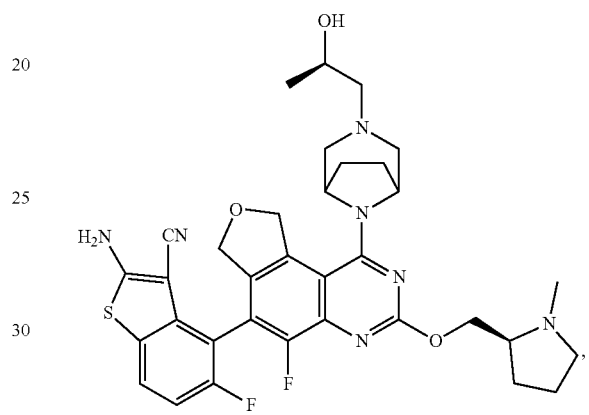
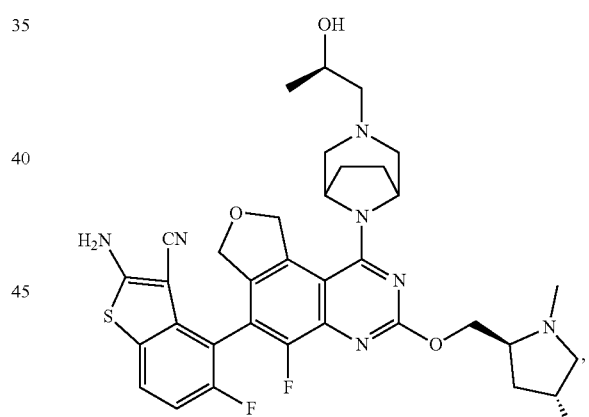
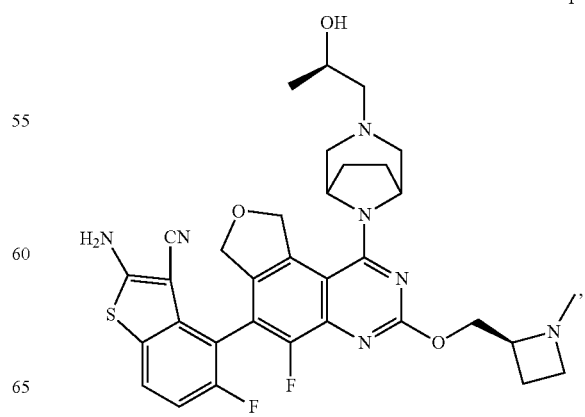

275
-continued
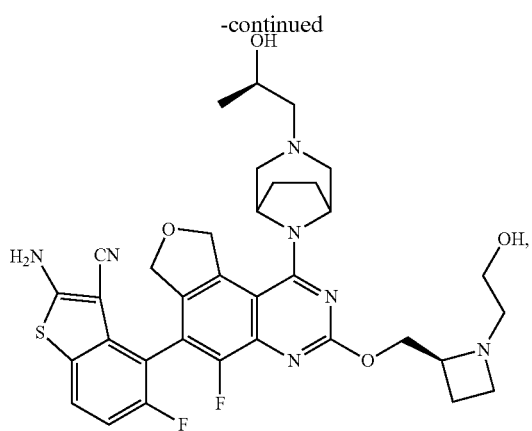
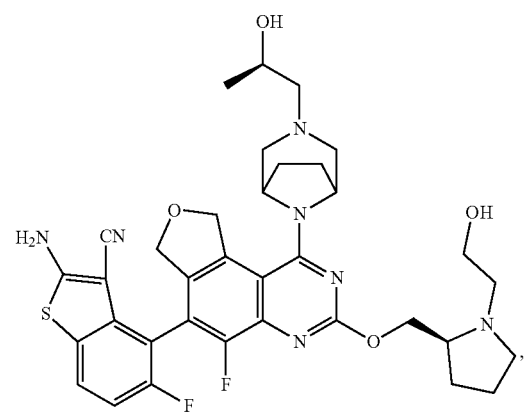
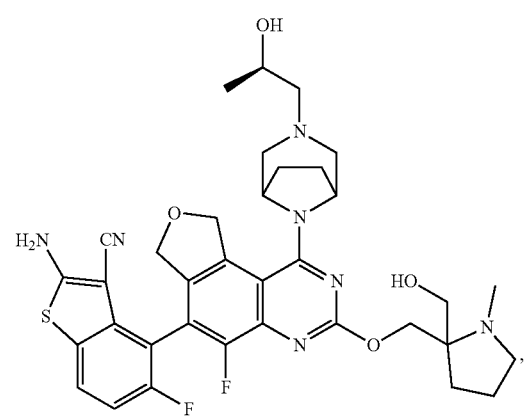
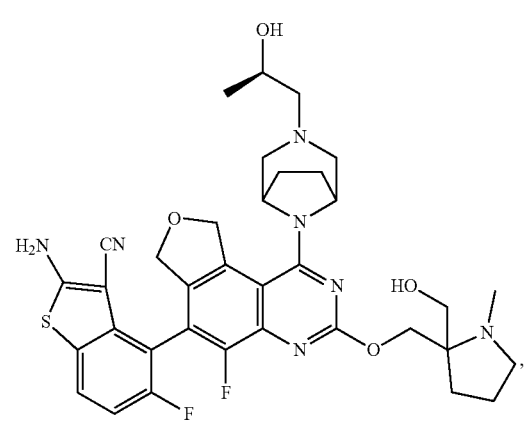
276
-continued
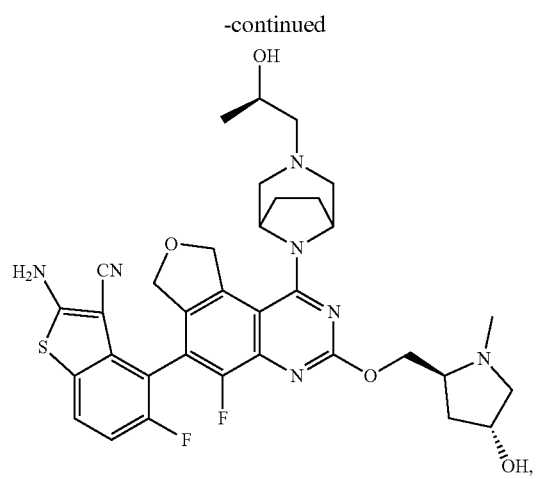
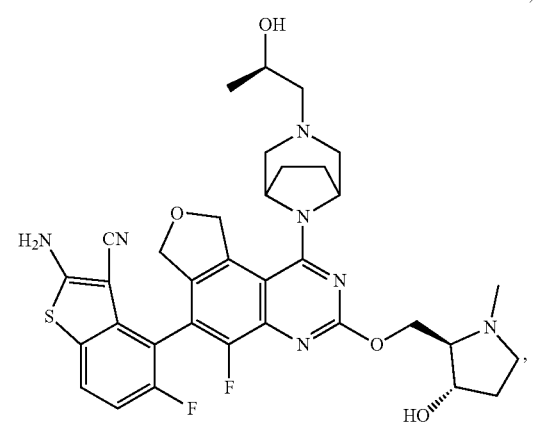
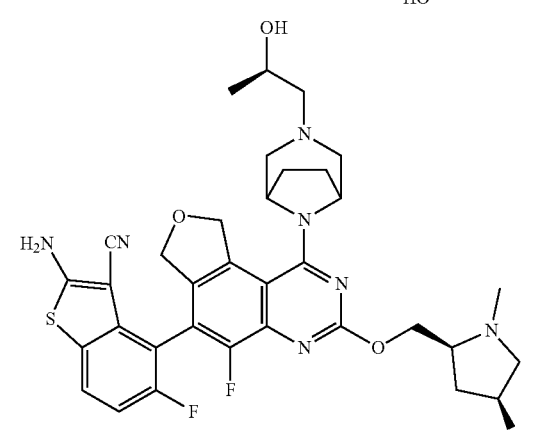
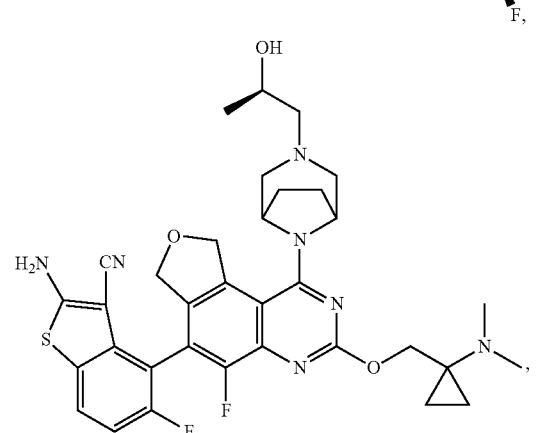

277
-continued
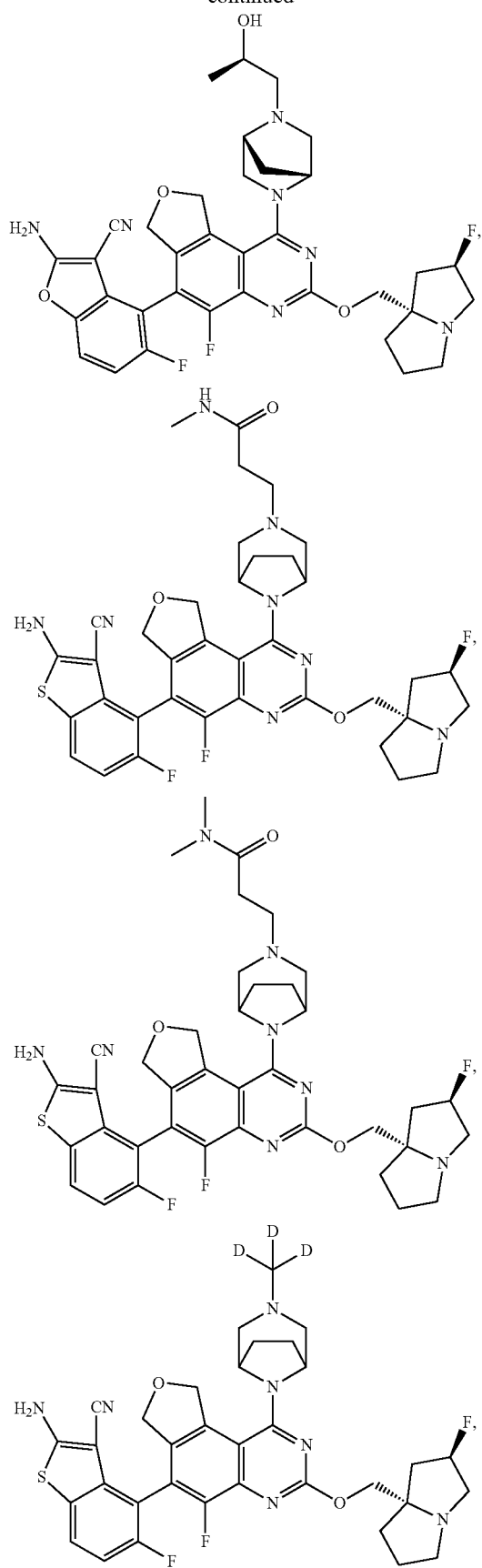
278
-continued
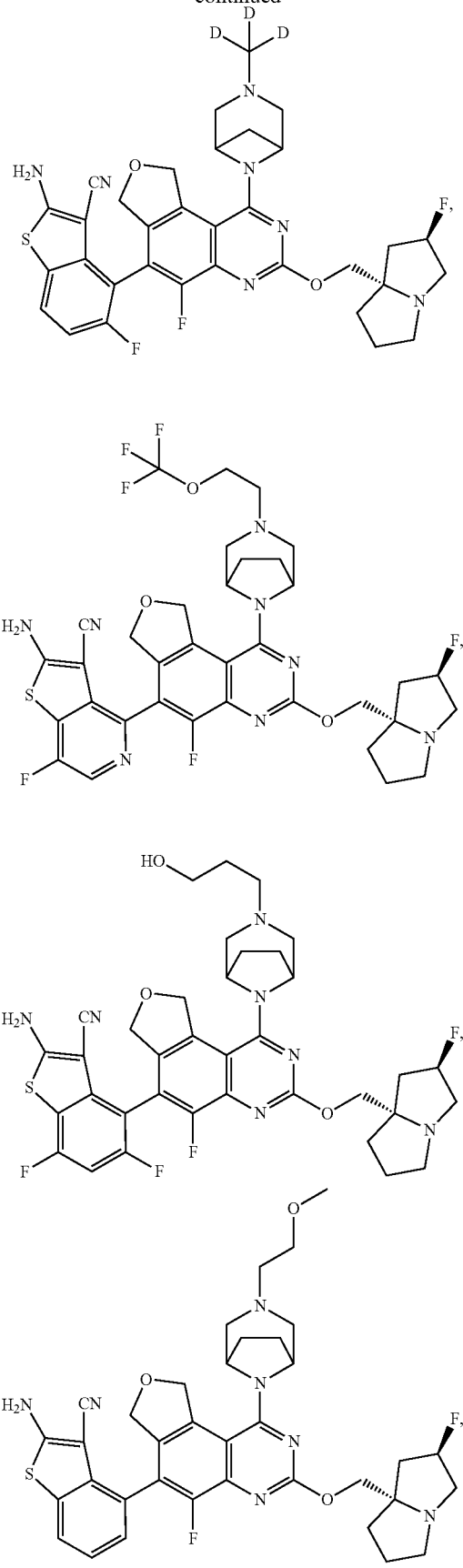

-continued
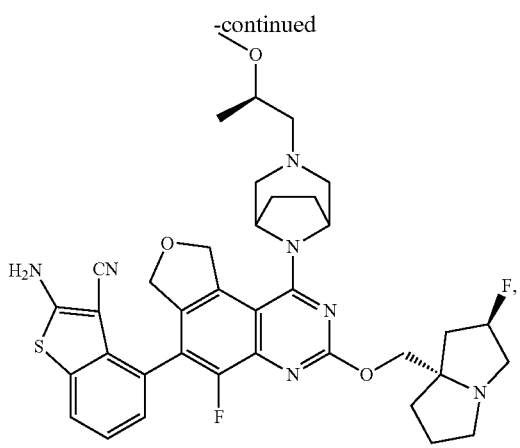
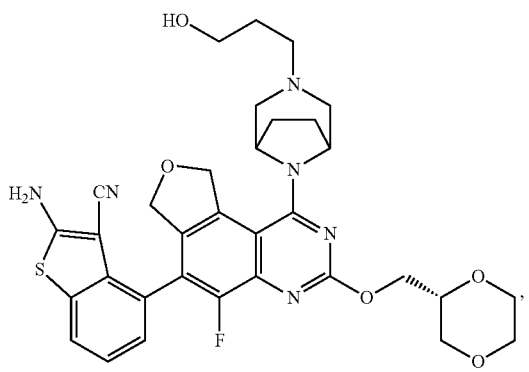
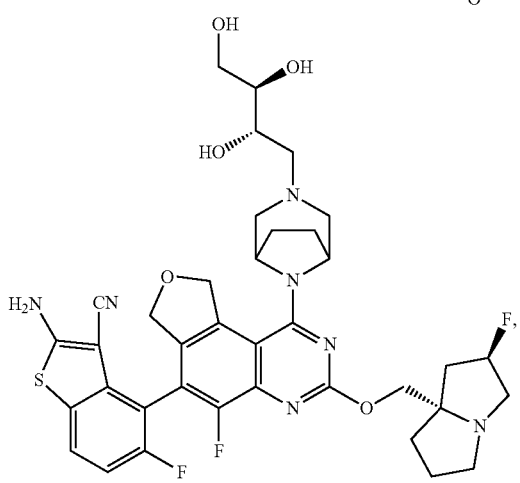
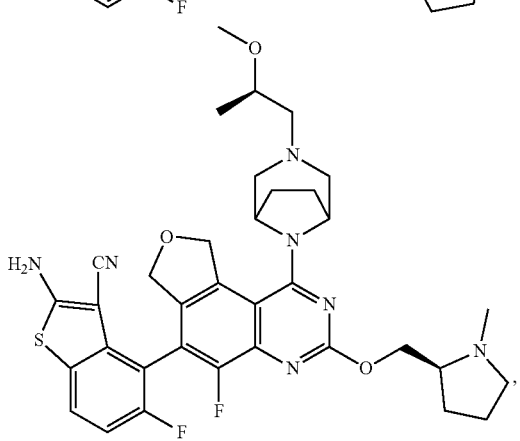
-continued
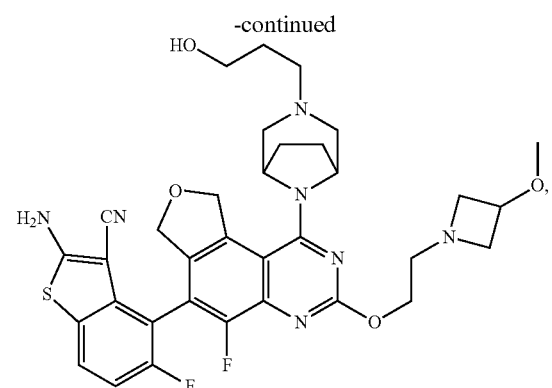
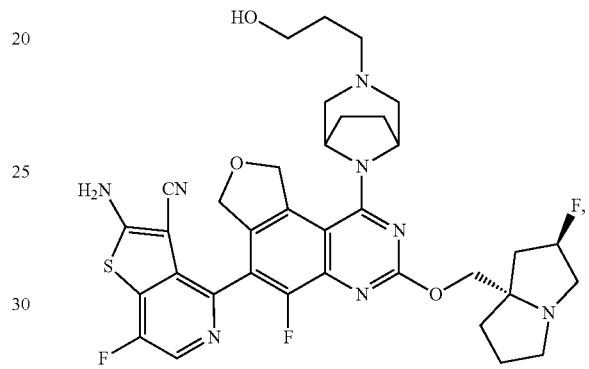
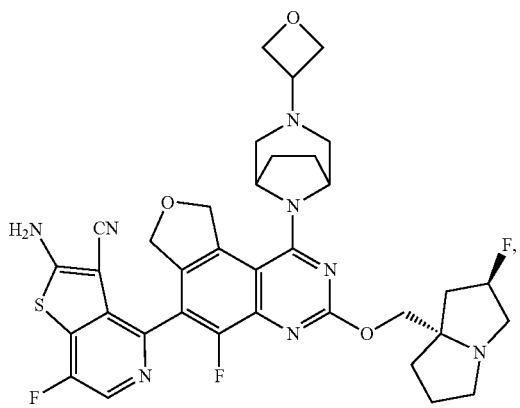
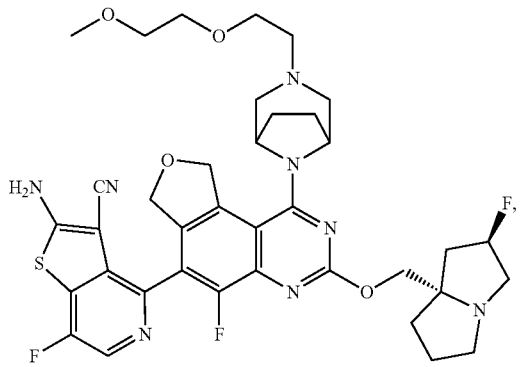

281
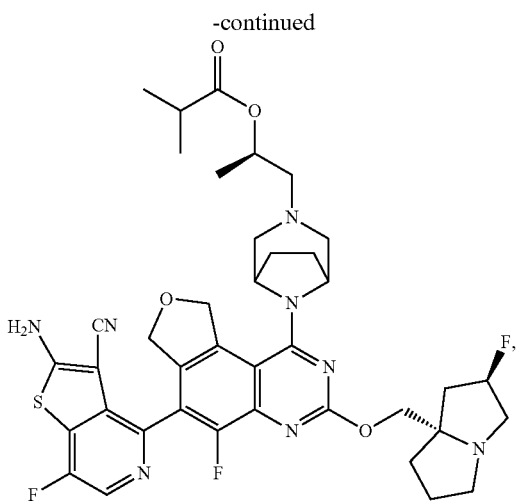
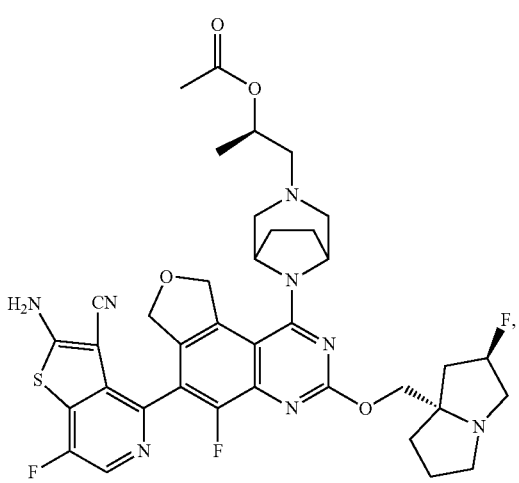
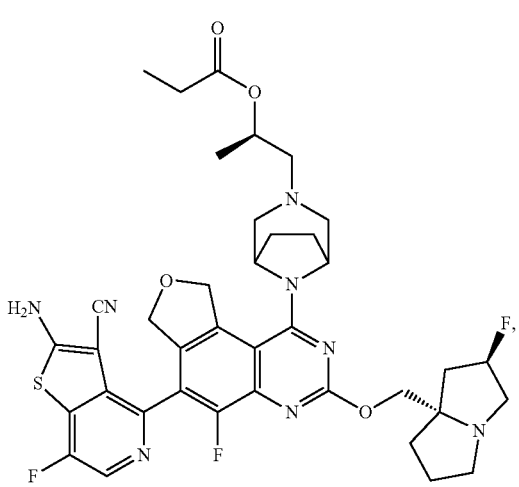
282
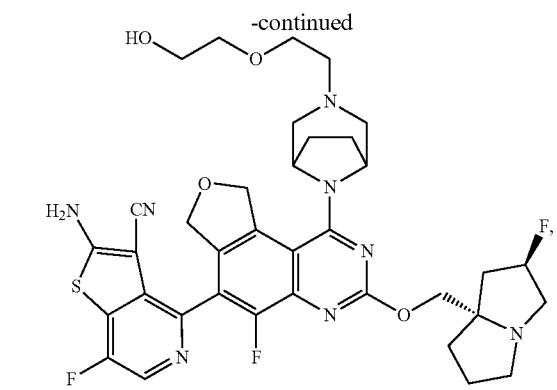
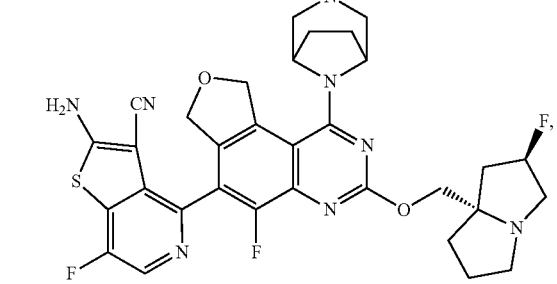
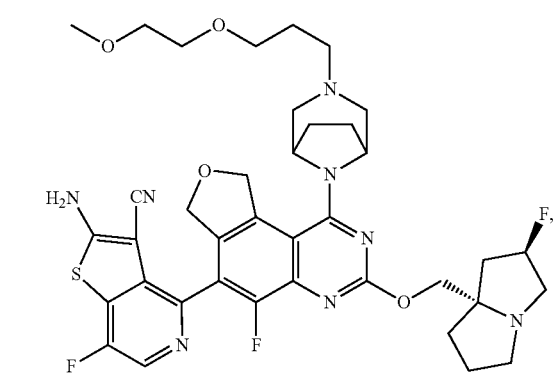
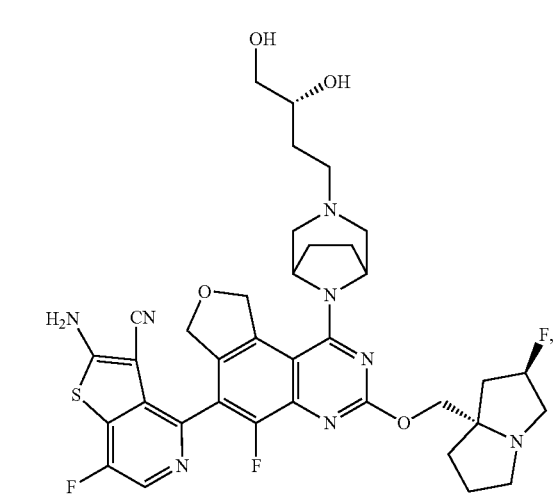

283
-continued
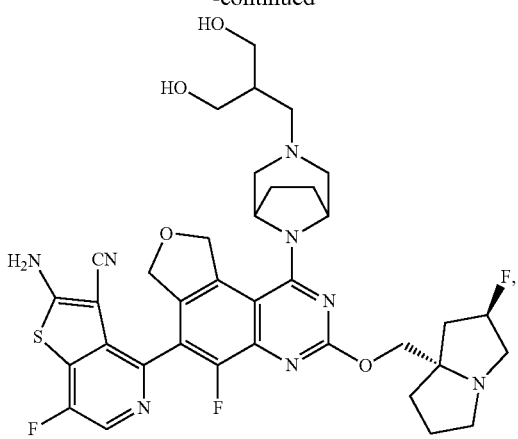
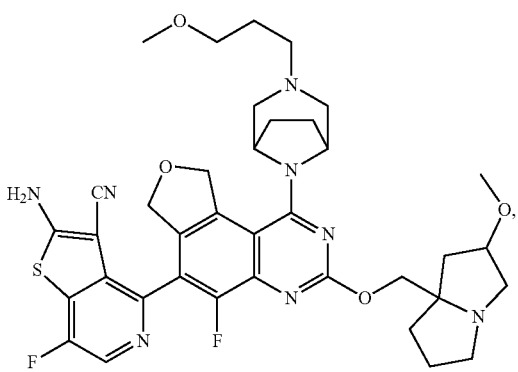
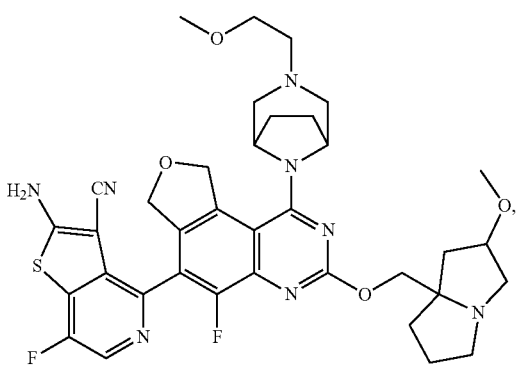
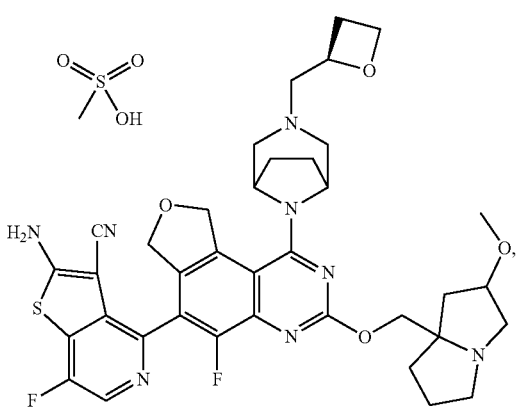
284
-continued
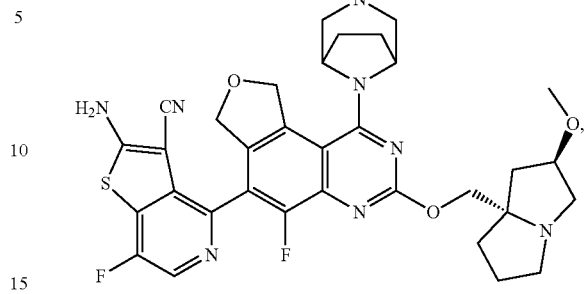
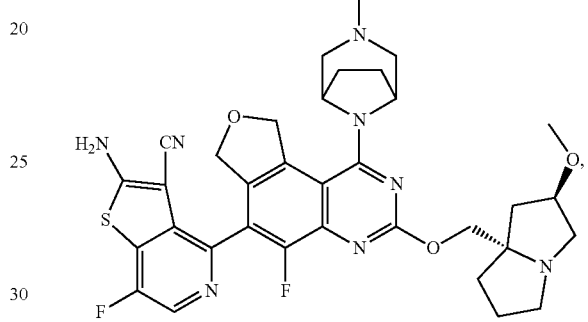
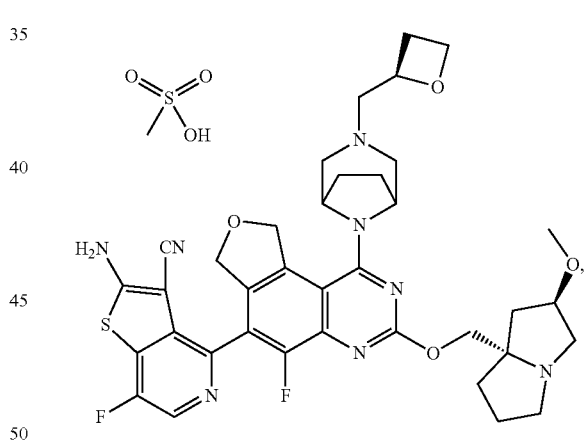
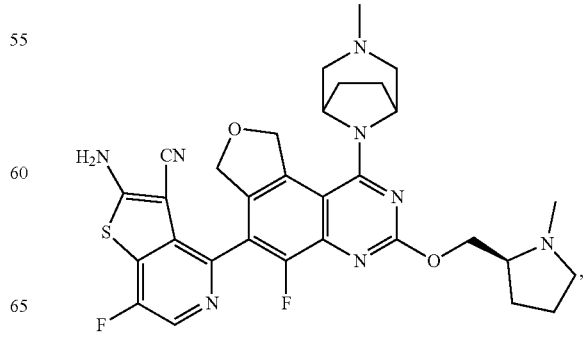

285
-continued
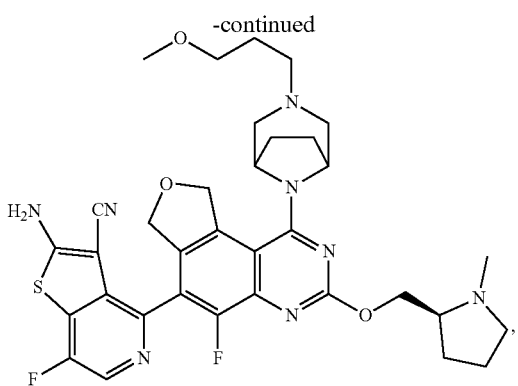
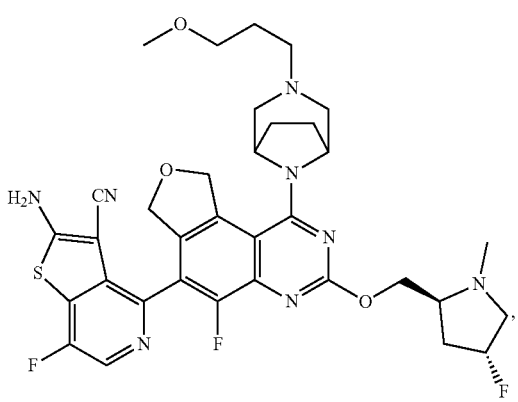
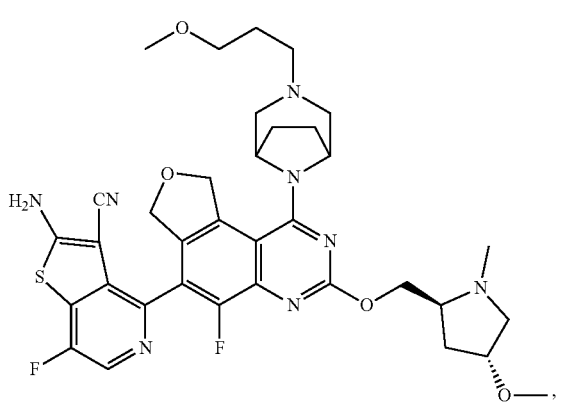
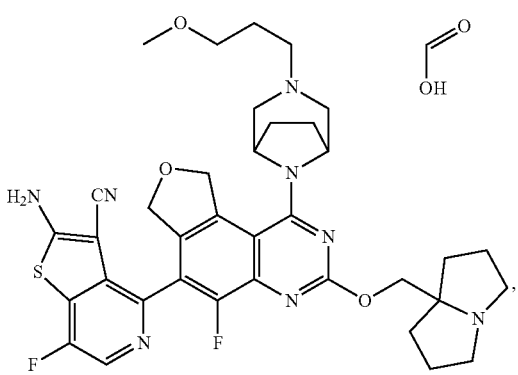
286
-continued
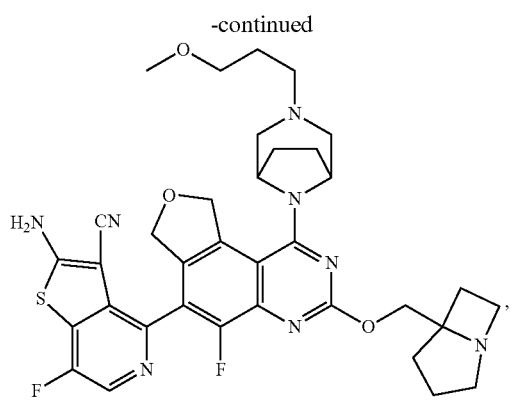
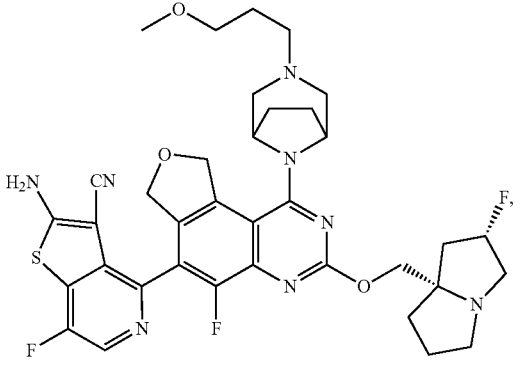
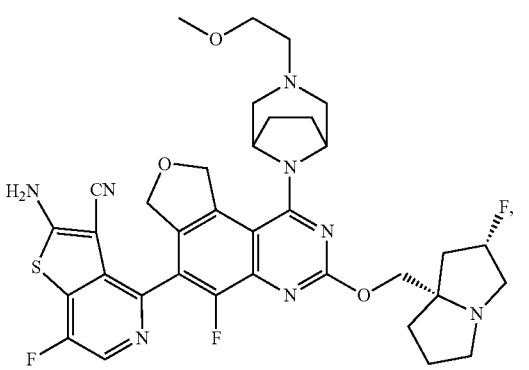
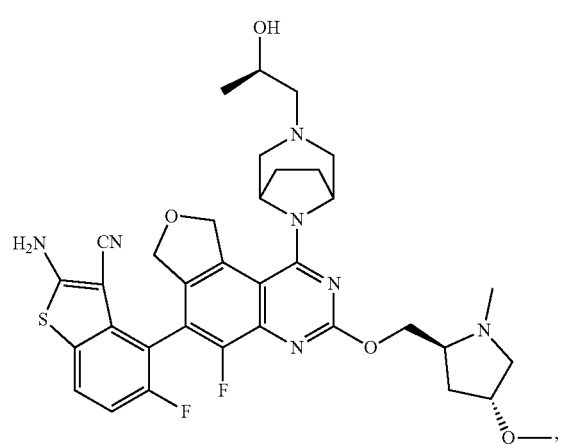

287
-continued
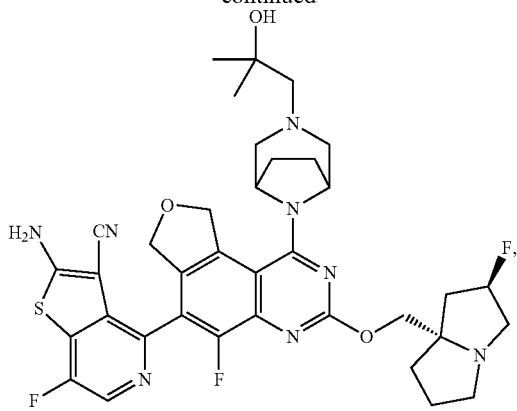
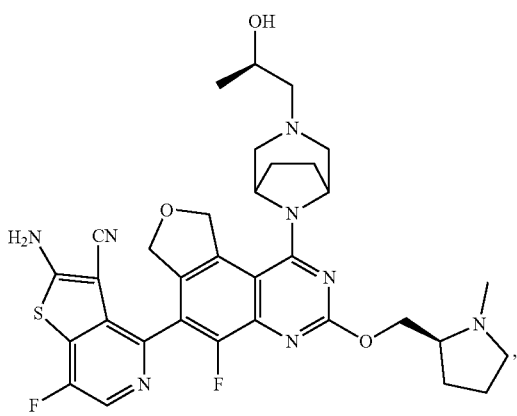
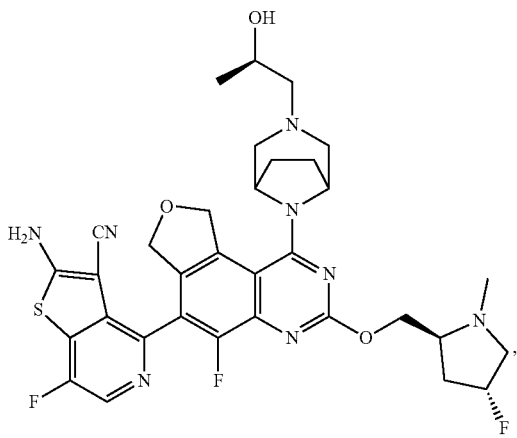
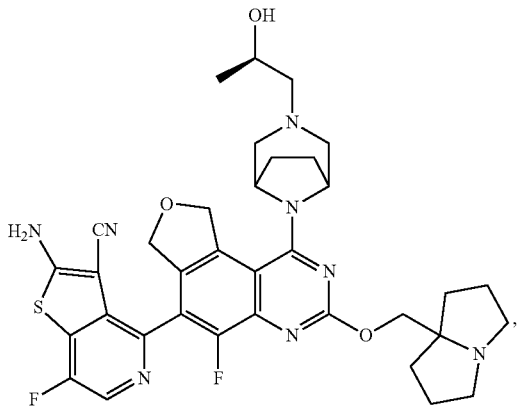
288
-continued
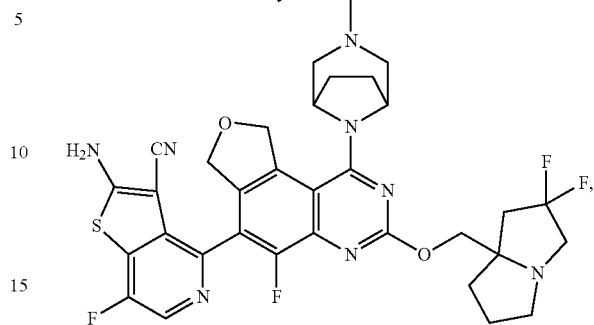
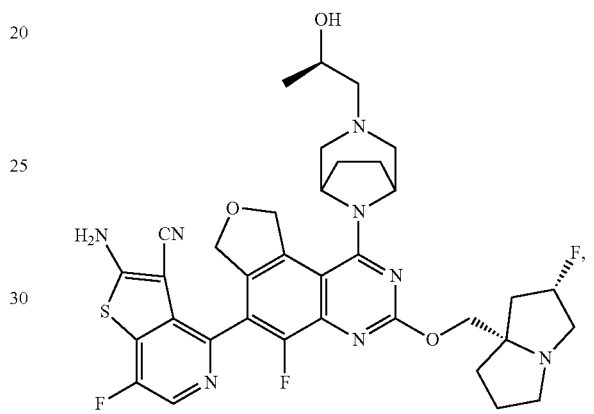
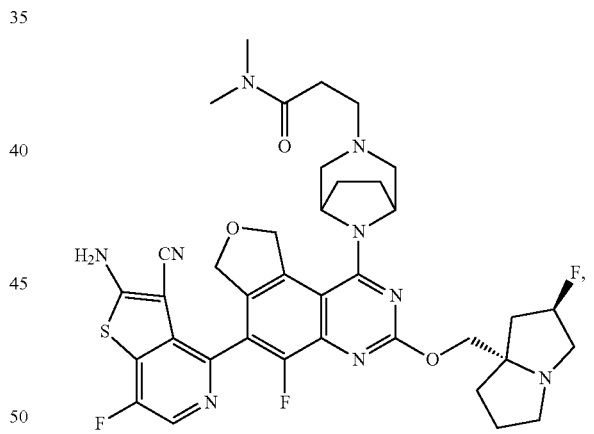
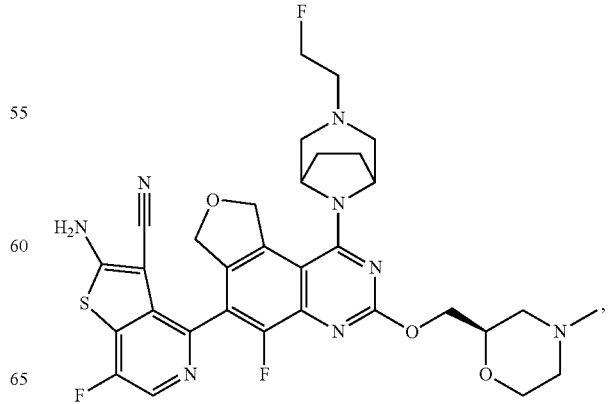

289
-continued
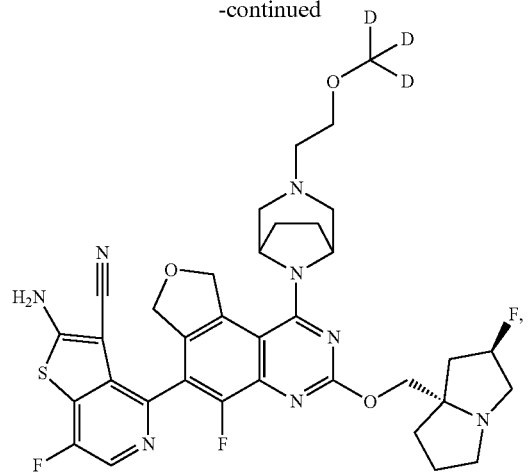
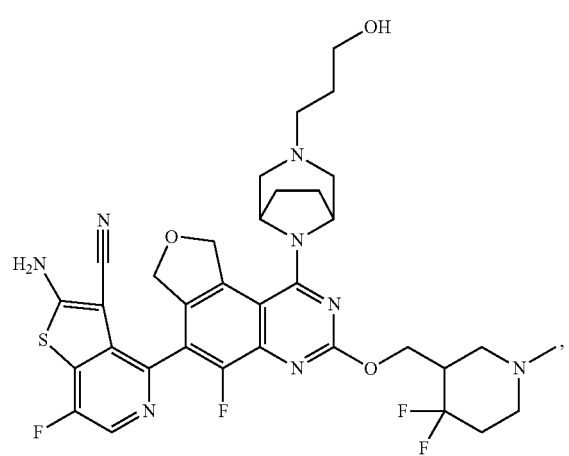
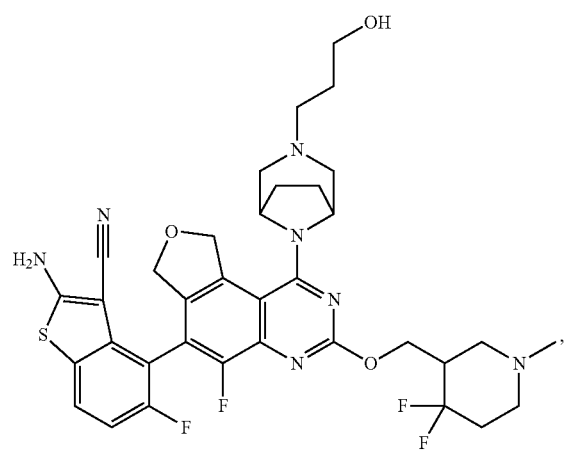
290
-continued
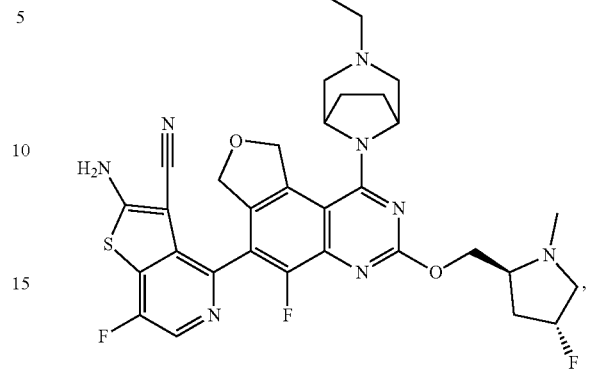
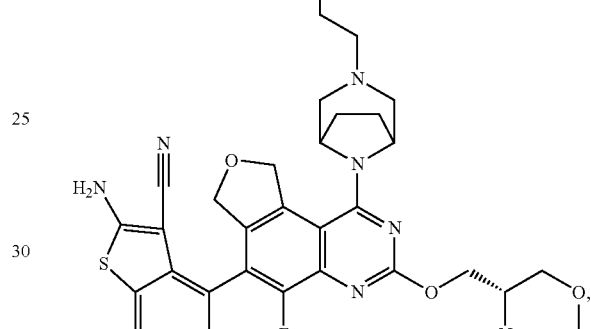
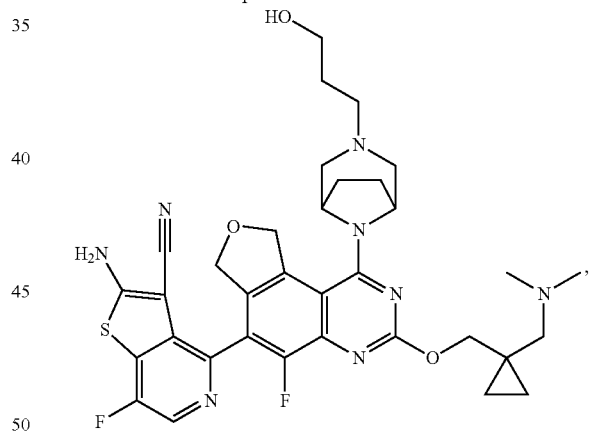
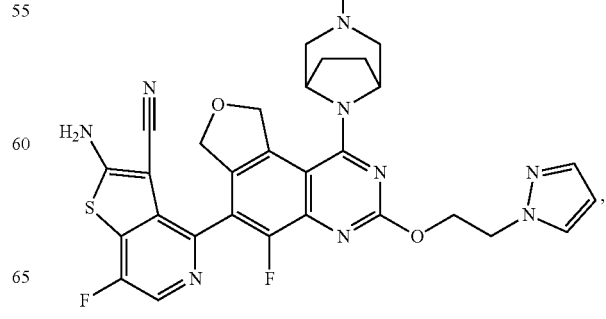

291
-continued
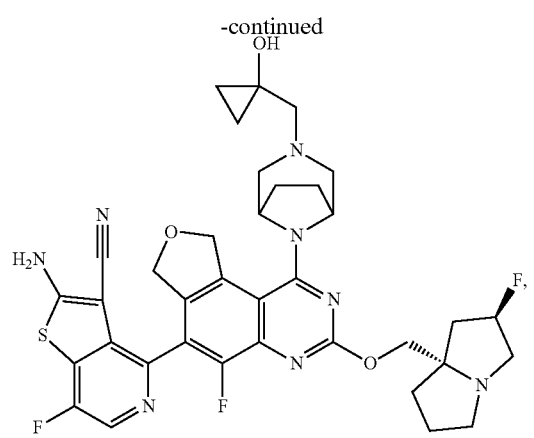
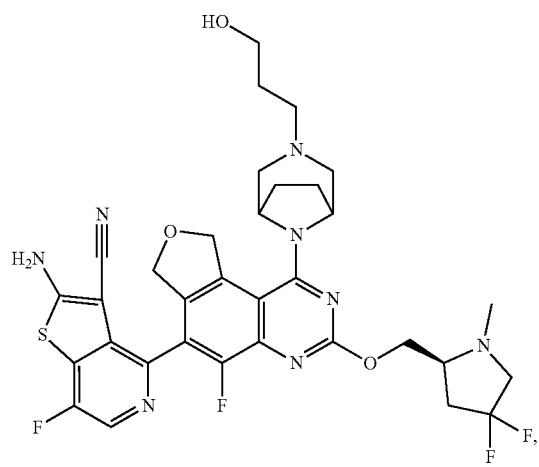
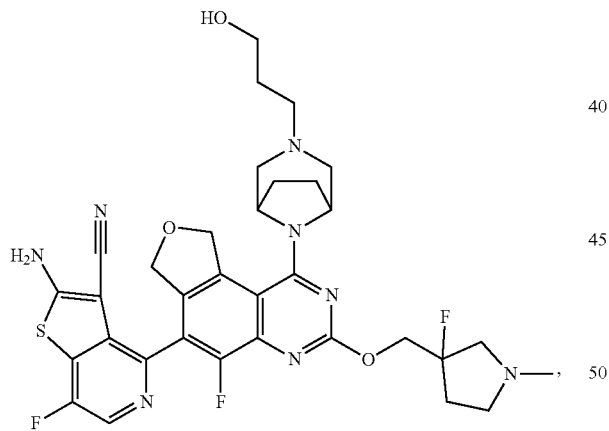
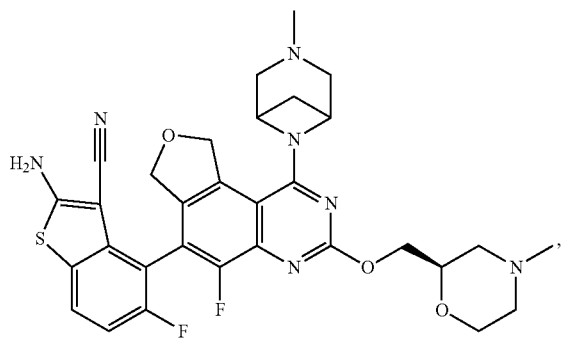
292
-continued
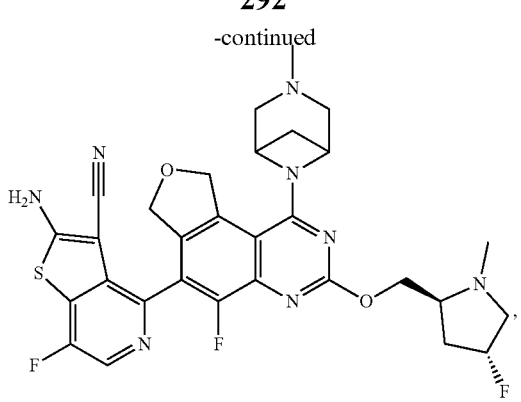
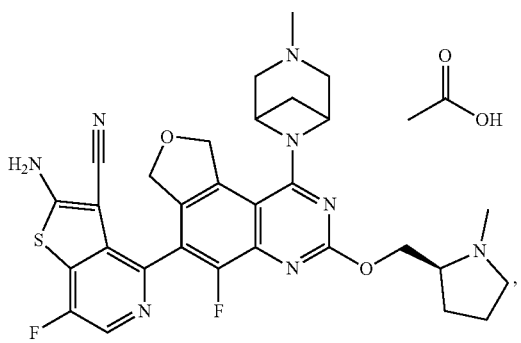
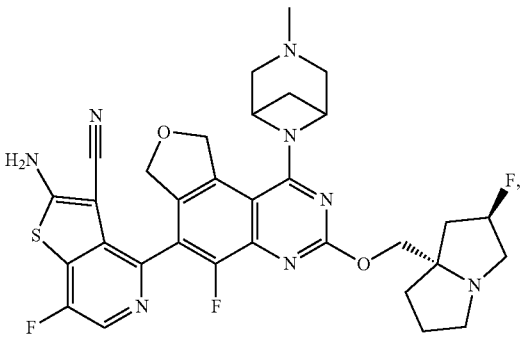
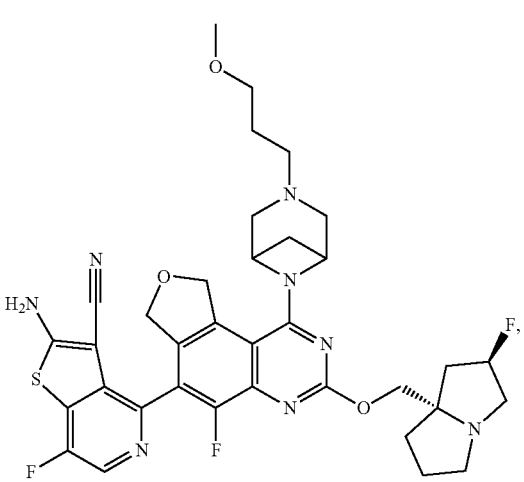

293
-continued
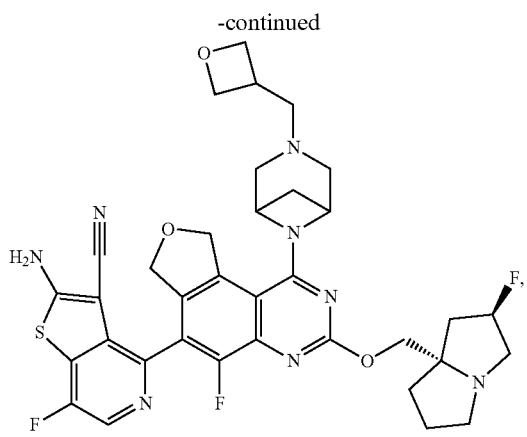
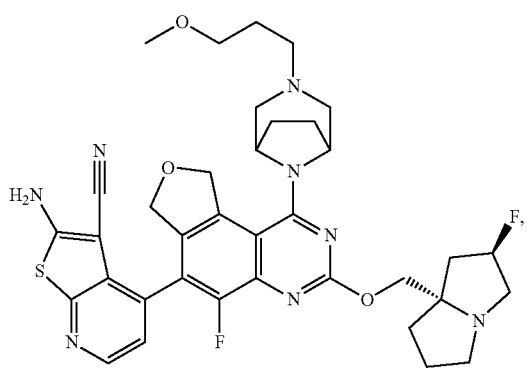
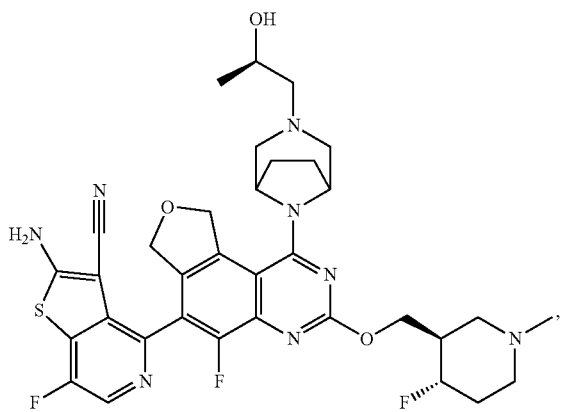
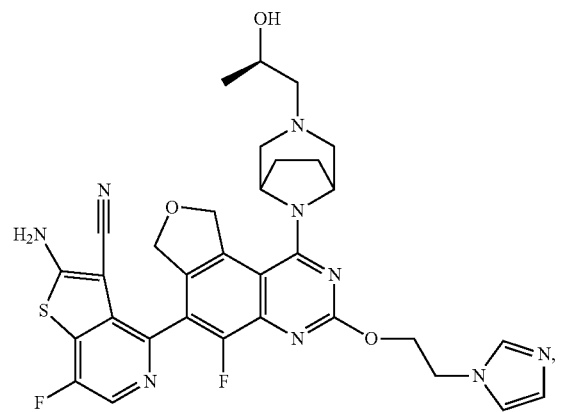
294
-continued
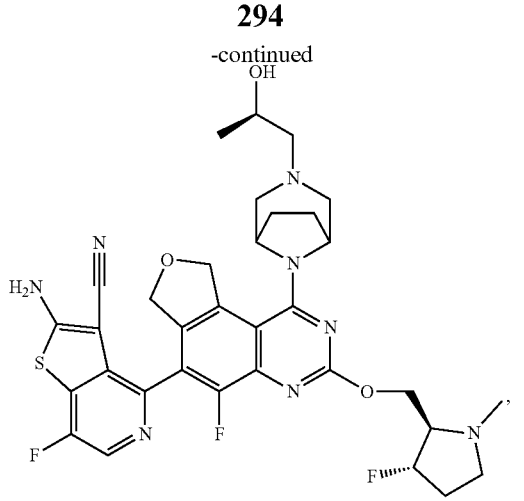
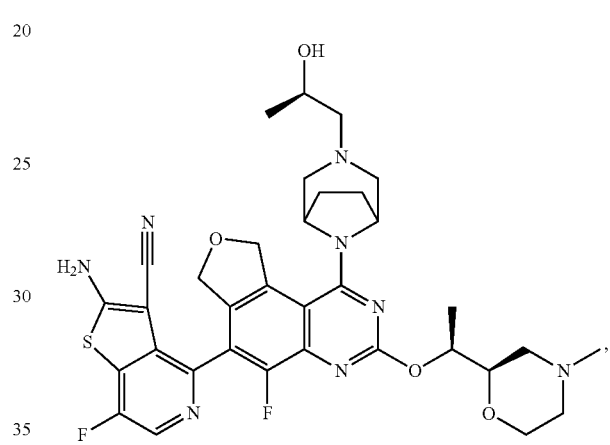
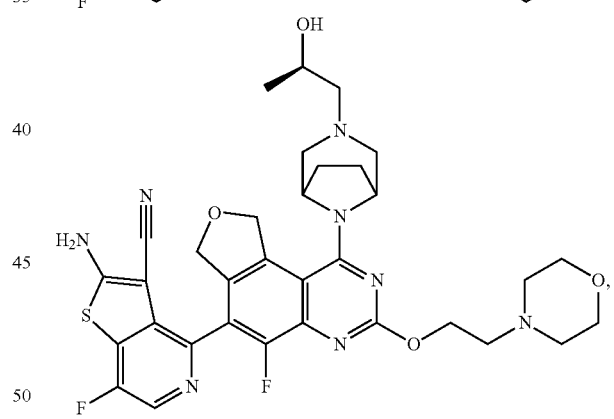
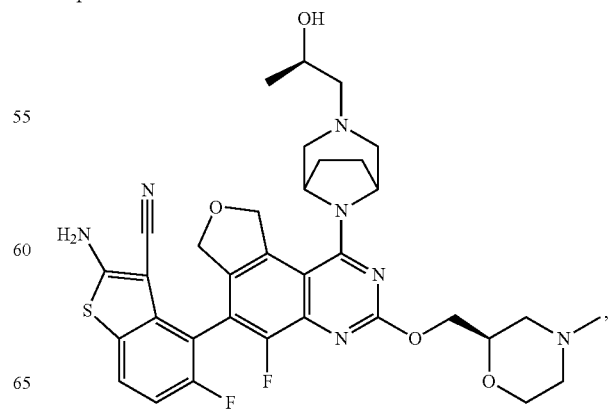

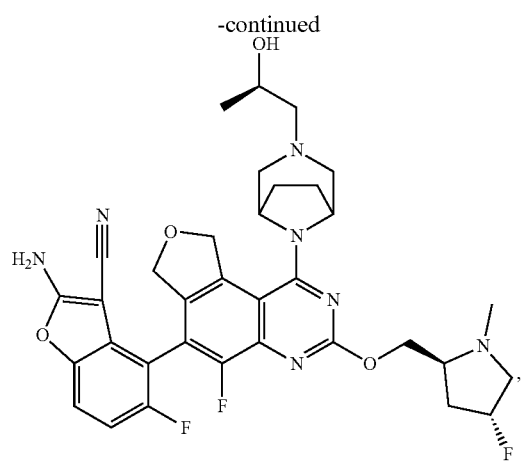
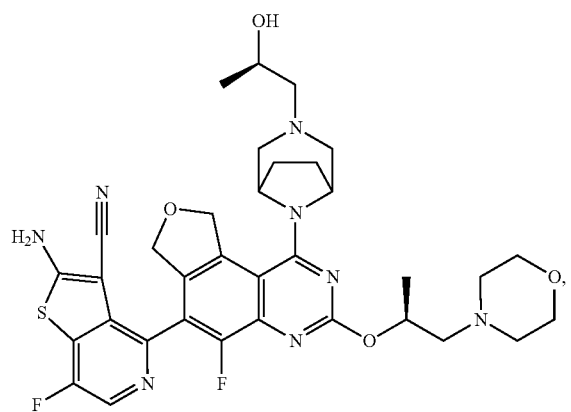
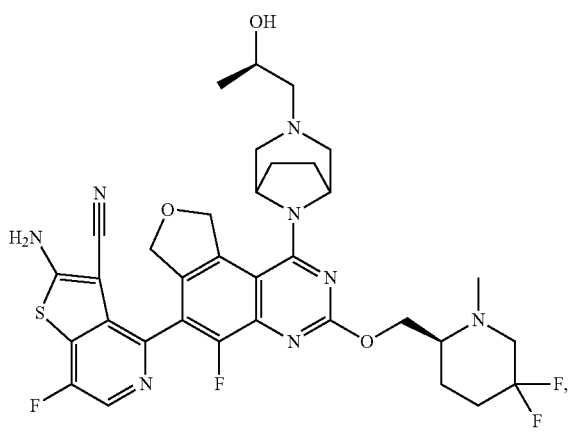
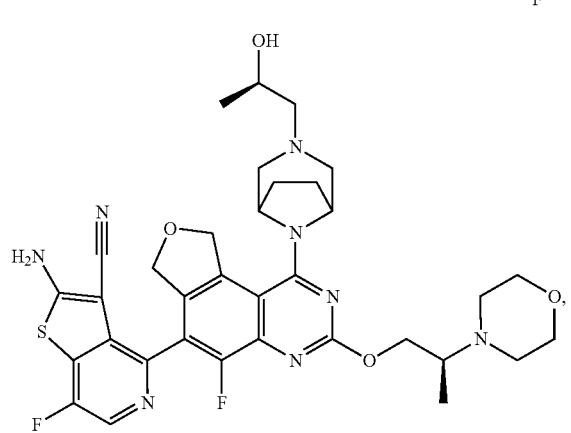
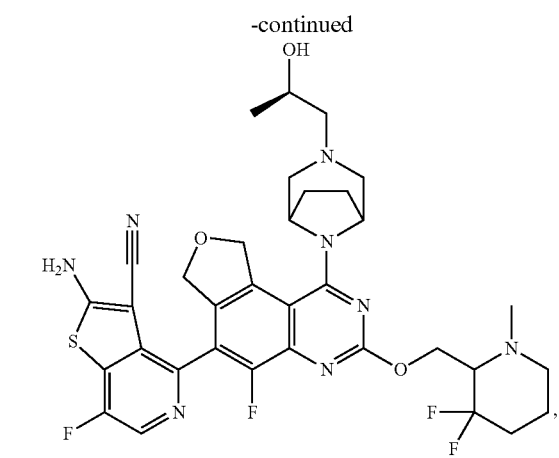
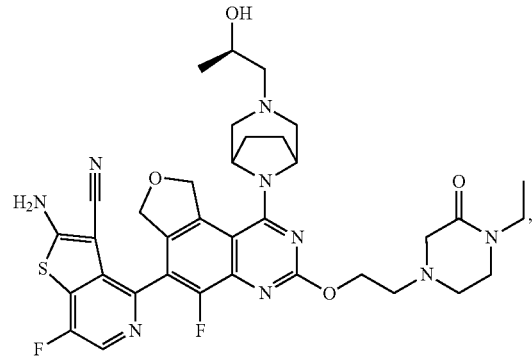
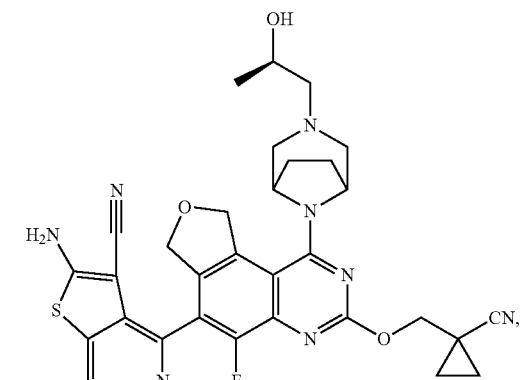
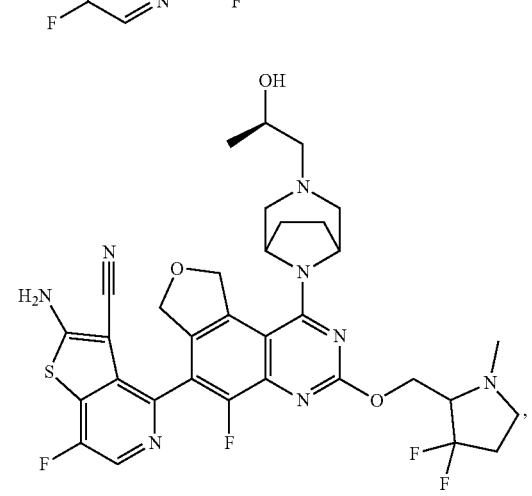

297
-continued
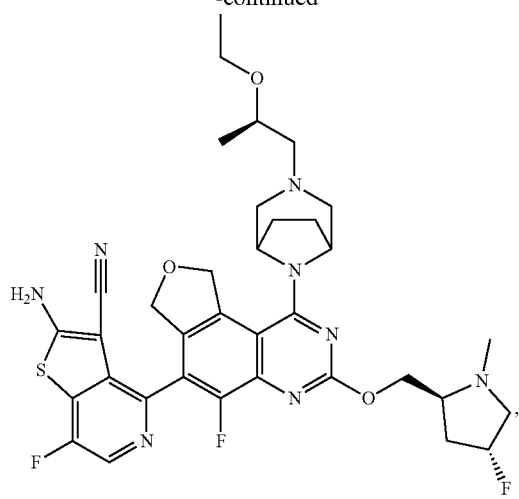
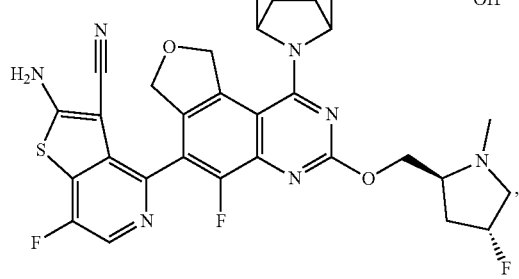
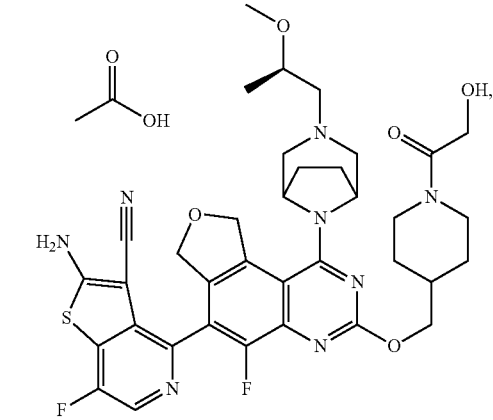
298
-continued
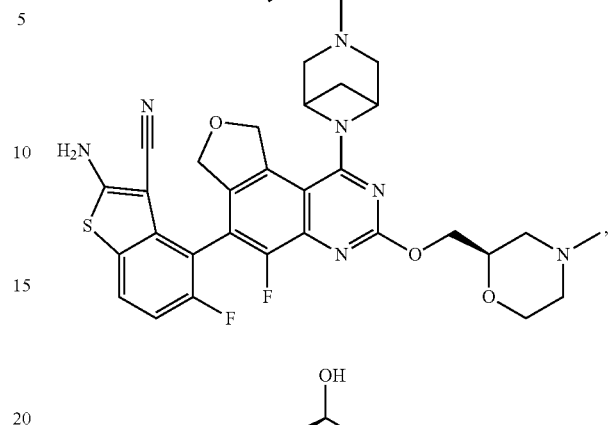
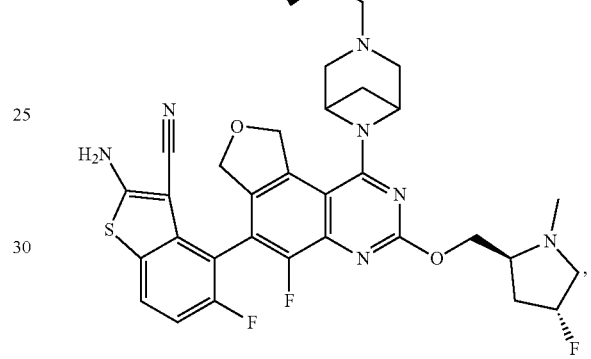
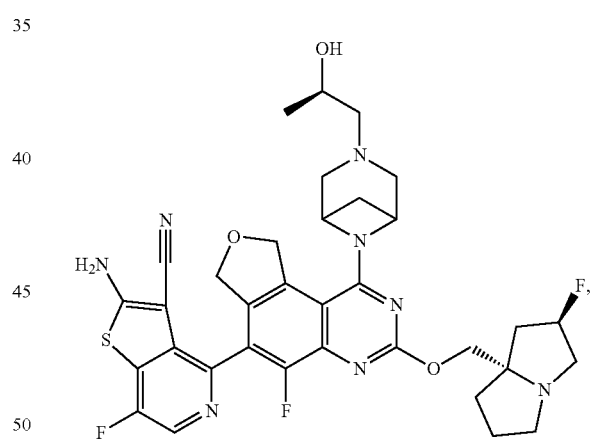
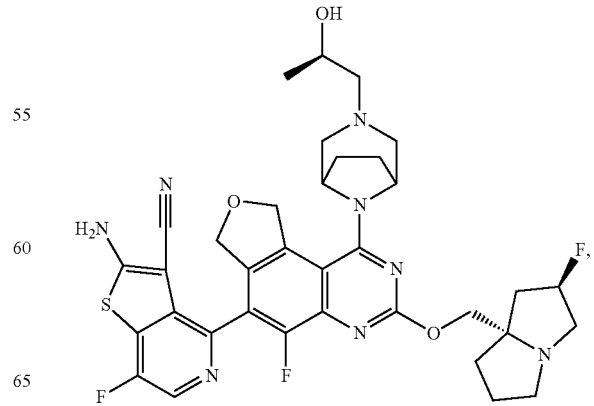

299
-continued
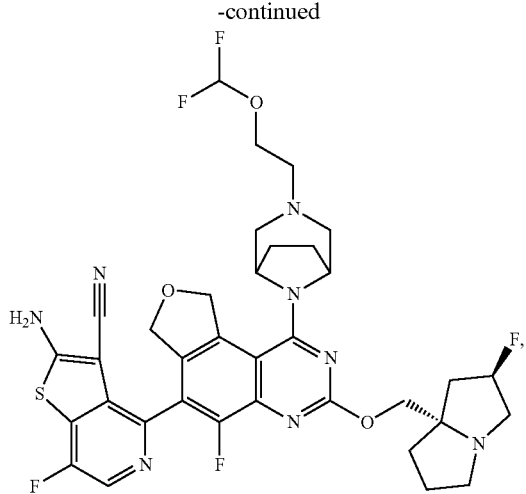
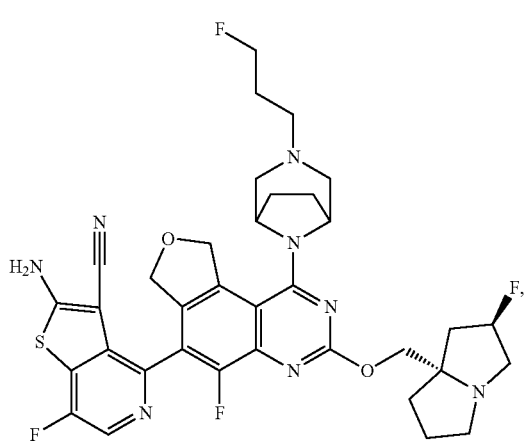
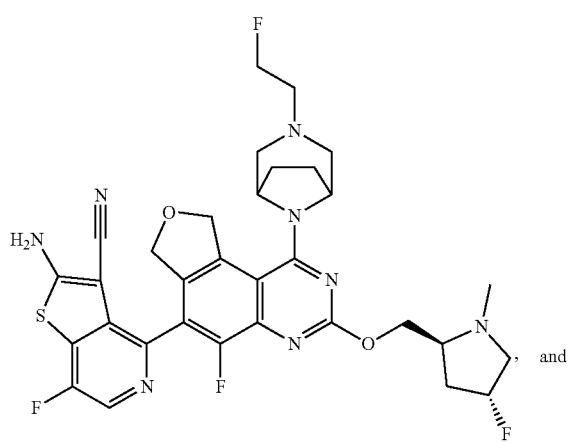, and
300
-continued
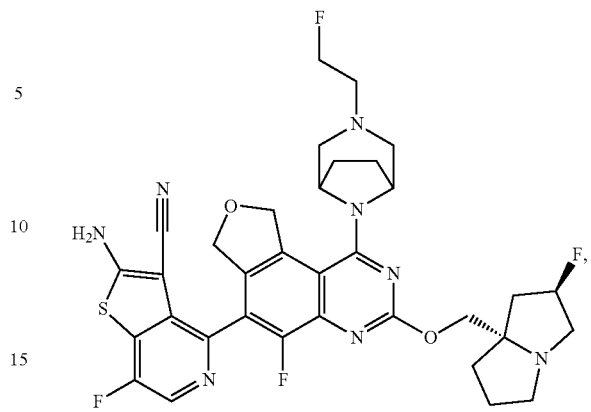
or a pharmaceutically acceptable salt thereof.
A further compound of Formulae I, Ia, II, IIa, III, IIIa, IV, or IVa or a pharmaceutically acceptable salt thereof, the compound is selected from
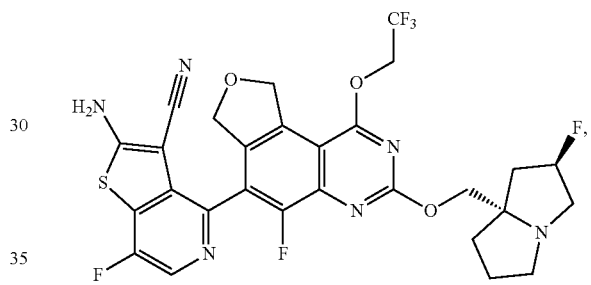
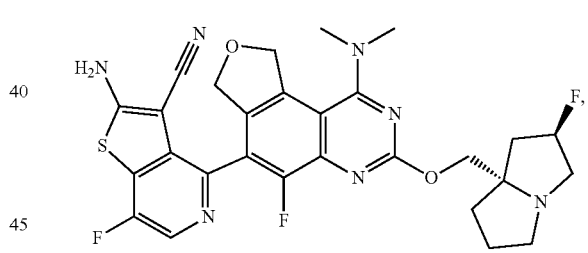
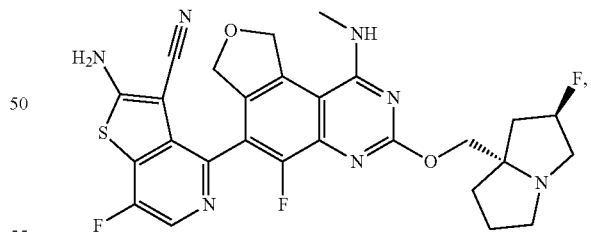
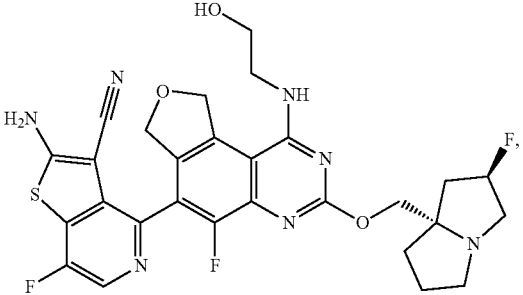

-continued

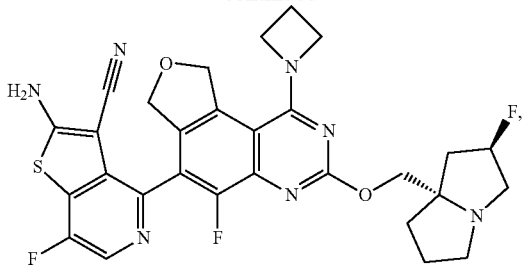

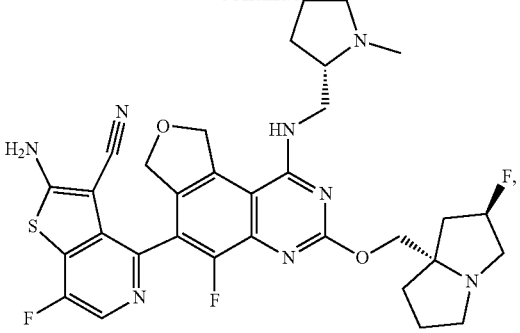

pharmaceutically acceptable salt thereof.

Also provided herein are pharmaceutical compositions comprising a compound according to any one of Formulae I-VIII (including Ia-VIIa), or a pharmaceutically acceptable salt thereof, examples of which include, but are not limited to, the compounds in Table A, and a pharmaceutically acceptable carrier, diluent, or excipient.

Further provided herein are methods of treating cancer, comprising administering to a patient in need thereof, an effective amount of a compound according to any one of Formulae I-VIII (including Ia-VIIa), or a pharmaceutically acceptable salt thereof. In this method, the cancer can be lung cancer, colorectal cancer, pancreatic cancer, bladder cancer, cervical cancer, endometrial cancer, ovarian cancer, cholangiocarcinoma, gastric, or esophageal cancer. In this method, the cancer can more specifically be non-small cell lung cancer, pancreatic cancer, or colorectal cancer. In an embodiment the cancer can be non-small cell lung cancer. In an embodiment the cancer can be pancreatic cancer. In an embodiment the cancer can be colorectal cancer.

Also provided herein is a method of treating cancer, comprising administering to a patient in need thereof, an effective amount of a compound according to any one of Formulae I-VIII (including Ia-VIIa), or a pharmaceutically acceptable salt thereof, in which the cancer has one or more cells that express a mutant KRas G12D protein. In this method, the cancer can be non-small cell lung cancer, pancreatic cancer, or colorectal cancer, in which the cancer has one or more cells that express a KRas G12D mutant protein. In an embodiment, the cancer is non-small cell lung carcinoma in which the cancer has one or more cells that express a KRas G12D mutant protein. In an embodiment, the cancer is mutant pancreatic cancer in which the cancer has one or more cells that express a KRas G12D mutant protein. In an embodiment, the cancer is colorectal carcinoma in which the cancer has one or more cells that express a KRas G12D mutant protein. This method also includes treating KRas G12D mutant bearing cancers of other origins.

Further provided herein is a method of treating a patient with a cancer that has a KRas G12D mutation comprising administering to a patient in need thereof an effective amount of a compound according to any one of Formulae I-VII or a pharmaceutically acceptable salt thereof. In this method, the cancer that has a KRas G12D mutation can be KRas G12D mutant lung cancer, KRas G12D mutant pancreatic cancer, KRas G12D mutant cervical cancer, KRas G12D mutant esophageal cancer, KRas G12D mutant endometrial cancer, KRas G12D mutant ovarian cancer, KRas G12D mutant cholangiocarcinoma, and KRas G12D mutant colorectal cancer. In an embodiment the cancer that has a KRas G12D mutation can be KRas G12D mutant non-small cell lung cancer. In an embodiment the cancer that has a KRas G12D mutation can be KRas G12D mutant pancreatic cancer. In an embodiment the cancer that has a KRas G12D mutation can be KRas G12D mutant colorectal cancer.

Additionally provided herein is a method of modulating a mutant KRas G12D enzyme in a patient in need thereof, by administering a compound according to any one of I-VIII (including Ia-VIIa), or a pharmaceutically acceptable salt thereof. In one embodiment this method comprises inhibiting a human mutant KRas G12D enzyme.

Also provided herein is a method of treating cancer in a patient in need thereof, wherein the patient has a cancer that was determined to express the KRas G12D mutant protein. The method comprises administering to a patient an effective amount of a compound according to any one of I-VIII (including Ia-VIIa), or a pharmaceutically acceptable salt thereof. The G12D mutational status of one or more cancer cells can be determined by a number of assays known in the art. Typically, one or more biopsies containing one or more cancer cells are obtained, and subjected to sequencing and/or polymerase chain reaction (PCR). Circulating cell-free DNA can also be used, e.g. in advanced cancers. Non-limiting examples of sequencing and PCR techniques used to determine the mutational status (e.g., G12D mutational status, in one or more cancer cells or in circulating cell-free DNA) include direct sequencing, next-generation sequencing, reverse transcription polymerase chain reaction (RT-PCR), multiplex PCR, and pyrosequencing and multi-analyte profiling.

Further provided herein is a compound or a pharmaceutically acceptable salt thereof according to any one of Formulae I-VII for use in therapy. The compound or a pharmaceutically acceptable salt thereof, can be for use in treating cancer. For this use in treating cancer, the cancer can be lung cancer, colorectal cancer, pancreatic cancer, bladder cancer, cervical cancer, endometrial cancer, ovarian cancer, cholangiocarcinoma, or esophageal cancer. The cancer can more specifically be non-small cell lung cancer, pancreatic cancer, or colorectal cancer. In an embodiment, the cancer is non-small cell lung cancer. In an embodiment, the cancer is pancreatic cancer. In an embodiment, the cancer is colorectal cancer. The cancer can have one or more cancer cells that express the mutant KRas G12D protein such as KRas G12D mutant lung cancer, KRas G12D mutant pancreatic cancer, KRas G12D mutant cervical cancer, KRas G12D mutant esophageal cancer, KRas G12D mutant endometrial cancer, KRas G12D mutant ovarian cancer, KRas G12D mutant cholangiocarcinoma, and KRas G12D mutant colorectal cancer. In these uses, the cancer is selected from: KRas G12D mutant non-small cell lung cancer, KRas G12D mutant colorectal cancer, and KRas G12D mutant pancreatic cancer. Additionally, the cancer can be non-small cell lung cancer, and one or more cells express KRas G12D mutant protein. Further, the cancer can be colorectal cancer, and one or more cells express KRas G12D mutant protein. Additionally, the cancer can be pancreatic cancer, and one or more cells express KRas G12D mutant protein. The patient can have a cancer that was determined to have one or more cells expressing the KRas G12D mutant protein prior to administration of the compound or a pharmaceutically acceptable salt thereof. The patient may have been treated with a different course of treatment prior to being treated as described herein.

The compounds provided herein according to any one of I-VIII (including Ia-VIIa), or a pharmaceutically acceptable salt thereof, may also be used in the manufacture of a medicament for treating cancer. When used in the manufacture of a medicament, the cancer can be lung cancer, colorectal cancer, pancreatic cancer, bladder cancer, cervical cancer, endometrial cancer, ovarian cancer, cholangiocarcinoma, or esophageal cancer. The cancer can more specifically be non-small cell lung cancer, pancreatic cancer, or colorectal cancer. In an embodiment, the cancer is non-small cell lung cancer. In an embodiment, the cancer is pancreatic cancer. In an embodiment, the cancer is colorectal cancer. The cancer can have one or more cancer cells that express the mutant KRas G12D protein. When the cancer cells express KRas G12D protein, the cancer can be selected from KRas G12D mutant non-small cell lung cancer, KRas G12D mutant colorectal cancer, and KRas G12D mutant pancreatic cancer.

Also provided herein is a method of treating cancer, comprising administering to a patient in need thereof, an effective amount of a compound according to any one of I-VIII (including Ia-VIIa), or a pharmaceutically acceptable salt thereof, and one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in which the cancer has one or more cells that express a mutant KRas G12D protein. Further provided herein is a compound according to any one of I-VIII (including Ia-VIIa), or a pharmaceutically acceptable salt thereof, for use in simultaneous, separate, or sequential combination with one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in the treatment of cancer. Additionally provided is a combination comprising a compound according to any one of I-VIII (including Ia-VIIa), or a pharmaceutically acceptable salt thereof, and one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, for simultaneous, separate, or sequential use in the treatment of cancer.

Also provided is a method of treating cancer, comprising administering to a patient in need thereof, an effective amount of a compound according to any one of I-VIII (including Ia-VIIa), or a pharmaceutically acceptable salt thereof, and a PD-1 or PD-L1 inhibitor, in which the cancer has one or more cells that express a mutant KRas G12D protein. Further provided is a compound according to any one of I-VIII (including Ia-VIIa), or a pharmaceutically acceptable salt thereof, for use in simultaneous, separate, or sequential combination with a PD-1 or PD-L1 inhibitor, for use in the treatment of cancer. Additionally provided is a combination comprising a compound according to any one of I-VIII (including Ia-VIIa), or a pharmaceutically acceptable salt thereof, and a PD-1 or PD-L1 inhibitor, for simultaneous, separate, or sequential use in the treatment of cancer. As used herein, the PD-1 or PD-L1 inhibitor can be pembrolizumab; the PD-1 or PD-L1 inhibitor can be nivolumab; the PD-1 or PD-L1 inhibitor can be cemiplimab; the PD-1 or PD-L1 inhibitor can be sintilimab; the PD-1 or PD-L1 inhibitor can be atezolizumab; the PD-1 or PD-L1 inhibitor can be avelumab; the PD-1 or PD-L1 inhibitor can be durvalumab; or the PD-1 or PD-L1 inhibitor can be lodapilimab. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; or the cancer can be mutant pancreatic cancer in which the cancer has one or more cells that express a KRas G12D mutant protein. This method also includes treating KRas G12D mutant bearing cancers of other origins.

Also provided is a method of treating cancer, comprising administering to a patient in need thereof, an effective amount of a compound according to any one of I-VIII (including Ia-VIIa), or a pharmaceutically acceptable salt thereof, and a CDK4/CDK6 inhibitor, or a pharmaceutically acceptable salt thereof, in which the cancer has one or more cells that express a mutant KRas G12D protein. Further provided is a compound according to any one of I-VIII (including Ia-VIIa), or a pharmaceutically acceptable salt thereof, for use in simultaneous, separate, or sequential combination with a CDK4/CDK6 inhibitor, or a pharmaceutically acceptable salt thereof, for use in the treatment of cancer, in which the cancer has one or more cells that express a mutant KRas G12D protein. Additionally provided is a combination comprising a compound according to any one of I-VIII (including Ia-VIIa), or a pharmaceutically acceptable salt thereof, and a CDK4/CDK6 inhibitor, or a pharmaceutically acceptable salt thereof, for simultaneous, separate, or sequential use in the treatment of cancer, in which the cancer has one or more cells that express a mutant KRas G12D protein. As used herein, the CDK4/CDK6 inhibitor can be abemaciclib; the CDK4/CDK6 inhibitor can be palbociclib; or the CDK4/CDK6 inhibitor can be ribociclib. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; the cancer can be mutant pancreatic cancer in which the cancer has one or more cells that express a KRas G12D mutant protein. This method also includes treating KRas G12D mutant bearing cancers of other origins.

Also provided is a method of treating cancer, comprising administering to a patient in need thereof, an effective amount of a compound according to any one of I-VIII (including Ia-VIIa), or a pharmaceutically acceptable salt thereof, and an EGFR inhibitor, or a pharmaceutically acceptable salt thereof, in which the cancer has one or more cells that express a mutant KRas G12D protein. Further provided is a compound according to any one of I-VIII (including Ia-VIIa), or a pharmaceutically acceptable salt thereof, for use in simultaneous, separate, or sequential combination with an EGFR inhibitor, or a pharmaceutically acceptable salt thereof, for the treatment of cancer. Additional provided is a combination comprising a compound according to any one of I-VIII (including Ia-VIIa), or a pharmaceutically acceptable salt thereof, and an EGFR inhibitor, or a pharmaceutically acceptable salt thereof, for simultaneous, separate, or sequential use in the treatment of cancer. As used herein, the EGFR inhibitor can be erlotinib; the EGFR inhibitor can be afatinib; the EGFR inhibitor can be gefitinib; the EGFR inhibitor can be cetuximab. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; or the cancer can be mutant pancreatic cancer in which the cancer has one or more cells that express a KRas G12D mutant protein. This method also includes treating KRas G12D mutant bearing cancers of other origins.

Also provided is a method of treating cancer, comprising administering to a patient in need thereof, an effective amount of a compound according to any one of I-VIII (including Ia-VIIa), or a pharmaceutically acceptable salt thereof, and an ERK inhibitor, or a pharmaceutically acceptable salt thereof, in which the cancer has one or more cells that express a mutant KRas G12D protein. Further provided is a compound according to any one of I-VIII (including Ia-VIIa), or a pharmaceutically acceptable salt thereof, for use in simultaneous, separate, or sequential combination with an ERK inhibitor, or a pharmaceutically acceptable salt thereof, for the treatment of cancer, in which the cancer has one or more cells that express a mutant KRas G12D protein. Additionally provided is a combination comprising a compound according to any one of I-VIII (including Ia-VIIa), or a pharmaceutically acceptable salt thereof, and an ERK inhibitor, or a pharmaceutically acceptable salt thereof, for simultaneous, separate, or sequential use in the treatment of cancer. As used herein, the ERK inhibitor can be LY3214996; the ERK inhibitor can be LTT462; or the ERK inhibitor can be KO-947. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; the cancer can be mutant pancreatic cancer in which the cancer has one or more cells that express a KRas G12D mutant protein. This method also includes treating KRas G12D mutant bearing cancers of other origins.

Also provided is a method of treating cancer, comprising administering to a patient in need thereof, an effective amount of a compound according to any one of I-VIII (including Ia-VIIa), or a pharmaceutically acceptable salt thereof, and an Aurora A inhibitor, in which the cancer has one or more cells that express a mutant KRas G12D protein. Further provided is a compound according to any one of I-VIII (including Ia-VIIa), or a pharmaceutically acceptable salt thereof, for use in simultaneous, separate, or sequential combination with an Aurora A inhibitor, or a pharmaceutically acceptable salt thereof, for the treatment of cancer, in which the cancer has one or more cells that express a mutant KRas G12D protein. Additionally provided is a combination comprising a compound according to any one of I-VIII (including Ia-VIIa), or a pharmaceutically acceptable salt thereof, and an Aurora A inhibitor, for simultaneous, separate, or sequential use in the treatment of cancer. As used herein, the Aurora A inhibitor can be alisertib, tozasertib, (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:2-methylpropan-2-amine (1:1) salt, and (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid: amine (1:1) salt, or a pharmaceutically acceptable salt thereof. In one embodiment, the Aurora A inhibitor is (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; the cancer can be mutant pancreatic cancer in which the cancer has one or more cells that express a KRas G12D mutant protein. This method also includes treating KRas G12D mutant bearing cancers of other origins.

Also provided is a method of treating cancer, comprising administering to a patient in need thereof, an effective amount of a compound according to any one of I-VIII (including Ia-VIIa), or a pharmaceutically acceptable salt thereof, and a SHP2 inhibitor, in which the cancer has one or more cells that express a mutant KRas G12D protein. Further provided is a compound according to any one of I-VIII (including Ia-VIIa), or a pharmaceutically acceptable salt thereof, for use in simultaneous, separate, or sequential combination with a SHP2 inhibitor, or a pharmaceutically acceptable salt thereof, for the treatment of cancer, in which the cancer has one or more cells that express a mutant KRas G12D protein. Additionally provided is a combination comprising a compound according to any one of I-VIII (including Ia-VIIa), or a pharmaceutically acceptable salt thereof, and a SHP2 inhibitor, for simultaneous, separate, or sequential use in the treatment of cancer. As used herein, the SHP2 inhibitor, or a pharmaceutically acceptable salt thereof, can be a Type I SHP2 Inhibitor or a Type II SHP2 Inhibitor. Examples of Type I SHP2 inhibitors include, but are not limited to, PHPS1, GS-493, NSC-87877, NSC-117199, and Cefsulodin, and pharmaceutically acceptable salts thereof. Examples of Type II SHP2 inhibitors include, but are not limited to, JAB-3068, JAB-3312, RMC-4550, RMC-4630, SHP099, SHP244, SHP389, SHP394, TNO155, RG-6433, and RLY-1971, and pharmaceutically acceptable salts thereof. Additional examples of SHP2 inhibitors include, but are not limited to, BBP-398, IACS-15509, IACS-13909, X37, ERAS-601, SH3809, HBI-2376, ETS-001, and PCC0208023, and pharmaceutically acceptable salts thereof. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; the cancer can be mutant pancreatic cancer in which the cancer has one or more cells that express a KRas G12D mutant protein. This method also includes treating KRas G12D mutant bearing cancers of other origins.

Also provided is a method of treating cancer, comprising administering to a patient in need thereof, an effective amount of a compound according to any one of I-VIII (including Ia-VIIa), or a pharmaceutically acceptable salt thereof, and a platinum agent, in which the cancer has one or more cells that express a mutant KRas G12D protein. Further provided is a compound according to any one of I-VIII (including Ia-VIIa), or a pharmaceutically acceptable salt thereof, for use in simultaneous, separate, or sequential combination with a platinum agent, or a pharmaceutically acceptable salt thereof, for the treatment of cancer, in which the cancer has one or more cells that express a mutant KRas G12D protein. Additionally provided is a combination comprising a compound according to any one of I-VIII (including Ia-VIIa), or a pharmaceutically acceptable salt thereof, and a platinum agent, for simultaneous, separate, or sequential use in the treatment of cancer. As used herein, the platinum agent can be cisplatin; the platinum agent can be carboplatin; or the platinum agent can be oxaliplatin. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; the cancer can be mutant pancreatic cancer in which the cancer has one or more cells that express a KRas G12D mutant protein. This method also includes treating KRas G12D mutant bearing cancers of other origins.

Also provided is a method of treating cancer, comprising administering to a patient in need thereof, an effective amount of a compound according to any one of I-VIII (including Ia-VIIa), or a pharmaceutically acceptable salt thereof, and pemetrexed, in which the cancer has one or more cells that express a mutant KRas G12D protein. Further provided is a compound according to any one of I-VIII (including Ia-VIIa), or a pharmaceutically acceptable salt thereof, for use in simultaneous, separate, or sequential combination with pemetrexed, for the treatment of cancer, in which the cancer has one or more cells that express a mutant KRas G12D protein. Additionally provided is a combination comprising a compound according to any one of I-VIII (including Ia-VIIa), or a pharmaceutically acceptable salt thereof, and pemetrexed, for simultaneous, separate, or sequential use in the treatment of cancer, in which the cancer has one or more cells that express a mutant KRas G12D protein. As described herein, the cancer has one or more cells that express a KRas G12D mutant protein. Further, a platinum agent can also be administered to the patient (and the platinum agent can be cisplatin, carboplatin, or oxaliplatin). As described herein, the cancer can be colorectal carcinoma in which the cancer has one or more cells that express a KRas G12D mutant protein or the cancer can be mutant pancreatic cancer in which the cancer has one or more cells that express a KRas G12D mutant protein. This method also includes treating KRas G12D mutant bearing cancers of other origins.

Also provided herein is a method of treating cancer, comprising administering to a patient in need thereof, an effective amount of a compound according to any one of Formulae I-VIII (including Ia-VIIa), or a pharmaceutically acceptable salt thereof, in which the cancer has one or more cells that express a mutant KRas G12C, G12D, and/or G12V protein. In this method, the cancer can be non-small cell lung cancer, pancreatic cancer, or colorectal cancer, in which the cancer has one or more cells that express a KRas G12C, G12D, and/or G12V mutant protein. In an embodiment, the cancer is non-small cell lung carcinoma in which the cancer has one or more cells that express a KRas G12C, G12D, and/or G12V mutant protein. In an embodiment, the cancer is mutant pancreatic cancer in which the cancer has one or more cells that express a KRas G12C, G12D, and/or G12V mutant protein. In an embodiment, the cancer is colorectal carcinoma in which the cancer has one or more cells that express a KRas G12C, G12D, and/or G12V mutant protein. This method also includes treating KRas G12C, G12D, and/or G12V mutant bearing cancers of other origins.

Further provided herein is a method of treating a patient with a cancer that has a KRas G12C, G12D, and/or G12V mutation comprising administering to a patient in need thereof an effective amount of a compound according to any one of Formulae I-VII or a pharmaceutically acceptable salt thereof. In this method, the cancer that has a KRas G12C, G12D, and/or G12V mutation can be KRas G12C, G12D, and/or G12V mutant lung cancer, KRas G12C, G12D, and/or G12V mutant pancreatic cancer, KRas G12C, G12D, and/or G12V mutant cervical cancer, KRas G12C, G12D, and/or G12V mutant esophageal cancer, KRas G12C, G12D, and/or G12V mutant endometrial cancer, KRas G12C, G12D, and/or G12V mutant ovarian cancer, KRas G12C, G12D, and/or G12V mutant cholangiocarcinoma, and KRas G12C, G12D, and/or G12V mutant colorectal cancer. In an embodiment the cancer that has a KRas G12C, G12D, and/or G12V mutation can be KRas G12C, G12D, and/or G12V mutant non-small cell lung cancer. In an embodiment the cancer that has a KRas G12C, G12D, and/or G12V mutation can be KRas G12C, G12D, and/or G12V mutant pancreatic cancer. In an embodiment the cancer that has a KRas G12C, G12D, and/or G12V mutation can be KRas G12C, G12D, and/or G12V mutant colorectal cancer.

Additionally provided herein is a method of modulating a mutant KRas G12C, G12D, and/or G12V enzyme in a patient in need thereof, by administering a compound according to any one of Formulae I-VIII (including Ia-VIIa), or a pharmaceutically acceptable salt thereof. In one embodiment this method comprises inhibiting a human mutant KRas G12C, G12D, and/or G12V enzyme.

Also provided herein is a method of treating cancer in a patient in need thereof, wherein the patient has a cancer that was determined to express the KRas G12C, G12D, and/or G12V mutant protein. The method comprises administering to a patient an effective amount of a compound according to any one of Formulae I-VIII (including Ia-VIIa), or a pharmaceutically acceptable salt thereof. The G12D mutational status of one or more cancer cells can be determined by a number of assays known in the art. Typically, one or more biopsies containing one or more cancer cells are obtained, and subjected to sequencing and/or polymerase chain reaction (PCR). Circulating cell-free DNA can also be used, e.g. in advanced cancers. Non-limiting examples of sequencing and PCR techniques used to determine the mutational status (e.g., G12D mutational status, in one or more cancer cells or in circulating cell-free DNA) include direct sequencing, next-generation sequencing, reverse transcription polymerase chain reaction (RT-PCR), multiplex PCR, and pyrosequencing and multi-analyte profiling.

Further provided herein is a compound or a pharmaceutically acceptable salt thereof according to any one of Formulae I-VII for use in therapy. The compound or a pharmaceutically acceptable salt thereof, can be for use in treating cancer. For this use in treating cancer, the cancer can be lung cancer, colorectal cancer, pancreatic cancer, bladder cancer, cervical cancer, endometrial cancer, ovarian cancer, cholangiocarcinoma, or esophageal cancer. The cancer can more specifically be non-small cell lung cancer, pancreatic cancer, or colorectal cancer. In an embodiment, the cancer is non-small cell lung cancer. In an embodiment, the cancer is pancreatic cancer. In an embodiment, the cancer is colorectal cancer. The cancer can have one or more cancer cells that express the mutant KRas G12C, G12D, and/or G12V protein such as KRas G12C, G12D, and/or G12V mutant lung cancer, KRas G12C, G12D, and/or G12V mutant pancreatic cancer, KRas G12C, G12D, and/or G12V mutant cervical cancer, KRas G12C, G12D, and/or G12V mutant esophageal cancer, KRas G12C, G12D, and/or G12V mutant endometrial cancer, KRas G12C, G12D, and/or G12V mutant ovarian cancer, KRas G12C, G12D, and/or G12V mutant cholangiocarcinoma, and KRas G12C, G12D, and/or G12V mutant colorectal cancer. In these uses, the cancer is selected from: KRas G12C, G12D, and/or G12V mutant non-small cell lung cancer, KRas G12C, G12D, and/or G12V mutant colorectal cancer, and KRas G12C, G12D, and/or G12V mutant pancreatic cancer. Additionally, the cancer can be non-small cell lung cancer, and one or more cells express KRas G12C, G12D, and/or G12V mutant protein. Further, the cancer can be colorectal cancer, and one or more cells express KRas G12C, G12D, and/or G12V mutant protein. Additionally, the cancer can be pancreatic cancer, and one or more cells express KRas G12C, G12D, and/or G12V mutant protein. The patient can have a cancer that was determined to have one or more cells expressing the KRas G12C, G12D, and/or G12V mutant protein prior to administration of the compound or a pharmaceutically acceptable salt thereof. The patient may have been treated with a different course of treatment prior to being treated as described herein.

The compounds provided herein according to any one of Formulae I-VIII (including Ia-VIIa), or a pharmaceutically acceptable salt thereof, may also be used in the manufacture of a medicament for treating cancer. When used in the manufacture of a medicament, the cancer can be lung cancer, colorectal cancer, pancreatic cancer, bladder cancer, cervical cancer, endometrial cancer, ovarian cancer, cholangiocarcinoma, or esophageal cancer. The cancer can more specifically be non-small cell lung cancer, pancreatic cancer, or colorectal cancer. In an embodiment, the cancer is non-small cell lung cancer. In an embodiment, the cancer is pancreatic cancer. In an embodiment, the cancer is colorectal cancer. The cancer can have one or more cancer cells that express the mutant KRas G12C, G12D, and/or G12V protein. When the cancer cells express KRas G12C, G12D, and/or G12V protein, the cancer can be selected from KRas G12C, G12D, and/or G12V mutant non-small cell lung cancer, KRas G12C, G12D, and/or G12V mutant colorectal cancer, and KRas G12C, G12D, and/or G12V mutant pancreatic cancer.

Also provided herein is a method of treating cancer, comprising administering to a patient in need thereof, an effective amount of a compound according to any one of Formulae I-VIII (including Ia-VIIa), or a pharmaceutically acceptable salt thereof, and one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in which the cancer has one or more cells that express a mutant KRas G12C, G12D, and/or G12V protein. Further provided herein is a compound according to any one of Formulae I-VIII (including Ia-VIIa), or a pharmaceutically acceptable salt thereof, for use in simultaneous, separate, or sequential combination with one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in the treatment of cancer. Additionally provided is a combination comprising a compound according to any one of Formulae I-VIII (including Ia-VIIa), or a pharmaceutically acceptable salt thereof, and one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, for simultaneous, separate, or sequential use in the treatment of cancer.

Also provided is a method of treating cancer, comprising administering to a patient in need thereof, an effective amount of a compound according to any one of Formulae I-VIII (including Ia-VIIa), or a pharmaceutically acceptable salt thereof, and a PD-1 or PD-L1 inhibitor, in which the cancer has one or more cells that express a mutant KRas G12C, G12D, and/or G12V protein. Further provided is a compound according to any one of Formulae I-VIII (including Ia-VIIa), or a pharmaceutically acceptable salt thereof, for use in simultaneous, separate, or sequential combination with a PD-1 or PD-L1 inhibitor, for use in the treatment of cancer. Additionally provided is a combination comprising a compound according to any one of Formulae I-VIII (including Ia-VIIa), or a pharmaceutically acceptable salt thereof, and a PD-1 or PD-L1 inhibitor, for simultaneous, separate, or sequential use in the treatment of cancer. As used herein, the PD-1 or PD-L1 inhibitor can be pembrolizumab; the PD-1 or PD-L1 inhibitor can be nivolumab; the PD-1 or PD-L1 inhibitor can be cemiplimab; the PD-1 or PD-L1 inhibitor can be sintilimab; the PD-1 or PD-L1 inhibitor can be atezolizumab; the PD-1 or PD-L1 inhibitor can be avelumab; the PD-1 or PD-L1 inhibitor can be durvalumab; or the PD-1 or PD-L1 inhibitor can be lodapilimab. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; or the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to any one of Formulae I-VIII (including Ia-VIIa), or a pharmaceutically acceptable salt thereof, and a CDK4/CDK6 inhibitor, or a pharmaceutically acceptable salt thereof, in which the cancer has one or more cells that express a mutant KRas G12C, G12D, and/or G12V protein. Further provided is a compound according to any one of Formulae I-VIII (including Ia-VIIa), or a pharmaceutically acceptable salt thereof, for use in simultaneous, separate, or sequential combination with a CDK4/CDK6 inhibitor, or a pharmaceutically acceptable salt thereof, for use in the treatment of cancer, in which the cancer has one or more cells that express a mutant KRas G12C, G12D, and/or G12V protein. Additionally provided is a combination comprising a compound according to any one of Formulae I-VIII (including Ia-VIIa), or a pharmaceutically acceptable salt thereof, and a CDK4/CDK6 inhibitor, or a pharmaceutically acceptable salt thereof, for simultaneous, separate, or sequential use in the treatment of cancer, in which the cancer has one or more cells that express a mutant KRas G12C, G12D, and/or G12V protein. As used herein, the CDK4/CDK6 inhibitor can be abemaciclib; the CDK4/CDK6 inhibitor can be palbociclib; or the CDK4/CDK6 inhibitor can be ribociclib. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to any one of Formulae I-VIII (including Ia-VIIa), or a pharmaceutically acceptable salt thereof, and an EGFR inhibitor, or a pharmaceutically acceptable salt thereof, in which the cancer has one or more cells that express a mutant KRas G12C, G12D, and/or G12V protein. Further provided is a compound according to any one of Formulae I-VIII (including Ia-VIIa), or a pharmaceutically acceptable salt thereof, for use in simultaneous, separate, or sequential combination with an EGFR inhibitor, or a pharmaceutically acceptable salt thereof, for the treatment of cancer. Additional provided is a combination comprising a compound according to any one of Formulae I-VIII (including Ia-VIIa), or a pharmaceutically acceptable salt thereof, and an EGFR inhibitor, or a pharmaceutically acceptable salt thereof, for simultaneous, separate, or sequential use in the treatment of cancer. As used herein, the EGFR inhibitor can be erlotinib; the EGFR inhibitor can be afatinib; the EGFR inhibitor can be gefitinib; the EGFR inhibitor can be cetuximab. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; or the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to any one of Formulae I-VIII (including Ia-VIIa), or a pharmaceutically acceptable salt thereof, and an ERK inhibitor, or a pharmaceutically acceptable salt thereof, in which the cancer has one or more cells that express a mutant KRas G12C, G12D, and/or G12V protein. Further provided is a compound according to any one of Formulae I-VIII (including Ia-VIIa), or a pharmaceutically acceptable salt thereof, for use in simultaneous, separate, or sequential combination with an ERK inhibitor, or a pharmaceutically acceptable salt thereof, for the treatment of cancer, in which the cancer has one or more cells that express a mutant KRas G12C, G12D, and/or G12V protein. Additionally provided is a combination comprising a compound according to any one of Formulae I-VIII (including Ia-VIIa), or a pharmaceutically acceptable salt thereof, and an ERK inhibitor, or a pharmaceutically acceptable salt thereof, for simultaneous, separate, or sequential use in the treatment of cancer. As used herein, the ERK inhibitor can be LY3214996; the ERK inhibitor can be LTT462; or the ERK inhibitor can be KO-947. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to any one of Formulae I-VIII (including Ia-VIIa), or a pharmaceutically acceptable salt thereof, and an Aurora A inhibitor, in which the cancer has one or more cells that express a mutant KRas G12C, G12D, and/or G12V protein. Further provided is a compound according to any one of Formulae I-VIII (including Ia-VIIa), or a pharmaceutically acceptable salt thereof, for use in simultaneous, separate, or sequential combination with an Aurora A inhibitor, or a pharmaceutically acceptable salt thereof, for the treatment of cancer, in which the cancer has one or more cells that express a mutant KRas G12C, G12D, and/or G12V protein. Additionally provided is a combination comprising a compound according to any one of Formulae I-VIII (including Ia-VIIa), or a pharmaceutically acceptable salt thereof, and an Aurora A inhibitor, for simultaneous, separate, or sequential use in the treatment of cancer. As used herein, the Aurora A inhibitor can be alisertib, tozasertib, (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:2-methyl-propan-2-amine (1:1) salt, and (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:amine (1:1) salt, or a pharmaceutically acceptable salt thereof. In one embodiment, the Aurora A inhibitor is (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to any one of Formulae I-VIII (including Ia-VIIa), or a pharmaceutically acceptable salt thereof, and a SHP2 inhibitor, in which the cancer has one or more cells that express a mutant KRas G12C, G12D, and/or G12V protein. Further provided is a compound according to any one of Formulae I-VIII (including Ia-VIIa), or a pharmaceutically acceptable salt thereof, for use in simultaneous, separate, or sequential combination with a SHP2 inhibitor, or a pharmaceutically acceptable salt thereof, for the treatment of cancer, in which the cancer has one or more cells that express a mutant KRas G12C, G12D, and/or G12V protein. Additionally provided is a combination comprising a compound according to any one of Formulae I-VIII (including Ia-VIIa), or a pharmaceutically acceptable salt thereof, and a SHP2 inhibitor, for simultaneous, separate, or sequential use in the treatment of cancer. As used herein, the SHP2 inhibitor, or a pharmaceutically acceptable salt thereof, can be a Type I SHP2 Inhibitor or a Type II SHP2 Inhibitor. Examples of Type I SHP2 inhibitors include, but are not limited to, PUPS1, GS-493, NSC-87877, NSC-117199, and Cefsulodin, and pharmaceutically acceptable salts thereof. Examples of Type II SHP2 inhibitors include, but are not limited to, JAB-3068, JAB-3312, RMC-4550, RMC-4630, SHP099, SHP244, SHP389, SHP394, TNO155, RG-6433, and RLY-1971, and pharmaceutically acceptable salts thereof. Additional examples of SHP2 inhibitors include, but are not limited to, BBP-398, IACS-15509, IACS-13909, X37, ERAS-601, SH3809, HBI-2376, ETS-001, and PCC0208023, and pharmaceutically acceptable salts thereof. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to any one of Formulae I-VIII (including Ia-VIIa), or a pharmaceutically acceptable salt thereof, and a platinum agent, in which the cancer has one or more cells that express a mutant KRas G12C, G12D, and/or G12V protein. Further provided is a compound according to any one of Formulae I-VIII (including Ia-VIIa), or a pharmaceutically acceptable salt thereof, for use in simultaneous, separate, or sequential combination with a platinum agent, or a pharmaceutically acceptable salt thereof, for the treatment of cancer, in which the cancer has one or more cells that express a mutant KRas G12C, G12D, and/or G12V protein. Additionally provided is a combination comprising a compound according to any one of Formulae I-VIII (including Ia-VIIa), or a pharmaceutically acceptable salt thereof, and a platinum agent, for simultaneous, separate, or sequential use in the treatment of cancer. As used herein, the platinum agent can be cisplatin; the platinum agent can be carboplatin; or the platinum agent can be oxaliplatin. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to any one of Formulae I-VIII (including Ia-VIIa), or a pharmaceutically acceptable salt thereof, and pemetrexed, in which the cancer has one or more cells that express a mutant KRas G12C, G12D, and/or G12V protein. Further provided is a compound according to any one of Formulae I-VIII (including Ia-VIIa), or a pharmaceutically acceptable salt thereof, for use in simultaneous, separate, or sequential combination with pemetrexed, for the treatment of cancer, in which the cancer has one or more cells that express a mutant KRas G12C, G12D, and/or G12V protein. Additionally provided is a combination comprising a compound according to any one of Formulae I-VIII (including Ia-VIIa), or a pharmaceutically acceptable salt thereof, and pemetrexed, for simultaneous, separate, or sequential use in the treatment of cancer, in which the cancer has one or more cells that express a mutant KRas G12C, G12D, and/or G12V protein. As described herein, the cancer has one or more cells that express a KRas G12C, G12D, and/or G12V mutant protein. Further, a platinum agent can also be administered to the patient (and the platinum agent can be cisplatin, carboplatin, or oxaliplatin). As described herein, the cancer can be colorectal carcinoma in which the cancer has one or more cells that express a KRas G12C, G12D, and/or G12V mutant protein or the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

The term "pharmaceutically acceptable salt" as used herein refers to a salt of a compound considered to be acceptable for clinical and/or veterinary use. Examples of pharmaceutically acceptable salts and common methodology for preparing them can be found in "Handbook of Pharmaceutical Salts: Properties, Selection and Use" P. Stahl, et al., 2nd Revised Edition, Wiley-VCH, 2011 and S. M. Berge, et al., "Pharmaceutical Salts", *Journal of Pharmaceutical Sciences*, 1977, 66(1), 1-19.

Pharmaceutical compositions containing the compounds of Formulae I-VII as described herein may be prepared using pharmaceutically acceptable additives. The term "pharmaceutically acceptable additive(s)" as used herein for the pharmaceutical compositions, refers to one or more carriers, diluents, and excipients that are compatible with the other additives of the composition or formulation and not deleterious to the patient. Examples of pharmaceutical compositions and processes for their preparation can be found in "Remington: The Science and Practice of Pharmacy", Loyd, V., et al. Eds., $22^{nd}$ Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose, alginates, gelatin, and polyvinyl-pyrrolidone; kaolin and bentonite; and polyethyl glycols.

As used herein, the term "effective amount" refers to an amount that is a dosage, which is effective in achieve a desired therapeutic result such as treating a disorder or disease, like a cancerous lesion or progression of abnormal cell growth and/or cell division. Factors considered in the determination of an effective amount or dose of a compound include: whether the compound or its salt will be administered; the co-administration of other agents, if used; the species of patient to be treated; the patient's size, age, gender, and general health; the degree of involvement or stage and/or the severity of the disorder; the response of the individual patient; the mode of administration; the bioavailability characteristics of the preparation administered; the dose regimen selected; and the use of other concomitant medication.

A treating physician, veterinarian, or other medical person will be able to determine an effective amount of the compound for treatment of a patient in need. Pharmaceutical compositions can be formulated as a tablet or capsule for oral administration, a solution for oral administration, or an injectable solution. The tablet, capsule, or solution can include a compound of the present invention in an amount effective for treating a patient in need of treatment for cancer.

As used herein, the terms "treating", "to treat", or "treatment", includes slowing, controlling, delaying, reducing, stopping, reversing, preventing, or ameliorating the progression or severity of an existing symptom, disorder, condition, which can include specifically slowing the growth of a cancerous lesion or progression of abnormal cell growth and/or cell division. Treating does not necessarily indicate a total elimination of all disorder or disease symptoms.

As used herein, the term "patient" refers to a mammal in need of treatment. Specifically, the patient can be a human that is in need of treatment for cancer, for example, KRas G12D mutant bearing cancers.

Certain abbreviations are defined as follows: "ACN" refers to acetonitrile; "AcOH" or "HOAc" refer to acetic acid; AIBN" refers to azobisisobutyronitrile; "Alloc" refers to the allyloxycarbonyl group; "aq." refers to aqueous; "atm" refers to atmosphere or atmospheres; "Boc-Gly-OH" refers to N-(tert-butoxycarbonyl)glycine; "BrettPhos" refers to 2-dicyclohexylphosphino-3,6-dimethoxy-2',4',6'-triisopropyl-1,1'-biphenyl; "BroP" refers to bromo tris(dimethylamino) phosphonium hexafluorophosphate; "Cbz" refers to the benzyloxycarbonyl group; "Cbz-Cl" refers to benzyl chloroformate; "conc." refers to concentrated; "CSI" refers to chlorosulfonyl isocyanate; "CV" refers to column volumes; "DCM" refers to dichloromethane; "DIAD" refers to diisopropyl azodicarboxylate; "DIBAL-H" refers to diisobutylaluminum hydride; "DIEA" and "DIPEA" refer to N,N-diisopropyl ethylamine; "(dippf)Rh(cod)BF$_4$" refers to [1,4-bis(diphenylphosphino)butane](1,5-cyclooctadiene) rhodium(I) tetrafluoroborate; "DMAP" refers to 4-dimethylaminopyridine; "DMEA" refers to N,N-dimethylethylamine; "DMEM" refers to Dulbecco's modified Eagle's medium; "DMF" refers to N,N-dimethylformamide; "DMSO" refers to dimethylsulfoxide; "DNA" refers to deoxyribonucleic acid; "DPEPhosPdCl$_2$" refers to dichloro-bis(diphenylphosphinophenyl)ether palladium (II); "DTT" refers to dithiothreitol; "EDTA" refers to ethylenediaminetetraacetic acid; "EGTA" refers to ethylene glycol-bis(β-aminoethyl ether)-N,N,N',N'-tetraacetic acid; "ELISA" refers to enzyme-linked immunosorbent assay; "ERK" refers to extracellular signal-regulated kinases; "EtOAc" refers to ethyl acetate; "Et$_2$O" refers to diethyl ether; "EtOH" refers to ethanol; "FA" refers to formic acid; "FBS" refers to fetal bovine serum; "Fmoc" refers to the fluorenylmethyloxycarbonyl group; "GDP" refers to guanosine diphosphate; "GTP" refers to guanosine triphosphate; "h" refers to hour or hours; "HATU" refers to 1-[Bis(dimethylamino)methylene]-1H-1,2,3-triazolo[4,5-b]pyridinium 3-oxide hexafluorophosphate; "Hex" or "hex" refers to hexane or hexanes; "HPLC" refers to high-performance liquid chromatography; "HRP" refers to horseradish peroxidase; "IPA" refers to isopropyl alcohol; "IPAm" refers to isopropyl amine; "KOAc" refers to potassium acetate; "LC-ES/MS" refers to liquid chromatograph-electrospray mass spectrometry; "LC-MS" refers to liquid chromatography mass spectrometry; "LiHMDS" refers to lithium bis(trimethylsilyl)amide; "L-prolinol" refers to [(2S)-pyrrolidin-2yl] methanol; "MAPK" refers to mitogen-activated protein kinases; "mCPBA" refers to 3-chloro-peroxybenzoic acid; "Me" refers to a methyl group; "MeOH" refers to methanol; "min" refers to minute or minutes; "MTBE" refers to methyl tert-butyl ether; "NaBH(OAc)$_3$ refers to sodium triacetoxyborohydride; "NaOMe" refers to sodium methoxide; "NBS" refers to N-bromosuccinimide; "NCS" refers to N-chlorosuccinimide; "N-methyl-L-prolinol" refers to [(2S)-1-methylpyrrolidin-2-yl]methanol; "NMM" refers to N-methylmorpholine; "NMP" refers to 1-methylpyrrolidin-2-one; "NIS" refers to N-iodosuccinimide; "PCR" refers to polymerase chain reaction; "Pd-117" refers to dichloro[bis(2-(diphenylphosphino)phenyl)ether]palladium(II), CAS 205319-06-8; "Pd-118" refers to 1,1'-bis(di-tert-butylphosphino)ferrocene palladium dichloride, CAS 95408-45-0; "Pd$_2$(dba)$_3$" refers to tris(dibenzylideneacetone)dipalladium (0); "Pd(dppf)Cl$_2$" refers to [1,1'-bis(diphenylphosphino) ferrocene]dichloropalladium(II); "Pd(OAc)$_2$ refers to palladium (II) acetate; Pd(PPh$_3$)$_4$ refers to tetrakis (triphenylphosphine)palladium(0); "PE" refers to petroleum ether or diethyl ether; "Ph" refers to phenyl; "RBF" refers to round bottom flask; "RPMI" refers to Roswell Park Memorial Institute; "RT" refers to room temperature; "RuPhos" refers to 2-dicyclohexylphosphino-2',6'-diisopropoxy-1,1'-biphenyl, CAS 787618-22-8; "sat." refers to saturated; "SCX" refers to strong cation exchange; "Selectfluor™" refers to 1-chloromethyl-4-fluoro-1,4-diazoniabicyclo [2.2.2]octane bis(tetrafluoroborate), "SPE" refers to solid phase extraction; "SPhos" refers to 2-dicyclohexylphosphino-2',6'-dimethoxy-1,1'-biphenyl; "TBAF" refers to tetrabutylammonium fluoride; "TBDMSCl" refers to tert-butyldimethylsilyl chloride; "TBDMS" refers to the tert-butyldimethylsilyl group; "tBu" refers to the tert-butyl group; "t-BuOH" refers to tert-butanol or tert-butyl alcohol; "A" refers to triethylamine; "TES" refers to triethylsilane; "Tf₂O" refers to trifluoromethanesulfonic anhydride; "TFA" refers to trifluoroacetic acid; "THF" refers to tetrahydrofuran; "TMEDA" refers to tetramethylethylenediamine; "t$_R$" refers to retention time; "XantPhos" refers to 4,5-bis(diphenylphosphino)-9,9-dimethylxanthene; "XPhos" refers to 2-(dicyclohexylphosphino)-2',4',6'-tri-isopropyl-1,1'-biphenyl; "XPhos Palladacycle G2" refers to chloro(2-dicyclohexylphosphino-2',4',6'-triisopropyl-1,1'-biphenyl)[2-(2'-amino-1,1'-biphenyl)]palladium(II), CAS 1310584-14-5; "XPhos Palladacycle Gen.4" or "XPhos Pd G4" refer to methanesulfonato(2-dicyclohexylphosphino-2',4',6'-triisopropyl-1,1'-biphenyl)(2'-methylamino-1,1'-biphenyl-2-yl) palladium(II), CAS 1599466-81-5.

Individual isomers, enantiomers, diastereomers, and atropisomers may be separated or resolved at any convenient point in the synthesis of compounds listed below, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). The molecules described herein include compounds that are atropisomers and which can exist in different conformations or as different rotomers. Atropisomers are compounds that exist in different conformations arising from restricted rotation about a single bond. Atropisomers can be isolated as separate chemical species if the energy barrier to rotation about the single bond is sufficiently high that the rate of interconversion is slow enough to allow the individual rotomers to be separated from each other. This description is intended to include all of the isomers, enantiomers, diastereomers, and atropisomers possible for the compounds disclosed herein or that could be made using the compounds disclosed herein. In the molecules described herein, only molecules in which the absolute conformation of a chiral center (or atropisomer conformation) is known have used naming conventions or chemical formula that are drawn to indicate the chirality or atropisomerism. Those of skill in the art will readily understand when other chiral centers are present in the molecules described herein and be able to identify the same.

Compounds of any one of Formulae I-VII that are chemically capable of forming salts are readily converted to and may be isolated as a pharmaceutically acceptable salt. Salt formation can occur upon the addition of a pharmaceutically acceptable acid to form the acid addition salt. Salts can also form simultaneously upon deprotection of a nitrogen or oxygen, i.e., removing the protecting group. Examples, reactions and conditions for salt formation can be found in Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

The compounds of the present invention, or salts thereof, may be prepared by a variety of procedures, some of which are illustrated in the Schemes, Preparations, and Examples below. The specific synthetic steps for each of the routes described may be combined in different ways, or in conjunction with steps from different routes, to prepare compounds or salts of the present invention. The products of each step in the Preparations below can be recovered by conventional methods, including extraction, evaporation, precipitation, chromatography, filtration, trituration, and crystallization.

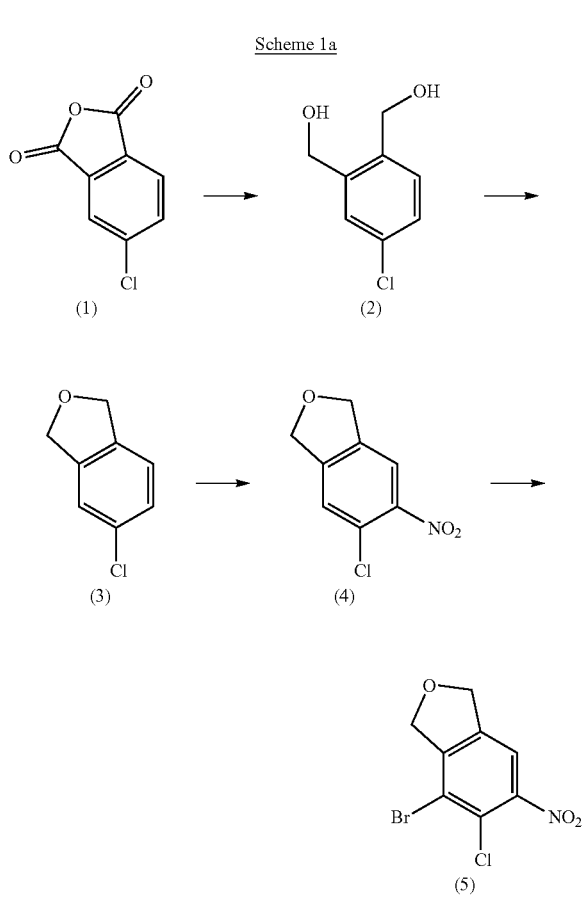

Scheme 1a depicts the preparation of dihydroisobenzofuran (5). Commercially available 4-chlorophthalic anhydride (1) may undergo reductive ring opening with LiAlH₄ in THF to give diol (2). Subsequent ring closure using a dialkyl carbonate such as dimethyl carbonate and a strong base such as NaOMe may be used to furnish heterocycle (3). Subsequent electrophilic aromatic substitution may yield nitroaryl compound (4) using KNO₃ or HNO₃ in conjunction with a strong acid like H₂SO₄. Heterocycle (4) may be brominated with a variety of suitable reagents such as, but not limited to, NBS, POBr₃, Bra, and 1,3-dibromo-5,5-dimethylimidazolidine-2,4-dione, to furnish 4-bromo-5-chloro-6-nitro-1,3-dihydroisobenzofuran (5).

-continued

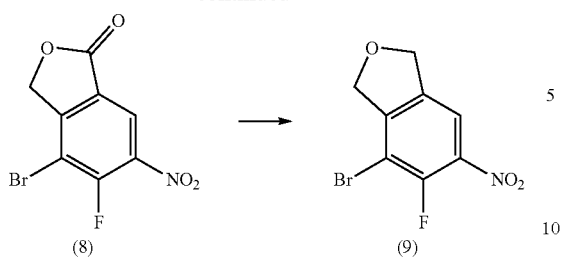

Scheme 1b illustrates the preparation of dihydroisobenzofuran (9). Using commercially available (2-bromo-5-fluorophenyl)methanol (6), a palladium-catalyzed carbonylation may be accomplished using a ligand such as XantPhos and a palladium source such as Pd(OAc)$_2$ with a suitable base, for example, triethylamine and a polar aprotic solvent such as acetonitrile to give lactone (7). A person skilled in the art will appreciate that a variety of bidentate phosphine ligands may be used. Subsequent nitration and bromination using conditions mentioned previously may afford functionalized isobenzofuranone (8). Reduction of compound (8) may be accomplished by using a hydride reagent such as DIBAL-H to give an intermediate lactol compound which is then further reduced by triethylsilane and TFA to afford 4-bromo-5-fluoro-6-nitro-1,3-dihydroisobenzofuran (9).

Scheme 2

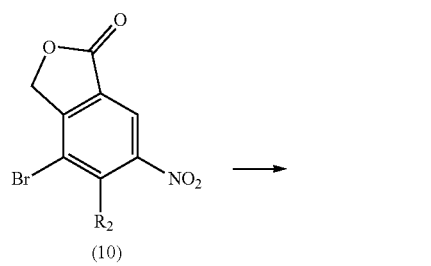

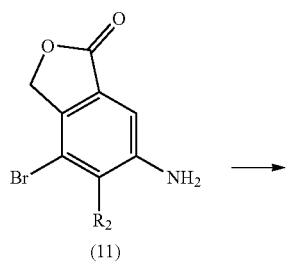

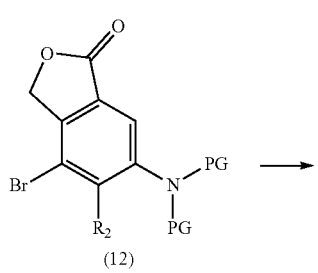

-continued

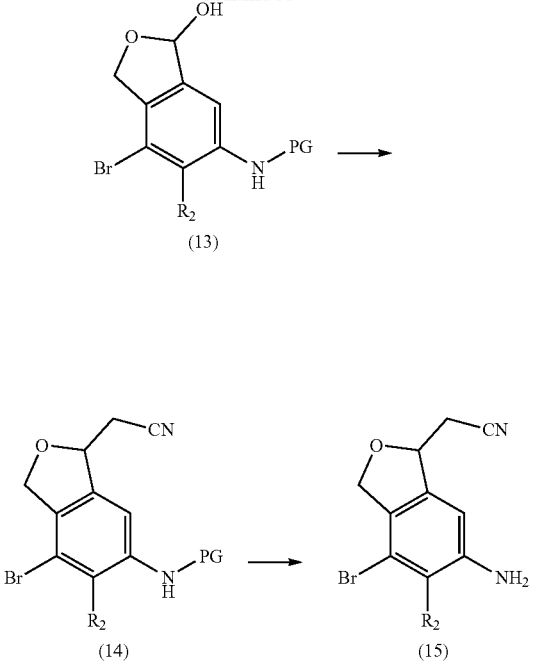

Scheme 2 depicts the preparation of cyanomethyl-substituted heterocyclic compounds of (15). Nitroaryl compounds of (10) may be reduced to the corresponding aniline compounds of (11) under hydrogenation conditions utilizing a Pt/C catalyst doped with sulfur. Alternatively, a person skilled in the art will also appreciate that the reduction may also be achieved with iron or zinc powder and NH$_4$Cl in a polar solvent such as THF, EtOH or MeOH. Protection of the amino moiety may be accomplished with di-tert-butyl dicarbonate, or Boc group, using a catalytic amount of DMAP under refluxing conditions in acetonitrile. A person skilled in the art will also be aware that other suitable carbamate protecting groups such as Alloc, Fmoc and Cbz may also be used in place of the Boc protecting group. Reduction of the lactone moiety of compounds (12) at low temperatures, obtained using a dry ice/acetone bath for instance, with an appropriate hydride agent, for example, DIBAL-H, may furnish the hydroxy compounds of (13). Cyanomethyl compounds of (14) may be obtained by using diethyl cyanomethyl phosphonate in a miscible solvent such as THE under Horner-Emmons reaction conditions. Deprotection of the amino group on cyanomethyl-substituted heterocycle (14) may be achieved by using HCl dissolved in 1,4-dioxane which upon basic work-up gives the aniline compounds of (15).

Scheme 3

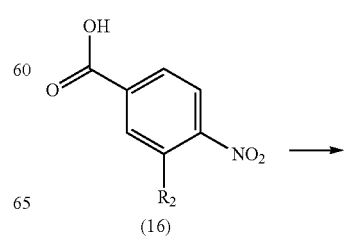

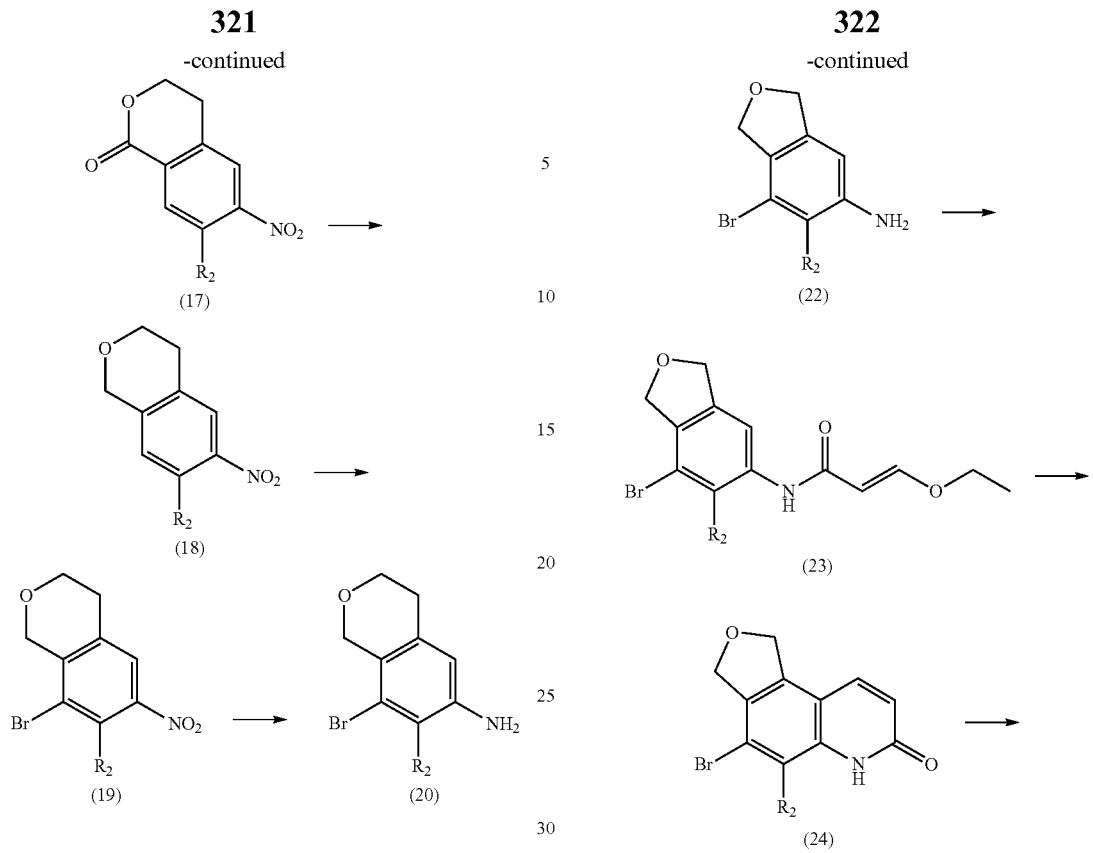

Scheme 3 depicts the preparation of isochromane compounds of (20). Starting from the benzoic acid compounds of (16), ring closure is achieved by a palladium-catalyzed C—H insertion reaction followed by oxidative addition to ethylene oxide, dissolved in THF, to afford isochromanone compounds of (17). A person skilled in the art would understand that a variety of N-acyl amino acids may be used as a ligand for the palladium. For example, N-acetyl valine may be used. A polar acidic solvent such as trifluoroethanol, TFA or hexafluoroisopropanol may be used as the solvent. Preferred is trifluoroethanol and hexafluoroisopropanol. Reduction of the carbonyl moiety may be achieved by utilizing a two-step procedure. In the first step, $LiBH_4$ in THF may be used to furnish an isochromanol intermediate which in the second step is then reacted with p-toluenesulfonic acid under refluxing conditions in toluene to give the isochromane compounds of (18). Subsequent bromination using conditions as mentioned previously, for example, NBS, may afford aryl bromide compounds of (19). Iron powder and $NH_4Cl$ in a mixed solvent system such as THF and water may be used to reduce the nitro moiety to give the aniline compounds of (20).

Scheme 4a illustrates the preparation of quinoline compounds of (25). Nitroaryl compounds of (21) may be reduced to the corresponding aniline compounds of (22) by aforementioned reaction conditions using iron or zinc powder. Acylation of amine compounds of (22) using 3-ethoxyprop-2-enoyl chloride in THF and a suitable base such as pyridine may yield the enamide compounds of (23). Cyclization using $H_2SO_4$ as the solvent followed by trituration in ice water affords quinolinone compounds of (24). Subsequent chlorination may be achieved with a suitable reagent such as (chloromethylene)dimethyliminium chloride or $POCl_3$ to furnish the chloroquinoline compounds of (25).

Scheme 4a

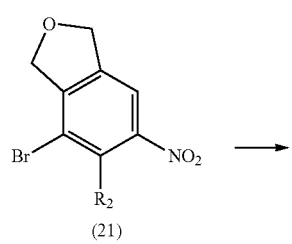

Scheme 4b

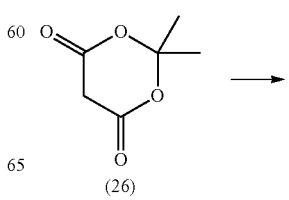

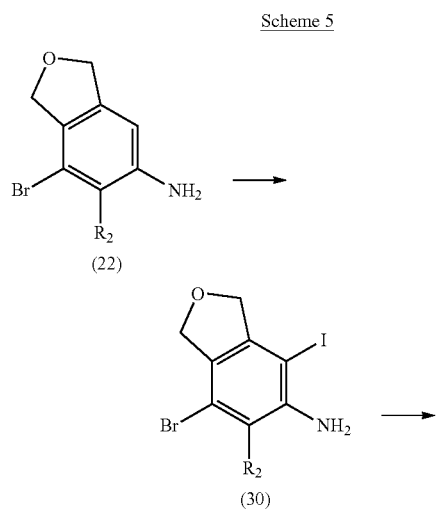

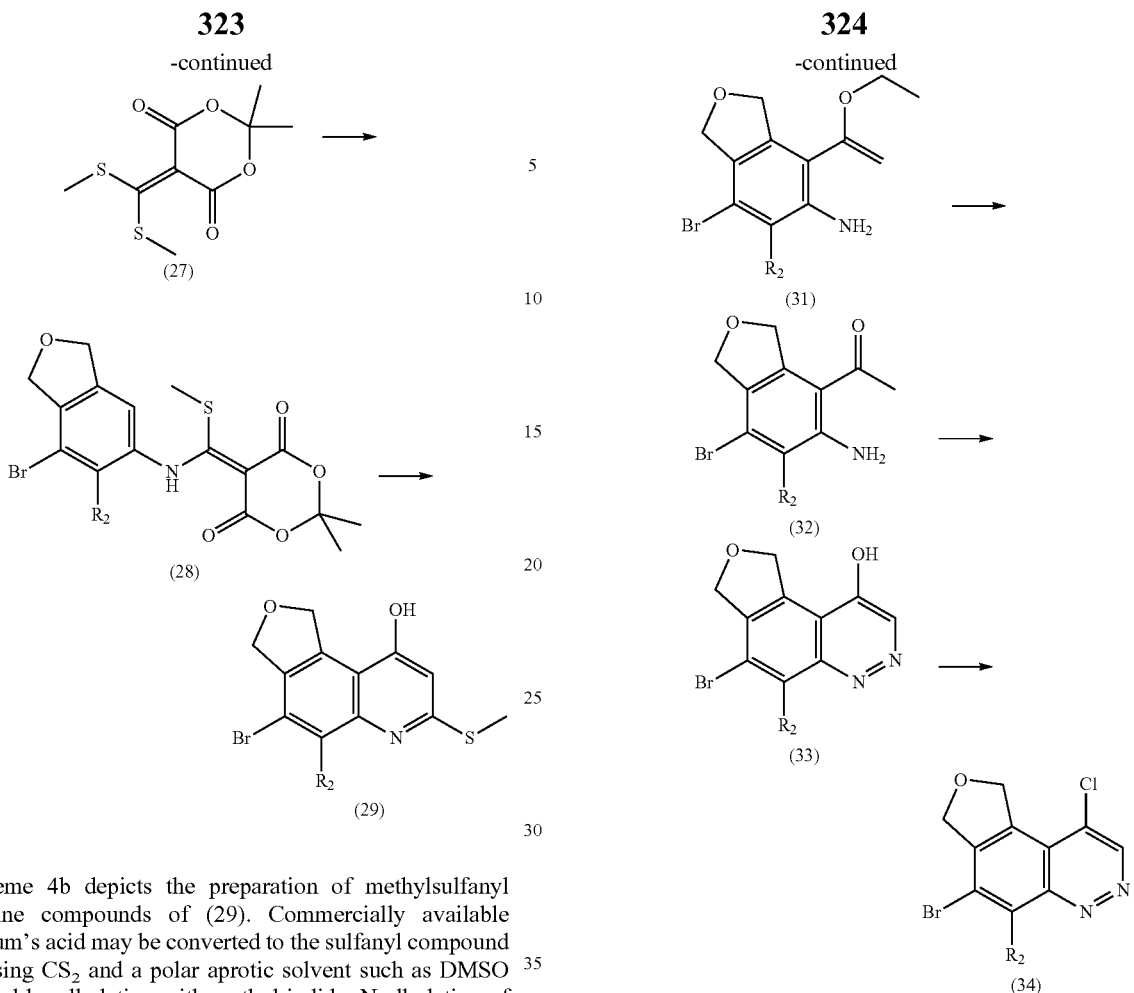

Scheme 4b depicts the preparation of methylsulfanyl quinoline compounds of (29). Commercially available Meldrum's acid may be converted to the sulfanyl compound (27) using $CS_2$ and a polar aprotic solvent such as DMSO followed by alkylation with methyl iodide. N-alkylation of the aniline compounds of (22) with methyl sulfanyl compound (27) by heating in a nonpolar solvent such as toluene followed by trituration in a suitable solvent system, for example, $Et_2O$/EtOAc, affords the functionalized compounds of (28). Refluxing at about 180° C. in a suitable high-boiling solvent, for instance, diphenyl ether may allow cyclization to occur to furnish quinolinol compounds of (29).

Scheme 5 shows the preparation of the cinnoline compounds of (34). Dihydroisobenzofuran compounds of (22) may be iodinated by several reagents known by those skilled in the art, such as NIS, $I_2$ and pyridinium iodo-chloride, to afford iodo-aniline compounds of (30). Stille coupling of iodide (30) using a $Pd^0$ source such as $Pd(PPh_3)_4$ and an appropriate tributylstannane, such as tributyl(1-ethoxyvinyl) stannane, may afford the vinyl compounds of (31). Acid hydrolysis using aqueous HCl may furnish acetophenone compounds of (32). A person of skill in the art will be familiar with conditions for diazotization of the amine moiety by use of sodium nitrite and TFA, followed by ring closure to obtain the hydroxycinnoline compounds of (33). Standard chlorination conditions, such as oxalyl chloride and DMF in DCM may be used to furnish the chlorocinnoline compounds of (34).

Scheme 6

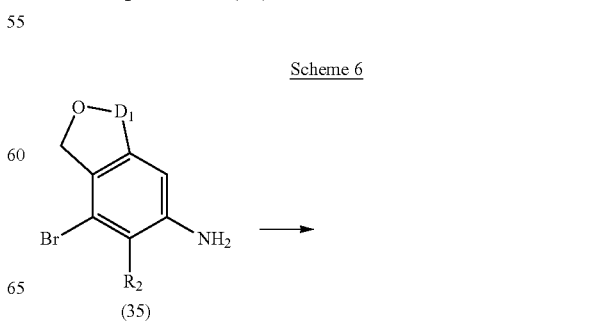

-continued

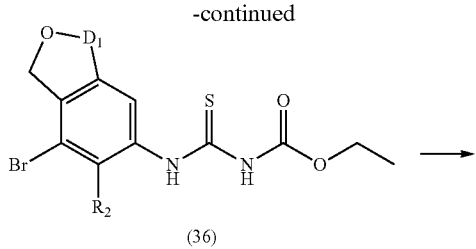

(36)

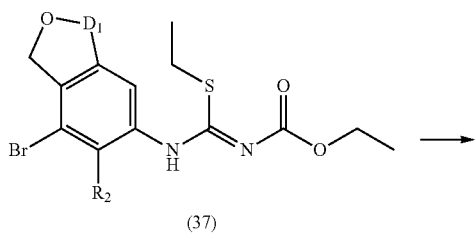

(37)

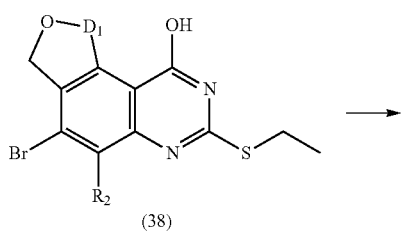

(38)

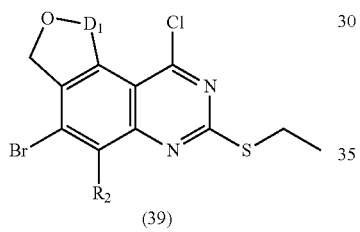

(39)

Scheme 6 depicts the preparation of the quinazolinyl compounds of (39). Thioacylation of the aniline compounds of (35) may be achieved with an appropriate isothiocyanate, for example ethoxycarbonyl isothiocyanate, to afford the carbamothioyl compounds of (36). S-Alkylation may be achieved by using a mild base, such as $K_2CO_3$, in a polar solvent such as acetone followed by the slow addition of ethyl iodide to give the sulfanyl compounds of (37). Ring closure in a solvent such as anhydrous NMP or diphenyl ether at 175° C. may furnish the hydroxyquinazoline compounds of (38) followed by chlorination using, for instance, oxalyl chloride, thionyl chloride, (chloromethylene)dimethyliminium chloride or $POCl_3$ plus adjusting the solvent as necessary may afford the chloroquinazolinyl compounds of (39).

Scheme 7

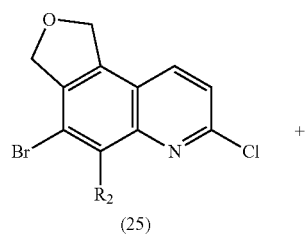

(25)

-continued

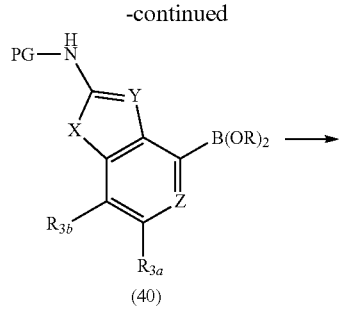

(40)

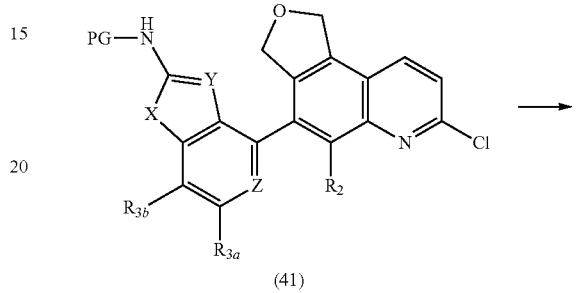

(41)

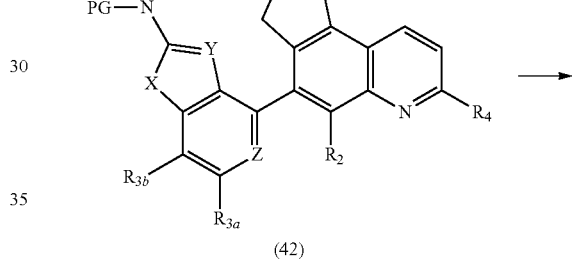

(42)

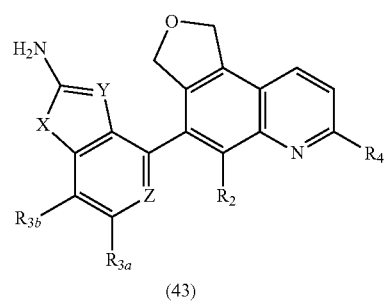

(43)

Scheme 7 illustrates the preparation of the bicyclic-substituted quinolinyl compounds of (43). Suzuki coupling of boronic ester compounds of (40) with bromoquinoline compounds of (25) using a base such as $Cs_2CO_3$ in THF with a suitable palladium complex well known by one skilled in the art, for example, dichloro[bis(2-(diphenylphosphino)phenyl)ether]palladium(II), may furnish the biaryl compounds of (41). A nucleophilic aromatic substitution reaction, commonly known as a $S_NAR$, of the chloro-moiety ortho to the quinoline nitrogen, using a strong base such as LiHMDS in THF and appropriate nucleophile, such as a primary or secondary alcohol, may yield the substituted-quinolinyl compounds of (42). Removal of the protecting group on the amine-moiety by using an appropriate acid, such as TFA in DCM, may furnish the functionalized quinolinyl compounds of (43).

Scheme 8

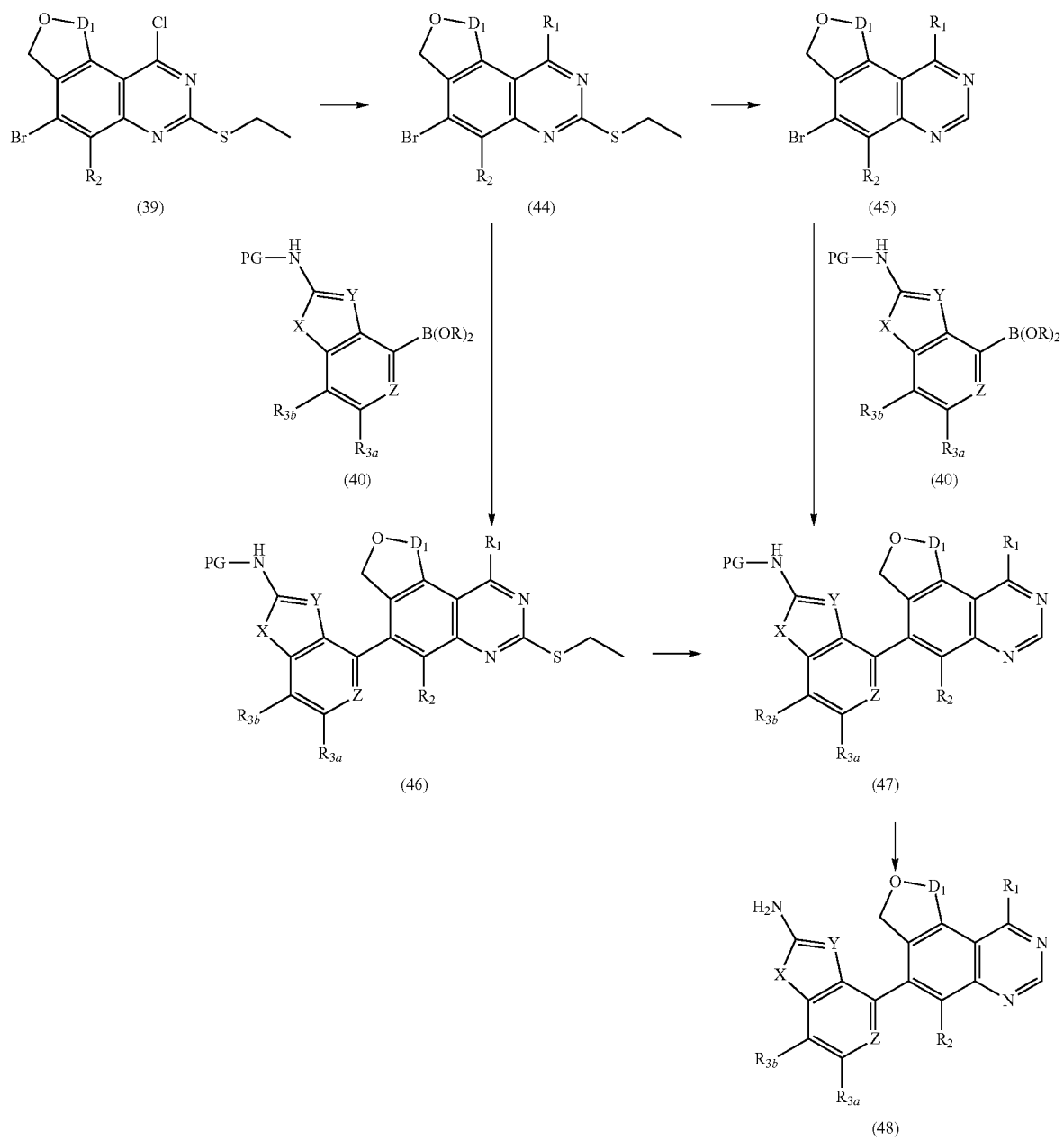

Scheme 8 depicts two routes for the preparation of bicyclic-substituted quinazoline compounds of (48). Chloroquinazolinyl compounds of (39) may undergo a $S_NAR$ with an appropriate nucleophile, such as a substituted piperazine. A person of skill in the art will be aware that a variety of non-nucleophilic bases may be employed, such as, but not limited to, DIPEA, TEA, or NMM in the reaction along with a polar, aprotic solvent such as acetonitrile or DMF to furnish the substituted quinazolinyl compounds of (44). In one route, the compounds of (44) may first undergo desulfurization with triethylsilane and $PdCl_2$ to afford quinazolinyl compounds of (45). An alternative method for desulfurization involves oxidation of the thioether compounds of (44) with mCPBA to afford an intermediate sulfone moiety which may then be removed using the well-known conditions to one with skill in the art, for instance, $NaBH_4$ in DCM/MeOH to furnish the quinazolinyl compounds of (45). This is then followed by a reaction with the bicyclic boronates of (40) using previously mentioned Suzuki coupling conditions to furnish bicyclic-substituted quinazolinyl compounds of (47). Another route utilizes the Suzuki coupling first to afford bicyclic-substituted quinazolinyl compounds of (46) before undergoing a desulfurization reaction to obtain the quinazolinyl compounds of (47). The amine moiety on the compounds of (47) may then be suitably deprotected using well known methods to one of skill in the art, for instance using TFA to remove a Boc-protecting group, to furnish the substituted quinazolinyl compounds of (48).

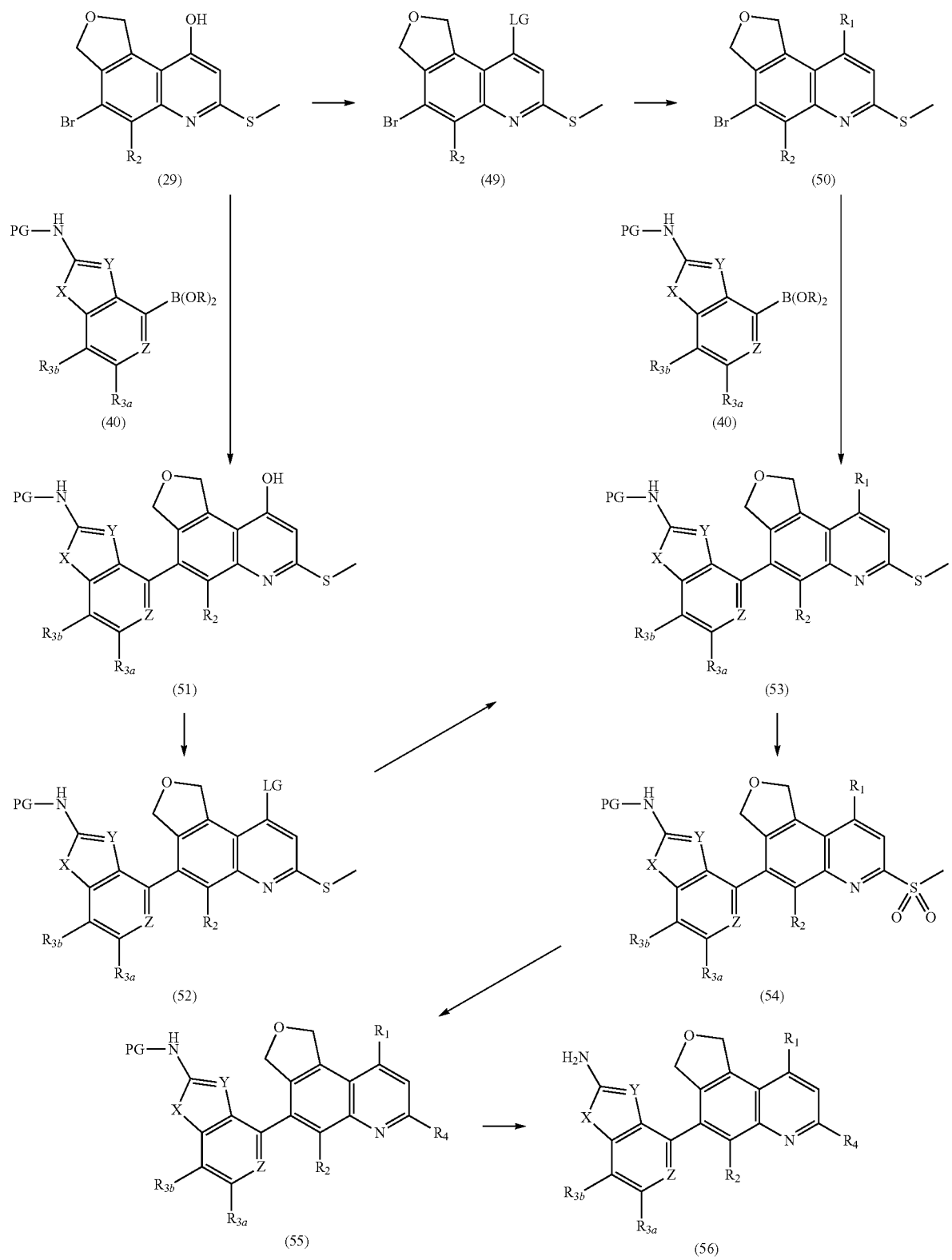
Scheme 9 illustrates the preparation of the dihydrofuroquinoline compounds of (56), also via two routes. Persons with skill in the art may choose the route based upon the order in which they desired to functionalize the dihydrofuroquinolinyl core. In one route, the hydroxy moiety of the quinolinyl compounds of (29) may be converted to a leaving group (LG) moiety, such as a chloride. Chlorination may be accomplished with oxalyl chloride and DMF in DCM to furnish the quinolinyl compounds of (49). Subsequent nucleophilic displacement at elevated temperatures, ~130° C., by a substituted piperazine using an appropriate hindered base such as DIPEA in an aprotic solvent such as DMSO may afford the substituted quinolinyl compounds of (50). Aryl coupling of the bromo-quinolinyl compounds of (50) with the bicyclic boronates of (40) under Suzuki conditions may furnish biaryl compounds of (53). Alternatively, to install the bicyclic aryl group first, the Suzuki coupling of bromide (29) with boronate (40) may be done using conditions well known by one with skill in the art, such as using $K_3PO_4$ as the base and the palladium complex 1,1'-bis(di-tert-butylphosphino)ferrocene palladium dichloride as well as refluxing in dioxane/water, to obtain the biaryl compounds of (51). Then the hydroxy moiety of the quinolinyl compounds of (51) may be converted to a leaving group (LG) moiety, for example, a chloride, a bromide or a triflate by standard methods that one with skill in the art would appreciate. For example, the triflate may be obtained from the hydroxy-quinoline compounds of (51) by using trifluoromethanesulfonic anhydride and DMAP in DCM at 0° C. which may then be used in a $S_NAR$, as previously described, using a substituted piperazine to give the dihydrofuroquinolinyl compounds of (53). The compounds of (53) may then be oxidized with mCPBA, or other suitable oxidizing agents known to those with skill in the art, along with an appropriate solvent, if needed, to furnish the sulfone compounds of (54). The sulfone moiety may then undergo nucleophilic displacement with a suitable nucleophile, such as a primary or secondary alcohol, using a strong base such as LiHMDS in THF to afford the substituted quinolinyl compounds of (55). Subsequent removal of the protecting group(s) may be achieved by methods appropriate to the protecting group used, such as Boc removal by TFA in DCM, to give the dihydrofuroquinoline compounds of (56).

Scheme 10

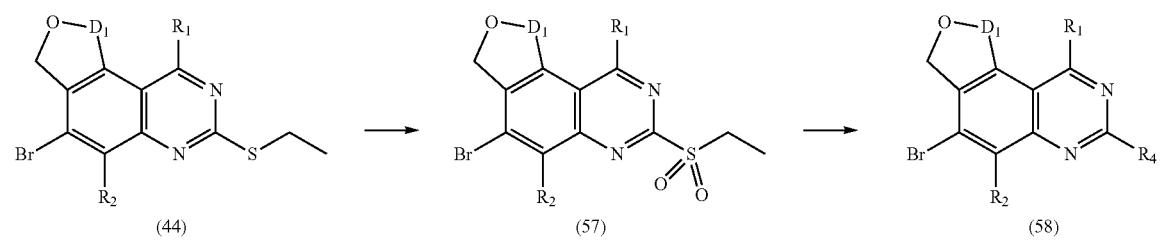

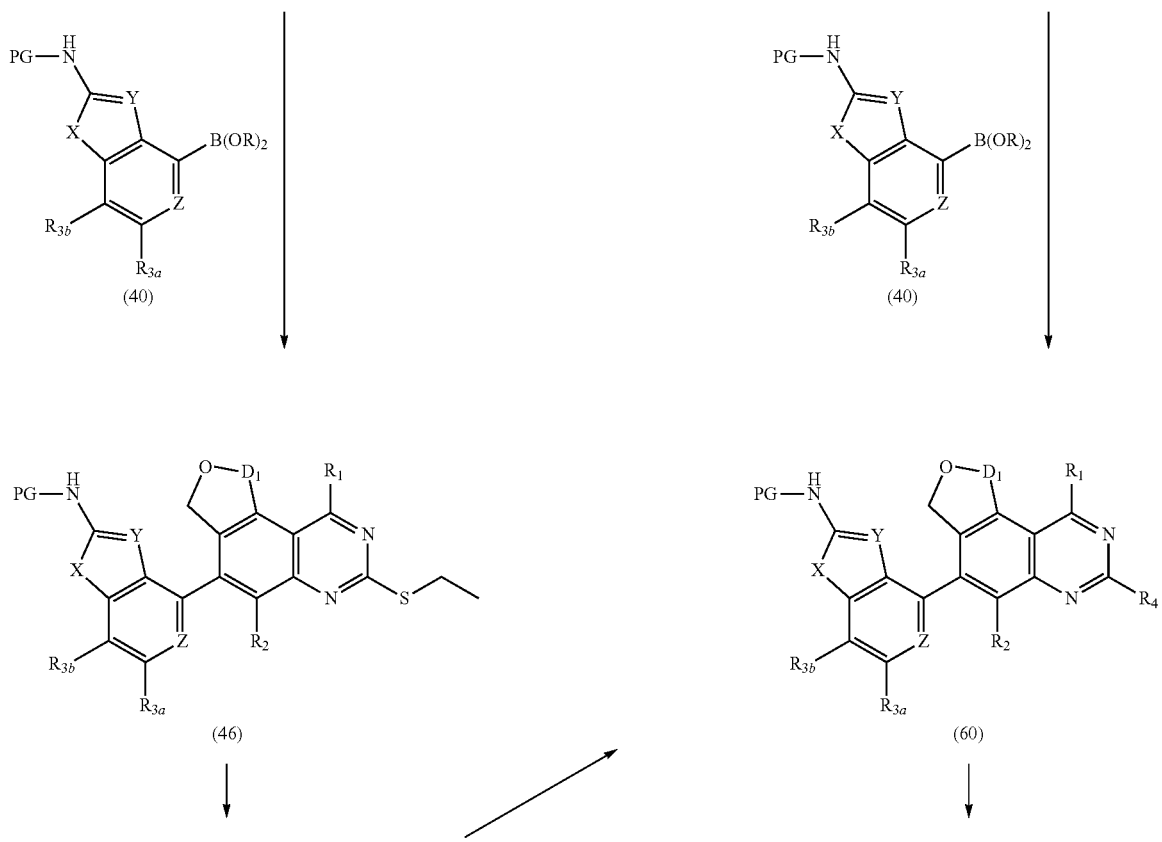

333

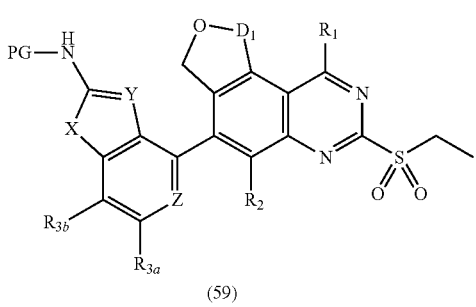

(59)

334

-continued

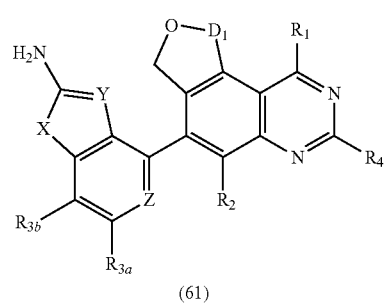

(61)

Scheme 10 depicts the preparation of dihydrofuroquinazoline compounds of (61) with route options to functionalize the quinazolinyl core in two different ways. One route to the intermediate compounds of (60) starts from the oxidation of the thioether compounds of (44), as previously mentioned with mCPBA, to furnish the sulfone compounds of (57). Nucleophilic displacement of the sulfone moiety may then provide the bifunctionalized quinazolinyl compounds of (58). Suzuki coupling of the bromide compounds of (58) with boronate compounds of (40), such as substituted benzothiophenes, benzothiazoles and benzofurans, may then yield the biaryl compounds of (60). The Suzuki coupling may also be achieved in the reverse, by reacting the bromide compounds of (58) with bis(neopentyl glycolato)diboron in the presence of a mild base such as KOAc and a palladium complex, such as dichloro[bis(2-(diphenylphosphino)phenyl)ether]palladium(II), to form the boronate ester on the quinazolinyl core followed by the coupling to a Boc-protected chlorothienopyridine, such as tert-butyl N-(4-chloro-thieno[3,2-c]pyridin-2-yl)carbamate, to furnish the biaryl compounds of (60). Another route to the intermediate compounds of (60) involves incorporating the Suzuki coupling up front so the bromide compounds of (44) may undergo arylation with the boronate compounds of (40) to provide the biaryl compounds of (46). Oxidation of the sulfide moiety on the compounds of (46) with previously mentioned standard conditions may then afford the sulfone compounds of (59) which through a $S_NAR$ with a nucleophile such as a primary or secondary alcohol may furnish the functionalized compounds of (60). Subsequent removal of the protecting group(s) may be achieved by methods appropriate to the protecting group used, such as Boc removal by TFA in DCM, to give the dihydrofuroquinazoline compounds of (61).

Preparation 1

5-Fluoro-3H-isobenzofuran-1-one

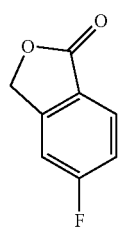 [SMILES: O=C1OCc2cc(F)ccc21]

To a stirred mixture of (2-bromo-5-fluorophenyl)methanol (500 g, 2.44 mol) and TEA (474.6 mL, 3.41 mol, 1.4 eq.) in ACN (2500 mL) was added Pd(OAc)$_2$ (10.95 g, 48.77 mmol, 0.02 eq.) and XantPhos (42.33 g, 73.16 mmol, 0.03 equiv.) at RT, then stirred for 3 days at 120° C. under 10 atm of carbon monoxide. The reaction was cooled to RT and concentrated. The residue was diluted with H$_2$O (1,000 mL), then extracted with EtOAc (2×2000 mL). The combined organic layers were washed with brine (2×1,000 mL), dried over anhydrous Na$_2$SO$_4$, filtered and concentrated. The residue was triturated with 10:1 hexanes/EtOAc (1,100 mL) and then filtered. The filter cake was dried at 50° C. for ~18 h to obtain the title compound as a yellow solid (300 g, 81%). MS (ES) m/z=153 (M+1).

Preparation 2

4-Bromo-5-fluoro-6-nitro-3H-isobenzofuran-1-one

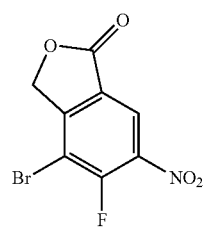 [SMILES: O=C1OCc2c1cc([N+](=O)[O-])c(F)c2Br]

To a stirred mixture of 5-fluoro-3H-isobenzofuran-1-one (300 g, 1.97 mol) in H$_2$SO$_4$ (1,500 mL) was added HNO$_3$ (273.38 g, 4.348 mol, 2.2 eq.) dropwise at 65° C. The reaction was stirred for 1 h then cooled to RT. 1,3-dibromo-5,5-dimethylimidazolidine-2,4-dione (2,255.43 g, 7.88 mol, 4 eq.) was added in portions over 20 min and was stirred at RT for ~18 h. The mixture was poured onto ice/water (pre-treated with 3 kg Na$_2$SO$_3$) and filtered. The filter cake was dissolved in EtOAc (3,000 mL), washed with sat. aq. Na$_2$CO$_3$ (2×1,000 mL), brine (2×1,000 mL), dried over anhydrous Na$_2$SO$_4$ and concentrated. The residue was triturated with 10:1 hexanes/EtOAc (660 mL) and was filtered and dried at 50° C. for ~18 h to obtain the title compound as a yellow solid (270 g, 49%) which was used in a subsequent step without further purification. $^1$H NMR (400 MHz, DMSO-d$_6$) δ 8.58 (s, 1H), 5.51 (s, 2H).

Preparation 3

5-Chloro-6-nitro-3H-isobenzofuran-1-one

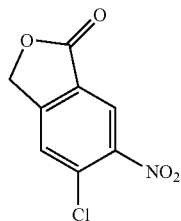 [SMILES: O=C1OCc2cc(Cl)c([N+](=O)[O-])cc21]

In a 1 L, 3-necked round bottom flask a solution of 5-chloro-3H-isobenzofuran-1-one (60 g, 355.91 mmol) in HNO$_3$ (46 mL) and H$_2$SO$_4$ (277 mL) was heated at 100° C. under N$_2$ for 4 h. The mixture was added slowly to ice water (1 L) and stirred for 30 min. The resulting precipitate was filtered and rinsed with H$_2$O (2×300 mL) and dried under vacuum at 45° C. to obtain the title compound (57 g, 70%) as a yellow solid. MS (ES) m/z=214 (M+1).

Preparation 4

4-Bromo-5-chloro-6-nitro-3H-isobenzofuran-1-one

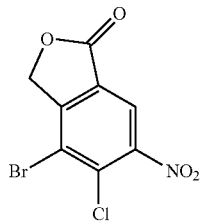 [SMILES: O=C1OCc2c1cc([N+](=O)[O-])c(Cl)c2Br]

In a 1 L, 3-necked RBF a solution of 5-chloro-6-nitro-3H-isobenzofuran-1-one (65 g, 283 mmol) was dissolved in H$_2$SO$_4$ (600 mL) and cooled to 0° C. NBS (60 g, 337 mmol) was added under N$_2$ portion wise at such a rate to keep the temperature at 0° C. The reaction was then stirred at 50° C. for ~18 h. The mixture was added slowly to ice water (1 L) and stirred for 30 min. The resulting precipitate was filtered and rinsed with H$_2$O (2×300 mL) and dried under vacuum at 45° C. to obtain the title compound (65 g, 72%) as a yellow solid. MS (ES) m/z=292 (M+1).

Preparation 5

4-Bromo-5-fluoro-6-nitro-1,3-dihydroisobenzofuran

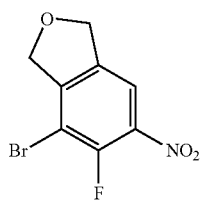 [SMILES: O=[N+]([O-])c1cc2c(c(Br)c1F)COC2]

To a stirred mixture of 4-bromo-5-fluoro-6-nitro-3H-isobenzofuran-1-one (270 g, 978 mmol) in DCM (2,500 mL) was added DIBAL-H (1M in THF, 1,467 mL, 1.467 mol, 1.5 eq.) dropwise at −78° C. under N$_2$. The reaction was stirred for 5 h at −78° C., then was quenched with 5N NaOH (300 mL) at −78° C. The resulting mixture was allowed to warm to RT, then was concentrated. The residue was diluted with EtOAc (2,500 mL), washed with brine (2×1,000 mL) and dried over anhydrous Na$_2$SO$_4$ and concentrated. The residue was triturated with 10:1 hexanes/EtOAc (550 mL) and filtered. The solids were dried (190 g, 683.4 mmol) then dissolved in DCM (1,500 mL) and treated dropwise with Et$_3$SiH (662 mL, 4.10 mol, 6 eq.) at 0° C. The reaction was stirred for 20 min at 0° C. TFA (152 mL, 2.05 mol, 3 eq.) was added dropwise at 0° C. The ice bath was removed, and the reaction was stirred at RT for ~18 h. The reaction was concentrated to an oil, which was diluted with EtOAc (2,000 mL), washed with sat. aq. Na$_2$CO$_3$ (2×500 mL) and brine (2×500 mL), dried over anhydrous Na$_2$SO$_4$, filtered and concentrated to obtain the title compound (110 g, 42%) which was used in a subsequent step without further purification. $^1$H NMR (400 MHz, DMSO-d$_6$) δ 8.16 (d, J=6.2 Hz, 1H), 5.18-5.15 (m, 2H), 5.11-5.06 (m, 2H).

Preparation 6

7-Bromo-6-fluoro-1,3-dihydroisobenzofuran-5-amine

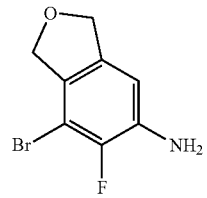 [SMILES: Nc1cc2c(c(Br)c1F)COC2]

To a stirred mixture of 4-bromo-5-fluoro-6-nitro-1,3-dihydroisobenzofuran (110 g, 420 mmol) and NH$_4$Cl (112.3 g, 2.10 mol, 5 eq.) in EtOH (1,000 mL) and H$_2$O (200 mL) was added Fe (117.22 g, 2.09 mol, 5 eq.) in portions at RT, then stirred for ~18 h at 80° C. The mixture was filtered and concentrated. The mixture was diluted with H$_2$O (500 mL) and extracted with EtOAc (2×1,000 mL). The combined organic layers were washed with brine (2×500 mL), dried over anhydrous Na$_2$SO$_4$, filtered and concentrated. The residue was purified on silica (25% to 50% EtOAc/Hex) to afford the title compound (70 g, 72%) as a yellow solid. MS (ES) m/z=231 (M+1).

Preparation 7

[4-Chloro-2-(hydroxymethyl)phenyl]methanol

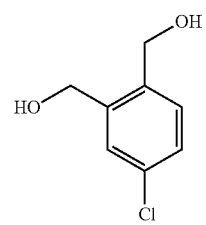

To a stirred mixture of LiAlH₄ (1.9 L, 2.74 mol, 2 eq., 2.5 M in THF) in THF (1 L) was added 4-chlorophthalic anhydride (250 g, 1.34 mol, 1.00 eq.) in THF (500 mL) dropwise at −20° C. under N₂. The resulting mixture was stirred for 30 min at 45° C. under N₂. The reaction was quenched by the addition of H₂O (1.5 L) and 15% NaOH (500 mL) at RT. The mixture was filtered, and the filter cake was washed with MTBE (3×250 mL). The filtrate was extracted with MTBE (3×1.5 L). The combined organic layers were washed with brine (2×2 L) and dried over anhydrous Na₂SO₄. After filtration, the filtrate was concentrated under reduced pressure to obtain the title compound (219.5 g, 93%) as an off-white solid. 1H NMR (300 MHz, DMSO-d₆) δ 7.45-7.36 (m, 2H), 7.28 (dd, J=8.2 Hz, 1H), 5.40-5.13 (m, 2H), 4.54 (s, 2H), 4.49 (s, 2H).

Preparation 8

5-Chloro-1,3-dihydroisobenzofuran

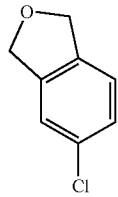

To a stirred mixture of [4-chloro-2-(hydroxymethyl)phenyl]methanol (219.5 g, 1.271 mol) and dimethyl carbonate (458.2 g, 5.082 mol, 4 eq.) in ACN (3 L) was added NaOMe (137.4 g, 2.544 mol, 2 eq.) in portions at RT. The resulting mixture was stirred for ~18 h at 80° C. under N₂. The mixture was concentrated under reduced pressure, diluted with H₂O (2 L) and extracted with EtOAc (3×2 L). The combined organic layers were washed with brine (2×2 L) and dried over anhydrous Na₂SO₄. After filtration, the filtrate was concentrated under reduced pressure. The residue was purified on silica (10:1 to 8:1 hex/EtOAc) to obtain the title compound (165 g, 82%) as a light-brown solid. ¹H NMR (300 MHz, DMSO-d₆) δ 7.42-7.37 (m, 1H), 7.33 (d, J=1.4 Hz, 2H), 4.99 (s, 4H).

Preparation 9

5-Chloro-6-nitro-1,3-dihydroisobenzofuran

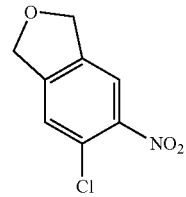 [SMILES: O=[N+]([O-])c1cc2c(cc1Cl)COC2]

A solution of 5-chloro-1,3-dihydroisobenzofuran (110 g, 712 mmol) in H₂SO₄ (700 mL) at −10° C. was charged with a solution of KNO₃ (64.74 g, 640 mmol, 0.9 eq.) in H₂SO₄ (200 mL) dropwise at −5° C.-0° C. The resulting mixture was stirred for additional 30 min at 0° C. and then was slowly added to stirred ice-cooled H₂O. The precipitated solids were collected by filtration and washed with H₂O (3×1 L). The filter cake was dried in vacuo to afford the title compound (110 g, 77%) as a light-brown solid which was used in a subsequent step without further purification. ¹H NMR (400 MHz, DMSO-d₆) δ 8.05 (s, 1H), 7.75 (s, 1H), 5.07-5.02 (m, 4H).

Preparation 10

4-Bromo-5-chloro-6-nitro-1,3-dihydroisobenzofuran

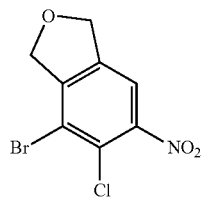

To a stirred solution of 5-chloro-6-nitro-1,3-dihydroisobenzofuran (125 g, 626 mmol) in H₂SO₄ (700 mL) was added 1,3-dibromo-5,5-dimethylimidazolidine-2,4-dione (179.1 g, 626.3 mmol, 1 eq.) in portions at −10° C. The mixture was stirred for 1 h at −10° C. then slowly was added to stirred ice-cooled H₂O. The precipitated solids were collected by filtration and washed with H₂O (3×0.5 L). The filter cake was dried in vacuo and purified on silica (10:1 to 5:1 Hex/EtOAc) to obtain the title compound (83.5 g, 47.9%) as a white solid. ¹H NMR (300 MHz, DMSO-d₆) δ 8.07 (d, J=1.1 Hz, 1H), 5.19 (dt, J=2.3, 1.1 Hz, 2H), 5.08 (t, 2H).

Preparation 11

7-Bromo-6-chloro-1,3-dihydroisobenzofuran-5-amine

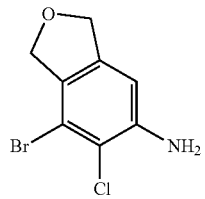 [SMILES: Nc1cc2c(c(Br)c1Cl)COC2]

To a stirred mixture of 4-bromo-5-chloro-6-nitro-1,3-dihydroisobenzofuran (37.0 g, 133 mmol) and NH₄Cl (42.64 g, 797.2 mmol, 6 eq.) in EtOH (200 mL) and H₂O (40 mL) was added Fe (44.52 g, 797.2 mmol, 6 equiv.) in portions at RT. The resulting mixture was stirred for ~18 h at 80° C. The resulting mixture was filtered hot and the filter cake was washed with EtOAc (3×500 mL). The filtrate was concentrated under reduced pressure and was purified on silica (15:1 to 10:1 Hex/EtOAc) to obtain the title compound (25 g, 76%) as a light-yellow solid. MS (ES) m/z=248 (M+1).

Preparation 12

N-(7-Bromo-6-chloro-1,3-dihydroisobenzofuran-5-yl)-3-ethoxy-prop-2-enamide

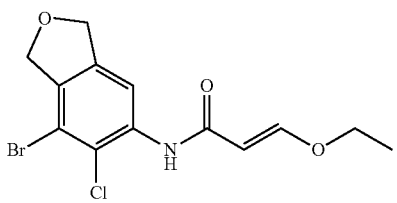 [SMILES: CCO/C=C/C(=O)Nc1cc2c(c(Br)c1Cl)COC2]

To a stirred solution of 7-bromo-6-chloro-1,3-dihydroisobenzofuran-5-amine (6.00 g, 24.1 mmol) and 3-ethoxyprop-2-enoyl chloride (4.06 g, 30.2 mmol) in THF (50 mL) was added pyridine (3.82 g, 48.3 mmol) dropwise at 0° C. The resulting mixture was stirred for 2 h at RT. The resulting mixture was concentrated under vacuum. The residue was purified by silica gel column chromatography, eluting with PE/EtOAc (5:1) to afford the product (6.00 g, 66.0%) as a yellow solid. MS (ES) m/z=346 (M+1).

Preparation 13

N-(7-Bromo-6-fluoro-1,3-dihydroisobenzofuran-5-yl)-3-ethoxy-prop-2-enamide

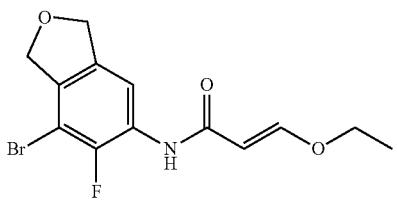 [SMILES: CCO/C=C/C(=O)Nc1cc2c(c(Br)c1F)COC2]

7-Bromo-6-fluoro-1,3-dihydroisobenzofuran-5-amine was used in a manner analogous to the method of Preparation 12 to afford the title compound (1.4 g, 89%) as a pale-yellow solid. MS (ES) m/z=332 (M+1).

Preparation 14

4-Bromo-5-chloro-3,6-dihydro-1H-furo[3,4-f]quinolin-7-one

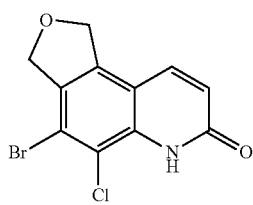 [SMILES: O=c1ccc2c3c(c(Br)c(Cl)c2[nH]1)COC3]

To a stirred solution of $H_2SO_4$ (20 mL) was added N-(7-Bromo-6-chloro-1,3-dihydroisobenzofuran-5-yl)-3-ethoxy-prop-2-enamide (6.10 g, 17.6 mmol) in portions at 0° C. The resulting mixture was stirred for ~18 h at RT. The mixture was slowly added to stirred ice-cooled water (200 mL). The precipitated solids were collected by filtration and washed with $H_2O$ (3×100 mL). The filter cake was dried under vacuum to afford the product (5.00 g, 87.0%) as a yellow solid. MS (ES) m/z=300 (M+1).

Preparation 15

4-Bromo-5-fluoro-3,6-dihydro-1H-furo[3,4-f]quinolin-7-one

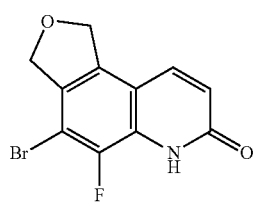 [SMILES: O=c1ccc2c3c(c(Br)c(F)c2[nH]1)COC3]

N-(7-Bromo-6-fluoro-1,3-dihydroisobenzofuran-5-yl)-3-ethoxy-prop-2-enamide was used in a manner analogous to that described for Preparation 14 to obtain the title compound (1.2 g, quantitative) as a tan solid. MS (ES) m/z=284 (M+1).

Preparation 16

4-Bromo-5,7-dichloro-1,3-dihydrofuro[3,4-f]quinoline

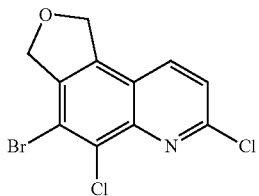 [SMILES: Clc1ccc2c3c(c(Br)c(Cl)c2n1)COC3]

To a stirred solution of 4-bromo-5-chloro-3,6-dihydro-1H-furo[3,4-f]quinolin-7-one (5.00 g, 16.6 mmol) in DMF (20 mL) was added $POCl_3$ (9.30 mL, 99.8 mmol) dropwise at 0° C. The resulting mixture was stirred for 2 h at 90° C. The mixture was slowly added to stirred ice-cooled water (200 mL). The precipitated solids were collected by filtration and washed with $H_2O$ (3×100 mL). The filter cake was dried under vacuum to afford the product (3.50 g, 62.7%) as a yellow solid. MS (ES) m/z=318 (M+1).

Preparation 17

4-Bromo-7-chloro-5-fluoro-1,3-dihydrofuro[3,4-f]quinoline

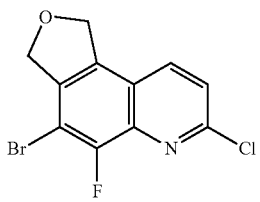 [SMILES: Fc1c(Br)c2c(c3ccc(Cl)nc13)COC2]

A suspension of 6-bromo-5-chloro-3-ethylsulfanyl-7,9-dihydrofuro[3,4-f]quinazolin-1-ol (1.2 g, 4.2 mmol) stirred in DCM (40 mL) was charged with (chloromethylene)dimethyliminium chloride (2.2 g, 17 mmol, 4 eq.) and stirred at RT for ~18 h. The reaction was diluted with DCM and washed with $H_2O$ and brine. The organic layer was dried over $Na_2SO_4$, filtered and concentrated to a solid which was triturated with a small amount of DCM. The solids were filtered and washed with a small amount of DCM and air-dried to give Batch 1. The filtrate was concentrated and purified on silica gel, eluting with EtOAc/hexanes (0% to 80%) to give Batch 2. Both batches were combined to afford the title compound (1.0 g, 78%) as a tan solid. MS (ES) m/z=304 (M+1).

Preparation 18

6-Amino-4-bromo-5-fluoro-3H-isobenzofuran-1-one

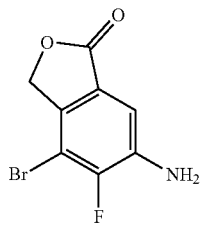 [SMILES: Nc1cc2c(c(Br)c1F)COC2=O]

A suspension of 4-bromo-5-fluoro-6-nitro-3H-isobenzofuran-1-one (1.11 g, 4.02 mmol) in AcOH (4 mL), $H_2O$ (2 mL) and EtOH (20 mL) was charged with iron (1.0 g, 18 mmol) and heated at 70° C. for 2 h. The reaction was cooled to RT, partitioned between DCM and sat. aq. $NaHCO_3$ and filtered through a pad of diatomaceous earth. The pad was rinsed with DCM, the filtrate partitioned, and the organics were dried over $MgSO_4$ and concentrated to afford the title compound (0.90 g, 91%) as a white solid. MS (ES) m/z=246 (M−1).

Preparation 19

6-Amino-4-bromo-5-chloro-3H-isobenzofuran-1-one

To a mixture of 4-bromo-5-chloro-6-nitro-3H-isobenzofuran-1-one (7.98 g, 27.3 mmol) in EtOH (200 mL) and $H_2O$ (40 mL) was added $NH_4Cl$ (5.84 g, 109 mmol), followed by iron powder (6.09 g, 109 mmol). The mixture was stirred at 80° C. in an oil bath for 20 h. The mixture was filtered through a pad of diatomaceous earth and washed with acetone. The filtrate was concentrated to ~50 mL. The resultant precipitate was collected by filtration and dried under vacuum overnight to afford a first batch of product (2.57 g) as beige solid. The diatomaceous earth mixture was stirred in acetone/MeOH (2/1) and filtered. The process was repeated twice. The combined filtrate was concentrated and dried in a vacuum oven at 60° C. overnight to afford a second batch of product (3.70 g). The batches were combined to give the title compound (6.27 g, 87.5%). MS (ES) m/z=279 (M+$H_2O$+1).

Preparation 20 tert-Butyl N-(7-bromo-6-fluoro-3-oxo-1H-isobenzofuran-5-yl)-N-tert-butoxycarbonyl-carbamate

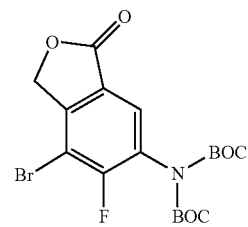 [SMILES: CC(C)(C)OC(=O)N(C(=O)OC(C)(C)C)c1cc2c(c(Br)c1F)COC2=O]

A mixture of 6-amino-4-bromo-5-fluoro-3H-isobenzofuran-1-one (36.0 g, 146 mmol), di-tert-butyl dicarbonate (100 g, 444 mmol) and DMAP (4.50 g, 37.0 mmol) in ACN (1,000 mL) was heated to reflux. After refluxing for 30 min, the reaction mixture was allowed to cool to RT. The solvent was removed under reduced pressure and the residue was dissolved in DCM (1,000 mL), washed with ice cold 10% citric acid, sat. aq. $NaHCO_3$, brine, and then was dried over $MgSO_4$, filtered and concentrated. The crude material was purified by silica column chromatography (100% A to 100% B; A=4% MTBE and 20% DCM in Hex, B=10% MTBE and 20% DCM in Hex) to afford the title compound (36.0 g, 55%). $^1$H NMR (300 MHz, DMSO-$d_6$) δ 8,11 (s, 1H), 5.49 (s, 2H), 1.40 (s, 18H).

Preparation 21 tert-Butyl N-(7-bromo-6-chloro-3-oxo-1H-isobenzofuran-5-yl)-N-tert-butoxycarbonyl-carbamate

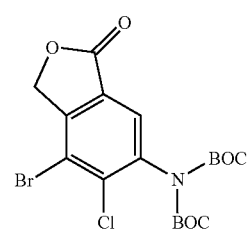

6-Amino-4-bromo-5-chloro-3H-isobenzofuran-1-one was used in a manner analogous to the method of Preparation 20 to afford the title compound (34.6 g, 61%) as an off-white solid. $^1$H NMR (300 MHz, DMSO-$d_6$) δ 8.10 (s, 1H), 5.48 (s, 2H), 1.40 (s, 18H).

Preparation 22 tert-Butyl N-(7-bromo-6-fluoro-3-hydroxy-1,3-dihydroisobenzofuran-5-yl)carbamate

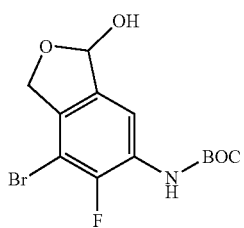 [SMILES: CC(C)(C)OC(=O)Nc1cc2c(c(Br)c1F)COC2O]

To a solution of tert-butyl N-(7-bromo-6-fluoro-3-oxo-1H-isobenzofuran-5-yl)-N-tert-butoxycarbonyl-carbamate (36.0 g, 80.7 mmol) in DCM (1,600 mL) at −70° C. was added DIBAL-H (1M in DCM, 245 mL, 245 mmol) dropwise over 2 h. The reaction mixture was stirred for 1h at −70° C. after addition. The reaction was quenched by adding NaOH solution (1M in $H_2O$, 164 mL, 164 mmol) dropwise at −70° C. The mixture was diluted with DCM (1,000 mL) and stirred up to RT. After addition of $MgSO_4$ (200 g), the mixture was stirred for 10 min and then left to stand over $MgSO_4$ overnight at RT. The mixture was filtered through diatomaceous earth and washed with 10% MeOH in DCM (1,000 mL). The filtrate was concentrated and purified by silica column chromatography (5-40% EtOAc/Hex) to afford the title compound (25.0 g, 89%) as white solid. MS (ES) m/z=346 (M−1).

Preparation 23 tert-Butyl N-(7-bromo-6-chloro-3-hydroxy-1,3-dihydroisobenzofuran-5-yl)carbamate

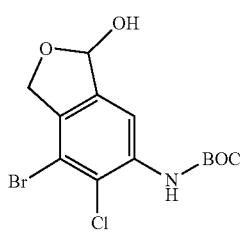 [SMILES: CC(C)(C)OC(=O)Nc1cc2c(c(Br)c1Cl)COC2O]

tert-Butyl N-(7-bromo-6-chloro-3-oxo-1H-isobenzofuran-5-yl)-N-tert-butoxycarbonyl-carbamate was used in a manner analogous to the method of Preparation 22 to afford the title compound (5.10 g, 65.4%) as a white solid. MS (ES) m/z=346 (M−$H_2O$+1).

Preparation 24 tert-Butyl N-[7-bromo-3-(cyanomethyl)-6-fluoro-1,3-dihydroisobenzofuran-5-yl]carbamate

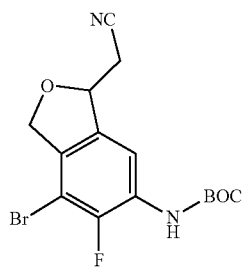 [SMILES: CC(C)(C)OC(=O)Nc1cc2c(c(Br)c1F)COC2CC#N]

To a flask was added tert-butyl N-(7-bromo-6-fluoro-3-hydroxy-1,3-dihydroisobenzofuran-5-yl)carbamate (9.70 g, 27.9 mmol), THF (200 mL), diethyl cyanomethylphosphonate (7.00 mL, 42.3 mmol) and $Cs_2CO_3$ (10.0 g, 30.7 mmol). The flask was fitted with a condenser and the mixture was heated to reflux. After 3 h, the mixture was allowed to cool and was filtered through diatomaceous earth and rinsed with EtOAc. The combined filtrate and washings were concentrated. The crude oil was diluted with EtOAc (500 mL) and $H_2O$ (500 mL) was added. The mixture was transferred to a separatory funnel and the layers were separated. The aqueous layer was back extracted with EtOAc (500 mL) and the combined organic layers were washed with brine, dried over $MgSO_4$, filtered and concentrated. The crude material was purified by flash silica column chromatography, eluting with 5-40% EtOAc/Hex to afford the title compound (9.15 g, 89%) as a white solid. $^1$H NMR (300 MHz, DMSO-$d_6$) δ 9.28 (s, 1H), 7.68 (s, 1H), 5.52 (s, H), 5.02 (m, 2H), 3.18 (m, 2H), 1.49 (s, 9H).

Preparation 25 tert-Butyl N-[7-bromo-6-chloro-3-(cyanomethyl)-1,3-dihydroisobenzofuran-5-yl]carbamate

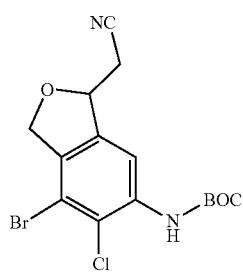 [SMILES: CC(C)(C)OC(=O)Nc1cc2c(c(Br)c1Cl)COC2CC#N]

tert-Butyl N-(7-bromo-6-chloro-3-hydroxy-1,3-dihydroisobenzofuran-5-yl)carbamate was used in a manner analogous to the method of Preparation 24 to afford the title compound (3.92 g, 72%) as white solid. MS (ES) m/z=385 (M−1).

Preparation 26

2-(6-Amino-4-bromo-5-fluoro-1,3-dihydroisobenzofuran-1-yl)acetonitrile

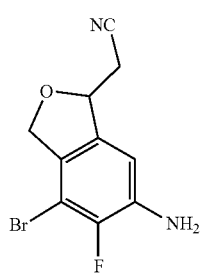

To a suspension of tert-butyl N-[7-bromo-3-(cyanomethyl)-6-fluoro-1,3-dihydroisobenzofuran-5-yl]carbamate (9.10 g, 24.5 mmol) in MeOH (150 mL) cooled in an ice bath was added HCl solution (4M in 1,4-dioxane, 64.0 mL, 256 mmol). The reaction was stirred at RT for 6 h. The mixture was cooled in an ice bath, neutralized first with 2N NaOH solution, and then with sat. aq. NaHCO$_3$. The mixture was concentrated and the resultant solid was collected and dried in vacuo at 60° C. overnight to afford the title compound as white solid (6.10 g, 92%). MS (ES) m/z=269 (M−1).

Preparation 27

2-(6-Amino-4-bromo-5-chloro-1,3-dihydroisobenzofuran-1-yl)acetonitrile

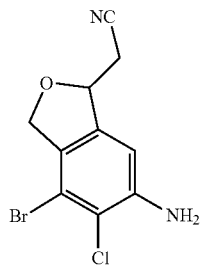

tert-Butyl N-[7-bromo-6-chloro-3-(cyanomethyl)-1,3-dihydroisobenzofuran-5-yl]carbamate was used in a manner analogous to the method of Preparation 26 to afford the title compound (2.64 g, 99%) as an off-white solid. MS (ES) m/z=287 (M+1).

Preparation 28

7-Methyl-6-nitro-isochroman-1-one

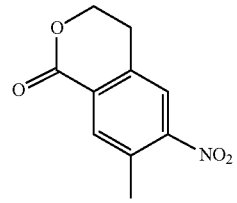

To a stirred mixture of 3-methyl-4-nitrobenzoic acid (70.0 g, 386 mmol) and N-acetyl-L-leucine (13.4 g, 77.3 mmol) in hexafluoroisopropanol (750 mL) was added KOAc (37.9 g, 386 mmol), and Pd(OAc)$_2$ (8.68 g, 38.6 mmol) followed by ethylene oxide (155 mL, 386 mmol, 1 eq., 2.5M in THF) at RT. The reaction mixture was stirred at 80° C. for 8 h under N$_2$. The mixture was diluted with EtOAc (1,000 mL). The organic layers were washed with brine (500 mL), dried over anhydrous Na$_2$SO$_4$ and filtered. The filtrate was concentrated under reduced pressure. The residue was purified by silica gel column chromatography, eluting with PE:EtOAc (3:1 to 1:1) to afford the product (56.0 g, 52.4%) as a yellow solid. MS (ES) m/z=249 (M+1).

Preparation 29

7-Methyl-6-nitro-isochromane

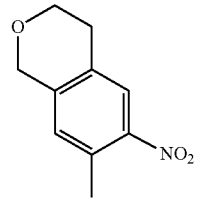

To a stirred mixture of 7-methyl-6-nitro-isochroman-1-one (66.0 g, 319 mmol) in THF (800 mL) was added LiBH$_4$ (2M in THF, 400 mL, 800 mmol) dropwise at −78° C. under N$_2$. The reaction mixture was allowed to warm to RT and was stirred for 3 h. The reaction was diluted by sat. aq. NH$_4$Cl (300 mL) and was extracted with EtOAc (2×600 mL). The combined organic layers were washed with brine (50 mL), dried over anhydrous Na$_2$SO$_4$, filtered and concentrated under reduced pressure. To the crude 2-[2-(hydroxymethyl)-4-methyl-5-nitrophenyl]ethanol (50.0 g, 237 mmol) was added 4-methylbenzene-1-sulfonic acid (44.8 g, 260 mmol) and toluene (500 mL). The resulting reaction mixture was heated at 115° C. for ~18 h. The reaction was allowed to cool down to RT. The mixture was diluted with EtOAc (1,000 mL) and was washed with brine (500 mL), then dried over anhydrous Na$_2$SO$_4$, filtered and concentrated under reduced pressure. The residue was purified by silica gel column chromatography, eluting with PE:EtOAc (3:1 to 1:1) to afford the product (30.0 g, 36.3%) as a yellow solid. $^1$H NMR (300 MHz, CDCl$_3$) δ 7.81 (s, 1H), 6.96 (s, 1H), 4.82-4.74 (m, 2H), 4.02-3.96 (m, 2H), 2.96-2.82 (m, 2H), 2.5 (s, 3H).

Preparation 30

8-Bromo-7-methyl-6-nitro-isochromane

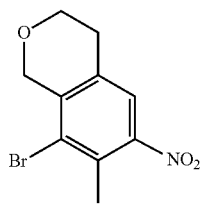

To a mixture of 7-methyl-6-nitro-isochromane (30 g, 150 mmol) in conc. $H_2SO_4$ (300 mL) was added NBS (32.1 g, 180 mmol) in portions at RT. The reaction was stirred at RT for ~18 h. The reaction mixture was poured into ice water (500 mL) and was filtered. The filter cake was washed with sat. aq. $Na_2CO_3$ (2×50 mL), then was dissolved in EtOAc (500 mL), washed with brine (2×50 mL), dried over anhydrous $Na_2SO_4$, filtered and concentrated under reduced pressure. The residue was purified by silica gel column chromatography, eluting with PE:EtOAc (3:1 to 1:1) to afford the product (23.0 g, 56.5%) as a yellow solid. $^1$H NMR (300 MHz, $CDCl_3$) δ 7.58 (s, 1H), 4.78-4.68 (m, 2H), 4.02-3.92 (m, 2H), 2.98-2.86 (m, 2H), 2.57 (s, 3H).

Preparation 31

8-Bromo-7-methyl-isochroman-6-amine

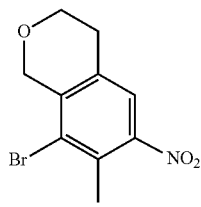

To a mixture of 8-bromo-7-methyl-6-nitro-isochromane (23.0 g, 84.5 mmol) and $NH_4Cl$ (22.6 g, 423 mmol) in EtOH (250 mL) and $H_2O$ (50 mL) was added iron powder (23.6 g, 423 mmol) at RT. The resulting reaction mixture was heated at 80° C. for 6 h. The mixture was filtered, and the filter cake was washed with EtOAc (2×200 mL). The filtrate was diluted with EtOAc (100 mL), washed with brine (500 mL), dried over anhydrous $Na_2SO_4$, filtered and was concentrated under reduced pressure. The residue was purified by silica gel column chromatography, eluting with PE:EtOAc (2:1 to 1:2) to afford the product (17.0 g, 83%) as a yellow solid. MS (ES) m/z=242 (M+1).

Preparation 32

Ethyl N-[(7-bromo-6-fluoro-1,3-dihydroisobenzofuran-5-yl)carbamothioyl]carbamate

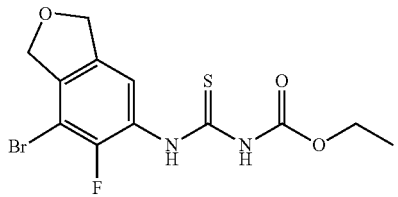 [SMILES: CCOC(=O)NC(=S)Nc1cc2c(c(Br)c1F)COC2]

A solution of 7-bromo-6-fluoro-1,3-dihydroisobenzofuran-5-amine (20.4 g, 87.9 mmol) in DCM (550 mL) was charged with ethoxycarbonyl isothiocyanate (9.7 mL, 82 mmol, 0.93 eq.) slowly via addition funnel and subsequently stirred at RT for ~4 h. The solids were filtered. The filtrate was concentrated, suspended in DCM (100 mL) and hexanes (350 mL) and stirred at RT. The resultant filtered solids and previous filtered solids were dried under vacuum at 50° C. for 2 h. The batches were combined to obtain the title compound (32.6 g, quantitative) as a white solid. MS (ES) m/z=363 (M+1).

The following compounds in Table 1 were prepared in a similar manner as described in Preparation 32. Various methods were used to purify the compounds, which would be apparent to one skilled in the art.

TABLE 1

| Preparation | Chemical Name | Structure | MS (ES) m/z (M + 1) |
|---|---|---|---|
| 33 | Ethyl N-[(7-bromo-6-chloro-1,3-dihydroisobenzofuran-5-yl)carbamothioyl]carbamate | 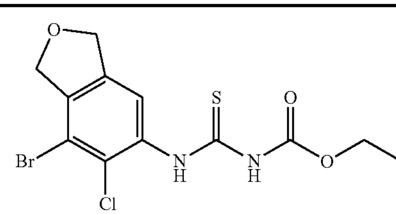 | 379 |

TABLE 1-continued

| Preparation | Chemical Name | Structure | MS (ES) m/z (M + 1) |
|---|---|---|---|
| 34 | Ethyl N-[[7-bromo-3-(cyanomethyl)-6-fluoro-1,3-dihydroisobenzofuran-5-yl]carbamothioyl]carbamate | 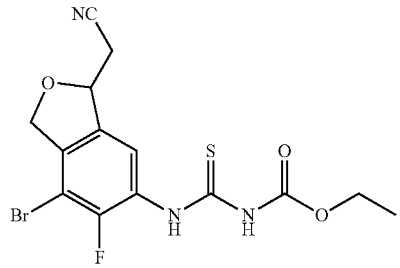 [SMILES: CCOC(=O)NC(=S)Nc1cc2c(c(Br)c1F)COC2CC#N] | 402 |
| 35 | Ethyl N-[[7-bromo-6-chloro-3-(cyanomethyl)-1,3-dihydroisobenzofuran-5-yl]carbamothioyl]carbamate | 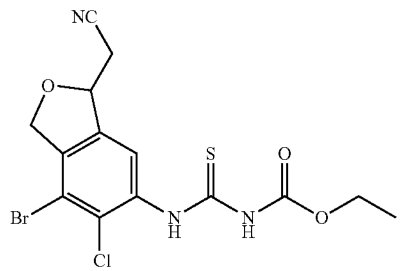 [SMILES: CCOC(=O)NC(=S)Nc1cc2c(c(Br)c1Cl)COC2CC#N] | 418 |
| 36 | Ethyl N-[(8-bromo-7-methyl-isochroman-6-yl)carbamothioyl]carbamate | 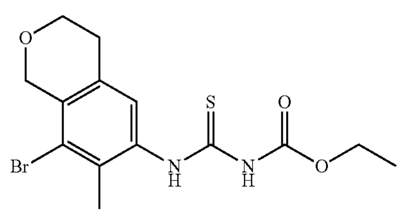 [SMILES: CCOC(=O)NC(=S)Nc1cc2c(c(Br)c1C)COCC2] | 373 |

Preparation 37

Ethyl (NZ)—N-[[(7-bromo-6-fluoro-1,3-dihydroisobenzofuran-5-yl)amino]-ethylsulfanyl-methylene]carbamate

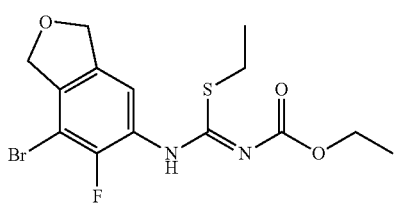

A 2 L 3-necked RBF, equipped with an overhead stirrer, dropping funnel and thermocouple was charged with a suspension of ethyl N-[(7-bromo-6-fluoro-1,3-dihydroisobenzofuran-5-yl)carbamothioyl]carbamate (32.6 g, 89.8 mmol) and acetone (450 mL). To this was added solid $K_2CO_3$ (37.2 g, 269 mmol, 3.00 eq.) in several portions, followed by the dropwise addition of EtI (7.2 mL, 90 mmol, 1.0 eq.) over 20 min. The mixture was stirred at RT for ~18 h. The solids were filtered and the filtrate was concentrated and partitioned between DCM (500 mL) and $H_2O$ (500 mL). The organics were further washed with brine and dried over anhydrous $Na_2SO_4$, filtered and concentrated. The residue was purified on silica (0 to 30% EtOAc/Hex) to obtain the title compound (30.9 g, 85.6%) as a white solid. MS (ES) m/z=391 (M+1).

The following compounds in Table 2 were prepared in a similar manner as described for Preparation 37. Various methods were used to purify the compounds, which would be apparent to one skilled in the art.

TABLE 2

| Preparation | Chemical Name | Structure | MS (ES) m/z (M + 1) |
|---|---|---|---|
| 38 | Ethyl (NZ)-N-[[(7-bromo-6-chloro-1,3-dihydroisobenzofuran-5-yl)amino]-ethylsulfanyl-methylene]carbamate | 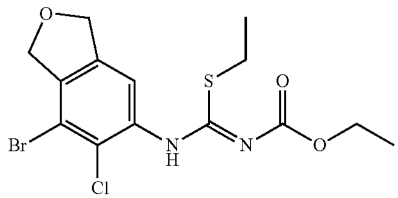 [SMILES: CCOC(=O)/N=C(/Nc1cc2c(c(Br)c1F)COC2)SCC] | 407 |
| 39 | Ethyl (NZ)-N-[[[7-bromo-3-(cyanomethyl)-6-fluoro-1,3-dihydroisobenzofuran-5-yl]amino]-ethylsulfanyl-methylene]carbamate | 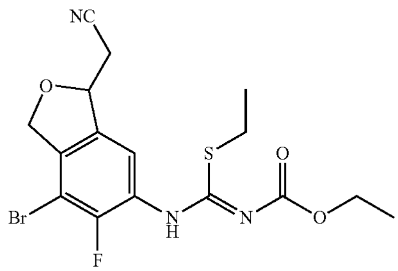 [SMILES: CCOC(=O)/N=C(/Nc1cc2c(c(Br)c1F)COC2CC#N)SCC] | 430 |
| 40 | Ethyl (NZ)-N-[[[7-bromo-6-chloro-3-(cyanomethyl)-1,3-dihydroisobenzofuran-5-yl]amino]-ethylsulfanyl-methylene]carbamate | 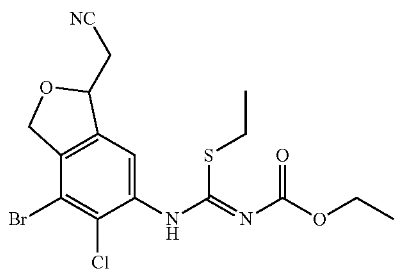 [SMILES: CCOC(=O)/N=C(/Nc1cc2c(c(Br)c1Cl)COC2CC#N)SCC] | 446 |
| 41 | Ethyl (NZ)-N-[[(8-bromo-7-methyl-isochroman-6-yl)amino]-ethylsulfanyl-methylene]carbamate | 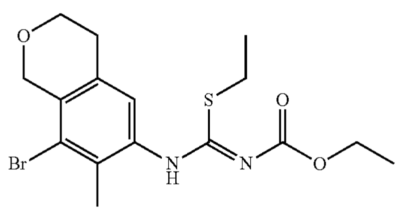 [SMILES: CCOC(=O)/N=C(/Nc1cc2c(c(Br)c1C)COCC2)SCC] | 401 |

Preparation 42

6-Bromo-3-ethylsulfanyl-5-fluoro-7,9-dihydrofuro[3,4-f]quinazolin-1-ol

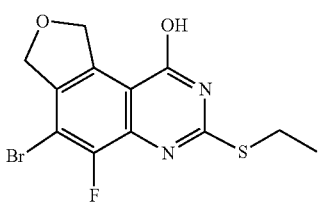

A 2 L 4-necked RBF was equipped with an overhead stirrer, dropping funnel, $N_2$ inlet and thermocouple and was purged with $N_2$. NMP (anhydrous, 300 mL) was added. The mixture was heated to 175° C. In a second flask, ethyl (NZ)—N-[[(7-bromo-6-fluoro-1,3-dihydroisobenzofuran-5-yl)amino]-ethylsulfanyl-methylene]carbamate (22.63 g, 57.83 mmol) and NMP (anhydrous, 100 mL) were combined and stirred under $N_2$ until a homogeneous solution was obtained. When the first flask had reached 175° C., the contents of the second flask were poured into the dropping funnel and were added dropwise but rapidly to the hot NMP. After 30 min, the heat was turned off and the reaction cooled to 45° C. $H_2O$ (500 mL) was slowly added and the mixture was stirred at RT for 1 h. The solids were filtered, rinsed with $H_2O$ (300 mL) and dried under vacuum at 50° C. for ~18 h to afford the title compound (15.2 g, 73%) as an off-white solid. MS (ES) m/z=363 (M+1).

The following compounds in Table 3 were prepared in a similar manner as described for Preparation 42. Various methods were used to purify the compounds, which would be apparent to one skilled in the art.

TABLE 3

| Preparation | Chemical Name | Structure | MS (ES) m/z (M + 1) |
|---|---|---|---|
| 43 | 6-Bromo-5-chloro-3-ethylsulfanyl-7,9-dihydrofuro[3,4-f]quinazolin-1-ol | 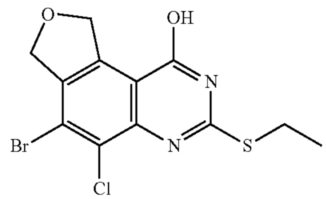 [SMILES: CCSc1nc(O)c2c3c(c(Br)c(F)c2n1)COC3] | 361 |
| 44 | 2-(6-Bromo-3-ethylsulfanyl-5-fluoro-1-hydroxy-7,9-dihydrofuro[3,4-f]quinazolin-9-yl)acetonitrile | 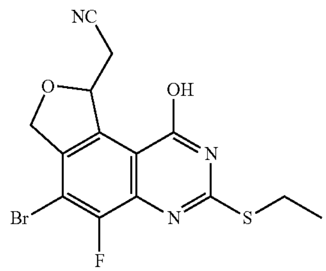 [SMILES: CCSc1nc(O)c2c3c(c(Br)c(F)c2n1)COC3CC#N] | 382 |
| 45 | 2-(6-Bromo-5-chloro-3-ethylsulfanyl-1-hydroxy-7,9-dihydrofuro[3,4-f]quinazolin-9-yl)acetonitrile | 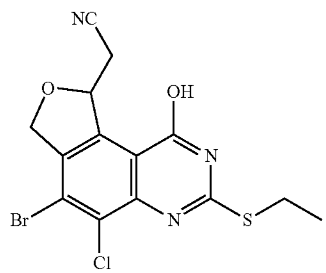 [SMILES: CCSc1nc(O)c2c3c(c(Br)c(Cl)c2n1)COC3CC#N] | 400 |
| 46 | 6-bromo-3-ethylsulfanyl-5-methyl-9,10-dihydro-7H-pyrano[4,3-f]quinazolin-1-ol | 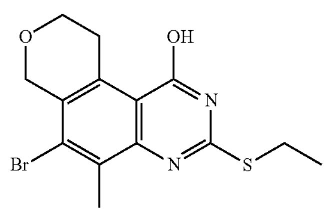 [SMILES: CCSc1nc(O)c2c3c(c(Br)c(C)c2n1)COCC3] | 355 |

Preparation 47

7-Bromo-6-fluoro-4-iodo-1,3-dihydroisobenzofuran-5-amine

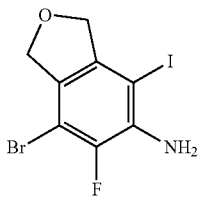 [SMILES: Nc1c(F)c(Br)c2c(c1I)COC2]

A mixture of 7-bromo-6-fluoro-1,3-dihydroisobenzofuran-5-amine (15.0 g, 64.6 mmol) and NIS (16.0 g, 71.1 mmol) in CHCl₃ (400 mL) was stirred at 50° C. under N₂ for ~18 h. The resulting mixture was concentrated under reduced pressure and the residue was purified by silica gel column chromatography, eluting with PE/EtOAc (10:1-5:1) to afford the product (16.0 g, 69.2%) as an orange solid. MS (ES) m/z=358 (M+1).

Preparation 48

7-Bromo-6-chloro-4-iodo-1,3-dihydroisobenzofuran-5-amine

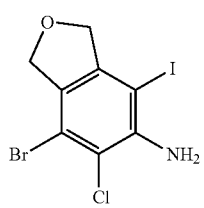 [SMILES: Nc1c(Cl)c(Br)c2c(c1I)COC2]

7-Bromo-6-chloro-1,3-dihydroisobenzofuran-5-amine was used in a manner analogous to the method of Prepara-

Preparation 49

Methyl 5-amino-7-bromo-6-fluoro-1,3-dihydroisobenzofuran-4-carboxylate

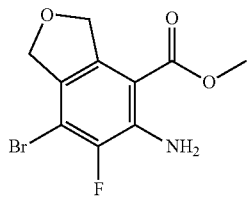 [SMILES: COC(=O)c1c(N)c(F)c(Br)c2c1COC2]

To a stirred solution of 7-bromo-6-fluoro-4-iodo-1,3-dihydroisobenzofuran-5-amine (1.62 g, 4.53 mmol) in MeOH (20 mL) and DMF (20 mL) was added TEA (1.89 mL, 13.6 mmol) and Pd(dppf)Cl$_2$ (331 mg, 0.45 mmol) at RT under CO atmosphere. The mixture was stirred at 60° C. for ~18 h under CO atmosphere using a CO balloon. The resulting mixture was concentrated under reduced pressure and was diluted with EtOAc (300 mL). The mixture was washed with H$_2$O (3×200 mL), brine (200 mL) and dried over anhydrous Na$_2$SO$_4$. After filtration, the filtrate was concentrated under reduced pressure. The residue was purified by silica gel column chromatography, eluting with EtOAc in PE, 20% to 40% gradient in 30 min to afford the product (1.00 g, 76.1%) as a yellow solid. MS (ES) m/z=290 (M+1).

Preparation 50

Methyl 5-amino-7-bromo-6-chloro-1,3-dihydroisobenzofuran-4-carboxylate

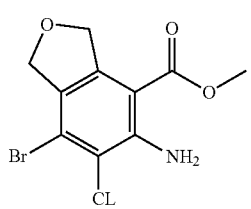

7-Bromo-6-chloro-4-iodo-1,3-dihydroisobenzofuran-5-amine was used in a manner analogous to the method of Preparation 49 to afford the title compound (6.2 g, 58%) as light-yellow solid. MS (ES) m/z=306 (M+1).

Preparation 51

7-Bromo-4-(1-ethoxyvinyl)-6-fluoro-1,3-dihydroisobenzofuran-5-amine

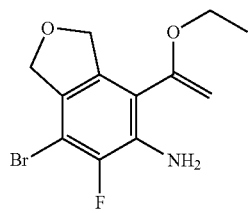 [SMILES: C=C(OCC)c1c(N)c(F)c(Br)c2c1COC2]

To a stirred mixture of 7-bromo-6-fluoro-4-iodo-1,3-dihydroisobenzofuran-5-amine (6.00 g, 16.8 mmol) and tributyl(1-ethoxyvinyl)stannane (22.7 g, 62.9 mmol) in DMF (60 mL) was added Pd(PPh$_3$)$_4$ (3.88 g, 3.34 mmol) in portions at RT. The reaction was then stirred for ~18 h at 80° C. The mixture was allowed to cool down to RT and was extracted with EtOAc (200 mL). The organic layers were washed with H$_2$O (3×50 mL), brine (50 mL) and dried over anhydrous Na$_2$SO$_4$. After filtration, the filtrate was concentrated under reduced pressure to afford the product (5.07 g, quantitative) which was used in the subsequent step without further purification. MS (ES) m/z=301 (M+1).

Preparation 52

1-(5-Amino-7-bromo-6-fluoro-1,3-dihydroisobenzofuran-4-yl)ethanone

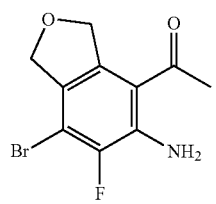

To a stirred mixture of 7-bromo-4-(1-ethoxyvinyl)-6-fluoro-1,3-dihydroisobenzofuran-5-amine (5.00 g, 16.6 mmol) in THF (50 mL) was added 1M HCl in water (50 mL) dropwise at 0° C., then stirred for 3 h at RT. The resulting mixture was extracted with EtOAc (100 mL) and the organic layers were washed with 1M aq. Na$_2$CO$_3$ solution (100 mL), brine (50 mL) and dried over anhydrous Na$_2$SO$_4$. After filtration, the filtrate was concentrated under reduced pressure. The residue was purified by silica gel column chromatography, eluting with PE:EtOAc (3:1 to 1:1) to afford the product (2.00 g, 44.1%) as a yellow solid. MS (ES) m/z=274 (M+1).

Preparation 53

6-Bromo-5-fluoro-7,9-dihydrofuro[3,4-f]quinazolin-1-ol

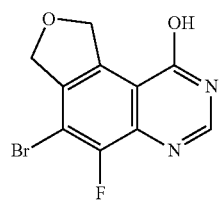

A mixture of methyl 5-amino-7-bromo-6-fluoro-1,3-dihydroisobenzofuran-4-carboxylate (6.00 g, 20.7 mmol) and formamide (48.0 mL, 1,200 mmol) was stirred for 12 h at 160° C. under N. The mixture was allowed to cool down to RT and diluted with $H_2O$ (300 mL) at 0° C. The precipitated solids were collected by filtration and washed with $H_2O$ (3×50 mL). The solids were dried under vacuum to afford the product (5.2 g, 88.1%) as a brown solid. MS (ES) m/z=285 (M+1).

Preparation 54

6-Bromo-5-chloro-7,9-dihydrofuro[3,4-f]quinazolin-1-ol

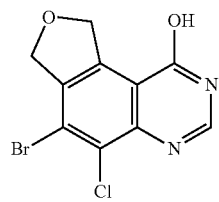 [SMILES: Oc1ncnc2c(Cl)c(Br)c3c(c12)COC3]

Methyl 5-amino-7-bromo-6-chloro-1,3-dihydroisobenzofuran-4-carboxylate was used in a manner analogous to the method of Preparation 53 to afford the title compound (3.5 g, 58%) as black solid. MS (ES) m/z=301 (M+1).

Preparation 55

4-Bromo-5-fluoro-1,3-dihydrofuro[3,4-f]cinnolin-9-ol

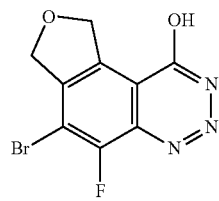

To a stirred mixture of 1-(5-amino-7-bromo-6-fluoro-1,3-dihydroisobenzofuran-4-yl)ethanone (2.00 g, 7.30 mmol) in TFA (40 mL) was added $NaNO_2$ (0.600 g, 8.76 mmol) at RT and stirred for 2 h at 70° C. The reaction was allowed to cool to RT and then concentrated under reduced pressure, $H_2O$ (100 mL) was added, and the resulting mixture was extracted with EtOAc (2×100 mL), the combined organic layers were washed with brine (50 mL) and dried over anhydrous $Na_2SO_4$. After filtration, the filtrate was concentrated under reduced pressure and the residue was purified by silica gel column chromatography, eluting with DCM:MeOH (10:1) to afford the product (1.20 g, 57.7%) as a yellow solid. MS (ES) m/z=285 (M+1).

Preparation 56

6-Bromo-5-fluoro-3-methyl-7,9-dihydrofuro[3,4-f]quinazolin-1-ol

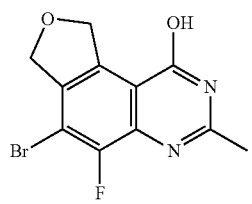 [SMILES: Cc1nc(O)c2c3c(c(Br)c(F)c2n1)COC3]

A stirred mixture of methyl 5-amino-7-bromo-6-fluoro-1,3-dihydro-2-benzofuran-4-carboxylate (350 mg, 1.21 mmol) and ACN (594 mg, 14.5 mmol) in 4M HCl in 1,4-dioxane (10 mL) was heated at 100° C. under $N_2$. The resulting mixture was stirred for ~18 h at 100° C. under $N_2$. The mixture was diluted with $H_2O$ (100 mL) and extracted with EtOAc (2×50 mL). The organic layers were concentrated under reduced pressure to afford the product (290 mg, 80.4%) as a yellow solid. MS (ES) m/z=299 (M+1).

Preparation 57

5-[Bis(methylsulfanyl)methylene]-2,2-dimethyl-1,3-dioxane-4,6-dione

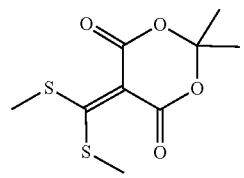

To a stirred mixture of Meldrum's acid (20 g, 138.76 mmol) and TEA (42.13 g, 416.30 mmol, 3 eq.) in DMSO (100 mL) was added $CS_2$ (15.85 g, 208.15 mmol, 1.5 eq.). The resulting mixture was stirred at RT for 3 h under $N_2$. $CH_3I$ (59.09 g, 416.30 mmol, 3 eq.) was added dropwise at 0° C. The temperature was allowed to warm to RT and reaction was stirred for ~18 h. The resulting mixture was diluted with EtOAc (1,000 mL), washed with $H_2O$ (2×200 mL), then brine (200 mL) and was dried over anhydrous $Na_2SO_4$. After filtration, the filtrate was concentrated under reduced pressure. The residue was purified on silica, eluting with PE:EtOAc (4:1 to 2:1) to afford the title compound (23 g, 67%) as a yellow solid. $^1H$ NMR (400 MHz, DMSO-$d_6$) δ 2.64 (s, 6H), 1.68 (s, 6H).

Preparation 58

5-[[(7-Bromo-6-chloro-1,3-dihydroisobenzofuran-5-yl)amino]-methylsulfanyl-methylene]-2,2-dimethyl-1,3-dioxane-4,6-dione

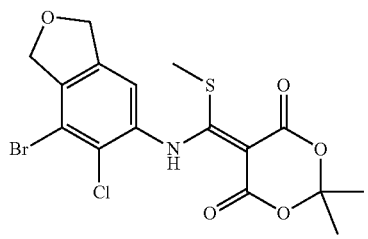 [SMILES: CSC(Nc1cc2c(c(Br)c1Cl)COC2)=C1C(=O)OC(C)(C)OC1=O]

A stirred mixture of 5-[bis(methylsulfanyl)methylene]-2,2-dimethyl-1,3-dioxane-4,6-dione (16.49 g, 66.40 mmol, 1.1 eq.) and 7-bromo-6-chloro-1,3-dihydroisobenzofuran-5-amine (15 g, 60 mmol, 1 eq.) in toluene (150 mL) was heated at 80° C. for 2 days. The reaction mixture was concentrated under reduced pressure and the residue was purified by trituration with 10:1 PE:EtOAc (250 mL). The solid was collected by filtration and dried under vacuum to afford the title compound (20 g, 73%) as a brown solid. $^1$H NMR (400 MHz, DMSO-$d_6$) δ 11.97 (s, 1H), 7.52 (s, 1H), 5.14 (s, 2H), 5.03 (s, 2H), 2.37 (s, 3H), 1.67 (s, 6H).

Preparation 59

4-Bromo-5-chloro-7-methylsulfanyl-1,3-dihydrofuro[3,4-f]quinolin-9-ol

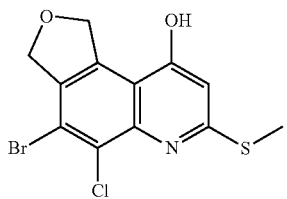 [SMILES: CSc1cc(O)c2c3c(c(Br)c(Cl)c2n1)COC3]

A solution of 5-[[(7-bromo-6-chloro-1,3-dihydroisobenzofuran-5-yl)amino]-methylsulfanyl-methylene]-2,2-dimethyl-1,3-dioxane-4,6-dione (18 g, 40 mmol, 1 eq.) in diphenyl ether (200 mL) was stirred for 1h at 180° C. The reaction was allowed to cool down to RT then was diluted with PE (500 mL) and stirred for 20 min at RT. After filtration, the filter cake was washed with PE (2×50 mL) and was dried under reduced pressure to afford the title compound (11.3 g, 81%) as a yellow solid which was used in the next step without further purification. MS (ES) m/z=346 (M+1).

Preparation 60

6-Bromo-1-chloro-3-ethylsulfanyl-5-fluoro-7,9-dihydrofuro[3,4-f]quinazoline

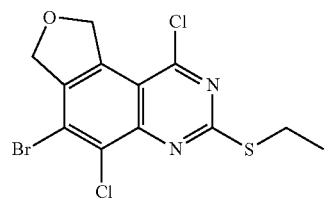 [SMILES: CCSc1nc(Cl)c2c3c(c(Br)c(Cl)c2n1)COC3]

A 5 L 3-necked RBF, equipped with a dropping funnel, thermocouple and an overhead stirrer was charged with a solution of DMF (50 mL, 646 mmol, 4 eq.) in DCM (1,000 mL) and was placed in an ice/water bath and cooled to ~4° C. Oxalyl chloride (50.0 mL, 576 mmol, 4 eq.) was added dropwise via addition funnel over ~40 min. When the addition was complete, the reaction was stirred at ~4° C. for 15 min. Solid 6-bromo-3-ethylsulfanyl-5-fluoro-7,9-dihydrofuro[3,4-f]quinazolin-1-ol (50.4 g, 140 mmol) was added in several portions to the reaction mixture and the resulting suspension was stirred at ~4° C. for 30 min. The ice bath was removed and the reaction was allowed to warm to RT and stir for 1 h. Then H$_2$O (1 L) was added and the mixture was stirred for 15 min. The mixture was partitioned and the organic layer was washed with brine (1 L) and dried over anhydrous Na$_2$SO$_4$, filtered and concentrated. The residue was purified on silica, eluting with DCM/Hex (60% to 90%) to obtain the title compound (45.1 g, 89%) as a white solid. MS (ES) m/z=363 (M+1).

The following compounds in Table 4 were prepared in a similar manner as described for Preparation 60. Various methods were used to purify the compounds, which would be apparent to one skilled in the art.

TABLE 4

| Preparation | Chemical Name | Structure | MS (ES) m/z (M + 1) |
|---|---|---|---|
| 61 | 6-Bromo-1,5-dichloro-3-ethylsulfanyl-7,9-dihydrofuro[3,4-f]quinazoline | 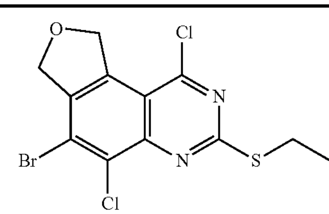 | 379 |

TABLE 4-continued

| Preparation | Chemical Name | Structure | MS (ES) m/z (M + 1) |
|---|---|---|---|
| 62 | 4-Bromo-9-chloro-5-fluoro-1,3-dihydrofuro[3,4-f]cinnoline | 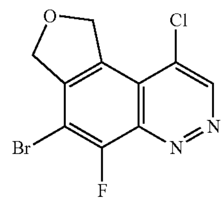 [SMILES: Fc1c(Br)c2c(c3c(Cl)cnnc13)COC2] | 303 |
| 63 | 6-Bromo-1-chloro-5-fluoro-7,9-dihydrofuro[3,4-f]quinazoline | 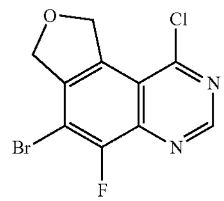 [SMILES: Fc1c(Br)c2c(c3c(Cl)ncnc13)COC2] | 303 |
| 64[a] | 4-bromo-5,9-dichloro-7-methylsulfanyl-1,3-dihydrofuro[3,4-f]quinoline | 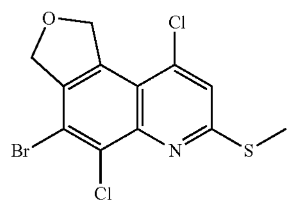 [SMILES: CSc1cc(Cl)c2c3c(c(Br)c(Cl)c2n1)COC3] | 366 |
| 65 | 6-bromo-1-chloro-3-ethylsulfanyl-5-methyl-9,10-dihydro-7H-pyrano[4,3-f]quinazoline | 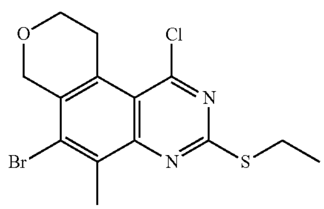 [SMILES: CCSc1nc(Cl)c2c3c(c(Br)c(C)c2n1)COCC3] | 375 |

[a] After removal of ice bath, the reaction was heated at 37° C. for ~24 h.

Preparation 66

2-(6-Bromo-1-chloro-3-ethylsulfanyl-5-fluoro-7,9-dihydrofuro[3,4-f]quinazolin-9-yl)acetonitrile

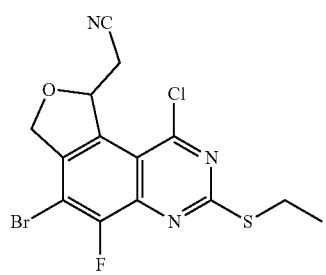 [SMILES: CCSc1nc(Cl)c2c3c(c(Br)c(F)c2n1)COC3CC#N]

To a solution of DMF (60 mL) and POCl$_3$ (50.00 mL, 538 mmol) was added 2-(6-bromo-3-ethylsulfanyl-5-fluoro-1-hydroxy-7,9-dihydrofuro[3,4-f]quinazolin-9-yl)acetonitrile (4.6 g, 12 mmol) portion wise. The mixture was heated at 90° C. in an oil bath for 1 h. The reaction mixture was cooled to RT, and then was slowly added to a mixture of ice-water with stirring. The resultant solid was collected by filtration, washed with cold water and dried in vacuum oven at 55° C. overnight to obtain the title compound (4.5 g, 75%) as a light-brown solid. MS (ES) m/z=402 (M+1).

Preparation 67

2-(6-Bromo-1,5-dichloro-3-ethylsulfanyl-7,9-dihydrofuro[3,4-f]quinazolin-9-yl)acetonitrile

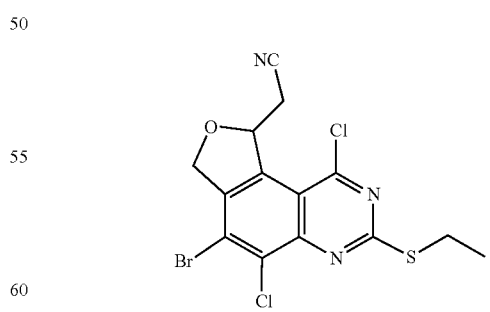

2-(6-Bromo-5-chloro-3-ethylsulfanyl-1-hydroxy-7,9-dihydrofuro[3,4-f]quinazolin-9-yl)acetonitrile was used in a manner analogous to the method of Preparation 66 to afford the title compound (0.9 g, 81%) as off-white solid. MS (ES) m/z=418 (M+1).

Preparation 68

6-Bromo-3-ethylsulfanyl-5-methyl-9,10-dihydro-7H-pyrano[4,3-f]quinazoline

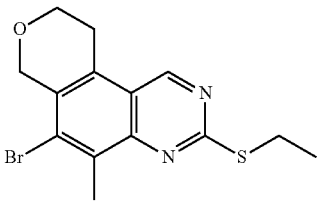 [SMILES: CCSc1ncc2c3c(c(Br)c(C)c2n1)COCC3]

A mixture of 6-bromo-1-chloro-3-ethylsulfanyl-5-methyl-9,10-dihydro-7H-pyrano[4,3-f]quinazoline (1.10 g, 2.94 mmol) and TMEDA (500 mg, 4.30 mmol) in THF (20 mL) was purged with argon. Pd(ddpf)Cl$_2$·DCM complex (120 mg, 0.144 mmol) and NaBH$_3$CN (280 mg, 4.46 mmol) were added. The reaction mixture was purged again with argon and heated to 45° C. After 2 h, the reaction mixture was cooled down to RT and diluted with EtOAc, washed with sat. aq. NH$_4$Cl, brine and dried over anhydrous Na$_2$SO$_4$. The mixture was filtered and concentrated under reduced pressure. The residue was purified by silica gel column chromatography, eluting with EtOAc in hexanes (0 to 40%) to afford the product (998 mg, quantitative) as a yellow solid. MS (ES) m/z=339 (M+1).

Preparation 300

6-Bromo-5-chloro-3-ethylsulfanyl-7,9-dihydrofuro[3,4-f]quinazoline

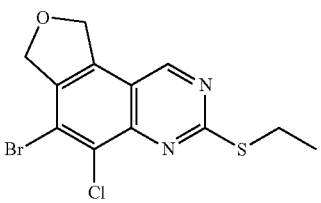 [SMILES: CCSc1ncc2c3c(c(Br)c(Cl)c2n1)COC3]

6-Bromo-1,5-dichloro-3-ethylsulfanyl-7,9-dihydrofuro[3,4-f]quinazoline was used in an analogous manner to the method of Preparation 68 to obtain the title compound (0.38 g, 51%) as a white solid. MS (ES) m/z=345,347 (M+1, Br).

Preparation 301

6-Bromo-3-ethylsulfanyl-5-fluoro-7,9-dihydrofuro[3,4-f]quinazoline

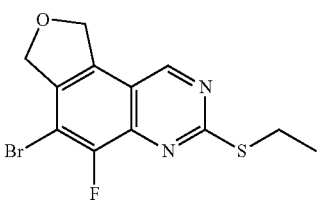 [SMILES: CCSc1ncc2c3c(c(Br)c(F)c2n1)COC3]

6-Bromo-1-chloro-3-ethylsulfanyl-5-fluoro-7,9-dihydrofuro[3,4-f]quinazoline was used in an analogous manner to the method of Preparation 68 to obtain the title compound (1.00 g, 92%). MS (ES) m/z=329,331 (M+1, Br).

Preparation 69

Methyl 4-bromo-5-fluoro-benzothiophene-2-carboxylate

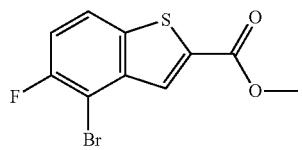

A solution of methyl thioglycolate (0.18 mL, 2.0 mmol, 1 eq.) in THF (5 mL) was flushed with N$_2$ and charged with NaH (60 mass %) in mineral oil (0.101 g, 2.53 mmol, 1.24 eq.) at RT. Gas evolution was observed, and a precipitate formed in the flask. The reaction was stirred at RT for 20 min. A solution of 2-bromo-3,6-difluorobenzaldehyde (0.475 g, 2.04 mmol) in THF (5 mL) was added slowly via syringe over ~2 min. The reaction was stirred at RT for 9 h. Additional methyl thioglycolate (0.1 mL, 1 mmol, 0.5 eq.) and sodium hydride (60 mass %) in mineral oil (0.050 g, 1.3 mmol, 0.6 eq.) were added and stirring was continued at RT for ~18 h. The mixture was diluted with EtOAc and washed with sat. aq. NH$_4$Cl and brine. The organics were dried over anhydrous Na$_2$SO$_4$, filtered and concentrated. The residue was purified on silica, eluting with 2% MTBE/Hex to obtain the title compound (0.346 g, 59%) as a white solid. $^1$H NMR (400 MHz, DMSO-d$_6$) δ 8.23-8.19 (dd, J=4.49, 8.9 Hz, 1H), 8.05 (s, 1H), 7.62 (t, J=9.0 Hz, 1H), 3.93 (s, 3H).

Preparation 70

4-Bromo-5-fluoro-benzothiophene-2-carboxylic acid

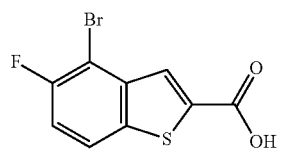 [SMILES: O=C(O)c1cc2c(Br)c(F)ccc2s1]

A solution of methyl 4-bromo-5-fluoro-benzothiophene-2-carboxylate (19.2 g, 66.4 mmol, 1 eq.) in MeOH (130 mL) and THF (130 mL) was charged with 5N NaOH (66 mL, 330 mmol, 5 eq.) and stirred at RT for 40 min. The mixture was concentrated and H$_2$O (500 mL) was added. The pH was adjusted to ~2 with 5N HCl. The mixture was extracted with EtOAc (2×500 mL) and the combined organic layers were dried over anhydrous Na$_2$SO$_4$, filtered and concentrated. The solids were dried under vacuum at 50° C. to afford the title compound (17.6 g, 96%) as a white solid. MS (ES) m/z=229 (M−1-CO$_2$).

Preparation 71 tert-Butyl N-(4-bromo-5-fluoro-benzothiophen-2-yl)carbamate

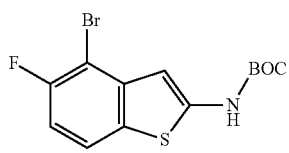 [SMILES: CC(C)(C)OC(=O)Nc1cc2c(Br)c(F)ccc2s1]

A solution of 4-bromo-5-fluoro-benzothiophene-2-carboxylic acid (1.5 g, 5.5 mmol) in t-butanol (30 mL) was charged with TEA (1.5 mL, 11 mmol, 2.0 eq.) and diphenylphosphoryl azide (1.5 mL, 6.9 mmol, 1.3 eq.) and heated at 95° C. for 1 h. The mixture was cooled and concentrated. The residue was purified on silica, eluting with MTBE/Hex (4% to 20%) to obtain the title compound (0.987 g, 52%) as a white solid. MS (ES) m/z=290 (M+1).

Preparation 72 tert-Butyl N-[4-(5,5-dimethyl-1,3,2-dioxaborinan-2-yl)-5-fluoro-benzothiophen-2-yl]carbamate

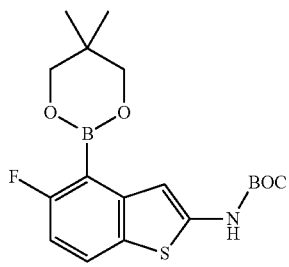 [SMILES: CC1(C)COB(c2c(F)ccc3sc(NC(=O)OC(C)(C)C)cc23)OC1]

A mixture of tert-butyl N-(4-bromo-5-fluoro-benzothiophen-2-yl)carbamate (3.08 g, 8.90 mmol) and bis(neopentyl glycolato)diboron (4.02 g, 17.8 mmol, 2 eq.) and KOAc (2.62 g, 26.7 mmol, 3 eq.) in 1,4-dioxane (70 mL, 819.9 mmol) was sparged with $N_2$ for 20 min. To the mixture was added Pd(ddpf)$Cl_2$ (0.69 g, 0.90 mmol, 0.1 eq.). The reaction was sonicated for 3 min, then put through a vacuum/$N_2$ refill cycle (3×) and was heated at 100° C. for 3 h. The mixture was cooled to RT, filtered through diatomaceous earth and was rinsed with 1:4 EtOAc/Hex. The filtrate was concentrated and the residue was purified on silica (0-40% MTBE/Hex) to obtain the title compound (2.95 g, 87%) as a white solid. $^1$H NMR (400 MHz, DMSO-$d_6$) δ 10.81-10.79 (bs, 1H), 7.84-7.74 (dd, J=5.07, 8.59, 1H), 7.14 (s, 1H), 6.94-6.88 (m, 1H), 3.89 (bs, 4H), 1.49 (s, 10H), 1.03 (s, 6H).

Preparation 73

2-Bromo-3-fluoro-6-methoxy-benzaldehyde

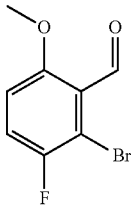

In a 2 L 3-necked RBF equipped with a thermocouple, dropping funnel and condenser, a solution of 2-bromo-3,6-difluoro-benzaldehyde (95.0 g, 430 mmol) in MeOH (850 mL) was charged dropwise with NaOMe (30 mass %) in MeOH (95 mL, 475 mmol, 1.1 eq.) over ~15 min and stirred at 60° C. for 5 h. The reaction was cooled to RT.
The reaction mixture was poured slowly into $H_2O$ (2 L) while stirring. A thick precipitate formed in the flask. The mixture was stirred at RT for 15 min and was filtered. The filter cake was dried under vacuum at 50° C. for ~18 h to afford the title compound (75.4 g, 75%) as a white solid. MS (ES) m/z=232 (M+1).

Preparation 74

2-Bromo-3-fluoro-6-hydroxy-benzaldehyde

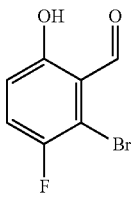 [SMILES: O=Cc1c(O)ccc(F)c1Br]

A 3-necked 2 L RBF, equipped with a thermometer, overhead stirrer and dropping funnel was charged with a solution of 2-bromo-3-fluoro-6-methoxy-benzaldehyde (79.2 g, 340 mmol) in DCM (700 ml). The flask was placed in a dry ice/acetone bath and was cooled to −76° C. $BBr_3$ (1.0 M in DCM, 340 mL, 340 mmol, 1 eq.) was added dropwise at such a rate to keep internal temperature below −70° C. The reaction was stirred in the dry ice/acetone bath for 15 min, then the ice bath was removed and the reaction was left to stir at RT for ~18 h. The reaction flask was placed in an ice/water bath. Once the internal temperature settled at ~2.5° C., $H_2O$ (250 mL) was added dropwise via an addition funnel. The ice bath was removed and the reaction was allowed to come to RT and was stirred another 15 min. The reaction mixture was partitioned and the aqueous phase was treated with DCM (200 mL) and brine (100 mL) and was partitioned again. The combined organic layers were dried over anhydrous $Na_2SO_4$, filtered and concentrated to a tan solid. Hexanes (250 mL) were added and the slurry was stirred for 30 min. The solids were filtered and the filtrate, upon standing, precipitated additional solids that were filtered and combined with the previously filtered solids (Batch 1). The combined batches were dried under vacuum at 50° C. overnight. The filtrate was concentrated and purified on silica (5% to 30% DCM/Hex) to obtain more product (Batch 2). The two batches were combined to afford the title compound (66.7 g, 90%) as white solid. GCMS (EI) m/z=219 (M)+.

Preparation 75

4-Bromo-5-fluoro-benzofuran-2-carboxylic acid

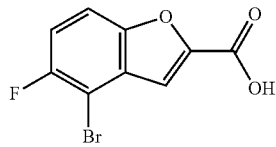 [SMILES: O=C(O)c1cc2c(Br)c(F)ccc2o1]

In a 2 L, 3-necked RBF, equipped with overhead stirrer, thermocouple, a solution of 2-bromo-3-fluoro-6-hydroxy-benzaldehyde (64.45 g, 294.3 mmol) in DMF (600 mL, 7,760 mmol) was charged with $K_2CO_3$ (89.5 g, 648 mmol, 2.2 eq.), NaI (8.83 g, 58.9 mmol, 0.2 eq.) and ethyl bromoacetate (36 mL, 324.2 mmol, 1.1 eq.) was heated at 70° C. for ~18 h. The temperature was increased to 120° C. for 4 h. The reaction was cooled to ~45° C., then the heat was removed and the reaction was allowed to cool. When the internal temperature reached ~45° C., a thick precipitate formed in the flask. $H_2O$ (1 L) was added in a slow stream via addition funnel to obtain a nearly homogeneous mixture. The pH was adjusted to ~3 with conc. HCl and the mixture was stirred at RT for 30 min. Solids were filtered, rinsed with $H_2O$ (500 mL) and dried under vacuum at 50° C. to obtain the title compound (52.4 g, 69%) as a white solid. MS (ES), m/z=212 (M−1−$CO_2$).

Preparation 76 tert-Butyl N-(4-bromo-5-fluoro-benzofuran-2-yl)carbamate

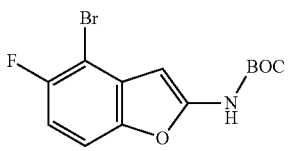

4-Bromo-5-fluoro-benzofuran-2-carboxylic acid was used in a manner analogous to the method of Preparation 71 and then the product was purified on silica, eluting with MTBE/Hex (5% to 30%) to obtain the title compound (29.1 g, 35%) as a yellow solid, MS (ES), m/z=274 (M+1-tBu).

Preparation 77 tert-Butyl N-[4-(5,5-dimethyl-1,3,2-dioxaborinan-2-yl)-5-fluoro-benzofuran-2-yl]carbamate

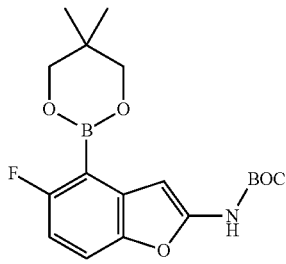 [SMILES: CC1(C)COB(c2c(F)ccc3oc(NC(=O)OC(C)(C)C)cc23)OC1]

tert-Butyl N-(4-bromo-5-fluoro-benzofuran-2-yl)carbamate was used in an analogous manner to the method of Preparation 72 to obtain the title compound (21.3 g, 71%) as a light-tan solid. MS (ES), m/z=240 (M+1, mass of boronic acid was observed). $^1$H NMR (400 MHz, DMSO-$d_6$) δ 10.74 (bs, 1H), 8.43 (s, 1H), 7.82 (dd, J=5.1, 8.8 Hz, 1H), 6.91 (dd, J=8.8, 9.5 Hz, 1H), 7.15 (s, 1H), 3.81 (s, 4H), 1.50 (s, 9H), 1.03 (s, 6H).

Preparation 78 tert-Butyl N-[3-cyano-4-(5,5-dimethyl-1,3,2-dioxaborinan-2-yl)benzothiophen-2-yl]carbamate

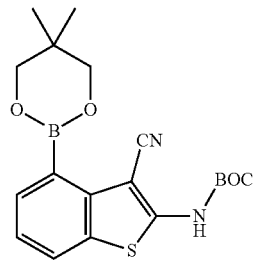 [SMILES: CC1(C)COB(c2cccc3sc(NC(=O)OC(C)(C)C)c(C#N)c23)OC1]

A mixture of tert-butyl N-(4-bromo-3-cyano-benzothiophen-2-yl)carbamate (United States Patent Application Publication US 2021/0179633 A1, Preparation 7) (19.0 g, 53.8 mmol), bis(neopentyl glycolato)diboron (18.2 g, 80.6 mmol) and KOAc (15.8 g, 161 mmol) in 1,4-dioxane (350 mL) was sparged with $N_2$ for 40 min. Pd-117 (3.93 g, 5.38 mmol) was added, and the resulting mixture was heated at 95° C. for 1.5 h. The reaction was cooled, filtered through diatomaceous earth and rinsed with DCM. The filtrate was concentrated and the residue was purified on silica, eluting with EtOAc/Hex (10-50%) to give the title compound (11.7 g, 56%) as an off-white solid. MS (ES), m/z=317 (M−1, mass of boronic acid was observed). $^1$H NMR (400 MHz, DMSO-$d_6$) δ 11.28 (s, 1H), 7.95 (dd, J=1.0, 8.0 Hz, 1H), 7.54 (dd, J=1.0, 7.2 Hz, 1H), 7.31 (t, J=7.6 Hz, 1H), 3.78 (s, 4H), 1.53 (s, 9H), 1.04 (s, 6H).

Preparation 79 tert-Butyl N-(4-chlorothieno[3,2-c]pyridin-2-yl)carbamate

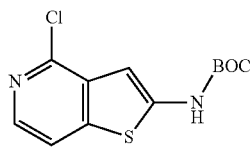 [SMILES: CC(C)(C)OC(=O)Nc1cc2c(Cl)nccc2s1]

To a suspension of 4-chlorothieno[3,2-c]pyridine-2-carboxylic acid (78 g, 365.1 mmol) in t-BuOH (1,500 mL) was added TEA (155 mL, 1,110 mmol) and diphenylphosphoryl azide (100 g, 356.1 mmol). The mixture was stirred and heated to ~80° C. After 14 h, the reaction was allowed to cool to RT and the solids were allowed to settle. The liquid above the solids was decanted and the solids were filtered and rinsed with DCM. The filtrate and decanted solution were combined and concentrated. The crude material was purified on silica, eluting with MTBE/Hex (10-50%) to afford the title compound (65 g, 58.3%) as a white solid. MS (ES) m/z=285 (M+1).

Preparation 80 tert-Butyl N-(4-chloro-3-cyano-thieno[3,2-c]pyridin-2-yl)carbamate

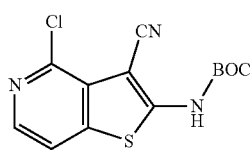

tert-Butyl N-(4-chlorothieno[3,2-c]pyridin-2-yl)carbamate (5.0 g, 18 mmol) in THF (120 mL) was cooled with an ice/water bath. CSI (4.7 mL, 53 mmol) was added dropwise all at once at a steady rate and stirred under $N_2$. After 1.5 h, the cold reaction mixture was transferred to an addition funnel and was added dropwise over a 14 min period to cold DMF (125 mL) in an ice bath. After addition, the ice bath was removed, and the reaction was stirred at RT for 1 h. The reaction was diluted with EtOAc and washed with brine and sat. aq. NaHCO$_3$. The aqueous layer was extracted with EtOAc (2×) and the combined organic layers were dried over Na$_2$SO$_4$. The solvent was evaporated and the oil containing DMF was evaporated over a stream of $N_2$ to obtain a brown solid. EtOH (25 mL) was added to the solid and it was sonicated, filtered and the solids were rinsed with DCM and air dried to obtain the product (2.2 g, 37%) as a white solid. MS (ES) m/z=310 (M+1).

Preparation 227 tert-Butyl N-(4-bromo-7-fluoro-benzofuran-2-yl)carbamate

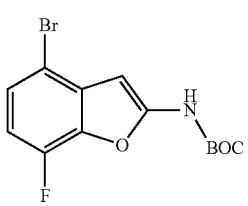 [SMILES: CC(C)(C)OC(=O)Nc1cc2c(Br)ccc(F)c2o1]

Ethyl 4-bromo-7-fluoro-benzofuran-2-carboxylate. 6-Bromo-3-fluoro-2-hydroxy-benzaldehyde (2.9 g, 13 mmol) was combined with potassium carbonate (2.0 g, 14 mmol) and sodium iodide (0.40 g, 2.7 mmol) in DMF (45 mL). Ethyl bromoacetate (1.6 mL, 14 mmol) was added and the reaction mixture was stirred at room temperature overnight. Potassium carbonate (2.0 g, 14 mmol) was added. The reaction mixture was stirred at 120° C. for 3 h and cooled to room temperature. The reaction mixture was diluted with water (60 mL), stirred for 30 min, and filtered the resulting solid. The solids were washed with water and dried in a vacuum oven (40° C.) to give ethyl 4-bromo-7-fluoro-benzofuran-2-carboxylate (1.2 g, 32%) as a light tan solid. MS (ES) m/z=287,289 (M+1, Br).

4-Bromo-7-fluoro-benzofuran-2-carboxylic acid. Ethyl 4-bromo-7-fluoro-benzofuran-2-carboxylate was used in an analogous manner to the method of Preparation 70 to obtain 4-bromo-7-fluoro-benzofuran-2-carboxylic acid (0.97 g, 90%) as a white solid. MS (ES) m/z=256,258 (M−1,Br).

tert-Butyl N-(4-bromo-7-fluoro-benzofuran-2-yl)carbamate. 4-Bromo-7-fluoro-benzofuran-2-carboxylic acid was used in an analogous manner to the method of Preparation 79 to obtain the title compound (0.42 g, 66%). MS (ES) m/z=328,330 (M−1,Br).

Preparation 228 tert-Butyl N-(4-bromo-3-cyano-7-fluoro-benzofuran-2-yl)carbamate

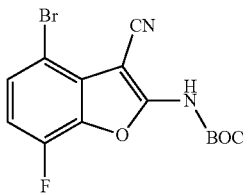 [SMILES: CC(C)(C)OC(=O)Nc1oc2c(F)ccc(Br)c2c1C#N]

tert-Butyl N-(4-bromo-7-fluoro-benzofuran-2-yl)carbamate was used in an analogous manner to the method of Preparation 80 to obtain the title compound (1.75 g, 63%). MS (ES) m/z=354,356 (M+1,Br).

Preparation 229 tert-Butyl N-(4-chloro-7-methyl-thieno[3,2-c]pyridin-2-yl)carbamate

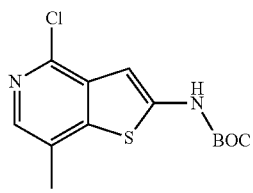 [SMILES: Cc1cnc(Cl)c2cc(NC(=O)OC(C)(C)C)sc12]

Methyl 4-chloro-7-methyl-thieno[3,2-c]pyridine-2-carboxylate. 2,4-Dichloro-5-methyl-pyridine-3-carbaldehyde (7.25 g, 38.2 mmol), potassium carbonate (10.5 g, 76.0 mmol), and DMF (127 mL) were combined, heated at 70° C. overnight, and cooled to room temperature. The reaction mixture was added to water (500 mL) and filtered. The solids were rinsed with water and dried to give methyl 4-chloro-7-methyl-thieno[3,2-c]pyridine-2-carboxylate (8.30 g, 90%) as a white solid. MS (ES) m/z=242 (M+1).

4-Chloro-7-methyl-thieno[3,2-c]pyridine-2-carboxylic acid. Methyl 4-chloro-7-methyl-thieno[3,2-c]pyridine-2-carboxylate was used in an analogous manner to the method of Preparation 70 to obtain 4-chloro-7-methyl-thieno[3,2-c]pyridine-2-carboxylic acid (6.5 g, 84%) as a white solid. MS (ES) m/z=228 (M+1).

tert-Butyl N-(4-chloro-7-methyl-thieno[3,2-c]pyridin-2-yl)carbamate. 4-Chloro-7-methyl-thieno[3,2-c]pyridine-2-carboxylic acid was used in an analogous manner to the method of Preparation 79 to obtain the title compound (0.83 g, 63%). MS (ES) m/z=299 (M+1).

Preparation 230 tert-Butyl N-(4-chloro-3-cyano-7-methyl-thieno[3,2-c]pyridin-2-yl)carbamate

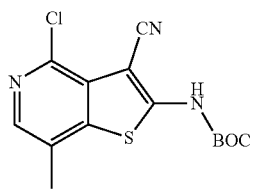 [SMILES: Cc1cnc(Cl)c2c(C#N)c(NC(=O)OC(C)(C)C)sc12]

tert-Butyl N-(4-chloro-7-methyl-thieno[3,2-c]pyridin-2-yl)carbamate was used in an analogous manner to the method of Preparation 80 to obtain the title compound (0.542 g, 31%). MS (ES) m/z=324 (M+1).

Preparation 231 tert-Butyl N-(4-chloro-3-cyano-7-fluoro-thieno[3,2-c]pyridin-2-yl)carbamate

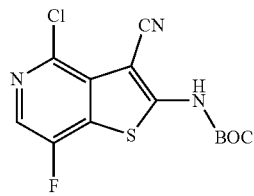 [SMILES: CC(C)(C)OC(=O)Nc1sc2c(F)cnc(Cl)c2c1C#N]

Ethyl N-(3-cyano-7-fluoro-thieno[3,2-c]pyridin-2-yl)carbamate. A solution of 2-(4-chloro-5-fluoropyridin-3-yl)acetonitrile (11.8 g, 56.1 mmol) in DMF (112 mL) was cooled to 0° C. Potassium tert-butoxide (7.00 g, 61.1 mmol) was added. After 15 min, ethoxycarbonyl isothiocyanate (7.45 mL, 61.8 mmol) was added dropwise. The reaction mixture was allowed to slowly warm to room temperature overnight. The reaction mixture was poured into a mixture of ice/water (1.5 L), stirred until all ice had melted, and filtered through diatomaceous earth. The solids were dried in a vacuum oven (60° C.) overnight and separated from the diatomaceous earth to give ethyl N-(3-cyano-7-fluoro-thieno[3,2-c]pyridin-2-yl)carbamate (11.9 g, 79%) as a solid. MS (ES) m/z=266 (M+1).

2-Amino-7-fluoro-thieno[3,2-c]pyridine-3-carbonitrile. A suspension of ethyl N-(3-cyano-7-fluoro-thieno[3,2-c]pyridin-2-yl)carbamate (11.9 g, 44.4 mmol) in DMSO (90 mL) was cooled to 0° C. NaOH (5 M in water, 90 mL) was added dropwise over 15 min. The reaction mixture was heated to 105° C. for 1 h, then cooled to room temperature. The reaction mixture was poured into a mixture of ice/water (1.8 L), stirred until all ice had melted, and filtered through diatomaceous earth. The solids were dried in a vacuum oven (50° C.) overnight and separated from the diatomaceous earth to give crude 2-amino-7-fluoro-thieno[3,2-c]pyridine-3-carbonitrile.

tert-Butyl N-(3-cyano-7-fluoro-thieno[3,2-c]pyridin-2-yl)carbamate. A mixture of crude 2-amino-7-fluoro-thieno[3,2-c]pyridine-3-carbonitrile (8.6 g, 44.4 mmol), DCM (90 mL), DMF (90 mL) and N,N-diisopropylethylamine (15.5 mL, 88.9 mmol) was cooled to 0° C. 4-dimethylaminopyridine (0.54 g, 4.42 mmol) and di-tert-butyl dicarbonate (14.6 g, 66.7 mmol) were added. The reaction mixture was stirred at room temperature for 2 h. The solvents were removed under reduced pressure and the remaining material was diluted with DCM (400 mL) and 5% aq. citric acid (250 mL). The aqueous phase was washed twice with DCM. The combined organic phases were washed with sat. aq. NaHCO₃, dried over MgSO₄, filtered, and concentrated to give tert-butyl N-(3-cyano-7-fluoro-thieno[3,2-c]pyridin-2-yl)carbamate (7.5 g, 58%) as a brown solid. MS (ES) m/z=294 (M+1).

tert-Butyl N-(3-cyano-7-fluoro-5-oxido-thieno[3,2-c]pyridin-5-ium-2-yl)carbamate. 3-Chloroperoxybenzoic acid (9.00 g, 40.2 mmol) was added to a solution of tert-butyl N-(3-cyano-7-fluoro-thieno[3,2-c]pyridin-2-yl)carbamate (7.85 g, 26.8 mmol) in DCM (180 mL). The reaction mixture was stirred at room temperature overnight, then cooled to 0° C. for ~15 min. Solids were collected by filtration and dried in a vacuum oven (60° C.). The filtrate was diluted with MeOH and silica gel, concentrated, and the residue was purified on silica, eluting with 0-6% MeOH in DCM. Fractions containing desired material were combined with the solids from the filtration and concentrated to give tert-butyl N-(3-cyano-7-fluoro-5-oxido-thieno[3,2-c]pyridin-5-ium-2-yl)carbamate (7.26 g, 88%) as an off-white solid. MS (ES) m/z=310 (M+1).

tert-Butyl N-(4-chloro-3-cyano-7-fluoro-thieno[3,2-c]pyridin-2-yl)carbamate. A suspension of tert-butyl N-(3-cyano-7-fluoro-5-oxido-thieno[3,2-c]pyridin-5-ium-2-yl)carbamate (5.27 g, 17.0 mmol) in 1,2-dichloroethane (34 mL) was cooled to 0° C. A solution of phosphoryl chloride (32 mL, 344 mmol) in 1,2-dichloroethane (34 mL) was added dropwise. The reaction mixture was stirred at room temperature for 30 min, at 45° C. for 90 min, and cooled to room temperature. The reaction mixture was diluted with 1,2-dichloroethane (100 mL) and added to a mixture of sat. aq. NaHCO₃ (500 mL), NaOH (5 M in water, 40 mL), and ice. Solid NaHCO₃ was added to the stirred mixture to maintain pH ~6-7. Once bubbling ceased, the phases were separated. The aqueous phase was extracted 3× with DCM. The combined organic phases were dried over MgSO₄ and filtered. The filtrate was diluted with MeOH and silica gel, concentrated, and the residue was purified on silica, eluting with 50-100% DCM in hexanes. Fractions containing desired material were concentrated to give the title compound (3.87 g, 69%) as a white solid. MS (ES) m/z=328 (M+1).

Preparation 81 tert-Butyl N-(4-bromobenzofuran-2-yl)carbamate

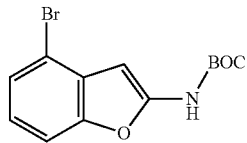 [SMILES: CC(C)(C)OC(=O)Nc1cc2c(Br)cccc2o1]

4-Bromobenzofuran-2-carboxylic acid was used in an analogous manner to the method of Preparation 71 to obtain the title compound (6.48 g, 50%). MS (ES) m/z=310 (M−1).

Preparation 82

N'-(4-Bromo-3-cyano-benzofuran-2-yl)-N,N-dimethyl-formamidine

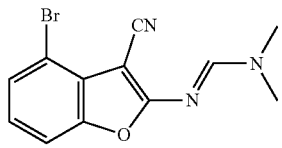 [SMILES: CN(C)/C=N/c1oc2cccc(Br)c2c1C#N]

To a RBF was added tert-butyl N-(4-bromobenzofuran-2-yl)carbamate (6.48 g, 20.8 mmol) and THF (0.3 M, 69.2 mL). The solution was cooled to −78° C. under N₂ and CSI (6.0 mL, 68.5 mmol, 3.3 eq.) was added slowly over 5 min. The reaction was stirred for 30 min, then it was transferred via cannula into stirred DMF (100 mL) at RT and rinsed with THF. The reaction mixture was stirred for 16 h at RT. The reaction was then chilled in ice bath and sat. aq. NaHCO₃ (~160 mL) was added slowly until effervescence subsided, then the mixture was diluted with EtOAc. The organic phase was washed with sat. aq. NaHCO₃ (2×), brine (3×) and was dried over MgSO₄, filtered, and concentrated. The resulting material was mixed with EtOAc to loosen solids. Hexane was added and the mixture was sonicated to break up larger clumps. The solids were filtered, rinsed with 20% EtOAc/Hexanes and dried in vacuo to obtain the title compound (3.39 g, 55.9%) as a light-green solid, MS (ES) m/z=292 (M+1).

Preparation 83

N'-[3-Cyano-4-(5,5-dimethyl-1,3,2-dioxaborinan-2-yl)benzofuran-2-yl]-N,N-dimethyl-formamidine

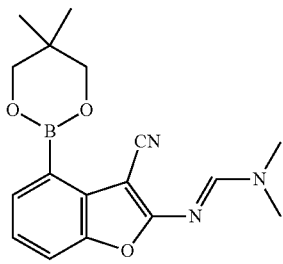 [SMILES: CN(C)/C=N/c1oc2cccc(B3OCC(C)(C)CO3)c2c1C#N]

To a RBF was added N'-(4-bromo-3-cyano-benzofuran-2-yl)-N,N-dimethyl-formamidine (3.38 g, 11.6 mmol), bis(neopentyl glycolato)diboron (7.84 g, 34.7 mmol, 3.0 eq.), KOAc (3.75 g, 38.2 mmol, 3.3 eq.), and 1,4-dioxane (96 mL). The mixture was sparged with N₂ and Pd-117 (0.83 g, 1.16 mmol, 0.1 eq.) was added and the reaction was stirred for 2.5 h at 100° C. The reaction mixture was cooled, filtered through diatomaceous earth and rinsed with 20% EtOAc/hexane. The filtrate was concentrated and the residue was purified on silica, eluting with EtOAc/Hex (0-100%). Fractions containing desired material were concentrated and EtOAc was added to the resulting solid. Solids were filtered and rinsed with EtOAc and hexanes and dried in vacuo at RT to obtain the title compound (2.64 g, 70%) as a tan solid. MS (ES) m/z=258 (M+1) of corresponding boronic acid. ¹H NMR (400 MHz, DMSO-d₆) δ 8.52 (s, 1H), 7.48-7.44 (m, 2H), 7.17 (dd, J=7.4, 8.0 Hz, 1H), 3.78 (s, 4H), 3.2 (s, 3H), 3.1 (s, 3H) 1.00 (s, 6H).

Preparation 232 tert-Butyl N-[3-cyano-4-(5,5-dimethyl-1,3,2-dioxaborinan-2-yl)-7-fluoro-benzofuran-2-yl]carbamate

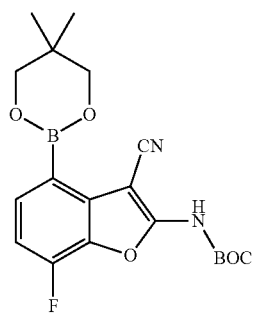 [SMILES: CC1(C)COB(c2ccc(F)c3oc(NC(=O)OC(C)(C)C)c(C#N)c23)OC1]

tert-Butyl N-(4-bromo-3-cyano-7-fluoro-benzofuran-2-yl)carbamate was used in an analogous manner to the method of Preparation 83 to obtain the title compound (0.75 g, 73%). MS (ES) m/z=321 (M+1, corresponding boronic acid).

Preparation 84

Methyl (2R,4R)-4-hydroxy-1-(9-phenylfluoren-9-yl)pyrrolidine-2-carboxylate

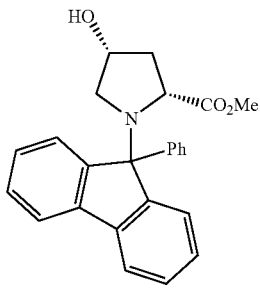 [SMILES: COC(=O)[C@H]1C[C@@H](O)CN1C1(c2ccccc2)c2ccccc2-c2ccccc21]

To a stirred mixture of methyl (2R,4R)-4-hydroxypyrrolidine-2-carboxylate hydrochloride (20.0 g, 138 mmol) and 9-bromo-9-phenylfluorene (53.1 g, 165 mmol) in DCM (400 mL) was added chlorotrimethylsilane (37.4 g, 344 mmol), TEA (13.9 g, 138 mmol) and Pb(NO$_3$)$_2$ (41.1 g, 124 mmol) portion wise at RT. The resulting mixture was stirred for ~18h at 70° C. under N$_2$. The reaction was cooled to RT and was concentrated under reduced pressure. The residue was purified by silica gel column chromatography, eluting with PE/EtOAc (1:1) to afford the product (42 g, 79.2%) as a white solid. MS (ES) m/z=386 (M+1).

Preparation 85

Methyl (2R)-4-oxo-1-(9-phenylfluoren-9-yl)pyrrolidine-2-carboxylate

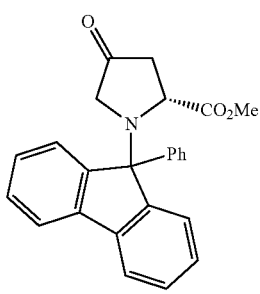 [SMILES: COC(=O)[C@H]1CC(=O)CN1C1(c2ccccc2)c2ccccc2-c2ccccc21]

To a stirred solution of methyl (2R,4R)-4-hydroxy-1-(9-phenylfluoren-9-yl)pyrrolidine-2-carboxylate (30.0 g, 77.8 mmol) and oxalyl chloride (83.0 g, 654 mmol) in DCM (1,000 mL) was added TEA (243 g, 2397 mmol) and DMSO (85.1 g, 1090 mmol) at −40° C. The resulting mixture was stirred for 8 h at −40° C. under N$_2$. The mixture was allowed to warm to RT and was concentrated under reduced pressure. The residue was purified by silica gel column chromatography, eluting with PE/EtOAc (2:1) to afford methyl the product (25.7 g, 85.6%) as a yellow solid. $^1$H NMR (400 MHz, DMSO-d$_6$) δ 7.87 (dd, J=14.0 Hz, 2H), 7.51-7.23 (m, 11H), 3.76-3.59 (m, 2H), 3.36 (s, 1H), 3.04 (s, 3H), 2.66 (dd, J=17.9, 8.5 Hz, 1H), 2.28-2.16 (m, 1H).

Preparation 86

Methyl (2S,3R)-3-fluoro-4-oxo-1-(9-phenylfluoren-9-yl)pyrrolidine-2-carboxylate

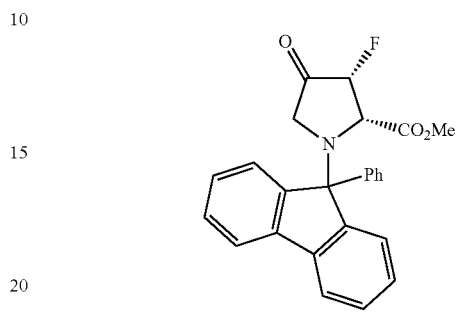

To a stirred solution of methyl (2R)-4-oxo-1-(9-phenylfluoren-9-yl)pyrrolidine-2-carboxylate (40.0 g, 104 mmol) and TEA (31.7 g, 312 mmol) in DCM (1000 mL) was added trimethylsilyl trifluoromethanesulfonate (119 g, 208 mmol) dropwise at −40° C. The resulting mixture was stirred for 2 h at −40° C. under N$_2$. Concentrated under reduced pressure, diluted with pentane (1,000 mL) and washed with sat. aq. NaHCO$_3$ (2×500 mL) and brine and the organics dried over anhydrous Na$_2$SO$_4$. The solution was concentrated under vacuum to give the crude silyl enol ether (47.3 g, quantitative). To a solution of crude silyl enol ether (13.0 g, 28.5 mmol) in DCM (200 mL) was added Selectfluor (131 g, 37.0 mmol) in portions at RT. The resulting mixture was stirred at RT ~18 h. The mixture was then concentrated under reduced pressure and the residue was purified by silica gel column chromatography, eluting with PE/EtOAc (1:1) to afford the title compound (3.96 g, 34.4%) as a light-yellow solid. $^1$H NMR (300 MHz, CDCl$_3$) δ 7.83-7.70 (m, 2H), 7.51-7.28 (m, 11H), 5.10 (dd, J50.9, 7.9 Hz, 1H), 4.10-3.96 (m, 2H), 3.74-3.61 (m, 1H), 3.25 (s, 3H).

Preparation 87

Methyl (2S,3R,4S)-3-fluoro-4-hydroxy-1-(9-phenylfluoren-9-yl)pyrrolidine-2-carboxylate

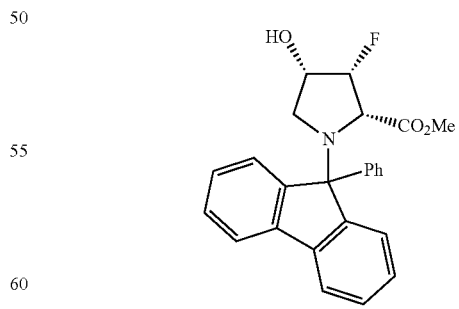

To a stirred solution of methyl (2S,3R)-3-fluoro-4-oxo-1-(9-phenylfluoren-9-yl)pyrrolidine-2-carboxylate (8.00 g, 19.93 mmol) in THF (60 mL) and EtOH (60 mL) was added NaBH$_4$ (0.83 g, 21.9 mmol) in portions at 0° C. under N$_2$. The resulting mixture was stirred for 1 h at 0° C. under N$_2$.

The mixture was extracted with EtOAc (3×100 mL). The combined organic layers were washed with H₂O (2×10 mL), dried over anhydrous Na₂SO₄, filtered and concentrated under reduced pressure. The residue was purified with silica gel, eluting with PE:EtOAc (4:1 to 2:1) to afford the title compound (6.66 g, 83%) as a light-yellow solid. MS (ES) m/z=426 (M+Na).

Preparation 88

Methyl (2S,3R,4R)-3-fluoro-4-(4-nitrobenzoyloxy)-1-(9-phenylfluoren-9-yl)pyrrolidine-2-carboxylate

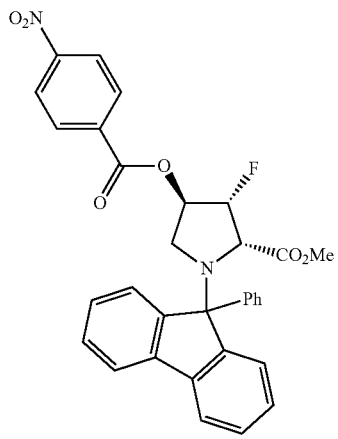 [SMILES: COC(=O)[C@H]1[C@@H](F)[C@H](OC(=O)c2ccc([N+](=O)[O-])cc2)CN1C1(c2ccccc2)c2ccccc2-c2ccccc21]

To a stirred mixture of PPh₃ (3.25 g, 12.4 mmol) and DIAD (2.41 g, 11.9 mmol) in THF (100 mL) was added methyl (2S,3R,4S)-3-fluoro-4-hydroxy-1-(9-phenylfluoren-9-yl)pyrrolidine-2-carboxylate (1.00 g, 2.48 mmol) and 4-nitrobenzoic acid (0.41 g, 2.48 mmol) dropwise at 0° C. under N₂. The reaction was stirred for 1 h at 0° C., then diluted with H₂O and extracted with EtOAc (3×200 mL). The combined organic layers were washed with H₂O (2×50 mL), dried over anhydrous Na₂SO₄, filtered and concentrated under reduced pressure. The residue was purified with silica gel, eluting with PE:EtOAc (4:1 to 2:1) to afford the title compound (450 mg, 38.6%) as a yellow solid. ¹H NMR (400 MHz, CDCl₃) δ 8.30-8.26 (m, 2H), 8.16-8.10 (m, 2H), 7.76-7.72 (m, 1H), 7.70-7.66 (m, 1H), 7.53-7.49 (m, 2H), 7.41-7.35 (m, 4H), 7.28-7.24 (m, 4H), 7.22-7.18 (m, 1H), 5.74-5.70 (m, 1H), 5.15-5.09 (m, 1H), 4.06-4.02 (m, 1H), 3.68-3.64 (m, 1H), 3.35 (s, 3H), 3.10-3.06 (m, 1H).

Preparation 89

Methyl (2S,3R,4R)-3-fluoro-4-hydroxy-1-(9-phenylfluoren-9-yl)pyrrolidine-2-carboxylate

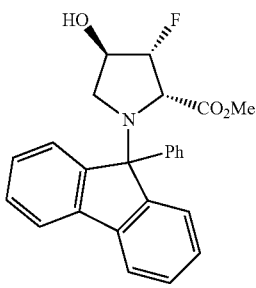 [SMILES: COC(=O)[C@H]1[C@@H](F)[C@H](O)CN1C1(c2ccccc2)c2ccccc2-c2ccccc21]

To a stirred mixture of methyl (2S,3R,4R)-3-fluoro-4-(4-nitrobenzoyloxy)-1-(9-phenylfluoren-9-yl)pyrrolidine-2-carboxylate (3.00 g, 5.43 mmol) in THF (100 mL) and H₂O (25 mL) was added a solution of LiOH H₂O (255 mg, 6.08 mmol) dissolved in H₂O (25 mL) dropwise at 0° C. After stirring for 2 h at 0° C. the reaction mixture was adjusted to pH 7 with formic acid and extracted with EtOAc (3×200 mL). The combined organic layers were washed with brine (2×50 mL), dried over anhydrous Na₂SO₄, filtered and concentrated under reduced pressure. The residue was purified on silica gel, eluting with PE:EtOAc (1:1) to afford the title compound (1.76 g, 80.7%) as a yellow solid. MS (ES) m/z=426 (M+Na).

Preparation 90

(3R,4R,5S)-4-Fluoro-5-(hydroxymethyl)-1-(9-phenylfluoren-9-yl)pyrrolidin-3-ol

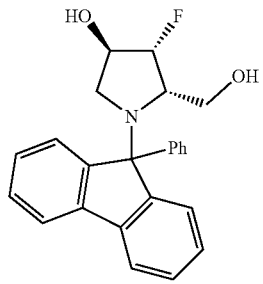 [SMILES: OC[C@H]1[C@@H](F)[C@H](O)CN1C1(c2ccccc2)c2ccccc2-c2ccccc21]

To a stirred mixture of methyl (2S,3R,4R)-3-fluoro-4-hydroxy-1-(9-phenylfluoren-9-yl)pyrrolidine-2-carboxylate (3.00 g, 7.44 mmol) in THF (100 mL) was added 1M LiAlH₄ in THF (15.0 mL, 15.0 mmol) dropwise at -60° C. under N₂. The reaction was stirred for 2 h at -60° C. The reaction mixture was diluted with EtOAc (200 mL), washed with aq. potassium sodium tartrate (100 mL), then brine and dried over Na₂SO₄. After filtration, the filtrate was concentrated under reduced pressure. The residue was purified on silica gel, eluting with PE:EtOAc (1:1) to afford the title compound (1.85 g, 66.3%) as a light-yellow solid. 1H NMR (400 MHz, CDCl₃) δ 7.78 (dt, J=7.6, 0.9 Hz, 1H), 7.74-7.63 (m, 2H), 7.61-7.43 (m, 4H), 7.37-7.20 (m, 6H), 4.61-4.43 (m, 2H), 3.54 (d, J=10.0 Hz, 1H), 3.25-3.22 (m, 1H), 2.89-2.63 (m, 3H), 2.25 (s, 1H).

Preparation 91

((2S,3R,4R)-3-Fluoro-4-((methylsulfonyl)oxy)-1-(9-phenyl-9H-fluoren-9-yl)pyrrolidin-2-yl)methyl methanesulfonate

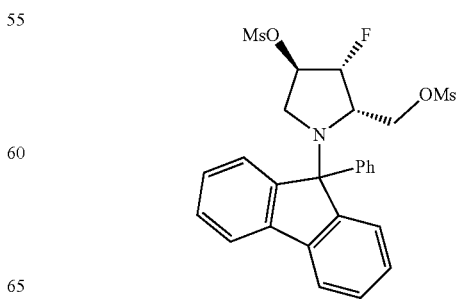

To a stirred mixture of (3R,4R,5S)-4-fluoro-5-(hydroxymethyl)-1-(9-phenylfluoren-9-yl)pyrrolidin-3-ol (1.00 g, 2.66 mmol) in THF (50 mL) was added TEA (1.62 g, 16.0 mmol) and methanesulfonyl chloride (1.22 g, 10.7 mmol) dropwise at 0° C. under $N_2$. When the reaction was complete by LC-MS, the resulting mixture was diluted with $H_2O$ (150 mL) and extracted with EtOAc (3×100 mL). The combined organic layers were washed with $H_2O$ (2×30 mL), dried over anhydrous $Na_2SO_4$, filtered and concentrated under reduced pressure. The residue was purified with silica gel, eluting with PE:EtOAc (4:1 to 2:1) to afford the title compound (1.32 g, 93.4%) as a white solid. MS (ES) m/z=532 (M+1).

Preparation 92

(1S,4S,7S)-7-Fluoro-2-(9-phenyl-9H-fluoren-9-yl)-2,5-diazabicyclo[2.2.1]heptane

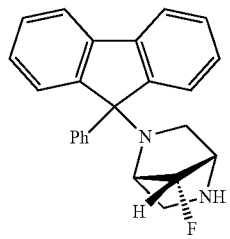 [SMILES: F[C@H]1[C@@H]2CN(C3(c4ccccc4)c4ccccc4-c4ccccc43)[C@H]1CN2]

A mixture of [(2S,3R,4R)-3-fluoro-4-(methanesulfonyloxy)-1-(9-phenylfluoren-9-yl)pyrrolidin-2-yl]methyl methanesulfonate (4.00 g, 7.52 mmol) in 2.0M $NH_3$ in IPA (210 mL, 420 mmol) was heated at 100° C. overnight. The mixture was allowed to cool to RT and was concentrated under reduced pressure. The residue was purified with silica gel, eluting with DCM:MeOH (12:1 to 10:1) to afford the title compound (1.00 g, 37.3%) as a light-yellow solid. MS (ES) m/z=357 (M+1).

Preparation 93

Benzyl (1S,4S,7S)-7-fluoro-2-(9-phenyl-9H-fluoren-9-yl)-2,5-diazabicyclo[2.2.1]heptane

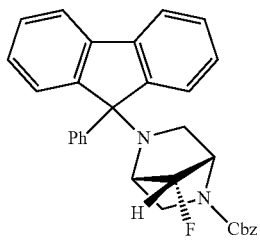 [SMILES: O=C(OCc1ccccc1)N1C[C@H]2[C@@H](F)[C@@H]1CN2C1(c2ccccc2)c2ccccc2-c2ccccc21]

To a stirred mixture of (1S,4S,7S)-7-fluoro-2-(9-phenylfluoren-9-yl)-2,5-diazabicyclo[2.2.1]heptane (1.20 g, 3.37 mmol) and DIEA (1.31 g, 10.1 mmol) in DCM (100 mL) was added Cbz-Cl (0.86 g, 5.05 mmol) in portions at 0° C. The resulting mixture was stirred for 2 h at RT, then was concentrated under reduced pressure. The residue was purified by silica gel column chromatography, eluting with PE/EtOAc (9:1-5:1) to afford the product (1.41 g, 85.4%) as a white solid. MS (ES) m/z=491 (M+1).

Preparation 94

Benzyl (1S,4S,7R)-7-fluoro-2,5-diazabicyclo[2.2.1]heptane-2-carboxylate

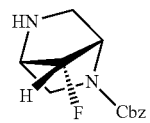 [SMILES: O=C(OCc1ccccc1)N1C[C@@H]2NC[C@H]1[C@@H]2F]

To a stirred solution of benzyl (1S,4S,7R)-7-fluoro-5-(9-phenylfluoren-9-yl)-2,5-diazabicyclo[2.2.1]heptane-2-carboxylate (1.41 g, 2.88 mmol) in DCM (16 mL) was added TFA (8.00 mL, 106 mmol) at RT. The resulting mixture was stirred for 1 h, then was concentrated under reduced pressure. The residue was dissolved in EtOAc (300 mL) and washed with sat. aq. $NaHCO_3$ (3×100 mL). The organic layer was dried over anhydrous $Na_2SO_4$, filtered and concentrated under reduced pressure to afford the product as a white solid (1.3 g, crude) which was used in a subsequent step without further purification. MS (ES) m/z=251 (M+1).

Preparation 95

((2S,4R)-4-Fluoro-1-methylpyrrolidin-2-yl)methanol

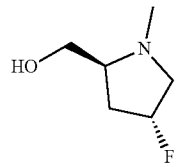

To a stirred solution of 1-(tert-butyl) 2-methyl (2S,4R)-4-fluoropyrrolidine-1,2-dicarboxylate (20.0 g, 80.9 mmol, 1.0 eq.) in THF (200 mL) was added $LiAlH_4$ (485.3 mL, 485.3 mmol, 6.0 eq., 1M in THF) dropwise at −50° C. under $N_2$. The resulting mixture was stirred for 1 h at −50° C. under $N_2$. Then the mixture was stirred for 2 h at 70° C. under $N_2$. The mixture was cooled to 0° C. and quenched by the addition of $H_2O$. The resulting mixture was extracted with EtOAc. The combined organic layers were washed with sat. aq. NaCl and were dried over anhydrous $Na_2SO_4$. After filtration, the filtrate was concentrated under reduced pressure. The residue was purified by silica gel column chromatography, eluting with DCM/MeOH (5:1) to afford the product (2.94 g, 27.3%) as a yellow oil. $^1$H NMR (400 MHz, $CDCl_3$) δ 5.13 (dm, J=55.7 Hz, 1H), 3.74 (dd, J=3.3, 11.4 Hz, 1H), 3.54 (ddd, J=26.4, 11.9, 5.1 Hz, 1H), 3.48 (dd, J=2.0, 11.2 Hz, 1H), 2.89 (s, 1H), 2.82 (m, 1H), 2.67 (ddd, J=32.4, 11.9, 2.5 Hz, 1H), 2.43 (s, 3H), 2.13 (m, 1H), 2.06 (m, 1H).

Preparation 96

[2-(Hydroxymethyl)-1-methylpyrrolidin-2-yl]methanol

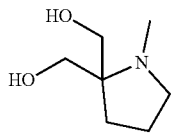

[2-(Hydroxymethyl)pyrrolidin-2-yl]methanol (500 mg, 3.81 mmol, 1.0 eq.) and HCHO (343 mg, 11.4 mmol, 3.0 eq.) in MeOH (10.00 mL) was stirred for 0.5 h at RT. Then NaBH$_3$CN (479 mg, 7.62 mmol, 2.00 eq.) was slowly added at 0° C. The resulting mixture was stirred for 4 h at RT. The reaction was quenched with H$_2$O (5 mL) at 0° C. and then diluted with H$_2$O. The mixture was extracted with EtOAc (3×200 mL). The combined organic layers were washed with brine (3×100 mL) and dried over anhydrous Na$_2$SO$_4$. After filtration, the filtrate was concentrated under reduced pressure. The residue was purified on silica gel, eluting with DCM/MeOH/NH$_4$OH (100:10:1 to 100:20:1) to afford the product (400 mg, 72.3%) as a yellow oil. (M+1). $^1$H NMR (300 MHz, DMSO-d$_6$+D$_2$O) δ 4.31-4.08 (m, 2H), 3.38-3.23 (m, 4H), 2.72 (t, J=6.3 Hz, 2H), 2.33 s, 3H), 1.76-1.50 (m, 4H).

Preparation 97

1-[tert-Butyl(dimethyl)silyl]oxypropan-2-one

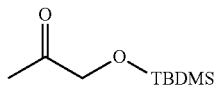

A solution of 1-hydroxypropan-2-one (25.00 g, 337.48 mmol, 1.0 eq.), tert-butyldimethylchlorosilane (76.30 g, 506.22 mmol, 1.50 eq.) and imidazole (50.54 g, 742.45 mmol, 2.20 eq.) in DCM (100 mL) was stirred for 4 h at RT under N$_2$. The resulting mixture was diluted with EtOAc (400 mL), washed with H$_2$O (3×500 mL), and concentrated under reduced pressure. The residue was purified by silica gel column chromatography, eluting with EtOAc/PE (0-5%) to afford the product (56.00 g, 88.10%) as a colorless oil. $^1$H NMR (400 MHz, CDCl$_3$) δ 4.15 (s, 2H), 2.17 (s, 3H), 0.93 (s, 9H), 0.09 (s, 6H).

Preparation 98

1-Benzyl-4-[[tert-butyl(dimethyl)silyl]oxymethyl]-3-methoxy-4-methyl-azetidin-2-one

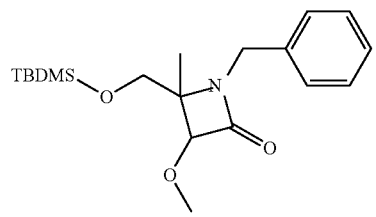

A mixture of 1-[tert-butyl(dimethyl)silyl]oxypropan-2-one (30.00 g, 159.28 mmol, 1.00 eq.), benzylamine (17.07 g, 159.30 mmol, 1.00 eq.) and 4 Å molecular sieves (30 g) in DCM (300 mL) was stirred for 12 h at 45° C. under N$_2$. To the mixture was added TEA (37.23 g, 367.92 mmol, 2.31 eq.) and then methoxyacetyl chloride (22.47 g, 207.06 mmol, 1.30 eq.) was added dropwise over 30 min at −78° C. The reaction was allowed to warm to RT and stirred for 12 h. The mixture was filtered and the filter cake was washed with DCM (200 mL). The filtrate was diluted with H$_2$O (300 mL) and was extracted with DCM (3×300 mL). The combined organic layers were washed with sat. aq. NaCl (200 mL), dried over anhydrous Na$_2$SO$_4$, filtered and concentrated under reduced pressure. The residue was purified by silica gel column chromatography, eluting with EtOAc/PE (10%) to afford the product (9.00 g, 12.12%) as a light-yellow oil. $^1$H NMR (400 MHz, CDCl$_3$) δ 7.37-7.18 (m, 5H), 4.45-4.27 (m, 2H), 4.10 (s, 1H), 3.71-3.56 (m, 2H), 3.50 (s, 3H), 1.22 (s, 3H), 0.86 (s, 9H), 0.05--0.09 (m, 6H).

Preparation 99 (1-Benzyl-3-methoxy-2-methyl-azetidin-2-yl)methoxy-tert-butyl-dimethyl-silane

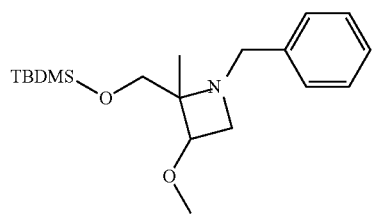

To a stirred mixture of AlCl$_3$ (1.85 g, 13.85 mmol, 1.21 eq.) in THF (20 mL) was added a solution of LiAlH$_4$ (0.64 g, 16.82 mmol, 1.47 eq.) in THF (10 mL) dropwise at −10° C. under N$_2$. The resulting mixture was allowed to warm to RT and stir for 3 h. After cooling to −10° C. a solution of 1-benzyl-4-[[tert-butyl(dimethyl)silyl]oxymethyl]-3-methoxy-4-methyl-azetidin-2-one (4.00 g, 11.4 mmol, 1.0 eq.) in THF (10 mL) was added dropwise. The mixture was allowed to warm to RT and stir for additional 1 h. Then H$_2$O (0.64 mL) was added followed by 15% NaOH (0.64 mL) and additional H$_2$O (1.92 mL). The mixture was filtered and the filter cake was washed with THF (100 mL). The filtrate was concentrated under reduced pressure. The residue was purified by silica gel column chromatography, eluting with EtOAc/PE (0-10%) to afford the product (1.56 g, 40.63%) as a colorless oil. $^1$H NMR (400 MHz, CDCl$_3$) δ 7.27-7.10 (m, 5H), 3.80-3.65 (m, 3H), 3.61 (dd, J=6.4, 4.7 Hz 1H), 3.53 (d, J=13.2 Hz, 1H), 3.23 (d, J=4.9 Hz, 4H), 2.98 (dd, J=7.7, 4.7 Hz, 1H), 1.22 (s, 3H), 0.83 (s, 9H), 0.00 (d, 6H).

Preparation 100 tert-Butyl-[(3-methoxy-1,2-dimethyl-azetidin-2-yl)methoxy]-dimethyl-silane

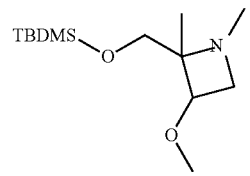

Preparation 101

(3-Methoxy-1,2-dimethyl-azetidin-2-yl)methanol

To a solution of (1-benzyl-3-methoxy-2-methyl-azetidin-2-yl)methoxy-tert-butyl-dimethyl-silane (1.1 g, 3.28 mmol, 1.00 eq.) in MeOH (10 mL) was added Pd/C (110 mg, 10% wt) under N₂. The mixture was hydrogenated at RT for 24 h under H₂ atmosphere using a hydrogen balloon. To the above mixture was added (HCHO)$_n$ (0.20 g, 6.66 mmol, 2.03 eq.) at RT. The resulting mixture was placed under a H₂ atmosphere again (balloon) and stirred for additional 10 h at RT. The mixture was filtered and the filter cake was washed with MeOH (50 mL). The filtrate was concentrated under reduced pressure to give the product (0.8 g, crude) as a colorless oil, which was used in a subsequent step without further purification.

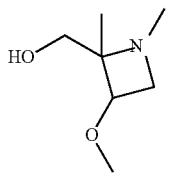

A solution of tert-butyl-[(3-methoxy-1,2-dimethyl-azetidin-2-yl)methoxy]-dimethyl-silane (800 mg, 3.08 mmol, 1 eq.) in 4M HCl/MeOH (10.00 mL) was stirred for 10 h at RT under N₂. The resulting mixture was concentrated under reduced pressure. The residue was purified by silica gel column chromatography, eluting with DCM/MeOH/NH₃H₂O (15:3:0.2) to afford the product (250 mg, 55.84%) as a light-yellow solid. ¹H NMR (400 MHz, CDCl₃) δ 3.84 (dd, J=6.3, 4.8 Hz, 1H), 3.78-3.66 (m, 2H), 3.46 (dd, J=8.0, 6.3 Hz, 1H), 3.36-3.28 (m, 4H), 2.35 (s, 3H), 1.18 (s, 3H).

Preparation 102 tert-Butyl 8-(6-bromo-3-ethylsulfanyl-5-fluoro-7,9-dihydrofuro[3,4-f]quinazolin-1-yl)-3,8-diazabicyclo[3.2.1]octane-3-carboxylate

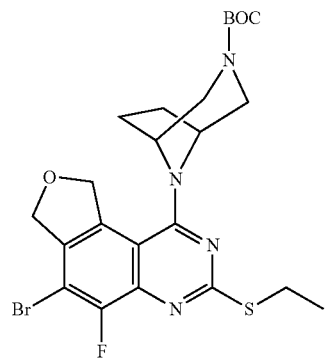 [SMILES: CCSc1nc(N2C3CCC2CN(C(=O)OC(C)(C)C)C3)c2c3c(c(Br)c(F)c2n1)COC3]

A suspension of 6-bromo-1-chloro-3-ethylsulfanyl-5-fluoro-7,9-dihydrofuro[3,4-f]quinazoline (21.0 g, 57.8 mmol) in ACN (580 mL) was charged with tert-butyl 3,8-diazabicyclo[3.2.1]octane-3-carboxylate (15.2 g, 69.5 mmol, 1.20 eq.) and DIPEA (40 mL, 229 mmol, 4 eq.) and was stirred at RT for 90 min. H₂O (1 L) was added slowly via addition funnel and the mixture was stirred at RT for 1 h. The solids were filtered, rinsed with H₂O (500 mL) and dried under vacuum at 50° C. to obtain the title compound (31 g, quantitative) as a white solid, MS (ES) m/z=539 (M+1).

The following compounds in Table 5 were prepared in similar manner as described in Preparation 102. Various methods were used to purify the compounds, which would be apparent to one skilled in the art.

TABLE 5

| Preparation | Chemical Name | Structure | MS (ES) m/z (M + 1) |
|---|---|---|---|
| 103 | tert-Butyl 8-(6-bromo-5-chloro-3-ethylsulfanyl-7,9-dihydrofuro[3,4-f]quinazolin-1-yl)-3,8-diazabicyclo[3.2.1]octane-3-carboxylate | 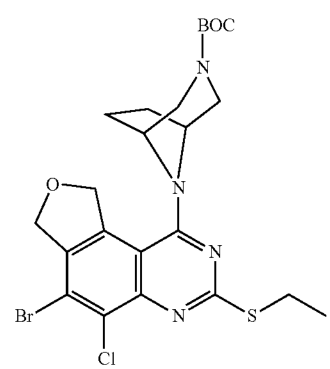 [SMILES: CCSc1nc(N2C3CCC2CN(C(=O)OC(C)(C)C)C3)c2c3c(c(Br)c(Cl)c2n1)COC3] | 555 |

TABLE 5-continued

| Preparation | Chemical Name | Structure | MS (ES) m/z (M + 1) |
|---|---|---|---|
| 104 | tert-Butyl (1R,4R)-5-(6-bromo-3-ethylsulfanyl-5-fluoro-7,9-dihydrofuro[3,4-f]quinazolin-1-yl)-2,5-diazabicyclo[2.2.1]heptane-2-carboxylate | 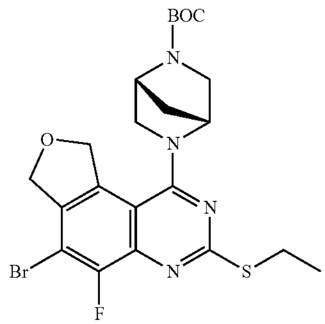 [SMILES: CCSc1nc(N2C[C@H]3C[C@@H]2CN3C(=O)OC(C)(C)C)c2c3c(c(Br)c(F)c2n1)COC3] | 525 |
| 105 | tert-Butyl 6-(6-bromo-3-ethylsulfanyl-5-fluoro-7,9-dihydrofuro[3,4-f]quinazolin-1-yl)-3,6-diazabicyclo[3.1.1]heptane-3-carboxylate | 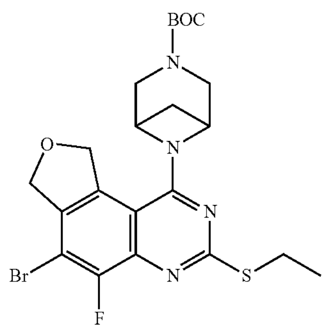 [SMILES: CCSc1nc(N2C3CC2CN(C(=O)OC(C)(C)C)C3)c2c3c(c(Br)c(F)c2n1)COC3] | 525 |
| 106 | tert-Butyl 8-(4-bromo-5-fluoro-1,3-dihydrofuro[3,4-f]cinnolin-9-yl)-3,8-diazabicyclo[3.2.1]octane-3-carboxylate | 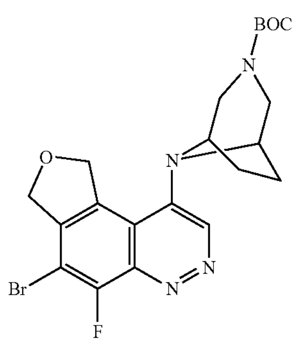 [SMILES: CC(C)(C)OC(=O)N1CC2CCC(C1)N2c1cnnc2c(F)c(Br)c3c(c12)COC3] | 479 |
| 107 | Benzyl (1S,4S,7R)-5-(6-bromo-5-fluoro-7,9-dihydrofuro[3,4-f]quinazolin-1-yl)-7-fluoro-2,5-diazabicyclo[2.2.1]heptane-2-carboxylate | 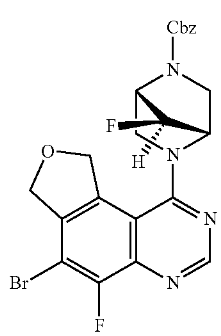 [SMILES: O=C(OCc1ccccc1)N1C[C@H]2[C@@H](F)[C@@H]1CN2c1ncnc2c(F)c(Br)c3c(c12)COC3] | 517 |

TABLE 5-continued

| Preparation | Chemical Name | Structure | MS (ES) m/z (M + 1) |
|---|---|---|---|
| 233 | 6-Bromo-N-[[1-(dimethylamino)cyclopentyl]methyl]-3-ethylsulfanyl-5-fluoro-7,9-dihydrofuro[3,4-f]quinazolin-1-amine | 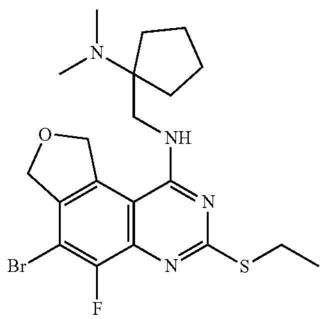 [SMILES: CCSc1nc(NCC2(N(C)C)CCCC2)c2c3c(c(Br)c(F)c2n1)COC3] | 469 |
| 234 | 6-Bromo-3-ethylsulfanyl-5-fluoro-1-methoxy-7,9-dihydrofuro[3,4-f]quinazoline | 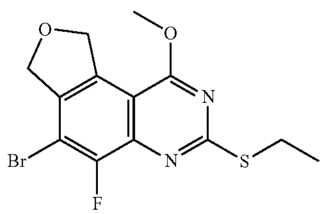 [SMILES: CCSc1nc(OC)c2c3c(c(Br)c(F)c2n1)COC3] | 359 |

Preparation 108 tert-Butyl (1R,4R)-5-(6-bromo-5-chloro-7,9-dihydrofuro[3,4-f]quinazolin-1-yl)-2,5-diazabicyclo[2.2.1]heptane-2-carboxylate

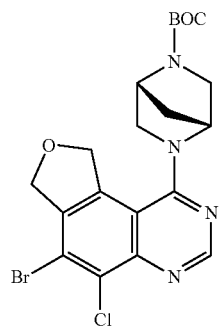 [SMILES: CC(C)(C)OC(=O)N1C[C@H]2C[C@@H]1CN2c1ncnc2c(Cl)c(Br)c3c(c12)COC3]

To a stirred mixture of 6-bromo-5-chloro-7H,9H-furo[3,4-f]quinazolin-1-ol (3 g, 9.95 mmol) and BrOP (5.79 g, 14.92 mmol) in 1,4-dioxane (30 mL) was added TEA (6.92 mL, 49.75 mmol) dropwise at RT. The resulting mixture was stirred for 4 h at 80° C. under $N_2$. Cooled to RT, and added tert-butyl (1R,4R)-2,5-diazabicyclo[2.2.1]heptane-2-carboxylate (3.95 g, 19.90 mmol). Heating was resumed at 80° C. under $N_2$. After 2h, the mixture was allowed to cool to RT, diluted with $H_2O$ (200 mL) and extracted with EtOAc (3×500 mL). The combined organic layers were washed with brine (3×200 mL), dried over anhydrous $Na_2SO_4$, filtered and concentrated under reduced pressure. The residue was purified by silica gel column chromatography, eluting with PE/EtOAc (3:1 to 2:1) to afford the title compound (780 mg, 14.6%) as a yellow solid. MS (ES) m/z=481 (M+1).

Preparation 109 tert-Butyl (1R,4R)-5-[6-bromo-9-(cyanomethyl)-3-ethylsulfanyl-5-fluoro-7,9-dihydrofuro[3,4-f]quinazolin-1-yl]-2,5-diazabicyclo[2.2.1]heptane-2-carboxylate

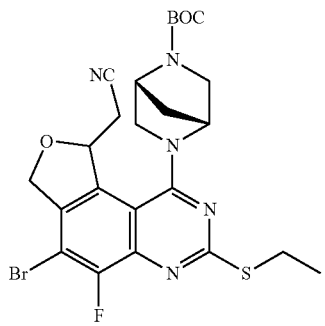 [SMILES: CCSc1nc(N2C[C@H]3C[C@@H]2CN3C(=O)OC(C)(C)C)c2c3c(c(Br)c(F)c2n1)COC3CC#N]

A suspension of 2-(6-bromo-1-chloro-3-ethylsulfanyl-5-fluoro-7,9-dihydrofuro[3,4-f]quinazolin-9-yl)acetonitrile (4.40 g, 8.85 mmol) in DMF (80 mL) cooled in an ice bath was charged with tert-butyl (1R,4R)-2,5-diazabicyclo[2.2.1]heptane-2-carboxylate (2.00 g, 9.78 mmol) and DIPEA (3.10 mL, 17.8 mmol). The reaction was stirred at RT for 2 h. DMF was removed under reduced pressure. The residue was dissolved in EtOAc (500 mL), washed with sat. aq. $NaHCO_3$ and brine, dried over anhydrous $MgSO_4$, filtered and concentrated. The residue was purified by silica column chromatography, eluting with EtOAc/Hex (10-100%) to afford the title compound (4.00 g, 80%) as a light-brown solid. MS (ES) m/z=564 (M+1).

Preparation 110 tert-Butyl (1R,4R)-5-[6-bromo-5-chloro-9-(cyanomethyl)-3-ethylsulfanyl-7,9-dihydrofuro[3,4-f]quinazolin-1-yl]-2,5-diazabicyclo[2.2.1]heptane-2-carboxylate

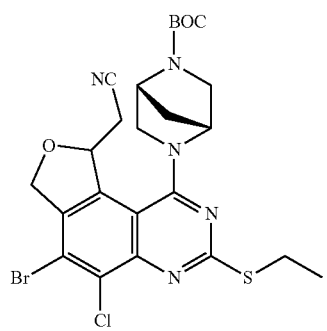 [SMILES: CCSc1nc(N2C[C@H]3C[C@@H]2CN3C(=O)OC(C)(C)C)c2c3c(c(Br)c(Cl)c2n1)COC3CC#N]

2-(6-Bromo-1,5-dichloro-3-ethylsulfanyl-7,9-dihydrofuro[3,4-f]quinazolin-9-yl)acetonitrile was used in an analogous manner to the method of Preparation 108 to obtain the title compound (0.53 g, 76%) as yellow solid. MS (ES) m/z=580 (M+1).

Preparation 111 tert-Butyl 8-(4-bromo-5-chloro-7-methylsulfanyl-1,3-dihydrofuro[3,4-f]quinolin-9-yl)-3,8-diazabicyclo[3.2.1]octane-3-carboxylate

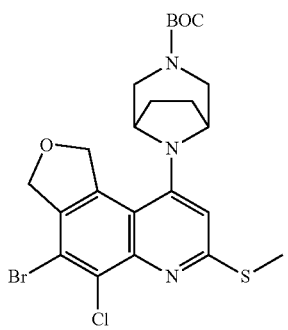 [SMILES: CSc1cc(N2C3CCC2CN(C(=O)OC(C)(C)C)C3)c2c3c(c(Br)c(Cl)c2n1)COC3]

In a dry reaction vessel, DMSO (198 mL) was purged with $N_2$ using a gas dispersion tube for 5 min. DIPEA (3.9 mL, 22 mmol) was added and purged for an additional 3 min. Solid 4-bromo-5,9-dichloro-7-methylsulfanyl-1,3-dihydrofuro[3,4-f]quinoline (8.1 g, 22 mmol) and tert-butyl 3,8-diazabicyclo[3.2.1]octane-3-carboxylate (19 g, 89 mmol, 4 eq.) was added and the reaction vessel was sealed and heated to 130° C. for 48 h. After cooling to RT, the reaction was poured into a separatory funnel and diluted with DCM (1.5 L), washed with $H_2O$ (3×500 mL), separated and concentrated. The residue was purified on silica (100% DCM to 5% EtOAc/DCM) to obtain the title compound (5.36 g. 45%) as a white solid. MS (ES) m/z=540 (M+1).

Preparation 112 tert-Butyl (1R,4R)-5-(6-bromo-5-fluoro-3-methyl-7,9-dihydrofuro[3,4-f]quinazolin-1-yl)-2,5-diazabicyclo[2.2.1]heptane-2-carboxylate

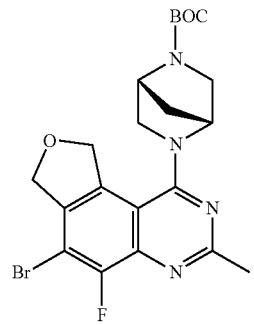 [SMILES: Cc1nc(N2C[C@H]3C[C@@H]2CN3C(=O)OC(C)(C)C)c2c3c(c(Br)c(F)c2n1)COC3]

A mixture of 6-bromo-5-fluoro-3-methyl-7,9-dihydrofuro[3,4-f]quinazolin-1-ol (280 mg, 0.936 mmol), phosphonitrilic chloride trimer (423 mg, 1.22 mmol) and DIEA (605 mg, 4.68 mmol) in ACN was stirred for 5 h at 50° C. under $N_2$. After cooling to RT, added tert-butyl (1R,4R)-2,5-diazabicyclo[2.2.1]heptane-2-carboxylate (119 mg, 0.602 mmol) and DIEA (605 mg, 4.68 mmol) and the resulting mixture was stirred for additional 2 h at RT. The mixture was diluted with $H_2O$ (150 mL), extracted with EtOAc (3×50 mL) and was concentrated under reduced pressure. The residue was purified by silica gel column chromatography, eluting with PE/EtOAc (3:1 to 1:1) to afford the title compound (280 mg, 62.3%) as a yellow solid. MS (ES) m/z=479 (M+1).

Preparation 113

6-Bromo-1-[(1R,4R)-2,5-diazabicyclo[2.2.1]heptan-2-yl]-3-ethylsulfanyl-5-fluoro-7,9-dihydrofuro[3,4-f]quinazoline

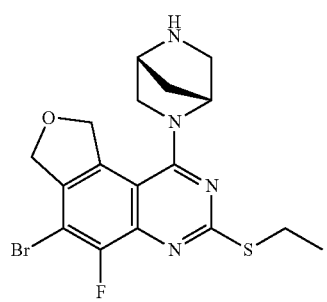 [SMILES: CCSc1nc(N2C[C@H]3C[C@@H]2CN3)c2c3c(c(Br)c(F)c2n1)COC3]

tert-Butyl (1R,4R)-5-(6-bromo-3-ethylsulfanyl-5-fluoro-7,9-dihydrofuro[3,4-f]quinazolin-1-yl)-2,5-diazabicyclo[2.2.1]heptane-2-carboxylate (500 mg, 0.951 mmol) was stirred in DCM (5 mL, 78.00 mmol). TFA (2 mL, 26.45 mmol) was added. The reaction vessel was capped and stirred at RT for ~18 h. The reaction solution was placed over an 10 g SCX column, washed with 3 column volumes of MeOH, then eluting with 3 column volumes of 2N $NH_3$ in MeOH. The basic fraction was concentrated to give the title compound (426 mg, quantitative) as a thick oil. MS (ES) m/z=426 (M+1).

Preparation 114 tert-Butyl 8-(6-bromo-3-ethylsulfonyl-5-fluoro-7,9-dihydrofuro[3,4-f]quinazolin-1-yl)-3,8-diazabicyclo[3.2.1]octane-3-carboxylate

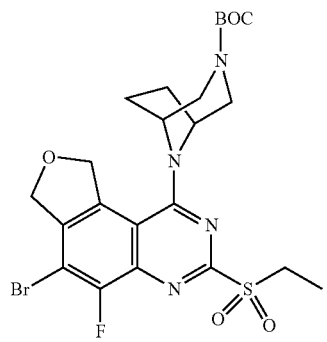 [SMILES: CCS(=O)(=O)c1nc(N2C3CCC2CN(C(=O)OC(C)(C)C)C3)c2c3c(c(Br)c(F)c2n1)COC3]

A solution of tert-butyl 8-(6-bromo-3-ethylsulfanyl-5-fluoro-7,9-dihydrofuro[3,4-f]quinazolin-1-yl)-3,8-diazabicyclo[3.2.1]octane-3-carboxylate (4.3 g, 8.0 mmol) in DCM (40 mL) was charged with mCPBA (6.21 g, 25.2 mmol, 3.2 eq.) and stirred at RT for 90 min. The mixture was diluted with DCM and washed with sat. aq. NaHCO$_3$, and brine. The organics were dried over anhydrous Na$_2$SO$_4$, filtered and concentrated. The residue was purified on silica, eluting with EtOAc/Hex (20-80%) to obtain the title compound (3.0 g, 66%) as a white solid. MS (ES) m/z=571 (M+1).

Preparation 235 tert-Butyl 8-(6-bromo-5-chloro-3-ethylsulfonyl-7,9-dihydrofuro[3,4-f]quinazolin-1-yl)-3,8-diazabicyclo[3.2.1]octane-3-carboxylate

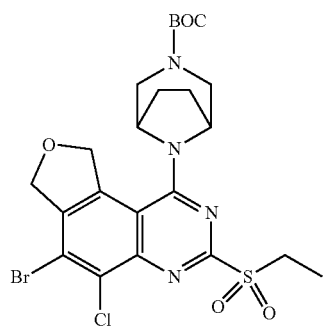 [SMILES: CCS(=O)(=O)c1nc(N2C3CCC2CN(C(=O)OC(C)(C)C)C3)c2c3c(c(Br)c(Cl)c2n1)COC3]

tert-Butyl 8-(6-bromo-5-chloro-3-ethylsulfanyl-7,9-dihydrofuro[3,4-f]quinazolin-1-yl)-3,8-diazabicyclo[3.2.1]octane-3-carboxylate was used in an analogous manner to the method of Preparation 114 to obtain the title compound (13.5 g, 86%). MS (ES) m/z=587,589 (M+1, Br).

Preparation 302

6-Bromo-3-ethylsulfonyl-5-fluoro-7,9-dihydrofuro[3,4-f]quinazoline

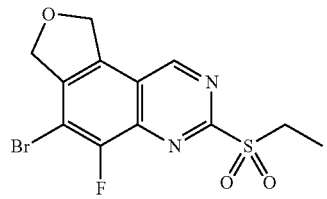 [SMILES: CCS(=O)(=O)c1ncc2c3c(c(Br)c(F)c2n1)COC3]

6-Bromo-3-ethylsulfanyl-5-fluoro-7,9-dihydrofuro[3,4-f]quinazoline was used in an analogous manner to the method of Preparation 114 to obtain the title compound (1.00 g, 92%). MS (ES) m/z=361,363 (M+1, Br).

Preparation 115 tert-Butyl 8-[6-bromo-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate

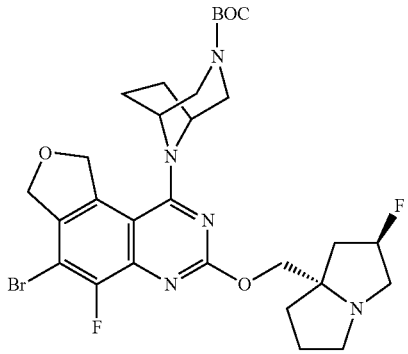 [SMILES: CC(C)(C)OC(=O)N1CC2CCC(C1)N2c1nc(OC[C@@]23CCCN2C[C@H](F)C3)nc2c(F)c(Br)c3c(c12)COC3]

To a mixture of [(2R,8S)-2-Fluoro-1,2,3,5,6,7-hexahydropyrrolizin-8-yl]methanol (2.26 g, 13.8 mmol) in THF (110 mL) under N$_2$ was added dropwise LiHMDS in THF (13.7 mL, 13.7 mmol, 1.0 M) and stirred for 20 min. To this solution was added dropwise via syringe, tert-butyl 8-(6-bromo-3-ethylsulfonyl-5-fluoro-7,9-dihydrofuro[3,4-f]quinazolin-1-yl)-3,8-diazabicyclo[3.2.1]octane-3-carboxylate (6.54 g, 11.4 mmol) in THF (40 mL). After 35 min, the reaction was diluted with EtOAc (250 mL) and washed with brine. The aqueous was extracted with EtOAc (2×200 mL) and the combined organics were dried over Na$_2$SO$_4$ and concentrated to a tan solid. The crude material was purified by silica, eluting with 0-10% MeOH/DCM to afford the title compound (7.0 g, 96%) as a light-tan solid. MS (ES) m/z=636 (M+1).

Preparation 236 tert-Butyl 8-[6-bromo-5-fluoro-3-[(2-methoxy-1,2,3,5,6,7-hexahydropyrrolizin-8-yl)methoxy]-7,9-dihydrofuro[3,4-f]quinazolin-1-yl]-3,8-diazabicyclo[3.2.1]octane-3-carboxylate

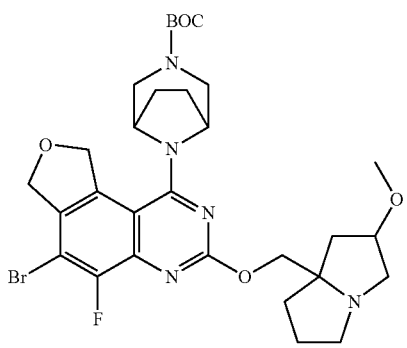 [SMILES: COC1CN2CCCC2(COc2nc(N3C4CCC3CN(C(=O)OC(C)(C)C)C4)c3c4c(c(Br)c(F)c3n2)COC4)C1]

(2-Methoxy-1,2,3,5,6,7-hexahydropyrrolizin-8-yl)methanol was used in an analogous manner to the method of Preparation 115 to obtain the title compound (4.5 g, 85%). MS (ES) m/z=648,650 (M+1, Br).

Preparation 237 tert-Butyl 8-[6-bromo-5-chloro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate

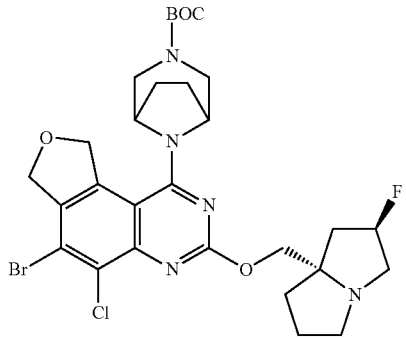 [SMILES: CC(C)(C)OC(=O)N1CC2CCC(C1)N2c1nc(OC[C@@]23CCCN2C[C@H](F)C3)nc2c(Cl)c(Br)c3c(c12)COC3]

tert-Butyl 8-(6-bromo-5-chloro-3-ethylsulfonyl-7,9-dihydrofuro[3,4-f]quinazolin-1-yl)-3,8-diazabicyclo[3.2.1]octane-3-carboxylate was used in an analogous manner to the method of Preparation 115 to obtain the title compound (12.8 g, 85%). MS (ES) m/z=652,654 (M+1, Br).

Preparation 116

6-Bromo-1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazoline

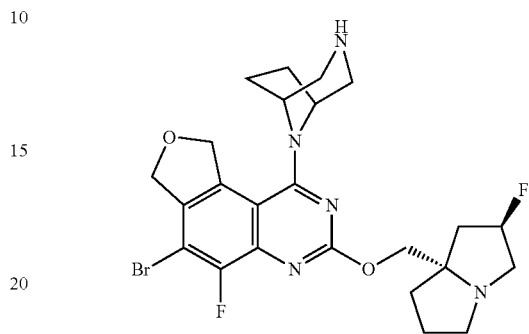

tert-Butyl 8-[6-bromo-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate was used in an analogous manner to the method of Preparation 113 and was isolated by partitioning between DCM and sat. aq. NaHCO₃ to obtain the title compound (0.83 g, 99%) as a pale-yellow foam. MS (ES) m/z=536 (M+1).

Preparation 117

3-[8-[6-Bromo-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]propoxy-tert-butyl-dimethyl-silane

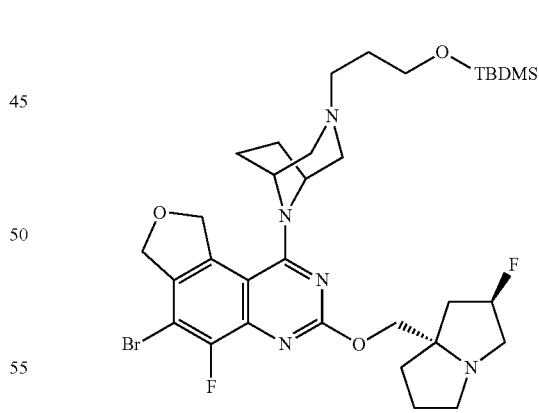

A solution of 6-bromo-1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazoline (0.900 g, 1.68 mmol) in DCM (17 mL) was treated with 3-[(tert-butyldimethylsilyl)oxy]-1-propanal (0.998 g, 5.03 mmol) and NaBH(OAc)₃ (1.12 g, 5.02 mmol) and was stirred at RT for 2 h. The reaction mixture was treated with sat. aq. NaHCO₃ and was stirred for 15 min. H₂O was added and the layers were separated. The aqueous layer was extracted 2× with DCM. The organic layers were combined, dried over Na₂SO₄ and concentrated in vacuo. The residue was purified on silica, eluting with 0% to 4% 7N NH₃/MeOH in DCM to afford the title compound (0.844 g, 71%) as an off-white solid. MS (ES) m/z=708 (M+1).

The following compounds in Table 6 were prepared in a similar manner as described for Preparation 117, using the appropriate aldehyde. Various methods were used to purify the compounds, which would be apparent to one skilled in the art.

TABLE 6

| Preparation | Chemical Name | Structure | MS (ES) m/z (M + 1) |
|---|---|---|---|
| 118 | 6-Bromo-5-fluoro-3-[[(2R,8S)-2-fluoro-1,2,3,5,6,7-hexahydropyrrolizin-8-yl]methoxy]-1-(3-methyl-3,8-diazabicyclo[3.2.1]octan-8-yl)-7,9-dihydrofuro[3,4-f]quinazoline | 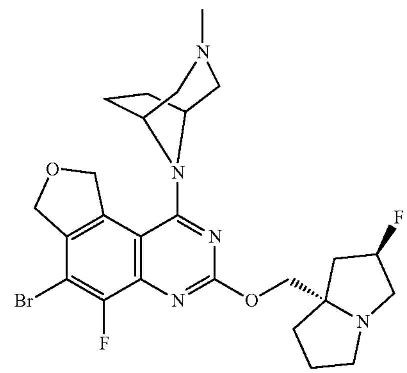 [SMILES: CN1CC2CCC(C1)N2c1nc(OC[C@@]23CCCN2C[C@H](F)C3)nc2c(F)c(Br)c3c(c12)COC3] | 550 |
| 119 | 6-Bromo-1-(3-ethyl-3,8-diazabicyclo[3.2.1]octan-8-yl)-5-fluoro-3-[(2R,8S)-2-fluoro-1,2,3,5,6,7-hexahydropyrrolizin-8-yl]methoxy]-7,9-dihydrofuro[3,4-f]quinazoline | 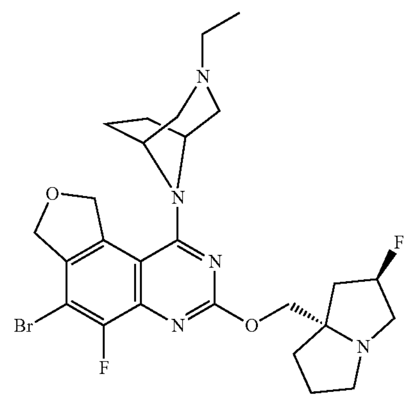 [SMILES: CCN1CC2CCC(C1)N2c1nc(OC[C@@]23CCCN2C[C@H](F)C3)nc2c(F)c(Br)c3c(c12)COC3] | 564 |
| 120 | 2-[8-[6-Bromo-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]ethoxy-tert-butyl-dimethyl-silane | 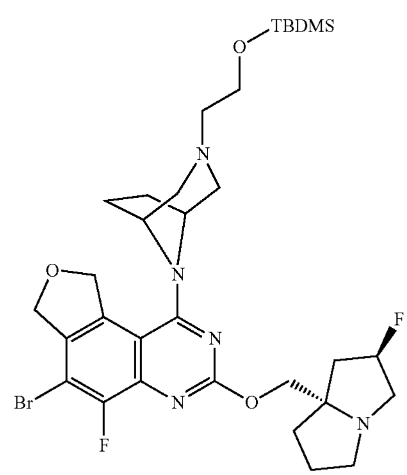 | 694 |

TABLE 6-continued

| Preparation | Chemical Name | Structure | MS (ES) m/z (M + 1) |
|---|---|---|---|
| 121 | 6-Bromo-3-ethylsulfanyl-5-fluoro-1-[(1R,4R)-5-methyl-2,5-diazabicyclo[2.2.1]heptan-2-yl]-7,9-dihydrofuro[3,4-f]quinazoline | 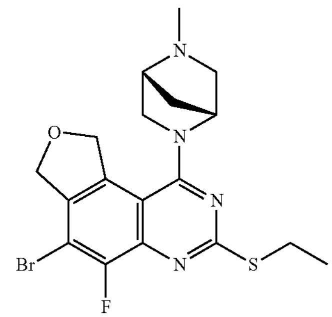 [SMILES: CCSc1nc(N2C[C@H]3C[C@@H]2CN3C)c2c3c(c(Br)c(F)c2n1)COC3] | 439 |

Preparation 122 tert-Butyl 6-[6-bromo-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,6-diazabicyclo[3.1.1]heptane-3-carboxylate tert-Butyl 6-(6-bromo-3-ethylsulfonyl-5-fluoro-7,9-dihydrofuro[3,4-f]quinazolin-1-yl)-3,6-diazabicyclo[3.1.1]heptane-3-carboxylate was used in an analogous manner to the method of Preparation 115 to obtain the title compound (0.8 g, 84%) as light-yellow foam. MS (ES) m/z=622 (M+1).

Preparation 303 tert-Butyl 8-[6-bromo-3-[[(2R)-1,4-dioxan-2-yl]methoxy]-5-fluoro-7,9-dihydrofuro[3,4-f]quinazolin-1-yl]-3,8-diazabicyclo[3.2.1]octane-3-carboxylate

[(2S)-1,4-Dioxan-2-yl]methanol was used in an analogous manner to the method of Preparation 115 to obtain the title compound (1.72 g, 97%) as white solid. MS (ES) m/z=595,597 (M+1, Br).

Preparation 304

6-Bromo-5-fluoro-3-[[(2R,8S)-2-fluoro-1,2,3,5,6,7-hexahydropyrrolizin-8-yl]methoxy]-7,9-dihydrofuro[3,4-f]quinazolinediazabicyclo[3.2.1]octane-3-carboxylate 6-Bromo-3-ethylsulfonyl-5-fluoro-7,9-dihydrofuro[3,4-f]quinazoline was used in an analogous manner to the method of Preparation 115 to obtain the title compound (0.11 g, 62%) as off-white solid. MS (ES) m/z=426,428 (M+1, Br).

Preparation 123 tert-Butyl 8-[6-[2-(tert-butoxycarbonylamino)-5-fluoro-benzothiophen-4-yl]-3-ethylsulfanyl-5-fluoro-7,9-dihydrofuro[3,4-f]quinazolin-1-yl]-3,8-diazabicyclo[3.2.1]octane-3-carboxylate A 250 mL 3-necked RBF, equipped with a thermocouple, condenser and $N_2$ sparge line, was charged with a suspension of tert-butyl 8-(6-bromo-3-ethylsulfanyl-5-fluoro-7,9-dihydrofuro[3,4-f]quinazolin-1-yl)-3,8-diazabicyclo[3.2.1]octane-3-carboxylate (5.00 g, 9.27 mmol) and tert-butyl N-[4-(5,5-dimethyl-1,3,2-dioxaborinan-2-yl)-5-fluoro-benzothiophen-2-yl]carbamate (5.53 g, 13.9 mmol, 1.5 eq.) in 1,4-dioxane (100 mL) and $H_2O$ (31 mL). The heat was set to 70° C. and started. At the same time, $N_2$ sparge was started. When the internal temperature had reached ~45° C., the sparge line was removed and $K_3PO_4$ (2.95 g, 13.9 mmol, 1.5 eq.) and Pd-118 (0.620 g, 0.932 mmol, 0.10 eq.) were added. The reaction temperature was allowed to reach 70° C. and was stirred for 90 min. The reaction was cooled to RT, then the mixture was diluted with EtOAc, washed with $H_2O$ and partitioned. The aqueous phase was extracted with EtOAc (100 mL), and the combined organics were washed with brine, dried over anhydrous $Na_2SO_4$, filtered and concentrated. MTBE (50 mL) was added and the mixture was sonicated for 20 min. Solids were filtered to obtain product as batch 1. The filtrate was concentrated and the residue was purified on silica, eluting with EtOAc/Hexanes (0-30%). Product-containing fractions were concentrated to a tan foam which was dissolved in DCM (20 mL) and treated dropwise with hexanes (60 mL) while stirring rapidly for 1 h. The resulting solids were filtered and rinsed with hexanes (50 mL) to obtain product as batch 2. The two batches were combined to give the title compound (6.4 g, 88%) as a white solid. MS (ES) m/z=726 (M+1).

The following compounds in Table 7 were prepared in similar manner as described in Preparation 123. Various methods were used to purify the compounds, which would be apparent to one skilled in the art.

TABLE 7

| Preparation | Chemical Name | Structure | MS (ES) m/z (M + 1) |
|---|---|---|---|
| 124 | tert-Butyl (1R,4R)-5-[6-[2-(tert-butoxycarbonylamino)-5-fluoro-benzothiophen-4-yl]-3-ethylsulfanyl-5-fluoro-7,9-dihydrofuro[3,4-f]quinazolin-1-yl]-2,5-diazabicyclo[2.2.1]heptane-2-carboxylate | 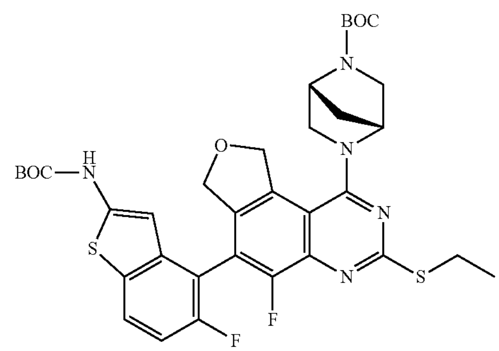 [SMILES: CCSc1nc(N2C[C@H]3C[C@@H]2CN3C(=O)OC(C)(C)C)c2c3c(c(-c4c(F)ccc5sc(NC(=O)OC(C)(C)C)cc45)c(F)c2n1)COC3] | 712 |
| 125 | tert-Butyl 6-[6-[2-(tert-butoxycarbonylamino)-5-fluoro-benzothiophen-4-yl]-3-ethylsulfanyl-5-fluoro-7,9-dihydrofuro[3,4-f]quinazolin-1-yl]-3,6-diazabicyclo[3.1.1]heptane-3-carboxylate | 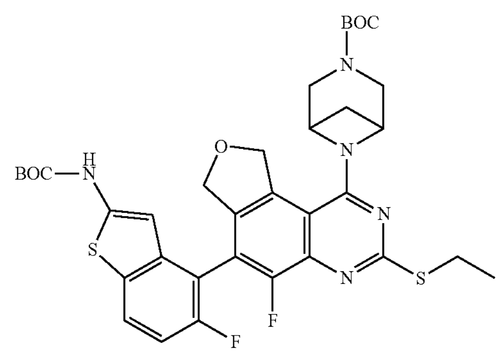 [SMILES: CCSc1nc(N2C3CC2CN(C(=O)OC(C)(C)C)C3)c2c3c(c(-c4c(F)ccc5sc(NC(=O)OC(C)(C)C)cc45)c(F)c2n1)COC3] | 712 |
| 238 | tert-Butyl 6-[6-[2-(tert-butoxycarbonylamino)-5-fluoro-benzofuran-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,6-diazabicyclo[3.1.1]heptane-3-carboxylate | 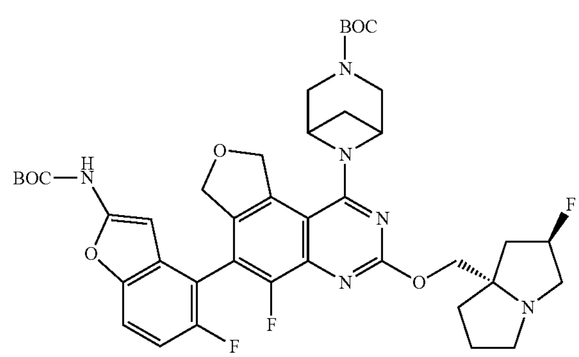 [SMILES: CC(C)(C)OC(=O)Nc1cc2c(-c3c4c(c5c(N6C7CC6CN(C(=O)OC(C)(C)C)C7)nc(OC[C@@]67CCCN6C[C@H](F)C7)nc5c3F)COC4)c(F)ccc2o1] | 793 |

TABLE 7-continued

| Preparation | Chemical Name | Structure | MS (ES) m/z (M + 1) |
|---|---|---|---|
| 239 | tert-Butyl 8-[6-[2-(tert-butoxycarbonylamino)-3-cyano-7-fluoro-benzofuran-4-yl]-3-ethylsulfanyl-5-fluoro-7,9-dihydrofuro[3,4-f]quinazolin-1-yl]-3,8-diazabicyclo[3.2.1]octane-3-carboxylate | 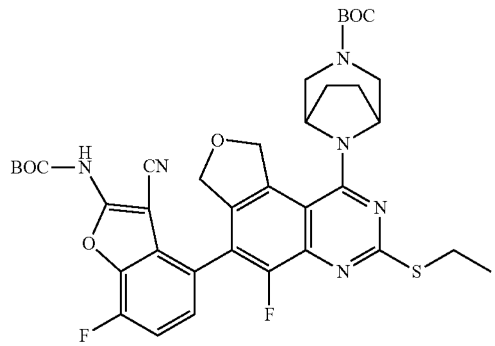 [SMILES: CCSc1nc(N2C3CCC2CN(C(=O)OC(C)(C)C)C3)c2c3c(c(-c4ccc(F)c5oc(NC(=O)OC(C)(C)C)c(C#N)c45)c(F)c2n1)COC3] | 735 |
| 240 | tert-Butyl 8-[6-[2-(tert-butoxycarbonylamino)-3-cyano-benzothiophen-4-yl]-5-chloro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate | 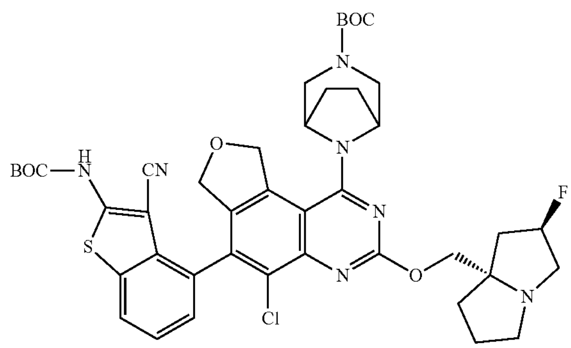 [SMILES: CC(C)(C)OC(=O)Nc1sc2cccc(-c3c4c(c5c(N6C7CCC6CN(C(=O)OC(C)(C)C)C7)nc(OC[C@@]67CCCN6C[C@H](F)C7)nc5c3Cl)COC4)c2c1C#N] | 846 |
| 241 | tert-Butyl (1R,4R)-5-[6-[2-(tert-butoxycarbonylamino)-5-fluoro-benzofuran-4-yl]-3-ethylsulfanyl-5-fluoro-7,9-dihydrofuro[3,4-f]quinazolin-1-yl]-2,5-diazabicyclo[2.2.1]heptane-2-carboxylate | 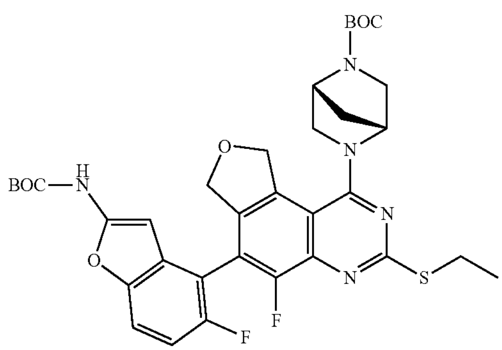 [SMILES: CCSc1nc(N2C[C@H]3C[C@@H]2CN3C(=O)OC(C)(C)C)c2c3c(c(-c4c(F)ccc5oc(NC(=O)OC(C)(C)C)cc45)c(F)c2n1)COC3] | 696 |
| 242 | tert-Butyl N-[4-[1-[[1-(dimethylamino)cyclopentyl]methylamino]-3-ethylsulfanyl-5-fluoro-7,9-dihydrofuro[3,4-f]quinazolin-6-yl]-5-fluoro-benzothiophen-2-yl]carbamate | 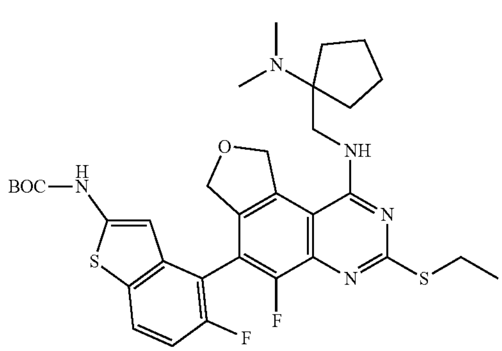 [SMILES: CCSc1nc(NCC2(N(C)C)CCCC2)c2c3c(c(-c4c(F)ccc5sc(NC(=O)OC(C)(C)C)cc45)c(F)c2n1)COC3] | 656 |

TABLE 7-continued

| Preparation | Chemical Name | Structure | MS (ES) m/z (M + 1) |
|---|---|---|---|
| 243 | tert-Butyl N-[4-(3-ethylsulfanyl-5-fluoro-1-methoxy-7,9-dihydrofuro[3,4-f]quinazolin-6-yl)-5-fluoro-benzothiophen-2-yl]carbamate | 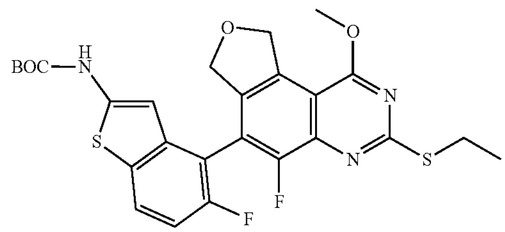 [SMILES: CCSc1nc(OC)c2c3c(c(-c4c(F)ccc5sc(NC(=O)OC(C)(C)C)cc45)c(F)c2n1)COC3] | 546 |
| 305 | tert-Butyl 8-[6-[2-(tert-butoxycarbonylamino)-3-cyano-benzothiophen-4-yl]-3-[[(2R)-1,4-dioxan-2-yl]methoxy]-5-fluoro-7,9-dihydrofuro[3,4-f]quinazolin-1-yl]-3,8-diazabicyclo[3.2.1]octane-3-carboxylate | 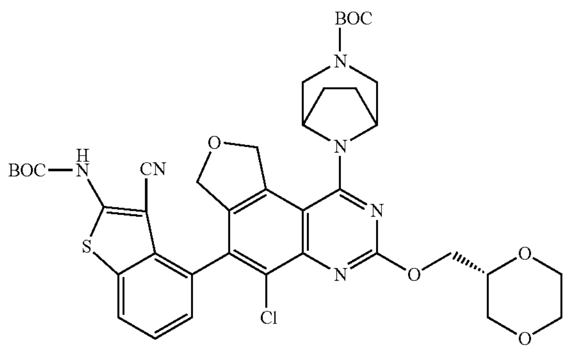 [SMILES: CC(C)(C)OC(=O)Nc1sc2cccc(-c3c4c(c5c(N6C7CCC6CN(C(=O)OC(C)(C)C)C7)nc(OC[C@H]6COCCO6)nc5c3Cl)COC4)c2c1C#N] | 789 |
| 306 | tert-Butyl N-[4-(5-chloro-3-ethylsulfanyl-7,9-dihydrofuro[3,4-f]quinazolin-6-yl)-3-cyano-7-fluoro-benzothiophen-2-yl]carbamate | 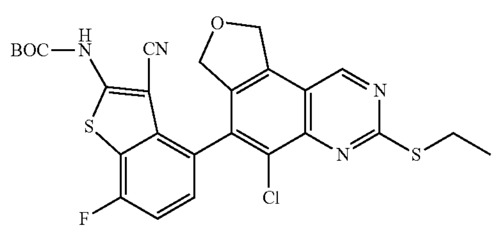 [SMILES: CCSc1ncc2c3c(c(-c4ccc(F)c5sc(NC(=O)OC(C)(C)C)c(C#N)c45)c(Cl)c2n1)COC3] | 557 |

Preparation 126 tert-Butyl 8-[6-[2-(tert-butoxycarbonylamino)-3-cyano-7-fluoro-benzothiophen-4-yl]-5-chloro-3-ethylsulfanyl-7,9-dihydrofuro[3,4-f]quinazolin-1-yl]-3,8-diazabicyclo[3.2.1]octane-3-carboxylate

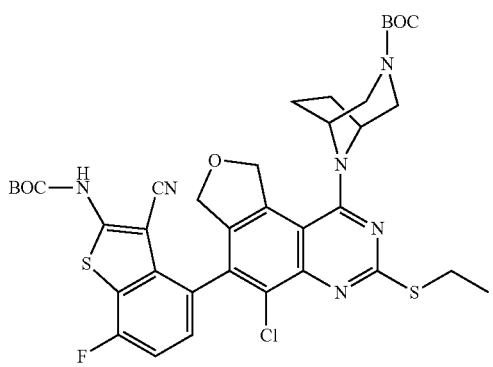 [SMILES: CCSc1nc(N2C3CCC2CN(C(=O)OC(C)(C)C)C3)c2c3c(c(-c4ccc(F)c5sc(NC(=O)OC(C)(C)C)c(C#N)c45)c(Cl)c2n1)COC3]

A solution of tert-butyl 8-(6-bromo-5-chloro-3-ethylsulfanyl-7,9-dihydrofuro[3,4-f]quinazolin-1-yl)-3,8-diazabicyclo[3.2.1]octane-3-carboxylate (0.785 g, 1.36 mmol) in THF (10 mL) was charged with tert-butyl N-[3-cyano-4-(5,5-dimethyl-1,3,2-dioxaborinan-2-yl)-7-fluoro-benzothiophen-2-yl]carbamate (0.826 g, 2.04 mmol, 1.5 eq.) and $Cs_2CO_3$ (1.39 g, 4.27 mmol, 3.15 eq.). The mixture was stirred and sparged with $N_2$ for 10 min. Pd-117 (0.202 g, 0.274 mmol, 0.20 eq.) was added and the mixture was sparged for another 5 min, then the reaction flask was fitted with a reflux condenser and heated at 70° C. for 6 h. The reaction was cooled to RT, diluted with $H_2O$ (1 mL) and was stirred for 5 min. The mixture was filtered through a 3.0 g ISOLUTE® cartridge (Biotage, LLC; Charlotte, NC), eluting with EtOAc until the effluent came off clear and colorless. The filtrate was concentrated and purified on silica, eluting with 200 EtOAc/Hex to obtain the title compound (0.743 g, 70) as a white solid. MS (ES) m/z=767 (M+1).

The following compounds in Table 8 were prepared in similar manner as described for Preparation 126. Various methods were used to purify the compounds, which would be apparent to one skilled in the art.

TABLE 8

| Preparation | Chemical Name | Structure | MS (ES) m/z (M + 1) |
|---|---|---|---|
| 127 | tert-Butyl N-[3-cyano-4-[3-ethylsulfanyl-5-fluoro-1-[(1R,4R)-5-methyl-2,5-diazabicyclo[2.2.1]heptan-2-yl]-7,9-dihydrofuro[3,4-f]quinazolin-6-yl]-7-fluoro-benzothiophen-2-yl]carbamate | 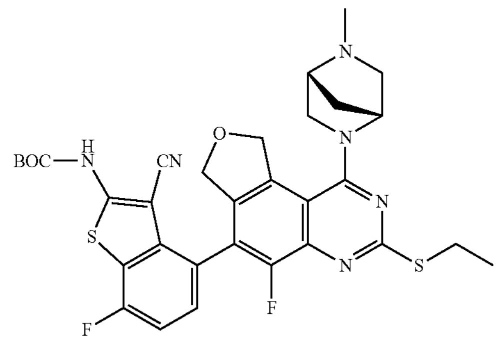 [SMILES: CCSc1nc(N2C[C@H]3C[C@@H]2CN3C)c2c3c(c(-c4ccc(F)c5sc(NC(=O)OC(C)(C)C)c(C#N)c45)c(F)c2n1)COC3] | 651 |
| 128 | tert-Butyl (1R,4R)-5-[6-[2-(tert-butoxycarbonylamino)-3-cyano-7-fluoro-benzothiophen-4-yl]-5-fluoro-3-methyl-7,9-dihydrofuro[3,4-f]quinazolin-1-yl]-2,5-diazabicyclo[2.2.1]heptane-2-carboxylate | 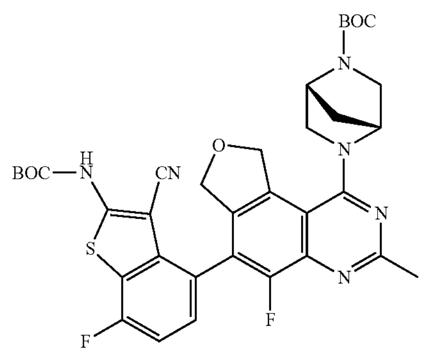 [SMILES: Cc1nc(N2C[C@H]3C[C@@H]2CN3C(=O)OC(C)(C)C)c2c3c(c(-c4ccc(F)c5sc(NC(=O)OC(C)(C)C)c(C#N)c45)c(F)c2n1)COC3] | 691 |
| 129 | tert-Butyl 8-[4-[2-(tert-butoxycarbonylamino)-3-cyano-7-fluoro-benzothiophen-4-yl]-5-fluoro-1,3-dihydrofuro[3,4-f]cinnolin-9-yl]-3,8-diazabicyclo[3.2.1]octane-3-carboxylate | 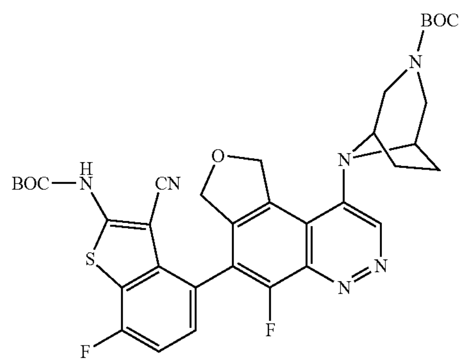 [SMILES: CC(C)(C)OC(=O)Nc1sc2c(F)ccc(-c3c4c(c5c(N6C7CCC6CN(C(=O)OC(C)(C)C)C7)cnnc5c3F)COC4)c2c1C#N] | 691 |
| 130 | Benzyl (1S,4S,7R)-5-[6-[2-(tert-butoxycarbonylamino)-3-cyano-7-fluoro-benzothiophen-4-yl]-5-fluoro-7,9-dihydrofuro[3,4-f]quinazolin-1-yl]-7-fluoro-2,5-diazabicyclo[2.2.1]heptane-2-carboxylate | 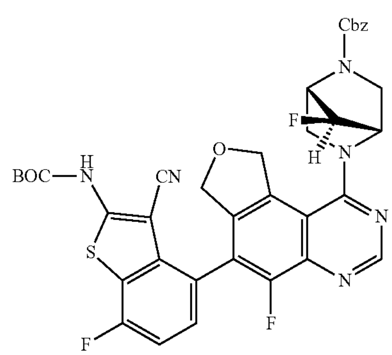 [SMILES: CC(C)(C)OC(=O)Nc1sc2c(F)ccc(-c3c4c(c5c(N6C[C@H]7[C@H](F)[C@@H]6CN7C(=O)OCc6ccccc6)ncnc5c3F)COC4)c2c1C#N] | 729 |

TABLE 8-continued

| Preparation | Chemical Name | Structure | MS (ES) m/z (M + 1) |
|---|---|---|---|
| 131 | tert-Butyl 8-[4-[2-(tert-butoxycarbonylamino)-3-cyano-7-fluoro-benzothiophen-4-yl]-5-chloro-7-methylsulfanyl-1,3-dihydrofuro[3,4-f]quinolin-9-yl]-3,8-diazabicyclo[3.2.1]octane-3-carboxylate | 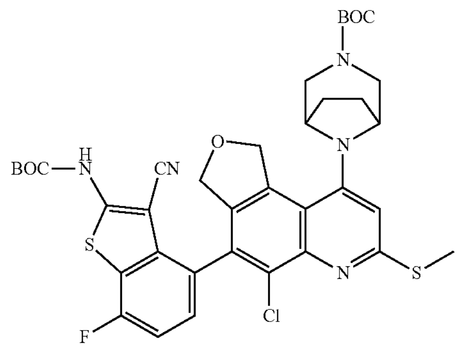 [SMILES: CSc1cc(N2C3CCC2CN(C(=O)OC(C)(C)C)C3)c2c3c(c(-c4ccc(F)c5sc(NC(=O)OC(C)(C)C)c(C#N)c45)c(Cl)c2n1)COC3] | 752 |
| 132 | tert-Butyl N-[4-(5-chloro-9-hydroxy-7-methylsulfanyl-1,3-dihydrofuro[3,4-f]quinolin-4-yl)-3-cyano-7-fluoro-benzothiophen-2-yl]carbamate | 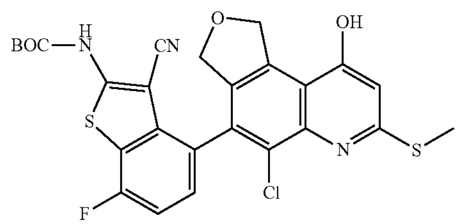 [SMILES: CSc1cc(O)c2c3c(c(-c4ccc(F)c5sc(NC(=O)OC(C)(C)C)c(C#N)c45)c(Cl)c2n1)COC3] | 558 |
| 133 | tert-Butyl 8-[6-[2-(tert-butoxycarbonylamino)-3-cyano-benzothiophen-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate | 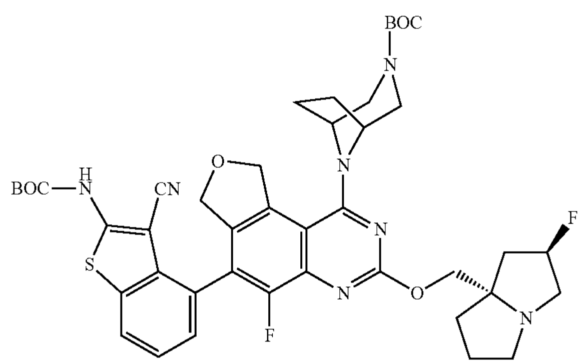 [SMILES: CC(C)(C)OC(=O)Nc1sc2cccc(-c3c4c(c5c(N6C7CCC6CN(C(=O)OC(C)(C)C)C7)nc(OC[C@@]67CCCN6C[C@H](F)C7)nc5c3F)COC4)c2c1C#N] | 830 |
| 134 | tert-Butyl (1R,4R)-5-[6-[2-(tert-butoxycarbonylamino)-3-cyano-7-fluoro-benzothiophen-4-yl]-5-chloro-7,9-dihydrofuro[3,4-f]quinazolin-1-yl]-2,5-diazabicyclo[2.2.1]heptane-2-carboxylate | 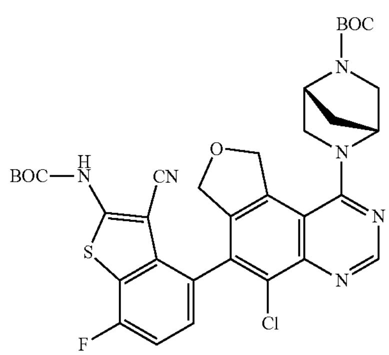 [SMILES: CC(C)(C)OC(=O)Nc1sc2c(F)ccc(-c3c4c(c5c(N6C[C@H]7C[C@@H]6CN7C(=O)OC(C)(C)C)ncnc5c3Cl)COC4)c2c1C#N] | 693 |

TABLE 8-continued

| Preparation | Chemical Name | Structure | MS (ES) m/z (M + 1) |
|---|---|---|---|
| 135 | tert-Butyl N-[3-cyano-4-[5-fluoro-3-[[(2R,8S)-2-fluoro-1,2,3,5,6,7-hexahydropyrrolizin-8-yl]methoxy]-1-(3-methyl-3,8-diazabicyclo[3.2.1]octan-8-yl)-7,9-dihydrofuro[3,4-f]quinazolin-6-yl]benzothiophen-2-yl]carbamate | 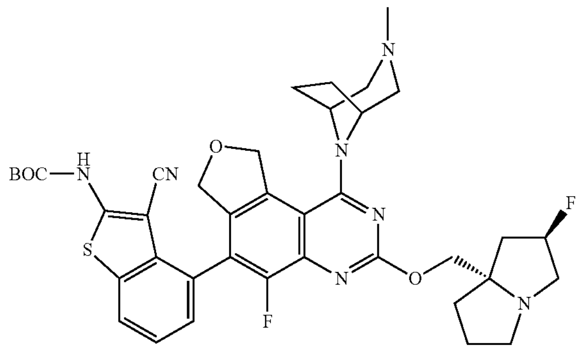 [SMILES: CN1CC2CCC(C1)N2c1nc(OC[C@@]23CCCN2C[C@H](F)C3)nc2c(F)c(-c3cccc4sc(NC(=O)OC(C)(C)C)c(C#N)c34)c3c(c12)COC3] | 744 |
| 136 | tert-Butyl N-[3-cyano-4-[1-(3-ethyl-3,8-diazabicyclo[3.2.1]octan-8-yl)-5-fluoro-3-[(2R,8S)-2-fluoro-1,2,3,5,6,7-hexahydropyrrolizin-8-yl]methoxy]-7,9-dihydrofuro[3,4-f]quinazolin-6-yl]benzothiophen-2-yl]carbamate | 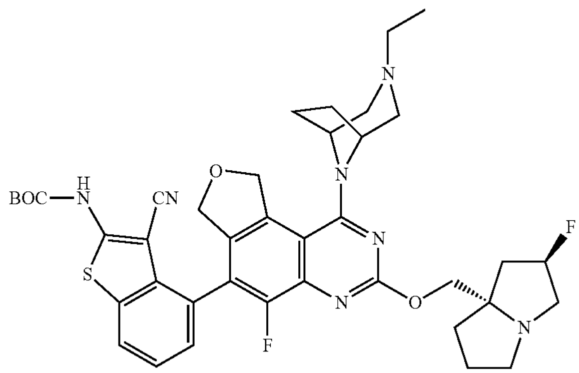 [SMILES: CCN1CC2CCC(C1)N2c1nc(OC[C@@]23CCCN2C[C@H](F)C3)nc2c(F)c(-c3cccc4sc(NC(=O)OC(C)(C)C)c(C#N)c34)c3c(c12)COC3] | 758 |
| 137 | tert-Butyl N-[4-[1-[3-[2-[tert-butyl(dimethyl)silyl]oxy-ethyl]-3,8-diazabicyclo[3.2.1]octan-8-yl]-5-fluoro-3-[(2R,8S)-2-fluoro-1,2,3,5,6,7-hexahydropyrrolizin-8-yl]methoxy]-7,9-dihydrofuro[3,4-f]quinazolin-6-yl]-3-cyano-benzothiophen-2-yl]carbamate | 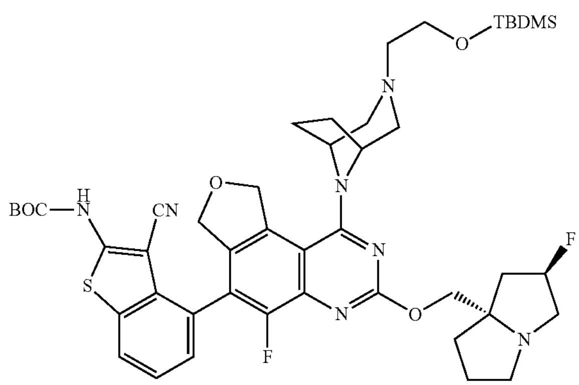 | 888 |
| 138 | tert-Butyl N-[3-cyano-4-(3-ethylsulfanyl-5-methyl-9,10-dihydro-7H-pyrano[4,3-f]quinazolin-6-yl)-7-fluoro-benzothiophen-2-yl]carbamate | 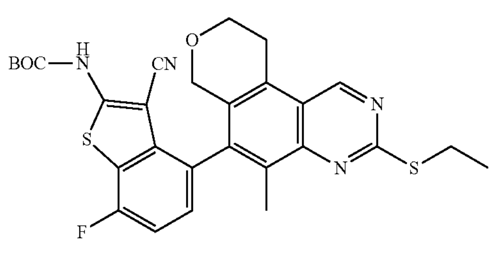 [SMILES: CCSc1ncc2c3c(c(-c4ccc(F)c5sc(NC(=O)OC(C)(C)C)c(C#N)c45)c(C)c2n1)COCC3] | 551 |
| 139 | tert-Butyl N-[4-[5-chloro-7-[[(2R)-tetrahydrofuran-2-yl]methoxy]-1,3-dihydrofuro[3,4-f]quinolin-4-yl]-3-cyano-7-fluoro-benzothiophen-2-yl]carbamate | 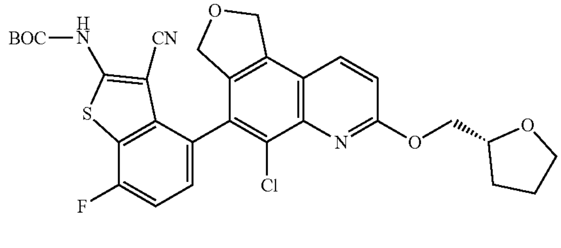 [SMILES: CC(C)(C)OC(=O)Nc1sc2c(F)ccc(-c3c4c(c5ccc(OC[C@H]6CCCO6)nc5c3Cl)COC4)c2c1C#N] | 596 |

TABLE 8-continued

| Preparation | Chemical Name | Structure | MS (ES) m/z (M + 1) |
|---|---|---|---|
| 140 | tert-Butyl N-[4-[5-chloro-7-(2-morpholinoethoxy)-1,3-dihydrofuro[3,4-f]quinolin-4-yl]-3-cyano-7-fluoro-benzothiophen-2-yl]carbamate | 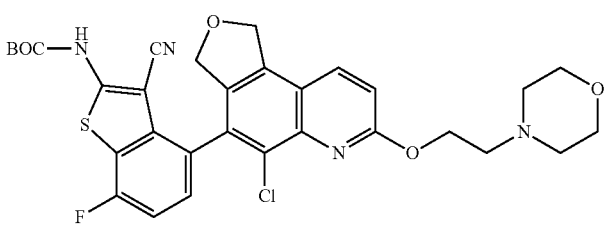 [SMILES: CC(C)(C)OC(=O)Nc1sc2c(F)ccc(-c3c4c(c5ccc(OCCN6CCOCC6)nc5c3Cl)COC4)c2c1C#N] | 625 |
| 141 | tert-Butyl N-[4-[5-chloro-7-[[(2S,4R)-4-hydroxy-1-methyl-pyrrolidin-2-yl]methoxy]-1,3-dihydrofuro[3,4-f]quinolin-4-yl]-3-cyano-7-fluoro-benzothiophen-2-yl]carbamate | 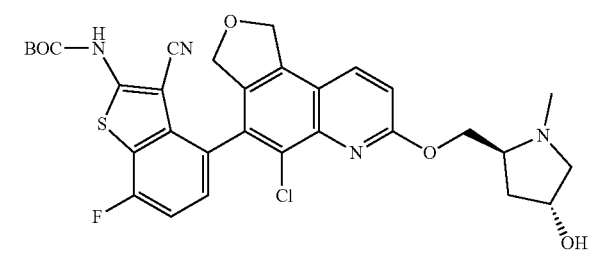 [SMILES: CN1C[C@H](O)C[C@H]1COc1ccc2c3c(c(-c4ccc(F)c5sc(NC(=O)OC(C)(C)C)c(C#N)c45)c(Cl)c2n1)COC3] | 625 |
| 142 | tert-Butyl N-[4-[5-chloro-7-[[(2R)-4-methylmorpholin-2-yl]methoxy]-1,3-dihydrofuro[3,4-f]quinolin-4-yl]-3-cyano-7-fluoro-benzothiophen-2-yl]carbamate | 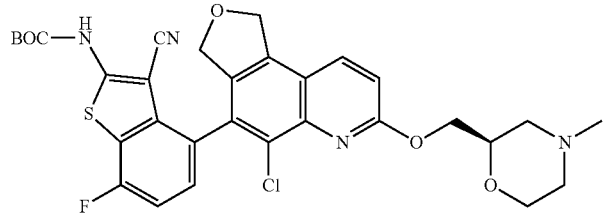 [SMILES: CN1CCO[C@@H](COc2ccc3c4c(c(-c5ccc(F)c6sc(NC(=O)OC(C)(C)C)c(C#N)c56)c(Cl)c3n2)COC4)C1] | 625 |
| 143 | tert-Butyl N-[4-[5-chloro-7-[(3S)-tetrahydrofuran-3-yl]oxy-1,3-dihydrofuro[3,4-f]quinolin-4-yl]-3-cyano-7-fluoro-benzothiophen-2-yl]carbamate | 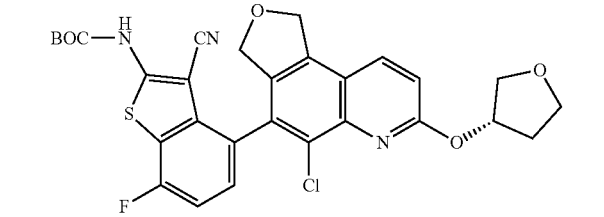 [SMILES: CC(C)(C)OC(=O)Nc1sc2c(F)ccc(-c3c4c(c5ccc(O[C@H]6CCOC6)nc5c3Cl)COC4)c2c1C#N] | 582 |
| 144 | tert-Butyl N-[4-[5-chloro-7-[[(3S)-4-methylmorpholin-3-yl]methoxy]-1,3-dihydrofuro[3,4-f]quinolin-4-yl]-3-cyano-7-fluoro-benzothiophen-2-yl]carbamate | 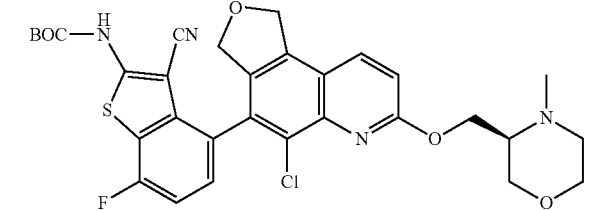 [SMILES: CN1CCOC[C@H]1COc1ccc2c3c(c(-c4ccc(F)c5sc(NC(=O)OC(C)(C)C)c(C#N)c45)c(Cl)c2n1)COC3] | 625 |
| 145 | tert-Butyl N-[4-[7-[3-[tert-butyl(dimethyl)silyl]oxycyclobutyl]methoxy]-5-chloro-1,3-dihydrofuro[3,4-f]quinolin-4-yl]-3-cyano-7-fluoro-benzothiophen-2-yl]carbamate | 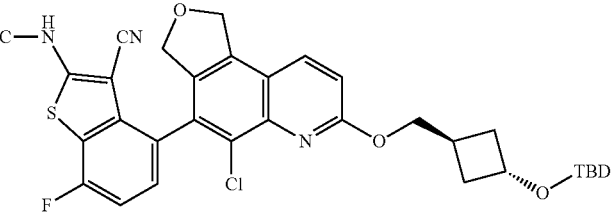 | 710 |

TABLE 8-continued

| Preparation | Chemical Name | Structure | MS (ES) m/z (M + 1) |
|---|---|---|---|
| 146 | tert-Butyl N-[4-[5-chloro-7-(oxetan-3-ylmethoxy)-1,3-dihydrofuro[3,4-f]quinolin-4-yl]-3-cyano-7-fluoro-benzothiophen-2-yl]carbamate | 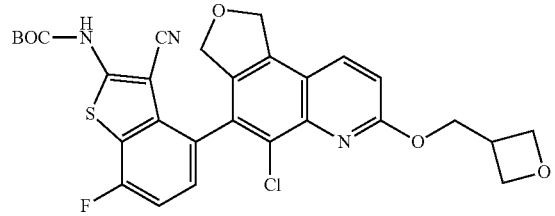 [SMILES: CC(C)(C)OC(=O)Nc1sc2c(F)ccc(-c3c4c(c5ccc(OCC6COC6)nc5c3Cl)COC4)c2c1C#N] | 582 |
| 147 | tert-Butyl N-[4-[5-chloro-7-[(2R)-2-hydroxypropoxy]-1,3-dihydrofuro[3,4-f]quinolin-4-yl]-3-cyano-7-fluoro-benzothiophen-2-yl]carbamate | 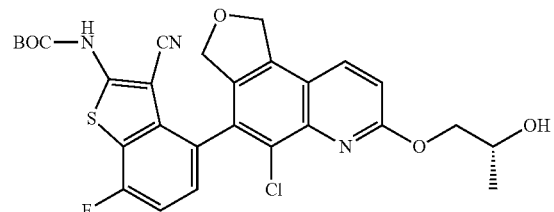 | 570 |
| 148 | tert-Butyl N-[4-[5-chloro-7-[[(2S,4R)-4-fluoro-1-methyl-pyrrolidin-2-yl]methoxy]-1,3-dihydrofuro[3,4-f]quinolin-4-yl]-3-cyano-7-fluoro-benzothiophen-2-yl]carbamate | 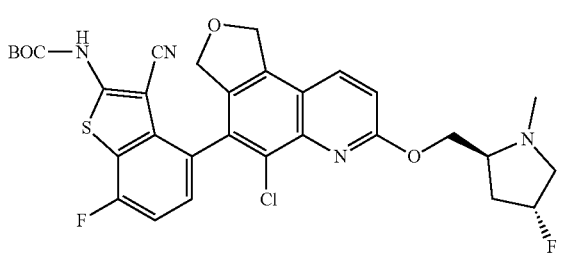 [SMILES: CN1C[C@H](F)C[C@H]1COc1ccc2c3c(c(-c4ccc(F)c5sc(NC(=O)OC(C)(C)C)c(C#N)c45)c(Cl)c2n1)COC3] | 627 |
| 149 | tert-Butyl N-[4-[5-chloro-7-(1,2,3,5,6,7-hexahydropyrrolizin-8-ylmethoxy)-1,3-dihydrofuro[3,4-f]quinolin-4-yl]-3-cyano-7-fluoro-benzothiophen-2-yl]carbamate | 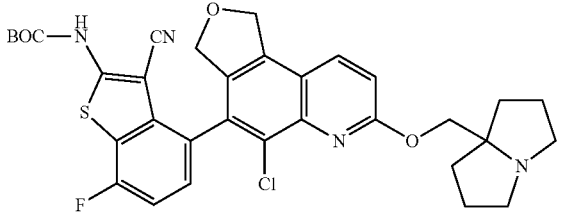 [SMILES: CC(C)(C)OC(=O)Nc1sc2c(F)ccc(-c3c4c(c5ccc(OCC67CCCN6CCC7)nc5c3Cl)COC4)c2c1C#N] | 635 |
| 150 | tert-Butyl N-[4-[5-chloro-7-[2-(hydroxymethyl)-1-methyl-pyrrolidin-2-yl]methoxy]-1,3-dihydrofuro[3,4-f]quinolin-4-yl]-3-cyano-7-fluoro-benzothiophen-2-yl]carbamate | 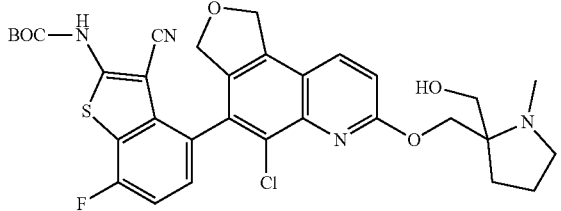 [SMILES: CN1CCCC1(CO)COc1ccc2c3c(c(-c4ccc(F)c5sc(NC(=O)OC(C)(C)C)c(C#N)c45)c(Cl)c2n1)COC3] | 639 |
| 151 | tert-Butyl N-[4-[5-chloro-7-[(3-methoxy-1,2-dimethyl-azetidin-2-yl)methoxy]-1,3-dihydrofuro[3,4-f]quinolin-4-yl]-3-cyano-7-fluoro-benzothiophen-2-yl]carbamate | 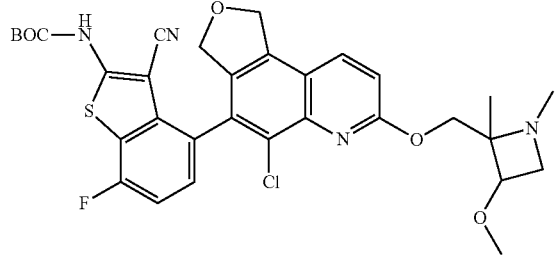 [SMILES: COC1CN(C)C1(C)COc1ccc2c3c(c(-c4ccc(F)c5sc(NC(=O)OC(C)(C)C)c(C#N)c45)c(Cl)c2n1)COC3] | 639 |

TABLE 8-continued

| Preparation | Chemical Name | Structure | MS (ES) m/z (M + 1) |
|---|---|---|---|
| 152 | tert-Butyl N-[4-[5-chloro-7-(2-hydroxyethoxy)-1,3-dihydrofuro[3,4-f]quinolin-4-yl]-3-cyano-7-fluoro-benzothiophen-2-yl]carbamate | 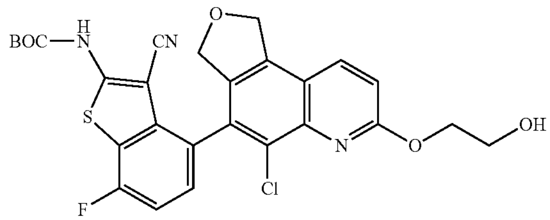 [SMILES: CC(C)(C)OC(=O)Nc1sc2c(F)ccc(-c3c4c(c5ccc(OCCO)nc5c3Cl)COC4)c2c1C#N] | 556 |
| 153 | tert-Butyl (2S)-2-[[4-[2-(tert-butoxycarbonylamino)-3-cyano-7-fluoro-benzothiophen-4-yl]-5-chloro-1,3-dihydrofuro[3,4-f]quinolin-7-yl]oxymethyl]pyrrolidine-1-carboxylate | 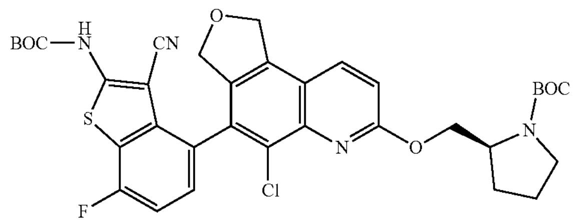 [SMILES: CC(C)(C)OC(=O)Nc1sc2c(F)ccc(-c3c4c(c5ccc(OC[C@@H]6CCCN6C(=O)OC(C)(C)C)nc5c3Cl)COC4)c2c1C#N] | 695 |
| 154 | tert-Butyl N-[4-[5-chloro-7-[(2S)-1-methylpyrrolidin-2-yl]methoxy]-1,3-dihydrofuro[3,4-f]quinolin-4-yl]-3-cyano-7-fluoro-benzothiophen-2-yl]carbamate | 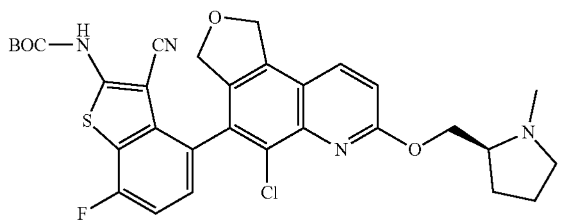 [SMILES: CN1CCC[C@H]1COc1ccc2c3c(c(-c4ccc(F)c5sc(NC(=O)OC(C)(C)C)c(C#N)c45)c(Cl)c2n1)COC3] | 609 |
| 155 | tert-Butyl N-[3-cyano-7-fluoro-4-[5-fluoro-7-[[(2S)-1-methylpyrrolidin-2-yl]methoxy]-1,3-dihydrofuro[3,4-f]quinolin-4-yl]benzothiophen-2-yl]carbamate, Isomer 1 | 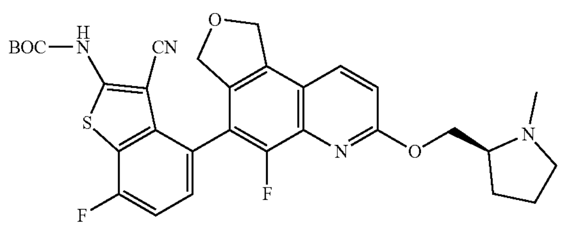 [SMILES: CN1CCC[C@H]1COc1ccc2c3c(c(-c4ccc(F)c5sc(NC(=O)OC(C)(C)C)c(C#N)c45)c(F)c2n1)COC3] | 593 |

Preparation 156 tert-Butyl N-[4-[1-[3-[3-[tert-butyl(dimethyl)silyl]oxypropyl]-3,8-diazabicyclo[3.2.1]octan-8-yl]-5-fluoro-3-[[(2R,8S)-2-fluoro-1,2,3,5,6,7-hexahydro-pyrrolizin-8-yl]methoxy]-7,9-dihydrofuro[3,4-f]quinazolin-6-yl]-1,3-benzothiazol-2-yl]carbamate

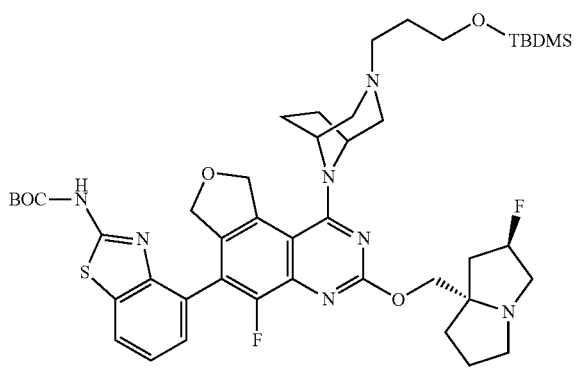

A mixture of 3-[8-[6-bromo-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]propoxy-tert-butyl-dimethyl-silane (0.110 g, 0.155 mmol), [2-(tert-butoxycarbonylamino)-1,3-benzothiazol-4-yl]boronic acid (U.S. Pat. No. 10,968,214 B2; Preparation 17) (0.064 g, 0.217 mmol) and $K_2CO_3$ (0.064 g, 0.466 mmol) in 1,4-dioxane (1.5 mL) and $H_2O$ (0.5 mL) was sparged with $N_2$ for 5 min before Pd(PPh$_3$)$_4$ (0.036 g, 0.310 mmol) was added. The resulting mixture was heated at 100° C. for 1.5 h, then cooled to RT and was partitioned between DCM and $H_2O$. The layers were separated, and the aqueous layer was extracted 2× with DCM. The organic layers were combined, passed through a hydrophobic frit (ISOLUTE® phase separator cartridge), and concentrated in vacuo. The residue was purified on silica (gradient 0 to 4% 7N $NH_3$/MeOH in DCM) to obtain the title compound (0.098 g, 55%) as a pale-yellow solid. MS (ES) m/z=878 (M+1).

Preparation 157 tert-Butyl 8-[6-[2-(tert-butoxycarbonylamino)-3-cyano-7-fluoro-benzothiophen-4-yl]-5-chloro-3-ethylsulfanyl-7,9-dihydrofuro[3,4-f]quinazolin-1-yl]-3,8-diazabicyclo[3.2.1]octane-3-carboxylate, Isomer 2

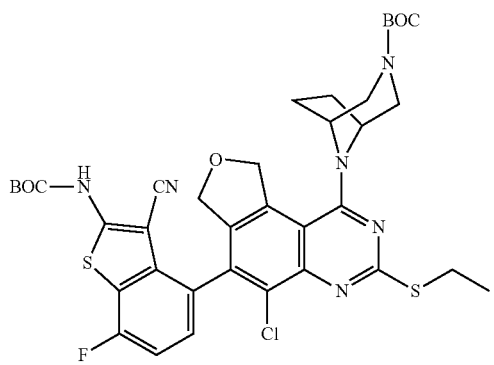 [SMILES: CCSc1nc(N2C3CCC2CN(C(=O)OC(C)(C)C)C3)c2c3c(c(-c4ccc(F)c5sc(NC(=O)OC(C)(C)C)c(C#N)c45)c(Cl)c2n1)COC3]

tert-Butyl 8-[6-[2-(tert-butoxycarbonylamino)-3-cyano-7-fluoro-benzothiophen-4-yl]-5-chloro-3-ethylsulfanyl-7,9-dihydrofuro[3,4-f]quinazolin-1-yl]-3,8-diazabicyclo[3.2.1]octane-3-carboxylate (5.30 g, 6.94 mmol) was purified by SFC (Chiralpak® IC, 21×250 mm, 35% MeOH (with 0.5% DMEA), 65% CO$_2$, 80 mL/min). The second eluting isomer ($t_{R2}$=10.77 min) was collected, concentrated and lyophilized to afford the title compound (1.37 g, 42%) as a white solid with 96% ee. MS (ES) m/z=767 (M+1).

Preparation 323

O3-tert-Butyl 08-methyl 8-(6-bromo-3-ethylsulfanyl-5-fluoro-7,9-dihydrofuro[3,4-f]quinazolin-1-yl)-3-azabicyclo[3.2.1]octane-3,8-dicarboxylate

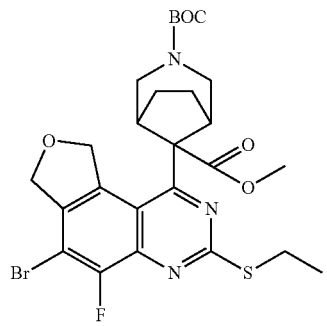 [SMILES: CCSc1nc(C2(C(=O)OC)C3CCC2CN(C(=O)OC(C)(C)C)C3)c2c3c(c(Br)c(F)c2n1)COC3]

6-Bromo-1-chloro-3-ethylsulfanyl-5-fluoro-7,9-dihydrofuro[3,4-f]quinazoline (0.10 g, 0.28 mmol), O3-tert-butyl O8-methyl 3-azabicyclo[3.2.1]octane-3,8-dicarboxylate (0.22 g, 0.82 mmol), and bis(tri-tert-butylphosphine)palladium(0) (0.022 g, 0.042 mmol) were combined under nitrogen. Toluene (4 mL) was added and the mixture was sparged with nitrogen for 3 min and cooled to 0° C. LiHMDS (0.8 mL, 0.8 mmol, 1M in THF) was added dropwise over 1.5 min and the reaction mixture was allowed to warm to room temperature. After 3 h, the reaction was poured into brine and extracted with ethyl acetate (2×). The combined organics were dried over MgSO$_4$, filtered and concentrated.

6-Bromo-1-chloro-3-ethylsulfanyl-5-fluoro-7,9-dihydrofuro[3,4-f]quinazoline (0.30 g, 0.83 mmol), O3-tert-butyl O8-methyl 3-azabicyclo[3.2.1]octane-3,8-dicarboxylate (0.67 g, 2.5 mmol), and bis(tri-tert-butylphosphine)palladium(0) (0.065 g, 0.12 mmol) were combined under nitrogen. Toluene (11 mL) was added and the mixture was sparged with nitrogen for 3 min and cooled to 0° C. LiHMDS (2.4 mL, 2.4 mmol, 1M in THF) was added dropwise over 3 min and the reaction mixture was allowed to warm to room temperature. After 3 h, the reaction was poured into brine and extracted with ethyl acetate (2×). The combined organics were dried over MgSO$_4$, filtered and concentrated.

The two residues were combined and purified by silica gel column chromatography, eluting with 0 to 30% ethyl acetate in hexanes to afford the product (0.55 g, 83%). MS (ES) m/z=596,598 (M+1,Br).

Preparation 324 tert-Butyl 8-(6-bromo-3-ethylsulfanyl-5-fluoro-7,9-dihydrofuro[3,4-f]quinazolin-1-yl)-3-azabicyclo[3.2.1]octane-3-carboxylate

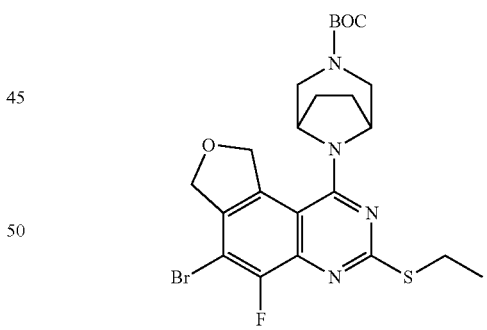

A mixture of O3-tert-butyl O8-methyl 8-(6-bromo-3-ethylsulfanyl-5-fluoro-7,9-dihydrofuro[3,4-f]quinazolin-1-yl)-3-azabicyclo[3.2.1]octane-3,8-dicarboxylate (0.99 g, 1.7 mmol) and LiCl (1.1 g, 25 mmol) in DMSO (9 mL) was stirred under microwave irradiation at 150° C. for 10 min. The reaction was diluted with water and extracted with ethyl acetate (2×). The combined organics were washed with brine, dried over MgSO$_4$, filtered and concentrated. The residue was purified by silica gel column chromatography, eluting with 0 to 30% ethyl acetate in hexanes to afford the product (0.11 g, 12%) as the faster eluting isomer. MS (ES) m/z=538,540 (M+1,Br).

Preparation 158 tert-Butyl 8-[6-[2-(tert-butoxycarbonylamino)-3-cyano-thieno[3,2-c]pyridin-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate

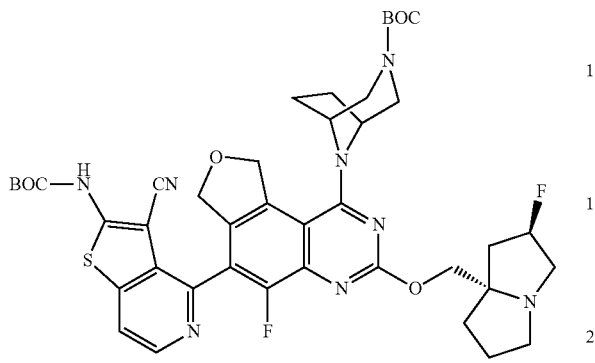

A mixture of tert-butyl 8-[6-bromo-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate (0.500 g, 0.786 mmol), KOAc (0.231 g, 2.35 mmol) and bis(neopentyl glycolato)diboron (0.266 g, 1.18 mmol) in 1,4-dioxane (8 mL) was sparged with $N_2$ for 10 min. Pd-117 (0.057 g, 0.078 mmol) was added, and the resulting mixture was heated at 95° C. for 2 h. The reaction mixture was cooled to RT. $H_2O$ (2.6 mL) was added, and the mixture was sparged with $N_2$ for 10 min. tert-Butyl N-(4-chloro-3-cyano-thieno[3,2-c]pyridin-2-yl)carbamate (0.245 g, 0.791 mmol), XPhos Pd G4 (0.071 g, 0.078 mmol) and $K_3PO_4$ (0.250 g, 1.18 mmol) were added, and the resulting mixture was heated at 85° C. for 1 h. The reaction mixture was cooled to RT and was partitioned between DCM and $H_2O$. The layers were separated, and the aqueous layer was extracted 2× with DCM. The organic layers were combined, dried over $Na_2SO_4$ and concentrated in vacuo. The residue was purified on silica (gradient 0 to 6% 7N $NH_3$/MeOH in DCM) to obtain the title compound (0.404 g, 62%) as a yellowish-tan solid. MS (ES) m/z=831 (M+1).

Preparation 244 tert-Butyl 8-[6-[2-(tert-butoxycarbonylamino)-3-cyano-7-fluoro-thieno[3,2-c]pyridin-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate

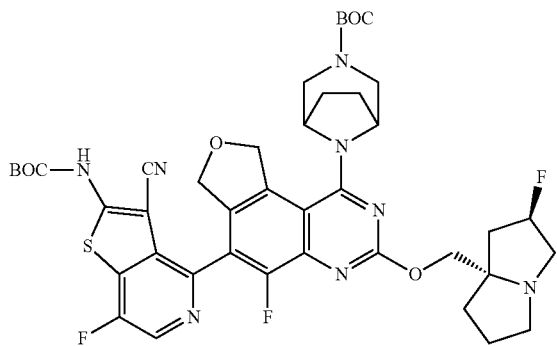 [SMILES: CC(C)(C)OC(=O)Nc1sc2c(F)cnc(-c3c4c(c5c(N6C7CCC6CN(C(=O)OC(C)(C)C)C7)nc(OC[C@@]67CCCN6C[C@H](F)C7)nc5c3F)COC4)c2c1C#N]

tert-Butyl N-(4-chloro-3-cyano-7-fluoro-thieno[3,2-c]pyridin-2-yl)carbamate was used in an analogous manner to the method of Preparation 158 to obtain the title compound (0.667 g, 46%). MS (ES) m/z=849 (M+1).

Preparation 245 tert-Butyl 8-[6-[2-(tert-butoxycarbonylamino)-3-cyano-7-fluoro-thieno[3,2-c]pyridin-4-yl]-5-fluoro-3-[(2-methoxy-1,2,3,5,6,7-hexahydropyrrolizin-8-yl)methoxy]-7,9-dihydrofuro[3,4-f]quinazolin-1-yl]-3,8-diazabicyclo[3.2.1]octane-3-carboxylate

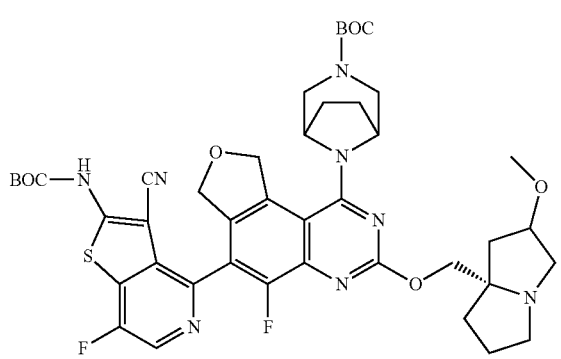 [SMILES: COC1CN2CCC[C@@]2(COc2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)C1]

tert-Butyl 8-[6-bromo-5-fluoro-3-[(2-methoxy-1,2,3,5,6,7-hexahydropyrrolizin-8-yl)methoxy]-7,9-dihydrofuro[3,4-f]quinazolin-1-yl]-3,8-diazabicyclo[3.2.1]octane-3-carboxylate and tert-butyl N-(4-chloro-3-cyano-7-fluoro-thieno[3,2-c]pyridin-2-yl)carbamate were used in an analogous manner to the method of Preparation 158 to obtain the title compound (0.43 g, 42%). MS (ES) m/z=861 (M+1).

Preparation 246 tert-Butyl 8-[6-[2-(tert-butoxycarbonylamino)-3-cyano-7-methyl-thieno[3,2-c]pyridin-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate

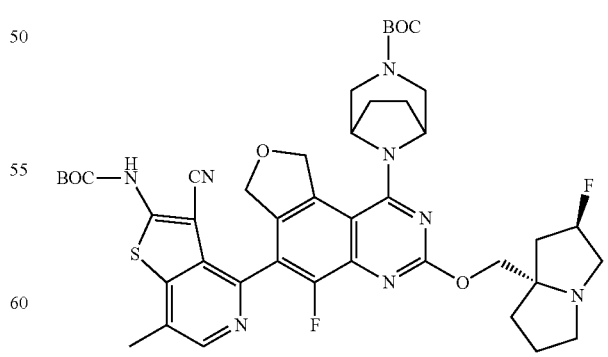

tert-Butyl N-(4-chloro-3-cyano-7-methyl-thieno[3,2-c]pyridin-2-yl)carbamate was used in an analogous manner to the method of Preparation 158 to obtain the title compound (0.10 g, 24%). MS (ES) m/z=845 (M+1).

Preparation 159 tert-Butyl 6-[6-[2-(tert-butoxycarbonylamino)-3-cyano-thieno[3,2-c]pyridin-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,6-diazabicyclo[3.1.1]heptane-3-carboxylate

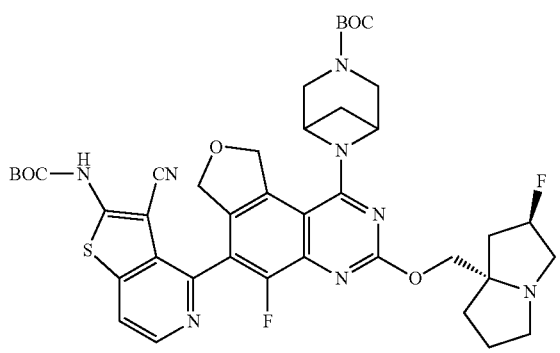 [SMILES: CC(C)(C)OC(=O)Nc1sc2ccnc(-c3c4c(c5c(N6C7CC6CN(C(=O)OC(C)(C)C)C7)nc(OC[C@@]67CCCN6C[C@H](F)C7)nc5c3F)COC4)c2c1C#N]

tert-Butyl 6-[6-bromo-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,6-diazabicyclo[3.1.1]heptane-3-carboxylate was used in an analogous manner to the method of Preparation 158 to obtain the title compound (0.101 g, 42.5%) as light-yellow solid. MS (ES) m/z=617 (M+1).

Preparation 307 tert-Butyl 8-[6-[2-(tert-butoxycarbonylamino)-3-cyano-7-fluoro-thieno[3,2-c]pyridin-4-yl]-3-ethylsulfanyl-5-fluoro-7,9-dihydrofuro[3,4-f]quinazolin-1-yl]-3,8-diazabicyclo[3.2.1]octane-3-carboxylate

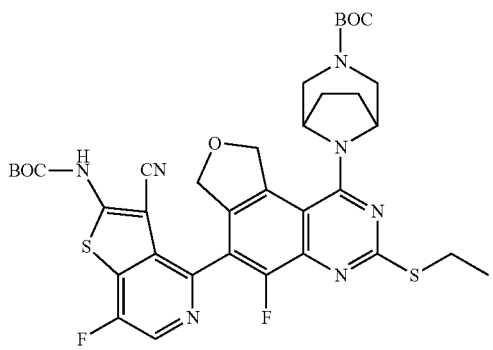 [SMILES: CCSc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3]

tert-Butyl 8-(6-bromo-3-ethylsulfanyl-5-fluoro-7,9-dihydrofuro[3,4-f]quinazolin-1-yl)-3,8-diazabicyclo[3.2.1]octane-3-carboxylate and tert-butyl N-(4-chloro-3-cyano-7-fluoro-thieno[3,2-c]pyridin-2-yl)carbamate were used in an analogous manner to the method of Preparation 158 to obtain the title compound (2.15 g, 61%) as white solid. MS (ES) m/z=752 (M+1).

Preparation 308 tert-Butyl N-[3-cyano-7-fluoro-4-[5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]thieno[3,2-c]pyridin-2-yl]carbamate

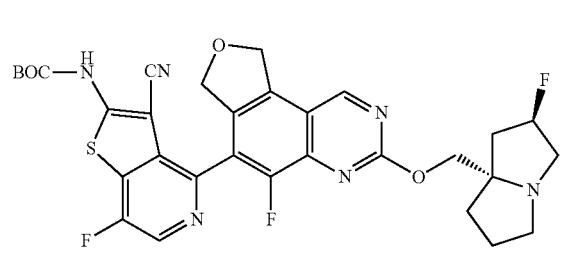 [SMILES: CC(C)(C)OC(=O)Nc1sc2c(F)cnc(-c3c4c(c5cnc(OC[C@@]67CCCN6C[C@H](F)C7)nc5c3F)COC4)c2c1C#N]

6-bromo-5-fluoro-3-[[(2R,8S)-2-fluoro-1,2,3,5,6,7-hexahydropyrrolizin-8-yl]methoxy]-7,9-dihydrofuro[3,4-f]quinazoline and tert-butyl N-(4-chloro-3-cyano-7-fluoro-thieno[3,2-c]pyridin-2-yl)carbamate were used in an analogous manner to the method of Preparation 158 to obtain the title compound (0.080 g, 35%). MS (ES) m/z=639 (M+1).

Preparation 325 tert-Butyl 6-[6-[2-(tert-butoxycarbonylamino)-3-cyano-7-fluoro-thieno[3,2-c]pyridin-4-yl]-3-ethylsulfanyl-5-fluoro-7,9-dihydrofuro[3,4-f]quinazolin-1-yl]-3,6-diazabicyclo[3.1.1]heptane-3-carboxylate

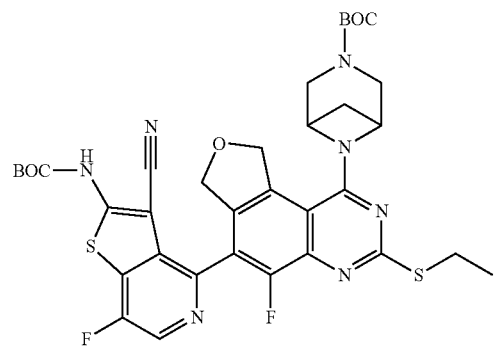 [SMILES: CCSc1nc(N2C3CC2CN(C(=O)OC(C)(C)C)C3)c2c3c(c(-c4ncc(F)c5sc(NC(=O)OC(C)(C)C)c(C#N)c45)c(F)c2n1)COC3]

tert-Butyl 6-(6-bromo-3-ethylsulfanyl-5-fluoro-7,9-dihydrofuro[3,4-f]quinazolin-1-yl)-3,6-diazabicyclo[3.1.1]heptane-3-carboxylate and tert-butyl N-(4-chloro-3-cyano-7-fluoro-thieno[3,2-c]pyridin-2-yl)carbamate were used in an analogous manner to the method of Preparation 158 to obtain the title compound. MS (ES) m/z=738 (M+1).

Preparation 326 tert-Butyl N-[3-cyano-4-(3-ethylsulfanyl-5-fluoro-7,9-dihydrofuro[3,4-f]quinazolin-6-yl)-7-fluoro-thieno[3,2-c]pyridin-2-yl]carbamate

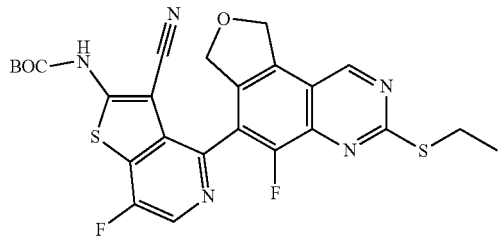 [SMILES: CCSc1ncc2c3c(c(-c4ncc(F)c5sc(NC(=O)OC(C)(C)C)c(C#N)c45)c(F)c2n1)COC3]

6-Bromo-3-ethylsulfanyl-5-fluoro-7,9-dihydrofuro[3,4-f]quinazoline and tert-butyl N-(4-chloro-3-cyano-7-fluoro-thieno[3,2-c]pyridin-2-yl)carbamate were used in an analogous manner to the method of Preparation 158 to obtain the title compound (43.0 g, 72%) as brown solid. MS (ES) m/z=542 (M+1).

Preparation 327 tert-Butyl 8-[6-[2-(tert-butoxycarbonylamino)-3-cyano-7-fluoro-thieno[3,2-c]pyridin-4-yl]-3-ethylsulfanyl-5-fluoro-7,9-dihydrofuro[3,4-f]quinazolin-1-yl]-3-azabicyclo[3.2.1]octane-3-carboxylate

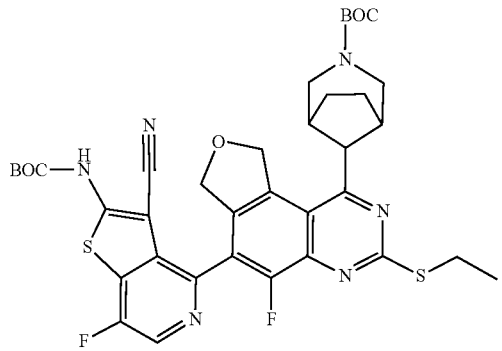 [SMILES: CCSc1nc(C2C3CCC2CN(C(=O)OC(C)(C)C)C3)c2c3c(c(-c4ncc(F)c5sc(NC(=O)OC(C)(C)C)c(C#N)c45)c(F)c2n1)COC3]

tert-Butyl 8-(6-bromo-3-ethylsulfanyl-5-fluoro-7,9-dihydrofuro[3,4-f]quinazolin-1-yl)-3-azabicyclo[3.2.1]octane-3-carboxylate and tert-butyl N-(4-chloro-3-cyano-7-fluoro-thieno[3,2-c]pyridin-2-yl)carbamate were used in an analogous manner to the method of Preparation 158 to obtain the title compound (0.050 g, 9%). MS (ES) m/z=751 (M+1).

Preparation 160 tert-Butyl 8-[6-[3-cyano-2-[dimethylaminomethyleneamino]benzofuran-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate

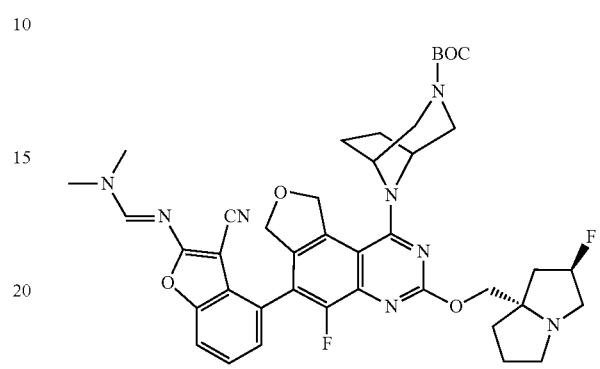

To a RBF was added tert-butyl 8-[6-bromo-5-fluoro-3-[[(2R,8S)-2-fluoro-1,2,3,5,6,7-tert-butyl 8-[6-bromo-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate (1.10 g, 1.73 mmol), N'-[3-cyano-4-(5,5-dimethyl-1,3,2-dioxaborinan-2-yl)benzofuran-2-yl]-N,N-dimethyl-formamidine (0.67 g, 2.07 mmol, 1.2 eq.), K₃PO₄ (0.550 g, 2.59 mmol, 1.5 eq.), Pd-118 (0.11 g, 0.173 mmol, 0.10 eq.), 1,4-dioxane (8.6 mL), and H₂O (1.7 mL). The mixture sparged with N₂, then heated at 90° C. for 3 h. The reaction was cooled, diluted with EtOAc and was washed with sat. aq. NaHCO₃, and brine, then dried over MgSO₄, filtered, and concentrated. The residue was purified on silica (0-10% MeOH/DCM) to obtain the title compound (0.78 g, 58.7%). MS (ES) m/z=769 (M+1).

Preparation 161 tert-Butyl 8-[6-[2-(tert-butoxycarbonylamino)-5-fluoro-benzofuran-4-yl]-3-ethylsulfanyl-5-fluoro-7,9-dihydrofuro[3,4-f]quinazolin-1-yl]-3,8-diazabicyclo[3.2.1]octane-3-carboxylate

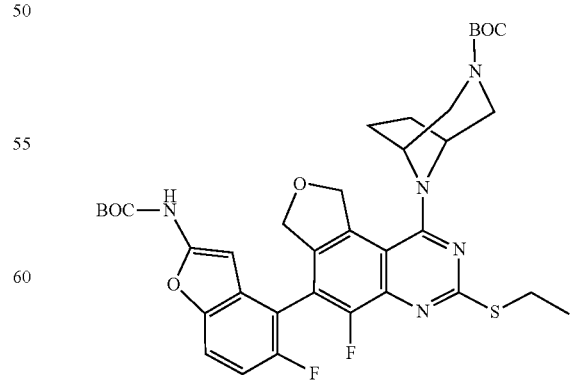

tert-Butyl 8-(6-bromo-3-ethylsulfanyl-5-fluoro-7,9-dihydrofuro[3,4-f]quinazolin-1-yl)-3,8-diazabicyclo[3.2.1]octane-3-carboxylate and tert-butyl N-[4-(5,5-dimethyl-1,3,2-dioxaborinan-2-yl)-5-fluoro-benzofuran-2-yl]carbamate were used in an analogous manner to the method of Preparation 160 to obtain the title compound (0.375 g, 95.0%). MS (ES) m/z=710 (M+1).

Preparation 162

[4-[2-(tert-Butoxycarbonylamino)-3-cyano-7-fluoro-benzothiophen-4-yl]-5-chloro-7-methylsulfanyl-1,3-dihydrofuro[3,4-f]quinolin-9-yl]trifluoromethanesulfonate

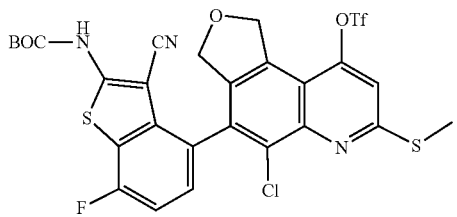 [SMILES: CSc1cc(OS(=O)(=O)C(F)(F)F)c2c3c(c(-c4ccc(F)c5sc(NC(=O)OC(C)(C)C)c(C#N)c45)c(Cl)c2n1)COC3]

To a stirred mixture of tert-butyl N-[4-(5-chloro-9-hydroxy-7-methylsulfanyl-1,3-dihydrofuro[3,4-f]quinolin-4-yl)-3-cyano-7-fluoro-benzothiophen-2-yl]carbamate (7.5 g, 13.44 mmol, 1 eq.) and 2,6-lutidine (3.31 g, 30.91 mmol, 2.3 eq.) in DCM (100 mL) were added DMAP (0.25 g, 2.01 mmol, 0.15 eq.) and Tf$_2$O (7.58 g, 26.88 mmol, 2 eq.) dropwise at 0° C. under N$_2$. The resulting mixture was stirred for 2 h at 0° C. The mixture was concentrated under reduced pressure and the residue was purified on silica, eluting with PE:EtOAc (3:1 to 1:1) to afford the title compound (8.0 g, 86%) as a light-yellow solid. MS (ES) m/z=690 (M+1).

Preparation 163 tert-Butyl N-[4-(9-bromo-5-chloro-7-methylsulfanyl-1,3-dihydrofuro[3,4-f]quinolin-4-yl)-3-cyano-7-fluoro-benzothiophen-2-yl]carbamate

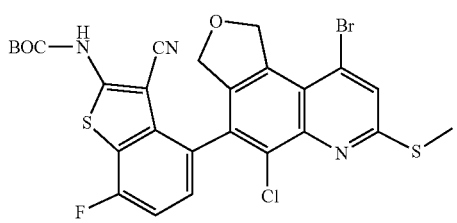 [SMILES: CSc1cc(Br)c2c3c(c(-c4ccc(F)c5sc(NC(=O)OC(C)(C)C)c(C#N)c45)c(Cl)c2n1)COC3]

To a stirred solution of [4-[2-(tert-butoxycarbonylamino)-3-cyano-7-fluoro-benzothiophen-4-yl]-5-chloro-7-methylsulfanyl-1,3-dihydrofuro[3,4-f]quinolin-9-yl]trifluoromethanesulfonate (8.0 g, 11.5 mmol, 1 eq.) in ACN (100 mL) was added LiBr (20.13 g, 231.8 mmol, 20 eq.). The resulting mixture was stirred for 18 h at 85° C. The mixture was concentrated under reduced pressure, then poured into H$_2$O (200 mL). After filtration, the filtrate cake was dried under vacuum at 40° C. to afford the crude, which was then suspended in 1,4-dioxane (70 mL) and charged with di-tert-butyl dicarbonate (3.77 g, 17.28 mmol, 1.5 eq.) and DMAP (0.31 g, 2.53 mmol, 0.22 eq.). The resulting mixture was stirred for 2 h at RT, then concentrated under reduced pressure. The residue was purified on silica, eluting with DCM/EtOAc (15:1 to 10:1) to obtain the title compound (6.0 g, 84%) as a yellow solid. MS (ES) m/z=620 (M−1).

Preparation 164 tert-Butyl 8-[6-(2-amino-3-cyano-benzofuran-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate

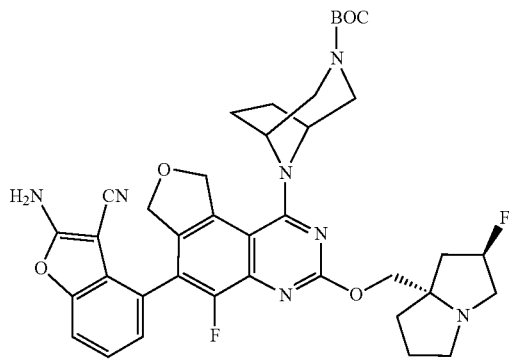 [SMILES: CC(C)(C)OC(=O)N1CC2CCC(C1)N2c1nc(OC[C@@]23CCCN2C[C@H](F)C3)nc2c(F)c(-c3cccc4oc(N)c(C#N)c34)c3c(c12)COC3]

To a RBF was added tert-butyl 8-[6-[3-cyano-2-[dimethylaminomethyleneamino]benzofuran-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate (780 mg, 1.02 mmol), MeOH (20 mL), and 1M NaOH (2.5 mL, 2.5 mmol, 2.5 eq.). The mixture was heated to 60° C. and stirred for 5 h. The reaction was cooled to 0° C. and 5N HCl was added to adjust to pH 4. The reaction mixture was placed over a 20 g SCX column, washed with 3 column volumes of MeOH then eluting with 3 column volumes of 2N NH$_3$ in MeOH. The basic fractions were concentrated to give the title compound (588 mg, 81.2%) as an oil. MS (ES) m/z=715 (M+1).

Preparation 165 tert-Butyl N-[2-[4-[2-(tert-butoxycarbonylamino)-3-cyano-7-fluoro-benzothiophen-4-yl]-5-chloro-7-methylsulfanyl-1,3-dihydrofuro[3,4-f]quinolin-9-yl]ethyl]carbamate

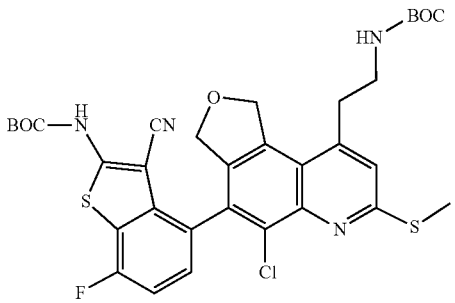 [SMILES: CSc1cc(CCNC(=O)OC(C)(C)C)c2c3c(c(-c4ccc(F)c5sc(NC(=O)OC(C)(C)C)c(C#N)c45)c(Cl)c2n1)COC3]

A mixture of tert-butyl N-[4-(9-bromo-5-chloro-7-methylsulfanyl-1,3-dihydrofuro[3,4-f]quinolin-4-yl)-3-cyano-7-fluoro-benzothiophen-2-yl]carbamate (0.500 g, 0.805 mmol), tert-butyl N-[2-(4,4,5,5-tetramethyl-1,3,2-dioxaborolan-2-yl)ethyl]carbamate (0.466 g, 1.65 mmol) and Cs$_2$CO$_3$ (0.787 g, 2.42 mmol) in 1,4-dioxane (8 mL) and water (0.8 mL) was sparged with N$_2$ for 15 min. Pd(ddpf)Cl$_2$ (0.059 g, 0.081 mmol) was added, and the resulting mixture was heated at 70° C. for ~18 h. The reaction mixture was cooled to RT and partitioned between DCM and H$_2$O. The layers were separated, and the aqueous layer was extracted 2× with DCM and 2× with CHCl$_3$:IPA (4:1). The organic layers were combined, dried over Na$_2$SO$_4$ and concentrated in vacuo. The residue was purified on silica, eluting with EtOAc/Hex (10-70%) to obtain the title compound (0.367 g, 67%) as a white solid. MS (ES) m/z=685 (M+1).

Preparation 166 tert-Butyl N-[4-[2-(tert-butoxycarbonylamino)-3-cyano-7-fluoro-benzothiophen-4-yl]-5-fluoro-7-methylsulfanyl-1,3-dihydrofuro[3,4-f]quinolin-9-yl]-3,8-diazabicyclo[3.2.1]octane-3-carboxylate

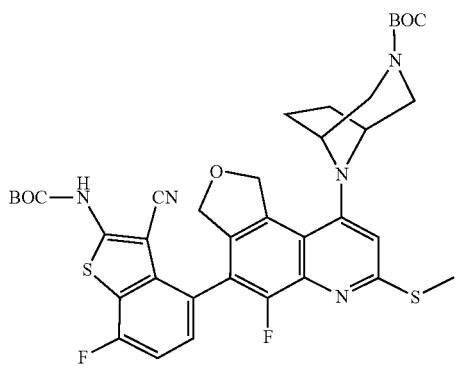 [SMILES: CSc1cc(N2C3CCC2CN(C(=O)OC(C)(C)C)C3)c2c3c(c(-c4ccc(F)c5sc(NC(=O)OC(C)(C)C)c(C#N)c45)c(F)c2n1)COC3]

A suspension of tert-butyl 3,8-diazabicyclo[3.2.1]octane-3-carboxylate (0.416 g, 1.90 mmol, 2.5 eq.), tert-butyl N-[4-(9-bromo-5-fluoro-7-methylsulfanyl-1,3-dihydrofuro[3,4-f]quinolin-4-yl)-3-cyano-7-fluoro-benzothiophen-2-yl]carbamate (0.446 g, 0.70 mmol) and Cs$_2$CO$_3$ (0.481 g, 1.47 mmol, 2 eq.) in DMF (25 mL) was purged with N$_2$ for ~5 min. Pd$_2$(dba)$_3$ (0.085 g, 0.15 mmol, 0.2 eq.) and BrettPhos (0.165 g, 0.292 mmol, 0.4 eq.) were added and the flask was sealed and heated to 100° C. for 6 h. The reaction mixture was cooled to RT, diluted with EtOAc and washed with brine. The aqueous layer was extracted with EtOAc and the combined organics were dried over Na$_2$SO$_4$ and concentrated. The residue was purified on silica, eluting with EtOAc/Hex (0% to 60%) to obtain the title compound (0.221 g, 39%) as a yellow solid. MS (ES) m/z=737 (M+1).

Preparation 167 tert-Butyl (1R,4R)-5-[6-[2-(tert-butoxycarbonylamino)-3-cyano-7-fluoro-benzothiophen-4-yl]-5-methyl-7,9-dihydrofuro[3,4-f]quinazolin-1-yl]-2,5-diazabicyclo[2.2.1]heptane-2-carboxylate

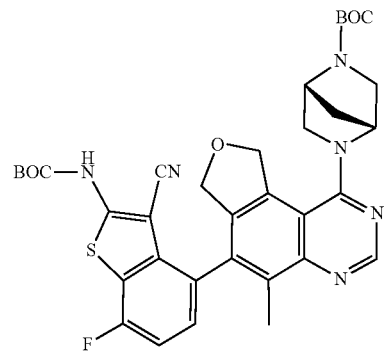 [SMILES: Cc1c(-c2ccc(F)c3sc(NC(=O)OC(C)(C)C)c(C#N)c23)c2c(c3c(N4C[C@H]5C[C@@H]4CN5C(=O)OC(C)(C)C)ncnc13)COC2]

To a stirred mixture of tert-butyl (1R,4R)-5-[6-[2-(tert-butoxycarbonylamino)-3-cyano-7-fluoro-benzothiophen-4-yl]-5-chloro-7,9-dihydrofuro[3,4-f]quinazolin-1-yl]-2,5-diazabicyclo[2.2.1]heptane-2-carboxylate (470 mg, 0.68 mmol), K$_2$CO$_3$ (281 mg, 2.03 mmol) and methylboronic acid (406 mg, 6.78 mmol) in 1,4-dioxane (20 mL) was added RuPhos (94.9 mg, 0.20 mmol) and XPhos Palladacycle Gen.4 (117 mg, 0.14 mmol) in portions at RT. The resulting mixture was stirred for 2 h at 100° C. under N$_2$. The mixture was allowed to cool to RT, diluted with H$_2$O (100 mL) and extracted with EtOAc (3×100 mL). The combined organic layers were washed with brine (3×100 mL) and dried over anhydrous Na$_2$SO$_4$, filtered and concentrated under reduced pressure. The residue was purified by silica gel column chromatography, eluting with PE/EtOAc (1:1 to 1:2) to afford the title compound (350 mg, 69.0%) as a red solid. MS (ES) m/z=673 (M+1).

Preparation 168 tert-Butyl 8-[6-[2-(tert-butoxycarbonylamino)-5-fluoro-benzothiophen-4-yl]-5-fluoro-7,9-dihydrofuro[3,4-f]quinazolin-1-yl]-3,8-diazabicyclo[3.2.1]octane-3-carboxylate

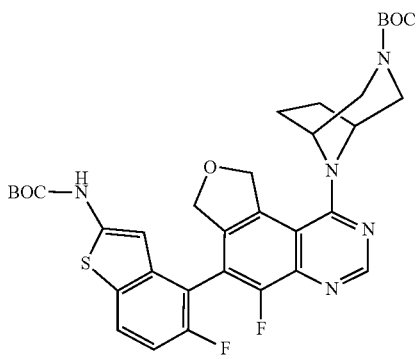 [SMILES: CC(C)(C)OC(=O)Nc1cc2c(-c3c4c(c5c(N6C7CCC6CN(C(=O)OC(C)(C)C)C7)ncnc5c3F)COC4)c(F)ccc2s1]

A solution of tert-butyl 8-[6-[2-(tert-butoxycarbonylamino)-5-fluoro-benzothiophen-4-yl]-3-ethylsulfanyl-5- fluoro-7,9-dihydrofuro[3,4-f]quinazolin-1-yl]-3,8-diazabicyclo[3.2.1]octane-3-carboxylate (28.6 g, 37.4 mmol) in THF (375 mL) was charged with TES (24 mL, 150 mmol, 4.00 eq.) and PdCl₂ (0.688 g, 3.69 mmol, 0.10 eq.) and stirred at RT for 4 h. H₂O (100 mL) was added dropwise, and the mixture was stirred at RT for 15 min. The mixture was filtered through diatomaceous earth, rinsed with EtOAc (100 mL). The filtrate was partitioned, and the organic layer was washed with brine and dried over anhydrous Na₂SO₄, filtered and concentrated. The residue was purified on silica, eluting with EtOAc/Hexanes (10-60%) to obtain the title compound (22.35 g, 90%) as a white foam. MS (ES) m/z=666 (M+1).

The following compounds in Table 9 were prepared in similar manner to Preparation 168. Various methods were used to purify the compounds, which would be apparent to one skilled in the art.

TABLE 9

| Preparation | Chemical Name | Structure | MS (ES) m/z (M + 1) |
| --- | --- | --- | --- |
| 169 | tert-Butyl (1R,4R)-5-[6-[2-(tert-butoxycarbonylamino)-5-fluoro-benzothiophen-4-yl]-5-fluoro-7,9-dihydrofuro[3,4-f]quinazolin-1-yl]-2,5-diazabicyclo[2.2.1]heptane-2-carboxylate | 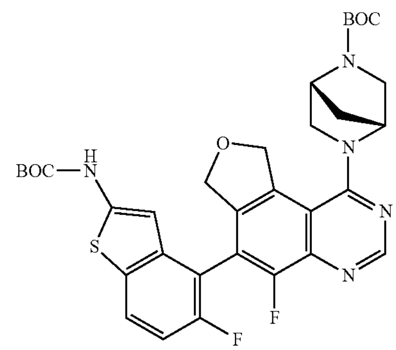 [SMILES: CC(C)(C)OC(=O)Nc1cc2c(-c3c4c(c5c(N6C[C@H]7C[C@@H]6CN7C(=O)OC(C)(C)C)ncnc5c3F)COC4)c(F)ccc2s1] | 652 |
| 170 | tert-Butyl N-[3-cyano-7-fluoro-4-[5-fluoro-1-[(1R,4R)-5-methyl-2,5-diazabicyclo[2.2.1]heptan-2-yl]-7,9-dihydrofuro[3,4-f]quinazolin-6-yl]benzothiophen-2-yl]carbamate | 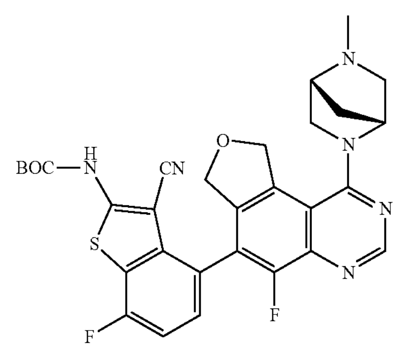 [SMILES: CN1C[C@H]2C[C@@H]1CN2c1ncnc2c(F)c(-c3ccc(F)c4sc(NC(=O)OC(C)(C)C)c(C#N)c34)c3c(c12)COC3] | 591 |
| 171 | tert-Butyl 8-[6-[2-(tert-butoxycarbonylamino)-5-fluoro-benzofuran-4-yl]-5-fluoro-7,9-dihydrofuro[3,4-f]quinazolin-1-yl]-3,8-diazabicyclo[3.2.1]octane-3-carboxylate | 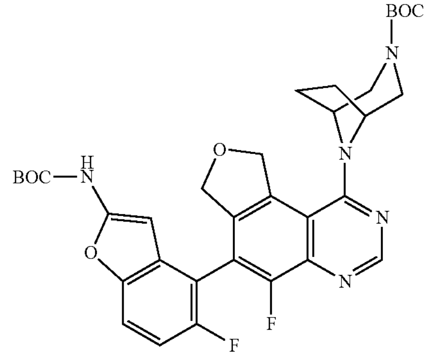 [SMILES: CC(C)(C)OC(=O)Nc1cc2c(-c3c4c(c5c(N6C7CCC6CN(C(=O)OC(C)(C)C)C7)ncnc5c3F)COC4)c(F)ccc2o1] | 650 |

Preparation 172 tert-Butyl 8-[6-[2-(tert-butoxycarbonylamino)-3-cyano-5-fluoro-benzothiophen-4-yl]-5-fluoro-7,9-dihydrofuro[3,4-f]quinazolin-1-yl]-3,8-diazabicyclo[3.2.1]octane-3-carboxylate

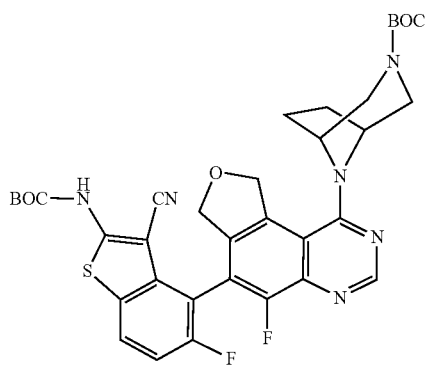 [SMILES: CC(C)(C)OC(=O)Nc1sc2ccc(F)c(-c3c4c(c5c(N6C7CCC6CN(C(=O)OC(C)(C)C)C7)ncnc5c3F)COC4)c2c1C#N]

In a 250 mL 3-necked RBF, equipped with a thermocouple, $N_2$ inlet and dropping funnel, tert-butyl 8-[6-[2-(tert-butoxycarbonylamino)-5-fluoro-benzothiophen-4-yl]-5-fluoro-7,9-dihydrofuro[3,4-f]quinazolin-1-yl]-3,8-diazabicyclo[3.2.1]octane-3-carboxylate (0.640 g, 0.961 mmol) was dissolved in THF (10 mL). The flask was placed in a −45° C. bath (ACN/Dry ice) and flushed with $N_2$. Once the internal temperature had reached −45° C. chlorosulfonyl isocyanate (0.42 mL, 4.8 mmol, 5.0 eq.) was added dropwise at such a rate to keep the internal temperature below −30° C. After 90 min, the cold reaction mixture was poured into DMF (15 mL) and stirred at RT for 1 h. The mixture was diluted with EtOAc, then was washed with 0.2M LiCl (3×300 mL) and brine. The organics were dried over anhydrous $Na_2SO_4$, filtered and concentrated. The residue was purified on silica, eluting with EtOAc/hexanes (10% to 100%) to obtain the title compound (0.553 g, 83%) as a white solid. MS (ES) m/z=691 (M+1).

The following compounds in Table 10 were prepared in a similar manner as described for Preparation 172. Various methods were used to purify the compounds, which would be apparent to one skilled in the art.

TABLE 10

| Preparation | Chemical Name | Structure | MS (ES) m/z (M + 1) |
|---|---|---|---|
| 173 | tert-Butyl (1R,4R)-5-[6-[2-(tert-butoxycarbonylamino)-3-cyano-5-fluoro-benzothiophen-4-yl]-5-fluoro-7,9-dihydrofuro[3,4-f]quinazolin-1-yl]-2,5-diazabicyclo[2.2.1]heptane-2-carboxylate | 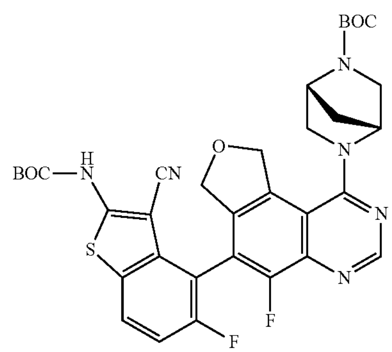 [SMILES: CC(C)(C)OC(=O)Nc1sc2ccc(F)c(-c3c4c(c5c(N6C[C@H]7C[C@@H]6CN7C(=O)OC(C)(C)C)ncnc5c3F)COC4)c2c1C#N] | 677 |
| 174 | tert-Butyl 6-[6-[2-(tert-butoxycarbonylamino)-3-cyano-5-fluoro-benzothiophen-4-yl]-3-ethylsulfanyl-5-fluoro-7,9-dihydrofuro[3,4-f]quinazolin-1-yl]-3,6-diazabicyclo[3.1.1]heptane-3-carboxylate | 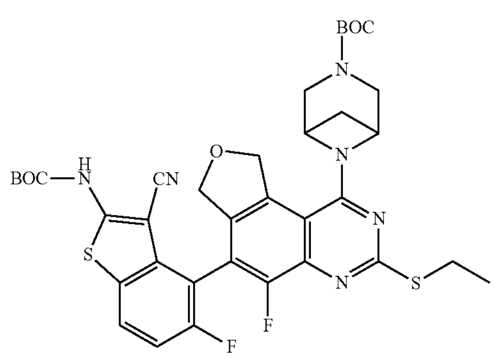 [SMILES: CCSc1nc(N2C3CC2CN(C(=O)OC(C)(C)C)C3)c2c3c(c(-c4c(F)ccc5sc(NC(=O)OC(C)(C)C)c(C#N)c45)c(F)c2n1)COC3] | 737 |

TABLE 10-continued

| Preparation | Chemical Name | Structure | MS (ES) m/z (M + 1) |
|---|---|---|---|
| 175 | tert-Butyl 8-[6-[3-cyano-2-[dimethylaminomethyleneamino]-5-fluoro-benzofuran-4-yl]-5-fluoro-7,9-dihydrofuro[3,4-f]quinazolin-1-yl]-3,8-diazabicyclo[3.2.1]octane-3-carboxylate | 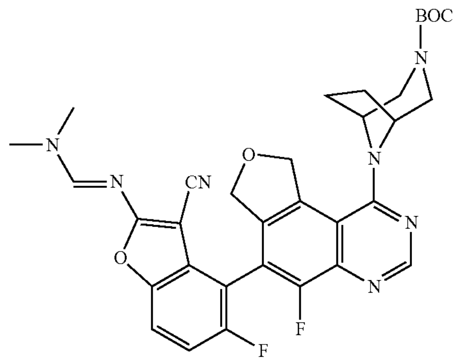 [SMILES: CN(C)/C=N/c1oc2ccc(F)c(-c3c4c(c5c(N6C7CCC6CN(C(=O)OC(C)(C)C)C7)ncnc5c3F)COC4)c2c1C#N] | 630 |
| 247 | tert-Butyl 8-[6-[2-(tert-butoxycarbonylamino)-3-cyano-5-fluoro-benzothiophen-4-yl]-3-ethylsulfanyl-5-fluoro-7,9-dihydrofuro[3,4-f]quinazolin-1-yl]-3,8-diazabicyclo[3.2.1]octane-3-carboxylate | 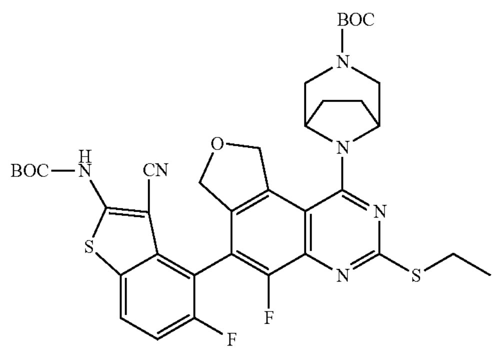 | 751 |
| 248[1] | tert-Butyl 8-[6-[2-(tert-butoxycarbonylamino)-3-cyano-5-fluoro-benzothiophen-4-yl]-3-ethylsulfanyl-5-fluoro-7,9-dihydrofuro[3,4-f]quinazolin-1-yl]-3,8-diazabicyclo[3.2.1]octane-3-carboxylate, Isomer 2 | 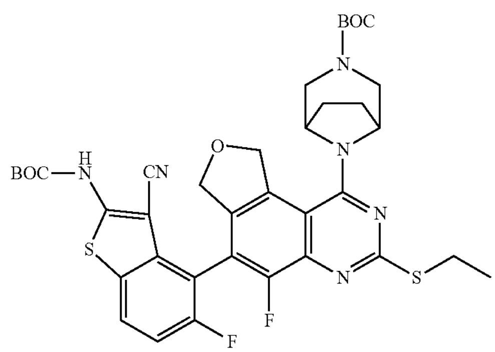 | 751 |
| 249 | tert-Butyl 8-[6-[2-(tert-butoxycarbonylamino)-3-cyano-5-fluoro-benzofuran-4-yl]-3-ethylsulfanyl-5-fluoro-7,9-dihydrofuro[3,4-f]quinazolin-1-yl]-3,8-diazabicyclo[3.2.1]octane-3-carboxylate | 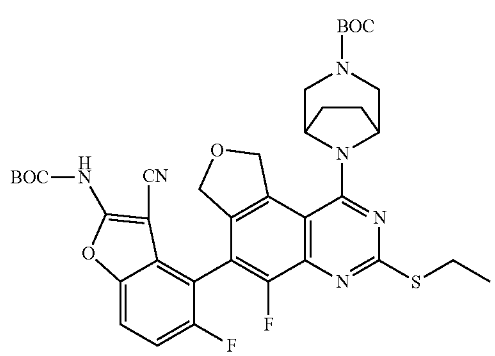 [SMILES: CCSc1nc(N2C3CCC2CN(C(=O)OC(C)(C)C)C3)c2c3c(c(-c4c(F)ccc5oc(NC(=O)OC(C)(C)C)c(C#N)c45)c(F)c2n1)COC3] | 735 |

TABLE 10-continued

| Preparation | Chemical Name | Structure | MS (ES) m/z (M + 1) |
|---|---|---|---|
| 250 | tert-Butyl 6-[6-[2-(tert-butoxycarbonylamino)-3-cyano-5-fluoro-benzofuran-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,6-diazabicyclo[3.1.1]heptane-3-carboxylate | 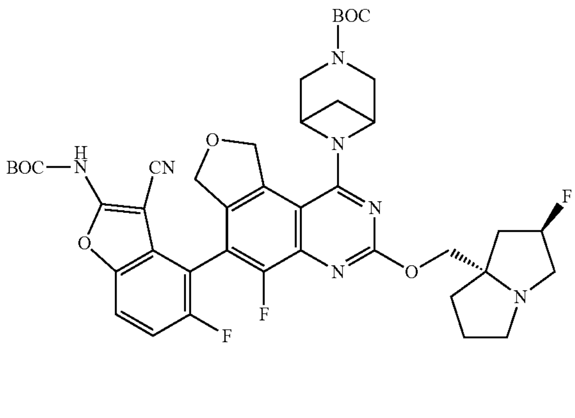 [SMILES: CC(C)(C)OC(=O)Nc1oc2ccc(F)c(-c3c4c(c5c(N6C7CC6CN(C(=O)OC(C)(C)C)C7)nc(OC[C@@]67CCCN6C[C@H](F)C7)nc5c3F)COC4)c2c1C#N] | 818 |
| 251[2] | tert-Butyl 6-[6-[2-(tert-butoxycarbonylamino)-3-cyano-5-fluoro-benzothiophen-4-yl]-3-ethylsulfanyl-5-fluoro-7,9-dihydrofuro[3,4-f]quinazolin-1-yl]-3,6-diazabicyclo[3.1.1]heptane-3-carboxylate, Isomer 2 | 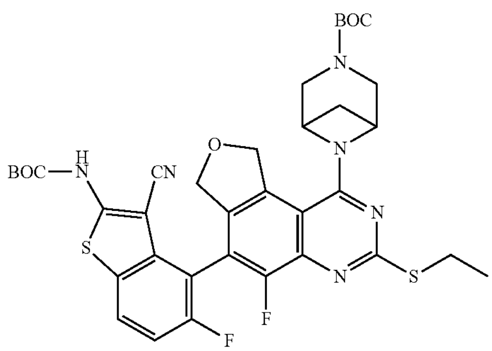 [SMILES: CCSc1nc(N2C3CC2CN(C(=O)OC(C)(C)C)C3)c2c3c(c(-c4c(F)ccc5sc(NC(=O)OC(C)(C)C)c(C#N)c45)c(F)c2n1)COC3] | 737 |
| 252 | tert-Butyl (1R,4R)-5-[6-[2-(tert-butoxycarbonylamino)-3-cyano-5-fluoro-benzofuran-4-yl]-3-ethylsulfanyl-5-fluoro-7,9-dihydrofuro[3,4-f]quinazolin-1-yl]-2,5-diazabicyclo[2.2.1]heptane-2-carboxylate | 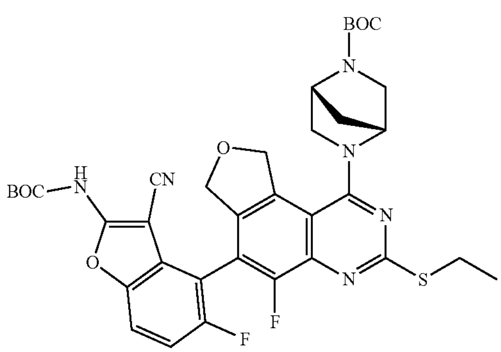 [SMILES: CCSc1nc(N2C[C@H]3C[C@@H]2CN3C(=O)OC(C)(C)C)c2c3c(c(-c4c(F)ccc5oc(NC(=O)OC(C)(C)C)c(C#N)c45)c(F)c2n1)COC3] | 721 |
| 253 | tert-Butyl N-[3-cyano-4-[1-[1-(dimethylamino)cyclopentyl]methylamino]-3-ethylsulfanyl-5-fluoro-7,9-dihydrofuro[3,4-f]quinazolin-6-yl]-5-fluoro-benzothiophen-2-yl]carbamate | 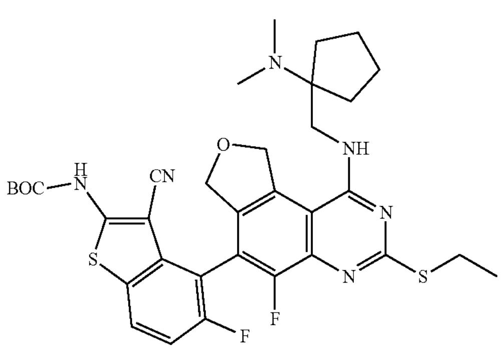 [SMILES: CCSc1nc(NCC2(N(C)C)CCCC2)c2c3c(c(-c4c(F)ccc5sc(NC(=O)OC(C)(C)C)c(C#N)c45)c(F)c2n1)COC3] | 681 |

TABLE 10-continued

| Preparation | Chemical Name | Structure | MS (ES) m/z (M + 1) |
|---|---|---|---|
| 254 | tert-Butyl N-[3-cyano-4-(3-ethylsulfanyl-5-fluoro-1-methoxy-7,9-dihydrofuro[3,4-f]quinazolin-6-yl)-5-fluoro-benzothiophen-2-yl]carbamate | 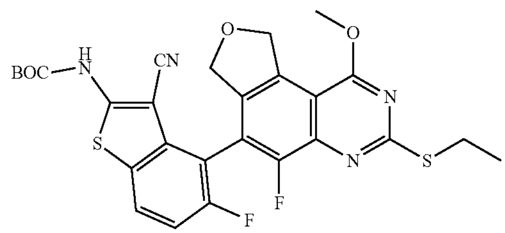 [SMILES: CCSc1nc(OC)c2c3c(c(-c4c(F)ccc5sc(NC(=O)OC(C)(C)C)c(C#N)c45)c(F)c2n1)COC3] | 571 |

[1]Chiralpak® AD-H, 50 × 250 mm, 30% EtOH: 70% $CO_2$, 180 mL/min
[2]Chiralpak® AD-H, 30 × 250 mm, 35% IPA(0.2% DEA): 65% $CO_2$, 50 mL/min Preparation 255 tert-Butyl 8-[6-[2-(tert-butoxycarbonylamino)-3-cyano-5-fluoro-benzothiophen-4-yl]-5-fluoro-7,9-dihydrofuro[3,4-f]quinazolin-1-yl]-3,8-diazabicyclo[3.2.1]octane-3-carboxylate, Isomer 2

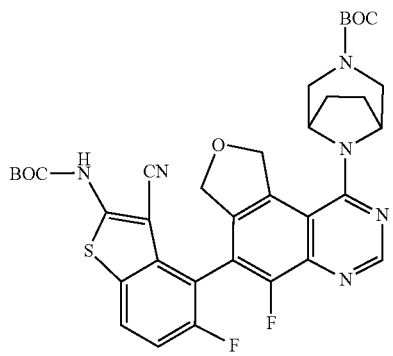 [SMILES: CC(C)(C)OC(=O)Nc1sc2ccc(F)c(-c3c4c(c5c(N6C7CCC6CN(C(=O)OC(C)(C)C)C7)ncnc5c3F)COC4)c2c1C#N]

tert-Butyl 8-[6-[2-(tert-butoxycarbonylamino)-3-cyano-5-fluoro-benzothiophen-4-yl]-3-ethylsulfanyl-5-fluoro-7,9-dihydrofuro[3,4-f]quinazolin-1-yl]-3,8-diazabicyclo[3.2.1]octane-3-carboxylate was used in an analogous manner to the method of Preparation 168, followed by chiral purification (Chiralpak® AD-H, 30×250 mm, 30% IPA:70% $CO_2$, 100 mL/min) to obtain the title compound (1.02 g, 35%). MS (ES) m/z=691 (M+1).

Preparation 176 tert-Butyl 8-[6-(2-amino-3-cyano-5-fluoro-benzofuran-4-yl)-5-fluoro-7,9-dihydrofuro[3,4-f]quinazolin-1-yl]-3,8-diazabicyclo[3.2.1]octane-3-carboxylate

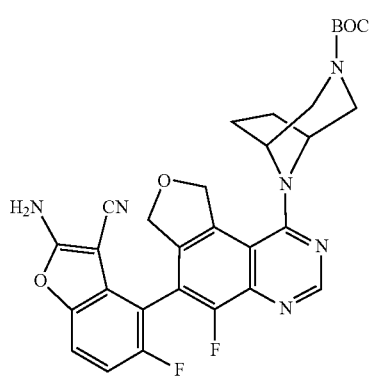 [SMILES: CC(C)(C)OC(=O)N1CC2CCC(C1)N2c1ncnc2c(F)c(-c3c(F)ccc4oc(N)c(C#N)c34)c3c(c12)COC3]

To a RBF was added tert-butyl 8-[6-[3-cyano-2-[dimethylaminomethyleneamino]-5-fluoro-benzofuran-4-yl]-5-fluoro-7,9-dihydrofuro[3,4-f]quinazolin-1-yl]-3,8-diazabicyclo[3.2.1]octane-3-carboxylate (0.225 g, 0.357 mmol), MeOH (2 mL), and 1M NaOH (0.9 mL, 0.893 mmol, 2.5 eq.) and was heated at 60° C. for 90 min. The reaction was cooled to 0° C. and 5N HCl was added to adjust to pH 4. The mixture was washed with brine, extracted with EtOAc (3×), dried over $MgSO_4$, filtered, and concentrated to afford the title compound (0.188 g, 92%). MS (ES) m/z=576 (M+1).

Preparation 177 tert-Butyl 8-[6-[2-(tert-butoxycarbonylamino)-3-cyano-7-fluoro-benzothiophen-4-yl]-3-ethylsulfanyl-7,9-dihydrofuro[3,4-f]quinazolin-1-yl]-3,8-diazabicyclo[3.2.1]octane-3-carboxylate

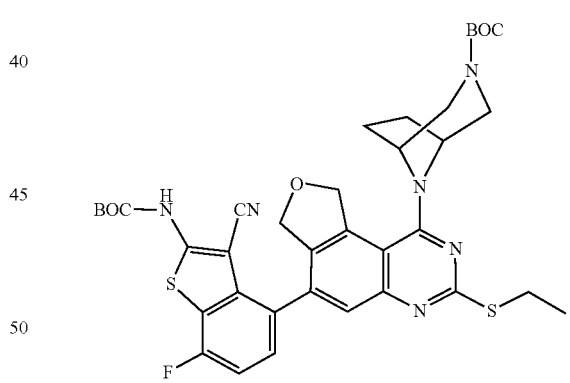

A solution of tert-butyl 8-[6-[2-(tert-butoxycarbonylamino)-3-cyano-7-fluoro-benzothiophen-4-yl]-5-chloro-3-ethylsulfanyl-7,9-dihydrofuro[3,4-f]quinazolin-1-yl]-3,8-diazabicyclo[3.2.1]octane-3-carboxylate (0.390 g, 0.498 mmol), in 1,4-dioxane (5 mL) and IPA (1 mL) was charged with $Cs_2CO_3$ (0.489 g, 1.50 mmol, 3.0 eq) and chloro(2-dicyclohexylphosphino-2',4',6'-triisopropyl-1,1'-biphenyl)[2-(2'-amino-1,1'-biphenyl)]palladium(II) (0.041 g, 0.051 mmol, 0.10 eq.) and was heated at 100° C. for ~18 h. The reaction was cooled to RT. The mixture was diluted with EtOAc and was washed with sat. aq. $NH_4Cl$, and brine. The organics were dried over anhydrous $Na_2SO_4$, filtered and concentrated. The residue was purified by silica gel chromatography, eluting with EtOAc/Hex (10-50%) to obtain the title compound (0.289 g, 60%) as a 75% pure off-white solid, which was used in a subsequent step without further purification. MS (ES) m/z=733 (M+1).

Preparation 256 tert-Butyl 8-[6-[2-(tert-butoxycarbonylamino)-3-cyano-benzothiophen-4-yl]-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate

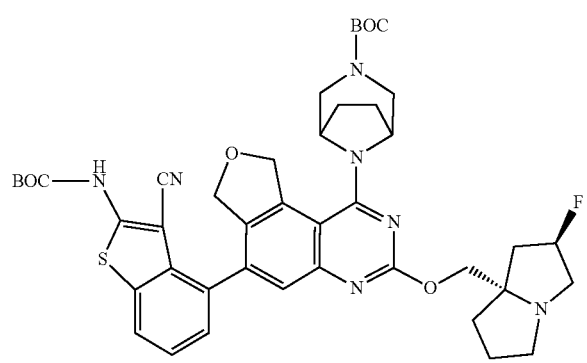 [SMILES: CC(C)(C)OC(=O)Nc1sc2cccc(-c3cc4nc(OC[C@@]56CCCN5C[C@H](F)C6)nc(N5C6CCC5CN(C(=O)OC(C)(C)C)C6)c4c4c3COC4)c2c1C#N]

tert-Butyl 8-[6-[2-(tert-butoxycarbonylamino)-3-cyano-benzothiophen-4-yl]-5-chloro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate was used in an analogous manner to the method of Preparation 177 to obtain the title compound (0.57 g, 83%). MS (ES) m/z=812 (M+1).

Preparation 178 tert-Butyl 8-[6-[2-(tert-butoxycarbonylamino)-3-cyano-7-fluoro-benzothiophen-4-yl]-3-ethylsulfonyl-5-fluoro-7,9-dihydrofuro[3,4-f]quinazolin-1-yl]-3,8-diazabicyclo[3.2.1]octane-3-carboxylate

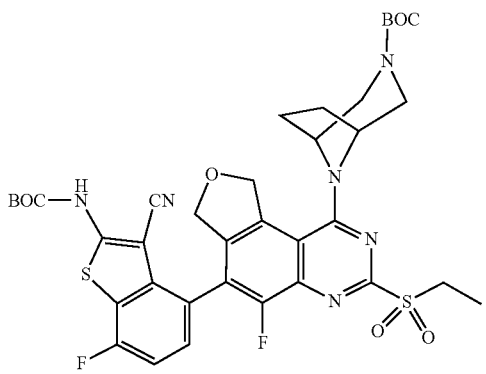 [SMILES: CCS(=O)(=O)c1nc(N2C3CCC2CN(C(=O)OC(C)(C)C)C3)c2c3c(c(-c4ccc(F)c5sc(NC(=O)OC(C)(C)C)c(C#N)c45)c(F)c2n1)COC3]

A solution of tert-butyl 8-[6-[2-(tert-butoxycarbonylamino)-3-cyano-7-fluoro-benzothiophen-4-yl]-3-ethylsulfanyl-5-fluoro-7,9-dihydrofuro[3,4-f]quinazolin-1-yl]-3,8-diazabicyclo[3.2.1]octane-3-carboxylate (1.13 g, 1.47 mmol) in DCM (15 mL) was charged with mCPBA (0.842 g, 4.88 mmol, 3.3 eq.) and was stirred at RT for 2 h. The mixture was diluted with DCM and washed with sat. aq. NaHCO$_3$, and brine. The organics were dried over anhydrous Na$_2$SO$_4$, filtered and concentrated. The residue was purified on silica, eluting with 40% EtOAc/Hex to obtain the title compound (1.15 g, 75%) as a white solid, MS (ES) m/z=783 (M+1).

The following compounds in Table 11 were prepared in a similar manner as described for Preparation 178. Various methods were used to purify the compounds, which would be apparent to one skilled in the art.

TABLE 11

| Preparation | Chemical Name | Structure | MS (ES) m/z (M + 1) |
|---|---|---|---|
| 179 | tert-Butyl 8-[6-[2-(tert-butoxycarbonylamino)-3-cyano-7-fluoro-benzothiophen-4-yl]-3-ethylsulfonyl-7,9-dihydrofuro[3,4-f]quinazolin-1-yl]-3,8-diazabicyclo[3.2.1]octane-3-carboxylate | 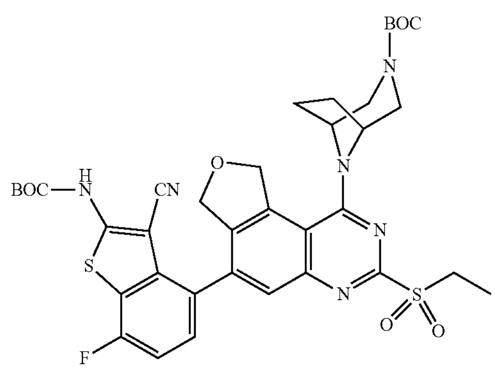 [SMILES: CCS(=O)(=O)c1nc(N2C3CCC2CN(C(=O)OC(C)(C)C)C3)c2c3c(c(-c4ccc(F)c5sc(NC(=O)OC(C)(C)C)c(C#N)c45)cc2n1)COC3] | 765 |

TABLE 11-continued

| Preparation | Chemical Name | Structure | MS (ES) m/z (M + 1) |
|---|---|---|---|
| 180 | tert-butyl 8-[6-[2-(tert-butoxycarbonylamino)-3-cyano-7-fluoro-benzothiophen-4-yl]-5-chloro-3-ethylsulfonyl-7,9-dihydrofuro[3,4-f]quinazolin-1-yl]-3,8-diazabicyclo[3.2.1]octane-3-carboxylate | 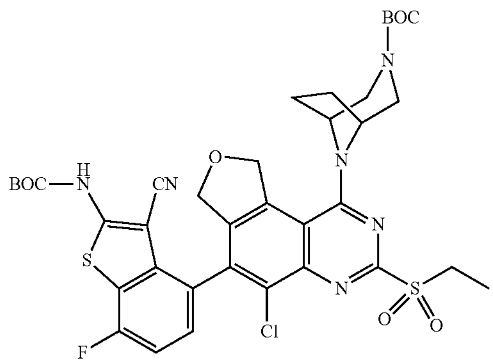 [SMILES: CCS(=O)(=O)c1nc(N2C3CCC2CN(C(=O)OC(C)(C)C)C3)c2c3c(c(-c4ccc(F)c5sc(NC(=O)OC(C)(C)C)c(C#N)c45)c(Cl)c2n1)COC3] | 799 |
| 181 | tert-Butyl 6-[6-[2-(tert-butoxycarbonylamino)-3-cyano-5-fluoro-benzothiophen-4-yl]-5-fluoro-7,9-dihydrofuro[3,4-f]quinazolin-1-yl]-3,6-diazabicyclo[3.1.1]heptane-3-carboxylate | 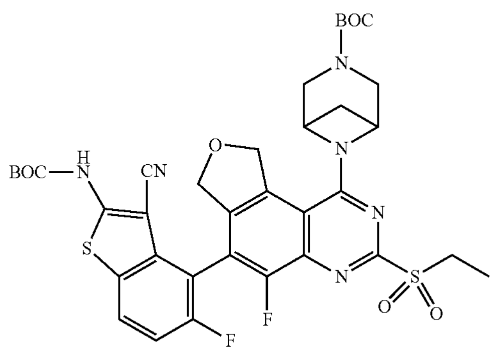 [SMILES: CCS(=O)(=O)c1nc(N2C3CC2CN(C(=O)OC(C)(C)C)C3)c2c3c(c(-c4c(F)ccc5sc(NC(=O)OC(C)(C)C)c(C#N)c45)c(F)c2n1)COC3] | 769 |
| 182 | tert-Butyl (1R,4R)-5-[6-bromo-9-(cyanomethyl)-3-ethylsulfonyl-5-fluoro-7,9-dihydrofuro[3,4-f]quinazolin-1-yl]-2,5-diazabicyclo[2.2.1]heptane-2-carboxylate | 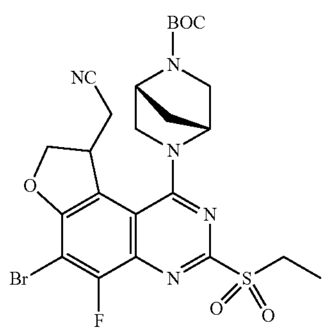 [SMILES: CCS(=O)(=O)c1nc(N2C[C@H]3C[C@@H]2CN3C(=O)OC(C)(C)C)c2c3c(c(Br)c(F)c2n1)OCC3CC#N] | 596 |
| 183 | tert-Butyl (1R,4R)-5-[6-bromo-5-chloro-9-(cyanomethyl)-3-ethylsulfonyl-7,9-dihydrofuro[3,4-f]quinazolin-1-yl]-2,5-diazabicyclo[2.2.1]heptane-2-carboxylate | 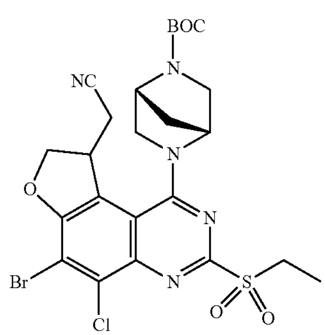 [SMILES: CCS(=O)(=O)c1nc(N2C[C@H]3C[C@@H]2CN3C(=O)OC(C)(C)C)c2c3c(c(Br)c(Cl)c2n1)OCC3CC#N] | 612 |

TABLE 11-continued

| Preparation | Chemical Name | Structure | MS (ES) m/z (M + 1) |
|---|---|---|---|
| 184 | tert-Butyl 6-(6-bromo-3-ethylsulfonyl-5-fluoro-7,9-dihydrofuro[3,4-f]quinazolin-1-yl)-3,6-diazabicyclo[3.1.1]heptane-3-carboxylate | 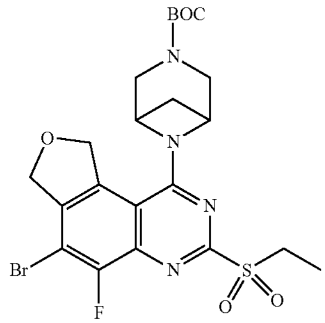 [SMILES: CCS(=O)(=O)c1nc(N2C3CC2CN(C(=O)OC(C)(C)C)C3)c2c3c(c(Br)c(F)c2n1)COC3] | 557 |
| 185 | tert-Butyl 8-[4-[2-(tert-butoxycarbonylamino)-3-cyano-7-fluoro-benzothiophen-4-yl]-5-chloro-7-methylsulfonyl-1,3-dihydrofuro[3,4-f]quinolin-9-yl]-3,8-diazabicyclo[3.2.1]octane-3-carboxylate | 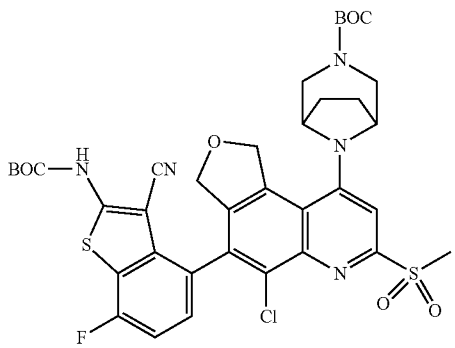 [SMILES: CC(C)(C)OC(=O)Nc1sc2c(F)ccc(-c3c4c(c5c(N6C7CCC6CN(C(=O)OC(C)(C)C)C7)cc(S(C)(=O)=O)nc5c3Cl)COC4)c2c1C#N] | 784 |
| 186[1] | tert-Butyl 8-[6-[2-(tert-butoxycarbonylamino)-3-cyano-7-fluoro-benzothiophen-4-yl]-5-chloro-3-ethylsulfonyl-7,9-dihydrofuro[3,4-f]quinazolin-1-yl]-3,8-diazabicyclo[3.2.1]octane-3-carboxylate | 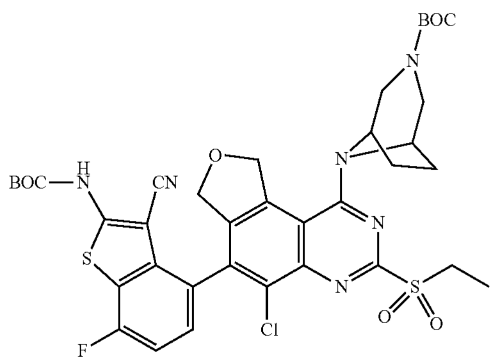 [SMILES: CCS(=O)(=O)c1nc(N2C3CCC2CN(C(=O)OC(C)(C)C)C3)c2c3c(c(-c4ccc(F)c5sc(NC(=O)OC(C)(C)C)c(C#N)c45)c(Cl)c2n1)COC3] | 799 |
| 187 | tert-Butyl N-[2-[4-[2-(tert-butoxycarbonylamino)-3-cyano-7-fluoro-benzothiophen-4-yl]-5-chloro-7-methylsulfonyl-1,3-dihydrofuro[3,4-f]quinolin-9-yl]ethyl]carbamate | 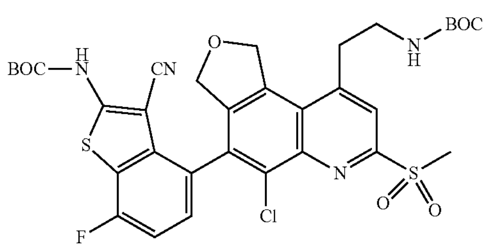 [SMILES: CC(C)(C)OC(=O)NCCc1cc(S(C)(=O)=O)nc2c(Cl)c(-c3ccc(F)c4sc(NC(=O)OC(C)(C)C)c(C#N)c34)c3c(c12)COC3] | 717 |
| 188 | tert-Butyl N-[3-cyano-4-(3-ethylsulfonyl-5-methyl-9,10-dihydro-7H-pyrano[4,3-f]quinazolin-6-yl)-7-fluoro-benzothiophen-2-yl]carbamate | 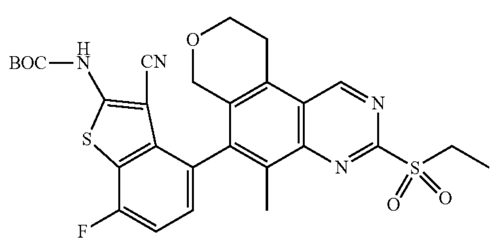 [SMILES: CCS(=O)(=O)c1ncc2c3c(c(-c4ccc(F)c5sc(NC(=O)OC(C)(C)C)c(C#N)c45)c(C)c2n1)COCC3] | 583 |

TABLE 11-continued

| Preparation | Chemical Name | Structure | MS (ES) m/z (M + 1) |
|---|---|---|---|
| 189 | tert-Butyl 8-[4-[2-(tert-butoxycarbonylamino)-3-cyano-7-fluoro-benzothiophen-4-yl]-5-fluoro-7-methylsulfonyl-1,3-dihydrofuro[3,4-f]quinolin-9-yl]-3,8-diazabicyclo[3.2.1]octane-3-carboxylate | 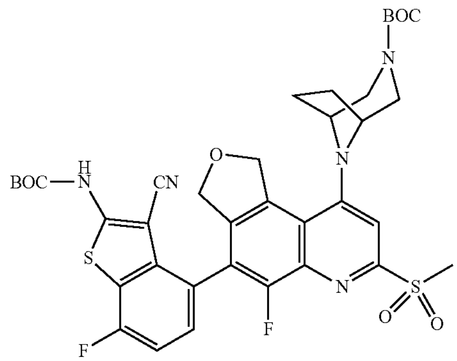 [SMILES: CC(C)(C)OC(=O)Nc1sc2c(F)ccc(-c3c4c(c5c(N6C7CCC6CN(C(=O)OC(C)(C)C)C7)cc(S(C)(=O)=O)nc5c3F)COC4)c2c1C#N] | 769 |
| 257 | tert-Butyl 8-[6-[2-(tert-butoxycarbonylamino)-3-cyano-5-fluoro-benzothiophen-4-yl]-3-ethylsulfonyl-5-fluoro-7,9-dihydrofuro[3,4-f]quinazolin-1-yl]-3,8-diazabicyclo[3.2.1]octane-3-carboxylate | 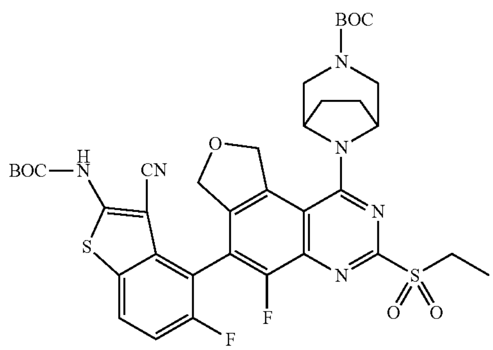 | 783 |
| 258[2] | tert-Butyl 8-[6-[2-(tert-butoxycarbonylamino)-3-cyano-5-fluoro-benzothiophen-4-yl]-3-ethylsulfonyl-5-fluoro-7,9-dihydrofuro[3,4-f]quinazolin-1-yl]-3,8-diazabicyclo[3.2.1]octane-3-carboxylate | 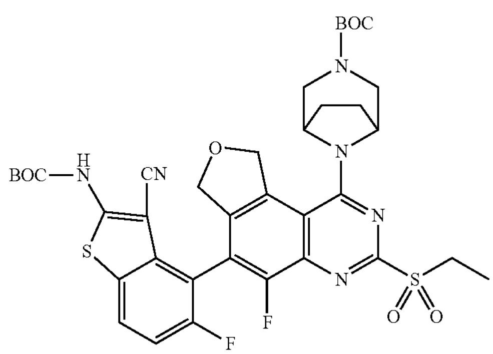 | 783 |
| 259 | tert-Butyl 8-[6-[2-(tert-butoxycarbonylamino)-3-cyano-5-fluoro-benzofuran-4-yl]-3-ethylsulfonyl-5-fluoro-7,9-dihydrofuro[3,4-f]quinazolin-1-yl]-3,8-diazabicyclo[3.2.1]octane-3-carboxylate | 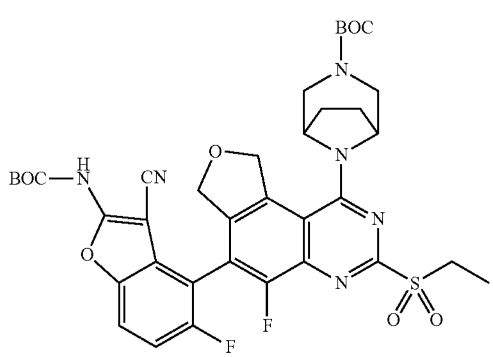 [SMILES: CCS(=O)(=O)c1nc(N2C3CCC2CN(C(=O)OC(C)(C)C)C3)c2c3c(c(-c4c(F)ccc5oc(NC(=O)OC(C)(C)C)c(C#N)c45)c(F)c2n1)COC3] | 767 |

TABLE 11-continued

| Preparation | Chemical Name | Structure | MS (ES) m/z (M + 1) |
|---|---|---|---|
| 260 | tert-Butyl 8-[6-[2-(tert-butoxycarbonylamino)-3-cyano-7-fluoro-benzofuran-4-yl]-3-ethylsulfonyl-5-fluoro-7,9-dihydrofuro[3,4-f]quinazolin-1-yl]-3,8-diazabicyclo[3.2.1]octane-3-carboxylate | 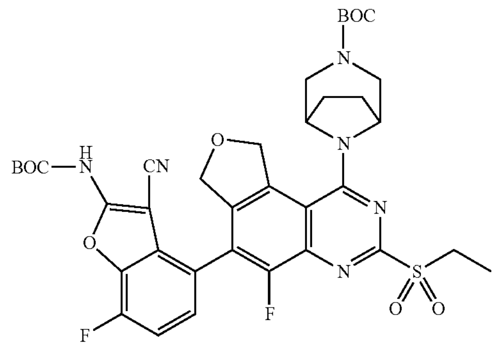 [SMILES: CCS(=O)(=O)c1nc(N2C3CCC2CN(C(=O)OC(C)(C)C)C3)c2c3c(c(-c4ccc(F)c5oc(NC(=O)OC(C)(C)C)c(C#N)c45)c(F)c2n1)COC3] | 767 |
| 261[3] | tert-Butyl 6-[6-[2-(tert-butoxycarbonylamino)-3-cyano-5-fluoro-benzothiophen-4-yl]-3-ethylsulfonyl-5-fluoro-7,9-dihydrofuro[3,4-f]quinazolin-1-yl]-3,6-diazabicyclo[3.1.1]heptane-3-carboxylate | 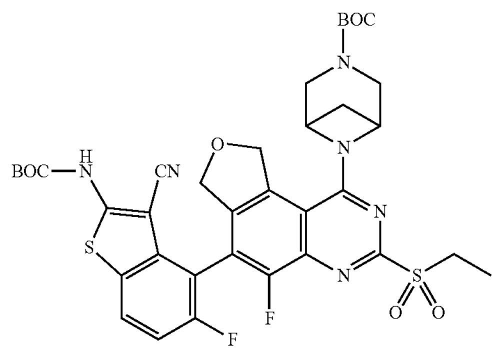 [SMILES: CCS(=O)(=O)c1nc(N2C3CC2CN(C(=O)OC(C)(C)C)C3)c2c3c(c(-c4c(F)ccc5sc(NC(=O)OC(C)(C)C)c(C#N)c45)c(F)c2n1)COC3] | 769 |
| 262 | tert-Butyl (1R,4R)-5-[6-[2-(tert-butoxycarbonylamino)-3-cyano-5-fluoro-benzofuran-4-yl]-3-ethylsulfonyl-5-fluoro-7,9-dihydrofuro[3,4-f]quinazolin-1-yl]-2,5-diazabicyclo[2.2.1]heptane-2-carboxylate | 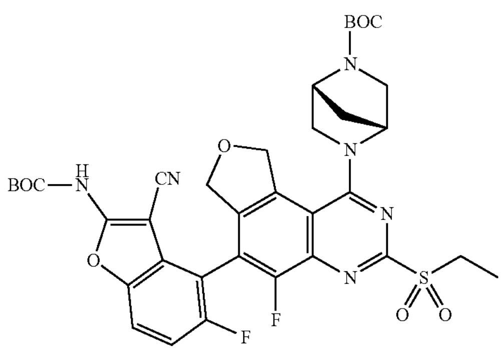 [SMILES: CCS(=O)(=O)c1nc(N2C[C@H]3C[C@@H]2CN3C(=O)OC(C)(C)C)c2c3c(c(-c4c(F)ccc5oc(NC(=O)OC(C)(C)C)c(C#N)c45)c(F)c2n1)COC3] | 753 |
| 263 | tert-Butyl N-[3-cyano-4-[1-[1-(dimethylamino)cyclopentyl]methylamino]-3-ethylsulfonyl-5-fluoro-7,9-dihydrofuro[3,4-f]quinazolin-6-yl]-5-fluoro-benzothiophen-2-yl]carbamate | 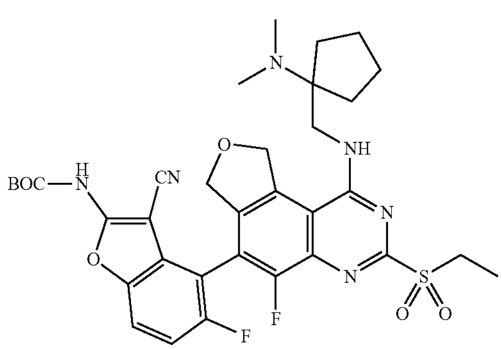 [SMILES: CCS(=O)(=O)c1nc(NCC2(N(C)C)CCCC2)c2c3c(c(-c4c(F)ccc5oc(NC(=O)OC(C)(C)C)c(C#N)c45)c(F)c2n1)COC3] | 713 |

TABLE 11-continued

| Preparation | Chemical Name | Structure | MS (ES) m/z (M + 1) |
|---|---|---|---|
| 264 | tert-Butyl N-[3-cyano-4-(3-ethylsulfonyl-5-fluoro-1-methoxy-7,9-dihydrofuro[3,4-f]quinazolin-6-yl)-5-fluoro-benzothiophen-2-yl]carbamate | 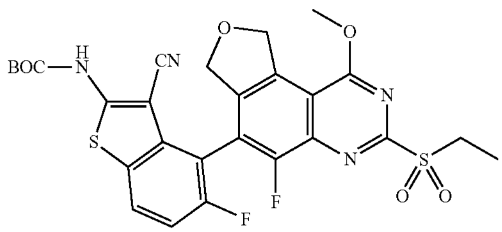 [SMILES: CCS(=O)(=O)c1nc(OC)c2c3c(c(-c4c(F)ccc5sc(NC(=O)OC(C)(C)C)c(C#N)c45)c(F)c2n1)COC3] | 603 |
| 309 | tert-Butyl 8-[6-[2-(tert-butoxycarbonylamino)-3-cyano-7-fluoro-thieno[3,2-c]pyridin-4-yl]-3-ethylsulfonyl-5-fluoro-7,9-dihydrofuro[3,4-f]quinazolin-1-yl]-3,8-diazabicyclo[3.2.1]octane-3-carboxylate | 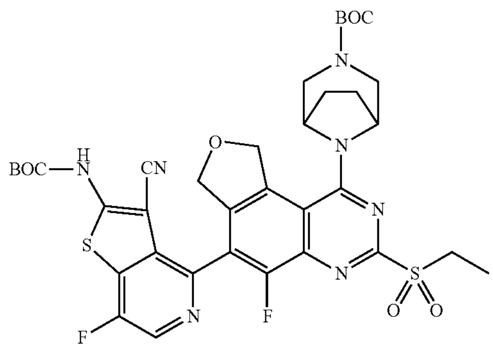 [SMILES: CCS(=O)(=O)c1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3] | 784 |
| 310 | tert-Butyl N-[4-(5-chloro-3-ethylsulfonyl-7,9-dihydrofuro[3,4-f]quinazolin-6-yl)-3-cyano-7-fluoro-benzothiophen-2-yl]carbamate | 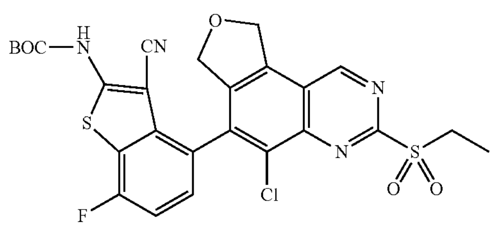 [SMILES: CCS(=O)(=O)c1ncc2c3c(c(-c4ccc(F)c5sc(NC(=O)OC(C)(C)C)c(C#N)c45)c(Cl)c2n1)COC3] | 589 |
| 328 | tert-Butyl 6-[6-[2-(tert-butoxycarbonylamino)-3-cyano-7-fluoro-thieno[3,2-c]pyridin-4-yl]-3-ethylsulfonyl-5-fluoro-7,9-dihydrofuro[3,4-f]quinazolin-1-yl]-3,6-diazabicyclo[3.1.1]heptane-3-carboxylate | 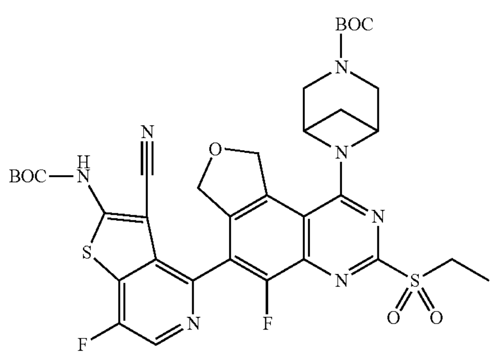 [SMILES: CCS(=O)(=O)c1nc(N2C3CC2CN(C(=O)OC(C)(C)C)C3)c2c3c(c(-c4ncc(F)c5sc(NC(=O)OC(C)(C)C)c(C#N)c45)c(F)c2n1)COC3] | 770 |
| 329 | tert-Butyl N-[3-cyano-4-(3-ethylsulfonyl-5-fluoro-7,9-dihydrofuro[3,4-f]quinazolin-6-yl)-7-fluoro-thieno[3,2-c]pyridin-2-yl]carbamate | 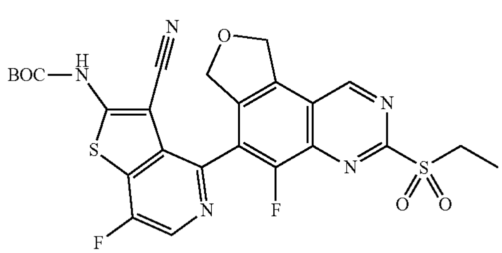 [SMILES: CCS(=O)(=O)c1ncc2c3c(c(-c4ncc(F)c5sc(NC(=O)OC(C)(C)C)c(C#N)c45)c(F)c2n1)COC3] | 574 |

TABLE 11-continued

| Preparation | Chemical Name | Structure | MS (ES) m/z (M + 1) |
|---|---|---|---|
| 330 | 6-Bromo-3-ethylsulfinyl-5-fluoro-7,9-dihydrofuro[3,4-f]quinazolin-1-ol | 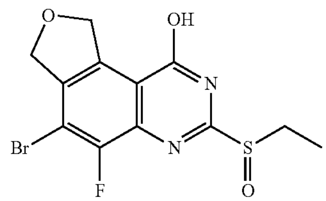 [SMILES: CCS(=O)c1nc(O)c2c3c(c(Br)c(F)c2n1)COC3] | 361, 363 |
| 331 | 6-Bromo-1-chloro-3-ethylsulfonyl-5-fluoro-7,9-dihydrofuro[3,4-f]quinazoline | 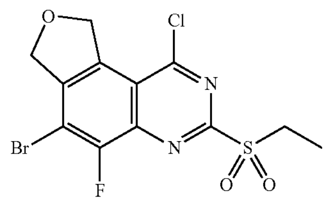 [SMILES: CCS(=O)(=O)c1nc(Cl)c2c3c(c(Br)c(F)c2n1)COC3] | 419 M + Na+ |
| 332 | tert-Butyl 8-[6-[2-(tert-butoxycarbonylamino)-3-cyano-7-fluoro-thieno[3,2-c]pyridin-4-yl]-3-ethylsulfonyl-5-fluoro-7,9-dihydrofuro[3,4-f]quinazolin-1-yl]-3-azabicyclo[3.2.1]octane-3-carboxylate | 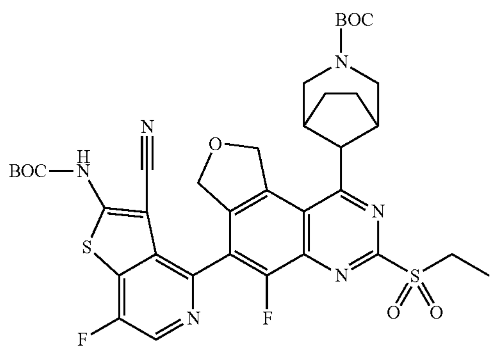 [SMILES: CCS(=O)(=O)c1nc(C2C3CCC2CN(C(=O)OC(C)(C)C)C3)c2c3c(c(-c4ncc(F)c5sc(NC(=O)OC(C)(C)C)c(C#N)c45)c(F)c2n1)COC3] | 742 |

[1] single atropisomer (from precursor in Preparation 157)
[2] single atropisomer (from precursor in Preparation 248)
[3] single atropisomer (from precursor in Preparation 251)

Preparation 190 tert-Butyl 6-[6-[2-(tert-butoxycarbonylamino)-3-cyano-5-fluoro-benzothiophen-4-yl]-5-fluoro-7,9-dihydrofuro[3,4-f]quinazolin-1-yl]-3,6-diazabicyclo[3.1.1]heptane-3-carboxylate

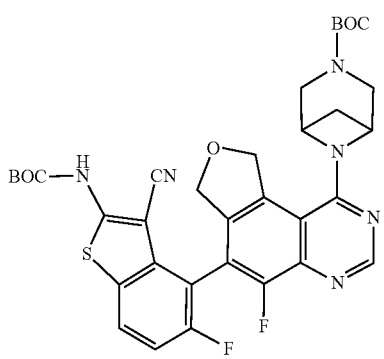 [SMILES: CC(C)(C)OC(=O)Nc1sc2ccc(F)c(-c3c4c(c5c(N6C7CC6CN(C(=O)OC(C)(C)C)C7)ncnc5c3F)COC4)c2c1C#N]

To a stirring solution of tert-butyl 6-[6-[2-(tert-butoxycarbonylamino)-3-cyano-5-fluoro-benzothiophen-4-yl]-3-ethylsulfonyl-5-fluoro-7,9-dihydrofuro[3,4-f]quinazolin-1-yl]-3,6-diazabicyclo[3.1.1]heptane-3-carboxylate (1.16 g, 1.50 mmol) in DCM (15 mL) and MeOH (15 mL) at RT was added NaBH$_4$ (0.58 g, 15 mmol, 10 eq.). After 15 min, the reaction mixture was diluted with DCM (300 mL), then sat. aq. NaHCO$_3$ (100 mL) and H$_2$O (500 mL) were added. The reaction mixture was stirred at RT until gas evolution stopped. The organic layer was separated and the aqueous layer was extracted with DCM (300 mL). The organic layers were combined and then were dried over anhydrous Na$_2$SO$_4$, filtered and concentrated. The residue was purified on silica, eluting with MeOH/DCM (0-2%) to obtain the title compound (0.80 g, 77%). MS (ES) m/z=677 (M+1).

The following compounds in Table 12 were prepared in a similar manner as described in Preparation 190. Various methods were used to purify the compounds, which would be apparent to one skilled in the art.

TABLE 12

| Preparation | Chemical Name | Structure | MS (ES) m/z (M + 1) |
|---|---|---|---|
| 191 | tert-Butyl (1R,4R)-5-[6-bromo-9-(cyanomethyl)-5-fluoro-7,9-dihydrofuro[3,4-f]quinazolin-1-yl]-2,5-diazabicyclo[2.2.1]heptane-2-carboxylate | 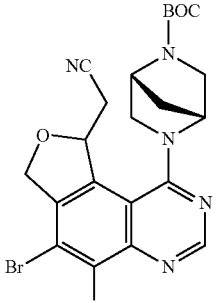 | 504 |
| 192 | tert-Butyl (1R,4R)-5-[6-bromo-5-chloro-9-(cyanomethyl)-7,9-dihydrofuro[3,4-f]quinazolin-1-yl]-2,5-diazabicyclo[2.2.1]heptane-2-carboxylate | 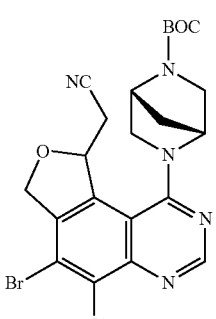 | 520 |

Preparation 193 tert-Butyl (1R,4R)-5-[6-[2-(tert-butoxycarbonylamino)-3-cyano-7-fluoro-benzothiophen-4-yl]-9-(cyanomethyl)-5-fluoro-7,9-dihydrofuro[3,4-f]quinazolin-1-yl]-2,5-diazabicyclo[2.2.1]heptane-2-carboxylate

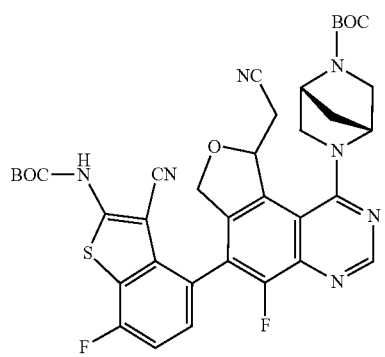 [SMILES: CC(C)(C)OC(=O)Nc1sc2c(F)ccc(-c3c4c(c5c(N6C[C@H]7C[C@@H]6CN7C(=O)OC(C)(C)C)ncnc5c3F)C(CC#N)OC4)c2c1C#N]

To a sealed flask were added tert-butyl(1R,4R)-5-[6-bromo-9-(cyanomethyl)-5-fluoro-7,9-dihydrofuro[3,4-f]quinazolin-1-yl]-2,5-diazabicyclo[2.2.1]heptane-2-carboxylate (1.00 g, 1.98 mmol) in THF (20.0 mL) and tert-butyl N-[3-cyano-4-(5,5-dimethyl-1,3,2-dioxaborinan-2-yl)-7-fluoro-benzothiophen-2-yl]carbamate (1.20 g, 2.97 mmol). The flask was sparged with $N_2$ for 15 min and then Pd-117 (430 mg, 0.601 mmol) was added, followed by $Cs_2CO_3$ (1.30 g, 3.99 mmol). The flask was sealed and heated with stirring at 70° C. in an oil bath for 2 h. The reaction mixture was cooled to RT and diluted with THF, filtered through a pad of diatomaceous earth. The filter cake was washed with 10% MeOH in DCM. The filtrate was concentrated, and the residue was purified by silica column chromatography with acetone/hexanes (0-40%) to afford crude product, which was repurified on silica with 1% to 5% 7N $NH_3$/MeOH in DCM to afford title compound (0.795 g, 56%) as a yellow solid. MS (ES) m/z=716 (M+1).

Preparation 194 tert-Butyl (1R,4R)-5-[6-[2-(tert-butoxycarbonylamino)-3-cyano-7-fluoro-benzothiophen-4-yl]-5-chloro-9-(cyanomethyl)-7,9-dihydrofuro[3,4-f]quinazolin-1-yl]-2,5-diazabicyclo[2.2.1]heptane-2-carboxylate

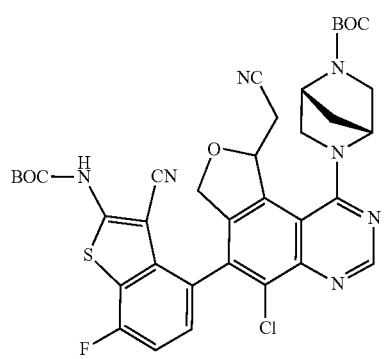

tert-Butyl (1R,4R)-5-[6-bromo-5-chloro-9-(cyanomethyl)-7,9-dihydrofuro[3,4-f]quinazolin-1-yl]-2,5-diazabicyclo[2.2.1]heptane-2-carboxylate was used in an analogous manner to the method of Preparation 193 to obtain the title compound (0.25 g, 54.7%) as yellow solid. MS (ES) m/z=732 (M+1).

Preparation 333

6-Bromo-3-ethylsulfonyl-5-fluoro-N-[[(2S)-1-methylpyrrolidin-2-yl]methyl]-7,9-dihydrofuro[3,4-f]quinazolin-1-amine

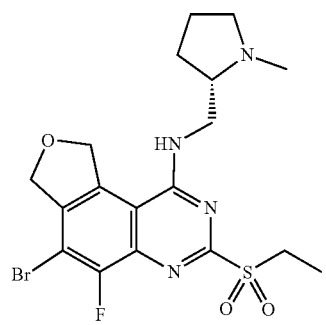 [SMILES: CCS(=O)(=O)c1nc(NC[C@@H]2CCCN2C)c2c3c(c(Br)c(F)c2n1)COC3]

6-Bromo-1-chloro-3-ethylsulfonyl-5-fluoro-7,9-dihydrofuro[3,4-f]quinazoline and [(2S)-1-methylpyrrolidin-2-yl]methanamine were used in an analogous manner to the method of Preparation 102 to obtain the title compound. MS (ES) m/z=473,475 (M+1,Br).

Preparation 195 tert-Butyl 8-[6-[2-(tert-butoxycarbonylamino)-3-cyano-7-fluoro-benzothiophen-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate

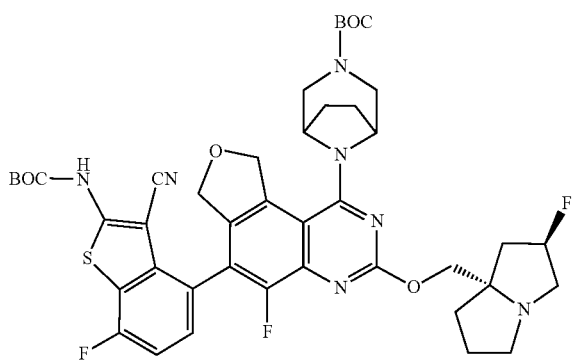 [SMILES: CC(C)(C)OC(=O)Nc1sc2c(F)ccc(-c3c4c(c5c(N6C7CCC6CN(C(=O)OC(C)(C)C)C7)nc(OC[C@@]67CCCN6C[C@H](F)C7)nc5c3F)COC4)c2c1C#N]

To [(2R,8S)-2-fluoro-1,2,3,5,6,7-hexahydropyrrolizin-8-yl]methanol (1.15 g, 7.01 mmol) in THF (30 mL) under N₂ at RT was added dropwise LiHMDS (6.7 mL, 6.7 mmol, 1M in THF) and stirred for 20 min at RT. To this solution was added dropwise via syringe, tert-butyl 8-[6-[2-(tert-butoxycarbonylamino)-3-cyano-7-fluoro-benzothiophen-4-yl]-3-ethylsulfonyl-5-fluoro-7,9-dihydrofuro[3,4-f]quinazolin-1-yl]-3,8-diazabicyclo[3.2.1]octane-3-carboxylate (2.3 g, 2.9 mmol) in THF (20 mL). After 40 min, the reaction was diluted with EtOAc and washed with brine. The aqueous layer was extracted 2× EtOAc and the combined organics were dried over anhydrous Na₂SO₄, filtered, and concentrated to a tan solid. The material was purified by silica (0% to 3.5% 7N NH₃/MeOH in DCM) to afford the title compound (2.26 g, 91%) as a yellow solid. MS (ES) m/z=848 (M+1).

The following compounds in Table 13 were prepared in a similar manner described in Preparation 195. Various methods were used to purify the compounds, which would be apparent to one skilled in the art.

TABLE 13

| Preparation | Chemical Name | Structure | MS (ES) m/z (M + 1) |
|---|---|---|---|
| 196 | tert-Butyl 8-[6-[2-(tert-butoxycarbonylamino)-3-cyano-7-fluoro-benzothiophen-4-yl]-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate) | 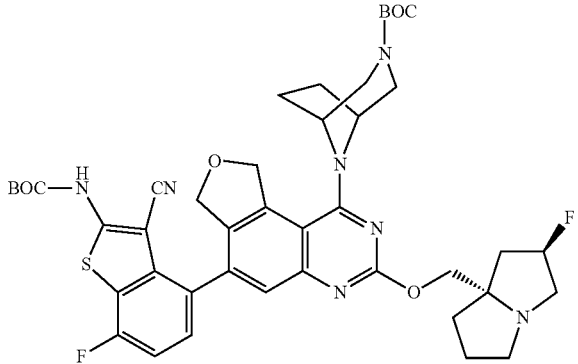 [SMILES: CC(C)(C)OC(=O)Nc1sc2c(F)ccc(-c3cc4nc(OC[C@@]56CCCN5C[C@H](F)C6)nc(N5C6CCC5CN(C(=O)OC(C)(C)C)C6)c4c4c3COC4)c2c1C#N] | 831 |
| 197 | tert-Butyl 8-[6-[2-(tert-butoxycarbonylamino)-3-cyano-7-fluoro-benzothiophen-4-yl]-5-chloro-3-[[(2R)-1,4-dioxan-2-yl]methoxy]-7,9-dihydrofuro[3,4-f]quinazolin-1-yl]-3,8-diazabicyclo[3.2.1]octane-3-carboxylate | 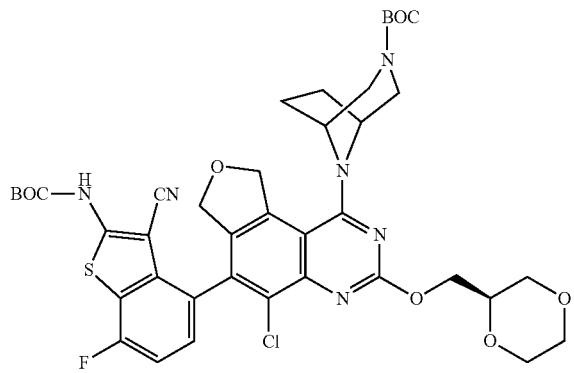 [SMILES: CC(C)(C)OC(=O)Nc1sc2c(F)ccc(-c3c4c(c5c(N6C7CCC6CN(C(=O)OC(C)(C)C)C7)nc(OC[C@H]6COCCO6)nc5c3Cl)COC4)c2c1C#N] | 823 |

TABLE 13-continued

| Preparation | Chemical Name | Structure | MS (ES) m/z (M + 1) |
|---|---|---|---|
| 198 | tert-Butyl 8-[6-[2-(tert-butoxycarbonylamino)-3-cyano-7-fluoro-benzothiophen-4-yl]-5-fluoro-3-(2-methoxyethoxy)-7,9-dihydrofuro[3,4-f]quinazolin-1-yl]-3,8-diazabicyclo[3.2.1]octane-3-carboxylate | 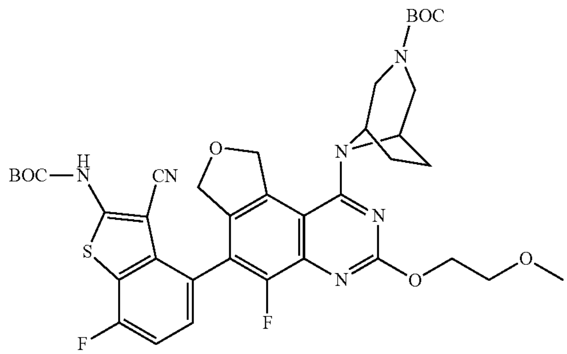 [SMILES: COCCOc1nc(N2C3CCC2CN(C(=O)OC(C)(C)C)C3)c2c3c(c(-c4ccc(F)c5sc(NC(=O)OC(C)(C)C)c(C#N)c45)c(F)c2n1)COC3] | 765 |
| 199 | tert-Butyl 8-[6-[2-(tert-butoxycarbonylamino)-3-cyano-7-fluoro-benzothiophen-4-yl]-5-fluoro-3-[[(2S)-1-(2-fluoroethyl)pyrrolidin-2-yl]methoxy]-7,9-dihydrofuro[3,4-f]quinazolin-1-yl]-3,8-diazabicyclo[3.2.1]octane-3-carboxylate | 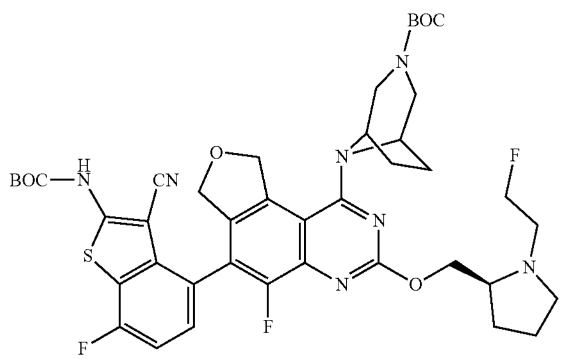 [SMILES: CC(C)(C)OC(=O)Nc1sc2c(F)ccc(-c3c4c(c5c(N6C7CCC6CN(C(=O)OC(C)(C)C)C7)nc(OC[C@@H]6CCCN6CCF)nc5c3F)COC4)c2c1C#N] | 836 |
| 200[1] | tert-Butyl 8-[4-[2-(tert-butoxycarbonylamino)-3-cyano-7-fluoro-benzothiophen-4-yl]-5-chloro-7-[[(2S)-1-methylpyrrolidin-2-yl]methoxy]-1,3-dihydrofuro[3,4-f]quinolin-9-yl]-3,8-diazabicyclo[3.2.1]octane-3-carboxylate | 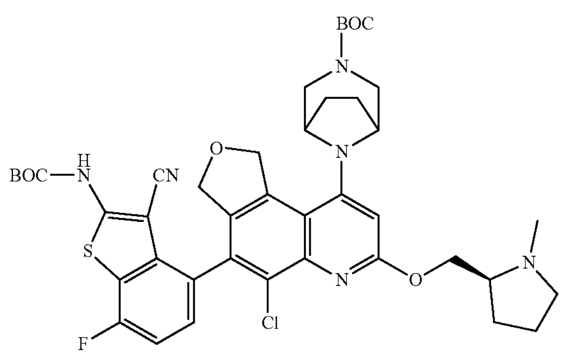 [SMILES: CN1CCC[C@H]1COc1cc(N2C3CCC2CN(C(=O)OC(C)(C)C)C3)c2c3c(c(-c4ccc(F)c5sc(NC(=O)OC(C)(C)C)c(C#N)c45)c(Cl)c2n1)COC3] | 820 |
| 201[2] | tert-Butyl 8-[6-[2-(tert-butoxycarbonylamino)-3-cyano-7-fluoro-benzothiophen-4-yl]-5-chloro-3-[2-(dimethylamino)ethoxy]-7,9-dihydrofuro[3,4-f]quinazolin-1-yl]-3,8-diazabicyclo[3.2.1]octane-3-carboxylate | 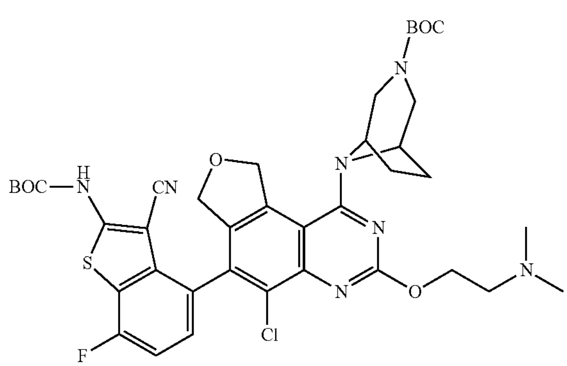 [SMILES: CN(C)CCOc1nc(N2C3CCC2CN(C(=O)OC(C)(C)C)C3)c2c3c(c(-c4ccc(F)c5sc(NC(=O)OC(C)(C)C)c(C#N)c45)c(Cl)c2n1)COC3] | 794 |

TABLE 13-continued

| Preparation | Chemical Name | Structure | MS (ES) m/z (M + 1) |
|---|---|---|---|
| 202[1] | tert-Butyl N-[2-[4-[2-(tert-butoxycarbonylamino)-3-cyano-7-fluoro-benzothiophen-4-yl]-5-chloro-7-[(2S)-1-methylpyrrolidin-2-yl]methoxy]-1,3-dihydrofuro[3,4-f]quinolin-9-yl]ethyl]carbamate | 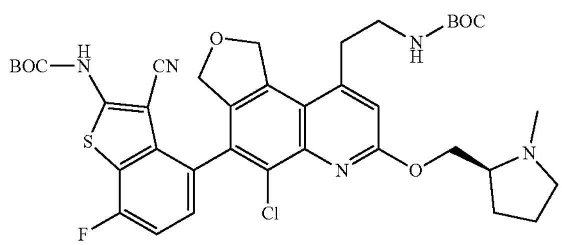 [SMILES: CN1CCC[C@H]1COc1cc(CCNC(=O)OC(C)(C)C)c2c3c(c(-c4ccc(F)c5sc(NC(=O)OC(C)(C)C)c(C#N)c45)c(Cl)c2n1)COC3] | 752 |
| 203[1] | tert-Butyl 8-[4-[2-(tert-butoxycarbonylamino)-3-cyano-7-fluoro-benzothiophen-4-yl]-5-chloro-7-[[(2S)-1-methylazetidin-2-yl]methoxy]-1,3-dihydrofuro[3,4-f]quinolin-9-yl]-3,8-diazabicyclo[3.2.1]octane-3-carboxylate | 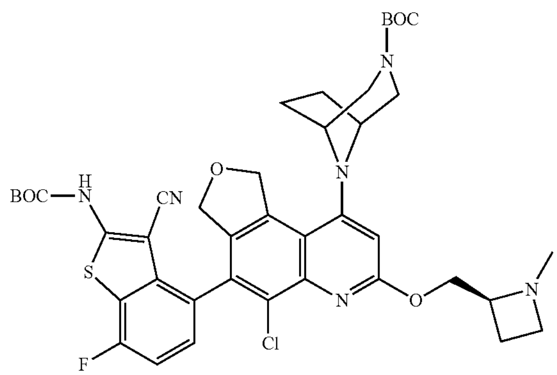 [SMILES: CN1CC[C@H]1COc1cc(N2C3CCC2CN(C(=O)OC(C)(C)C)C3)c2c3c(c(-c4ccc(F)c5sc(NC(=O)OC(C)(C)C)c(C#N)c45)c(Cl)c2n1)COC3] | 805 |
| 204[1] | tert-Butyl 8-[6-[2-(tert-butoxycarbonylamino)-3-cyano-7-fluoro-benzothiophen-4-yl]-5-chloro-3-[(1S)-2-hydroxy-1-methyl-ethoxy]-7,9-dihydrofuro[3,4-f]quinazolin-1-yl]-3,8-diazabicyclo[3.2.1]octane-3-carboxylate | 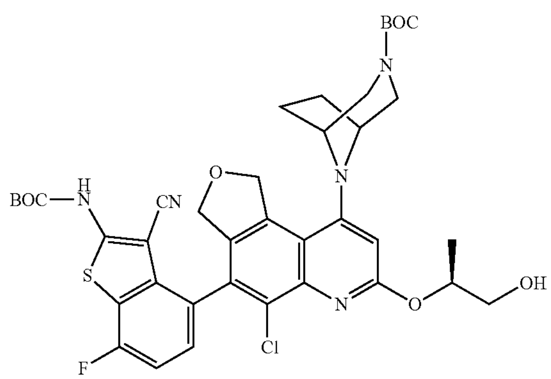 [SMILES: C[C@@H](CO)Oc1cc(N2C3CCC2CN(C(=O)OC(C)(C)C)C3)c2c3c(c(-c4ccc(F)c5sc(NC(=O)OC(C)(C)C)c(C#N)c45)c(Cl)c2n1)COC3] | 781 |
| 205 | tert-Butyl N-[3-cyano-7-fluoro-4-[5-methyl-3-[[(2S)-1-methylpyrrolidin-2-yl]methoxy]-9,10-dihydro-7H-pyrano[4,3-f]quinazolin-6-yl]benzothiophen-2-yl]carbamate | 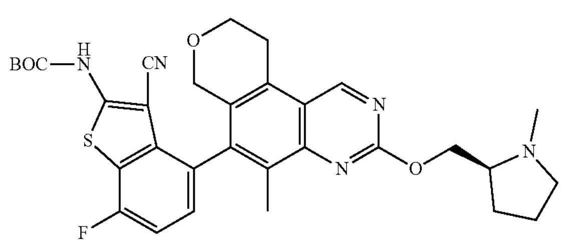 [SMILES: Cc1c(-c2ccc(F)c3sc(NC(=O)OC(C)(C)C)c(C#N)c23)c2c(c3cnc(OC[C@@H]4CCCN4C)nc13)CCOC2] | 604 |
| 206[3] | 4-Bromo-5-chloro-7-[[(2R)-tetrahydrofuran-2-yl]methoxy]-1,3-dihydrofuro[3,4-f]quinoline | 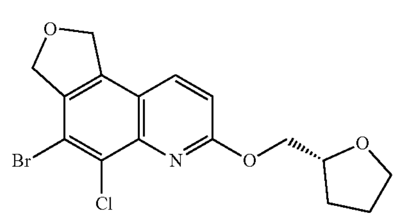 [SMILES: Clc1c(Br)c2c(c3ccc(OC[C@H]4CCCO4)nc13)COC2] | 384 |

TABLE 13-continued

| Preparation | Chemical Name | Structure | MS (ES) m/z (M + 1) |
|---|---|---|---|
| 207[1] | 4-Bromo-5-chloro-7-(2-morpholinoethoxy)-1,3-dihydrofuro[3,4-f]quinoline | 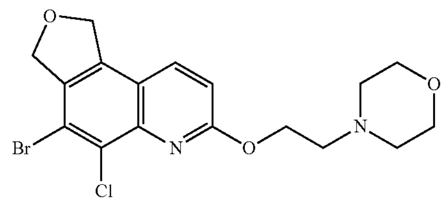 [SMILES: Clc1c(Br)c2c(c3ccc(OCCN4CCOCC4)nc13)COC2] | 413 |
| 208[1] | (3R,5S)-5-[(4-Bromo-5-chloro-1,3-dihydrofuro[3,4-f]quinolin-7-yl)oxymethyl]-1-methyl-pyrrolidin-3-ol | 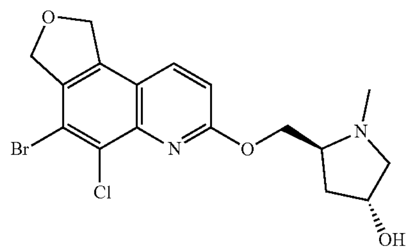 [SMILES: CN1C[C@H](O)C[C@H]1COc1ccc2c3c(c(Br)c(Cl)c2n1)COC3] | 413 |
| 209[1] | 4-Bromo-5-chloro-7-[[(2R)-4-methylmorpholin-2-yl]methoxy]-1,3-dihydrofuro[3,4-f]quinoline | 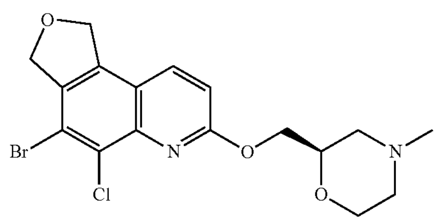 [SMILES: CN1CCO[C@@H](COc2ccc3c4c(c(Br)c(Cl)c3n2)COC4)C1] | 413 |
| 210[1] | 4-Bromo-5-chloro-7-[(3S)-tetrahydrofuran-3-yl]oxy-1,3-dihydrofuro[3,4-f]quinoline | 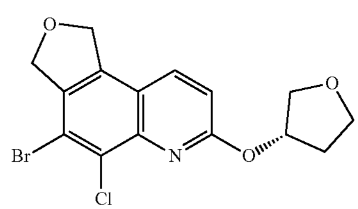 [SMILES: Clc1c(Br)c2c(c3ccc(O[C@H]4CCOC4)nc13)COC2] | 370 |
| 211[1] | 4-Bromo-5-chloro-7-[[(3S)-4-methylmorpholin-3-yl]methoxy]-1,3-dihydrofuro[3,4-f]quinoline | 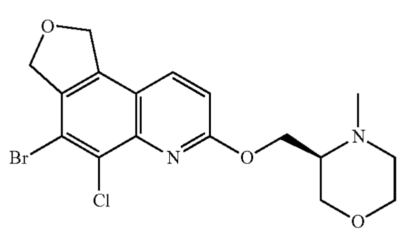 [SMILES: CN1CCOC[C@H]1COc1ccc2c3c(c(Br)c(Cl)c2n1)COC3] | 413 |
| 212[1] | [3-[(4-Bromo-5-chloro-1,3-dihydrofuro[3,4-f]quinolin-7-yl)oxymethyl]cyclobutoxy]-tert-butyl-dimethyl-silane | 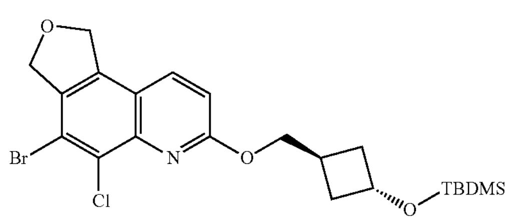 | 498 |
| 213[1] | 4-Bromo-5-chloro-7-(oxetan-3-ylmethoxy)-1,3-dihydrofuro[3,4-f]quinoline | 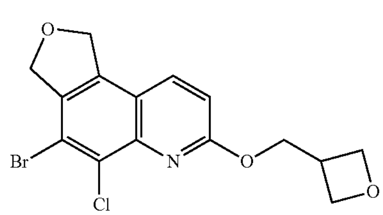 [SMILES: Clc1c(Br)c2c(c3ccc(OCC4COC4)nc13)COC2] | 370 |

TABLE 13-continued

| Preparation | Chemical Name | Structure | MS (ES) m/z (M + 1) |
|---|---|---|---|
| 214[1] | (2R)-1-[(4-Bromo-5-chloro-1,3-dihydrofuro[3,4-f]quinolin-7-yl)oxy]propan-2-ol | 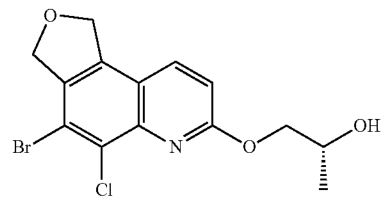 [SMILES: C[C@@H](O)COc1ccc2c3c(c(Br)c(Cl)c2n1)COC3] | 358 |
| 215[1] | 4-Bromo-5-chloro-7-[[(2S,4R)-4-fluoro-1-methyl-pyrrolidin-2-yl]methoxy]-1,3-dihydrofuro[3,4-f]quinoline | 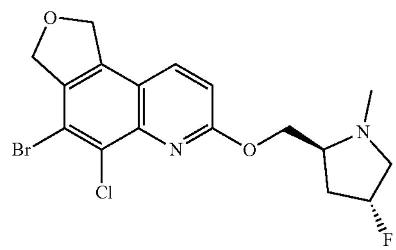 [SMILES: CN1C[C@H](F)C[C@H]1COc1ccc2c3c(c(Br)c(Cl)c2n1)COC3] | 415 |
| 216[1] | 4-Bromo-5-chloro-7-(1,2,3,5,6,7-hexahydropyrrolizin-8-ylmethoxy)-1,3-dihydrofuro[3,4-f]quinoline | 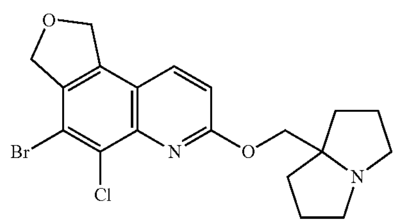 [SMILES: Clc1c(Br)c2c(c3ccc(OCC45CCCN4CCC5)nc13)COC2] | 423 |
| 217[1] | [2-[(4-Bromo-5-chloro-1,3-dihydrofuro[3,4-f]quinolin-7-yl)oxymethyl]-1-methyl-pyrrolidin-2-yl]methanol | 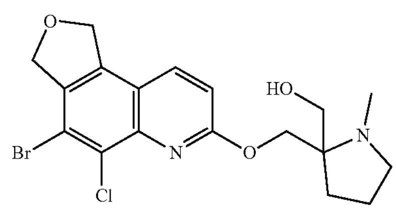 [SMILES: CN1CCCC1(CO)COc1ccc2c3c(c(Br)c(Cl)c2n1)COC3] | 427 |
| 218[1] | 4-Bromo-5-chloro-7-[(3-methoxy-1,2-dimethyl-azetidin-2-yl)methoxy]-1,3-dihydrofuro[3,4-f]quinoline | 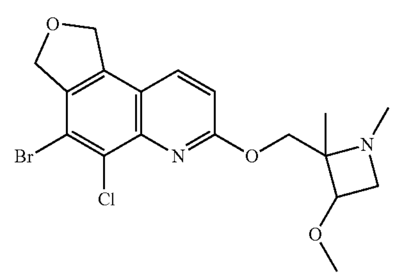 [SMILES: COC1CN(C)C1(C)COc1ccc2c3c(c(Br)c(Cl)c2n1)COC3] | 427 |
| 219[1] | 2-[(4-Bromo-5-chloro-1,3-dihydrofuro[3,4-f]quinolin-7-yl)oxy]ethanol | 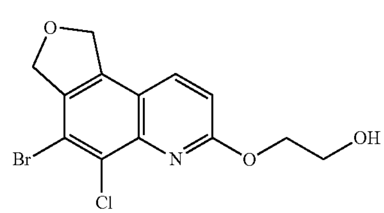 [SMILES: OCCOc1ccc2c3c(c(Br)c(Cl)c2n1)COC3] | 344 |

TABLE 13-continued

| Preparation | Chemical Name | Structure | MS (ES) m/z (M + 1) |
|---|---|---|---|
| 220[1] | tert-Butyl (2S)-2-[(4-bromo-5-chloro-1,3-dihydrofuro[3,4-f]quinolin-7-yl)oxymethyl]pyrrolidine-1-carboxylate | 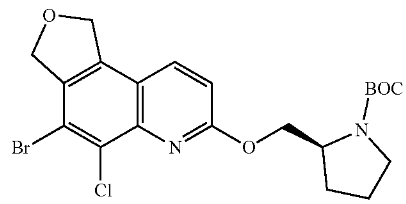 [SMILES: CC(C)(C)OC(=O)N1CCC[C@H]1COc1ccc2c3c(c(Br)c(Cl)c2n1)COC3] | 483 |
| 221[3] | 4-Bromo-5-chloro-7-[[(2S)-1-methylpyrrolidin-2-yl]methoxy]-1,3-dihydrofuro[3,4-f]quinoline | 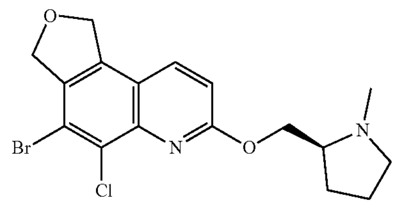 [SMILES: CN1CCC[C@H]1COc1ccc2c3c(c(Br)c(Cl)c2n1)COC3] | 397 |
| 222[4] | tert-Butyl 8-[4-[2-(tert-butoxycarbonylamino)-3-cyano-7-fluoro-benzothiophen-4-yl]-5-fluoro-7-[(2R,8S)-2-fluoro-1,2,3,5,6,7-hexahydropyrrolizin-8-yl]methoxy]-1,3-dihydrofuro[3,4-f]quinolin-9-yl]-3,8-diazabicyclo[3.2.1]octane-3-carboxylate | 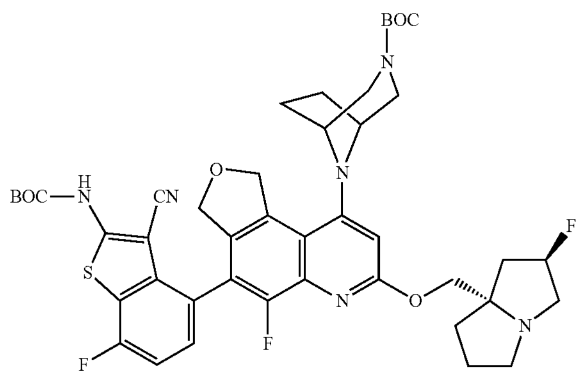 [SMILES: CC(C)(C)OC(=O)Nc1sc2c(F)ccc(-c3c4c(c5c(N6C7CCC6CN(C(=O)OC(C)(C)C)C7)cc(OC[C@@]67CCCN6C[C@H](F)C7)nc5c3F)COC4)c2c1C#N] | 847 |
| 265 | tert-Butyl 6-[6-[2-(tert-butoxycarbonylamino)-3-cyano-5-fluoro-benzothiophen-4-yl]-5-fluoro-3-[(2R,8S)-2-fluoro-1,2,3,5,6,7-hexahydropyrrolizin-8-yl]methoxy]-7,9-dihydrofuro[3,4-f]quinazolin-1-yl]-3,6-diazabicyclo[3.1.1]heptane-3-carboxylate | 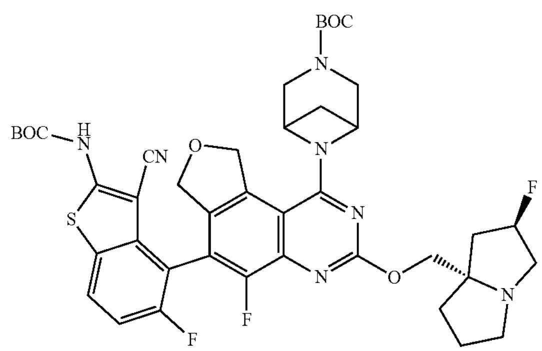 [SMILES: CC(C)(C)OC(=O)Nc1sc2ccc(F)c(-c3c4c(c5c(N6C7CC6CN(C(=O)OC(C)(C)C)C7)nc(OC[C@@]67CCCN6C[C@H](F)C7)nc5c3F)COC4)c2c1C#N] | 834 |
| 266[5] | tert-Butyl 6-[6-[2-(tert-butoxycarbonylamino)-3-cyano-5-fluoro-benzothiophen-4-yl]-5-fluoro-3-[(2R,8S)-2-fluoro-1,2,3,5,6,7-hexahydropyrrolizin-8-yl]methoxy]-7,9-dihydrofuro[3,4-f]quinazolin-1-yl]-3,6-diazabicyclo[3.1.1]heptane-3-carboxylate, Isomer 2 | 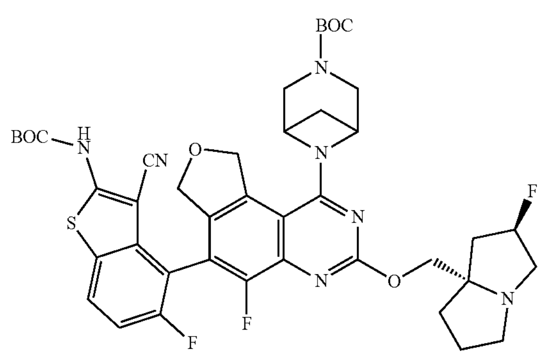 [SMILES: CC(C)(C)OC(=O)Nc1sc2ccc(F)c(-c3c4c(c5c(N6C7CC6CN(C(=O)OC(C)(C)C)C7)nc(OC[C@@]67CCCN6C[C@H](F)C7)nc5c3F)COC4)c2c1C#N] | 834 |

TABLE 13-continued

| Preparation | Chemical Name | Structure | MS (ES) m/z (M + 1) |
|---|---|---|---|
| 267 | tert-Butyl 8-[6-[2-(tert-butoxycarbonylamino)-3-cyano-5-fluoro-benzothiophen-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate | 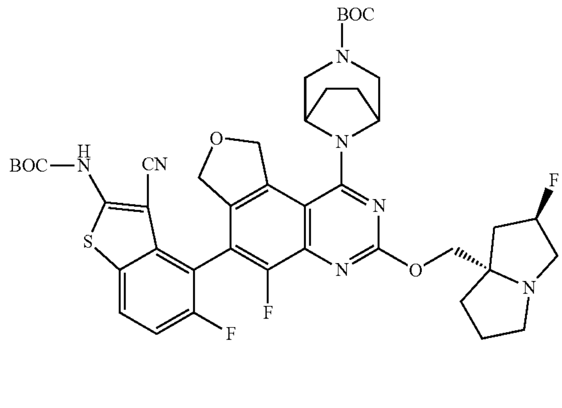 [SMILES: CC(C)(C)OC(=O)Nc1sc2ccc(F)c(-c3c4c(c5c(N6C7CCC6CN(C(=O)OC(C)(C)C)C7)nc(OC[C@@]67CCCN6C[C@H](F)C7)nc5c3F)COC4)c2c1C#N] | 848 |
| 268[6] | tert-Butyl 8-[6-[2-(tert-butoxycarbonylamino)-3-cyano-5-fluoro-benzothiophen-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate | 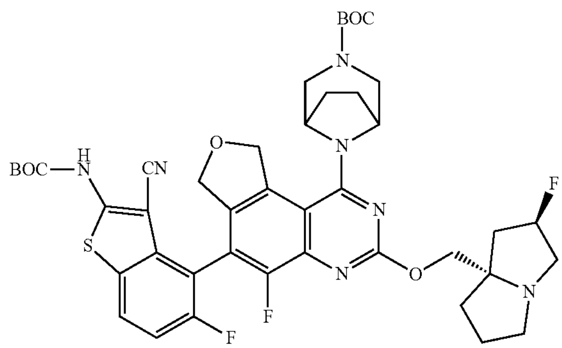 [SMILES: CC(C)(C)OC(=O)Nc1sc2ccc(F)c(-c3c4c(c5c(N6C7CCC6CN(C(=O)OC(C)(C)C)C7)nc(OC[C@@]67CCCN6C[C@H](F)C7)nc5c3F)COC4)c2c1C#N] | 848 |
| 269 | tert-Butyl 8-[6-[2-(tert-butoxycarbonylamino)-3-cyano-5-fluoro-benzofuran-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate | 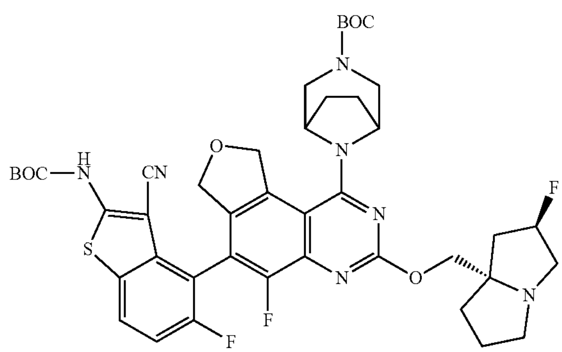 [SMILES: CC(C)(C)OC(=O)Nc1sc2ccc(F)c(-c3c4c(c5c(N6C7CCC6CN(C(=O)OC(C)(C)C)C7)nc(OC[C@@]67CCCN6C[C@H](F)C7)nc5c3F)COC4)c2c1C#N] | 832 |
| 270 | tert-Butyl 8-[6-[2-(tert-butoxycarbonylamino)-3-cyano-7-fluoro-benzofuran-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate | 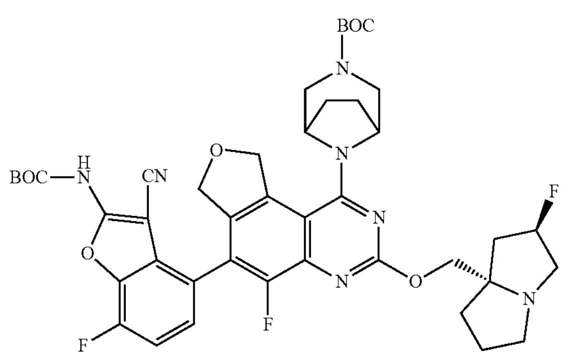 [SMILES: CC(C)(C)OC(=O)Nc1oc2c(F)ccc(-c3c4c(c5c(N6C7CCC6CN(C(=O)OC(C)(C)C)C7)nc(OC[C@@]67CCCN6C[C@H](F)C7)nc5c3F)COC4)c2c1C#N] | 832 |

TABLE 13-continued

| Preparation | Chemical Name | Structure | MS (ES) m/z (M + 1) |
|---|---|---|---|
| 271[6] | tert-Butyl 8-[6-[2-(tert-butoxycarbonylamino)-3-cyano-5-fluoro-benzothiophen-4-yl]-5-fluoro-3-[[(2S)-1-methylpyrrolidin-2-yl]methoxy]-7,9-dihydrofuro[3,4-f]quinazolin-1-yl]-3,8-diazabicyclo[3.2.1]octane-3-carboxylate | 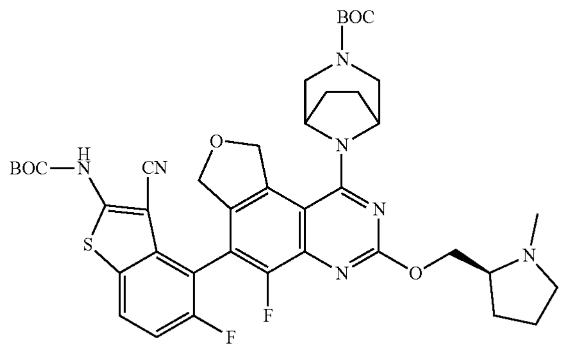 [SMILES: CN1CCC[C@H]1COc1nc(N2C3CCC2CN(C(=O)OC(C)(C)C)C3)c2c3c(c(-c4c(F)ccc5sc(NC(=O)OC(C)(C)C)c(C#N)c45)c(F)c2n1)COC3] | 804 |
| 272[6] | tert-Butyl 8-[6-[2-(tert-butoxycarbonylamino)-3-cyano-5-fluoro-benzothiophen-4-yl]-3-[3-(dimethylamino)azetidin-1-yl]-5-fluoro-7,9-dihydrofuro[3,4-f]quinazolin-1-yl]-3,8-diazabicyclo[3.2.1]octane-3-carboxylate | 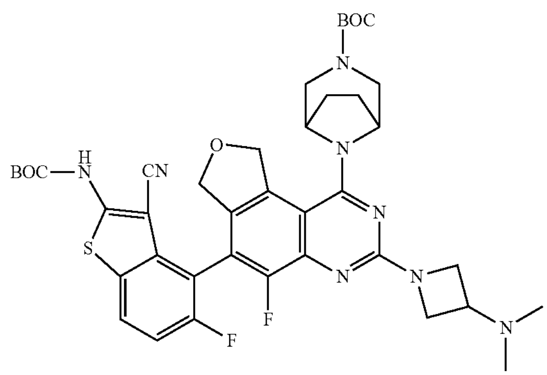 [SMILES: CN(C)C1CN(c2nc(N3C4CCC3CN(C(=O)OC(C)(C)C)C4)c3c4c(c(-c5c(F)ccc6sc(NC(=O)OC(C)(C)C)c(C#N)c56)c(F)c3n2)COC4)C1] | 789 |
| 273[6] | tert-Butyl 8-[6-[2-(tert-butoxycarbonylamino)-3-cyano-5-fluoro-benzothiophen-4-yl]-5-fluoro-3-[[(2S,4R)-4-fluoro-1-methyl-pyrrolidin-2-yl]methoxy]-7,9-dihydrofuro[3,4-f]quinazolin-1-yl]-3,8-diazabicyclo[3.2.1]octane-3-carboxylate | 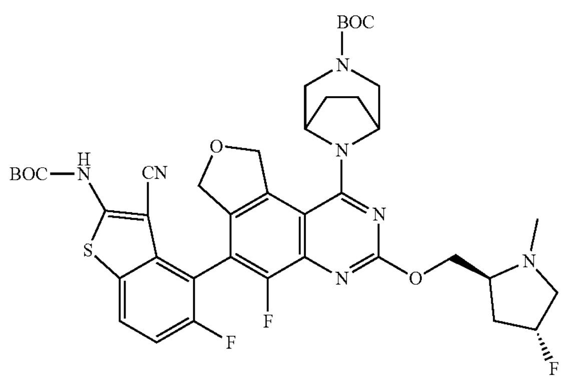 [SMILES: CN1C[C@H](F)C[C@H]1COc1nc(N2C3CCC2CN(C(=O)OC(C)(C)C)C3)c2c3c(c(-c4c(F)ccc5sc(NC(=O)OC(C)(C)C)c(C#N)c45)c(F)c2n1)COC3] | 822 |
| 274[6] | tert-Butyl 8-[6-[2-(tert-butoxycarbonylamino)-3-cyano-5-fluoro-benzothiophen-4-yl]-5-fluoro-3-[[(2S)-1-(2-fluoroethyl)pyrrolidin-2-yl]methoxy]-7,9-dihydrofuro[3,4-f]quinazolin-1-yl]-3,8-diazabicyclo[3.2.1]octane-3-carboxylate | 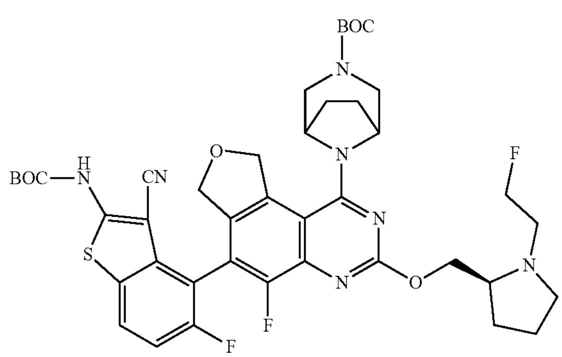 [SMILES: CC(C)(C)OC(=O)Nc1sc2ccc(F)c(-c3c4c(c5c(N6C7CCC6CN(C(=O)OC(C)(C)C)C7)nc(OC[C@@H]6CCCN6CCF)nc5c3F)COC4)c2c1C#N] | 836 |

TABLE 13-continued

| Preparation | Chemical Name | Structure | MS (ES) m/z (M + 1) |
|---|---|---|---|
| 275[6] | tert-Butyl 8-[6-[2-(tert-butoxycarbonylamino)-3-cyano-5-fluoro-benzothiophen-4-yl]-3-[[(2R)-1,4-dioxan-2-yl]methoxy]-5-fluoro-7,9-dihydrofuro[3,4-f]quinazolin-1-yl]-3,8-diazabicyclo[3.2.1]octane-3-carboxylate | 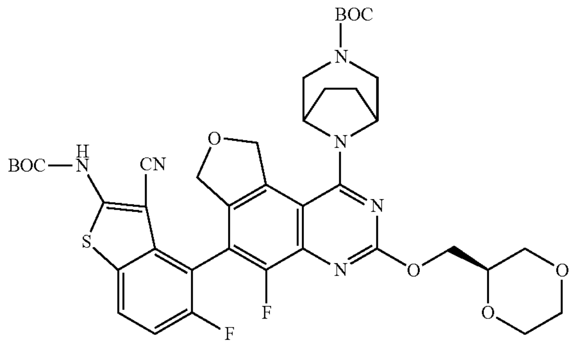 [SMILES: CC(C)(C)OC(=O)Nc1sc2ccc(F)c(-c3c4c(c5c(N6C7CCC6CN(C(=O)OC(C)(C)C)C7)nc(OC[C@H]6COCCO6)nc5c3F)COC4)c2c1C#N] | 807 |
| 276[6] | tert-Butyl 8-[6-[2-(tert-butoxycarbonylamino)-3-cyano-5-fluoro-benzothiophen-4-yl]-5-fluoro-3-[[(2R)-tetrahydrofuran-2-yl]methoxy]-7,9-dihydrofuro[3,4-f]quinazolin-1-yl]-3,8-diazabicyclo[3.2.1]octane-3-carboxylate | 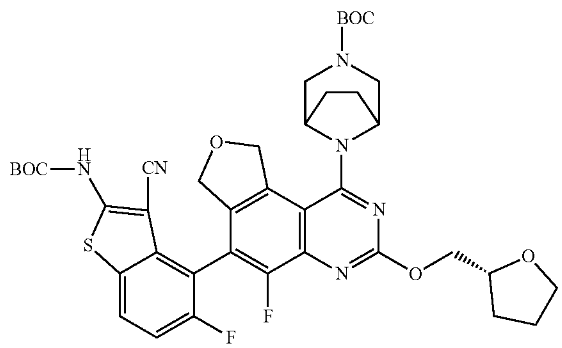 [SMILES: CC(C)(C)OC(=O)Nc1sc2ccc(F)c(-c3c4c(c5c(N6C7CCC6CN(C(=O)OC(C)(C)C)C7)nc(OC[C@H]6CCCO6)nc5c3F)COC4)c2c1C#N] | 791 |
| 277[6] | tert-Butyl 8-[6-[2-(tert-butoxycarbonylamino)-3-cyano-5-fluoro-benzothiophen-4-yl]-3-[2-(dimethylamino)ethoxy]-5-fluoro-7,9-dihydrofuro[3,4-f]quinazolin-1-yl]-3,8-diazabicyclo[3.2.1]octane-3-carboxylate | 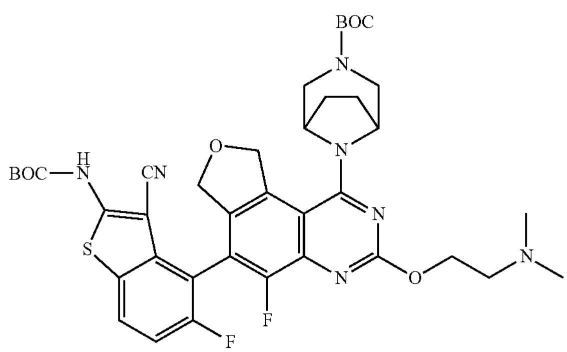 [SMILES: CN(C)CCOc1nc(N2C3CCC2CN(C(=O)OC(C)(C)C)C3)c2c3c(c(-c4c(F)ccc5sc(NC(=O)OC(C)(C)C)c(C#N)c45)c(F)c2n1)COC3] | 778 |
| 278[6] | tert-Butyl 8-[6-[2-(tert-butoxycarbonylamino)-3-cyano-5-fluoro-benzothiophen-4-yl]-5-fluoro-3-[2-[(3S)-3-fluoropyrrolidin-1-yl]ethoxy]-7,9-dihydrofuro[3,4-f]quinazolin-1-yl]-3,8-diazabicyclo[3.2.1]octane-3-carboxylate | 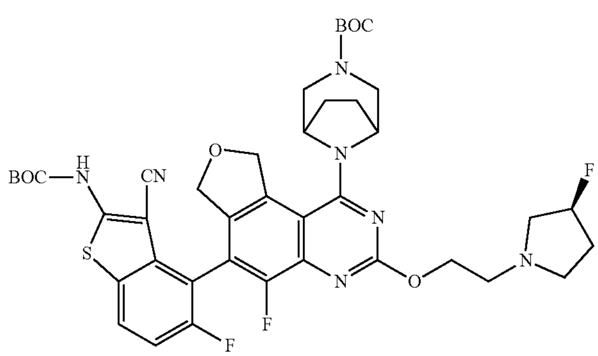 [SMILES: CC(C)(C)OC(=O)Nc1sc2ccc(F)c(-c3c4c(c5c(N6C7CCC6CN(C(=O)OC(C)(C)C)C7)nc(OCCN6CC[C@H](F)C6)nc5c3F)COC4)c2c1C#N] | 822 |

TABLE 13-continued

| Preparation | Chemical Name | Structure | MS (ES) m/z (M + 1) |
|---|---|---|---|
| 279[6] | tert-Butyl 8-[6-[2-(tert-butoxycarbonylamino)-3-cyano-5-fluoro-benzothiophen-4-yl]-5-fluoro-3-(2-morpholinoethoxy)-7,9-dihydrofuro[3,4-f]quinazolin-1-yl]-3,8-diazabicyclo[3.2.1]octane-3-carboxylate | 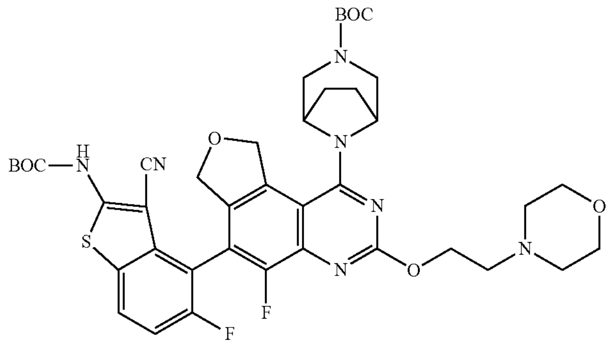 [SMILES: CC(C)(C)OC(=O)Nc1sc2ccc(F)c(-c3c4c(c5c(N6C7CCC6CN(C(=O)OC(C)(C)C)C7)nc(OCCN6CCOCC6)nc5c3F)COC4)c2c1C#N] | 820 |
| 280[6] | tert-Butyl 8-[6-[2-(tert-butoxycarbonylamino)-3-cyano-5-fluoro-benzothiophen-4-yl]-5-fluoro-3-[2-[(3S)-3-methoxypyrrolidin-1-yl]ethoxy]-7,9-dihydrofuro[3,4-f]quinazolin-1-yl]-3,8-diazabicyclo[3.2.1]octane-3-carboxylate | 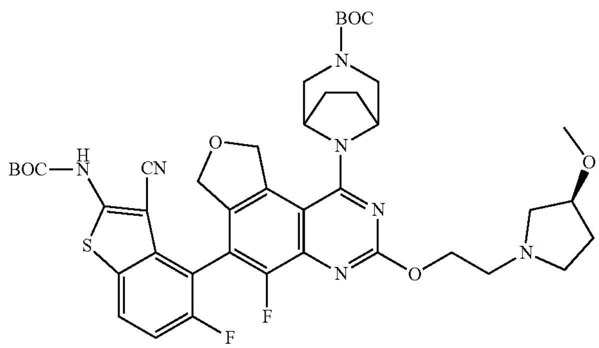 [SMILES: CO[C@H]1CCN(CCOc2nc(N3C4CCC3CN(C(=O)OC(C)(C)C)C4)c3c4c(c(-c5c(F)ccc6sc(NC(=O)OC(C)(C)C)c(C#N)c56)c(F)c3n2)COC4)C1] | 834 |
| 281[6] | tert-Butyl 8-[6-[2-(tert-butoxycarbonylamino)-3-cyano-5-fluoro-benzothiophen-4-yl]-5-fluoro-3-[[(2S)-1-methylazetidin-2-yl]methoxy]-7,9-dihydrofuro[3,4-f]quinazolin-1-yl]-3,8-diazabicyclo[3.2.1]octane-3-carboxylate | 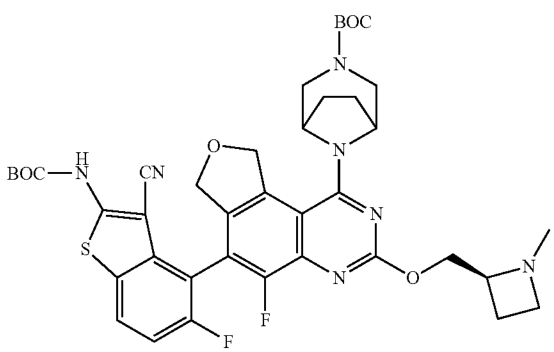 [SMILES: CN1CC[C@H]1COc1nc(N2C3CCC2CN(C(=O)OC(C)(C)C)C3)c2c3c(c(-c4c(F)ccc5sc(NC(=O)OC(C)(C)C)c(C#N)c45)c(F)c2n1)COC3] | 790 |
| 282[6] | tert-Butyl 8-[6-[2-(tert-butoxycarbonylamino)-3-cyano-5-fluoro-benzothiophen-4-yl]-5-fluoro-3-[(2S)-1-(2-hydroxyethyl)azetidin-2-yl]methoxy]-7,9-dihydrofuro[3,4-f]quinazolin-1-yl]-3,8-diazabicyclo[3.2.1]octane-3-carboxylate | 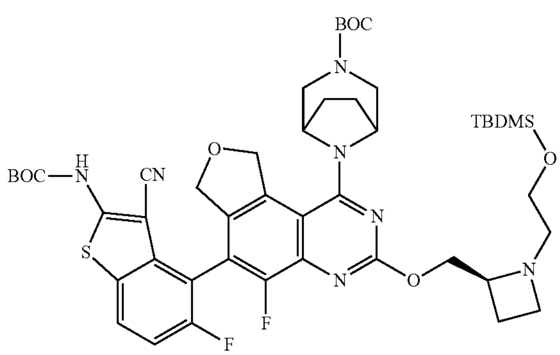 | 934 |

TABLE 13-continued

| Preparation | Chemical Name | Structure | MS (ES) m/z (M + 1) |
|---|---|---|---|
| 283[6] | tert-Butyl 8-[6-[2-(tert-butoxycarbonylamino)-3-cyano-5-fluoro-benzothiophen-4-yl]-5-fluoro-3-[(2S)-1-(2-hydroxyethyl)pyrrolidin-2-yl]methoxy]-7,9-dihydrofuro[3,4-f]quinazolin-1-yl]-3,8-diazabicyclo[3.2.1]octane-3-carboxylate | 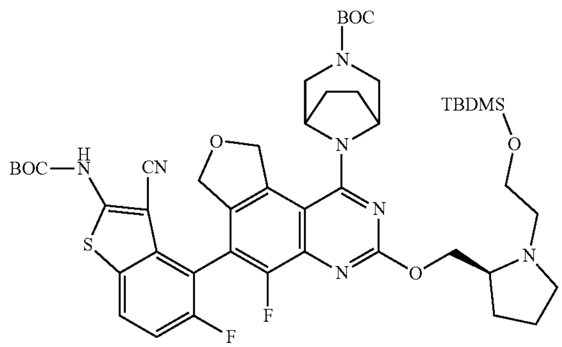 | 948 |
| 284[6] | tert-Butyl 8-[6-[2-(tert-butoxycarbonylamino)-3-cyano-5-fluoro-benzothiophen-4-yl]-5-fluoro-3-[[2-(hydroxymethyl)-1-methyl-pyrrolidin-2-yl]methoxy]-7,9-dihydrofuro[3,4-f]quinazolin-1-yl]-3,8-diazabicyclo[3.2.1]octane-3-carboxylate | 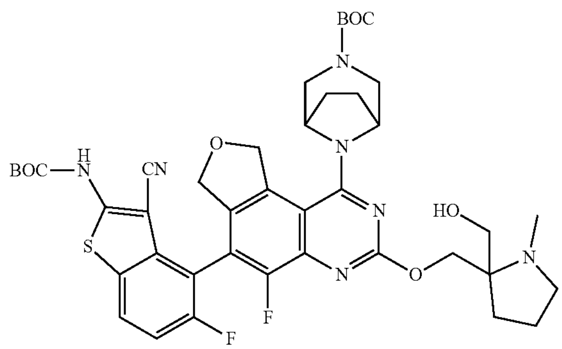 [SMILES: CN1CCCC1(CO)COc1nc(N2C3CCC2CN(C(=O)OC(C)(C)C)C3)c2c3c(c(-c4c(F)ccc5sc(NC(=O)OC(C)(C)C)c(C#N)c45)c(F)c2n1)COC3] | 834 |
| 285[6] | tert-Butyl 8-[6-[2-(tert-butoxycarbonylamino)-3-cyano-5-fluoro-benzothiophen-4-yl]-5-fluoro-3-[[(2S,4R)-4-hydroxy-1-methyl-pyrrolidin-2-yl]methoxy]-7,9-dihydrofuro[3,4-f]quinazolin-1-yl]-3,8-diazabicyclo[3.2.1]octane-3-carboxylate | 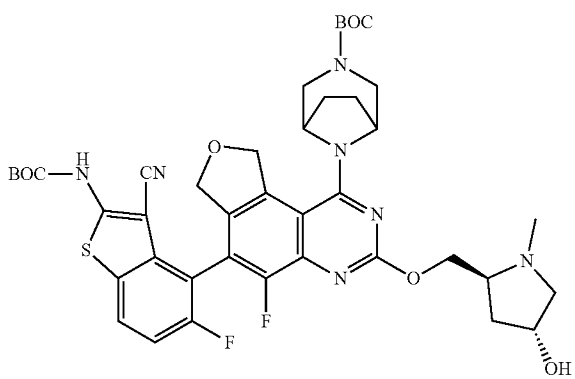 [SMILES: CN1C[C@H](O)C[C@H]1COc1nc(N2C3CCC2CN(C(=O)OC(C)(C)C)C3)c2c3c(c(-c4c(F)ccc5sc(NC(=O)OC(C)(C)C)c(C#N)c45)c(F)c2n1)COC3] | 820 |
| 286[6] | tert-Butyl 8-[6-[2-(tert-butoxycarbonylamino)-3-cyano-5-fluoro-benzothiophen-4-yl]-5-fluoro-3-[(2R,3S)-3-hydroxy-1-methyl-pyrrolidin-2-yl]methoxy]-7,9-dihydrofuro[3,4-f]quinazolin-1-yl]-3,8-diazabicyclo[3.2.1]octane-3-carboxylate | 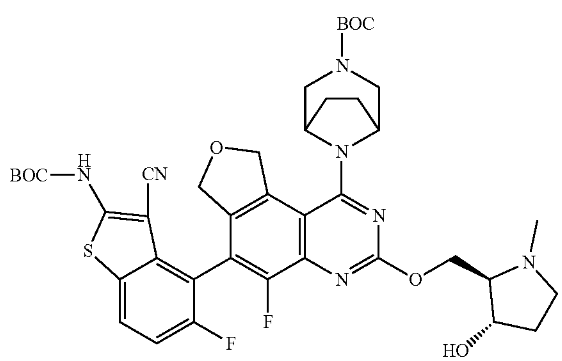 [SMILES: CN1CC[C@H](O)[C@H]1COc1nc(N2C3CCC2CN(C(=O)OC(C)(C)C)C3)c2c3c(c(-c4c(F)ccc5sc(NC(=O)OC(C)(C)C)c(C#N)c45)c(F)c2n1)COC3] | 820 |

TABLE 13-continued

| Preparation | Chemical Name | Structure | MS (ES) m/z (M + 1) |
|---|---|---|---|
| 287[6] | tert-Butyl 8-[6-[2-(tert-butoxycarbonylamino)-3-cyano-5-fluoro-benzothiophen-4-yl]-5-fluoro-3-[[(2S,4S)-4-fluoro-1-methyl-pyrrolidin-2-yl]methoxy]-7,9-dihydrofuro[3,4-f]quinazolin-1-yl]-3,8-diazabicyclo[3.2.1]octane-3-carboxylate | 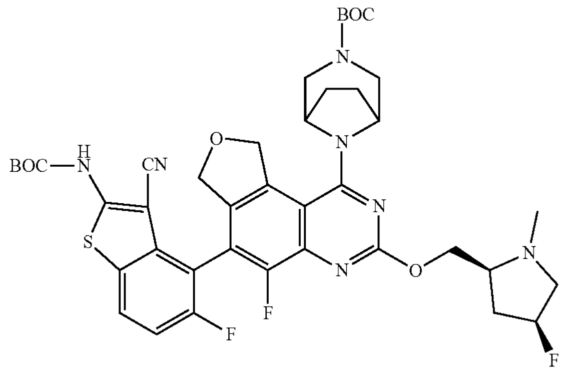 [SMILES: CN1C[C@@H](F)C[C@H]1COc1nc(N2C3CCC2CN(C(=O)OC(C)(C)C)C3)c2c3c(c(-c4c(F)ccc5sc(NC(=O)OC(C)(C)C)c(C#N)c45)c(F)c2n1)COC3] | 822 |
| 288[6] | tert-Butyl 8-[6-[2-(tert-butoxycarbonylamino)-3-cyano-5-fluoro-benzothiophen-4-yl]-3-[1-(dimethylamino)cyclopropyl]methoxy]-5-fluoro-7,9-dihydrofuro[3,4-f]quinazolin-1-yl]-3,8-diazabicyclo[3.2.1]octane-3-carboxylate | 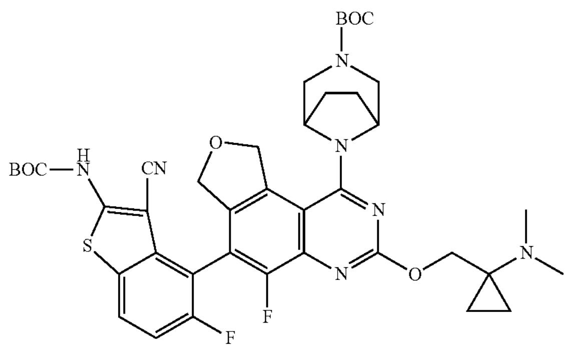 [SMILES: CN(C)C1(COc2nc(N3C4CCC3CN(C(=O)OC(C)(C)C)C4)c3c4c(c(-c5c(F)ccc6sc(NC(=O)OC(C)(C)C)c(C#N)c56)c(F)c3n2)COC4)CC1] | 804 |
| 289[7] | tert-Butyl 6-[6-[2-(tert-butoxycarbonylamino)-3-cyano-5-fluoro-benzothiophen-4-yl]-5-fluoro-3-[(2S)-1-methylpyrrolidin-2-yl]methoxy]-7,9-dihydrofuro[3,4-f]quinazolin-1-yl]-3,6-diazabicyclo[3.1.1]heptane-3-carboxylate | 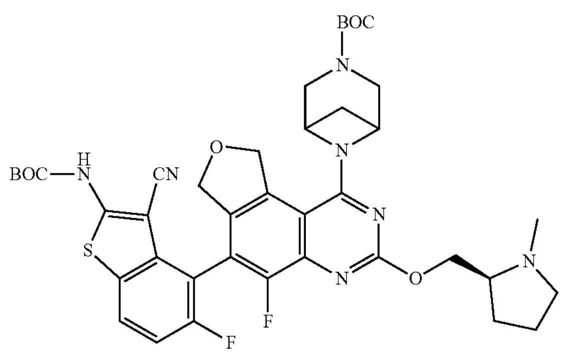 [SMILES: CN1CCC[C@H]1COc1nc(N2C3CC2CN(C(=O)OC(C)(C)C)C3)c2c3c(c(-c4c(F)ccc5sc(NC(=O)OC(C)(C)C)c(C#N)c45)c(F)c2n1)COC3] | 790 |
| 290[7] | tert-Butyl 6-[6-[2-(tert-butoxycarbonylamino)-3-cyano-5-fluoro-benzothiophen-4-yl]-5-fluoro-3-[[(2S,4R)-4-fluoro-1-methyl-pyrrolidin-2-yl]methoxy]-7,9-dihydrofuro[3,4-f]quinazolin-1-yl]-3,6-diazabicyclo[3.1.1]heptane-3-carboxylate | 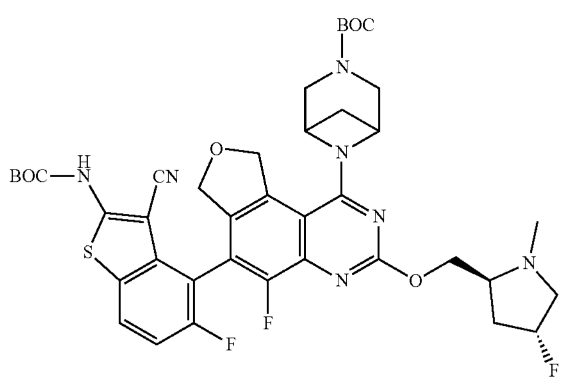 [SMILES: CN1C[C@H](F)C[C@H]1COc1nc(N2C3CC2CN(C(=O)OC(C)(C)C)C3)c2c3c(c(-c4c(F)ccc5sc(NC(=O)OC(C)(C)C)c(C#N)c45)c(F)c2n1)COC3] | 808 |

TABLE 13-continued

| Preparation | Chemical Name | Structure | MS (ES) m/z (M + 1) |
|---|---|---|---|
| 291[7] | tert-Butyl 6-[6-[2-(tert-butoxycarbonylamino)-3-cyano-5-fluoro-benzothiophen-4-yl]-5-fluoro-3-[[(2R)-tetrahydrofuran-2-yl]methoxy]-7,9-dihydrofuro[3,4-f]quinazolin-1-yl]-3,6-diazabicyclo[3.1.1]heptane-3-carboxylate | 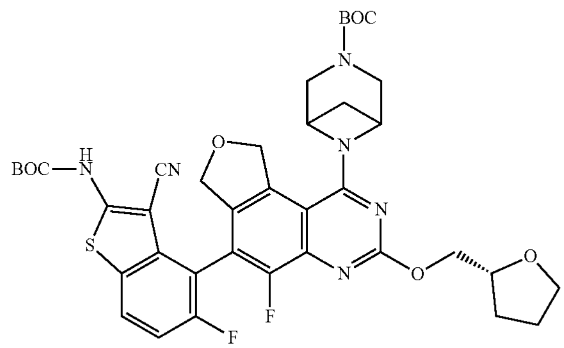 [SMILES: CC(C)(C)OC(=O)Nc1sc2ccc(F)c(-c3c4c(c5c(N6C7CC6CN(C(=O)OC(C)(C)C)C7)nc(OC[C@H]6CCCO6)nc5c3F)COC4)c2c1C#N] | 777 |
| 292[7] | tert-Butyl 6-[6-[2-(tert-butoxycarbonylamino)-3-cyano-5-fluoro-benzothiophen-4-yl]-5-fluoro-3-[[(2S)-1-(2-hydroxyethyl)pyrrolidin-2-yl]methoxy]-7,9-dihydrofuro[3,4-f]quinazolin-1-yl]-3,6-diazabicyclo[3.1.1]heptane-3-carboxylate | 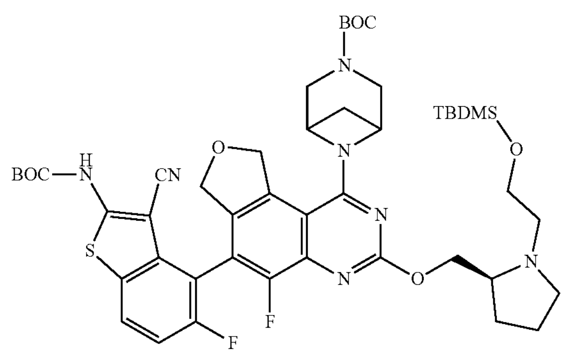 | 934 |
| 293 | tert-Butyl (1R,4R)-5-[6-[2-(tert-butoxycarbonylamino)-3-cyano-5-fluoro-benzofuran-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-2,5-diazabicyclo[2.2.1]heptane-2-carboxylate | 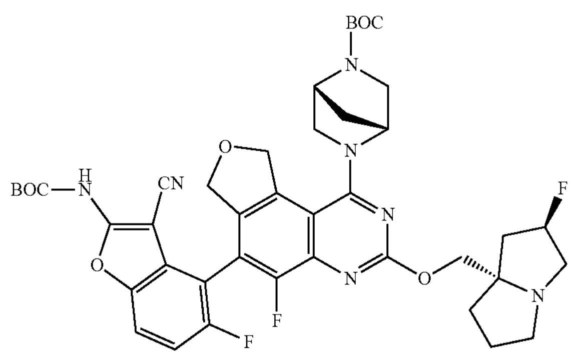 [SMILES: CC(C)(C)OC(=O)Nc1oc2ccc(F)c(-c3c4c(c5c(N6C[C@H]7C[C@@H]6CN7C(=O)OC(C)(C)C)nc(OC[C@@]67CCCN6C[C@H](F)C7)nc5c3F)COC4)c2c1C#N] | 818 |
| 294 | tert-Butyl N-[3-cyano-4-[1-[[1-(dimethylamino)cyclopentyl]methylamino]-5-fluoro-3-[(2R,8S)-2-fluoro-1,2,3,5,6,7-hexahydropyrrolizin-8-yl]methoxy]-7,9-dihydrofuro[3,4-f]quinazolin-6-yl]-5-fluoro-benzothiophen-2-yl]carbamate | 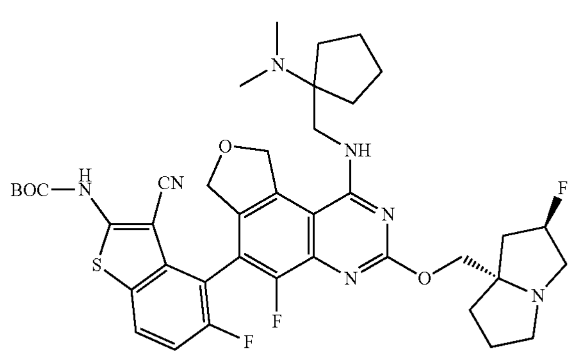 [SMILES: CN(C)C1(CNc2nc(OC[C@@]34CCCN3C[C@H](F)C4)nc3c(F)c(-c4c(F)ccc5sc(NC(=O)OC(C)(C)C)c(C#N)c45)c4c(c23)COC4)CCCC1] | 778 |

TABLE 13-continued

| Preparation | Chemical Name | Structure | MS (ES) m/z (M + 1) |
|---|---|---|---|
| 295 | tert-Butyl N-[3-cyano-5-fluoro-4-[5-fluoro-3-[[(2R,8S)-2-fluoro-1,2,3,5,6,7-hexahydropyrrolizin-8-yl]methoxy]-1-methoxy-7,9-dihydrofuro[3,4-f]quinazolin-6-yl]benzothiophen-2-yl]carbamate | 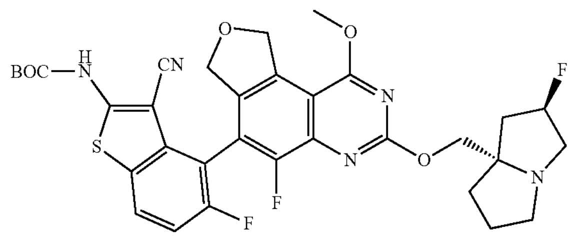 [SMILES: COc1nc(OC[C@@]23CCCN2C[C@H](F)C3)nc2c(F)c(-c3c(F)ccc4sc(NC(=O)OC(C)(C)C)c(C#N)c34)c3c(c12)COC3] | 668 |
| 311[6] | tert-Butyl 8-[6-[2-(tert-butoxycarbonylamino)-3-cyano-5-fluoro-benzothiophen-4-yl]-5-fluoro-3-[[(2S,4R)-4-methoxy-1-methyl-pyrrolidin-2-yl]methoxy]-7,9-dihydrofuro[3,4-f]quinazolin-1-yl]-3,8-diazabicyclo[3.2.1]octane-3-carboxylate | 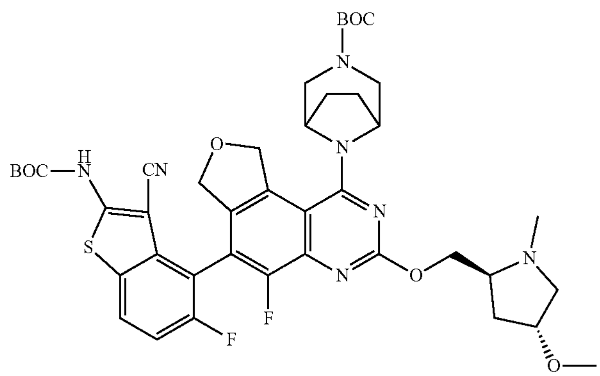 [SMILES: CO[C@@H]1C[C@@H](COc2nc(N3C4CCC3CN(C(=O)OC(C)(C)C)C4)c3c4c(c(-c5c(F)ccc6sc(NC(=O)OC(C)(C)C)c(C#N)c56)c(F)c3n2)COC4)N(C)C1] | 834 |
| 312[6] | tert-Butyl 8-[6-[2-(tert-butoxycarbonylamino)-3-cyano-5-fluoro-benzothiophen-4-yl]-5-fluoro-3-[2-(3-methoxyazetidin-1-yl)ethoxy]-7,9-dihydrofuro[3,4-f]quinazolin-1-yl]-3,8-diazabicyclo[3.2.1]octane-3-carboxylate | 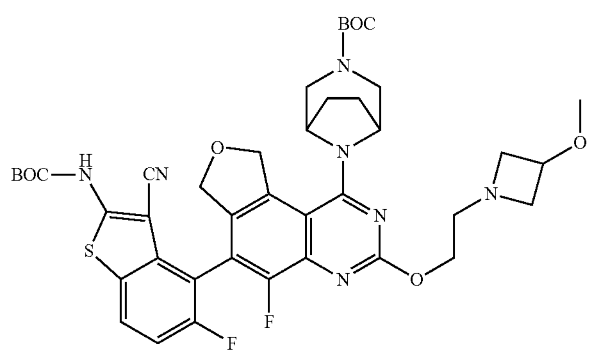 [SMILES: COC1CN(CCOc2nc(N3C4CCC3CN(C(=O)OC(C)(C)C)C4)c3c4c(c(-c5c(F)ccc6sc(NC(=O)OC(C)(C)C)c(C#N)c56)c(F)c3n2)COC4)C1] | 820 |
| 313 | tert-Butyl 8-[6-[2-(tert-butoxycarbonylamino)-3-cyano-7-fluoro-thieno[3,2-c]pyridin-4-yl]-5-fluoro-3-[[(2R,8S)-2-methoxy-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate | 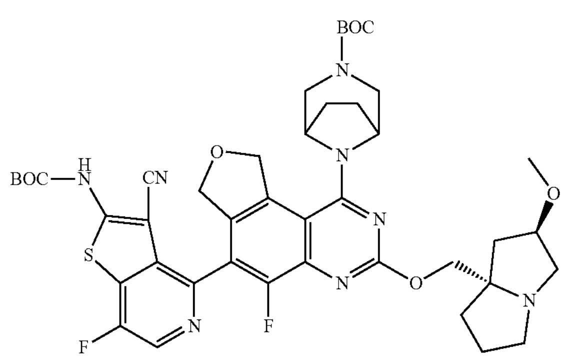 [SMILES: CO[C@H]1CN2CCC[C@@]2(COc2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)C1] | 861 |

TABLE 13-continued

| Preparation | Chemical Name | Structure | MS (ES) m/z (M + 1) |
|---|---|---|---|
| 314 | tert-Butyl 8-[6-[2-(tert-butoxycarbonylamino)-3-cyano-7-fluoro-thieno[3,2-c]pyridin-4-yl]-5-fluoro-3-[(2S)-1-methylpyrrolidin-2-yl]methoxy]-7,9-dihydrofuro[3,4-f]quinazolin-1-yl]-3,8-diazabicyclo[3.2.1]octane-3-carboxylate | 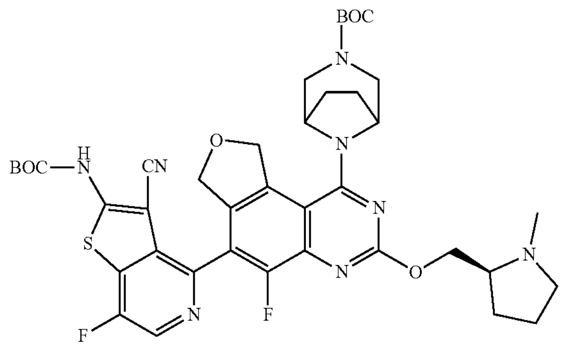 [SMILES: CN1CCC[C@H]1COc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3] | 805 |
| 315 | tert-Butyl 8-[6-[2-(tert-butoxycarbonylamino)-3-cyano-7-fluoro-thieno[3,2-c]pyridin-4-yl]-5-fluoro-3-[[(2S,4R)-4-fluoro-1-methyl-pyrrolidin-2-yl]methoxy]-7,9-dihydrofuro[3,4-f]quinazolin-1-yl]-3,8-diazabicyclo[3.2.1]octane-3-carboxylate | 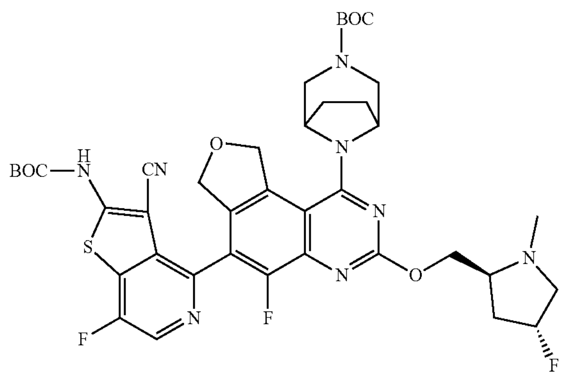 [SMILES: CN1C[C@H](F)C[C@H]1COc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3] | 823 |
| 316 | tert-Butyl 8-[6-[2-(tert-butoxycarbonylamino)-3-cyano-7-fluoro-thieno[3,2-c]pyridin-4-yl]-5-fluoro-3-[[(2S,4R)-4-methoxy-1-methyl-pyrrolidin-2-yl]methoxy]-7,9-dihydrofuro[3,4-f]quinazolin-1-yl]-3,8-diazabicyclo[3.2.1]octane-3-carboxylate | 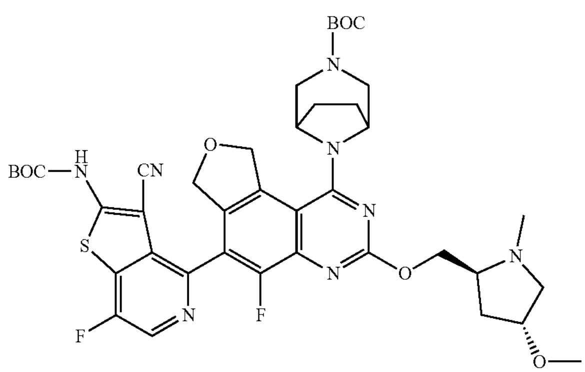 [SMILES: CO[C@@H]1C[C@@H](COc2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)N(C)C1] | 835 |
| 317 | tert-Butyl 8-[6-[2-(tert-butoxycarbonylamino)-3-cyano-7-fluoro-thieno[3,2-c]pyridin-4-yl]-5-fluoro-3-(1,2,3,5,6,7-hexahydropyrrolizin-8-ylmethoxy)-7,9-dihydrofuro[3,4-f]quinazolin-1-yl]-3,8-diazabicyclo[3.2.1]octane-3-carboxylate | 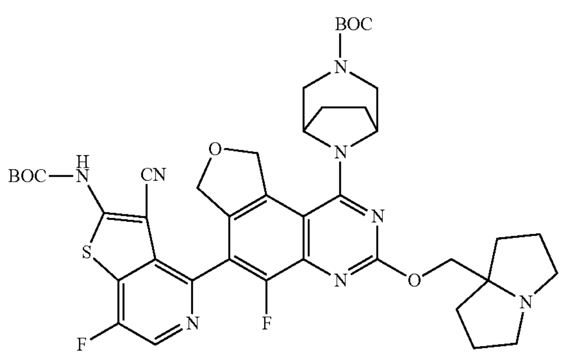 [SMILES: CC(C)(C)OC(=O)Nc1sc2c(F)cnc(-c3c4c(c5c(N6C7CCC6CN(C(=O)OC(C)(C)C)C7)nc(OCC67CCCN6CCC7)nc5c3F)COC4)c2c1C#N] | 831 |

TABLE 13-continued

| Preparation | Chemical Name | Structure | MS (ES) m/z (M + 1) |
|---|---|---|---|
| 318 | tert-Butyl 8-[6-[2-(tert-butoxycarbonylamino)-3-cyano-7-fluoro-thieno[3,2-c]pyridin-4-yl]-3-[(6,6-difluoro-2,3,5,7-tetrahydro-1H-pyrrolizin-8-yl)methoxy]-5-fluoro-7,9-dihydrofuro[3,4-f]quinazolin-1-yl]-3,8-diazabicyclo[3.2.1]octane-3-carboxylate | 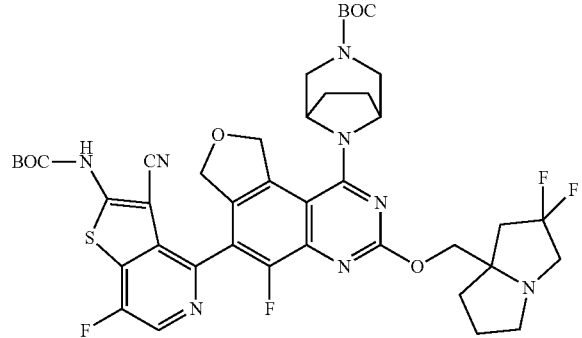 [SMILES: CC(C)(C)OC(=O)Nc1sc2c(F)cnc(-c3c4c(c5c(N6C7CCC6CN(C(=O)OC(C)(C)C)C7)nc(OCC67CCCN6CC(F)(F)C7)nc5c3F)COC4)c2c1C#N] | 867 |
| 319 | tert-Butyl 8-[3-(1-azabicyclo[3.2.0]heptan-5-ylmethoxy)-6-[2-(tert-butoxycarbonylamino)-3-cyano-7-fluoro-thieno[3,2-c]pyridin-4-yl]-5-fluoro-7,9-dihydrofuro[3,4-f]quinazolin-1-yl]-3,8-diazabicyclo[3.2.1]octane-3-carboxylate | 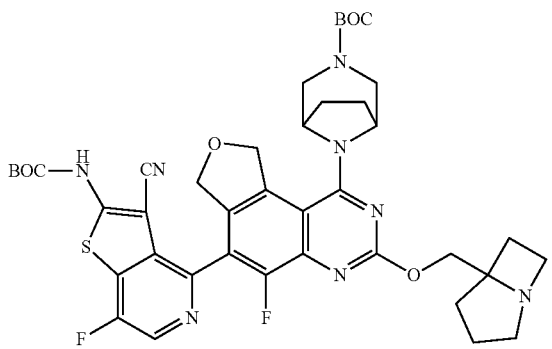 [SMILES: CC(C)(C)OC(=O)Nc1sc2c(F)cnc(-c3c4c(c5c(N6C7CCC6CN(C(=O)OC(C)(C)C)C7)nc(OCC67CCCN6CC7)nc5c3F)COC4)c2c1C#N] | 817 |
| 320 | tert-Butyl 8-[6-[2-(tert-butoxycarbonylamino)-3-cyano-7-fluoro-thieno[3,2-c]pyridin-4-yl]-5-fluoro-3-[[(2SR,8SR)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate | 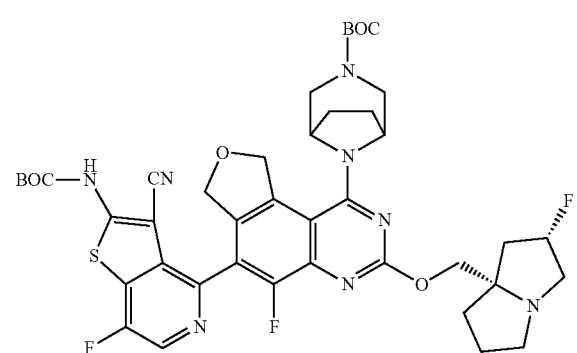 [SMILES: CC(C)(C)OC(=O)Nc1sc2c(F)cnc(-c3c4c(c5c(N6C7CCC6CN(C(=O)OC(C)(C)C)C7)nc(OC[C@@]67CCCN6C[C@@H](F)C7)nc5c3F)COC4)c2c1C#N] | 849 |
| 321 | tert-Butyl N-[4-[5-chloro-3-[[(2S)-1-methylpyrrolidin-2-yl]methoxy]-7,9-dihydrofuro[3,4-f]quinazolin-6-yl]-3-cyano-7-fluoro-benzothiophen-2-yl]carbamate | 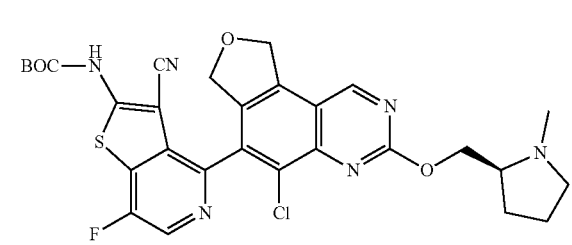 [SMILES: CN1CCC[C@H]1COc1ncc2c3c(c(-c4ncc(F)c5sc(NC(=O)OC(C)(C)C)c(C#N)c45)c(Cl)c2n1)COC3] | 610 |
| 322 | tert-Butyl N-[4-[5-chloro-3-[[(2R,8S)-2-fluoro-1,2,3,5,6,7-hexahydropyrrolizin-8-yl]methoxy]-7,9-dihydrofuro[3,4-f]quinazolin-6-yl]-3-cyano-7-fluoro-benzothiophen-2-yl]carbamate | 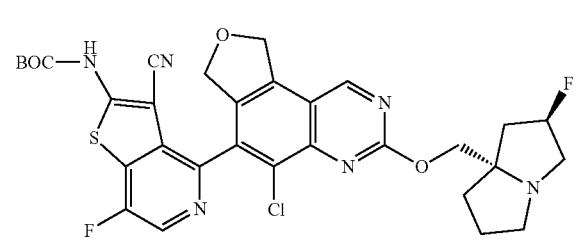 [SMILES: CC(C)(C)OC(=O)Nc1sc2c(F)cnc(-c3c4c(c5cnc(OC[C@@]67CCCN6C[C@H](F)C7)nc5c3Cl)COC4)c2c1C#N] | 654 |

TABLE 13-continued

| Preparation | Chemical Name | Structure | MS (ES) m/z (M + 1) |
|---|---|---|---|
| 334 | tert-Butyl 8-[6-[2-(tert-butoxycarbonylamino)-3-cyano-7-fluoro-thieno[3,2-c]pyridin-4-yl]-5-fluoro-3-[[(2R)-4-methylmorpholin-2-yl]methoxy]-7,9-dihydrofuro[3,4-f]quinazolin-1-yl]-3,8-diazabicyclo[3.2.1]octane-3-carboxylate | 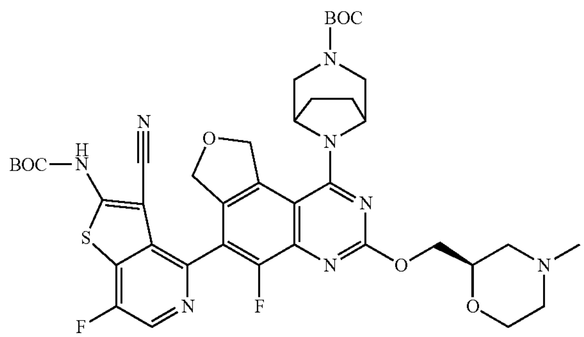 | 821 |
| 335 | tert-Butyl 8-[6-[2-(tert-butoxycarbonylamino)-3-cyano-7-fluoro-thieno[3,2-c]pyridin-4-yl]-5-fluoro-3-[[(3R,4S)-4-fluoro-1-methyl-3-piperidyl]methoxy]-7,9-dihydrofuro[3,4-f]quinazolin-1-yl]-3,8-diazabicyclo[3.2.1]octane-3-carboxylate | 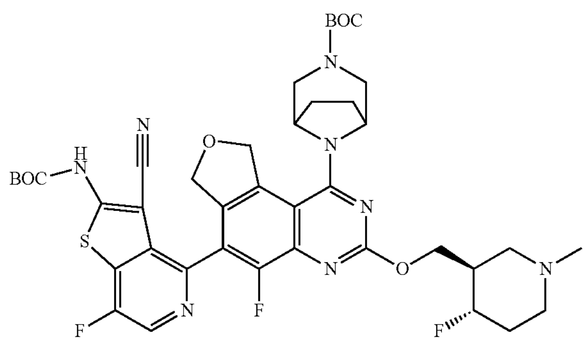 [SMILES: CN1CC[C@H](F)[C@@H](COc2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)C1] | 837 |
| 336 | tert-Butyl 8-[6-[2-(tert-butoxycarbonylamino)-3-cyano-7-fluoro-thieno[3,2-c]pyridin-4-yl]-5-fluoro-3-(2-imidazol-1-ylethoxy)-7,9-dihydrofuro[3,4-f]quinazolin-1-yl]-3,8-diazabicyclo[3.2.1]octane-3-carboxylate | 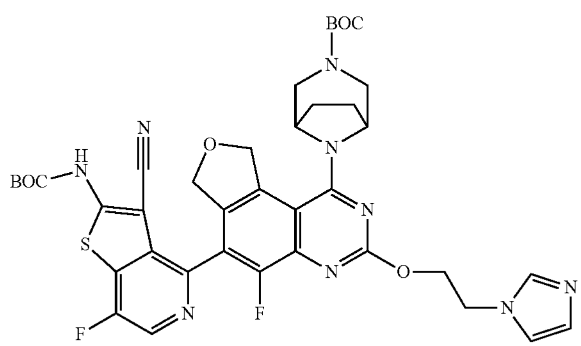 [SMILES: CC(C)(C)OC(=O)Nc1sc2c(F)cnc(-c3c4c(c5c(N6C7CCC6CN(C(=O)OC(C)(C)C)C7)nc(OCCn6ccnc6)nc5c3F)COC4)c2c1C#N] | 802 |
| 337 | tert-Butyl 8-[6-[2-(tert-butoxycarbonylamino)-3-cyano-7-fluoro-thieno[3,2-c]pyridin-4-yl]-5-fluoro-3-[[(2R,3S)-3-fluoro-1-methyl-pyrrolidin-2-yl]methoxy]-7,9-dihydrofuro[3,4-f]quinazolin-1-yl]-3,8-diazabicyclo[3.2.1]octane-3-carboxylate | 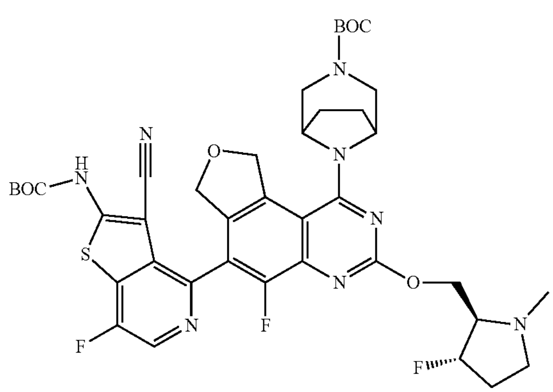 [SMILES: CN1CC[C@H](F)[C@H]1COc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3] | 823 |

TABLE 13-continued

| Preparation | Chemical Name | Structure | MS (ES) m/z (M + 1) |
|---|---|---|---|
| 338 | tert-Butyl 8-[6-[2-(tert-butoxycarbonylamino)-3-cyano-7-fluoro-thieno[3,2-c]pyridin-4-yl]-5-fluoro-3-[(1S)-1-[(2R)-4-methylmorpholin-2-yl]ethoxy]-7,9-dihydrofuro[3,4-f]quinazolin-1-yl]-3,8-diazabicyclo[3.2.1]octane-3-carboxylate | 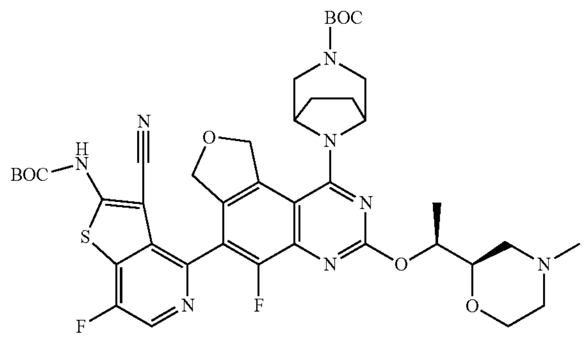 [SMILES: C[C@H](Oc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3)[C@H]1CN(C)CCO1] | 835 |
| 339 | tert-Butyl 8-[6-[2-(tert-butoxycarbonylamino)-3-cyano-7-fluoro-thieno[3,2-c]pyridin-4-yl]-5-fluoro-3-(2-morpholinoethoxy)-7,9-dihydrofuro[3,4-f]quinazolin-1-yl]-3,8-diazabicyclo[3.2.1]octane-3-carboxylate | 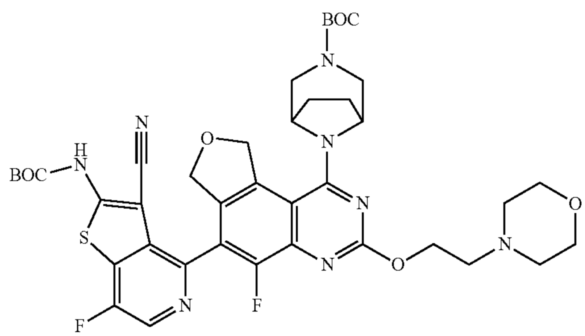 [SMILES: CC(C)(C)OC(=O)Nc1sc2c(F)cnc(-c3c4c(c5c(N6C7CCC6CN(C(=O)OC(C)(C)C)C7)nc(OCCN6CCOCC6)nc5c3F)COC4)c2c1C#N] | 821 |
| 340 | tert-Butyl 8-[6-[2-(tert-butoxycarbonylamino)-3-cyano-7-fluoro-thieno[3,2-c]pyridin-4-yl]-3-[(4,4-difluoro-1-methyl-3-piperidyl)methoxy]-5-fluoro-7,9-dihydrofuro[3,4-f]quinazolin-1-yl]-3,8-diazabicyclo[3.2.1]octane-3-carboxylate | 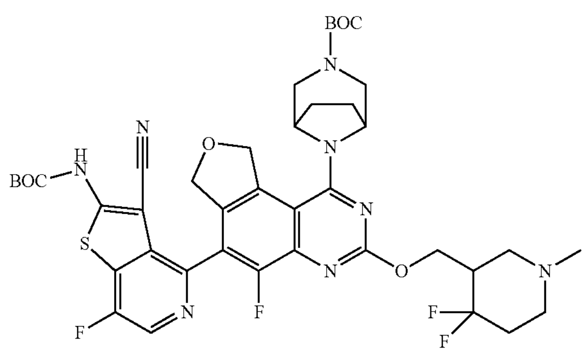 [SMILES: CN1CCC(F)(F)C(COc2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)C1] | 855 |
| 341[6] | tert-Butyl 8-[6-[2-(tert-butoxycarbonylamino)-3-cyano-5-fluoro-benzothiophen-4-yl]-3-[(4,4-difluoro-1-methyl-3-piperidyl)methoxy]-5-fluoro-7,9-dihydrofuro[3,4-f]quinazolin-1-yl]-3,8-diazabicyclo[3.2.1]octane-3-carboxylate | 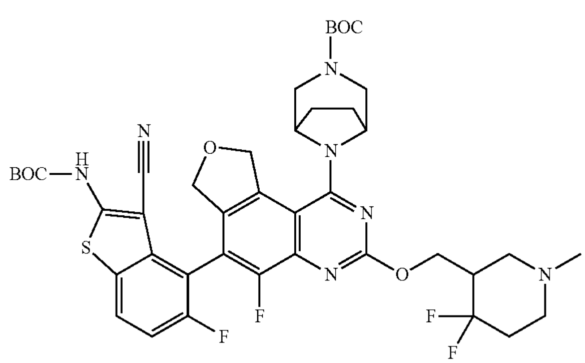 [SMILES: CN1CCC(F)(F)C(COc2nc(N3C4CCC3CN(C(=O)OC(C)(C)C)C4)c3c4c(c(-c5c(F)ccc6sc(NC(=O)OC(C)(C)C)c(C#N)c56)c(F)c3n2)COC4)C1] | 854 |

TABLE 13-continued

| Preparation | Chemical Name | Structure | MS (ES) m/z (M + 1) |
|---|---|---|---|
| 342[6] | tert-Butyl 8-[6-[2-(tert-butoxycarbonylamino)-3-cyano-5-fluoro-benzothiophen-4-yl]-5-fluoro-3-[[(2R)-4-methylmorpholin-2-yl]methoxy]-7,9-dihydrofuro[3,4-f]quinazolin-1-yl]-3,8-diazabicyclo[3.2.1]octane-3-carboxylate | 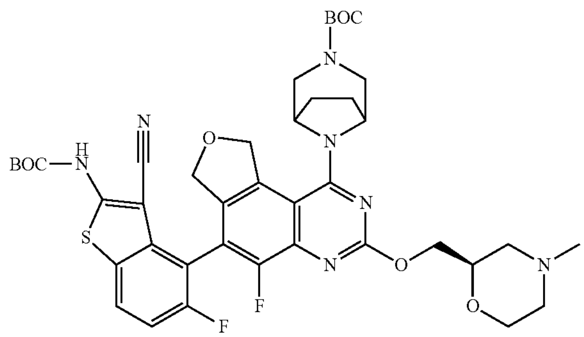 [SMILES: CN1CCO[C@@H](COc2nc(N3C4CCC3CN(C(=O)OC(C)(C)C)C4)c3c4c(c(-c5c(F)ccc6sc(NC(=O)OC(C)(C)C)c(C#N)c56)c(F)c3n2)COC4)C1] | 820 |
| 343 | tert-Butyl 8-[6-[2-(tert-butoxycarbonylamino)-3-cyano-5-fluoro-benzofuran-4-yl]-5-fluoro-3-[[(2S,4R)-4-fluoro-1-methyl-pyrrolidin-2-yl]methoxy]-7,9-dihydrofuro[3,4-f]quinazolin-1-yl]-3,8-diazabicyclo[3.2.1]octane-3-carboxylate | 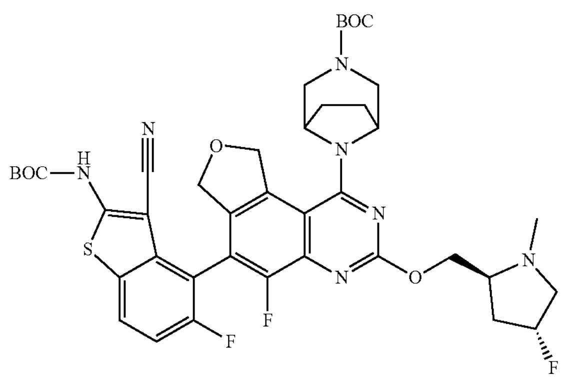 [SMILES: CN1C[C@H](F)C[C@H]1COc1nc(N2C3CCC2CN(C(=O)OC(C)(C)C)C3)c2c3c(c(-c4c(F)ccc5sc(NC(=O)OC(C)(C)C)c(C#N)c45)c(F)c2n1)COC3] | 806 |
| 344 | tert-Butyl 8-[6-[2-(tert-butoxycarbonylamino)-3-cyano-7-fluoro-thieno[3,2-c]pyridin-4-yl]-5-fluoro-3-[(1S)-1-methyl-2-morpholino-ethoxy]-7,9-dihydrofuro[3,4-f]quinazolin-1-yl]-3,8-diazabicyclo[3.2.1]octane-3-carboxylate | 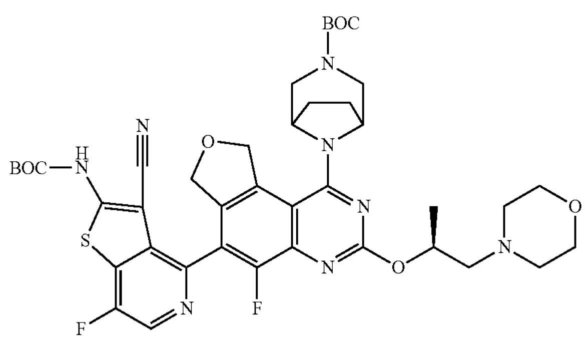 [SMILES: C[C@@H](CN1CCOCC1)Oc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3] | 835 |
| 345 | tert-Butyl 8-[6-[2-(tert-butoxycarbonylamino)-3-cyano-7-fluoro-thieno[3,2-c]pyridin-4-yl]-3-[(2S)-5,5-difluoro-1-methyl-2-piperidyl]methoxy]-5-fluoro-7,9-dihydrofuro[3,4-f]quinazolin-1-yl]-3,8-diazabicyclo[3.2.1]octane-3-carboxylate | 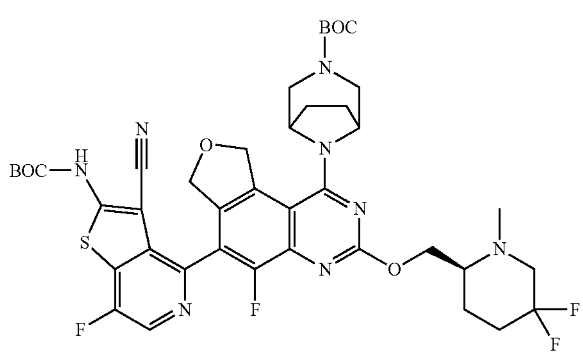 [SMILES: CN1CC(F)(F)CC[C@H]1COc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3] | 855 |

TABLE 13-continued

| Preparation | Chemical Name | Structure | MS (ES) m/z (M + 1) |
|---|---|---|---|
| 346 | tert-Butyl 8-[6-[2-(tert-butoxycarbonylamino)-3-cyano-5-fluoro-benzothiophen-4-yl]-5-fluoro-3-[[(3S)-4-methylmorpholin-3-yl]methoxy]-7,9-dihydrofuro[3,4-f]quinazolin-1-yl]-3,8-diazabicyclo[3.2.1]octane-3-carboxylate | 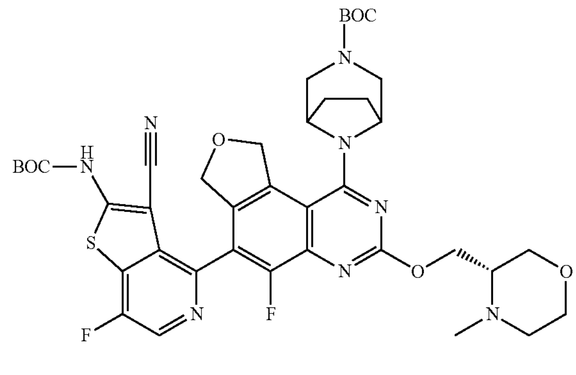 [SMILES: CN1CCOC[C@H]1COc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3] | 820 |
| 347 | tert-Butyl 8-[6-[2-(tert-butoxycarbonylamino)-3-cyano-7-fluoro-thieno[3,2-c]pyridin-4-yl]-3-[[1-[(dimethylamino)methyl]cyclopropyl]methoxy]-5-fluoro-7,9-dihydrofuro[3,4-f]quinazolin-1-yl]-3,8-diazabicyclo[3.2.1]octane-3-carboxylate | 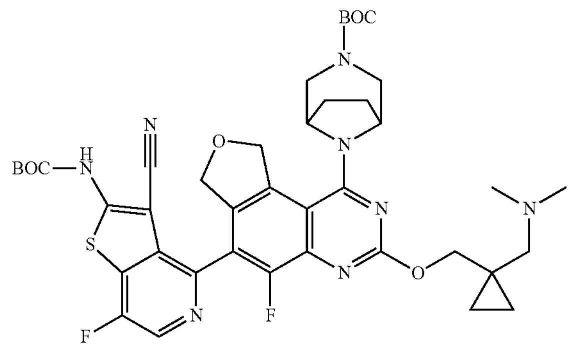 [SMILES: CN(C)CC1(COc2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)CC1] | 819 |
| 348 | tert-Butyl 8-[6-[2-(tert-butoxycarbonylamino)-3-cyano-7-fluoro-thieno[3,2-c]pyridin-4-yl]-5-fluoro-3-(2-pyrazol-1-ylethoxy)-7,9-dihydrofuro[3,4-f]quinazolin-1-yl]-3,8-diazabicyclo[3.2.1]octane-3-carboxylate | 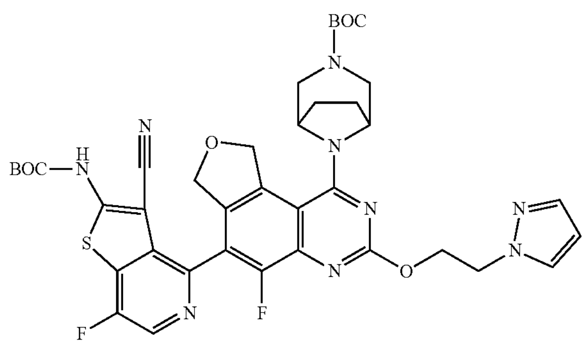 [SMILES: CC(C)(C)OC(=O)Nc1sc2c(F)cnc(-c3c4c(c5c(N6C7CCC6CN(C(=O)OC(C)(C)C)C7)nc(OCCn6cccn6)nc5c3F)COC4)c2c1C#N] | 802 |
| 349 | tert-Butyl 8-[6-[2-(tert-butoxycarbonylamino)-3-cyano-7-fluoro-thieno[3,2-c]pyridin-4-yl]-5-fluoro-3-[(2S)-2-morpholinopropoxy]-7,9-dihydrofuro[3,4-f]quinazolin-1-yl]-3,8-diazabicyclo[3.2.1]octane-3-carboxylate | 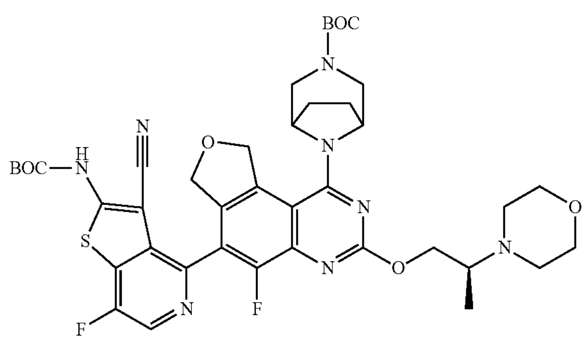 [SMILES: C[C@@H](COc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3)N1CCOCC1] | 835 |

TABLE 13-continued

| Preparation | Chemical Name | Structure | MS (ES) m/z (M + 1) |
|---|---|---|---|
| 350 | tert-Butyl 8-[6-[2-(tert-butoxycarbonylamino)-3-cyano-7-fluoro-thieno[3,2-c]pyridin-4-yl]-3-[[(2S)-4,4-difluoro-1-methyl-pyrrolidin-2-yl]methoxy]-5-fluoro-7,9-dihydrofuro[3,4-f]quinazolin-1-yl]-3,8-diazabicyclo[3.2.1]octane-3-carboxylate | 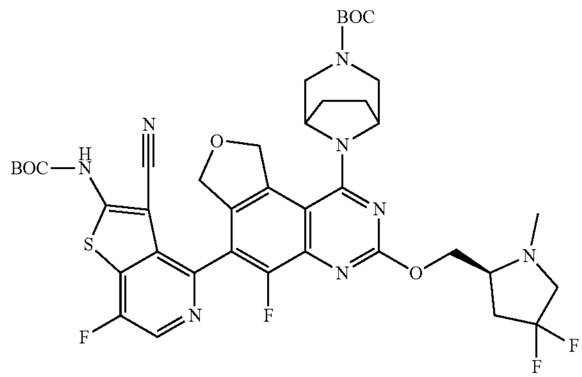 [SMILES: CN1CC(F)(F)C[C@H]1COc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3] | 841 |
| 351 | tert-Butyl 8-[6-[2-(tert-butoxycarbonylamino)-3-cyano-7-fluoro-thieno[3,2-c]pyridin-4-yl]-5-fluoro-3-[(3-fluoro-1-methyl-pyrrolidin-3-yl)methoxy]-7,9-dihydrofuro[3,4-f]quinazolin-1-yl]-3,8-diazabicyclo[3.2.1]octane-3-carboxylate | 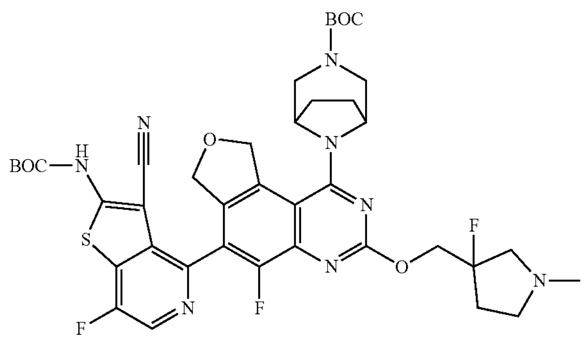 [SMILES: CN1CCC(F)(COc2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)C1] | 722 |
| 352 | tert-Butyl 8-[6-[2-(tert-butoxycarbonylamino)-3-cyano-7-fluoro-thieno[3,2-c]pyridin-4-yl]-3-[(3,3-difluoro-1-methyl-2-piperidyl)methoxy]-5-fluoro-7,9-dihydrofuro[3,4-f]quinazolin-1-yl]-3,8-diazabicyclo[3.2.1]octane-3-carboxylate | 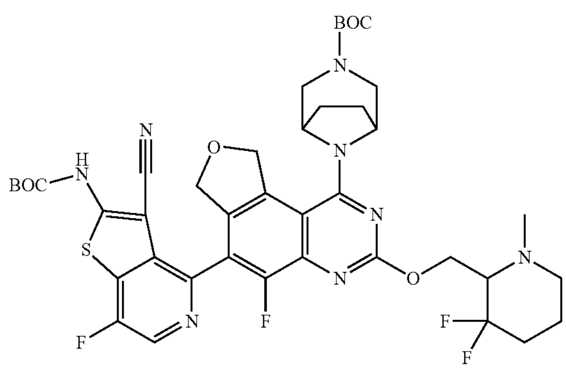 [SMILES: CN1CCCC(F)(F)C1COc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3] | 855 |
| 353 | tert-Butyl 8-[6-[2-(tert-butoxycarbonylamino)-3-cyano-7-fluoro-thieno[3,2-c]pyridin-4-yl]-3-[2-(4-ethyl-3-oxo-piperazin-1-yl)ethoxy]-5-fluoro-7,9-dihydrofuro[3,4-f]quinazolin-1-yl]-3,8-diazabicyclo[3.2.1]octane-3-carboxylate | 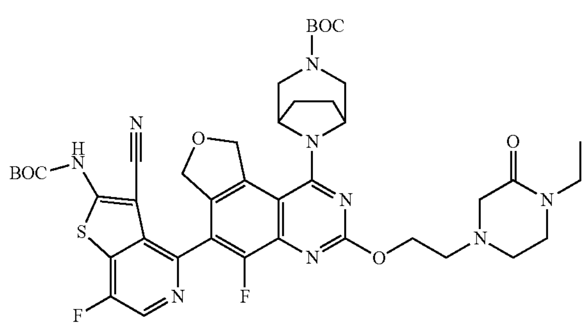 [SMILES: CCN1CCN(CCOc2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)CC1=O] | 862 |

TABLE 13-continued

| Preparation | Chemical Name | Structure | MS (ES) m/z (M + 1) |
|---|---|---|---|
| 354 | tert-Butyl 8-[6-[2-(tert-butoxycarbonylamino)-3-cyano-7-fluoro-thieno[3,2-c]pyridin-4-yl]-3-[(1-cyanocyclopropyl)methoxy]-5-fluoro-7,9-dihydrofuro[3,4-f]quinazolin-1-yl]-3,8-diazabicyclo[3.2.1]octane-3-carboxylate | 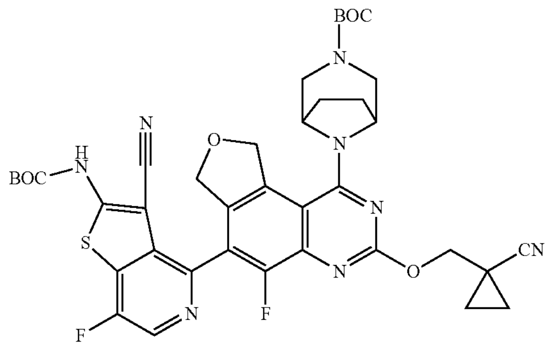 [SMILES: CC(C)(C)OC(=O)Nc1sc2c(F)cnc(-c3c4c(c5c(N6C7CCC6CN(C(=O)OC(C)(C)C)C7)nc(OCC6(C#N)CC6)nc5c3F)COC4)c2c1C#N] | 787 |
| 355 | tert-Butyl 8-[6-[2-(tert-butoxycarbonylamino)-3-cyano-7-fluoro-thieno[3,2-c]pyridin-4-yl]-3-[(3,3-difluoro-1-methyl-pyrrolidin-2-yl)methoxy]-5-fluoro-7,9-dihydrofuro[3,4-f]quinazolin-1-yl]-3,8-diazabicyclo[3.2.1]octane-3-carboxylate | 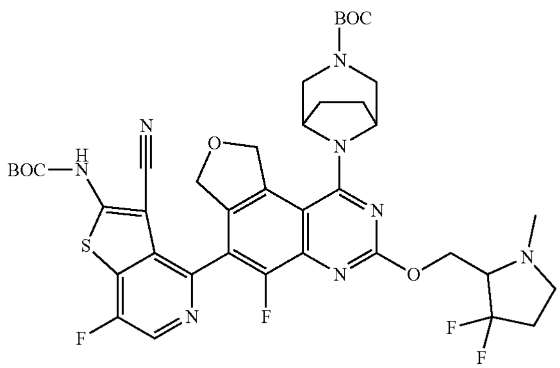 [SMILES: CN1CCC(F)(F)C1COc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3] | 841 |
| 356 | tert-Butyl 8-[6-[2-(tert-butoxycarbonylamino)-3-cyano-7-fluoro-thieno[3,2-c]pyridin-4-yl]-5-fluoro-3-[[1-(2-hydroxyacetyl)-4-piperidyl]methoxy]-7,9-dihydrofuro[3,4-f]quinazolin-1-yl]-3,8-diazabicyclo[3.2.1]octane-3-carboxylate | 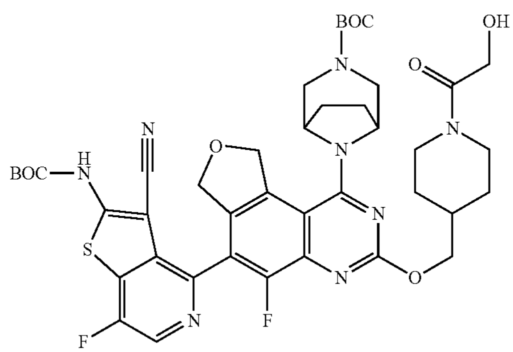 [SMILES: CC(C)(C)OC(=O)Nc1sc2c(F)cnc(-c3c4c(c5c(N6C7CCC6CN(C(=O)OC(C)(C)C)C7)nc(OCC6CCN(C(=O)CO)CC6)nc5c3F)COC4)c2c1C#N] | |
| 357 | tert-Butyl 6-[6-[2-(tert-butoxycarbonylamino)-3-cyano-5-fluoro-benzothiophen-4-yl]-5-fluoro-3-[[(2R)-4-methylmorpholin-2-yl]methoxy]-7,9-dihydrofuro[3,4-f]quinazolin-1-yl]-3,6-diazabicyclo[3.1.1]heptane-3-carboxylate | 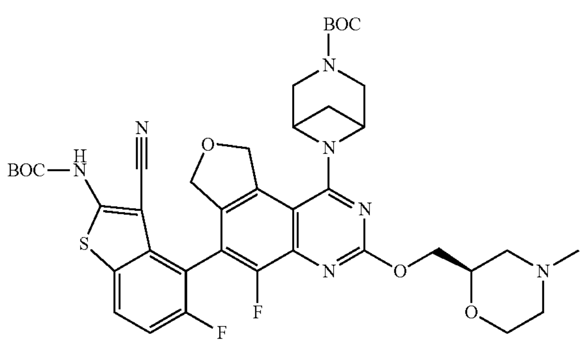 [SMILES: CN1CCO[C@@H](COc2nc(N3C4CC3CN(C(=O)OC(C)(C)C)C4)c3c4c(c(-c5c(F)ccc6sc(NC(=O)OC(C)(C)C)c(C#N)c56)c(F)c3n2)COC4)C1] | 806 |

TABLE 13-continued

| Preparation | Chemical Name | Structure | MS (ES) m/z (M + 1) |
|---|---|---|---|
| 358 | tert-Butyl 6-[6-[2-(tert-butoxycarbonylamino)-3-cyano-5-fluoro-benzothiophen-4-yl]-5-fluoro-3-[[(2S,4R)-4-fluoro-1-methyl-pyrrolidin-2-yl]methoxy]-7,9-dihydrofuro[3,4-f]quinazolin-1-yl]-3,6-diazabicyclo[3.1.1]heptane-3-carboxylate | 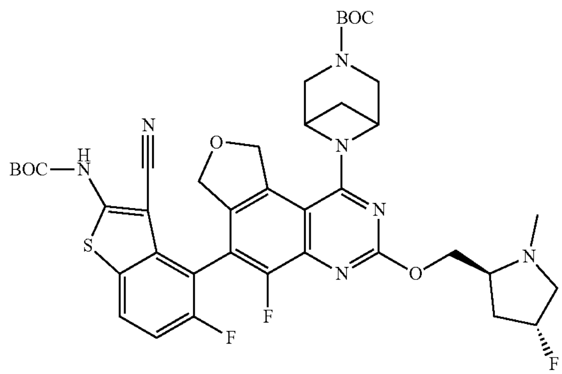 [SMILES: CN1C[C@H](F)C[C@H]1COc1nc(N2C3CC2CN(C(=O)OC(C)(C)C)C3)c2c3c(c(-c4c(F)ccc5sc(NC(=O)OC(C)(C)C)c(C#N)c45)c(F)c2n1)COC3] | 808 |
| 359 | tert-Butyl 6-[6-[2-(tert-butoxycarbonylamino)-3-cyano-7-fluoro-thieno[3,2-c]pyridin-4-yl]-5-fluoro-3-[[(2S,4R)-4-fluoro-1-methyl-pyrrolidin-2-yl]methoxy]-7,9-dihydrofuro[3,4-f]quinazolin-1-yl]-3,6-diazabicyclo[3.1.1]heptane-3-carboxylate | 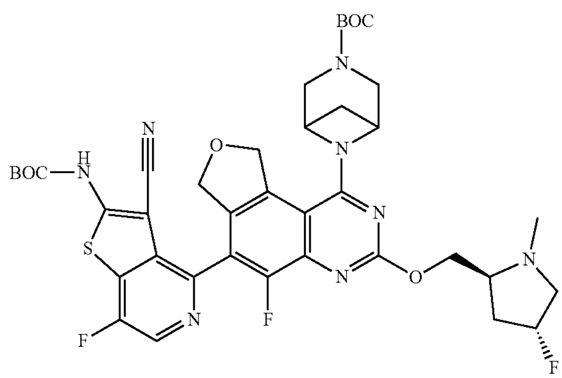 [SMILES: CN1C[C@H](F)C[C@H]1COc1nc(N2C3CC2CN(C(=O)OC(C)(C)C)C3)c2c3c(c(-c4ncc(F)c5sc(NC(=O)OC(C)(C)C)c(C#N)c45)c(F)c2n1)COC3] | 809 |
| 360 | tert-Butyl 6-[6-[2-(tert-butoxycarbonylamino)-3-cyano-7-fluoro-thieno[3,2-c]pyridin-4-yl]-5-fluoro-3-[(2S)-1-methylpyrrolidin-2-yl]methoxy]-7,9-dihydrofuro[3,4-f]quinazolin-1-yl]-3,6-diazabicyclo[3.1.1]heptane-3-carboxylate | 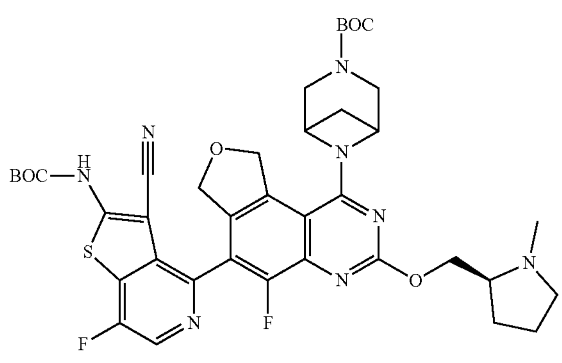 [SMILES: CN1CCC[C@H]1COc1nc(N2C3CC2CN(C(=O)OC(C)(C)C)C3)c2c3c(c(-c4ncc(F)c5sc(NC(=O)OC(C)(C)C)c(C#N)c45)c(F)c2n1)COC3] | 791 |
| 361 | tert-Butyl 6-[6-[2-(tert-butoxycarbonylamino)-3-cyano-7-fluoro-thieno[3,2-c]pyridin-4-yl]-5-fluoro-3-[(2R,8S)-2-fluoro-1,2,3,5,6,7-hexahydropyrrolizin-8-yl]methoxy]-7,9-dihydrofuro[3,4-f]quinazolin-1-yl]-3,6-diazabicyclo[3.1.1]heptane-3-carboxylate | 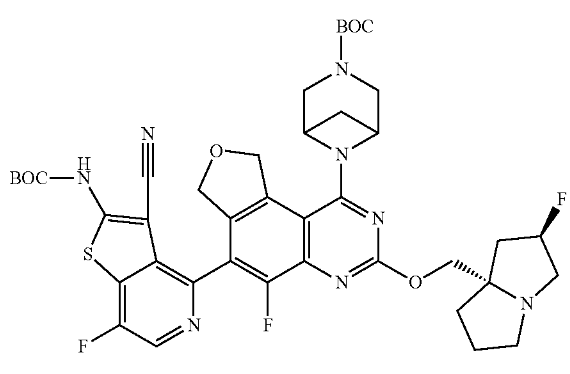 [SMILES: CC(C)(C)OC(=O)Nc1sc2c(F)cnc(-c3c4c(c5c(N6C7CC6CN(C(=O)OC(C)(C)C)C7)nc(OC[C@@]67CCCN6C[C@H](F)C7)nc5c3F)COC4)c2c1C#N] | 835 |

TABLE 13-continued

| Preparation | Chemical Name | Structure | MS (ES) m/z (M + 1) |
|---|---|---|---|
| 362 | tert-Butyl N-[3-cyano-7-fluoro-4-[5-fluoro-3-[[(2S)-1-methylpyrrolidin-2-yl]methoxy]-7,9-dihydrofuro[3,4-f]quinazolin-6-yl]thieno[3,2-c]pyridin-2-yl]carbamate | 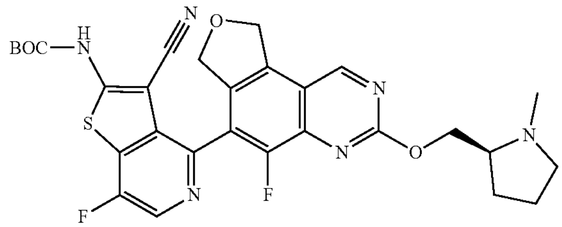 [SMILES: CN1CCC[C@H]1COc1ncc2c3c(c(-c4ncc(F)c5sc(NC(=O)OC(C)(C)C)c(C#N)c45)c(F)c2n1)COC3] | 595 |
| 363 | tert-Butyl N-[3-cyano-4-[3-[[(2S,4R)-4-(difluoromethoxy)-1-methyl-pyrrolidin-2-yl]methoxy]-5-fluoro-7,9-dihydrofuro[3,4-f]quinazolin-6-yl]-7-fluoro-thieno[3,2-c]pyridin-2-yl]carbamate | 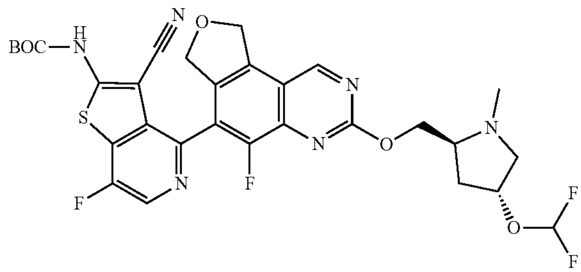 [SMILES: CN1C[C@H](OC(F)F)C[C@H]1COc1ncc2c3c(c(-c4ncc(F)c5sc(NC(=O)OC(C)(C)C)c(C#N)c45)c(F)c2n1)COC3] | 661 |
| 364 | tert-Butyl 3-[[6-[2-(tert-butoxycarbonylamino)-3-cyano-7-fluoro-thieno[3,2-c]pyridin-4-yl]-5-fluoro-7,9-dihydrofuro[3,4-f]quinazolin-3-yl]oxymethyl]-3-fluoro-azetidine-1-carboxylate | 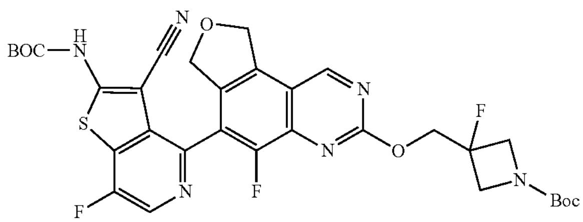 [SMILES: CC(C)(C)OC(=O)Nc1sc2c(F)cnc(-c3c4c(c5cnc(OCC6(F)CN(C(=O)OC(C)(C)C)C6)nc5c3F)COC4)c2c1C#N] | 585 |
| 365 | tert-Butyl N-[3-cyano-4-[3-[(4,4-difluoro-1-methyl-3-piperidyl)methoxy]-5-fluoro-7,9-dihydrofuro[3,4-f]quinazolin-6-yl]-7-fluoro-thieno[3,2-c]pyridin-2-yl]carbamate | 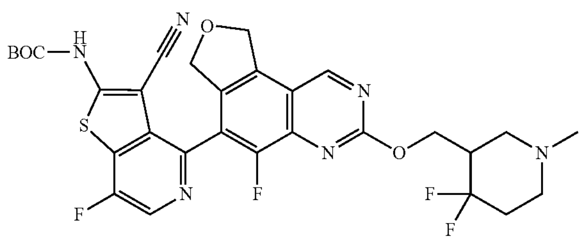 [SMILES: CN1CCC(F)(F)C(COc2ncc3c4c(c(-c5ncc(F)c6sc(NC(=O)OC(C)(C)C)c(C#N)c56)c(F)c3n2)COC4)C1] | 645 |
| 366 | tert-Butyl N-[3-cyano-7-fluoro-4-[5-fluoro-3-[[(2S,4S)-4-methoxy-1-methyl-pyrrolidin-2-yl]methoxy]-7,9-dihydrofuro[3,4-f]quinazolin-6-yl]thieno[3,2-c]pyridin-2-yl]carbamate | 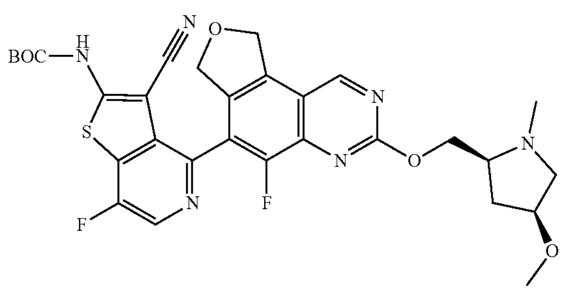 [SMILES: CO[C@H]1C[C@@H](COc2ncc3c4c(c(-c5ncc(F)c6sc(NC(=O)OC(C)(C)C)c(C#N)c56)c(F)c3n2)COC4)N(C)C1] | 625 |
| 367 | tert-Butyl N-[3-cyano-7-fluoro-4-[5-fluoro-3-[[(2S,4R)-4-methoxy-1-methyl-pyrrolidin-2-yl]methoxy]-7,9-dihydrofuro[3,4-f]quinazolin-6-yl]thieno[3,2-c]pyridin-2-yl]carbamate | 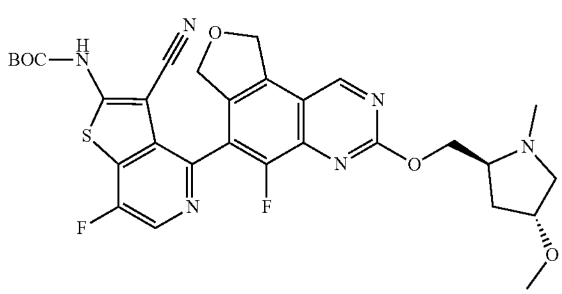 [SMILES: CO[C@@H]1C[C@@H](COc2ncc3c4c(c(-c5ncc(F)c6sc(NC(=O)OC(C)(C)C)c(C#N)c56)c(F)c3n2)COC4)N(C)C1] | 625 |

TABLE 13-continued

| Preparation | Chemical Name | Structure | MS (ES) m/z (M + 1) |
|---|---|---|---|
| 368 | tert-Butyl N-[3-cyano-7-fluoro-4-[5-fluoro-3-[[(2S,4S)-4-fluoro-1-(2-methoxyethyl)pyrrolidin-2-yl]methoxy]-7,9-dihydrofuro[3,4-f]quinazolin-6-yl]thieno[3,2-c]pyridin-2-yl]carbamate | 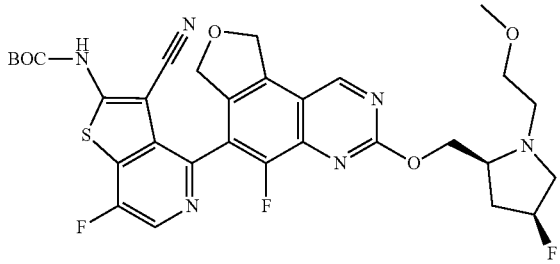 [SMILES: COCCN1C[C@@H](F)C[C@H]1COc1ncc2c3c(c(-c4ncc(F)c5sc(NC(=O)OC(C)(C)C)c(C#N)c45)c(F)c2n1)COC3] | 657 |
| 369 | tert-Butyl N-[4-[3-[[(2S,4S)-1-[2-[tert-butyl(dimethyl)silyl]oxy-ethyl]-4-fluoro-pyrrolidin-2-yl]methoxy]-5-fluoro-7,9-dihydrofuro[3,4-f]quinazolin-6-yl]-3-cyano-7-fluoro-thieno[3,2-c]pyridin-2-yl]carbamate | 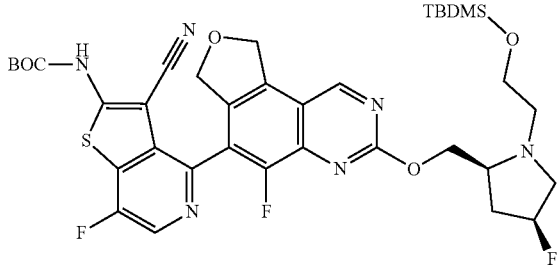 | 757 |
| 370 | tert-Butyl N-[4-[3-[[(2S,4R)-1-[2-[tert-butyl(dimethyl)silyl]oxy-ethyl]-4-fluoro-pyrrolidin-2-yl]methoxy]-5-fluoro-7,9-dihydrofuro[3,4-f]quinazolin-6-yl]-3-cyano-7-fluoro-thieno[3,2-c]pyridin-2-yl]carbamate | 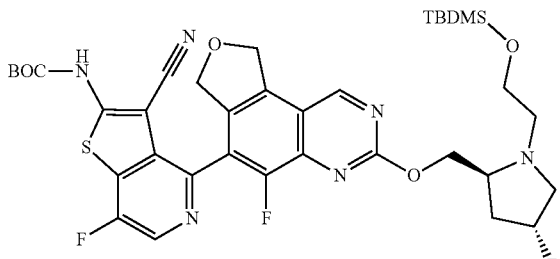 | 757 |
| 371 | tert-Butyl N-[3-cyano-7-fluoro-4-[5-fluoro-3-[[(2S,4S)-1-methyl-4-tetrahydropyran-2-yloxy-pyrrolidin-2-yl]methoxy]-7,9-dihydrofuro[3,4-f]quinazolin-6-yl]thieno[3,2-c]pyridin-2-yl]carbamate | 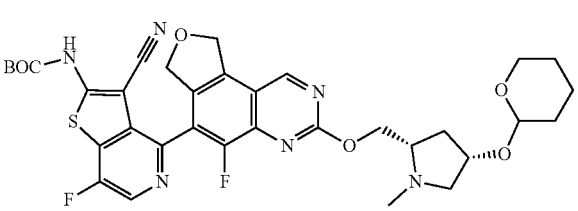 [SMILES: CN1C[C@@H](OC2CCCCO2)C[C@H]1COc1ncc2c3c(c(-c4ncc(F)c5sc(NC(=O)OC(C)(C)C)c(C#N)c45)c(F)c2n1)COC3] | 695 |
| 372 | tert-Butyl N-[3-cyano-7-fluoro-4-[5-fluoro-3-[[(2S,4R)-1-methyl-4-tetrahydropyran-2-yloxy-pyrrolidin-2-yl]methoxy]-7,9-dihydrofuro[3,4-f]quinazolin-6-yl]thieno[3,2-c]pyridin-2-yl]carbamate | 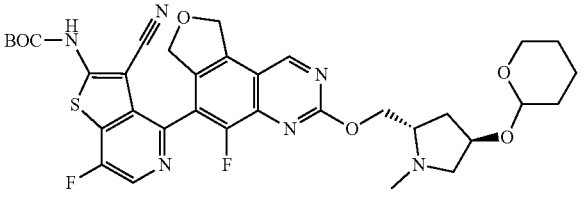 [SMILES: CN1C[C@H](OC2CCCCO2)C[C@H]1COc1ncc2c3c(c(-c4ncc(F)c5sc(NC(=O)OC(C)(C)C)c(C#N)c45)c(F)c2n1)COC3] | 695 |
| 373[8] | tert-Butyl 3-[[6-[2-(tert-butoxycarbonylamino)-3-cyano-7-fluoro-thieno[3,2-c]pyridin-4-yl]-5-fluoro-7,9-dihydrofuro[3,4-f]quinazolin-3-yl]oxymethyl]-3-fluoro-pyrrolidine-1-carboxylate, Isomer 1 | 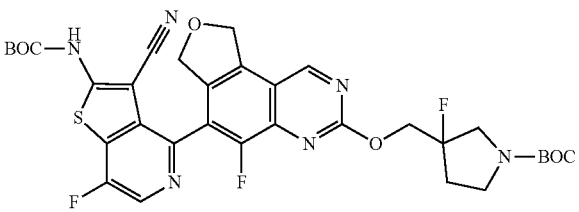 | 699 |

TABLE 13-continued

| Preparation | Chemical Name | Structure | MS (ES) m/z (M + 1) |
|---|---|---|---|
| 374[8] | tert-Butyl 3-[6-[2-(tert-butoxycarbonylamino)-3-cyano-7-fluoro-thieno[3,2-c]pyridin-4-yl]-5-fluoro-7,9-dihydrofuro[3,4-f]quinazolin-3-yl]oxymethyl]-3-fluoro-pyrrolidine-1-carboxylate, Isomer 2 | 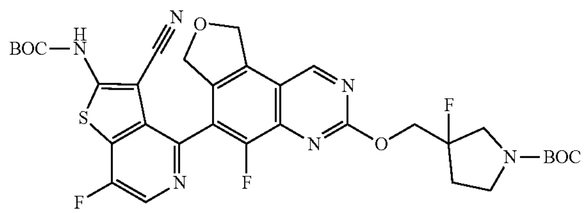 [SMILES: CC(C)(C)OC(=O)Nc1sc2c(F)cnc(-c3c4c(c5cnc(OCC6(F)CCN(C(=O)OC(C)(C)C)C6)nc5c3F)COC4)c2c1C#N] | 699 |
| 375 | tert-Butyl N-[3-cyano-4-[3-[[(2S)-5,5-difluoro-1-methyl-2-piperidyl]methoxy]-5-fluoro-7,9-dihydrofuro[3,4-f]quinazolin-6-yl]-7-fluoro-thieno[3,2-c]pyridin-2-yl]carbamate | 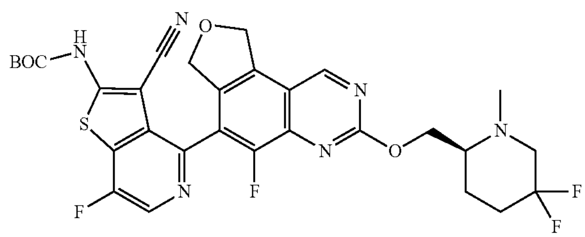 [SMILES: CN1CC(F)(F)CC[C@H]1COc1ncc2c3c(c(-c4ncc(F)c5sc(NC(=O)OC(C)(C)C)c(C#N)c45)c(F)c2n1)COC3] | 645 |
| 376 | tert-Butyl N-[3-cyano-4-[3-[[(2S)-4,4-difluoro-1-methyl-2-piperidyl]methoxy]-5-fluoro-7,9-dihydrofuro[3,4-f]quinazolin-6-yl]-7-fluoro-thieno[3,2-c]pyridin-2-yl]carbamate | 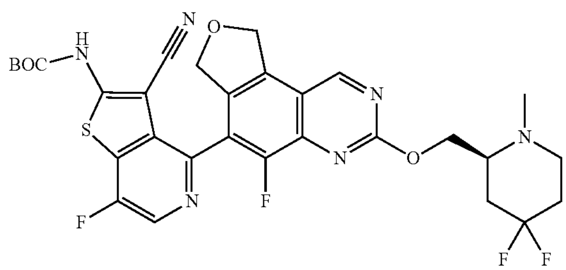 [SMILES: CN1CCC(F)(F)C[C@H]1COc1ncc2c3c(c(-c4ncc(F)c5sc(NC(=O)OC(C)(C)C)c(C#N)c45)c(F)c2n1)COC3] | 645 |
| 377 | tert-Butyl N-[3-cyano-7-fluoro-4-[5-fluoro-3-[[(1R,2S,5S)-3-methyl-3-azabicyclo[3.1.0]hexan-2-yl]methoxy]-7,9-dihydrofuro[3,4-f]quinazolin-6-yl]thieno[3,2-c]pyridin-2-yl]carbamate | 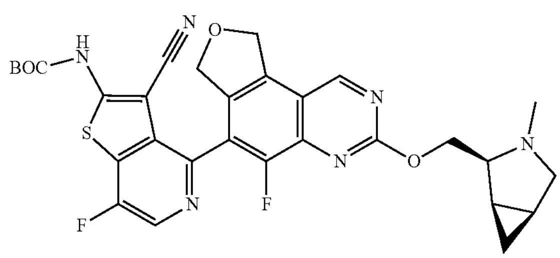 [SMILES: CN1C[C@H]2C[C@H]2[C@H]1COc1ncc2c3c(c(-c4ncc(F)c5sc(NC(=O)OC(C)(C)C)c(C#N)c45)c(F)c2n1)COC3] | 607 |
| 378 | tert-Butyl N-[3-cyano-7-fluoro-4-[5-fluoro-3-[[(2S,4S)-1-methyl-4-(trifluoromethyl)pyrrolidin-2-yl]methoxy]-7,9-dihydrofuro[3,4-f]quinazolin-6-yl]thieno[3,2-c]pyridin-2-yl]carbamate | 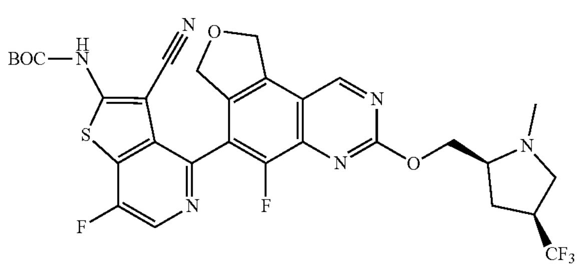 [SMILES: CN1C[C@@H](C(F)(F)F)C[C@H]1COc1ncc2c3c(c(-c4ncc(F)c5sc(NC(=O)OC(C)(C)C)c(C#N)c45)c(F)c2n1)COC3] | 663 |
| 379 | tert-Butyl N-[3-cyano-7-fluoro-4-[5-fluoro-3-[[(2S,4R)-1-methyl-4-(trifluoromethyl)pyrrolidin-2-yl]methoxy]-7,9-dihydrofuro[3,4-f]quinazolin-6-yl]thieno[3,2-c]pyridin-2-yl]carbamate | 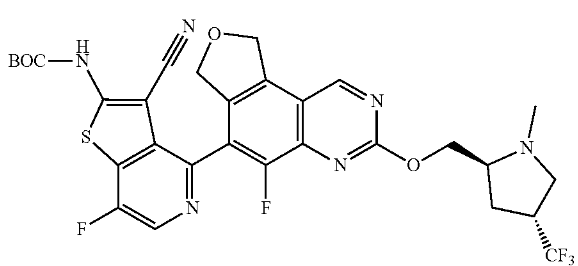 [SMILES: CN1C[C@H](C(F)(F)F)C[C@H]1COc1ncc2c3c(c(-c4ncc(F)c5sc(NC(=O)OC(C)(C)C)c(C#N)c45)c(F)c2n1)COC3] | 663 |

TABLE 13-continued

| Preparation | Chemical Name | Structure | MS (ES) m/z (M + 1) |
|---|---|---|---|
| 380 | tert-Butyl N-[3-cyano-7-fluoro-4-[5-fluoro-3-[[(2R,8S)-2-methoxy-1,2,3,5,6,7-hexahydropyrrolizin-8-yl]methoxy]-7,9-dihydrofuro[3,4-f]quinazolin-6-yl]thieno[3,2-c]pyridin-2-yl]carbamate | 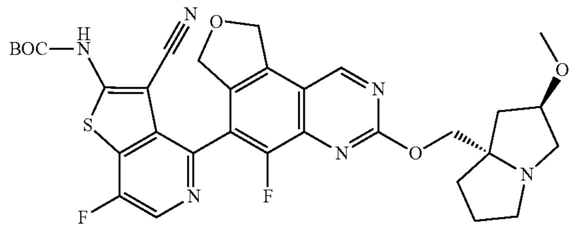 [SMILES: CO[C@H]1CN2CCC[C@@]2(COc2ncc3c4c(c(-c5ncc(F)c6sc(NC(=O)OC(C)(C)C)c(C#N)c56)c(F)c3n2)COC4)C1] | 651 |
| 381 | tert-Butyl N-[3-cyano-4-[3-[[(8S)-6,6-difluoro-2,3,5,7-tetrahydro-1H-pyrrolizin-8-yl]methoxy]-5-fluoro-7,9-dihydrofuro[3,4-f]quinazolin-6-yl]-7-fluoro-thieno[3,2-c]pyridin-2-yl]carbamate | 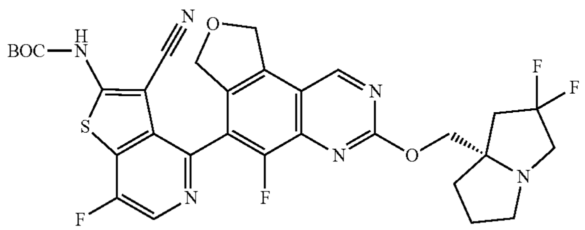 [SMILES: CC(C)(C)OC(=O)Nc1sc2c(F)cnc(-c3c4c(c5cnc(OC[C@@]67CCCN6CC(F)(F)C7)nc5c3F)COC4)c2c1C#N] | 657 |
| 382 | tert-Butyl N-[4-[3-[[3-[tert-butyl(dimethyl)silyl]oxycyclobutyl]methoxy]-5-fluoro-7,9-dihydrofuro[3,4-f]quinazolin-6-yl]-3-cyano-7-fluoro-thieno[3,2-c]pyridin-2-yl]carbamate | 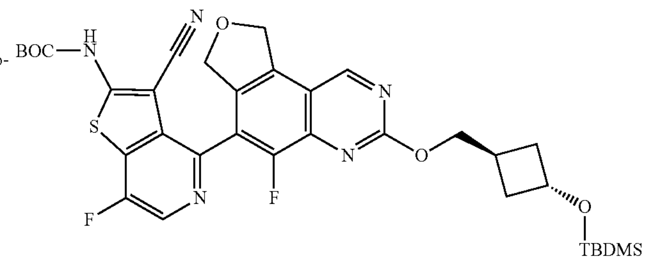 | 696 |
| 383 | tert-Butyl N-[4-[3-[[3-[tert-butyl(dimethyl)silyl]oxycyclobutyl]methoxy]-5-fluoro-7,9-dihydrofuro[3,4-f]quinazolin-6-yl]-3-cyano-7-fluoro-thieno[3,2-c]pyridin-2-yl]carbamate | 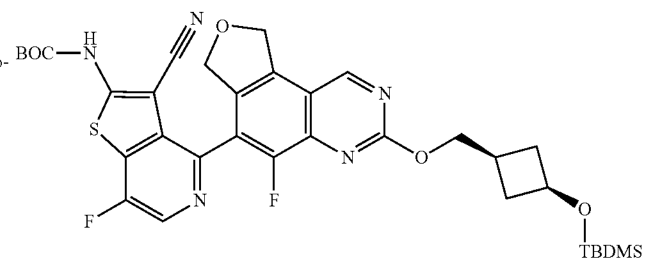 | 696 |
| 384 | tert-Butyl N-[3-cyano-7-fluoro-4-[5-fluoro-3-[[(3S)-4-methylmorpholin-3-yl]methoxy]-7,9-dihydrofuro[3,4-f]quinazolin-6-yl]thieno[3,2-c]pyridin-2-yl]carbamate | 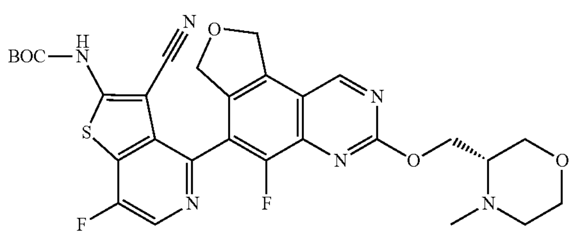 [SMILES: CN1CCOC[C@H]1COc1ncc2c3c(c(-c4ncc(F)c5sc(NC(=O)OC(C)(C)C)c(C#N)c45)c(F)c2n1)COC3] | 611 |
| 385 | tert-Butyl N-[3-cyano-7-fluoro-4-[5-fluoro-3-[[(3R)-4-methylmorpholin-3-yl]methoxy]-7,9-dihydrofuro[3,4-f]quinazolin-6-yl]thieno[3,2-c]pyridin-2-yl]carbamate | 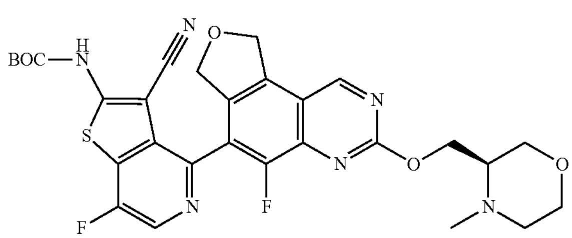 [SMILES: CN1CCOC[C@@H]1COc1ncc2c3c(c(-c4ncc(F)c5sc(NC(=O)OC(C)(C)C)c(C#N)c45)c(F)c2n1)COC3] | 611 |

TABLE 13-continued

| Preparation | Chemical Name | Structure | MS (ES) m/z (M + 1) |
|---|---|---|---|
| 386 | tert-Butyl N-[3-cyano-7-fluoro-4-[5-fluoro-3-[[(2R)-tetrahydrofuran-2-yl]methoxy]-7,9-dihydrofuro[3,4-f]quinazolin-6-yl]thieno[3,2-c]pyridin-2-yl]carbamate | 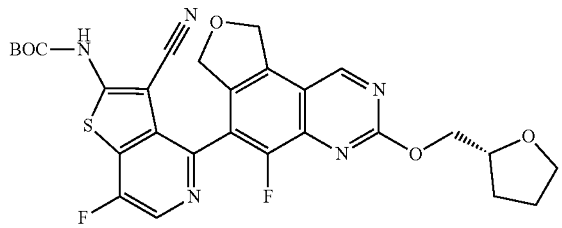 [SMILES: CC(C)(C)OC(=O)Nc1sc2c(F)cnc(-c3c4c(c5cnc(OC[C@H]6CCCO6)nc5c3F)COC4)c2c1C#N] | 582 |
| 387 | tert-Butyl N-[3-cyano-7-fluoro-4-[5-fluoro-3-[[(2S)-tetrahydrofuran-2-yl]methoxy]-7,9-dihydrofuro[3,4-f]quinazolin-6-yl]thieno[3,2-c]pyridin-2-yl]carbamate | 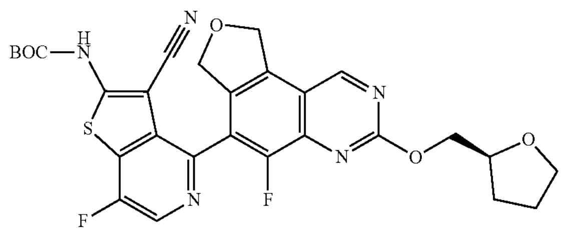 [SMILES: CC(C)(C)OC(=O)Nc1sc2c(F)cnc(-c3c4c(c5cnc(OC[C@@H]6CCCO6)nc5c3F)COC4)c2c1C#N] | 582 |
| 388 | tert-Butyl N-[3-cyano-7-fluoro-4-[5-fluoro-3-[[(2S,4S)-4-fluoro-1-methyl-pyrrolidin-2-yl]methoxy]-7,9-dihydrofuro[3,4-f]quinazolin-6-yl]thieno[3,2-c]pyridin-2-yl]carbamate | 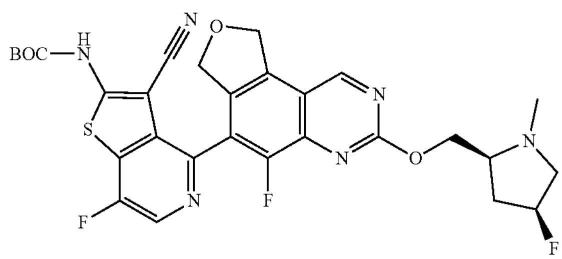 [SMILES: CN1C[C@@H](F)C[C@H]1COc1ncc2c3c(c(-c4ncc(F)c5sc(NC(=O)OC(C)(C)C)c(C#N)c45)c(F)c2n1)COC3] | 613 |
| 389 | tert-Butyl N-[3-cyano-7-fluoro-4-[5-fluoro-3-[[(2S,4R)-4-fluoro-1-methyl-pyrrolidin-2-yl]methoxy]-7,9-dihydrofuro[3,4-f]quinazolin-6-yl]thieno[3,2-c]pyridin-2-yl]carbamate | 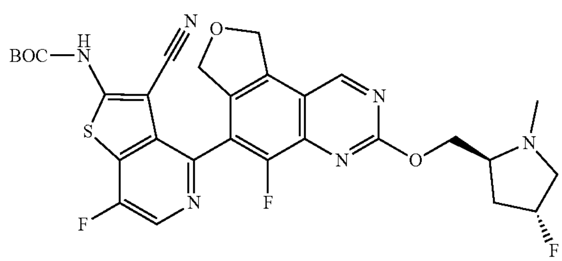 [SMILES: CN1C[C@H](F)C[C@H]1COc1ncc2c3c(c(-c4ncc(F)c5sc(NC(=O)OC(C)(C)C)c(C#N)c45)c(F)c2n1)COC3] | 613 |
| 390 | tert-Butyl N-[3-cyano-7-fluoro-4-[5-fluoro-3-[[(2S)-1-methylazetidin-2-yl]methoxy]-7,9-dihydrofuro[3,4-f]quinazolin-6-yl]thieno[3,2-c]pyridin-2-yl]carbamate | 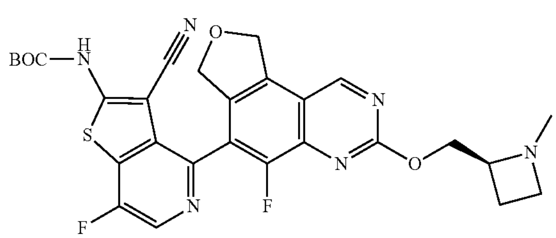 [SMILES: CN1CC[C@H]1COc1ncc2c3c(c(-c4ncc(F)c5sc(NC(=O)OC(C)(C)C)c(C#N)c45)c(F)c2n1)COC3] | 581 |
| 391 | tert-Butyl N-[3-cyano-7-fluoro-4-[5-fluoro-3-[[(2R)-1-methylazetidin-2-yl]methoxy]-7,9-dihydrofuro[3,4-f]quinazolin-6-yl]thieno[3,2-c]pyridin-2-yl]carbamate | 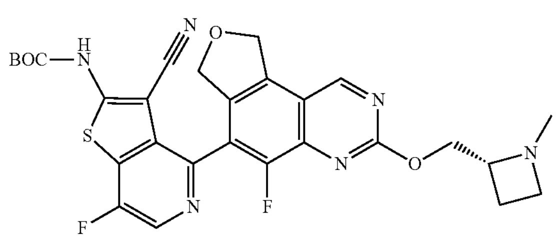 [SMILES: CN1CC[C@@H]1COc1ncc2c3c(c(-c4ncc(F)c5sc(NC(=O)OC(C)(C)C)c(C#N)c45)c(F)c2n1)COC3] | 581 |

TABLE 13-continued

| Preparation | Chemical Name | Structure | MS (ES) m/z (M + 1) |
|---|---|---|---|
| 392 | tert-Butyl N-[3-cyano-7-fluoro-4-[5-fluoro-3-(2-morpholinoethoxy)-7,9-dihydrofuro[3,4-f]quinazolin-6-yl]thieno[3,2-c]pyridin-2-yl]carbamate | 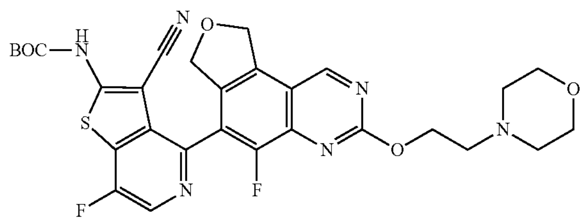 [SMILES: CC(C)(C)OC(=O)Nc1sc2c(F)cnc(-c3c4c(c5cnc(OCCN6CCOCC6)nc5c3F)COC4)c2c1C#N] | 611 |
| 393 | tert-Butyl N-[3-cyano-7-fluoro-4-[5-fluoro-3-[[(2R)-4-methylmorpholin-2-yl]methoxy]-7,9-dihydrofuro[3,4-f]quinazolin-6-yl]thieno[3,2-c]pyridin-2-yl]carbamate | 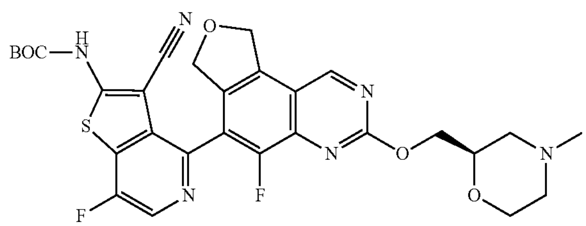 [SMILES: CN1CCO[C@@H](COc2ncc3c4c(c(-c5ncc(F)c6sc(NC(=O)OC(C)(C)C)c(C#N)c56)c(F)c3n2)COC4)C1] | 611 |
| 394 | tert-Butyl N-[3-cyano-7-fluoro-4-[5-fluoro-3-[[(2S)-4-methylmorpholin-2-yl]methoxy]-7,9-dihydrofuro[3,4-f]quinazolin-6-yl]thieno[3,2-c]pyridin-2-yl]carbamate | 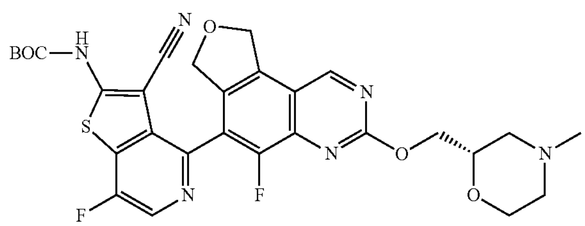 [SMILES: CN1CCO[C@H](COc2ncc3c4c(c(-c5ncc(F)c6sc(NC(=O)OC(C)(C)C)c(C#N)c56)c(F)c3n2)COC4)C1] | 611 |
| 395 | tert-Butyl N-[3-cyano-7-fluoro-4-[5-fluoro-3-[[(3R)-tetrahydrofuran-3-yl]methoxy]-7,9-dihydrofuro[3,4-f]quinazolin-6-yl]thieno[3,2-c]pyridin-2-yl]carbamate | 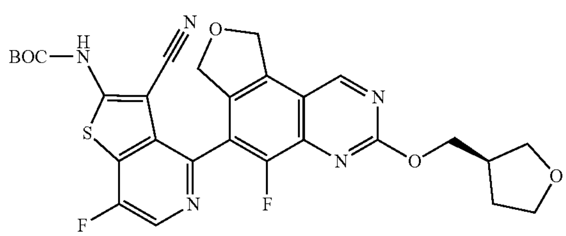 [SMILES: CC(C)(C)OC(=O)Nc1sc2c(F)cnc(-c3c4c(c5cnc(OC[C@@H]6CCOC6)nc5c3F)COC4)c2c1C#N] | 582 |
| 396 | tert-Butyl N-[3-cyano-7-fluoro-4-[5-fluoro-3-[[(3S)-tetrahydrofuran-3-yl]methoxy]-7,9-dihydrofuro[3,4-f]quinazolin-6-yl]thieno[3,2-c]pyridin-2-yl]carbamate | 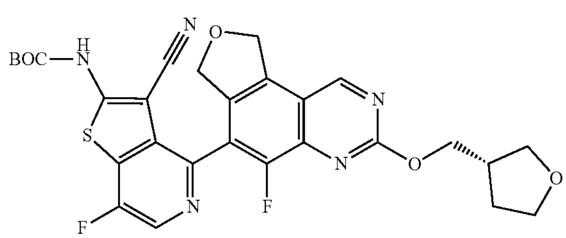 [SMILES: CC(C)(C)OC(=O)Nc1sc2c(F)cnc(-c3c4c(c5cnc(OC[C@H]6CCOC6)nc5c3F)COC4)c2c1C#N] | 582 |
| 397 | 6-Bromo-5-fluoro-3-[[(2R,8S)-2-fluoro-1,2,3,5,6,7-hexahydropyrrolizin-8-yl]methoxy]-7,9-dihydrofuro[3,4-f]quinazolin-1-ol | 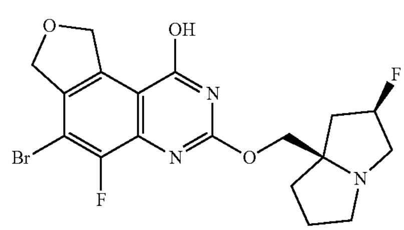 [SMILES: Oc1nc(OC[C@]23CCCN2C[C@H](F)C3)nc2c(F)c(Br)c3c(c12)COC3] | 442, 444 |

TABLE 13-continued

| Preparation | Chemical Name | Structure | MS (ES) m/z (M + 1) |
|---|---|---|---|
| 398 | 6-Bromo-5-fluoro-3-[[(2R,8S)-2-fluoro-1,2,3,5,6,7-hexahydropyrrolizin-8-yl]methoxy]-N-[[(2S)-1-methylpyrrolidin-2-yl]methyl]-7,9-dihydrofuro[3,4-f]quinazolin-1-amine | 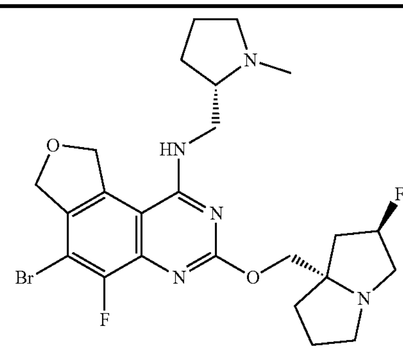 | 538, 540 |
| 399 | tert-Butyl 8-[6-[2-(tert-butoxycarbonylamino)-3-cyano-7-fluoro-thieno[3,2-c]pyridin-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3-azabicyclo[3.2.1]octane-3-carboxylate | 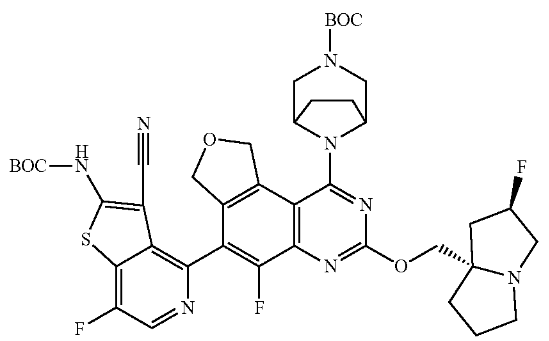 [SMILES: CC(C)(C)OC(=O)Nc1sc2c(F)cnc(-c3c4c(c5c(N6C7CCC6CN(C(=O)OC(C)(C)C)C7)nc(OC[C@@]67CCCN6C[C@H](F)C7)nc5c3F)COC4)c2c1C#N] | 848 |
| 416 | tert-Butyl N-[3-cyano-4-[3-[[1-[(dimethylamino)methyl]cyclopropyl]methoxy]-5-fluoro-7,9-dihydrofuro[3,4-f]quinazolin-6-yl]-7-fluoro-thieno[3,2-c]pyridin-2-yl]carbamate | 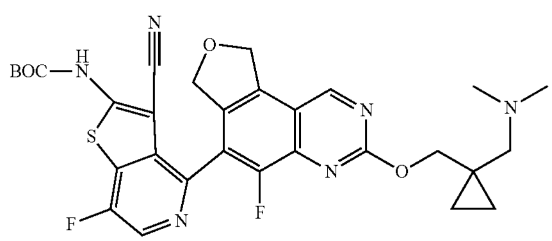 [SMILES: CN(C)CC1(COc2ncc3c4c(c(-c5ncc(F)c6sc(NC(=O)OC(C)(C)C)c(C#N)c56)c(F)c3n2)COC4)CC1] | 609 |

[1] The reaction was heated at 55° C. for ~ 18 h.
[2] single atropisomer (from precursor in Preparation 157)
[3] The reaction was heated at 80° C. for 1 h.
[4] The reaction was heated at 60° C. ~ 48 h.
[5] Chiralpak ® AD-H, 21 x 150 mm, 25% IPA (0.5% DMEA): 75% CO₂, 70 mL/min
[6] single atropisomer (from precursor in Preparation 248)
[7] single atropisomer (from precursor in Preparation 251)
[8] Chiralcel ® OD, 20 x 250 mm, 20% EtOH (0.5% DMEA): 80% CO₂, 80 mL/min Preparation 223

4-Bromo-5-fluoro-7-[[(2S)-1-methylpyrrolidin-2-yl]methoxy]-1,3-dihydrofuro[3,4-f]quinoline

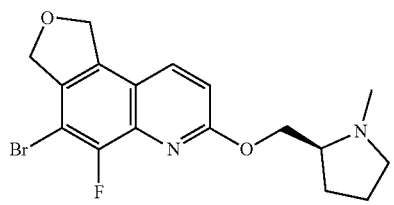

A solution of LHMDS (1M in THF, 7.3 mL, 7.3 mmol) and N-methyl-1-prolinol (0.9 mL, 7 mmol) in DMF (15 mL) was stirred for 5 min. A suspension of 4-bromo-7-chloro-5-fluoro-1,3-dihydrofuro[3,4-f]quinoline (1.0 g, 3.3 mmol) in DMF (30 mL) was added and stirred at RT for ~18 h. The reaction solution was added to H₂O (150 mL) and the resulting solid was filtered, washed with H₂O and placed under vacuum at 40° C. overnight to obtain the title compound (1.1 g, 85%) as a white solid. MS (ES) m/z=381 (M+1).

Preparation 224 tert-Butyl 8-[6-[2-(tert-butoxycarbonylamino)-3-cyano-7-fluoro-benzothiophen-4-yl]-5-chloro-3-cyano-7,9-dihydrofuro[3,4-f]quinazolin-1-yl]-3,8-diazabicyclo[3.2.1]octane-3-carboxylate

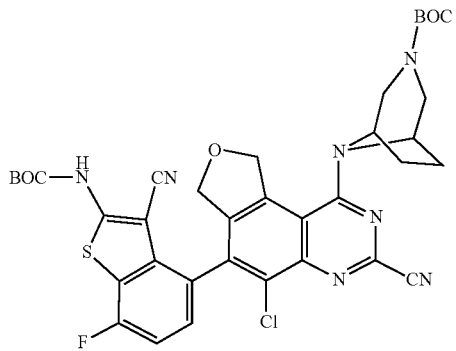 [SMILES: CC(C)(C)OC(=O)Nc1sc2c(F)ccc(-c3c4c(c5c(N6C7CCC6CN(C(=O)OC(C)(C)C)C7)nc(C#N)nc5c3Cl)COC4)c2c1C#N]

A mixture of tert-butyl 8-[6-[2-(tert-butoxycarbonylamino)-3-cyano-7-fluoro-benzothiophen-4-yl]-5-chloro-3-ethylsulfonyl-7,9-dihydrofuro[3,4-f]quinazolin-1-yl]-3,8-diazabicyclo[3.2.1]octane-3-carboxylate, Isomer 2 (Preparation 157; 765 mg, 0.957 mmol) and NaCN (93.8 mg, 1.91 mmol) in DMSO (10 mL) was stirred at RT for 1 h. The resulting mixture was diluted with EtOAc (200 mL), washed with H$_2$O (3×200 mL), brine (200 mL), then was dried over anhydrous Na$_2$SO$_4$, filtered and was concentrated under reduced pressure to afford the title compound (650 mg, 93%) as a yellow solid. MS (ES) m/z=732 (M+1).

Preparation 225

Methyl 6-[2-(tert-butoxycarbonylamino)-3-cyano-7-fluoro-benzothiophen-4-yl]-1-(3-tert-butoxycarbonyl-3,8-diazabicyclo[3.2.1]octan-8-yl)-5-chloro-7,9-dihydrofuro[3,4-f]quinazoline-3-carboxylate

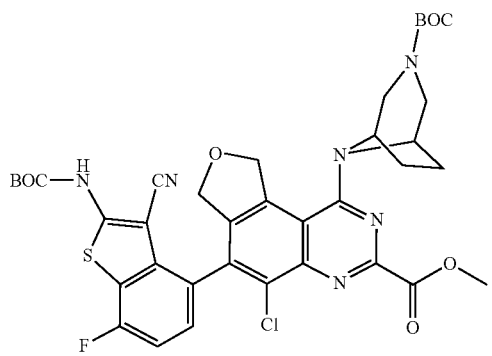 [SMILES: COC(=O)c1nc(N2C3CCC2CN(C(=O)OC(C)(C)C)C3)c2c3c(c(-c4ccc(F)c5sc(NC(=O)OC(C)(C)C)c(C#N)c45)c(Cl)c2n1)COC3]

To a stirred solution of tert-butyl 8-[6-[2-(tert-butoxycarbonylamino)-3-cyano-7-fluoro-benzothiophen-4-yl]-5-chloro-3-cyano-7,9-dihydrofuro[3,4-f]quinazolin-1-yl]-3,8-diazabicyclo[3.2.1]octane-3-carboxylate (650 mg, 0.888 mmol) in MeOH (10 mL) was added a solution of NaOH (71.0 mg, 1.78 mmol) in H$_2$O (10 mL) dropwise at RT. The resulting mixture was stirred for 2 h at RT. The mixture was cooled to 0° C. and was acidified to pH 2-3 with 1N HCl solution and was stirred for 2 h at RT. The resulting mixture was concentrated under reduced pressure and extracted with EtOAc (300 mL). The combined organic layers were washed with H$_2$O (3×200 mL), brine (200 mL) and dried over anhydrous Na$_2$SO$_4$. After filtration, the filtrate was concentrated under reduced pressure to afford the title compound (580 mg, 85%) as a yellow solid. MS (ES) m/z=765 (M+1).

Preparation 226 tert-Butyl 8-[6-[2-(tert-butoxycarbonylamino)-3-cyano-7-fluoro-benzothiophen-4-yl]-5-chloro-3-(hydroxymethyl)-7,9-dihydrofuro[3,4-f]quinazolin-1-yl]-3,8-diazabicyclo[3.2.1]octane-3-carboxylate

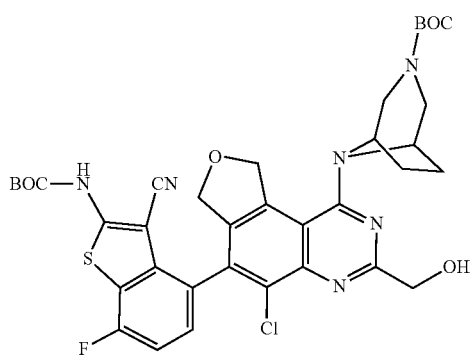 [SMILES: CC(C)(C)OC(=O)Nc1sc2c(F)ccc(-c3c4c(c5c(N6C7CCC6CN(C(=O)OC(C)(C)C)C7)nc(CO)nc5c3Cl)COC4)c2c1C#N]

To a stirred mixture of methyl 6-[2-(tert-butoxycarbonylamino)-3-cyano-7-fluoro-benzothiophen-4-yl]-1-(3-tert-butoxycarbonyl-3,8-diazabicyclo[3.2.1]octan-8-yl)-5-chloro-7,9-dihydrofuro[3,4-f]quinazoline-3-carboxylate (200 mg, 0.261 mmol) in EtOH (20 mL) at 0° C. was added NaBH$_4$ (19.8 mg, 0.522 mmol) in portions. The resulting mixture was stirred for 1h at RT under N$_2$. The reaction was quenched with H$_2$O at 0° C. The resulting mixture was concentrated under reduced pressure and was extracted with EtOAc (300 mL). The organic layer was washed with H$_2$O (3×200 mL), brine (200 mL) and dried over anhydrous Na$_2$SO$_4$. After filtration, the filtrate was concentrated under reduced pressure to afford the title compound (150 mg, 78%) as a yellow solid. MS (ES) m/z=737 (M+1).

Preparation 296 tert-Butyl 8-[6-(2-amino-3-cyano-5-fluoro-benzofuran-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate, Isomer 1

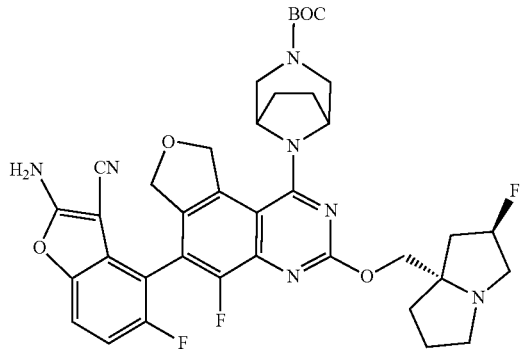 [SMILES: CC(C)(C)OC(=O)N1CC2CCC(C1)N2c1nc(OC[C@@]23CCCN2C[C@H](F)C3)nc2c(F)c(-c3c(F)ccc4oc(N)c(C#N)c34)c3c(c12)COC3]

A mixture of tert-butyl 8-[6-[2-(tert-butoxycarbonylamino)-3-cyano-5-fluoro-benzofuran-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate (0.548 g, 0.659 mmol) and hexafluoroisopropanol (3 mL) was stirred under microwave irradiation at 110° C. for 4 min. The mixture was concentrated and purified by reversed phase flash purification on C18, eluting with 0% to 100% ACN in 10 mM aq. NH$_4$HCO$_3$ with 5% MeOH to obtain the racemate, followed by chiral purification (Chiralpak® IC, 21×250 mm, 35% EtOH (w/0.5% DMEA): 65% CO$_2$, 80 mL/min) to obtain the title compound (0.126 g) as a white solid. MS (ES) m/z=732 (M+1).

Preparation 297 tert-Butyl 6-[6-(2-amino-3-cyano-5-fluoro-benzofuran-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,6-diazabicyclo[3.1.1]heptane-3-carboxylate

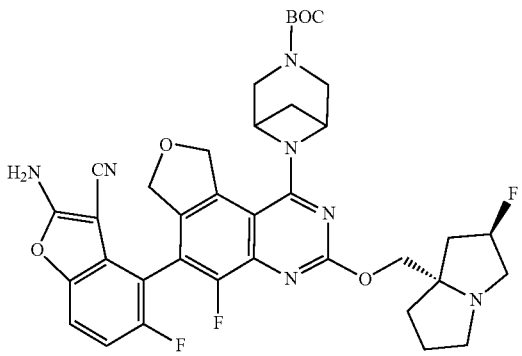 [SMILES: CC(C)(C)OC(=O)N1CC2CC(C1)N2c1nc(OC[C@@]23CCCN2C[C@H](F)C3)nc2c(F)c(-c3c(F)ccc4oc(N)c(C#N)c34)c3c(c12)COC3]

tert-Butyl 6-[6-[2-(tert-butoxycarbonylamino)-3-cyano-5-fluoro-benzofuran-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,6-diazabicyclo[3.1.1]heptane-3-carboxylate was used in an analogous manner to the method of Preparation 296 to obtain the title compound (0.28 g). MS (ES) m/z=718 (M+1).

Preparation 298 tert-Butyl (1R,4R)-5-[6-(2-amino-3-cyano-5-fluoro-benzofuran-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-2,5-diazabicyclo[2.2.1]heptane-2-carboxylate, Isomer 2

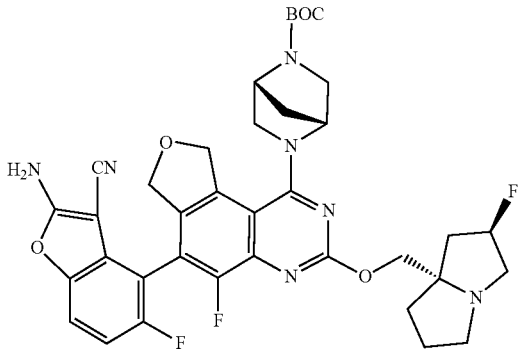 [SMILES: CC(C)(C)OC(=O)N1C[C@H]2C[C@@H]1CN2c1nc(OC[C@@]23CCCN2C[C@H](F)C3)nc2c(F)c(-c3c(F)ccc4oc(N)c(C#N)c34)c3c(c12)COC3]

tert-Butyl (1R,4R)-5-[6-[2-(tert-butoxycarbonylamino)-3-cyano-5-fluoro-benzofuran-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-2,5-diazabicyclo[2.2.1]heptane-2-carboxylate was used in an analogous manner to the method of Preparation 296, followed by chiral purification (Chiralpak® IC, 21×250 mm, 40% MeOH:60% CO$_2$, 70 mL/min) to obtain the title compound (0.14 g). MS (ES) m/z=718 (M+1).

Preparation 299 tert-Butyl N-[4-[1-[3-[3-[tert-butyl(dimethyl)silyl]oxypropyl]-3,8-diazabicyclo[3.2.1]octan-8-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-5,7-difluoro-1,3-benzothiazol-2-yl]carbamate

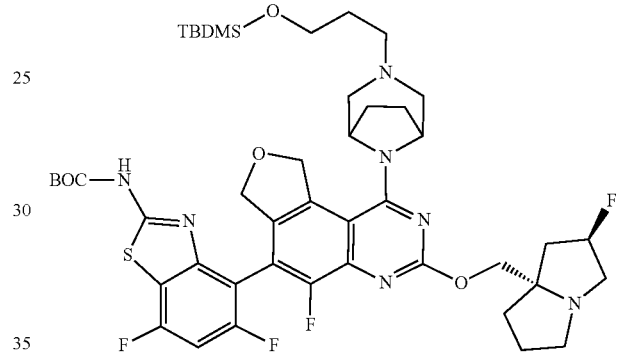

[2-(tert-Butoxycarbonylamino)-5,7-difluoro-1,3-benzothiazol-4-yl]boronic acid was used in an analogous manner to the method of Preparation 156 to obtain the title compound (0.50 g). MS (ES) m/z=914 (M+1).

Preparation 400

6-Bromo-5-fluoro-3-[[(2R,8S)-2-fluoro-1,2,3,5,6,7-hexahydropyrrolizin-8-yl]methoxy]-1-(2,2,2-trifluoroethoxy)-7,9-dihydrofuro[3,4-f]quinazoline

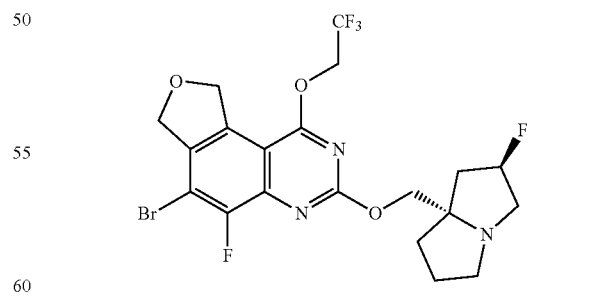

6-Bromo-5-fluoro-3-[[(2R,8S)-2-fluoro-1,2,3,5,6,7-hexahydropyrrolizin-8-yl]methoxy]-7,9-dihydrofuro[3,4-f]quinazolin-1-ol and trifluoroethanol were used in an analogous manner to the method of Preparation 112 to obtain the title compound (2.2 g, 77%) as light yellow solid. MS (ES) m/z=524,526 (M+1,Br).

Preparation 401 tert-Butyl N-[3-cyano-7-fluoro-4-[5-fluoro-3-[[(2R,8S)-2-fluoro-1,2,3,5,6,7-hexahydropyrrolizin-8-yl]methoxy]-1-(2,2,2-trifluoroethoxy)-7,9-dihydrofuro[3,4-f]quinazolin-6-yl]thieno[3,2-c]pyridin-2-yl]carbamate

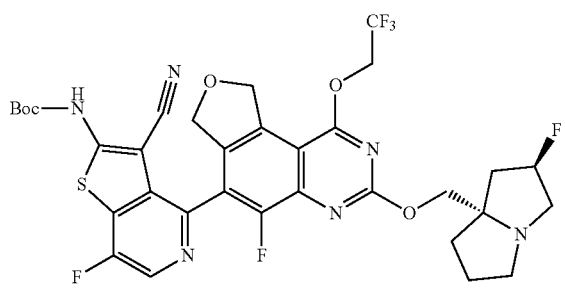 [SMILES: CC(C)(C)OC(=O)Nc1sc2c(F)cnc(-c3c4c(c5c(OCC(F)(F)F)nc(OC[C@@]67CCCN6C[C@H](F)C7)nc5c3F)COC4)c2c1C#N]

6-Bromo-5-fluoro-3-[[(2R,8S)-2-fluoro-1,2,3,5,6,7-hexahydropyrrolizin-8-yl]methoxy]-1-(2,2,2-trifluoroethoxy)-7,9-dihydrofuro[3,4-f]quinazoline and tert-butyl N-(4-chloro-3-cyano-7-fluoro-thieno[3,2-c]pyridin-2-yl)carbamate were used in an analogous manner to the method of Preparation 158 to obtain the title compound (1.5 g) as light yellow solid. MS (ES) m/z=737 (M+1).

Preparation 402 tert-Butyl N-[3-cyano-7-fluoro-4-[5-fluoro-3-[[(2R,8S)-2-fluoro-1,2,3,5,6,7-hexahydropyrrolizin-8-yl]methoxy]-1-[[(2S)-1-methylpyrrolidin-2-yl]methylamino]-7,9-dihydrofuro[3,4-f]quinazolin-6-yl]thieno[3,2-c]pyridin-2-yl]carbamate

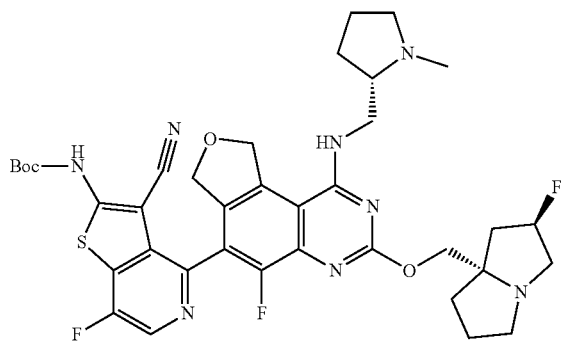 [SMILES: CN1CCC[C@H]1CNc1nc(OC[C@@]23CCCN2C[C@H](F)C3)nc2c(F)c(-c3ncc(F)c4sc(NC(=O)OC(C)(C)C)c(C#N)c34)c3c(c12)COC3]

6-Bromo-5-fluoro-3-[[(2R,8S)-2-fluoro-1,2,3,5,6,7-hexahydropyrrolizin-8-yl]methoxy]-N-[[(2S)-1-methylpyrrolidin-2-yl]methyl]-7,9-dihydrofuro[3,4-f]quinazolin-1-amine and tert-butyl N-(4-chloro-3-cyano-7-fluoro-thieno[3,2-c]pyridin-2-yl)carbamate were used in an analogous manner to the method of Preparation 158 to obtain the title compound. MS (ES) m/z=751 (M+1).

Preparation 403 tert-Butyl N-[3-cyano-4-[1-(dimethylamino)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-thieno[3,2-c]pyridin-2-yl]carbamate

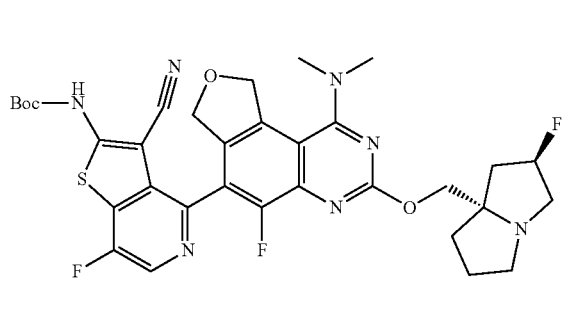 [SMILES: CN(C)c1nc(OC[C@@]23CCCN2C[C@H](F)C3)nc2c(F)c(-c3ncc(F)c4sc(NC(=O)OC(C)(C)C)c(C#N)c34)c3c(c12)COC3]

tert-Butyl N-[3-cyano-7-fluoro-4-[5-fluoro-3-[[(2R,8S)-2-fluoro-1,2,3,5,6,7-hexahydropyrrolizin-8-yl]methoxy]-1-(2,2,2-trifluoroethoxy)-7,9-dihydrofuro[3,4-f]quinazolin-6-yl]thieno[3,2-c]pyridin-2-yl]carbamate and dimethylamine were used in an analogous manner to the method of Preparation 111 to obtain the title compound. MS (ES) m/z=682 (M+1).

Preparation 404 tert-Butyl N-[3-cyano-7-fluoro-4-[5-fluoro-3-[[(2R,8S)-2-fluoro-1,2,3,5,6,7-hexahydropyrrolizin-8-yl]methoxy]-1-(methylamino)-7,9-dihydrofuro[3,4-f]quinazolin-6-yl]thieno[3,2-c]pyridin-2-yl]carbamate

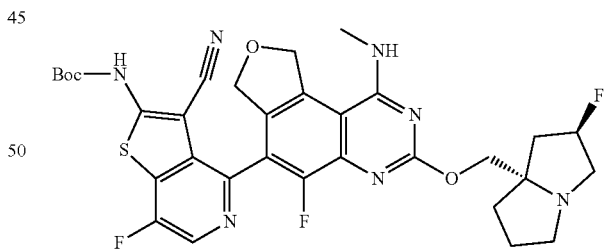

tert-Butyl N-[3-cyano-7-fluoro-4-[5-fluoro-3-[[(2R,8S)-2-fluoro-1,2,3,5,6,7-hexahydropyrrolizin-8-yl]methoxy]-1-(2,2,2-trifluoroethoxy)-7,9-dihydrofuro[3,4-f]quinazolin-6-yl]thieno[3,2-c]pyridin-2-yl]carbamate and methylamine were used in an analogous manner to the method of Preparation 111 to obtain the title compound. MS (ES) m/z=668 (M+1).

Preparation 405 tert-Butyl N-[3-cyano-7-fluoro-4-[5-fluoro-3-[[(2R,8S)-2-fluoro-1,2,3,5,6,7-hexahydropyrrolizin-8-yl]methoxy]-1-(2-hydroxyethylamino)-7,9-dihydrofuro[3,4-f]quinazolin-6-yl]thieno[3,2-c]pyridin-2-yl]carbamate

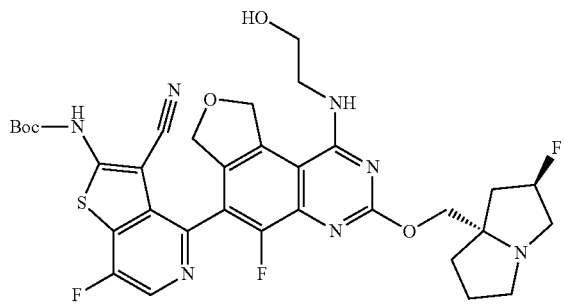 [SMILES: CC(C)(C)OC(=O)Nc1sc2c(F)cnc(-c3c4c(c5c(NCCO)nc(OC[C@@]67CCCN6C[C@H](F)C7)nc5c3F)COC4)c2c1C#N]

tert-Butyl N-[3-cyano-7-fluoro-4-[5-fluoro-3-[[(2R,8S)-2-fluoro-1,2,3,5,6,7-hexahydropyrrolizin-8-yl]methoxy]-1-(2,2,2-trifluoroethoxy)-7,9-dihydrofuro[3,4-f]quinazolin-6-yl]thieno[3,2-c]pyridin-2-yl]carbamate and ethanolamine were used in an analogous manner to the method of Preparation 111 to obtain the title compound. MS (ES) m/z=698 (M+1).

Preparation 406 tert-Butyl N-[4-[1-(azetidin-1-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-3-cyano-7-fluoro-thieno[3,2-c]pyridin-2-yl]carbamate

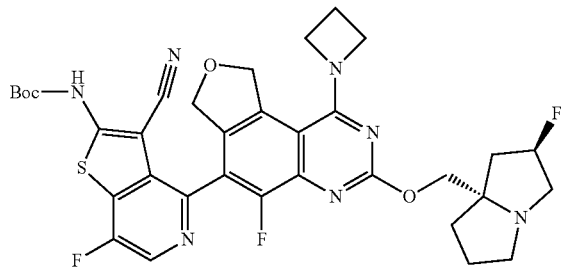 [SMILES: CC(C)(C)OC(=O)Nc1sc2c(F)cnc(-c3c4c(c5c(N6CCC6)nc(OC[C@@]67CCCN6C[C@H](F)C7)nc5c3F)COC4)c2c1C#N]

tert-Butyl N-[3-cyano-7-fluoro-4-[5-fluoro-3-[[(2R,8S)-2-fluoro-1,2,3,5,6,7-hexahydropyrrolizin-8-yl]methoxy]-1-(2,2,2-trifluoroethoxy)-7,9-dihydrofuro[3,4-f]quinazolin-6-yl]thieno[3,2-c]pyridin-2-yl]carbamate and azetidine were used in an analogous manner to the method of Preparation 111 to obtain the title compound. MS (ES) m/z=694 (M+1).

Preparation 407 tert-Butyl N-[3-cyano-7-fluoro-4-[5-fluoro-3-[[(2R,8S)-2-fluoro-1,2,3,5,6,7-hexahydropyrrolizin-8-yl]methoxy]-1-(3-methoxyazetidin-1-yl)-7,9-dihydrofuro[3,4-f]quinazolin-6-yl]thieno[3,2-c]pyridin-2-yl]carbamate

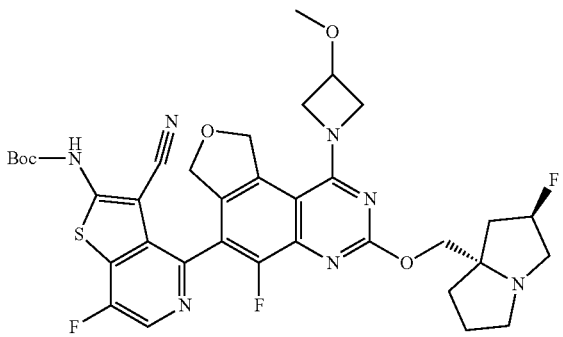 [SMILES: COC1CN(c2nc(OC[C@@]34CCCN3C[C@H](F)C4)nc3c(F)c(-c4ncc(F)c5sc(NC(=O)OC(C)(C)C)c(C#N)c45)c4c(c23)COC4)C1]

tert-Butyl N-[3-cyano-7-fluoro-4-[5-fluoro-3-[[(2R,8S)-2-fluoro-1,2,3,5,6,7-hexahydropyrrolizin-8-yl]methoxy]-1-(2,2,2-trifluoroethoxy)-7,9-dihydrofuro[3,4-f]quinazolin-6-yl]thieno[3,2-c]pyridin-2-yl]carbamate and 3-methoxyazetidine were used in an analogous manner to the method of Preparation 111 to obtain the title compound. MS (ES) m/z=724 (M+1).

Preparation 408 tert-Butyl N-[3-cyano-7-fluoro-4-[5-fluoro-3-[[(2R,8S)-2-fluoro-1,2,3,5,6,7-hexahydropyrrolizin-8-yl]methoxy]-1-morpholino-7,9-dihydrofuro[3,4-f]quinazolin-6-yl]thieno[3,2-c]pyridin-2-yl]carbamate

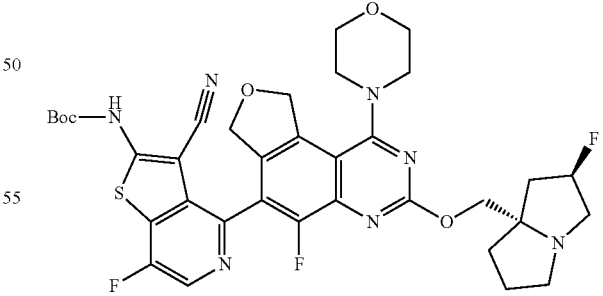

tert-Butyl N-[3-cyano-7-fluoro-4-[5-fluoro-3-[[(2R,8S)-2-fluoro-1,2,3,5,6,7-hexahydropyrrolizin-8-yl]methoxy]-1-(2,2,2-trifluoroethoxy)-7,9-dihydrofuro[3,4-f]quinazolin-6-yl]thieno[3,2-c]pyridin-2-yl]carbamate and morpholine were used in an analogous manner to the method of Preparation 111 to obtain the title compound. MS (ES) m/z=724 (M+1).

Preparation 409 tert-Butyl N-[3-cyano-7-fluoro-4-[5-fluoro-3-[[(2R,8S)-2-fluoro-1,2,3,5,6,7-hexahydropyrrolizin-8-yl]methoxy]-1-(2-methoxyethoxy)-7,9-dihydrofuro[3,4-f]quinazolin-6-yl]thieno[3,2-c]pyridin-2-yl]carbamate

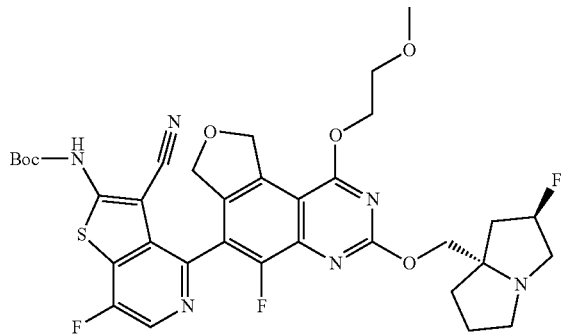 [SMILES: COCCOc1nc(OC[C@@]23CCCN2C[C@H](F)C3)nc2c(F)c(-c3ncc(F)c4sc(NC(=O)OC(C)(C)C)c(C#N)c34)c3c(c12)COC3]

tert-Butyl N-[3-cyano-7-fluoro-4-[5-fluoro-3-[[(2R,8S)-2-fluoro-1,2,3,5,6,7-hexahydropyrrolizin-8-yl]methoxy]-1-(2,2,2-trifluoroethoxy)-7,9-dihydrofuro[3,4-f]quinazolin-6-yl]thieno[3,2-c]pyridin-2-yl]carbamate and 2-methoxyethanol were used in an analogous manner to the method of Preparation 195 to obtain the title compound. MS (ES) m/z=713 (M+1).

Preparation 410 tert-butyl N-[3-cyano-7-fluoro-4-[5-fluoro-3-[[(2R,8S)-2-fluoro-1,2,3,5,6,7-hexahydropyrrolizin-8-yl]methoxy]-1-hydroxy-7,9-dihydrofuro[3,4-f]quinazolin-6-yl]thieno[3,2-c]pyridin-2-yl]carbamate

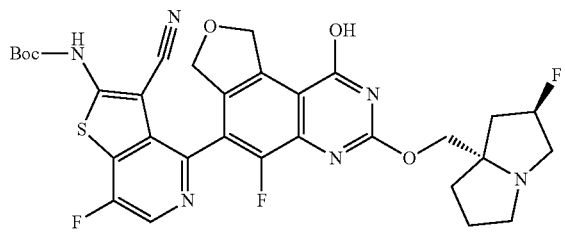 [SMILES: CC(C)(C)OC(=O)Nc1sc2c(F)cnc(-c3c4c(c5c(O)nc(OC[C@@]67CCCN6C[C@H](F)C7)nc5c3F)COC4)c2c1C#N]

To a solution of tert-butyl N-[3-cyano-7-fluoro-4-[5-fluoro-3-[[(2R,8S)-2-fluoro-1,2,3,5,6,7-hexahydropyrrolizin-8-yl]methoxy]-1-(2,2,2-trifluoroethoxy)-7,9-dihydrofuro[3,4-f]quinazolin-6-yl]thieno[3,2-c]pyridin-2-yl]carbamate (0.15 g, 0.20 mmol) in THF (2 mL) was added a solution of NaOH (0.041 g, 1.02 mmol) in H₂O (0.2 mL) dropwise under nitrogen. After 2h, the mixture was diluted with H₂O (50 mL) and extracted with EtOAc (2×100 mL). The combined organic layers were washed with brine (2×100 mL), dried over anhydrous Na₂SO₄, filtered and concentrated under reduced pressure. The residue was diluted with DMF (2 mL) and purified by reversed phase flash purification on C18, eluting with 24% to 37% ACN in 10 mM aq. NH₄HCO₃ with 0.05% NH₄OH, to give the title compound (0.022 g, 16%) as a white solid. MS (ES) m/z=655 (M+1).

Preparation 411 tert-Butyl N-(4-hydroxythieno[2,3-b]pyridin-2-yl)carbamate

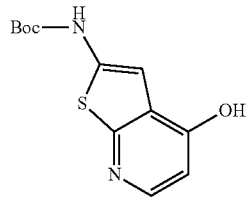 [SMILES: CC(C)(C)OC(=O)Nc1cc2c(O)ccnc2s1]

A mixture of 4-hydroxythieno[2,3-b]pyridine-2-carboxylic acid; hydrochloride (1.96 g, 8.5 mmol) and triethylamine (4.8 mL, 34 mmol, 4.0 eq) in tert-butanol (40 mL) was heated to form a solution, then cooled to RT. Diphenylphosphoryl azide (2.5 mL, 11 mmol, 1.3 eq) was added. The reaction mixture was stirred at RT for 10 min, then heated at 85° C. overnight. The mixture was concentrated in vacuo. The residue was purified on silica, eluting with 10-100% acetone in hexanes to obtain the title compound (1.70 g, 76%). MS (ES) m/z=267 (M+1).

Preparation 412

(2-Aminothieno[2,3-b]pyridin-4-yl) trifluoromethanesulfonate

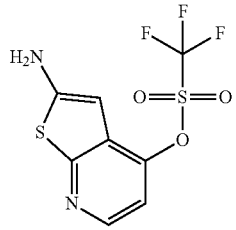

To a suspension of tert-butyl N-(4-hydroxythieno[2,3-b]pyridin-2-yl)carbamate (1.45 g, 5.4 mmol) in DCM (110 mL) was added 2,6-lutidine (1.2 mL, 10 mmol, 1.9 eq) and 4-dimethylaminopyridine (0.067 g, 0.54 mmol, 0.10 eq). The reaction mixture was cooled in an ice bath, treated dropwise with trifluoromethanesulfonic anhydride (1.2 mL, 7.0 mmol, 1.3 eq), and stirred in the ice bath for 1 h. Additional 2,6-lutidine (1.2 mL, 10 mmol, 1.9 eq) and trifluoromethanesulfonic anhydride (1.2 mL, 7.0 mmol, 1.3 eq) were added. The reaction mixture was stirred in the ice bath for 30 min, then quenched with saturated aqueous sodium bicarbonate. The layers were separated and the aqueous layer was extracted twice with DCM. The combined organics were dried over sodium sulfate and concentrated in vacuo. The residue was purified on silica, eluting with 0-75% MTBE in hexanes to give impure fractions. The impure fractions were concentrated in vacuo and further purified on silica, eluting with 50-100% DCM in hexanes. The aqueous layer was extracted four times with 4:1 CHCl₃: isopropanol. The combined organics were dried over sodium sulfate and concentrated in vacuo. The residue was purified on silica, eluting with 10-50% MTBE in hexanes. Clean fractions from the second and third silica purifications were combined and concentrated in vacuo to obtain the title compound (0.71 g, 44%) as an off-white solid. MS (ES) m/z=299 (M+1).

Preparation 413

[2-[Bis(tert-butoxycarbonyl)amino]thieno[2,3-b]pyridin-4-yl]trifluoromethanesulfonate

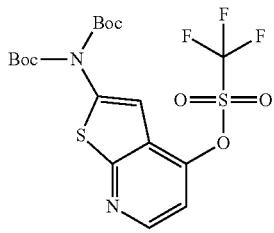 [SMILES: CC(C)(C)OC(=O)N(C(=O)OC(C)(C)C)c1cc2c(OS(=O)(=O)C(F)(F)F)ccnc2s1]

To a solution of (2-aminothieno[2,3-b]pyridin-4-yl) trifluoromethanesulfonate (0.67 g, 2.26 mmol) in 1,4-dioxane (45 mL) was added di-tert-butyl dicarbonate (1.23 g, 5.64 mmol, 2.5 eq) and 4-dimethylaminopyridine (0.028 g, 0.227 mmol, 0.10 eq). The reaction mixture was stirred at RT for 6 days, and concentrated in vacuo. The residue was purified on silica, eluting with 0-50% MTBE in hexanes to obtain the title compound (0.93 g, 82%). MS (ES) m/z=499 (M+1).

Preparation 414

[2-(tert-Butoxycarbonylamino)-3-cyano-thieno[2,3-b]pyridin-4-yl]trifluoromethanesulfonate

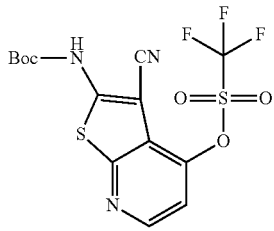 [SMILES: CC(C)(C)OC(=O)Nc1sc2nccc(OS(=O)(=O)C(F)(F)F)c2c1C#N]

A solution of [2-[bis(tert-butoxycarbonyl)amino]thieno[2,3-b]pyridin-4-yl]trifluoromethanesulfonate (0.550 g, 1.10 mmol) in acetonitrile (11 mL) was cooled in an ice bath. Chlorosulfonyl isocyanate (0.3 mL, 3 mmol, 3 eq) was added dropwise and the reaction mixture was stirred in the ice bath for 5 h, placed in a −20° C. freezer overnight, allowed to warm to RT, and stirred for 3.5 h. The reaction mixture was cooled in an ice bath, added dropwise to N,N-dimethylformamide (8.5 mL, cooled in an ice bath), stirred for 1 h, slowly poured into cold saturated aqueous sodium bicarbonate, and diluted with EtOAc. The layers were separated and the aqueous layer was extracted twice with EtOAc. The combined organics were washed with saturated aqueous sodium chloride, dried over sodium sulfate and concentrated in vacuo. The residue was purified on silica, eluting with 0-50% DCM in hexanes to obtain the title compound (0.118 g, 25%) as an off-white solid. MS (ES) m/z=424 (M+1).

Preparation 415 tert-Butyl 8-[6-[2-(tert-butoxycarbonylamino)-3-cyano-thieno[2,3-b]pyridin-4-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate

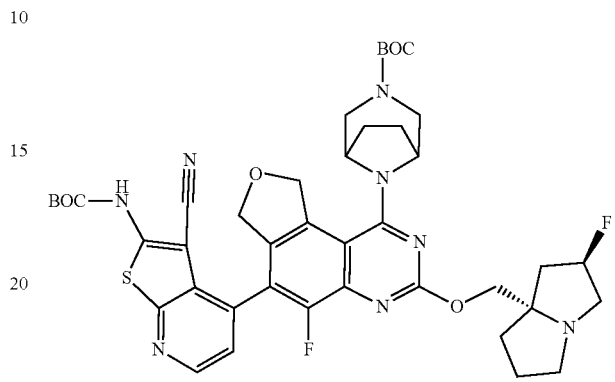

Reaction mixture A: A mixture of tert-butyl 8-[6-bromo-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate (0.370 g, 0.581 mmol), KOAc (0.171 g, 1.74 mmol) and bis(neopentyl glycolato)diboron (0.197 g, 0.872 mmol) in 1,4-dioxane (6 mL) was sparged with $N_2$ for 10 min. Dichloro[bis(2-(diphenylphosphino)phenyl)ether]palladium(II) (0.043 g, 0.059 mmol) was added, and the resulting mixture was sealed and heated at 95° C. for 2.5 h. The reaction mixture was cooled to RT and kept overnight.

Reaction mixture B: A mixture of tert-butyl 8-[6-bromo-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octane-3-carboxylate (0.370 g, 0.581 mmol), KOAc (0.171 g, 1.74 mmol) and bis(neopentyl glycolato)diboron (0.197 g, 0.872 mmol) in 1,4-dioxane (6 mL) was sparged with $N_2$ for 10 min. Dichloro[bis(2-(diphenylphosphino)phenyl)ether]palladium(II) (0.043 g, 0.059 mmol) was added, and the resulting mixture was sealed and heated at 95° C. overnight. The reaction mixture was cooled to RT.

Reaction mixture C: A mixture of [2-(tert-butoxycarbonylamino)-3-cyano-thieno[2,3-b]pyridin-4-yl]trifluoromethanesulfonate (0.162 g, 0.383 mmol), 1,4-dioxane (4 mL) and water (1.2 mL) was sparged with $N_2$ for 15 min. Potassium phosphate (0.162 g, 0.763 mmol) and XPhos Pd G4 (CAS #1599466-81-5; 0.035 g, 0.039 mmol) were added, and the resulting mixture was sealed and heated at 85° C. Reaction mixture A was added via syringe and heated for 1 h before cooling to RT. The reaction mixture was again heated at 85° C. One-third of Reaction mixture B was added via syringe and heated for 1 h. The remainder of Reaction mixture B was added via syringe and heated for 1 h. The reaction mixture was partitioned between DCM and water. The layers were separated, and the aqueous layer was extracted 2× with DCM. The organic layers were combined, dried over $Na_2SO_4$, and concentrated in vacuo. The residue was purified by silica, eluting with 1-5% 7N ammoniated methanol/DCM to afford the title compound (0.200 g, 45%). MS (ES) m/z=831 (M+1).

Example 1

2-Amino-4-[1-(3,8-diazabicyclo[3.2.1]octan-8-yl)-5-fluoro-7,9-dihydrofuro[3,4-f]quinazolin-6-yl]-5-fluoro-benzothiophene-3-carbonitrile, Isomer 2

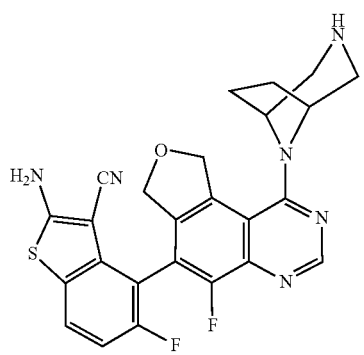 [SMILES: N#Cc1c(N)sc2ccc(F)c(-c3c4c(c5c(N6C7CCC6CNC7)ncnc5c3F)COC4)c12]

A solution of tert-butyl 8-[6-[2-(tert-butoxycarbonylamino)-3-cyano-5-fluoro-benzothiophen-4-yl]-5-fluoro-7,9-dihydrofuro[3,4-f]quinazolin-1-yl]-3,8-diazabicyclo[3.2.1]octane-3-carboxylate (0.605 g, 0.876 mmol) in DCM (5 mL) was charged with TFA (4 mL) and stirred at RT for 25 min. The mixture was concentrated, DCM was added and the mixture was concentrated again, repeating 3×. The mixture was filtered through an SCX column, eluting with MeOH (4 CV), followed by 7N $NH_3$/MeOH (4 CV) to obtain the crude product which was purified on silica gel, eluting with a gradient of 10 to 10% 7N $NH_{13}$/MeOH in DCM to obtain the racemate, followed by chiral purification (Chiralpak® AS-H, 21×250 mm, 35% MeOH (w/0.5% DMEA): 65% $CO_2$, 80 mL/min) to obtain the title compound (0.129 g, 30%) as a white solid. MS (ES) m/z=491 (M+1).

The Example compounds in Table 14 were prepared in a similar manner as described for Preparation 296 or Example 1. Various methods were used to purify the compounds, which would be apparent to one skilled in the art. Chiral purification methods (if applicable) for the Examples of Table 14 are located in Table 18.

TABLE 14

| Example | Chemical Name | Structure | MS (ES) m/z (M + 1) |
|---|---|---|---|
| 2 | 2-Amino-4-[1-(3,8-diazabicyclo[3.2.1]octan-8-yl)-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-benzothiophene-3-carbonitrile | 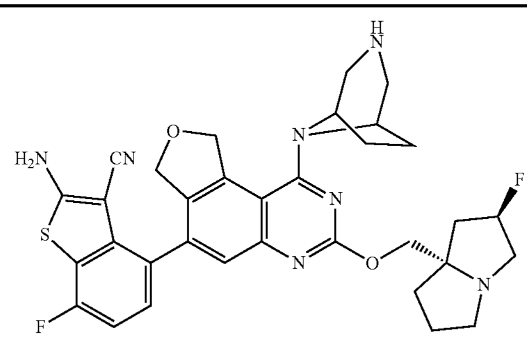 | 630 |
| 3 | 2-Amino-4-[1-[(1R,4R)-2,5-diazabicyclo[2.2.1]heptan-2-yl]-5-fluoro-7,9-dihydrofuro[3,4-f]quinazolin-6-yl]-5-fluoro-benzothiophene-3-carbonitrile, Isomer 2 | 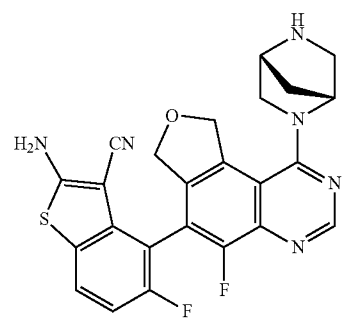 [SMILES: N#Cc1c(N)sc2ccc(F)c(-c3c4c(c5c(N6C[C@H]7C[C@@H]6CN7)ncnc5c3F)COC4)c12] | 477 |
| 4[1] | 2-Amino-4-[9-(cyanomethyl)-1-[(1R,4R)-2,5-diazabicyclo[2.2.1]heptan-2-yl]-5-fluoro-7,9-dihydrofuro[3,4-f]quinazolin-6-yl]-7-fluoro-benzothiophene-3-carbonitrile, Isomer 1 | 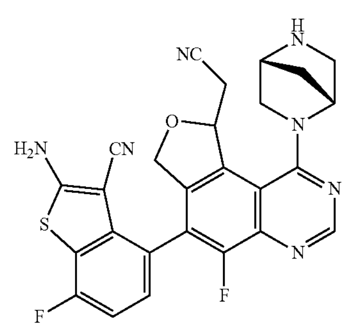 [SMILES: N#CCC1OCc2c(-c3ccc(F)c4sc(N)c(C#N)c34)c(F)c3ncnc(N4C[C@H]5C[C@@H]4CN5)c3c21] | 516 |

TABLE 14-continued

| Example | Chemical Name | Structure | MS (ES) m/z (M + 1) |
|---|---|---|---|
| 5[1] | 2-Amino-4-[5-chloro-9-(cyanomethyl)-1-[(1R,4R)-2,5-diazabicyclo[2.2.1]heptan-2-yl]-7,9-dihydrofuro[3,4-f]quinazolin-6-yl]-7-fluoro-benzothiophene-3-carbonitrile, Isomer 2 | 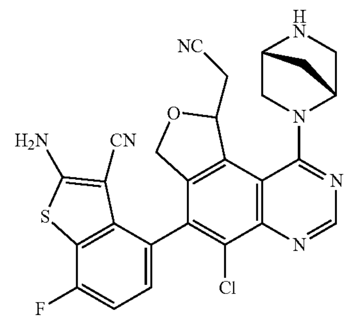 [SMILES: N#CCC1OCc2c(-c3ccc(F)c4sc(N)c(C#N)c34)c(Cl)c3ncnc(N4C[C@H]5C[C@@H]4CN5)c3c21] | 532 |
| 6 | 2-Amino-7-fluoro-4-[5-fluoro-1-[(1R,4R)-5-methyl-2,5-diazabicyclo[2.2.1]heptan-2-yl]-7,9-dihydrofuro[3,4-f]quinazolin-6-yl]benzothiophene-3-carbonitrile | 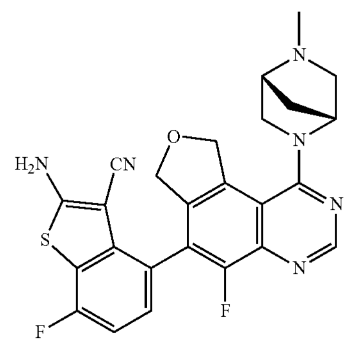 [SMILES: CN1C[C@H]2C[C@@H]1CN2c1ncnc2c(F)c(-c3ccc(F)c4sc(N)c(C#N)c34)c3c(c12)COC3] | 491 |
| 7 | 2-Amino-4-[5-chloro-1-(3,8-diazabicyclo[3.2.1]octan-8-yl)-3-[[(2R)-1,4-dioxan-2-yl]methoxy]-7,9-dihydrofuro[3,4-f]quinazolin-6-yl]-7-fluoro-benzothiophene-3-carbonitrile | 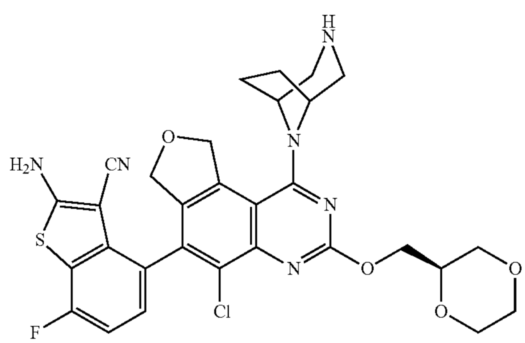 [SMILES: N#Cc1c(N)sc2c(F)ccc(-c3c4c(c5c(N6C7CCC6CNC7)nc(OC[C@H]6COCCO6)nc5c3Cl)COC4)c12] | 623 |
| 8 | 2-Amino-4-[5-chloro-7-[[(2R)-tetrahydrofuran-2-yl]methoxy]-1,3-dihydrofuro[3,4-f]quinolin-4-yl]-7-fluoro-benzothiophene-3-carbonitrile | 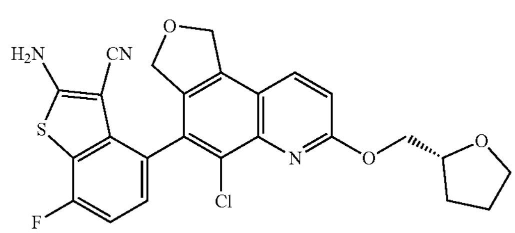 [SMILES: N#Cc1c(N)sc2c(F)ccc(-c3c4c(c5ccc(OC[C@H]6CCCO6)nc5c3Cl)COC4)c12] | 496 |
| 9 | 2-Amino-4-[1-(3,6-diazabicyclo[3.1.1]heptan-6-yl)-5-fluoro-7,9-dihydrofuro[3,4-f]quinazolin-6-yl]-5-fluoro-benzothiophene-3-carbonitrile, Isomer 2 | 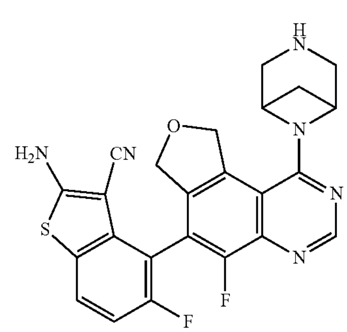 [SMILES: N#Cc1c(N)sc2ccc(F)c(-c3c4c(c5c(N6C7CNCC6C7)ncnc5c3F)COC4)c12] | 477 |

TABLE 14-continued

| Example | Chemical Name | Structure | MS (ES) m/z (M + 1) |
|---|---|---|---|
| 10 | 2-Amino-4-[1-(3,8-diazabicyclo[3.2.1]octan-8-yl)-5-fluoro-3-(2-methoxyethoxy)-7,9-dihydrofuro[3,4-f]quinazolin-6-yl]-7-fluoro-benzothiophene-3-carbonitrile | 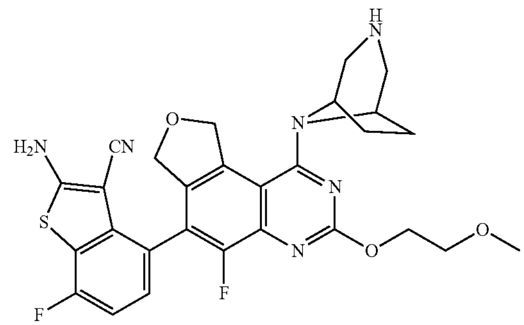 [SMILES: COCCOc1nc(N2C3CCC2CNC3)c2c3c(c(-c4ccc(F)c5sc(N)c(C#N)c45)c(F)c2n1)COC3] | 565 |
| 11 | 2-Amino-4-[1-(3,8-diazabicyclo[3.2.1]octan-8-yl)-5-fluoro-3-[[(2S)-1-(2-fluoroethyl)pyrrolidin-2-yl]methoxy]-7,9-dihydrofuro[3,4-f]quinazolin-6-yl]-7-fluoro-benzothiophene-3-carbonitrile | 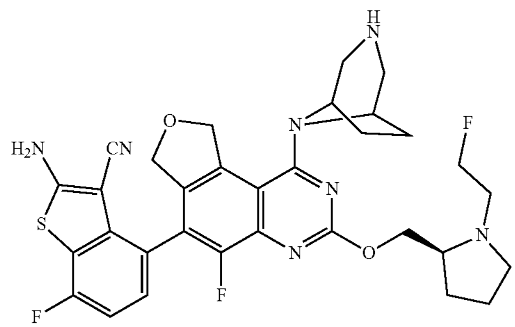 [SMILES: N#Cc1c(N)sc2c(F)ccc(-c3c4c(c5c(N6C7CCC6CNC7)nc(OC[C@@H]6CCCN6CCF)nc5c3F)COC4)c12] | 636 |
| 12 | 2-Amino-4-[1-[(1R,4R)-2,5-diazabicyclo[2.2.1]heptan-2-yl]-5-fluoro-3-methyl-7,9-dihydrofuro[3,4-f]quinazolin-6-yl]-7-fluoro-benzothiophene-3-carbonitrile | 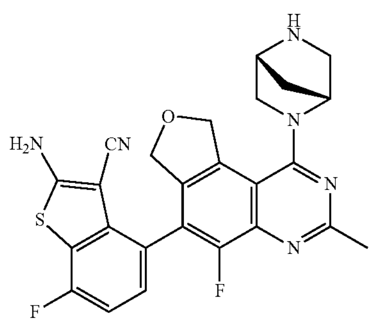 [SMILES: Cc1nc(N2C[C@H]3C[C@@H]2CN3)c2c3c(c(-c4ccc(F)c5sc(N)c(C#N)c45)c(F)c2n1)COC3] | 491 |
| 13 | 2-Amino-4-[9-(3,8-diazabicyclo[3.2.1]octan-8-yl)-5-fluoro-1,3-dihydrofuro[3,4-f]cinnolin-4-yl]-7-fluoro-benzothiophene-3-carbonitrile | 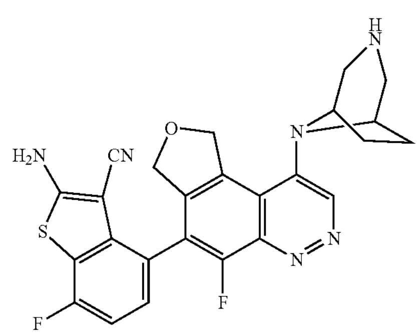 [SMILES: N#Cc1c(N)sc2c(F)ccc(-c3c4c(c5c(N6C7CCC6CNC7)cnnc5c3F)COC4)c12] | 491 |

TABLE 14-continued

| Example | Chemical Name | Structure | MS (ES) m/z (M + 1) |
|---|---|---|---|
| 14 | 2-Amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]benzofuran-3-carbonitrile | 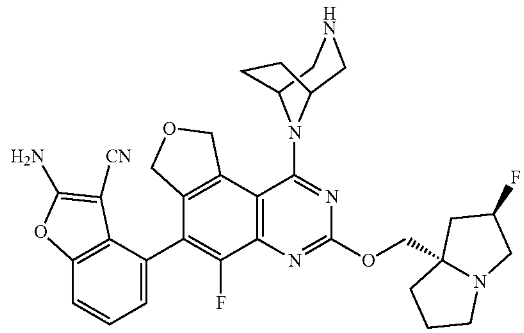 [SMILES: N#Cc1c(N)oc2cccc(-c3c4c(c5c(N6C7CCC6CNC7)nc(OC[C@@]67CCCN6C[C@H](F)C7)nc5c3F)COC4)c12] | 614 |
| 15 | 2-Amino-4-[1-(3,8-diazabicyclo[3.2.1]octan-8-yl)-5-fluoro-7,9-dihydrofuro[3,4-f]quinazolin-6-yl]-5-fluoro-benzofuran-3-carbonitrile, Isomer 2 | 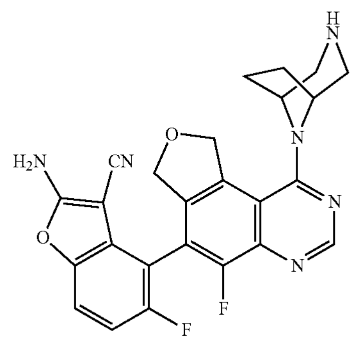 [SMILES: N#Cc1c(N)oc2ccc(F)c(-c3c4c(c5c(N6C7CCC6CNC7)ncnc5c3F)COC4)c12] | 475 |
| 16 | 2-Amino-4-[5-chloro-9-(3,8-diazabicyclo[3.2.1]octan-8-yl)-7-[[(2S)-1-methylpyrrolidin-2-yl]methoxy]-1,3-dihydrofuro[3,4-f]quinolin-4-yl]-7-fluoro-benzothiophene-3-carbonitrile | 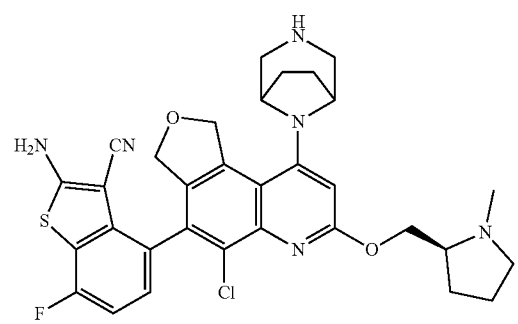 [SMILES: CN1CCC[C@H]1COc1cc(N2C3CCC2CNC3)c2c3c(c(-c4ccc(F)c5sc(N)c(C#N)c45)c(Cl)c2n1)COC3] | 619 |
| 17[2] | 2-Amino-4-[5-chloro-1-(3,8-diazabicyclo[3.2.1]octan-8-yl)-3-[2-(dimethylamino)ethoxy]-7,9-dihydrofuro[3,4-f]quinazolin-6-yl]-7-fluoro-benzothiophene-3-carbonitrile | 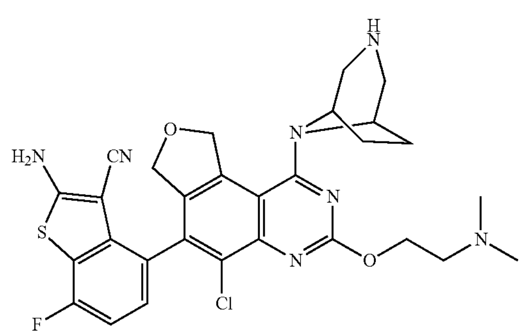 [SMILES: CN(C)CCOc1nc(N2C3CCC2CNC3)c2c3c(c(-c4ccc(F)c5sc(N)c(C#N)c45)c(Cl)c2n1)COC3] | 594 |

TABLE 14-continued

| Example | Chemical Name | Structure | MS (ES) m/z (M + 1) |
|---------|---------------|-----------|---------------------|
| 18 | 2-Amino-4-[5-chloro-1-(3,8-diazabicyclo[3.2.1]octan-8-yl)-3-(hydroxymethyl)-7,9-dihydrofuro[3,4-f]quinazolin-6-yl]-7-fluoro-benzothiophene-3-carbonitrile, Isomer 2 | 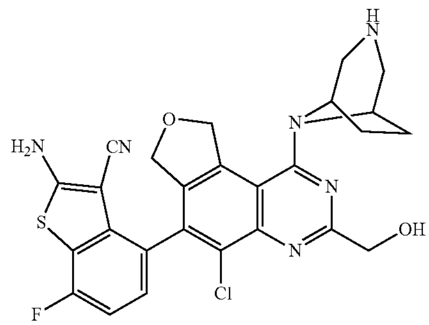 [SMILES: N#Cc1c(N)sc2c(F)ccc(-c3c4c(c5c(N6C7CCC6CNC7)nc(CO)nc5c3Cl)COC4)c12] | 537 |
| 19 | 2-Amino-4-[9-(2-aminoethyl)-5-chloro-7-[[(2S)-1-methylpyrrolidin-2-yl]methoxy]-1,3-dihydrofuro[3,4-f]quinolin-4-yl]-7-fluoro-benzothiophene-3-carbonitrile | 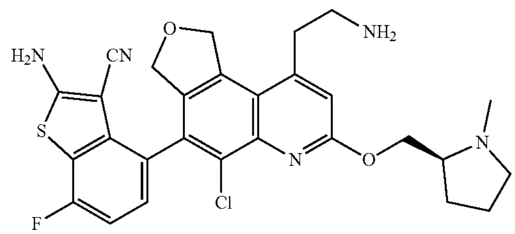 [SMILES: CN1CCC[C@H]1COc1cc(CCN)c2c3c(c(-c4ccc(F)c5sc(N)c(C#N)c45)c(Cl)c2n1)COC3] | 552 |
| 20 | 2-Amino-4-[5-chloro-9-(3,8-diazabicyclo[3.2.1]octan-8-yl)-7-[[(2S)-1-methylazetidin-2-yl]methoxy]-1,3-dihydrofuro[3,4-f]quinolin-4-yl]-7-fluoro-benzothiophene-3-carbonitrile | 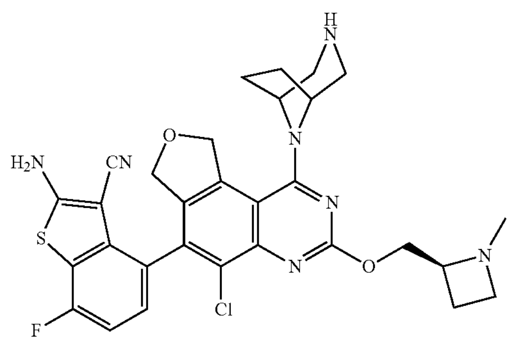 [SMILES: CN1CC[C@H]1COc1nc(N2C3CCC2CNC3)c2c3c(c(-c4ccc(F)c5sc(N)c(C#N)c45)c(Cl)c2n1)COC3] | 605 |
| 21 | 2-Amino-4-[5-chloro-1-(3,8-diazabicyclo[3.2.1]octan-8-yl)-3-[(1S)-2-hydroxy-1-methyl-ethoxy]-7,9-dihydrofuro[3,4-f]quinazolin-6-yl]-7-fluoro-benzothiophene-3-carbonitrile | 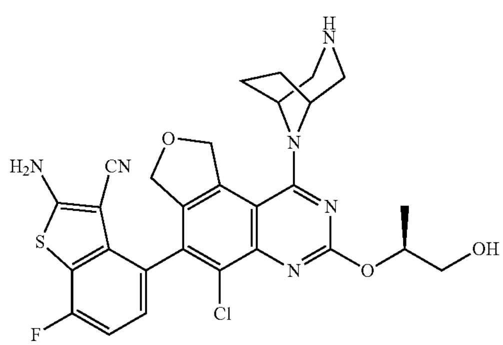 [SMILES: C[C@@H](CO)Oc1nc(N2C3CCC2CNC3)c2c3c(c(-c4ccc(F)c5sc(N)c(C#N)c45)c(Cl)c2n1)COC3] | 581 |
| 22 | 2-Amino-4-[1-[(1R,4R)-2,5-diazabicyclo[2.2.1]heptan-2-yl]-5-methyl-7,9-dihydrofuro[3,4-f]quinazolin-6-yl]-7-fluoro-benzothiophene-3-carbonitrile, Isomer 1 | 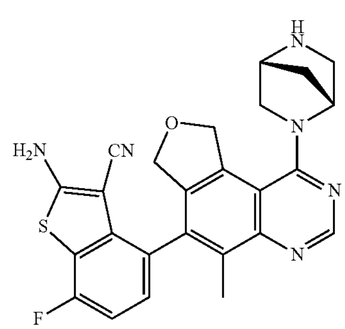 [SMILES: Cc1c(-c2ccc(F)c3sc(N)c(C#N)c23)c2c(c3c(N4C[C@H]5C[C@@H]4CN5)ncnc13)COC2] | 473 |

TABLE 14-continued

| Example | Chemical Name | Structure | MS (ES) m/z (M + 1) |
|---|---|---|---|
| 23 | 2-Amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]benzothiophene-3-carbonitrile | 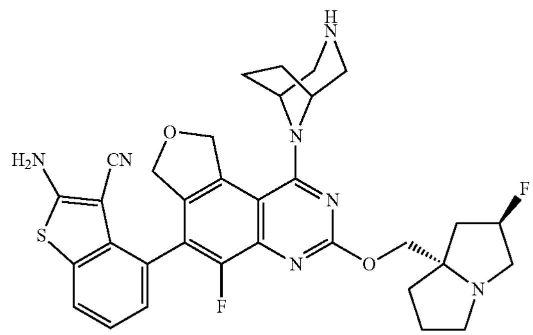 [SMILES: N#Cc1c(N)sc2cccc(-c3c4c(c5c(N6C7CCC6CNC7)nc(OC[C@@]67CCCN6C[C@H](F)C7)nc5c3F)COC4)c12] | 630 |
| 24 | 2-Amino-4-[4-[5-fluoro-3-[[(2R,8S)-2-fluoro-1,2,3,5,6,7-hexahydropyrrolizin-8-yl]methoxy]-1-(3-methyl-3,8-diazabicyclo[3.2.1]octan-8-yl)-7,9-dihydrofuro[3,4-f]quinazolin-6-yl]benzothiophene-3-carbonitrile | 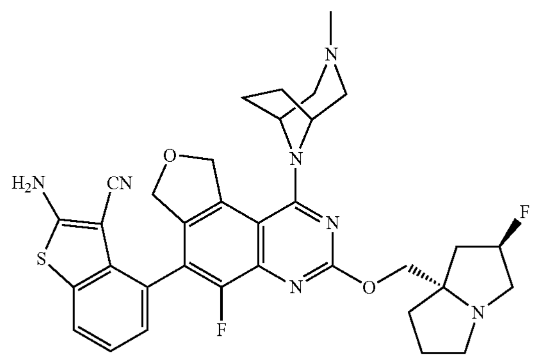 [SMILES: CN1CC2CCC(C1)N2c1nc(OC[C@@]23CCCN2C[C@H](F)C3)nc2c(F)c(-c3cccc4sc(N)c(C#N)c34)c3c(c12)COC3] | 644 |
| 25 | 2-Amino-4-[1-(3-ethyl-3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]benzothiophene-3-carbonitrile | 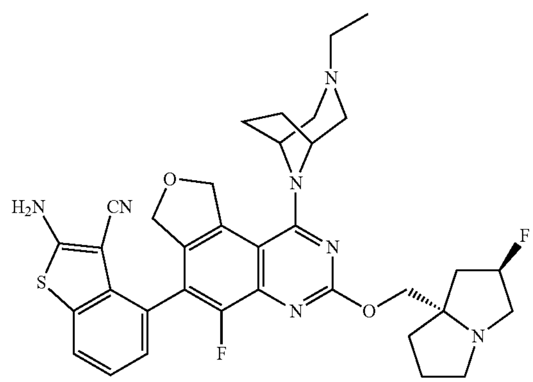 [SMILES: CCN1CC2CCC(C1)N2c1nc(OC[C@@]23CCCN2C[C@H](F)C3)nc2c(F)c(-c3cccc4sc(N)c(C#N)c34)c3c(c12)COC3] | 658 |
| 26 | 2-Amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]thieno[3,2-c]pyridine-3-carbonitrile | 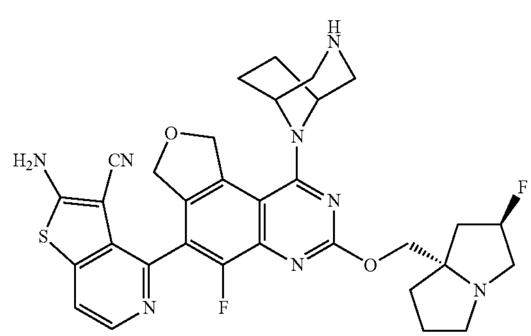 [SMILES: N#Cc1c(N)sc2ccnc(-c3c4c(c5c(N6C7CCC6CNC7)nc(OC[C@@]67CCCN6C[C@H](F)C7)nc5c3F)COC4)c12] | 631 |

TABLE 14-continued

| Example | Chemical Name | Structure | MS (ES) m/z (M + 1) |
|---|---|---|---|
| 27 | 2-Amino-4-[1-(3,6-diazabicyclo[3.1.1]heptan-6-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]thieno[3,2-c]pyridine-3-carbonitrile | 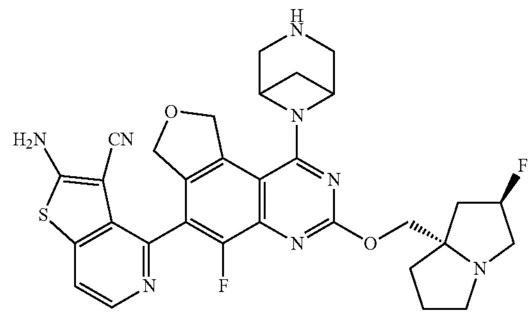 [SMILES: N#Cc1c(N)sc2ccnc(-c3c4c(c5c(N6C7CNCC6C7)nc(OC[C@@]67CCCN6C[C@H](F)C7)nc5c3F)COC4)c12] | 617 |
| 28 | 3-[8-[6-(2-Amino-1,3-benzothiazol-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]propan-1-ol | 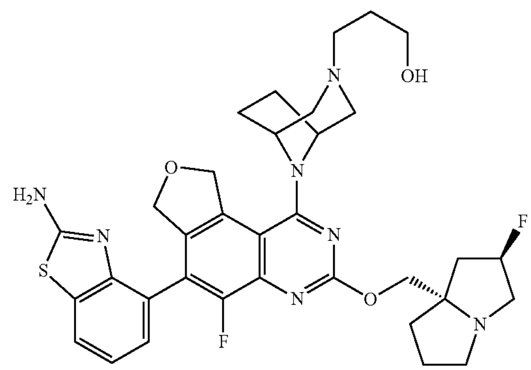 [SMILES: Nc1nc2c(-c3c4c(c5c(N6C7CCC6CN(CCCO)C7)nc(OC[C@@]67CCCN6C[C@H](F)C7)nc5c3F)COC4)cccc2s1] | 664 |
| 29 | 2-Amino-7-fluoro-4-[5-methyl-3-[[(2S)-1-methylpyrrolidin-2-yl]methoxy]-9,10-dihydro-7H-pyrano[4,3-f]quinazolin-6-yl]benzothiophene-3-carbonitrile, Isomer 1 | 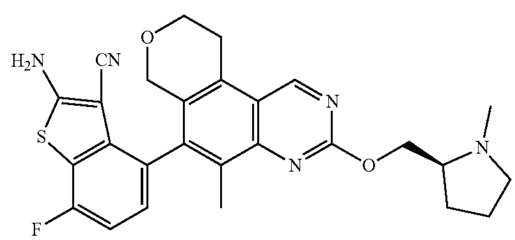 [SMILES: Cc1c(-c2ccc(F)c3sc(N)c(C#N)c23)c2c(c3cnc(OC[C@@H]4CCCN4C)nc13)CCOC2] | 502[a] |
| 30 | 2-Amino-4-[5-chloro-7-(2-morpholinoethoxy)-1,3-dihydrofuro[3,4-f]quinolin-4-yl]-7-fluoro-benzothiophene-3-carbonitrile, Isomer 1 | 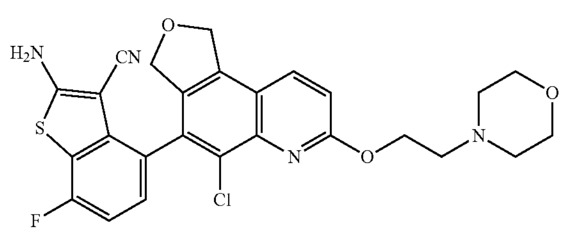 [SMILES: N#Cc1c(N)sc2c(F)ccc(-c3c4c(c5ccc(OCCN6CCOCC6)nc5c3Cl)COC4)c12] | 525 |
| 31 | 2-Amino-4-[5-chloro-7-[[(2S,4R)-4-hydroxy-1-methyl-pyrrolidin-2-yl]methoxy]-1,3-dihydrofuro[3,4-f]quinolin-4-yl]-7-fluoro-benzothiophene-3-carbonitrile, Isomer 1 | 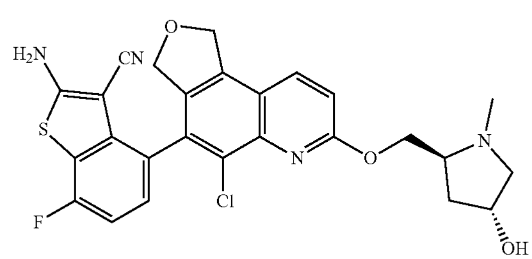 [SMILES: CN1C[C@H](O)C[C@H]1COc1ccc2c3c(c(-c4ccc(F)c5sc(N)c(C#N)c45)c(Cl)c2n1)COC3] | 525 |

TABLE 14-continued

| Example | Chemical Name | Structure | MS (ES) m/z (M + 1) |
|---------|---------------|-----------|---------------------|
| 32 | 2-Amino-4-[5-chloro-7-[[(2R)-4-methylmorpholin-2-yl]methoxy]-1,3-dihydrofuro[3,4-f]quinolin-4-yl]-7-fluoro-benzothiophene-3-carbonitrile, Isomer 2 | 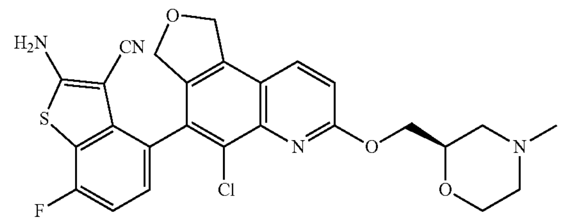 [SMILES: CN1CCO[C@@H](COc2ccc3c4c(c(-c5ccc(F)c6sc(N)c(C#N)c56)c(Cl)c3n2)COC4)C1] | 525 |
| 33 | 2-Amino-4-[5-chloro-7-[(3S)-tetrahydrofuran-3-yl]oxy-1,3-dihydrofuro[3,4-f]quinolin-4-yl]-7-fluoro-benzothiophene-3-carbonitrile, Isomer 2 | 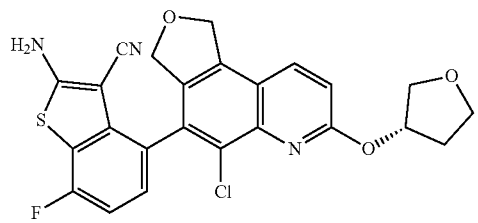 [SMILES: N#Cc1c(N)sc2c(F)ccc(-c3c4c(c5ccc(O[C@H]6CCOC6)nc5c3Cl)COC4)c12] | 482 |
| 34 | 2-Amino-4-[5-chloro-7-[[(3S)-4-methylmorpholin-3-yl]methoxy]-1,3-dihydrofuro[3,4-f]quinolin-4-yl]-7-fluoro-benzothiophene-3-carbonitrile, Isomer 1 | 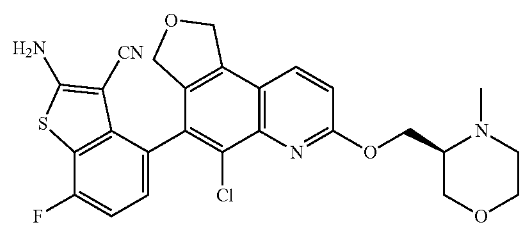 [SMILES: CN1CCOC[C@H]1COc1ccc2c3c(c(-c4ccc(F)c5sc(N)c(C#N)c45)c(Cl)c2n1)COC3] | 525 |
| 35 | 2-Amino-4-[5-chloro-7-[(3-hydroxycyclobutyl)methoxy]-1,3-dihydrofuro[3,4-f]quinolin-4-yl]-7-fluoro-benzothiophene-3-carbonitrile, Isomer 1 | 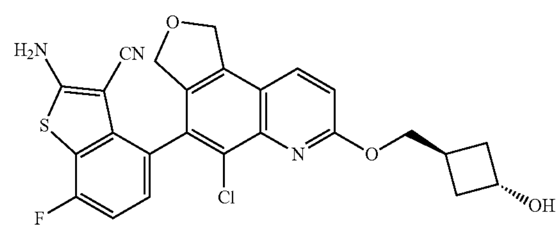 [SMILES: N#Cc1c(N)sc2c(F)ccc(-c3c4c(c5ccc(OC[C@H]6C[C@H](O)C6)nc5c3Cl)COC4)c12] | 496 |
| 36 | 2-Amino-4-[5-chloro-7-(oxetan-3-ylmethoxy)-1,3-dihydrofuro[3,4-f]quinolin-4-yl]-7-fluoro-benzothiophene-3-carbonitrile, Isomer 1 | 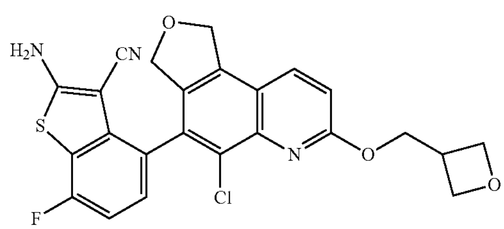 [SMILES: N#Cc1c(N)sc2c(F)ccc(-c3c4c(c5ccc(OCC6COC6)nc5c3Cl)COC4)c12] | 482 |
| 37 | 2-Amino-4-[5-chloro-7-[(2R)-2-hydroxypropoxy]-1,3-dihydrofuro[3,4-f]quinolin-4-yl]-7-fluoro-benzothiophene-3-carbonitrile | 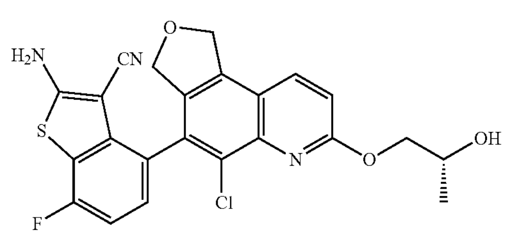 [SMILES: C[C@@H](O)COc1ccc2c3c(c(-c4ccc(F)c5sc(N)c(C#N)c45)c(Cl)c2n1)COC3] | 470 |

TABLE 14-continued

| Example | Chemical Name | Structure | MS (ES) m/z (M + 1) |
|---|---|---|---|
| 38 | 2-Amino-4-[5-chloro-7-[[(2S,4R)-4-fluoro-1-methyl-pyrrolidin-2-yl]methoxy]-1,3-dihydrofuro[3,4-f]quinolin-4-yl]-7-fluoro-benzothiophene-3-carbonitrile, Isomer 1 | 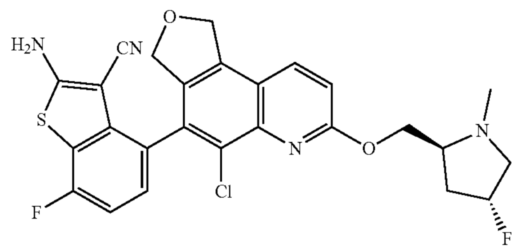 [SMILES: CN1C[C@H](F)C[C@H]1COc1ccc2c3c(c(-c4ccc(F)c5sc(N)c(C#N)c45)c(Cl)c2n1)COC3] | 527 |
| 39 | 2-Amino-4-[5-chloro-7-(1,2,3,5,6,7-hexahydropyrrolizin-8-ylmethoxy)-1,3-dihydrofuro[3,4-f]quinolin-4-yl]-7-fluoro-benzothiophene-3-carbonitrile, Isomer 1 | 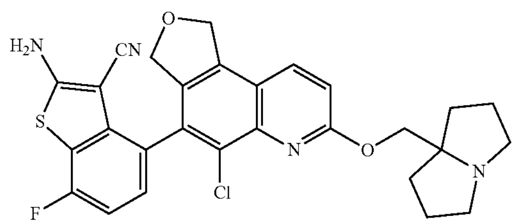 [SMILES: N#Cc1c(N)sc2c(F)ccc(-c3c4c(c5ccc(OCC67CCCN6CCC7)nc5c3Cl)COC4)c12] | 535 |
| 40 | 2-Amino-4-[5-chloro-7-[[2-(hydroxymethyl)-1-methyl-pyrrolidin-2-yl]methoxy]-1,3-dihydrofuro[3,4-f]quinolin-4-yl]-7-fluoro-benzothiophene-3-carbonitrile, Isomer 1 | 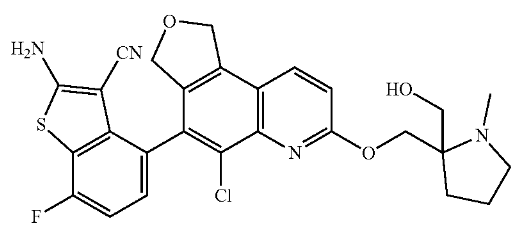 [SMILES: CN1CCCC1(CO)COc1ccc2c3c(c(-c4ccc(F)c5sc(N)c(C#N)c45)c(Cl)c2n1)COC3] | 539 |
| 41 | 2-Amino-4-[5-chloro-7-[(3-methoxy-1,2-dimethyl-azetidin-2-yl)methoxy]-1,3-dihydrofuro[3,4-f]quinolin-4-yl]-7-fluoro-benzothiophene-3-carbonitrile, Isomer 1 | 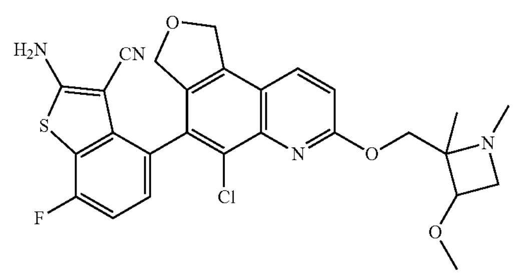 [SMILES: COC1CN(C)C1(C)COc1ccc2c3c(c(-c4ccc(F)c5sc(N)c(C#N)c45)c(Cl)c2n1)COC3] | 539 |
| 42 | 2-Amino-4-[5-chloro-7-(2-hydroxyethoxy)-1,3-dihydrofuro[3,4-f]quinolin-4-yl]-7-fluoro-benzothiophene-3-carbonitrile | 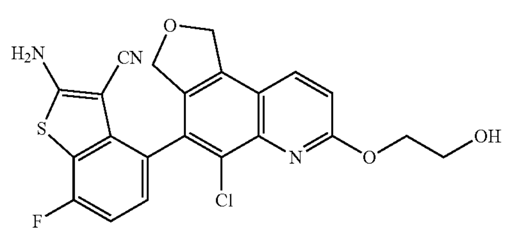 [SMILES: N#Cc1c(N)sc2c(F)ccc(-c3c4c(c5ccc(OCCO)nc5c3Cl)COC4)c12] | 456 |
| 43 | 2-Amino-4-[5-chloro-7-[[(2S)-pyrrolidin-2-yl]methoxy]-1,3-dihydrofuro[3,4-f]quinolin-4-yl]-7-fluoro-benzothiophene-3-carbonitrile, Isomer 1 | 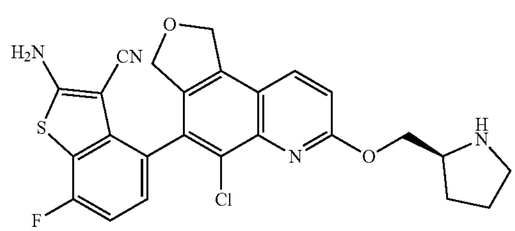 [SMILES: N#Cc1c(N)sc2c(F)ccc(-c3c4c(c5ccc(OC[C@@H]6CCCN6)nc5c3Cl)COC4)c12] | 495 |

TABLE 14-continued

| Example | Chemical Name | Structure | MS (ES) m/z (M + 1) |
|---|---|---|---|
| 44 | 2-Amino-4-[5-chloro-7-[[(2S)-1-methylpyrrolidin-2-yl]methoxy]-1,3-dihydrofuro[3,4-f]quinolin-4-yl]-7-fluoro-benzothiophene-3-carbonitrile, Isomer 1 | 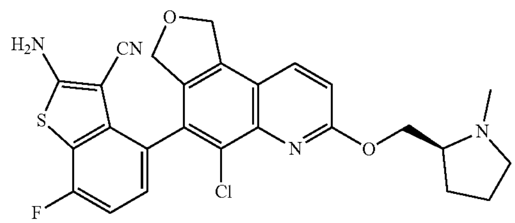 [SMILES: CN1CCC[C@H]1COc1ccc2c3c(c(-c4ccc(F)c5sc(N)c(C#N)c45)c(Cl)c2n1)COC3] | 509 |
| 45 | 2-Amino-4-[9-(3,8-diazabicyclo[3.2.1]octan-8-yl)-5-fluoro-7-[[(2R,8S)-2-fluoro-1,2,3,5,6,7-hexahydropyrrolizin-8-yl]methoxy]-1,3-dihydrofuro[3,4-f]quinolin-4-yl]-7-fluoro-benzothiophene-3-carbonitrile, Isomer 1 | 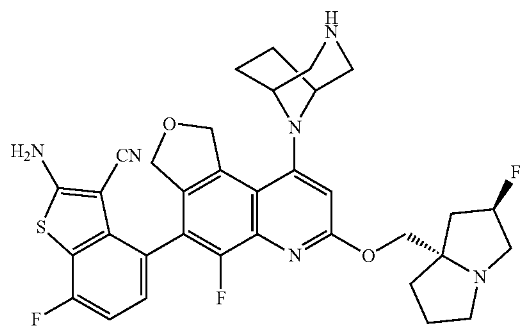 [SMILES: N#Cc1c(N)sc2c(F)ccc(-c3c4c(c5c(N6C7CCC6CNC7)cc(OC[C@@]67CCCN6C[C@H](F)C7)nc5c3F)COC4)c12] | 647 |
| 58 | 2-Amino-4-[1-(3,6-diazabicyclo[3.1.1]heptan-6-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-5-fluoro-benzothiophene-3-carbonitrile | 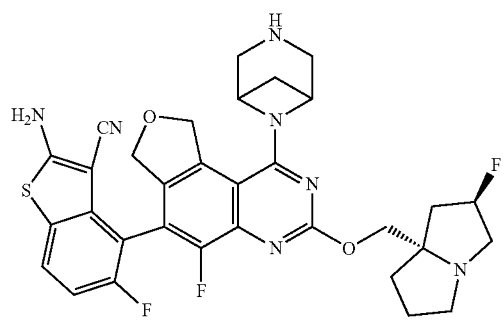 [SMILES: N#Cc1c(N)sc2ccc(F)c(-c3c4c(c5c(N6C7CNCC6C7)nc(OC[C@@]67CCCN6C[C@H](F)C7)nc5c3F)COC4)c12] | 634 |
| 59[3] | 2-Amino-4-[1-(3,6-diazabicyclo[3.1.1]heptan-6-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-5-fluoro-benzothiophene-3-carbonitrile | 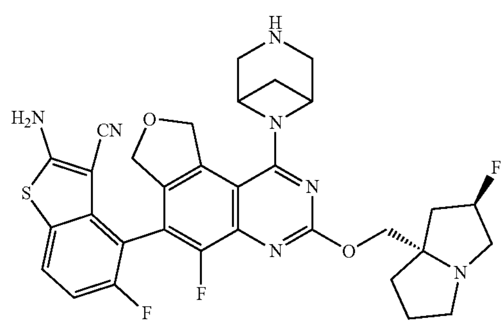 [SMILES: N#Cc1c(N)sc2ccc(F)c(-c3c4c(c5c(N6C7CNCC6C7)nc(OC[C@@]67CCCN6C[C@H](F)C7)nc5c3F)COC4)c12] | 634 |
| 60 | 2-Amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-5-fluoro-benzothiophene-3-carbonitrile | 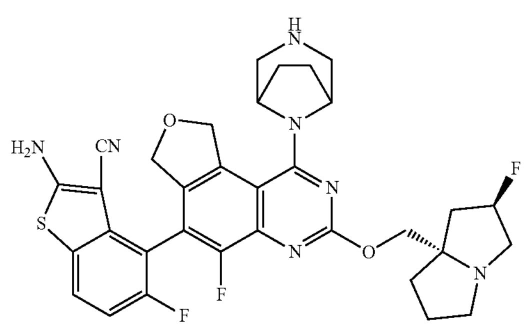 [SMILES: N#Cc1c(N)sc2ccc(F)c(-c3c4c(c5c(N6C7CCC6CNC7)nc(OC[C@@]67CCCN6C[C@H](F)C7)nc5c3F)COC4)c12] | 648 |

TABLE 14-continued

| Example | Chemical Name | Structure | MS (ES) m/z (M + 1) |
|---|---|---|---|
| 61[4] | 2-Amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-5-fluoro-benzothiophene-3-carbonitrile | 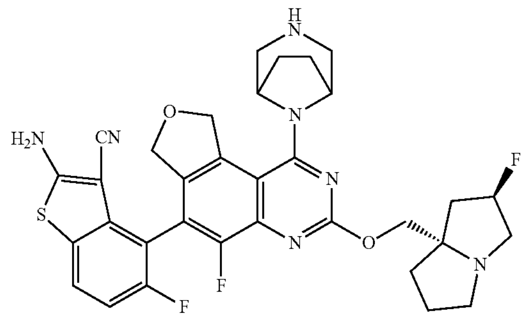 [SMILES: N#Cc1c(N)sc2ccc(F)c(-c3c4c(c5c(N6C7CCC6CNC7)nc(OC[C@@]67CCCN6C[C@H](F)C7)nc5c3F)COC4)c12] | 648 |
| 62[5] | 2-Amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-5-fluoro-benzofuran-3-carbonitrile | 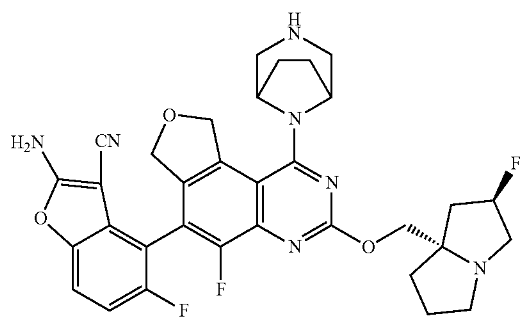 [SMILES: N#Cc1c(N)oc2ccc(F)c(-c3c4c(c5c(N6C7CCC6CNC7)nc(OC[C@@]67CCCN6C[C@H](F)C7)nc5c3F)COC4)c12] | 632 |
| 63 | 2-Amino-4-[1-(3,6-diazabicyclo[3.1.1]heptan-6-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-5-fluoro-benzofuran-3-carbonitrile | 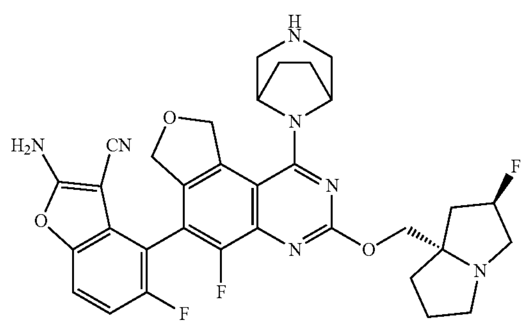 [SMILES: N#Cc1c(N)oc2ccc(F)c(-c3c4c(c5c(N6C7CCC6CNC7)nc(OC[C@@]67CCCN6C[C@H](F)C7)nc5c3F)COC4)c12] | 618 |
| 64 | 2-Amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-thieno[3,2-c]pyridine-3-carbonitrile | 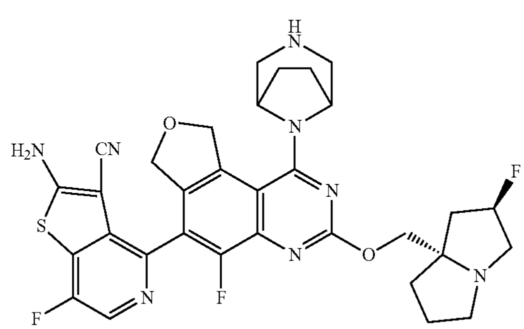 [SMILES: N#Cc1c(N)sc2c(F)cnc(-c3c4c(c5c(N6C7CCC6CNC7)nc(OC[C@@]67CCCN6C[C@H](F)C7)nc5c3F)COC4)c12] | 649 |

TABLE 14-continued

| Example | Chemical Name | Structure | MS (ES) m/z (M + 1) |
|---|---|---|---|
| 65 | 2-Amino-4-[1-(3,8-diazabicyclo[3.2.1]octan-8-yl)-5-fluoro-3-[(2-methoxy-1,2,3,5,6,7-hexahydropyrrolizin-8-yl)methoxy]-7,9-dihydrofuro[3,4-f]quinazolin-6-yl]-7-fluoro-thieno[3,2-c]pyridine-3-carbonitrile | 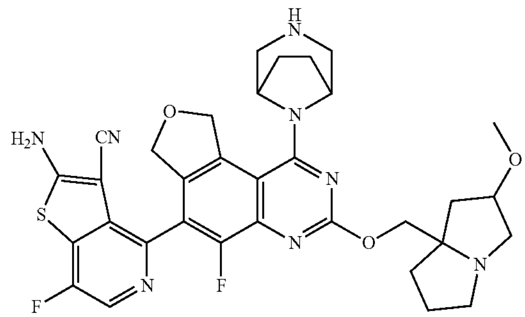 [SMILES: COC1CN2CCCC2(COc2nc(N3C4CCC3CNC4)c3c4c(c(-c5ncc(F)c6sc(N)c(C#N)c56)c(F)c3n2)COC4)C1] | 661 |
| 66 | 2-Amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-7-methyl-thieno[3,2-c]pyridine-3-carbonitrile | 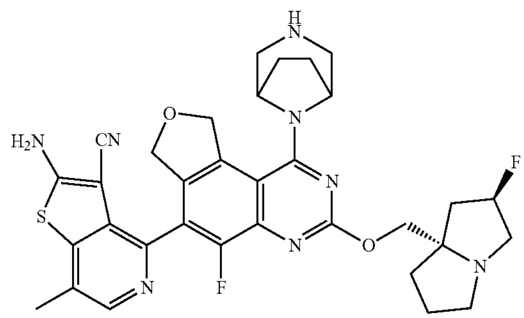 [SMILES: Cc1cnc(-c2c3c(c4c(N5C6CCC5CNC6)nc(OC[C@@]56CCCN5C[C@H](F)C6)nc4c2F)COC3)c2c(C#N)c(N)sc12] | 645 |
| 67 | 2-Amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-benzofuran-3-carbonitrile | 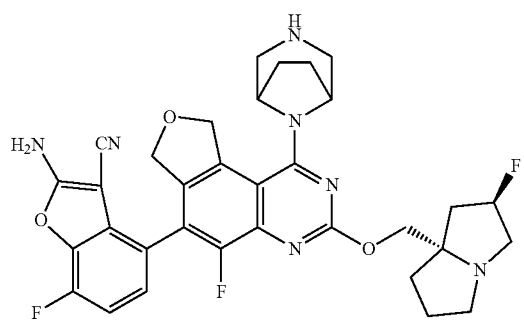 [SMILES: N#Cc1c(N)oc2c(F)ccc(-c3c4c(c5c(N6C7CCC6CNC7)nc(OC[C@@]67CCCN6C[C@H](F)C7)nc5c3F)COC4)c12] | 632 |
| 68 | 2-Amino-4-[1-(3,8-diazabicyclo[3.2.1]octan-8-yl)-3-[[(2R,8S)-2-fluoro-1,2,3,5,6,7-hexahydropyrrolizin-8-yl]methoxy]-7,9-dihydrofuro[3,4-f]quinazolin-6-yl]benzothiophene-3-carbonitrile | 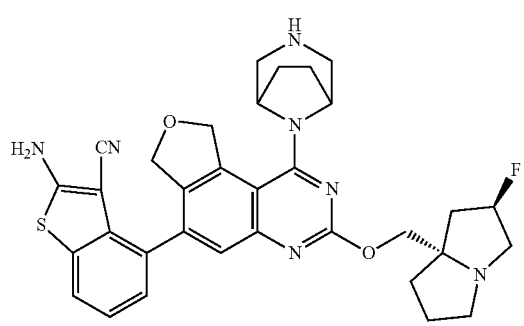 [SMILES: N#Cc1c(N)sc2cccc(-c3cc4nc(OC[C@@]56CCCN5C[C@H](F)C6)nc(N5C6CCC5CNC6)c4c4c3COC4)c12] | 612 |

TABLE 14-continued

| Example | Chemical Name | Structure | MS (ES) m/z (M + 1) |
|---|---|---|---|
| 69[4] | 2-Amino-4-[1-(3,8-diazabicyclo[3.2.1]octan-8-yl)-5-fluoro-3-[[(2S)-1-methylpyrrolidin-2-yl]methoxy]-7,9-dihydrofuro[3,4-f]quinazolin-6-yl]-5-fluoro-benzothiophene-3-carbonitrile | 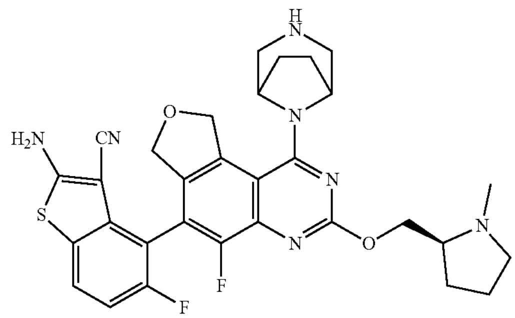 [SMILES: CN1CCC[C@H]1COc1nc(N2C3CCC2CNC3)c2c3c(c(-c4c(F)ccc5sc(N)c(C#N)c45)c(F)c2n1)COC3] | 604 |
| 70[4] | 2-Amino-4-[1-(3,8-diazabicyclo[3.2.1]octan-8-yl)-3-[3-(dimethylamino)azetidin-1-yl]-5-fluoro-7,9-dihydrofuro[3,4-f]quinazolin-6-yl]-5-fluoro-benzothiophene-3-carbonitrile | 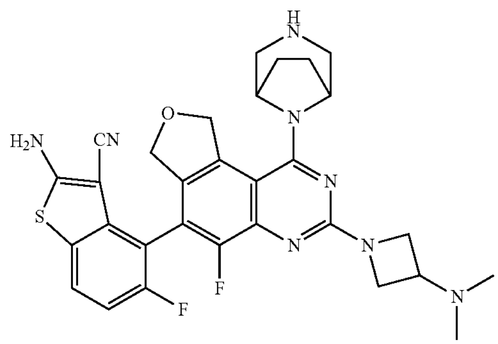 [SMILES: CN(C)C1CN(c2nc(N3C4CCC3CNC4)c3c4c(c(-c5c(F)ccc6sc(N)c(C#N)c56)c(F)c3n2)COC4)C1] | 589 |
| 71[4] | 2-Amino-4-[1-(3,8-diazabicyclo[3.2.1]octan-8-yl)-5-fluoro-3-[[(2S,4R)-4-fluoro-1-methyl-pyrrolidin-2-yl]methoxy]-7,9-dihydrofuro[3,4-f]quinazolin-6-yl]-5-fluoro-benzothiophene-3-carbonitrile | 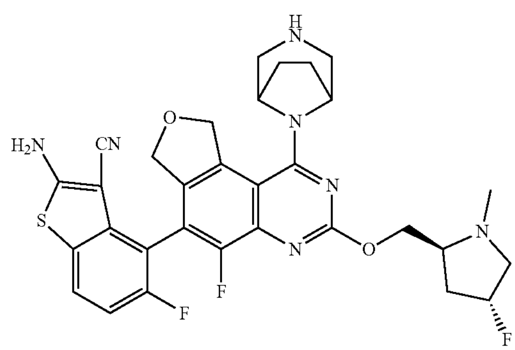 [SMILES: CN1C[C@H](F)C[C@H]1COc1nc(N2C3CCC2CNC3)c2c3c(c(-c4c(F)ccc5sc(N)c(C#N)c45)c(F)c2n1)COC3] | 622 |
| 72[4] | 2-Amino-4-[1-(3,8-diazabicyclo[3.2.1]octan-8-yl)-5-fluoro-3-[[(2S)-1-(2-fluoroethyl)pyrrolidin-2-yl]methoxy]-7,9-dihydrofuro[3,4-f]quinazolin-6-yl]-5-fluoro-benzothiophene-3-carbonitrile | 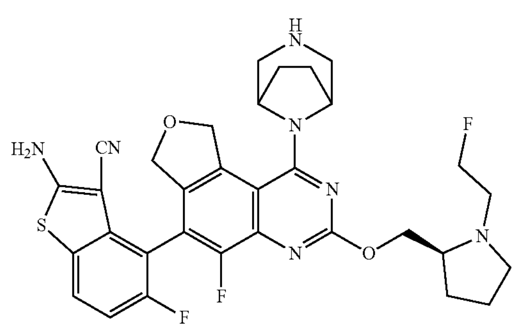 [SMILES: N#Cc1c(N)sc2ccc(F)c(-c3c4c(c5c(N6C7CCC6CNC7)nc(OC[C@@H]6CCCN6CCF)nc5c3F)COC4)c12] | 636 |

TABLE 14-continued

| Example | Chemical Name | Structure | MS (ES) m/z (M + 1) |
|---|---|---|---|
| 73[4] | 2-Amino-4-[1-(3,8-diazabicyclo[3.2.1]octan-8-yl)-3-[[(2R)-1,4-dioxan-2-yl]methoxy]-5-fluoro-7,9-dihydrofuro[3,4-f]quinazolin-6-yl]-5-fluoro-benzothiophene-3-carbonitrile | 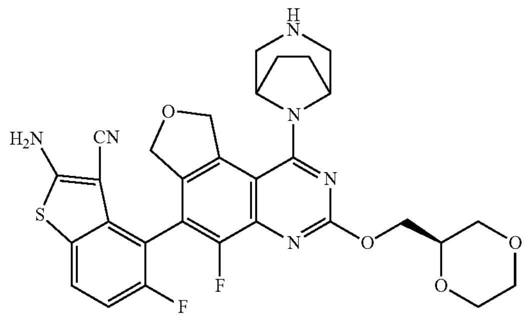 [SMILES: N#Cc1c(N)sc2ccc(F)c(-c3c4c(c5c(N6C7CCC6CNC7)nc(OC[C@H]6COCCO6)nc5c3F)COC4)c12] | 607 |
| 74[4] | 2-Amino-4-[1-(3,8-diazabicyclo[3.2.1]octan-8-yl)-5-fluoro-3-[[(2R)-tetrahydrofuran-2-yl]methoxy]-7,9-dihydrofuro[3,4-f]quinazolin-6-yl]-5-fluoro-benzothiophene-3-carbonitrile | 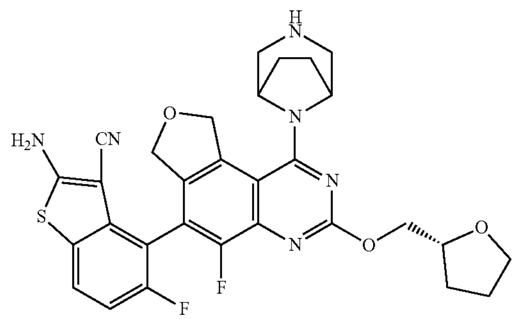 [SMILES: N#Cc1c(N)sc2ccc(F)c(-c3c4c(c5c(N6C7CCC6CNC7)nc(OC[C@H]6CCCO6)nc5c3F)COC4)c12] | 591 |
| 75[4] | 2-Amino-4-[1-(3,8-diazabicyclo[3.2.1]octan-8-yl)-3-[2-(dimethylamino)ethoxy]-5-fluoro-7,9-dihydrofuro[3,4-f]quinazolin-6-yl]-5-fluoro-benzothiophene-3-carbonitrile | 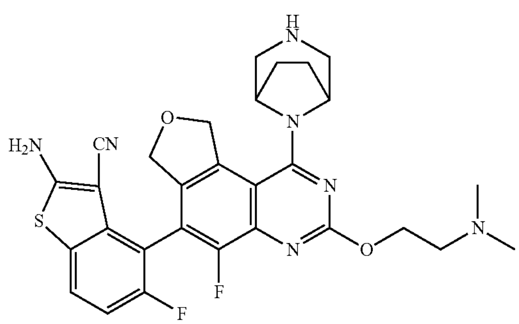 [SMILES: CN(C)CCOc1nc(N2C3CCC2CNC3)c2c3c(c(-c4c(F)ccc5sc(N)c(C#N)c45)c(F)c2n1)COC3] | 578 |
| 76[4] | 2-Amino-4-[1-(3,8-diazabicyclo[3.2.1]octan-8-yl)-5-fluoro-3-[2-[(3S)-3-fluoropyrrolidin-1-yl]ethoxy]-7,9-dihydrofuro[3,4-f]quinazolin-6-yl]-5-fluoro-benzothiophene-3-carbonitrile | 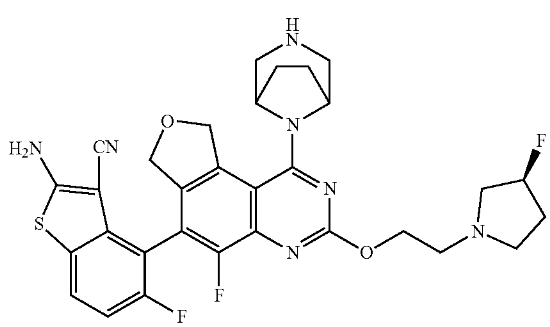 [SMILES: N#Cc1c(N)sc2ccc(F)c(-c3c4c(c5c(N6C7CCC6CNC7)nc(OCCN6CC[C@H](F)C6)nc5c3F)COC4)c12] | 622 |

TABLE 14-continued

| Example | Chemical Name | Structure | MS (ES) m/z (M + 1) |
|---|---|---|---|
| 77[4] | 2-Amino-4-[1-(3,8-diazabicyclo[3.2.1]octan-8-yl)-5-fluoro-3-(2-morpholinoethoxy)-7,9-dihydrofuro[3,4-f]quinazolin-6-yl]-5-fluoro-benzothiophene-3-carbonitrile | 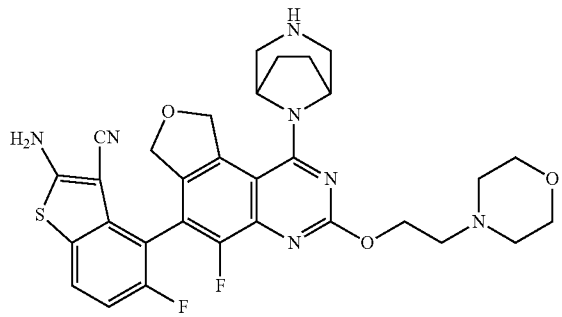 [SMILES: N#Cc1c(N)sc2ccc(F)c(-c3c4c(c5c(N6C7CCC6CNC7)nc(OCCN6CCOCC6)nc5c3F)COC4)c12] | 620 |
| 78[4] | 2-Amino-4-[1-(3,8-diazabicyclo[3.2.1]octan-8-yl)-5-fluoro-3-[2-[(3S)-3-methoxypyrrolidin-1-yl]ethoxy]-7,9-dihydrofuro[3,4-f]quinazolin-6-yl]-5-fluoro-benzothiophene-3-carbonitrile | 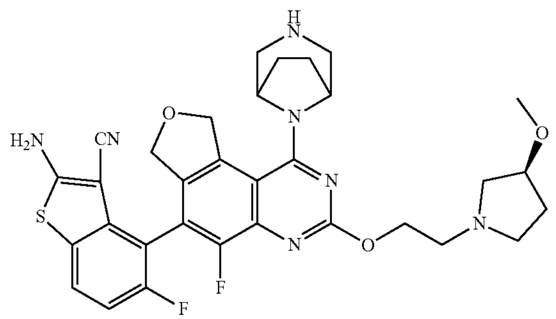 [SMILES: CO[C@H]1CCN(CCOc2nc(N3C4CCC3CNC4)c3c4c(c(-c5c(F)ccc6sc(N)c(C#N)c56)c(F)c3n2)COC4)C1] | 634 |
| 79[4] | 2-Amino-4-[1-(3,8-diazabicyclo[3.2.1]octan-8-yl)-5-fluoro-3-[[(2S)-1-methylazetidin-2-yl]methoxy]-7,9-dihydrofuro[3,4-f]quinazolin-6-yl]-5-fluoro-benzothiophene-3-carbonitrile | 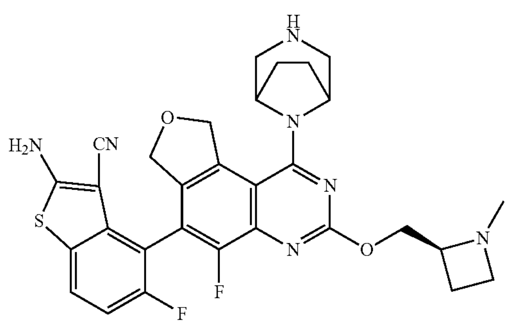 [SMILES: CN1CC[C@H]1COc1nc(N2C3CCC2CNC3)c2c3c(c(-c4c(F)ccc5sc(N)c(C#N)c45)c(F)c2n1)COC3] | 590 |
| 80[4] | 2-Amino-4-[1-(3,8-diazabicyclo[3.2.1]octan-8-yl)-5-fluoro-3-[[(2S)-1-(2-hydroxyethyl)azetidin-2-yl]methoxy]-7,9-dihydrofuro[3,4-f]quinazolin-6-yl]-5-fluoro-benzothiophene-3-carbonitrile | 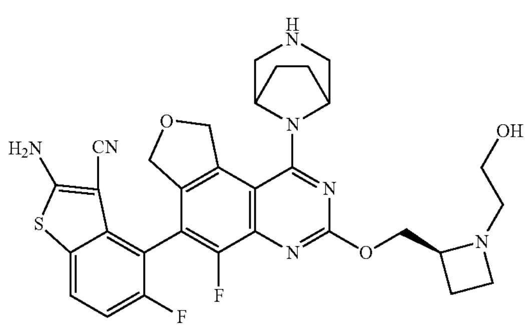 [SMILES: N#Cc1c(N)sc2ccc(F)c(-c3c4c(c5c(N6C7CCC6CNC7)nc(OC[C@@H]6CCN6CCO)nc5c3F)COC4)c12] | 620 |

TABLE 14-continued

| Example | Chemical Name | Structure | MS (ES) m/z (M + 1) |
|---|---|---|---|
| 81[4] | 2-Amino-4-[1-(3,8-diazabicyclo[3.2.1]octan-8-yl)-5-fluoro-3-[[(2S)-1-(2-hydroxyethyl)pyrrolidin-2-yl]methoxy]-7,9-dihydrofuro[3,4-f]quinazolin-6-yl]-5-fluoro-benzothiophene-3-carbonitrile | 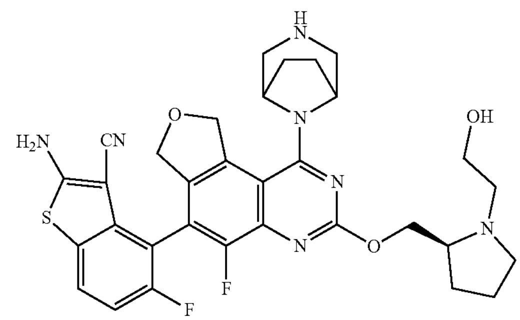 [SMILES: N#Cc1c(N)sc2ccc(F)c(-c3c4c(c5c(N6C7CCC6CNC7)nc(OC[C@@H]6CCCN6CCO)nc5c3F)COC4)c12] | 634 |
| 82[4] | 2-Amino-4-[1-(3,8-diazabicyclo[3.2.1]octan-8-yl)-5-fluoro-3-[[(2S)-1-(2-hydroxyethyl)pyrrolidin-2-yl]methoxy]-7,9-dihydrofuro[3,4-f]quinazolin-6-yl]-5-fluoro-benzothiophene-3-carbonitrile | 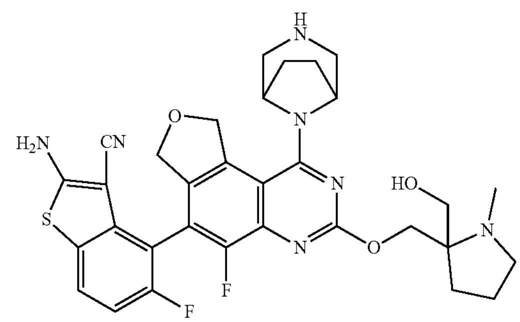 [SMILES: CN1CCCC1(CO)COc1nc(N2C3CCC2CNC3)c2c3c(c(-c4c(F)ccc5sc(N)c(C#N)c45)c(F)c2n1)COC3] | 634 |
| 83[4] | 2-Amino-4-[1-(3,8-diazabicyclo[3.2.1]octan-8-yl)-5-fluoro-3-[[(2S,4R)-4-hydroxy-1-methyl-pyrrolidin-2-yl]methoxy]-7,9-dihydrofuro[3,4-f]quinazolin-6-yl]-5-fluoro-benzothiophene-3-carbonitrile | 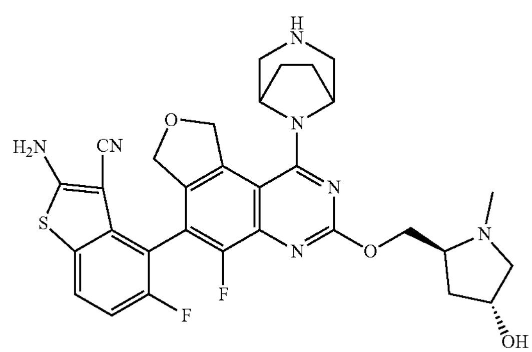 [SMILES: CN1C[C@H](O)C[C@H]1COc1nc(N2C3CCC2CNC3)c2c3c(c(-c4c(F)ccc5sc(N)c(C#N)c45)c(F)c2n1)COC3] | 620 |
| 84[4] | 2-Amino-4-[1-(3,8-diazabicyclo[3.2.1]octan-8-yl)-5-fluoro-3-[[(2R,3S)-3-hydroxy-1-methyl-pyrrolidin-2-yl]methoxy]-7,9-dihydrofuro[3,4-f]quinazolin-6-yl]-5-fluoro-benzothiophene-3-carbonitrile | 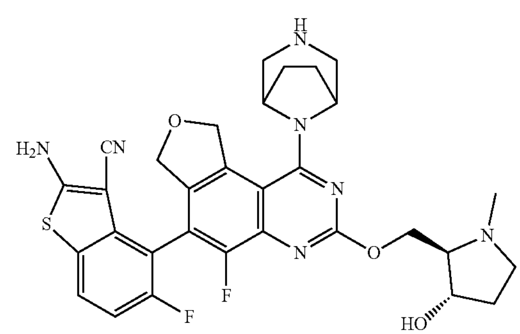 [SMILES: CN1CC[C@H](O)[C@H]1COc1nc(N2C3CCC2CNC3)c2c3c(c(-c4c(F)ccc5sc(N)c(C#N)c45)c(F)c2n1)COC3] | 620 |

TABLE 14-continued

| Example | Chemical Name | Structure | MS (ES) m/z (M + 1) |
|---|---|---|---|
| 85[4] | 2-Amino-4-[1-(3,8-diazabicyclo[3.2.1]octan-8-yl)-5-fluoro-3-[[(2S,4S)-4-fluoro-1-methyl-pyrrolidin-2-yl]methoxy]-7,9-dihydrofuro[3,4-f]quinazolin-6-yl]-5-fluoro-benzothiophene-3-carbonitrile | 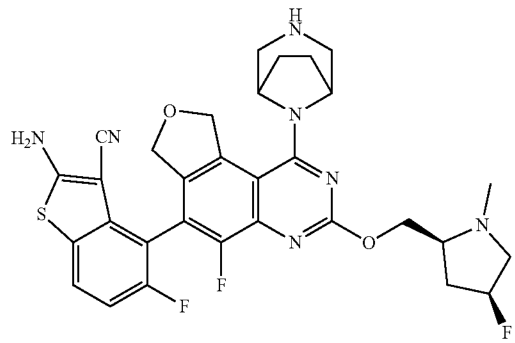 [SMILES: CN1C[C@@H](F)C[C@H]1COc1nc(N2C3CCC2CNC3)c2c3c(c(-c4c(F)ccc5sc(N)c(C#N)c45)c(F)c2n1)COC3] | 622 |
| 86[4] | 2-Amino-4-[1-(3,8-diazabicyclo[3.2.1]octan-8-yl)-3-[[1-(dimethylamino)cyclopropyl]methoxy]-5-fluoro-7,9-dihydrofuro[3,4-f]quinazolin-6-yl]-5-fluoro-benzothiophene-3-carbonitrile | 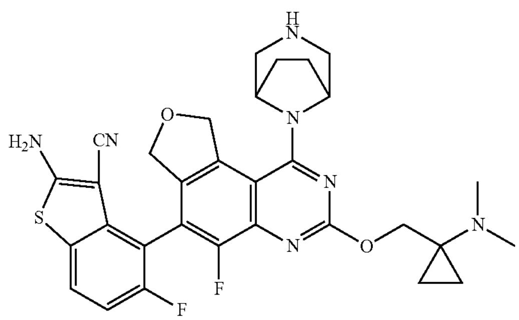 [SMILES: CN(C)C1(COc2nc(N3C4CCC3CNC4)c3c4c(c(-c5c(F)ccc6sc(N)c(C#N)c56)c(F)c3n2)COC4)CC1] | 604 |
| 87[6] | 2-Amino-4-[1-(3,6-diazabicyclo[3.1.1]heptan-6-yl)-5-fluoro-3-[[(2S)-1-methylpyrrolidin-2-yl]methoxy]-7,9-dihydrofuro[3,4-f]quinazolin-6-yl]-5-fluoro-benzothiophene-3-carbonitrile | 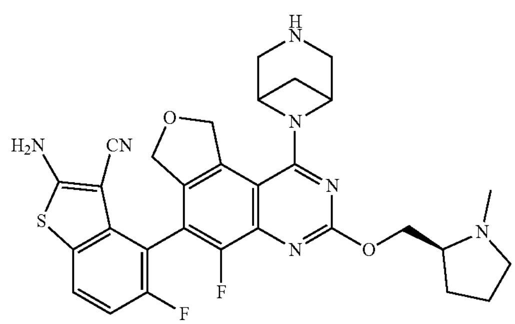 [SMILES: CN1CCC[C@H]1COc1nc(N2C3CNCC2C3)c2c3c(c(-c4c(F)ccc5sc(N)c(C#N)c45)c(F)c2n1)COC3] | 590 |
| 88[6] | 2-Amino-4-[1-(3,6-diazabicyclo[3.1.1]heptan-6-yl)-5-fluoro-3-[[(2S,4R)-4-fluoro-1-methyl-pyrrolidin-2-yl]methoxy]-7,9-dihydrofuro[3,4-f]quinazolin-6-yl]-5-fluoro-benzothiophene-3-carbonitrile | 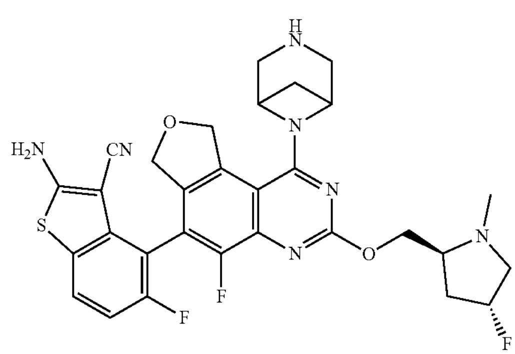 [SMILES: CN1C[C@H](F)C[C@H]1COc1nc(N2C3CNCC2C3)c2c3c(c(-c4c(F)ccc5sc(N)c(C#N)c45)c(F)c2n1)COC3] | 608 |

TABLE 14-continued

| Example | Chemical Name | Structure | MS (ES) m/z (M + 1) |
|---|---|---|---|
| 89[6] | 2-Amino-4-[1-(3,6-diazabicyclo[3.1.1]heptan-6-yl)-5-fluoro-3-[[(2R)-tetrahydrofuran-2-yl]methoxy]-7,9-dihydrofuro[3,4-f]quinazolin-6-yl]-5-fluoro-benzothiophene-3-carbonitrile | 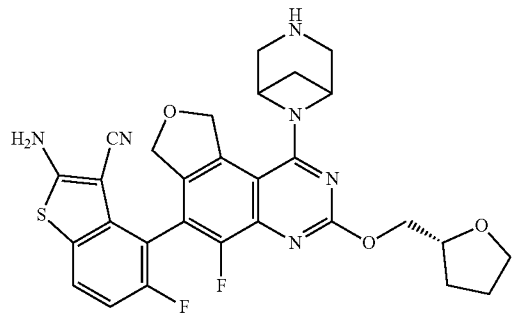 [SMILES: N#Cc1c(N)sc2ccc(F)c(-c3c4c(c5c(N6C7CNCC6C7)nc(OC[C@H]6CCCO6)nc5c3F)COC4)c12] | 577 |
| 90[6] | 2-Amino-4-[1-(3,6-diazabicyclo[3.1.1]heptan-6-yl)-5-fluoro-3-[[(2S)-1-(2-hydroxyethyl)pyrrolidin-2-yl]methoxy]-7,9-dihydrofuro[3,4-f]quinazolin-6-yl]-5-fluoro-benzothiophene-3-carbonitrile | 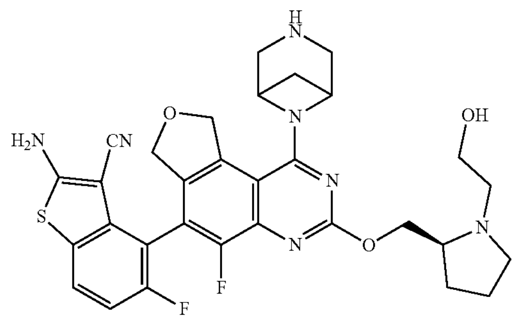 [SMILES: N#Cc1c(N)sc2ccc(F)c(-c3c4c(c5c(N6C7CNCC6C7)nc(OC[C@@H]6CCCN6CCO)nc5c3F)COC4)c12] | 620 |
| 91[7] | 2-Amino-4-[1-(3,8-diazabicyclo[3.2.1]octan-8-yl)-5-fluoro-7,9-dihydrofuro[3,4-f]quinazolin-6-yl]-5-fluoro-benzothiophene-3-carbonitrile | 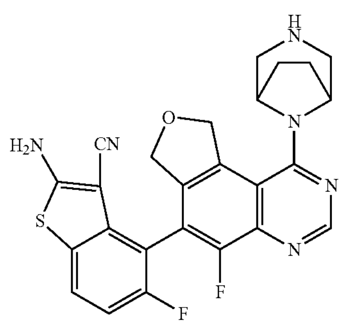 [SMILES: N#Cc1c(N)sc2ccc(F)c(-c3c4c(c5c(N6C7CCC6CNC7)ncnc5c3F)COC4)c12] | 491 |
| 92[8] | 2-Amino-4-[1-[(1R,4R)-2,5-diazabicyclo[2.2.1]heptan-2-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-5-fluoro-benzofuran-3-carbonitrile | 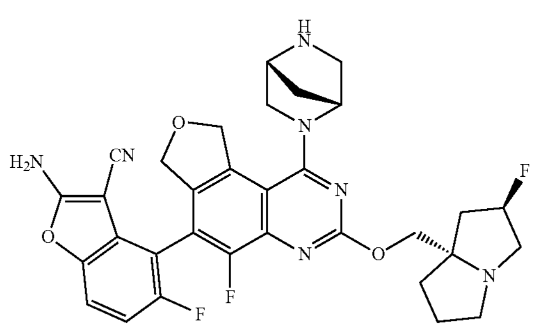 [SMILES: N#Cc1c(N)oc2ccc(F)c(-c3c4c(c5c(N6C[C@H]7C[C@@H]6CN7)nc(OC[C@@]67CCCN6C[C@H](F)C7)nc5c3F)COC4)c12] | 618 |

TABLE 14-continued

| Example | Chemical Name | Structure | MS (ES) m/z (M + 1) |
|---|---|---|---|
| 93 | 2-Amino-4-[1-[[1-(dimethylamino)cyclopentyl]methylamino]-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-5-fluoro-benzothiophene-3-carbonitrile | 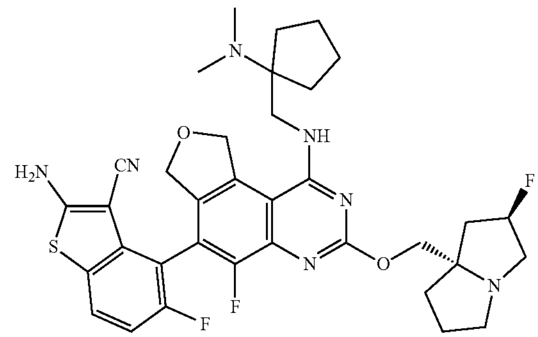 [SMILES: CN(C)C1(CNc2nc(OC[C@@]34CCCN3C[C@H](F)C4)nc3c(F)c(-c4c(F)ccc5sc(N)c(C#N)c45)c4c(c23)COC4)CCCC1] | 678 |
| 94 | 2-Amino-5-fluoro-4-[5-fluoro-3-[[(2R,8S)-2-fluoro-1,2,3,5,6,7-hexahydropyrrolizin-8-yl]methoxy]-1-methoxy-7,9-dihydrofuro[3,4-f]quinazolin-6-yl]benzothiophene-3-carbonitrile | 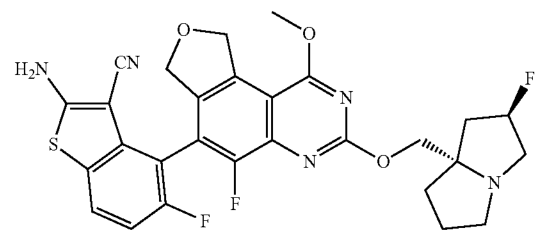 [SMILES: COc1nc(OC[C@@]23CCCN2C[C@H](F)C3)nc2c(F)c(-c3c(F)ccc4sc(N)c(C#N)c34)c3c(c12)COC3] | 568 |
| 195 | 2-Amino-4-[1-(3,8-diazabicyclo[3.2.1]octan-8-yl)-3-[[(2R)-1,4-dioxan-2-yl]methoxy]-5-fluoro-7,9-dihydrofuro[3,4-f]quinazolin-6-yl]benzothiophene-6-carbonitrile | 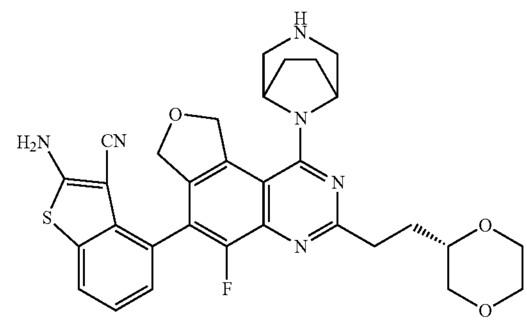 [SMILES: N#Cc1c(N)sc2cccc(-c3c4c(c5c(N6C7CCC6CNC7)nc(CC[C@H]6COCCO6)nc5c3F)COC4)c12] | 589 |
| 196[4] | 2-Amino-4-[1-(3,8-diazabicyclo[3.2.1]octan-8-yl)-5-fluoro-3-[[(2S,4R)-4-methoxy-1-methyl-pyrrolidin-2-yl]methoxy]-7,9-dihydrofuro[3,4-f]quinazolin-6-yl]-5-fluoro-benzothiophene-3-carbonitrile | 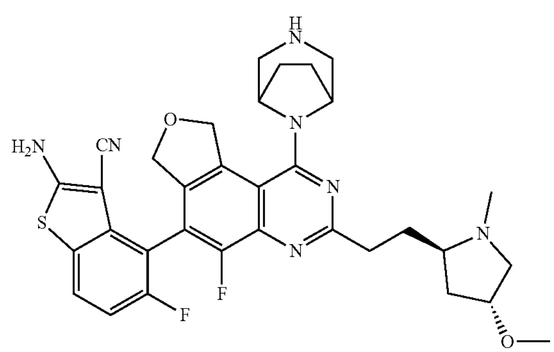 [SMILES: CO[C@@H]1C[C@@H](CCc2nc(N3C4CCC3CNC4)c3c4c(c(-c5c(F)ccc6sc(N)c(C#N)c56)c(F)c3n2)COC4)N(C)C1] | 634 |
| 197[4] | 2-Amino-4-[1-(3,8-diazabicyclo[3.2.1]octan-8-yl)-5-fluoro-3-[2-(3-methoxyazetidin-1-yl)ethoxy]-7,9-dihydrofuro[3,4-f]quinazolin-6-yl]-5-fluoro-benzothiophene-3-carbonitrile | 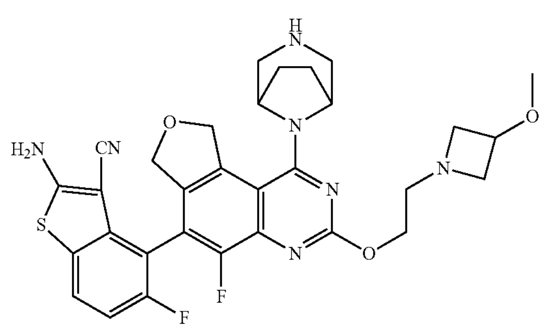 [SMILES: COC1CN(CCOc2nc(N3C4CCC3CNC4)c3c4c(c(-c5c(F)ccc6sc(N)c(C#N)c56)c(F)c3n2)COC4)C1] | 620 |

| Example | Chemical Name | Structure | MS (ES) m/z (M + 1) |
|---|---|---|---|
| 198 | 2-Amino-4-[1-(3,8-diazabicyclo[3.2.1]octan-8-yl)-5-fluoro-3-[[(2R,8S)-2-methoxy-1,2,3,5,6,7-hexahydropyrrolizin-8-yl]methoxy]-7,9-dihydrofuro[3,4-f]quinazolin-6-yl]-7-fluoro-thieno[3,2-c]pyridine-3-carbonitrile | 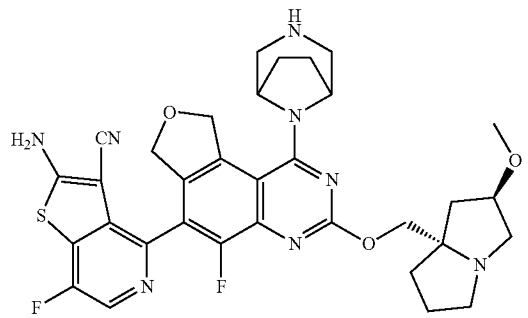 [SMILES: CO[C@H]1CN2CCC[C@@]2(COc2nc(N3C4CCC3CNC4)c3c4c(c(-c5ncc(F)c6sc(N)c(C#N)c56)c(F)c3n2)COC4)C1] | 661 |
| 199 | 2-Amino-4-[1-(3,8-diazabicyclo[3.2.1]octan-8-yl)-5-fluoro-3-[[(2S)-1-methylpyrrolidin-2-yl]methoxy]-7,9-dihydrofuro[3,4-f]quinazolin-6-yl]-7-fluoro-thieno[3,2-c]pyridine-3-carbonitrile | 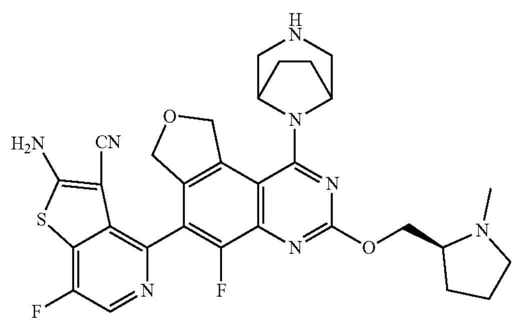 [SMILES: CN1CCC[C@H]1COc1nc(N2C3CCC2CNC3)c2c3c(c(-c4ncc(F)c5sc(N)c(C#N)c45)c(F)c2n1)COC3] | 605 |
| 200 | 2-Amino-4-[1-(3,8-diazabicyclo[3.2.1]octan-8-yl)-5-fluoro-3-[[(2S,4R)-4-fluoro-1-methyl-pyrrolidin-2-yl]methoxy]-7,9-dihydrofuro[3,4-f]quinazolin-6-yl]-7-fluoro-thieno[3,2-c]pyridine-3-carbonitrile | 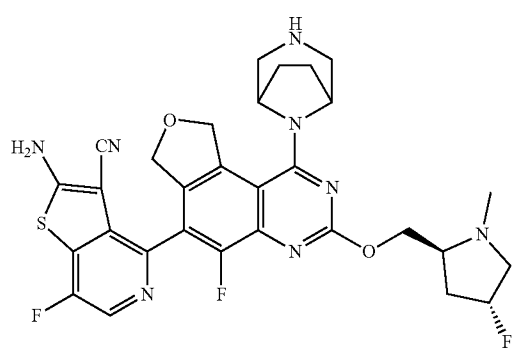 [SMILES: CN1C[C@H](F)C[C@H]1COc1nc(N2C3CCC2CNC3)c2c3c(c(-c4ncc(F)c5sc(N)c(C#N)c45)c(F)c2n1)COC3] | 623 |
| 201 | 2-Amino-4-[1-(3,8-diazabicyclo[3.2.1]octan-8-yl)-5-fluoro-3-[[(2S,4R)-4-methoxy-1-methyl-pyrrolidin-2-yl]methoxy]-7,9-dihydrofuro[3,4-f]quinazolin-6-yl]-7-fluoro-thieno[3,2-c]pyridine-3-carbonitrile | 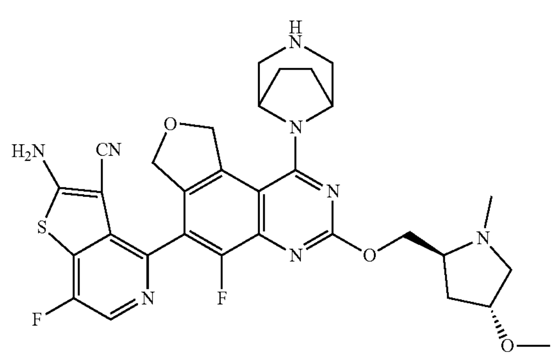 [SMILES: CO[C@@H]1C[C@@H](COc2nc(N3C4CCC3CNC4)c3c4c(c(-c5ncc(F)c6sc(N)c(C#N)c56)c(F)c3n2)COC4)N(C)C1] | 635 |

TABLE 14-continued

| Example | Chemical Name | Structure | MS (ES) m/z (M + 1) |
|---|---|---|---|
| 202 | 2-Amino-4-[1-(3,8-diazabicyclo[3.2.1]octan-8-yl)-5-fluoro-3-(1,2,3,5,6,7-hexahydropyrrolizin-8-ylmethoxy)-7,9-dihydrofuro[3,4-f]quinazolin-6-yl]-7-fluoro-thieno[3,2-c]pyridine-3-carbonitrile | 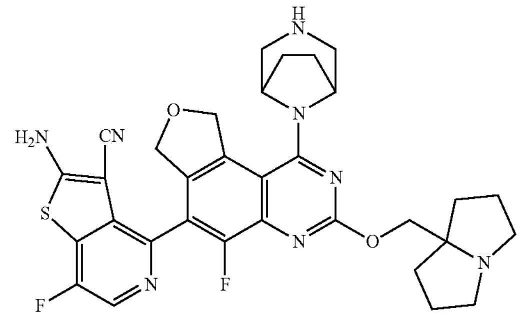 [SMILES: N#Cc1c(N)sc2c(F)cnc(-c3c4c(c5c(N6C7CCC6CNC7)nc(OCC67CCCN6CCC7)nc5c3F)COC4)c12] | 631 |
| 203 | 2-Amino-4-[1-(3,8-diazabicyclo[3.2.1]octan-8-yl)-3-[(6,6-difluoro-2,3,5,7-tetrahydro-1H-pyrrolizin-8-yl)methoxy]-5-fluoro-7,9-dihydrofuro[3,4-f]quinazolin-6-yl]-7-fluoro-thieno[3,2-c]pyridine-3-carbonitrile | 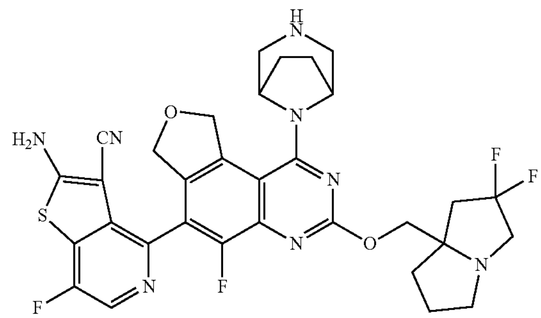 [SMILES: N#Cc1c(N)sc2c(F)cnc(-c3c4c(c5c(N6C7CCC6CNC7)nc(OCC67CCCN6CC(F)(F)C7)nc5c3F)COC4)c12] | 667 |
| 204 | 2-Amino-4-[3-(1-azabicyclo[3.2.0]heptan-5-ylmethoxy)-1-(3,8-diazabicyclo[3.2.1]octan-8-yl)-5-fluoro-7,9-dihydrofuro[3,4-f]quinazolin-6-yl]-7-fluoro-thieno[3,2-c]pyridine-3-carbonitrile | 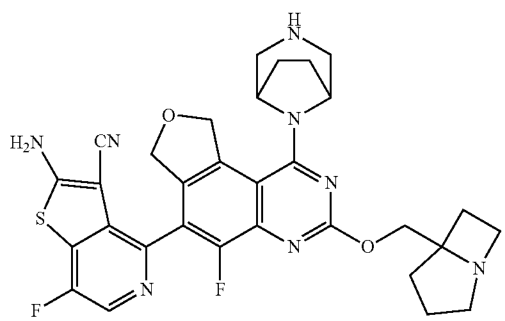 [SMILES: N#Cc1c(N)sc2c(F)cnc(-c3c4c(c5c(N6C7CCC6CNC7)nc(OCC67CCCN6CC7)nc5c3F)COC4)c12] | 617 |
| 205 | 2-Amino-4-[1-(3,8-diazabicyclo[3.2.1]octan-8-yl)-5-fluoro-3-[[(2SR,8SR)-2-fluoro-1,2,3,5,6,7-hexahydropyrrolizin-8-yl]methoxy]-7,9-dihydrofuro[3,4-f]quinazolin-6-yl]-7-fluoro-thieno[3,2-c]pyridine-3-carbonitrile | 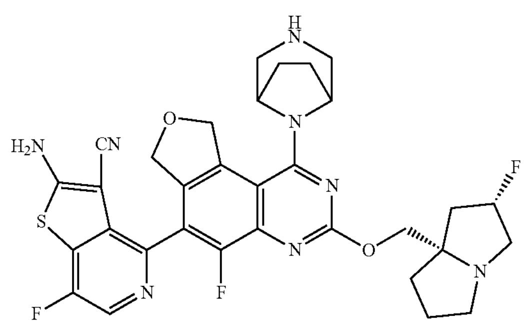 [SMILES: N#Cc1c(N)sc2c(F)cnc(-c3c4c(c5c(N6C7CCC6CNC7)nc(OC[C@@]67CCCN6C[C@@H](F)C7)nc5c3F)COC4)c12] | 649 |
| 206 | 2-Amino-4-[5-chloro-3-[[(2S)-1-methylpyrrolidin-2-yl]methoxy]-7,9-dihydrofuro[3,4-f]quinazolin-6-yl]-7-fluoro-benzothiophene-3-carbonitrile | 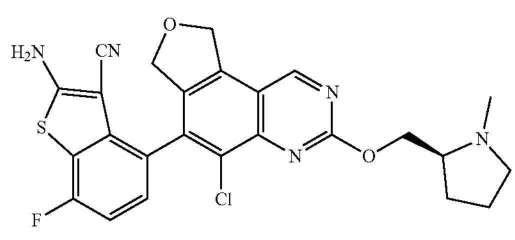 [SMILES: CN1CCC[C@H]1COc1ncc2c3c(c(-c4ccc(F)c5sc(N)c(C#N)c45)c(Cl)c2n1)COC3] | 510 |

TABLE 14-continued

| Example | Chemical Name | Structure | MS (ES) m/z (M + 1) |
|---|---|---|---|
| 207 | 2-Amino-4-[5-chloro-3-[[(2S)-1-methylpyrrolidin-2-yl]methoxy]-7,9-dihydrofuro[3,4-f]quinazolin-6-yl]-7-fluoro-benzothiophene-3-carbonitrile, Isomer 1 | 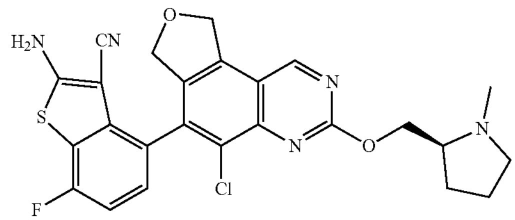 [SMILES: CN1CCC[C@H]1COc1ncc2c3c(c(-c4ccc(F)c5sc(N)c(C#N)c45)c(Cl)c2n1)COC3] | 510 |
| 208 | 2-Amino-4-[5-chloro-3-[[(2S)-1-methylpyrrolidin-2-yl]methoxy]-7,9-dihydrofuro[3,4-f]quinazolin-6-yl]-7-fluoro-benzothiophene-3-carbonitrile, Isomer 2 | 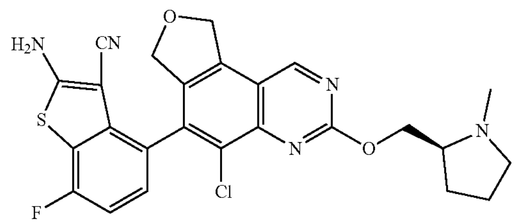 [SMILES: CN1CCC[C@H]1COc1ncc2c3c(c(-c4ccc(F)c5sc(N)c(C#N)c45)c(Cl)c2n1)COC3] | 510 |
| 209 | 2-Amino-4-[5-chloro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-benzothiophene-3-carbonitrile, Isomer 1 | 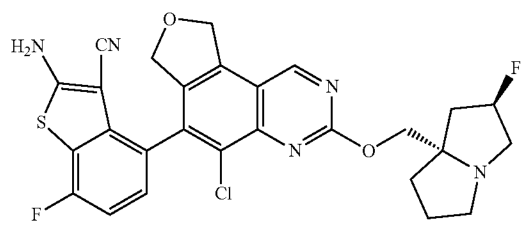 [SMILES: N#Cc1c(N)sc2c(F)ccc(-c3c4c(c5cnc(OC[C@@]67CCCN6C[C@H](F)C7)nc5c3Cl)COC4)c12] | 554 |
| 210 | 2-Amino-4-[5-chloro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-benzothiophene-3-carbonitrile, Isomer 2 | 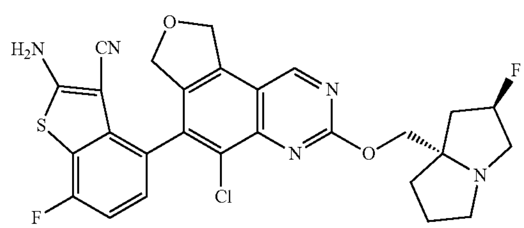 [SMILES: N#Cc1c(N)sc2c(F)ccc(-c3c4c(c5cnc(OC[C@@]67CCCN6C[C@H](F)C7)nc5c3Cl)COC4)c12] | 554 |
| 211 | 2-Amino-7-fluoro-4-[5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]thieno[3,2-c]pyridine-3-carbonitrile | 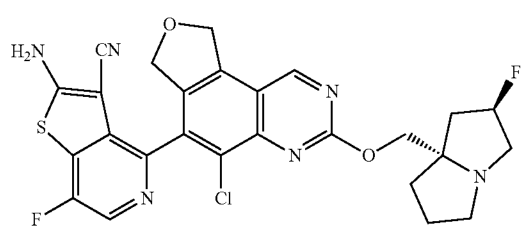 [SMILES: N#Cc1c(N)sc2c(F)cnc(-c3c4c(c5cnc(OC[C@@]67CCCN6C[C@H](F)C7)nc5c3Cl)COC4)c12] | 539 |
| 251 | 2-Amino-4-[1-(3,8-diazabicyclo[3.2.1]octan-8-yl)-5-fluoro-3-[[(2R)-4-methylmorpholin-2-yl]methoxy]-7,9-dihydrofuro[3,4-f]quinazolin-6-yl]-7-fluoro-thieno[3,2-c]pyridine-3-carbonitrile | 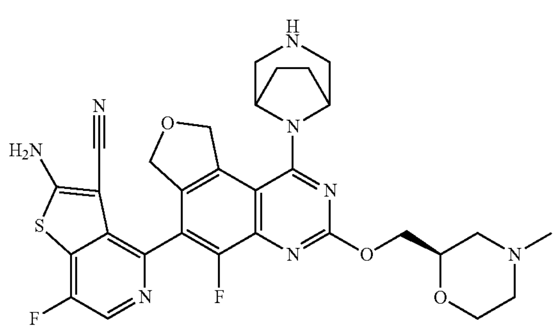 [SMILES: CN1CCO[C@@H](COc2nc(N3C4CCC3CNC4)c3c4c(c(-c5ncc(F)c6sc(N)c(C#N)c56)c(F)c3n2)COC4)C1] | 621 |

TABLE 14-continued

| Example | Chemical Name | Structure | MS (ES) m/z (M + 1) |
|---|---|---|---|
| 252 | 2-Amino-4-[1-(3,8-diazabicyclo[3.2.1]octan-8-yl)-5-fluoro-3-[[(3R,4S)-4-fluoro-1-methyl-3-piperidyl]methoxy]-7,9-dihydrofuro[3,4-f]quinazolin-6-yl]-7-fluoro-thieno[3,2-c]pyridine-3-carbonitrile | 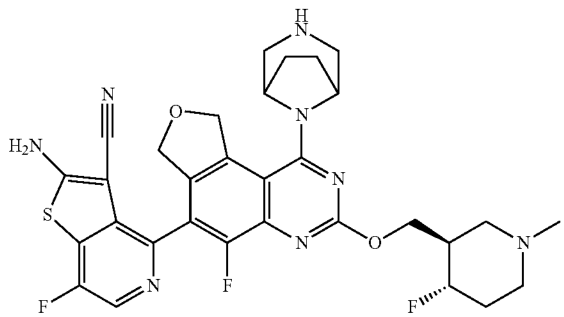 [SMILES: CN1CC[C@H](F)[C@@H](COc2nc(N3C4CCC3CNC4)c3c4c(c(-c5ncc(F)c6sc(N)c(C#N)c56)c(F)c3n2)COC4)C1] | 637 |
| 253 | 2-Amino-4-[1-(3,8-diazabicyclo[3.2.1]octan-8-yl)-5-fluoro-3-(2-imidazol-1-ylethoxy)-7,9-dihydrofuro[3,4-f]quinazolin-6-yl]-7-fluoro-thieno[3,2-c]pyridine-3-carbonitrile | 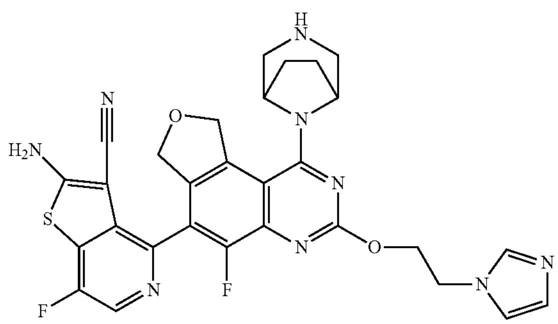 [SMILES: N#Cc1c(N)sc2c(F)cnc(-c3c4c(c5c(N6C7CCC6CNC7)nc(OCCn6ccnc6)nc5c3F)COC4)c12] | 602 |
| 254 | 2-Amino-4-[1-(3,8-diazabicyclo[3.2.1]octan-8-yl)-5-fluoro-3-[[(2R,3S)-3-fluoro-1-methyl-pyrrolidin-2-yl]methoxy]-7,9-dihydrofuro[3,4-f]quinazolin-6-yl]-7-fluoro-thieno[3,2-c]pyridine-3-carbonitrile | 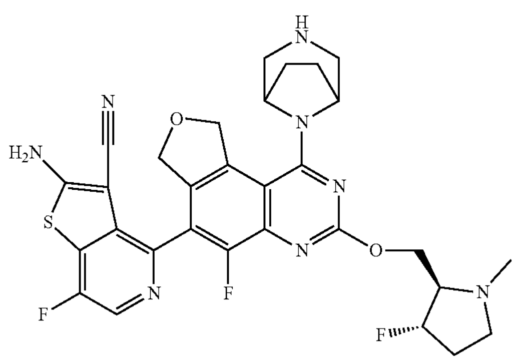 [SMILES: CN1CC[C@H](F)[C@H]1COc1nc(N2C3CCC2CNC3)c2c3c(c(-c4ncc(F)c5sc(N)c(C#N)c45)c(F)c2n1)COC3] | 623 |
| 255 | 2-Amino-4-[1-(3,8-diazabicyclo[3.2.1]octan-8-yl)-5-fluoro-3-[(1S)-1-[(2R)-4-methylmorpholin-2-yl]ethoxy]-7,9-dihydrofuro[3,4-f]quinazolin-6-yl]-7-fluoro-thieno[3,2-c]pyridine-3-carbonitrile | 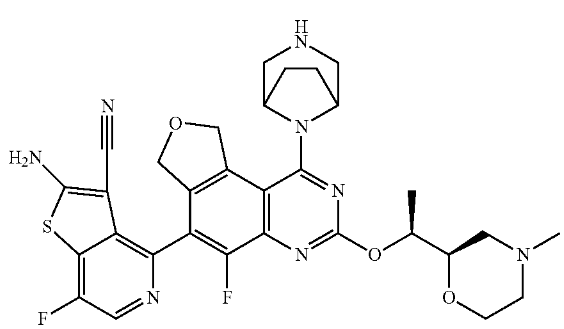 [SMILES: C[C@H](Oc1nc(N2C3CCC2CNC3)c2c3c(c(-c4ncc(F)c5sc(N)c(C#N)c45)c(F)c2n1)COC3)[C@H]1CN(C)CCO1] | 635 |

TABLE 14-continued

| Example | Chemical Name | Structure | MS (ES) m/z (M + 1) |
|---|---|---|---|
| 256 | 2-Amino-4-[1-(3,8-diazabicyclo[3.2.1]octan-8-yl)-5-fluoro-3-(2-morpholinoethoxy)-7,9-dihydrofuro[3,4-f]quinazolin-6-yl]-7-fluoro-thieno[3,2-c]pyridine-3-carbonitrile | 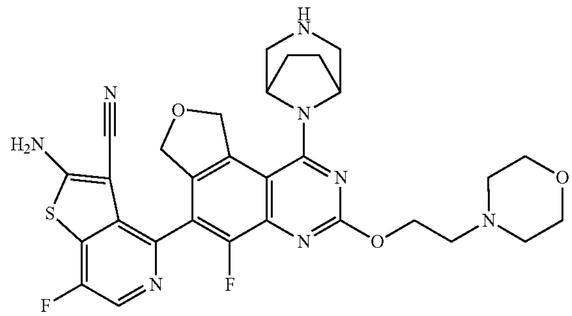 [SMILES: N#Cc1c(N)sc2c(F)cnc(-c3c4c(c5c(N6C7CCC6CNC7)nc(OCCN6CCOCC6)nc5c3F)COC4)c12] | 621 |
| 257 | 2-Amino-4-[1-(3,8-diazabicyclo[3.2.1]octan-8-yl)-3-[(4,4-difluoro-1-methyl-3-piperidyl)methoxy]-5-fluoro-7,9-dihydrofuro[3,4-f]quinazolin-6-yl]-7-fluoro-thieno[3,2-c]pyridine-3-carbonitrile | 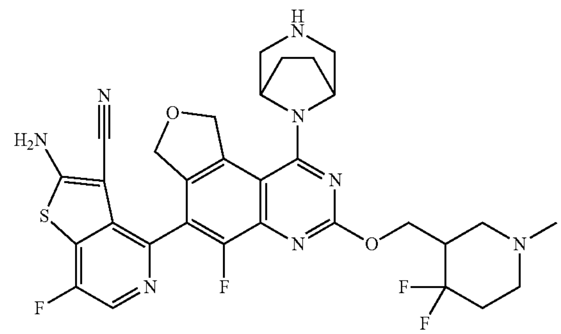 [SMILES: CN1CCC(F)(F)C(COc2nc(N3C4CCC3CNC4)c3c4c(c(-c5ncc(F)c6sc(N)c(C#N)c56)c(F)c3n2)COC4)C1] | 655 |
| 258[4] | 2-Amino-4-[1-(3,8-diazabicyclo[3.2.1]octan-8-yl)-3-[(4,4-difluoro-1-methyl-3-piperidyl)methoxy]-5-fluoro-7,9-dihydrofuro[3,4-f]quinazolin-6-yl]-5-fluoro-benzothiophene-3-carbonitrile | 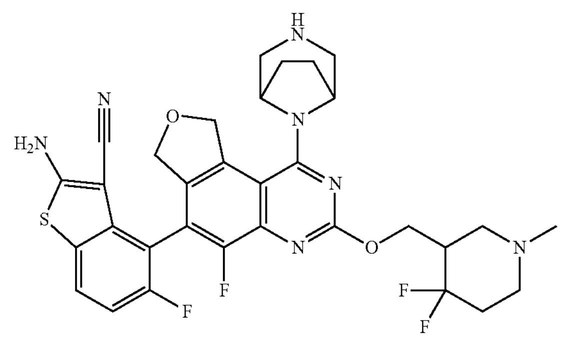 [SMILES: CN1CCC(F)(F)C(COc2nc(N3C4CCC3CNC4)c3c4c(c(-c5c(F)ccc6sc(N)c(C#N)c56)c(F)c3n2)COC4)C1] | 654 |
| 259[4] | 2-Amino-4-[1-(3,8-diazabicyclo[3.2.1]octan-8-yl)-5-fluoro-3-[[(2R)-4-methylmorpholin-2-yl]methoxy]-7,9-dihydrofuro[3,4-f]quinazolin-6-yl]-5-fluoro-benzothiophene-3-carbonitrile | 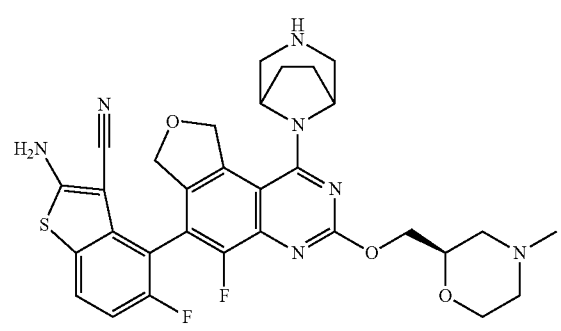 [SMILES: CN1CCO[C@@H](COc2nc(N3C4CCC3CNC4)c3c4c(c(-c5c(F)ccc6sc(N)c(C#N)c56)c(F)c3n2)COC4)C1] | 620 |

TABLE 14-continued

| Example | Chemical Name | Structure | MS (ES) m/z (M + 1) |
|---|---|---|---|
| 260 | 2-Amino-4-[1-(3,8-diazabicyclo[3.2.1]octan-8-yl)-5-fluoro-3-[[(2S,4R)-4-fluoro-1-methyl-pyrrolidin-2-yl]methoxy]-7,9-dihydrofuro[3,4-f]quinazolin-6-yl]-5-fluoro-benzofuran-3-carbonitrile | 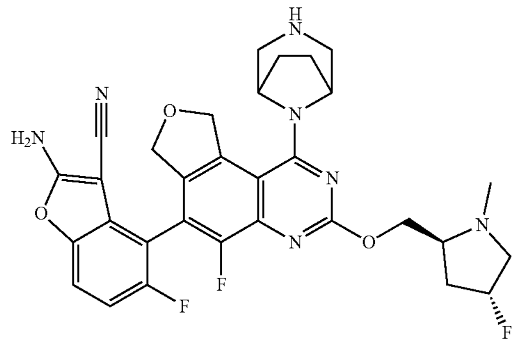 | 606 |
| 261 | 2-Amino-4-[1-(3,8-diazabicyclo[3.2.1]octan-8-yl)-5-fluoro-3-[(1S)-1-methyl-2-morpholino-ethoxy]-7,9-dihydrofuro[3,4-f]quinazolin-6-yl]-7-fluoro-thieno[3,2-c]pyridine-3-carbonitrile | 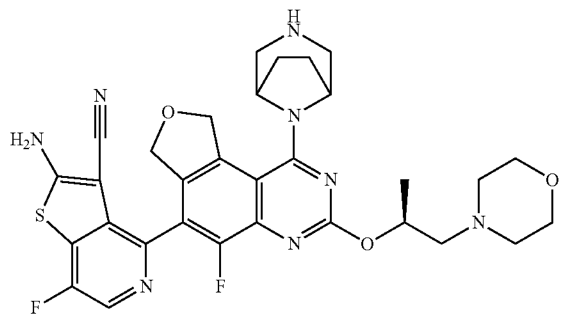 [SMILES: C[C@@H](CN1CCOCC1)Oc1nc(N2C3CCC2CNC3)c2c3c(c(-c4ncc(F)c5sc(N)c(C#N)c45)c(F)c2n1)COC3] | 635 |
| 262 | 2-Amino-4-[1-(3,8-diazabicyclo[3.2.1]octan-8-yl)-3-[[(2S)-5,5-difluoro-1-methyl-2-piperidyl]methoxy]-5-fluoro-7,9-dihydrofuro[3,4-f]quinazolin-6-yl]-7-fluoro-thieno[3,2-c]pyridine-3-carbonitrile | 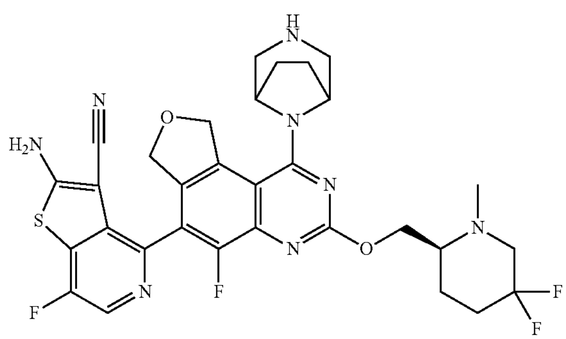 [SMILES: CN1CC(F)(F)CC[C@H]1COc1nc(N2C3CCC2CNC3)c2c3c(c(-c4ncc(F)c5sc(N)c(C#N)c45)c(F)c2n1)COC3] | 655 |
| 263 | 2-Amino-4-[1-(3,8-diazabicyclo[3.2.1]octan-8-yl)-5-fluoro-3-[[(3S)-4-methylmorpholin-3-yl]methoxy]-7,9-dihydrofuro[3,4-f]quinazolin-6-yl]-5-fluoro-benzothiophene-3-carbonitrile | 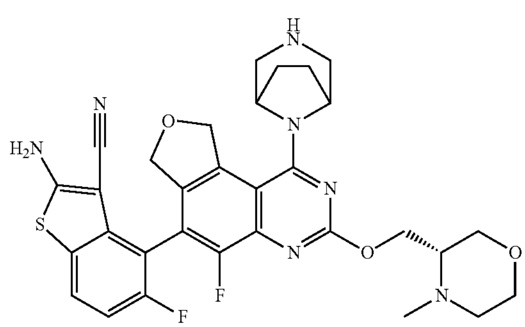 [SMILES: CN1CCOC[C@H]1COc1nc(N2C3CCC2CNC3)c2c3c(c(-c4c(F)ccc5sc(N)c(C#N)c45)c(F)c2n1)COC3] | 620 |

TABLE 14-continued

| Example | Chemical Name | Structure | MS (ES) m/z (M + 1) |
|---------|---------------|-----------|---------------------|
| 264 | 2-Amino-4-[1-(3,8-diazabicyclo[3.2.1]octan-8-yl)-3-[[1-[(dimethylamino)methyl]cyclopropyl]methoxy]-5-fluoro-7,9-dihydrofuro[3,4-f]quinazolin-6-yl]-7-fluoro-thieno[3,2-c]pyridine-3-carbonitrile | 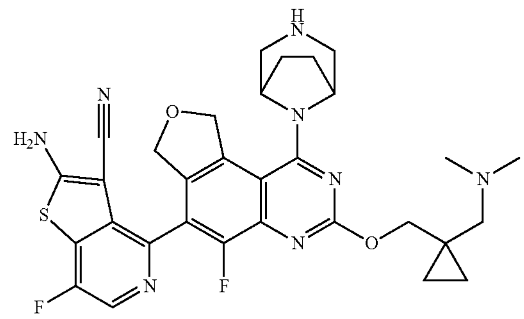 [SMILES: CN(C)CC1(COc2nc(N3C4CCC3CNC4)c3c4c(c(-c5ncc(F)c6sc(N)c(C#N)c56)c(F)c3n2)COC4)CC1] | 619 |
| 265 | 2-Amino-4-[1-(3,8-diazabicyclo[3.2.1]octan-8-yl)-5-fluoro-3-(2-pyrazol-1-ylethoxy)-7,9-dihydrofuro[3,4-f]quinazolin-6-yl]-7-fluoro-thieno[3,2-c]pyridine-3-carbonitrile | 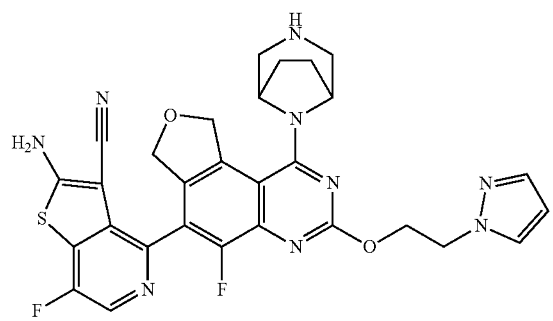 [SMILES: N#Cc1c(N)sc2c(F)cnc(-c3c4c(c5c(N6C7CCC6CNC7)nc(OCCn6cccn6)nc5c3F)COC4)c12] | 602 |
| 266 | 2-Amino-4-[1-(3,8-diazabicyclo[3.2.1]octan-8-yl)-5-fluoro-3-[(2S)-2-morpholinopropoxy]-7,9-dihydrofuro[3,4-f]quinazolin-6-yl]-7-fluoro-thieno[3,2-c]pyridine-3-carbonitrile | 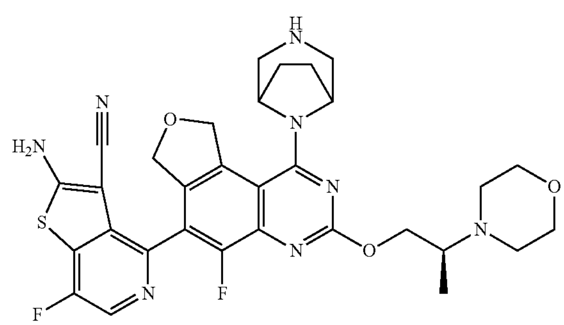 [SMILES: C[C@@H](COc1nc(N2C3CCC2CNC3)c2c3c(c(-c4ncc(F)c5sc(N)c(C#N)c45)c(F)c2n1)COC3)N1CCOCC1] | 635 |
| 267 | 2-Amino-4-[1-(3,8-diazabicyclo[3.2.1]octan-8-yl)-3-[[(2S)-4,4-difluoro-1-methyl-pyrrolidin-2-yl]methoxy]-5-fluoro-7,9-dihydrofuro[3,4-f]quinazolin-6-yl]-7-fluoro-thieno[3,2-c]pyridine-3-carbonitrile | 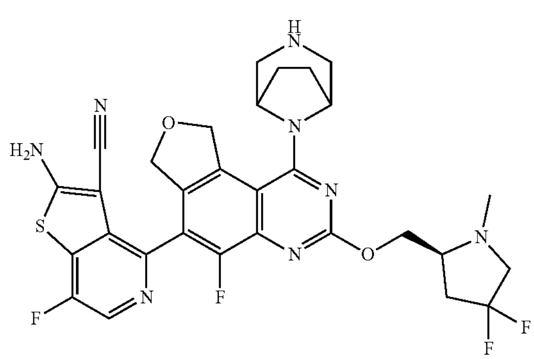 [SMILES: CN1CC(F)(F)C[C@H]1COc1nc(N2C3CCC2CNC3)c2c3c(c(-c4ncc(F)c5sc(N)c(C#N)c45)c(F)c2n1)COC3] | 641 |

TABLE 14-continued

| Example | Chemical Name | Structure | MS (ES) m/z (M + 1) |
|---|---|---|---|
| 268 | 2-Amino-4-[1-(3,8-diazabicyclo[3.2.1]octan-8-yl)-5-fluoro-3-[(3-fluoro-1-methyl-pyrrolidin-3-yl)methoxy]-7,9-dihydrofuro[3,4-f]quinazolin-6-yl]-7-fluoro-thieno[3,2-c]pyridine-3-carbonitrile | 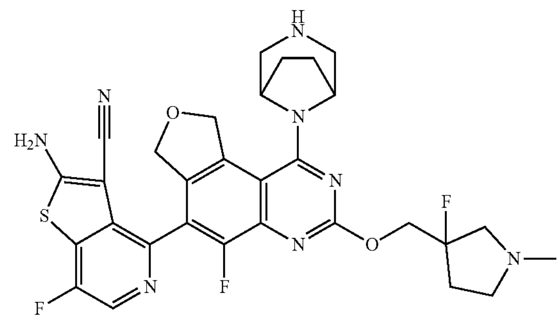 [SMILES: CN1CCC(F)(COc2nc(N3C4CCC3CNC4)c3c4c(c(-c5ncc(F)c6sc(N)c(C#N)c56)c(F)c3n2)COC4)C1] | 623 |
| 269 | 2-Amino-4-[1-(3,8-diazabicyclo[3.2.1]octan-8-yl)-3-[(3,3-difluoro-1-methyl-2-piperidyl)methoxy]-5-fluoro-7,9-dihydrofuro[3,4-f]quinazolin-6-yl]-7-fluoro-thieno[3,2-c]pyridine-3-carbonitrile | 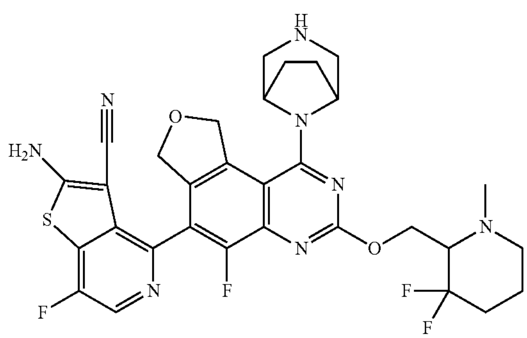 [SMILES: CN1CCCC(F)(F)C1COc1nc(N2C3CCC2CNC3)c2c3c(c(-c4ncc(F)c5sc(N)c(C#N)c45)c(F)c2n1)COC3] | 655 |
| 270 | 2-Amino-4-[1-(3,8-diazabicyclo[3.2.1]octan-8-yl)-3-[2-(4-ethyl-3-oxo-piperazin-1-yl)ethoxy]-5-fluoro-7,9-dihydrofuro[3,4-f]quinazolin-6-yl]-7-fluoro-thieno[3,2-c]pyridine-3-carbonitrile | 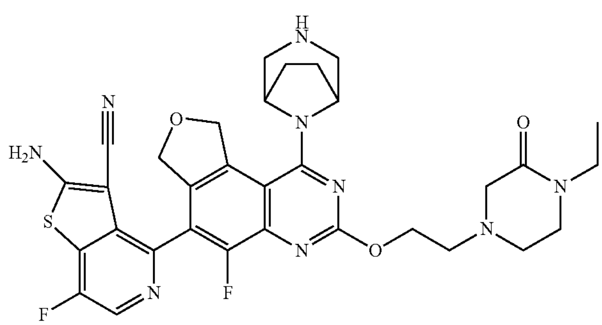 [SMILES: CCN1CCN(CCOc2nc(N3C4CCC3CNC4)c3c4c(c(-c5ncc(F)c6sc(N)c(C#N)c56)c(F)c3n2)COC4)CC1=O] | 662 |
| 271 | 2-Amino-4-[3-[(1-cyanocyclopropyl)methoxy]-1-(3,8-diazabicyclo[3.2.1]octan-8-yl)-5-fluoro-7,9-dihydrofuro[3,4-f]quinazolin-6-yl]-7-fluoro-thieno[3,2-c]pyridine-3-carbonitrile | 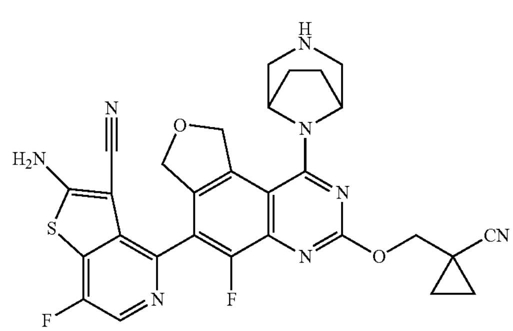 [SMILES: N#Cc1c(N)sc2c(F)cnc(-c3c4c(c5c(N6C7CCC6CNC7)nc(OCC6(C#N)CC6)nc5c3F)COC4)c12] | 587 |

TABLE 14-continued

| Example | Chemical Name | Structure | MS (ES) m/z (M + 1) |
|---|---|---|---|
| 272 | 2-Amino-4-[1-(3,8-diazabicyclo[3.2.1]octan-8-yl)-3-[(3,3-difluoro-1-methyl-pyrrolidin-2-yl)methoxy]-5-fluoro-7,9-dihydrofuro[3,4-f]quinazolin-6-yl]-7-fluoro-thieno[3,2-c]pyridine-3-carbonitrile | 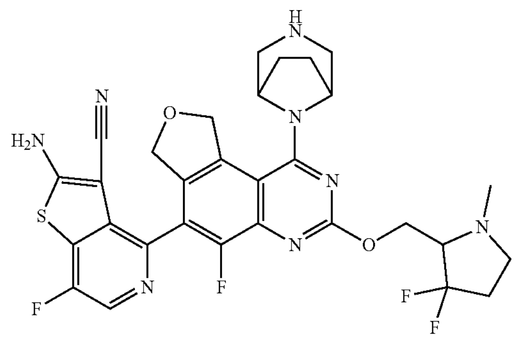 [SMILES: CN1CCC(F)(F)C1COc1nc(N2C3CCC2CNC3)c2c3c(c(-c4ncc(F)c5sc(N)c(C#N)c45)c(F)c2n1)COC3] | 641 |
| 273 | 2-Amino-4-[1-(3,8-diazabicyclo[3.2.1]octan-8-yl)-5-fluoro-3-[[1-(2-hydroxyacetyl)-4-piperidyl]methoxy]-7,9-dihydrofuro[3,4-f]quinazolin-6-yl]-7-fluoro-thieno[3,2-c]pyridine-3-carbonitrile | 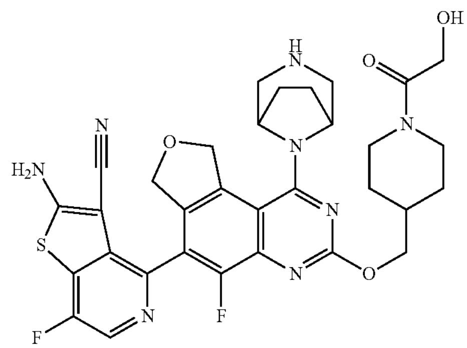 [SMILES: N#Cc1c(N)sc2c(F)cnc(-c3c4c(c5c(N6C7CCC6CNC7)nc(OCC6CCN(C(=O)CO)CC6)nc5c3F)COC4)c12] | 663 |
| 274 | 2-Amino-4-[1-(3,6-diazabicyclo[3.1.1]heptan-6-yl)-5-fluoro-3-[[(2R)-4-methylmorpholin-2-yl]methoxy]-7,9-dihydrofuro[3,4-f]quinazolin-6-yl]-5-fluoro-benzothiophene-3-carbonitrile | 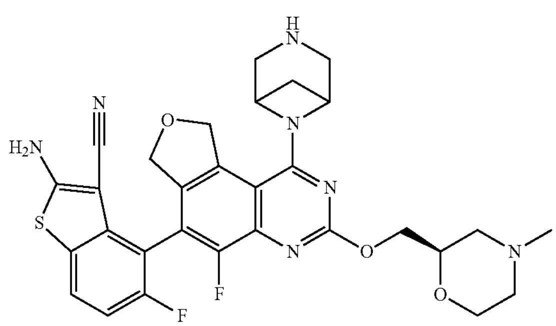 [SMILES: CN1CCO[C@@H](COc2nc(N3C4CNCC3C4)c3c4c(c(-c5c(F)ccc6sc(N)c(C#N)c56)c(F)c3n2)COC4)C1] | 606 |
| 275 | 2-Amino-4-[1-(3,6-diazabicyclo[3.1.1]heptan-6-yl)-5-fluoro-3-[[(2S,4R)-4-fluoro-1-methyl-pyrrolidin-2-yl]methoxy]-7,9-dihydrofuro[3,4-f]quinazolin-6-yl]-5-fluoro-benzothiophene-3-carbonitrile | 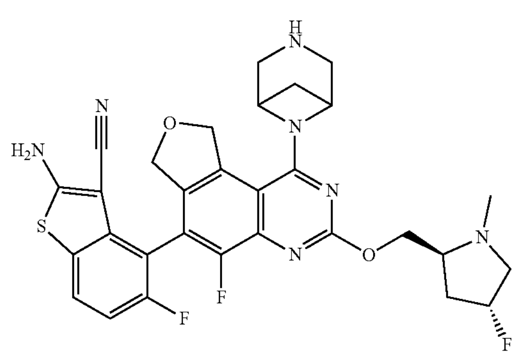 [SMILES: CN1C[C@H](F)C[C@H]1COc1nc(N2C3CNCC2C3)c2c3c(c(-c4c(F)ccc5sc(N)c(C#N)c45)c(F)c2n1)COC3] | 608 |

TABLE 14-continued

| Example | Chemical Name | Structure | MS (ES) m/z (M + 1) |
|---|---|---|---|
| 276 | 2-Amino-4-[1-(3,6-diazabicyclo[3.1.1]heptan-6-yl)-5-fluoro-3-[[(2S,4R)-4-fluoro-1-methyl-pyrrolidin-2-yl]methoxy]-7,9-dihydrofuro[3,4-f]quinazolin-6-yl]-7-fluoro-thieno[3,2-c]pyridine-3-carbonitrile | 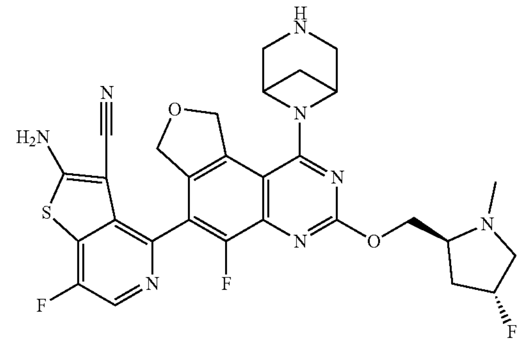 [SMILES: CN1C[C@H](F)C[C@H]1COc1nc(N2C3CNCC2C3)c2c3c(c(-c4ncc(F)c5sc(N)c(C#N)c45)c(F)c2n1)COC3] | 609 |
| 277 | 2-Amino-4-[1-(3,6-diazabicyclo[3.1.1]heptan-6-yl)-5-fluoro-3-[[(2S)-1-methylpyrrolidin-2-yl]methoxy]-7,9-dihydrofuro[3,4-f]quinazolin-6-yl]-7-fluoro-thieno[3,2-c]pyridine-3-carbonitrile | 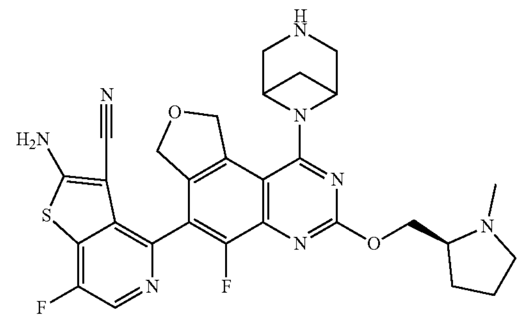 [SMILES: CN1CCC[C@H]1COc1nc(N2C3CNCC2C3)c2c3c(c(-c4ncc(F)c5sc(N)c(C#N)c45)c(F)c2n1)COC3] | 591 |
| 278 | 2-Amino-4-[1-(3,6-diazabicyclo[3.1.1]heptan-6-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-thieno[3,2-c]pyridine-3-carbonitrile | 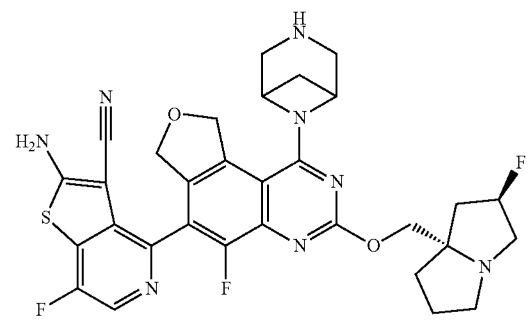 [SMILES: N#Cc1c(N)sc2c(F)cnc(-c3c4c(c5c(N6C7CNCC6C7)nc(OC[C@@]67CCCN6C[C@H](F)C7)nc5c3F)COC4)c12] | 635 |
| 279 | 2-Amino-7-fluoro-4-[5-fluoro-3-[[(2S)-1-methylpyrrolidin-2-yl]methoxy]-7,9-dihydrofuro[3,4-f]quinazolin-6-yl]thieno[3,2-c]pyridine-3-carbonitrile | 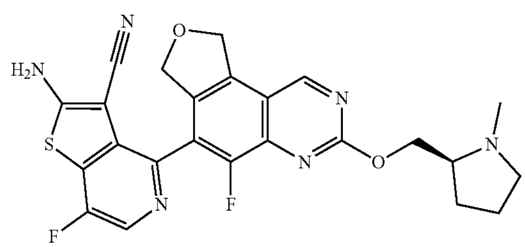 [SMILES: CN1CCC[C@H]1COc1ncc2c3c(c(-c4ncc(F)c5sc(N)c(C#N)c45)c(F)c2n1)COC3] | 495 |
| 280 | 2-Amino-4-[3-[[(2S,4R)-4-(difluoromethoxy)-1-methyl-pyrrolidin-2-yl]methoxy]-5-fluoro-7,9-dihydrofuro[3,4-f]quinazolin-6-yl]-7-fluoro-thieno[3,2-c]pyridine-3-carbonitrile | 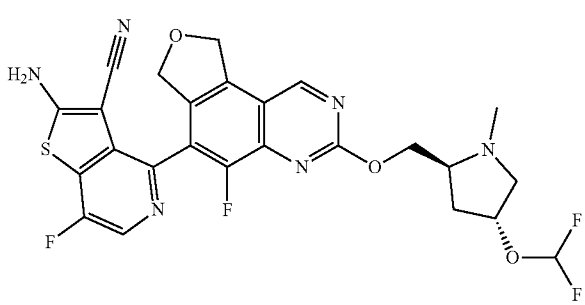 [SMILES: CN1C[C@H](OC(F)F)C[C@H]1COc1ncc2c3c(c(-c4ncc(F)c5sc(N)c(C#N)c45)c(F)c2n1)COC3] | 561 |

TABLE 14-continued

| Example | Chemical Name | Structure | MS (ES) m/z (M + 1) |
|---------|---------------|-----------|---------------------|
| 281 | 2-Amino-7-fluoro-4-[5-fluoro-3-[(3-fluoroazetidin-3-yl)methoxy]-7,9-dihydrofuro[3,4-f]quinazolin-6-yl]thieno[3,2-c]pyridine-3-carbonitrile | 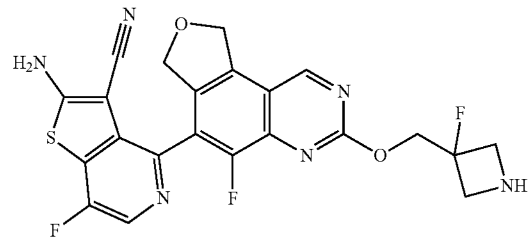 [SMILES: N#Cc1c(N)sc2c(F)cnc(-c3c4c(c5cnc(OCC6(F)CNC6)nc5c3F)COC4)c12] | 485 |
| 282 | 2-Amino-4-[3-[(4,4-difluoro-1-methyl-3-piperidyl)methoxy]-5-fluoro-7,9-dihydrofuro[3,4-f]quinazolin-6-yl]-7-fluoro-thieno[3,2-c]pyridine-3-carbonitrile | 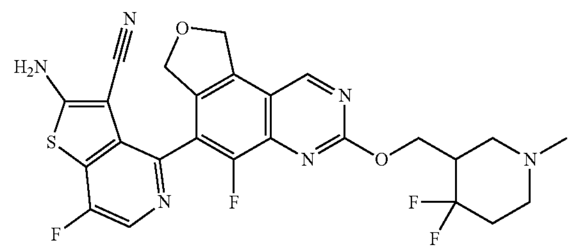 [SMILES: CN1CCC(F)(F)C(COc2ncc3c4c(c(-c5ncc(F)c6sc(N)c(C#N)c56)c(F)c3n2)COC4)C1] | 545 |
| 283 | 2-Amino-7-fluoro-4-[5-fluoro-3-[[(2S,4S)-4-methoxy-1-methyl-pyrrolidin-2-yl]methoxy]-7,9-dihydrofuro[3,4-f]quinazolin-6-yl]thieno[3,2-c]pyridine-3-carbonitrile | 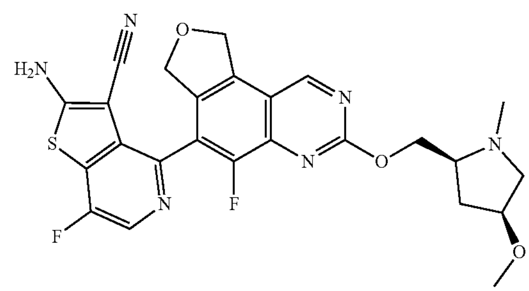 [SMILES: CO[C@H]1C[C@@H](COc2ncc3c4c(c(-c5ncc(F)c6sc(N)c(C#N)c56)c(F)c3n2)COC4)N(C)C1] | 525 |
| 284 | 2-Amino-7-fluoro-4-[5-fluoro-3-[[(2S,4R)-4-methoxy-1-methyl-pyrrolidin-2-yl]methoxy]-7,9-dihydrofuro[3,4-f]quinazolin-6-yl]thieno[3,2-c]pyridine-3-carbonitrile | 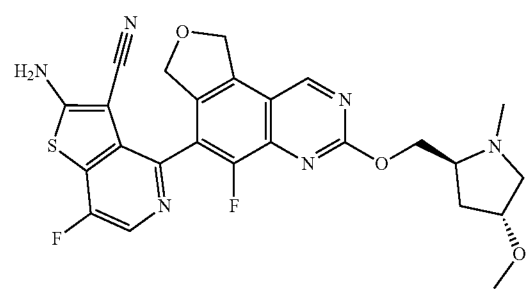 [SMILES: CO[C@@H]1C[C@@H](COc2ncc3c4c(c(-c5ncc(F)c6sc(N)c(C#N)c56)c(F)c3n2)COC4)N(C)C1] | 525 |
| 285 | 2-Amino-7-fluoro-4-[5-fluoro-3-[[(2S,4S)-4-fluoro-1-(2-methoxyethyl)pyrrolidin-2-yl]methoxy]-7,9-dihydrofuro[3,4-f]quinazolin-6-yl]thieno[3,2-c]pyridine-3-carbonitrile | 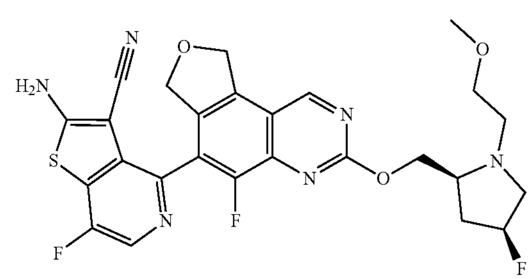 [SMILES: COCCN1C[C@@H](F)C[C@H]1COc1ncc2c3c(c(-c4ncc(F)c5sc(N)c(C#N)c45)c(F)c2n1)COC3] | 557 |

TABLE 14-continued

| Example | Chemical Name | Structure | MS (ES) m/z (M + 1) |
|---|---|---|---|
| 286 | 2-Amino-7-fluoro-4-[5-fluoro-3-[[(2S,4S)-4-fluoro-1-(2-hydroxyethyl)pyrrolidin-2-yl]methoxy]-7,9-dihydrofuro[3,4-f]quinazolin-6-yl]thieno[3,2-c]pyridine-3-carbonitrile | 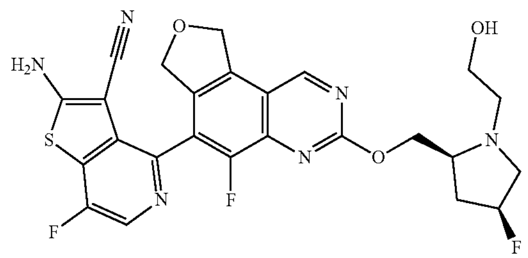 [SMILES: N#Cc1c(N)sc2c(F)cnc(-c3c4c(c5cnc(OC[C@@H]6C[C@H](F)CN6CCO)nc5c3F)COC4)c12] | 543 |
| 287 | 2-Amino-7-fluoro-4-[5-fluoro-3-[[(2S,4R)-4-fluoro-1-(2-hydroxyethyl)pyrrolidin-2-yl]methoxy]-7,9-dihydrofuro[3,4-f]quinazolin-6-yl]thieno[3,2-c]pyridine-3-carbonitrile | 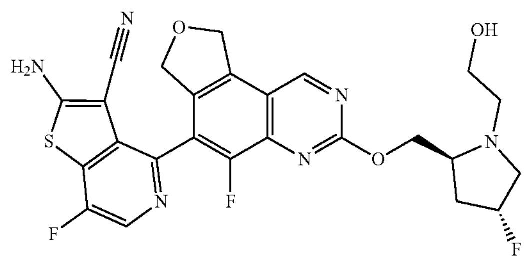 [SMILES: N#Cc1c(N)sc2c(F)cnc(-c3c4c(c5cnc(OC[C@@H]6C[C@@H](F)CN6CCO)nc5c3F)COC4)c12] | 543 |
| 288 | 2-Amino-7-fluoro-4-[5-fluoro-3-[[(2S,4S)-4-hydroxy-1-methyl-pyrrolidin-2-yl]methoxy]-7,9-dihydrofuro[3,4-f]quinazolin-6-yl]thieno[3,2-c]pyridine-3-carbonitrile | 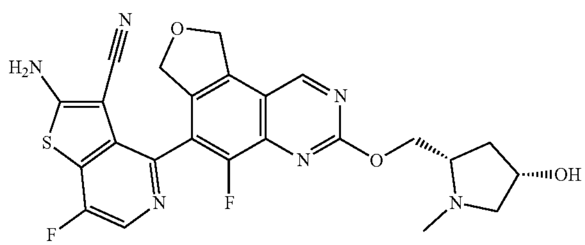 [SMILES: CN1C[C@@H](O)C[C@H]1COc1ncc2c3c(c(-c4ncc(F)c5sc(N)c(C#N)c45)c(F)c2n1)COC3] | 511 |
| 289 | 2-Amino-7-fluoro-4-[5-fluoro-3-[[(2S,4R)-4-hydroxy-1-methyl-pyrrolidin-2-yl]methoxy]-7,9-dihydrofuro[3,4-f]quinazolin-6-yl]thieno[3,2-c]pyridine-3-carbonitrile | 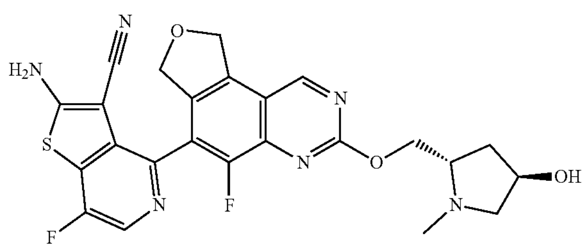 [SMILES: CN1C[C@H](O)C[C@H]1COc1ncc2c3c(c(-c4ncc(F)c5sc(N)c(C#N)c45)c(F)c2n1)COC3] | 511 |
| 290 | 2-Amino-7-fluoro-4-[5-fluoro-3-[(3-fluoropyrrolidin-3-yl)methoxy]-7,9-dihydrofuro[3,4-f]quinazolin-6-yl]thieno[3,2-c]pyridine-3-carbonitrile, Isomer 1 | 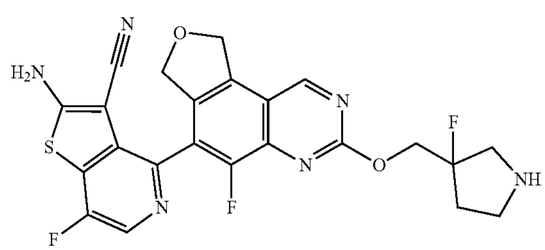 [SMILES: N#Cc1c(N)sc2c(F)cnc(-c3c4c(c5cnc(OCC6(F)CCNC6)nc5c3F)COC4)c12] | 499 |
| 291 | 2-Amino-7-fluoro-4-[5-fluoro-3-[(3-fluoropyrrolidin-3-yl)methoxy]-7,9-dihydrofuro[3,4-f]quinazolin-6-yl]thieno[3,2-c]pyridine-3-carbonitrile, Isomer 2 | 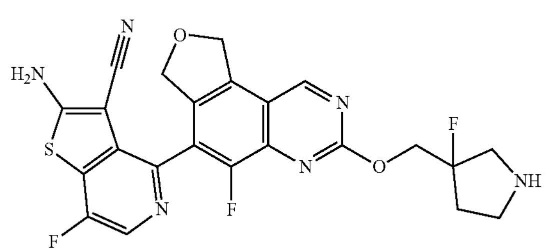 [SMILES: N#Cc1c(N)sc2c(F)cnc(-c3c4c(c5cnc(OCC6(F)CCNC6)nc5c3F)COC4)c12] | 499 |

TABLE 14-continued

| Example | Chemical Name | Structure | MS (ES) m/z (M + 1) |
|---|---|---|---|
| 292 | 2-Amino-4-[3-[[(2S)-5,5-difluoro-1-methyl-2-piperidyl]methoxy]-5-fluoro-7,9-dihydrofuro[3,4-f]quinazolin-6-yl]-7-fluoro-thieno[3,2-c]pyridine-3-carbonitrile | 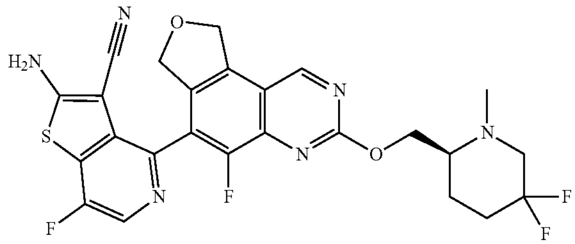 [SMILES: CN1CC(F)(F)CC[C@H]1COc1ncc2c3c(c(-c4ncc(F)c5sc(N)c(C#N)c45)c(F)c2n1)COC3] | 545 |
| 293 | 2-Amino-4-[3-[[(2S)-4,4-difluoro-1-methyl-2-piperidyl]methoxy]-5-fluoro-7,9-dihydrofuro[3,4-f]quinazolin-6-yl]-7-fluoro-thieno[3,2-c]pyridine-3-carbonitrile | 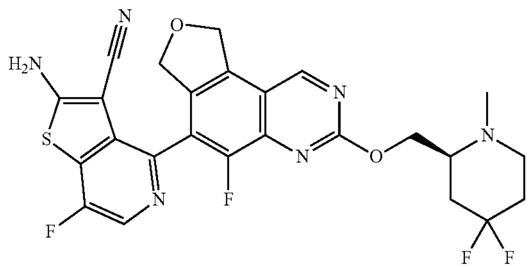 [SMILES: CN1CCC(F)(F)C[C@H]1COc1ncc2c3c(c(-c4ncc(F)c5sc(N)c(C#N)c45)c(F)c2n1)COC3] | 545 |
| 294 | 2-Amino-7-fluoro-4-[5-fluoro-3-[[(1R,2S,5S)-3-methyl-3-azabicyclo[3.1.0]hexan-2-yl]methoxy]-7,9-dihydrofuro[3,4-f]quinazolin-6-yl]thieno[3,2-c]pyridine-3-carbonitrile | 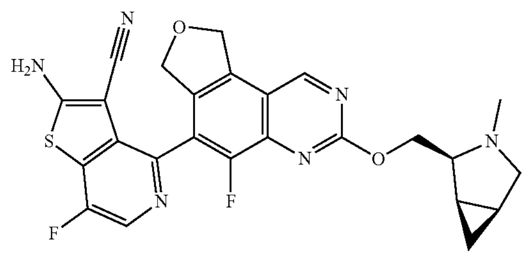 [SMILES: CN1C[C@H]2C[C@H]2[C@H]1COc1ncc2c3c(c(-c4ncc(F)c5sc(N)c(C#N)c45)c(F)c2n1)COC3] | 507 |
| 295 | 2-Amino-7-fluoro-4-[5-fluoro-3-[[(2S,4S)-1-methyl-4-(trifluoromethyl)pyrrolidin-2-yl]methoxy]-7,9-dihydrofuro[3,4-f]quinazolin-6-yl]thieno[3,2-c]pyridine-3-carbonitrile | 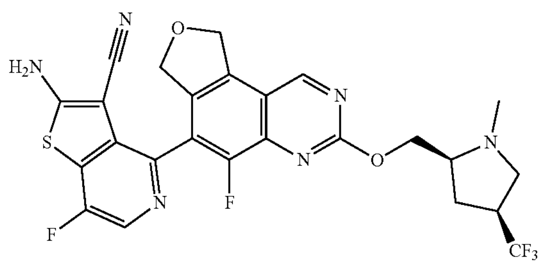 [SMILES: CN1C[C@@H](C(F)(F)F)C[C@H]1COc1ncc2c3c(c(-c4ncc(F)c5sc(N)c(C#N)c45)c(F)c2n1)COC3] | 563 |
| 296 | 2-Amino-7-fluoro-4-[5-fluoro-3-[[(2S,4R)-1-methyl-4-(trifluoromethyl)pyrrolidin-2-yl]methoxy]-7,9-dihydrofuro[3,4-f]quinazolin-6-yl]thieno[3,2-c]pyridine-3-carbonitrile | 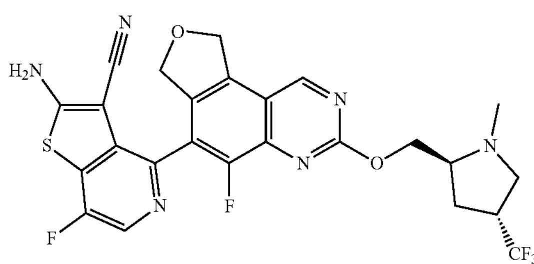 [SMILES: CN1C[C@H](C(F)(F)F)C[C@H]1COc1ncc2c3c(c(-c4ncc(F)c5sc(N)c(C#N)c45)c(F)c2n1)COC3] | 563 |
| 297 | 2-Amino-7-fluoro-4-[5-fluoro-3-[[(2R,8S)-2-methoxy-1,2,3,5,6,7-hexahydropyrrolizin-8-yl]methoxy]-7,9-dihydrofuro[3,4-f]quinazolin-6-yl]thieno[3,2-c]pyridine-3-carbonitrile | 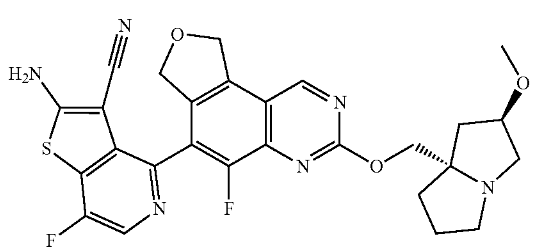 [SMILES: CO[C@H]1CN2CCC[C@@]2(COc2ncc3c4c(c(-c5ncc(F)c6sc(N)c(C#N)c56)c(F)c3n2)COC4)C1] | 551 |

TABLE 14-continued

| Example | Chemical Name | Structure | MS (ES) m/z (M + 1) |
|---------|---------------|-----------|---------------------|
| 298 | 2-Amino-4-[3-[[(8S)-6,6-difluoro-2,3,5,7-tetrahydro-1H-pyrrolizin-8-yl]methoxy]-5-fluoro-7,9-dihydrofuro[3,4-f]quinazolin-6-yl]-7-fluoro-thieno[3,2-c]pyridine-3-carbonitrile | 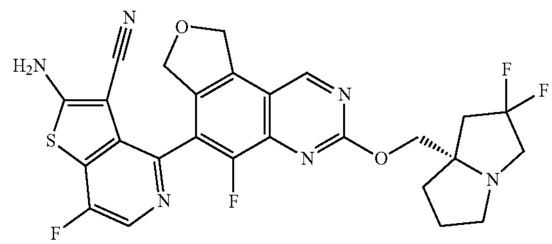 [SMILES: N#Cc1c(N)sc2c(F)cnc(-c3c4c(c5cnc(OC[C@@]67CCCN6CC(F)(F)C7)nc5c3F)COC4)c12] | 557 |
| 299 | 2-Amino-7-fluoro-4-[5-fluoro-3-[(3-hydroxycyclobutyl)methoxy]-7,9-dihydrofuro[3,4-f]quinazolin-6-yl]thieno[3,2-c]pyridine-3-carbonitrile | 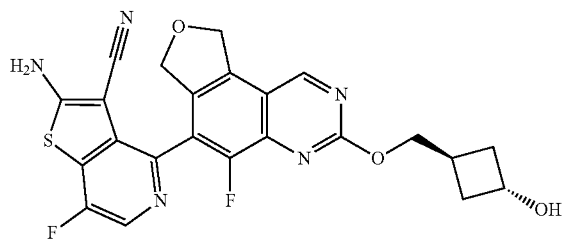 [SMILES: N#Cc1c(N)sc2c(F)cnc(-c3c4c(c5cnc(OC[C@H]6C[C@H](O)C6)nc5c3F)COC4)c12] | 482 |
| 300 | 2-Amino-7-fluoro-4-[5-fluoro-3-[(3-hydroxycyclobutyl)methoxy]-7,9-dihydrofuro[3,4-f]quinazolin-6-yl]thieno[3,2-c]pyridine-3-carbonitrile | 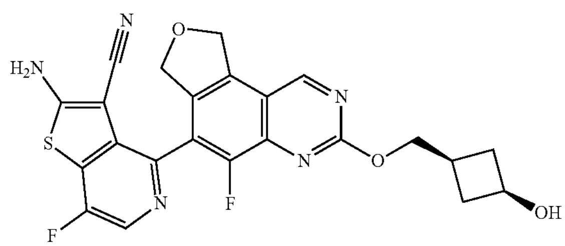 [SMILES: N#Cc1c(N)sc2c(F)cnc(-c3c4c(c5cnc(OC[C@H]6C[C@@H](O)C6)nc5c3F)COC4)c12] | 482 |
| 301 | 2-Amino-7-fluoro-4-[5-fluoro-3-[[(3S)-4-methylmorpholin-3-yl]methoxy]-7,9-dihydrofuro[3,4-f]quinazolin-6-yl]thieno[3,2-c]pyridine-3-carbonitrile | 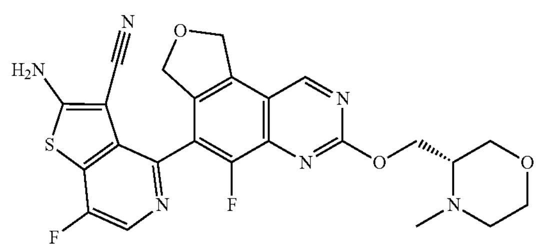 [SMILES: CN1CCOC[C@H]1COc1ncc2c3c(c(-c4ncc(F)c5sc(N)c(C#N)c45)c(F)c2n1)COC3] | 511 |
| 302 | 2-Amino-7-fluoro-4-[5-fluoro-3-[[(3R)-4-methylmorpholin-3-yl]methoxy]-7,9-dihydrofuro[3,4-f]quinazolin-6-yl]thieno[3,2-c]pyridine-3-carbonitrile | 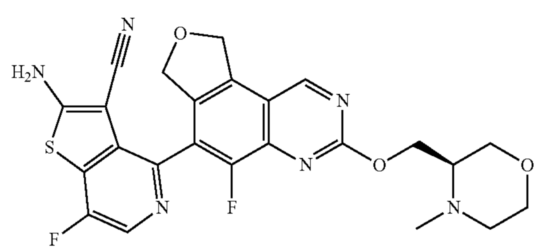 [SMILES: CN1CCOC[C@@H]1COc1ncc2c3c(c(-c4ncc(F)c5sc(N)c(C#N)c45)c(F)c2n1)COC3] | 511 |
| 303 | 2-Amino-7-fluoro-4-[5-fluoro-3-[[(2R)-tetrahydrofuran-2-yl]methoxy]-7,9-dihydrofuro[3,4-f]quinazolin-6-yl]thieno[3,2-c]pyridine-3-carbonitrile | 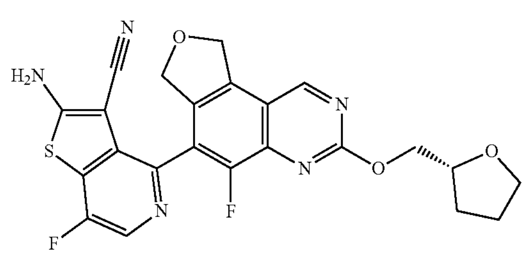 [SMILES: N#Cc1c(N)sc2c(F)cnc(-c3c4c(c5cnc(OC[C@H]6CCCO6)nc5c3F)COC4)c12] | 482 |

TABLE 14-continued

| Example | Chemical Name | Structure | MS (ES) m/z (M + 1) |
|---|---|---|---|
| 304 | 2-Amino-7-fluoro-4-[5-fluoro-3-[[(2S)-tetrahydrofuran-2-yl]methoxy]-7,9-dihydrofuro[3,4-f]quinazolin-6-yl]thieno[3,2-c]pyridine-3-carbonitrile | 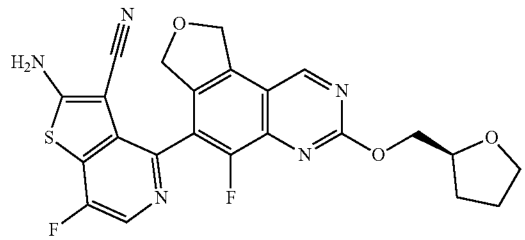 [SMILES: N#Cc1c(N)sc2c(F)cnc(-c3c4c(c5cnc(OC[C@@H]6CCCO6)nc5c3F)COC4)c12] | 482 |
| 305 | 2-Amino-7-fluoro-4-[5-fluoro-3-[[(2S,4S)-4-fluoro-1-methyl-pyrrolidin-2-yl]methoxy]-7,9-dihydrofuro[3,4-f]quinazolin-6-yl]thieno[3,2-c]pyridine-3-carbonitrile | 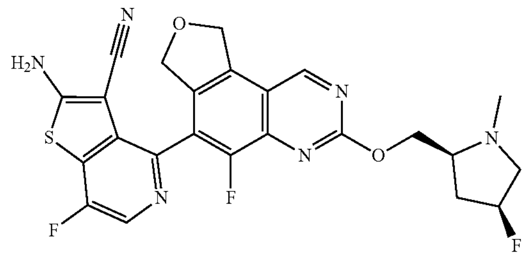 [SMILES: CN1C[C@@H](F)C[C@H]1COc1ncc2c3c(c(-c4ncc(F)c5sc(N)c(C#N)c45)c(F)c2n1)COC3] | 513 |
| 306 | 2-Amino-7-fluoro-4-[5-fluoro-3-[[(2S,4R)-4-fluoro-1-methyl-pyrrolidin-2-yl]methoxy]-7,9-dihydrofuro[3,4-f]quinazolin-6-yl]thieno[3,2-c]pyridine-3-carbonitrile | 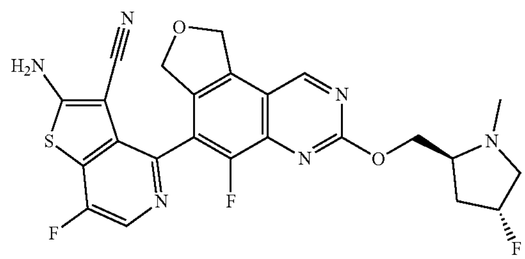 [SMILES: CN1C[C@H](F)C[C@H]1COc1ncc2c3c(c(-c4ncc(F)c5sc(N)c(C#N)c45)c(F)c2n1)COC3] | 513 |
| 307 | 2-Amino-7-fluoro-4-[5-fluoro-3-[[(2S)-1-methylazetidin-2-yl]methoxy]-7,9-dihydrofuro[3,4-f]quinazolin-6-yl]thieno[3,2-c]pyridine-3-carbonitrile | 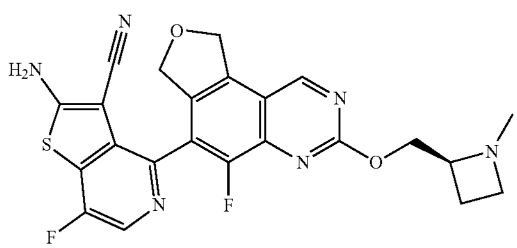 [SMILES: CN1CC[C@H]1COc1ncc2c3c(c(-c4ncc(F)c5sc(N)c(C#N)c45)c(F)c2n1)COC3] | 481 |
| 308 | 2-Amino-7-fluoro-4-[5-fluoro-3-[[(2R)-1-methylazetidin-2-yl]methoxy]-7,9-dihydrofuro[3,4-f]quinazolin-6-yl]thieno[3,2-c]pyridine-3-carbonitrile | 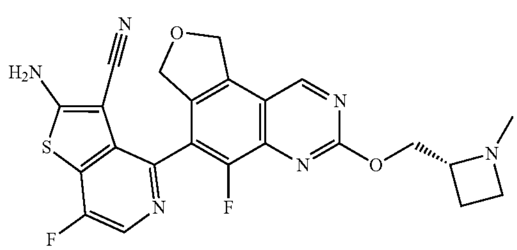 [SMILES: CN1CC[C@@H]1COc1ncc2c3c(c(-c4ncc(F)c5sc(N)c(C#N)c45)c(F)c2n1)COC3] | 481 |
| 309 | 2-Amino-7-fluoro-4-[5-fluoro-3-(2-morpholinoethoxy)-7,9-dihydrofuro[3,4-f]quinazolin-6-yl]thieno[3,2-c]pyridine-3-carbonitrile | 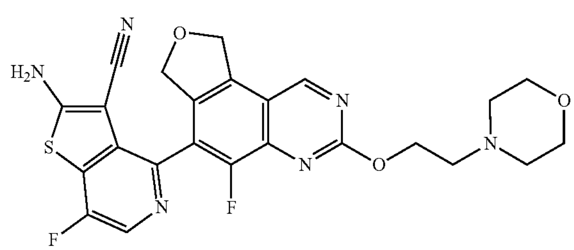 [SMILES: N#Cc1c(N)sc2c(F)cnc(-c3c4c(c5cnc(OCCN6CCOCC6)nc5c3F)COC4)c12] | 511 |

TABLE 14-continued

| Example | Chemical Name | Structure | MS (ES) m/z (M + 1) |
|---|---|---|---|
| 310 | 2-Amino-7-fluoro-4-[5-fluoro-3-[[(2R)-4-methylmorpholin-2-yl]methoxy]-7,9-dihydrofuro[3,4-f]quinazolin-6-yl]thieno[3,2-c]pyridine-3-carbonitrile | 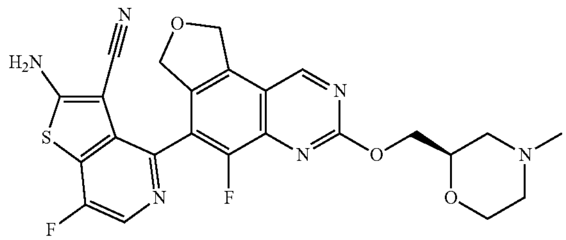 [SMILES: CN1CCO[C@@H](COc2ncc3c4c(c(-c5ncc(F)c6sc(N)c(C#N)c56)c(F)c3n2)COC4)C1] | 511 |
| 311 | 2-Amino-7-fluoro-4-[5-fluoro-3-[[(2S)-4-methylmorpholin-2-yl]methoxy]-7,9-dihydrofuro[3,4-f]quinazolin-6-yl]thieno[3,2-c]pyridine-3-carbonitrile | 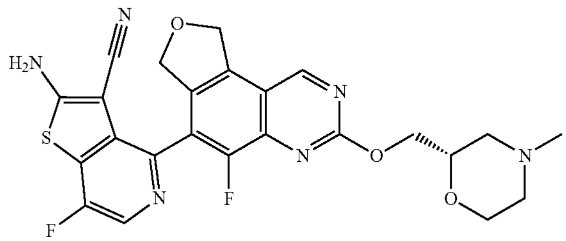 [SMILES: CN1CCO[C@H](COc2ncc3c4c(c(-c5ncc(F)c6sc(N)c(C#N)c56)c(F)c3n2)COC4)C1] | 511 |
| 312 | 2-Amino-7-fluoro-4-[5-fluoro-3-[[(3R)-tetrahydrofuran-3-yl]methoxy]-7,9-dihydrofuro[3,4-f]quinazolin-6-yl]thieno[3,2-c]pyridine-3-carbonitrile | 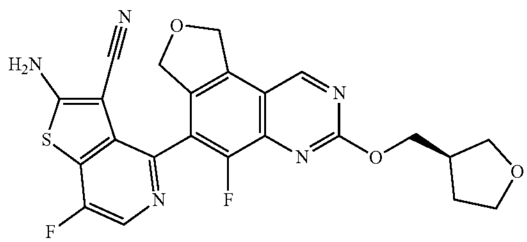 [SMILES: N#Cc1c(N)sc2c(F)cnc(-c3c4c(c5cnc(OC[C@@H]6CCOC6)nc5c3F)COC4)c12] | 482 |
| 313 | 2-Amino-7-fluoro-4-[5-fluoro-3-[[(3S)-tetrahydrofuran-3-yl]methoxy]-7,9-dihydrofuro[3,4-f]quinazolin-6-yl]thieno[3,2-c]pyridine-3-carbonitrile | 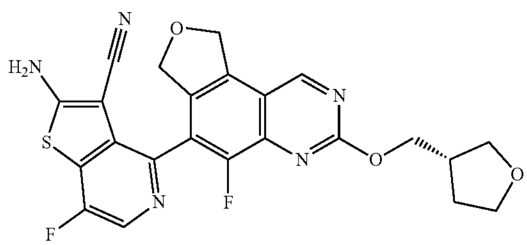 [SMILES: N#Cc1c(N)sc2c(F)cnc(-c3c4c(c5cnc(OC[C@H]6CCOC6)nc5c3F)COC4)c12] | 482 |
| 314 | 2-Amino-7-fluoro-4-[5-fluoro-3-[[(2R,8S)-2-fluoro-1,2,3,5,6,7-hexahydropyrrolizin-8-yl]methoxy]-1-(2,2,2-trifluoroethoxy)-7,9-dihydrofuro[3,4-f]quinazolin-6-yl]thieno[3,2-c]pyridine-3-carbonitrile | 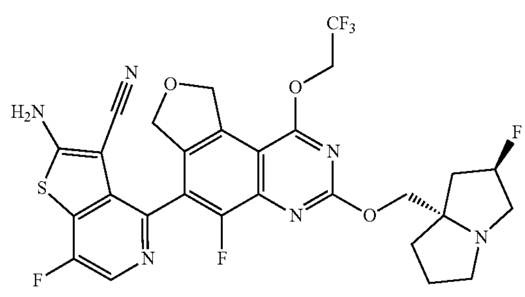 [SMILES: N#Cc1c(N)sc2c(F)cnc(-c3c4c(c5c(OCC(F)(F)F)nc(OC[C@@]67CCCN6C[C@H](F)C7)nc5c3F)COC4)c12] | 637 |
| 315 | 2-Amino-4-[1-(dimethylamino)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-thieno[3,2-c]pyridine-3-carbonitrile | 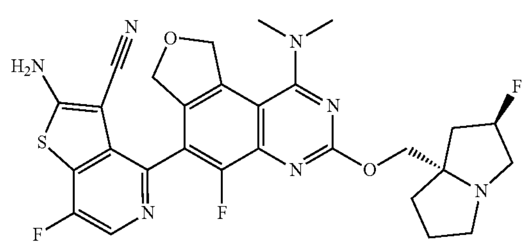 [SMILES: CN(C)c1nc(OC[C@@]23CCCN2C[C@H](F)C3)nc2c(F)c(-c3ncc(F)c4sc(N)c(C#N)c34)c3c(c12)COC3] | 582 |

| Example | Chemical Name | Structure | MS (ES) m/z (M + 1) |
|---|---|---|---|
| 316 | 2-Amino-7-fluoro-4-[5-fluoro-3-[[(2R,8S)-2-fluoro-1,2,3,5,6,7-hexahydropyrrolizin-8-yl]methoxy]-1-(methylamino)-7,9-dihydrofuro[3,4-f]quinazolin-6-yl]thieno[3,2-c]pyridine-3-carbonitrile | 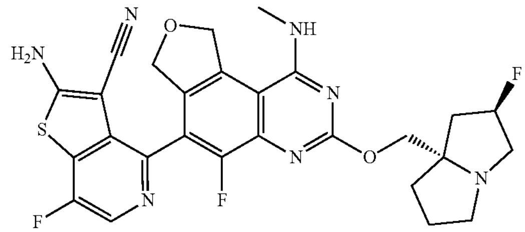 [SMILES: CNc1nc(OC[C@@]23CCCN2C[C@H](F)C3)nc2c(F)c(-c3ncc(F)c4sc(N)c(C#N)c34)c3c(c12)COC3] | 568 |
| 317 | 2-Amino-7-fluoro-4-[5-fluoro-3-[[(2R,8S)-2-fluoro-1,2,3,5,6,7-hexahydropyrrolizin-8-yl]methoxy]-1-(2-hydroxyethylamino)-7,9-dihydrofuro[3,4-f]quinazolin-6-yl]thieno[3,2-c]pyridine-3-carbonitrile | 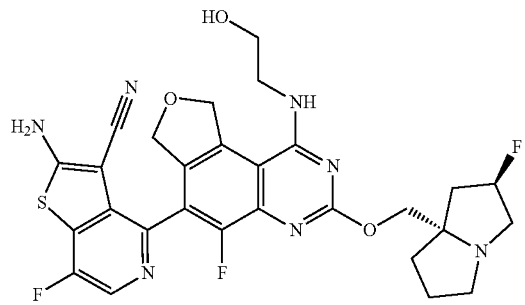 [SMILES: N#Cc1c(N)sc2c(F)cnc(-c3c4c(c5c(NCCO)nc(OC[C@@]67CCCN6C[C@H](F)C7)nc5c3F)COC4)c12] | 598 |
| 318 | 2-Amino-4-[1-(azetidin-1-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-thieno[3,2-c]pyridine-3-carbonitrile | 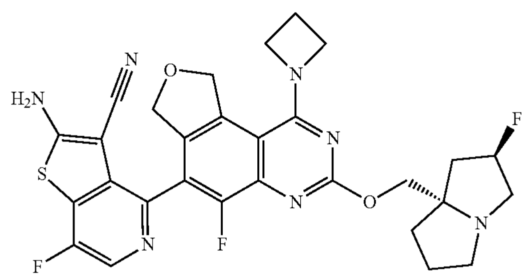 [SMILES: N#Cc1c(N)sc2c(F)cnc(-c3c4c(c5c(N6CCC6)nc(OC[C@@]67CCCN6C[C@H](F)C7)nc5c3F)COC4)c12] | 594 |
| 319 | 2-Amino-7-fluoro-4-[5-fluoro-3-[[(2R,8S)-2-fluoro-1,2,3,5,6,7-hexahydropyrrolizin-8-yl]methoxy]-1-(3-methoxyazetidin-1-yl)-7,9-dihydrofuro[3,4-f]quinazolin-6-yl]thieno[3,2-c]pyridine-3-carbonitrile | 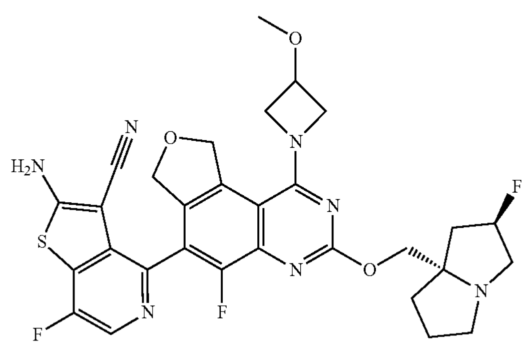 [SMILES: COC1CN(c2nc(OC[C@@]34CCCN3C[C@H](F)C4)nc3c(F)c(-c4ncc(F)c5sc(N)c(C#N)c45)c4c(c23)COC4)C1] | 624 |
| 320 | 2-Amino-7-fluoro-4-[5-fluoro-3-[[(2R,8S)-2-fluoro-1,2,3,5,6,7-hexahydropyrrolizin-8-yl]methoxy]-1-morpholino-7,9-dihydrofuro[3,4-f]quinazolin-6-yl]thieno[3,2-c]pyridine-3-carbonitrile | 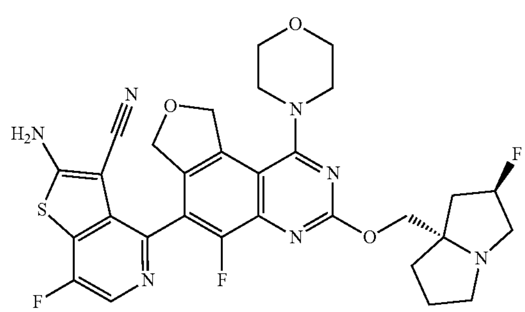 [SMILES: N#Cc1c(N)sc2c(F)cnc(-c3c4c(c5c(N6CCOCC6)nc(OC[C@@]67CCCN6C[C@H](F)C7)nc5c3F)COC4)c12] | 624 |

TABLE 14-continued

| Example | Chemical Name | Structure | MS (ES) m/z (M + 1) |
|---|---|---|---|
| 321 | 2-Amino-7-fluoro-4-[5-fluoro-3-[[(2R,8S)-2-fluoro-1,2,3,5,6,7-hexahydropyrrolizin-8-yl]methoxy]-1-(2-methoxyethoxy)-7,9-dihydrofuro[3,4-f]quinazolin-6-yl]thieno[3,2-c]pyridine-3-carbonitrile | 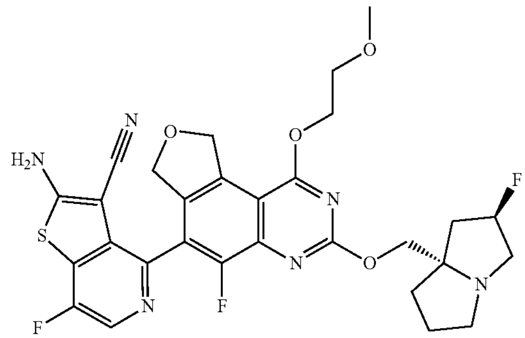 [SMILES: COCCOc1nc(OC[C@@]23CCCN2C[C@H](F)C3)nc2c(F)c(-c3ncc(F)c4sc(N)c(C#N)c34)c3c(c12)COC3] | 613 |
| 322 | 2-Amino-7-fluoro-4-[5-fluoro-3-[[(2R,8S)-2-fluoro-1,2,3,5,6,7-hexahydropyrrolizin-8-yl]methoxy]-1-hydroxy-7,9-dihydrofuro[3,4-f]quinazolin-6-yl]thieno[3,2-c]pyridine-3-carbonitrile | 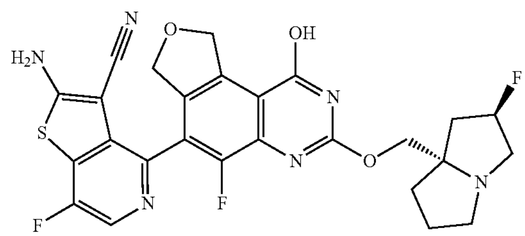 [SMILES: N#Cc1c(N)sc2c(F)cnc(-c3c4c(c5c(O)nc(OC[C@@]67CCCN6C[C@H](F)C7)nc5c3F)COC4)c12] | 555 |
| 323 | 2-Amino-7-fluoro-4-[5-fluoro-3-[[(2R,8S)-2-fluoro-1,2,3,5,6,7-hexahydropyrrolizin-8-yl]methoxy]-1-[[(2S)-1-methylpyrrolidin-2-yl]methylamino]-7,9-dihydrofuro[3,4-f]quinazolin-6-yl]thieno[3,2-c]pyridine-3-carbonitrile | 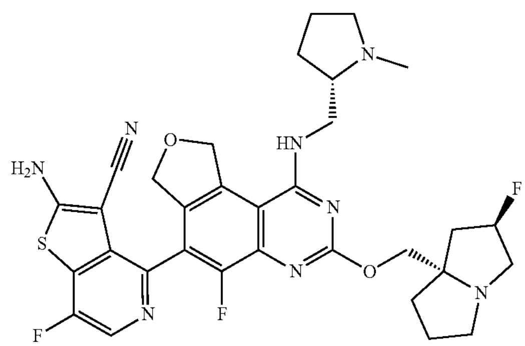 [SMILES: CN1CCC[C@H]1CNc1nc(OC[C@@]23CCCN2C[C@H](F)C3)nc2c(F)c(-c3ncc(F)c4sc(N)c(C#N)c34)c3c(c12)COC3] | 651 |
| 324 | 2-Amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]thieno[2,3-b]pyridine-3-carbonitrile | 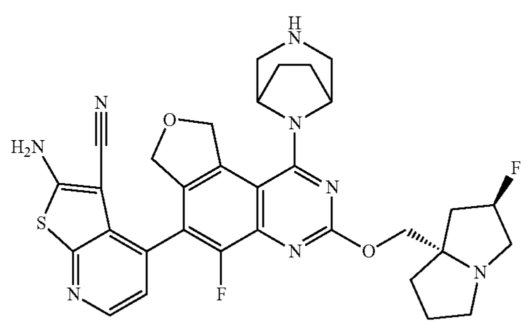 [SMILES: N#Cc1c(N)sc2nccc(-c3c4c(c5c(N6C7CCC6CNC7)nc(OC[C@@]67CCCN6C[C@H](F)C7)nc5c3F)COC4)c12] | 631 |
| 325 | 2-Amino-4-[1-(3-azabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-thieno[3,2-c]pyridine-3-carbonitrile | 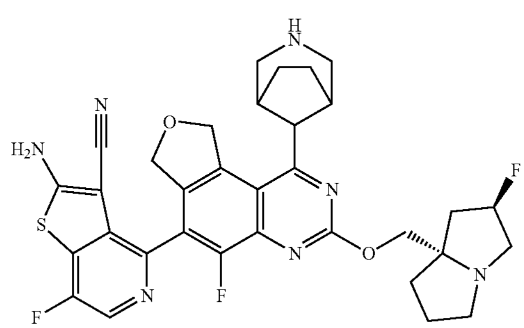 | 648 |

TABLE 14-continued

| Example | Chemical Name | Structure | MS (ES) m/z (M + 1) |
|---|---|---|---|
| 375 | 2-Amino-4-[3-[[1-[(dimethylamino)methyl]cyclopropyl]methoxy]-5-fluoro-7,9-dihydrofuro[3,4-f]quinazolin-6-yl]-7-fluoro-thieno[3,2-c]pyridine-3-carbonitrile | 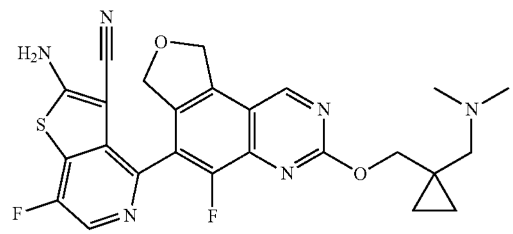 [SMILES: CN(C)CC1(COc2ncc3c4c(c(-c5ncc(F)c6sc(N)c(C#N)c56)c(F)c3n2)COC4)CC1] | 509 |

[1] single diastereomer
[2] single atropisomer (from precursor in Preparation 157)
[3] single atropisomer (from precursor in Preparation 266)
[4] single atropisomer (from precursor in Preparation 248)
[5] single atropisomer (from precursor in Preparation 296)
[6] single atropisomer (from precursor in Preparation 251)
[7] single atropisomer (from precursor in Preparation 255)
[8] single atropisomer (from precursor in Preparation 298)
[a] measured in MS (ES)*

Example 46

2-Amino-4-[5-fluoro-3-[[(2R,8S)-2-fluoro-1,2,3,5,6,7-hexahydropyrrolizin-8-yl]methoxy]-1-[3-(2-hydroxyethyl)-3,8-diazabicyclo[3.2.1]octan-8-yl]-7,9-dihydrofuro[3,4-f]quinazolin-6-yl]benzothiophene-3-carbonitrile

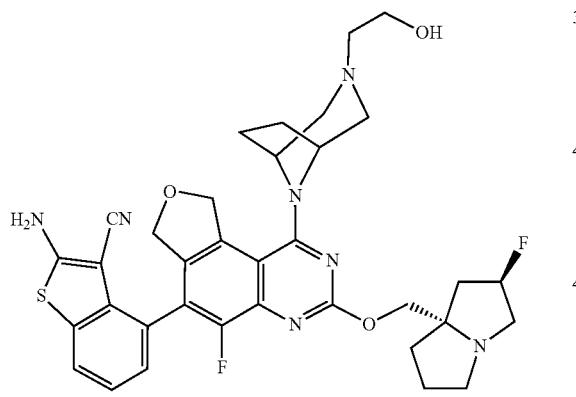

A solution of tert-butyl N-[4-[1-[3-[2-[tert-butyl(dimethyl)silyl]oxyethyl]-3,8-diazabicyclo[3.2.1]octan-8-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-3-cyano-benzothiophen-2-yl]carbamate (0.250 g, 0.281 mmol) in THF (2 mL) was treated with 1M TBAF in THF (0.7 mL, 0.7 mmol) and was stirred at RT for 1.5 h. A second portion of 1M TBAF in THF (0.7 mL, 0.7 mmol) was added and the mixture was stirred for ~18 h. The mixture was concentrated and dried in vacuo. The residue was dissolved in DCM (5 mL), treated with TFA (2 mL) and stirred at RT for ~18 h. The mixture was concentrated. DCM was added, and the mixture was concentrated again. The residue was dissolved in DCM/MeOH and loaded onto SCX, eluting with MeOH and DCM, then with 1:1 2N NH$_3$/MeOH:DCM. The ammoniated eluent was concentrated in vacuo, and residue was further purified by reversed phase flash chromatography on C18, eluting with 5-50% ACN in 10 mM aq. NH$_4$HCO$_3$ with 5% MeOH) to obtain the title compound (0.111 g, 59%) as an off-white solid. MS (ES) m/z=674 (M+1).

Example 47

2-Amino-7-fluoro-4-[5-fluoro-1-[(1S,4S,7S)-7-fluoro-2,5-diazabicyclo[2.2.1]heptan-2-yl]-7,9-dihydrofuro[3,4-f]quinazolin-6-yl]benzothiophene-3-carbonitrile

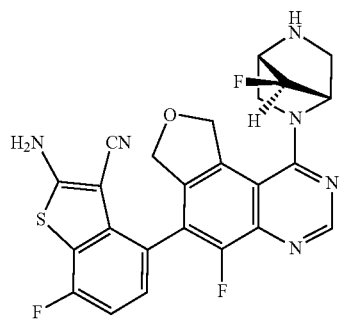 [SMILES: N#Cc1c(N)sc2c(F)ccc(-c3c4c(c5c(N6C[C@@H]7NC[C@H]6[C@H]7F)ncnc5c3F)COC4)c12]

Benzyl (1S,4S,7R)-5-[6-[2-(tert-butoxycarbonylamino)-3-cyano-7-fluoro-benzothiophen-4-yl]-5-fluoro-7,9-dihydrofuro[3,4-f]quinazolin-1-yl]-7-fluoro-2,5-diazabicyclo[2.2.1]heptane-2-carboxylate (280 mg, 0.384 mmol) was stirred in TFA (10.0 mL) at RT. The resulting mixture was then stirred for 5 h at 70° C. The mixture was concentrated under reduced pressure and was diluted with DMF (3 mL). The mixture was then basified to pH 9 with NH$_3$H$_2$O. The mixture was purified on C18, eluting with a gradient of 46% to 65% ACN in 10 mM aq. NH$_4$HCO$_3$. to afford the title compound (39.5 mg, 20.2%) as a white solid. MS (ES) m/z=495 (M+1).

Example 48

2-Amino-4-[5-fluoro-3-[[(2R,8S)-2-fluoro-1,2,3,5,6,7-hexahydropyrrolizin-8-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile

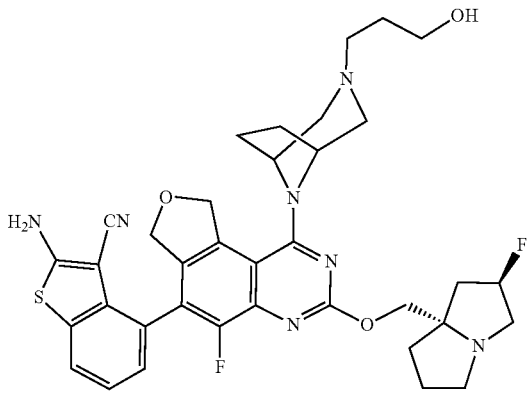 [SMILES: N#Cc1c(N)sc2cccc(-c3c4c(c5c(N6C7CCC6CN(CCCO)C7)nc(OC[C@@]67CCCN6C[C@H](F)C7)nc5c3F)COC4)c12]

A solution of 2-amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]benzothiophene-3-carbonitrile (0.800 g, 1.27 mmol) in DCM (13 mL) and MeOH (2.5 mL) was treated with 3-[(tert-butyldimethylsilyl)oxy]-1-propanal (0.756 g, 3.81 mmol) and NaBH(OAc)$_3$ (0.850 g, 3.81 mmol). After stirring at RT for 1 h, the reaction mixture was poured directly onto SCX, eluting first with MeOH and DCM, then with 1:1 2N NH$_3$/MeOH:DCM. The ammoniated fractions were concentrated. The residue was dissolved in DCM/MeOH and passed over SCX a second time. The residue from concentration of the ammoniated fraction was purified on silica (eluting with 0% to 5% 7N NH$_3$/MeOH in DCM) followed by reversed phase flash chromatography on C18 (eluting with 5% to 51% ACN in 10 mM aq. NH$_4$HCO$_3$ with 5% MeOH) to obtain the title compound (0.541 g, 62%) as a light-beige solid. MS (ES) m/z=688 (M+1).

The Example compounds in Table 15 were prepared in a similar manner as described for Example 48. Various methods were used to purify the compounds, which would be apparent to one skilled in the art. Chiral purification methods (if applicable) for the Examples of Table 15 are located in Table 18.

TABLE 15

| Example | Chemical Name | Structure | MS (ES) m/z (M + 1) |
|---|---|---|---|
| 49[1] | 2-Amino-5-fluoro-4-[5-fluoro-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile | 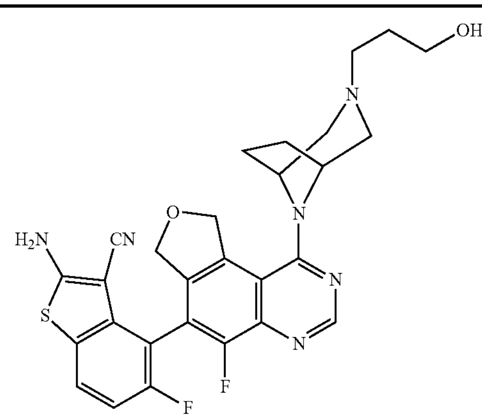 | 549 |
| 50 | 2-Amino-4-[5-fluoro-3-[[(2R,8S)-2-fluoro-1,2,3,5,6,7-hexahydropyrrolizin-8-yl]methoxy]-1-[3-(oxetan-3-yl)-3,8-diazabicyclo[3.2.1]octan-8-yl]-7,9-dihydrofuro[3,4-f]quinazolin-6-yl]benzothiophene-3-carbonitrile | 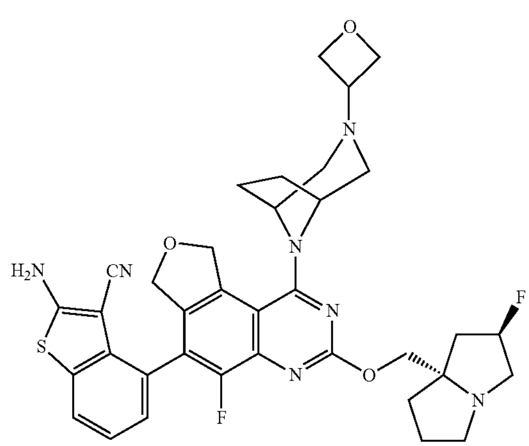 [SMILES: N#Cc1c(N)sc2cccc(-c3c4c(c5c(N6C7CCC6CN(C6COC6)C7)nc(OC[C@@]67CCCN6C[C@H](F)C7)nc5c3F)COC4)c12] | 686 |

TABLE 15-continued

| Example | Chemical Name | Structure | MS (ES) m/z (M + 1) |
|---|---|---|---|
| 51[2] | 2-Amino-4-[5-fluoro-3-[[(2R,8S)-2-fluoro-1,2,3,5,6,7-hexahydropyrrolizin-8-yl]methoxy]-1-(3-methyl-3,8-diazabicyclo[3.2.1]octan-8-yl)-7,9-dihydrofuro[3,4-f]quinazolin-6-yl]thieno[3,2-c]pyridine-3-carbonitrile | 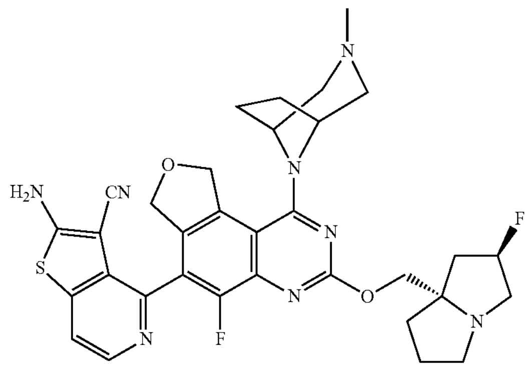 [SMILES: CN1CC2CCC(C1)N2c1nc(OC[C@@]23CCCN2C[C@H](F)C3)nc2c(F)c(-c3nccc4sc(N)c(C#N)c34)c3c(c12)COC3] | 645 |
| 52 | 2-Amino-4-[5-fluoro-3-[[(2R,8S)-2-fluoro-1,2,3,5,6,7-hexahydropyrrolizin-8-yl]methoxy]-1-(3-methyl-3,6-diazabicyclo[3.1.1]heptan-6-yl)-7,9-dihydrofuro[3,4-f]quinazolin-6-yl]thieno[3,2-c]pyridine-3-carbonitrile | 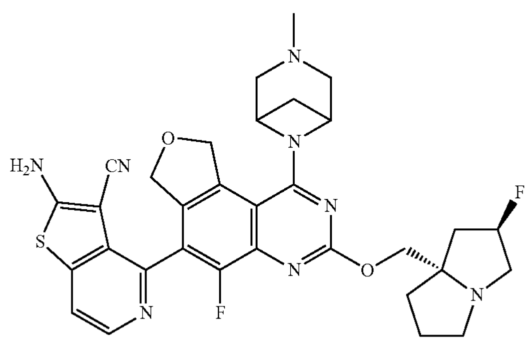 [SMILES: CN1CC2CC(C1)N2c1nc(OC[C@@]23CCCN2C[C@H](F)C3)nc2c(F)c(-c3nccc4sc(N)c(C#N)c34)c3c(c12)COC3] | 631 |
| 53 | 2-Amino-5-fluoro-4-[5-fluoro-1-(3-methyl-3,6-diazabicyclo[3.1.1]heptan-6-yl)-7,9-dihydrofuro[3,4-f]quinazolin-6-yl]benzothiophene-3-carbonitrile, Isomer 2 | 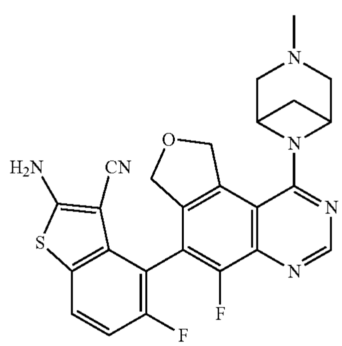 [SMILES: CN1CC2CC(C1)N2c1ncnc2c(F)c(-c3c(F)ccc4sc(N)c(C#N)c34)c3c(c12)COC3] | 491 |
| 54 | 2-Amino-4-[5-fluoro-3-[[(2R,8S)-2-fluoro-1,2,3,5,6,7-hexahydropyrrolizin-8-yl]methoxy]-1-(3-methyl-3,8-diazabicyclo[3.2.1]octan-8-yl)-7,9-dihydrofuro[3,4-f]quinazolin-6-yl]benzofuran-3-carbonitrile | 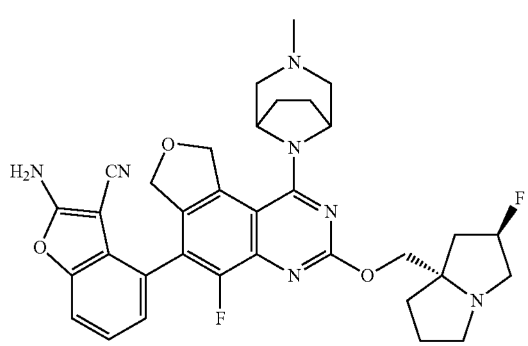 [SMILES: CN1CC2CCC(C1)N2c1nc(OC[C@@]23CCCN2C[C@H](F)C3)nc2c(F)c(-c3cccc4oc(N)c(C#N)c34)c3c(c12)COC3] | 628 |

TABLE 15-continued

| Example | Chemical Name | Structure | MS (ES) m/z (M + 1) |
|---|---|---|---|
| 95[3] | 2-Amino-5-fluoro-4-[5-fluoro-3-[[(2R,8S)-2-fluoro-1,2,3,5,6,7-hexahydropyrrolizin-8-yl]methoxy]-1-(3-methyl-3,6-diazabicyclo[3.1.1]heptan-6-yl)-7,9-dihydrofuro[3,4-f]quinazolin-6-yl]benzothiophene-3-carbonitrile | 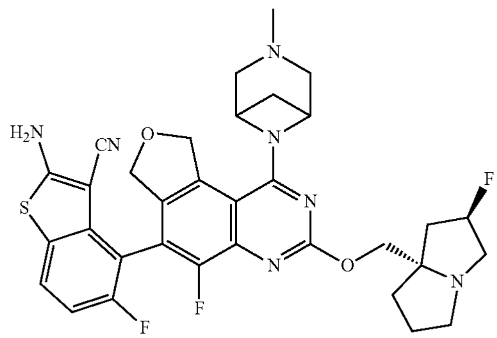 [SMILES: CN1CC2CC(C1)N2c1nc(OC[C@@]23CCCN2C[C@H](F)C3)nc2c(F)c(-c3c(F)ccc4sc(N)c(C#N)c34)c3c(c12)COC3] | 648 |
| 96[3] | 2-Amino-5-fluoro-4-[5-fluoro-3-[[(2R,8S)-2-fluoro-1,2,3,5,6,7-hexahydropyrrolizin-8-yl]methoxy]-1-[3-(3-hydroxybutyl)-3,6-diazabicyclo[3.1.1]heptan-6-yl]-7,9-dihydrofuro[3,4-f]quinazolin-6-yl]benzothiophene-3-carbonitrile | 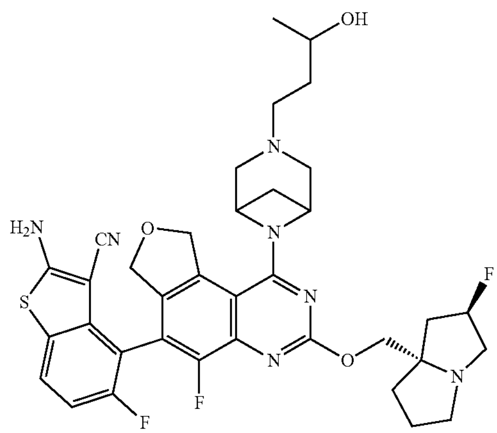 [SMILES: CC(O)CCN1CC2CC(C1)N2c1nc(OC[C@@]23CCCN2C[C@H](F)C3)nc2c(F)c(-c3c(F)ccc4sc(N)c(C#N)c34)c3c(c12)COC3] | 706 |
| 97[3] | 2-Amino-5-fluoro-4-[5-fluoro-3-[[(2R,8S)-2-fluoro-1,2,3,5,6,7-hexahydropyrrolizin-8-yl]methoxy]-1-[3-(3-hydroxy-2-methyl-propyl)-3,6-diazabicyclo[3.1.1]heptan-6-yl]-7,9-dihydrofuro[3,4-f]quinazolin-6-yl]benzothiophene-3-carbonitrile | 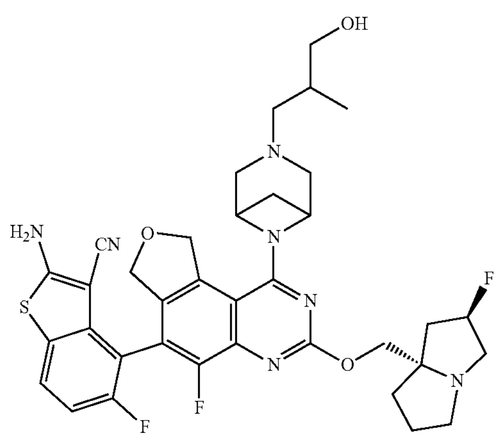 [SMILES: CC(CO)CN1CC2CC(C1)N2c1nc(OC[C@@]23CCCN2C[C@H](F)C3)nc2c(F)c(-c3c(F)ccc4sc(N)c(C#N)c34)c3c(c12)COC3] | 706 |

TABLE 15-continued

| Example | Chemical Name | Structure | MS (ES) m/z (M + 1) |
|---|---|---|---|
| 98[3] | 2-Amino-5-fluoro-4-[5-fluoro-3-[[(2R,8S)-2-fluoro-1,2,3,5,6,7-hexahydropyrrolizin-8-yl]methoxy]-1-[3-(3-hydroxypropyl)-3,6-diazabicyclo[3.1.1]heptan-6-yl]-7,9-dihydrofuro[3,4-f]quinazolin-6-yl]benzothiophene-3-carbonitrile | 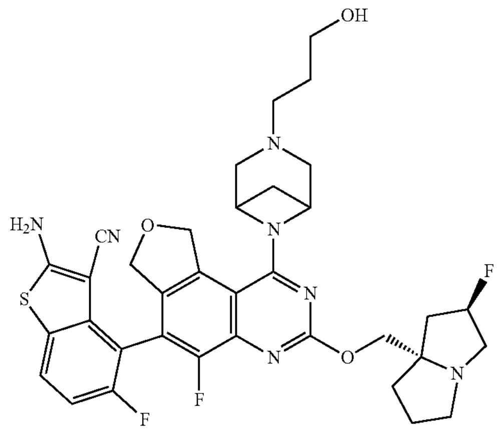 [SMILES: N#Cc1c(N)sc2ccc(F)c(-c3c4c(c5c(N6C7CC6CN(CCCO)C7)nc(OC[C@@]67CCCN6C[C@H](F)C7)nc5c3F)COC4)c12] | 692 |
| 99 | 2-Amino-4-[5-fluoro-3-[[(2R,8S)-2-fluoro-1,2,3,5,6,7-hexahydropyrrolizin-8-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile, Isomer 1 | 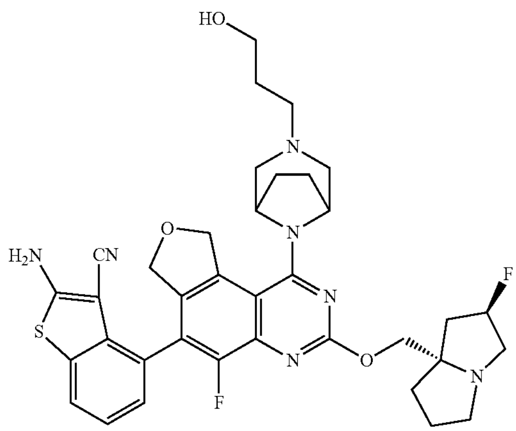 [SMILES: N#Cc1c(N)sc2cccc(-c3c4c(c5c(N6C7CCC6CN(CCCO)C7)nc(OC[C@@]67CCCN6C[C@H](F)C7)nc5c3F)COC4)c12] | 688 |
| 100 | 2-Amino-7-fluoro-4-[5-fluoro-3-[[(2R,8S)-2-fluoro-1,2,3,5,6,7-hexahydropyrrolizin-8-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile | 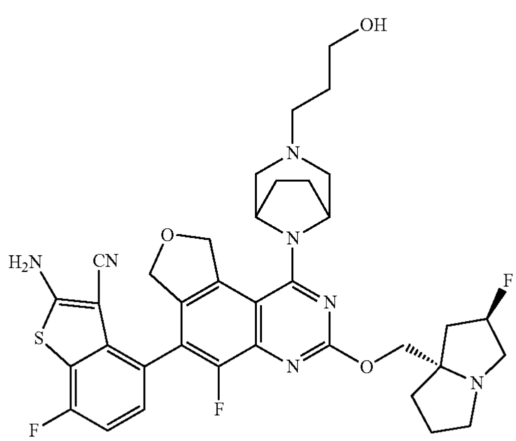 [SMILES: N#Cc1c(N)sc2c(F)ccc(-c3c4c(c5c(N6C7CCC6CN(CCCO)C7)nc(OC[C@@]67CCCN6C[C@H](F)C7)nc5c3F)COC4)c12] | 706 |

TABLE 15-continued

| Example | Chemical Name | Structure | MS (ES) m/z (M + 1) |
|---|---|---|---|
| 101 | 2-Amino-7-fluoro-4-[5-fluoro-3-[[(2R,8S)-2-fluoro-1,2,3,5,6,7-hexahydropyrrolizin-8-yl]methoxy]-1-[3-[[(2R)-oxetan-2-yl]methyl]-3,8-diazabicyclo[3.2.1]octan-8-yl]-7,9-dihydrofuro[3,4-f]quinazolin-6-yl]benzothiophene-3-carbonitrile | 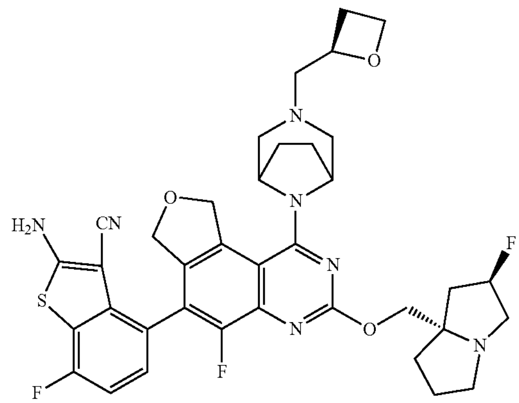 [SMILES: N#Cc1c(N)sc2c(F)ccc(-c3c4c(c5c(N6C7CCC6CN(C[C@H]6CCO6)C7)nc(OC[C@@]67CCCN6C[C@H](F)C7)nc5c3F)COC4)c12] | 718 |
| 102 | 2-Amino-7-fluoro-4-[5-fluoro-3-[[(2R,8S)-2-fluoro-1,2,3,5,6,7-hexahydropyrrolizin-8-yl]methoxy]-1-[3-[[(2R)-oxetan-2-yl]methyl]-3,8-diazabicyclo[3.2.1]octan-8-yl]-7,9-dihydrofuro[3,4-f]quinazolin-6-yl]benzothiophene-3-carbonitrile, Isomer 1 | 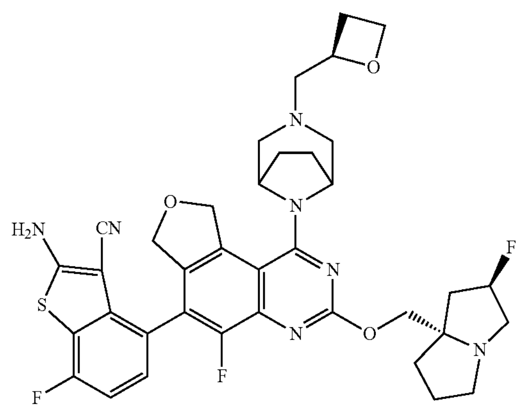 [SMILES: N#Cc1c(N)sc2c(F)ccc(-c3c4c(c5c(N6C7CCC6CN(C[C@H]6CCO6)C7)nc(OC[C@@]67CCCN6C[C@H](F)C7)nc5c3F)COC4)c12] | 718 |
| 103 | 2-Amino-7-fluoro-4-[5-fluoro-3-[[(2R,8S)-2-fluoro-1,2,3,5,6,7-hexahydropyrrolizin-8-yl]methoxy]-1-[3-[[(2R)-oxetan-2-yl]methyl]-3,8-diazabicyclo[3.2.1]octan-8-yl]-7,9-dihydrofuro[3,4-f]quinazolin-6-yl]benzothiophene-3-carbonitrile, Isomer 2 | 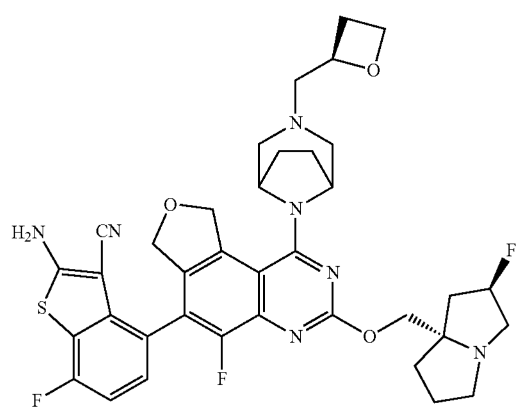 [SMILES: N#Cc1c(N)sc2c(F)ccc(-c3c4c(c5c(N6C7CCC6CN(C[C@H]6CCO6)C7)nc(OC[C@@]67CCCN6C[C@H](F)C7)nc5c3F)COC4)c12] | 718 |

TABLE 15-continued

| Example | Chemical Name | Structure | MS (ES) m/z (M + 1) |
|---------|---------------|-----------|---------------------|
| 104 | 2-Amino-7-fluoro-4-[5-fluoro-3-[[(2R,8S)-2-fluoro-1,2,3,5,6,7-hexahydropyrrolizin-8-yl]methoxy]-1-[3-(oxetan-3-ylmethyl)-3,8-diazabicyclo[3.2.1]octan-8-yl]-7,9-dihydrofuro[3,4-f]quinazolin-6-yl]benzothiophene-3-carbonitrile | 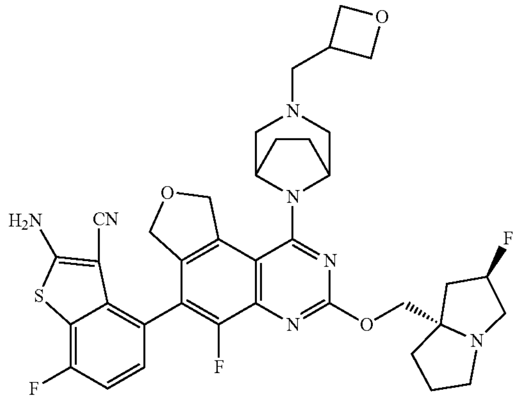 [SMILES: N#Cc1c(N)sc2c(F)ccc(-c3c4c(c5c(N6C7CCC6CN(CC6COC6)C7)nc(OC[C@@]67CCCN6C[C@H](F)C7)nc5c3F)COC4)c12] | 718 |
| 105 | 2-Amino-7-fluoro-4-[5-fluoro-3-[[(2R,8S)-2-fluoro-1,2,3,5,6,7-hexahydropyrrolizin-8-yl]methoxy]-1-[3-(oxetan-3-ylmethyl)-3,8-diazabicyclo[3.2.1]octan-8-yl]-7,9-dihydrofuro[3,4-f]quinazolin-6-yl]benzothiophene-3-carbonitrile, Isomer 1 | 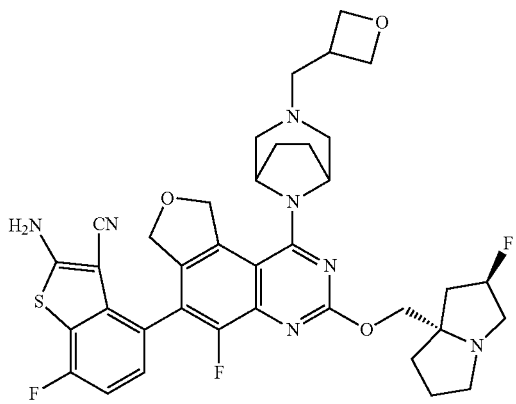 [SMILES: N#Cc1c(N)sc2c(F)ccc(-c3c4c(c5c(N6C7CCC6CN(CC6COC6)C7)nc(OC[C@@]67CCCN6C[C@H](F)C7)nc5c3F)COC4)c12] | 718 |
| 106 | 2-Amino-7-fluoro-4-[5-fluoro-3-[[(2R,8S)-2-fluoro-1,2,3,5,6,7-hexahydropyrrolizin-8-yl]methoxy]-1-[3-(oxetan-3-ylmethyl)-3,8-diazabicyclo[3.2.1]octan-8-yl]-7,9-dihydrofuro[3,4-f]quinazolin-6-yl]benzothiophene-3-carbonitrile, Isomer 2 | 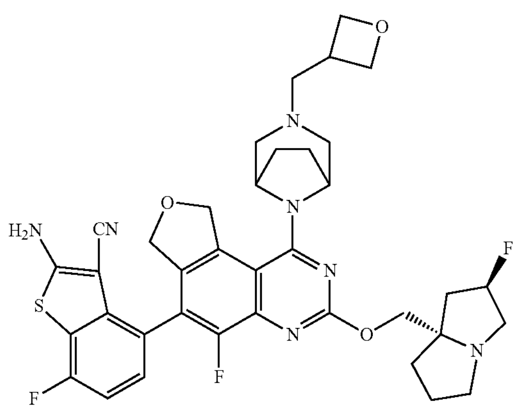 | 718 |

TABLE 15-continued

| Example | Chemical Name | Structure | MS (ES) m/z (M + 1) |
|---------|---------------|-----------|---------------------|
| 107 | 2-Amino-5-fluoro-4-[5-fluoro-3-[[(2R,8S)-2-fluoro-1,2,3,5,6,7-hexahydropyrrolizin-8-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile, Isomer 2 | 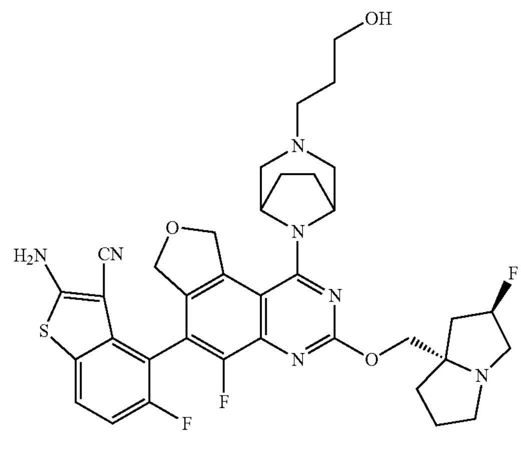 [SMILES: N#Cc1c(N)sc2ccc(F)c(-c3c4c(c5c(N6C7CCC6CN(CCCO)C7)nc(OC[C@@]67CCCN6C[C@H](F)C7)nc5c3F)COC4)c12] | 718 |
| 108[4] | 2-Amino-5-fluoro-4-[5-fluoro-3-[[(2R,8S)-2-fluoro-1,2,3,5,6,7-hexahydropyrrolizin-8-yl]methoxy]-1-(3-methyl-3,8-diazabicyclo[3.2.1]octan-8-yl)-7,9-dihydrofuro[3,4-f]quinazolin-6-yl]benzothiophene-3-carbonitrile | 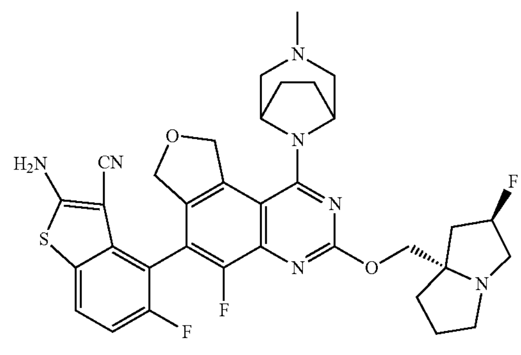 [SMILES: CN1CC2CCC(C1)N2c1nc(OC[C@@]23CCCN2C[C@H](F)C3)nc2c(F)c(-c3c(F)ccc4sc(N)c(C#N)c34)c3c(c12)COC3] | 662 |
| 109[4] | 2-Amino-5-fluoro-4-[5-fluoro-3-[[(2R,8S)-2-fluoro-1,2,3,5,6,7-hexahydropyrrolizin-8-yl]methoxy]-1-[3-(2-methoxyethyl)-3,8-diazabicyclo[3.2.1]octan-8-yl]-7,9-dihydrofuro[3,4-f]quinazolin-6-yl]benzothiophene-3-carbonitrile | 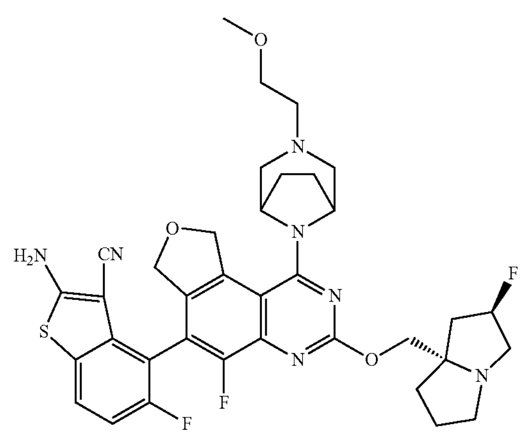 [SMILES: COCCN1CC2CCC(C1)N2c1nc(OC[C@@]23CCCN2C[C@H](F)C3)nc2c(F)c(-c3c(F)ccc4sc(N)c(C#N)c34)c3c(c12)COC3] | 706 |

TABLE 15-continued

| Example | Chemical Name | Structure | MS (ES) m/z (M + 1) |
|---|---|---|---|
| 110 | 2-Amino-5-fluoro-4-[5-fluoro-3-[[(2R,8S)-2-fluoro-1,2,3,5,6,7-hexahydropyrrolizin-8-yl]methoxy]-1-[3-[[1-(2-hydroxyethyl)pyrazol-4-yl]methyl]-3,8-diazabicyclo[3.2.1]octan-8-yl]-7,9-dihydrofuro[3,4-f]quinazolin-6-yl]benzothiophene-3-carbonitrile | 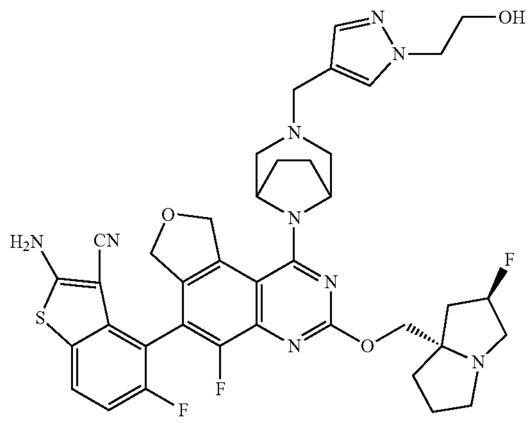 [SMILES: N#Cc1c(N)sc2ccc(F)c(-c3c4c(c5c(N6C7CCC6CN(Cc6cnn(CCO)c6)C7)nc(OC[C@@]67CCCN6C[C@H](F)C7)nc5c3F)COC4)c12] | 772 |
| 111 | 2-Amino-5-fluoro-4-[5-fluoro-3-[[(2R,8S)-2-fluoro-1,2,3,5,6,7-hexahydropyrrolizin-8-yl]methoxy]-1-[3-[[1-(2-hydroxyethyl)imidazol-4-yl]methyl]-3,8-diazabicyclo[3.2.1]octan-8-yl]-7,9-dihydrofuro[3,4-f]quinazolin-6-yl]benzothiophene-3-carbonitrile | 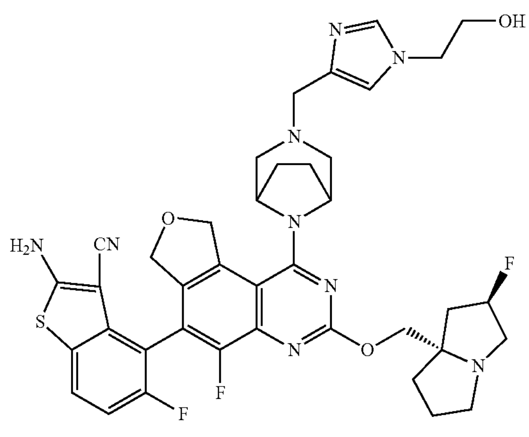 [SMILES: N#Cc1c(N)sc2ccc(F)c(-c3c4c(c5c(N6C7CCC6CN(Cc6cn(CCO)cn6)C7)nc(OC[C@@]67CCCN6C[C@H](F)C7)nc5c3F)COC4)c12] | 772 |
| 112 | 2-Amino-5-fluoro-4-[5-fluoro-3-[[(2R,8S)-2-fluoro-1,2,3,5,6,7-hexahydropyrrolizin-8-yl]methoxy]-1-[3-[(2R,3R)-2,3,4-trihydroxybutyl]-3,8-diazabicyclo[3.2.1]octan-8-yl]-7,9-dihydrofuro[3,4-f]quinazolin-6-yl]benzothiophene-3-carbonitrile | 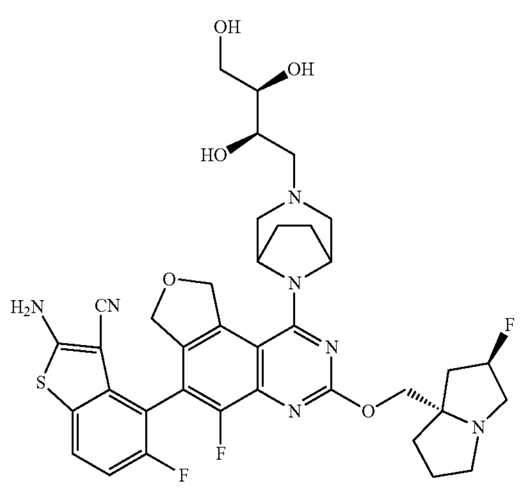 [SMILES: N#Cc1c(N)sc2ccc(F)c(-c3c4c(c5c(N6C7CCC6CN(C[C@@H](O)[C@H](O)CO)C7)nc(OC[C@@]67CCCN6C[C@H](F)C7)nc5c3F)COC4)c12] | 752 |

TABLE 15-continued

| Example | Chemical Name | Structure | MS (ES) m/z (M + 1) |
|---|---|---|---|
| 113[4] | 2-Amino-5-fluoro-4-[5-fluoro-3-[[(2R,8S)-2-fluoro-1,2,3,5,6,7-hexahydropyrrolizin-8-yl]methoxy]-1-[3-(3-methoxypropyl)-3,8-diazabicyclo[3.2.1]octan-8-yl]-7,9-dihydrofuro[3,4-f]quinazolin-6-yl]benzothiophene-3-carbonitrile | 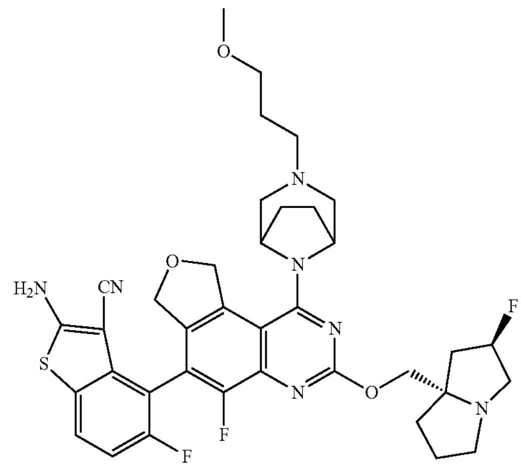 [SMILES: COCCCN1CC2CCC(C1)N2c1nc(OC[C@@]23CCCN2C[C@H](F)C3)nc2c(F)c(-c3c(F)ccc4sc(N)c(C#N)c34)c3c(c12)COC3] | 720 |
| 114[5] | 2-Amino-5-fluoro-4-[5-fluoro-3-[[(2R,8S)-2-fluoro-1,2,3,5,6,7-hexahydropyrrolizin-8-yl]methoxy]-1-[3-(3-hydroxypropyl)-3,8-diazabicyclo[3.2.1]octan-8-yl]-7,9-dihydrofuro[3,4-f]quinazolin-6-yl]benzofuran-3-carbonitrile | 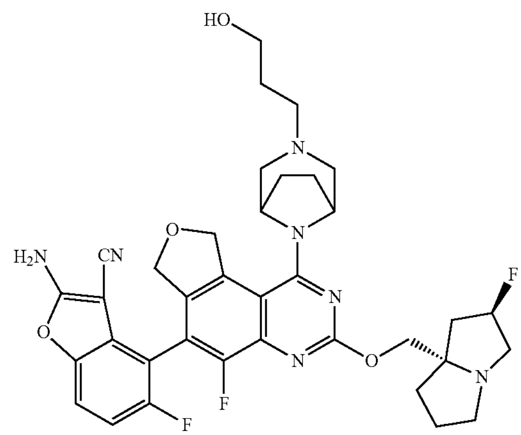 [SMILES: N#Cc1c(N)oc2ccc(F)c(-c3c4c(c5c(N6C7CCC6CN(CCCO)C7)nc(OC[C@@]67CCCN6C[C@H](F)C7)nc5c3F)COC4)c12] | 690 |
| 115 | 2-Amino-5-fluoro-4-[5-fluoro-3-[[(2R,8S)-2-fluoro-1,2,3,5,6,7-hexahydropyrrolizin-8-yl]methoxy]-1-(3-methyl-3,6-diazabicyclo[3.1.1]heptan-6-yl)-7,9-dihydrofuro[3,4-f]quinazolin-6-yl]benzofuran-3-carbonitrile | 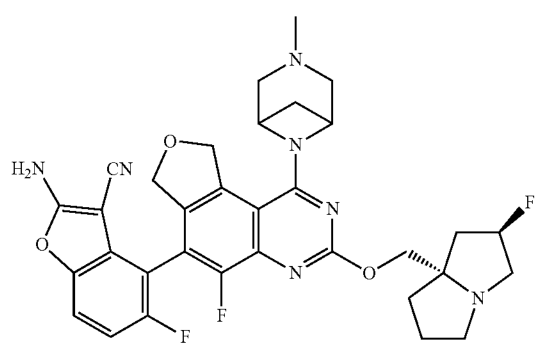 [SMILES: CN1CC2CC(C1)N2c1nc(OC[C@@]23CCCN2C[C@H](F)C3)nc2c(F)c(-c3c(F)ccc4oc(N)c(C#N)c34)c3c(c12)COC3] | 632 |
| 116 | 2-Amino-5-fluoro-4-[5-fluoro-3-[[(2R,8S)-2-fluoro-1,2,3,5,6,7-hexahydropyrrolizin-8-yl]methoxy]-1-(3-methyl-3,6-diazabicyclo[3.1.1]heptan-6-yl)-7,9-dihydrofuro[3,4-f]quinazolin-6-yl]benzofuran-3-carbonitrile, Isomer 1 | 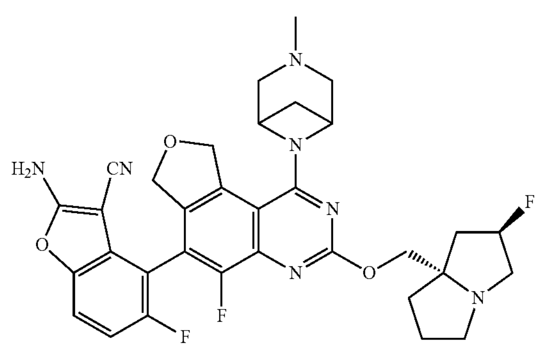 [SMILES: CN1CC2CC(C1)N2c1nc(OC[C@@]23CCCN2C[C@H](F)C3)nc2c(F)c(-c3c(F)ccc4oc(N)c(C#N)c34)c3c(c12)COC3] | 632 |

TABLE 15-continued

| Example | Chemical Name | Structure | MS (ES) m/z (M + 1) |
|---|---|---|---|
| 117 | 2-Amino-4-[5-fluoro-3-[[(2R,8S)-2-fluoro-1,2,3,5,6,7-hexahydropyrrolizin-8-yl]methoxy]-1-[3-(oxetan-3-ylmethyl)-3,8-diazabicyclo[3.2.1]octan-8-yl]-7,9-dihydrofuro[3,4-f]quinazolin-6-yl]thieno[3,2-c]pyridine-3-carbonitrile | 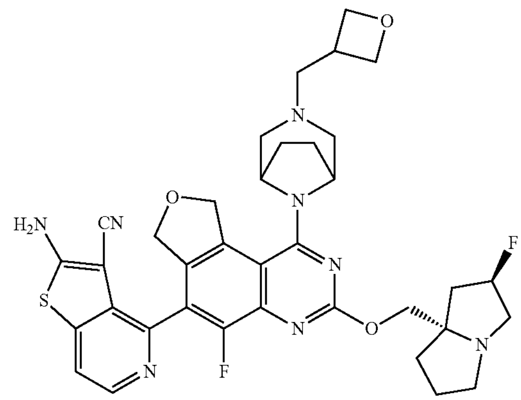 [SMILES: N#Cc1c(N)sc2ccnc(-c3c4c(c5c(N6C7CCC6CN(CC6COC6)C7)nc(OC[C@@]67CCCN6C[C@H](F)C7)nc5c3F)COC4)c12] | 701 |
| 118 | 2-Amino-4-[5-fluoro-3-[[(2R,8S)-2-fluoro-1,2,3,5,6,7-hexahydropyrrolizin-8-yl]methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 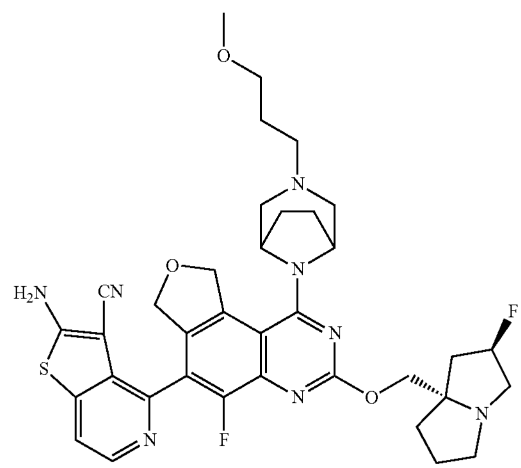 [SMILES: COCCCN1CC2CCC(C1)N2c1nc(OC[C@@]23CCCN2C[C@H](F)C3)nc2c(F)c(-c3nccc4sc(N)c(C#N)c34)c3c(c12)COC3] | 703 |
| 119 | 2-Amino-4-[5-fluoro-3-[[(2R,8S)-2-fluoro-1,2,3,5,6,7-hexahydropyrrolizin-8-yl]methoxy]-1-[3-(2-methoxyethyl)-3,8-diazabicyclo[3.2.1]octan-8-yl]-7,9-dihydrofuro[3,4-f]quinazolin-6-yl]thieno[3,2-c]pyridine-3-carbonitrile | 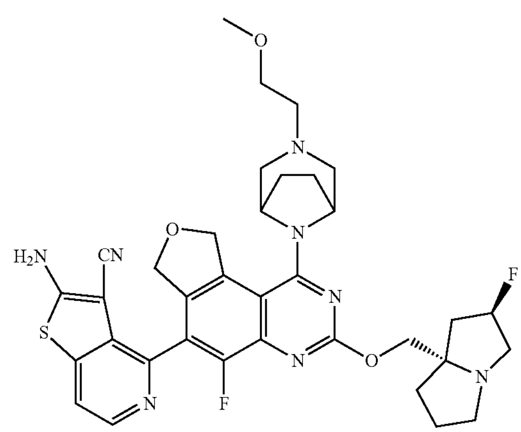 [SMILES: COCCN1CC2CCC(C1)N2c1nc(OC[C@@]23CCCN2C[C@H](F)C3)nc2c(F)c(-c3nccc4sc(N)c(C#N)c34)c3c(c12)COC3] | 689 |

TABLE 15-continued

| Example | Chemical Name | Structure | MS (ES) m/z (M + 1) |
|---|---|---|---|
| 120 | 2-Amino-4-[5-fluoro-3-[[(2R,8S)-2-fluoro-1,2,3,5,6,7-hexahydropyrrolizin-8-yl]methoxy]-1-[3-[(2R)-2-methoxypropyl]-3,8-diazabicyclo[3.2.1]octan-8-yl]-7,9-dihydrofuro[3,4-f]quinazolin-6-yl]thieno[3,2-c]pyridine-3-carbonitrile | 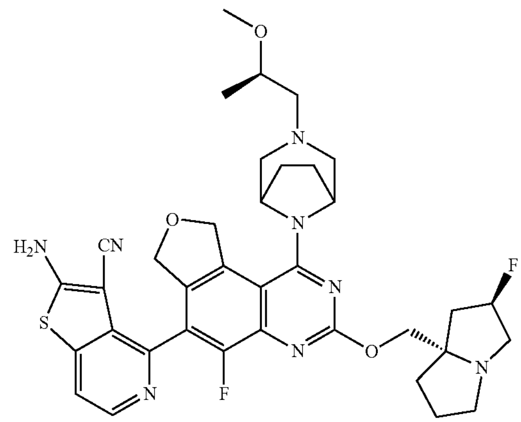 [SMILES: CO[C@H](C)CN1CC2CCC(C1)N2c1nc(OC[C@@]23CCCN2C[C@H](F)C3)nc2c(F)c(-c3nccc4sc(N)c(C#N)c34)c3c(c12)COC3] | 703 |
| 121 | 2-Amino-7-fluoro-4-[5-fluoro-3-[[(2R,8S)-2-fluoro-1,2,3,5,6,7-hexahydropyrrolizin-8-yl]methoxy]-1-(3-methyl-3,8-diazabicyclo[3.2.1]octan-8-yl)-7,9-dihydrofuro[3,4-f]quinazolin-6-yl]thieno[3,2-c]pyridine-3-carbonitrile | 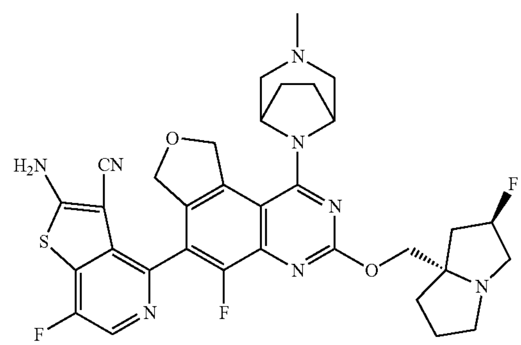 | 663 |
| 122 | 2-Amino-7-fluoro-4-[5-fluoro-3-[[(2R,8S)-2-fluoro-1,2,3,5,6,7-hexahydropyrrolizin-8-yl]methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 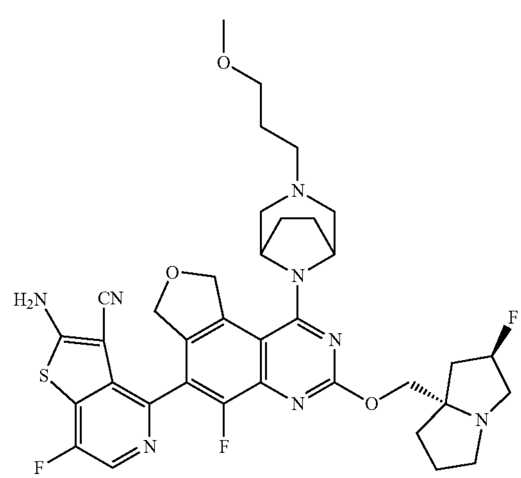 [SMILES: COCCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] | 721 |

TABLE 15-continued

| Example | Chemical Name | Structure | MS (ES) m/z (M + 1) |
|---|---|---|---|
| 123 | 2-Amino-7-fluoro-4-[5-fluoro-3-[[(2R,8S)-2-fluoro-1,2,3,5,6,7-hexahydropyrrolizin-8-yl]methoxy]-1-[3-[[(2R)-oxetan-2-yl]methyl]-3,8-diazabicyclo[3.2.1]octan-8-yl]-7,9-dihydrofuro[3,4-f]quinazolin-6-yl]thieno[3,2-c]pyridine-3-carbonitrile | 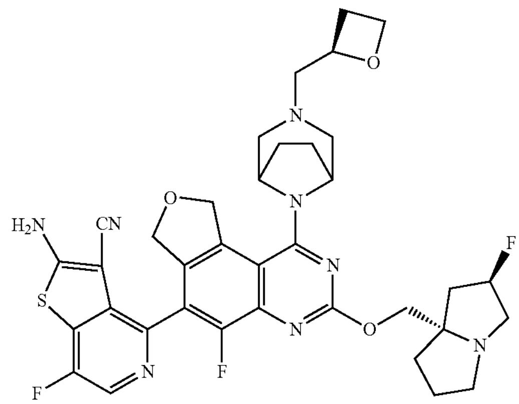 [SMILES: N#Cc1c(N)sc2c(F)cnc(-c3c4c(c5c(N6C7CCC6CN(C[C@H]6CCO6)C7)nc(OC[C@@]67CCCN6C[C@H](F)C7)nc5c3F)COC4)c12] | 719 |
| 124 | 2-Amino-7-fluoro-4-[5-fluoro-3-[[(2R,8S)-2-fluoro-1,2,3,5,6,7-hexahydropyrrolizin-8-yl]methoxy]-1-[3-(2-methoxyethyl)-3,8-diazabicyclo[3.2.1]octan-8-yl]-7,9-dihydrofuro[3,4-f]quinazolin-6-yl]thieno[3,2-c]pyridine-3-carbonitrile | 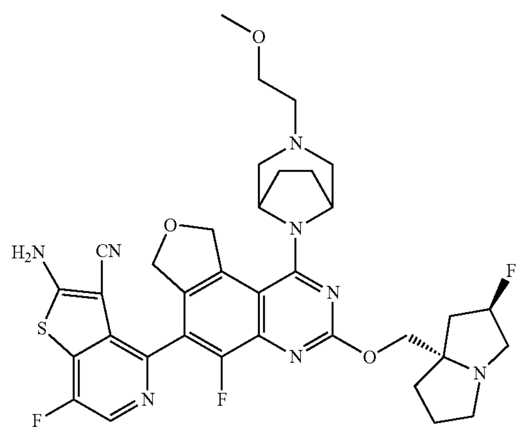 [SMILES: COCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] | 707 |
| 125 | 2-Amino-7-fluoro-4-[5-fluoro-3-[[(2R,8S)-2-fluoro-1,2,3,5,6,7-hexahydropyrrolizin-8-yl]methoxy]-1-[3-(2-hydroxyethyl)-3,8-diazabicyclo[3.2.1]octan-8-yl]-7,9-dihydrofuro[3,4-f]quinazolin-6-yl]thieno[3,2-c]pyridine-3-carbonitrile | 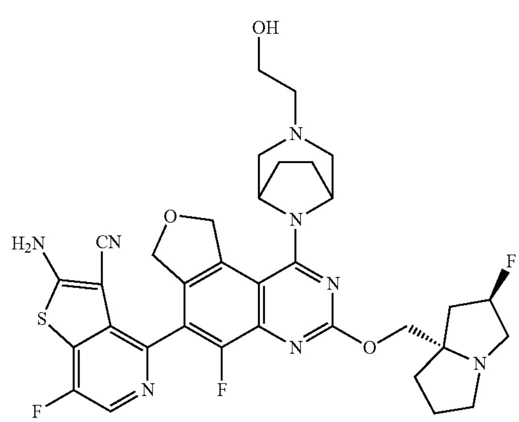 [SMILES: N#Cc1c(N)sc2c(F)cnc(-c3c4c(c5c(N6C7CCC6CN(CCO)C7)nc(OC[C@@]67CCCN6C[C@H](F)C7)nc5c3F)COC4)c12] | 693 |

TABLE 15-continued

| Example | Chemical Name | Structure | MS (ES) m/z (M + 1) |
|---|---|---|---|
| 126 | 2-Amino-7-fluoro-4-[5-fluoro-3-[[(2R,8S)-2-fluoro-1,2,3,5,6,7-hexahydropyrrolizin-8-yl]methoxy]-1-[3-[(2R)-2-methoxypropyl]-3,8-diazabicyclo[3.2.1]octan-8-yl]-7,9-dihydrofuro[3,4-f]quinazolin-6-yl]thieno[3,2-c]pyridine-3-carbonitrile | 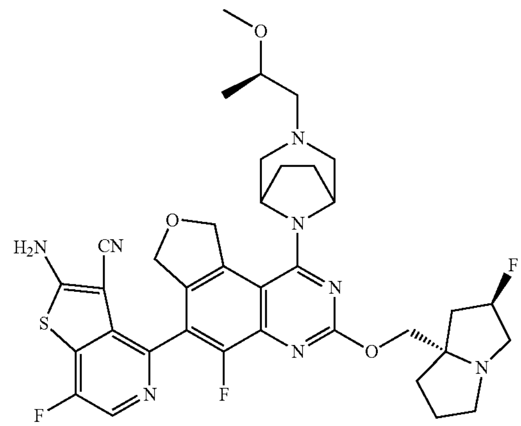 [SMILES: CO[C@H](C)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] | 721 |
| 127 | 2-Amino-4-[1-(3-ethyl-3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-thieno[3,2-c]pyridine-3-carbonitrile | 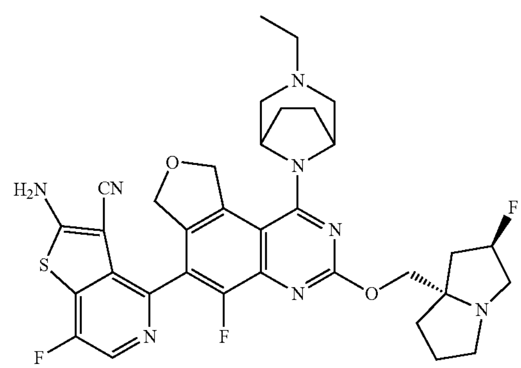 [SMILES: CCN1CC2CCC(C1)N2c1nc(OC[C@@]23CCCN2C[C@H](F)C3)nc2c(F)c(-c3ncc(F)c4sc(N)c(C#N)c34)c3c(c12)COC3] | 677 |
| 128 | 2-Amino-7-fluoro-4-[5-fluoro-3-[[(2R,8S)-2-fluoro-1,2,3,5,6,7-hexahydropyrrolizin-8-yl]methoxy]-1-[3-[(2S)-2-methoxypropyl]-3,8-diazabicyclo[3.2.1]octan-8-yl]-7,9-dihydrofuro[3,4-f]quinazolin-6-yl]thieno[3,2-c]pyridine-3-carbonitrile | 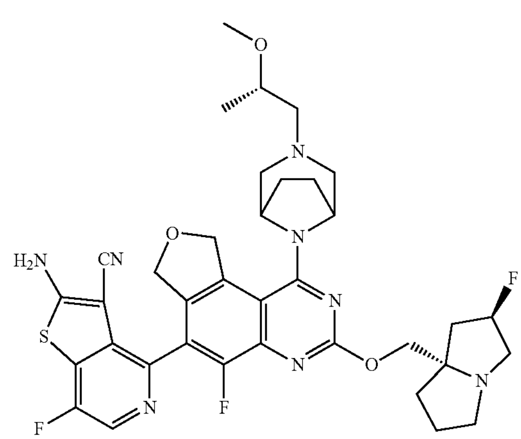 [SMILES: CO[C@@H](C)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] | 721 |

TABLE 15-continued

| Example | Chemical Name | Structure | MS (ES) m/z (M + 1) |
|---|---|---|---|
| 129 | 2-Amino-7-fluoro-4-[5-fluoro-3-[[(2R,8S)-2-fluoro-1,2,3,5,6,7-hexahydropyrrolizin-8-yl]methoxy]-1-[3-[[(2S)-oxetan-2-yl]methyl]-3,8-diazabicyclo[3.2.1]octan-8-yl]-7,9-dihydrofuro[3,4-f]quinazolin-6-yl]thieno[3,2-c]pyridine-3-carbonitrile | 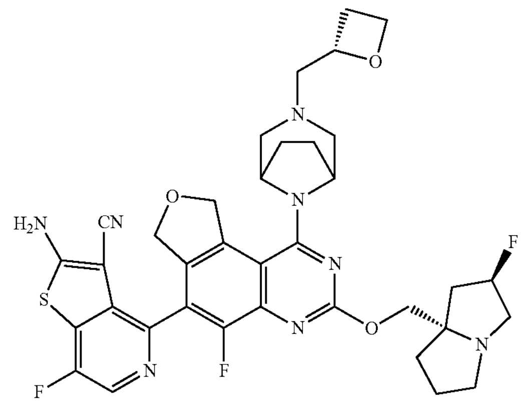 [SMILES: N#Cc1c(N)sc2c(F)cnc(-c3c4c(c5c(N6C7CCC6CN(C[C@@H]6CCO6)C7)nc(OC[C@@]67CCCN6C[C@H](F)C7)nc5c3F)COC4)c12] | 719 |
| 130 | 2-Amino-7-fluoro-4-[5-fluoro-3-[[(2R,8S)-2-fluoro-1,2,3,5,6,7-hexahydropyrrolizin-8-yl]methoxy]-1-[3-(oxetan-3-ylmethyl)-3,8-diazabicyclo[3.2.1]octan-8-yl]-7,9-dihydrofuro[3,4-f]quinazolin-6-yl]thieno[3,2-c]pyridine-3-carbonitrile | 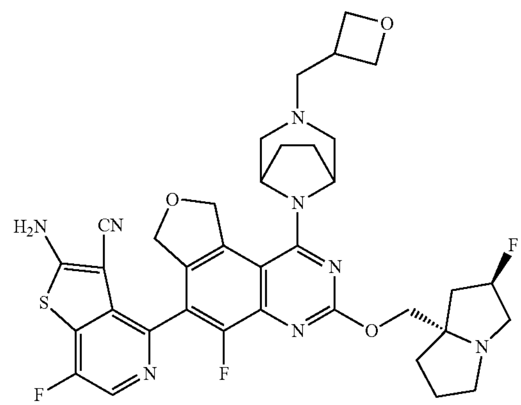 | 719 |
| 131 | 2-Amino-7-fluoro-4-[5-fluoro-1-[3-(2-methoxyethyl)-3,8-diazabicyclo[3.2.1]octan-8-yl]-3-[(2-methoxy-1,2,3,5,6,7-hexahydropyrrolizin-8-yl)methoxy]-7,9-dihydrofuro[3,4-f]quinazolin-6-yl]thieno[3,2-c]pyridine-3-carbonitrile | 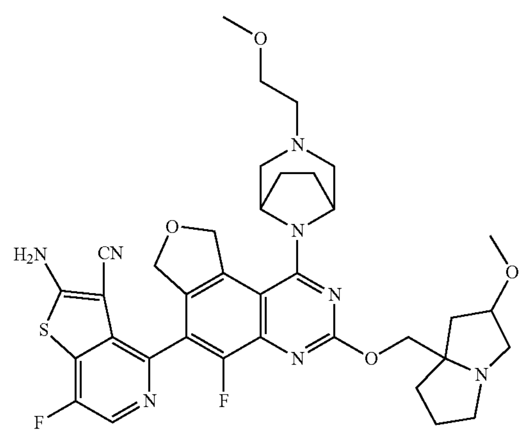 [SMILES: COCCN1CC2CCC(C1)N2c1nc(OCC23CCCN2CC(OC)C3)nc2c(F)c(-c3ncc(F)c4sc(N)c(C#N)c34)c3c(c12)COC3] | 719 |
| 132 | 2-Amino-4-[5-fluoro-3-[[(2R,8S)-2-fluoro-1,2,3,5,6,7-hexahydropyrrolizin-8-yl]methoxy]-1-(3-methyl-3,8-diazabicyclo[3.2.1]octan-8-yl)-7,9-dihydrofuro[3,4-f]quinazolin-6-yl]-7-methyl-thieno[3,2-c]pyridine-3-carbonitrile | 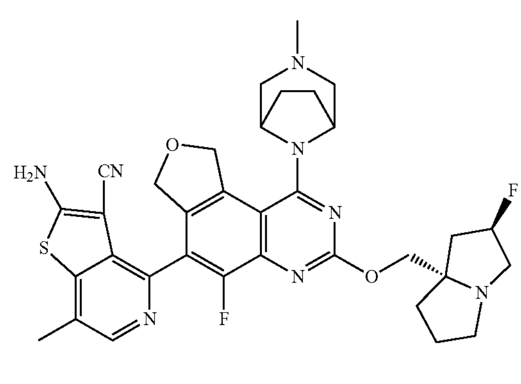 [SMILES: Cc1cnc(-c2c3c(c4c(N5C6CCC5CN(C)C6)nc(OC[C@@]56CCCN5C[C@H](F)C6)nc4c2F)COC3)c2c(C#N)c(N)sc12] | 659 |

TABLE 15-continued

| Example | Chemical Name | Structure | MS (ES) m/z (M + 1) |
|---|---|---|---|
| 133 | 2-Amino-4-[5-fluoro-3-[[(2R,8S)-2-fluoro-1,2,3,5,6,7-hexahydropyrrolizin-8-yl]methoxy]-1-[3-(2-methoxyethyl)-3,8-diazabicyclo[3.2.1]octan-8-yl]-7,9-dihydrofuro[3,4-f]quinazolin-6-yl]-7-methyl-thieno[3,2-c]pyridine-3-carbonitrile | 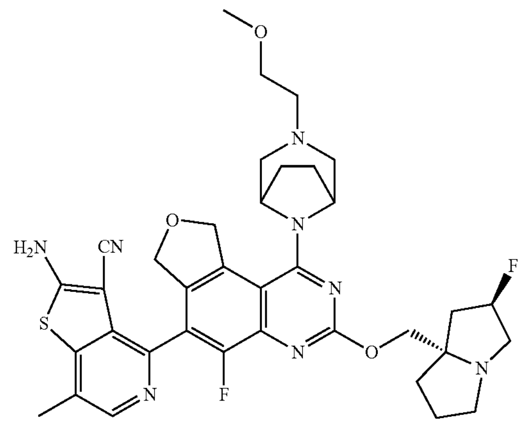 [SMILES: COCCN1CC2CCC(C1)N2c1nc(OC[C@@]23CCCN2C[C@H](F)C3)nc2c(F)c(-c3ncc(C)c4sc(N)c(C#N)c34)c3c(c12)COC3] | 703 |
| 134 | 2-Amino-4-[5-fluoro-3-[[(2R,8S)-2-fluoro-1,2,3,5,6,7-hexahydropyrrolizin-8-yl]methoxy]-1-[3-(oxetan-3-ylmethyl)-3,8-diazabicyclo[3.2.1]octan-8-yl]-7,9-dihydrofuro[3,4-f]quinazolin-6-yl]-7-methyl-thieno[3,2-c]pyridine-3-carbonitrile | 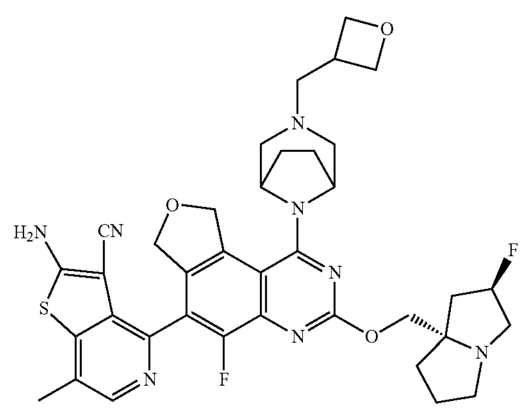 [SMILES: Cc1cnc(-c2c3c(c4c(N5C6CCC5CN(CC5COC5)C6)nc(OC[C@@]56CCCN5C[C@H](F)C6)nc4c2F)COC3)c2c(C#N)c(N)sc12] | 715 |
| 135 | 2-Amino-7-fluoro-4-[5-fluoro-3-[[(2R,8S)-2-fluoro-1,2,3,5,6,7-hexahydropyrrolizin-8-yl]methoxy]-1-[3-(oxetan-3-ylmethyl)-3,8-diazabicyclo[3.2.1]octan-8-yl]-7,9-dihydrofuro[3,4-f]quinazolin-6-yl]benzofuran-3-carbonitrile | 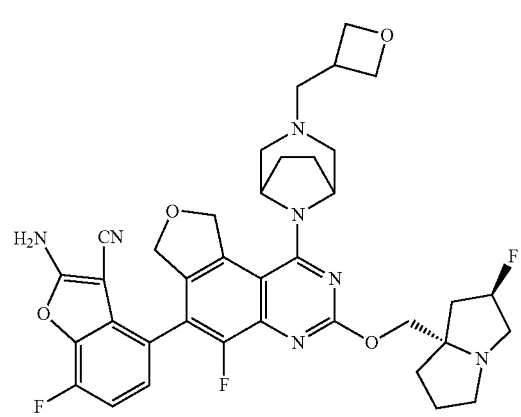 | 702 |

TABLE 15-continued

| Example | Chemical Name | Structure | MS (ES) m/z (M + 1) |
|---|---|---|---|
| 136 | 2-Amino-7-fluoro-4-[5-fluoro-3-[[(2R,8S)-2-fluoro-1,2,3,5,6,7-hexahydropyrrolizin-8-yl]methoxy]-1-(3-methyl-3,8-diazabicyclo[3.2.1]octan-8-yl)-7,9-dihydrofuro[3,4-f]quinazolin-6-yl]benzofuran-3-carbonitrile | 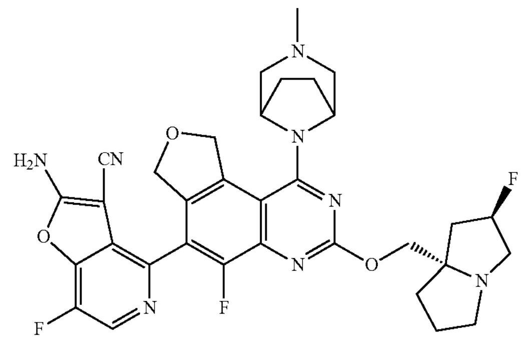 [SMILES: CN1CC2CCC(C1)N2c1nc(OC[C@@]23CCCN2C[C@H](F)C3)nc2c(F)c(-c3ncc(F)c4oc(N)c(C#N)c34)c3c(c12)COC3] | 646 |
| 137 | 2-Amino-4-[3-[[(2R,8S)-2-fluoro-1,2,3,5,6,7-hexahydropyrrolizin-8-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile | 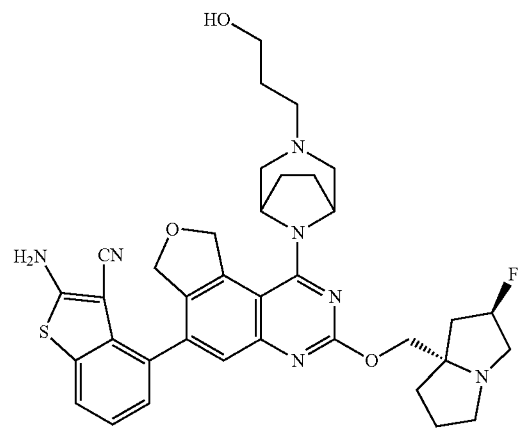 [SMILES: N#Cc1c(N)sc2cccc(-c3cc4nc(OC[C@@]56CCCN5C[C@H](F)C6)nc(N5C6CCC5CN(CCCO)C6)c4c4c3COC4)c12] | 670 |
| 138[4] | 2-Amino-5-fluoro-4-[5-fluoro-1-[3-(3-hydroxypropyl)-3,8-diazabicyclo[3.2.1]octan-8-yl]-3-[[(2S)-1-methylpyrrolidin-2-yl]methoxy]-7,9-dihydrofuro[3,4-f]quinazolin-6-yl]benzothiophene-3-carbonitrile | 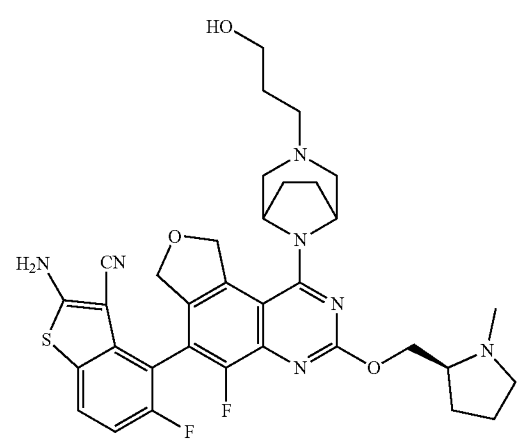 [SMILES: CN1CCC[C@H]1COc1nc(N2C3CCC2CN(CCCO)C3)c2c3c(c(-c4c(F)ccc5sc(N)c(C#N)c45)c(F)c2n1)COC3] | 662 |

TABLE 15-continued

| Example | Chemical Name | Structure | MS (ES) m/z (M + 1) |
|---|---|---|---|
| 139[4] | 2-Amino-4-[3-[3-(dimethylamino)azetidin-1-yl]-5-fluoro-1-[3-(3-hydroxypropyl)-3,8-diazabicyclo[3.2.1]octan-8-yl]-7,9-dihydrofuro[3,4-f]quinazolin-6-yl]-5-fluoro-benzothiophene-3-carbonitrile | 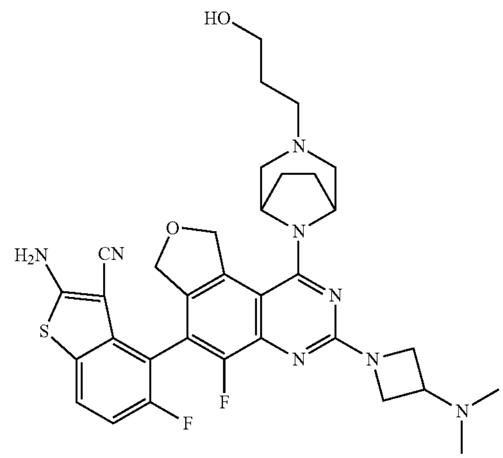 [SMILES: CN(C)C1CN(c2nc(N3C4CCC3CN(CCCO)C4)c3c4c(c(-c5c(F)ccc6sc(N)c(C#N)c56)c(F)c3n2)COC4)C1] | 647 |
| 140[4] | 2-Amino-5-fluoro-4-[5-fluoro-3-[[(2S,4R)-4-fluoro-1-methyl-pyrrolidin-2-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile | 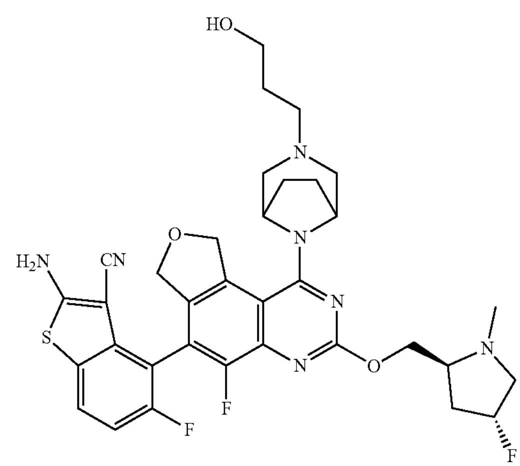 [SMILES: CN1C[C@H](F)C[C@H]1COc1nc(N2C3CCC2CN(CCCO)C3)c2c3c(c(-c4c(F)ccc5sc(N)c(C#N)c45)c(F)c2n1)COC3] | 680 |
| 141[4] | 2-Amino-5-fluoro-4-[5-fluoro-3-[[(2S)-1-(2-fluoroethyl)pyrrolidin-2-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile | 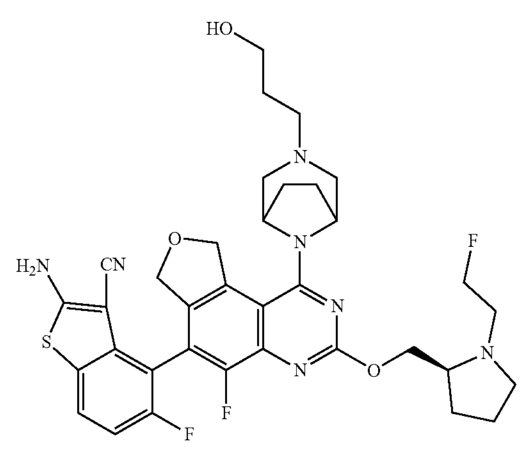 [SMILES: N#Cc1c(N)sc2ccc(F)c(-c3c4c(c5c(N6C7CCC6CN(CCCO)C7)nc(OC[C@@H]6CCCN6CCF)nc5c3F)COC4)c12] | 694 |

TABLE 15-continued

| Example | Chemical Name | Structure | MS (ES) m/z (M + 1) |
|---|---|---|---|
| 142[4] | 2-Amino-4-[3-[[(2R)-1,4-dioxan-2-yl]methoxy]-5-fluoro-1-[3-(3-hydroxypropyl)-3,8-diazabicyclo[3.2.1]octan-8-yl]-7,9-dihydrofuro[3,4-f]quinazolin-6-yl]-5-fluoro-benzothiophene-3-carbonitrile | 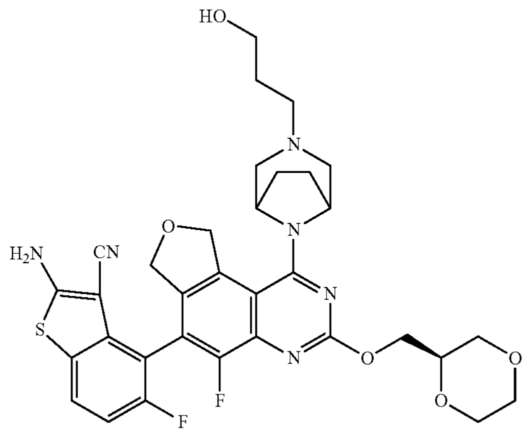 [SMILES: N#Cc1c(N)sc2ccc(F)c(-c3c4c(c5c(N6C7CCC6CN(CCCO)C7)nc(OC[C@H]6COCCO6)nc5c3F)COC4)c12] | 665 |
| 143[4] | 2-Amino-5-fluoro-4-[5-fluoro-1-[3-(3-hydroxypropyl)-3,8-diazabicyclo[3.2.1]octan-8-yl]-3-[[(2R)-tetrahydrofuran-2-yl]methoxy]-7,9-dihydrofuro[3,4-f]quinazolin-6-yl]benzothiophene-3-carbonitrile | 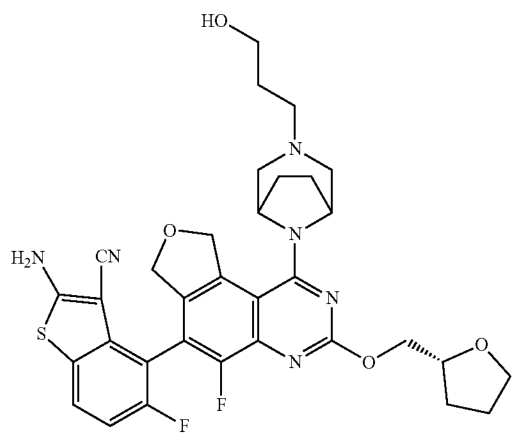 [SMILES: N#Cc1c(N)sc2ccc(F)c(-c3c4c(c5c(N6C7CCC6CN(CCCO)C7)nc(OC[C@H]6CCCO6)nc5c3F)COC4)c12] | 649 |
| 144[4] | 2-Amino-4-[3-[2-(dimethylamino)ethoxy]-5-fluoro-1-[3-(3-hydroxypropyl)-3,8-diazabicyclo[3.2.1]octan-8-yl]-7,9-dihydrofuro[3,4-f]quinazolin-6-yl]-5-fluoro-benzothiophene-3-carbonitrile | 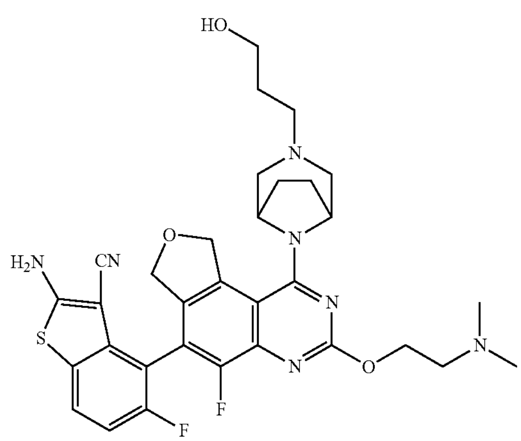 [SMILES: CN(C)CCOc1nc(N2C3CCC2CN(CCCO)C3)c2c3c(c(-c4c(F)ccc5sc(N)c(C#N)c45)c(F)c2n1)COC3] | 636 |

TABLE 15-continued

| Example | Chemical Name | Structure | MS (ES) m/z (M + 1) |
|---|---|---|---|
| 145[4] | 2-Amino-5-fluoro-4-[5-fluoro-3-[2-[(3S)-3-fluoropyrrolidin-1-yl]ethoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile | 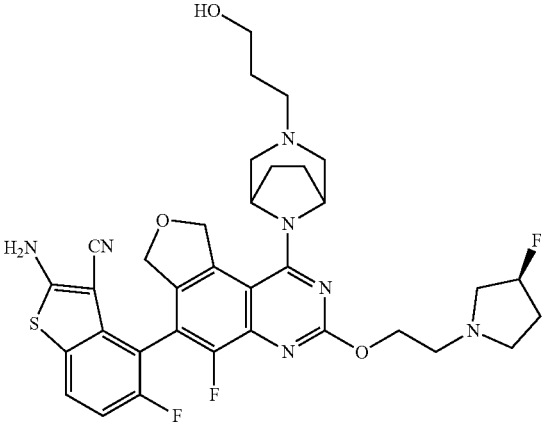 [SMILES: N#Cc1c(N)sc2ccc(F)c(-c3c4c(c5c(N6C7CCC6CN(CCCO)C7)nc(OCCN6CC[C@H](F)C6)nc5c3F)COC4)c12] | 680 |
| 146[4] | 2-Amino-5-fluoro-4-[5-fluoro-1-[3-(3-hydroxypropyl)-3,8-diazabicyclo[3.2.1]octan-8-yl]-3-(2-morpholinoethoxy)-7,9-dihydrofuro[3,4-f]quinazolin-6-yl]benzothiophene-3-carbonitrile | 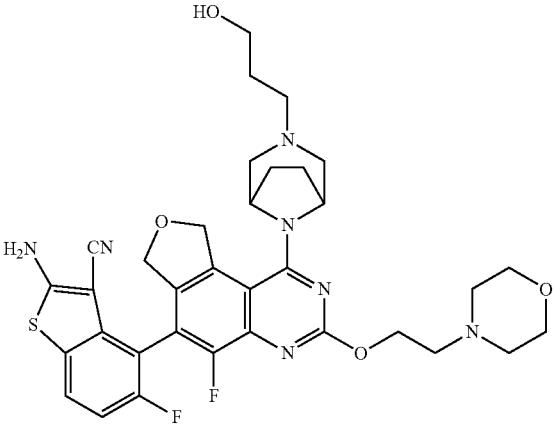 [SMILES: N#Cc1c(N)sc2ccc(F)c(-c3c4c(c5c(N6C7CCC6CN(CCCO)C7)nc(OCCN6CCOCC6)nc5c3F)COC4)c12] | 678 |
| 147[4] | 2-Amino-5-fluoro-4-[5-fluoro-1-[3-(3-hydroxypropyl)-3,8-diazabicyclo[3.2.1]octan-8-yl]-3-[2-[(3S)-3-methoxypyrrolidin-1-yl]ethoxy]-7,9-dihydrofuro[3,4-f]quinazolin-6-yl]benzothiophene-3-carbonitrile | 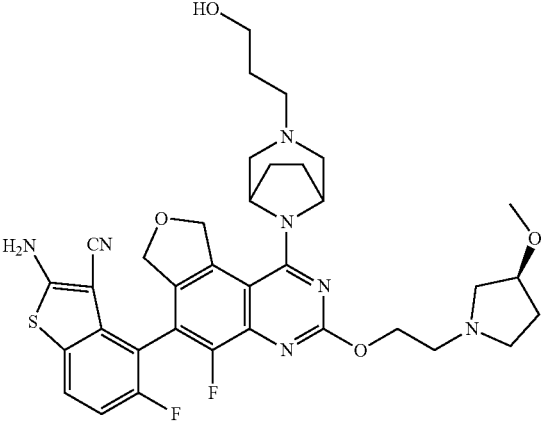 [SMILES: CO[C@H]1CCN(CCOc2nc(N3C4CCC3CN(CCCO)C4)c3c4c(c(-c5c(F)ccc6sc(N)c(C#N)c56)c(F)c3n2)COC4)C1] | 692 |

TABLE 15-continued

| Example | Chemical Name | Structure | MS (ES) m/z (M + 1) |
|---|---|---|---|
| 148[4] | 2-Amino-5-fluoro-4-[5-fluoro-1-[3-(3-hydroxypropyl)-3,8-diazabicyclo[3.2.1]octan-8-yl]-3-[[(2S)-1-methylazetidin-2-yl]methoxy]-7,9-dihydrofuro[3,4-f]quinazolin-6-yl]benzothiophene-3-carbonitrile | 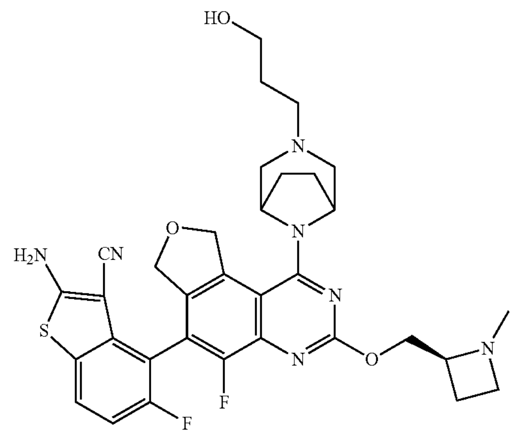 [SMILES: CN1CC[C@H]1COc1nc(N2C3CCC2CN(CCCO)C3)c2c3c(c(-c4c(F)ccc5sc(N)c(C#N)c45)c(F)c2n1)COC3] | 648 |
| 149[4] | 2-Amino-5-fluoro-4-[5-fluoro-3-[[(2S)-1-methylpyrrolidin-2-yl]methoxy]-1-[3-(oxetan-3-ylmethyl)-3,8-diazabicyclo[3.2.1]octan-8-yl]-7,9-dihydrofuro[3,4-f]quinazolin-6-yl]benzothiophene-3-carbonitrile | 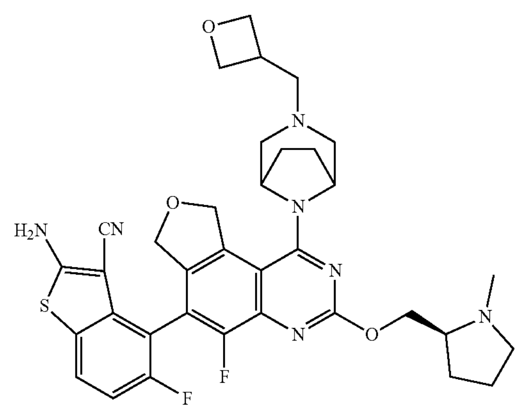 [SMILES: CN1CCC[C@H]1COc1nc(N2C3CCC2CN(CC2COC2)C3)c2c3c(c(-c4c(F)ccc5sc(N)c(C#N)c45)c(F)c2n1)COC3] | 674 |
| 150[4] | 2-Amino-5-fluoro-4-[5-fluoro-1-[3-(2-methoxyethyl)-3,8-diazabicyclo[3.2.1]octan-8-yl]-3-[[(2S)-1-methylpyrrolidin-2-yl]methoxy]-7,9-dihydrofuro[3,4-f]quinazolin-6-yl]benzothiophene-3-carbonitrile | 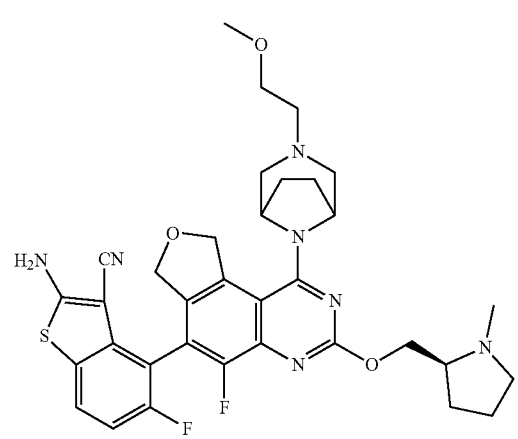 [SMILES: COCCN1CC2CCC(C1)N2c1nc(OC[C@@H]2CCCN2C)nc2c(F)c(-c3c(F)ccc4sc(N)c(C#N)c34)c3c(c12)COC3] | 662 |

TABLE 15-continued

| Example | Chemical Name | Structure | MS (ES) m/z (M + 1) |
|---|---|---|---|
| 151[4] | 2-Amino-5-fluoro-4-[5-fluoro-1-[3-(3-methoxypropyl)-3,8-diazabicyclo[3.2.1]octan-8-yl]-3-[[(2S)-1-methylpyrrolidin-2-yl]methoxy]-7,9-dihydrofuro[3,4-f]quinazolin-6-yl]benzothiophene-3-carbonitrile | 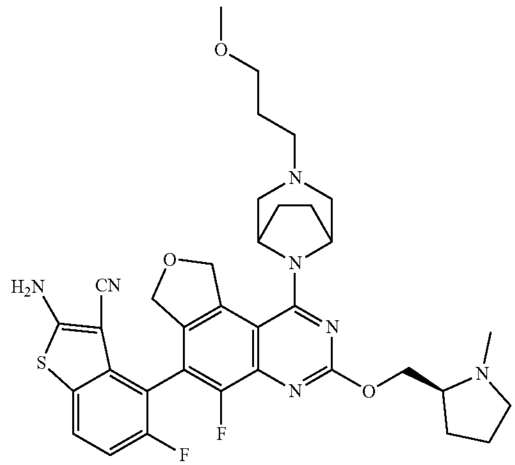 [SMILES: COCCCN1CC2CCC(C1)N2c1nc(OC[C@@H]2CCCN2C)nc2c(F)c(-c3c(F)ccc4sc(N)c(C#N)c34)c3c(c12)COC3] | 676 |
| 152[6] | 2-Amino-5-fluoro-4-[5-fluoro-1-(3-methyl-3,6-diazabicyclo[3.1.1]heptan-6-yl)-3-[[(2S)-1-methylpyrrolidin-2-yl]methoxy]-7,9-dihydrofuro[3,4-f]quinazolin-6-yl]benzothiophene-3-carbonitrile | 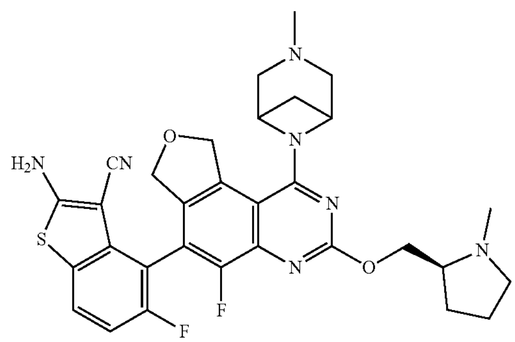 [SMILES: CN1CC2CC(C1)N2c1nc(OC[C@@H]2CCCN2C)nc2c(F)c(-c3c(F)ccc4sc(N)c(C#N)c34)c3c(c12)COC3] | 604 |
| 153[6] | 2-Amino-5-fluoro-4-[5-fluoro-3-[[(2S,4R)-4-fluoro-1-methyl-pyrrolidin-2-yl]methoxy]-1-(3-methyl-3,6-diazabicyclo[3.1.1]heptan-6-yl)-7,9-dihydrofuro[3,4-f]quinazolin-6-yl]benzothiophene-3-carbonitrile | 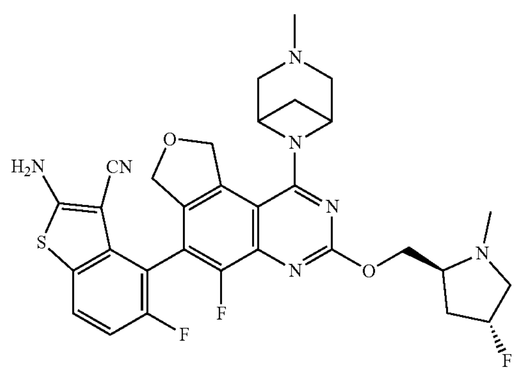 [SMILES: CN1CC2CC(C1)N2c1nc(OC[C@@H]2C[C@@H](F)CN2C)nc2c(F)c(-c3c(F)ccc4sc(N)c(C#N)c34)c3c(c12)COC3] | 622 |
| 154[6] | 2-Amino-5-fluoro-4-[5-fluoro-1-(3-methyl-3,6-diazabicyclo[3.1.1]heptan-6-yl)-3-[[(2R)-tetrahydrofuran-2-yl]methoxy]-7,9-dihydrofuro[3,4-f]quinazolin-6-yl]benzothiophene-3-carbonitrile | 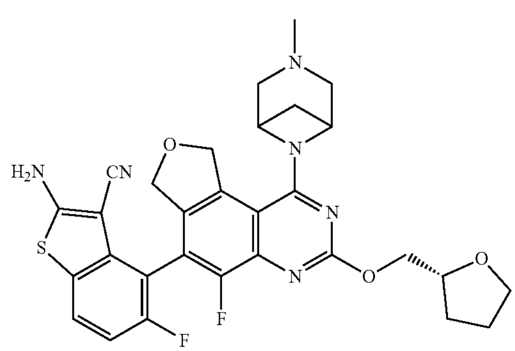 [SMILES: CN1CC2CC(C1)N2c1nc(OC[C@H]2CCCO2)nc2c(F)c(-c3c(F)ccc4sc(N)c(C#N)c34)c3c(c12)COC3] | 591 |

TABLE 15-continued

| Example | Chemical Name | Structure | MS (ES) m/z (M + 1) |
|---|---|---|---|
| 155[6] | 2-Amino-5-fluoro-4-[5-fluoro-3-[[(2S)-1-(2-hydroxyethyl)pyrrolidin-2-yl]methoxy]-1-(3-methyl-3,6-diazabicyclo[3.1.1]heptan-6-yl)-7,9-dihydrofuro[3,4-f]quinazolin-6-yl]benzothiophene-3-carbonitrile | 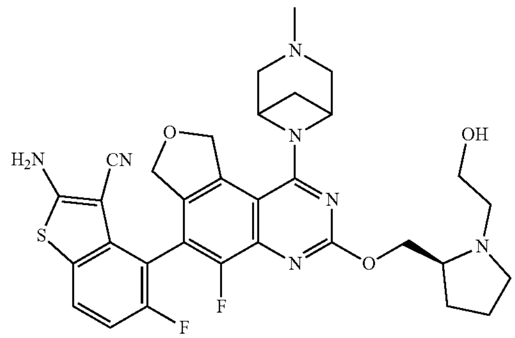 [SMILES: CN1CC2CC(C1)N2c1nc(OC[C@@H]2CCCN2CCO)nc2c(F)c(-c3c(F)ccc4sc(N)c(C#N)c34)c3c(c12)COC3] | 634 |
| 156[7] | 2-Amino-5-fluoro-4-[5-fluoro-1-[3-(4-hydroxybutyl)-3,8-diazabicyclo[3.2.1]octan-8-yl]-7,9-dihydrofuro[3,4-f]quinazolin-6-yl]benzothiophene-3-carbonitrile | 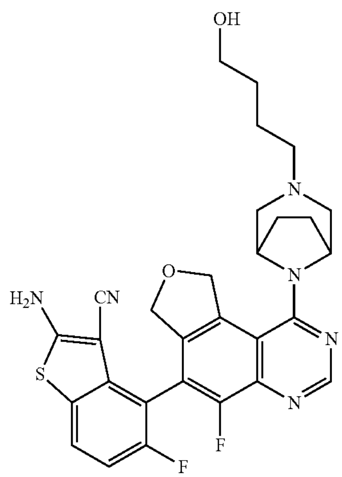 [SMILES: N#Cc1c(N)sc2ccc(F)c(-c3c4c(c5c(N6C7CCC6CN(CCCCO)C7)ncnc5c3F)COC4)c12] | 563 |
| 157[7] | 2-Amino-5-fluoro-4-[5-fluoro-1-[3-[[2-(hydroxymethyl)cyclopropyl]methyl]-3,8-diazabicyclo[3.2.1]octan-8-yl]-7,9-dihydrofuro[3,4-f]quinazolin-6-yl]benzothiophene-3-carbonitrile | 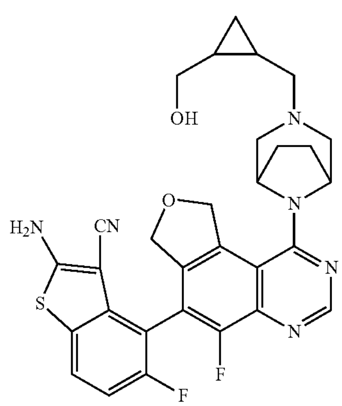 [SMILES: N#Cc1c(N)sc2ccc(F)c(-c3c4c(c5c(N6C7CCC6CN(CC6CC6CO)C7)ncnc5c3F)COC4)c12] | 575 |

TABLE 15-continued

| Example | Chemical Name | Structure | MS (ES) m/z (M + 1) |
|---|---|---|---|
| 212 | 2-Amino-4-[5-fluoro-3-[[(2R,8S)-2-fluoro-1,2,3,5,6,7-hexahydropyrrolizin-8-yl]methoxy]-1-[3-(2-methoxyethyl)-3,8-diazabicyclo[3.2.1]octan-8-yl]-7,9-dihydrofuro[3,4-f]quinazolin-6-yl]benzothiophene-3-carbonitrile | 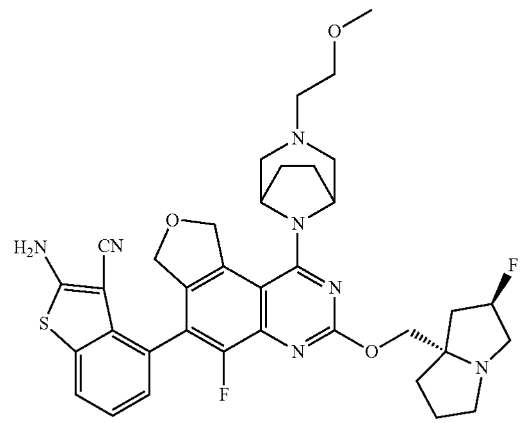 [SMILES: COCCN1CC2CCC(C1)N2c1nc(OC[C@@]23CCCN2C[C@H](F)C3)nc2c(F)c(-c3cccc4sc(N)c(C#N)c34)c3c(c12)COC3] | 688 |
| 213 | 2-Amino-4-[5-fluoro-3-[[(2R,8S)-2-fluoro-1,2,3,5,6,7-hexahydropyrrolizin-8-yl]methoxy]-1-[3-[(2R)-2-methoxypropyl]-3,8-diazabicyclo[3.2.1]octan-8-yl]-7,9-dihydrofuro[3,4-f]quinazolin-6-yl]benzothiophene-3-carbonitrile | 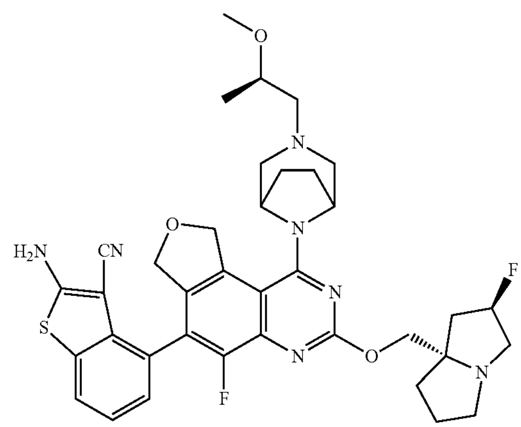 [SMILES: CO[C@H](C)CN1CC2CCC(C1)N2c1nc(OC[C@@]23CCCN2C[C@H](F)C3)nc2c(F)c(-c3cccc4sc(N)c(C#N)c34)c3c(c12)COC3] | 702 |
| 214 | 2-Amino-4-[3-[[(2R)-1,4-dioxan-2-yl]methoxy]-5-fluoro-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile, Isomer 2 | 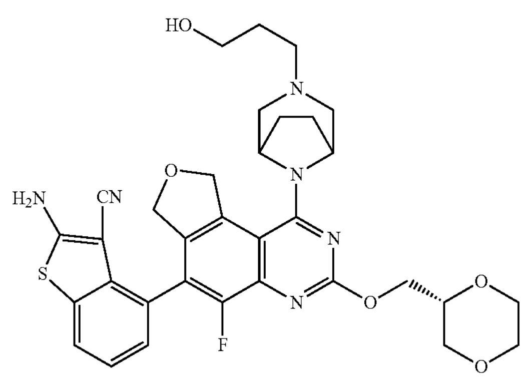 [SMILES: N#Cc1c(N)sc2cccc(-c3c4c(c5c(N6C7CCC6CN(CCCO)C7)nc(OC[C@H]6COCCO6)nc5c3F)COC4)c12] | 647 |

TABLE 15-continued

| Example | Chemical Name | Structure | MS (ES) m/z (M + 1) |
|---------|---------------|-----------|---------------------|
| 215 | 2-Amino-5-fluoro-4-[5-fluoro-3-[[(2R,8S)-2-fluoro-1,2,3,5,6,7-hexahydropyrrolizin-8-yl]methoxy]-1-[3-[(2S,3R)-2,3,4-trihydroxybutyl]-3,8-diazabicyclo[3.2.1]octan-8-yl]-7,9-dihydrofuro[3,4-f]quinazolin-6-yl]benzothiophene-3-carbonitrile | 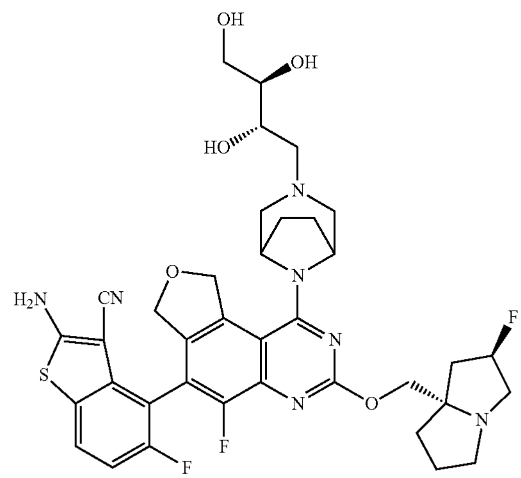 [SMILES: N#Cc1c(N)sc2ccc(F)c(-c3c4c(c5c(N6C7CCC6CN(C[C@H](O)[C@H](O)CO)C7)nc(OC[C@@]67CCCN6C[C@H](F)C7)nc5c3F)COC4)c12] | 752 |
| 216[4] | 2-Amino-5-fluoro-4-[5-fluoro-1-[3-[(2R)-2-methoxypropyl]-3,8-diazabicyclo[3.2.1]octan-8-yl]-3-[[(2S)-1-methylpyrrolidin-2-yl]methoxy]-7,9-dihydrofuro[3,4-f]quinazolin-6-yl]benzothiophene-3-carbonitrile | 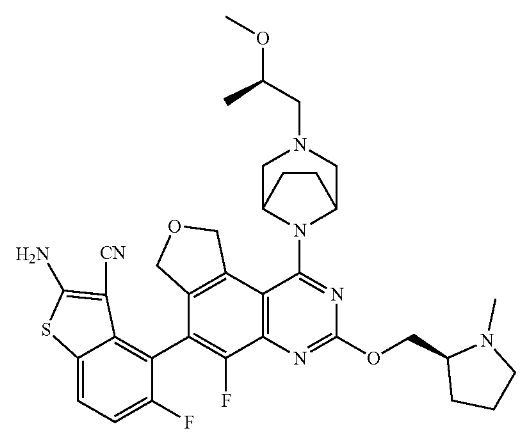 [SMILES: CO[C@H](C)CN1CC2CCC(C1)N2c1nc(OC[C@@H]2CCCN2C)nc2c(F)c(-c3c(F)ccc4sc(N)c(C#N)c34)c3c(c12)COC3] | 676 |
| 217[4] | 2-Amino-5-fluoro-4-[5-fluoro-1-[3-(3-hydroxypropyl)-3,8-diazabicyclo[3.2.1]octan-8-yl]-3-[2-(3-methoxyazetidin-1-yl)ethoxy]-7,9-dihydrofuro[3,4-f]quinazolin-6-yl]benzothiophene-3-carbonitrile | 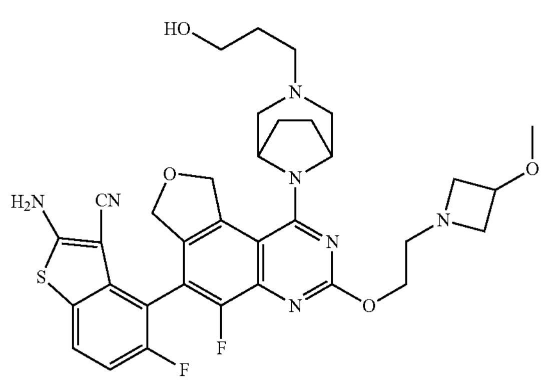 [SMILES: COC1CN(CCOc2nc(N3C4CCC3CN(CCCO)C4)c3c4c(c(-c5c(F)ccc6sc(N)c(C#N)c56)c(F)c3n2)COC4)C1] | 678 |

TABLE 15-continued

| Example | Chemical Name | Structure | MS (ES) m/z (M + 1) |
|---|---|---|---|
| 218 | 2-Amino-7-fluoro-4-[5-fluoro-3-[[(2R,8S)-2-fluoro-1,2,3,5,6,7-hexahydropyrrolizin-8-yl]methoxy]-1-[3-(3-hydroxypropyl)-3,8-diazabicyclo[3.2.1]octan-8-yl]-7,9-dihydrofuro[3,4-f]quinazolin-6-yl]thieno[3,2-c]pyridine-3-carbonitrile | 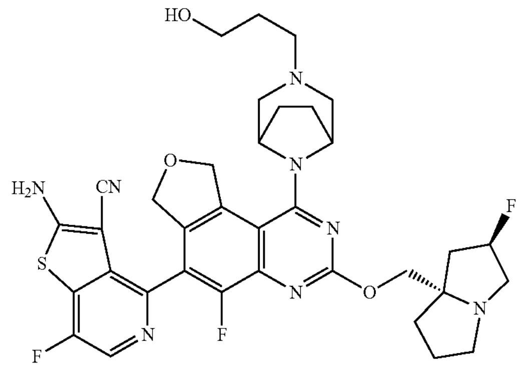 [SMILES: N#Cc1c(N)sc2c(F)cnc(-c3c4c(c5c(N6C7CCC6CN(CCCO)C7)nc(OC[C@@]67CCCN6C[C@H](F)C7)nc5c3F)COC4)c12] | 707 |
| 219 | 2-Amino-7-fluoro-4-[5-fluoro-3-[[(2R,8S)-2-fluoro-1,2,3,5,6,7-hexahydropyrrolizin-8-yl]methoxy]-1-[3-(oxetan-3-yl)-3,8-diazabicyclo[3.2.1]octan-8-yl]-7,9-dihydrofuro[3,4-f]quinazolin-6-yl]thieno[3,2-c]pyridine-3-carbonitrile | 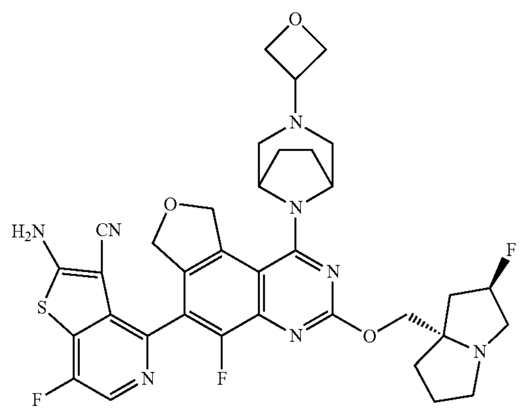 [SMILES: N#Cc1c(N)sc2c(F)cnc(-c3c4c(c5c(N6C7CCC6CN(C6COC6)C7)nc(OC[C@@]67CCCN6C[C@H](F)C7)nc5c3F)COC4)c12] | 705 |
| 220 | 2-Amino-7-fluoro-4-[5-fluoro-3-[[(2R,8S)-2-fluoro-1,2,3,5,6,7-hexahydropyrrolizin-8-yl]methoxy]-1-[3-[2-(2-methoxyethoxy)ethyl]-3,8-diazabicyclo[3.2.1]octan-8-yl]-7,9-dihydrofuro[3,4-f]quinazolin-6-yl]thieno[3,2-c]pyridine-3-carbonitrile | 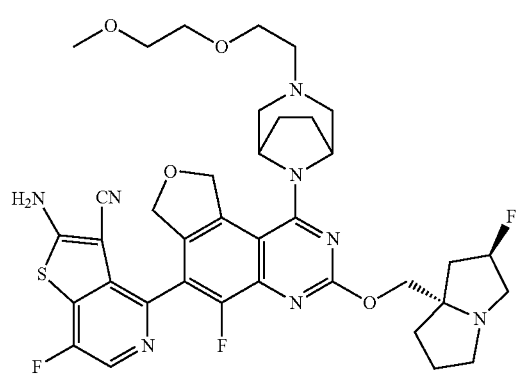 [SMILES: COCCOCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] | 751 |

TABLE 15-continued

| Example | Chemical Name | Structure | MS (ES) m/z (M + 1) |
|---|---|---|---|
| 221 | [(1R)-2-[8-[6-(2-Amino-3-cyano-7-fluoro-thieno[3,2-c]pyridin-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]-1-methyl-ethyl] 2-methylpropanoate | 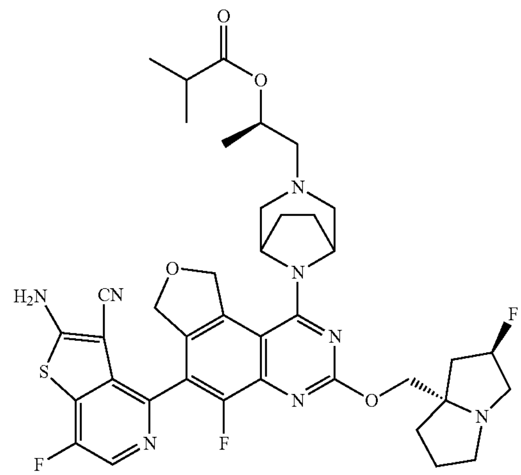 [SMILES: CC(C)C(=O)O[C@H](C)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] | 777 |
| 222 | [(1R)-2-[8-[6-(2-Amino-3-cyano-7-fluoro-thieno[3,2-c]pyridin-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]-1-methyl-ethyl] acetate | 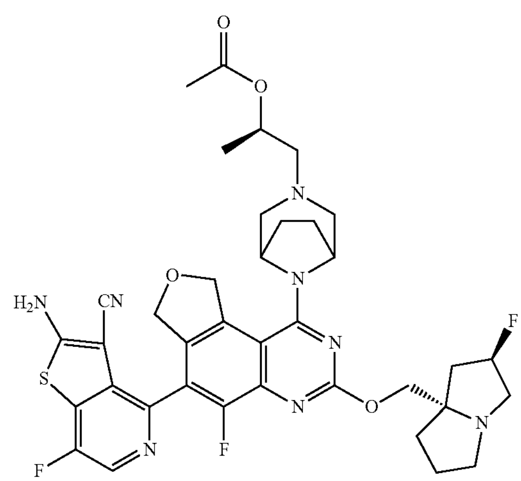 [SMILES: CC(=O)O[C@H](C)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] | 749 |
| 223 | [(1R)-2-[8-[6-(2-Amino-3-cyano-7-fluoro-thieno[3,2-c]pyridin-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]-1-methyl-ethyl] propanoate | 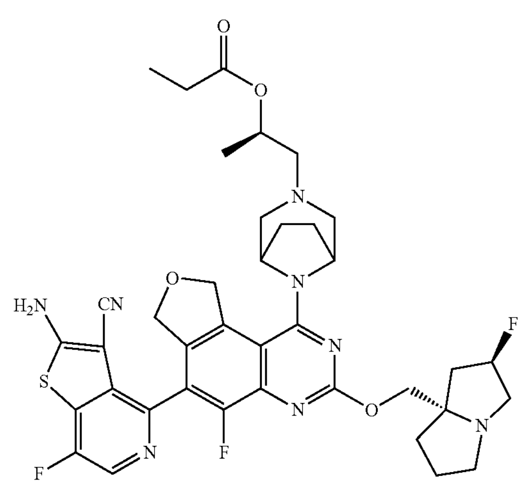 [SMILES: CCC(=O)O[C@H](C)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] | 763 |

TABLE 15-continued

| Example | Chemical Name | Structure | MS (ES) m/z (M + 1) |
|---|---|---|---|
| 224 | 2-Amino-7-fluoro-4-[5-fluoro-3-[[(2R,8S)-2-fluoro-1,2,3,5,6,7-hexahydropyrrolizin-8-yl]methoxy]-1-[3-[2-(2-hydroxyethoxy)ethyl]-3,8-diazabicyclo[3.2.1]octan-8-yl]-7,9-dihydrofuro[3,4-f]quinazolin-6-yl]thieno[3,2-c]pyridine-3-carbonitrile | 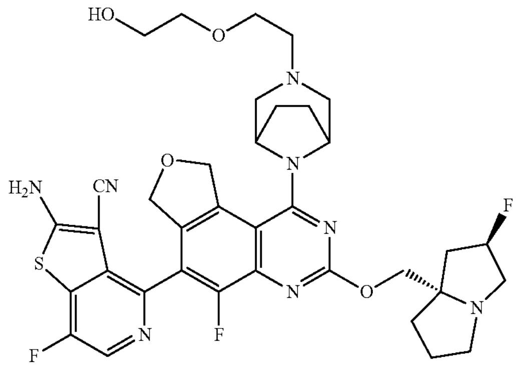 [SMILES: N#Cc1c(N)sc2c(F)cnc(-c3c4c(c5c(N6C7CCC6CN(CCOCCO)C7)nc(OC[C@@]67CCCN6C[C@H](F)C7)nc5c3F)COC4)c12] | 737 |
| 225 | 2-Amino-7-fluoro-4-[5-fluoro-3-[[(2R,8S)-2-fluoro-1,2,3,5,6,7-hexahydropyrrolizin-8-yl]methoxy]-1-[3-[3-(2-hydroxyethoxy)propyl]-3,8-diazabicyclo[3.2.1]octan-8-yl]-7,9-dihydrofuro[3,4-f]quinazolin-6-yl]thieno[3,2-c]pyridine-3-carbonitrile | 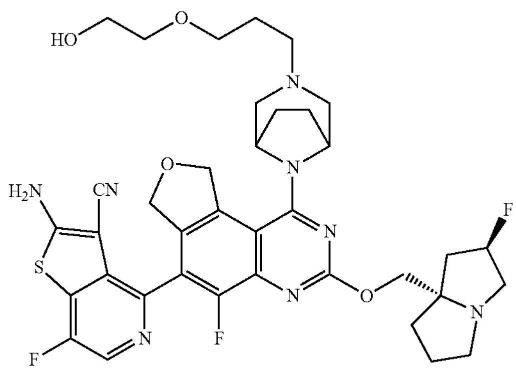 [SMILES: N#Cc1c(N)sc2c(F)cnc(-c3c4c(c5c(N6C7CCC6CN(CCCOCCO)C7)nc(OC[C@@]67CCCN6C[C@H](F)C7)nc5c3F)COC4)c12] | 751 |
| 226 | 2-Amino-7-fluoro-4-[5-fluoro-3-[[(2R,8S)-2-fluoro-1,2,3,5,6,7-hexahydropyrrolizin-8-yl]methoxy]-1-[3-[3-(2-methoxyethoxy)propyl]-3,8-diazabicyclo[3.2.1]octan-8-yl]-7,9-dihydrofuro[3,4-f]quinazolin-6-yl]thieno[3,2-c]pyridine-3-carbonitrile | 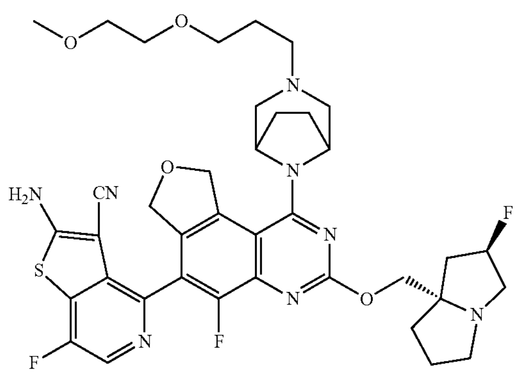 [SMILES: COCCOCCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] | 765 |
| 227 | 2-Amino-4-[1-[3-[(3R)-3,4-dihydroxybutyl]-3,8-diazabicyclo[3.2.1]octan-8-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-thieno[3,2-c]pyridine-3-carbonitrile | 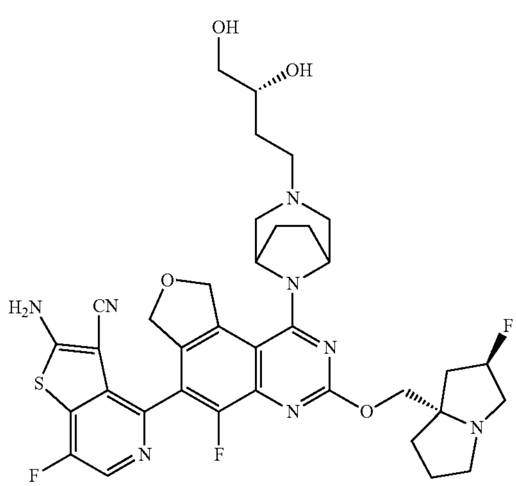 [SMILES: N#Cc1c(N)sc2c(F)cnc(-c3c4c(c5c(N6C7CCC6CN(CC[C@@H](O)CO)C7)nc(OC[C@@]67CCCN6C[C@H](F)C7)nc5c3F)COC4)c12] | 737 |

TABLE 15-continued

| Example | Chemical Name | Structure | MS (ES) m/z (M + 1) |
|---------|---------------|-----------|---------------------|
| 228 | 2-Amino-7-fluoro-4-[5-fluoro-3-[[(2R,8S)-2-fluoro-1,2,3,5,6,7-hexahydropyrrolizin-8-yl]methoxy]-1-[3-[3-hydroxy-2-(hydroxymethyl)propyl]-3,8-diazabicyclo[3.2.1]octan-8-yl]-7,9-dihydrofuro[3,4-f]quinazolin-6-yl]thieno[3,2-c]pyridine-3-carbonitrile | 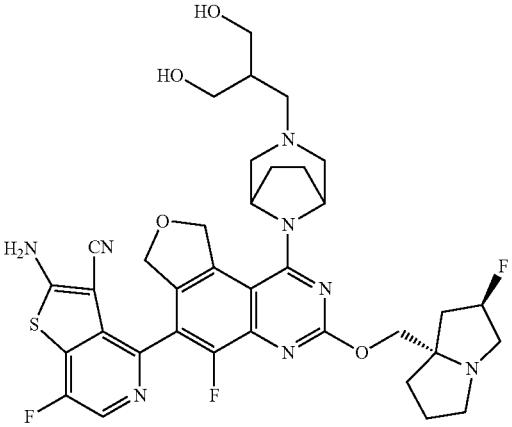 [SMILES: N#Cc1c(N)sc2c(F)cnc(-c3c4c(c5c(N6C7CCC6CN(CC(CO)CO)C7)nc(OC[C@@]67CCCN6C[C@H](F)C7)nc5c3F)COC4)c12] | 737 |
| 229 | 2-Amino-7-fluoro-4-[5-fluoro-3-[(2-methoxy-1,2,3,5,6,7-hexahydropyrrolizin-8-yl)methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 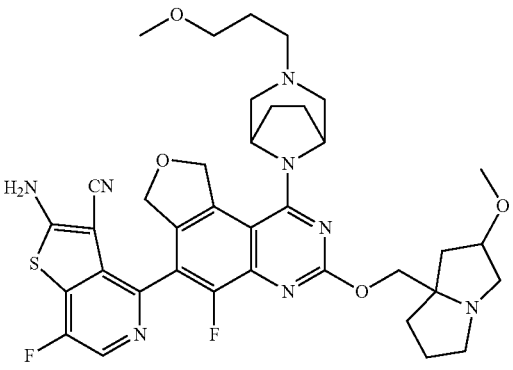 [SMILES: COCCCN1CC2CCC(C1)N2c1nc(OCC23CCCN2CC(OC)C3)nc2c(F)c(-c3ncc(F)c4sc(N)c(C#N)c34)c3c(c12)COC3] | 733 |
| 230 | 2-Amino-7-fluoro-4-[5-fluoro-1-[3-(2-methoxyethyl)-3,8-diazabicyclo[3.2.1]octan-8-yl]-3-[(2-methoxy-1,2,3,5,6,7-hexahydropyrrolizin-8-yl)methoxy]-7,9-dihydrofuro[3,4-f]quinazolin-6-yl]thieno[3,2-c]pyridine-3-carbonitrile | 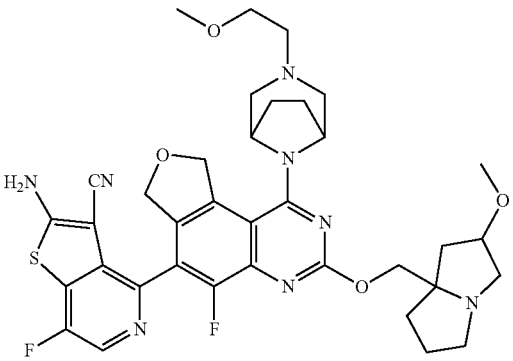 [SMILES: COCCN1CC2CCC(C1)N2c1nc(OCC23CCCN2CC(OC)C3)nc2c(F)c(-c3ncc(F)c4sc(N)c(C#N)c34)c3c(c12)COC3] | 719 |

TABLE 15-continued

| Example | Chemical Name | Structure | MS (ES) m/z (M + 1) |
|---|---|---|---|
| 231 | 2-Amino-7-fluoro-4-[5-fluoro-3-[(2-methoxy-1,2,3,5,6,7-hexahydropyrrolizin-8-yl)methoxy]-1-[3-[[(2R)-oxetan-2-yl]methyl]-3,8-diazabicyclo[3.2.1]octan-8-yl]-7,9-dihydrofuro[3,4-f]quinazolin-6-yl]thieno[3,2-c]pyridine-3-carbonitrile methanesulfonic acid | 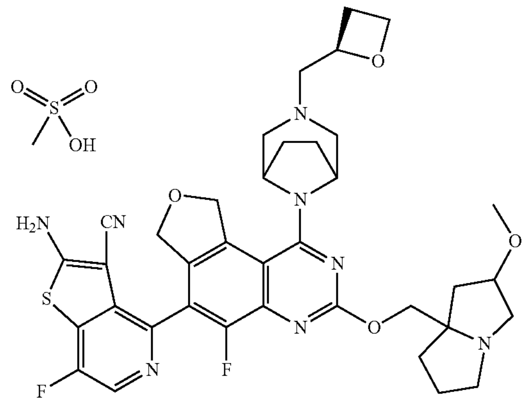 | 731 |
| 232 | 2-Amino-7-fluoro-4-[5-fluoro-3-[[(2R,8S)-2-methoxy-1,2,3,5,6,7-hexahydropyrrolizin-8-yl]methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 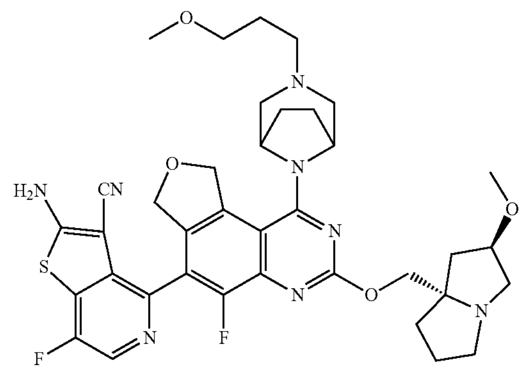 [SMILES: COCCCN1CC2CCC(C1)N2c1nc(OC[C@@]23CCCN2C[C@H](OC)C3)nc2c(F)c(-c3ncc(F)c4sc(N)c(C#N)c34)c3c(c12)COC3] | 733 |
| 233 | 2-Amino-7-fluoro-4-[5-fluoro-1-[3-(2-methoxyethyl)-3,8-diazabicyclo[3.2.1]octan-8-yl]-3-[[(2R,8S)-2-methoxy-1,2,3,5,6,7-hexahydropyrrolizin-8-yl]methoxy]-7,9-dihydrofuro[3,4-f]quinazolin-6-yl]thieno[3,2-c]pyridine-3-carbonitrile | 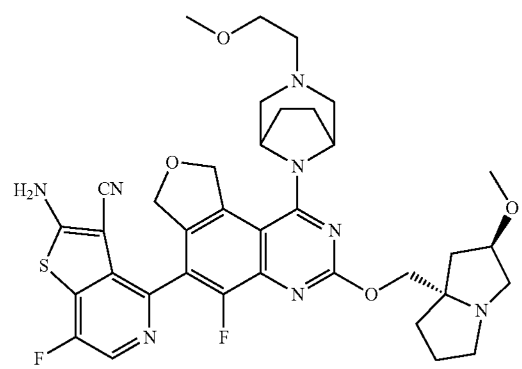 [SMILES: COCCN1CC2CCC(C1)N2c1nc(OC[C@@]23CCCN2C[C@H](OC)C3)nc2c(F)c(-c3ncc(F)c4sc(N)c(C#N)c34)c3c(c12)COC3] | 719 |
| 234 | 2-amino-7-fluoro-4-[5-fluoro-3-[[(2R,8S)-2-methoxy-1,2,3,5,6,7-hexahydropyrrolizin-8-yl]methoxy]-1-[3-[[(2R)-oxetan-2-yl]methyl]-3,8-diazabicyclo[3.2.1]octan-8-yl]-7,9-dihydrofuro[3,4-f]quinazolin-6-yl]thieno[3,2-c]pyridine-3-carbonitrile methanesulfonic acid | 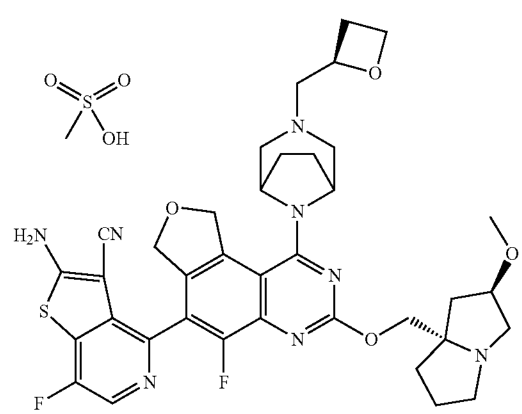 | 731 |

TABLE 15-continued

| Example | Chemical Name | Structure | MS (ES) m/z (M + 1) |
|---|---|---|---|
| 235 | 2-Amino-7-fluoro-4-[5-fluoro-1-(3-methyl-3,8-diazabicyclo[3.2.1]octan-8-yl)-3-[[(2S)-1-methylpyrrolidin-2-yl]methoxy]-7,9-dihydrofuro[3,4-f]quinazolin-6-yl]thieno[3,2-c]pyridine-3-carbonitrile | 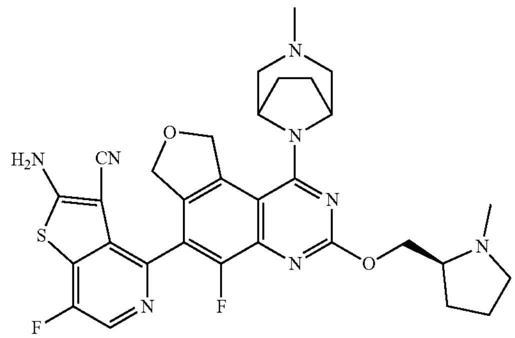 [SMILES: CN1CC2CCC(C1)N2c1nc(OC[C@@H]2CCCN2C)nc2c(F)c(-c3ncc(F)c4sc(N)c(C#N)c34)c3c(c12)COC3] | 619 |
| 236 | 2-Amino-7-fluoro-4-[5-fluoro-1-[3-(3-methoxypropyl)-3,8-diazabicyclo[3.2.1]octan-8-yl]-3-[[(2S)-1-methylpyrrolidin-2-yl]methoxy]-7,9-dihydrofuro[3,4-f]quinazolin-6-yl]thieno[3,2-c]pyridine-3-carbonitrile | 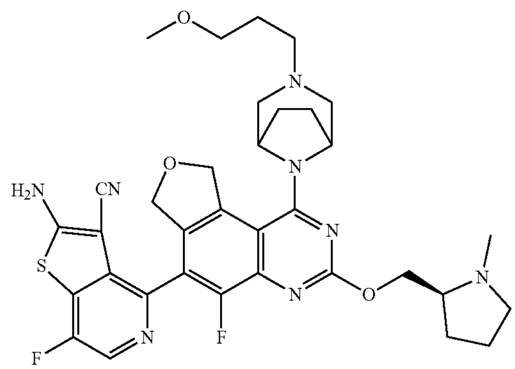 [SMILES: COCCCN1CC2CCC(C1)N2c1nc(OC[C@@H]2CCCN2C)nc2c(F)c(-c3ncc(F)c4sc(N)c(C#N)c34)c3c(c12)COC3] | 677 |
| 237 | 2-Amino-7-fluoro-4-[5-fluoro-3-[[(2S,4R)-4-fluoro-1-methyl-pyrrolidin-2-yl]methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 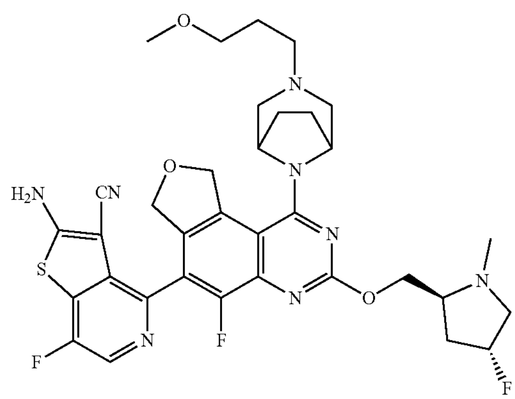 [SMILES: COCCCN1CC2CCC(C1)N2c1nc(OC[C@@H]2C[C@@H](F)CN2C)nc2c(F)c(-c3ncc(F)c4sc(N)c(C#N)c34)c3c(c12)COC3] | 695 |
| 238 | 2-Amino-7-fluoro-4-[5-fluoro-3-[[(2S,4R)-4-methoxy-1-methyl-pyrrolidin-2-yl]methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 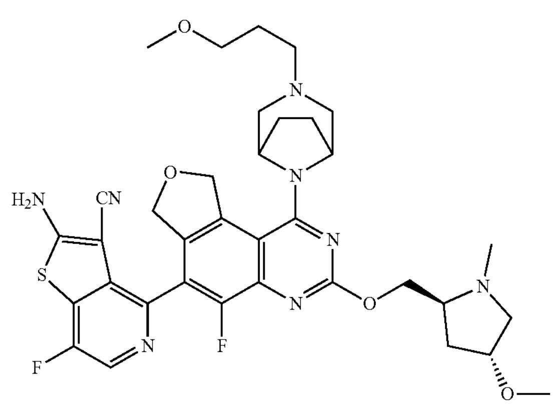 [SMILES: COCCCN1CC2CCC(C1)N2c1nc(OC[C@@H]2C[C@@H](OC)CN2C)nc2c(F)c(-c3ncc(F)c4sc(N)c(C#N)c34)c3c(c12)COC3] | 707 |

TABLE 15-continued

| Example | Chemical Name | Structure | MS (ES) m/z (M + 1) |
|---|---|---|---|
| 239 | 2-Amino-7-fluoro-4-[5-fluoro-3-(1,2,3,5,6,7-hexahydropyrrolizin-8-ylmethoxy)-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile formic acid | 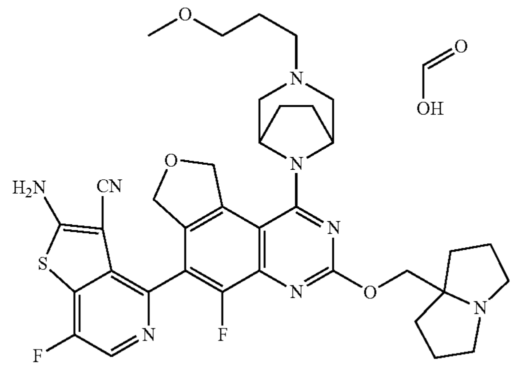 [SMILES: COCCCN1CC2CCC(C1)N2c1nc(OCC23CCCN2CCC3)nc2c(F)c(-c3ncc(F)c4sc(N)c(C#N)c34)c3c(c12)COC3 ; O=CO] | 703 |
| 240 | 2-Amino-4-[3-(1-azabicyclo[3.2.0]heptan-5-ylmethoxy)-5-fluoro-1-[3-(3-methoxypropyl)-3,8-diazabicyclo[3.2.1]octan-8-yl]-7,9-dihydrofuro[3,4-f]quinazolin-6-yl]-7-fluoro-thieno[3,2-c]pyridine-3-carbonitrile | 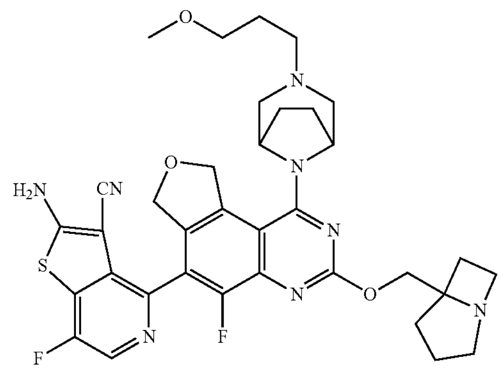 [SMILES: COCCCN1CC2CCC(C1)N2c1nc(OCC23CCCN2CC3)nc2c(F)c(-c3ncc(F)c4sc(N)c(C#N)c34)c3c(c12)COC3] | 689 |
| 241 | 2-Amino-7-fluoro-4-[5-fluoro-3-[[(2SR,8SR)-2-fluoro-1,2,3,5,6,7-hexahydropyrrolizin-8-yl]methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 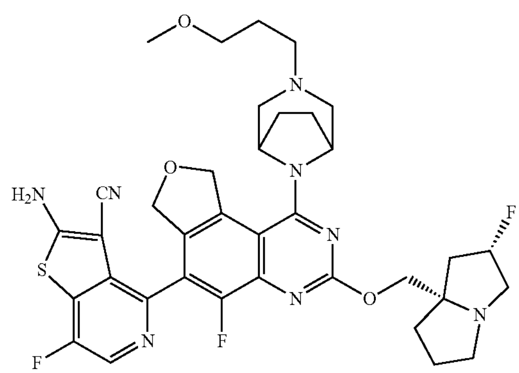 [SMILES: COCCCN1CC2CCC(C1)N2c1nc(OC[C@@]23CCCN2C[C@@H](F)C3)nc2c(F)c(-c3ncc(F)c4sc(N)c(C#N)c34)c3c(c12)COC3] | 721 |
| 242 | 2-Amino-7-fluoro-4-[5-fluoro-3-[[(2SR,8SR)-2-fluoro-1,2,3,5,6,7-hexahydropyrrolizin-8-yl]methoxy]-1-[3-(2-methoxyethyl)-3,8-diazabicyclo[3.2.1]octan-8-yl]-7,9-dihydrofuro[3,4-f]quinazolin-6-yl]thieno[3,2-c]pyridine-3-carbonitrile | 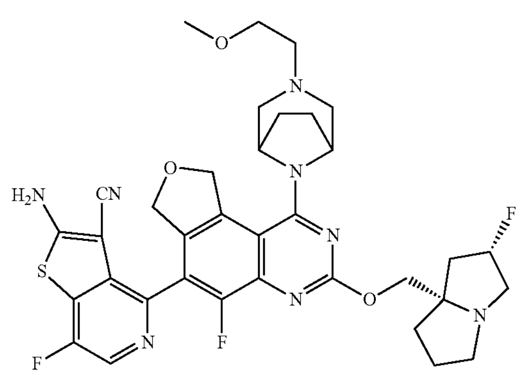 [SMILES: COCCN1CC2CCC(C1)N2c1nc(OC[C@@]23CCCN2C[C@@H](F)C3)nc2c(F)c(-c3ncc(F)c4sc(N)c(C#N)c34)c3c(c12)COC3] | 707 |

TABLE 15-continued

| Example | Chemical Name | Structure | MS (ES) m/z (M + 1) |
|---|---|---|---|
| 326 | 2-Amino-7-fluoro-4-[5-fluoro-1-[3-(2-fluoroethyl)-3,8-diazabicyclo[3.2.1]octan-8-yl]-3-[[(2R)-4-methylmorpholin-2-yl]methoxy]-7,9-dihydrofuro[3,4-f]quinazolin-6-yl]thieno[3,2-c]pyridine-3-carbonitrile | 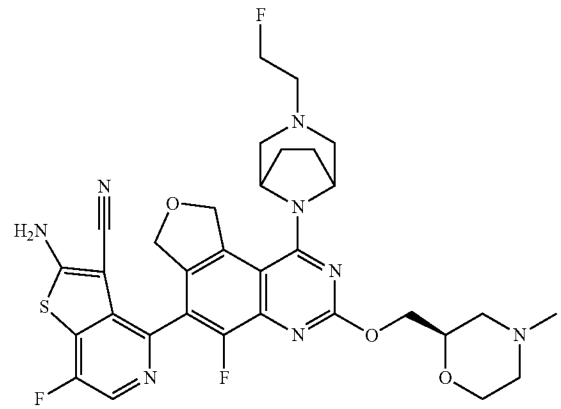 [SMILES: CN1CCO[C@@H](COc2nc(N3C4CCC3CN(CCF)C4)c3c4c(c(-c5ncc(F)c6sc(N)c(C#N)c56)c(F)c3n2)COC4)C1] | 667 |
| 327 | 2-Amino-7-fluoro-4-[5-fluoro-3-[[(2R,8S)-2-fluoro-1,2,3,5,6,7-hexahydropyrrolizin-8-yl]methoxy]-1-[3-[2-(trideuteriomethoxy)ethyl]-3,8-diazabicyclo[3.2.1]octan-8-yl]-7,9-dihydrofuro[3,4-f]quinazolin-6-yl]thieno[3,2-c]pyridine-3-carbonitrile | 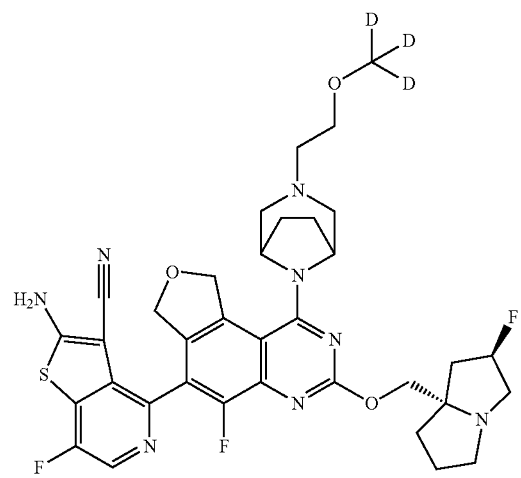 [SMILES: [2H]C([2H])([2H])OCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] | 710 |
| 328 | 2-Amino-4-[3-[(4,4-difluoro-1-methyl-3-piperidyl)methoxy]-5-fluoro-1-[3-(3-hydroxypropyl)-3,8-diazabicyclo[3.2.1]octan-8-yl]-7,9-dihydrofuro[3,4-f]quinazolin-6-yl]-7-fluoro-thieno[3,2-c]pyridine-3-carbonitrile, Isomer 1 | 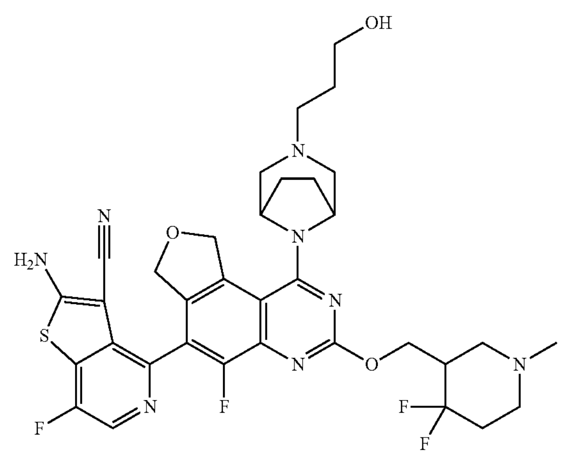 [SMILES: CN1CCC(F)(F)C(COc2nc(N3C4CCC3CN(CCCO)C4)c3c4c(c(-c5ncc(F)c6sc(N)c(C#N)c56)c(F)c3n2)COC4)C1] | 713 |

TABLE 15-continued

| Example | Chemical Name | Structure | MS (ES) m/z (M + 1) |
|---|---|---|---|
| 329 | 2-Amino-4-[3-[(4,4-difluoro-1-methyl-3-piperidyl)methoxy]-5-fluoro-1-[3-(3-hydroxypropyl)-3,8-diazabicyclo[3.2.1]octan-8-yl]-7,9-dihydrofuro[3,4-f]quinazolin-6-yl]-7-fluoro-thieno[3,2-c]pyridine-3-carbonitrile, Isomer 2 | 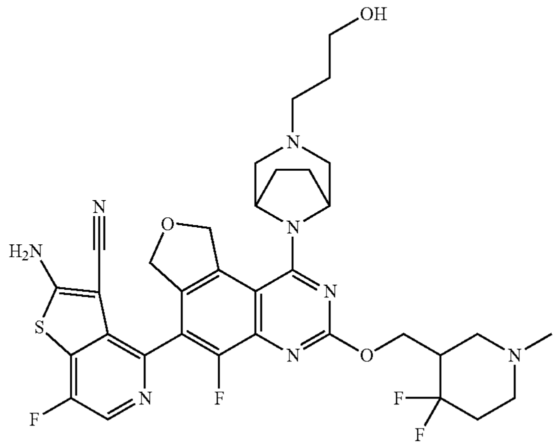 [SMILES: CN1CCC(F)(F)C(COc2nc(N3C4CCC3CN(CCCO)C4)c3c4c(c(-c5ncc(F)c6sc(N)c(C#N)c56)c(F)c3n2)COC4)C1] | 713 |
| 330[4] | 2-Amino-4-[3-[(4,4-difluoro-1-methyl-3-piperidyl)methoxy]-5-fluoro-1-[3-(3-hydroxypropyl)-3,8-diazabicyclo[3.2.1]octan-8-yl]-7,9-dihydrofuro[3,4-f]quinazolin-6-yl]-5-fluoro-benzothiophene-3-carbonitrile, Isomer 1 | 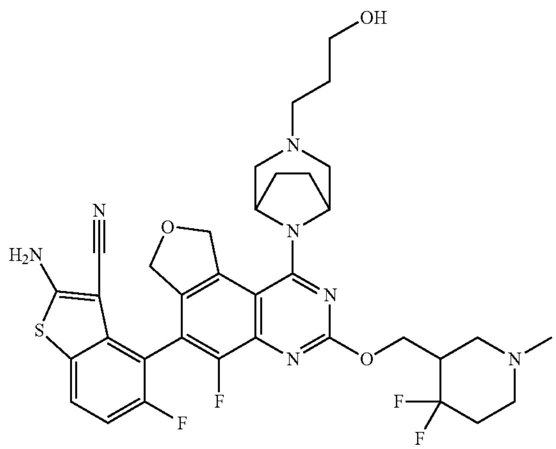 [SMILES: CN1CCC(F)(F)C(COc2nc(N3C4CCC3CN(CCCO)C4)c3c4c(c(-c5c(F)ccc6sc(N)c(C#N)c56)c(F)c3n2)COC4)C1] | 712 |
| 331[4] | 2-Amino-4-[3-[(4,4-difluoro-1-methyl-3-piperidyl)methoxy]-5-fluoro-1-[3-(3-hydroxypropyl)-3,8-diazabicyclo[3.2.1]octan-8-yl]-7,9-dihydrofuro[3,4-f]quinazolin-6-yl]-5-fluoro-benzothiophene-3-carbonitrile, Isomer 2 | 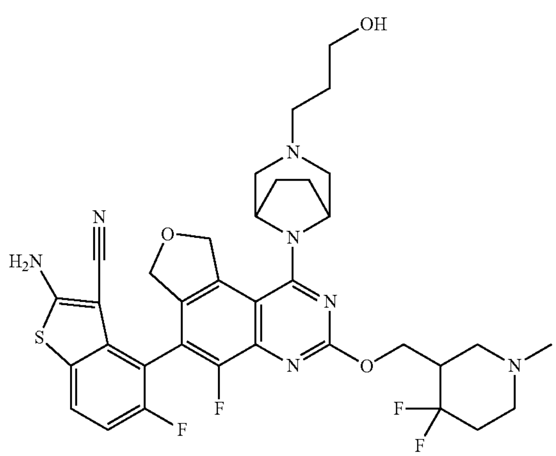 [SMILES: CN1CCC(F)(F)C(COc2nc(N3C4CCC3CN(CCCO)C4)c3c4c(c(-c5c(F)ccc6sc(N)c(C#N)c56)c(F)c3n2)COC4)C1] | 712 |

TABLE 15-continued

| Example | Chemical Name | Structure | MS (ES) m/z (M + 1) |
|---|---|---|---|
| 332 | 2-Amino-7-fluoro-4-[5-fluoro-3-[[(2S,4R)-4-fluoro-1-methyl-pyrrolidin-2-yl]methoxy]-1-[3-(3-hydroxypropyl)-3,8-diazabicyclo[3.2.1]octan-8-yl]-7,9-dihydrofuro[3,4-f]quinazolin-6-yl]thieno[3,2-c]pyridine-3-carbonitrile | 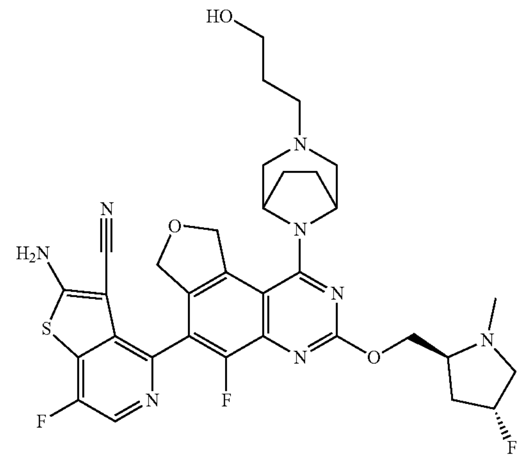 [SMILES: CN1C[C@H](F)C[C@H]1COc1nc(N2C3CCC2CN(CCCO)C3)c2c3c(c(-c4ncc(F)c5sc(N)c(C#N)c45)c(F)c2n1)COC3] | 681 |
| 333 | 2-Amino-5-fluoro-4-[5-fluoro-1-[3-(3-hydroxypropyl)-3,8-diazabicyclo[3.2.1]octan-8-yl]-3-[[(3S)-4-methylmorpholin-3-yl]methoxy]-7,9-dihydrofuro[3,4-f]quinazolin-6-yl]benzothiophene-3-carbonitrile | 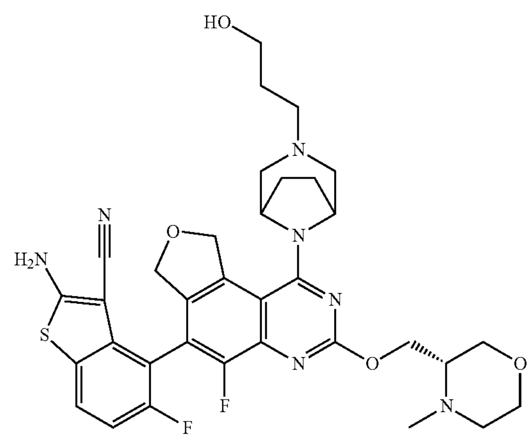 [SMILES: CN1CCOC[C@H]1COc1nc(N2C3CCC2CN(CCCO)C3)c2c3c(c(-c4c(F)ccc5sc(N)c(C#N)c45)c(F)c2n1)COC3] | 678 |
| 334 | 2-Amino-4-[3-[[1-[(dimethylamino)methyl]cyclopropyl]methoxy]-5-fluoro-1-[3-(3-hydroxypropyl)-3,8-diazabicyclo[3.2.1]octan-8-yl]-7,9-dihydrofuro[3,4-f]quinazolin-6-yl]-7-fluoro-thieno[3,2-c]pyridine-3-carbonitrile | 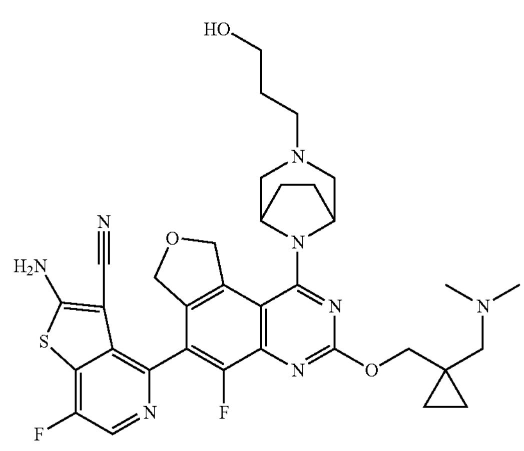 [SMILES: CN(C)CC1(COc2nc(N3C4CCC3CN(CCCO)C4)c3c4c(c(-c5ncc(F)c6sc(N)c(C#N)c56)c(F)c3n2)COC4)CC1] | 677 |

TABLE 15-continued

| Example | Chemical Name | Structure | MS (ES) m/z (M + 1) |
|---|---|---|---|
| 335 | 2-Amino-7-fluoro-4-[5-fluoro-1-[3-(3-hydroxypropyl)-3,8-diazabicyclo[3.2.1]octan-8-yl]-3-(2-pyrazol-1-ylethoxy)-7,9-dihydrofuro[3,4-f]quinazolin-6-yl]thieno[3,2-c]pyridine-3-carbonitrile | 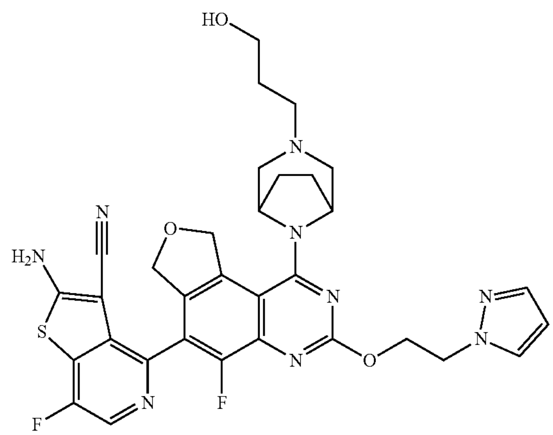 [SMILES: N#Cc1c(N)sc2c(F)cnc(-c3c4c(c5c(N6C7CCC6CN(CCCO)C7)nc(OCCn6cccn6)nc5c3F)COC4)c12] | 660 |
| 336 | 2-Amino-7-fluoro-4-[5-fluoro-3-[[(2R,8S)-2-fluoro-1,2,3,5,6,7-hexahydropyrrolizin-8-yl]methoxy]-1-[3-[(1-hydroxycyclopropyl)methyl]-3,8-diazabicyclo[3.2.1]octan-8-yl]-7,9-dihydrofuro[3,4-f]quinazolin-6-yl]thieno[3,2-c]pyridine-3-carbonitrile | 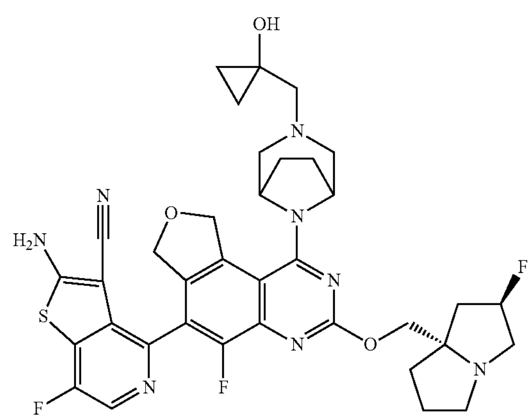 [SMILES: N#Cc1c(N)sc2c(F)cnc(-c3c4c(c5c(N6C7CCC6CN(CC6(O)CC6)C7)nc(OC[C@@]67CCCN6C[C@H](F)C7)nc5c3F)COC4)c12] | 719 |
| 337 | 2-Amino-4-[3-[[(2S)-4,4-difluoro-1-methyl-pyrrolidin-2-yl]methoxy]-5-fluoro-1-[3-(3-hydroxypropyl)-3,8-diazabicyclo[3.2.1]octan-8-yl]-7,9-dihydrofuro[3,4-f]quinazolin-6-yl]-7-fluoro-thieno[3,2-c]pyridine-3-carbonitrile | 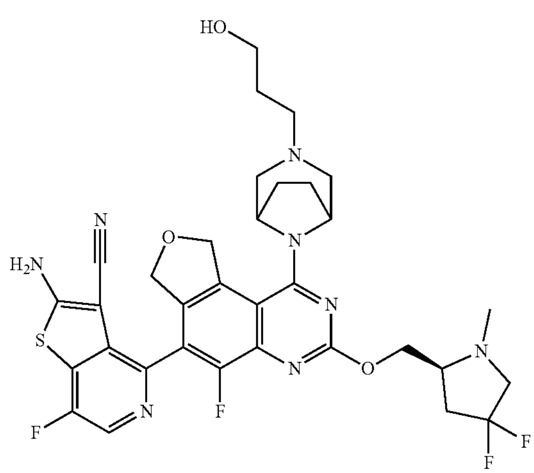 [SMILES: CN1CC(F)(F)C[C@H]1COc1nc(N2C3CCC2CN(CCCO)C3)c2c3c(c(-c4ncc(F)c5sc(N)c(C#N)c45)c(F)c2n1)COC3] | 699 |

TABLE 15-continued

| Example | Chemical Name | Structure | MS (ES) m/z (M + 1) |
|---|---|---|---|
| 338 | 2-Amino-7-fluoro-4-[5-fluoro-3-[(3-fluoro-1-methyl-pyrrolidin-3-yl)methoxy]-1-[3-(3-hydroxypropyl)-3,8-diazabicyclo[3.2.1]octan-8-yl]-7,9-dihydrofuro[3,4-f]quinazolin-6-yl]thieno[3,2-c]pyridine-3-carbonitrile | 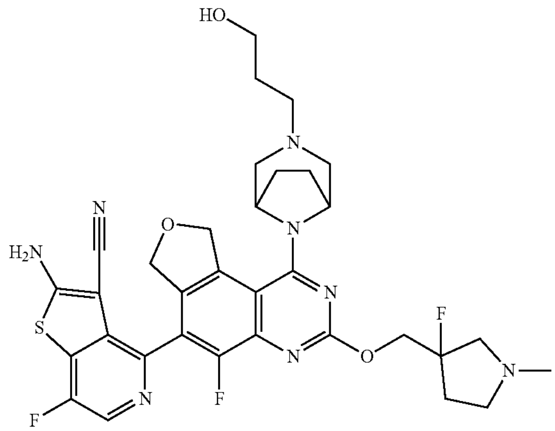 [SMILES: CN1CCC(F)(COc2nc(N3C4CCC3CN(CCCO)C4)c3c4c(c(-c5ncc(F)c6sc(N)c(C#N)c56)c(F)c3n2)COC4)C1] | 681 |
| 339 | 2-Amino-5-fluoro-4-[5-fluoro-1-(3-methyl-3,6-diazabicyclo[3.1.1]heptan-6-yl)-3-[[(2R)-4-methylmorpholin-2-yl]methoxy]-7,9-dihydrofuro[3,4-f]quinazolin-6-yl]benzothiophene-3-carbonitrile | 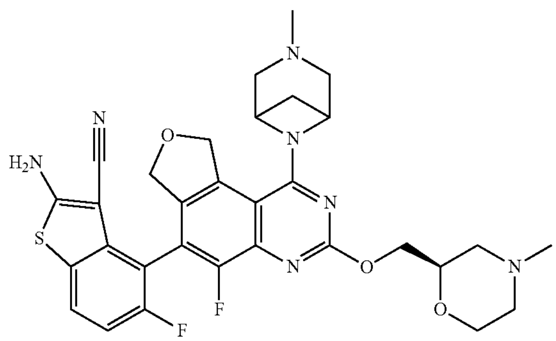 [SMILES: CN1CC2CC(C1)N2c1nc(OC[C@H]2CN(C)CCO2)nc2c(F)c(-c3c(F)ccc4sc(N)c(C#N)c34)c3c(c12)COC3] | 620 |
| 340 | 2-Amino-5-fluoro-4-[5-fluoro-1-(3-methyl-3,6-diazabicyclo[3.1.1]heptan-6-yl)-3-[[(2R)-4-methylmorpholin-2-yl]methoxy]-7,9-dihydrofuro[3,4-f]quinazolin-6-yl]benzothiophene-3-carbonitrile, Isomer 2 | 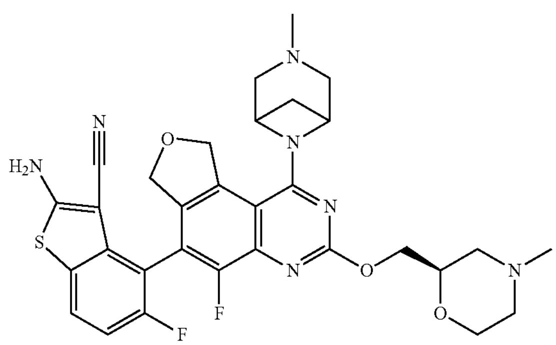 [SMILES: CN1CC2CC(C1)N2c1nc(OC[C@H]2CN(C)CCO2)nc2c(F)c(-c3c(F)ccc4sc(N)c(C#N)c34)c3c(c12)COC3] | 620 |
| 341 | 2-Amino-7-fluoro-4-[5-fluoro-3-[[(2S,4R)-4-fluoro-1-methyl-pyrrolidin-2-yl]methoxy]-1-(3-methyl-3,6-diazabicyclo[3.1.1]heptan-6-yl)-7,9-dihydrofuro[3,4-f]quinazolin-6-yl]thieno[3,2-c]pyridine-3-carbonitrile | 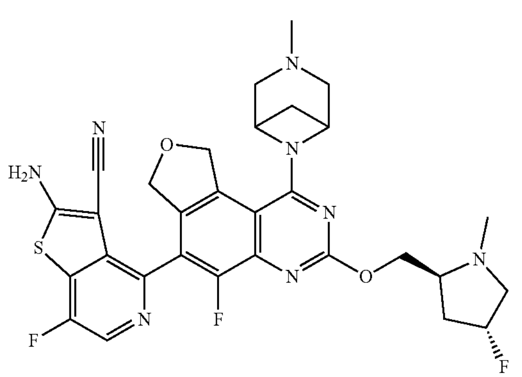 [SMILES: CN1CC2CC(C1)N2c1nc(OC[C@@H]2C[C@@H](F)CN2C)nc2c(F)c(-c3ncc(F)c4sc(N)c(C#N)c34)c3c(c12)COC3] | 623 |

TABLE 15-continued

| Example | Chemical Name | Structure | MS (ES) m/z (M + 1) |
|---|---|---|---|
| 342 | 2-Amino-7-fluoro-4-[5-fluoro-1-(3-methyl-3,6-diazabicyclo[3.1.1]heptan-6-yl)-3-[[(2S)-1-methylpyrrolidin-2-yl]methoxy]-7,9-dihydrofuro[3,4-f]quinazolin-6-yl]thieno[3,2-c]pyridine-3-carbonitrile; acetic acid | 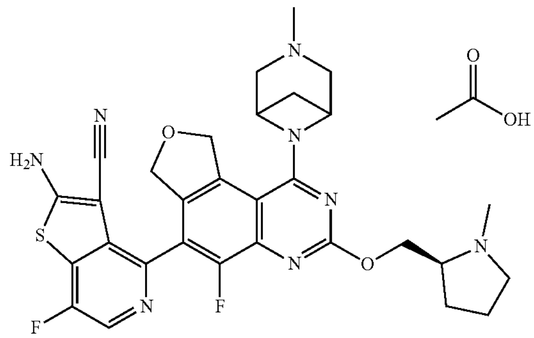 | 605 |
| 343 | 2-Amino-7-fluoro-4-[5-fluoro-3-[[(2R,8S)-2-fluoro-1,2,3,5,6,7-hexahydropyrrolizin-8-yl]methoxy]-1-(3-methyl-3,6-diazabicyclo[3.1.1]heptan-6-yl)-7,9-dihydrofuro[3,4-f]quinazolin-6-yl]thieno[3,2-c]pyridine-3-carbonitrile | 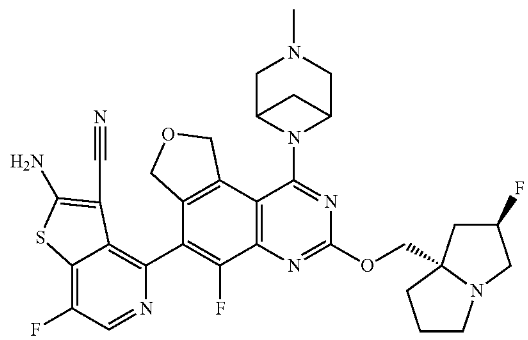 [SMILES: CN1CC2CC(C1)N2c1nc(OC[C@@]23CCCN2C[C@H](F)C3)nc2c(F)c(-c3ncc(F)c4sc(N)c(C#N)c34)c3c(c12)COC3] | 649 |
| 344 | 2-Amino-7-fluoro-4-[5-fluoro-3-[[(2R,8S)-2-fluoro-1,2,3,5,6,7-hexahydropyrrolizin-8-yl]methoxy]-1-[3-(3-methoxypropyl)-3,6-diazabicyclo[3.1.1]heptan-6-yl]-7,9-dihydrofuro[3,4-f]quinazolin-6-yl]thieno[3,2-c]pyridine-3-carbonitrile | 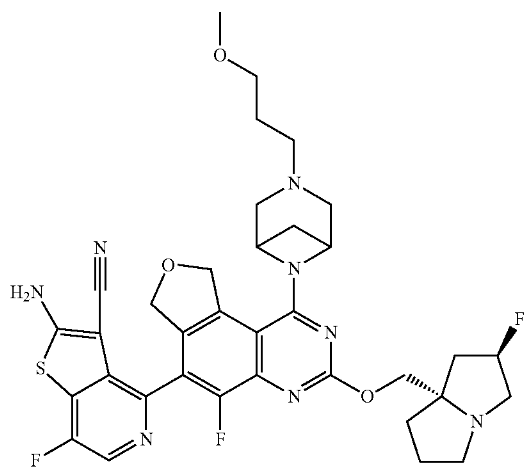 [SMILES: COCCCN1CC2CC(C1)N2c1nc(OC[C@@]23CCCN2C[C@H](F)C3)nc2c(F)c(-c3ncc(F)c4sc(N)c(C#N)c34)c3c(c12)COC3] | 707 |
| 345 | 2-Amino-7-fluoro-4-[5-fluoro-3-[[(2R,8S)-2-fluoro-1,2,3,5,6,7-hexahydropyrrolizin-8-yl]methoxy]-1-[3-(oxetan-3-ylmethyl)-3,6-diazabicyclo[3.1.1]heptan-6-yl]-7,9-dihydrofuro[3,4-f]quinazolin-6-yl]thieno[3,2-c]pyridine-3-carbonitrile | 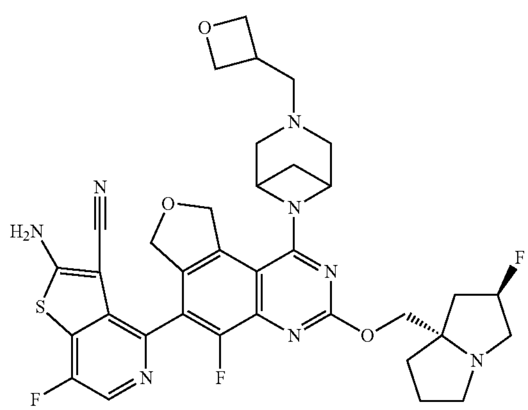 [SMILES: N#Cc1c(N)sc2c(F)cnc(-c3c4c(c5c(N6C7CC6CN(CC6COC6)C7)nc(OC[C@@]67CCCN6C[C@H](F)C7)nc5c3F)COC4)c12] | 705 |

TABLE 15-continued

| Example | Chemical Name | Structure | MS (ES) m/z (M + 1) |
|---|---|---|---|
| 346 | 2-Amino-7-fluoro-4-[5-fluoro-3-[(3-fluoro-1-methyl-pyrrolidin-3-yl)methoxy]-7,9-dihydrofuro[3,4-f]quinazolin-6-yl]thieno[3,2-c]pyridine-3-carbonitrile, Isomer 1 | 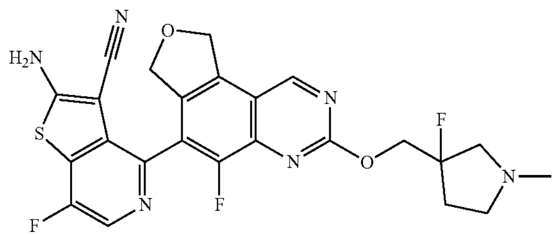 [SMILES: CN1CCC(F)(COc2ncc3c4c(c(-c5ncc(F)c6sc(N)c(C#N)c56)c(F)c3n2)COC4)C1] | 513 |
| 347 | 2-Amino-7-fluoro-4-[5-fluoro-3-[(3-fluoro-1-methyl-pyrrolidin-3-yl)methoxy]-7,9-dihydrofuro[3,4-f]quinazolin-6-yl]thieno[3,2-c]pyridine-3-carbonitrile, Isomer 2 | 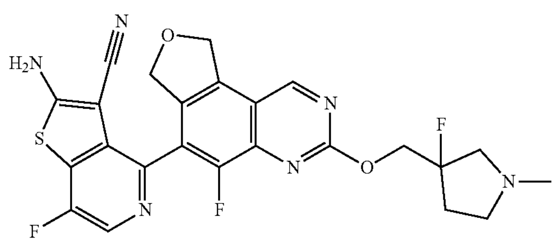 [SMILES: CN1CCC(F)(COc2ncc3c4c(c(-c5ncc(F)c6sc(N)c(C#N)c56)c(F)c3n2)COC4)C1] | 513 |
| 348 | 2-Amino-4-[5-fluoro-3-[[(2R,8S)-2-fluoro-1,2,3,5,6,7-hexahydropyrrolizin-8-yl]methoxy]-1-[3-(3-methoxypropyl)-3,8-diazabicyclo[3.2.1]octan-8-yl]-7,9-dihydrofuro[3,4-f]quinazolin-6-yl]thieno[2,3-b]pyridine-3-carbonitrile | 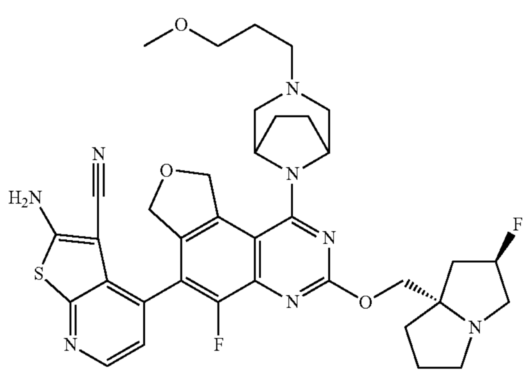 [SMILES: COCCCN1CC2CCC(C1)N2c1nc(OC[C@@]23CCCN2C[C@H](F)C3)nc2c(F)c(-c3ccnc4sc(N)c(C#N)c34)c3c(c12)COC3] | 703 |

[1] single atropisomer (from precursor in Example 1)
[2] Prepared using 37 wt % aq. formaldehyde, no MeOH co-solvent.
[3] single atropisomer (from precursor in Preparation 266)
[4] single atropisomer (from precursor in Preparation 248)
[5] single atropisomer (from precursor in Preparation 296)
[6] single atropisomer (from precursor in Preparation 251)
[7] single atropisomer (from precursor in Preparation 255)

Example 55

2-Amino-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile

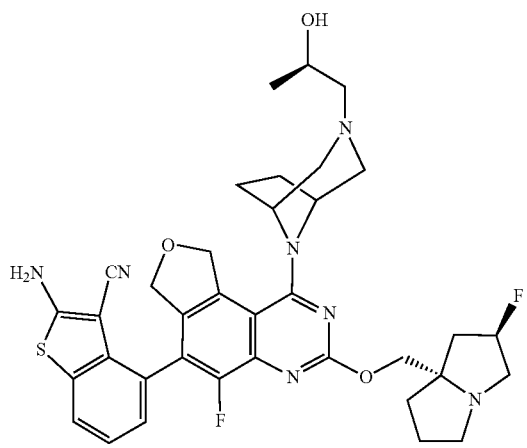 [SMILES: C[C@@H](O)CN1CC2CCC(C1)N2c1nc(OC[C@@]23CCCN2C[C@H](F)C3)nc2c(F)c(-c3cccc4sc(N)c(C#N)c34)c3c(c12)COC3]

A solution of 2-amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]benzothiophene-3-carbonitrile (0.120 g, 0.191 mmol) in MeOH (4 mL) was treated with (R)-(+)-propylene oxide (0.056 g, 0.945 mmol). The mixture was heated in a sealed tube at 70° C. for 2 h, then was concentrated. The residue was purified by reversed phase flash chromatography on C18 (eluting with 5% to 64% ACN in 10 mM aq. $NH_4HCO_3$ with 5% MeOH) to obtain the title compound (0.089 g, 62%) as a light-beige solid. MS (ES) m/z=688 (M+1).

The Example compounds in Table 16 were prepared in a similar manner as described for Example 48 or Example 55. Various methods were used to purify the compounds, which would be apparent to one skilled in the art. Chiral purification methods (if applicable) for the Examples of Table 16 are located in Table 18.

TABLE 16

| Example | Chemical Name | Structure | MS (ES) m/z (M + 1) |
|---|---|---|---|
| 158 | 2-Amino-5-fluoro-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,6-diazabicyclo[3.1.1]heptan-6-yl]-7,9-dihydrofuro[3,4-f]quinazolin-6-yl]benzothiophene-3-carbonitrile, Isomer 1 | 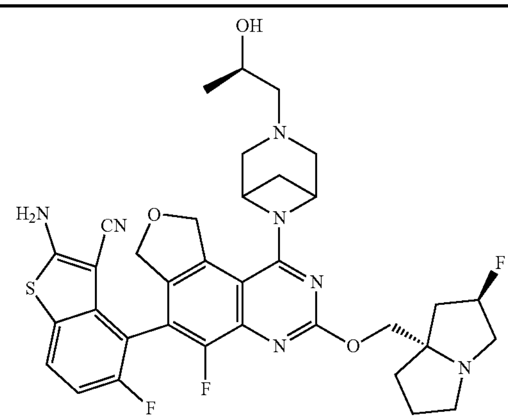 | 692 |
| 159 | 2-Amino-4-[5-fluoro-3-[[(2R,8S)-2-fluoro-1,2,3,5,6,7-hexahydropyrrolizin-8-yl]methoxy]-1-[3-(2-hydroxy-2-methyl-propyl)-3,8-diazabicyclo[3.2.1]octan-8-yl]-7,9-dihydrofuro[3,4-f]quinazolin-6-yl]benzothiophene-3-carbonitrile | 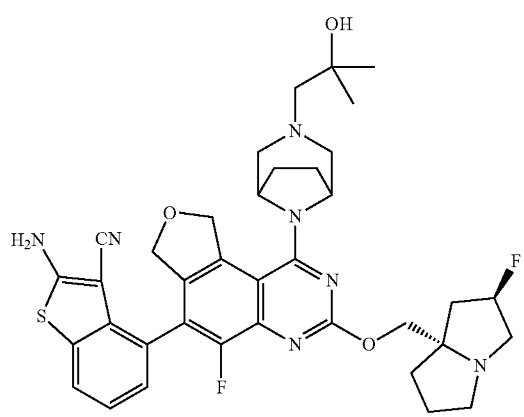 [SMILES: CC(C)(O)CN1CC2CCC(C1)N2c1nc(OC[C@@]23CCCN2C[C@H](F)C3)nc2c(F)c(-c3cccc4sc(N)c(C#N)c34)c3c(c12)COC3] | 702 |

TABLE 16-continued

| Example | Chemical Name | Structure | MS (ES) m/z (M + 1) |
|---|---|---|---|
| 160 | 2-Amino-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile, Isomer 1 | 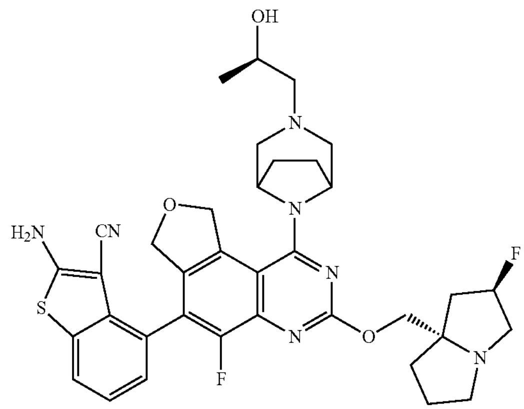 | 688 |
| 161 | 2-Amino-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile, Isomer 2 | 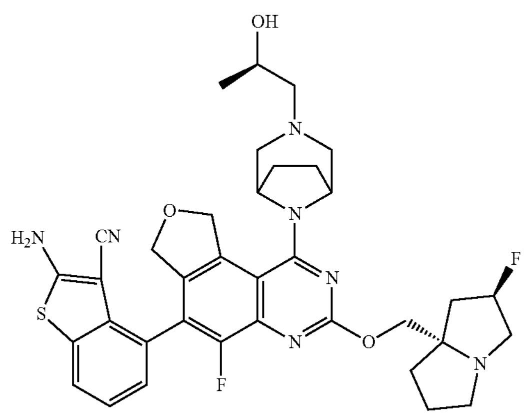 | 688 |
| 162 | 2-Amino-7-fluoro-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 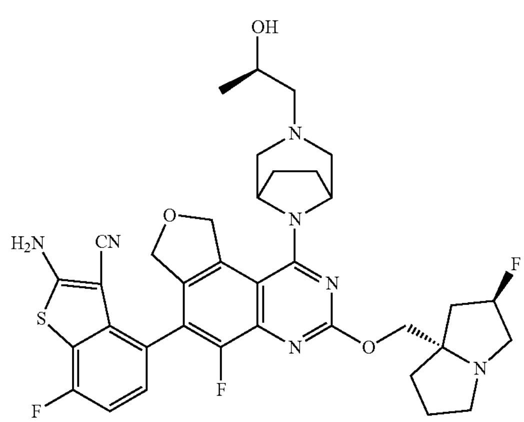 | 705 |

TABLE 16-continued

| Example | Chemical Name | Structure | MS (ES) m/z (M + 1) |
|---|---|---|---|
| 163 | 2-Amino-5-fluoro-4-[5-fluoro-3-[[(2R,8S)-2-fluoro-1,2,3,5,6,7-hexahydropyrrolizin-8-yl]methoxy]-1-[3-[(2S)-3,3,3-trifluoro-2-hydroxy-propyl]-3,8-diazabicyclo[3.2.1]octan-8-yl]-7,9-dihydrofuro[3,4-f]quinazolin-6-yl]benzothiophene-3-carbonitrile, Isomer 1 | 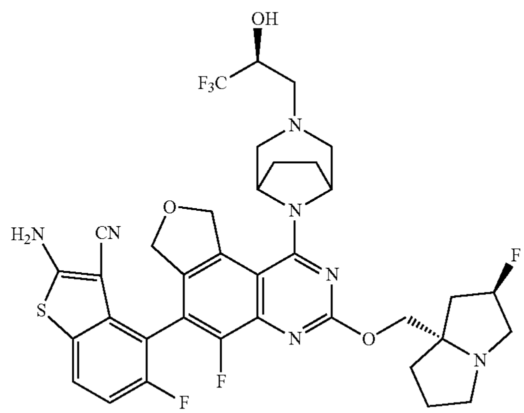 [SMILES: N#Cc1c(N)sc2ccc(F)c(-c3c4c(c5c(N6C7CCC6CN(C[C@H](O)C(F)(F)F)C7)nc(OC[C@@]67CCCN6C[C@H](F)C7)nc5c3F)COC4)c12] | 760 |
| 164 | 2-Amino-5-fluoro-4-[5-fluoro-3-[[(2R,8S)-2-fluoro-1,2,3,5,6,7-hexahydropyrrolizin-8-yl]methoxy]-1-[3-[(2S)-3,3,3-trifluoro-2-hydroxy-propyl]-3,8-diazabicyclo[3.2.1]octan-8-yl]-7,9-dihydrofuro[3,4-f]quinazolin-6-yl]benzothiophene-3-carbonitrile, Isomer 2 | 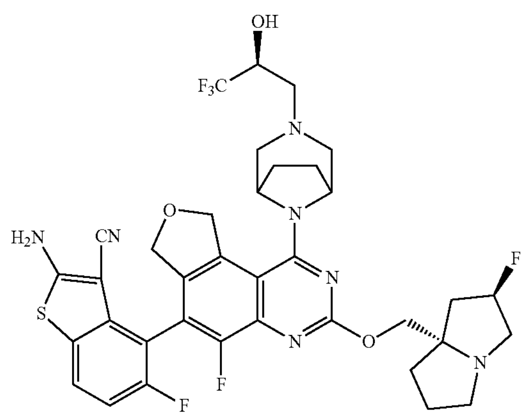 [SMILES: N#Cc1c(N)sc2ccc(F)c(-c3c4c(c5c(N6C7CCC6CN(C[C@H](O)C(F)(F)F)C7)nc(OC[C@@]67CCCN6C[C@H](F)C7)nc5c3F)COC4)c12] | 760 |
| 165 | 2-Amino-5-fluoro-4-[5-fluoro-3-[[(2R,8S)-2-fluoro-1,2,3,5,6,7-hexahydropyrrolizin-8-yl]methoxy]-1-[3-[(2R)-3-fluoro-2-hydroxy-propyl]-3,8-diazabicyclo[3.2.1]octan-8-yl]-7,9-dihydrofuro[3,4-f]quinazolin-6-yl]benzothiophene-3-carbonitrile | 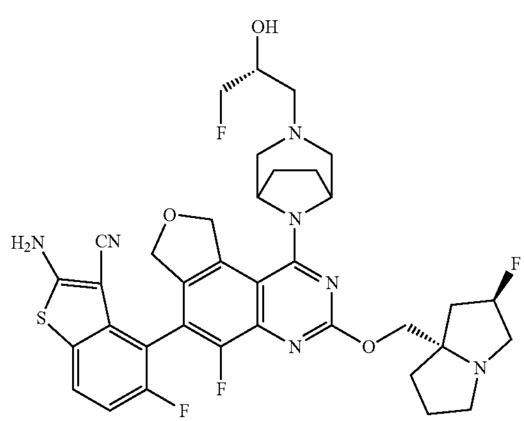 | 724 |

TABLE 16-continued

| Example | Chemical Name | Structure | MS (ES) m/z (M + 1) |
|---|---|---|---|
| 166 | 2-Amino-5-fluoro-4-[5-fluoro-3-[[(2R,8S)-2-fluoro-1,2,3,5,6,7-hexahydropyrrolizin-8-yl]methoxy]-1-[3-(3-fluoro-2-hydroxy-propyl)-3,8-diazabicyclo[3.2.1]octan-8-yl]-7,9-dihydrofuro[3,4-f]quinazolin-6-yl]benzothiophene-3-carbonitrile, Isomer 2 | 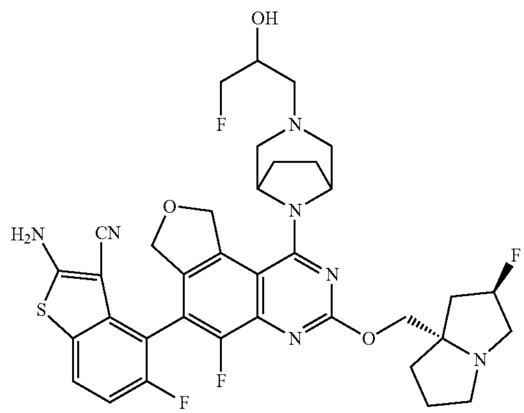 | 724 |
| 167 | 2-Amino-5-fluoro-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 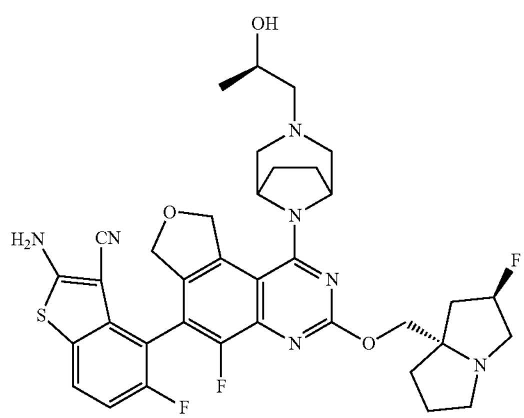 [SMILES: C[C@@H](O)CN1CC2CCC(C1)N2c1nc(OC[C@@]23CCCN2C[C@H](F)C3)nc2c(F)c(-c3c(F)ccc4sc(N)c(C#N)c34)c3c(c12)COC3] | 706 |
| 168 | 2-Amino-5-fluoro-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile, Isomer 2 | 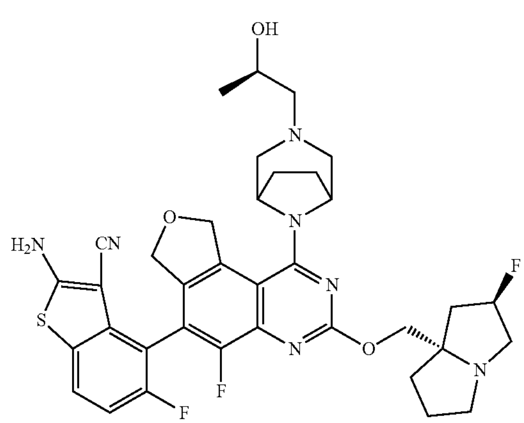 [SMILES: C[C@@H](O)CN1CC2CCC(C1)N2c1nc(OC[C@@]23CCCN2C[C@H](F)C3)nc2c(F)c(-c3c(F)ccc4sc(N)c(C#N)c34)c3c(c12)COC3] | 706 |

TABLE 16-continued

| Example | Chemical Name | Structure | MS (ES) m/z (M + 1) |
|---------|---------------|-----------|---------------------|
| 169[1] | 2-Amino-5-fluoro-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzofuran-3-carbonitrile | 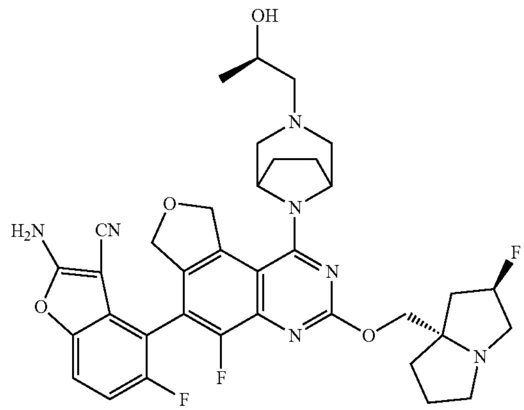 | 690 |
| 170 | 2-Amino-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 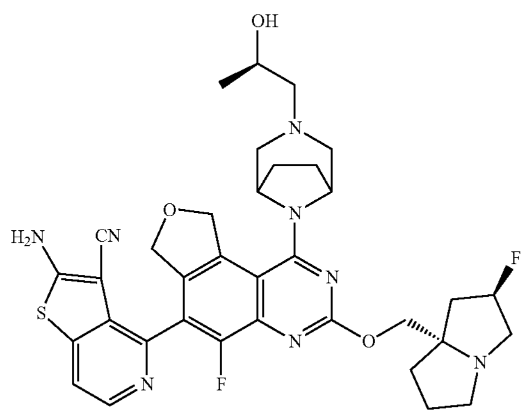 [SMILES: C[C@@H](O)CN1CC2CCC(C1)N2c1nc(OC[C@@]23CCCN2C[C@H](F)C3)nc2c(F)c(-c3nccc4sc(N)c(C#N)c34)c3c(c12)COC3] | 689 |
| 171 | 2-Amino-7-fluoro-4-[5-fluoro-3-[[(2R,8S)-2-fluoro-1,2,3,5,6,7-hexahydropyrrolizin-8-yl]methoxy]-1-[3-[(2S)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 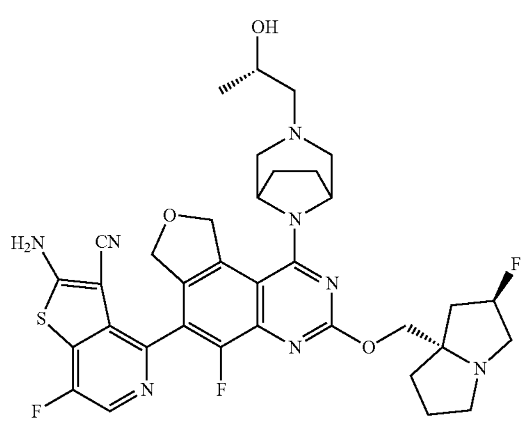 [SMILES: C[C@H](O)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] | 707 |

TABLE 16-continued

| Example | Chemical Name | Structure | MS (ES) m/z (M + 1) |
|---|---|---|---|
| 172 | 2-Amino-7-fluoro-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 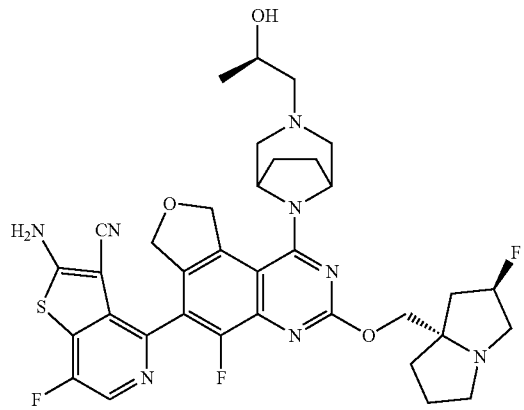 | 707 |
| 173 | 2-Amino-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]-7-methyl-thieno[3,2-c]pyridine-3-carbonitrile | 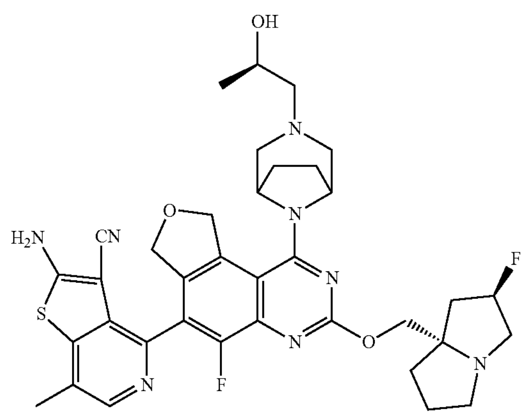 [SMILES: Cc1cnc(-c2c3c(c4c(N5C6CCC5CN(C[C@@H](C)O)C6)nc(OC[C@@]56CCCN5C[C@H](F)C6)nc4c2F)COC3)c2c(C#N)c(N)sc12] | 703 |
| 174 | 2-Amino-7-fluoro-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzofuran-3-carbonitrile | 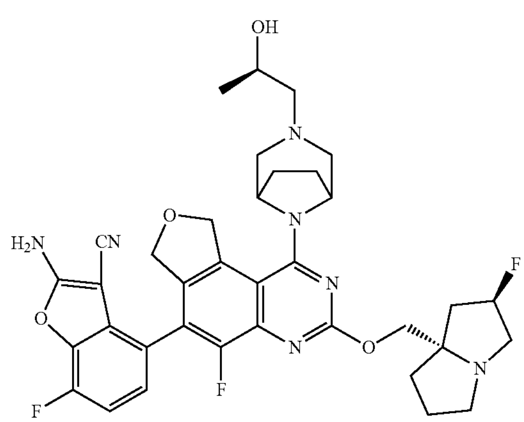 | 690 |

TABLE 16-continued

| Example | Chemical Name | Structure | MS (ES) m/z (M + 1) |
|---|---|---|---|
| 175 | 2-Amino-4-[3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 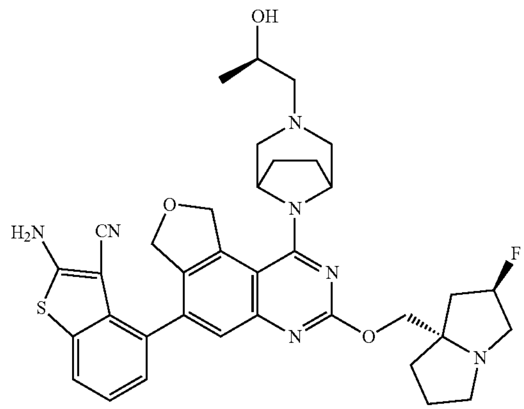 [SMILES: C[C@@H](O)CN1CC2CCC(C1)N2c1nc(OC[C@@]23CCCN2C[C@H](F)C3)nc2cc(-c3cccc4sc(N)c(C#N)c34)c3c(c12)COC3] | 670 |
| 176 | 2-Amino-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzofuran-3-carbonitrile | 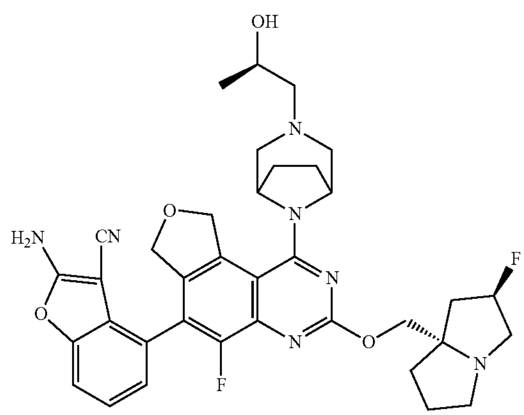 [SMILES: C[C@@H](O)CN1CC2CCC(C1)N2c1nc(OC[C@@]23CCCN2C[C@H](F)C3)nc2c(F)c(-c3cccc4oc(N)c(C#N)c34)c3c(c12)COC3] | 672 |
| 177[2] | 2-Amino-5-fluoro-4-[5-fluoro-1-[3-[(2R)-2-hydroxypropyl]-3,8-diazabicyclo[3.2.1]octan-8-yl]-3-[[(2S)-1-methylpyrrolidin-2-yl]methoxy]-7,9-dihydrofuro[3,4-f]quinazolin-6-yl]benzothiophene-3-carbonitrile | 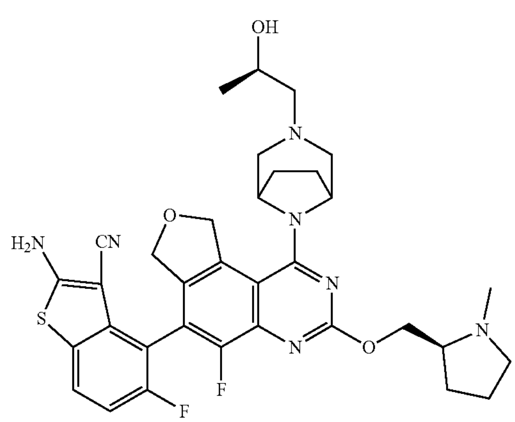 [SMILES: C[C@@H](O)CN1CC2CCC(C1)N2c1nc(OC[C@@H]2CCCN2C)nc2c(F)c(-c3c(F)ccc4sc(N)c(C#N)c34)c3c(c12)COC3] | 662 |

TABLE 16-continued

| Example | Chemical Name | Structure | MS (ES) m/z (M + 1) |
|---|---|---|---|
| 178[2] | 2-Amino-5-fluoro-4-[5-fluoro-3-[[(2S,4R)-4-fluoro-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 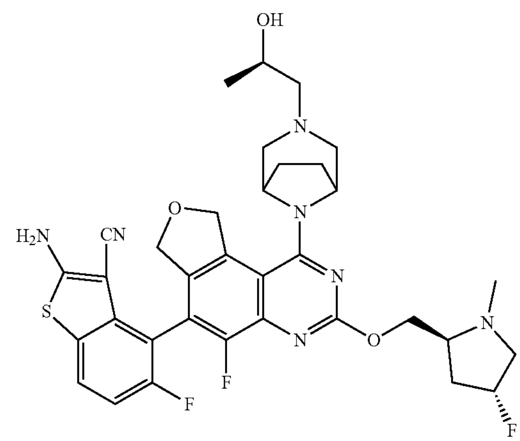 [SMILES: C[C@@H](O)CN1CC2CCC(C1)N2c1nc(OC[C@@H]2C[C@@H](F)CN2C)nc2c(F)c(-c3c(F)ccc4sc(N)c(C#N)c34)c3c(c12)COC3] | 680 |
| 179[2] | 2-Amino-5-fluoro-4-[5-fluoro-1-[3-[(2R)-2-hydroxypropyl]-3,8-diazabicyclo[3.2.1]octan-8-yl]-3-[[(2S)-1-methylazetidin-2-yl]methoxy]-7,9-dihydrofuro[3,4-f]quinazolin-6-yl]benzothiophene-3-carbonitrile | 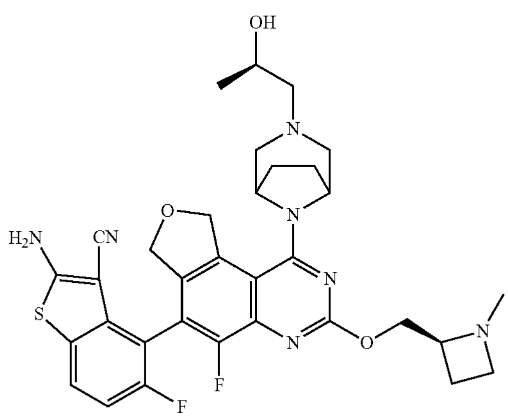 [SMILES: C[C@@H](O)CN1CC2CCC(C1)N2c1nc(OC[C@@H]2CCN2C)nc2c(F)c(-c3c(F)ccc4sc(N)c(C#N)c34)c3c(c12)COC3] | 648 |
| 180[2] | 2-Amino-5-fluoro-4-[5-fluoro-3-[[(2S)-1-(2-hydroxyethyl)azetidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 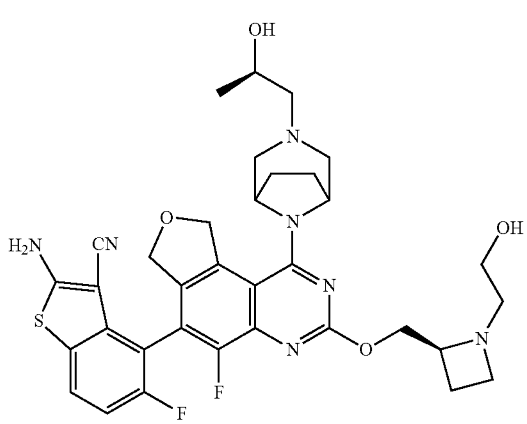 [SMILES: C[C@@H](O)CN1CC2CCC(C1)N2c1nc(OC[C@@H]2CCN2CCO)nc2c(F)c(-c3c(F)ccc4sc(N)c(C#N)c34)c3c(c12)COC3] | 678 |

TABLE 16-continued

| Example | Chemical Name | Structure | MS (ES) m/z (M + 1) |
|---|---|---|---|
| 181[2] | 2-Amino-5-fluoro-4-[5-fluoro-3-[[(2S)-1-(2-hydroxyethyl)pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 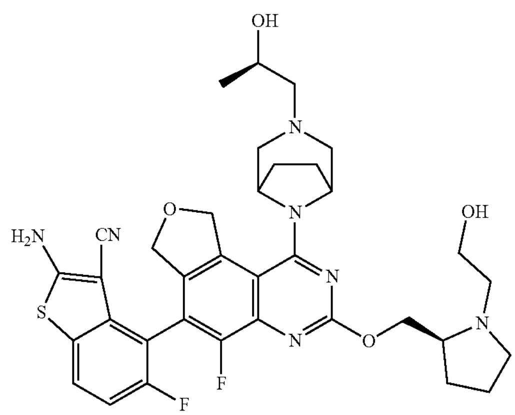 [SMILES: C[C@@H](O)CN1CC2CCC(C1)N2c1nc(OC[C@@H]2CCCN2CCO)nc2c(F)c(-c3c(F)ccc4sc(N)c(C#N)c34)c3c(c12)COC3] | 692 |
| 182[2] | 2-Amino-5-fluoro-4-[5-fluoro-3-[[2-(hydroxymethyl)-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile, Isomer 1 | 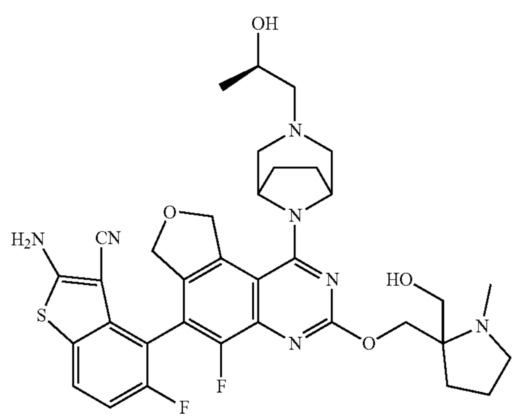 [SMILES: C[C@@H](O)CN1CC2CCC(C1)N2c1nc(OCC2(CO)CCCN2C)nc2c(F)c(-c3c(F)ccc4sc(N)c(C#N)c34)c3c(c12)COC3] | 692 |
| 183[2] | 2-Amino-5-fluoro-4-[5-fluoro-3-[[2-(hydroxymethyl)-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile, Isomer 2 | 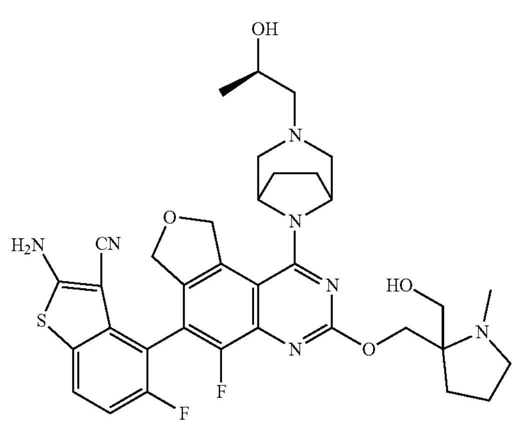 [SMILES: C[C@@H](O)CN1CC2CCC(C1)N2c1nc(OCC2(CO)CCCN2C)nc2c(F)c(-c3c(F)ccc4sc(N)c(C#N)c34)c3c(c12)COC3] | 692 |

TABLE 16-continued

| Example | Chemical Name | Structure | MS (ES) m/z (M + 1) |
|---|---|---|---|
| 184[2] | 2-Amino-5-fluoro-4-[5-fluoro-3-[[(2S,4R)-4-hydroxy-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 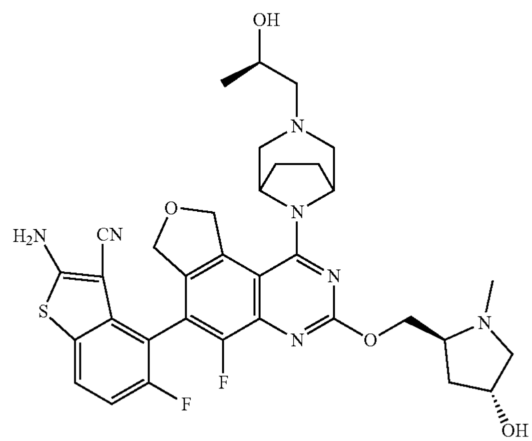 [SMILES: C[C@@H](O)CN1CC2CCC(C1)N2c1nc(OC[C@@H]2C[C@@H](O)CN2C)nc2c(F)c(-c3c(F)ccc4sc(N)c(C#N)c34)c3c(c12)COC3] | 678 |
| 185[2] | 2-Amino-5-fluoro-4-[5-fluoro-3-[[(2R,3S)-3-hydroxy-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 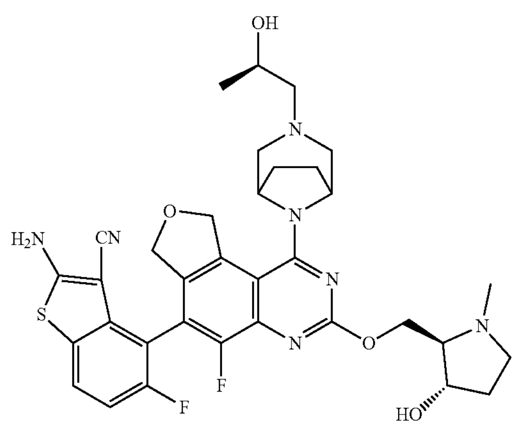 [SMILES: C[C@@H](O)CN1CC2CCC(C1)N2c1nc(OC[C@@H]2[C@@H](O)CCN2C)nc2c(F)c(-c3c(F)ccc4sc(N)c(C#N)c34)c3c(c12)COC3] | 678 |
| 186[2] | 2-Amino-5-fluoro-4-[5-fluoro-3-[[(2S,4S)-4-fluoro-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 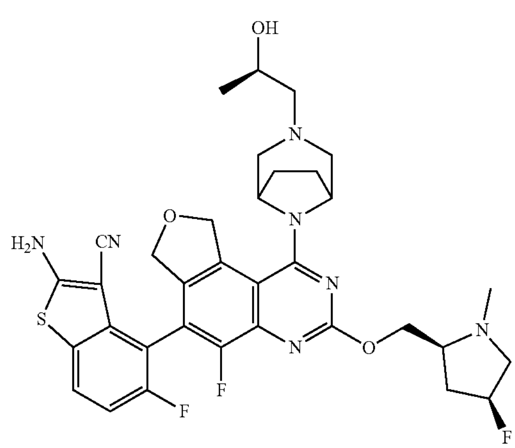 [SMILES: C[C@@H](O)CN1CC2CCC(C1)N2c1nc(OC[C@@H]2C[C@H](F)CN2C)nc2c(F)c(-c3c(F)ccc4sc(N)c(C#N)c34)c3c(c12)COC3] | 680 |

TABLE 16-continued

| Example | Chemical Name | Structure | MS (ES) m/z (M + 1) |
|---|---|---|---|
| 187[2] | 2-Amino-4-[3-[[1-(dimethylamino)cyclopropyl]methoxy]-5-fluoro-1-[3-[(2R)-2-hydroxypropyl]-3,8-diazabicyclo[3.2.1]octan-8-yl]-7,9-dihydrofuro[3,4-f]quinazolin-6-yl]-5-fluoro-benzothiophene-3-carbonitrile | 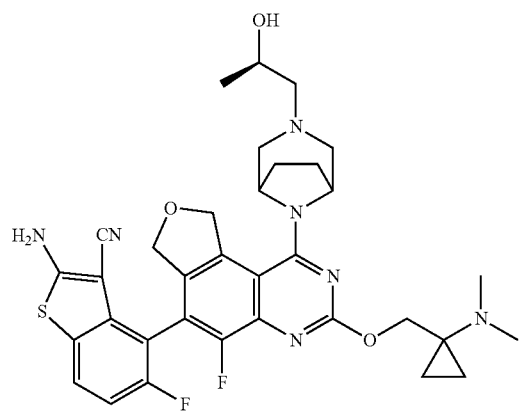 [SMILES: C[C@@H](O)CN1CC2CCC(C1)N2c1nc(OCC2(N(C)C)CC2)nc2c(F)c(-c3c(F)ccc4sc(N)c(C#N)c34)c3c(c12)COC3] | 662 |
| 188[3] | 2-Amino-5-fluoro-4-[5-fluoro-3-[[(2R,8S)-2-fluoro-1,2,3,5,6,7-hexahydropyrrolizin-8-yl]methoxy]-1-[(1R,4R)-5-[(2R)-2-hydroxypropyl]-2,5-diazabicyclo[2.2.1]heptan-2-yl]-7,9-dihydrofuro[3,4-f]quinazolin-6-yl]benzofuran-3-carbonitrile | 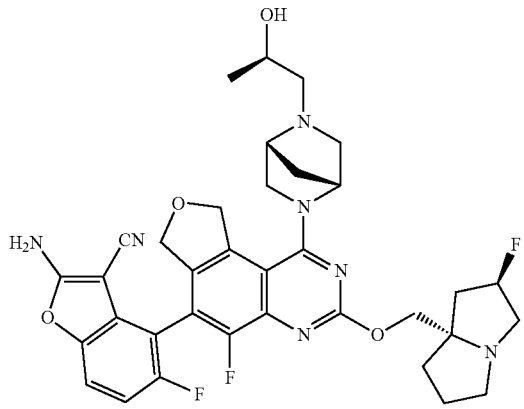 [SMILES: C[C@@H](O)CN1C[C@H]2C[C@@H]1CN2c1nc(OC[C@@]23CCCN2C[C@H](F)C3)nc2c(F)c(-c3c(F)ccc4oc(N)c(C#N)c34)c3c(c12)COC3] | 676 |
| 243[2] | 2-Amino-5-fluoro-4-[5-fluoro-1-[3-[(2R)-2-hydroxypropyl]-3,8-diazabicyclo[3.2.1]octan-8-yl]-3-[[(2S,4R)-4-methoxy-1-methyl-pyrrolidin-2-yl]methoxy]-7,9-dihydrofuro[3,4-f]quinazolin-6-yl]benzothiophene-3-carbonitrile | 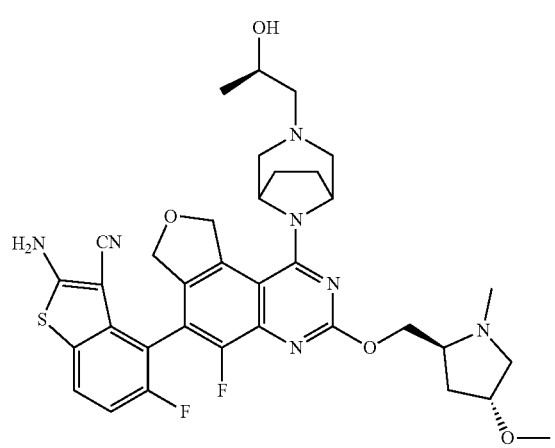 [SMILES: CO[C@@H]1C[C@@H](COc2nc(N3C4CCC3CN(C[C@@H](C)O)C4)c3c4c(c(-c5c(F)ccc6sc(N)c(C#N)c56)c(F)c3n2)COC4)N(C)C1] | 692 |

TABLE 16-continued

| Example | Chemical Name | Structure | MS (ES) m/z (M + 1) |
|---|---|---|---|
| 244 | 2-Amino-7-fluoro-4-[5-fluoro-3-[[(2R,8S)-2-fluoro-1,2,3,5,6,7-hexahydropyrrolizin-8-yl]methoxy]-1-[3-(2-hydroxy-2-methyl-propyl)-3,8-diazabicyclo[3.2.1]octan-8-yl]-7,9-dihydrofuro[3,4-f]quinazolin-6-yl]thieno[3,2-c]pyridine-3-carbonitrile | 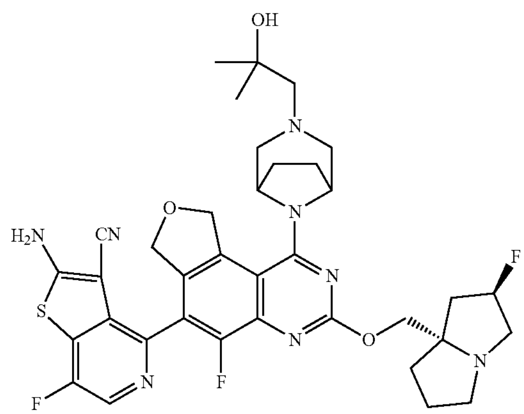 [SMILES: CC(C)(O)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] | 721 |
| 245 | 2-Amino-7-fluoro-4-[5-fluoro-1-[3-[(2R)-2-hydroxypropyl]-3,8-diazabicyclo[3.2.1]octan-8-yl]-3-[[(2S)-1-methylpyrrolidin-2-yl]methoxy]-7,9-dihydrofuro[3,4-f]quinazolin-6-yl]thieno[3,2-c]pyridine-3-carbonitrile | 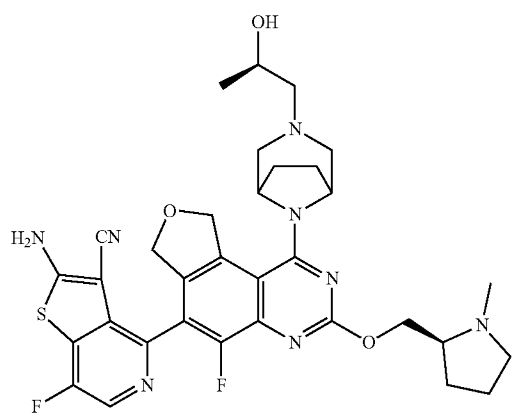 [SMILES: C[C@@H](O)CN1CC2CCC(C1)N2c1nc(OC[C@@H]2CCCN2C)nc2c(F)c(-c3ncc(F)c4sc(N)c(C#N)c34)c3c(c12)COC3] | 663 |
| 246 | 2-Amino-7-fluoro-4-[5-fluoro-3-[[(2S,4R)-4-fluoro-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 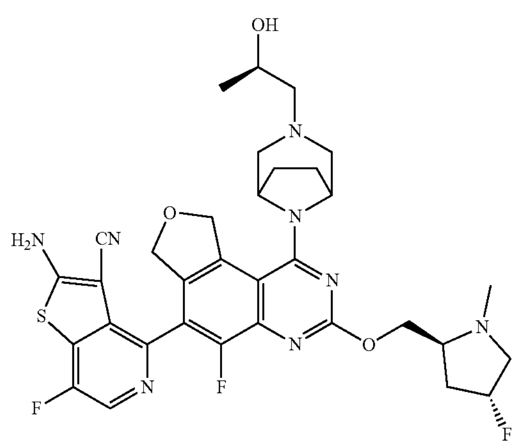 [SMILES: C[C@@H](O)CN1CC2CCC(C1)N2c1nc(OC[C@@H]2C[C@@H](F)CN2C)nc2c(F)c(-c3ncc(F)c4sc(N)c(C#N)c34)c3c(c12)COC3] | 681 |

TABLE 16-continued

| Example | Chemical Name | Structure | MS (ES) m/z (M + 1) |
|---|---|---|---|
| 247 | 2-Amino-7-fluoro-4-[5-fluoro-3-(1,2,3,5,6,7-hexahydropyrrolizin-8-ylmethoxy)-1-[3-[(2R)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 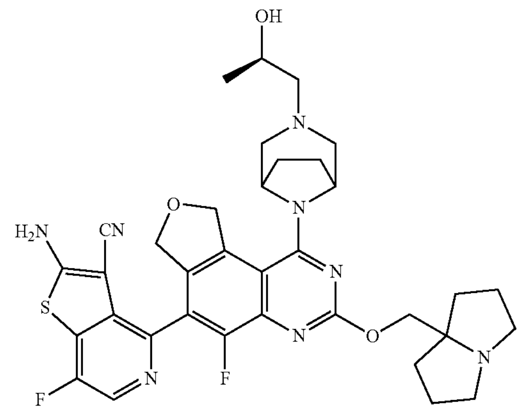 [SMILES: C[C@@H](O)CN1CC2CCC(C1)N2c1nc(OCC23CCCN2CCC3)nc2c(F)c(-c3ncc(F)c4sc(N)c(C#N)c34)c3c(c12)COC3] | 689 |
| 248 | 2-Amino-4-[3-[(6,6-difluoro-2,3,5,7-tetrahydro-1H-pyrrolizin-8-yl)methoxy]-5-fluoro-1-[3-[(2R)-2-hydroxypropyl]-3,8-diazabicyclo[3.2.1]octan-8-yl]-7,9-dihydrofuro[3,4-f]quinazolin-6-yl]-7-fluoro-thieno[3,2-c]pyridine-3-carbonitrile | 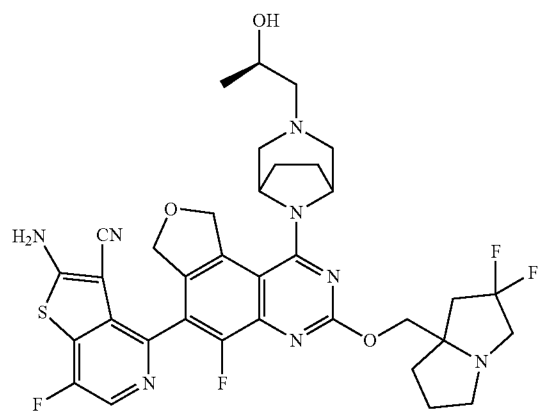 [SMILES: C[C@@H](O)CN1CC2CCC(C1)N2c1nc(OCC23CCCN2CC(F)(F)C3)nc2c(F)c(-c3ncc(F)c4sc(N)c(C#N)c34)c3c(c12)COC3] | 725 |
| 249 | 2-Amino-7-fluoro-4-[5-fluoro-3-[[(2SR,8SR)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 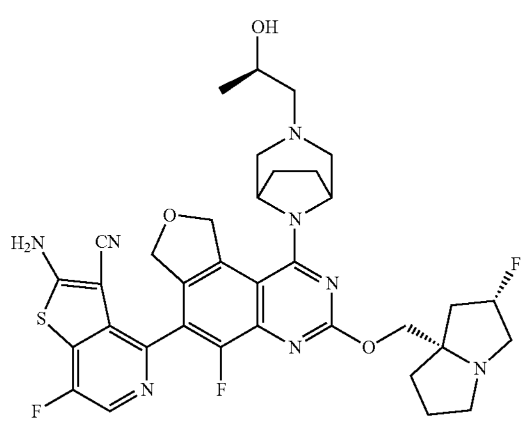 [SMILES: C[C@@H](O)CN1CC2CCC(C1)N2c1nc(OC[C@@]23CCCN2C[C@@H](F)C3)nc2c(F)c(-c3ncc(F)c4sc(N)c(C#N)c34)c3c(c12)COC3] | 707 |

TABLE 16-continued

| Example | Chemical Name | Structure | MS (ES) m/z (M + 1) |
|---|---|---|---|
| 349 | 2-Amino-7-fluoro-4-[5-fluoro-3-[[(3RS,4SR)-4-fluoro-1-methyl-3-piperidyl]methoxy]-1-[3-[(2R)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 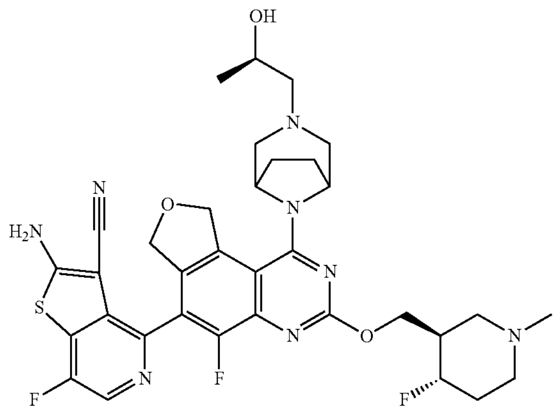 [SMILES: C[C@@H](O)CN1CC2CCC(C1)N2c1nc(OC[C@H]2CN(C)CC[C@@H]2F)nc2c(F)c(-c3ncc(F)c4sc(N)c(C#N)c34)c3c(c12)COC3] | 695 |
| 350 | 2-Amino-7-fluoro-4-[5-fluoro-1-[3-[(2R)-2-hydroxypropyl]-3,8-diazabicyclo[3.2.1]octan-8-yl]-3-(2-imidazol-1-ylethoxy)-7,9-dihydrofuro[3,4-f]quinazolin-6-yl]thieno[3,2-c]pyridine-3-carbonitrile | 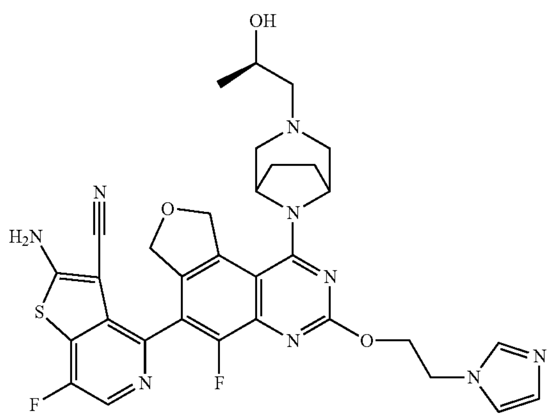 [SMILES: C[C@@H](O)CN1CC2CCC(C1)N2c1nc(OCCn2ccnc2)nc2c(F)c(-c3ncc(F)c4sc(N)c(C#N)c34)c3c(c12)COC3] | 660 |
| 351 | 2-Amino-7-fluoro-4-[5-fluoro-3-[[(2R,3S)-3-fluoro-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 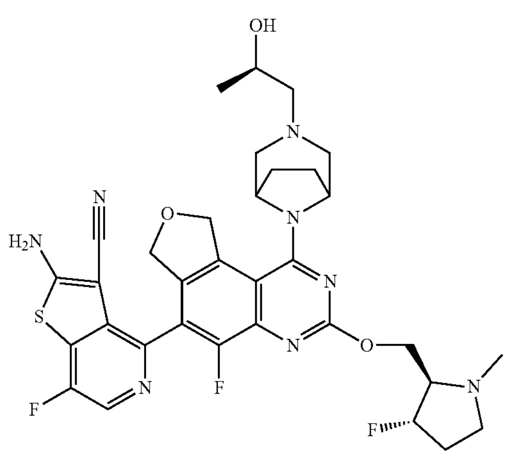 [SMILES: C[C@@H](O)CN1CC2CCC(C1)N2c1nc(OC[C@@H]2[C@@H](F)CCN2C)nc2c(F)c(-c3ncc(F)c4sc(N)c(C#N)c34)c3c(c12)COC3] | 681 |

TABLE 16-continued

| Example | Chemical Name | Structure | MS (ES) m/z (M + 1) |
|---|---|---|---|
| 352 | 2-Amino-7-fluoro-4-[5-fluoro-1-[3-[(2R)-2-hydroxypropyl]-3,8-diazabicyclo[3.2.1]octan-8-yl]-3-[(1SR)-1-[(2RS)-4-methylmorpholin-2-yl]ethoxy]-7,9-dihydrofuro[3,4-f]quinazolin-6-yl]thieno[3,2-c]pyridine-3-carbonitrile | 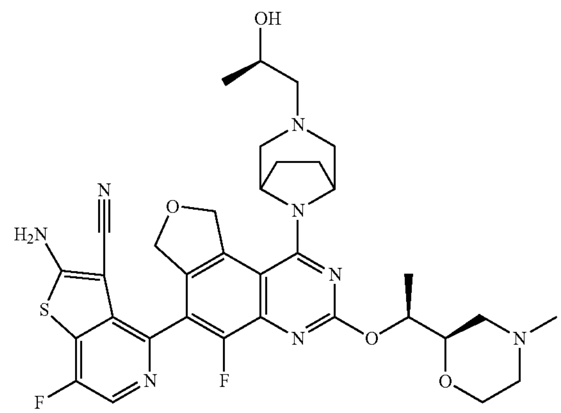 [SMILES: C[C@H](Oc1nc(N2C3CCC2CN(C[C@@H](C)O)C3)c2c3c(c(-c4ncc(F)c5sc(N)c(C#N)c45)c(F)c2n1)COC3)[C@H]1CN(C)CCO1] | 693 |
| 353 | 2-Amino-7-fluoro-4-[5-fluoro-1-[3-[(2R)-2-hydroxypropyl]-3,8-diazabicyclo[3.2.1]octan-8-yl]-3-(2-morpholinoethoxy)-7,9-dihydrofuro[3,4-f]quinazolin-6-yl]thieno[3,2-c]pyridine-3-carbonitrile | 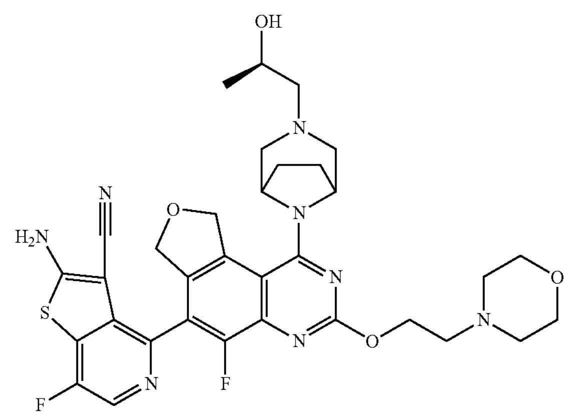 [SMILES: C[C@@H](O)CN1CC2CCC(C1)N2c1nc(OCCN2CCOCC2)nc2c(F)c(-c3ncc(F)c4sc(N)c(C#N)c34)c3c(c12)COC3] | 679 |
| 354[2] | 2-Amino-5-fluoro-4-[5-fluoro-1-[3-[(2R)-2-hydroxypropyl]-3,8-diazabicyclo[3.2.1]octan-8-yl]-3-[[(2R)-4-methylmorpholin-2-yl]methoxy]-7,9-dihydrofuro[3,4-f]quinazolin-6-yl]benzothiophene-3-carbonitrile | 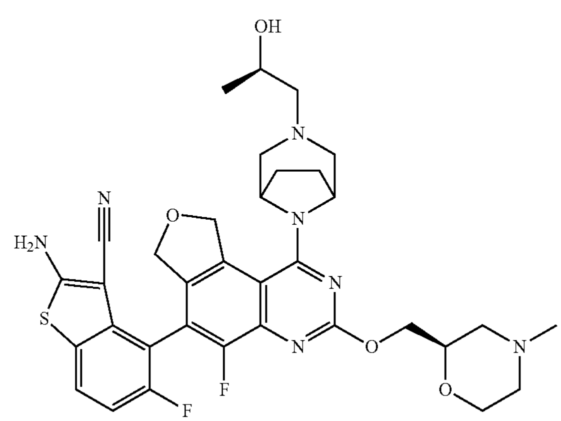 [SMILES: C[C@@H](O)CN1CC2CCC(C1)N2c1nc(OC[C@H]2CN(C)CCO2)nc2c(F)c(-c3c(F)ccc4sc(N)c(C#N)c34)c3c(c12)COC3] | 678 |

TABLE 16-continued

| Example | Chemical Name | Structure | MS (ES) m/z (M + 1) |
|---|---|---|---|
| 355 | 2-Amino-5-fluoro-4-[5-fluoro-3-[[(2S,4R)-4-fluoro-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzofuran-3-carbonitrile | 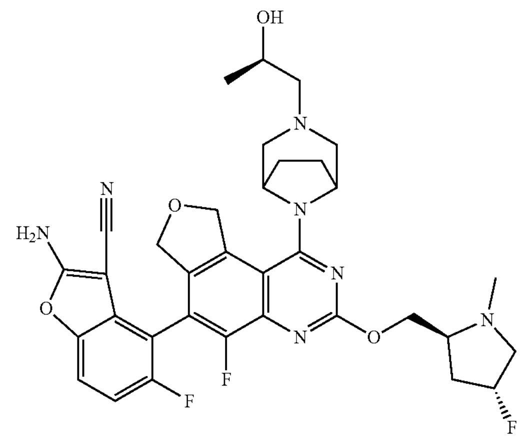 [SMILES: C[C@@H](O)CN1CC2CCC(C1)N2c1nc(OC[C@@H]2C[C@@H](F)CN2C)nc2c(F)c(-c3c(F)ccc4oc(N)c(C#N)c34)c3c(c12)COC3] | 664 |
| 356 | 2-Amino-7-fluoro-4-[5-fluoro-1-[3-[(2R)-2-hydroxypropyl]-3,8-diazabicyclo[3.2.1]octan-8-yl]-3-[(1S)-1-methyl-2-morpholino-ethoxy]-7,9-dihydrofuro[3,4-f]quinazolin-6-yl]thieno[3,2-c]pyridine-3-carbonitrile | 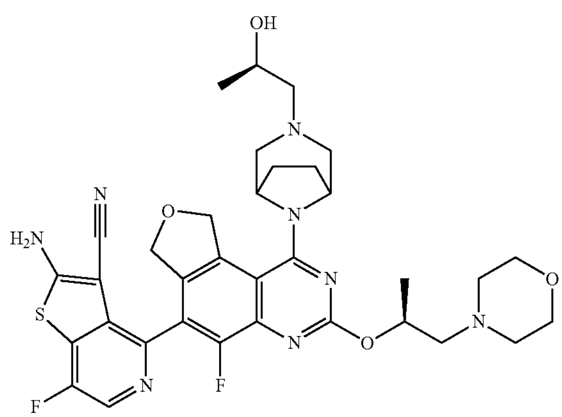 [SMILES: C[C@@H](O)CN1CC2CCC(C1)N2c1nc(O[C@@H](C)CN2CCOCC2)nc2c(F)c(-c3ncc(F)c4sc(N)c(C#N)c34)c3c(c12)COC3] | 693 |
| 357 | 2-Amino-4-[3-[[(2S)-5,5-difluoro-1-methyl-2-piperidyl]methoxy]-5-fluoro-1-[3-[(2R)-2-hydroxypropyl]-3,8-diazabicyclo[3.2.1]octan-8-yl]-7,9-dihydrofuro[3,4-f]quinazolin-6-yl]-7-fluoro-thieno[3,2-c]pyridine-3-carbonitrile | 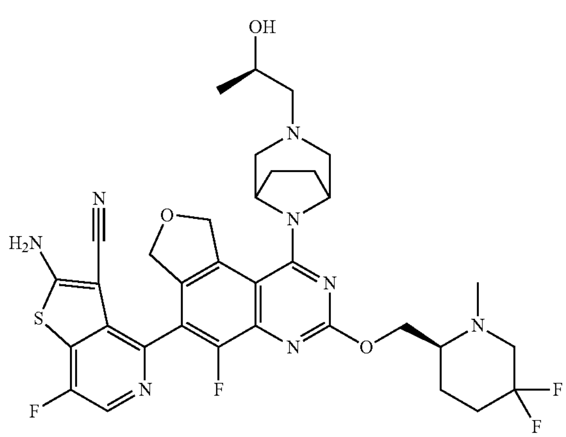 [SMILES: C[C@@H](O)CN1CC2CCC(C1)N2c1nc(OC[C@@H]2CCC(F)(F)CN2C)nc2c(F)c(-c3ncc(F)c4sc(N)c(C#N)c34)c3c(c12)COC3] | 713 |

TABLE 16-continued

| Example | Chemical Name | Structure | MS (ES) m/z (M + 1) |
|---|---|---|---|
| 358 | 2-Amino-7-fluoro-4-[5-fluoro-1-[3-[(2R)-2-hydroxypropyl]-3,8-diazabicyclo[3.2.1]octan-8-yl]-3-[(2S)-2-morpholinopropoxy]-7,9-dihydrofuro[3,4-f]quinazolin-6-yl]thieno[3,2-c]pyridine-3-carbonitrile | 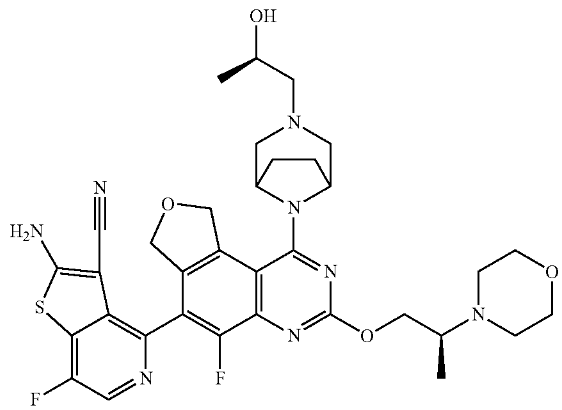 [SMILES: C[C@@H](O)CN1CC2CCC(C1)N2c1nc(OC[C@H](C)N2CCOCC2)nc2c(F)c(-c3ncc(F)c4sc(N)c(C#N)c34)c3c(c12)COC3] | 693 |
| 359 | 2-Amino-4-[3-[(3,3-difluoro-1-methyl-2-piperidyl)methoxy]-5-fluoro-1-[3-[(2R)-2-hydroxypropyl]-3,8-diazabicyclo[3.2.1]octan-8-yl]-7,9-dihydrofuro[3,4-f]quinazolin-6-yl]-7-fluoro-thieno[3,2-c]pyridine-3-carbonitrile | 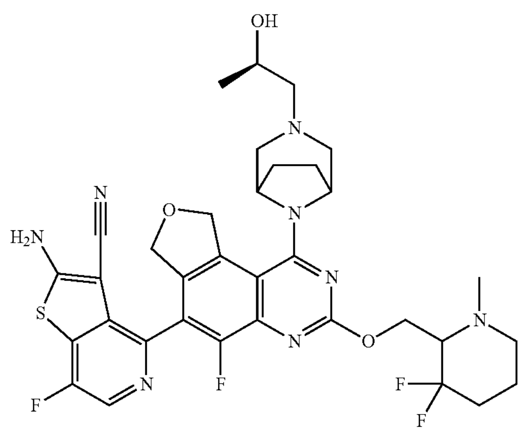 [SMILES: C[C@@H](O)CN1CC2CCC(C1)N2c1nc(OCC2N(C)CCCC2(F)F)nc2c(F)c(-c3ncc(F)c4sc(N)c(C#N)c34)c3c(c12)COC3] | 713 |
| 360 | 2-Amino-4-[3-[2-(4-ethyl-3-oxo-piperazin-1-yl)ethoxy]-5-fluoro-1-[3-[(2R)-2-hydroxypropyl]-3,8-diazabicyclo[3.2.1]octan-8-yl]-7,9-dihydrofuro[3,4-f]quinazolin-6-yl]-7-fluoro-thieno[3,2-c]pyridine-3-carbonitrile | 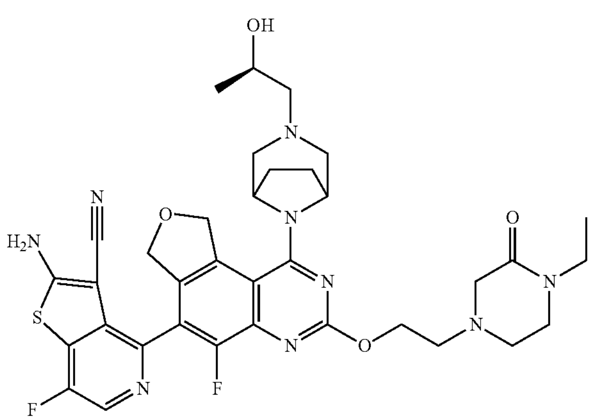 [SMILES: CCN1CCN(CCOc2nc(N3C4CCC3CN(C[C@@H](C)O)C4)c3c4c(c(-c5ncc(F)c6sc(N)c(C#N)c56)c(F)c3n2)COC4)CC1=O] | 720 |

TABLE 16-continued

| Example | Chemical Name | Structure | MS (ES) m/z (M + 1) |
|---------|---------------|-----------|---------------------|
| 361 | 2-Amino-4-[3-[(1-cyanocyclopropyl)methoxy]-5-fluoro-1-[3-[(2R)-2-hydroxypropyl]-3,8-diazabicyclo[3.2.1]octan-8-yl]-7,9-dihydrofuro[3,4-f]quinazolin-6-yl]-7-fluoro-thieno[3,2-c]pyridine-3-carbonitrile | 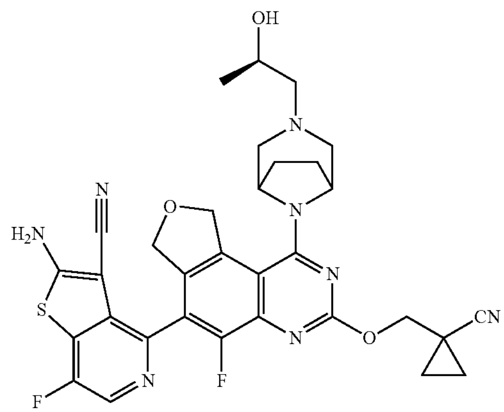 [SMILES: C[C@@H](O)CN1CC2CCC(C1)N2c1nc(OCC2(C#N)CC2)nc2c(F)c(-c3ncc(F)c4sc(N)c(C#N)c34)c3c(c12)COC3] | 645 |
| 362 | 2-Amino-4-[3-[(3,3-difluoro-1-methyl-pyrrolidin-2-yl)methoxy]-5-fluoro-1-[3-[(2R)-2-hydroxypropyl]-3,8-diazabicyclo[3.2.1]octan-8-yl]-7,9-dihydrofuro[3,4-f]quinazolin-6-yl]-7-fluoro-thieno[3,2-c]pyridine-3-carbonitrile | 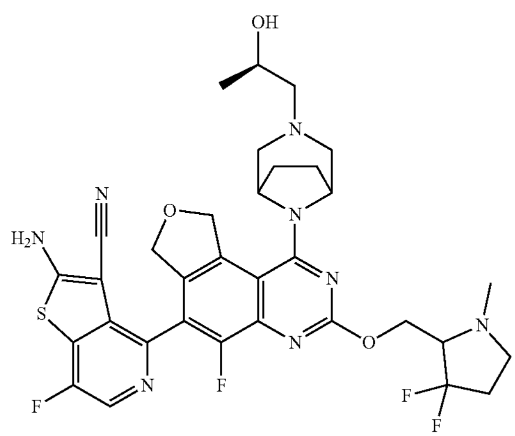 [SMILES: C[C@@H](O)CN1CC2CCC(C1)N2c1nc(OCC2N(C)CCC2(F)F)nc2c(F)c(-c3ncc(F)c4sc(N)c(C#N)c34)c3c(c12)COC3] | 699 |
| 363 | 2-Amino-4-[1-[3-[(2R)-2-ethoxypropyl]-3,8-diazabicyclo[3.2.1]octan-8-yl]-5-fluoro-3-[[(2S,4R)-4-fluoro-1-methyl-pyrrolidin-2-yl]methoxy]-7,9-dihydrofuro[3,4-f]quinazolin-6-yl]-7-fluoro-thieno[3,2-c]pyridine-3-carbonitrile | 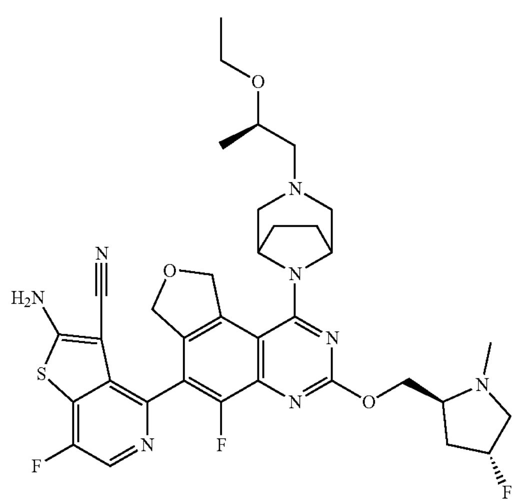 [SMILES: CCO[C@H](C)CN1CC2CCC(C1)N2c1nc(OC[C@@H]2C[C@@H](F)CN2C)nc2c(F)c(-c3ncc(F)c4sc(N)c(C#N)c34)c3c(c12)COC3] | 709 |

TABLE 16-continued

| Example | Chemical Name | Structure | MS (ES) m/z (M + 1) |
|---|---|---|---|
| 364 | 2-Amino-7-fluoro-4-[5-fluoro-3-[[(2S,4R)-4-fluoro-1-methyl-pyrrolidin-2-yl]methoxy]-1-[3-[(2R)-2-methoxypropyl]-3,8-diazabicyclo[3.2.1]octan-8-yl]-7,9-dihydrofuro[3,4-f]quinazolin-6-yl]thieno[3,2-c]pyridine-3-carbonitrile; acetic acid | 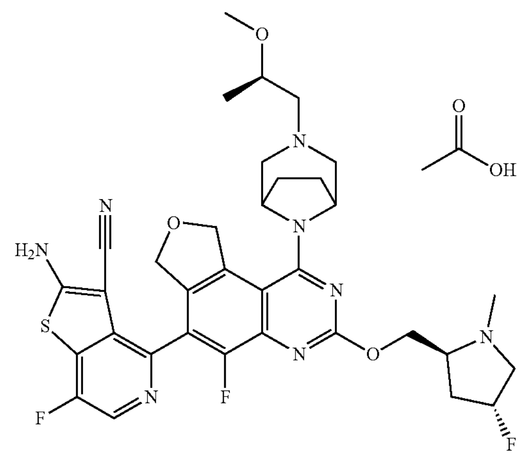 | 695 |
| 365 | 2-Amino-7-fluoro-4-[5-fluoro-3-[[1-(2-hydroxyacetyl)-4-piperidyl]methoxy]-1-[3-[(2R)-2-methoxypropyl]-3,8-diazabicyclo[3.2.1]octan-8-yl]-7,9-dihydrofuro[3,4-f]quinazolin-6-yl]thieno[3,2-c]pyridine-3-carbonitrile; acetic acid | 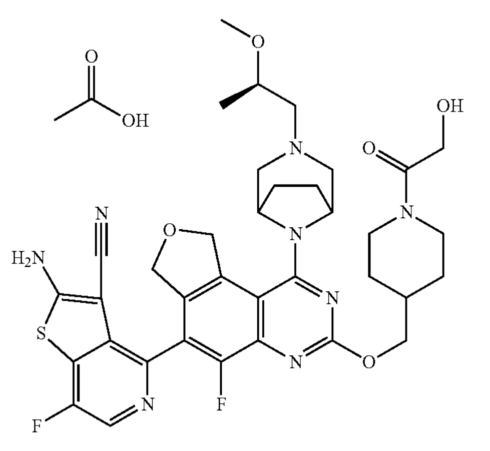 | 735 |
| 366 | 2-Amino-5-fluoro-4-[5-fluoro-1-[3-[(2R)-2-hydroxypropyl]-3,6-diazabicyclo[3.1.1]heptan-6-yl]-3-[[(2R)-4-methylmorpholin-2-yl]methoxy]-7,9-dihydrofuro[3,4-f]quinazolin-6-yl]benzothiophene-3-carbonitrile, Isomer 1 | 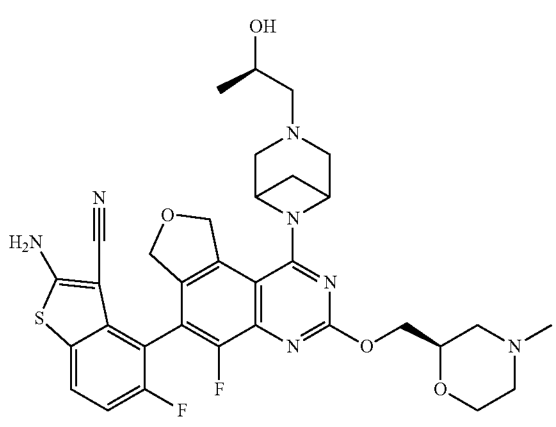 [SMILES: C[C@@H](O)CN1CC2CC(C1)N2c1nc(OC[C@H]2CN(C)CCO2)nc2c(F)c(-c3c(F)ccc4sc(N)c(C#N)c34)c3c(c12)COC3] | 664 |

TABLE 16-continued

| Example | Chemical Name | Structure | MS (ES) m/z (M + 1) |
|---------|---------------|-----------|---------------------|
| 367 | 2-Amino-5-fluoro-4-[5-fluoro-3-[[(2S,4R)-4-fluoro-1-methyl-pyrrolidin-2-yl]methoxy]-1-[3-[(2R)-2-hydroxypropyl]-3,6-diazabicyclo[3.1.1]heptan-6-yl]-7,9-dihydrofuro[3,4-f]quinazolin-6-yl]benzothiophene-3-carbonitrile | 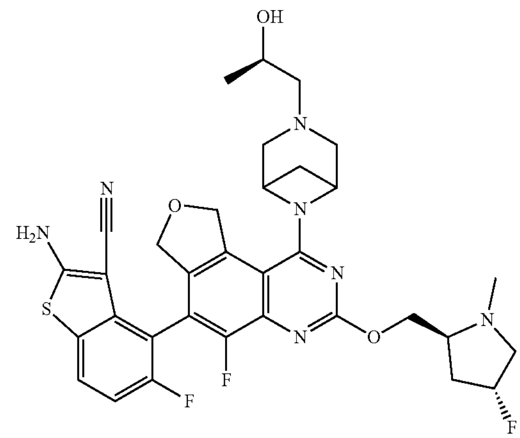 [SMILES: C[C@@H](O)CN1CC2CC(C1)N2c1nc(OC[C@@H]2C[C@@H](F)CN2C)nc2c(F)c(-c3c(F)ccc4sc(N)c(C#N)c34)c3c(c12)COC3] | 666 |
| 368 | 2-Amino-5-fluoro-4-[5-fluoro-3-[[(2S,4R)-4-fluoro-1-methyl-pyrrolidin-2-yl]methoxy]-1-[3-[(2R)-2-hydroxypropyl]-3,6-diazabicyclo[3.1.1]heptan-6-yl]-7,9-dihydrofuro[3,4-f]quinazolin-6-yl]benzothiophene-3-carbonitrile, Isomer 1 | 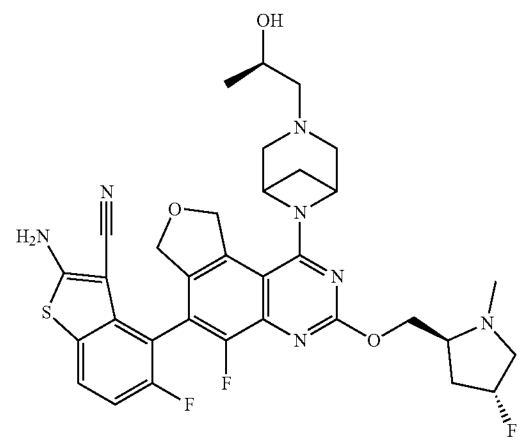 [SMILES: C[C@@H](O)CN1CC2CC(C1)N2c1nc(OC[C@@H]2C[C@@H](F)CN2C)nc2c(F)c(-c3c(F)ccc4sc(N)c(C#N)c34)c3c(c12)COC3] | 666 |
| 369 | 2-Amino-7-fluoro-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,6-diazabicyclo[3.1.1]heptan-6-yl]-7,9-dihydrofuro[3,4-f]quinazolin-6-yl]thieno[3,2-c]pyridine-3-carbonitrile | 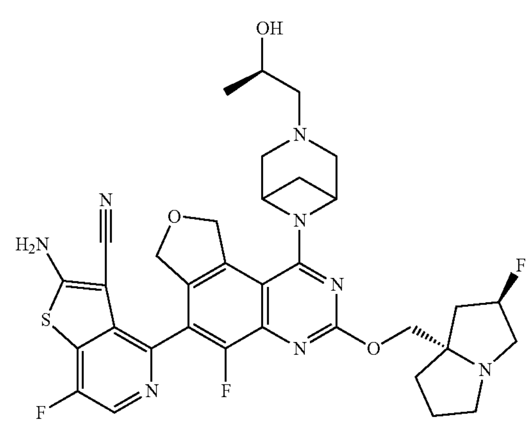 [SMILES: C[C@@H](O)CN1CC2CC(C1)N2c1nc(OC[C@@]23CCCN2C[C@H](F)C3)nc2c(F)c(-c3ncc(F)c4sc(N)c(C#N)c34)c3c(c12)COC3] | 693 |

TABLE 16-continued

| Example | Chemical Name | Structure | MS (ES) m/z (M + 1) |
|---|---|---|---|
| 370 | 2-Amino-7-fluoro-4-[5-fluoro-3-[[(2R,8S)-2-fluoro-1,2,3,5,6,7-hexahydropyrrolizin-8-yl]methoxy]-1-[3-[(2R)-2-hydroxypropyl]-3-azabicyclo[3.2.1]octan-8-yl]-7,9-dihydrofuro[3,4-f]quinazolin-6-yl]thieno[3,2-c]pyridine-3-carbonitrile | 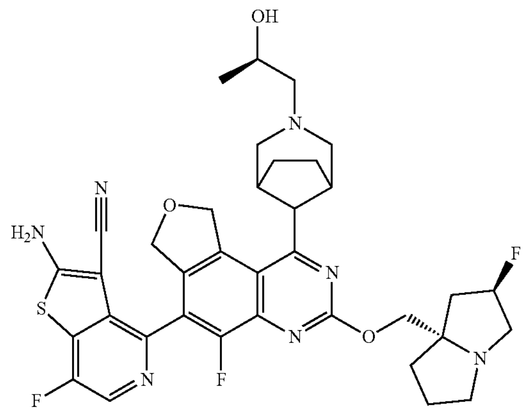 [SMILES: C[C@@H](O)CN1CC2CCC(C1)C2c1nc(OC[C@@]23CCCN2C[C@H](F)C3)nc2c(F)c(-c3ncc(F)c4sc(N)c(C#N)c34)c3c(c12)COC3] | 706 |

[1] single atropisomer (from precursor in Preparation 296)
[2] single atropisomer (from precursor in Preparation 248)
[3] single atropisomer (from precursor in Preparation 298)

Examples 56 and 57

2-Amino-4-[5-fluoro-3-[[(2R,8S)-2-fluoro-1,2,3,5,6,7-hexahydropyrrolizin-8-yl]methoxy]-1-[3-[(2S)-2-hydroxypropyl]-3,8-diazabicyclo[3.2.1]octan-8-yl]-7,9-dihydrofuro[3,4-f]quinazolin-6-yl]benzothiophene-3-carbonitrile and 2-Amino-4-[5-fluoro-1-[3-[(2S)-2-hydroxypropyl]-3,8-diazabicyclo[3.2.1]octan-8-yl]-3-methoxy-7,9-dihydrofuro[3,4-f]quinazolin-6-yl]benzothiophene-3-carbonitrile

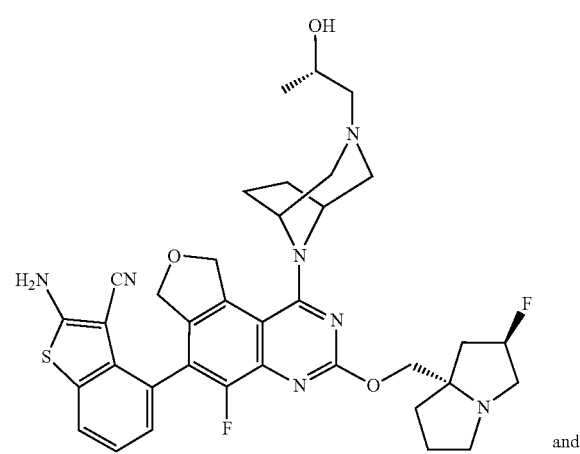

and

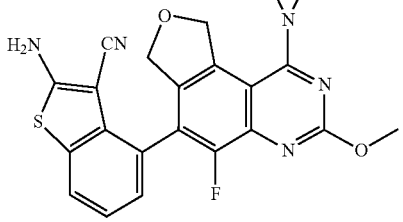

2-Amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]benzothiophene-3-carbonitrile was used in a manner analogous to the method described in Example 55 using (S)-(−)-propylene oxide and heating the reaction at 70° C. for ~18 h. Upon purification of the residue by reversed phase flash purification on C18, eluting with 5% to 50% ACN in 10 mM aq. NH$_4$HCO$_3$ with 5% MeOH, two products were isolated to give 2-amino-4-[5-fluoro-3-[[(2R,8S)-2-fluoro-1,2,3,5,6,7-hexahydropyrrolizin-8-yl]methoxy]-1-[3-[(2S)-2-hydroxypropyl]-3,8-diazabicyclo[3.2.1]octan-8-yl]-7,9-dihydrofuro[3,4-f]quinazolin-6-yl]benzothiophene-3-carbonitrile (0.033 g, 37%) as a peach-colored solid, MS (ES) m/z=688 (M+1), and 2-amino-4-[5-fluoro-1-[3-[(2S)-2-hydroxypropyl]-3,8-diazabicyclo[3.2.1]octan-8-yl]-3-methoxy-7,9-dihydrofuro[3,4-f]quinazolin-6-yl]benzothiophene-3-carbonitrile (0.020 g, 26%) as an off-white solid. MS (ES) m/z=561 (M+1).

Example 189

3-[8-[6-(2-amino-3-cyano-5-fluoro-benzothiophen-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]-N-methyl-propanamide

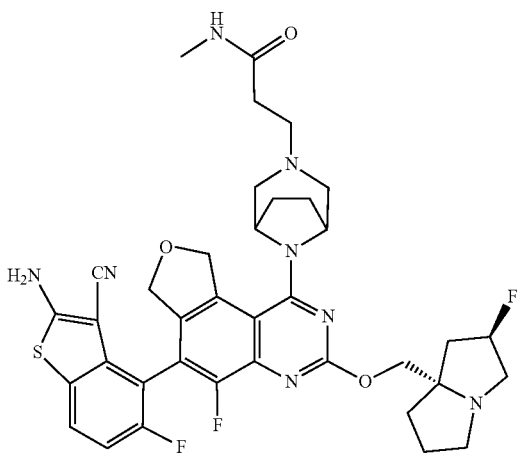 [SMILES: CNC(=O)CCN1CC2CCC(C1)N2c1nc(OC[C@@]23CCCN2C[C@H](F)C3)nc2c(F)c(-c3c(F)ccc4sc(N)c(C#N)c34)c3c(c12)COC3]

A mixture of 2-amino-4-[1-(3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-5-fluoro-benzothiophene-3-carbonitrile (single atropisomer, from precursor in Preparation 248, 0.060 g, 0.093 mmol), 3-chloro-N-methylpropanamide (0.056 g, 0.465 mmol), potassium iodide (0.0077 g, 0.046 mmol), and triethylamine (0.019 g, 0.186 mmol) in acetonitrile (3 mL) was heated at 80° C. for ~12 h. The mixture was concentrated, diluted with DMF (2 mL), and purified by reversed phase flash purification on C18, eluting with 35% to 51% ACN in 10 mM aq. $NH_4HCO_3$ with 0.1% $NH_4OH$, to give the title compound (0.021 g, 30%) as a white solid. MS (ES) m/z=733 (M+1).

The Example compounds in Table 17 were prepared in a similar manner as described for Example 189. Various methods were used to purify the compounds, which would be apparent to one skilled in the art. Chiral purification methods (if applicable) for the Examples of Table 17 are located in Table 18.

TABLE 17

| Example | Chemical Name | Structure | MS (ES) m/z (M + 1) |
|---|---|---|---|
| 190[1] | 3-[8-[6-(2-Amino-3-cyano-5-fluoro-benzothiophen-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]-N,N-dimethyl-propanamide | 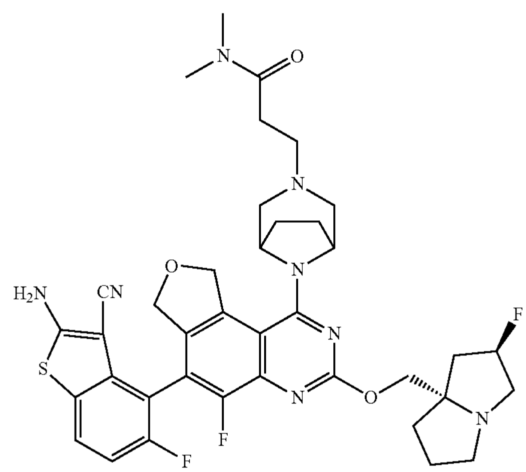 [SMILES: CN(C)C(=O)CCN1CC2CCC(C1)N2c1nc(OC[C@@]23CCCN2C[C@H](F)C3)nc2c(F)c(-c3c(F)ccc4sc(N)c(C#N)c34)c3c(c12)COC3] | 747 |
| 191[1] | 2-Amino-5-fluoro-4-[5-fluoro-3-[[(2R,8S)-2-fluoro-1,2,3,5,6,7-hexahydropyrrolizin-8-yl]methoxy]-1-[3-(trideuteriomethyl)-3,8-diazabicyclo[3.2.1]octan-8-yl]-7,9-dihydrofuro[3,4-f]quinazolin-6-yl]benzothiophene-3-carbonitrile | 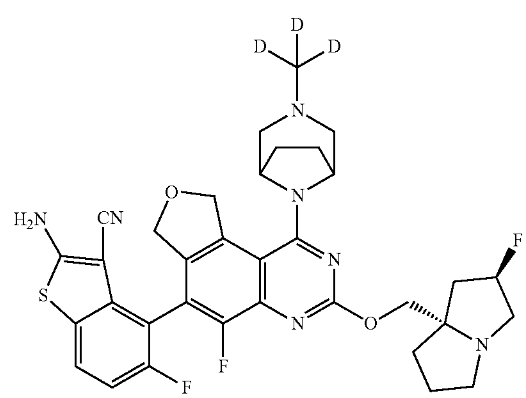 [SMILES: [2H]C([2H])([2H])N1CC2CCC(C1)N2c1nc(OC[C@@]23CCCN2C[C@H](F)C3)nc2c(F)c(-c3c(F)ccc4sc(N)c(C#N)c34)c3c(c12)COC3] | 665 |

TABLE 17-continued

| Example | Chemical Name | Structure | MS (ES) m/z (M + 1) |
|---|---|---|---|
| 192[2] | 2-Amino-5-fluoro-4-[5-fluoro-3-[[(2R,8S)-2-fluoro-1,2,3,5,6,7-hexahydropyrrolizin-8-yl]methoxy]-1-[3-(trideuteriomethyl)-3,6-diazabicyclo[3.1.1]heptan-6-yl]-7,9-dihydrofuro[3,4-f]quinazolin-6-yl]benzothiophene-3-carbonitrile | 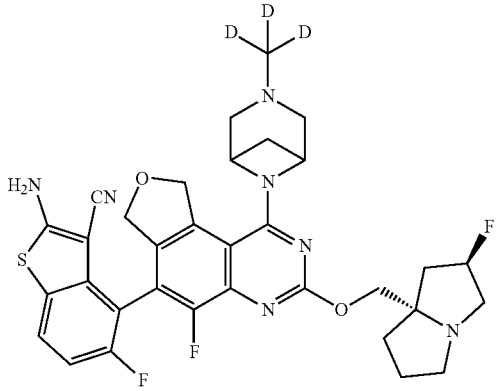 [SMILES: [2H]C([2H])([2H])N1CC2CC(C1)N2c1nc(OC[C@@]23CCCN2C[C@H](F)C3)nc2c(F)c(-c3c(F)ccc4sc(N)c(C#N)c34)c3c(c12)COC3] | 692 |
| 193 | 2-Amino-7-fluoro-4-[5-fluoro-3-[[(2R,8S)-2-fluoro-1,2,3,5,6,7-hexahydropyrrolizin-8-yl]methoxy]-1-[3-[2-(trifluoromethoxy)ethyl]-3,8-diazabicyclo[3.2.1]octan-8-yl]-7,9-dihydrofuro[3,4-f]quinazolin-6-yl]thieno[3,2-c]pyridine-3-carbonitrile | 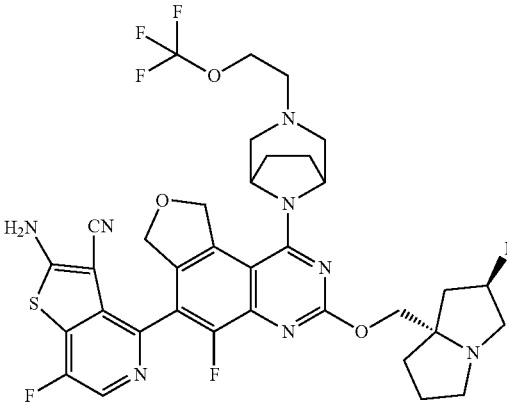 | 761 |
| 250 | 3-[8-[6-(2-Amino-3-cyano-7-fluoro-thieno[3,2-c]pyridin-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]-N,N-dimethyl-propanamide | 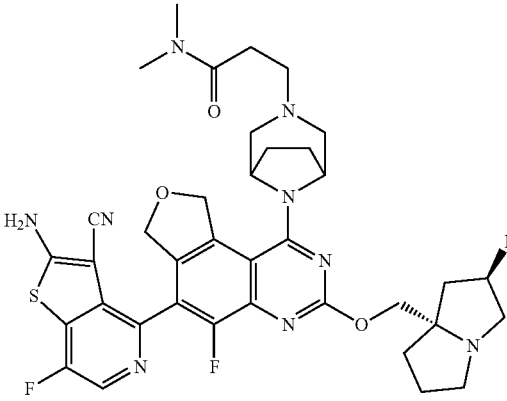 | 748 |

TABLE 17-continued

| Example | Chemical Name | Structure | MS (ES) m/z (M + 1) |
|---|---|---|---|
| 371 | 2-Amino-4-[1-[3-[2-(difluoromethoxy)ethyl]-3,8-diazabicyclo[3.2.1]octan-8-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-thieno[3,2-c]pyridine-3-carbonitrile | 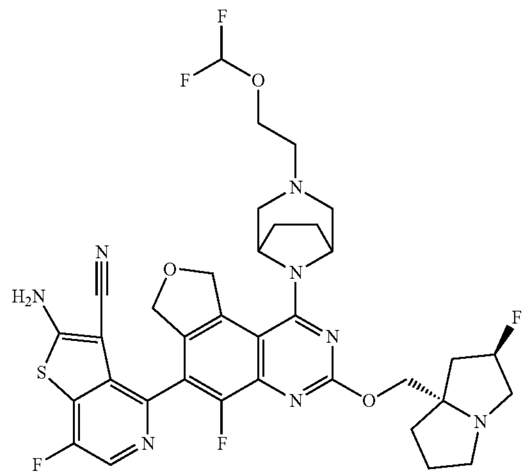 [SMILES: N#Cc1c(N)sc2c(F)cnc(-c3c4c(c5c(N6C7CCC6CN(CCOC(F)F)C7)nc(OC[C@@]67CCCN6C[C@H](F)C7)nc5c3F)COC4)c12] | 743 |
| 372 | 2-Amino-7-fluoro-4-[5-fluoro-3-[[(2R,8S)-2-fluoro-1,2,3,5,6,7-hexahydropyrrolizin-8-yl]methoxy]-1-[3-(3-fluoropropyl)-3,8-diazabicyclo[3.2.1]octan-8-yl]-7,9-dihydrofuro[3,4-f]quinazolin-6-yl]thieno[3,2-c]pyridine-3-carbonitrile | 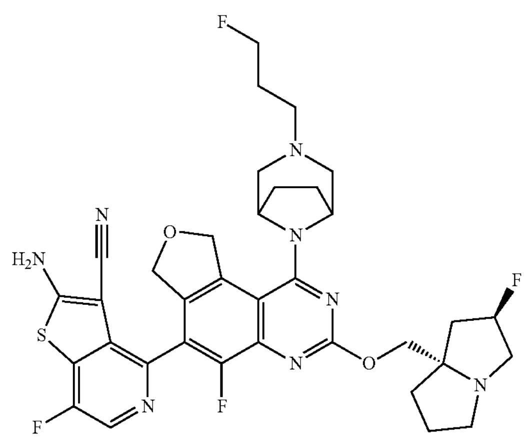 [SMILES: N#Cc1c(N)sc2c(F)cnc(-c3c4c(c5c(N6C7CCC6CN(CCCF)C7)nc(OC[C@@]67CCCN6C[C@H](F)C7)nc5c3F)COC4)c12] | 709 |
| 373 | 2-Amino-7-fluoro-4-[5-fluoro-1-[3-(2-fluoroethyl)-3,8-diazabicyclo[3.2.1]octan-8-yl]-3-[[(2S,4R)-4-fluoro-1-methyl-pyrrolidin-2-yl]methoxy]-7,9-dihydrofuro[3,4-f]quinazolin-6-yl]thieno[3,2-c]pyridine-3-carbonitrile | 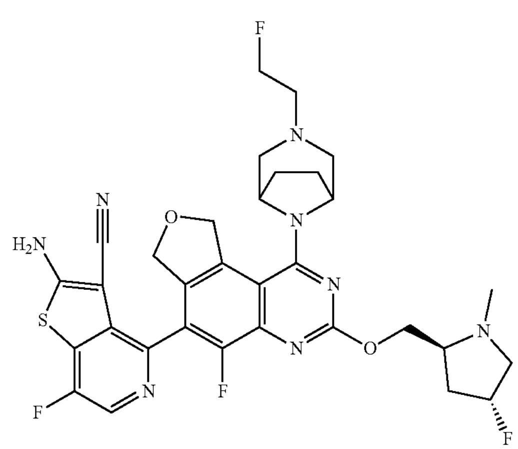 [SMILES: CN1C[C@H](F)C[C@H]1COc1nc(N2C3CCC2CN(CCF)C3)c2c3c(c(-c4ncc(F)c5sc(N)c(C#N)c45)c(F)c2n1)COC3] | 669 |

TABLE 17-continued

| Example | Chemical Name | Structure | MS (ES) m/z (M + 1) |
|---|---|---|---|
| 374 | 2-Amino-7-fluoro-4-[5-fluoro-1-[3-(2-fluoroethyl)-3,8-diazabicyclo[3.2.1]octan-8-yl]-3-[[(2R,8S)-2-fluoro-1,2,3,5,6,7-hexahydropyrrolizin-8-yl]methoxy]-7,9-dihydrofuro[3,4-f]quinazolin-6-yl]thieno[3,2-c]pyridine-3-carbonitrile | 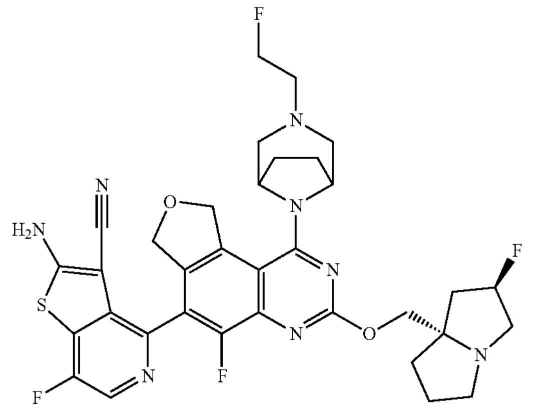 [SMILES: N#Cc1c(N)sc2c(F)cnc(-c3c4c(c5c(N6C7CCC6CN(CCF)C7)nc(OC[C@@]67CCCN6C[C@H](F)C7)nc5c3F)COC4)c12] | 695 |

[1]single atropisomer (from precursor in Preparation 248)
[2]single atropisomer (from precursor in Preparation 266)

Example 194

3-[8-[6-(2-Amino-5,7-difluoro-1,3-benzothiazol-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl] propan-1-ol

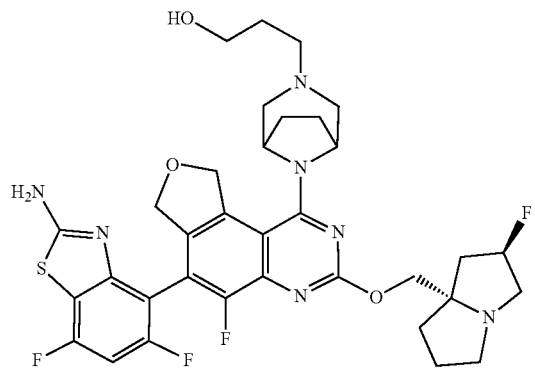 [SMILES: Nc1nc2c(-c3c4c(c5c(N6C7CCC6CN(CCCO)C7)nc(OC[C@@]67CCCN6C[C@H](F)C7)nc5c3F)COC4)c(F)cc(F)c2s1]

tert-Butyl N-[4-[1-[3-[3-[tert-butyl(dimethyl)silyl]oxypropyl]-3,8-diazabicyclo[3.2.1]octan-8-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-5,7-difluoro-1,3-benzothiazol-2-yl]carbamate was used in an analogous manner to the method of Example 1 to obtain the title compound (0.028 g, 16%). MS (ES) m/z=700 (M+1). Chiral purification methods for the Example compounds in Tables 14-17 are in Table 18.

TABLE 18

Purification Methods.

| Example | Method | Stationary Phase | Mobile Phase |
|---|---|---|---|
| 3 | SFC | Chiralpak ® IC[a] | 40% MeOH (w/0.5% DMEA): $CO_2$ |
| 4 | SFC | Chiralpak ® AD-H[a] | 35% IPA (w/0.5% DMEA): $CO_2$ |
| 5 | SFC | Chiralpak ® AD-H[a] | 35% EtOH (w/0.5% DMEA): $CO_2$ |
| 9 | SFC | Chiralpak ® AS-H[a] | 30% EtOH (w/0.5% DMEA): $CO_2$ |
| 15 | SFC | Chiralpak ® IC[a] | 40% MeOH (w/0.5% DMEA): $CO_2$ |
| 21 | SFC | Chiralpak ® IC[a] | 40% EtOH (w/0.5% DMEA): $CO_2$ |
| 22 | Chiral HPLC | CHIRAL ART Cellulose SB ™,[c] | A: Hexanes (10 mM $NH_3$—MeOH); B: EtOH; Isocratic 30% B |
| 29 | SFC | Lux ® Cellulose[d] | 40% EtOH (w/0.5% DMEA): $CO_2$ |
| 30 | Chiral HPLC | Chiralpak ® IE[a] | A: Hexanes (10 mM $NH_3$—MeOH); B: EtOH; Isocratic 20% B |
| 31 | Chiral HPLC | Chiralpak ® IE[a] | A: Hexanes (10 mM $NH_3$—MeOH); B: EtOH; Isocratic 30% B |
| 34 | Chiral HPLC | Chiralpak ® IE[a] | A: Hex (10 mM $NH_3$—MeOH); B: EtOH; Isocratic 20% B |
| 35 | Chiral HPLC | Chiralpak ® IE[a] | A: Hex(10 mM $NH_3$—MeOH); B: EtOH; Isocratic 20% B |
| 36 | Chiral HPLC | Chiralpak ® IE[a] | A: Hex (10 mM $NH_3$—MeOH); B: EtOH; Isocratic 70% B |
| 38 | Chiral HPLC | Chiralpak ® IE[a] | A: Hex (10 mM $NH_3$—MeOH); B: EtOH; Isocratic 20% B |
| 39 | Chiral HPLC | Chiralpak ® IE[a] | A: Hex (10 mM $NH_3$—MeOH); B: DCM:EtOH = 9:1; Isocratic 20% B |
| 40 | 1) Chiral HPLC 2) Chiral HPLC | 1) Chiralpak ® IE[a] 2) CHIRAL ART Amylose-C NEO ™,[c] | 1) A: Hex (10 mM $NH_3$—MeOH); B: EtOH; Isocratic 30% B 2) Hex (10 mM $NH_3$—MeOH); B: EtOH; Isocratic 15% B |

TABLE 18-continued

Purification Methods.

| Example | Method | Stationary Phase | Mobile Phase |
|---|---|---|---|
| 41 | 1) Chiral HPLC<br>2) Chiral HPLC | 1) Chiralpak ® IE[a]<br>2) Chiralpak ® IE[a] | 1) A: Hex (10 mM NH$_3$—MeOH); B: EtOH: MeOH = 1:3; Isocratic 20% B<br>2) A: MTBE (10 mM NH$_3$—MeOH); B: EtOH: IPA = 1:1; Isocratic 20% B |
| 43 | SFC | Chiralpak ® IG[a] | 50% EtOH (0.5% 2M NH$_3$—MeOH): CO$_2$ |
| 44 | SFC | Chiralcel ® OJ-H[a] | 25% EtOH (0.5% DMEA): CO$_2$ |
| 53 | SFC | Chiralpak ® AS-H[a] | 25% MeOH (w/0.5% DMEA): CO$_2$ |
| 99 | SFC | Chiralpak ® AD-H[a] | 30% IPA (w/0.5% DMEA): CO$_2$ |
| 102 | SFC | Chiralpak ® AD-H[a] | 30% IPA (w/0.5% DMEA): CO$_2$ |
| 103 | SFC | Chiralpak ® AD-H[a] | 30% IPA (w/0.5% DMEA): CO$_2$ |
| 105 | SFC | Chiralpak ® AD-H[a] | 40% IPA (w/0.5% DMEA): CO$_2$ |
| 106 | SFC | Chiralpak ® AD-H[a] | 40% IPA (w/0.5% DMEA): CO$_2$ |
| 107 | SFC | Chiralpak ® AS-H[a] | 30% EtOH (w/0.5% DMEA): CO$_2$ |
| 116 | SFC | Chiralpak ® ICa | 40% IPA (w/0.5% DMEA): CO$_2$ |
| 158 | SFC | Chiralpak ® ICa | 50% EtOH (w/0.5% DMEA): CO$_2$ |
| 160 | SFC | Chiralpak ® AD-H[a] | 35% IPA (w/0.5% DMEA): CO$_2$ |
| 161 | SFC | Chiralpak ® AD-H[a] | 35% IPA (w/0.5% DMEA): CO$_2$ |
| 166 | SFC | Chiralpak ® AS-H[a] | 25% MeOH (w/0.5% DMEA): CO$_2$ |
| 168 | SFC | Chiralpak ® AD-H[a] | 30% IPA (w/0.5% DMEA): CO$_2$ |
| 182 | Chiral HPLC | Chiralpak ® IE[a] | A: 1:1 Hex:MTBE (0 w/ 0.1% DMEA); B: EtOH; Isocratic 15% B |
| 183 | Chiral HPLC | Chiralpak ® IE[a] | A: 1:1 Hex:MTBE (0 w/ 0.1% DMEA); B: EtOH; Isocratic 15% B |
| 207 | SFC | Chiralpak ® AD-H[a] | 35% IPA (w/0.5% DMEA): CO$_2$ |
| 208 | SFC | Chiralpak ® AD-H[a] | 35% IPA (w/0.5% DMEA): CO$_2$ |
| 209 | SFC | Lux ® Cellulose[d] | 50% MeOH (w/0.5% DMEA): CO$_2$ |
| 210 | SFC | Lux ® Cellulose[d] | 50% MeOH (w/0.5% DMEA): CO$_2$ |
| 214 | SFC | Chiralpak ® AS-H[a] | 25% MeOH (w/0.5% DMEA): CO$_2$ |
| 328 | SFC | Chiralpak ® AD-H[a] | 30% EtOH (w/0.5% DMEA): CO$_2$ |
| 329 | SFC | Chiralpak ® AD-H[a] | 30% EtOH (w/0.5% DMEA): CO$_2$ |
| 330 | SFC | Chiralpak ® IH[a] | 40% MeOH (w/0.5% DMEA): CO$_2$ |
| 331 | SFC | Chiralpak ® IH[a] | 40% MeOH (w/0.5% DMEA): CO$_2$ |
| 340 | SFC | Chiralpak ® AS-H[a] | 30% MeOH (w/0.5% DMEA): CO$_2$ |
| 366 | SFC | Chiralpak ® IC-H[a] | 35% MeOH (w/0.5% DMEA): CO$_2$ |
| 368 | SFC | Chiralpak ® IC-H[a] | 35% EtOH (w/0.5% DMEA): CO$_2$ |

[a]Chiralpak ® Columns available from Daicel Chiral Technologies; West Chester, PA.
[b]XBridge Columns available from Waters Corp.; Milford, MA.
[c]Chiral ART Columns available from YMC America, Inc.; Devens, MA.
[d]Lux ® Columns available from Phenomenex, Inc.; Torrance, CA.

Biological Assays

The following assays demonstrate that the exemplified compounds are potent inhibitors of Kras G12D and inhibit growth of certain tumors in vitro and/or in vivo.

Example 376

PANC-1 Cellular Active RAS GTPase ELISA (KRas G12D Mutation)

The purpose of this assay is to measure the ability of test compounds to inhibit constitutive RAS GTPase activity in human PANC-1 (RRID:CVCL_0480) pancreatic ductal adenocarcinoma cells (Supplier: ATCC #CRL-1469). The RAS GTPase ELISA kit (Active Motif Cat #52097) contains a 96-well glutathione-coated capture plate and kit-supplied Glutathione-S-Transferase (GST)-fused to Raf-Ras Binding Domain (RBD) protein. Activated pan-RAS (GTP-bound) in cell extracts specifically bind to the Raf-RBD. Bound RAS is detected with a primary Ras antibody that recognizes human K-Ras (and H-Ras). An HRP-conjugated anti-rat IgG secondary antibody recognizes the primary antibody, and a development substrate solution facilitates a chemiluminescent readout.

PANC-1 cells are plated at a concentration of 75,000 cells/well in 80 µL complete media (DMEM, high-glucose, L-glutamine, GIBCO; 10% heat-inactivated fetal bovine serum, GIBCO) and incubated overnight at 37° C./5% CO$_2$. Approximately 24 hours later, 20 µL of (1:3) serially-diluted (in complete media) test compound (1-50 µM top concentration) and 20 µL of serially-diluted (in complete media) controls (Maximum signal wells: 0.5% DMSO and Minimum signal wells: 10 µM reference positive control compound) are added to the cell plate and incubated for 2 hours at 37° C./5% CO$_2$. Complete Lysis/Binding Buffer is prepared containing Protease Inhibitor cocktail (PIC) and stored on ice. One hour before cell plate incubation is completed, GST-Raf-RBD is diluted in lysis/binding buffer, and 50 µL of mixed buffer per well is added to the supplied opaque white ELISA assay plate and is incubated for a minimum of 1 hour at 4° C., with gently rocking. After 2 hours, the cells are washed with 100 µL ice-cold Ca2+/Mg2+-free PBS and lysed with 100 µL of kit supplied lysis/binding buffer (AM11). After 30-50 minutes of vigorous plate shaking at ambient temperature, cell plate is centrifuged at 410×g (approx. 1500 rpm) for 10 minutes. Wash buffer diluted to 1× with ultrapure H$_2$O and 0.2 µm filtered is prepared at ambient temperature during the centrifugation step and then used to wash (3×100 µL) the GST-Raf-RBD coated assay plate. Next, 50 µL of cell lysate is added to the GST-Raf-RBD coated assay plate and incubated for 1 hour at ambient temperature with gentle shaking. During this incubation period, 1× Antibody Binding Buffer is prepared from thawed concentrate. The assay plate is washed 3×100 µL with 1× Wash Buffer, and then 50 µL of Primary RAS Antibody (kit supplied #101678), diluted 1:500 in 1× Antibody Binding buffer, is added. After a one hour of ambient incubation with gentle shaking, the assay plate is washed 3×100 µL with 1× Wash Buffer. Subsequently, 50 µL of Anti-rat HRP-conjugated IgG secondary antibody (0.25 µg/µL) (diluted 1:5000 in 1× Antibody Binding buffer) is added to each well of the assay plate and incubated an additional hour at ambient temperature with gentle shaking. Finally, the assay plate is washed 4×100 µL with 1× Wash buffer, followed by addition of 50 µL of mixed ambient temperature chemiluminescent working solution (combination of Reaction buffer with a chemiluminescence substrate). Data from each well's luminescent emission is recorded with a 2104 EnVision™ Plate Reader (Perkin Elmer) using a luminescence program optimized for the assay plate dimensions.

The signal is converted to percent inhibition using the following equation: % Inhibition=100−[(Test Compound Signal −Median Minimum Signal)/(Median Maximum Signal −Median Minimum Signal)×100]. The Maximum signal is a control well without inhibitor (DMSO). The Minimum signal is a control well containing a reference inhibitor sufficient to fully inhibit activity. The $IC_{50}$ is determined by fitting the percent inhibition at each inhibitor concentration to the four parameter nonlinear logistic equation using Genedata Screener®, v17: $y=(A+((B-A)/(1+((x/C)^D))))$ where, y=% inhibition, A=minimum asymptote, B=maximum asymptote, C=relative $IC_{50}$ or the inhibitor concentration producing 50% inhibition within the fitted range of both asymptotes, and D=Hill Slope.

In the above assay, compounds of Examples 1-5, 7-12, 14-18, 20-26, 28-59, 62, 64, 67, 68, 93-192, 194, 206-209, 211-239, 241-250, 279, 323, 327, 328, 331, 332, 334, 336, 340-345, 348, 351, 354-356, 358, 363, 364, 367-372, and 374 all exhibited an ability to inhibit constitutive RAS GTPase activity indicating inhibition of KRas G12D mutant enzyme with a relative $IC_{50}$ of <100 nM. This data shows that compounds of Formulae I-VIII (including Ia-VIIa) as described herein are potent inhibitors of KRAS-GTP activity in this human pancreatic cancer cell culture demonstrating the ability to inhibit KRas G12D mutants.

Example 377

MKN-45 Cellular Active RAS GTPase ELISA
(KRas Wild-type)

The purpose of this assay is to measure the ability of test compounds to inhibit constitutive RAS GTPase activity in human MKN-45 gastric adenocarcinoma cell (Supplier: JCRB, SupplierID: JCRB 0254, Lot:05222009). The RAS GTPase ELISA kit (Active Motif Cat #52097) contains a 96-well glutathione-coated capture plate and kit-supplied Glutathione-S-Transferase (GST)-fused to Raf-Ras Binding Domain (RBD) protein. Activated pan-RAS (GTP-bound) in cell extracts specifically bind to the Raf-RBD. Bound RAS is detected with a primary Ras antibody that recognizes human K-Ras (and H-Ras). An HRP-conjugated anti-rat IgG secondary antibody recognizes the primary antibody, and a development substrate solution facilitates a chemiluminescent readout.

MKN-45 cells are plated at a concentration of 75,000 cells/well in 80 µL complete media (DMEM, high-glucose, L-glutamine, GIBCO; 10% heat-inactivated fetal bovine serum, GIBCO) and incubated overnight at 37° C./5% $CO_2$. Approximately 24 hours later, 20 µL of (1:3) serially-diluted (in complete media) test compound (1-10 µM top concentration) and 20 µL of serially-diluted (in complete media) controls (Maximum signal wells: 0.1% DMSO and Minimum signal wells: 10 µM reference positive control compound) are added to the cell plate and incubated for 2 hours at 37° C./5% $CO_2$. Complete Lysis/Binding Buffer is prepared containing Protease Inhibitor cocktail (PIC) and stored on ice. One hour before cell plate incubation is completed, GST-Raf-RBD is diluted in lysis/binding buffer, and 50 µL of mixed buffer per well is added to the supplied opaque white ELISA assay plate and is incubated for a minimum of 1 hour at 4° C., with gently rocking. After 2 hours, the cells are washed with 100 µL ice-cold Ca2+/Mg2+-free PBS and lysed with 100 µL of kit supplied lysis/binding buffer (AM11). After 30-50 minutes of vigorous plate shaking at ambient temperature, cell plate is centrifuged at 410×g (approx. 1500 rpm) for 10 minutes. Wash buffer diluted to 1× with ultrapure $H_2O$ during the centrifugation step and then used to wash (3×100 µL) the GST-Raf-RBD coated assay plate. Next, 50 µL of cell lysate is added to the GST-Raf-RBD coated assay plate and incubated for 1 hour at ambient temperature with gentle shaking. During this incubation period, 1× Antibody Binding Buffer is prepared from thawed concentrate. The assay plate is washed 3×100 µL with 1× Wash Buffer, and then 50 µL of Primary RAS Antibody (kit supplied #101678), diluted 1:500 in 1× Antibody Binding buffer, is added. After a one hour of ambient incubation with gentle shaking, the assay plate is washed 3×100 µL with 1× Wash Buffer. Subsequently, 50 µL of Anti-rat HRP-conjugated IgG secondary antibody (0.25 µg/µL) (diluted 1:5000 in 1× Antibody Binding buffer) is added to each well of the assay plate and incubated an additional hour at ambient temperature with gentle shaking. Finally, the assay plate is washed 4×100 µL with 1× Wash buffer, followed by addition of 50 µL of mixed ambient temperature chemiluminescent working solution (combination of Reaction buffer with a chemiluminescence substrate). Data from each well's luminescent emission is recorded with a 2104 EnVision™ Plate Reader (Perkin Elmer) using a luminescence program optimized for the assay plate dimensions.

The signal is converted to percent inhibition using the following equation: % Inhibition=100−[(Test Compound Signal −Median Minimum Signal)/(Median Maximum Signal −Median Minimum Signal)×100]. The Maximum signal is a control well without inhibitor (DMSO). The Minimum signal is a control well containing a reference inhibitor sufficient to fully inhibit activity. The $IC_{50}$ is determined by fitting the percent inhibition at each inhibitor concentration to the four parameter nonlinear logistic equation using Genedata Screener®, v17: $y=(A+((B-A)/(1+((x/C)^D))))$ where, y=% inhibition, A=minimum asymptote, B=maximum asymptote, C=relative $IC_{50}$ or the inhibitor concentration producing 50% inhibition within the fitted range of both asymptotes, and D=Hill Slope.

Compounds of Examples 1, 3, 5, 7, 9-11, 13-18, 20, 22-28, 45, 46, 48, 49, 51-58, 62, 64, 68, 95, 96, 98-100, 103, 106-108, 110, 113, 114, 116-127, 130-146, 148-151, 153, 156-158, 161, 162, 170-187, 189-192, 194, 212-214, 216-218, 220, 224-229, 231, 232, 234-239, 241-243, 247-249, 327, 328, 330-332, 334-338, 340, 341, 343, 344, 348, 349, 351, 354-356, 358, 363, 364, 366, 367, and 372-374 were tested in both assays above (PANC-1 Cellular Active RAS GTPase ELISA and MKN-45 Cellular Active RAS GTPase ELISA) and all showed a significant (i.e., greater than 10-fold) selective inhibition preference for KRas G12D mutant over KRas wild-type.

Example 378

Cellular Phospho-ERK AlphaLISA® Assay for
KRAS Inhibition

The purpose of these assays is to quantify the ability of test compounds to selectively inhibit KRAS signaling in cells with amplified KRAS and expressing activating KRAS G12 mutations (Table 19). Cancer cell lines used in this study were selected based on the presence of homozygous activating KRAS G12 mutations, or amplification of the KRAS gene. In addition, these assays were performed in a set of RAS-less mouse embryonic fibroblast (MEF) cells which were engineered to only express KRAS wild type, HRAS, and NRAS, respectively (Table 19). MEF cells were used to confirm KRAS selectivity of the test compounds.

TABLE 19

Cell Line Information

| Cell Line Name | RAS Mutation/Features | Assay Seeding Density (Cells/Well) |
|---|---|---|
| MKN45 | WT KRAS Amplification/Human Gastric Cancer | 20,000 |
| SW620 | KRAS G12V/Human Colorectal Cancer | 20,000 |
| HPAC | KRAS G12D/Human Pancreatic Cancer | 2,500 |
| NCI-1373 | KRAS G12C/Human Lung Cancer | 5,000 |
| MEF-NRAS | RAS-less MEFs Expressing NRAS only | 20,000 |
| MEF-HRAS | RAS-less MEFs Expressing HRAS only | 10,000 |
| MEF-KRAS | RAS-less MEFs Expressing KRAS only | 2,500 |

The compounds' activity is determined by measuring changes in the phosphorylation levels of the downstream effector Extracellular Signal-regulated Kinase-1 and 2 (ERK1/2) in the compound treated cells. Phosphorylation levels of ERK-1/2 are measured using the AlphaLISA© SureFire© Ultra™ p-ERK 1/2 (Thr202/Tyr204) Assay Kit (#ALSU-PERK-A50K, PerkinElmer® Waltham, MA). The AlphaLISA© assay is a quantitative sandwich immunoassay that can be used to detect phosphorylation of target proteins from cellular lysates using bead-based Alpha technology. The assay kit contains two antibodies, one that binds the phospho-Thr202/Tyr204 epitope on ERK-1/2, and another one that recognizes a separate site on the protein. One of these antibodies is biotinylated and associated with streptavidin-coated Alpha Donor beads, the other antibody is conjugated to AlphaLISA© Acceptor beads. When ERK-1/2 is phosphorylated in cellular lysate, the Donor and Acceptor beads are brought into proximity with each other. When the Donor bead is excited by 600 nm wavelength light, a photosensitizer inside the bead converts ambient oxygen to an excited singlet state. When the Acceptor bead is within 200 nm of this reaction, the singlet oxygen reacts with the Acceptor leading to a chemiluminescent emission. The amount of light measured is proportional to the amount of phosphorylated ERK-1/2 in the lysate. The AlphaLISA© SureFire© Ultra™ p-ERK 1/2 (Thr202/Tyr204) Assay Kit contains AlphaLISA© antibody-conjugated Donor and Acceptor Beads, Lysis buffer concentrate, and a set of proprietary buffers (Activation Buffer, Reaction Buffer 1, Reaction Buffer 2, and Dilution Buffer).

To perform the assays, test compounds and controls are acoustically dispensed (Labcyte ECHO®, San Jose, CA) into a white 384-well assay plate (Proxiplate-384, PerkinElmer #6008280) in a 10-point 3-fold dilution series in 30 nL DMSO. Cells are then added to the assay plate in 8 µL per well assay medium (HBSS, Sigma #55021C, 10% FBS, GIBCO #10082-147) at a cell line specific density. The final compound concentrations range from 0.5 to 10,000 nM and the final DMSO concentration is 0.375% in each well. Maximum signal control wells contain 0.375% DMSO only (negative control), and minimum signal control wells contain 10,000 nM control compound (positive control). Cells in suspension are incubated with the test and reference compounds for 2 h at 37° C./5% $CO_2$. Following the 2 h incubation, cells are lysed by adding 2 µL of the AlphaLISA® Lysis buffer concentrate (5×) supplemented with protease/phosphatase inhibitor cocktail (Thermo Scientific #78442). The assay plate is covered with an opaque lid and shaken at 750 rpm on a multi-plate shaker (Heidolph, Schwabach, Germany) for 30 min at room temperature to induce cell lysis. During the lysis, the AlphaLISA® Acceptor beads are diluted 1:50 in a prepared buffer mixture (1:1 AlphaLISA® Reaction Buffers 1 and 2 with a 1:25 dilution of AlphaLISA® Activation Buffer). Following cell lysis, plates are centrifuged briefly, and 5 µL per well prepared Acceptor beads are added. The plate is then covered and incubated in the dark for 2 h at room temperature. During the Acceptor bead incubation, Donor beads are prepared by diluting the Alpha streptavidin Donor beads 1:50 in AlphaLISA® Dilution buffer. Following the Acceptor bead incubation, 5 µL per well of Donor bead mixture is added to the plates. Plates are then covered and allowed to incubate in the dark at room temperature for 2 h. After this incubation period, the AlphaLISA signal is read using a PHERAstar® FSX multimode plate reader (BMG Labtech, Ortenberg, Germany) equipped with an AlphaLISA® compatible optics cube. Raw signal obtained from the AlphaLISA® assay is analyzed using Genedata Screener® 17.0.3. Within the program, data is normalized to 32 wells treated with inhibition control (max inhibition/positive control) and 32 wells treated with 0.375% DMSO only (minimum inhibition/negative control) to calculate the % Activity of the compound:

$$\% \text{ Activity} = 100 \times \left(1 - \frac{(\text{treated value} - \text{positive control})}{(\text{negative control} - \text{positive control})}\right) \quad \text{eq. 1}$$

% Activity values are fit to a four-parameter non-linear logistic equation using Genedata Screener® 17.0.3. to determine $IC_{50}$ values:

$$y = \text{Bottom} + \frac{\text{Top} - \text{Bottom}}{1 + \left(\frac{10^{Log(IC_{50})}}{10^x}\right)^h} \quad \text{eq. 2}$$

Where y=% Activity, Bottom=minimum asymptote, Top=maximum asymptote, x=compound concentration, $IC_{50}$=the compound concentration where half maximal activity is achieved, and h=the Hill Coefficient.

In the above assays, compounds of Examples indicated herein exhibited an ability to reduce levels of phosphorylated ERK-1/2 in cells expressing KRAS and KRAS variants indicating inhibition of constitutive RAS activity in cells expressing KRAS G12C (Examples 2,24,29,32,35,37,40,42-45,48, 55, 56, 59, 68, 93, 95-97, 101, 103, 106-109, 113, 114, 116, 129, 152, 159, 161, 162, 164-166, 168, 169, 172, 190-192, 206, 208, 211-213, 218, 219, 243, 244, 280-289, 292-318, 320, 321, 343, 346, 347, 370, and 375), KRAS G12D (Examples 2, 14, 24, 29, 35, 37, 42-45, 48, 55, 56, 59, 68, 93, 95-97, 101, 103, 106-109, 113, 114, 116, 129, 152, 159, 161, 162, 164-166, 168, 169, 175, 188, 190-193, 212, 213, 218-220, 229, 231, 233, 243, 244, 280-289, 292-313, 316, 318, 343, 346, 347, 370, and 375), KRAS G12V (Examples 29, 30, 32, 35, 37-40, 42-45, 59, 93, 97, 108, 109, 165, 166, 168, 209, 211, 219, 280-289, 292-318, 320, 321, 346, 347, 370, and 375), or KRAS WT (Examples 2, 29, 30, 32, 35, 37-40, 42-45, 48, 56, 59, 62, 93, 95-97, 101, 103, 107-109, 113, 114, 116, 129, 159, 161, 162, 164-166, 168, 169, 190-192, 209, 211, 218, 219, 244, 280-289, 292-314, 316-318, 320, 321346, 347, 370, and 375), with a relative IC50 of <500 nM. Compounds of Examples 2, 14, 24, 45, 48, 49, 55, 56, 59, 68, 95-97, 101, 103, 106-109, 113, 114, 116, 121-124, 126, 129, 130, 142, 152, 159, 161, 162, 164-166, 168, 169, 172, 175, 188, 190-193, 211-213, 218-220, 229, 231, 233, 243, 244, 280-289, 293, 295-302, 305-311, 314-322, 343, 346, 347, 370 and 375 were tested in the Mouse Embryonic Fibroblasts cell line assays above (MEF-NRAS, MEF-HRAS) and all exhibited a relative IC50 of >2 µM.

This data shows that compounds of Formulae I-VIII (including Ia-VIIa) as described herein are potent inhibitors of KRAS human cancer cells expressing KRAS demonstrating the ability to inhibit KRAS G12C, G12D or G12V mutants with a significant selective inhibition preference for KRAS mutants over HRAS or NRAS.

TABLE 10

| | Abbreviations |
|---|---|
| KRAS | Kirsten Rat Sarcoma Virus |
| NRAS | Neuroblastoma RAS Viral Oncogene Homolog |
| HRAS | H$^a$rvey Rat Sarcoma Virus |
| MEF | Mouse Embryonic Fibroblasts |
| ERK | Extracellular Signal-Regulated Kinase |
| AlphaLISA | Alph$^a$-Linked Immunosorbent Assay |
| DMSO | Dimethyl Sulfoxide |
| HBSS | H$^a$nk's Balanced Salt Solution |
| FBS | Fetal Bovine Serum |
| $CO_2$ | Carbon Dioxide |

What is claimed is:

1. A compound of the formula:

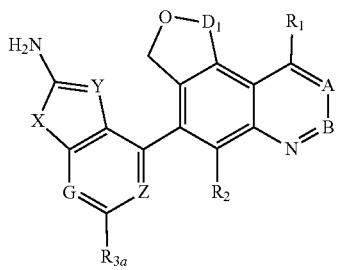

wherein:
A is —C(H)— or —N—;
B is —C($R_4$)— or —N—;
$D_1$ is —$CH_2$—;
X is —S—;
Y is —C(CN)— or —N—;
Z is —C($R_{3c}$)— or —N—;
G is —C($R_{3b}$)— or —N—;
$R_1$ is methoxy, $C_{1-4}$ alkyl, $C_{2-4}$ heteroalkyl, azetidine, N-linked piperazine, piperidine, morpholine, or a group of the formula selected from

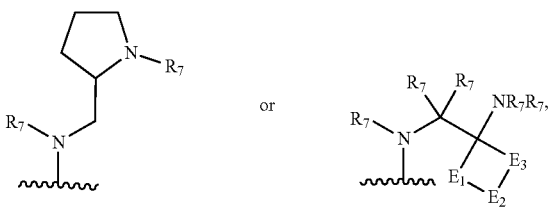

wherein the $C_{1-4}$ alkyl, $C_{2-4}$ heteroalkyl, azetidine, piperidine, or N-linked piperazine are optionally substituted with one or more of amino, hydroxyl, methyl, trideuteromethyl, methoxy, oxetane, or $C_{1-3}$ alkyl, wherein the $C_{1-3}$ alkyl is optionally substituted by one or more halogen, hydroxyl, methyl, hydroxymethyl, methoxy, trifluoromethoxy, difluoromethoxy, —O-trideuteromethyl, cyclopropyl, oxetane, pyrazole, imidazole, amino, —CONR$_7$R$_7$, —O—(CH$_2$)$_p$—OC$_{1-3}$ alkyl, —O—(CH$_2$)$_p$—OH, or —O—CO—C$_{1-3}$ alkyl, wherein the piperidine or the N-linked piperazine are optionally bridged by a $C_{1-3}$ alkyl and wherein the cyclopropyl, imidazole, or pyrazole are each optionally substituted with a hydroxyl or a $C_{1-3}$ alkyl substituted with one or more hydroxyl;
$E_1$ is —(CR$_7$R$_7$-)$_n$, $E_2$ is —CR$_7$R$_7$—, —NR$_7$— or —O— and $E_3$ is —(CR$_7$R$_7$-)$_m$, wherein m+n is 1, 2, 3 or 4;
p is 1, 2, or 3;
$R_2$ is H, halogen, or methyl;
$R_{3a}$, $R_{3b}$, and $R_{3c}$ are each independently H or halogen;
$R_4$ is H, methyl, —$CH_2$—OH, —O—$R_5$-$R_6$, —O—$R_6$, or azetidine optionally substituted with NR$_7$R$_7$, wherein $R_5$ is —$CH_2$—, —CH(CH$_3$)—, or —$CH_2$—$CH_2$—, wherein $R_6$ is H, $C_{1-3}$ alkyl, $C_{2-3}$ heteroalkyl, $C_{3-6}$ cycloalkyl, $C_{4-6}$ heterocycloalkyl, 2-oxo-1,3-dihydrobenzimidazole, imidazole or pyrazole, wherein the $C_{1-3}$ alkyl, $C_{3-6}$ cycloalkyl, or $C_{4-6}$ heterocycloalkyl are optionally substituted with one or more oxo, halogen, hydroxyl, methoxy, difluoromethoxy, NR$_7$R$_7$, $C_{1-4}$ alkyl, $C_{1-4}$ alkenyl, —CN, or —CO—$CH_2$OH, wherein the $C_{1-4}$ alkyl is optionally substituted with one or more halogen, hydroxyl, methoxy, or NR$_7$R$_7$, wherein the $C_{3-6}$ cycloalkyl or $C_{4-6}$ heterocycloalkyl are optionally fused with the $C_{1-4}$ alkyl to form a bicyclic ring, or the $C_{3-6}$ cycloalkyl or $C_{4-6}$ heterocycloalkyl are optionally bridged with a $C_{1-3}$ alkyl; and
each $R_7$ is independently H, or $C_{1-3}$ alkyl;
or a pharmaceutically acceptable salt thereof.

2. The compound according to claim 1, wherein G is —N—, or a pharmaceutically acceptable salt thereof.

3. The compound according to claim 1, wherein G is —N—, and Z is —C($R_{3c}$)—, or a pharmaceutically acceptable salt thereof.

4. The compound according to claim 1, wherein G is —C($R_{3b}$)—, or a pharmaceutically acceptable salt thereof.

5. The compound according to claim 4, wherein $R_{3b}$ is F, or a pharmaceutically acceptable salt thereof.

6. The compound according to claim 1, wherein G is —C($R_{3b}$)—, and Z is —N—, or a pharmaceutically acceptable salt thereof.

7. The compound according to claim 1, wherein G is —C($R_{3b}$)—; $R_{3a}$, $R_{3b}$, and $R_{3c}$ are each independently H, or halogen; $R_1$ is $C_{1-4}$ alkyl, $C_{2-4}$ heteroalkyl, N-linked piperazine, piperidine, or a group of the formula

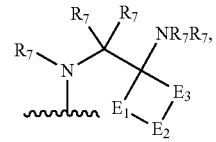

wherein the $C_{1-4}$ alkyl, $C_{2-4}$ heteroalkyl, piperidine, or N-linked piperazine are optionally substituted with one or more of amino, hydroxyl, methyl, trideuteromethyl, oxetane, or $C_{1-3}$ alkyl, wherein the $C_{1-3}$ alkyl is optionally substituted by one or more halogen, hydroxyl, methyl, hydroxymethyl, methoxy, trifluoromethoxy, cyclopropyl, oxetane, pyrazole, imidazole, amino, —CONR$_7$R$_7$, —O—(CH$_2$)$_p$—OC$_{1-3}$ alkyl, —O—(CH$_2$)$_p$—OH, or —O—CO—C$_{1-3}$ alkyl, wherein the piperidine or the N-linked piperazine are optionally bridged by a $C_{1-3}$ alkyl and wherein the cyclopropyl, imidazole, or pyrazole are each optionally substituted with a $C_{1-3}$ alkyl substituted with one or more hydroxyl; and R$_4$ is H, methyl, —CH$_2$—OH, —O—R$_5$-R$_6$, —O—R$_6$, or azetidine optionally substituted with NR$_7$R$_7$, wherein R$_5$ is —CH$_2$—, —CH(CH$_3$)—, or —CH$_2$—CH$_2$—, wherein R$_6$ is H, C$_{1-3}$ alkyl, C$_{2-3}$ heteroalkyl, C$_{3-6}$ cycloalkyl, C$_{4-6}$ heterocycloalkyl or 2-oxo-1,3-dihydrobenzimidazole, wherein the C$_{1-3}$ alkyl, C$_{3-6}$ cycloalkyl, or C$_{4-6}$ heterocycloalkyl are optionally substituted with one or more halogen, hydroxyl, methoxy, NR$_7$R$_7$, C$_{1-4}$ alkyl, or C$_{1-4}$ alkenyl, wherein the C$_{1-4}$ alkyl is optionally substituted with one or more halogen or hydroxyl, wherein the C$_{3-6}$ cycloalkyl or C$_{4-6}$ heterocycloalkyl are optionally fused with the C$_{1-4}$ alkyl to form a bicyclic ring, or the C$_{3-6}$ cycloalkyl or C$_{4-6}$ heterocycloalkyl are optionally bridged with a C$_{1-3}$ alkyl; or a pharmaceutically acceptable salt thereof.

8. The compound according to claim 1, wherein G is —C(R$_{3b}$)—; R$_{3a}$, R$_{3b}$, and R$_{3c}$ are each independently H, or halogen; and R$_1$ is C$_{1-4}$ alkyl, C$_{2-4}$ heteroalkyl, N-linked piperazine, piperidine, or a group of the formula

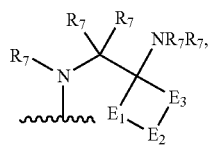

wherein the C$_{1-4}$ alkyl, C$_{2-4}$ heteroalkyl, piperidine, or N-linked piperazine are optionally substituted with one or more of amino, hydroxyl, methyl, trideuteromethyl, oxetane, or C$_{1-3}$ alkyl, wherein the C$_{1-3}$ alkyl is optionally substituted by one or more halogen, hydroxyl, methyl, hydroxymethyl, methoxy, trifluoromethoxy, cyclopropyl, oxetane, pyrazole, imidazole, amino, or —CONR$_7$R$_7$, wherein the piperidine or the N-linked piperazine are optionally bridged by a C$_{1-3}$ alkyl and wherein the cyclopropyl, imidazole, or pyrazole are each optionally substituted with a C$_{1-3}$ alkyl substituted with one or more hydroxyl; and R$_4$ is H, methyl, —CH$_2$—OH, —O—R$_5$-R$_6$, —O—R$_6$, or azetidine optionally substituted with NR$_7$R$_7$, wherein R$_5$ is —CH$_2$—, —CH(CH$_3$)—, or —CH$_2$—CH$_2$—, wherein R$_6$ is H, C$_{1-3}$ alkyl, C$_{2-3}$ heteroalkyl, C$_{3-6}$ cycloalkyl, C$_{4-6}$ heterocycloalkyl or 2-oxo-1,3-dihydrobenzimidazole, wherein the C$_{1-3}$ alkyl, C$_{3-6}$ cycloalkyl, or C$_{4-6}$ heterocycloalkyl are optionally substituted with one or more halogen, hydroxyl, methoxy, NR$_7$R$_7$, C$_{1-4}$ alkyl, or C$_{1-4}$ alkenyl, wherein the C$_{1-4}$ alkyl is optionally substituted with one or more halogen or hydroxyl, wherein the C$_{3-6}$ cycloalkyl or C$_{4-6}$ heterocycloalkyl are optionally fused with the C$_{1-4}$ alkyl to form a bicyclic ring, or the C$_{3-6}$ cycloalkyl or C$_{4-6}$ heterocycloalkyl are optionally bridged with a C$_{1-3}$ alkyl; or a pharmaceutically acceptable salt thereof.

9. The compound according to claim 1, wherein G is —C(R$_{3b}$)—; R$_{3a}$, R$_{3b}$, and R$_{3c}$ are each independently H, or halogen; R$_1$ is C$_{1-4}$ alkyl, C$_{2-4}$ heteroalkyl, or N-linked piperazine, wherein the C$_{1-4}$ alkyl, C$_{2-4}$ heteroalkyl, or N-linked piperazine are optionally substituted with one or more of amino, hydroxyl, methyl, oxetane, or C$_{1-3}$ alkyl, wherein the C$_{1-3}$ alkyl is optionally substituted by one or more halogen, hydroxyl, methyl, hydroxymethyl, methoxy, cyclopropyl, oxetane, or amino, and wherein the N-linked piperazine is optionally bridged by the C$_{1-3}$ alkyl; and R$_4$ is H, methyl, —CH$_2$—OH, —O—R$_5$-R$_6$, or —O—R$_6$, wherein R$_5$ is —CH$_2$—, —CH$_2$ (CH$_3$)—, or —CH$_2$—CH$_2$—, wherein R$_6$ is H, C$_{1-3}$ alkyl, C$_{2-3}$ heteroalkyl, C$_{4-6}$ cycloalkyl, or C$_{4-6}$ heterocycloalkyl, wherein the C$_{1-3}$ alkyl, C$_{4-6}$ cycloalkyl, or C$_{4-6}$ heterocycloalkyl are optionally substituted with one or more halogen, hydroxyl, methoxy, C$_{1-4}$ alkyl, or C$_{1-4}$ alkenyl, wherein the C$_{1-4}$ alkyl is optionally substituted with one or more halogen or hydroxyl, wherein the C$_{4-6}$ cycloalkyl or C$_{4-6}$ heterocycloalkyl are optionally fused with the C$_{1-4}$ alkyl to form a bicyclic ring, or a pharmaceutically acceptable salt thereof.

10. The compound according to claim 1, wherein Y is —C(CN)—, or a pharmaceutically acceptable salt thereof.

11. The compound according to claim 1, wherein Z is —C(R$_{3c}$)—, or a pharmaceutically acceptable salt thereof.

12. The compound according to claim 1, wherein R$_{3a}$ and R$_{3c}$ are each independently H or F, or a pharmaceutically acceptable salt thereof.

13. The compound according to claim 1, wherein R$_{3a}$ is H, or a pharmaceutically acceptable salt thereof.

14. The compound according to claim 1, wherein Z is —N—, or a pharmaceutically acceptable salt thereof.

15. The compound according to claim 1, wherein A is —N—, or a pharmaceutically acceptable salt thereof.

16. The compound according to claim 1, wherein A is —C(H)—, or a pharmaceutically acceptable salt thereof.

17. The compound according to claim 1, wherein B is —C(R$_4$)—, or a pharmaceutically acceptable salt thereof.

18. The compound according to claim 1, wherein B is —C(H)—, or a pharmaceutically acceptable salt thereof.

19. The compound according to claim 1, wherein R$_1$ is N-linked piperazine, or a pharmaceutically acceptable salt thereof.

20. The compound according to claim 1, wherein R$_1$ is N-linked piperazine optionally substituted with one or more of amino, hydroxyl, methyl, trideuteromethyl, oxetane, or C$_{1-3}$ alkyl, wherein the C$_{1-3}$ alkyl is optionally substituted by one or more halogen, hydroxyl, methyl, hydroxymethyl, methoxy, trifluoromethoxy, cyclopropyl, oxetane, pyrazole, imidazole, amino, or —CONR$_7$R$_7$, and optionally bridged by a C$_{1-3}$ alkyl and wherein the cyclopropyl, imidazole, or pyrazole are each optionally substituted with a C$_{1-3}$ alkyl substituted with one or more hydroxyl, or a pharmaceutically acceptable salt thereof.

21. The compound according to claim 1, wherein R$_1$ is C$_{1-4}$ alkyl, C$_{2-4}$ heteroalkyl, N-linked piperazine, piperidine, or a group of the formula

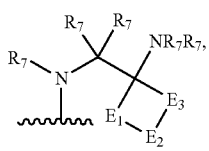

wherein the $C_{1-4}$ alkyl, $C_{2-4}$ heteroalkyl, piperidine, or N-linked piperazine are optionally substituted with one or more of amino, hydroxyl, methyl, trideuteromethyl, oxetane, or $C_{1-3}$ alkyl, wherein the $C_{1-3}$ alkyl is optionally substituted by one or more halogen, hydroxyl, methyl, hydroxymethyl, methoxy, trifluoromethoxy, cyclopropyl, oxetane, pyrazole, imidazole, amino, or —$CONR_7R_7$, wherein the piperidine or the N-linked piperazine are optionally bridged by a $C_{1-3}$ alkyl and wherein the cyclopropyl, imidazole, or pyrazole are each optionally substituted with a $C_{1-3}$ alkyl substituted with one or more hydroxyl; or a pharmaceutically acceptable salt thereof.

22. The compound according to claim 1, wherein $R_1$ is N-linked piperazine substituted with one or more of methyl, trideuteromethyl, or $C_{1-3}$ alkyl, wherein the $C_{1-3}$ alkyl is optionally substituted by one or more halogen, hydroxyl, methyl, hydroxymethyl, methoxy, trifluoromethoxy, difluoromethoxy, —O-trideuteromethyl, cyclopropyl, oxetane, pyrazole, imidazole, —$CONR_7R_7$, —O—$(CH_2)_p$—$OC_{1-3}$ alkyl, —O—$(CH_2)_p$—OH, or —O—CO—$C_{1-3}$ alkyl, and wherein the cyclopropyl, imidazole, or pyrazole are each optionally substituted with a hydroxyl or a $C_{1-3}$ alkyl substituted with one or more hydroxyl, and wherein the N-linked piperazine is bridged by a $C_{1-3}$ alkyl, or a pharmaceutically acceptable salt thereof.

23. The compound according to claim 1, wherein $R_1$ is selected from

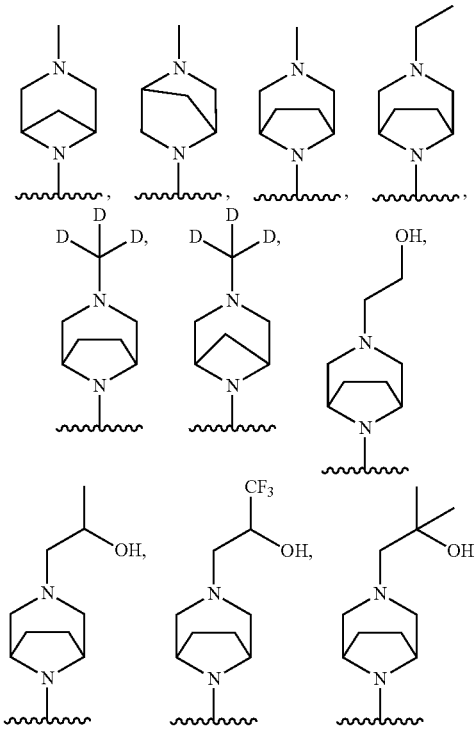

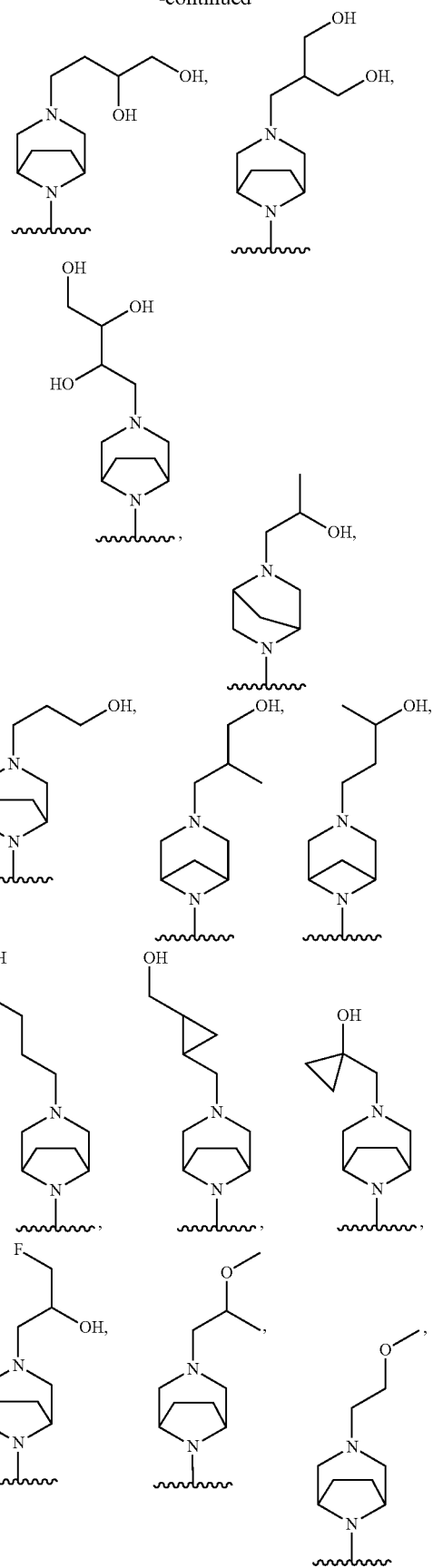

741
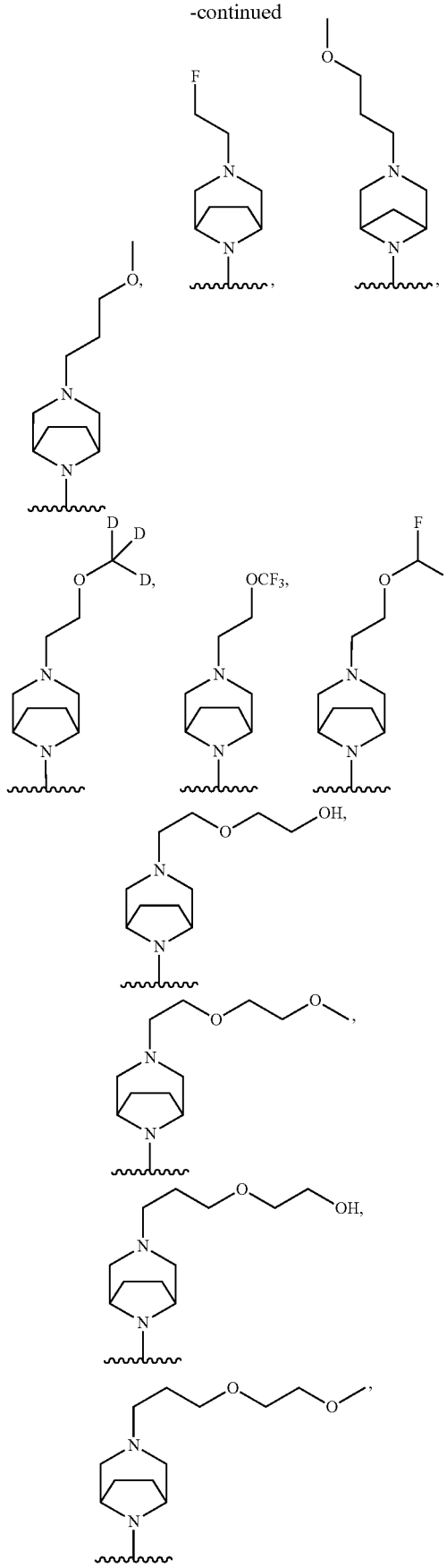
742
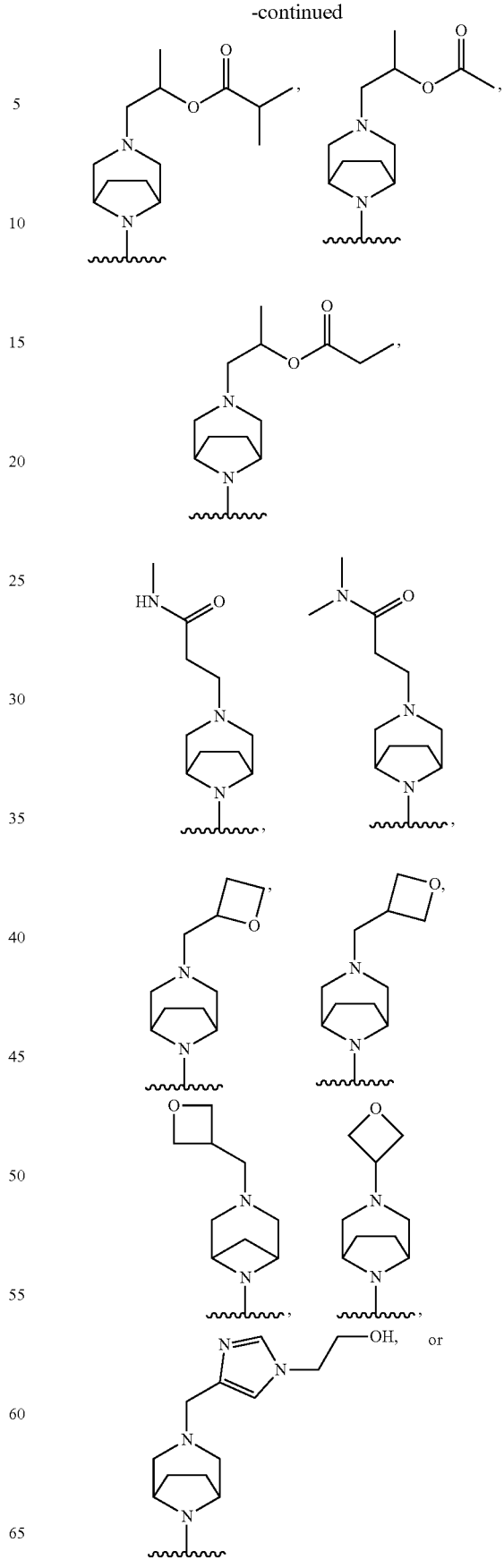

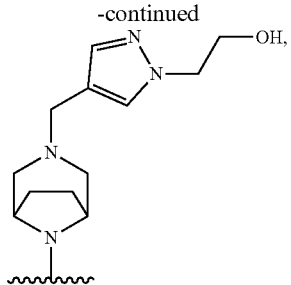

or a pharmaceutically acceptable salt thereof.

24. The compound according to claim 1, wherein $R_4$ is —O—CH$_2$—R$_6$ or a pharmaceutically acceptable salt thereof.

25. The compound according to claim 24, wherein $R_6$ is azetidine, pyrrolidine, piperidine, oxetane, tetrahydrofuran, morpholine, cyclobutane, or 1,4-dioxane, or a pharmaceutically acceptable salt thereof.

26. The compound according to claim 1, wherein $R_4$ is selected from

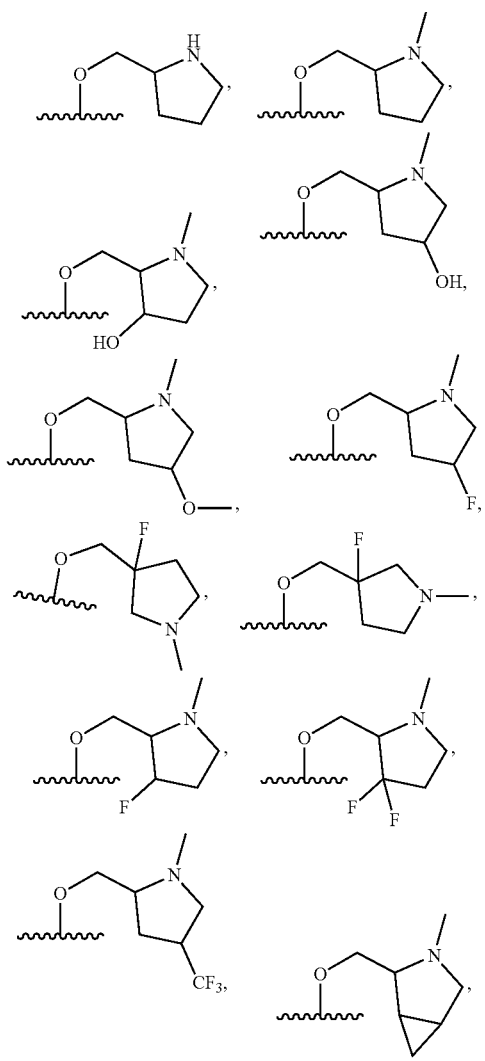
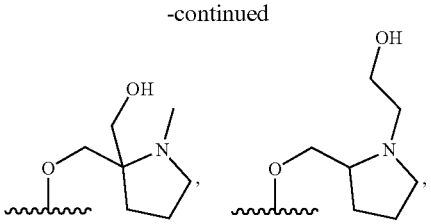
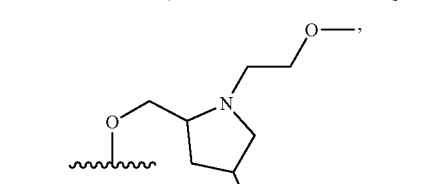
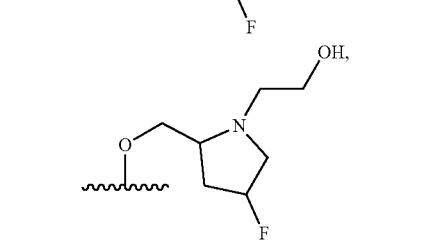
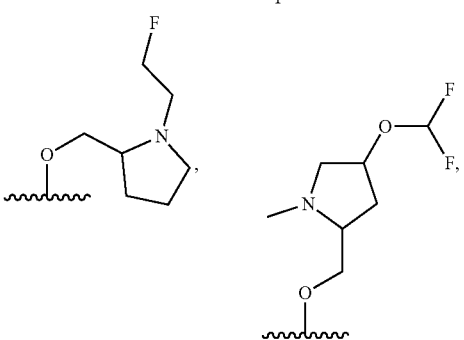
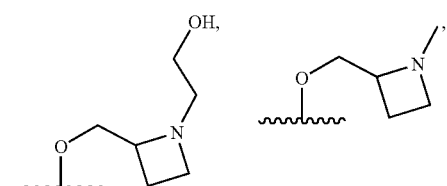
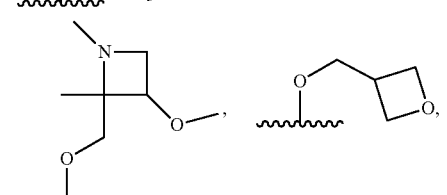
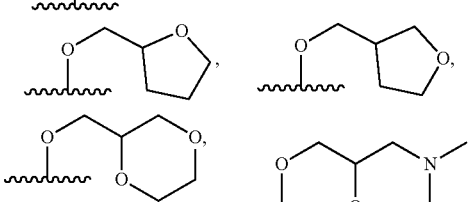
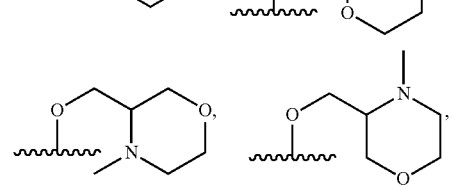

745
-continued

746
-continued or a pharmaceutically acceptable salt thereof.

27. The compound according to claim 1, wherein $R_2$ is F or Cl or a pharmaceutically acceptable salt thereof.

28. The compound according to claim 1, wherein $R_2$ is F, or a pharmaceutically acceptable salt thereof.

29. The compound according to claim 1, wherein $R_2$ is Cl, or a pharmaceutically acceptable salt thereof.

30. The compound according to claim 1, wherein Y is —C(CN)—, Z is —C($R_{3c}$)—, $R_2$ is F or Cl, $R_{3a}$ is H, $R_{3b}$ is H, and $R_{3c}$ is F, or a pharmaceutically acceptable salt thereof.

31. The compound according to claim 1, wherein the compound is selected from

| Example | Chemical Name | Structure |
|---|---|---|
| 24 | 2-Amino-4-[5-fluoro-3-[[(2R,8S)-2-fluoro-1,2,3,5,6,7-hexahydropyrrolizin-8-yl]methoxy]-1-(3-methyl-3,8-diazabicyclo[3.2.1]octan-8-yl)-7,9-dihydrofuro[3,4-f]quinazolin-6-yl]benzothiophene-3-carbonitrile | 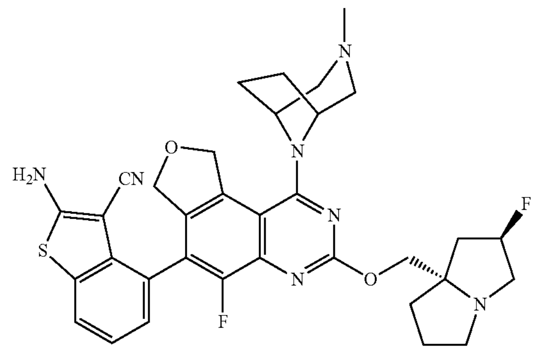 [SMILES: CN1CC2CCC(C1)N2c1nc(OC[C@@]23CCCN2C[C@H](F)C3)nc2c(F)c(-c3cccc4sc(N)c(C#N)c34)c3c(c12)COC3] |
| 25 | 2-Amino-4-[1-(3-ethyl-3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]benzothiophene-3-carbonitrile | 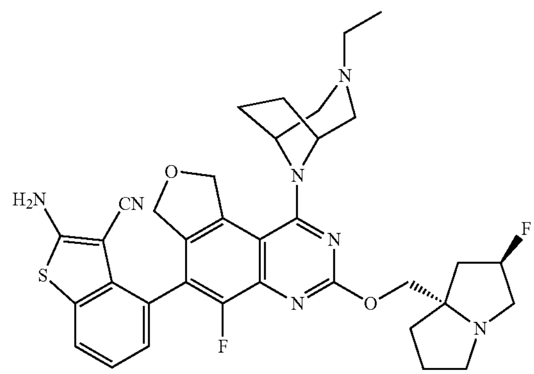 [SMILES: CCN1CC2CCC(C1)N2c1nc(OC[C@@]23CCCN2C[C@H](F)C3)nc2c(F)c(-c3cccc4sc(N)c(C#N)c34)c3c(c12)COC3] |
| 28 | 3-[8-[6-(2-Amino-1,3-benzothiazol-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]propan-1-ol | 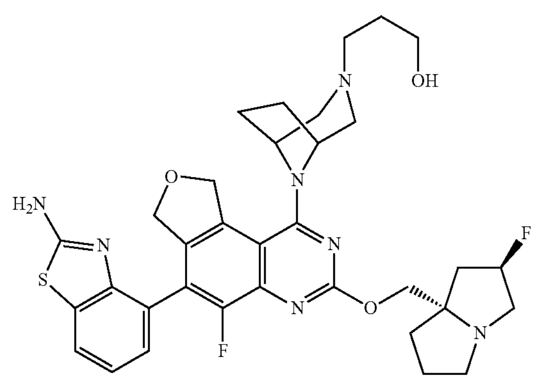 [SMILES: Nc1nc2c(-c3c4c(c5c(N6C7CCC6CN(CCCO)C7)nc(OC[C@@]67CCCN6C[C@H](F)C7)nc5c3F)COC4)cccc2s1] |

-continued

| Example | Chemical Name | Structure |
|---|---|---|
| 46 | 2-Amino-4-[5-fluoro-3-[[(2R,8S)-2-fluoro-1,2,3,5,6,7-hexahydropyrrolizin-8-yl]methoxy]-1-[3-(2-hydroxyethyl)-3,8-diazabicyclo[3.2.1]octan-8-yl]-7,9-dihydrofuro[3,4-f]quinazolin-6-yl]benzothiophene-3-carbonitrile | 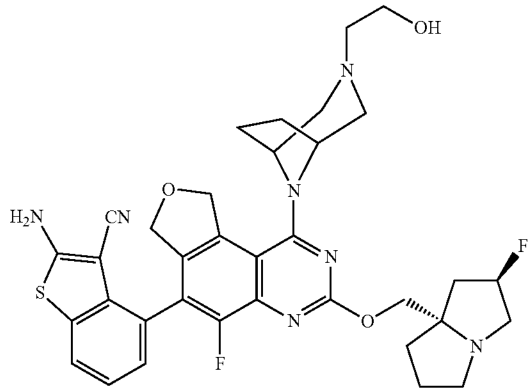 [SMILES: N#Cc1c(N)sc2cccc(-c3c4c(c5c(N6C7CCC6CN(CCO)C7)nc(OC[C@@]67CCCN6C[C@H](F)C7)nc5c3F)COC4)c12] |
| 48 | 2-Amino-4-[5-fluoro-3-[[(2R,8S)-2-fluoro-1,2,3,5,6,7-hexahydropyrrolizin-8-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile | 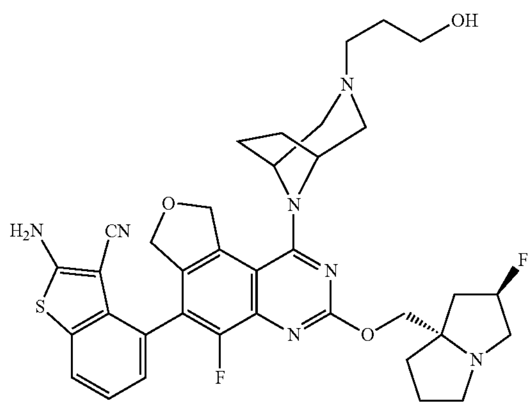 [SMILES: N#Cc1c(N)sc2cccc(-c3c4c(c5c(N6C7CCC6CN(CCCO)C7)nc(OC[C@@]67CCCN6C[C@H](F)C7)nc5c3F)COC4)c12] |
| 49 | 2-Amino-5-fluoro-4-[5-fluoro-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile | 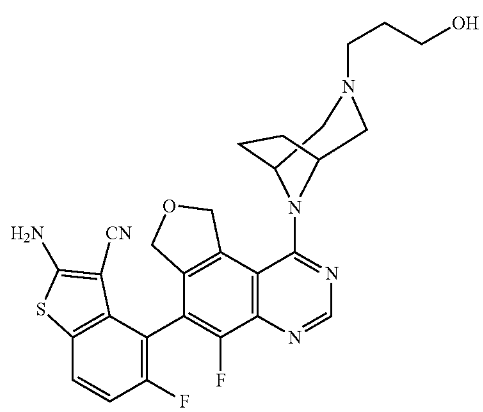 [SMILES: N#Cc1c(N)sc2ccc(F)c(-c3c4c(c5c(N6C7CCC6CN(CCCO)C7)ncnc5c3F)COC4)c12] |
| 51 | 2-Amino-4-[5-fluoro-3-[[(2R,8S)-2-fluoro-1,2,3,5,6,7-hexahydropyrrolizin-8-yl]methoxy]-1-(3-methyl-3,8-diazabicyclo[3.2.1]octan-8-yl)-7,9-dihydrofuro[3,4-f]quinazolin-6-yl]thieno[3,2-c]pyridine-3-carbonitrile | 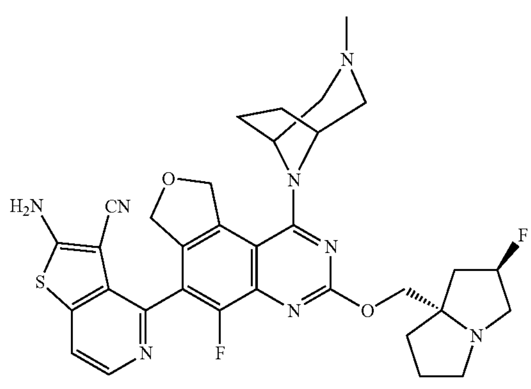 [SMILES: CN1CC2CCC(C1)N2c1nc(OC[C@@]23CCCN2C[C@H](F)C3)nc2c(F)c(-c3nccc4sc(N)c(C#N)c34)c3c(c12)COC3] |

-continued

| Example | Chemical Name | Structure |
|---|---|---|
| 52 | 2-Amino-4-[5-fluoro-3-[[(2R,8S)-2-fluoro-1,2,3,5,6,7-hexahydropyrrolizin-8-yl]methoxy]-1-(3-methyl-3,6-diazabicyclo[3.1.1]heptan-6-yl)-7,9-dihydrofuro[3,4-f]quinazolin-6-yl]thieno[3,2-c]pyridine-3-carbonitrile | 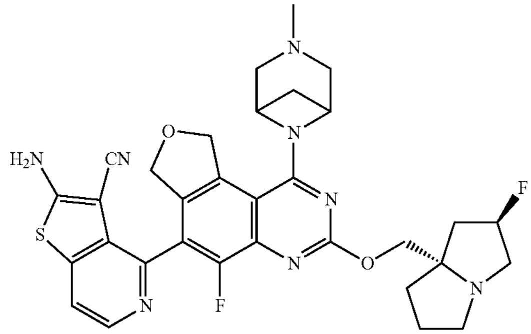 [SMILES: CN1CC2CC(C1)N2c1nc(OC[C@@]23CCCN2C[C@H](F)C3)nc2c(F)c(-c3nccc4sc(N)c(C#N)c34)c3c(c12)COC3] |
| 53 | 2-Amino-5-fluoro-4-[5-fluoro-1-(3-methyl-3,6-diazabicyclo[3.1.1]heptan-6-yl)-7,9-dihydrofuro[3,4-f]quinazolin-6-yl]benzothiophene-3-carbonitrile, Isomer 2 | 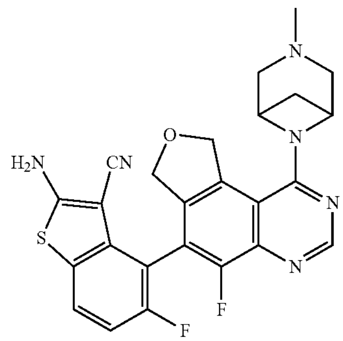 [SMILES: CN1CC2CC(C1)N2c1ncnc2c(F)c(-c3c(F)ccc4sc(N)c(C#N)c34)c3c(c12)COC3] |
| 55 | 2-Amino-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 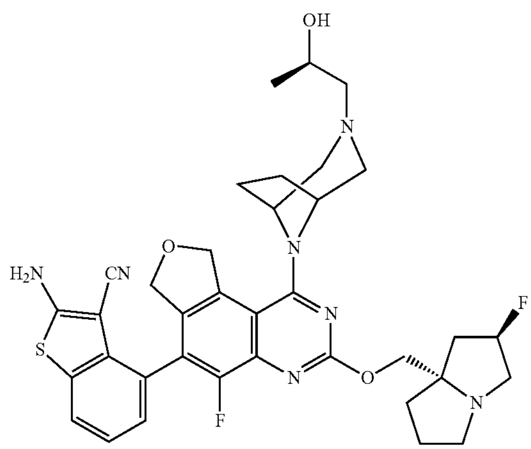 [SMILES: C[C@@H](O)CN1CC2CCC(C1)N2c1nc(OC[C@@]23CCCN2C[C@H](F)C3)nc2c(F)c(-c3cccc4sc(N)c(C#N)c34)c3c(c12)COC3] |
| 56 | 2-Amino-4-[5-fluoro-3-[[(2R,8S)-2-fluoro-1,2,3,5,6,7-hexahydropyrrolizin-8-yl]methoxy]-1-[3-[(2S)-2-hydroxypropyl]-3,8-diazabicyclo[3.2.1]octan-8-yl]-7,9-dihydrofuro[3,4-f]quinazolin-6-yl]benzothiophene-3-carbonitrile | 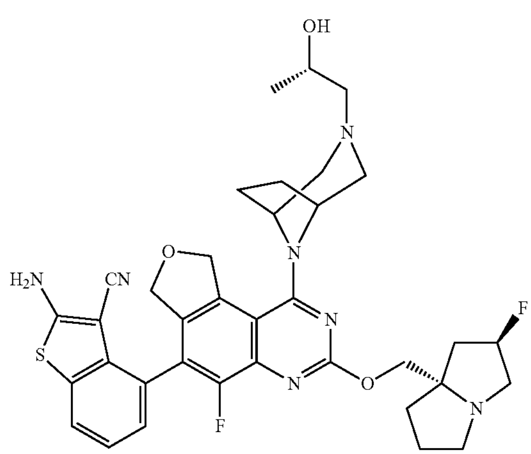 [SMILES: C[C@H](O)CN1CC2CCC(C1)N2c1nc(OC[C@@]23CCCN2C[C@H](F)C3)nc2c(F)c(-c3cccc4sc(N)c(C#N)c34)c3c(c12)COC3] |

-continued

| Example | Chemical Name | Structure |
|---|---|---|
| 57 | 2-Amino-4-[5-fluoro-1-[3-[(2S)-2-hydroxypropyl]-3,8-diazabicyclo[3.2.1]octan-8-yl]-3-methoxy-7,9-dihydrofuro[3,4-f]quinazolin-6-yl]benzothiophene-3-carbonitrile | 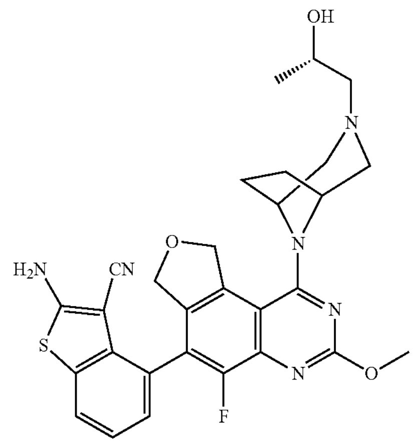 [SMILES: COc1nc(N2C3CCC2CN(C[C@H](C)O)C3)c2c3c(c(-c4cccc5sc(N)c(C#N)c45)c(F)c2n1)COC3] |
| 95 | 2-Amino-5-fluoro-4-[5-fluoro-3-[[(2R,8S)-2-fluoro-1,2,3,5,6,7-hexahydropyrrolizin-8-yl]methoxy]-1-(3-methyl-3,6-diazabicyclo[3.1.1]heptan-6-yl)-7,9-dihydrofuro[3,4-f]quinazolin-6-yl]benzothiophene-3-carbonitrile | 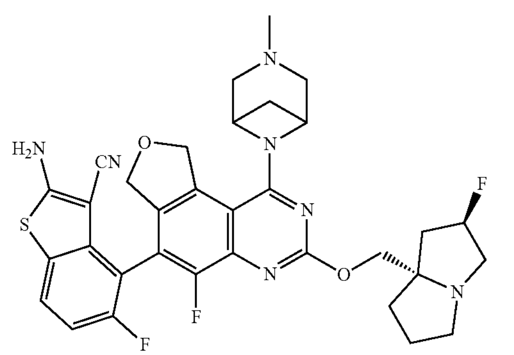 [SMILES: CN1CC2CC(C1)N2c1nc(OC[C@@]23CCCN2C[C@H](F)C3)nc2c(F)c(-c3c(F)ccc4sc(N)c(C#N)c34)c3c(c12)COC3] |
| 96 | 2-Amino-5-fluoro-4-[5-fluoro-3-[[(2R,8S)-2-fluoro-1,2,3,5,6,7-hexahydropyrrolizin-8-yl]methoxy]-1-[3-(3-hydroxybutyl)-3,6-diazabicyclo[3.1.1]heptan-6-yl]-7,9-dihydrofuro[3,4-f]quinazolin-6-yl]benzothiophene-3-carbonitrile | 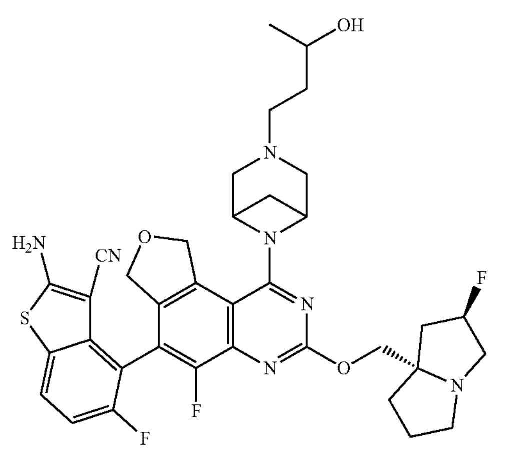 [SMILES: CC(O)CCN1CC2CC(C1)N2c1nc(OC[C@@]23CCCN2C[C@H](F)C3)nc2c(F)c(-c3c(F)ccc4sc(N)c(C#N)c34)c3c(c12)COC3] |

| Example | Chemical Name | Structure |
|---|---|---|
| 98 | 2-Amino-5-fluoro-4-[5-fluoro-3-[[(2R,8S)-2-fluoro-1,2,3,5,6,7-hexahydropyrrolizin-8-yl]methoxy]-1-[3-(3-hydroxypropyl)-3,6-diazabicyclo[3.1.1]heptan-6-yl]-7,9-dihydrofuro[3,4-f]quinazolin-6-yl]benzothiophene-3-carbonitrile | 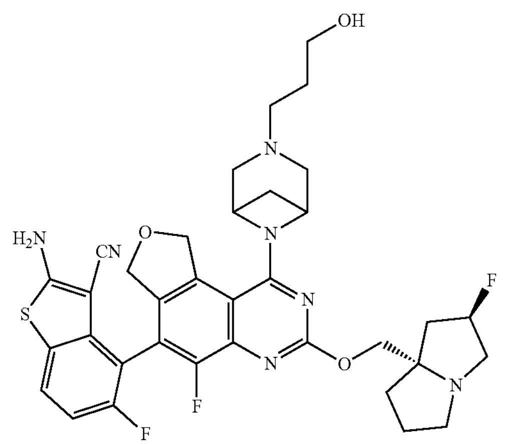 [SMILES: N#Cc1c(N)sc2ccc(F)c(-c3c4c(c5c(N6C7CC6CN(CCCO)C7)nc(OC[C@@]67CCCN6C[C@H](F)C7)nc5c3F)COC4)c12] |
| 99 | 2-Amino-4-[5-fluoro-3-[[(2R,8S)-2-fluoro-1,2,3,5,6,7-hexahydropyrrolizin-8-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile, Isomer 1 | 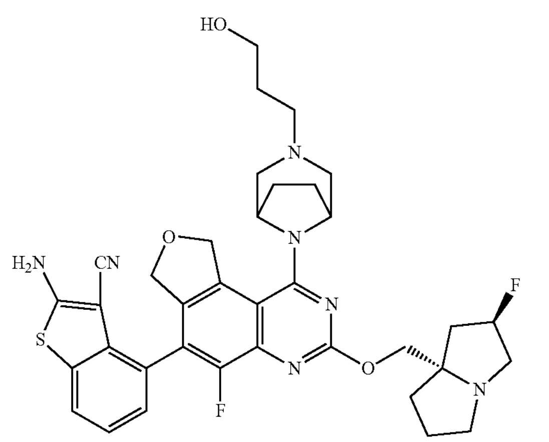 [SMILES: N#Cc1c(N)sc2cccc(-c3c4c(c5c(N6C7CCC6CN(CCCO)C7)nc(OC[C@@]67CCCN6C[C@H](F)C7)nc5c3F)COC4)c12] |
| 100 | 2-Amino-7-fluoro-4-[5-fluoro-3-[[(2R,8S)-2-fluoro-1,2,3,5,6,7-hexahydropyrrolizin-8-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile | 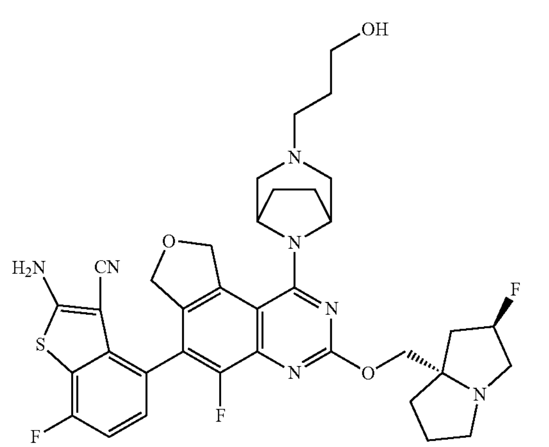 [SMILES: N#Cc1c(N)sc2c(F)ccc(-c3c4c(c5c(N6C7CCC6CN(CCCO)C7)nc(OC[C@@]67CCCN6C[C@H](F)C7)nc5c3F)COC4)c12] |

| Example | Chemical Name | Structure |
|---|---|---|
| 103 | 2-Amino-7-fluoro-4-[5-fluoro-3-[[(2R,8S)-2-fluoro-1,2,3,5,6,7-hexahydropyrrolizin-8-yl]methoxy]-1-[3-[(2R)-oxetan-2-yl]methyl]-3,8-diazabicyclo[3.2.1]octan-8-yl]-7,9-dihydrofuro[3,4-f]quinazolin-6-yl]benzothiophene-3-carbonitrile, Isomer 2 | 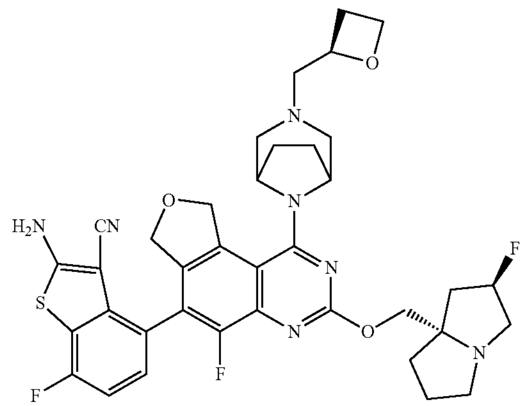 [SMILES: N#Cc1c(N)sc2c(F)ccc(-c3c4c(c5c(N6C7CCC6CN(C[C@H]6CCO6)C7)nc(OC[C@@]67CCCN6C[C@H](F)C7)nc5c3F)COC4)c12] |
| 106 | 2-Amino-7-fluoro-4-[5-fluoro-3-[[(2R,8S)-2-fluoro-1,2,3,5,6,7-hexahydropyrrolizin-8-yl]methoxy]-1-[3-(oxetan-3-ylmethyl)-3,8-diazabicyclo[3.2.1]octan-8-yl]-7,9-dihydrofuro[3,4-f]quinazolin-6-yl]benzothiophene-3-carbonitrile, Isomer 2 | 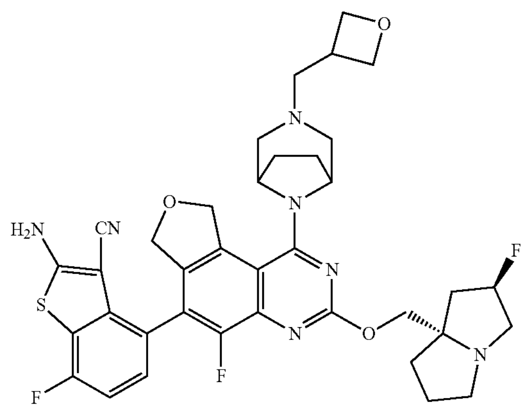 [SMILES: N#Cc1c(N)sc2c(F)ccc(-c3c4c(c5c(N6C7CCC6CN(CC6COC6)C7)nc(OC[C@@]67CCCN6C[C@H](F)C7)nc5c3F)COC4)c12] |
| 107 | 2-Amino-5-fluoro-4-[5-fluoro-3-[[(2R,8S)-2-fluoro-1,2,3,5,6,7-hexahydropyrrolizin-8-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile, Isomer 2 | 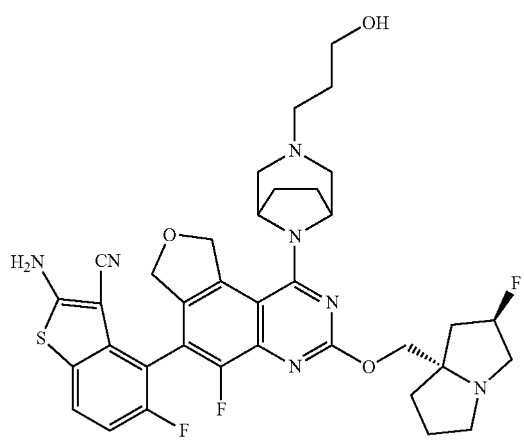 [SMILES: N#Cc1c(N)sc2ccc(F)c(-c3c4c(c5c(N6C7CCC6CN(CCCO)C7)nc(OC[C@@]67CCCN6C[C@H](F)C7)nc5c3F)COC4)c12] |
| 108 | 2-Amino-5-fluoro-4-[5-fluoro-3-[[(2R,8S)-2-fluoro-1,2,3,5,6,7-hexahydropyrrolizin-8-yl]methoxy]-1-(3-methyl-3,8-diazabicyclo[3.2.1]octan-8-yl)-7,9-dihydrofuro[3,4-f]quinazolin-6-yl]benzothiophene-3-carbonitrile | 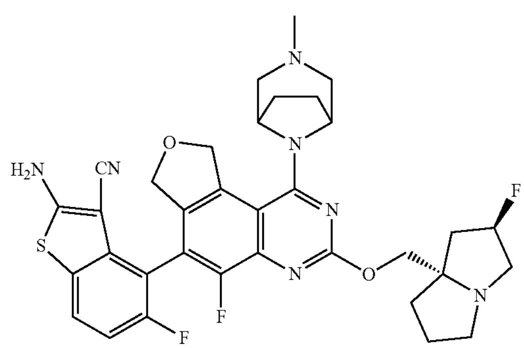 [SMILES: CN1CC2CCC(C1)N2c1nc(OC[C@@]23CCCN2C[C@H](F)C3)nc2c(F)c(-c3c(F)ccc4sc(N)c(C#N)c34)c3c(c12)COC3] |

| Example | Chemical Name | Structure |
|---|---|---|
| 110 | 2-Amino-5-fluoro-4-[5-fluoro-3-[[(2R,8S)-2-fluoro-1,2,3,5,6,7-hexahydropyrrolizin-8-yl]methoxy]-1-[3-[1-(2-hydroxyethyl)pyrazol-4-yl]methyl]-3,8-diazabicyclo[3.2.1]octan-8-yl]-7,9-dihydrofuro[3,4-f]quinazolin-6-yl]benzothiophene-3-carbonitrile | 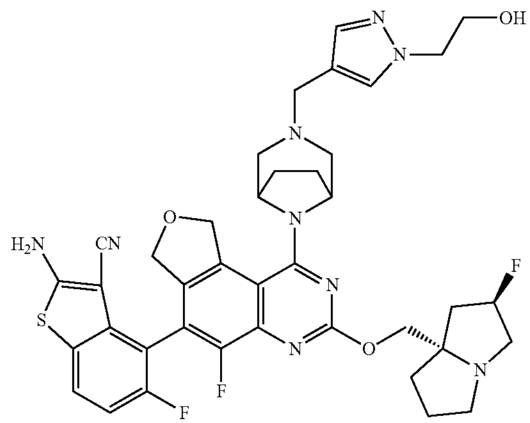 [SMILES: N#Cc1c(N)sc2ccc(F)c(-c3c4c(c5c(N6C7CCC6CN(Cc6cnn(CCO)c6)C7)nc(OC[C@@]67CCCN6C[C@H](F)C7)nc5c3F)COC4)c12] |
| 113 | 2-Amino-5-fluoro-4-[5-fluoro-3-[[(2R,8S)-2-fluoro-1,2,3,5,6,7-hexahydropyrrolizin-8-yl]methoxy]-1-[3-(3-methoxypropyl)-3,8-diazabicyclo[3.2.1]octan-8-yl]-7,9-dihydrofuro[3,4-f]quinazolin-6-yl]benzothiophene-3-carbonitrile | 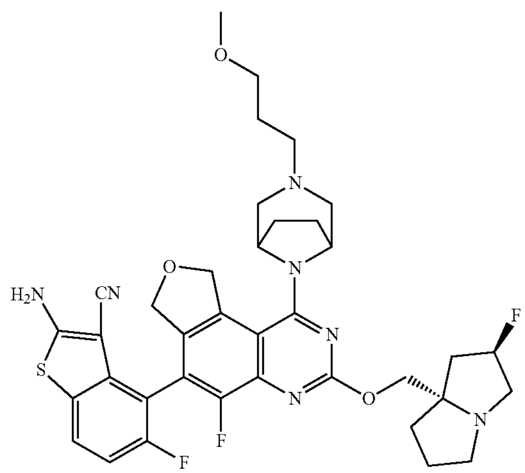 [SMILES: COCCCN1CC2CCC(C1)N2c1nc(OC[C@@]23CCCN2C[C@H](F)C3)nc2c(F)c(-c3c(F)ccc4sc(N)c(C#N)c34)c3c(c12)COC3] |
| 117 | 2-Amino-4-[5-fluoro-3-[[(2R,8S)-2-fluoro-1,2,3,5,6,7-hexahydropyrrolizin-8-yl]methoxy]-1-[3-(oxetan-3-ylmethyl)-3,8-diazabicyclo[3.2.1]octan-8-yl]-7,9-dihydrofuro[3,4-f]quinazolin-6-yl]thieno[3,2-c]pyridine-3-carbonitrile | 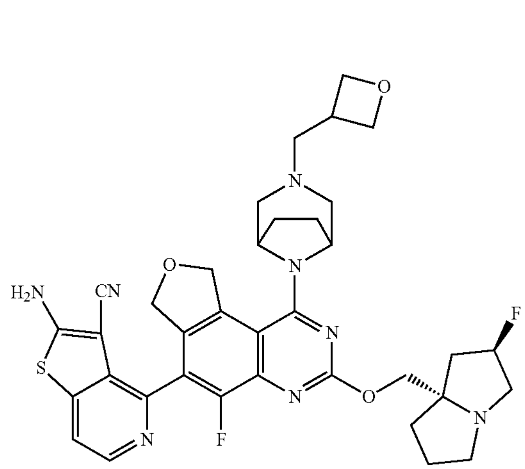 [SMILES: N#Cc1c(N)sc2ccnc(-c3c4c(c5c(N6C7CCC6CN(CC6COC6)C7)nc(OC[C@@]67CCCN6C[C@H](F)C7)nc5c3F)COC4)c12] |

| Example | Chemical Name | Structure |
|---|---|---|
| 118 | 2-Amino-4-[5-fluoro-3-[[(2R,8S)-2-fluoro-1,2,3,5,6,7-hexahydropyrrolizin-8-yl]methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 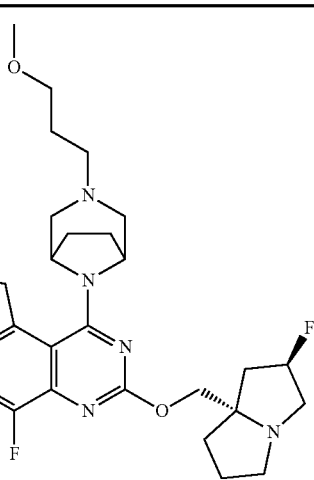 |
| 119 | 2-Amino-4-[5-fluoro-3-[[(2R,8S)-2-fluoro-1,2,3,5,6,7-hexahydropyrrolizin-8-yl]methoxy]-1-[3-(2-methoxyethyl)-3,8-diazabicyclo[3.2.1]octan-8-yl]-7,9-dihydrofuro[3,4-f]quinazolin-6-yl]thieno[3,2-c]pyridine-3-carbonitrile | 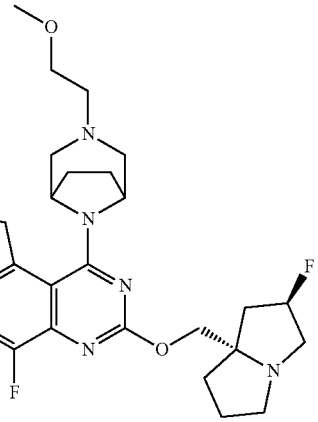 |
| 120 | 2-Amino-4-[5-fluoro-3-[[(2R,8S)-2-fluoro-1,2,3,5,6,7-hexahydropyrrolizin-8-yl]methoxy]-1-[3-[(2R)-2-methoxypropyl]-3,8-diazabicyclo[3.2.1]octan-8-yl]-7,9-dihydrofuro[3,4-f]quinazolin-6-yl]thieno[3,2-c]pyridine-3-carbonitrile | 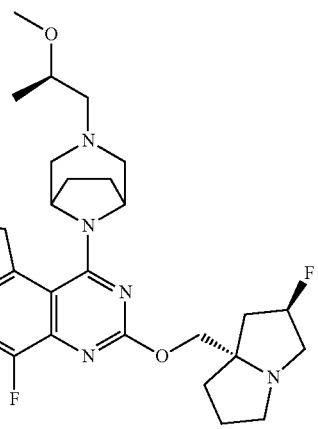 |

| Example | Chemical Name | Structure |
|---|---|---|
| 121 | 2-Amino-7-fluoro-4-[5-fluoro-3-[[(2R,8S)-2-fluoro-1,2,3,5,6,7-hexahydropyrrolizin-8-yl]methoxy]-1-(3-methyl-3,8-diazabicyclo[3.2.1]octan-8-yl)-7,9-dihydrofuro[3,4-f]quinazolin-6-yl]thieno[3,2-c]pyridine-3-carbonitrile | 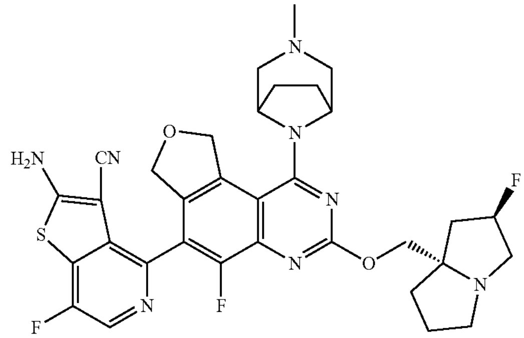 [SMILES: CN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 122 | 2-Amino-7-fluoro-4-[5-fluoro-3-[[(2R,8S)-2-fluoro-1,2,3,5,6,7-hexahydropyrrolizin-8-yl]methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 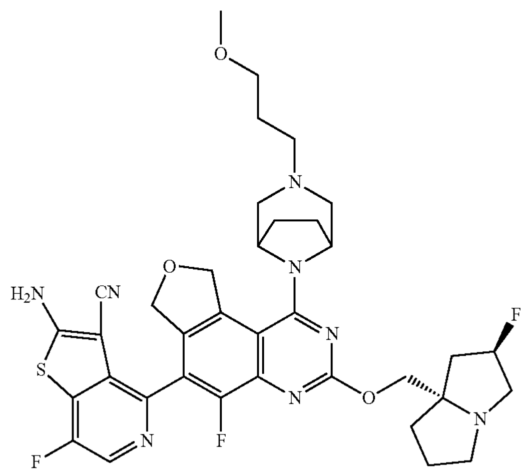 [SMILES: COCCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 123 | 2-Amino-7-fluoro-4-[5-fluoro-3-[[(2R,8S)-2-fluoro-1,2,3,5,6,7-hexahydropyrrolizin-8-yl]methoxy]-1-[3-[(2R)-oxetan-2-yl]methyl]-3,8-diazabicyclo[3.2.1]octan-8-yl]-7,9-dihydrofuro[3,4-f]quinazolin-6-yl]thieno[3,2-c]pyridine-3-carbonitrile | 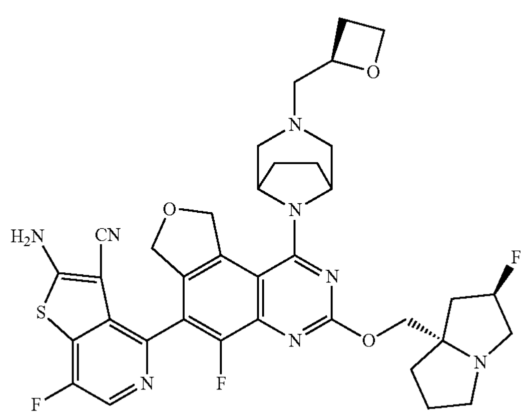 [SMILES: N#Cc1c(N)sc2c(F)cnc(-c3c4c(c5c(N6C7CCC6CN(C[C@H]6CCO6)C7)nc(OC[C@@]67CCCN6C[C@H](F)C7)nc5c3F)COC4)c12] |

| Example | Chemical Name | Structure |
|---------|---------------|-----------|
| 124 | 2-Amino-7-fluoro-4-[5-fluoro-3-[[(2R,8S)-2-fluoro-1,2,3,5,6,7-hexahydropyrrolizin-8-yl]methoxy]-1-[3-(2-methoxyethyl)-3,8-diazabicyclo[3.2.1]octan-8-yl]-7,9-dihydrofuro[3,4-f]quinazolin-6-yl]thieno[3,2-c]pyridine-3-carbonitrile | 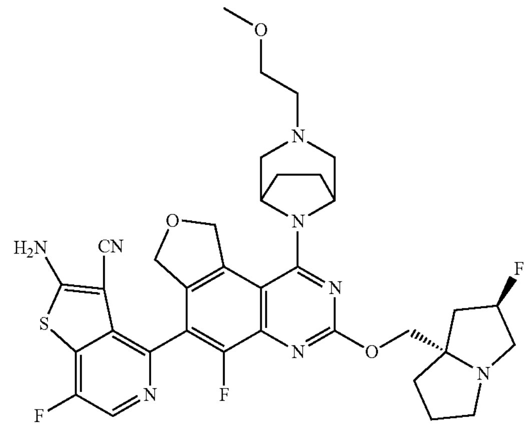 [SMILES: COCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 125 | 2-Amino-7-fluoro-4-[5-fluoro-3-[[(2R,8S)-2-fluoro-1,2,3,5,6,7-hexahydropyrrolizin-8-yl]methoxy]-1-[3-(2-hydroxyethyl)-3,8-diazabicyclo[3.2.1]octan-8-yl]-7,9-dihydrofuro[3,4-f]quinazolin-6-yl]thieno[3,2-c]pyridine-3-carbonitrile | 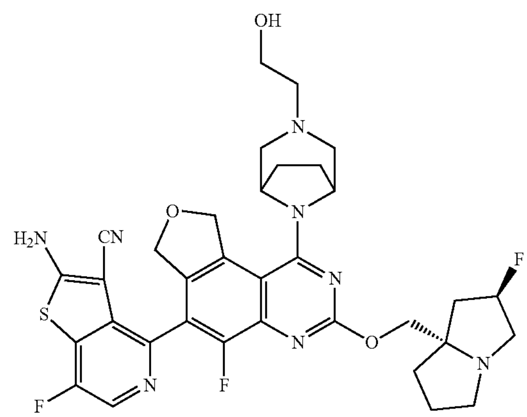 [SMILES: N#Cc1c(N)sc2c(F)cnc(-c3c4c(c5c(N6C7CCC6CN(CCO)C7)nc(OC[C@@]67CCCN6C[C@H](F)C7)nc5c3F)COC4)c12] |
| 126 | 2-Amino-7-fluoro-4-[5-fluoro-3-[[(2R,8S)-2-fluoro-1,2,3,5,6,7-hexahydropyrrolizin-8-yl]methoxy]-1-[3-[(2R)-2-methoxypropyl]-3,8-diazabicyclo[3.2.1]octan-8-yl]-7,9-dihydrofuro[3,4-f]quinazolin-6-yl]thieno[3,2-c]pyridine-3-carbonitrile | 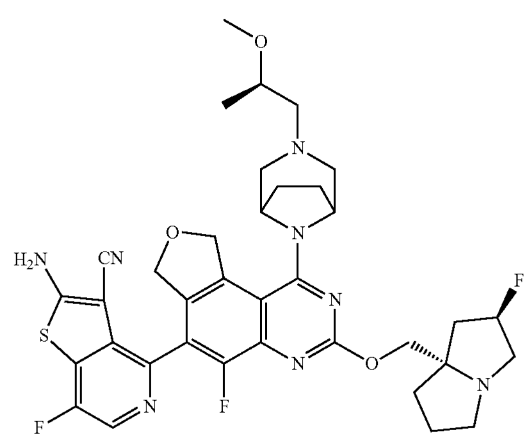 [SMILES: CO[C@H](C)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] |

-continued

| Example | Chemical Name | Structure |
|---|---|---|
| 127 | 2-Amino-4-[1-(3-ethyl-3,8-diazabicyclo[3.2.1]octan-8-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-thieno[3,2-c]pyridine-3-carbonitrile | 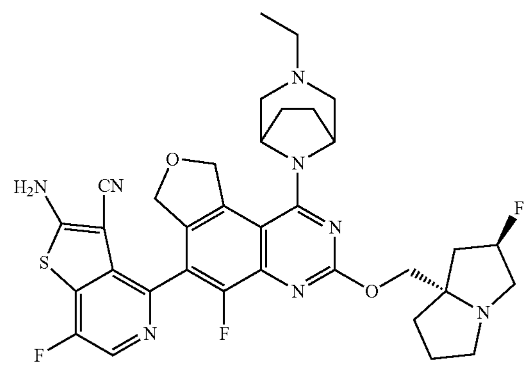 [SMILES: CCN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 130 | 2-Amino-7-fluoro-4-[5-fluoro-3-[[(2R,8S)-2-fluoro-1,2,3,5,6,7-hexahydropyrrolizin-8-yl]methoxy]-1-[3-(oxetan-3-ylmethyl)-3,8-diazabicyclo[3.2.1]octan-8-yl]-7,9-dihydrofuro[3,4-f]quinazolin-6-yl]thieno[3,2-c]pyridine-3-carbonitrile | 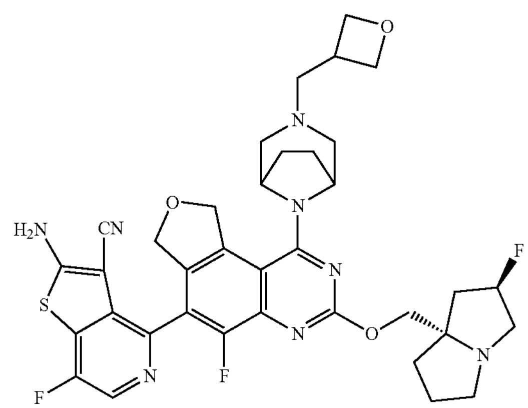 [SMILES: N#Cc1c(N)sc2c(F)cnc(-c3c4c(c5c(N6C7CCC6CN(CC6COC6)C7)nc(OC[C@@]67CCCN6C[C@H](F)C7)nc5c3F)COC4)c12] |
| 131 | 2-Amino-7-fluoro-4-[5-fluoro-1-[3-(2-methoxyethyl)-3,8-diazabicyclo[3.2.1]octan-8-yl]-3-[(2-methoxy-1,2,3,5,6,7-hexahydropyrrolizin-8-yl)methoxy]-7,9-dihydrofuro[3,4-f]quinazolin-6-yl]thieno[3,2-c]pyridine-3-carbonitrile | 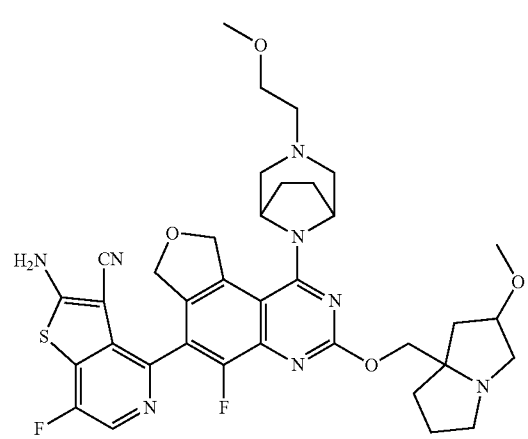 [SMILES: COCCN1CC2CCC(C1)N2c1nc(OCC23CCCN2CC(OC)C3)nc2c(F)c(-c3ncc(F)c4sc(N)c(C#N)c34)c3c(c12)COC3] |

-continued

| Example | Chemical Name | Structure |
|---|---|---|
| 137 | 2-Amino-4-[3-[[(2R,8S)-2-fluoro-1,2,3,5,6,7-hexahydropyrrolizin-8-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile | 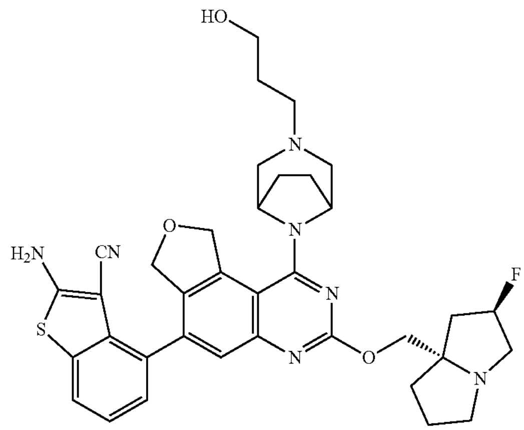 [SMILES: N#Cc1c(N)sc2cccc(-c3cc4nc(OC[C@@]56CCCN5C[C@H](F)C6)nc(N5C6CCC5CN(CCCO)C6)c4c4c3COC4)c12] |
| 138 | 2-Amino-5-fluoro-4-[5-fluoro-1-[3-(3-hydroxypropyl)-3,8-diazabicyclo[3.2.1]octan-8-yl]-3-[[(2S)-1-methylpyrrolidin-2-yl]methoxy]-7,9-dihydrofuro[3,4-f]quinazolin-6-yl]benzothiophene-3-carbonitrile | 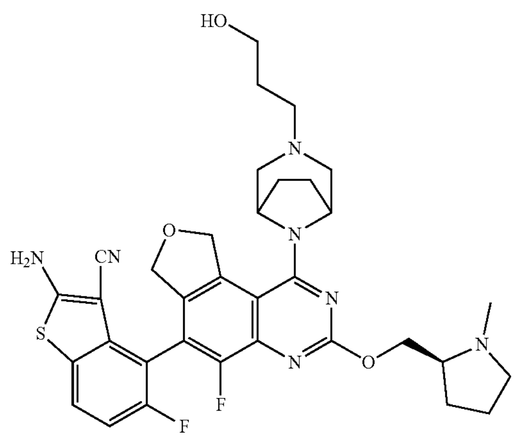 [SMILES: CN1CCC[C@H]1COc1nc(N2C3CCC2CN(CCCO)C3)c2c3c(c(-c4c(F)ccc5sc(N)c(C#N)c45)c(F)c2n1)COC3] |
| 139 | 2-Amino-4-[3-[3-(dimethylamino)azetidin-1-yl]-5-fluoro-1-[3-(3-hydroxypropyl)-3,8-diazabicyclo[3.2.1]octan-8-yl]-7,9-dihydrofuro[3,4-f]quinazolin-6-yl]-5-fluoro-benzothiophene-3-carbonitrile | 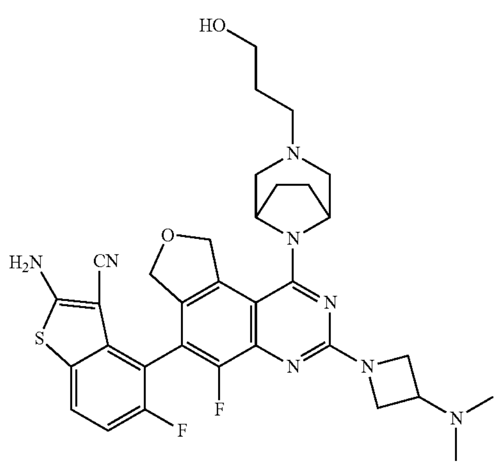 [SMILES: CN(C)C1CN(c2nc(N3C4CCC3CN(CCCO)C4)c3c4c(c(-c5c(F)ccc6sc(N)c(C#N)c56)c(F)c3n2)COC4)C1] |

| Example | Chemical Name | Structure |
|---|---|---|
| 140 | 2-Amino-5-fluoro-4-[5-fluoro-3-[[(2S,4R)-4-fluoro-1-methyl-pyrrolidin-2-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile | 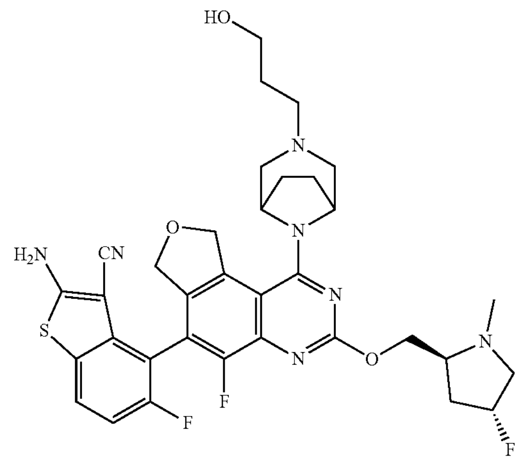 [SMILES: CN1C[C@H](F)C[C@H]1COc1nc(N2C3CCC2CN(CCCO)C3)c2c3c(c(-c4c(F)ccc5sc(N)c(C#N)c45)c(F)c2n1)COC3] |
| 141 | 2-Amino-5-fluoro-4-[5-fluoro-3-[[(2S)-1-(2-fluoroethyl)pyrrolidin-2-yl]methoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile | 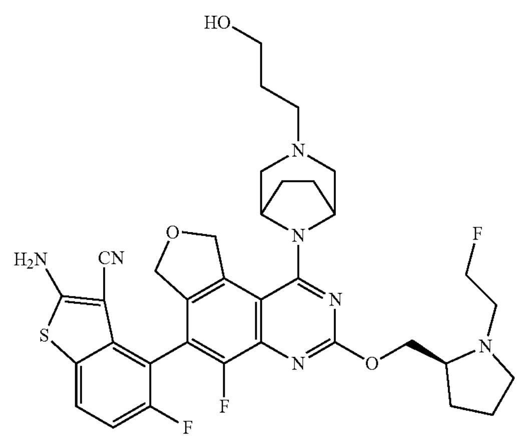 [SMILES: N#Cc1c(N)sc2ccc(F)c(-c3c4c(c5c(N6C7CCC6CN(CCCO)C7)nc(OC[C@@H]6CCCN6CCF)nc5c3F)COC4)c12] |
| 142 | 2-Amino-4-[3-[[(2R)-1,4-dioxan-2-yl]methoxy]-5-fluoro-1-[3-(3-hydroxypropyl)-3,8-diazabicyclo[3.2.1]octan-8-yl]-7,9-dihydrofuro[3,4-f]quinazolin-6-yl]-5-fluoro-benzothiophene-3-carbonitrile | 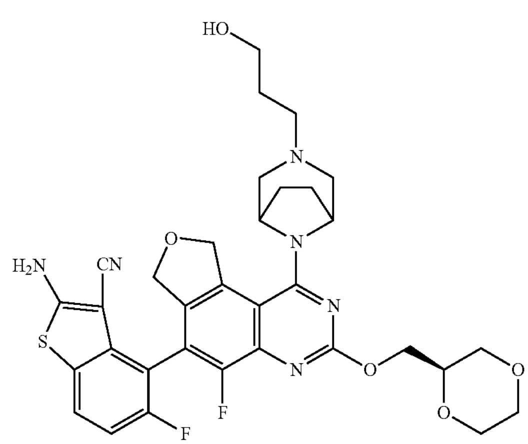 [SMILES: N#Cc1c(N)sc2ccc(F)c(-c3c4c(c5c(N6C7CCC6CN(CCCO)C7)nc(OC[C@H]6COCCO6)nc5c3F)COC4)c12] |

| Example | Chemical Name | Structure |
| --- | --- | --- |
| 143 | 2-Amino-5-fluoro-4-[5-fluoro-1-[3-(3-hydroxypropyl)-3,8-diazabicyclo[3.2.1]octan-8-yl]-3-[[(2R)-tetrahydrofuran-2-yl]methoxy]-7,9-dihydrofuro[3,4-f]quinazolin-6-yl]benzothiophene-3-carbonitrile | 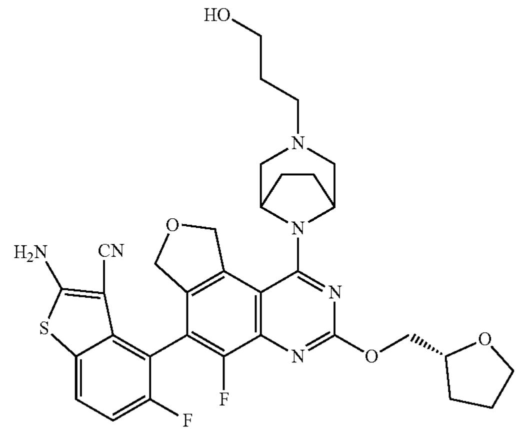 [SMILES: N#Cc1c(N)sc2ccc(F)c(-c3c4c(c5c(N6C7CCC6CN(CCCO)C7)nc(OC[C@H]6CCCO6)nc5c3F)COC4)c12] |
| 144 | 2-Amino-4-[3-[2-(dimethylamino)ethoxy]-5-fluoro-1-[3-(3-hydroxypropyl)-3,8-diazabicyclo[3.2.1]octan-8-yl]-7,9-dihydrofuro[3,4-f]quinazolin-6-yl]-5-fluoro-benzothiophene-3-carbonitrile | 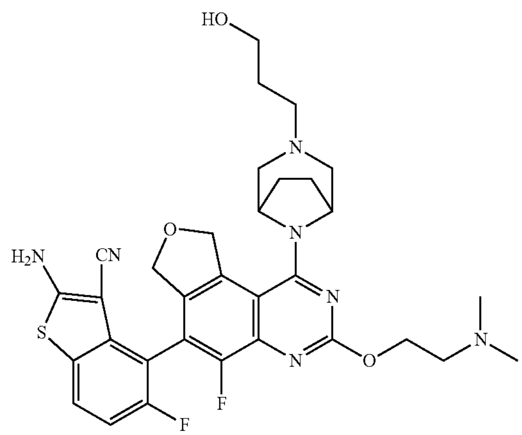 [SMILES: CN(C)CCOc1nc(N2C3CCC2CN(CCCO)C3)c2c3c(c(-c4c(F)ccc5sc(N)c(C#N)c45)c(F)c2n1)COC3] |
| 145 | 2-Amino-5-fluoro-4-[5-fluoro-3-[2-[(3S)-3-fluoropyrrolidin-1-yl]ethoxy]-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile | 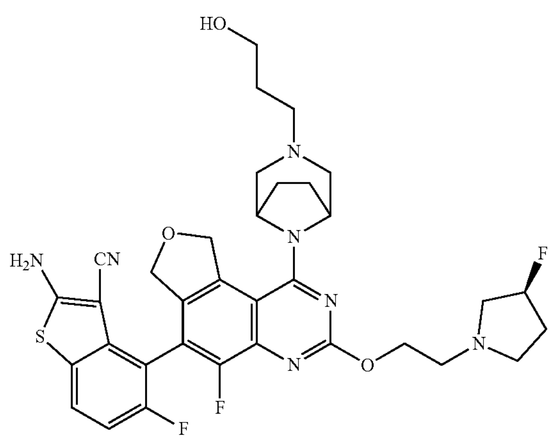 [SMILES: N#Cc1c(N)sc2ccc(F)c(-c3c4c(c5c(N6C7CCC6CN(CCCO)C7)nc(OCCN6CC[C@H](F)C6)nc5c3F)COC4)c12] |

| Example | Chemical Name | Structure |
|---|---|---|
| 146 | 2-Amino-5-fluoro-4-[5-fluoro-1-[3-(3-hydroxypropyl)-3,8-diazabicyclo[3.2.1]octan-8-yl]-3-(2-morpholinoethoxy)-7,9-dihydrofuro[3,4-f]quinazolin-6-yl]benzothiophene-3-carbonitrile | 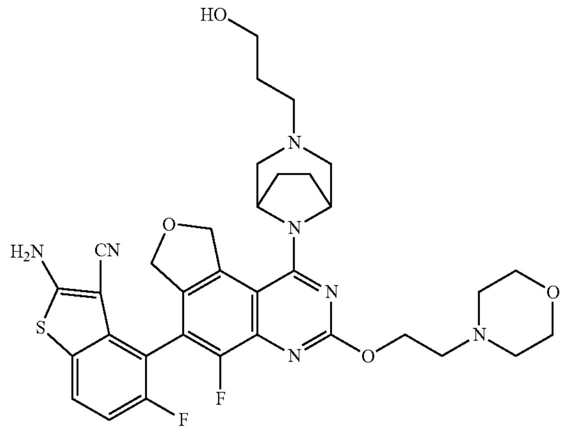 [SMILES: N#Cc1c(N)sc2ccc(F)c(-c3c4c(c5c(N6C7CCC6CN(CCCO)C7)nc(OCCN6CCOCC6)nc5c3F)COC4)c12] |
| 148 | 2-Amino-5-fluoro-4-[5-fluoro-1-[3-(3-hydroxypropyl)-3,8-diazabicyclo[3.2.1]octan-8-yl]-3-[[(2S)-1-methylazetidin-2-yl]methoxy]-7,9-dihydrofuro[3,4-f]quinazolin-6-yl]benzothiophene-3-carbonitrile | 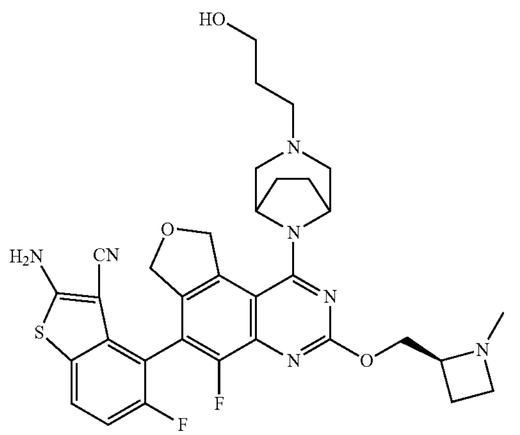 [SMILES: CN1CC[C@H]1COc1nc(N2C3CCC2CN(CCCO)C3)c2c3c(c(-c4c(F)ccc5sc(N)c(C#N)c45)c(F)c2n1)COC3] |
| 149 | 2-Amino-5-fluoro-4-[5-fluoro-3-[[(2S)-1-methylpyrrolidin-2-yl]methoxy]-1-[3-(oxetan-3-ylmethyl)-3,8-diazabicyclo[3.2.1]octan-8-yl]-7,9-dihydrofuro[3,4-f]quinazolin-6-yl]benzothiophene-3-carbonitrile | 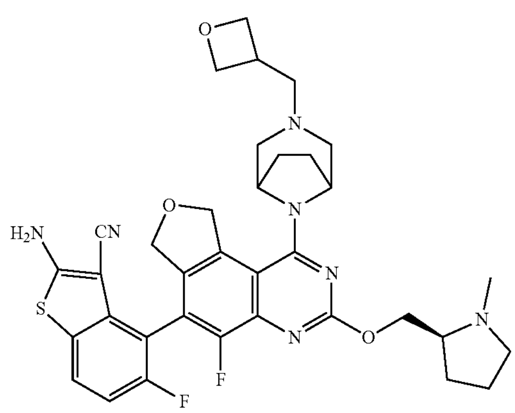 [SMILES: CN1CCC[C@H]1COc1nc(N2C3CCC2CN(CC2COC2)C3)c2c3c(c(-c4c(F)ccc5sc(N)c(C#N)c45)c(F)c2n1)COC3] |

| Example | Chemical Name | Structure |
|---|---|---|
| 150 | 2-Amino-5-fluoro-4-[5-fluoro-1-[3-(2-methoxyethyl)-3,8-diazabicyclo[3.2.1]octan-8-yl]-3-[[(2S)-1-methylpyrrolidin-2-yl]methoxy]-7,9-dihydrofuro[3,4-f]quinazolin-6-yl]benzothiophene-3-carbonitrile | 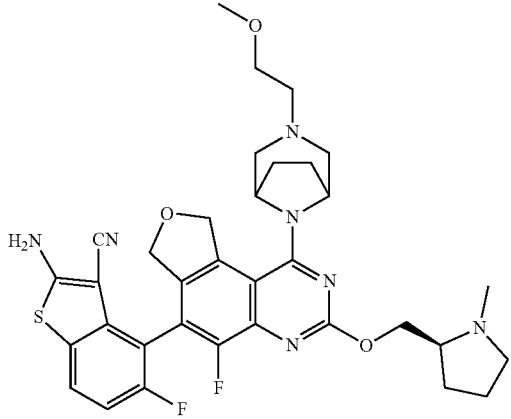 [SMILES: COCCN1CC2CCC(C1)N2c1nc(OC[C@@H]2CCCN2C)nc2c(F)c(-c3c(F)ccc4sc(N)c(C#N)c34)c3c(c12)COC3] |
| 151 | 2-Amino-5-fluoro-4-[5-fluoro-1-[3-(3-methoxypropyl)-3,8-diazabicyclo[3.2.1]octan-8-yl]-3-[[(2S)-1-methylpyrrolidin-2-yl]methoxy]-7,9-dihydrofuro[3,4-f]quinazolin-6-yl]benzothiophene-3-carbonitrile | 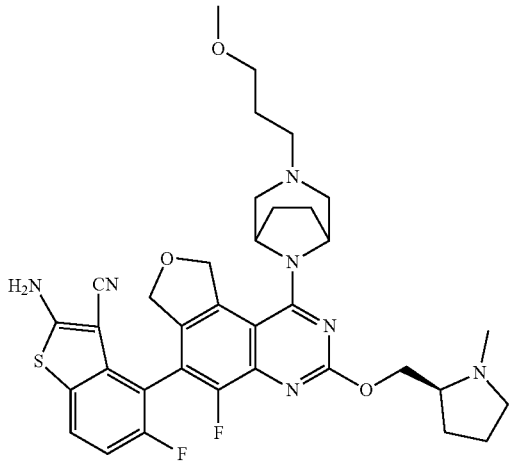 [SMILES: COCCCN1CC2CCC(C1)N2c1nc(OC[C@@H]2CCCN2C)nc2c(F)c(-c3c(F)ccc4sc(N)c(C#N)c34)c3c(c12)COC3] |
| 153 | 2-Amino-5-fluoro-4-[5-fluoro-3-[[(2S,4R)-4-fluoro-1-methyl-pyrrolidin-2-yl]methoxy]-1-(3-methyl-3,6-diazabicyclo[3.1.1]heptan-6-yl)-7,9-dihydrofuro[3,4-f]quinazolin-6-yl]benzothiophene-3-carbonitrile | 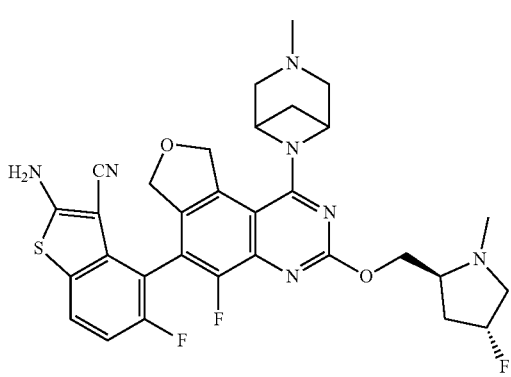 [SMILES: CN1CC2CC(C1)N2c1nc(OC[C@@H]2C[C@@H](F)CN2C)nc2c(F)c(-c3c(F)ccc4sc(N)c(C#N)c34)c3c(c12)COC3] |

-continued

| Example | Chemical Name | Structure |
|---|---|---|
| 156 | 2-Amino-5-fluoro-4-[5-fluoro-1-[3-(4-hydroxybutyl)-3,8-diazabicyclo[3.2.1]octan-8-yl]-7,9-dihydrofuro[3,4-f]quinazolin-6-yl]benzothiophene-3-carbonitrile | 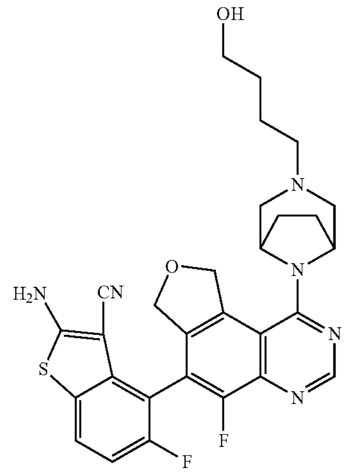 [SMILES: N#Cc1c(N)sc2ccc(F)c(-c3c4c(c5c(N6C7CCC6CN(CCCCO)C7)ncnc5c3F)COC4)c12] |
| 157 | 2-Amino-5-fluoro-4-[5-fluoro-1-[3-[[2-(hydroxymethyl)cyclopropyl]methyl]-3,8-diazabicyclo[3.2.1]octan-8-yl]-7,9-dihydrofuro[3,4-f]quinazolin-6-yl]benzothiophene-3-carbonitrile | 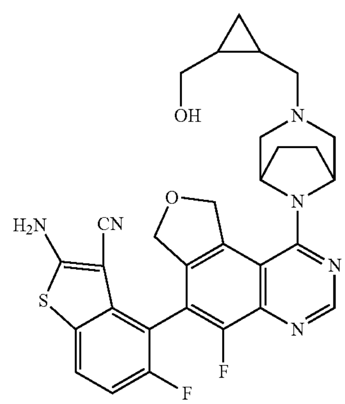 [SMILES: N#Cc1c(N)sc2ccc(F)c(-c3c4c(c5c(N6C7CCC6CN(CC6CC6CO)C7)ncnc5c3F)COC4)c12] |
| 158 | 2-Amino-5-fluoro-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,6-diazabicyclo[3.1.1]heptan-6-yl]-7,9-dihydrofuro[3,4-f]quinazolin-6-yl]benzothiophene-3-carbonitrile, Isomer 1 | 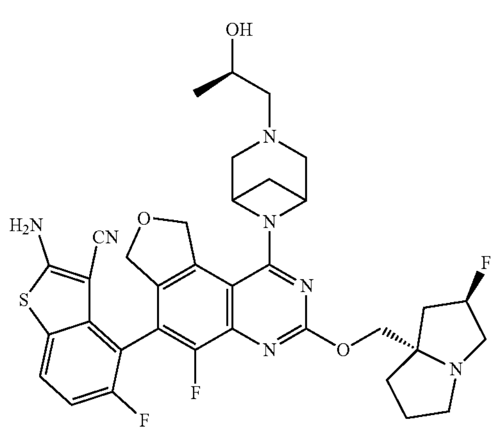 [SMILES: C[C@@H](O)CN1CC2CC(C1)N2c1nc(OC[C@@]23CCCN2C[C@H](F)C3)nc2c(F)c(-c3c(F)ccc4sc(N)c(C#N)c34)c3c(c12)COC3] |

| Example | Chemical Name | Structure |
|---|---|---|
| 161 | 2-Amino-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile, Isomer 2 | 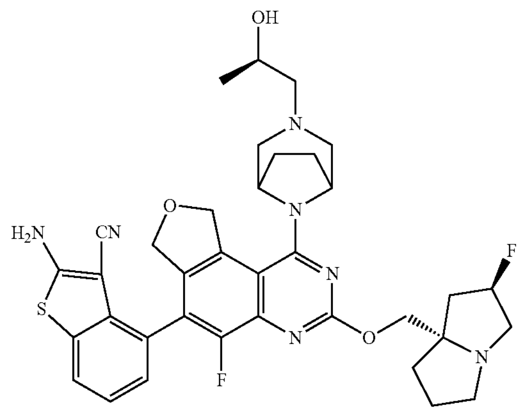 [SMILES: C[C@@H](O)CN1CC2CCC(C1)N2c1nc(OC[C@@]23CCCN2C[C@H](F)C3)nc2c(F)c(-c3cccc4sc(N)c(C#N)c34)c3c(c12)COC3] |
| 162 | 2-Amino-7-fluoro-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 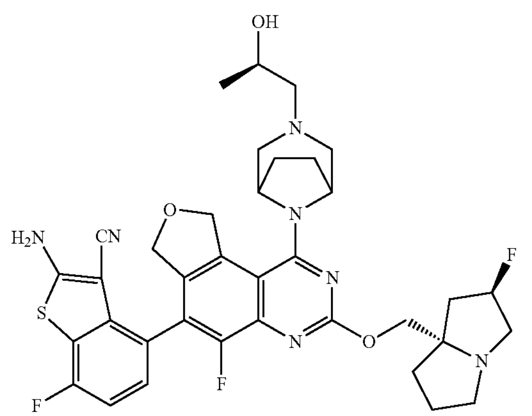 [SMILES: C[C@@H](O)CN1CC2CCC(C1)N2c1nc(OC[C@@]23CCCN2C[C@H](F)C3)nc2c(F)c(-c3ccc(F)c4sc(N)c(C#N)c34)c3c(c12)COC3] |
| 170 | 2-Amino-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 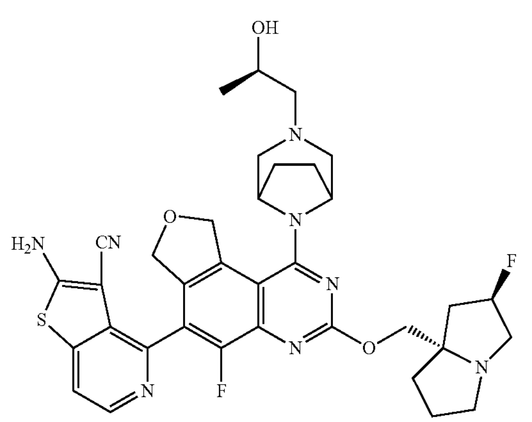 [SMILES: C[C@@H](O)CN1CC2CCC(C1)N2c1nc(OC[C@@]23CCCN2C[C@H](F)C3)nc2c(F)c(-c3nccc4sc(N)c(C#N)c34)c3c(c12)COC3] |

-continued

| Example | Chemical Name | Structure |
|---|---|---|
| 171 | 2-Amino-7-fluoro-4-[5-fluoro-3-[[(2R,8S)-2-fluoro-1,2,3,5,6,7-hexahydropyrrolizin-8-yl]methoxy]-1-[3-[(2S)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 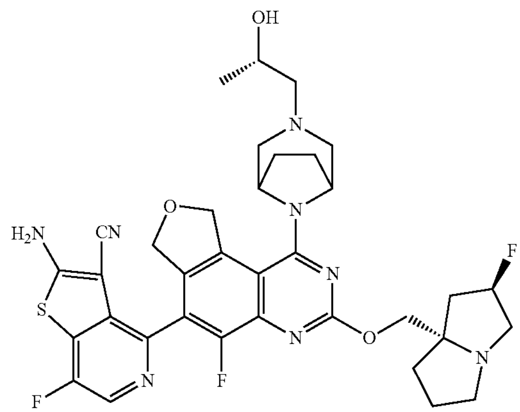 [SMILES: C[C@H](O)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 172 | 2-Amino-7-fluoro-4-[5-fluoro-3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 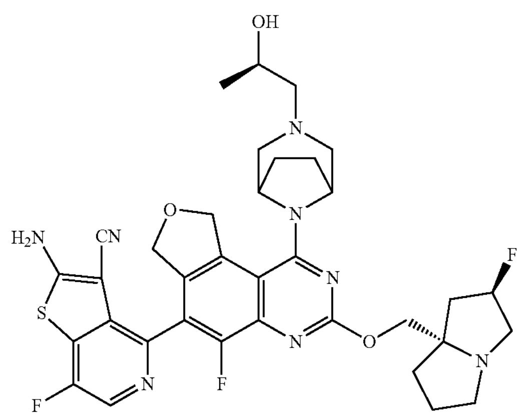 [SMILES: C[C@@H](O)CN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 175 | 2-Amino-4-[3-[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 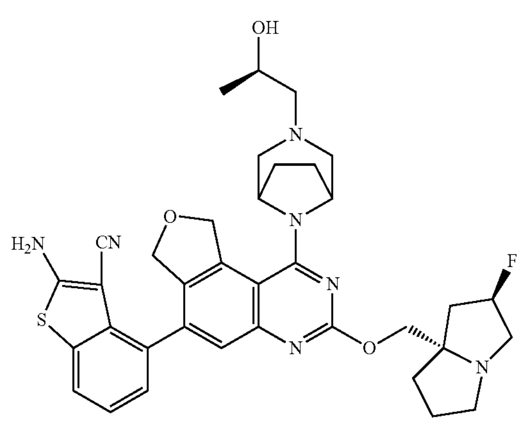 [SMILES: C[C@@H](O)CN1CC2CCC(C1)N2c1nc(OC[C@@]23CCCN2C[C@H](F)C3)nc2cc(-c3cccc4sc(N)c(C#N)c34)c3c(c12)COC3] |

| Example | Chemical Name | Structure |
|---|---|---|
| 177 | 2-Amino-5-fluoro-4-[5-fluoro-1-[3-[(2R)-2-hydroxypropyl]-3,8-diazabicyclo[3.2.1]octan-8-yl]-3-[[(2S)-1-methylpyrrolidin-2-yl]methoxy]-7,9-dihydrofuro[3,4-f]quinazolin-6-yl]benzothiophene-3-carbonitrile | 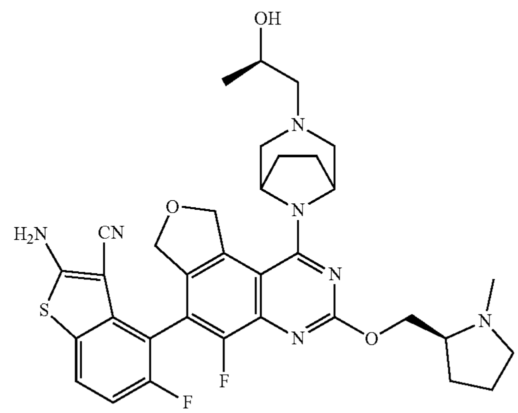 [SMILES: C[C@@H](O)CN1CC2CCC(C1)N2c1nc(OC[C@@H]2CCCN2C)nc2c(F)c(-c3c(F)ccc4sc(N)c(C#N)c34)c3c(c12)COC3] |
| 178 | 2-Amino-5-fluoro-4-[5-fluoro-3-[[(2S,4R)-4-fluoro-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 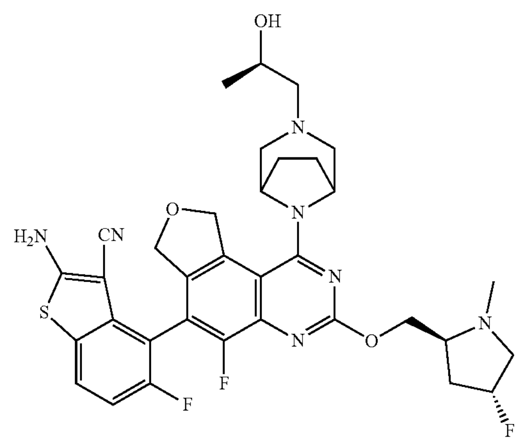 [SMILES: C[C@@H](O)CN1CC2CCC(C1)N2c1nc(OC[C@@H]2C[C@@H](F)CN2C)nc2c(F)c(-c3c(F)ccc4sc(N)c(C#N)c34)c3c(c12)COC3] |
| 179 | 2-Amino-5-fluoro-4-[5-fluoro-1-[3-[(2R)-2-hydroxypropyl]-3,8-diazabicyclo[3.2.1]octan-8-yl]-3-[[(2S)-1-methylazetidin-2-yl]methoxy]-7,9-dihydrofuro[3,4-f]quinazolin-6-yl]benzothiophene-3-carbonitrile | 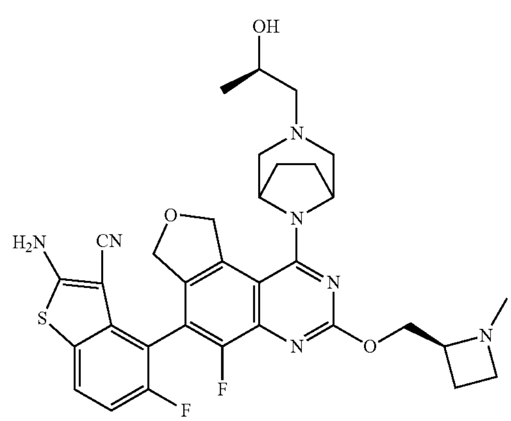 [SMILES: C[C@@H](O)CN1CC2CCC(C1)N2c1nc(OC[C@@H]2CCN2C)nc2c(F)c(-c3c(F)ccc4sc(N)c(C#N)c34)c3c(c12)COC3] |

| Example | Chemical Name | Structure |
|---|---|---|
| 180 | 2-Amino-5-fluoro-4-[5-fluoro-3-[[(2S)-1-(2-hydroxyethyl)azetidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 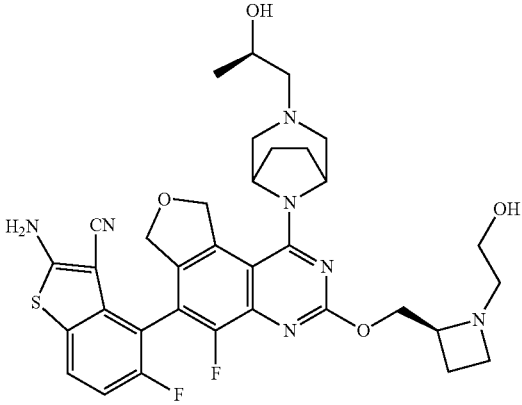 [SMILES: C[C@@H](O)CN1CC2CCC(C1)N2c1nc(OC[C@@H]2CCN2CCO)nc2c(F)c(-c3c(F)ccc4sc(N)c(C#N)c34)c3c(c12)COC3] |
| 181 | 2-Amino-5-fluoro-4-[5-fluoro-3-[[(2S)-1-(2-hydroxyethyl)pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 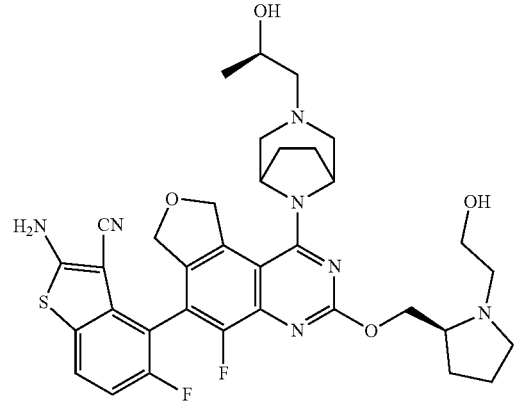 [SMILES: C[C@@H](O)CN1CC2CCC(C1)N2c1nc(OC[C@@H]2CCCN2CCO)nc2c(F)c(-c3c(F)ccc4sc(N)c(C#N)c34)c3c(c12)COC3] |
| 182 | 2-Amino-5-fluoro-4-[5-fluoro-3-[[2-(hydroxymethyl)-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile, Isomer 1 | 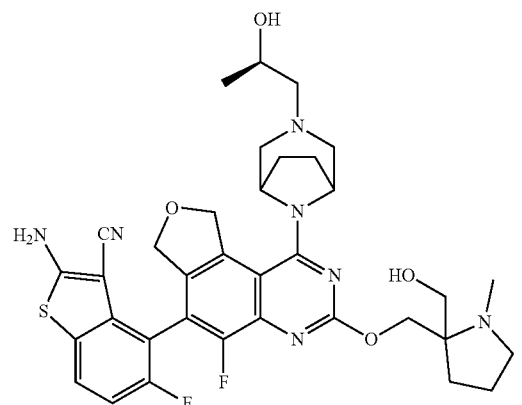 |

| Example | Chemical Name | Structure |
|---|---|---|
| 183 | 2-Amino-5-fluoro-4-[5-fluoro-3-[[2-(hydroxymethyl)-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile, Isomer 2 | 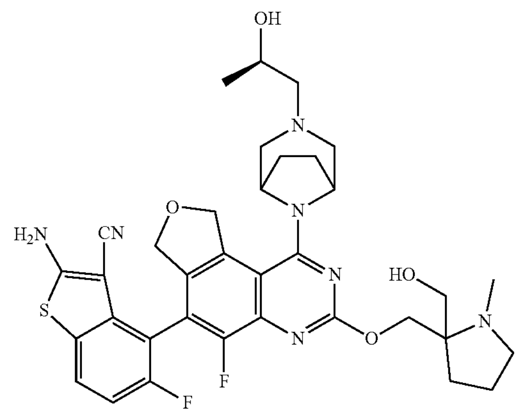 [SMILES: C[C@@H](O)CN1CC2CCC(C1)N2c1nc(OCC2(CO)CCCN2C)nc2c(F)c(-c3c(F)ccc4sc(N)c(C#N)c34)c3c(c12)COC3] |
| 184 | 2-Amino-5-fluoro-4-[5-fluoro-3-[[(2S,4R)-4-hydroxy-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 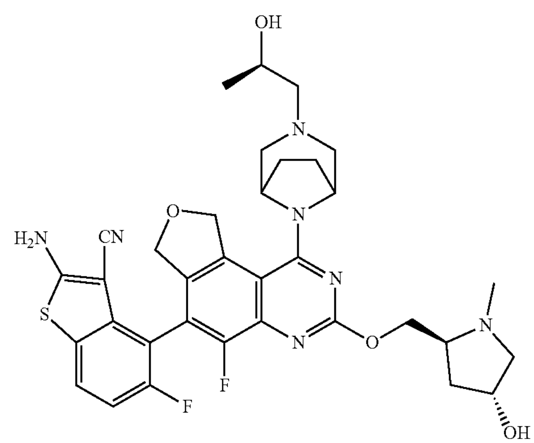 [SMILES: C[C@@H](O)CN1CC2CCC(C1)N2c1nc(OC[C@@H]2C[C@@H](O)CN2C)nc2c(F)c(-c3c(F)ccc4sc(N)c(C#N)c34)c3c(c12)COC3] |
| 185 | 2-Amino-5-fluoro-4-[5-fluoro-3-[[(2R,3S)-3-hydroxy-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 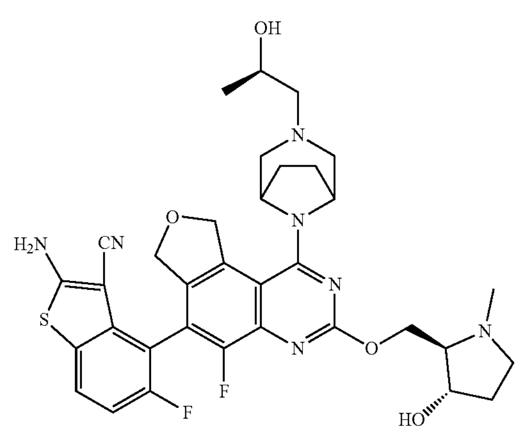 [SMILES: C[C@@H](O)CN1CC2CCC(C1)N2c1nc(OC[C@@H]2[C@@H](O)CCN2C)nc2c(F)c(-c3c(F)ccc4sc(N)c(C#N)c34)c3c(c12)COC3] |

| Example | Chemical Name | Structure |
|---|---|---|
| 186 | 2-Amino-5-fluoro-4-[5-fluoro-3-[(2S,4S)-4-fluoro-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile | 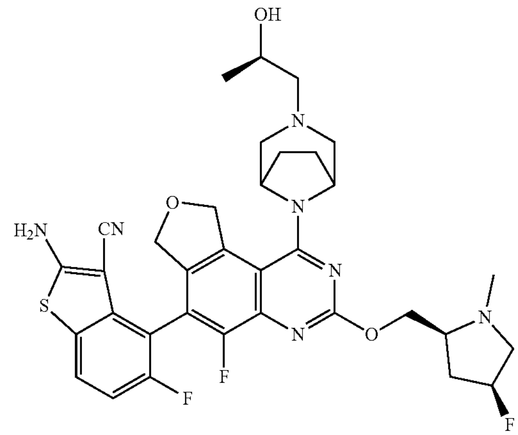 [SMILES: C[C@@H](O)CN1CC2CCC(C1)N2c1nc(OC[C@@H]2C[C@H](F)CN2C)nc2c(F)c(-c3c(F)ccc4sc(N)c(C#N)c34)c3c(c12)COC3] |
| 187 | 2-Amino-4-[3-[[1-(dimethylamino)cyclopropyl]methoxy]-5-fluoro-1-[3-[(2R)-2-hydroxypropyl]-3,8-diazabicyclo[3.2.1]octan-8-yl]-7,9-dihydrofuro[3,4-f]quinazolin-6-yl]-5-fluoro-benzothiophene-3-carbonitrile | 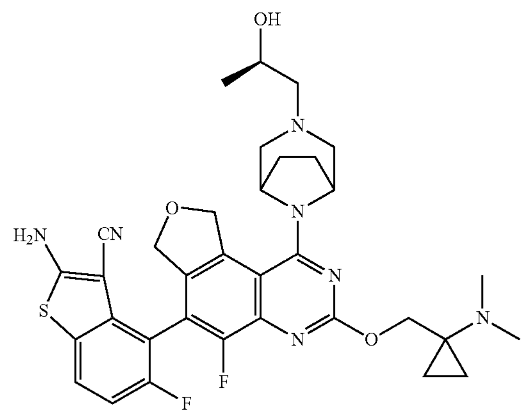 [SMILES: C[C@@H](O)CN1CC2CCC(C1)N2c1nc(OCC2(N(C)C)CC2)nc2c(F)c(-c3c(F)ccc4sc(N)c(C#N)c34)c3c(c12)COC3] |
| 189 | 3-[8-[6-(2-amino-3-cyano-5-fluoro-benzothiophen-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]-N-methyl-propanamide | 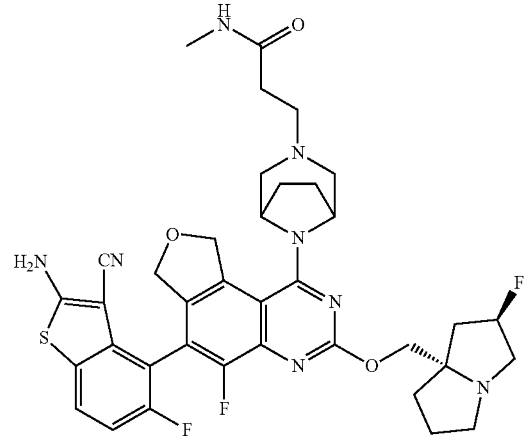 [SMILES: CNC(=O)CCN1CC2CCC(C1)N2c1nc(OC[C@@]23CCCN2C[C@H](F)C3)nc2c(F)c(-c3c(F)ccc4sc(N)c(C#N)c34)c3c(c12)COC3] |

| Example | Chemical Name | Structure |
|---|---|---|
| 190 | 3-[8-[6-(2-Amino-3-cyano-5-fluoro-benzothiophen-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]-N,N-dimethyl-propanamide | 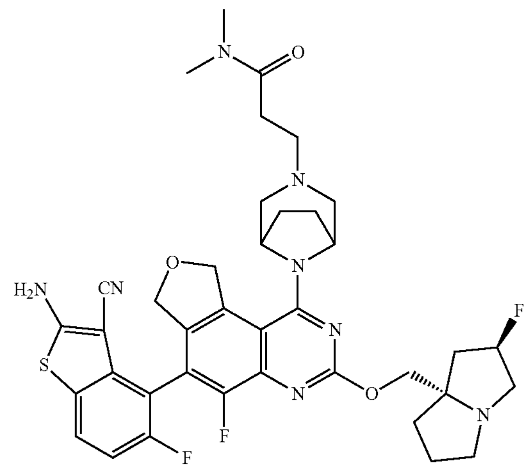 [SMILES: CN(C)C(=O)CCN1CC2CCC(C1)N2c1nc(OC[C@@]23CCCN2C[C@H](F)C3)nc2c(F)c(-c3c(F)ccc4sc(N)c(C#N)c34)c3c(c12)COC3] |
| 191 | 2-Amino-5-fluoro-4-[5-fluoro-3-[[(2R,8S)-2-fluoro-1,2,3,5,6,7-hexahydropyrrolizin-8-yl]methoxy]-1-[3-(trideuteriomethyl)-3,8-diazabicyclo[3.2.1]octan-8-yl]-7,9-dihydrofuro[3,4-f]quinazolin-6-yl]benzothiophene-3-carbonitrile | 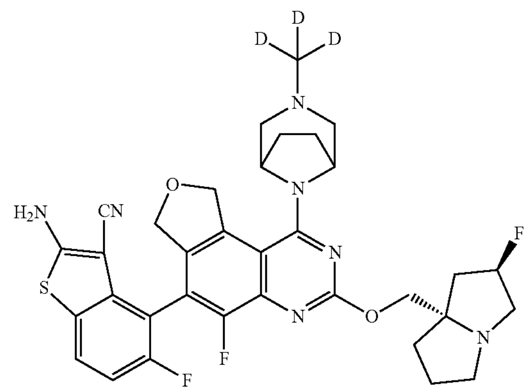 [SMILES: [2H]C([2H])([2H])N1CC2CCC(C1)N2c1nc(OC[C@@]23CCCN2C[C@H](F)C3)nc2c(F)c(-c3c(F)ccc4sc(N)c(C#N)c34)c3c(c12)COC3] |
| 192 | 2-Amino-5-fluoro-4-[5-fluoro-3-[[(2R,8S)-2-fluoro-1,2,3,5,6,7-hexahydropyrrolizin-8-yl]methoxy]-1-[3-(trideuteriomethyl)-3,6-diazabicyclo[3.1.1]heptan-6-yl]-7,9-dihydrofuro[3,4-f]quinazolin-6-yl]benzothiophene-3-carbonitrile | 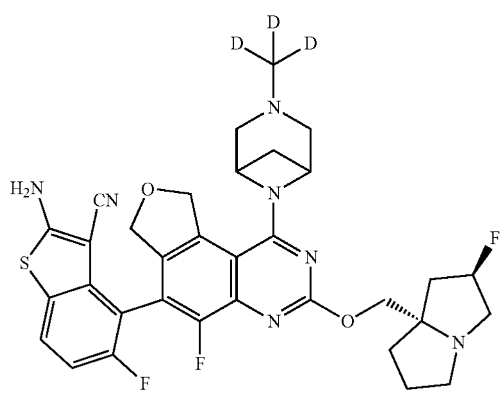 [SMILES: [2H]C([2H])([2H])N1CC2CC(C1)N2c1nc(OC[C@@]23CCCN2C[C@H](F)C3)nc2c(F)c(-c3c(F)ccc4sc(N)c(C#N)c34)c3c(c12)COC3] |
| 194 | 3-[8-[6-(2-Amino-5,7-difluoro-1,3-benzothiazol-4-yl)-5-fluoro-3-[[(2R,8S)-2-fluoro-1,2,3,5,6,7-hexahydropyrrolizin-8-yl]methoxy]-7,9-dihydrofuro[3,4-f]quinazolin-1-yl]-3,8-diazabicyclo[3.2.1]octan-3-yl]propan-1-ol | 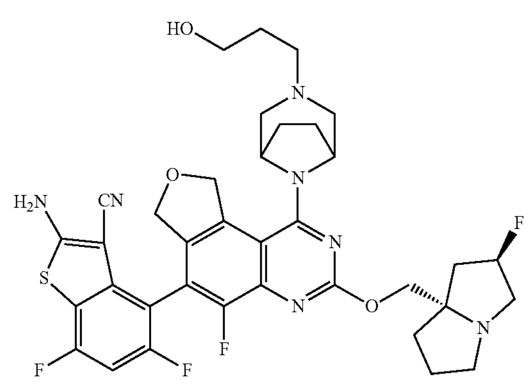 [SMILES: N#Cc1c(N)sc2c(F)cc(F)c(-c3c4c(c5c(N6C7CCC6CN(CCCO)C7)nc(OC[C@@]67CCCN6C[C@H](F)C7)nc5c3F)COC4)c12] |

| Example | Chemical Name | Structure |
| --- | --- | --- |
| 212 | 2-Amino-4-[5-fluoro-3-[[(2R,8S)-2-fluoro-1,2,3,5,6,7-hexahydropyrrolizin-8-yl]methoxy]-1-[3-(2-methoxyethyl)-3,8-diazabicyclo[3.2.1]octan-8-yl]-7,9-dihydrofuro[3,4-f]quinazolin-6-yl]benzothiophene-3-carbonitrile | 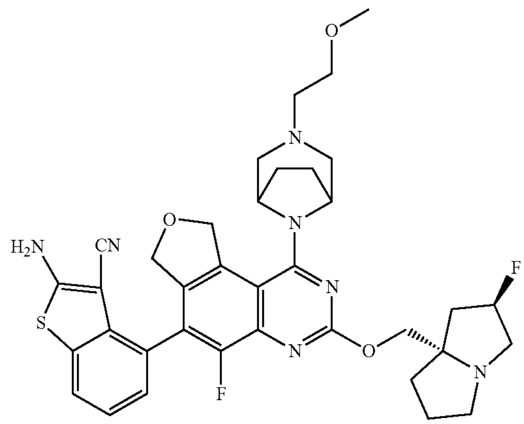 [SMILES: COCCN1CC2CCC(C1)N2c1nc(OC[C@@]23CCCN2C[C@H](F)C3)nc2c(F)c(-c3cccc4sc(N)c(C#N)c34)c3c(c12)COC3] |
| 213 | 2-Amino-4-[5-fluoro-3-[[(2R,8S)-2-fluoro-1,2,3,5,6,7-hexahydropyrrolizin-8-yl]methoxy]-1-[3-[(2R)-2-methoxypropyl]-3,8-diazabicyclo[3.2.1]octan-8-yl]-7,9-dihydrofuro[3,4-f]quinazolin-6-yl]benzothiophene-3-carbonitrile | 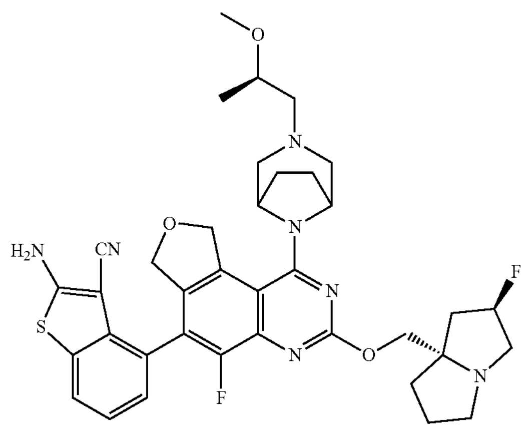 [SMILES: CO[C@H](C)CN1CC2CCC(C1)N2c1nc(OC[C@@]23CCCN2C[C@H](F)C3)nc2c(F)c(-c3cccc4sc(N)c(C#N)c34)c3c(c12)COC3] |
| 214 | 2-Amino-4-[3-[[(2R)-1,4-dioxan-2-yl]methoxy]-5-fluoro-1-[3-(3-hydroxypropyl)-3,8-diazabicyclo[3.2.1]octan-8-yl]-7,9-dihydrofuro[3,4-f]quinazolin-6-yl]benzothiophene-3-carbonitrile, Isomer 2 | 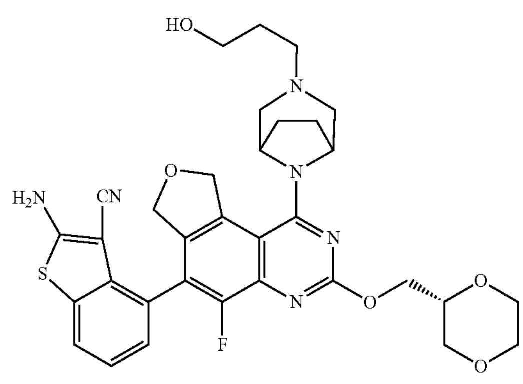 [SMILES: N#Cc1c(N)sc2cccc(-c3c4c(c5c(N6C7CCC6CN(CCCO)C7)nc(OC[C@H]6COCCO6)nc5c3F)COC4)c12] |

-continued

| Example | Chemical Name | Structure |
|---|---|---|
| 216 | 2-Amino-5-fluoro-4-[5-fluoro-1-[3-[(2R)-2-methoxypropyl]-3,8-diazabicyclo[3.2.1]octan-8-yl]-3-[(2S)-1-methylpyrrolidin-2-yl]methoxy]-7,9-dihydrofuro[3,4-f]quinazolin-6-yl]benzothiophene-3-carbonitrile | 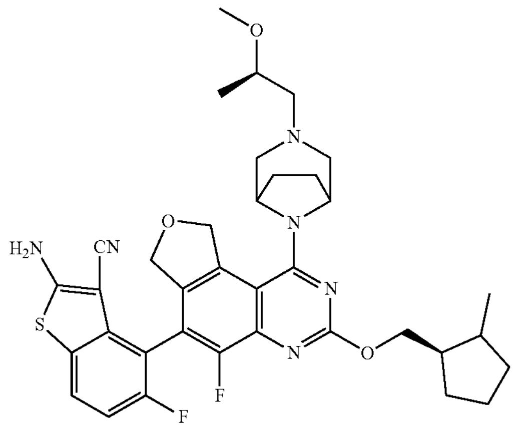 [SMILES: CO[C@H](C)CN1CC2CCC(C1)N2c1nc(OC[C@@H]2CCCC2C)nc2c(F)c(-c3c(F)ccc4sc(N)c(C#N)c34)c3c(c12)COC3] |
| 217 | 2-Amino-5-fluoro-4-[5-fluoro-1-[3-(3-hydroxypropyl)-3,8-diazabicyclo[3.2.1]octan-8-yl]-3-[2-(3-methoxyazetidin-1-yl)ethoxy]-7,9-dihydrofuro[3,4-f]quinazolin-6-yl]benzothiophene-3-carbonitrile | 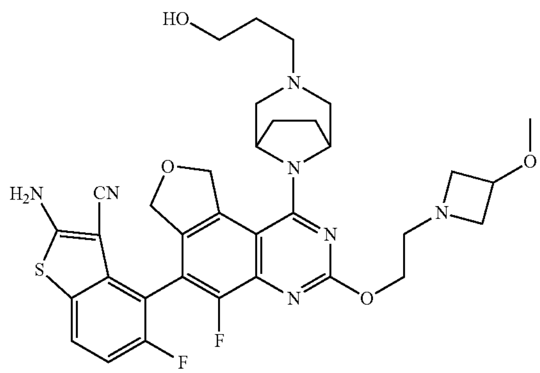 [SMILES: COC1CN(CCOc2nc(N3C4CCC3CN(CCCO)C4)c3c4c(c(-c5c(F)ccc6sc(N)c(C#N)c56)c(F)c3n2)COC4)C1] |
| 218 | 2-Amino-7-fluoro-4-[5-fluoro-3-[[(2R,8S)-2-fluoro-1,2,3,5,6,7-hexahydropyrrolizin-8-yl]methoxy]-1-[3-(3-hydroxypropyl)-3,8-diazabicyclo[3.2.1]octan-8-yl]-7,9-dihydrofuro[3,4-f]quinazolin-6-yl]thieno[3,2-c]pyridine-3-carbonitrile | 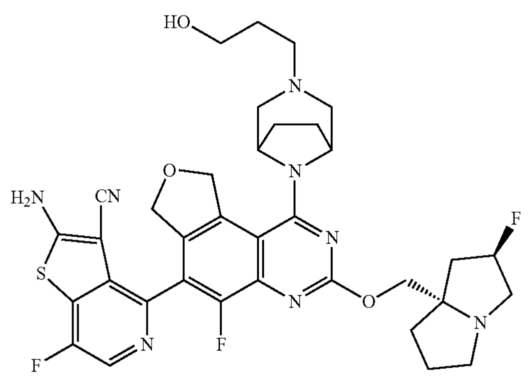 [SMILES: N#Cc1c(N)sc2c(F)cnc(-c3c4c(c5c(N6C7CCC6CN(CCCO)C7)nc(OC[C@@]67CCCN6C[C@H](F)C7)nc5c3F)COC4)c12] |
| 220 | 2-Amino-7-fluoro-4-[5-fluoro-3-[[(2R,8S)-2-fluoro-1,2,3,5,6,7-hexahydropyrrolizin-8-yl]methoxy]-1-[3-[2-(2-methoxyethoxy)ethyl]-3,8-diazabicyclo[3.2.1]octan-8-yl]-7,9-dihydrofuro[3,4-f]quinazolin-6-yl]thieno[3,2-c]pyridine-3-carbonitrile | 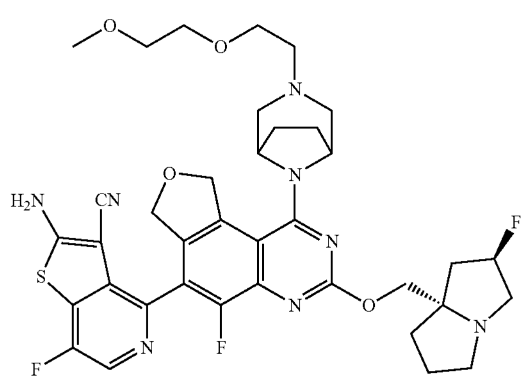 [SMILES: COCCOCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] |

| Example | Chemical Name | Structure |
|---|---|---|
| 224 | 2-Amino-7-fluoro-4-[5-fluoro-3-[[(2R,8S)-2-fluoro-1,2,3,5,6,7-hexahydropyrrolizin-8-yl]methoxy]-1-[3-[2-(2-hydroxyethoxy)ethyl]-3,8-diazabicyclo[3.2.1]octan-8-yl]-7,9-dihydrofuro[3,4-f]quinazolin-6-yl]thieno[3,2-c]pyridine-3-carbonitrile | 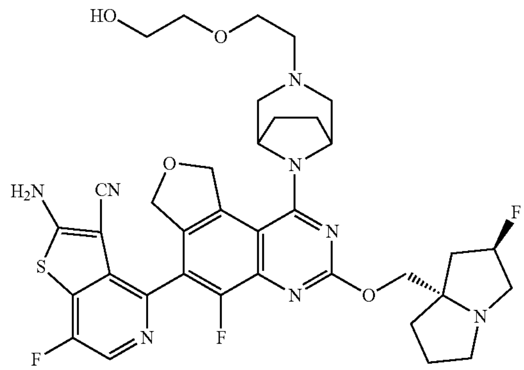 [SMILES: N#Cc1c(N)sc2c(F)cnc(-c3c4c(c5c(N6C7CCC6CN(CCOCCO)C7)nc(OC[C@@]67CCCN6C[C@H](F)C7)nc5c3F)COC4)c12] |
| 225 | 2-Amino-7-fluoro-4-[5-fluoro-3-[[(2R,8S)-2-fluoro-1,2,3,5,6,7-hexahydropyrrolizin-8-yl]methoxy]-1-[3-[3-(2-hydroxyethoxy)propyl]-3,8-diazabicyclo[3.2.1]octan-8-yl]-7,9-dihydrofuro[3,4-f]quinazolin-6-yl]thieno[3,2-c]pyridine-3-carbonitrile | 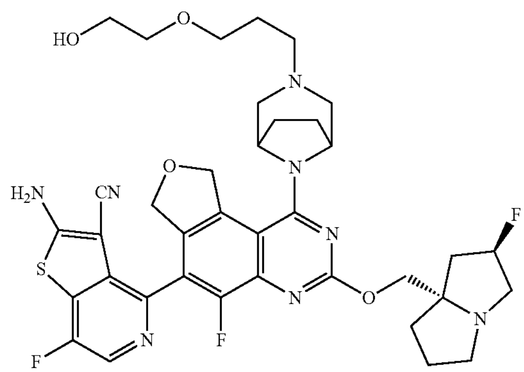 [SMILES: N#Cc1c(N)sc2c(F)cnc(-c3c4c(c5c(N6C7CCC6CN(CCCOCCO)C7)nc(OC[C@@]67CCCN6C[C@H](F)C7)nc5c3F)COC4)c12] |
| 226 | 2-Amino-7-fluoro-4-[5-fluoro-3-[[(2R,8S)-2-fluoro-1,2,3,5,6,7-hexahydropyrrolizin-8-yl]methoxy]-1-[3-[3-(2-methoxyethoxy)propyl]-3,8-diazabicyclo[3.2.1]octan-8-yl]-7,9-dihydrofuro[3,4-f]quinazolin-6-yl]thieno[3,2-c]pyridine-3-carbonitrile | 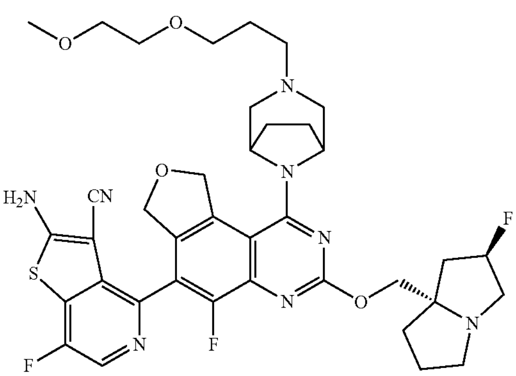 [SMILES: COCCOCCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 227 | 2-Amino-4-[1-[3-[(3R)-3,4-dihydroxybutyl]-3,8-diazabicyclo[3.2.1]octan-8-yl]-5-fluoro-3-[[(2R,8S)-2-fluoro-1,2,3,5,6,7-hexahydropyrrolizin-8-yl]methoxy]-7,9-dihydrofuro[3,4-f]quinazolin-6-yl]-7-fluoro-thieno[3,2-c]pyridine-3-carbonitrile | 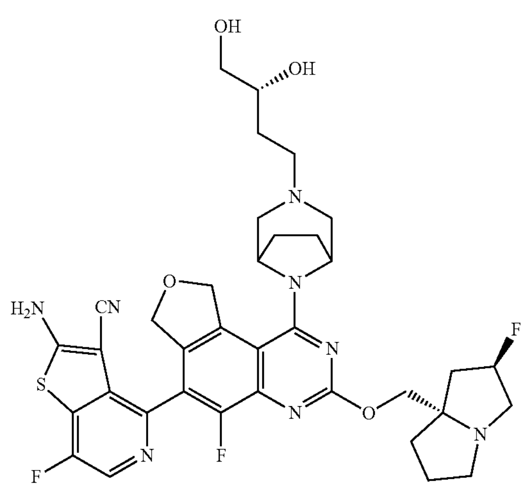 [SMILES: N#Cc1c(N)sc2c(F)cnc(-c3c4c(c5c(N6C7CCC6CN(CC[C@@H](O)CO)C7)nc(OC[C@@]67CCCN6C[C@H](F)C7)nc5c3F)COC4)c12] |

-continued

| Example | Chemical Name | Structure |
|---|---|---|
| 228 | 2-Amino-7-fluoro-4-[5-fluoro-3-[[(2R,8S)-2-fluoro-1,2,3,5,6,7-hexahydropyrrolizin-8-yl]methoxy]-1-[3-[3-hydroxy-2-(hydroxymethyl)propyl]-3,8-diazabicyclo[3.2.1]octan-8-yl]-7,9-dihydrofuro[3,4-f]quinazolin-6-yl]thieno[3,2-c]pyridine-3-carbonitrile | 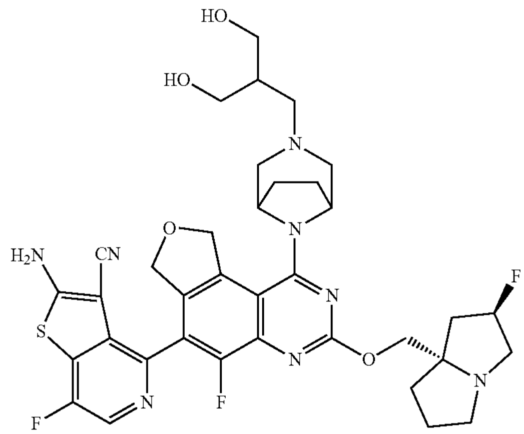 [SMILES: N#Cc1c(N)sc2c(F)cnc(-c3c4c(c5c(N6C7CCC6CN(CC(CO)CO)C7)nc(OC[C@@]67CCCN6C[C@H](F)C7)nc5c3F)COC4)c12] |
| 229 | 2-Amino-7-fluoro-4-[5-fluoro-3-[(2-methoxy-1,2,3,5,6,7-hexahydropyrrolizin-8-yl)methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 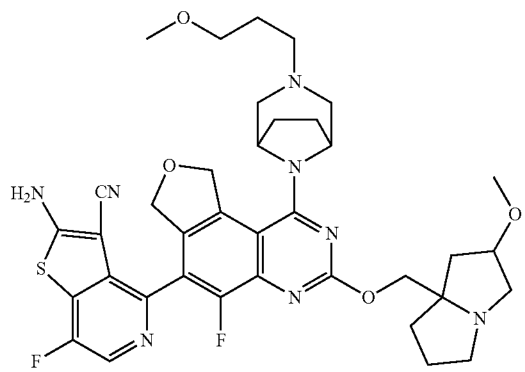 [SMILES: COCCCN1CC2CCC(C1)N2c1nc(OCC23CCCN2CC(OC)C3)nc2c(F)c(-c3ncc(F)c4sc(N)c(C#N)c34)c3c(c12)COC3] |
| 231 | 2-Amino-7-fluoro-4-[5-fluoro-3-[(2-methoxy-1,2,3,5,6,7-hexahydropyrrolizin-8-yl)methoxy]-1-[3-[[(2R)-oxetan-2-yl]methyl]-3,8-diazabicyclo[3.2.1]octan-8-yl]-7,9-dihydrofuro[3,4-f]quinazolin-6-yl]thieno[3,2-c]pyridine-3-carbonitrile methanesulfonic acid | 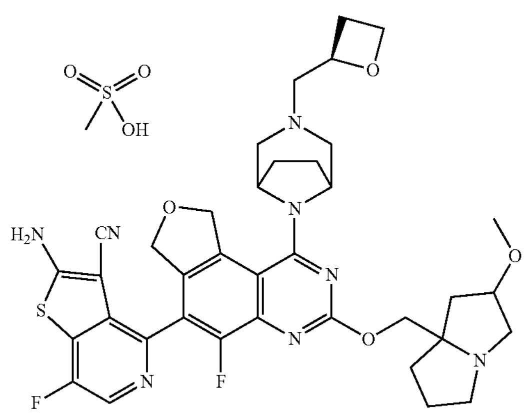 |
| 232 | 2-Amino-7-fluoro-4-[5-fluoro-3-[[(2R,8S)-2-methoxy-1,2,3,5,6,7-hexahydropyrrolizin-8-yl]methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 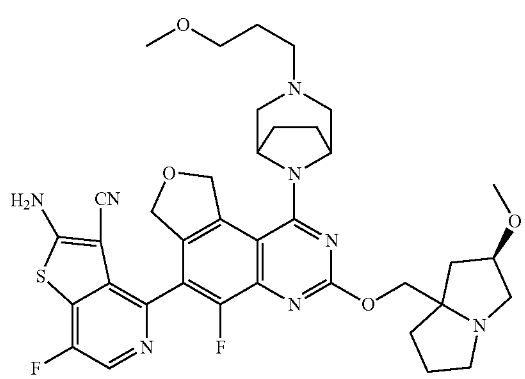 [SMILES: COCCCN1CC2CCC(C1)N2c1nc(OCC23CCCN2C[C@H](OC)C3)nc2c(F)c(-c3ncc(F)c4sc(N)c(C#N)c34)c3c(c12)COC3] |

| Example | Chemical Name | Structure |
|---|---|---|
| 234 | 2-amino-7-fluoro-4-[5-fluoro-3-[[(2R,8S)-2-methoxy-1,2,3,5,6,7-hexahydropyrrolizin-8-yl]methoxy]-1-[3-[(2R)-oxetan-2-yl]methyl]-3,8-diazabicyclo[3.2.1]octan-8-yl]-7,9-dihydrofuro[3,4-f]quinazolin-6-yl]thieno[3,2-c]pyridine-3-carbonitrile methanesulfonic acid | 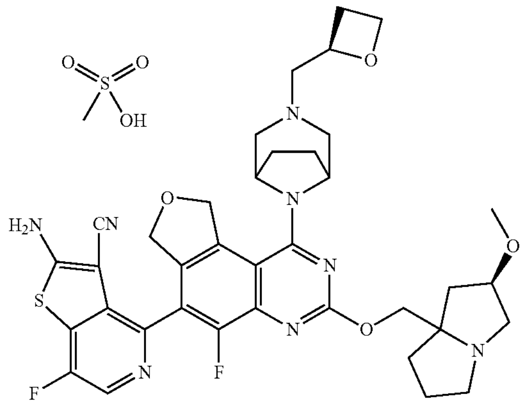 |
| 235 | 2-Amino-7-fluoro-4-[5-fluoro-1-(3-methyl-3,8-diazabicyclo[3.2.1]octan-8-yl)-3-[[(2S)-1-methylpyrrolidin-2-yl]methoxy]-7,9-dihydrofuro[3,4-f]quinazolin-6-yl]thieno[3,2-c]pyridine-3-carbonitrile | 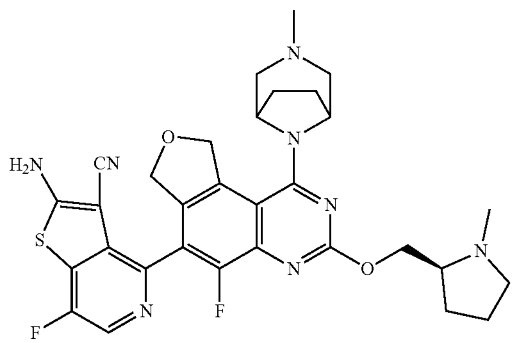 [SMILES: CN1CC2CCC(C1)N2c1nc(OC[C@@H]2CCCN2C)nc2c(F)c(-c3ncc(F)c4sc(N)c(C#N)c34)c3c(c12)COC3] |
| 236 | 2-Amino-7-fluoro-4-[5-fluoro-1-[3-(3-methoxypropyl)-3,8-diazabicyclo[3.2.1]octan-8-yl]-3-[[(2S)-1-methylpyrrolidin-2-yl]methoxy]-7,9-dihydrofuro[3,4-f]quinazolin-6-yl]thieno[3,2-c]pyridine-3-carbonitrile | 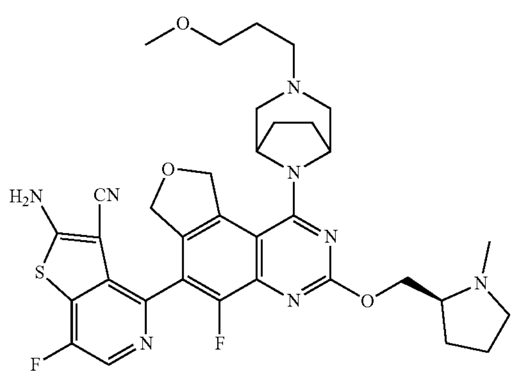 [SMILES: COCCCN1CC2CCC(C1)N2c1nc(OC[C@@H]2CCCN2C)nc2c(F)c(-c3ncc(F)c4sc(N)c(C#N)c34)c3c(c12)COC3] |
| 237 | 2-Amino-7-fluoro-4-[5-fluoro-3-[[(2S,4R)-4-fluoro-1-methyl-pyrrolidin-2-yl]methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 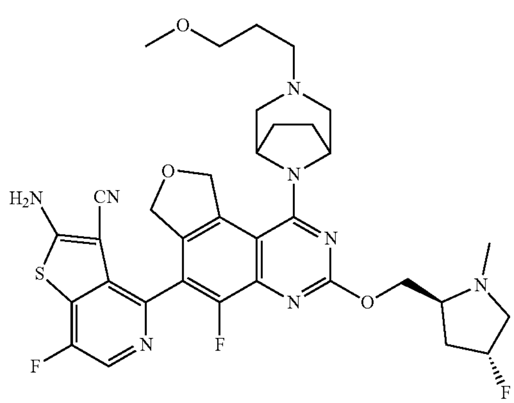 [SMILES: COCCCN1CC2CCC(C1)N2c1nc(OC[C@@H]2C[C@@H](F)CN2C)nc2c(F)c(-c3ncc(F)c4sc(N)c(C#N)c34)c3c(c12)COC3] |

-continued

| Example | Chemical Name | Structure |
|---|---|---|
| 238 | 2-Amino-7-fluoro-4-[5-fluoro-3-[[(2S,4R)-4-methoxy-1-methyl-pyrrolidin-2-yl]methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 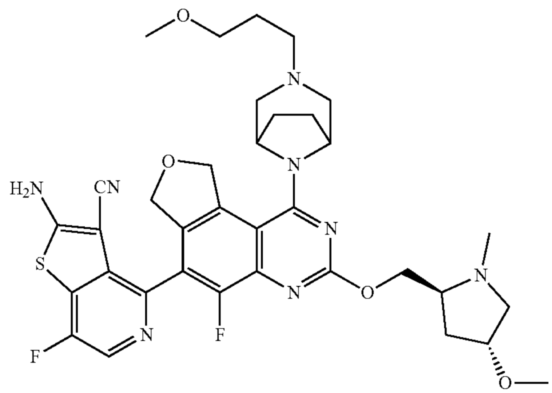 [SMILES: COCCCN1CC2CCC(C1)N2c1nc(OC[C@@H]2C[C@@H](OC)CN2C)nc2c(F)c(-c3ncc(F)c4sc(N)c(C#N)c34)c3c(c12)COC3] |
| 239 | 2-Amino-7-fluoro-4-[5-fluoro-3-(1,2,3,5,6,7-hexahydropyrrolizin-8-ylmethoxy)-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile formic acid | 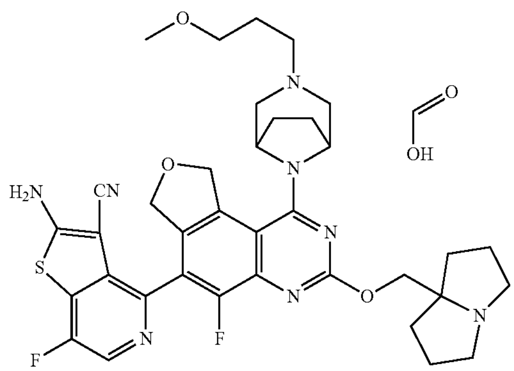 [SMILES: COCCCN1CC2CCC(C1)N2c1nc(OCC23CCCN2CCC3)nc2c(F)c(-c3ncc(F)c4sc(N)c(C#N)c34)c3c(c12)COC3 ; O=CO] |
| 241 | 2-Amino-7-fluoro-4-[5-fluoro-3-[[(2SR,8SR)-2-fluoro-1,2,3,5,6,7-hexahydropyrrolizin-8-yl]methoxy]-1-[3-(3-methoxypropyl)-3,8-diazabicyclo[3.2.1]octan-8-yl]-7,9-dihydrofuro[3,4-f]quinazolin-6-yl]thieno[3,2-c]pyridine-3-carbonitrile | 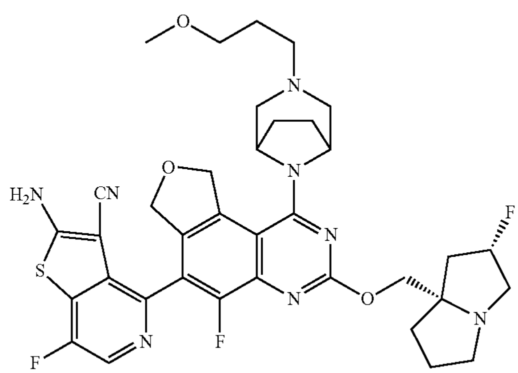 [SMILES: COCCCN1CC2CCC(C1)N2c1nc(OC[C@@]23CCCN2C[C@@H](F)C3)nc2c(F)c(-c3ncc(F)c4sc(N)c(C#N)c34)c3c(c12)COC3] |
| 242 | 2-Amino-7-fluoro-4-[5-fluoro-3-[[(2SR,8SR)-2-fluoro-1,2,3,5,6,7-hexahydropyrrolizin-8-yl]methoxy]-1-[3-(2-methoxyethyl)-3,8-diazabicyclo[3.2.1]octan-8-yl]-7,9-dihydrofuro[3,4-f]quinazolin-6-yl]thieno[3,2-c]pyridine-3-carbonitrile | 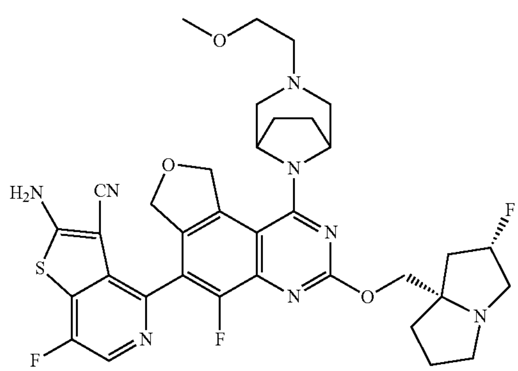 [SMILES: COCCN1CC2CCC(C1)N2c1nc(OC[C@@]23CCCN2C[C@@H](F)C3)nc2c(F)c(-c3ncc(F)c4sc(N)c(C#N)c34)c3c(c12)COC3] |

| Example | Chemical Name | Structure |
|---|---|---|
| 243 | 2-Amino-5-fluoro-4-[5-fluoro-1-[3-[(2R)-2-hydroxypropyl]-3,8-diazabicyclo[3.2.1]octan-8-yl]-3-[[(2S,4R)-4-methoxy-1-methyl-pyrrolidin-2-yl]methoxy]-7,9-dihydrofuro[3,4-f]quinazolin-6-yl]benzothiophene-3-carbonitrile | 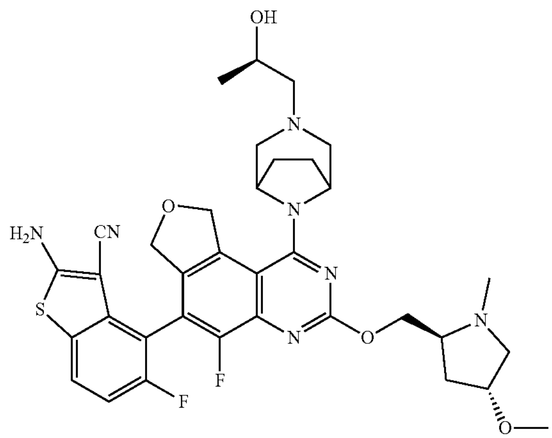 [SMILES: CO[C@@H]1C[C@@H](COc2nc(N3C4CCC3CN(C[C@@H](C)O)C4)c3c4c(c(-c5c(F)ccc6sc(N)c(C#N)c56)c(F)c3n2)COC4)N(C)C1] |
| 247 | 2-Amino-7-fluoro-4-[5-fluoro-3-(1,2,3,5,6,7-hexahydropyrrolizin-8-ylmethoxy)-1-[3-[(2R)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 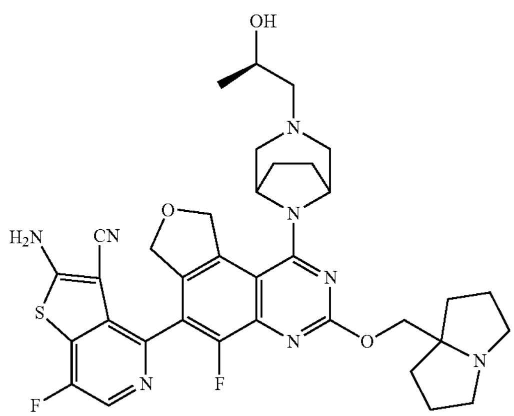 [SMILES: C[C@@H](O)CN1CC2CCC(C1)N2c1nc(OCC23CCCN2CCC3)nc2c(F)c(-c3ncc(F)c4sc(N)c(C#N)c34)c3c(c12)COC3] |
| 248 | 2-Amino-4-[3-[(6,6-difluoro-2,3,5,7-tetrahydro-1H-pyrrolizin-8-yl)methoxy]-5-fluoro-1-[3-[(2R)-2-hydroxypropyl]-3,8-diazabicyclo[3.2.1]octan-8-yl]-7,9-dihydrofuro[3,4-f]quinazolin-6-yl]-7-fluoro-thieno[3,2-c]pyridine-3-carbonitrile | 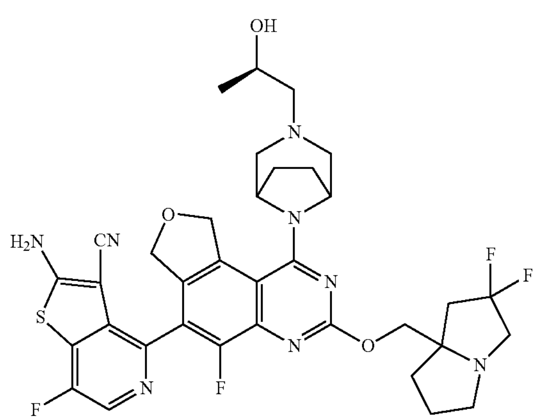 [SMILES: C[C@@H](O)CN1CC2CCC(C1)N2c1nc(OCC23CCCN2CC(F)(F)C3)nc2c(F)c(-c3ncc(F)c4sc(N)c(C#N)c34)c3c(c12)COC3] |

-continued

| Example | Chemical Name | Structure |
|---|---|---|
| 249 | 2-Amino-7-fluoro-4-[5-fluoro-3-[[(2SR,8SR)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 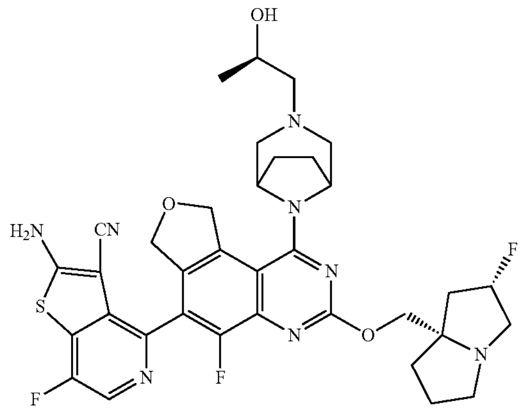 [SMILES: C[C@@H](O)CN1CC2CCC(C1)N2c1nc(OC[C@@]23CCCN2C[C@@H](F)C3)nc2c(F)c(-c3ncc(F)c4sc(N)c(C#N)c34)c3c(c12)COC3] |
| 327 | 2-Amino-7-fluoro-4-[5-fluoro-3-[[(2R,8S)-2-fluoro-1,2,3,5,6,7-hexahydropyrrolizin-8-yl]methoxy]-1-[3-[2-(trideuteriomethoxy)ethyl]-3,8-diazabicyclo[3.2.1]octan-8-yl]-7,9-dihydrofuro[3,4-f]quinazolin-6-yl]thieno[3,2-c]pyridine-3-carbonitrile | 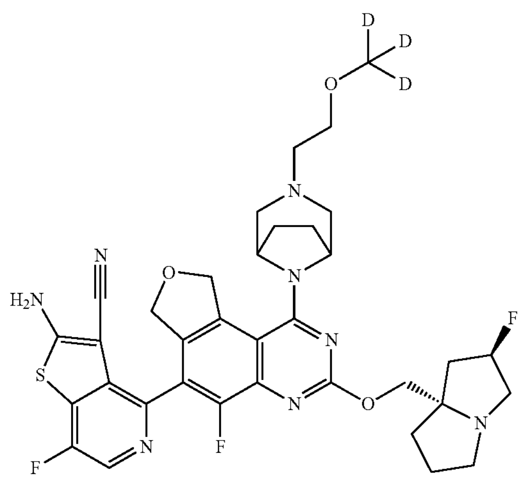 [SMILES: [2H]C([2H])([2H])OCCN1CC2CCC(C1)N2c1nc(OC[C@@]23CCCN2C[C@H](F)C3)nc2c(F)c(-c3ncc(F)c4sc(N)c(C#N)c34)c3c(c12)COC3] |
| 328 | 2-Amino-4-[3-[(4,4-difluoro-1-methyl-3-piperidyl)methoxy]-5-fluoro-1-[3-(3-hydroxypropyl)-3,8-diazabicyclo[3.2.1]octan-8-yl]-7,9-dihydrofuro[3,4-f]quinazolin-6-yl]-7-fluoro-thieno[3,2-c]pyridine-3-carbonitrile, Isomer 1 | 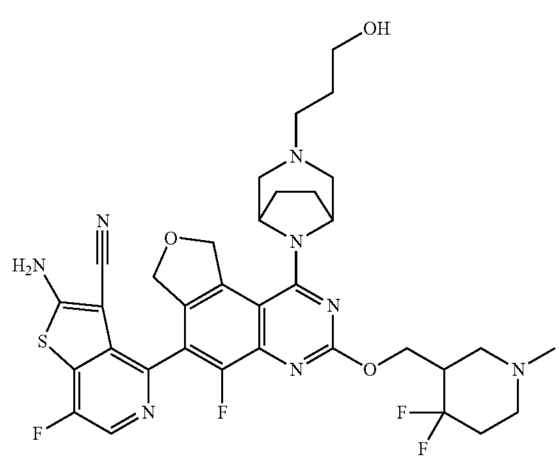 [SMILES: CN1CCC(F)(F)C(COc2nc(N3C4CCC3CN(CCCO)C4)c3c4c(c(-c5ncc(F)c6sc(N)c(C#N)c56)c(F)c3n2)COC4)C1] |

| Example | Chemical Name | Structure |
|---|---|---|
| 331 | 2-Amino-4-[3-[(4,4-difluoro-1-methyl-3-piperidyl)methoxy]-5-fluoro-1-[3-(3-hydroxypropyl)-3,8-diazabicyclo[3.2.1]octan-8-yl]-7,9-dihydrofuro[3,4-f]quinazolin-6-yl]-5-fluoro-benzothiophene-3-carbonitrile, Isomer 2 | 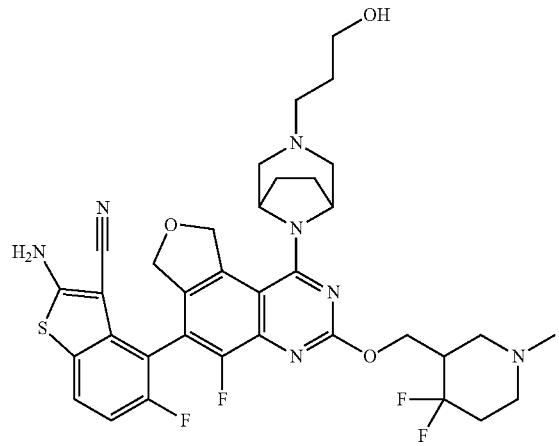 [SMILES: CN1CCC(F)(F)C(COc2nc(N3C4CCC3CN(CCCO)C4)c3c4c(c(-c5c(F)ccc6sc(N)c(C#N)c56)c(F)c3n2)COC4)C1] |
| 332 | 2-Amino-7-fluoro-4-[5-fluoro-3-[[(2S,4R)-4-fluoro-1-methyl-pyrrolidin-2-yl]methoxy]-1-[3-(3-hydroxypropyl)-3,8-diazabicyclo[3.2.1]octan-8-yl]-7,9-dihydrofuro[3,4-f]quinazolin-6-yl]thieno[3,2-c]pyridine-3-carbonitrile | 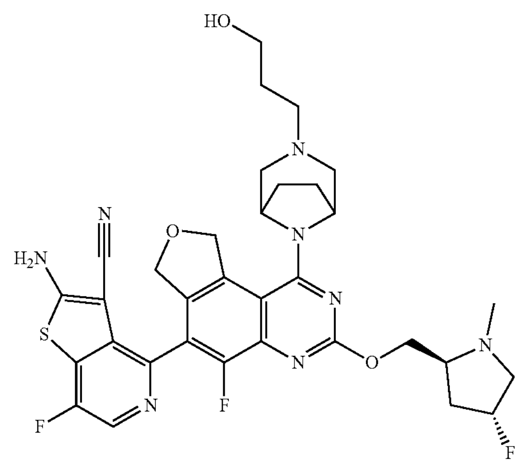 [SMILES: CN1C[C@H](F)C[C@H]1COc1nc(N2C3CCC2CN(CCCO)C3)c2c3c(c(-c4ncc(F)c5sc(N)c(C#N)c45)c(F)c2n1)COC3] |
| 334 | 2-Amino-4-[3-[[1-[(dimethylamino)methyl]cyclopropyl]methoxy]-5-fluoro-1-[3-(3-hydroxypropyl)-3,8-diazabicyclo[3.2.1]octan-8-yl]-7,9-dihydrofuro[3,4-f]quinazolin-6-yl]-7-fluoro-thieno[3,2-c]pyridine-3-carbonitrile | 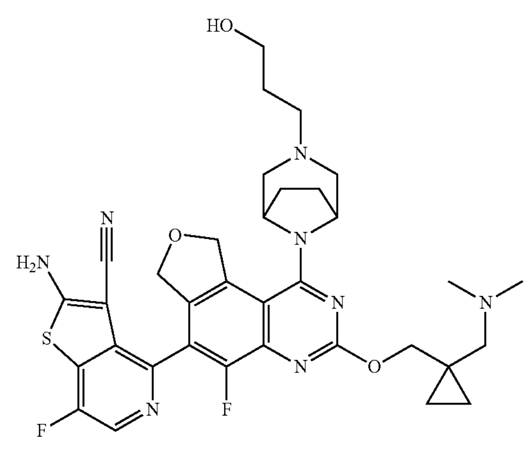 [SMILES: CN(C)CC1(COc2nc(N3C4CCC3CN(CCCO)C4)c3c4c(c(-c5ncc(F)c6sc(N)c(C#N)c56)c(F)c3n2)COC4)CC1] |

| Example | Chemical Name | Structure |
|---|---|---|
| 336 | 2-Amino-7-fluoro-4-[5-fluoro-3-[[(2R,8S)-2-fluoro-1,2,3,5,6,7-hexahydropyrrolizin-8-yl]methoxy]-1-[3-[(1-hydroxycyclopropyl)methyl]-3,8-diazabicyclo[3.2.1]octan-8-yl]-7,9-dihydrofuro[3,4-f]quinazolin-6-yl]thieno[3,2-c]pyridine-3-carbonitrile | 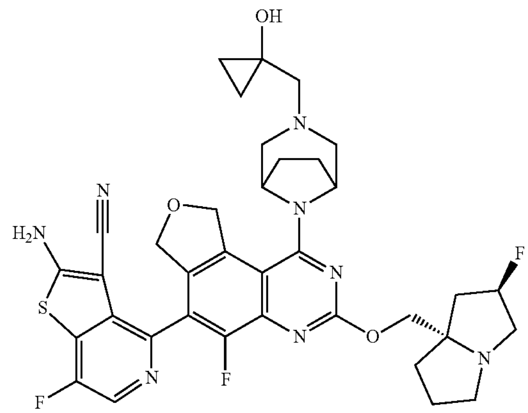 [SMILES: N#Cc1c(N)sc2c(F)cnc(-c3c4c(c5c(N6C7CCC6CN(CC6(O)CC6)C7)nc(OC[C@@]67CCCN6C[C@H](F)C7)nc5c3F)COC4)c12] |
| 340 | 2-Amino-5-fluoro-4-[5-fluoro-1-(3-methyl-3,6-diazabicyclo[3.1.1]heptan-6-yl)-3-[[(2R)-4-methylmorpholin-2-yl]methoxy]-7,9-dihydrofuro[3,4-f]quinazolin-6-yl]benzothiophene-3-carbonitrile, Isomer 2 | 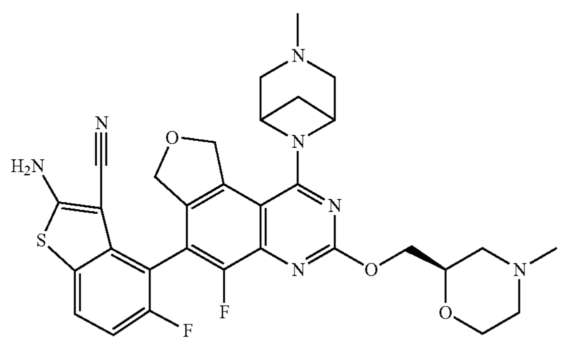 [SMILES: CN1CC2CC(C1)N2c1nc(OC[C@H]2CN(C)CCO2)nc2c(F)c(-c3c(F)ccc4sc(N)c(C#N)c34)c3c(c12)COC3] |
| 341 | 2-Amino-7-fluoro-4-[5-fluoro-3-[[(2S,4R)-4-fluoro-1-methyl-pyrrolidin-2-yl]methoxy]-1-(3-methyl-3,6-diazabicyclo[3.1.1]heptan-6-yl)-7,9-dihydrofuro[3,4-f]quinazolin-6-yl]thieno[3,2-c]pyridine-3-carbonitrile | 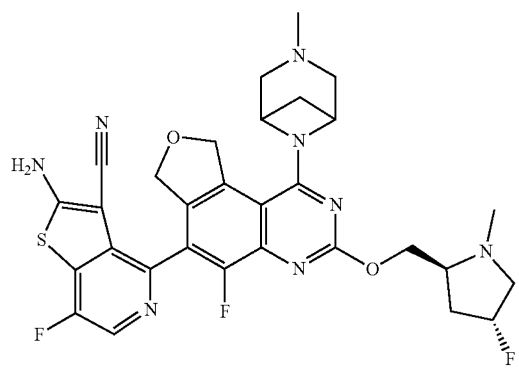 [SMILES: CN1CC2CC(C1)N2c1nc(OC[C@@H]2C[C@@H](F)CN2C)nc2c(F)c(-c3ncc(F)c4sc(N)c(C#N)c34)c3c(c12)COC3] |
| 343 | 2-Amino-7-fluoro-4-[5-fluoro-3-[[(2R,8S)-2-fluoro-1,2,3,5,6,7-hexahydropyrrolizin-8-yl]methoxy]-1-(3-methyl-3,6-diazabicyclo[3.1.1]heptan-6-yl)-7,9-dihydrofuro[3,4-f]quinazolin-6-yl]thieno[3,2-c]pyridine-3-carbonitrile | 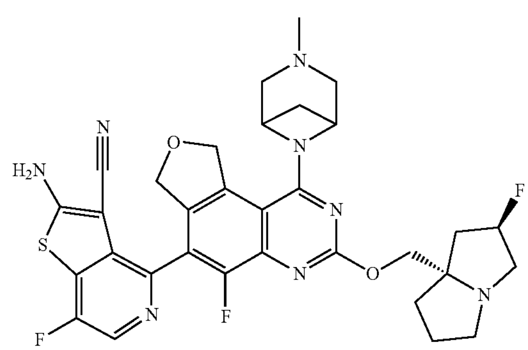 [SMILES: CN1CC2CC(C1)N2c1nc(OC[C@@]23CCCN2C[C@H](F)C3)nc2c(F)c(-c3ncc(F)c4sc(N)c(C#N)c34)c3c(c12)COC3] |

| Example | Chemical Name | Structure |
|---|---|---|
| 344 | 2-Amino-7-fluoro-4-[5-fluoro-3-[[(2R,8S)-2-fluoro-1,2,3,5,6,7-hexahydropyrrolizin-8-yl]methoxy]-1-[3-(3-methoxypropyl)-3,6-diazabicyclo[3.1.1]heptan-6-yl]-7,9-dihydrofuro[3,4-f]quinazolin-6-yl]thieno[3,2-c]pyridine-3-carbonitrile | 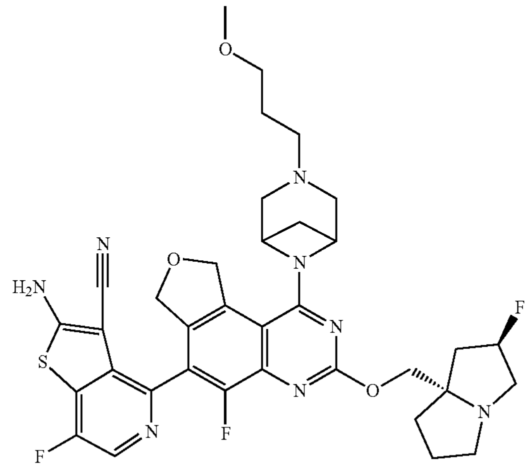 [SMILES: COCCCN1CC2CC(C1)N2c1nc(OC[C@@]23CCCN2C[C@H](F)C3)nc2c(F)c(-c3ncc(F)c4sc(N)c(C#N)c34)c3c(c12)COC3] |
| 348 | 2-Amino-4-[5-fluoro-3-[[(2R,8S)-2-fluoro-1,2,3,5,6,7-hexahydropyrrolizin-8-yl]methoxy]-1-[3-(3-methoxypropyl)-3,8-diazabicyclo[3.2.1]octan-8-yl]-7,9-dihydrofuro[3,4-f]quinazolin-6-yl]thieno[2,3-b]pyridine-3-carbonitrile | 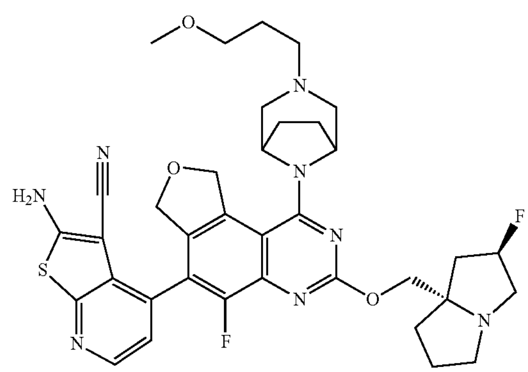 [SMILES: COCCCN1CC2CCC(C1)N2c1nc(OC[C@@]23CCCN2C[C@H](F)C3)nc2c(F)c(-c3ccnc4sc(N)c(C#N)c34)c3c(c12)COC3] |
| 351 | 2-Amino-7-fluoro-4-[5-fluoro-3-[[(2R,3S)-3-fluoro-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]thieno[3,2-c]pyridine-3-carbonitrile | 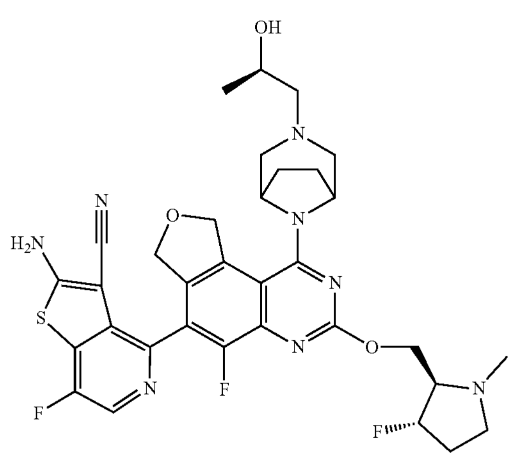 [SMILES: C[C@@H](O)CN1CC2CCC(C1)N2c1nc(OC[C@@H]2[C@@H](F)CCN2C)nc2c(F)c(-c3ncc(F)c4sc(N)c(C#N)c34)c3c(c12)COC3] |

| Example | Chemical Name | Structure |
|---|---|---|
| 354 | 2-Amino-5-fluoro-4-[5-fluoro-1-[3-[(2R)-2-hydroxypropyl]-3,8-diazabicyclo[3.2.1]octan-8-yl]-3-[[(2R)-4-methylmorpholin-2-yl]methoxy]-7,9-dihydrofuro[3,4-f]quinazolin-6-yl]benzothiophene-3-carbonitrile | 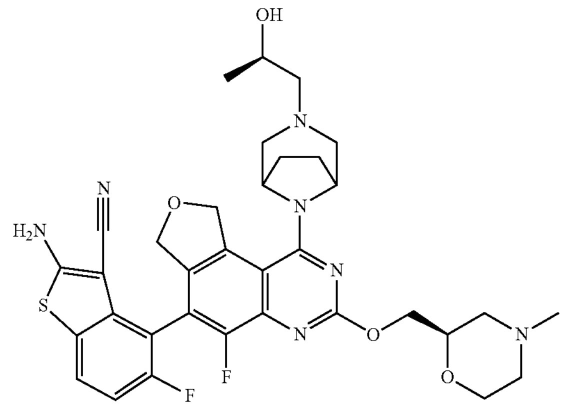 [SMILES: C[C@@H](O)CN1CC2CCC(C1)N2c1nc(OC[C@H]2CN(C)CCO2)nc2c(F)c(-c3c(F)ccc4sc(N)c(C#N)c34)c3c(c12)COC3] |
| 356 | 2-Amino-7-fluoro-4-[5-fluoro-1-[3-[(2R)-2-hydroxypropyl]-3,8-diazabicyclo[3.2.1]octan-8-yl]-3-[(1S)-1-methyl-2-morpholino-ethoxy]-7,9-dihydrofuro[3,4-f]quinazolin-6-yl]thieno[3,2-c]pyridine-3-carbonitrile | 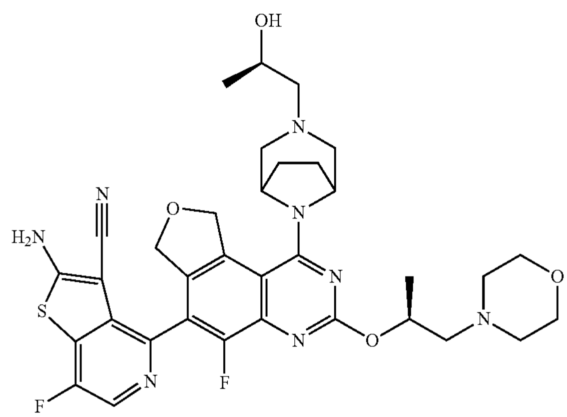 [SMILES: C[C@@H](O)CN1CC2CCC(C1)N2c1nc(O[C@@H](C)CN2CCOCC2)nc2c(F)c(-c3ncc(F)c4sc(N)c(C#N)c34)c3c(c12)COC3] |
| 358 | 2-Amino-7-fluoro-4-[5-fluoro-1-[3-[(2R)-2-hydroxypropyl]-3,8-diazabicyclo[3.2.1]octan-8-yl]-3-[(2S)-2-morpholinopropoxy]-7,9-dihydrofuro[3,4-f]quinazolin-6-yl]thieno[3,2-c]pyridine-3-carbonitrile | 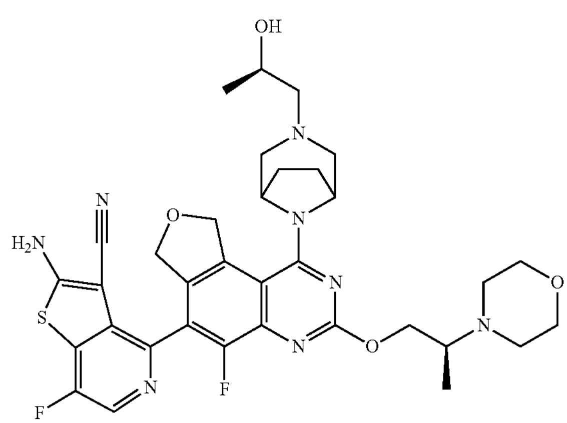 [SMILES: C[C@@H](O)CN1CC2CCC(C1)N2c1nc(OC[C@H](C)N2CCOCC2)nc2c(F)c(-c3ncc(F)c4sc(N)c(C#N)c34)c3c(c12)COC3] |

| Example | Chemical Name | Structure |
|---|---|---|
| 363 | 2-Amino-4-[1-[3-[(2R)-2-ethoxypropyl]-3,8-diazabicyclo[3.2.1]octan-8-yl]-5-fluoro-3-[[(2S,4R)-4-fluoro-1-methyl-pyrrolidin-2-yl]methoxy]-7,9-dihydrofuro[3,4-f]quinazolin-6-yl]-7-fluoro-thieno[3,2-c]pyridine-3-carbonitrile | 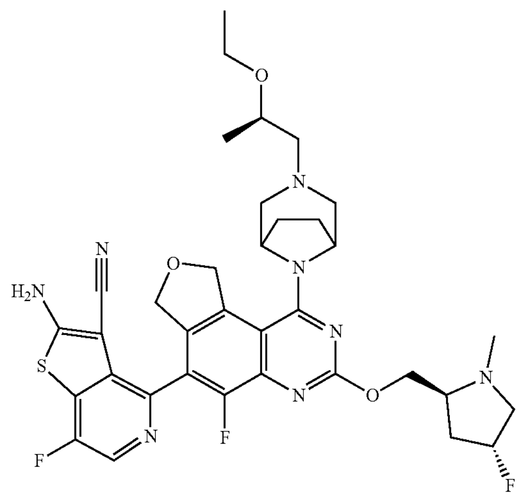 [SMILES: CCO[C@H](C)CN1CC2CCC(C1)N2c1nc(OC[C@@H]2C[C@@H](F)CN2C)nc2c(F)c(-c3ncc(F)c4sc(N)c(C#N)c34)c3c(c12)COC3] |
| 364 | 2-Amino-7-fluoro-4-[5-fluoro-3-[[(2S,4R)-4-fluoro-1-methyl-pyrrolidin-2-yl]methoxy]-1-[3-[(2R)-2-methoxypropyl]-3,8-diazabicyclo[3.2.1]octan-8-yl]-7,9-dihydrofuro[3,4-f]quinazolin-6-yl]thieno[3,2-c]pyridine-3-carbonitrile; acetic acid | 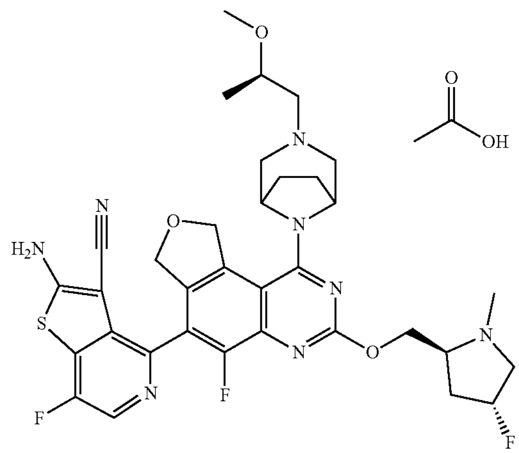 |
| 367 | 2-Amino-5-fluoro-4-[5-fluoro-3-[[(2S,4R)-4-fluoro-1-methyl-pyrrolidin-2-yl]methoxy]-1-[3-[(2R)-2-hydroxypropyl]-3,6-diazabicyclo[3.1.1]heptan-6-yl]-7,9-dihydrofuro[3,4-f]quinazolin-6-yl]benzothiophene-3-carbonitrile | 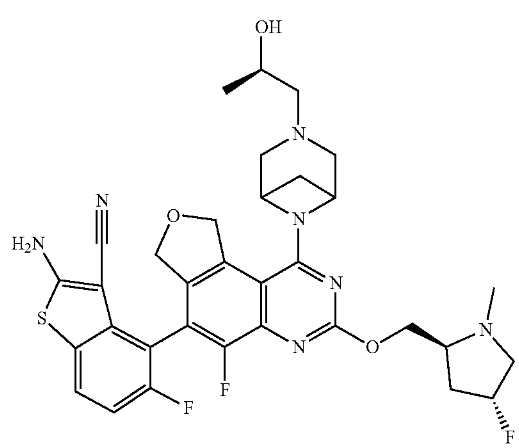 [SMILES: C[C@@H](O)CN1CC2CC(C1)N2c1nc(OC[C@@H]2C[C@@H](F)CN2C)nc2c(F)c(-c3c(F)ccc4sc(N)c(C#N)c34)c3c(c12)COC3] |

-continued

| Example | Chemical Name | Structure |
|---|---|---|
| 372 | 2-Amino-7-fluoro-4-[5-fluoro-3-[[(2R,8S)-2-fluoro-1,2,3,5,6,7-hexahydropyrrolizin-8-yl]methoxy]-1-[3-(3-fluoropropyl)-3,8-diazabicyclo[3.2.1]octan-8-yl]-7,9-dihydrofuro[3,4-f]quinazolin-6-yl]thieno[3,2-c]pyridine-3-carbonitrile | 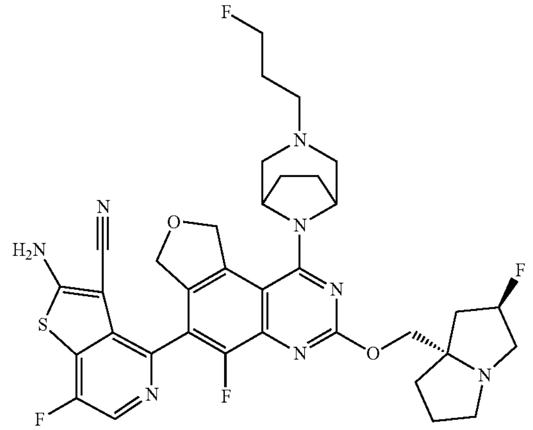 [SMILES: N#Cc1c(N)sc2c(F)cnc(-c3c4c(c5c(N6C7CCC6CN(CCCF)C7)nc(OC[C@@]67CCCN6C[C@H](F)C7)nc5c3F)COC4)c12] |
| 374 | 2-Amino-7-fluoro-4-[5-fluoro-1-[3-(2-fluoroethyl)-3,8-diazabicyclo[3.2.1]octan-8-yl]-3-[[(2R,8S)-2-fluoro-1,2,3,5,6,7-hexahydropyrrolizin-8-yl]methoxy]-7,9-dihydrofuro[3,4-f]quinazolin-6-yl]thieno[3,2-c]pyridine-3-carbonitrile | | or a pharmaceutically acceptable salt thereof.

32. A pharmaceutical composition comprising a compound according to claim 1, or a pharmaceutically acceptable salt thereof, and a pharmaceutically acceptable carrier, diluent or excipient.

33. A pharmaceutical composition comprising a compound according to claim 31, or a pharmaceutically acceptable salt thereof, and a pharmaceutically acceptable carrier, diluent or excipient.

\* \* \* \* \*

UNITED STATES PATENT AND TRADEMARK OFFICE
CERTIFICATE OF CORRECTION

PATENT NO. : 12,351,591 B2
APPLICATION NO. : 18/189713
DATED : July 8, 2025
INVENTOR(S) : Barda et al.

Page 1 of 4

It is certified that error appears in the above-identified patent and that said Letters Patent is hereby corrected as shown below:

In the Claims

In Column 738, in Claim 9, Line 25, delete "ring," and insert -- ring; --.

In Column 745, in Claim 26, Lines 1-7, delete " 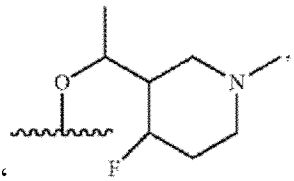 " and insert

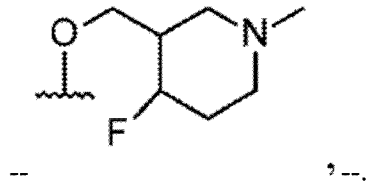

-- ? --.

In Column 757, in Claim 31, Example 103, Lines 1-15, delete "2-Amino-7-fluoro-4-[5-fluoro-3-[[(2R,8S)-2-fluoro-1,2,3,5,6,7-hexahydropyrrolizin-8-yl]methoxy]-1-[3-[(2R)-oxetan-2-yl]methyl]-3,8-diazabicyclo[3.2.1]octan-8-yl]-7,9-dihydrofuro[3,4-f]quinazolin-6-yl]benzothiophene-3-carbonitrile, Isomer 2" and insert -- 2-Amino-7-fluoro-4-[5-fluoro-3-[[(2R,8S)-2-fluoro-1,2,3,5,6,7-hexahydropyrrolizin-8-yl]methoxy]-1-[3-[[(2R)-oxetan-2-yl]methyl]-3,8-diazabicyclo[3.2.1]octan-8-yl]-7,9-dihydrofuro[3,4-f]quinazolin-6-yl]benzothiophene-3-carbonitrile, Isomer 2 --.

In Column 759, in Claim 31, Example 110, Lines 1-15, delete "2-Amino-5-fluoro-4-[5-fluoro-3-[[(2R,8S)-2-fluoro-1,2,3,5,6,7-hexahydropyrrolizin-8-yl]methoxy]-1-[3-[1-(2-hydroxyethyl)pyrazol-4-yl]methyl]-3,8-diazabicyclo[3.2.1]octan-8-yl]-7,9-dihydrofuro[3,4-f]quinazolin-6-yl]benzothiophene-3-carbonitrile" and insert -- 2-Amino-5-fluoro-4-[5-fluoro-3-[[(2R,8S)-2-fluoro-1,2,3,5,6,7-

Signed and Sealed this
Tenth Day of February, 2026

John A. Squires
*Director of the United States Patent and Trademark Office* hexahydropyrrolizin-8-yl]methoxy]-1-[3-[[1-(2-hydroxyethyl)pyrazol-4-yl]methyl]-3,8-diazabicyclo[3.2.1]octan-8-yl]-7,9-dihydrofuro[3,4-f]quinazolin-6-yl]benzothiophene-3-carbonitrile --.

In Column 763, in Claim 31, Example 123, Lines 50-60, delete "2-Amino-7-fluoro-4-[5-fluoro-3-[[(2R,8S)-2-fluoro-1,2,3,5,6,7-hexahydropyrrolizin-8-yl]methoxy]-1-[3-[(2R)-oxetan-2-yl]methyl]-3,8-diazabicyclo[3.2.1]octan-8-yl]-7,9-dihydrofuro[3,4-f]quinazolin-6-yl]thieno[3,2-c]pyridine-3-carbonitrile" and insert -- 2-Amino-7-fluoro-4-[5-fluoro-3-[[(2R,8S)-2-fluoro-1,2,3,5,6,7-hexahydropyrrolizin-8-yl]methoxy]-1-[3-[[(2R)-oxetan-2-yl]methyl]-3,8-diazabicyclo[3.2.1]octan-8-yl]-7,9-dihydrofuro[3,4-f]quinazolin-6-yl]thieno[3,2-c]pyridine-3-carbonitrile --.

In Column 783, in Claim 31, Example 175, Lines 50-60, delete "2-Amino-4-[3-[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile" and insert -- "2-Amino-4-[3-[[(2R,8S)-2-fluoro-1,2,3,5,6,7-hexahydropyrrolizin-8-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile --.

In Column 785, in Claim 31, Example 179, Lines 50-60, delete "2-Amino-5-fluoro-4-[5-fluoro-1-[3-[(2R)-2-hydroxypropyl]-3,8-diazabicyclo[3.2.1]octan-8-yl]-3-[(2S)-1-methylazetidin-2-yl]methoxy]-7,9-dihydrofuro[3,4-f]quinazolin-6-yl]benzothiophene-3-carbonitrile" and insert -- 2-Amino-5-fluoro-4-[5-fluoro-1-[3-[(2R)-2-hydroxypropyl]-3,8-diazabicyclo[3.2.1]octan-8-yl]-3-[[(2S)-1-methylazetidin-2-yl]methoxy]-7,9-dihydrofuro[3,4-f]quinazolin-6-yl]benzothiophene-3-carbonitrile --.

In Column 791, in Claim 31, Example 186, Lines 1-15, delete "2-Amino-5-fluoro-4-[5-fluoro-3-[(2S,4S)-4-fluoro-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile" and insert -- 2-Amino-5-fluoro-4-[5-fluoro-3-[[(2S,4S)-4-fluoro-1-methyl-pyrrolidin-2-yl]methoxy]-1-[3-[(2R)-2-hydroxypropyl]-3,8-diazabicyclo[3.2.1]octan-8-yl]-7,9-dihydrofuro[3,4-f]quinazolin-6-yl]benzothiophene-3-carbonitrile --.

In Column 797, in Claim 31, Example 216, Lines 1-15, delete "2-Amino-5-fluoro-4-[5-fluoro-1-[3-[(2R)-2-methoxypropyl]-3,8-diazabicyclo[3.2.1]octan-8-yl]-3-[(2S)-1-methylpyrrolidin-2-yl]methoxy]-7,9-dihydrofuro[3,4-f]quinazolin-6-yl]benzothiophene-3-carbonitrile" and insert -- 2-Amino-5-fluoro-4-[5-fluoro-1-[3-[(2R)-2-methoxypropyl]-3,8-diazabicyclo[3.2.1]octan-8-yl]-3-[[(2S)-1-methylpyrrolidin-2-yl]methoxy]-7,9-dihydrofuro[3,4-f]quinazolin-6-yl]benzothiophene-3-carbonitrile --.

CERTIFICATE OF CORRECTION (continued)
U.S. Pat. No. 12,351,591 B2

Page 3 of 4

In Column 797, in Claim 31, Example 216, Lines 1-15, delete " 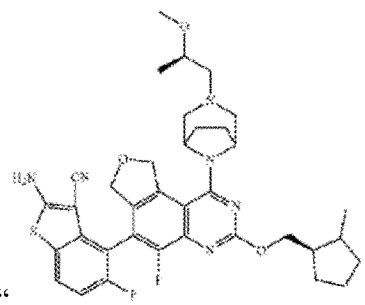 " and insert -- 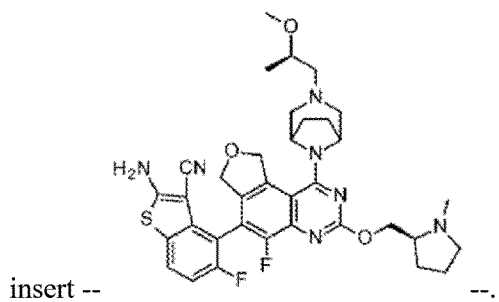 --.

In Column 801, in Claim 31, Example 232, Lines 50-65, delete " 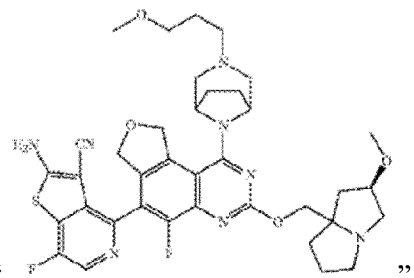 "

and insert -- 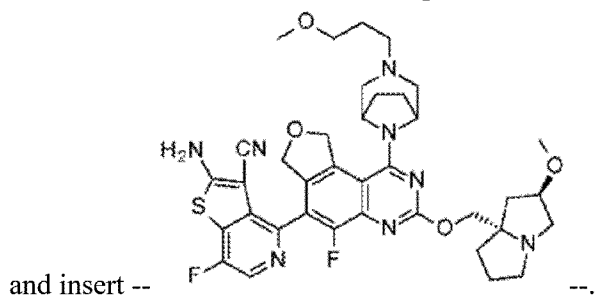 --.

In Column 803, in Claim 31, Example 234, Lines 1-15, delete "2-amino-7-fluoro-4-[5-fluoro-3-[[(2R,8S)-2-methoxy-1,2,3,5,6,7-hexahydropyrrolizin-8-yl]methoxy]-1-[3-[(2R)-oxetan-2-yl]methyl]-3,8-diazabicyclo[3.2.1]octan-8-yl]-7,9-dihydrofuro[3,4-f]quinazolin-6-yl]thieno[3,2-c]pyridine-3-carbonitrile methanesulfonic acid" and insert -- 2-amino-7-fluoro-4-[5-fluoro-3-[[(2R,8S)-2-methoxy-1,2,3,5,6,7-hexahydropyrrolizin-8-yl]methoxy]-1-[3-[[(2R)-oxetan-2-yl]methyl]-3,8-diazabicyclo[3.2.1]octan-8-yl]-7,9-dihydrofuro[3,4-f]quinazolin-6-yl]thieno[3,2-c]pyridine-3-carbonitrile methanesulfonic acid --.

CERTIFICATE OF CORRECTION (continued)
U.S. Pat. No. 12,351,591 B2

In Column 803, in Claim 31, Example 234, Lines 1-15, delete " 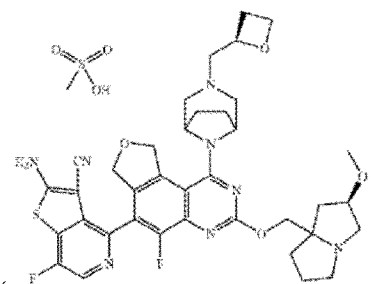 " and insert -- 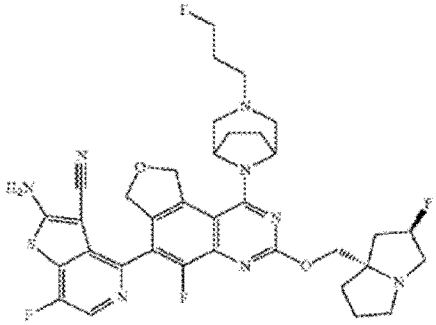 --.

In Column 821, in Claim 31, Lines 1-15, after " 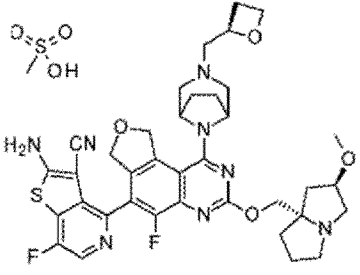 " insert -- , and --.